(12) United States Patent
Patel et al.

(10) Patent No.: US 10,176,292 B2
(45) Date of Patent: Jan. 8, 2019

(54) STING CRYSTALS AND MODULATORS

(71) Applicants: MEMORIAL SLOAN-KETTERING CANCER CENTER, New York, NY (US); THE ROCKEFELLER UNIVERSITY, New York, NY (US); RUTGERS, THE STATE UNIVERSITY OF NEW JERSEY, New Brunswick, NJ (US); UNIVERSITY OF BONN, Bonn (DE)

(72) Inventors: Dinshaw J. Patel, New York, NY (US); Thomas Tuschl, New York, NY (US); Roger Jones, New Brunswick, NJ (US); Gunther Hartmann, Bonn (DE); Winfried Barchet, Bonn (DE); Thomas Zillinger, Bonn (DE); Weiyi Wang, New York, NY (US); Pu Gao, New York, NY (US); Liang Deng, New York, NY (US); Manuel Ascano, Jr., New York, NY (US)

(73) Assignees: Memorial Sloan-Kettering Cancer Center, New York, NY (US); The Rockefeller University, New York, NY (US); Rutgers, The State University of New Jersey, New Brunswick, NJ (US); University of Bonn, Bonn (DE)

( * ) Notice: Subject to any disclaimer, the term of this patent is extended or adjusted under 35 U.S.C. 154(b) by 0 days.

(21) Appl. No.: 14/908,019

(22) PCT Filed: Jul. 31, 2014

(86) PCT No.: PCT/US2014/049140
§ 371 (c)(1),
(2) Date: Jan. 27, 2016

(87) PCT Pub. No.: WO2015/017652
PCT Pub. Date: Feb. 5, 2015

(65) Prior Publication Data
US 2016/0210400 A1 Jul. 21, 2016

Related U.S. Application Data

(60) Provisional application No. 61/860,818, filed on Jul. 31, 2013.

(51) Int. Cl.
| | |
|---|---|
| *G06F 19/16* | (2011.01) |
| *G06F 19/12* | (2011.01) |
| *G01N 33/68* | (2006.01) |
| *C07K 14/715* | (2006.01) |
| *A61K 31/352* | (2006.01) |
| *A61K 31/7084* | (2006.01) |
| *A61K 31/473* | (2006.01) |
| *C07K 14/70* | (2006.01) |
| *C07K 14/705* | (2006.01) |

(52) U.S. Cl.
CPC .......... *G06F 19/16* (2013.01); *A61K 31/352* (2013.01); *A61K 31/473* (2013.01); *A61K 31/7084* (2013.01); *C07K 14/705* (2013.01); *C07K 14/7156* (2013.01); *G01N 33/68* (2013.01); *G06F 19/12* (2013.01); *C07K 2299/00* (2013.01); *G01N 2333/52* (2013.01); *G01N 2400/00* (2013.01); *G01N 2500/04* (2013.01)

(58) Field of Classification Search
CPC ..... G06F 19/16; G06F 19/12; C07K 14/7156; C07K 14/705; G01N 33/68; A61K 31/473; A61K 31/352; A61K 31/7084; A61K 2500/04; A61K 2400/00
See application file for complete search history.

(56) References Cited

U.S. PATENT DOCUMENTS

| | | | |
|---|---|---|---|
| 5,547,941 | A | 8/1996 | Battistini et al. |
| 5,637,483 | A | 6/1997 | Dranoff et al. |
| 5,698,432 | A | 12/1997 | Oxford |
| 5,904,920 | A | 5/1999 | Dranoff et al. |
| 5,985,290 | A | 11/1999 | Jaffee et al. |
| 6,033,674 | A | 3/2000 | Jaffee et al. |
| 6,090,611 | A | 7/2000 | Covacci et al. |
| 6,183,121 | B1* | 2/2001 | Kim .................... C07K 14/005 378/71 |
| 6,277,368 | B1 | 8/2001 | Hiserodt et al. |
| 6,350,445 | B1 | 2/2002 | Jaffee et al. |
| 6,464,973 | B1 | 10/2002 | Levitsky et al. |
| 6,558,670 | B1 | 5/2003 | Friede et al. |
| 6,780,429 | B1 | 8/2004 | Matsuyama et al. |
| 7,569,555 | B2 | 8/2009 | Karaolis |
| 7,592,326 | B2 | 9/2009 | Karaolis |
| 7,709,458 | B2 | 5/2010 | Karaolis et al. |
| 8,012,469 | B2 | 9/2011 | Levitsky et al. |

(Continued)

FOREIGN PATENT DOCUMENTS

| | | |
|---|---|---|
| WO | WO-2005/030186 A2 | 4/2005 |
| WO | WO-2005/039535 A1 | 5/2005 |

(Continued)

OTHER PUBLICATIONS

Huang et al., The structural basis for the sensing and binding of cyclic di-GMP by STING. Nat Struct Mol Biol. (Epub Jun. 24, 2012), vol. 19(7), pp. 728-730.*

(Continued)

*Primary Examiner* — Suzanne M Noakes
*Assistant Examiner* — Jae W Lee
(74) *Attorney, Agent, or Firm* — Choate, Hall & Stewart LLP; Brenda Herschbach Jarrell; John P. Rearick

(57) ABSTRACT

The present invention provides STING crystals. The present invention also provides STING modulators that interact with sites present in and/or defined by such crystals. The present invention also provides methods of making and using such crystals and modulators. Other aspects and/or features of the present invention will be apparent to those skilled in the art, reading the present specification.

6 Claims, 48 Drawing Sheets
(28 of 48 Drawing Sheet(s) Filed in Color)
Specification includes a Sequence Listing.

(56) References Cited

U.S. PATENT DOCUMENTS

| | | | |
|---|---|---|---|
| 8,283,328 | B2 | 10/2012 | Krieg et al. |
| 8,304,396 | B2 | 11/2012 | Krieg et al. |
| 8,367,716 | B2 | 2/2013 | Karaolis |
| 8,450,293 | B2 | 5/2013 | Jones et al. |
| 9,061,048 | B2 | 6/2015 | Portnoy et al. |
| 9,597,391 | B2 | 3/2017 | Ebensen et al. |
| 9,840,533 | B2 | 12/2017 | Patel et al. |
| 2001/0041682 | A1 | 11/2001 | Stutts et al. |
| 2002/0140414 | A1 | 10/2002 | Sohn et al. |
| 2003/0003092 | A1 | 1/2003 | Krissansen et al. |
| 2003/0138413 | A1 | 7/2003 | Vicari et al. |
| 2006/0040887 | A1 | 2/2006 | Karaolis |
| 2006/0286549 | A1 | 12/2006 | Sohn et al. |
| 2007/0059683 | A1 | 3/2007 | Barber et al. |
| 2007/0155766 | A1 | 7/2007 | Zheng et al. |
| 2007/0224210 | A1 | 9/2007 | Krieg et al. |
| 2007/0244059 | A1 | 10/2007 | Karaolis |
| 2007/0281897 | A1 | 12/2007 | Karaolis |
| 2008/0076778 | A1 | 3/2008 | Ossovskaya et al. |
| 2008/0286296 | A1 | 11/2008 | Ebensen et al. |
| 2010/0150946 | A1 | 6/2010 | Jooss et al. |
| 2010/0310602 | A1 | 12/2010 | Reed et al. |
| 2011/0081674 | A1 | 4/2011 | Han et al. |
| 2011/0262485 | A1 | 10/2011 | Barber |
| 2011/0287948 | A1 | 11/2011 | Suresh et al. |
| 2012/0041057 | A1 | 2/2012 | Jones et al. |
| 2012/0164107 | A1 | 6/2012 | Portnoy et al. |
| 2012/0178710 | A1 | 7/2012 | Jones et al. |
| 2014/0205653 | A1 | 7/2014 | Dubensky, Jr. et al. |
| 2014/0329889 | A1 | 11/2014 | Vance et al. |
| 2014/0341976 | A1 | 11/2014 | Dubensky, Jr. et al. |
| 2015/0056224 | A1 | 2/2015 | Dubensky, Jr. et al. |
| 2016/0068560 | A1 | 3/2016 | Patel et al. |
| 2018/0118777 | A1 | 5/2018 | Patel et al. |
| 2018/0127454 | A1 | 5/2018 | Patel et al. |

FOREIGN PATENT DOCUMENTS

| | | | |
|---|---|---|---|
| WO | WO-2005/087238 | A2 | 9/2005 |
| WO | WO-2005/089777 | A1 | 9/2005 |
| WO | WO-2007/054279 | A2 | 5/2007 |
| WO | WO-2007/064945 | A2 | 6/2007 |
| WO | WO-2009/133560 | A1 | 11/2009 |
| WO | WO-2010/017248 | A2 | 2/2010 |
| WO | WO-2010/067262 | A1 | 6/2010 |
| WO | WO-2010/104883 | A1 | 9/2010 |
| WO | WO-2011/003025 | A1 | 1/2011 |
| WO | WO-2011/136828 | A1 | 11/2011 |
| WO | WO-2011/139769 | A2 | 11/2011 |
| WO | WO-2012/088155 | A1 | 6/2012 |
| WO | WO-2012/139209 | A1 | 10/2012 |
| WO | WO-2013/086331 | A1 | 6/2013 |
| WO | WO-2013/166000 | A1 | 11/2013 |
| WO | WO-2013/185052 | A1 | 12/2013 |
| WO | WO-2014/093936 | A1 | 6/2014 |
| WO | WO-2014/099824 | A1 | 6/2014 |
| WO | WO-2014/179335 | A1 | 11/2014 |
| WO | WO-2014/179760 | A1 | 11/2014 |
| WO | WO-2014/189805 | A1 | 11/2014 |
| WO | WO-2014/189806 | A1 | 11/2014 |
| WO | WO-2015/017652 | A1 | 2/2015 |
| WO | WO-2015/061294 | A2 | 4/2015 |
| WO | WO-2015/074145 | A1 | 5/2015 |
| WO | WO-2015/077354 | A1 | 5/2015 |
| WO | WO-2015/108595 | A1 | 7/2015 |
| WO | WO-2015/185565 | A1 | 12/2015 |

OTHER PUBLICATIONS

Huang et al. Supplemental Epub Jun. 24, 2012.*

Ekins et al. (In silico pharmacology for drug discovery: methods for virtual ligand screening and profiling. Br J Pharmacol. (2007), vol. 152(1), pp. 9-20.*

Ouyang et al. Structural analysis of the STING adaptor protein reveals a hydrophobic dimer interface and mode of cyclic di-GMP binding. Immunity. (Jun. 29, 2012), vol. 36(6), pp. 1073-1086.*

Ouyang et al. supplemental information Jun. 29, 2012.*

Weber, Overview of Crystallization Methods. Methods in Enzymology, 1997, vol. 276, pp. 13-22.*

Drenth, "Principles of Protein X-Ray Crystallography", 2nd Edition, 1999 Springer-Verlag New York Inc., Chapter 1, p. 19, 4th paragraph, lines 1-2.*

Klyushnichenko. Curr. Op. Drug Discovery, 2003, 6(6):848-54.*

Ablasser, A. et al. cGAS produces a 2'-5'-linked cyclic dinucleotide second messenger that activates STING. Nature 498, 380-384 (2013).

Adams, P.D. et al., PHENIX: a comprehensive Python-based system for macromolecular structure solution. Acta Crystallogr. D Biol. Crystallogr. 66, 213-221 (2010).

Adler-Moore, J. et al., Characterization of the murine Th2 response to immunization with liposomal M2e influenza vaccine, Vaccine, 29:4460-4468(2011).

Ahmed, S.S. et al., Assessing the safety of adjuvanted vaccines. Sciience Translation Medicine, 3(93):1-12 (2011).

Antonarakis, E.S. and Drake, C.G., Combining immunological and androgen-directed approaches: an emerging concept in prostate cancer immunotherapy, Current Opinion in Oncology, 24(3):258-265 (2012).

Ausmees, N. et al., Genetic data indicate that proteins containing the GGDEF domain possess diguanylate cyclase ctivity, FEMS Microbiology Letters 204(1):163-167 (2001).

Badovinac, V.P. et al., Accelerated CD8B+ T-cell memory and prime-boost response after dendritic-cell vaccination, Nature Medicine, 11(7):748-756 (2005).

Baguley, B.C., and Ching, L.M. DMXAA: an antivascular agent with multiple host responses. Int. J. Radiat. Oncol. Biol. Phys. 54, 1503-1511 (2002).

Bahjat, K.S. et al., Activation of Immature Hepatic NK Cells as Immunotherapy for Liver Metastatic Disease, The Journal of Immunology, 179(11):7376-7384 (2007).

Bahjat, K.S. et al., Cytosolic entry controls CD8+-T-Cell potency during bacterial infection, Infection and Immunity, 74(11):6387-6397 (2006).

Bahjat, K.S. et al., Suppression of cell-mediated immunity following recognition of phagosome-confined bacteria, PLoS Pathogens, 5(9):e1000568 (2009).

Bala, I. et al., PLGA nanoparticles in drug delivery: the state of the art, Critical Reviews in Therapeutic Drug Carrier Systems, 21(5):387-422 (2004).

Baldwin, S. et al., The importance of adjuvant formulation in the development of a tuberculosis vaccine, The Journal of Immunology, 188(5):2189-2197 (2012).

Barber, G.N., Cytoplasmic DNA innate immune pathways, Immunological Reviews, 243(1):99-108 (2011).

Barber, G.N., STING-dependent signaling, Nature Immunology, 12(10):929-930 (2011).

Barker, J.R. et al., STING-Dependent recognition of cyclic di-AMP mediates type I interferon responses during Chlamydia trachomatis infection, mBio, 4(3):e00018-00013 (2013).

Battistini, C. et al., Stereoselective synthesis of cyclic dinucleotide phosphorothioates, Tetrahedron, 49(5):1115-1132 (1993).

Blankenstein, T. et al., The determinants of tumour immunogenicity, Nature Reviews Cancer, 12(4):307-313 (2012).

Bowie, A.G. et al., Innate sensing of bacterial cyclic dinucleotides: more than just STING, Nature Immunology, 13(12):1137-1139 (2012).

Brahmer, J.R. et al., Phase I study of single-agent anti-programmed death-1 (MDX-1106) in refractory solid tumors: safety, clinical activity, pharmacodynamics, and immunologic correlates, Journal of Clinical Oncology, 28(19):3167-3175 (2010).

Brockstedt, D.G. et al., Killed but metabolically active microbes: a new vaccine paradigm for eliciting effector T-cell responses and protective immunity, Nature Medicine, 11(8):853-860 (2005).

Brockstedt, D.G. et al., Listeria-based cancer vaccines that segregate immunogenicity from toxicity, Proceedings of the National Academy of Sciences, U.S.A., 101(38):13832-13837 (2004).

(56) References Cited

OTHER PUBLICATIONS

Burckstummer, T. et al., An orthogonal proteomic-genomic screen identifies AIM2 as a cytoplasmic DNA sensor for the inflammasome. Nat. Immunol. 10, 266-272 (2009).
Burdette, D.L., and Vance, R.E. STING and the innate immune response to nucleic acids in the cytosol. Nat. Immunol. 14, 19-26 (2013).
Burdette, D.L., et al. STING is a direct innate immune sensor of cyclic di-GMP. Nature 478, 515-518 (2011).
Burger's Medicinal Chemistry and Drug Discovery, Fifth Edition, published 1994 by Wiley-Interscience, edited by Manfred E. Wolff, pp. 975-977.
Cai, X. et al. The cGAS-cGAMP-STING Pathway of Cytosolic DNA Sensing and Signaling. Mol. Cell 54, 289-296 (2014).
Cavlar, T. et al. Species-specific detection of the antiviral small-molecule compound CMA by STING. EMBO J. 32, 1440-1450 (2013).
Chan, C. et al., Structural basis of activity and allosteric control of diguanylate cyclase, Proceedings of the National Academy of Sciences of the United States of America, 101(49)17084-9 (2004).
Chen, W. et al., The potential of 3',5'-cyclic diguanylic acid (c-di-GMP) as an effective vaccine adjuvant, Vaccine, 28(18):3080-3085 (2010).
Civril, F. et al. Structural mechanism of cytosolic DNA sensing by cGAS. Nature 498, 332-337 (2013).
Coffman, R.L. et al., Vaccine adjuvants: putting innate immunity to work, Immunity, 33(4):492-503 (2010).
Coler, R.N. et al., Development and characterization of synthetic glucopyranosyl lipid adjuvant system as a vaccine adjuvant, PLoS One, 6(1):e16333 (2011).
Conlon, J., et al. Mouse, but not human STING, binds and signals in response to the vascular disrupting agent 5,6-Dimethylxanthenone-4-Acetic Acid. J. Immunol. 190, 5216-5225 (2013).
Coughlin, J.E. et al., Orally bioavailable anti-HBV dinucleotide acyloxyalkyl prodrugs, Bioorganic & Medicinal Chemistry Letters 20(5):1783-1786 (2010).
Creighton, T.E. et al., Mechanisms and catalysts of disulfide bond formation in proteins. Trends in Biotechnology, 13(1):18-23 (1995).
Crimmins, G.T. et al., Listeria monocytogenes multidrug resistance transporters activate a cytosolic surveillance pathway of innate immunity, Proceedings of the National Academy of Sciences, U.S.A., 105(29):10191-10196 (2008).
Crittenden, M. et al., Expression of inflammatory chemokines combined with local tumor destruction enhances tumor regression and long-term immunity, Cancer Research, 63(17):5505-5512 (2003).
Curran, M.A. and Allison, J.P., Tumor vaccines expressing Flt3 ligand synergize with CTLA-4 blockade to reject dreimplanted tumors, Cancer Research, 69(19):7747-7755 (2009).
Dai, P. et al. Modified vaccinia virus Ankara triggers type I IFN production in murine conventional dendritic cells via a cGAS/STING-mediated cytosolic DNA-sensing pathway. PLoS Pathog. 10, e1003989 (2014).
Dalby, B. et al., Advanced transfection with Lipofectamine 2000 reagent: primary neurons, siRNA, and high-throughput pplications, Methods, 33(2):95-103 (2004).
Danilchanka, O. and Mekalanos, J. J., Cyclic Dinucleotides and the Innate Immune Response. Cell 154, 962-970 (2013).
Davies, B.W. et al., Coordinated regulation of accessory genetic elements produces cyclic di-nucleotides for V. cholerae virulence. Cell 149, 358-370 (2012).
De Grujil, T.D. et al., Whole-cell cancer vaccination: from autologous to allogeneic tumor-and dendritic cell-based vaccines, Cancer Immunology, Immunotherapy, 57(10):1569-1577 (2008).
Desmet, C.J. and Ishii, K.J., Nucleic acid sensing at the interface between innate and adaptive immunity in vaccination, Nature Reviews Immunology, 12(7):479-491 (2012).

Dessureault, S. et al., A phase-I trial using a universal GM-CSF-producing and CD40L-expressing bystander cell line (GM.CD4OL) in the formulation of autologous tumor cell-based vaccines for cancer patients with stage IV disease, Annals of Surgical Oncology, 14(2):869-884 (2007).
Di Lorenzo, G. et al., Immunotherapy for the treatment of prostate cancer, Nature Reviews Clinical Oncology, 8:551-561 (2011).
Diner, E.J., et al. The innate immune DNA sensor cGAS produces a noncanonical cyclic dinucleotide that activates human STING. Cell reports 3, 1355-1361 (2013).
Donovan, J. et al., Structural basis for cytosolic double-stranded RNA surveillance by human oligoadenylate synthetase 1. Proc. Natl. Acad. Sci. USA 110, 1652-1657 (2013).
Drake, C.G. et al., Androgen ablation mitigates tolerance to a prostate/prostate cancer-restricted antigen, Cancer Cell, 7(3):239-249 (2005).
Dranoff, G. et al., Vaccination with irradiated tumor cells engineered to secrete murine granulocyte-macrophage colony-stimulating factor stimulates potent, specific, and long-lasting anti-tumor immunity, Proceedings of the National Academy of Sciences, 90(8):3539-3543 (1993).
Driessens, G. et al., Highly successful therapeutic vaccinations combining factor dendritic cells and tumor cells secreting granulocyte macrophage colony-stimulating factor, Cancer Research, 64(22):8435-8442 (2004).
Dubensky, T.W. and Reed, S.G., Adjuvants for cancer vaccines, Seminars in Immunology, 22(3):155-161 (2010).
Dubensky, T.W. et al., Abstract 4573: A novel tumor vaccine with cyclic dinucleotides—can induce potent anti-tumor esponses in vivo, Cancer Research, 73(8 Suppl):4573 (2013).
Dubensky, T.W. et al., Rationale, progress, and development of vaccines utilizing STING-activating cyclic dinucleotide djuvants Therapeutic Advances in Vaccines, 1(4):131-143 (2013).
Eager, R. and Nemunaitis, J., GM-CSF gene-transduced tumor vaccines, Molecular Therapy, 12(1):18-27 (2005).
Ebensen, T. et al., Bis-(3',5')-cyclic dimeric adenosine monophosphate: Strong Th1/Th2/Th17 promoting mucosal adjuvant, Vaccine, 29(32):5210-5220 (2011).
Ebensen, T. et al., The bacterial second messenger cdiGMP exhibits promising activity as a mucosal adjuvant. Clinical and Vaccine Immunology, 14(8):952-958 (2007).
Ebensen, T. et al., The bacterial second messenger cyclic diGMP exhibits potent adjuvant properties, Vaccine, 25:1464-1469 (2007).
Egli, M. et al., Atomic-resolution structure of the cellulose synthase regulator cyclic diguanylic acid. Proc. Natl. Acad. Sci. USA 87, 3235-3239 (1990).
Einstein, M.H. et al., Comparison of the immunogenicity and safety of Cervarix and Gardasil human papillomavirus (HPV) cervical cancer vaccines in healthy women aged 18-45 years, Human Vaccines, 5(10):705-719 (2009).
Emsley, P. et al., Features and development of Coot. Acta Crystallogr. D Biol. Crystallogr. 66, 486-501 (2010).
Ertem, G. and Ferris, J.P., Synthesis of RNA oligomers on heterogeneous templates, Nature, 379(6562):238-240 (1996).
Ettmayer, P. et al., Lessons learned from marketed and investigational prodrugs, Journal of Medicinal Chemistry, 47(10):2393-2404 (2004).
Fasso, M. et al., SPAS-1 (stimulator of prostatic adenocarcinoma-specific T cells)/SH3GLB2: A prostate tumor antigen dentified by CTLA-4 blockade, Proceedings of the National Academy of Sciences, U.S.A., 105(9):3509-3514 (2008).
Fernandes-Alnemri, T. et al., AIM2 activates the inflammasome and cell death in response to cytoplasmic DNA. Nature 458, 509-513 (2009).
Fujii, G. et al., The VesiVax system: a method for rapid vaccine development, Frontiers in Bioscience, 13:1968-1980 (2008).
Gaffney, B.L. et al., One-flask syntheses of c-di-GMP and the [Rp,Rp] and [Rp,Sp] thiophosphate analogues, Organic Letters,16;12(14):3269-71 (2010).
Gaffney, B.L., and Jones, R.A. One-flask syntheses of cyclic diguanosine monophosphate (c-di-GMP). Current Protocols in Nucleic Acid Chemistry 14, 14.18.11-14.18.17 (2012).

(56) References Cited

OTHER PUBLICATIONS

Gall, A., et al. Autoimmunity initiates in nonhematopoietic cells and progresses via lymphocytes in an IFN-dependent autoimmune disease. Immunity 36, 120-131 (2012).
Gao, J. et al., GM-CSF-surface-modified B16.F10 melanoma cell vaccine, Vaccine, 24(25):5265-5268 (2006).
Gao, P., et al. Structure-Function Analysis of STING Activation by c[G(2',5') pA(3',5')p] and Targeting by Antiviral DMXAA. Cell 154, 748-762 (2013).
Gao, P., et al., Binding-pocket and lid-region substitutions render human STING sensitive to the species-specific drug DMXAA, Cell Rep. 8(6):1668-1676 (2014).
Gao, P., et al., Cyclic [G(2',5')pA(3',5')p] is the metazoan second messenger produced by DNA-activated cyclic GMP-AMP synthase, Cell, 153(5):1094-107 (2013).
Gehrke, N., et al. Oxidative Damage of DNA Confers Resistance to Cytosolic Nuclease TREX1 Degradation and Potentiates STING-Dependent Immune Sensing. Immunity 39, 482-495 (2013).
Goldberg, M.V. et al., Role of PD-1 and its ligand, B7-H1, in early fate decisions of CD8 T cells, Blood, 110(1):186-192 (2007).
Grajkowski, A. et al., Convenient synthesis of a propargylated cyclic (3'-5') diguanylic acid and its "Click" conjugation to a biotinylated azide, Bioconjugate Chemistry, 21(11):2147-2152 (2010).
Gulley, J.L. et al., Immunologic and prognostic factors associated with overall survival employing a poxviral-based DSA vaccine in metastatic castrate-resistant prostate cancer, Cancer Immunology, Immunotherapy, 59(5):663-674 (2010).
Hartmann, R., et al., Crystal structure of the 2'-specific and double-stranded RNA-activated interferon-induced antiviral protein 2'-5'-oligoadenylate synthetase. Mol. Cell 12, 1173-1185 (2003).
Harty, J.T. and Badovinac, V.P., Shaping and reshaping CD8+ T-cell memory, Nature Reviews Immunology, 8(2):107-119 (2008).
Hayakawa Y., A facile synthesis of cyclic bis(3'?5')diguanylic acid., Tetrahedron, 59:6465-6471 (2003).
Head, M. and Jameson, M. B., The development of the tumor vascular-disrupting agent ASA404 (vadimezan, DMXAA): current status and future opportunities, Expert Opin. Inv. Drug. 19:295-304 (2010).
Hernandez, J.M. et al., Novel kidney cancer immunotherapy based on the granulocyte-macrophage colony-stimulating factor and carbonic anhydrase IX fusion gene, Clinical Cancer Research, 9(5):1906-1916 (2003).
Higashida, H. et al., Measurement of adenylyl cyclase by separating cyclic AMP on silica gel thin-layer chromatograghy. Anal. Biochem. 308, 106-111 (2002).
Hodi, F.S. et al., Improved survival with ipilimumab in patients with metastatic melanoma, The New England Journal of Medicine, 363(8):711-723 (2010).
Hornung, V. and Latz, E., Intracellular DNA recognition, Nat. Rev. Immunol. 10, 123-130 (2010).
Hornung, V. et al., AIM2 recognizes cytosolic dsDNA and forms a caspase-1-activating inflammasome with ASC. Nature 458, 514-518 (2009).
Hu, D.L. et al., c-di-GMP as a vaccine adjuvant enhances protection against systemic methicillin-resistant *Staphylococcus aureus* (MRSA) infection, Vaccine, 27(35):4867-4873 (2009).
Huang, Y.H., et al. The structural basis for the sensing and binding of cyclic di-GMP by STING. Nat. Struct. Mol. Bio. 19, 728-730 (2012).
Huffman, J.L. and Brennan, R.G. Prokaryotic transcription regulators: more than just the helix-turn-helix motif. 12, 98-106 (2002).
Hughes, G.A., Nanostructure-mediated drug delivery, Nanomedicine, 1(1):22-30 (2005).
Hurwitz, A.A. et al., The TRAMP Mouse as a model for prostate cancer, Current Protocols in Immunolog, Chapter 20:Unit 20.5 (2001).
Hyodo, M. et al., Synthesis of cyclic bis(3'-5')diguanylic acid (c-di-GMP) analogs, Tetrahedron, 62:3089-3094 (2006).
International Search Report for PCT/US2014/035909, 4 pages (dated Sep. 12, 2014).

International Search Report for PCT/US2014/049140, 5 pages (dated Dec. 22, 2014).
Ishikawa, H. and Barber, G.N., The STING pathway and regulation of innate immune signaling in response to DNA pathogens, Cell Mol Life Sci, 68(7):1157-1165 (2011).
Ishikawa, H., and Barber, G.N. STING is an endoplasmic reticulum adaptor that facilitates innate immune signalling. Nature 455, 674-678 (2008).
Ishikawa, H., et al. STING regulates intracellular DNA-mediated, type I interferon-dependent innate immunity. Nature 461, 788-792 (2009).
Iwasaki, A. and Medzhitov, R., Regulation of adaptive immunity by the innate immune system, Science, 327(5963):291-295 (2010).
Jemal, A. et al., Cancer statistics, 2010, CA Cancer J Clin, 60(5):277-300 (2010).
Jin, L. et al., Identification and Characterization of a Loss-of-Function Human MPYS Variant, Genes Immun, 12(4): 263-269 (2011).
Jin, L. et al., MPYS is required for IFN response factor 3 activation and type I IFN production in the response of cultured phagocytes to bacterial second messengers cyclic-di-AMP and cyclic-di-GMP, The Journal of Immunology, 187(5):2595-2601 (2011).
Jin, L., et al., MPYS, a novel membrane tetraspanner, is associated with major histocompatibility complex class II and mediates transduction of apoptotic signals. Mol. Cell Biol. 28, 5014-5026 (2008).
Jin, T., et al. Structures of the HIN domain:DNA complexes reveal ligand binding and activation mechanisms of the AIM2 inflammasome and IFI16 receptor. Immunity 36, 561-571 (2012).
Kantoff, P.W. et al., Overall survival analysis of a phase II randomized controlled trial of a poxviral-based PSA-targeted immunotherapy in metastatic castration-resistant prostate cancer., Journal of Clinical Oncology, 28(7):1099-1105 (2010).
Kantoff, P.W. et al., Sipuleucel-T immunotherapy for castration-resistant prostate cancer, The New England Journal of Medicine, 363(5):411-422 (2010).
Karaolis, D.K.R. et al., Bacterial c-di-GMP is an immunostimulatory molecule, The Journal of Immunology, 178(4):2171-2181 (2007).
Karaolis, D.K.R. et al., Cyclic Di-GMP stimulates protective innate immunity in bacterial pneumonia, Infection and Immunity, 75(10):4942-4950 (2007).
Kastenmuller, K. et al., Protective T cell immunity in mice following protein-TLR7/8 agonist-conjugate immunization requires aggregation, type I IFN, and multiple DC subsets, The Journal of Clinical Investigation, 121(5):1782-1796 (2011).
Kasturi, P. S., et al. Programming the magnitude and persistence of antibody responses with innate immunity, Nature, vol. 470, pp. 543-547 (2011).
Kawai, T. and Akira, S., The role of pattern-recognition receptors in innate immunity: update on Toll-like receptors, Nature Immunology, 11(5):373-384 (2010).
Keating, S.E. et al. Cytosolic DNA sensors regulating type I interferon induction. Trends Immunol. 32, 574-581 (2011).
Kerur, N., et al. IFI16 acts as a nuclear pathogen sensor to induce the inflammasome in response to Kaposi Sarcoma-associated herpesvirus infection. Cell Host Microbe 9, 363-375 (2011).
Kim, J.J. et al., Co-crystal structures of PKG Iβ (92-227) with cGMP and cAMP reveal the molecular details of cyclic-nucleotide binding, PLoS One, 6(4):e18413 (2011).
Kim, S., et al. Anticancer flavonoids are mouse-selective STING agonists. ACS Chem. Biol. 8, 1396-1401 (2013).
Kodym, R., et al. 2'-5'-Oligoadenylate synthetase is activated by a specific RNA sequence motif. Biochem. Biophys. Res. Commun. 388, 317-322 (2009).
Krasteva, P.V. et al. Sensing the messenger: the diverse ways that bacteria signal through c-di-GMP. Protein Sci. 21, 929-948 (2012).
Krishnamachari, Y. et al., Nanoparticle delivery systems in cancer vaccines, Pharm Res, 28:215-236 (2011).
Kubota, K. et al. Identification of 2'-phophodiesterase, which plays a role in 2-5A system reulated by interferon. J. Biol. Chem, 279, 37832-37841 (2004).

(56) References Cited

OTHER PUBLICATIONS

Kulshina, N. et al. Recognition of the bacterial second messenger cyclic diguanylate by its cognate riboswitch. Nat. Struct. Mol. Biol. 16, 1212-1217 (2009).
Lam, E.et al, Adenovirus detection by the cGAS/STING/TBK1 DNA sensing cascade, Journal of Virology, 88(2):974-981 (2014).
Lara, P.N., Jr., et al. Randomized phase III placebo-controlled trial of carboplatin and paclitaxel with or without the vascular disrupting agent vadimezan (ASA404) in advanced non-small-cell lung cancer. J. Clin. Oncol. 29, 2965-2971 (2011).
Lauvau, G. et al., Priming of memory but not effector CD8 T cells by a killed bacterial vaccine, Science, 294(5547):1735-1739 (2009).
Le, D.T. et al., A live-attenuated Listeria Vaccine (ANZ-100) and a live-attenuated Listeria Vaccine expressing mesothelin (CRS-207) for advanced cancers: phase I studies of safety and immune induction, Clin Cancer Res, 18(3):858-868 (2012).
Le, D.T. et al., Cellular vaccine approaches, Cancer J, 16(4):304-310 (2010).
Leber, J.H. et al., Distinct TLR- and NLR-Mediated transcriptional responses to an intracellular pathogen, PLoS Pathogens, 4(1):e6 (2008).
Lee, A.W. et al., A clinical grade cocktail of cytokines and PGE2 results in uniform maturation of human monocyte-derived dendritic cells: implications for immunotherapy, Vaccine, 20(Suppl 4):A8-A22 (2002).
Lee, E.R., et al. An allosteric self-splicing ribozyme triggered by a bacterial second messenger. Science 329, 845-848 (2010).
Li, X. et al, Cyclic GMP-AMP synthase is activated by double-stranded DNA-induced oligomerization, Immunity, 39(6):1019-1031 (2013).
Libanova, R. et al., The member of the cyclic di-nucleotide family bis-(3', 5')-cyclic dimeric inosine monophosphate exerts potent activity as mucosal adjuvant, Vaccine, 28(10):2249-2258 (2010).
Libanova, R., Cyclic di-nucleotides: new era for small molecules as adjuvants, Microbial Biotechnology, 5(2):168-176 (2012).
Lubong Sabado, R. et al., In vitro priming recapitulates in vivo HIV-1 specific T cell responses, revealing rapid loss of virus reactive CD4+ T cells in acute HIV-1 infection, PLoS One, 4(1):e4256 (2009).
Lunde, B.M. et al. RNA-binding proteins: modular design for efficient function. Nat. Rev. Mol Cell. Biol. 8, 479-490 (2007).
Luo, Y. et al, Selective binding of 2'-F-c-di-GMP to Ct-E88 and Cb-E43, new class I riboswitches from Clostridium tetani and Clostridium botulinum respectively, Molecular Biosystems, 9(6):1535-1539 (2013).
Lutz, E. et al., A lethally irradiated allogeneic granulocyte-macrophage colony stimulating factor-secreting tumor vaccine for pancreatic Adenocarcinoma: a phase II trial of safety, efficacy, and immune activation, Ann Surg, 253(2):328-335 (2011).
Madhun, A.S. et al., Intranasal c-di-GMP-adjuvanted plant-derived H5 influenza vaccine induces multifunctional Th1 CD4+ cells and strong mucosal and systemic antibody responses in mice, Vaccine, 29(31):4973-4982 (2011).
Mathew, E. et al., Cytosolic delivery of antisense oligonucleotides by listeriolysin O-containing liposomes, Gene Therapy, 10(13):1105-1115 (2003).
McCoy, A.J. et al. Phaser crystallographic software. J. Appl. Crystallogr. 40, 658-674 (2007).
McCune, C.S. et al., Active specific immunotherapy with tumor cells and Corynebacterium parvum: a phase I study, Cancer, 43(5):1619-1623 (1979).
McWhirter, S.M. et al., A host type I interferon response is induced by cytosolic sensing of the bacterial second messenger cyclic-di-GMP, The Journal of Experimental Medicine, 206(9):1899-1911 (2009).
Mellman, I. et al., Cancer immunotherapy comes of age, Nature, 480(7378):480-489 (2011).
Miyabe, H. et al., A new adjuvant delivery system 'cyclic di-GMP/YSK05 liposome' for cancer immunotherapy, Journal of Controlled Release, 184:20-27 (2014).

Muderhwa, J.M. et al., Oil-in-water liposomal emulsions: characterization and potential use in vaccine delivery, Journal of Pharmaceutical Sciences, 88(12):1332-1339 (1999).
Murshudov, G.N., et al. Refinement of macromolecular structures by the maximum-likelihood method. Acta Crystallogr. D Biol. Crystallogr. 53, 240-255 (1997).
Nelson, D.P. and Griswold, W.R., A computer program for calculating antibody affinity constants, Computer Methods and Programs in Biomedicine, 27(1):65-68 (1988).
Neumann, F. et al., Identification of an HLA-DR-restricted peptide epitope with a promiscuous binding pattern derived from the cancer testis antigen HOM-MEL-40/SSX2, Int J Cancer, 112(4):661-668 (2004).
Nicoletto, M.O. et al., BRCA-1 and BRCA-2 mutations as prognostic factors in clinical practice and genetic counselling, Cancer Treatmeant Reviews, 27(5):295-304 (2001).
O'Neill, L.A., Immunology. Sensing the dark side of DNA, Science, 339(6121):763-4 (2013).
O'Riordan, M. et al., Innate recognition of bacteria by a macrophage cytosolic surveillance pathway, Proceedings of the National Academy of Science U.S.A., 99(21):13861-13866 (2002).
Ogunniyi, A.D. et al., c-di-GMP is an effective immunomodulator and vaccine adjuvant against Pneumococcal infection, Vaccine, 26(36):4676-4685 (2008).
Olson, K. et al., Liposomal gD ectodomain (gD1-306) vaccine protects against HSV2 genital or rectal infection of female and male mice, Vaccine, 28(2):548-560 (2009).
Ora, M. et al., Hydrolytic reactions of cyclic bis(3'-5') diadenylics acid (c-di-AMP), Journal of Physical Organic Chemistry, 26, pp. 218-225 (2013).
Otwinowski, Z., and Minor, W. Processing of X-ray Diffraction Data Collected in Oscillation Mode. Methods in Enzymology 276, 307-326 (1997).
Ouyang et al., Structural Analysis of the STING Adaptor Protein Reveals a Hydrophobic Dimer 1-3 Interface and Mode of Cyclic di-GMP Binding, Immunity, 36: 1073-1086 (2012).
Paludan, S.R. and Bowie, A.G. Immune sensing of DNA. Immunity 38, 870-880 (2013).
Pardoll, D. and Drake, C., Immunotherapy earns its spot in the ranks of cancer therapy, The Journal of Experimental Medicine, 209(2):201-209 (2012).
Pardoll, D.M., The blockade of immune checkpoints in cancer immunotherapy, Nature Reviews Cancer, 12(4):252-264 (2012).
Parvatiyar, K. et al., DDX41 recognizes the bacterial secondary messengers cyclic di-GMP and cyclic di-AMP to activate a type I interferon immune response, Nat Immunol, 13(12):1155-1161 (2012).
Pham, N.L.L. et al., Exploiting cross-priming to generate protective CD8 T-cell immunity rapidly, Proceedings of the National Academy of Sciences U.S.A., 107(27):12198-12203 (2010).
Porter, R. S., et al. 19th Edition Merck Manual, pp. 1059-1062 (2011).
Prantner, D., et al. 5,6-Dimethylxanthenone-4-acetic acid (DMXAA) activates stimulator of interferon gene (STING)-dependent innate immune pathways and is regulated by mitochondrial membrane potential. J. Biol. Chem. 287, 39776-39788 (2012).
Rappuoli, R. et al., Vaccines for the twenty-first century society, Nature Reviews Immunology, 11(12):865-872 (2011).
Rasmussen, S.B., et al. Activation of autophagy by alpha-herpesviruses in myeloid cells is mediated by cytoplasmic viral DNA through a mechanism dependent on stimulator of IFN genes. J Immunol. 187, 5268-5276 (2011).
Reed, S.G. et al., New horizons in adjuvants for vaccine development, Trends in Immunology, 30(1):23-32 (2009).
Roberts, Z. J., et al. IFN-beta-dependent inhibition of tumor growth by the vascular disrupting agent 5,6-dimethylxanthenone-4-acetic acid (DMXAA). J. Interf. Cytok. Res. 28, 133-139 (2008).
Roembke, B.T. et al., A cyclic dinucleotide containing 2-aminopurine is a general fluorescent sensor for c-di-GMP and 3',3'-cGAMP, Molecular Biosystems, 10(6):1568-1575 (2014).
Romling, U. et al., Cyclic di-GMP: the First 25 Years of a Universal Bacterial Second Messenger, Microbiol. Mol. Biol. Rev. 77:1-52 (2013).

(56) References Cited

OTHER PUBLICATIONS

Ross, P. et al. Regulation of cellulose synthesis in Acetobacter xylinum by cyclic diguanylic acid. Nature 325, 279-281 (1987).
Ross, P. et al., The cyclic diguanylic acid regulatory system of cellulose synthesis in Acelobacter xylinum, Chemical Synthesis and Biological Activity of Cyclic Nucleotide Dimer, Trimer, and Phosphothioate Derivatives, The Journal of Biological Chemistry, 265(31):18933-18943 (1990).
Sadler, A.J., and Williams, B.R. Interferon-inducible antiviral effectors. Nat. Rev. Immunol. 8, 559-568 (2008).
Sauer, J. D., et al. The N-ethyl-N-nitrosourea-induced Goldenticket mouse mutant reveals an essential function of Sting in the in vivo interferon response to Listeria monocytogenes and cyclic dinucleotides. Infect. Immun. 79, 688-694 (2011).
Sawai, H. and Ohno, M., Synthesis of 2'-5' Linked Oligouridylates in Aqueous Medium Using the Pd2+ Ion, Chem Pharm Bull, 29(8):2237-2245 (1981).
Sawai, H. et al., Preparation and properties of oligocytidylates with 2'-5' internucleotide linkage, Bull Chem Soc Jpn, 58(1):361-366 (1985).
Schirmer, T., and Jenal, U. Structural and mechanistic determinants of c-di-GMP signalling. Nat. Rev. Microbiol. 7, 724-735 (2009).
Schmidt, N.W. et al., Memory CD8 T cell responses exceeding a large but definable threshold provide long-term immunity to malaria, Proceedings of the National Academy of Sciences U.S.A., 105(37):14017-14022 (2008).
Schoggins, J.W., et al. A diverse range of gene products are effectors of the type I interferon antiviral response. Nature 472, 481-485 (2011).
Schwartz, K.T. et al., Hyperinduction of host beta interferon by a Listeria monocytogenes strain naturally overexpressing the multidrug efflux pump MdrT, Infection and Immunity, 80(4):1537-1545 (2012).
Seder, R.A. et al., T-cell quality in memory and protection: implications for vaccine design, Natural Reviews Immunology, 8(4):247-258 (2008).
Shanahan, C.A. et al., Differential analog binding by two classes of c-di-GMP riboswitches, J Am Chem Soc, 133(39):15578-15592 (2011).
Shanahan, C.A. et al., Identification of c-di-GMP Derivatives Resistant to an EAL Domain Phosphodiesterase, Biochemistry, 52(2):365-377 (2013).
Shang, G., et al. Crystal structures of STING protein reveal basis for recognition of cyclic di-GMP. Nat. Struct. Mol. Bio. 19, 725-727 (2012).
Shu, C. et al., Structure of STING bound to cyclic di-GMP reveals the mechanism of cyclic dinucleotide recognition by the immune system, Nature Structural and Molecular Biology, 19(7):722-724 (2012).
Silverman, the Organic Chemistry of Drug Design and Drug Action, Published 1992 by Academic Press, pp. 352-397.
Singh, S. et al., Non-replicating adenovirus vectors expressing avian influenza virus hemagglutinin and nucleocapsid proteins induce chicken specific effector, memory and effector memory CD8B(+) T lymphocytes. Virology. 405(1):62-69 (2010).
Singh, S. et al.. Avian influenza viral nucleocapsid and hemagglutinin proteins induce chicken CD8+ memory T lymphocytes. Virology. 399:231-238 (2010).
Skoberne, M. et al., KBMA Listeria monocytogenes is an effective vector for DC-mediated induction of antitumor immunity, J Clin Invest, 118(12):3990-4001 (2008).
Smith, K.D. et al. Structural basis of ligand binding by a c-di-GMP riboswitch. Nat. Struct. Mol. Biol. 16, 1218-1223 (2009).
Sofia, M.J. et al., Nucleoside, Nucleotide, and Non-Nucleoside Inhibitors of Hepatitis C Virus NS5B RNA—Dependent RNA;—Polymerase, J Med Chem, 55(6):2481-2531 (2012).
Sofia, M.J., Nucleotide prodrugs for HCV therapy, Antiviral Chemistry & Chemotherapy, 22(1):23-49 (2011).
Stella, V.J., Prodrugs and therapeutics, Expert Opinion on Therapeutic Patents, 14(3):277-280 (2004).

Sudarsan, N. et al. Riboswitches in eubacteria sense the second messenger cyclic di-GMP. Science 321, 411-413 (2008).
Sun, J.C. and Bevan, M.J., Defective COB T Cell memory following acute infection without CD4 T cell help, Science, 300(5617):339-342 (2003).
Sun, L. et al., Cyclic GMP-AMP synthase is a cytosolic DNA sensor that activates the type I interferon pathway, Science, 339(6121):786-91 (2013).
Sun, W. et al. ERIS, an endoplasmic reticulum IFN stimulator, activates innate immune signaling through dimerization. Proc. Natl. Acad. Sci. USA 106, 8653-8658 (2009).
Suzuki, N. et al., Practical synthesis of cyclic bis(3'-5')diadenylic acid (c-di-AMP), Chem Lett, 40(10):1113-1114 (2011).
Takaoka, A. et al. DAI (DLM-1/ZBP1) is a cytosolic DNA sensor and an activator of innate immune response. Nature 448, 501-505 (2007).
Tamayo, R. et al., Roles of cyclic diguanylate in the regulation of bacterial pathogenesis, Annu Rev Microbiol, 61:131-148 (2007).
Tanaka, Y. and Chen, Z.J., STING specifies IRF3 phosphorylation by TBK1 in the cytosolic DNA signaling pathway, Sci Signal, 5(214):ra20 (2012).
Tannock et al., Docetaxel plus Prednisone or Mitoxantrone plus Prednisone for Advanced Prostate Cancer, N Engl J Med. 351(15):1502-1512 (2004).
Testa, B. et al., Prodrug research: futile or fertile?, Biochemical Pharmacology, 68(11):2097-2106 (2004).
Tewari, K. et al., Poly(I:C) is an effective adjuvant for antibody and multi-functional CD4+ T cell responses to Plasmodium falciparum circumsporozoite protein (CSP) and alphaDEC-CSP in non human primates, Vaccine, 28(45):7256-7266 (2010).
Tezuka, T. et al., Synthesis of 2'-modified cyclic bis{3'-5')diadenylic acids {c-di-AMPs) and their promotion of cell division in a freshwater green alga, Chem Lett, 41:1723-25 (2012).
Tijono et al., Identification of human-selective analogues of the vascular-disrupting agent 5,6-dimethylxanthenone-4-acetic acid (DMXAA), British Journal of Cancer, 108: 1306-1315 (2013).
Topalian, S.L. et al., Cancer immunotherapy comes of age, Journal of Clinical Oncology, 29(36):4828-4836 (2011).
Unterholzner, L. et al. IFI16 is an innate immune sensor for intracellular DNA. Nat. Immunol. 11, 997-1004 (2010).
Urata, H. et al., Regio- and Diastereo-Selectivity of Montmorillonite-Catalyzed Oligomerization of Racemic Adenosine 5'-Phosphorimidazolide, Nucleosides, Nucelotides and Nucleic Acids, 27: 421-430 (2008).
Van Elsas, A. et al., Elucidating the autoimmune and antitumor effector mechnaisms of a treatment based on cytotoxic T lymphocyte antigen-4 blockade in combination with a B16 melanoma vaccine: comparison of prophylaxis and therapy, The Journal of Experimental Medicine, 194(4):481-489 (2001).
Van Erp, R. et al., Application of a sol particle immunoassay to the determination of affinity constants of monoclonal antibodies, Journal of Immunoassay, 12(3):425-443 (1991).
Vance, R.E. et al., Patterns of pathogenesis: discrimination of pathogenic and nonpathogenic microbes by the innate immune system, Cell Host & Microbe, 6(1):10-21 (2009).
Venes, D. et al., 21st Edition Taber's Cyclopedic Medical Dictionary, pp. 1163 (2009).
Waitz, R. et al., Potent induction of tumor immunity by combining tumor cryoablation with anti-CTLA-4 therapy, Cancer Research, 72(2):430-439 (2012).
Ward, E.S. et al., Binding activities of a repertoire of single immunoglobulin variable domains secreted from *Escherichia coli*, Nature, 341(6242):544-546 (1989).
Wille-Reece, U. et al., HIV Gag protein conjugated to a Toll-like receptor 7/8 agonist improves the magnitude and quality of Th1 and CD8+ T cell responses in nonhuman primates, Proceedings of the National Academy of Science U.S.A., 102 (42):15190-15194 (2005).
Wille-Reece, U. et al., Immunization with HIV-1 Gag protein conjugated to a TLR7/8 agonist results in the generation of HIV-1 Gag-specific Th1 and CD8+ T cell responses, The Journal of Immunology, 174(12):7676-7683 (2005).

(56) References Cited

OTHER PUBLICATIONS

Wille-Reece, U. et al., Toll-like receptor agonists influence the magnitude and quality of memory T cell responses after prime-boost immunization in nonhuman primates, The Journal of Experimental Medicine, 203(5):1249-1258 (2006).
Wilson, K.M. et al., Simplified conjugation chemistry for coupling peptides to F(ab') fragments: autologous red cell agglutination assay for HIV-1 antibodies, Journal of Immunological Methods, 175(2):267-273 (1994).
Witte, C.E. et al., Innate immune pathways triggered by Listeria monocytogenes and their role in the induction of cell-mediated immunity, Advances in Immunology, 113:135-156 (2012).
Wolkowicz, U.M., and Cook, A.G. NF45 dimerizes with NF90, Zfr and SPNR via a conserved domain that has a nucleotidyltransferase fold. Nucleic Acids Res. 40, 9356-9368 (2012).
Woodward, J.J. et al. c-di-AMP Secreted by Intracellular Listeria monocytogenes Activates a Host Type I Interferon Response. Science (New York, N.Y 328, 1703-1705 (2010).
Woodward, J.J. et al., Supporting online material for c-di-AMP secreted by intracellular Listeria monocytogenes activates a host type I interferon response, Science Express, 15 pages (2010).
Woycechowsky, K.J. and Raines, R.T., Native disulfide bond formation in proteins, Curr Opin Chem Biol, (5):533-539 (2000).
Wu, J. et al. Cyclic GMP-AMP is an endogenous second messenger in innate immune signaling by cytosolic DNA. Science 339, 826-830 (2013).
Xiao, T. S., and Fitzgerald, K. A. The cGAS-STING Pathway for DNA Sensing. Mol. Cell 51, 135-139 (2013).
Yan, H. and Aguilar, A.L., Synthesis of 3',5'-cyclic diguanylic acid (cdiGMP) using 1-(4-chlorophenyl)-4-ethoxypi peridin-4-yl as a protecting group for 2'-hydroxy functions of ribonucleosides, Nucleosides Nucleotides & Nucleic Acids, 26(2):189-204 (2007).
Yan, H. et al., Synthesis and immunostimulatory properties of the phosphorothioate analogues of cdiGMP, Bioorganic & Medicinal Chemistry Letters, 18(20):5631-5634 (2008).
Yang, P. et al. The cytosolic nucleic acid sensor LRRFIP1 mediates the production of type I interferon via a beta-catenin-dependent pathway. Nat. Immunol. 11, 487-494 (2010).
Yarmush, M.L. et al., Coupling of antibody-binding fragments to solid-phase supports: site-directed binding of F(ab')2 fragments, Journal of Biochemical and Biophysical Methods, 25(4):285-297 (1992).
Yi, G. H., et al. Single Nucleotide Polymorphisms of Human STING Can Affect Innate Immune Response to Cyclic Dinucleotides, PLoS One, 8(10):e77846 (2013).
Yin, Q. et al., Cyclic ; di-GMP sensing via the innate immune signaling protein STING, Molecular Cell, 46(6):735-45 (2012).
Zhang, X., et al. Cyclic GMP-AMP Containing Mixed Phosphodiester Linkages Is an Endogenous High-Affinity Ligand for STING. Mol. Cell 51, 226-235 (2013).
Zhang, Z. et al. The helicase DDX41 senses intracellular DNA mediated by the adaptor STING in dendritic cells. Nat. Immunol. 12, 959-965 (2011).
Zhang, Z. et al., c-di-GMP Displays a monovalent metal ion-dependent polymorphism, J Am Chem Soc, 126(51):16700-16701 (2004).
Zhao, J. et al., Thiophosphate analogs of c-di-GMP: impact on polymorphism, Nucleosides Nucleotides & Nucleic Acids, 28(5):352-378 (2009).
Zhong, B. et al.The adaptor protein MITA links virus-sensing receptors to IRF3 transcription factor activation. Immunity 29, 538-550 (2008).
Zhou, J. et al., Endo-S-c-di-GMP analogues-polymorphism and binding studies with class I riboswitch, Molecules, 17(11):13376-13389 (2012).
Zhou, J. et al., Potent suppression of c-di-GMP synthesis via I-site allosteric inhibition of diguanylate cyclases with 2'-F-c-di-GMP, Bioorganic & Medicinal Chemistry, 21(14):4396-4404 (2013).
Abe et al., STING Recognition of Cytoplasmic DNA Instigates Cellular Defense. Mol Cell. Apr. 11, 2013;50(1):5-15.

Ahn et al., STING manifests self DNA-dependent inflammatory disease. Proc Natl Acad Sci U S A. Nov. 20, 2012;109(47):19386-19391.
Apetoh et al., Toll-like receptor 4-dependent contribution of the immune system to anticancer chemotherapy and radiotherapy. Nat Med. Sep. 2007;13(9):1050-1059.
Blank et al., PD-L1/B7H-1 Inhibits the Effector Phase of Tumor Rejection by T Cell Receptor(TCR) Transgenic CD8+ T Cells. Cancer Res. Feb. 1, 2004;64(3):1140-1145.
Chin, K-H. et al, Novel c-di-GMP recognition modes of the mouse innate immune adaptor protein STING, Acta. Crystl., D69: 352-366 (2013).
Corrales et al., Extremely potent immunotherapeutic activity of a STING agonist in the B16 melanoma model in vivo. J ImmunoTherapy, Nov. 10, 2013;1:1.
Diamond et al., Type I interferon is selectively required by dendritic cells for immune rejection of tumors. J Exp Med. Sep. 26, 2011;208(10):1989-2003.
Fridman et al., The immune contexture in human tumours: impact on clinical outcome. Nat Rev Cancer. Mar. 15, 2012;12(4):298-306.
Fuertes et al., Host type I IFN signals are required for antitumor CD8+ T cell responses through CD8{alpha}+ dendritic cells. J Exp Med. Sep. 26, 2011;208(10):2005-2016.
Fuertes et al., Type I IFN response and innate immune sensing of cancer. Trends Immunol. Feb. 2013;34(2):67-73.
Gajewski et al., Cancer immunotherapy strategies based on overcoming barriers within the tumor microenvironment. Curr Opin Immunol. Apr. 2013;25(2):268-276.
Gajewski et al., Gene Signature in Melanoma Associated With Clinical Activity: A Potential Clue to Unlock Cancer Immunotherapy. Cancer J. Jul.-Aug. 2010;16(4):399-403.
Gajewski, Identifying and Overcoming Immune Resistance Mechanisms in the Melanoma Tumor Microenvironment. Clin Cancer Res. Apr. 1, 2006;12(7 Pt 2):2326s-2330s.
Galon, J. et al., Type, Density, and Location of Immune Cells Within Human Colorectal Tumors Predict Clinical Outcome, Science, 313(5795):1960-1964 (2006).
Ghiringhelli et al., Activation of the NLRP3 inflammasome in dendritic cells induces IL-1beta-dependent adaptive immunity against tumors. Nat Med. Oct. 2009;15(10):1170-1178.
Gray et al., Evidence for cyclic diguanylate as a vaccine adjuvant with novel immunostimulatory activities. Cell Immunol. Jul.-Aug. 2012;278(1-2):113-119.
Hamid et al., A prospective phase II trial exploring the association between tumor microenvironment biomarkers and clinical activity of ipilimumab in advanced melanoma. J Transl Med. Nov. 28, 2011;9:204.
Harlin et al., Chemokine Expression in Melanoma Metastases Associated with CD8+ T-Cell Recruitment. Cancer Res. Apr. 1, 2009;69(7):3077-3085.
Henry et al., Type I interferon signaling is required for activation of the inflammasome during Francisella infection. J Exp Med. May 14, 2007;204(5):987-994.
Hoebe et al., Upregulation of costimulatory molecules induced by lipopolysaccharide and double-stranded RNA occurs by Trif-dependent and Trif-independent pathways. Nat Immunol. Dec. 2003;4(12):1223-1229.
Howgate, P. and Hampton, A., Conversion of 2',3'-O-isopropylideneadenosine into 9-(6-deoxy-beta-D-allofuranosyl)- and 9-(6-deoxy-alpha-L-talofuranosyl)-adenines, Carbohydrate Research, 21:309-315 (1972).
Hwang et al., Prognostic Significance of Tumor-infiltrating T-cells in Ovarian; Cancer: a Meta-analysis. Gynecol Oncol. Feb. 2012;124(2):192-198.
Ishii et al., A Toll-like receptor-independent antiviral response induced by double-stranded 8-form DNA. Nat Immunol. Jan. 2006;7(1):40-48.
Joshi, P.C. et al, Selectivity of montmorillonite catalyzed prebiotic reactions of D, L-nucleotides, Orig. Life Evol. Biosph., 37(1): 3-26 (2007).
Jounai et al., Recognition of damage-associated molecular patterns related to nucleic acids during inflammation and vaccination. Front Cell Infect Microbiol. Jan. 8, 2013;2:168.

(56) References Cited

OTHER PUBLICATIONS

Kawarada et al., NK- and CD8+T Cell-Mediated Eradication of Established Tumors by Peritumoral Injection of CpG-Containing Oligodeoxynucleotides. J Immunol. Nov. 1, 2001;167(9):5247-5253.

Konno et al., Cyclic Di Nucleotides Trigger ULK1 (ATG1) Phosphorylation of STING to Prevent Sustained Innate Immune Signaling. Cell. Oct. 24, 2013;155(3):688-698.

Kono and Rock, How dying cells alert the immune system to danger. Nat Rev Immunol. Apr. 2008;8(4):279-289.

Kroemer et al., Immunogenic Cell Death in Cancer Therapy. Annu Rev Immunol. 2013;31:51-72.

Lande et al., Plasmacytoid dendritic cells sense self-DNA coupled with antimicrobial peptide. Nature. Oct. 4, 2007;449(7162):564-569.

Li et al., Efficient Cross-presentation Depends on Autophagy in Tumor Cells. Cancer Res. Sep. 1, 2008;68(17):6889-6895.

Mahmoud et al., Tumor-Infiltrating CD8+ Lymphocytes Predict Clinical Outcome in Breast Cancer. J Clin Oncol. May 20, 2011;29(15):1949-1955.

Marichal et al., DNA released from dying host cells mediates aluminum adjuvant activity. Nat Med. Jul. 17, 2011;17(8):996-1002.

McKee et al., Host DNA released in response to aluminum adjuvant enhances MHC class II-mediated antigen presentation and prolongs CD4 T-cell interactions with dendritic cells. Proc Natl Acad Sci U S A. Mar. 19, 2013;110(12):E1122-E1131.

Meng, X-Y. et al, Molecular Docking: A powerful approach for structure-based drug discovery, Curr. Comput. Aided Drug Des., 7(2): 146-157 (2011).

Molinero et al., Epidermal Langerhans cells promote skin allograft rejection in mice with NF-KB-impaired T cells. Am J Transplant. Jan. 2008;8(1):21-31.

Nelson, V. et al., Synthesis of Hypoxanthine, Guanine, and 6-Thiopurine Nucleosides of 6-Deoxy-D-allofuranose, J Med Chem, 26:1071-1074 (1983).

Obeid et al., Calreticulin exposure dictates the immunogenicity of cancer cell death, Nat Med. Jan. 2007;13(1):54-61.

Oka et al., Mitochondrial DNA That Escapes from Autophagy Causes Inflammation and Heart Failure. Nature. May 10, 2012;485(7397):251-255.

Ouyang, S. et al., Crystal structure of STING CTD complex with c-di-GMP, retrieved from www.ebi.ac.uk, accession No. 4EF4, May 16, 2012.

Pagès et al., In Situ Cytotoxic and Memory T Cells Predict Outcome in Patients With Early-Stage Colorectal Cancer, J Clin Oncol., 27(35):5944-5951 (2009).

Roberson and Walker, Immortalization of Cloned Mouse Splenic Macrophages with a Retrovirus Containing the v-raf/mil and v-myc Oncogenes. Cell Immunol. Oct. 15, 1988;116(2):341-351.

Sancho et al., Identification of a dendritic cell receptor that couples sensing of necrosis to immunity. Nature. Apr. 16, 2009;458(7240):899-903.

Sawai, H. and Ohno, M., Synthesis of oligoinosinates with 2'-5' internucleotide linkage in aqueous solution using Pb2+ion, Bulletin of the Chemical Society of Japan, 54(9): 2759-2762 (1981).

Sharma et al., Innate immune recognition of an AT-rich stem-loop DNA motif in the Plasmodium falciparum genome. Immunity. Aug. 26, 2011;35(2):194-207.

Simm, R. et al, Phenotypic convergence mediated by GGDEF-domain-containing proteins, J. Bacteriol., 187(19): 6816-23 (2005) and Erratum, 1 page (2006).

Slansky et al., Enhanced Antigen-Specific Antitumor Immunity with Altered Peptide Ligands that Stabilize the MHC-Peptide-TCR Complex. Immunity. Oct. 2000;13(4):529-538.

Spranger et al., Up-Regulation of PD-L 1, IDO, and Tregs in the Melanoma Tumor; Microenvironment Is Driven by CD8+ T Cells. Sci Transl Med. Aug. 28, 2013;5(200):200ra116.

Stetson and Medzhitov, Recognition of Cytosolic DNA Activates an IRF3-Dependent Innate Immune Response. Immunity. Jan. 2006;24(1):93-103.

Takahashi, M. et al., Synthesis and characterization of 2'-modified-4'-thioRNA: a comprehensive comparison of nuclease stability, Nucleic Acids Research, 37(4):1353-1362 (2009).

Twitty et al., Tumor-Derived Autophagosome Vaccine: Induction of Cross Protective; Immune Responses Against Short-Lived Proteins Through a P62-Dependent Mechanism. Clin Cancer Res. Oct. 15, 2011;17(20):6467-6481.

Wolchok et al., Nivolumab plus Ipilimumab in Advanced Melanoma. N Engl J Med. Jul. 11, 2013;369(2):122-133.

Wu, J. et al., Corrected Supplemental Materials for Cyclic GMP-AMP is an Endogeneous Second Messenger in Innate Immune Signaling by Cytosolic DNA, Science, 21 pages (2013).

Wu, J. et al., Supplemental Materials for Cyclic GMP-AMP is an Endogeneous Second Messenger in Innate Immune Signaling by Cytosolic DNA, Science, 6 pages (2013).

Yanai et al., HMGB proteins function as universal sentinels for nucleic-acid-mediated innate immune responses. Nature. Nov. 5, 2009;462(7269):99-103.

Zhou et al., MyD88 Intrinsically Regulates CD4 T-Cell Responses. J Virol. Feb. 2009;83(4):1625-1634.

Zhou et al., MyD88 is critical for the development of innate and adaptive immunity during acute lymphocytic choriomeningitis virus infection. Eur J Immunol. Mar. 2005;35(3):822-830.

Dubensky, oral slide presentation Development of Cyclic Dinucleotides as STING-Targeted Molecular Adjuvants, Immunological Mechanisms of Vaccination seminar, Fairmont Château Laurier, Ottawa, Ontario Canada, 13 pages (Dec. 14, 2012).

Zhang, X. et al, Crystal structure of STING in complex with cGAMP, retrieved from http:www.ebi.ac.uk/pdbe/entry/pdb/4KSY, Database accession No. 4ksy, Protein Data Bank in Europe, 2 pages (released Jun. 12, 2013).

\* cited by examiner

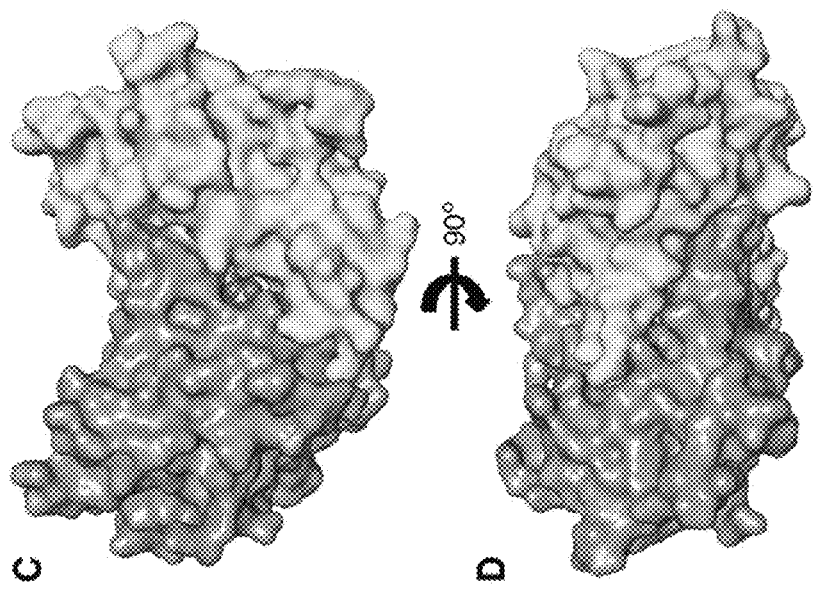
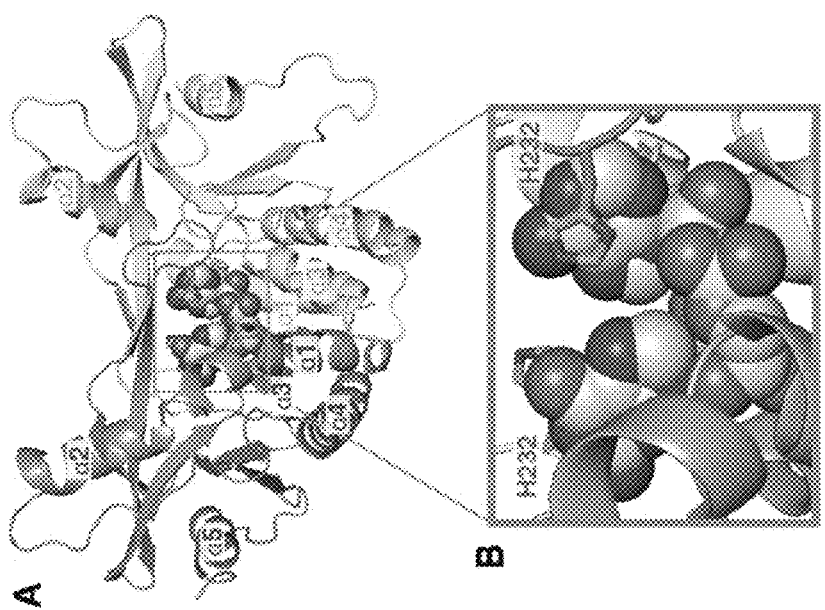

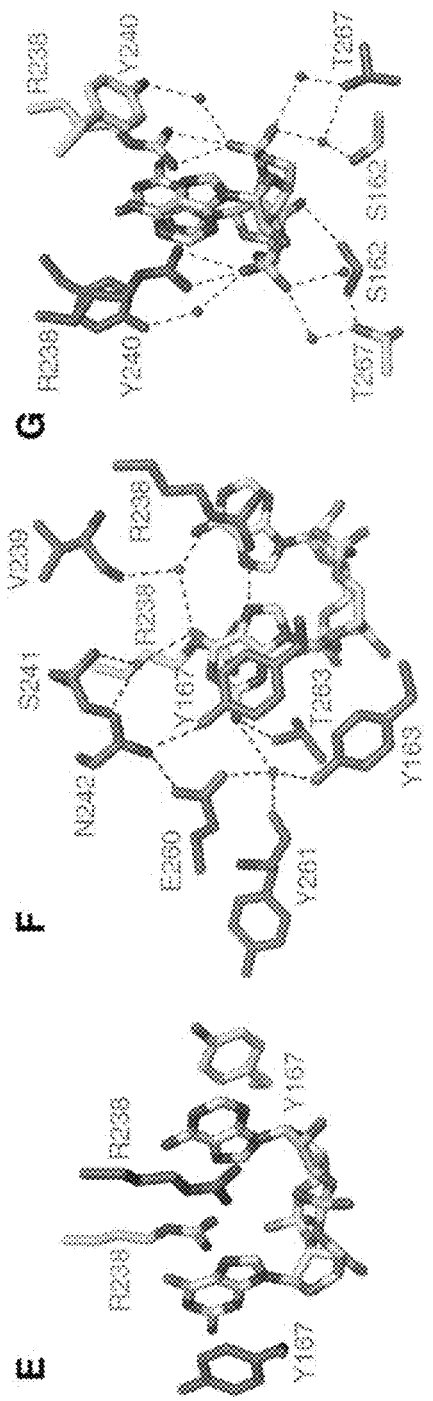
*Figure 1E*  *Figure 1F*  *Figure 1G*

D
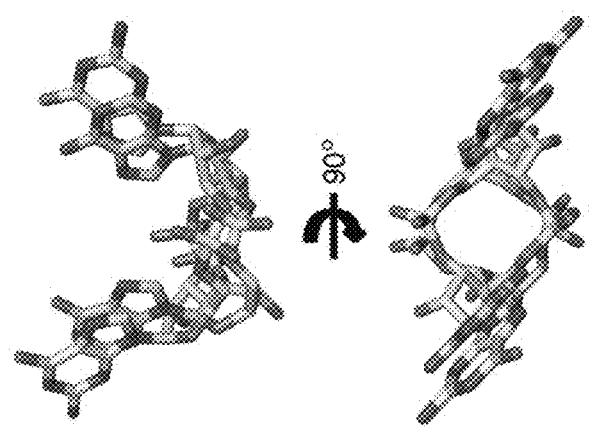
C
*Figure 2D*
*Figure 2C*

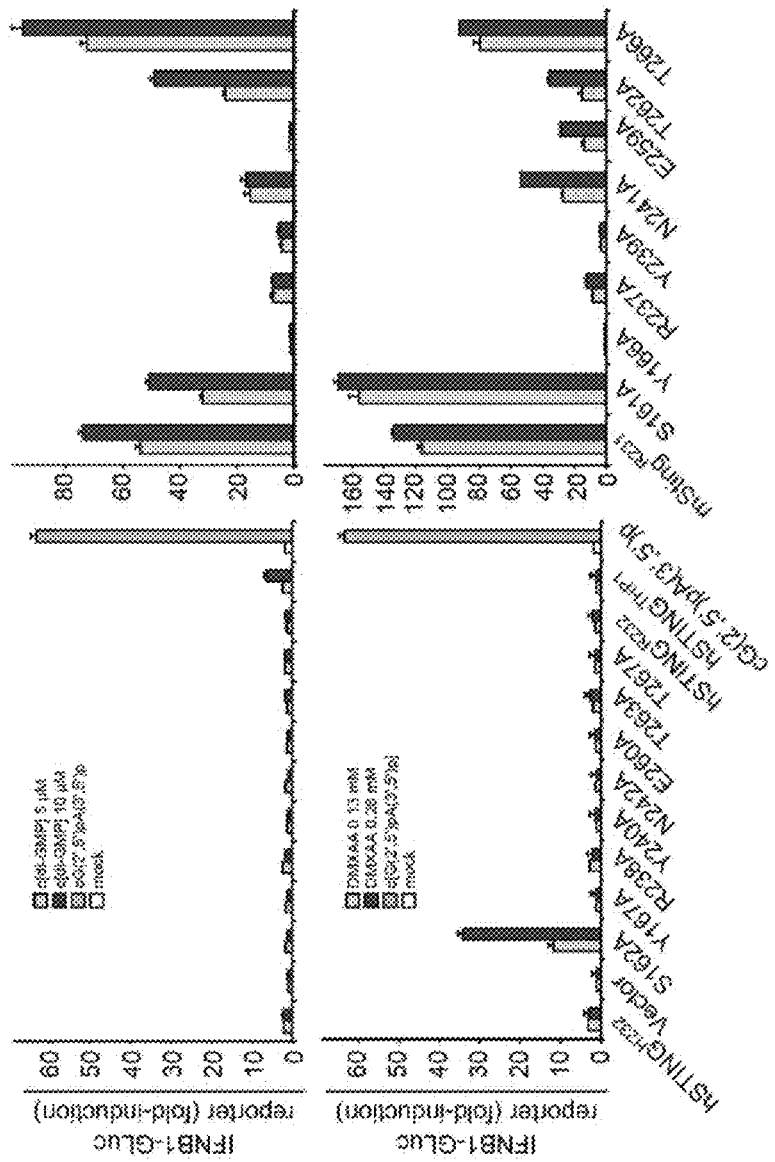

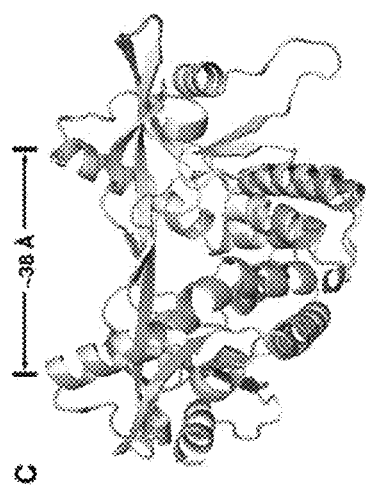
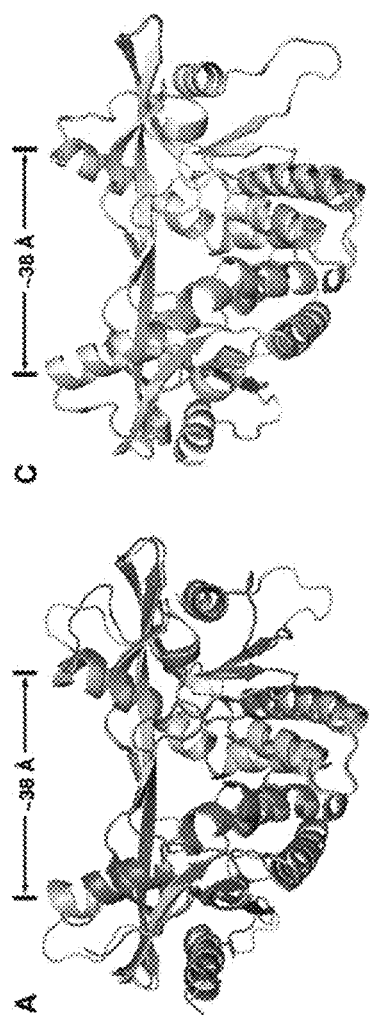
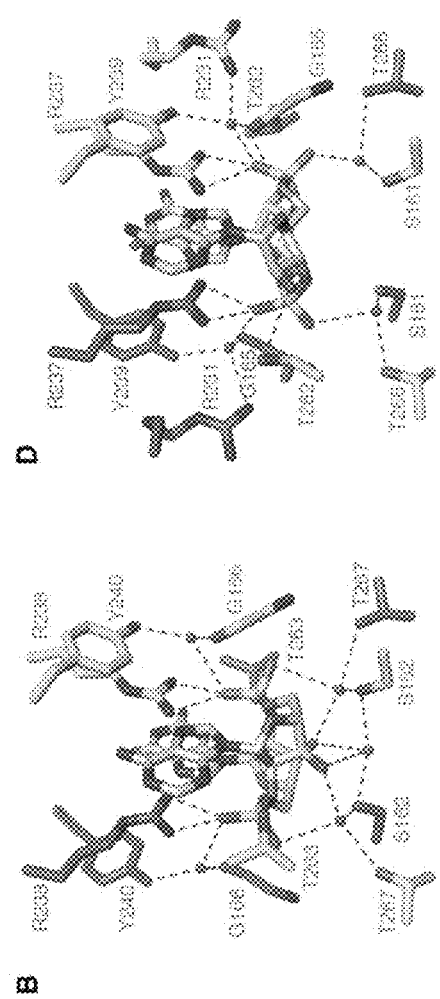
*Figure 9A*  *Figure 9C*
*Figure 9B*  *Figure 9D*

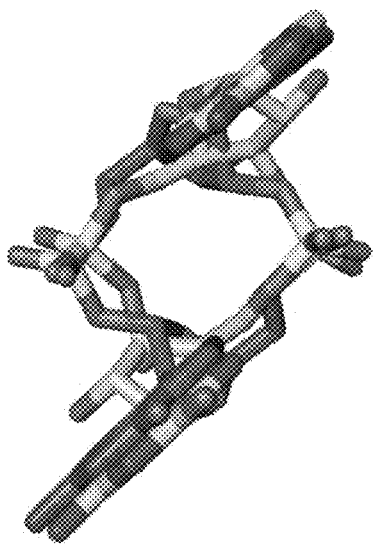
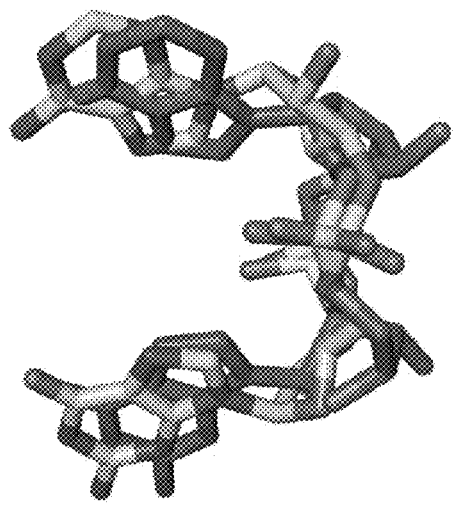
Figure 9E

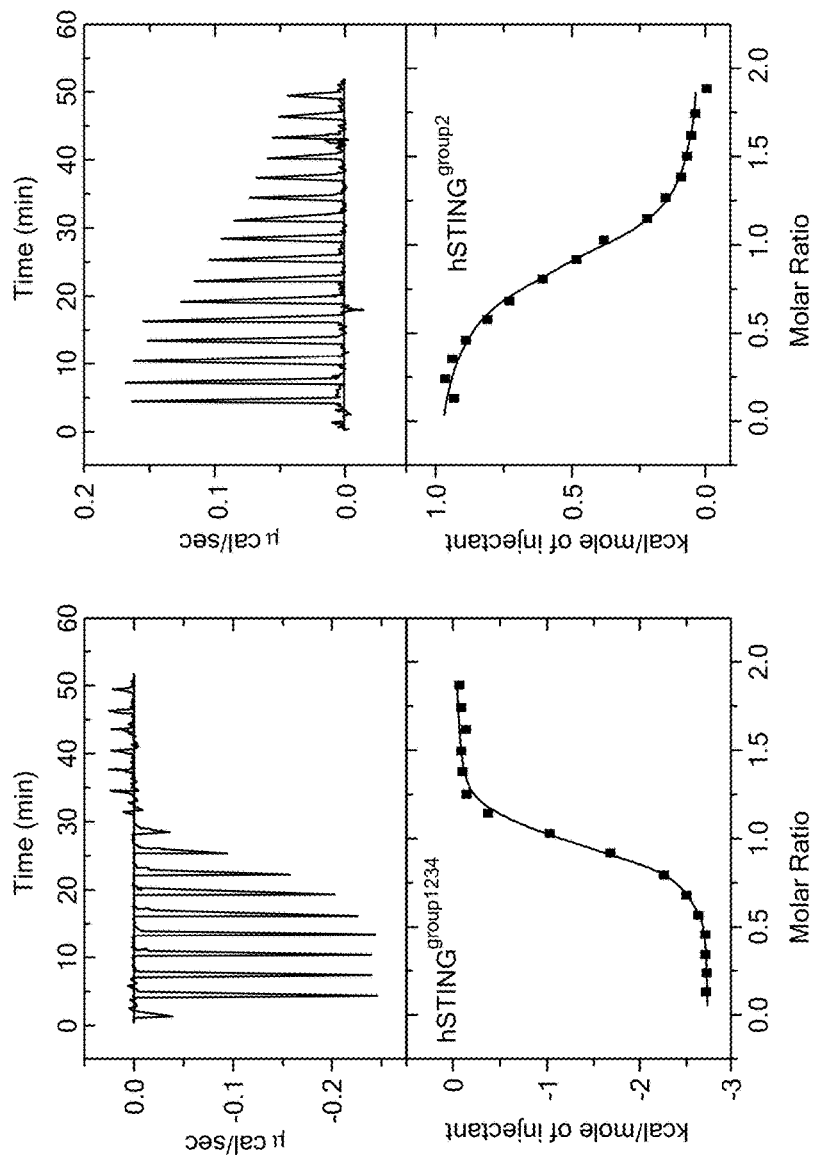
*Figure 15C*
*Figure 15B*
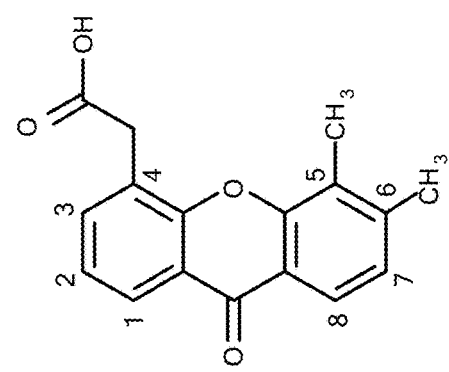
*Figure 15A*

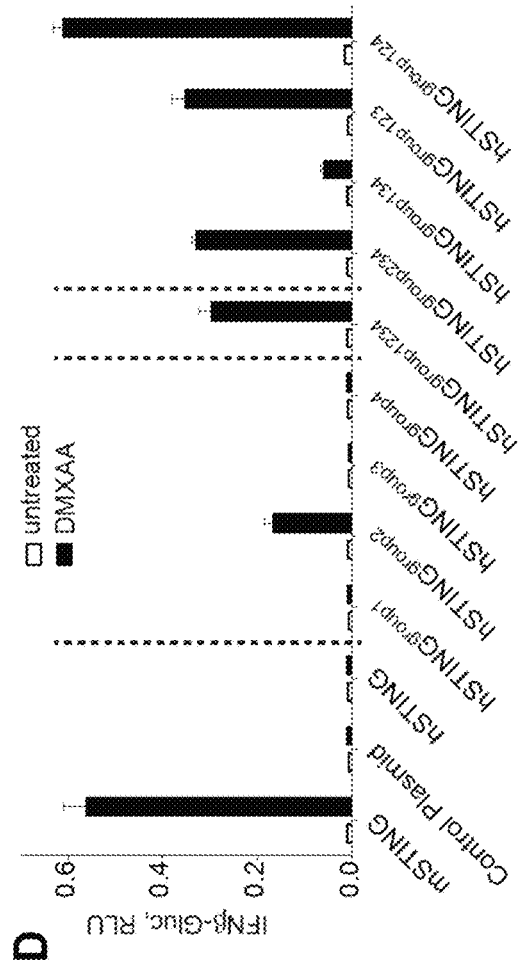
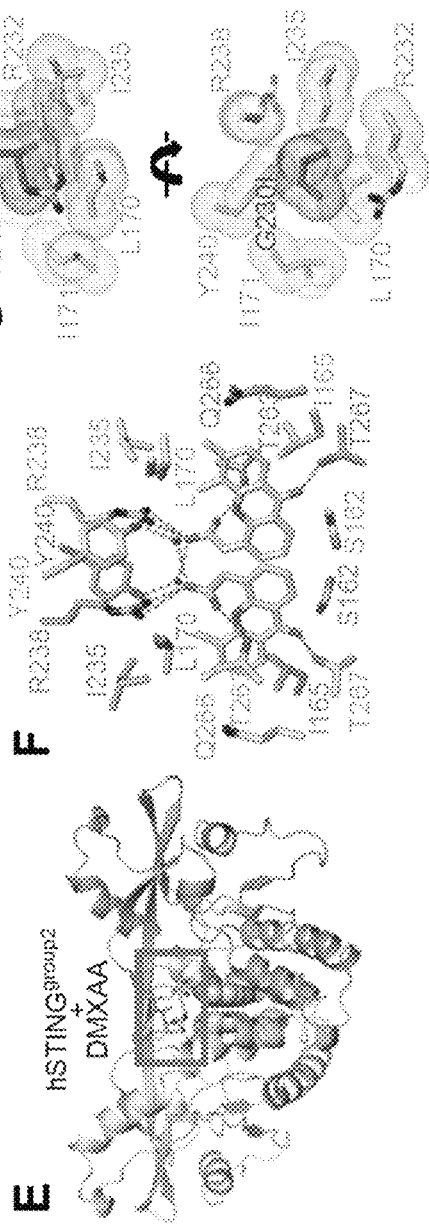
*Figure 15D*  *Figure 15E*  *Figure 15F*  *Figure 15G*

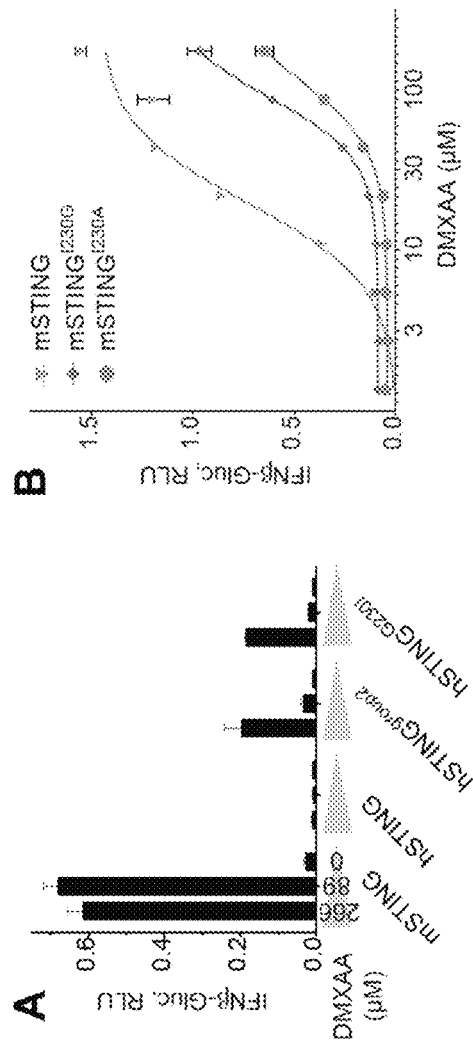
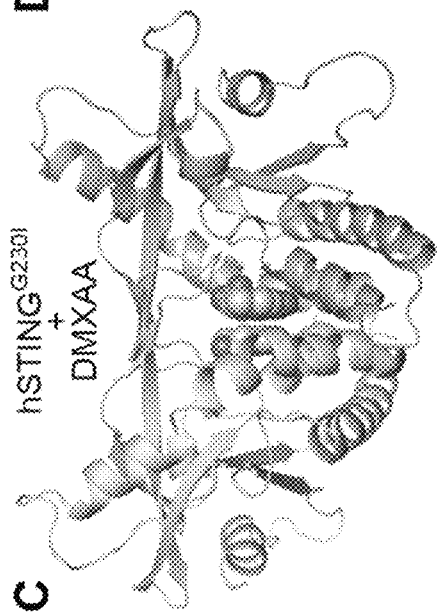
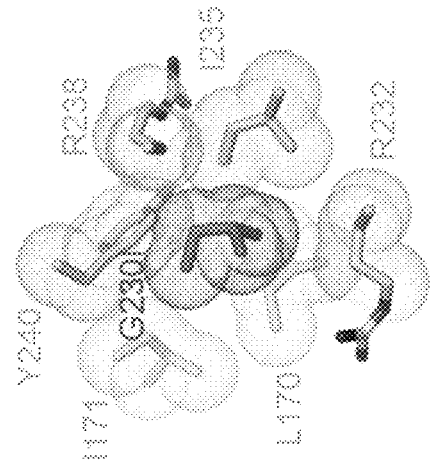
Figure 16A
Figure 16B
Figure 16C
Figure 16D

```
hSTING  MPHSSLHPSIPCPRGHGAQKAALVLLSACLVTLWGLGEPPEHTLRYLVLHLASLQLGLLL  60
mSTING  MPYSNLHPAIPRPRGHRSKYVALIFLVAGLMILWVAKDPNSTLKYIALHLASRELGLLL  60
        *   * * *   *  * **  * *   **  *     * ***  *       *  * hSTING  NGVCSLAEELRHIHSRYRGSYWRTVRACLGCPLRRGALLLLSIYFYYSLPNAVGPPFTWM  120
mSTING  RKLCCLAEELCHVQSRYQGSYWKAVRACLGCPIRCMAMILLSSFYF-LQNTADIYLSWM  119
         *   *****   ** **** *******    *  *** **  *   *  *

S162  G166
                                                 ▼    ▼
hSTING  LALGLSQSLNILLGLKGLAPAEISAVCEKGNFNVAHGLAWSYYIGYLRLILPELQARIR  180
mSTING  FGLLVLYSLSMLGLQSLTPAEVSAVCEEKKLNVAHGLAWSYYIGYLRLILPGLQARIR  179
          * *      *      **** ***** * *****************  ******
                                                                Q236
                                                                 ▼
hSTING  TYNQHYNNLLRGAVSQRLYILLPLDCGVPDNLSMADPNIRFLDKLPQQTGDRAGIKDRVY  240
mSTING  MFNQLHNKMLSGAGSRLYILFPLDCGVPDNLSVVDPNIRFRDMLPQQNIDRAGIKNRVY  239
         ***  *   * ** ***** ***********   **** * ****   ***** ***

Q266
                   ▼
hSTING  SNSIYELLENGQRAGTCVLEYATPLQTLFAMSQYSQAGFSREDRLEQAKLFCRTLEDILA  300
mSTING  SNSVYEILENGQPAGVCILEYATPLQTLFAMSQDAKAGFSREDRLEQAKLFCRTLEEILE  299
        *  ***  * ***********   ************** hSTING  DAPESQNNCRLIAYQEPADDSSFSLSQEVLRHLRQEEKEEVTGSLKTSAVPSTSTMSQE  360
mSTING  DVPESRNNCRLIVYQEPTDGNSFSLSQEVLRHIRQEEKEEVTMNAPMTSVAPPPSVLSQE  359
        * * **  ** *  ********  ******  *   ** *    *** hSTING  PELLISGMEKPLPLRTDFS  379  (SEQ. ID. No. 103)
mSTING  PRLLISGMDQPLPLRTDLI  378  (SEQ. ID. No. 2)
        * ****** *******
```

| group1 (E174G / T181M / Y182F / H185L / Y186H / L189M / R191S / V194G / Q196R)

| group2 (L222R / K224M / T229N / G230I / D237N / I244V)

| group3 (Y274D / S275A / Q276K / D297E / A300E / A302V / Q306R)

| group4 (V343M / G344N / S345A / L346P / K347M / A350V / V351A / S353P / T354P / T356V / M357L / E362R / E369D / K370Q / F378L / S379I)

▼ Mutations in ligand-binding pocket

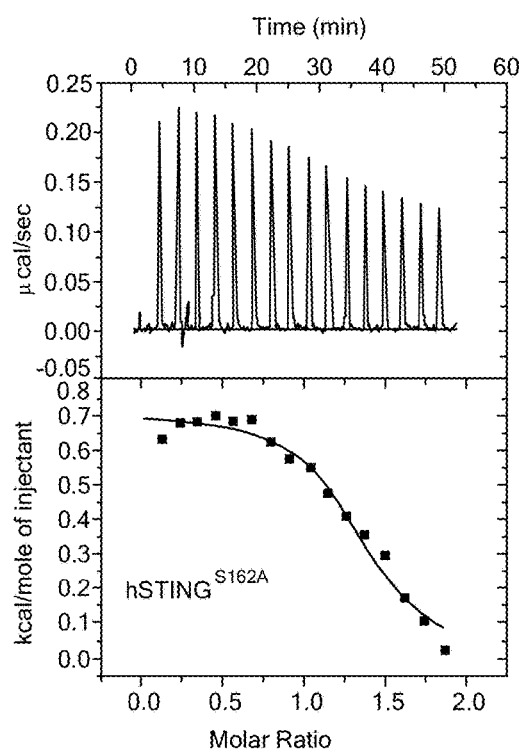
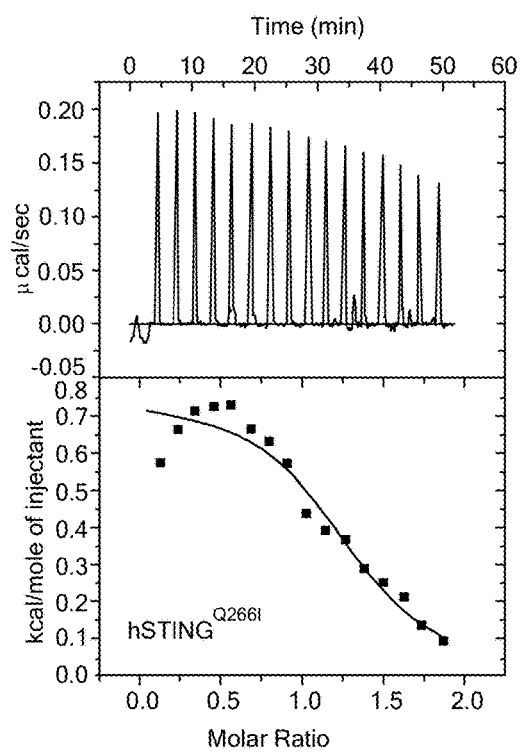
*Figure 21C*  *Figure 21D*

STING CRYSTALS AND MODULATORS

CROSS REFERENCE TO RELATED APPLICATIONS

This application is U.S. National Application under 35 U.S.C. § 371 of International Patent Application No. PCT/US2014/049140, filed Jul. 31, 2014, which claims priority to U.S. provisional patent application No. 61/860,818, filed Jul. 31, 2013, the entire contents of each of which is hereby incorporated by reference herein.

SEQUENCE LISTING

The instant application contains a Sequence Listing which has been submitted electronically in ASCII format and is hereby incorporated by reference in its entirety. Said ASCII copy, created on Sep. 19, 2014, is named 2003080-0706_SL.txt and is 38,861 bytes in size.

CRYSTALLOGRAPHIC DATA TABLES

The present specification makes reference to Table 1: c[G(2',5')pA(3',5')p]-hSTING$^{H232}$ complex (4LOH) coordinates ("Table_1.txt" created on Jul. 30, 2013 and 257 KB in size), which is filed electronically herewith as an ASCII .txt file, and is hereby incorporated herein by reference in its entirety. Table 1 lists atomic structure coordinates for a c[G(2',5')pA(3',5')p]-hSTING$^{H232}$ complex as derived by X-ray diffraction from the crystal (hSTING$^{H232}$ SEQ ID NO: 1). "Atom type" refers to the element whose coordinates are measured. The first letter in the column defines the element. "Resid" refers to the amino acid residue identity in the molecular model. "X, Y, Z" crystallographically define the atomic position of the element measured. "B" is a thermal factor that measures movement of the atom around its atomic center. "Occ" is an occupancy factor that refers to the fraction of the molecules in which each atom occupies the position specified by the coordinates. A value of "1" indicates that each atom has the same conformation, i.e., the same position, in all molecules of the crystal.

The present specification makes reference to Table 2: c[G(2',5')pA(2',5')p]-hSTING$^{H232}$ complex (4LOI) coordinates ("Table_2.txt" created on Jul. 30, 2013 and 260 KB in size), which is filed electronically herewith as an ASCII .txt file, and is hereby incorporated herein by reference in its entirety. Table 2 lists atomic structure coordinates for a c[G(2',5')pA(2',5')p]-hSTING$^{H232}$ complex as derived by X-ray diffraction from the crystal (hSTING$^{H232}$ SEQ ID NO: 1). "Atom type" refers to the element whose coordinates are measured. The first letter in the column defines the element. "Resid" refers to the amino acid residue identity in the molecular model. "X, Y, Z" crystallographically define the atomic position of the element measured. "B" is a thermal factor that measures movement of the atom around its atomic center. "Occ" is an occupancy factor that refers to the fraction of the molecules in which each atom occupies the position specified by the coordinates. A value of "1" indicates that each atom has the same conformation, i.e., the same position, in all molecules of the crystal.

The present specification makes reference to Table 3: c[G(2',5')pA(3',5')p]-mSting$^{R231}$ complex (4LOJ) coordinates ("Table_3.txt" created on Jul. 30, 2013 and 257 KB in size), which is filed electronically herewith as an ASCII .txt file, and is hereby incorporated herein by reference in its entirety. Table 3 lists atomic structure coordinates for a c[G(2',5')pA(3',5')p]-mSting$^{R231}$ complex as derived by X-ray diffraction from the crystal (mSting$^{R231}$ SEQ ID NO: 2). "Atom type" refers to the element whose coordinates are measured. The first letter in the column defines the element. "Resid" refers to the amino acid residue identity in the molecular model. "X, Y, Z" crystallographically define the atomic position of the element measured. "B" is a thermal factor that measures movement of the atom around its atomic center. "Occ" is an occupancy factor that refers to the fraction of the molecules in which each atom occupies the position specified by the coordinates. A value of "1" indicates that each atom has the same conformation, i.e., the same position, in all molecules of the crystal.

The present specification makes reference to Table 4: c[G(3',5')pA(3',5')p]-mSting$^{R231}$ complex (4LOK) coordinates ("Table_4.txt" created on Jul. 30, 2013 and 502 KB in size), which is filed electronically herewith as an ASCII .txt file, and is hereby incorporated herein by reference in its entirety. Table 4 lists atomic structure coordinates for a c[G(3',5')pA(3',5')p]-mSting$^{R231}$ complex as derived by X-ray diffraction from the crystal (mSting$^{R231}$ SEQ ID NO: 2). "Atom type" refers to the element whose coordinates are measured. The first letter in the column defines the element. "Resid" refers to the amino acid residue identity in the molecular model. "X, Y, Z" crystallographically define the atomic position of the element measured. "B" is a thermal factor that measures movement of the atom around its atomic center. "Occ" is an occupancy factor that refers to the fraction of the molecules in which each atom occupies the position specified by the coordinates. A value of "1" indicates that each atom has the same conformation, i.e., the same position, in all molecules of the crystal.

The present specification makes reference to Table 5: DMXAA-mStingR231 complex (4LOL) coordinates ("Table_5.txt" created on Jul. 30, 2013 and 473 KB in size), which is filed electronically herewith as an ASCII .txt file, and is hereby incorporated herein by reference in its entirety. Table 5 lists atomic structure coordinates for a DMXAA-mStingR231 complex as derived by X-ray diffraction from the crystal (mStingR231 SEQ ID NO: 2). "Atom type" refers to the element whose coordinates are measured. The first letter in the column defines the element. "Resid" refers to the amino acid residue identity in the molecular model. "X, Y, Z" crystallographically define the atomic position of the element measured. "B" is a thermal factor that measures movement of the atom around its atomic center. "Occ" is an occupancy factor that refers to the fraction of the molecules in which each atom occupies the position specified by the coordinates. A value of "1" indicates that each atom has the same conformation, i.e., the same position, in all molecules of the crystal.

LENGTHY TABLES

The patent contains a lengthy table section. A copy of the table is available in electronic form from the USPTO web site (http://seqdata.uspto.gov/?pageRequest=docDetail&DocID=US10176292B2). An electronic copy of the table will also be available from the USPTO upon request and payment of the fee set forth in 37 CFR 1.19(b)(3).

BACKGROUND

The protein TMEM173/STING (stimulator of interferon genes) (Ishikawa and Barber, 2008; Zhong et al. 2008; Sun et al. 2009; Burdette et al. 2011) is a central player in the innate immune response to nucleic acids, particularly cytosolic dsDNA (reviewed in Burdette and Vance, 2013). STING responds to various pathogens, as well as to mitochondrial damage, and its overactivation may contribute or possibly even trigger the onset of autoimmune disorders such as systemic lupus erythematosus. Drug discovery requires a mechanistic understanding of the cytosolic DNA-sensing pathway. Such discovery is desperately needed for development of agonists and antagonists of innate immunity, and will have a profound impact on anti-cancer and vaccine development, as well as therapies for autoimmune disorders.

SUMMARY

The present disclosure provides insights into STING structure and function; such insights define agents useful as modulators of human STING, and provide methods and compositions related thereto.

Among other things, the present invention identifies the source of one or more problems with prior efforts to modulate (agonist or antagonist) human STING, and provides solutions to such problems. The present invention also identifies the source of one or more problems with prior efforts to define or determine hSTING structure, or relevant aspects of hSTING-interacting agents, based on comparisons with STING orthologs. The present invention provides solutions to such problems. Thus, among other things, the present invention provides STING polypeptides, STING crystal (and/or crystallizable) compositions, STING binding agents, systems that tangibly embody or otherwise contrain or utilize information about such polypeptides, compositions, and/or binding agents, and methods of generating and/or using each of these.

The present invention provides, among other things, a STING modulator whose structure is an analog of c[G(2', 5')pA(3',5')p], 5,6-dimethylxanthenone-4-acetic acid (DMXAA), or 10-carboxymethyl-9-acridine (CMA), and includes a moiety that interacts with a residue corresponding to Ser162 and/or Ile165 of hSTING. In some embodiments, a STING modulator whose structure is an analog of c[G(2', 5')pA(3',5')p], 5,6-dimethylxanthenone-4-acetic acid (DMXAA), or 10-carboxymethyl-9-acridine (CMA), includes a moiety that interacts with a residue corresponding Gly230, Gln266, Ser162, or Ile165 of hSTING, or a combination thereof. In some embodiments, a provided STING modulator includes a moiety that interacts with a residue corresponding to Gln266 of hSTING. In some embodiments, a provided STING modulator includes a moiety that interacts with a residue corresponding to Gly230 of hSTING. In some embodiments, a provided STING modulator includes a moiety that interacts with a residue corresponding to Ser162 of hSTING.

In some embodiments, provided STING modulators, upon binding hSTING, an antiparallel β-pleated sheet forms over the binding pocket indicative of formation of a closed STING conformation.

In some embodiments, a STING modulator comprises one or more of the following features:
i.) direct hydrogen bonds to the side chain of Thr267 of hSTING;
ii.) direct hydrogen bonds to the side chain of Arg238 of hSTING; and
iii.) direct hydrogen bonds to the side chain of Thr263 of hSTING.

In some embodiments, a STING modulator comprises one or more of the following features:
i) direct hydrogen bonds to the side chain of Arg238 of hSTING; and
ii) water-mediated hydrogen bonds to Tyr240 of hSTING.

In some embodiments, a STING modulator comprises one or more of the following features:
i) hydrophobic interactions with a residue corresponding to Leu170 of hSTING;
ii) hydrophobic interactions with a residue corresponding to Ile235 of hSTING; and
iii) hydrophobic interactions with a residue corresponding to Ile165 of hSTING.

In certain embodiments, the one or more features of provided STING modulators include at least one feature selected from the group consisting of: spatial separation between the moiety and the potential interaction site; energy of the potential moiety-interaction site interaction, and/or combinations thereof.

In some embodiments, provided STING agents modulate hSTING.

In some embodiments, provided STING agents are specific to hSTING as compared with mSTING.

In some embodiments, the present invention provides methods of designing or characterizing a STING modulator comprising providing an image of a STING crystal that includes at least one potential interaction site; docking in the image at least one moiety that is a potential STING modulator structural element; and assessing one or more features of a potential moiety-interaction site interaction.

In some embodiments, the at least one potential interaction site includes a site of hSTING selected from the group consisting of Ser162, Ile165, R238, T263, T267, and combinations thereof. In some embodiments, the at least one potential interaction site includes a site of hSTING selected from the group consisting of Ser162, Ile165, Arg238, Thr263, Thr267, and combinations thereof. In some embodiments, the at least one potential interaction site includes a site of hSTING selected from the group consisting of Gly230, Gln266, Tyr240, Leu170, Ile235, and combinations thereof.

In some embodiments, the at least one potential interaction site is Ser162 of hSTING.

In some embodiments, the at least one potential interaction site is Ile165 of hSTING.

In some embodiments, the at least one potential interaction site is Gly230 of hSTING.

In some embodiments, provided methods further comprise a step of providing an image of a potential STING modulator comprising the moiety docked with the image of the STING crystal.

In some embodiments, provided methods further comprise further comprising a step of comparing the image with that of a STING crystal including a bound known modulator.

In some embodiments, the present invention provides a system comprising a computer or computer readable medium in which a STING crystal structure, or coordinates thereof, is embedded and/or displayed.

One feature of the present invention is that it permits assessment of potential and/or actual STING modulators based on both structural and functional attributes. For example, in some embodiments, the present invention provides methods of designing and/or characterizing a STING modulator, which methods comprise steps of (i) using a system comprising a computer or computer readable medium in which a STING crystal structure, or coordinates thereof, is embedded and/or displayed to assess one or more structural features of the STING modulator; and (ii) performing one or more in vitro, in vivo or cell-based assays to characterize the STING modulator. In some embodiments, the one or more structure features of the STING modulator comprise a moiety that interacts with a residue corresponding to Ser162 and/or Ile165 of hSTING. In some embodiments, the one or more structure features of the STING modulator comprise a moiety that interacts with a residue corresponding to Gly230 of hSTING. In some embodiments, the one or more structure features of the STING modulator comprise a moiety that interacts with a residue corresponding to Arg238, Thr263, Thr267, Gln266, Tyr240, Leu170, Ile235 of hSTING, or a combination thereof.

In some embodiments, the present invention provides a method of designing and/or characterizing a STING modulator, which method comprises steps of (i) determining the STING modulator binds in the binding pocket having a three-dimensional structure characterized by the structure coordinates of any one of Tables 1, 2, 3, 4, 5, 6, 7, 8, and/or 9; and (ii) assessing one or more structure features of the STING modulator. In some embodiments, the method further comprises the step of defining the three-dimensional shape of the modulator. In some embodiments, the three-dimensional shape of the modulator includes a moiety that interacts with a residue corresponding to Ser162 and/or Ile165 of hSTING. In certain embodiments, the three-dimensional shape of the modulator includes a moiety that interacts with a residue corresponding to Gly230 of hSTING. In some embodiments, the three-dimensional shape of the modulator includes a moiety that interacts with a residue corresponding to Arg238, Thr263, Thr267, Gln266, Tyr240, Leu170, Ile235 of hSTING, or a combination thereof.

In some embodiments, the present invention provides a modulator of STING characterized in that it binds in the binding pocket having a three-dimensional structure characterized by the structure coordinates of any one of Tables 1, 2, 3, 4, 5, 6, 7, 8, and/or 9.

In some embodiments, the present invention provides a designed STING modulator, comprising the crystallography coordinates of any one of Tables 1, 2, 3, 4, 5, 6, 7, 8, and/or 9, wherein the crystallography coordinates are within about a root mean square deviation of not more than about 1.5 Å from the backbone atoms of the amino acids according to Tables 1, 2, 3, 4, 5, 6, 7, 8, and/or 9.

In some embodiments, the present invention provides a computer system containing a set of information to perform a design or characterization of a STING modulator having a user interface comprising a display unit, the set of information comprising: (i) logic for inputting an information regarding a binding of a STING protein to a moiety known to bind STING protein; (ii) logic for designing a candidate STING modulator based on the binding of the STING protein to the moiety known to bind STING protein; (iii) logic for determining an information regarding a binding of the STING protein to the candidate STING modulator; and logic for making a conclusion regarding a STING agonist or antagonist properties of the candidate STING modulator based on the determination of step (iii).

In some embodiments, the present invention provides a computer-readable storage medium containing a set of information for a general purpose computer having a user interface comprising, a display unit, the set of information comprising: (i) logic for inputting an information regarding a binding of a STING protein to a chemical known to binding STING protein; (ii) logic for design a candidate STING modulator based on the binding of the STING protein to the chemical known to bind STING protein; (iii) logic for determining an information regarding a binding of the STING protein to the candidate STING modulator; and (iv) logic for making a conclusion regarding a STING agonist or antagonist properties of the candidate STING modulator based on the determination step of step (iii).

In some embodiments, the present invention provides an electronic signal or carrier wave that is propagated over the internet between computers comprising a set of information for a general purpose computer having a user interface comprising a display unit, the set of information comprising a computer-readable storage medium containing a set of information for a general purpose computer having a user interface comprising a display unit, the set of information comprising: (i) logic for inputting an information regarding a binding of a STING protein to an agent known to bind STING protein; (ii) logic for designing a candidate STING modulator based on the binding of the STING protein to the agent known to bind STING protein; (iii) logic for determining an information regarding a binding of the STING protein to the candidate STING modulator; and (iv) logic for making a conclusion regarding a STING agonist or antagonist properties of the candidate STING modulator based on the determination of step (iii).

In some embodiments, the present invention provides a crystalline or crystallizable composition comprising or consisting of a STING polypeptide. In some embodiments, the present invention provides methods of making and using such crystalline or crystallizable compositions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The Figures described below, that together make up the Drawings, are for illustration purposes only, not for limitation.

FIG. 1 depicts an exemplary crystal structure of c[G(2',5')pA(3',5')p] bound to hSTING$^{H232}$ and exemplary details of intermolecular contacts in the complex. FIG. 1A depicts an exemplary 2.25 Å crystal structure of cyclic [G(2',5')pA (3',5')p] bound to hSTING$^{H232}$ (aa 155-341). The symmetrical hSTING$^{H232}$ dimer is shown in a ribbon representation, with individual monomers colored in magenta and yellow. α-helices are labeled from α 1 to α 5. The c[G(2',5')pA(3', 5')p] in a space-filling representation is bound in the central cavity at the interface between the two monomers. FIG. 1B depicts an exemplary expanded view of the c[G(2',5')pA(3', 5')p] binding pocket in the complex. The position of H232 (in green) in a stick representation is labeled in this panel. FIG. 1C depicts an exemplary surface representation of the structure of the complex shown in panel A. FIG. 1D depicts an exemplary view in panel C rotated through 90°. FIG. 1E, FIG. 1F and FIG. 1G depict exemplary intermolecular contacts in the complex of c[G(2',5')pA(3',5')p] bound to hSTING$^{H232}$. The bound c[G(2',5')pA(3',5')p] is shown in biscuit color, with individual STING subunits in the symmetrical dimer shown in magenta and yellow. The bracketing of the purine rings of c[G(2',5')pA(3',5')p] by Y167 is shown in panel E, and intermolecular contacts to the base edges and backbone phosphates of the ligand by the subunits of STING are shown in panels F and G, respectively.

FIG. 2 depicts an exemplary comparison of hSTING$^{H232}$ complexes bound to c[G(2',5')pA(3',5')p] and c[di-GMP].

FIG. 2A discloses 'KDRVY' as SEQ ID NO: 102. FIG. 2C depicts an exemplary superposition of the c[G(2',5')pA(3',5')p] in green and c[di-GMP] in orange (PDB: 4EF4) in their complexes with hSTING$^{H232}$. FIG. 2D depicts an exemplary expanded view in stereo of the top right segment of panel B following superposition of the c[G(2',5')pA(3',5')p] bound structure of hSTING$^{H232}$ (both subunits in green) and c[di-GMP] bound structure of hSTING$^{H232}$ (both subunits in orange) (PDB: 4EF4).

FIG. 3 depicts an exemplary crystal structure of c[G(2',5')pA(3',5')p] bound to mSting$^{R231}$ and an exemplary comparison of its complex with the same ligand bound to hSTING$^{H23}$.

FIG. 4 depicts exemplary ITC data on binding of cGAMP linkage isomers to hSTING$^{H232}$ and hSTING$^{H232}$ mutants, as well as to hSTING$^{R232}$, hSTING$^{A230/R232}$, mSTING$^{R231}$ and mSting$^{A231}$.

FIG. 5 depicts an exemplary crystal structure of DMXAA ligand bound to mSting$^{R23}$.

FIG. 6 depicts exemplary results of cGAMP stimulation of the IFN pathway in mouse and human cells.

FIG. 7 depicts an exemplary mouse and human STING mutational analysis. FIG. 7C depicts exemplary results where HEK293T cells were transfected as in panel A and stimulated with cyclic di-GMP (5 and 10 μM) following digitonin permeabilization. Luciferase activity was determined 12 h after stimulation. As negative and positive controls, HEK293T cells transfected with hSTING$^{H232}$ were mock-treated (white bar) or stimulated with 5 μM c[G(2',5')pA(3',5')p] following digitonin permeabilization (green bar), respectively. FIG.

7D depicts an exemplary experiment where HEK293T cells were transfected as in panel C and after 12 h stimulated with medium containing DMXAA (136 and 266 µM). Luciferase activity was measured after additional 12 h.

FIG. 8 depicts exemplary surface views of the crystal structure of c[di-GMP] bound to hSTING$^{H232}$ and exemplary details of intermolecular contacts in the complex.

FIG. 9 depicts exemplary details of c[G(2',5')pA(2',5')p]-hSTING$^{H232}$ and c[G(3',5')pA(3',5')p]-mSting$^{R231}$ complexes. FIG. 9A depicts an exemplary superposition of the c[G(2',5')pA(2',5')p] (both subunits in red) and c[G(2',5')pA(3',5')p] (both subunits in green) bound structures of hSTING$^{H232}$ (aa 155-341). FIG. 9B depicts exemplary details of hydrogen-bonding interactions in the structure of the c[G(2',5')pA(2',5')p]-hSTING$^{H232}$ complex. Note the water-mediated hydrogen bonds between the 3'-OH groups and side chains of S162 and T267. FIG. 9C depicts an exemplary superposition of the c[G(3',5')pA(3',5')p] (both subunits in cyan) and c[G(2',5')pA(3',5')p] (both subunits in magenta) bound structures of mSting$^{R231}$ (aa 154-340). FIG. 9D depicts exemplary details of hydrogen-bonding interactions in the structure of the c[G(3',5')pA(3',5')p]-mSting$^{R231}$ complex. Note the direct hydrogen bonds between the 2'-OH groups and the side chains of T262. FIG. 9E depicts an exemplary superposition of the c[G(2',5')pA(2',5')p] in its complex with hSTING$^{H232}$ in red and c[G(3',5')pA(3',5')p] in its complex with mSting$^{R231}$ in cyan. The c[G(2',5')pA(2',5')p] is positioned deeper in the binding pocket than is its c[G(3',5')pA(3',5')p] counterpart.

FIG. 10 depicts an exemplary an exemplary crystal structure of CMA ligand bound to mSting$^{R231}$.

FIG. 12 depicts exemplary results showing that STING point mutants and natural STING variants display distinct dose-responses to cGAMP linkage isomers. The dotted line indicates the 5 µM cGAMP dose, whose corresponding values are that shown in FIG. 7. For dose dependence: Data points were determined in triplicate and are depicted as means±SEM.

FIG. 14 depicts exemplary results of hSTING position 162 variants and their sensitivity to cyclic dinucleaotides and DMXAA. 293T cells were transfected with reporter plasmids and hSTING variants as indicated. 12 h after transfection, cells were stimulated by incubation with 75 µg/ml DMXAA (panel A) or Digitonin-permeabilized for 30 min in the presence of cyclic dinucleotides (5 µM) as indicated (panel B). After another 12 h, cells were lysed and luciferase assay was performed. For bar graphs: Data points were determined in triplicate and are depicted as means±SEM.

FIG. 15 depicts exemplary results of how the replacement of non-conserved residues of hSTING with its murine counterparts enables recognition of DMXAA, as well as a crystal structure of DMXAA bound to hSTING$^{group2}$ and details of intermolecular interactions in the complex. FIG. 15A depicts the chemical formula of 5,6-dimethyl-xanthenone-4-acetic acid (DMXAA). FIGS. 15B and 15C depict isothermal titration calorimetry (ITC) binding curves for complex formation between DMXAA bound to hSTING$^{group1234}$ (aa 140-379) (panel B) and hSTING$^{group2}$ (panel C). FIG. 15D depicts 293T cells were transfected with IFN-β reporter constructs and STING variants as indicated. 12 hours after transfection, cells were stimulated with 0.18 mM DMXAA (50 μg/ml). Luciferase activity was determined after another 12 hours. Dotted lines separate (from left to right) wt controls, single group mutants, hSTING$^{group1234}$ and triple group mutants. Shown are raw values of *Gaussia* luciferase activity normalized to constitutive Firefly luciferase values. Values depicted are the means of triplicates +SEM and representative of 3 independent experiments. FIG. 15E depicts the 1.88 Å crystal structure of DMXAA bound to hSTING$^{group2}$ (aa 155-341). The symmetrical hSTING$^{group2}$ dimer is shown in a ribbon representation. The DMXAA in a space-filling representation is bound in the central cavity at the interface between the two monomers. FIG. 15F depicts intermolecular contacts in the complex. The bound DMXAA is shown with individual STING subunits in the symmetrical dimer. FIG. 15G depicts two expanded views of the hydrophobic interactions of the G230I substitution in the complex (box region in panel E). Other residues lining the hydrophobic pocket are shown in a lighter shade.

FIG. 16 depicts that G230 in hSTING and I229 in mSTING are relevant for DMXAA species selectivity. FIG. 16A depicts results where 293T cells were transfected with IFN-β reporter constructs and STING variants as indicated. 12 hours after transfection, cells were stimulated with ascending concentrations of DMXAA. Luciferase activity was determined after another 12 hours. Shown are the means of triplicates +SEM, representative of 3 independent experiments. FIG. 16B depicts results where 293T cells were transfected with mSTING variants and reporter constructs. Stimulation and luciferase assay was performed as described in panel A. Dose-responses are representative of 2 independent experiments. FIG. 16C depicts the 2.51 Å crystal structure of DMXAA bound to hSTINGG230I (aa 155-341). The representations are the same as used in FIG. 15E. FIG. 16D depicts detailed hydrophobic interactions in the complex of DMXAA bound to hSTINGG230I, with the same representations as in FIG. 15G.

FIG. 17 depicts exemplary results showing S162A and Q266I substitutions render hSTING sensitive to DMXAA.

FIG. 18 depicts findings that triple substitution of G230I/S162A/Q266I yields an hSTING Variant with higher affinity to DMXAA compared to mSTING, and robust stimulation of cytokines/chemokines in mouse cells.

FIG. 19 depicts sequence alignment of STING from mouse (SEQ ID NO: 2) and human (SEQ ID NO: 103) and the design of group substituents. The transmembrane domain (1-139 of hSTING; 1-138 of mSTING) and C-terminal domain (140-379 of hSTING; 139-378 of mSTING) are shown in gray and black, respectively. The group substituents are indicated in boxes. Arrows indicate the mutated residues within the ligand-binding pocket.

FIG. 20 depicts ITC binding assays for DMXAA with hSTING group1, group3, and group4 mutants and structural comparison of DMXAA Bound to hSTINGgroup2 and mSTING.

FIG. 21 depicts a structural comparison of DMXAA Bound to hSTING$^{G230I}$ and hSTING$^{group2}$, as well as ITC-based DMXAA-binding assays for hSTING S162A and Q266I Mutants. FIGS. 21C-D depict ITC binding curves for complex formation between DMXAA bound to hSTING$^{S162A}$ (aa 140-379) (panel C) and hSTING$^{Q266I}$ (panel D).

FIG. 22 depicts dose-responses of hSTING Variants and their respective S162A, Q266I Mutants to DMXAA and the structural comparison of DMXAA bound to hSTING$^{G230I}$ and hSTING$^{S162A/Q266I}$, as well as DMXAA stimulation of cytokines/chemokines in mouse cells. 293T cells were transfected with reporter constructs and indicated STING variants. After 12 hours, cells were stimulated with ascending concentration of DMXAA (A and B) directly added to medium. Luciferase assay was performed after another 12 hours. Dose-responses shown are representative of 2 independent experiments.

DEFINITIONS

Figures 2A, 2B:
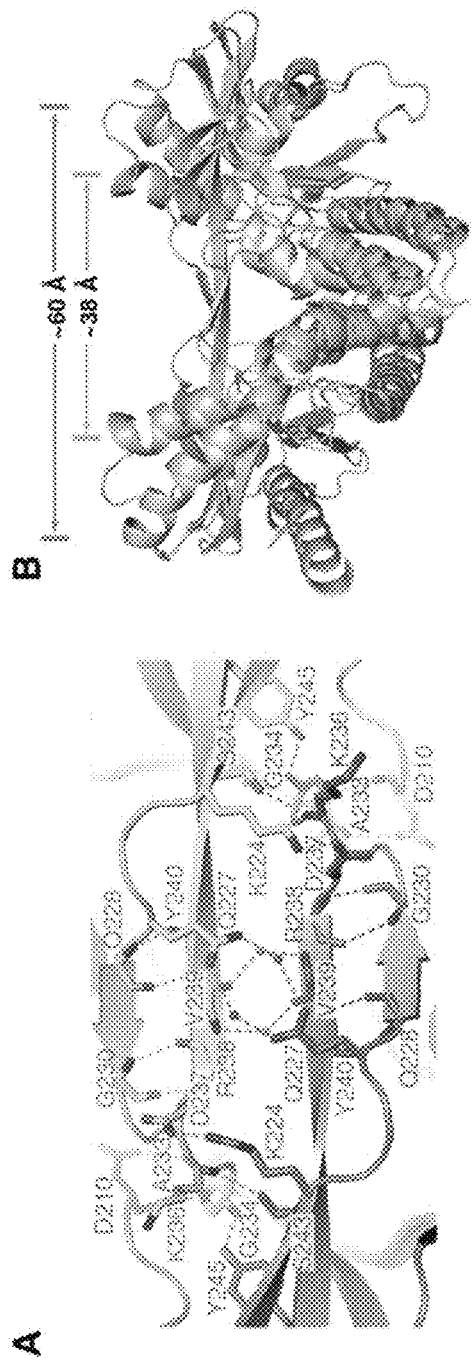
FIG. 2A depicts exemplary Details related to alignment and hydrogen-bonding patterns within the four-stranded anti-parallel β-sheet that forms a cap over the binding pocket on formation of the c[G(2',5')pA(3',5')p]-hSTING$^{H232}$ complex.
FIG. 2B depicts an exemplary superposition of the c[G(2',5')pA(3',5')p] bound structure of hSTING$^{H232}$ (aa 155-341) with both subunits in green and c-[d-GMP] bound structure of hSTING$^{H232}$ (aa 139-379) with both subunits in beige (PDB: 4EF4).

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Aliphatic: As used herein, the term "aliphatic" or "aliphatic group" means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkyl: As used herein, the term "alkyl" refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in some embodiments alkyl groups contain 1-3 carbon atoms, and in some embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Amino acid: As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog a substance that can be generated from the reference substance by chemical manipulation of the reference substance. In some embodiemnts, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Approximately: As used herein, the term "approximately" and "about" is intended to encompass normal statistical variation as would be understood by those of ordinary skill in the art as appropriate to the relevant context. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of continguous monomers spaced apart by one or more spacer regions whose length may or may not vary across polymers that share the sequence element. In certain embodiments, particular characteristic sequence elements may be referred to as "motifs".

Combination therapy: As used herein, the term "combination therapy" refers to those situations in which a subject is simultaneously exposed to two or more therapeutic agents. In some embodiments, such agents are administered simultaneously; in some embodiments, such agents are administered sequentially; in some embodiments, such agents are administered in overlapping regimens.

Comparable: The term "comparable", as used herein, refers to two or more agents, entities, situations, sets of conditions, etc that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc to be considered comparable.

Computer-readable medium: The term "computer-readable medium", as used herein, refers to non-volatile (i.e. secondary storage) computer data storage and/or memory to retain digital data even when not powered. Examples of computer-readable medium include, but are not limited to hard disk, floppy disk, flash memory (i.e. solid state memory), Ferroelectric RAM (F-RAM), Magnetoresistive RAM (MRAM), optical disc, standalone RAM disks, ZIP drives, magnetic tape and holographic memory.

Computer system: The term "computer system" or "computer", as used herein, refers to a computing device that can be used to implement the techniques described in this disclosure. An exemplary computing device 2500 and a mobile computing device are shown in FIG. 25.

Corresponding to: As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

Crystal structure: As used herein, the term "crystal structure" of a composition shall mean a computer readable medium in which is stored a representation of three dimensional positional information (i.e. coordinates) for atoms of the composition.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Docking: As used herein, the term "docking" refers to orienting, rotating, translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof. See Meng et al. J. Comp. Chem. 4: 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend et al., J. Mol. Recognition 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen et al., J. Med. Chem. 33:889-894 (1990)). Docking can also be performed by combining a Monte Carlo search technique with rapid energy evaluation using molecular affinity potentials. See Goodsell and Olson, Proteins: Structure, Function and Genetics 8:195-202 (1990). Software programs that carry out docking functions include but are not limited to MATCHMOL (Cory et al., J. Mol. Graphics 2: 39 (1984); MOLFIT (Redington, Comput. Chem. 16: 217 (1992)) and DOCK (Meng et al., supra).

Dosage form: As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

Designed: As used herein, the term "designed" refers to an agent (i) whose structure is or was selected by the hand of man; (ii) that is produced by a process requiring the hand of man; and/or (iii) that is distinct from natural substances and other known agents.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is correlated with a desired or beneficial outcome when administered across a relevant population (i.e., is a therapeutic dosing regimen).

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| | | | | | |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

Homology model: As used herein, the term "homology model" refers to a set of coordinates derived from known three-dimensional structure used as template. Generation of the homology model, termed "homology modeling", involves sequence alignment, residue replacement and residue conformation adjustment through energy minimization.

Human: In some embodiments, a human is an embryo, a fetus, an infant, a child, a teenager, an adult, or a senior citizen.

Hydrophilic: As used herein, the term "hydrophilic" and/or "polar" refers to a tendency to mix with, or dissolve easily in, water.

Hydrophobic: As used herein, the term "hydrophobic" and/or "non-polar", refers to a tendency to repel, not combine with, or an inability to dissolve easily in, water.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

Inhibition model: As used herein, the term "inhibition model" refers to a region or regions of proteins that can associate with another chemical entity or compound. Such regions are of significant utility in fields such as drug discovery. These regions are formed by amino acid residues key for ligand binding or may be residues that are spatially related and define a three-dimensional shape of the binding pocket. In some embodiments, the amino acid residues may be contiguous or non-contiguous in primary sequence. In some embodiments, the region or regions may be embodied as a dataset (e.g. an array of structure coordinates) recorded on computer readable media.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In some embodiments, isolation involves or requires disruption of covalent bonds (e.g., to isolate a polypeptide domain from a longer polypeptide and/or to isolate a nucleotide sequence element from a longer oligonucleotide or nucleic acid).

Modulator: The term "modulator" is used to refer to an entity whose presence in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof).

In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Patient: As used herein, the term "patient" or "subject" refers to a human or any non-human animal (e.g., mouse, rat, rabbit, dog, cat, cattle, swine, sheep, horse or primate) to whom therapy is administered. In many embodiments, a patient is a human being. In some embodiments, a patient is a human presenting to a medical provider for diagnosis or treatment of a disease, disorder or condition. In some embodiments, a patient displays one or more symptoms or characteristics of a disease, disorder or condition. In some embodiments, a patient does not display any symptom or characteristic of a disease, disorder, or condition. In some embodiments, a patient is someone with one or more features characteristic of susceptibility to or risk of a disease, disorder, or condition.

Pharmaceutically acceptable: The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

Polypeptide: The term "polypeptide", as used herein, generally has its art-recognized meaning of a polymer of at least three amino acids, linked to one another by peptide bonds. In some embodiments, the term is used to refer to specific functional classes of polypeptides, such as, for example, autoantigen polypeptides, nicotinic acetylcholine receptor polypeptides, alloantigen polypeptides, etc. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region, often including a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide as described herein may comprise or consist of a fragment of a parent polypeptide. In some embodiments, a useful polypeptide as described herein may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Reference: The term "reference" is often used herein to describe a standard or control agent or value against which an agent or value of interest is compared. In some embodiments, a reference agent is tested and/or a reference value is determined substantially simultaneously with the testing or determination of the agent or value of interest. In some embodiments, a reference agent or value is a historical reference, optionally embodied in a tangible medium. Typically, as would be understood by those skilled in the art, a reference agent or value is determined or characterized under conditions comparable to those utilized to determine or characterize the agent or value of interest.

Small molecule: As used herein, the term "small molecule" means a low molecular weight organic compound that may serve as an enzyme substrate or regulator of biological processes. In general, a "small molecule" is a molecule that is less than about 5 kilodaltons (kD) in size. In some embodiments, provided nanoparticles further include one or more small molecules. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, one or more small molecules are encapsulated within the nanoparticle. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc. In some embodiments, a small molecule is a therapeutic. In some embodiments, a small molecule is an adjuvant. In some embodiments, a small molecule is a drug.

Specific: The term "specific", when used herein with reference to an agent or entity having an activity, is understood by those skilled in the art to mean that the agent or entity discriminates between potential targets or states. For example, an agent is said to bind "specifically" to its target if it binds preferentially with that target in the presence of competing alternative targets. In some embodiments, the agent or entity does not detectably bind to the competing alternative target under conditions of binding to its target. In some embodiments, the agent or entity binds with higher on-rate, lower off-rate, increased affinity, decreased dissociation, and/or increased stability to its target as compared with the competing alternative target(s).

Figure 23:
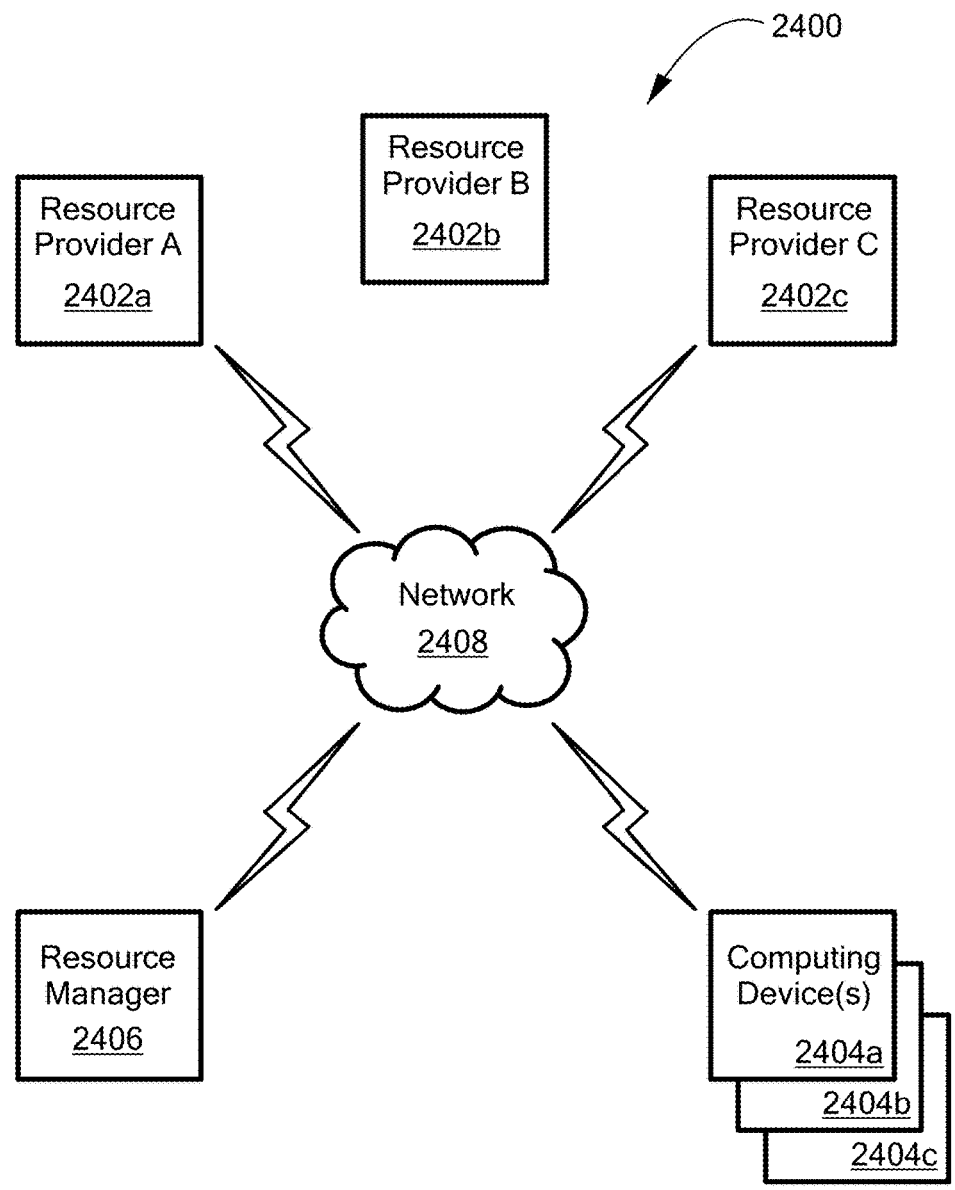
FIG. 23 depicts an exemplary block diagram of a computing device and a mobile computing device.

Storage environment: As used herein, the term "storage environment" comprises any environment comprising secondary storage, i.e. long-term persistent storage. In some embodiments, a storage environment comprises computer-readable medium. In some embodiments, a storage environment comprises a network environment for establishing a multi-channel context aware communication environment (i.e. cloud computing). For example, FIG. 23 is a block diagram of a network environment for establishing a multi-channel context aware communication environment.

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from allergy, etc.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic agent: As used herein, the phrase "therapeutic agent" refers to any agent that has a therapeutic effect and/or elicits a desired biological and/or pharmacological effect, when administered to a subject. In some embodiments, an agent is considered to be a therapeutic agent if its administration to a relevant population is statistically correlated with a desired or beneficial therapeutic outcome in the population, whether or not a particular subject to whom the agent is administered experiences the desired or beneficial therapeutic outcome.

Therapeutically effective amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition (e.g., allergy). In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweart, tears, urine, etc). Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

Therapeutic regimen: A "therapeutic regimen", as that term is used herein, refers to a dosing regimen whose administration across a relevant population is correlated with a desired or beneficial therapeutic outcome.

Treatment: As used herein, the term "treatment" (also "treat" or "treating") refers to any administration of a substance that partially or completely alleviates, ameliorates, relives, inhibits, delays onset of, reduces severity of, and/or reduces frequency, incidence or severity of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Three dimensional representation: As used herein, the term "three dimensional representation" refers to converting the lists of structure coordinates into structural models or graphical representation in three-dimensional space. In some embodiments, the three dimensional structure may be displayed or used to performing computer modeling or fitting operations. In some embodiments, the structure coordinates themselves, without the displayed model, may be used to perform computer-based modeling and fitting operations.

Unsaturated: As used herein, the term "unsaturated" means that a moiety has one or more units of unsaturation.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certain embodiments, neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

The symbol "⌇", except when used as a bond to depict unknown or mixed stereochemistry, denotes the point of attachment of a chemical moiety to the remainder of a molecule or chemical formula.

DETAILED DESCRIPTION OF CERTAIN EMBODIMENTS

STING

The protein TMEM173/STING (stimulator of interferon genes) (Ishikawa and Barber, 2008; Zhong et al. 2008; Sun et al. 2009; Burdette et al. 2011; Ishikawa et al., 2009; Jin et al., 2008) is a central player in the innate immune response to nucleic acids, particularly cytosolic dsDNA (reviewed in Burdette and Vance, 2013; Cai et al., 2014; Danilchanka and Mekalanos, 2013; O'Neill, 2013; Paludan and Bowie, 2013; Xiao and Fitzgerald, 2013). STING responds to various pathogens, as well as to mitochondrial damage, and its overactivation may contribute or possibly even trigger the onset of autoimmune disorders such as systemic lupus erythematosus (Gall et al. 2012; Gehrke et al., 2013). STING's role in the immune system is consistent with its higher expression in certain organs such as the thymus, spleen and placenta. STING is also expressed in THP1 human monocytic cells.

An initial screen designed to discover potential regulators of the type I interferon (IFN) antiviral response identified cyclic GMP-AMP (cGAMP) synthase (MB21D1/cGAS) as a gene with broad antiviral effect (Schoggins et al. 2011). Independently, biochemical fractionation identified cGAS as the metazoan cytosolic DNA sensor and synthase of cGAMP, the endogenous second messenger that activates the type I IFN pathway (Sun et al. 2013; Wu et al. 2013). A structure-function study demonstrated that only one specific isomer of cGAMP, namely c[G(2',5')pA(3',5')p] was produced by cGAS (Gao et al. 2013). This isomer of the second messenger contained an unanticipated 2',5'-linkage at the GpA step, a feature subsequently validated by several independent studies (Diner et al. 2013; Ablasser et al. 2013; Zhang et al. 2013). Structures of dsDNA-bound cGAS with ATP and GTP (Gao et al. 2013; Civril et al. 2013), pppGpA dinucleotide intermediate (Gao et al. 2013), and the product c[G(2',5')pA(3',5')p] (Gao et al. 2013), along with biochemical analysis of reaction intermediates, provided insights into the stepwise conversion of GTP and ATP in the first step to pppGpA (Gao et al. 2013; Ablasser et al. 2013) and subsequent cyclization to c[G(2',5')pA(3',5')p] (Gao et al. 2013; Ablasser et al. 2013).

The identification of c[G(2',5')pA(3',5')p] as a novel second messenger generated by dsDNA-bound cGAS in the presence of GTP and ATP (Gao et al., 2013) has prompted studies of the role of c[G(2',5')pA(3',5')p] in activating the IFN pathway via the downstream receptor STING (Diner et al. 2013; Ablasser et al. 2013; Zhang et al. 2013). Binding of c[G(2',5')pA(3',5')p] to STING activates a cascade of events whereby STING recruits and activates IκB kinase (IKK) and TANK-binding kinase (TBK1), which following their phosphorylation, respectively activate nuclear transcription factor κB (NF-κB) and interferon regulatory factor 3 (IRF3). These activated proteins translocate to the nucleus to induce transcription of the genes encoding type I IFN and cytokines for promoting intercellular host immune defense (reviewed in Keating et al. 2011; Paludan and Bowie, 2013). STING is a direct sensor of bacterial cyclic dinucleotides (CDNs) such as c[di-GMP] (Burdette et al., 2011), although it was subsequently demonstrated that the host-encoded cytosolic DNA-binding sensor cyclic GMP-AMP synthase (cGAS) (Sun et al., 2013) and its product cyclic GMP-AMP (cGAMP) (Wu et al., 2013) acted as the second messenger binding to STING in response to cells exposed to DNA.

In the human population, there are several STING variants, which may influence the responsiveness to cGAMP, its linkage isomers and other CDNs (Diner et al., 2013; Yi et al., 2013). Among them, R71/G230/R232/R293 (referred to as hSTING$^{R232}$) appears to be the most common variant (Yi et al., 2013). Thus, unless specified otherwise, the experiments described in the ensuing exemplification were based on this variant.

Human (h) and mouse (m) STING exhibit 68% amino acid identity and 81% similarity, with distinct sequence alleles reported in humans (Diner et al. 2013). Established numbering systems of human and mouse STING are offset by one residue, with hSTING$^{R232}$ and mSTING$^{R231}$ occupying corresponding positions. The amino acid sequences of hSTING (accession no. NP_938023.1; SEQ ID NO.: 1) and mSTING (accession no.; SEQ ID NO.: 2) are shown in Table A.

TABLE A

Human and Mouse Stimulator of Interferon Genes Protein (STING)

| | |
|---|---|
| Human STING Accession number: NP_938023.1 | MPHSSLHPSIPCPRGHGAQKAALVLLSACLVTLWGLG EPPEHTLRYLVLHLASLQLGLLLNGVCSLAEELRHIH SRYRGSYWRTVRACLGCPLRRGALLLLSIYFYYSLPN AVGPPFTWMLALLGLSQALNILLGLKGLAPAEISAVC EKGNFNVAHGLAWSYYIGYLRLILPELQARIRTYNQH YNNLLRGAVSQRLYILLPLDCGVPDNLSMADPNIRFL DKLPQQTGDHAGIKDRVYSNSIYELLENGQRAGTCVL EYATPLQTLFAMSQYSQAGFSREDRLEQAKLFCRTLE DILADAPESQNNCRLIAYQEPADDSSFSLSQEVLRHL RQEEKEEVTVGSLKTSAVPSTSTMSQEPELLISGMEK PLPLRTDFS (SEQ ID NO: 1) |
| Mouse STING Accession number: NP_082537.1 | MPYSNLHPAIPRPRGHRSKYVALIFLVASLMILWVAK DPPNHTLKYLALHLASHELGLLLKNLCCLAEELCHVQ SRYQGSYWKAVRACLGCPIHCMAMILLSSYFYFLQNT ADIYLSWMFGLLVLYKSLSMLLGLQSLTPAEVSAVCE EKKLNVAHGLAWSYYIGYLRLILPGLQARIRMFNQLH NNMLSGAGSRRLYILFPLDCGVPDNLSVVDPNIRFRD MLPQQNIDRAGIKNRVYSNSVYEILENGQPAGVCILE YATPLQTLFAMSQDAKAGFSREDRLEQAKLFCRTLEE ILEDVPESRNNCRLIVYQEPTDGNSFSLSQEVLRHIR QEEKEEVTMNAPMTSVAPPPSVLSQEPRLLISGMDQP LPLRTDLI (SEQ ID NO: 2) | hSTING is composed of a N-terminal transmembrane domain (aa 1-154), a central globular domain (aa 155-341) and a C-terminal tail (aa 342-379). Distinct sequence variants of either mouse or human STING have been studied with different functional assays and outcomes, complicating interpretation. Diner et al (2013) identified natural variant alleles of STING, namely the R232H variant to the genome reference of human STING (hSTING$^{H232}$, reference sequence) and the R231A variant of mouse Sting (mSTING$^{A231}$), which were activated by c[G(2',5')pA(3',5')p] but not by c[di-GMP] or c[G(3',5')pA(3',5')p]. By contrast, Zhang et al (2013) proposed based on structural, calorimetric-based binding and cellular assays that c[G(2',5')pA(3',5')p] is the highest affinity ligand for hSTING$^{R232}$, even though their in vitro calorimetric binding measurements did not support their results seen with IFN induction cellular assays. Ablasser et al (2013) investigated the contribution of 2',5'- and 3',5'-linkages in cGAMP and concluded that c[G(2',5')pA(3',5')p] was more potent than c[G(3',5')pA(3',5')] in activating hSTING from human fibroblasts and THP1 cells, and wild-type mSTING$^{R231}$.

Structural studies have been reported on hSTING$^{H232}$ in the free and c[di-GMP] bound states. STING forms a symmetrical dimer in both states with c[di-GMP] bound in a pocket within the dimer interface and anchored by a network of intermolecular hydrogen bonds (reviewed in Burdette and Vance, 2013). For all but one of the c[di-GMP]-hSTING$^{H232}$ complexes, the STING dimer adopts the same V-shaped conformation independent of the presence of the ligand and also does not completely surround the bound ligand. In the one exception, c[di-GMP]-bound hSTING$^{A230/R232}$ forms an anti-parallel β-pleated sheet cap over the binding pocket on complex formation and this conformational change further sequesters the bound ligand (Huang et al. 2012). More recently, the same conformational transition has been reported on formation of the complex between mSTING$^{R231}$ and the anti-viral drug CMA (Cavlar et al. 2013) and on formation of the complex between hSTING$^{R232}$ and c[G(2',5')pA(3',5')p] (Zhang et al. 2013).

The present disclosure provides valuable insights into the structural basis and functional output of ligand-binding by hSTING and mSTING. Given STING's central role in immunoregulation of the anti-viral response and in eliciting a macrophage-dependent tumoricidal program (Kim et al. 2013), such insights permit design, production, and or characterization of useful STING modulators. In some embodiments, such modulators are useful in medicine (e.g., in therapy and/or in prophylaxis) of one or more diseases, disorders, or conditions.

The present disclosure provides insights relevant to selectivity of hSTING$^{R232}$ for [G(2',5')pA(3',5')p], as well as its ability to recognize, bind to and/or discriminate between its linkage isomers.

The present disclosure also assesses the extent to which distinct STING alleles (e.g., hSTING$^{H232}$ and mSTING$^{A231}$) and/or variants differentially respond to particular modulator agents.

Among other things, the present disclosure provides crystal structures of various STING alleles and/or variants alone or complexed with one or more modulator or candidate modulator agents. Such crystal structures are useful, for example, to guide design of modulator agents, including modulator agents whose structures include moieties that can and/or do make specified interactions with complementary STING moieties. In some embodiments, such complementary STING moieties are present in some STING alleles or variants but not others. The present disclosure, therefore, among other things, provides technologies for designing, identifying and/or characterizing STING modulators that discriminate between or among STING alleles and/or variants.

STING Function

It is generally believed that STING coordinates multiple immune responses to infection, including the induction of interferons and STAT6-dependent response and selective autophagy response. STING plays an important role in innate immunity and mediates type I interferon production in response to intracellular DNA and a variety of intracellular pathogens, such as viruses, mycobacteria and intracellular parasites. For example, STING binds directly to cyclic di-GMP, and this recognition leads to the production of cytokines, such as type I interferon. Type I interferon protects infected cells and nearby cells from local infection in an autocrine and paracrine manner.

For example, binding of c[G(2',5')pA(3',5')p] to STING activates a cascade of events whereby STING recruits and activates IκB kinase (IKK) and TANK-binding kinase (TBK1), which following their phosphorylation, respectively activate nuclear transcription factor κB (NF-κB) and interferon regulatory factor 3 (IRF3). These activated proteins translocate to the nucleus to induce transcription of the genes encoding type I IFN and cytokines for promoting intercellular host immune defense (reviewed in Keating et al. 2011; Paludan and Bowie, 2013).

STING plays an important role in antiviral immunity and elicits powerful type I interferon immunity against viral infection. After viral entry, viral nucleic acids will be present in the cytosol of infected cells. Several DNA sensors, such as DAI, RNA polymerase III, IFI16, DDX41 and cGAS, can detect foreign nucleic acids. After recognizing viral DNA, DNA sensors initiate the downstream signaling pathways by activating STING-mediated interferon response. Viruses that activate a STING-dependent innate immune response include, but are not limited to, adenovirus, herpes simplex virus (e.g., HSV-1 and HSV-2), negative-stranded RNA virus-vesicular stomatitis virus (VSV), and combinations thereof.

A variety of assays are known to one of skill in the art that detect and/or characterize STING activities. In some embodiments, STING activity is or comprises interacting with a particular binding partner or partners. In some embodiments, STING activity is or comprises discriminating between potential partners. In some embodiments, STING activity is or comprises hSTING activity. In some embodiments, STING activity is or comprises mSTING activity.

In some embodiments, STING activity is or comprises phosphorylation of a particular substrate or substrates. In some embodiments, STING activity is or comprises phosphorylation of TBK1, IKK, IRF3, STAT6 and/or combinations thereof.

In some embodiments, STING activity is or comprises upregulation of gene expression of of IFN-β, CCL2, CCL20, and/or combinations thereof.

In some embodiments, a STING polypeptide shares at least one of these activities with a reference STING polypeptide, such as a wild type STING. In some embodiments, a STING polypeptide is considered to "share" an activity with a reference if it shows an activity that would be recognized by those skilled in the art as comparable to, or not significantly different from, that of a relevant reference in an appropriate assay that detects and/or characterizes the activity. While the kinase activity of a STING polypeptide compared to a reference may be significantly lower, it can be recognized by its ability to phosphorylate STING-specific sites in bona-fide STING substrates such as IKK and TBK1.

STING Crystal Structure

Among other things, the present invention provides a crystalline (i.e., containing at least one crystal) or crystallizable composition comprising a STING polypeptide. In some embodiments, such a provided composition consists of or consists essentially of the STING polypeptide. In some embodiments, a composition is considered to "consist of" a STING polypeptide if it includes only the polypeptide, one or more solvents, and optionally salts and/or metals. In some embodiments, such a provided composition includes one or more other agents such as one or more other polypeptides (e.g., one or more potential or actual STING binding partner polypeptides) and/or one or more interacting agents (e.g., small molecules).

In some embodiments, such a provided composition comprises a wild-type STING polypeptide. Exemplary wild-type STING polypeptides include, but are not limited to, hSTING (SEQ ID NO: 1) and mSTING (SEQ ID NO: 2). In some embodiments, such a provided composition comprises a STING polypeptide comprising an N-terminal truncation. In some embodiments, a STING polypeptide comprises an N-terminal truncation of hSTING comprising a truncation of amino acid residues 1-139 (hSTING$^{140\text{-}379}$). In some embodiments, a STING polypeptide comprises an N-terminal truncation of mSTING comprising a truncation of amino acid residues 1-138 (mSTING$^{139\text{-}378}$).

In some embodiments, a STING polypeptide comprises a C-terminal truncation.

In some embodiments, a STING polypeptide comprises both an N-terminal truncation and a C-terminal truncation. In some embodiments, a STING polypeptide comprises both an N-terminal truncation and a C-terminal truncation of hSTING comprising a trunctation of N-terminal residues 1-154 and C-terminal residues 342-379 (hSTING$^{H232}$ comprising residues 155-341). In some embodiments, a STING polypeptide comprises both an N-terminal truncation and a C-terminal truncation of mSTING comprising a trunctation of N-terminal residues 1-153 and C-terminal residues 341-378 (mSTING$^{R231}$ comprising residues 154-340).

In some embodiments, a STING polypeptide comprises both an N-terminal truncation and one or more internal deletions. In some embodiments, a STING polypeptide comprises an N-terminal truncation, a C-terminal truncation, one or more internal deletions, and/or combinations thereof.

Without wishing to be bound by any particular theory, truncation and/or internal deletion of the STING polypeptide favors crystallization because it can reduce flexibility, can result in more compact shape, and eliminate undesirable events like aggregation, if for example, the deleted region has a hydrophobic binding site for a protein-binding partner.

In some embodiments, provided compositions comprise a STING polypeptide bound to one or more binding partners. In some embodiments, such a provided composition comprises a STING polypeptide bound to c[G(2',5')pA(3',5')p] (see, e.g., Table 1: c[G(2',5')pA(3',5')p]-hSTING$^{H232}$ complex (4LOH) coordinates; and Table 3: c[G(2',5')pA(3',5')p]-mSting$^{R231}$ complex (4LOJ) coordinates).

In some embodiments, such a provided composition comprises a STING polypeptide bound to c[G(2',5')pA(2',5')p] (see, e.g., Table 2: c[G(2',5')pA(2',5')p]-hSTING$^{H232}$ complex (4LOI) coordinates).

In some embodiments, such a provided composition comprises a STING polypeptide bound to c[G(3',5')pA(3',5')p] (see, e.g., Table 4: c[G(3',5')pA(3',5')p]-mSting$^{R231}$ complex (4LOK) coordinates).

In some embodiments, such a provided composition comprises a STING polypeptide bound to DMXAA (see, e.g., Table 5: DMXAA-mSting$^{R231}$ complex (4LOL) coordinates).

In some embodiments, such a provided composition comprises a STING polypeptide bound to DMXAA (see, e.g., Table 6: DMXAA-hSting$^{group2}$ complex (4QXO) coordinates).

In some embodiments, such a provided composition comprises a STING polypeptide bound to DMXAA (see, e.g., Table 7: DMXAA-hSTING$^{G230I}$ complex (4QXP) coordinates).

In some embodiments, such a provided composition comprises a STING polypeptide bound to DMXAA (see, e.g., Table 8: DMXAA-hSTING$^{S162A/Q266I}$ complex (4QXQ) coordinates).

In some embodiments, such a provided composition comprises a STING polypeptide bound to DMXAA (see, e.g., Table 9: DMXAA-hSTING$^{S162A/G230I/Q266I}$ complex (4QXR) coordinates).

In some embodiments, provided composition comprise an STING polypeptide bound to one or more STING modulators. In some embodiments, provided composition comprises a STING polypeptide bound to one or more exemplary STING modulators including, but not limited to, analogs of of c[G(2',5')pA(3',5')p], DMXAA, CMA, and/or combinations thereof.

The present invention also provides structural information and/or analyses of STING polypeptide crystals and/or sets thereof. In some embodiments, such structural information includes, but is not limited to, diffraction patterns, and/or coordinates, as well as any data sets, images, models, and/or graphical representations thereof or generated therefrom. In some embodiments, such graphical representations may include, for example, space-filling models, molecular surface representations, shell or boundary models, ribbon models, stick models; and/or combinations thereof.

In some embodiments, provided information is or comprises differences observed between or among structures that differ from one another in the presence or absence of one or more binding partners and/or interacting agents. In some embodiments, provided information is or comprises differences observed between or among structures that differ from one another in the presence or absence of one or more binding partners and/or one or more modulators.

In some embodiments, such structural information and/or analyses may be embodied in a tangible medium (e.g., a computer-readable medium) or a storage environment. Thus, the present invention provides tangible embodiments of STING polypeptide crystal structure information, as well as its use, for example, by or with a computer system, in any of a variety of applications. For example, in some embodiments, such structural information and/or analyses may be accessed by, transported to or from, and/or otherwise utilized by a computer system or program running thereon.

STING Modulators

As discussed herein, among other things, the present disclosure defines and/or provides certain STING modulators. In some embodiments, the present disclosure provides technologies for identifying, designing, and/or characterizing STING modulators. In some embodiments, STING modulators are specific STING modulators. In some embodiments, STING modulators are specific modulators of one or more STING alleles or variants; in some such embodiments, STING modulators have differential effects on different STING alleles or variants and/or discriminate between or among such alleles or variants.

In some embodiments, the present disclosure provides STING modulators that are DMXAA analogs. DMXAA (5,6-dimethylxanthenone-4-acetic acid, Vadimezan) was initially identified as a small molecule exhibiting immune modulatory activities through induction of cytokines, and disrupting tumor vascularization in mouse xenotransplantation models (Baguley and Ching, 2002). The induction of interferon (IFN) β expression by DMXAA also slowed the growth of tumors in vivo (Head and Jameson, 2010; Roberts et al., 2008). DMXAA, in combination with paclitaxel and carboplatin showed promising efficacy, and was therefore evaluated in a phase II clinical trial against non-small-cell lung cancer, but subsequently failed in human phase III trials (Lara et al. 2011). Recently, it has been demonstrated that DMXAA-induced IFN production by murine macrophages was impaired by the absence of STING (Prantner et al. 2012), suggesting that DMXAA targets the STING pathway. Despite high sequence identity between mSting and hSTING, DMXAA, which only activates mSting and has no effect on hSTING (Conlon et al. 2013; Kim et al., 2013), which presumably hampered further therapeutic development of DMXAA as a human drug.

Figure 5A:
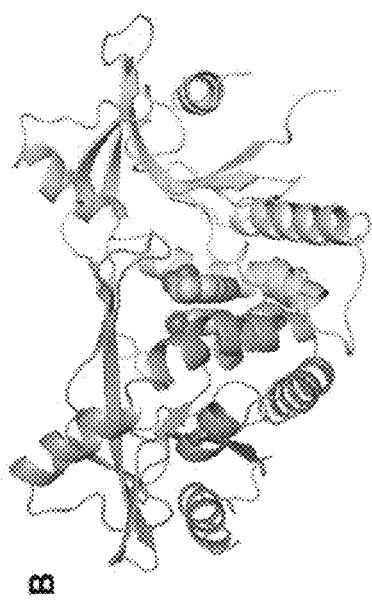
FIG. 5A depicts exemplary chemical formulas of dimethylxanthenone-4-acetic acid (DMXAA).

In some embodiments, DMXAA analogs include substitutions at position 1 and/or position 2 (FIG. 5A). In some embodiments, the H at position 1 and/or 2 is replaced by an OH or O-methyl group. In some embodiments, positions 1 and/or 2 could also be replaced by F, Cl, $NO_2$ groups to facilitate hydrogen bond formation with Ser162 of hSTING. Without wishing to be bound to a particular theory, hydrogen replacement by either an OH or O-methyl group facilitates hydrogen bond formation with Ser162 of hSTING.

In some embodiments, DMXAA analogs include substitutions at position 7 and/or position 8 (FIG. 5A). In some embodiments, the H at position 7 and/or 8 is replaced by methyl and/or larger alkyl groups. Without wishing to be bound to a particular theory, hydrogen replacement by methyl and/or larger alkyl groups facilitates hydrophobic contacts with Ile165 of hSTING. In some embodiments, the H at position 7 is replaced by polar groups (OH, $OCH_3$, F, Cl, $NO_2$). Without wishing to be bound to a particular theory, hydrogen replacement by polar groups facilitates hydrogen bond formation with Gln266 of hSTING.

The present disclosure describes systematic structure-function studies of mouse and human STING interaction with DMXAA. The present disclosure specifically defines interaction points between STING modulator compounds and STING moieties. In one example, the present disclosure specifically defines interaction points between DMXAA moieties and STING moieties. Moreover, the present disclosure describes modifications of hSTING and/or DMXAA structure (i.e., mutations of hSTING and analogs of DMXAA) that permit interaction between them. Thus, the present disclosure defines DMXAA analogs that can act as hSTING modulators, including as specific hSTING modulators (even relative to mSting).

The present disclosure also describes cyclic dinucleotide compounds (e.g., cGAMP-analogs and/or isomers) active as STING modulators, and particularly as hSTING modulators (e.g., specific hSTING modulators). Among other things, the present disclosure demonstrates that hSTING was more discriminating towards 2',5'-linkage-containing isomers versus those isomers containing all 3',5'-linkages.

The present disclosure also describes 10-carboxymethyl-9-acridine (CMA) analogs that are active as STING modulators, and particularly as hSTING modulators (e.g., specific hSTING modulators). In certain embodiments, alternative CMA analogs are provided and tested for STING modulatory activity as described herein.

In some embodiments, provided STING modulators are compounds whose structure include one or more moieties that interact with a residue corresponding to Ser162 and/or Ile165 of hSTING. In some embodiments, provided STING modulators are compounds whose structure include one or more moieties that interact with a residue corresponding to Gly230, Gln266, Ser162, and/or Ile165 of hSTING. In some embodiments, provided STING modulators are compounds whose structure include one or more moieties that interact with a residue corresponding to Gly230, Gln266, and/or Ser162 of hSTING. In some embodiments, provided STING modulators are compounds whose structures include one or more moieties that interact with a residue corresponding to Leu170, Ile235, Ile165, Thr267, Arg238, Tyr240, and/or Thr263 of hSTING. In some embodiments, provided STING modulators are compounds whose structures include one or more moieties that interact with a residue corresponding to Gly230, Gln266, Ser162, Ile165, Leu170, Ile235, Ile165, Thr267, Arg238, Tyr240, and/or Thr263 of hSTING.

In some embodiments, provided STING modulators are characterized by variety well understood and known by those skilled in the art including, but not limited to cGAMP stimulation of cells, ELISA, Isothermal Titration Calorimetry (ITC) Binding Assay, and/or combinations thereof. For example, in some embodiments, provided STING modulators show activity in an ITC binding assay such as is described in the Examples.

In some embodiments, in accordance with the present invention, STING modulators, and particularly hSTING modulators (e.g., specific hSTING modulators) are useful as agonists or antagonists of innate immunity. In some embodiments, in accordance with the present invention, STING modulators, and particularly hSTING modulators (e.g., specific hSTING modulators) are useful as anti-cancer agents. In some embodiments, in accordance with the present invention, STING modulators, and particularly hSTING modulators (e.g., specific hSTING modulators) are useful in vaccine development. In some embodiments, in accordance with the present invention, STING modulators, and particularly hSTING modulators (e.g., specific hSTING modulators) are useful as therapies for autoimmune disorders.

In some embodiments, a STING modulator is a compound described in International Patent Application No. PCT/US14/35909, the entire contents of which is hereby incorporated by reference.

STING Species Selectivity

In one aspect, the present invention defines the molecular basis underlying DMXAA species selectivity. The small molecule drug DMXAA specifically activates the STING nucleic acid-sensing pathway in a species-dependent manner. Functional and structural studies demonstrate that DMXAA activates mouse but not human STING (Conlon et al., 2013; Kim et al., 2013). DMXAA showed great promise in mouse cancer models, underscoring its potential for human application, notwithstanding the outcome of a phase III clinical trial for non-small cell lung carcinoma (Lara et al., 2011). Hence it is important to recognize that while DMXAA itself is apparently not a viable drug, pharmacological modulation of STING remains an ideal therapeutic strategy.

One model recently suggested that DMXAA species-selectivity might be due to non-conserved residues within mSTING that could directly bind to DMXAA (Conlon et al., 2013). However, previous structural studies established that DMXAA binds to mSTING within the same pocket as cGAMP and that DMXAA binding involves interactions with identical amino acids in both mSTING and hSTING (Gao et al., 2013b). Therefore, although the non-conserved residues do not participate in direct interaction with DMXAA, they potentially play alternative roles in DMXAA recognition. Results disclosed herein on ITC binding (FIGS. 15B, 15C and 20A) and IFN induction (FIG. 15D) studies established that the non-conserved residues located within the lid region of the ligand-binding pocket (group2) are important for the species-specific response to DMXAA. Furthermore, the structural studies described herein reveal the same 'closed' conformation for the complexes of DMXAA bound to hSTING$^{group2}$ (FIG. 15E) and mSTING (FIG. 20B), confirming the important role of group2 residues in DMXAA recognition and complex formation.

Figure 20A:
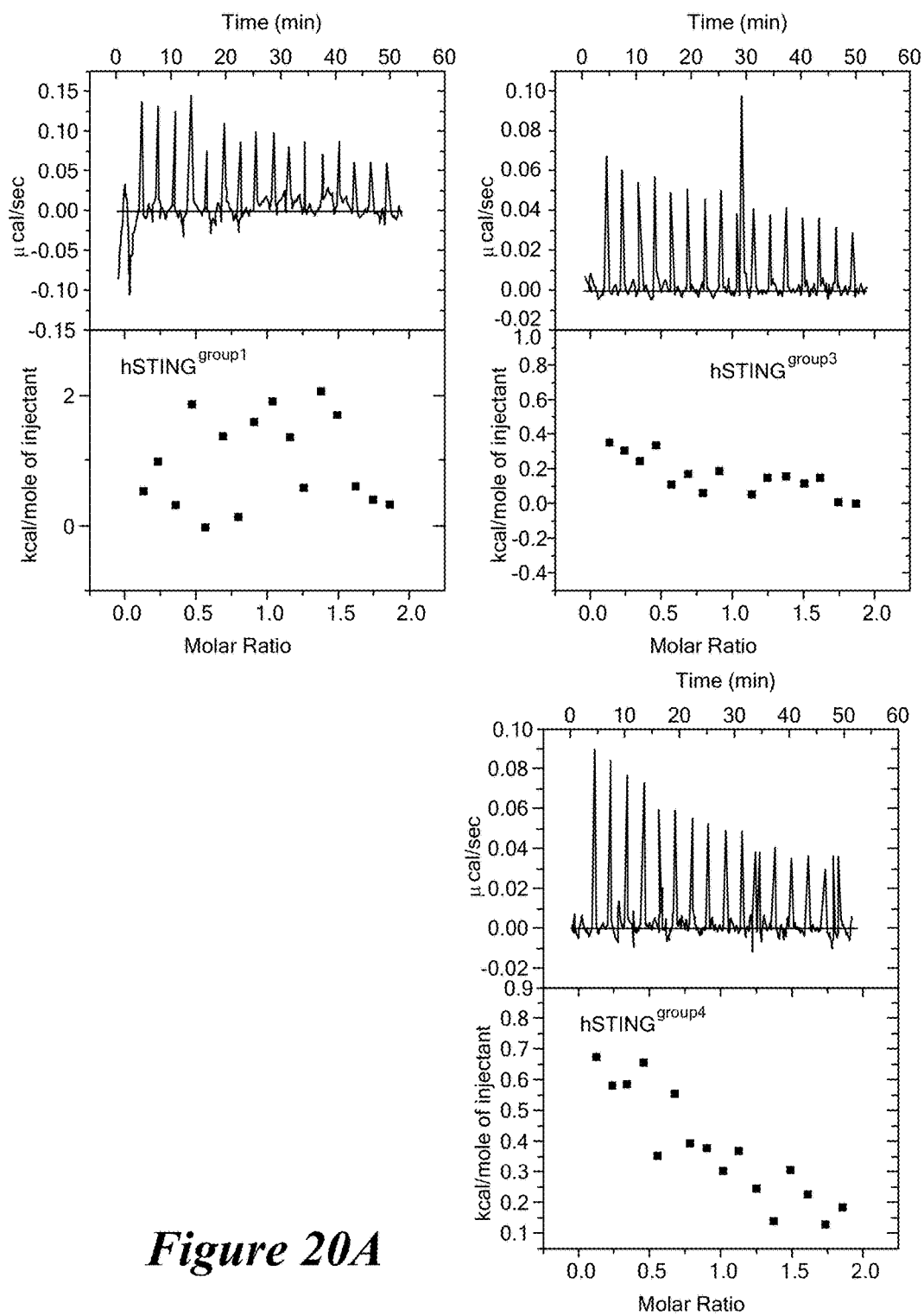
FIG. 20A depicts ITC binding curves for complex formation between DMXAA bound to hSTINGgroup1 (aa 140-379) (left), hSTINGgroup3 (middle), and hSTINGgroup4 (right).
Figure 20B:
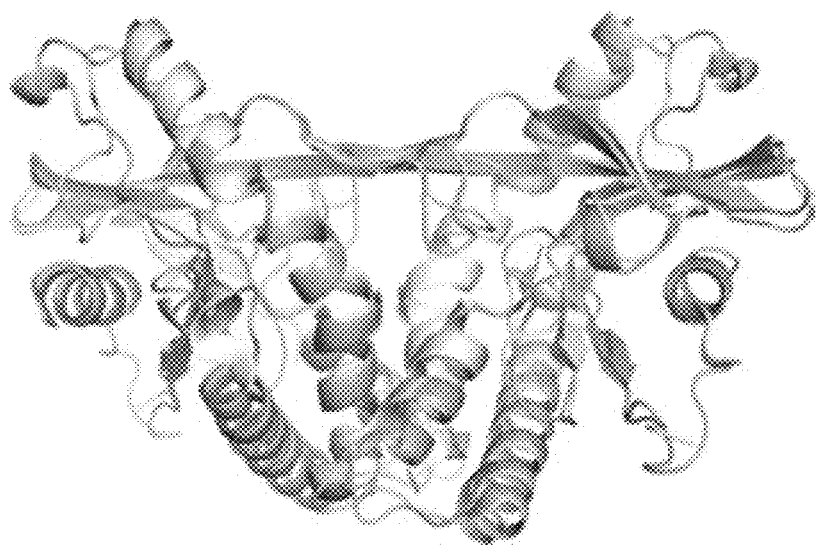
FIG. 20B depicts superposed structures of the complex of DMXAA bound with mSTING (PDB: 4LOL) and hSTINGgroup2 (aa 155-341).
Figure 20C:
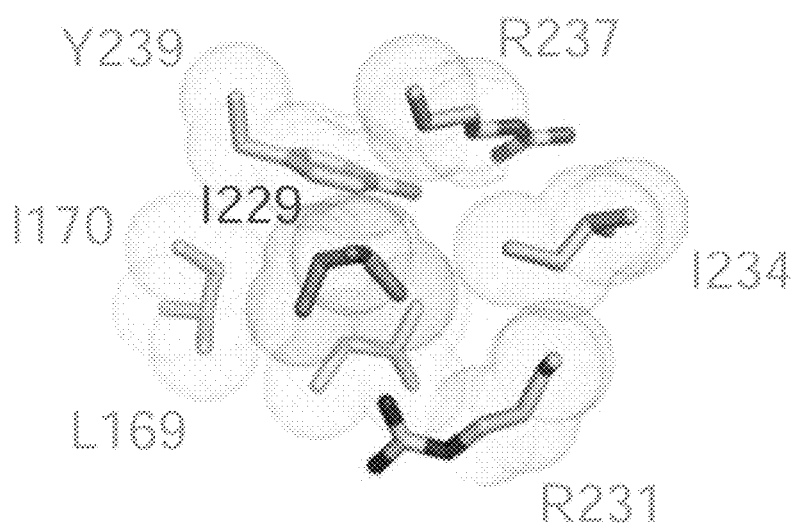
FIG. 20C depicts hydrophobic interactions of I229 with surrounding residues in the mSTING-DMXAA complex, with the same representations used in FIG. 15G.

Moreover, the present disclosure identifies a hydrophobic interaction between the substituted I230 and the residues from both the lid region and other parts of the protein in the hSTING$^{group2}$-DMXAA complex (FIG. 15G), a distinctive feature that was also found in the structure of the mSTING-DMXAA complex (FIG. 20C). All residues that form the hydrophobic pocket that contains I230 are conserved in both human and mouse STING proteins. The gain of function of hSTING$^{G230I}$ and inversely the loss of function of mSTING$^{I229G}$ or mSTING$^{I229A}$ in their abilities to induce IFN gene expression in response to DMXAA, further confirmed the role of this residue in species-specific recognition of DMXAA (FIG. 16A, B). A crystal structure of the hSTING$^{G230I}$-DMXAA complex also exhibited the active 'closed' conformation (FIGS. 16C, D), further supporting the conclusion that this single point substitution outside of the binding pocket of hSTING modulates sensitivity to the otherwise mouse-selective DMXAA ligand. Hydrophobic interactions could help facilitate formation of the lid region and other parts of the protein, allowing mSTING to form the 'closed' conformation more readily than hSTING in response to DMXAA.

Figures 17A, 17B:
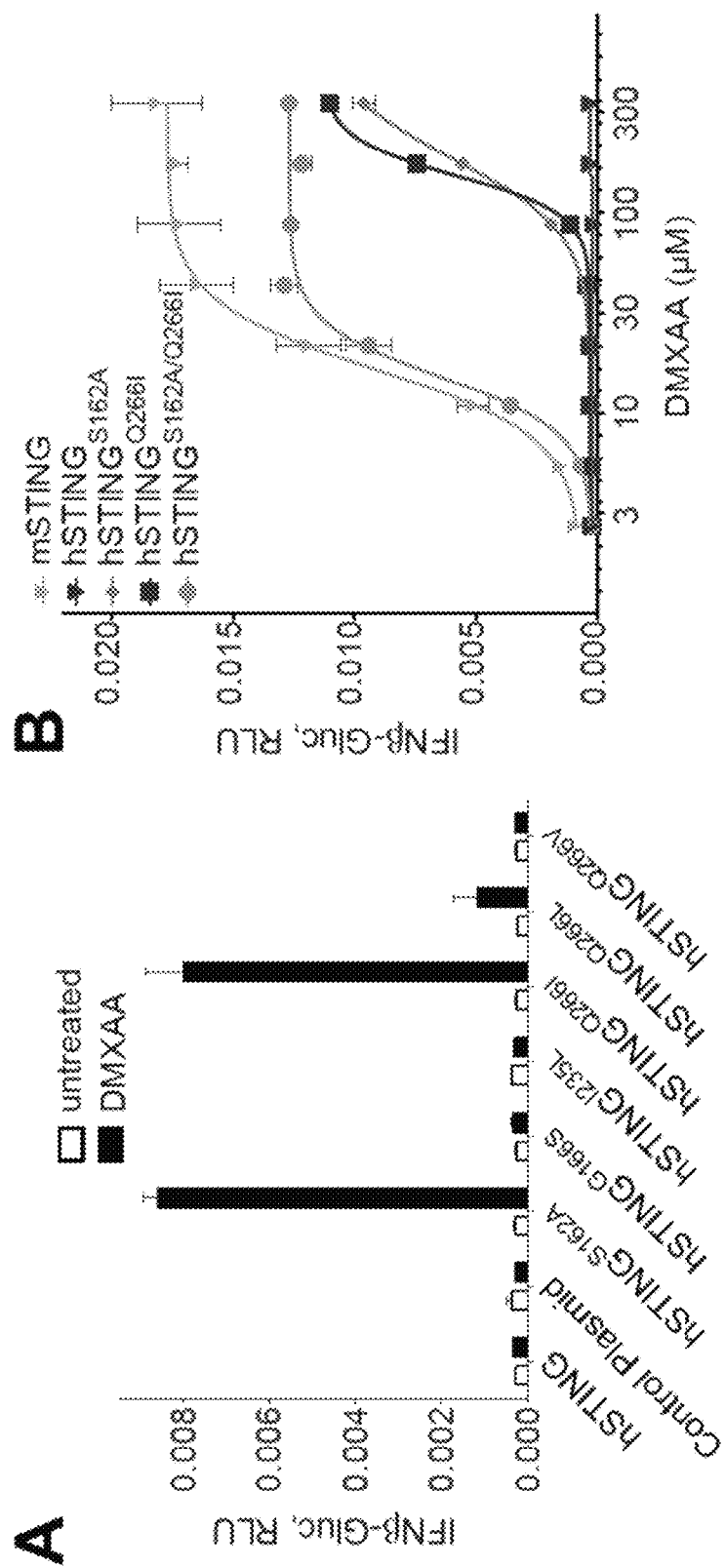
FIG. 17A depicts results where A293T cells were transfected with reporter constructs and indicated hSTING variants. 12 hours after transfection, cells were stimulated with 0.18 mM DMXAA for another 12 hours, followed by luciferase assay. Shown are means of triplicates +SEM, representative of 3 independent experiments.
FIG. 17B depicts DMXAA dose-response curves of 293T cells transfected with indicated STING variants and illustrating one representative of 3 independent experiments.
Figure 22A:
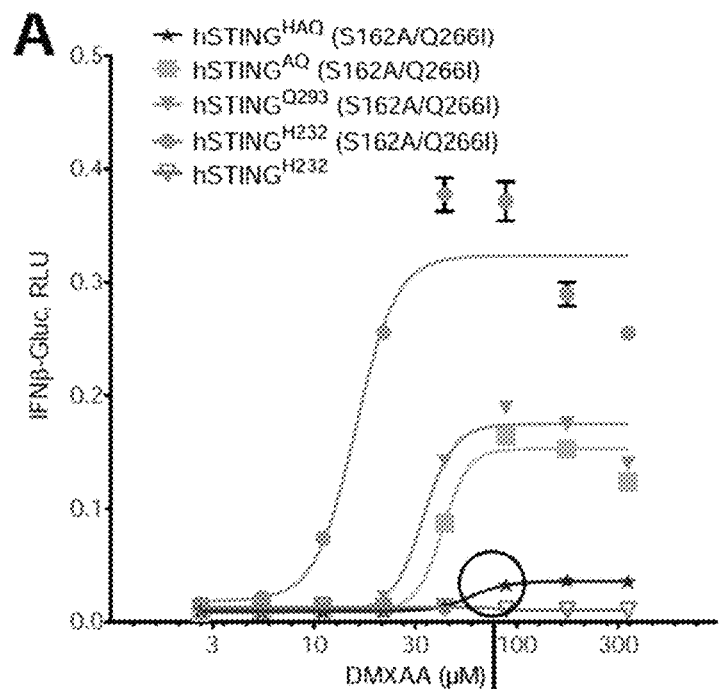
FIG. 22A depicts DMXAA dose-response of hSTING variants with S162A, Q266I double substituent. For improved clarity, only hSTING$^{H232}$ is shown as a representative for the corresponding wt variants. Circle refers to magnified view in (B).

The disclosed structural studies indicate that mSTING is induced more readily to assume the 'closed' conformation than hSTING in response to CDNs and their analogs. Due to this 'intrinsic disadvantage' of hSTING, better fitting DMXAA analogs need to be designed to allow hSTING to overcome the energy barrier of transitioning from an 'open' to a 'closed' state. To enable the rational design of suitable DMXAA modifications, the ensuing Examples systematically introduced hSTING substitutions within the binding pocket and tested their influence on DMXAA-induced IFN-β production. Following this strategy and guided by co-crystal structures of STING substituents with DMXAA, the present invention identifies two point substitutions within the ligand-binding pocket, S162A reported previously (Gao et al., 2013b) and Q266I, each of which strongly promote DMXAA recognition (FIG. 17A). These data suggest that modestly-altered DMXAA derivatives might be sufficient to bind and activate hSTING. By introducing the above substitutions into the predominant hSTING alleles, a dose-dependent response to DMXAA is restored in all cases (FIGS. 22A, B). However, the Q293-carrying hSTING variants still responded poorly to DMXAA (FIG. 17E), in line with previous reports showing an impaired CDN response by hSTING$^{Q293}$ and hSTING$^{HAQ}$ (Jin et al., 2011; Yi et al., 2013). This general effect of Q293 will most likely also affect the responsiveness to human-active DMXAA derivatives, suggesting a need for STING-genotyping in patients and possible adjustment of drug dosing in future studies.

Figures 18A, 18B:
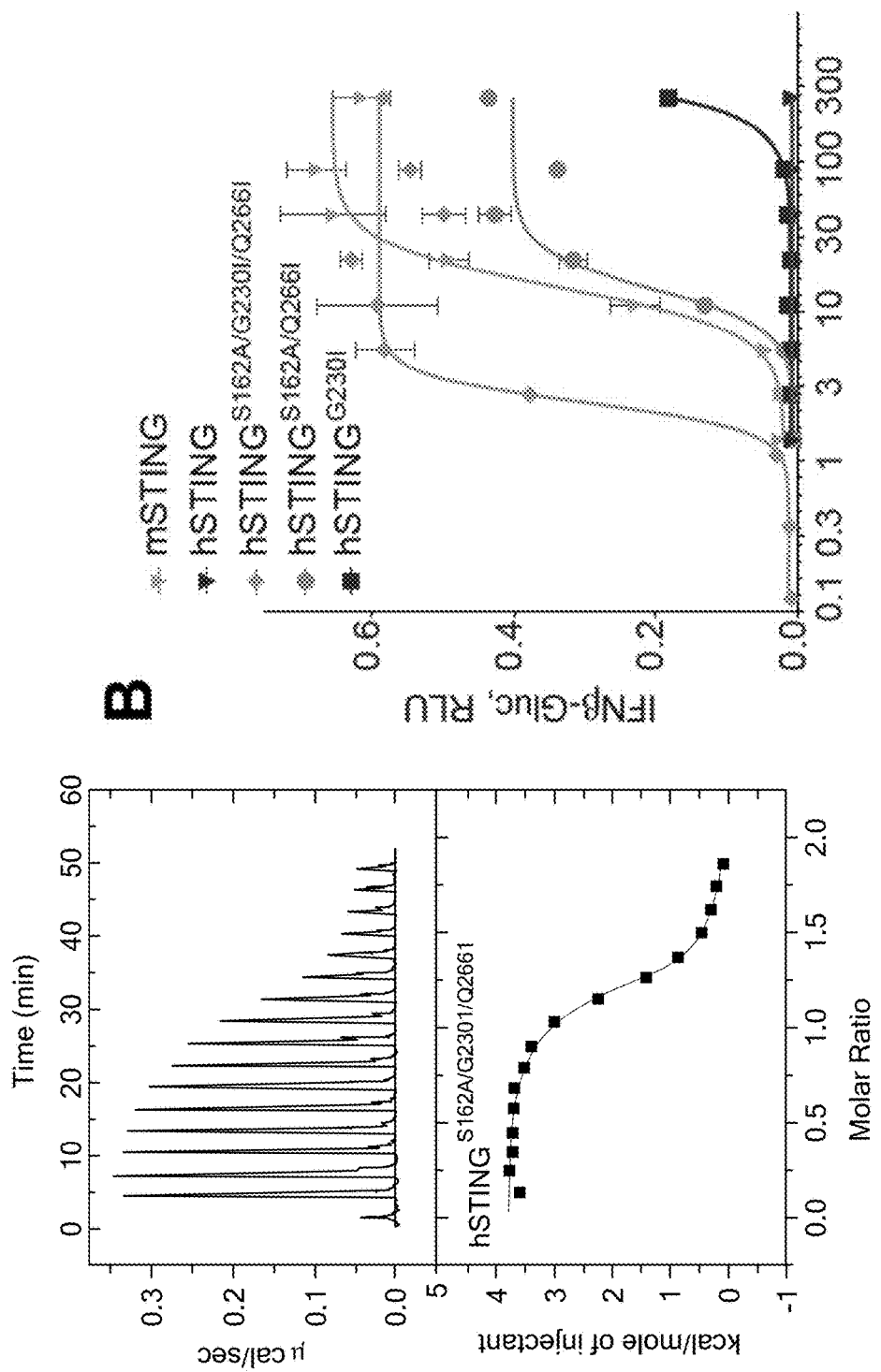
FIG. 18A depicts an ITC binding curve for complex formation between DMXAA bound to hSTING$^{S162A/G230I/Q266I}$ (aa 140-379).
FIG. 18B depicts results where 293T cells were transfected with reporter constructs and indicated STING variants. After 12 hours, cells were stimulated with ascending concentrations of DMXAA for another 12 hours, followed by luciferase assay. Individual data points are means of triplicates ±SEM. Representative of 3 independent experiments.
Figure 22B:
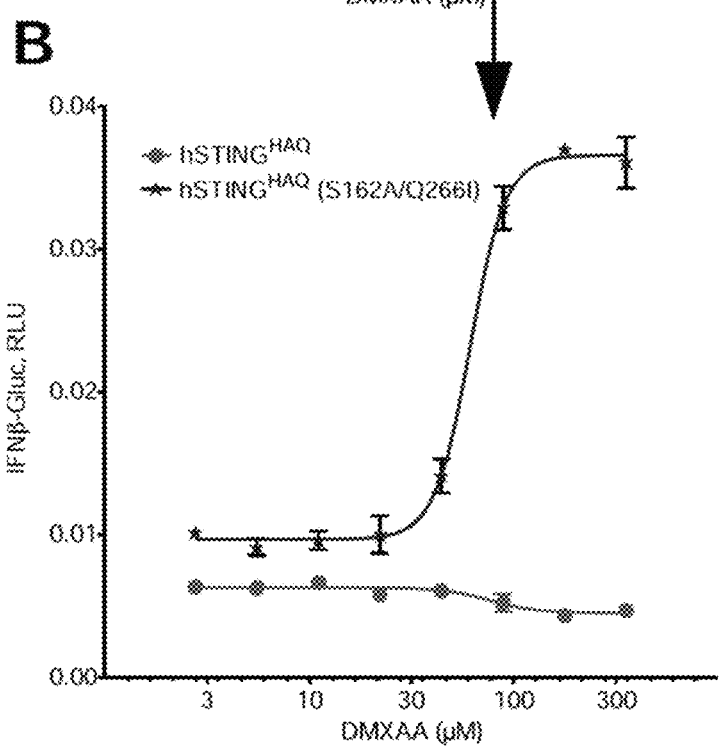
FIG. 22B depicts DMXAA dose-responses of hSTNG$^{HAQ}$ and hSTING$^{HAQ}$ S162A, Q266I on a magnified scale (circle denotes corresponding hSTING$^{HAQ}$ S162A, Q266I curve in (A)).
Figure 22C:
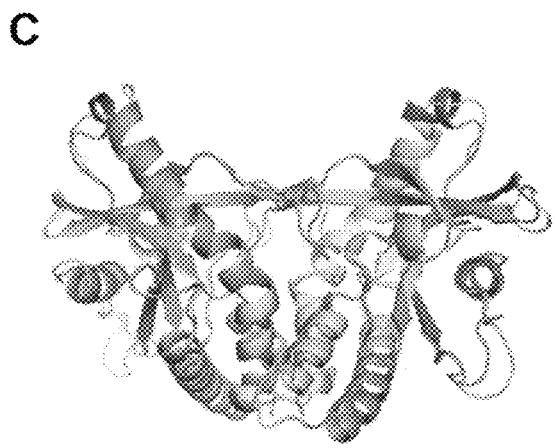
FIG. 22C depicts superposed structures of the complex of DMXAA bound with hSTING$^{G230I}$ (aa 155-341) and hSTING$^{S162A/Q266I}$ (aa 155-341).
Figure 22E:
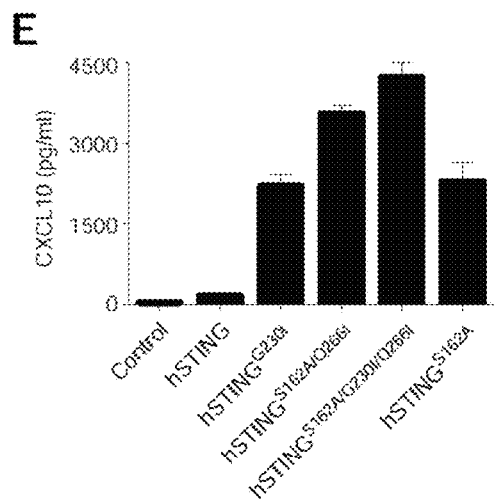
FIG. 22E depicts results where BMDCs were infected with retroviruses (same as in FIG. 18F). Cells were incubated with 50 µg/ml of DMXAA and supernatants were collected 18 hours after treatment. CXCL10 protein levels were determined by ELISA. Data shown are means±SEM (n=3), representative of two independent experiments.

The S162A/G230I/Q266I triple substitution of hSTING showed an order of magnitude higher activity than mSTING (FIG. 18B), indicating that all three substitutions confer a substantial synergistic effect to DMXAA recognition. hSTING$^{S162A/G230I/Q266I}$ might therefore be used as a benchmark hSTING synthetic allele in future drug development studies using humanized mouse models. In addition to the luciferase reporter assays in human 293T cells, the ensuing Examples describe IFN and proinflammatory cytokine/chemokine production for hSTING substitutions in BMDCs from the STING$^{Gt/Gt}$ mouse and similar results (FIGS. 18F and 22E).

The ensuing Examples also show DMXAA-induced type I IFN and proinflammatory cytokine/chemokine production in STING-deficient bone marrow-derived dendritic cells (BMDCs) reconstituted with the hSTING mutants by retroviral transduction. In some embodiments, reconstitution with hSTING$^{S162A/G230I/Q266I}$ resulted in the highest responsiveness to DMXAA stimulation in primary DCs with the induction of IFNB, IL-6, CCL5 and CXCL10 gene expression. These findings provide a guide for future rational drug design of DMXAA variants with potential IFN-β-stimulating activity in humans that are needed for the development of anti-cancer therapies and vaccine adjuvants Thus the present invention provides, among other things, a comprehensive structural, biophysical, and functional analysis of DMXAA association with select substitutions within hSTING. The present invention highlights the role of the lid residue at position 230 (229 in mSTING) and unveils the structural basis for the mSTING-selectivity of DMXAA. Provided structural and functional results also shed light on strategies to restore an efficient DMXAA-response of hSTING based on the binding pocket S162A and Q266I substitutions. Imitating the effects of these amino acid substitutions by rational design of reciprocal DMXAA derivatives should lead to the development of human-active STING agonists for anti-tumor, anti-viral, and vaccine adjuvant applications. The same principles may apply to generation of analogs of CMA, the other small molecule that to date can target mSTING but not hSTING (Cavlar et al., 2013).

Structure-Based Drug Design

In some embodiments, the present disclosure provides systems for identifying and/or characterizing STING modulators. In some embodiments, the present disclosure provides a method of designing, identifying and/or characterizing a STING modulator comprising the steps of: a) providing an image of a STING crystal that includes at least one potential interaction site; b) docking in the image at least one moiety that is a potential STING modulator structural element; and c) assessing one or more features of a potential moiety-interaction site interaction.

In some embodiments, the at least one potential interaction site includes a site selected from the group consisting of Ser162, Ile165, and combinations thereof. In some embodiments, the at least one potential interaction site includes a site selected from the group consisting of Ser162, Ile165, Gly230, Gln266, and combinations thereof. In some embodiments, the at least one potential interaction site includes Ser162. In some embodiments, the at least one potential interaction site includes Ile165. In some embodiments, the at least one potential interaction site includes Gly230. In some embodiments, the at least one potential interaction site includes Gln266. In some embodiments, the modulator is a compound disclosed herein.

In some embodiments, the one or more features include at least one feature selected from the group consisting of: spatial separation between the moiety and the potential interaction site; energy of the potential moiety-interaction site interaction, and/or combinations thereof.

In some embodiments, a method further comprises a step of providing an image of a potential STING modulator comprising the moiety docked with the image of the STING crystal. In some embodiments, a method further comprises a step of comparing the image with that of a STING crystal including a bound known modulator, substrate, or product.

Computer Systems

Figure 24:
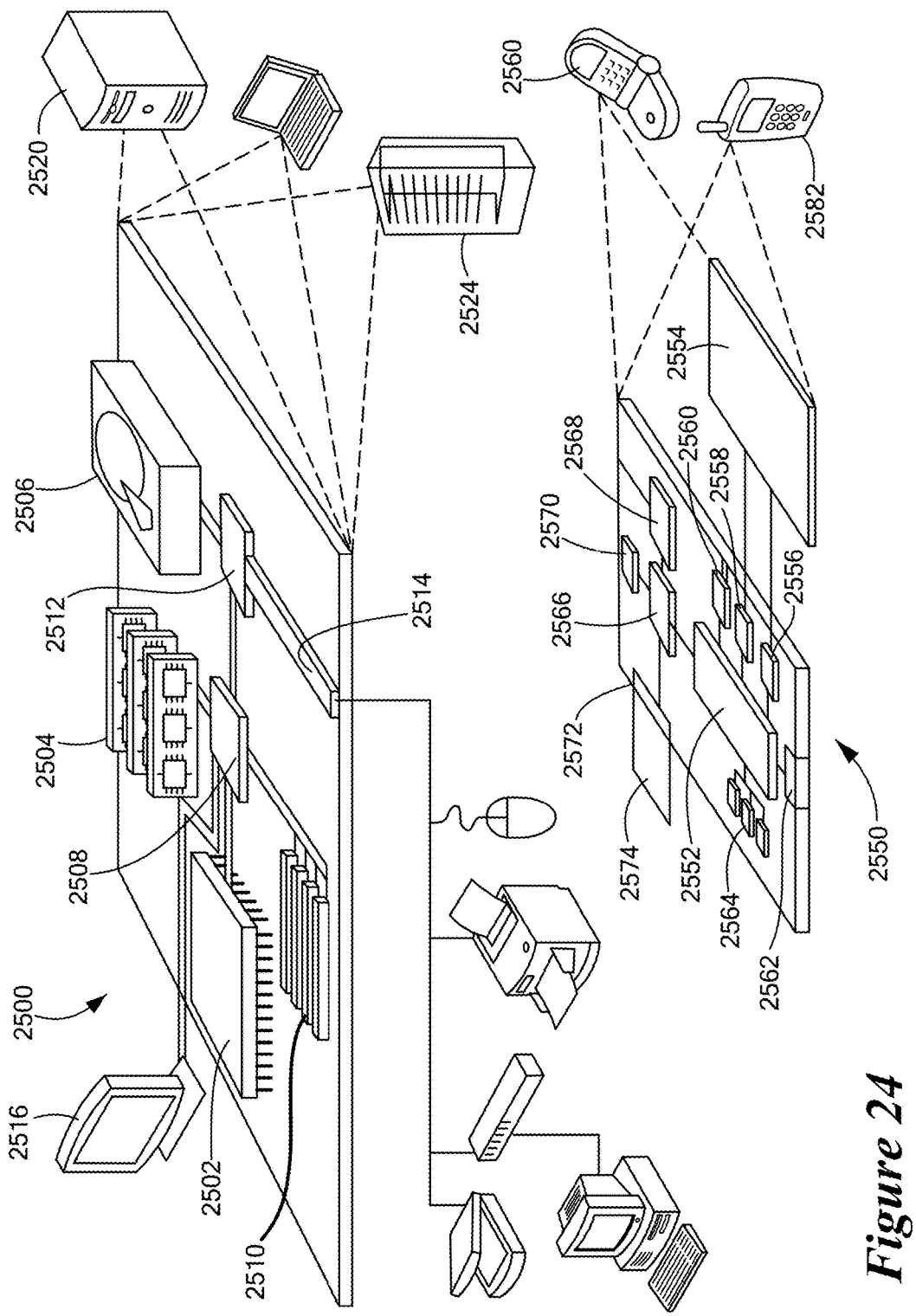
FIG. 24 depicts an exemplary block diagram of a network environment for establishing a multi-channel context aware communication environment.

As will be appreciated by those skilled in the art, reading the present disclosure, in some aspects, the present invention is ideally suited for use in computer-implemented inventions. FIG. 24 shows but one example of a computing device 2500 and a mobile computing device 2550 that can be used to implement certain techniques described in this disclosure. The computing device 2500 depicted in FIG. 24 is intended to represent any of a variety forms of digital computers, such as laptops, desktops, workstations, personal digital assistants, servers, blade servers, mainframes, and other appropriate computers. The depicted mobile computing device 2550 is intended to represent any appropriate form of mobile devices, such as personal digital assistants, cellular telephones, smart-phones, tablet computers, and other similar computing devices. Moreover, the components shown in FIG. 24 and elsewhere in the Figures, their connections and relationships, and their functions, are meant to be examples only, and are not meant to be limiting.

The computing device depicted in FIG. 24 2500 includes a processor 2502, a memory 2504, a storage device 2506, a high-speed interface 2508 connecting to the memory 2504 and multiple high-speed expansion ports 2510, and a low-speed interface 2512 connecting to a low-speed expansion port 2514 and the storage device 2506. Each of the processor 2502, the memory 2504, the storage device 2506, the high-speed interface 2508, the high-speed expansion ports 2510, and the low-speed interface 2512, are interconnected using various busses, and may be mounted on a common motherboard or in other manners as appropriate. The processor 2502 can process instructions for execution within the computing device 2500, including instructions stored in the memory 2504 or on the storage device 2506 to display graphical information for a GUI on an external input/output device, such as a display 2516 coupled to the high-speed interface 2508. In some implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 2504 depicted in FIG. 24 stores information within the computing device 2500. In some implementations, the memory 2504 is a volatile memory unit or units. In some implementations, the memory 2504 is a non-volatile memory unit or units. The memory 2504 may also be another form of computer-readable medium, such as a magnetic or optical disk.

The storage device 2506 depicted in FIG. 24 is capable of providing mass storage for the computing device 2500. In some implementations, the storage device 2506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2502), perform one or more methods, such as those described above. The instructions can also be stored by one or more storage devices such as computer- or machine-readable mediums (for example, the memory 2504, the storage device 2506, or memory on the processor 2502).

The high-speed interface 2508 manages bandwidth-intensive operations for the computing device 2500, while the low-speed interface 2512 manages lower bandwidth-intensive operations. Such allocation of functions is an example only. In some implementations, the high-speed interface 2508 is coupled to the memory 2504, the display 2516 (e.g., through a graphics processor or accelerator), and to the high-speed expansion ports 2510, which may accept various expansion cards (not shown). In the implementation, the low-speed interface 2512 is coupled to the storage device 2506 and the low-speed expansion port 2514. The low-speed expansion port 2514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 2500 may be implemented in a number of different forms, as shown in the figure. For example, it may be implemented as a standard server 2520, or multiple times in a group of such servers. In addition, it may be implemented in a personal computer such as a laptop computer 2522. It may also be implemented as part of a rack server system 2524. Alternatively, components from the computing device 2500 may be combined with other components in a mobile device (not shown), such as a mobile computing device 2550. Each of such devices may contain one or more of the computing device 2500 and the mobile computing device 2550, and an entire system may be made up of multiple computing devices communicating with each other.

The mobile computing device 2550 depicted in FIG. 24 includes a processor 2552, a memory 2564, an input/output device such as a display 2554, a communication interface 2566, and a transceiver 2568, among other components. The mobile computing device 2550 may also be provided with a storage device, such as a micro-drive or other device, to provide additional storage. Each of the processor 2552, the memory 2564, the display 2554, the communication interface 2566, and the transceiver 2568, are interconnected using various buses, and several of the components may be mounted on a common motherboard or in other manners as appropriate.

The processor 2552 depicted in FIG. 24 can execute instructions within the mobile computing device 2550, including instructions stored in the memory 2564. The processor 2552 may be implemented as a chipset of chips that include separate and multiple analog and digital processors. The processor 2552 may provide, for example, for coordination of the other components of the mobile computing device 2550, such as control of user interfaces, applications run by the mobile computing device 2550, and wireless communication by the mobile computing device 2550.

The processor 2552 may communicate with a user through a control interface 2558 and a display interface 2556 coupled to the display 2554. The display 2554 depicted in FIG. 24 may be, for example, a TFT (Thin-Film-Transistor Liquid Crystal Display) display or an OLED (Organic Light Emitting Diode) display, or other appropriate display technology. The display interface 2556 may comprise appropriate circuitry for driving the display 2554 to present graphical and other information to a user. The control interface 2558 may receive commands from a user and convert them for submission to the processor 2552. In addition, an external interface 2562 may provide communication with the processor 2552, so as to enable near area communication of the mobile computing device 2550 with other devices. The external interface 2562 may provide, for example, for wired communication in some implementations, or for wireless communication in other implementations, and multiple interfaces may also be used.

The memory 2564 depicted in FIG. 24 stores information within the mobile computing device 2550. The memory 2564 can be implemented as one or more of a computer-readable medium or media, a volatile memory unit or units, or a non-volatile memory unit or units. An expansion memory 2574 may also be provided and connected to the mobile computing device 2550 through an expansion interface 2572, which may include, for example, a SIMM (Single In Line Memory Module) card interface. The expansion memory 2574 may provide extra storage space for the mobile computing device 2550, or may also store applications or other information for the mobile computing device 2550. Specifically, the expansion memory 2574 may include instructions to carry out or supplement the processes described above, and may include secure information also. Thus, for example, the expansion memory 2574 may be provide as a security module for the mobile computing device 2550, and may be programmed with instructions that permit secure use of the mobile computing device 2550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier, that the instructions, when executed by one or more processing devices (for example, processor 2552), perform one or more methods, such as those described above. The instructions can also be stored by one or more storage devices, such as one or more computer- or machine-readable mediums (for example, the memory 2564, the expansion memory 2574, or memory on the processor 2552). In some implementations, the instructions can be received in a propagated signal, for example, over the transceiver 2568 or the external interface 2562.

The mobile computing device 2550 depicted in FIG. 24 may communicate wirelessly through the communication interface 2566, which may include digital signal processing circuitry where necessary. The communication interface 2566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2568 using a radio-frequency. In addition, short-range communication may occur, such as using a Bluetooth®, Wi-Fi™, or other such transceiver (not shown). In addition, a GPS (Global Positioning System) receiver module 2570 may provide additional navigation- and location-related wireless data to the mobile computing device 2550, which may be used as appropriate by applications running on the mobile computing device 2550.

The mobile computing device 2550 depicted in FIG. 24 may also communicate audibly using an audio codec 2560, which may receive spoken information from a user and convert it to usable digital information. The audio codec 2560 may likewise generate audible sound for a user, such as through a speaker, e.g., in a handset of the mobile computing device 2550. Such sound may include sound from voice telephone calls, may include recorded sound (e.g., voice messages, music files, etc.) and may also include sound generated by applications operating on the mobile computing device 2550.

The mobile computing device 2550 may be implemented in a number of different forms, as shown in FIG. 24. For example, it may be implemented as a cellular telephone 2580. It may also be implemented as part of a smart-phone 2582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some embodiments, there is provided an implementation of an exemplary cloud computing environment for subscription management in a multi-channel context aware communication environment. As shown in FIG. 23, the cloud computing environment 2400 may include one or more resource providers 2402a, 2402b, 2402c (collectively, 2402). Each resource provider 2402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 2402 may be connected to any other resource provider 2402 in the cloud computing environment 2400. In some implementations, the resource providers 2402 may be connected over a computer network 2408. Each resource provider 2402 may be connected to one or more computing device 2404a, 2404b, 2404c (collectively, 2404), over the computer network 2408.

The cloud computing environment 2400 depicted in FIG. 23 may include a resource manager 2406. The resource manager 2406 may be connected to the resource providers 2402 and the computing devices 2404 over the computer network 2408. In some implementations, the resource manager 2406 may facilitate the provision of computing resources by one or more resource providers 2402 to one or more computing devices 2404. The resource manager 2406 may receive a request for a computing resource from a particular computing device 2404. The resource manager 2406 may identify one or more resource providers 2402 capable of providing the computing resource requested by the computing device 2404. The resource manager 2406 may select a resource provider 2402 to provide the computing resource. The resource manager 2406 may facilitate a connection between the resource provider 2402 and a particular computing device 2404. In some implementations, the resource manager 2406 may establish a connection between a particular resource provider 2402 and a particular computing device 2404. In some implementations, the resource manager 2406 may redirect a particular computing device 2404 to a particular resource provider 2402 with the requested computing resource.

As will be appreciated by those skilled in the art, reading the present disclosure in some embodiments, the present invention provides a computer system comprising one or more of (a) atomic coordinate data as disclosed herein [+/−a root mean square deviation from the Cα atoms of note more than 1.5 Å (or 1.0 Å or 0.5 Å)]; (b) structure factor data (where a structure factor comprises the amplitude and phase of the diffracted wave) for STING, said structure factor data being derivable from the atomic coordinate data of Tables 1-5+/−a root mean square deviation from the Cα atoms of note more than 1.5 Å (or 1.0 Å or 0.5 Å); (c) atomic coordinate data of a STING modulator protein generated by homology modeling of the target based on the data disclosed herein +/−a root mean square deviation from the Cα atoms of not more than 1.5 Å (or 1.0 Å or 0.5 Å); (d) atomic coordinate data of a STING modulator protein generated by interpreting X-ray crystallographic data or NMR data by reference to the data disclosed herein +/−a root mean square deviation from the Cα atoms of note more than 1.5 Å (or 1.0 Å or 0.5 Å); or (e) structure factor data a derivable from the atomic coordinate data of (c) or (d). In certain embodiments, a computer system comprises: a computer-readable data storage medium comprising data storage material encoded with the computer-readable data; (a) a working memory for storing instructions for processing said computer-readable data; and (b) a central-processing unit coupled to said working memory and to said computer-readable data storage medium for processing said computer-readable data and thereby generating structures, characterizing structures and/or performing rational drug design.

In some embodiments, there is provided a machine-readable data storage medium, comprising a data storage material encoded with machine-readable data, wherein said data comprises all or part of a c[G(2',5')pA(3',5')p]-hSTING$^{H232}$ complex defined by structure coordinates of hST- ING$^{H232}$ amino acids (SEQ ID NO.:1), according Table 1; or a molecule or molecular complex comprising all or part of a c[G(2',5')pA(3',5')p]-hSTINGH232 complex defined by structure coordinates of corresponding amino acids that are identical to said hSTING$^{H232}$ amino acids, wherein the root mean square deviation of the backbone atoms between said corresponding amino acids and said hSTING$^{H232}$ amino acids is not more than about 3.0 Å, 2.5 Å, 2.0 Å, 1.5 Å, 1.0 Å; or a molecule or molecular complex comprising all or part of a c[G(2',5')pA(3',5')p]-hSTINGH23$^2$ complex defined by structure coordinates of a set of corresponding amino acids, wherein the root mean square deviation of the backbone atoms between said set of corresponding amino acids and said hSTING$^{H232}$ amino acids is not more than about 1.1, 0.9, 0.7, or 0.5 Å, and wherein at least one of said corresponding amino acids is not identical to the hSTING$^{H232}$ amino acid to which it corresponds.

In some embodiments, there is provided a machine-readable data storage medium, comprising a data storage material encoded with machine-readable data, wherein said data comprises all or part of a c[G(2',5')pA(2',5')p]-hSTING$^{H232}$ complex defined by structure coordinates of hSTING$^{H232}$ amino acids (SEQ ID NO.:1), according Table 2; or a molecule or molecular complex comprising all or part of a c[G(2',5')pA(2',5')p]-hSTING$^{H232}$ complex defined by structure coordinates of corresponding amino acids that are identical to said hSTING$^{H232}$ amino acids, wherein the root mean square deviation of the backbone atoms between said corresponding amino acids and said hSTING$^{H232}$ amino acids is not more than about 3.0 Å, 2.5 Å, 2.0 Å, 1.5 Å, 1.0 Å; or a molecule or molecular complex comprising all or part of a c[G(2',5')pA(2',5')p]-hSTING$^{H232}$ complex defined by structure coordinates of a set of corresponding amino acids, wherein the root mean square deviation of the backbone atoms between said set of corresponding amino acids and said hSTING$^{H232}$ amino acids is not more than about 1.1, 0.9, 0.7, or 0.5 Å, and wherein at least one of said corresponding amino acids is not identical to the hSTING$^{H232}$ amino acid to which it corresponds.

In some embodiments, there is provided a machine-readable data storage medium, comprising a data storage material encoded with machine-readable data, wherein said data comprises all or part of a c[G(2',5')pA(3',5')p]-mSting$^{R231}$ complex defined by structure coordinates of mSting$^{R231}$ amino acids (SEQ ID NO.:2), according Table 3; or a molecule or molecular complex comprising all or part of a c[G(2',5')pA(3',5')p]-mSting$^{R231}$ complex defined by structure coordinates of corresponding amino acids that are identical to said mSting$^{R231}$ amino acids, wherein the root mean square deviation of the backbone atoms between said corresponding amino acids and said mSting$^{R231}$ amino acids is not more than about 3.0 Å, 2.5 Å, 2.0 Å, 1.5 Å, 1.0 Å; or a molecule or molecular complex comprising all or part of a c[G(2',5')pA(3',5')p]-mSting$^{R231}$ complex defined by structure coordinates of a set of corresponding amino acids, wherein the root mean square deviation of the backbone atoms between said set of corresponding amino acids and said mSting$^{R231}$ amino acids is not more than about 1.1, 0.9, 0.7, or 0.5 Å, and wherein at least one of said corresponding amino acids is not identical to the mSting$^{R231}$ amino acid to which it corresponds.

In some embodiments, there is provided a machine-readable data storage medium, comprising a data storage material encoded with machine-readable data, wherein said data comprises all or part of a c[G(3',5')pA(3',5')p]-mSting$^{R231}$ complex defined by structure coordinates of mSting$^{R231}$ amino acids (SEQ ID NO.:2), according Table 4; or a molecule or molecular complex comprising all or part of a c[G(3',5')pA(3',5')p]-mSting$^{R231}$ complex defined by structure coordinates of corresponding amino acids that are identical to said mSting$^{R231}$ amino acids, wherein the root mean square deviation of the backbone atoms between said corresponding amino acids and said mSting$^{R231}$ amino acids is not more than about 3.0 Å, 2.5 Å, 2.0 Å, 1.5 Å, 1.0 Å; or a molecule or molecular complex comprising all or part of a c[G(2',5')pA(3',5')p]-mSting$^{R231}$ complex defined by structure coordinates of a set of corresponding amino acids, wherein the root mean square deviation of the backbone atoms between said set of corresponding amino acids and said mSting$^{R231}$ amino acids is not more than about 1.1, 0.9, 0.7, or 0.5 Å, and wherein at least one of said corresponding amino acids is not identical to the mSting$^{R231}$ amino acid to which it corresponds.

In some embodiments, there is provided a machine-readable data storage medium, comprising a data storage material encoded with machine-readable data, wherein said data comprises all or part of a DMXAA-mSting$^{R231}$ complex defined by structure coordinates of mSting$^{R231}$ amino acids (SEQ ID NO.:2), according Table 5; or a molecule or molecular complex comprising all or part of a DMXAA-mSting$^{R231}$ complex defined by structure coordinates of corresponding amino acids that are identical to said mSting$^{R231}$ amino acids, wherein the root mean square deviation of the backbone atoms between said corresponding amino acids and said mSting$^{R231}$ amino acids is not more than about 3.0 Å, 2.5 Å, 2.0 Å, 1.5 Å, 1.0 Å; or a molecule or molecular complex comprising all or part of a DMXAA-mSting$^{R231}$ complex defined by structure coordinates of a set of corresponding amino acids, wherein the root mean square deviation of the backbone atoms between said set of corresponding amino acids and said mSting$^{R231}$ amino acids is not more than about 1.1, 0.9, 0.7, or 0.5 Å, and wherein at least one of said corresponding amino acids is not identical to the mSting$^{R231}$ amino acid to which it corresponds.

In some embodiments, there is provided a machine-readable data storage medium, comprising a data storage material encoded with machine-readable data, wherein said data comprises all or part of a DMXAA-hSTING$^{group2}$ complex defined by structure coordinates of hSTING$^{group2}$ amino acids, according Table 6; or a molecule or molecular complex comprising all or part of a DMXAA-hSTING$^{group2}$ complex defined by structure coordinates of corresponding amino acids that are identical to said hSTING$^{group2}$ amino acids, wherein the root mean square deviation of the backbone atoms between said corresponding amino acids and said hSTING$^{group2}$ amino acids is not more than about 3.0 Å, 2.5 Å, 2.0 Å, 1.5 Å, 1.0 Å; or a molecule or molecular complex comprising all or part of a DMXAA-hSTING$^{group2}$ complex defined by structure coordinates of a set of corresponding amino acids, wherein the root mean square deviation of the backbone atoms between said set of corresponding amino acids and said hSTING$^{group2}$ amino acids is not more than about 1.1, 0.9, 0.7, or 0.5 Å, and wherein at least one of said corresponding amino acids is not identical to the hSTING$^{group2}$ amino acid to which it corresponds.

In some embodiments, there is provided a machine-readable data storage medium, comprising a data storage material encoded with machine-readable data, wherein said data comprises all or part of a DMXAA-hSTING$^{G230I}$ complex defined by structure coordinates of hSTING$^{G230I}$ amino acids, according Table 7; or a molecule or molecular complex comprising all or part of a DMXAA-hSTING$^{G230I}$ complex defined by structure coordinates of corresponding amino acids that are identical to said hSTING$^{G230I}$ amino acids, wherein the root mean square deviation of the backbone atoms between said corresponding amino acids and said hSTING$^{G230I}$ amino acids is not more than about 3.0 Å, 2.5 Å, 2.0 Å, 1.5 Å, 1.0 Å; or a molecule or molecular complex comprising all or part of a DMXAA-hSTING$^{G230I}$ complex defined by structure coordinates of a set of corresponding amino acids, wherein the root mean square deviation of the backbone atoms between said set of corresponding amino acids and said hSTING$^{G230I}$ amino acids is not more than about 1.1, 0.9, 0.7, or 0.5 Å, and wherein at least one of said corresponding amino acids is not identical to the hSTING$^{G230I}$ amino acid to which it corresponds.

In some embodiments, there is provided a machine-readable data storage medium, comprising a data storage material encoded with machine-readable data, wherein said data comprises all or part of a DMXAA-hSTING$^{S162A/Q266I}$ complex defined by structure coordinates of hSTING$^{S162A/Q266I}$ amino acids, according Table 8; or a molecule or molecular complex comprising all or part of a DMXAA-hSTING$^{S162A/Q266I}$ complex defined by structure coordinates of corresponding amino acids that are identical to said hSTING$^{S162A/Q266I}$ amino acids, wherein the root mean square deviation of the backbone atoms between said corresponding amino acids and said hSTING$^{S162A/Q266I}$ amino acids is not more than about 3.0 Å, 2.5 Å, 2.0 Å, 1.5 Å, 1.0 Å; or a molecule or molecular complex comprising all or part of a DMXAA-hSTING$^{S162A/Q266I}$ complex defined by structure coordinates of a set of corresponding amino acids, wherein the root mean square deviation of the backbone atoms between said set of corresponding amino acids and said hSTING$^{S162A/Q266I}$ amino acids is not more than about 1.1, 0.9, 0.7, or 0.5 Å, and wherein at least one of said corresponding amino acids is not identical to the hSTING$^{S162A/Q266I}$ amino acid to which it corresponds.

In some embodiments, there is provided a machine-readable data storage medium, comprising a data storage material encoded with machine-readable data, wherein said data comprises all or part of a DMXAA-hSTING$^{S162A/G230I/Q266I}$ complex defined by structure coordinates of hSTING$^{S162A/G230I/Q266I/Q266I}$ amino acids, according Table 9; or a molecule or molecular complex comprising all or part of a DMXAA-hSTING$^{S162A/G230I/Q266I}$ complex defined by structure coordinates of corresponding amino acids that are identical to said hSTING$^{S162A/G230I/Q266I}$ amino acids, wherein the root mean square deviation of the backbone atoms between said corresponding amino acids and said hSTING$^{S162A/G230I/Q266I}$ amino acids is not more than about 3.0 Å, 2.5 Å, 2.0 Å, 1.5 Å, 1.0 Å; or a molecule or molecular complex comprising all or part of a DMXAA-hSTING$^{S162A/G230I/Q266I}$ complex defined by structure coordinates of a set of corresponding amino acids, wherein the root mean square deviation of the backbone atoms between said set of corresponding amino acids and said hSTING$^{S162A/G230I/Q266I}$ amino acids is not more than about 1.1, 0.9, 0.7, or 0.5 Å, and wherein at least one of said corresponding amino acids is not identical to the hSTING$^{S162A/G230I/Q266I}$ amino acid to which it corresponds.

In some embodiments, the data storage material is encoded with machine-readable data comprising all or part of a superposition of a STING complex with one or more additional molecules and/or complexes. In some embodiments, data storage material is encoded with machine-readable data comprising all or part of a superposition of a STING protein and STING modulator complex. In some embodiments, one or more domain(s) of STING are superposed with one or more molecules and/or complexes. In some embodiments, the cyclic dinucleotide cleft domain of STING and DMXAA are superpositioned. In some embodiments, the cyclic dinucleotide cleft domain of STING and a candidate STING modulator are superpositioned.

In some embodiments, the present invention provides a computer system comprising executable code for computer-aided and/or structure-based drug design of STING modulators. In some embodiments, the present invention provides a computer system comprising executable code for docking STING modulators in at least one potential STING interaction site (e.g., dinucleotide cleft domain, ligand-binding pocket). In some embodiments, said executable code comprises instructions for providing an image of a STRING crystal that includes at least one potential interaction site; docking in the image at least one moiety that is a potential STING modulator structural element; and assessing one or more features of a potential moiety-interaction site interaction.

In some embodiments, said executable code comprises a determining step, wherein said determining step comprises a prediction of 1.) whether said moiety will bind to at least one potential STING interaction site; 2.) calculates the strength of binding affinity; and 3.) calculates moiety specificity. In some embodiments, the determining step further comprises predicting the conformation of the moiety when bound to at least one potential interaction site. In some embodiments, the determining step further comprises one or more predictions of conformational changes in a STING polypeptide when said moiety binds at least one potential interaction site.

In some embodiments, provided computer system comprise executable code for superimposing all or part of a STING crystal or crystallizable composition with another crystal or crystallizable composition.

In some embodiments, provided computer systems comprise executable code for modeling interactions with a STING crystal or crystallizable composition.

Identifying, Designing and/or Characterizing STING Modulators

As described herein, the present disclosure describes systems useful in the identification, design, and/or characterization of STING modulators and/or STING modulator candidates. In some embodiments, such systems are or comprise structure based drug design systems. In some embodiments, such systems are or comprise one or more activity assays.

In some embodiments, candidate STING modulator compounds are tested in accordance with systems described herein in order to identify and/or characterize those with desirable structural and/or functional attributes. In some embodiments, a population of candidate STING modulator compounds is provided through structure-based drug design predictions of interacting moieties. In some embodiments, a population of candidate STING modulator compounds is or comprises analogs of a reference compound selected from the group consisting of cyclic dinucleotides, DMXAA, CMA, and combinations thereof.

Pharmaceutical Compositions

The pharmaceutical compositions can be in a variety of forms including oral dosage forms, topic creams, topical patches, iontophoresis forms, suppository, nasal spray and inhaler, eye drops, intraocular injection forms, depot forms, as well as injectable and infusible solutions. Methods for preparing pharmaceutical composition are well known in the art.

Pharmaceutical compositions typically contain the active agent described herein (e.g. STING modulators) in an amount effective to achieve the desired therapeutic effect while avoiding or minimizing adverse side effects. Pharmaceutically acceptable preparations and salts of the active agent are provided herein and are well known in the art. For the administration of STING modulators and the like, the amount administered desirably is chosen that is therapeutically effective with few to no adverse side effects. The amount of the therapeutic or pharmaceutical composition which is effective in the treatment of a particular disease, disorder or condition depends on the nature and severity of the disease, the target site of action, the subject's weight, special diets being followed by the subject, concurrent medications being used, the administration route and other factors that are recognized by those skilled in the art. The dosage can be adapted by the clinician in accordance with conventional factors such as the extent of the disease and different parameters from the subject. Effective doses may be extrapolated from dose-response curves derived from in vitro or animal model test systems (e.g., as described by the U.S. Department of Health and Human Services, Food and Drug Administration, and Center for Drug Evaluation and Research in "Guidance for Industry: Estimating Maximum Safe Starting Dose in Initial Clinical Trials for Therapeutics in Adult Healthy Volunteers", *Pharmacology and Toxicology*, July 2005, the entire contents of which are incorporated herein by reference).

Various delivery systems are known and can be used to administer active agent described herein (e.g. STING modulators) or a pharmaceutical composition comprising the same. The pharmaceutical compositions described herein can be administered by any suitable route including, intravenous or intramuscular injection, intraventricular or intrathecal injection (for central nervous system administration), orally, topically, subcutaneously, intrapulmonary (e.g., inhalation), subconjunctivally, intraocularly, or via intranasal, intradermal, sublingual, vaginal, rectal or epidural routes.

Other delivery systems well known in the art can be used for delivery of the pharmaceutical compositions described herein, for example via aqueous solutions, encapsulation in microparticles, or microcapsules. The pharmaceutical compositions of the present invention can also be delivered in a controlled release system. For example, a polymeric material can be used (see, e.g., Smolen and Ball, Controlled Drug Bioavailability, Drug product design and performance, 1984, John Wiley & Sons; Ranade and Hollinger, Drug Delivery Systems, pharmacology and toxicology series, 2003, $2^{nd}$ edition, CRRC Press). Alternatively, a pump may be used (Saudek et al., *N. Engl. J. Med.* 321:574 (1989)). The compositions described herein may also be coupled to a class of biodegradable polymers useful in achieving controlled release of the drug, for example, polylactic acid, polyorthoesters, cross-linked amphipathic block copolymers and hydrogels, polyhydroxy butyric acid, and polydihydropyrans.

As described above, pharmaceutical compositions desirably include a pharmaceutically acceptable carrier. The term carrier refers to diluents, adjuvants, excipients or vehicles with which STING modulators are administered. Such pharmaceutical carriers include sterile liquids such as water and oils including mineral oil, vegetable oil (e.g., soybean oil or corn oil), animal oil or oil of synthetic origin. Aqueous glycerol and dextrose solutions as well as saline solutions may also be employed as liquid carriers of the pharmaceutical compositions of the present invention. The choice of the carrier depends on factors well recognized in the art, such as the nature of the peptide, peptide derivative or peptidomimetic, its solubility and other physiological properties as well as the target site of delivery and application. Examples of suitable pharmaceutical carriers are described in Remington: The Science and Practice of Pharmacy by Alfonso R. Gennaro, 2003, $21^{th}$ edition, Mack Publishing Company. Moreover, suitable carriers for oral administration are known in the art and are described, for example, in U.S. Pat. Nos. 6,086,918, 6,673,574, 6,960,355, and 7,351,741 and in WO2007/131286, the disclosures of which are hereby incorporated by reference.

Further pharmaceutically suitable materials that may be incorporated in pharmaceutical preparations include absorption enhancers including those intended to increase paracellular absorption, pH regulators and buffers, osmolarity adjusters, preservatives, stabilizers, antioxidants, surfactants, thickeners, emollient, dispersing agents, flavoring agents, coloring agents, and wetting agents.

Examples of suitable pharmaceutical excipients include, water, glucose, sucrose, lactose, glycol, ethanol, glycerol monostearate, gelatin, starch flour (e.g., rice flour), chalk, sodium stearate, malt, sodium chloride, and the like. The pharmaceutical compositions comprising STING modulators can take the form of solutions, capsules, tablets, creams, gels, powders sustained release formulations and the like. The composition can be formulated as a suppository, with traditional binders and carriers such as triglycerides (see Remington: The Science and Practice of Pharmacy by Alfonso R. Gennaro, 2003, $21^{th}$ edition, Mack Publishing Company). Such compositions contain a therapeutically effective amount of the therapeutic composition, together with a suitable amount of carrier so as to provide the form for proper administration to the subject. The formulations are designed to suit the mode of administration and the target site of action (e.g., a particular organ or cell type).

The pharmaceutical compositions comprising the active agent described herein (e.g. STING modulators) also include compositions formulated as neutral or salt forms. Pharmaceutically acceptable salts include those that form with free amino groups and those that react with free carboxyl groups. Non-toxic alkali metal, alkaline earth metal, and ammonium salts commonly used in the pharmaceutical industry include sodium, potassium, lithium, calcium, magnesium, barium, ammonium, and protamine zinc salts, which are prepared by methods well known in the art. Also included are non-toxic acid addition salts, which are generally prepared by reacting the compounds of the present invention with suitable organic or inorganic acid. Representative salts include the hydrobromide, hydrochloride, valerate, oxalate, oleate, laureate, borate, benzoate, sulfate, bisulfate, acetate, phosphate, tysolate, citrate, maleate, fumarate, tartrate, succinate, napsylate salts, and the like.

Examples of fillers or binders that may be used in accordance with the present invention include acacia, alginic acid, calcium phosphate (dibasic), carboxymethylcellulose, carboxymethylcellulose sodium, hydroxyethylcellulose, hydroxypropylcellulose, hydroxypropylmethylcellulose, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. In certain embodiments, a filler or binder is microcrystalline cellulose.

Examples of disintegrating agents that may be used include alginic acid, carboxymethylcellulose, carboxymethylcellulose sodium, hydroxypropylcellulose (low substituted), microcrystalline cellulose, powdered cellulose, colloidal silicon dioxide, sodium croscarmellose, crospovidone, methylcellulose, polacrilin potassium, povidone, sodium alginate, sodium starch glycolate, starch, disodium disulfite, disodium edathamil, disodium edetate, disodiumethylenediaminetetraacetate (EDTA) crosslinked polyvinylpyrrolidones, pregelatinized starch, carboxymethyl starch, sodium carboxymethyl starch, microcrystalline cellulose.

Examples of lubricants include calcium stearate, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL-leucine.

Examples of silica flow conditioners include colloidal silicon dioxide, magnesium aluminum silicate and guar gum. Another most preferred silica flow conditioner consists of silicon dioxide.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol.

In some embodiments, the present invention contemplates oral formulations containing the active agent described herein (e.g. STING modulators). For example, pharmaceutical compositions described herein may include a cyclodextrin or cyclodextrin derivative. Cyclodextrins are generally made up of five or more α-D-glycopyranoside unites linked 1→4. Typically, cyclodextrins contain a number of glucose monomers ranging from six to eight units in a ring, creating a cone shape (α-cyclodextrin: six membered sugar ring molecule, β-cyclodextrin: seven sugar ring molecule, γ-cyclodextrin: eight sugar ring molecule). Exemplary cyclodextrins and cyclodextrin derivatives are disclosed in U.S. Pat. No. 7,723,304, U.S. Publication No. 2010/0196452, and U.S. Publication No. 2010/0144624, the entire contents of each of which are incorporated herein by reference. For example, in some embodiments, a cyclodextrin in accordance with the present invention is an alkylated cyclodextrin, hydroxyalkylated cyclodextrin, or acylated cyclodextrin. In some embodiments, a cyclodextrin is a hydroxypropyl β-cyclodextrin. Exemplary cyclodextrin derivatives are disclosed in Szejtli, J. Chem Rev, (1998), 98, 1743-1753; and Szente, L and Szejtli, J., Advance Drug Delivery Reviews, 36 (1999) 17-28, the entire contents of each of which are hereby incorporated by reference. Examples of cyclodextin derivatives include methylated cyclodextrins (e.g., RAMEB; randomly methylated β-cyclodextrin); hydroxyalkylated cyclodextrins (hydroxypropyl-β-cyclodextrin and hydroxypropyl γ-cyclodextrin); acetylated cyclodextrins (acetyl-γ-cyclodextrin); reactive cyclodextrins (chlorotriazinyl β-cyclodextrin); and branched cyclodextrins (glucosyl- and maltosyl β-cyclodextrin); acetyl-γ-cyclodextrin; acetyl-β-cyclodextrin, sulfobutyl-βcyclodextrin, sulfated α-, β- and γ-cyclodextrins; sulfoalkylated cyclodextrins; and hydroxypropyl β-cyclodextrin.

Dosing

Typically, active agent described herein (e.g. STING modulators) in an amount ranging from 0.001 to 100 mg/kg/day is administered to the subject. For example, in some embodiments, about 0.01 mg/kg/day to about 25 mg/kg/day, about 1 mg/kg/day to about 20 mg/kg/day, 0.2 mg/kg/day to about 10 mg/kg/day, about 0.02 mg/kg/day to about 0.1 mg/kg/day, or about 1 mg/kg/day to about 100 mg/kg/day is administered to the subject. In some embodiments, active agent described herein (e.g. STING modulators) in an amount of about 10 µg/kg/day, 50 µg/kg/day, 100 µg/kg/day, 200 µg/kg/day, 300 µg/kg/day, 400 µg/kg/day, 500 µg/kg/day, 600 µg/kg/day, 700 µg/kg/day, 800 µg/kg/day, 900 µg/kg/day, or 1000 µg/kg/day is administered to the subject.

In some embodiments, the STING modulator is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the STING modulator is administered at an effective dose ranging from about 1-500 µg/kg/day. In some embodiments, the STING modulator is administered at an effective dose ranging from about 1-100 µg/kg/day. In some embodiments, the STING modulator is administered at an effective dose ranging from about 1-60 µg/kg/day. In some embodiments, the STING modulator is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 ug/kg/day.

In some embodiments, a therapeutically effective amount of an STING modulator may be an amount ranging from about 10-1,000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, an STING modulator is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, an STING modulator is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg. In some embodiments, the therapeutically effective amount described herein is provided in one dose. In some embodiments, the therapeutically effective amount described herein is provided in one day.

In other embodiments, a therapeutically effective amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of cancer. In some embodiments, a pharmaceutical formulation is or comprises a unit dose amount for administration in accordance with a dosing regimen correlated with achievement of the reduced incidence or risk of infectious disease (i.e., vaccine). In some embodiments, a pharmaceutical formulation is or comprises a unit dose amount for administration in accordance with a dosing regimen correlated with achievement of the reduced incidence or risk of autoimmune disorders.

In some embodiments, a formulation comprising a STING modulator as described herein administered as a single dose. In some embodiments, a formulation comprising a STING modulator as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a STING modulator as described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a STING modulator as described herein is administered at regular intervals indefinitely. In some embodiments, a formulation comprising a STING modulator as described herein is administered at regular intervals for a defined period. In some embodiments, a formulation comprising a STING modulator as described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapy

In some embodiments, the present invention provides STING modulator agents for use in combination with one or more additional therapeutic and/or diagnostic agents and/or modalities. In some embodiments, provided agents are useful in combination with one or more other therapeutic agents or modalities known to be useful in the treatment or prevention of one or more STING-associated diseases, disorders, or conditions, and/or with the relief of one or more symptoms of such diseases, disorders, or conditions. For example, in some embodiments, provided agents are useful in combination with one or more chemotherapeutic, autoimmune medications and/or infectious disease agents. In some embodiments, provided agents are useful in combination with one or more other agents or modalities that is or are approved by the United States Food and Drug Administration or one or more other non-US agencies.

In some embodiments, agents utilized in combination may be included in a single pharmaceutical compositions. More commonly, however, agents utilized in combination are administered in accordance with overlapping regimens so that a subject is simultaneously exposed to both (or all)

agents, and/or is exposed to individual agents in a predetermined order and/or with a predetermined timing.

For purposes of the present disclosure, the term "palliative" refers to treatment that is focused on the relief of symptoms of a disease and/or side effects of a therapeutic regimen, but is not curative. For example, in some embodiments, palliative treatment encompasses painkillers and antinausea medications. Alternatively or additionally, in some embodiments, chemotherapy, radiotherapy, and surgery can all be used palliatively (that is, to reduce symptoms without going for cure; e.g., for shrinking tumors and reducing pressure, bleeding, pain, and/or other symptoms or signs of cancer).

In some embodiments, a STING modulator is administered in combination with one or more known therapeutic agents (e.g., autoimmune medications) currently used for treatment of autoimmune disorders (e.g., systemic lupus erythematosus).

In some embodiments, a STING modulator is administered in combination with one or more known therapeutic agents (e.g., anti-viral medications) currently used for treatment of infectious disease (e.g., pathogenic infection).

In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

Applications for STING Modulators

In certain embodiments provided modulators are useful in medicine. In some embodiments, provided modulators are useful in treating immune disease, disorders, or conditions. In some embodiments, the present invention provides a method for the treatment or prevention of an immune disease, disorder, or condition comprising administering to a subject in need thereof a provided modulator or a pharmaceutical composition thereof.

In some embodiments, the immune disease, disorder, or condition is an autoimmune disease, disorder, or condition. In certain embodiments, the immune disease, disorder, or condition is selected from the group consisting of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc. In some embodiments, the immune disease, disorder, or condition is characterized by inflammation. In some embodiments, the immune disease, disorder, or condition is caused by, sustained by, or related to cGAS activation. In some embodiments, the immune disease, disorder, or condition is caused by, sustained by, or related to STING activation.

In some embodiments the autoimmune disorder or disease is selected from Acute disseminated encephalomyelitis (ADEM), Addison's disease, Agammaglobulinemia, Alopecia areata, Amyotrophic lateral sclerosis (Also Lou Gehrig's disease; Motor Neuron Disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticarial, Autoimmune uveitis, Balo disease/Balo concentric sclerosis, Behçet's disease, Berger's disease, Bickerstaffs encephalitis, Blau syndrome, Bullous pemphigoid Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid Cogan syndrome, Cold agglutinin disease, Complement component 2 deficiency, Contact dermatitis, Cranial arteritis, CREST syndrome, Crohn's disease (idiopathic inflammatory bowel disease "IBD"), Cushing's Syndrome, Cutaneous leukocytoclastic angiitis, Dego's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura, IgA nephropathy, Inclusion body myositis, Chronic inflammatory demyelinating polyneuropathy, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lupoid hepatitis aka Autoimmune hepatitis, Lupus erythematosus, Majeed syndrome, Ménière's disease, Microscopic polyangiitis, Miller-Fisher syndrome see Guillain-Barré Syndrome, Mixed connective tissue disease, Morphea, Mucha-Habermann disease aka Pityriasis lichenoides et varioliformis acuta, Multiple sclerosis, Myasthenia gravis, Myositis, Narcolepsy, Neuromyelitis optica (also Devic's disease), Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome, Schnitzler syndrome, Scleritis, Scleroderma, Serum Sickness, Sjögren's syndrome, Spondyloarthropathy, Still's disease, Subacute bacterial endocarditis (SBE), Susac's syndrome, Sweet's syndrome, Sydenham chorea see PANDAS, Sympathetic ophthalmia, Systemic lupus erythematosis, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), Undifferentiated connective tissue disease different from Mixed connective tissue disease, Undifferentiated spondyloarthropathy, Urticarial vasculitis, Vasculitis, Vitiligo, and Wegener's granulomatosis.

In certain embodiments, administration of a STING modulator to a patient in need thereof results in a decrease of cGAS activity. In some embodiments, administration of a STING modulator to a patient in need thereof results in a decrease of STING activity. In some embodiments, compounds used in the provided methods are prepared by chemical synthesis.

In certain embodiments, the present invention provides a method of inhibiting STING comprising contacting STING with a provided modulator.

In certain embodiments, the present invention provides a method of modulating activity of an STING polypeptide, the method comprising contacting the STING polypeptide with a STING modulator designed by the methods disclosed herein, which modulating agent is not a known modulator, substrate, or product of STING.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits comprising the molecules (compounds and compositions as described above) of the invention. In one embodiment, the kit comprises one or more functional antibodies or function fragments thereof.

Kits of the invention may comprise one or more STING parent molecules, or any mimic, analog or variant thereof. Kits may also comprise any of the STING variants, analogs or mutants described herein. The kit may further comprise packaging and instructions and/or a delivery agent to form a formulation composition. The delivery agent may comprise a saline, a buffered solution, a lipid or any delivery agent disclosed herein.

In one embodiment, the buffer solution may include sodium chloride, calcium chloride, phosphate and/or EDTA. In another embodiment, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No. 20120258046; herein incorporated by reference in its entirety). In a further embodiment, the buffer solutions may be precipitated or it may be lyophilized. The amount of each component may be varied to enable consistent, reproducible higher concentration saline or simple buffer formulations. The components may also be varied in order to increase the stability of the compound or composition in the buffer solution over a period of time and/or under a variety of conditions. In one aspect, the present invention provides kits for research applications related to STING activity or cGAMP signaling, provided in an amount effective to study the concomitant signaling pathways when introduced into a target cell. The kits may further comprise a second or further modulator or composition described herein. Such second or further molecules may modulate the immune response or an inflammatory process or comprise one or more therapeutic molecules. In one embodiment, a kit comprises at least one STING polypeptide and at least one cGAMP molecule. In one embodiment, the kits of the present invention comprise packaging and instructions.

EXEMPLIFICATION

Unless otherwise described in a particular Example, the reagents, protocols and constructs used in each Example are as described below. In each case, one of skill in the art will recognize that variations of particular reagents or procedures would be acceptable equivalents and it is contemplated that these alternatives are considered as part of the present description. The Examples below are intended only to provide specific exemplary enbodiments, and are not limiting.

The following coordinates have been deposited in the RCSB Protein Data Bank, with which the skilled artisan will be familiar, and correspond to Tables 1-9 incorporated by reference herein. With respect to Tables 1-5, see also Gao, P., et al. *Cell* 154, 748-762 (2013), including supplementary materials, the entire contents of which are hereby incorporated by reference herein. Furthermore, in the context of FIGS. 1-3, 5, and 8-10, the data presented in Tables 1-5 of U.S. provisional patent application No. 61/860,818, filed Jul. 31, 2013, are hereby incorporated by reference.

| Sample | PDB code[1] | Table |
|---|---|---|
| c[G(2',5')pA(3',5')p]-hSTING$^{H232}$ complex | 4LOH | 1 |
| c[G(2',5')pA(2',5')p]-hSTING$^{H232}$ complex | 4LOI | 2 |
| c[G(2',5')pA(3',5')p]-mSting$^{R231}$ complex | 4LOJ | 3 |
| c[G(3',5')pA(3',5')p]-mSting$^{R231}$ complex | 4LOK | 4 |
| DMXAA-mSting$^{R231}$ complex | 4LOL | 5 |
| DMXAA-hSTING$^{group2}$ complex | 4QXO | 6 |
| DMXAA-hSTING$^{G230I}$ complex | 4QXP | 7 |
| DMXAA-hSTING$^{S162A/Q266I}$ complex | 4QXQ | 8 |
| DMXAA-hSTING$^{S162A/G230I/Q266I}$ complex | 4QXR | 9 |

[1]One method of accessing the RCSB Protein Data Bank is online at www.rcsb.org.

Tables 6-9 are found at the end of the specification and are hereby incorporated by reference herein in their entirety. Table 6 lists atomic structure coordinates for a DMXAA-hSTING$^{group2}$ complex as derived from X-ray diffraction from the corresponding crystal. Table 7 lists atomic structure coordinates for a DMXAA-hSTING$^{G230I}$ complex as derived from X-ray diffraction from the corresponding crystal. Table 8 lists atomic structure coordinates for a DMXAA-hSTING$^{S162A/Q266I}$ complex as derived from X-ray diffraction from the corresponding crystal. Table 9 lists atomic structure coordinates for a DMXAA-hSTING$^{S162A/G230I/Q266I}$ complex as derived from X-ray diffraction from the corresponding crystal.

Plasmid Construction

The human and murine STING sequences (reference sequences) used in the following Examples were inserted into a modified pMAX-cloning (Amaxa, Cologne, Germany) by standard cloning techniques, in frame with a N-terminal FLAG-tag. Site-directed mutagenesis was performed by the Quikchange method (Agilent, Santa Clara, Calif.) using Pfu Ultra Hot Start DNA Polymerase (Agilent) or Phusion Polymerase (NEB, Ipswich, Mass.). Luciferase reporter constructs were as described (Gao et al., 2013). Constructs (FIG. 147) were verified by restriction digest and Sanger sequencing (Seqlab, Göttingen, Germany).

TABLE S7

Primer sequences for STING cloning and mutagenesis

| Primer Name | Sequence(5'-3') | SEQ ID NO. |
|---|---|---|
| mSTINGfwSalI | ATATATGTCGACATGCCATACTCCAACCTGCATCCA | 3 |
| mSTINGrevNotI | ATATATGCGGCCGCTCAGATGAGGTCAGTGCGGAGT | 4 |
| hSTINGfwSalI | ATATATGTCGACACCATGCCCCACTCCAGCCTGCA | 5 |
| hSTINGrevNotI | ATATATGCGGCCGCTCAAGAGAAATCCGTGCGGAGA | 6 |
| hSTINGfw-39bpFlag-GibA | GCCACCATGGATTACAAGGATGACGACGATAAGGTCG ACATGCCCCACTCCAGCCTGCA | 7 |
| hSTINGrev458-GibA | AAATTCCCTTTTTCACACACTGCAG | 8 |
| hSTINGfw420-GibA | CCCAGCTGAGATCTCTGCA | 9 |
| hSTINGrev-40bp-GibA | TGTGGTTTGTCCAAACTCATCGAGCTCGATGCGGCCG CGGTCAAGAGAAATCCGTGCGGAGA | 10 |
| mmSTING t481g_antisense | CCCAATGTAGTATGCCCAGGCCAGCCCG | 11 |
| mmSTING t481g | CGGGCTGGCCTGGGCATACTACATTGGG | 12 |
| mmSTING t496g_a497c | CTGGTCATACTACATTGGGGCCTTGCGGTTGATCTTACCA | 13 |
| mmSTING t496g_a497c_antisense | TGGTAAGATCAACCGCAAGGCCCCAATGTAGTATGACCAG | 14 |
| mmSTING c709g_g710c | CGACCGTGCTGGCATCAAGAATGCGGTTTATTCCAACAG | 15 |
| mmSTING c709g_g710c_antisense | CTGTTGGAATAAACCGCATTCTTGATGCCAGCACGGTCG | 16 |
| mmSTING t715g_a716c_antisense | TCGTAGACGCTGTTGGAAGCAACCCGATTCTTGATGCCAG | 17 |
| mmSTING t715g_a716c | CTGGCATCAAGAATCGGGTTGCTTCCAACAGCGTCTACGA | 18 |
| mmSTING a721g_a722c_antisense | CAGAATCTCGTAGACGCTGGCGGAATAAACCCGATTCTTG | 19 |
| mmSTING a721g_a722c | CAAGAATCGGGTTTATTCCGCCAGCGTCTACGAGATTCTG | 20 |
| mmSTING a776c_antisense | GGGGGTGGCGTACGCCAGGATACAGAC | 21 |
| mmSTING a776c | GTCTGTATCCTGGCGTACGCCACCCCC | 22 |
| mmSTING a784g | CCTGGAGTACGCCGCCCCCTTGCAGAC | 23 |
| mmSTING a784g_antisense | GTCTGCAAGGGGCGGCGTACTCCAGG | 24 |
| mmSTING a796g_antisense | CATGGCAAACAGGGCCTGCAAGGGGTGG | 25 |
| mmSTING a796g | CCACCCCTTGCAGGCCCTGTTTGCCATG | 26 |
| hSTING t484g_c485g_antisense | AGATATCCGATGTAATATCCCCATGCCAGCCCATGGGC | 27 |
| hSTING t484g_c485g | GCCCATGGGCTGGCATGGGGATATTACATCGGATATCT | 28 |
| hSTING t484a_a486g | GCCCATGGGCTGGCATGGACGTATTACATCGGATATCTG | 29 |
| hSTING t484a_a486g_antisense | CAGATATCCGATGTAATACGTCCATGCCAGCCCATGGGC | 30 |

TABLE S7-continued

Primer sequences for STING cloning and mutagenesis

| Primer Name | Sequence(5'-3') | SEQ ID NO. |
|---|---|---|
| hSTING c485t | CCATGGGCTGGCATGGTTATATTACATCGGATATC | 31 |
| hSTING c485t_antisense | GATATCCGATGTAATATAACCATGCCAGCCCATGG | 32 |
| hSTINGfw-39bpFlag-GibA | GCCACCATGGATTACAAGGATGACGACGATAAGGTCGACAT GCCCCACTCCAGCCTGCA | 33 |
| hSTINGrev458-GibA | AAATTCCCTTTTTCACACACTGCAG | 34 |
| hSTINGfw420-GibA | CCCAGCTGAGATCTCTGCA | 35 |
| hSTINGrev-40bp-GibA | TGTGGTTTGTCCAAACTCATCGAGCTCGATGCGGCCGCGGT CAAGAGAAATCCGTGCGGAGA | 36 |
| revbefgroup1 | TGGCAGGATCAGCCGCAG | 37 |
| fwbefgroup1 | CTGCGGCTGATCCTGCCA | 38 |
| revbefgroup2 | ACAGTCCAATGGGAGGAGAATATACAG | 39 |
| fwbefgroup2 | CTGTATATTCTCCTCCCATTGGACTGT | 40 |
| revbefgroup3 | TGGCGTACTCCAGGACACAGG | 41 |
| fwbefgroup3 | CCTGTGTCCTGGAGTACGCCA | 42 |
| revbefgroup4 | ACAGCGAGAAGCTGCTGTCAT | 43 |
| fwbefgroup4 | ATGACAGCAGCTTCTCGCTGT | 44 |
| revbeforore266 | TGGCGTACTCCAGGACACAG | 45 |
| fwbefore266 | AGCTTCTGGAGAACGGGCAG | 46 |
| fwafter266 | TGCCATGTCACAATACAGTCAAGCT | 47 |
| revafter266 | GGCCTGCTCAAGCCTATCCTC | 48 |
| G230R232fw | CTGCCCCAGCAGACCGGTGACCGTGCTGGCATCAAGGATC | 49 |
| G230R232rev | GATCCTTGATGCCAGCACGGTCACCGGTCTGCTGGGGCAG | 50 |
| A230R232fw | CTGCCCCAGCAGACCGCTGACCGTGCTGGCATCAAGGATC | 51 |
| A230R232rev | GATCCTTGATGCCAGCACGGTCAGCGGTCTGCTGGGGCAG | 52 |
| G230H232fw | CTGCCCCAGCAGACCGGTGACCATGCTGGCATCAAGGATC | 53 |
| G230H232rev | GATCCTTGATGCCAGCATGGTCACCGGTCTGCTGGGGCAG | 54 |
| group2toGfw | CTGCCCCAGCAGAACGGTGACCGTGCTGGCATCAAGAATC | 55 |
| group2toGrev | GATTCTTGATGCCAGCACGGTCACCGTTCTGCTGGGGCAG | 56 |
| Q266Ifw | GTGACATGGCAAACAAAGTTATCAAGGGGGTGGCGTACTCC | 57 |
| Q266Irev | GGAGTACGCCACCCCCTTGATAACTTTGTTTGCCATGTCAC | 58 |
| S162Afw | CCCATGGGCTGGCATGGGCATATTACATCGGATATC | 59 |
| S162Arev | GATATCCGATGTAATATGCCCATGCCAGCCCATGGG | 60 |
| G230I 232H_fw | CTGCCCCAGCAGACCATTGACCATGCTGGCAT | 61 |
| G230I 232H_rev | ATGCCAGCATGGTCAATGGTCTGCTGGGGCAG | 62 |
| G230I 232R_fw | TCCTTGATGCCAGCACGGTCAATGGTCTGCTGGGGCAG | 63 |
| G230I 232R_rev | CTGCCCCAGCAGACCATTGACCGTGCTGGCATCAAGGA | 64 |
| I165Afw | GGGCTGGCATGGTCATATTACGCCGGATATCTGCGGCT | 65 |
| I165Arev | AGCCGCAGATATCCGGCGTAATATGACCATGCCAGCCC | 66 |
| G166Sfw | CTGGCATGGTCATATTACATCAGCTATCTGCGGCTGATCC | 67 |

TABLE S7-continued

Primer sequences for STING cloning and mutagenesis

| Primer Name | Sequence(5'-3') | SEQ ID NO. |
|---|---|---|
| G166Srev | GGATCAGCCGCAGATAGCTGATGTAATATGACCATGCCAG | 68 |
| I235Lfw | AGACCGGTGACCGTGCTGGCCTCAAGGATCGGG | 69 |
| I235Lrev | CCCGATCCTTGAGGCCAGCACGGTCACCGGTCT | 70 |
| Q266Ifw | GGAGTACGCCACCCCCTTGATAACTTTGTTTGCCATGTCAC | 71 |
| Q266Irev | GTGACATGGCAAACAAAGTTATCAAGGGGGTGGCGTACTCC | 72 |
| Q266Lfw | CGCCACCCCCTTGCTGACTTTGTTTGCCAT | 73 |
| Q266Lrev | ATGGCAAACAAAGTCAGCAAGGGGGTGGCG | 74 |
| Q266Vfw | GTACGCCACCCCCTTGGTGACTTTGTTTGCCATGT | 75 |
| Q266Vrev | ACATGGCAAACAAAGTCACCAAGGGGGTGGCGTAC | 76 |
| mSTING_I229Gfw | ATGCTGCCCCAGCAAACGGCGACCGTGCTGG | 77 |
| mSTING_I229Grev | CCAGCACGGTCGCCGTTTTGCTGGGGCAGCAT | 78 |
| mSTING_I229Afw | ATGCTGCCCCAGCAAACGCCGACCGTGCTGG | 79 |
| mSTING_I229Arev | CCAGCACGGTCGGCGTTTTGCTGGGGCAGCAT | 80 |

Human STING mutants were assembled from C-terminal mutated constructs (140-C) and N-terminal reference sequence by Gibson Assembly (NEB) and confirmed by Sanger sequencing. STING$^{THP1}$ and STING$^{R232}$ cDNAs were cloned from THP1 cells and Peripheral Blood Mononuclear Cells of a voluntary human donor with informed consent, respectively.

Protein Expression and Purification

Unless otherwise specified, sequences used in the following Examples corresponding to residues aa 140-379 and 155-341 of hSTING$^{H232}$, hSTING$^{R232}$, hSTING$^{A230/R232}$, hSTING$^{group2}$, hSTING$^{G230I}$, hSTING$^{S162A/Q266I}$, and hSTING$^{S162A/G230I/Q266I}$; and residues 139-378 and 154-340 of mSTING$^{R231}$ were inserted into a modified pRSFDuet-1 vector (Novagen), in which the target protein was separated from the preceding His$_6$-SUMO tag ('His$_6$' disclosed as SEQ ID NO: 91) by an ubiquitin-like protease (ULP) cleavage site. The gene sequences were subsequently confirmed by sequencing. The fusion proteins were expressed in BL21 (DE3) RIL cell strain. The cells were grown at 37° C. until OD600 reached approx. 0.6. The temperature was then shifted to 18° C. and the cells were induced by addition of isopropyl β-D-1-thiogalactopyranoside (IPTG) to the culture medium at a final concentration of 0.3 mM. After induction, the cells were grown overnight. The fusion proteins were purified over a Ni-NTA affinity column. The His$_6$-SUMO tag ('His$_6$' disclosed as SEQ ID NO: 91) was removed by ULP1 cleavage during dialysis against buffer containing 40 mM Tris-HCl, 300 mM NaCl, pH 7.5. After dialysis, the His$_6$-SUMO tag ('His$_6$' disclosed as SEQ ID NO: 91) was removed by Ni-NTA affinity column and the sample was further fractionated over a gel filtration 16/60 G200 Superdex column. The final sample of hSTING$^{H232}$, hSTING$^{R232}$ and hSTING$^{A230/R232}$, mSTING$^{R231}$, hSTING$^{group2}$, hSTING$^{G230I}$, hSTING$^{S162A/Q266I}$, and hSTING$^{S162A/G230I/Q266I}$ contain about 13-16 mg/ml protein, 20 mM Tris-HCl, 150 mM NaCl, pH 7.5. All the mutants were cloned and purified using the same protocol as used for preparation of the wild-type protein.

Crystallization

Crystals were grown in the following Examples using the sitting drop vapor diffusion method and diffraction data collected at synchrotron beam lines. For crystallization of hSTING$^{H232}$ (155-341) with c[G(2',5')pA(3',5')p] and c[G(2',5')pA(2',5')p], the protein was incubated with c[G(2',5')pA(3',5')p] (2 mM) or c[G(2',5')pA(2',5')p] (2 mM) and MgCl$_2$ (5 mM) for 0.5 h at room temperature. The crystals were generated by sitting drop vapor diffusion method at 20° C., by mixing equal volume reservoir solution (for c[G(2',5')pA(3',5')p]: 0.01 M NiCl$_2$, 0.1 M Tris, 20% PEG2000, pH 8.5; for c[G(2',5')pA(2',5')p]: 1.6 M NaH$_2$PO$_4$, 0.4 M Na$_2$HPO$_4$, 0.1 M phosphate-citrate, pH 4.2) with the sample.

For crystallization of mSTING$^{R231}$ (154-340) with c[G(2',5')pA(3',5')p], c[G(3',5')pA(3',5')p] and DMXAA, the protein was incubated with c[G(2',5')pA(3',5')p] (2 mM) or c[G(3',5')pA(3',5')p] (2 mM) or DMXAA (4 mM) for 0.5 h at room temperature. The crystals were generated by sitting drop vapor diffusion method at 20° C., by mixing equal volume reservoir solution (for c[G(2',5')pA(3',5')p]: 0.2 M di-ammonium tartrate, 20% PEG3350; for c[G(3',5')pA(3',5')p]: 0.2 M sodium formate, 20% PEG3350; for DMXAA: 1.6 M ammonium sulfate, 0.1 M Tris-HCl, pH 8.0) with the samples.

For crystallization of DMXAA with hSTING mutants (aa 155-341), the protein samples were mixed and incubated with DMXAA (1:2 molar ratio) for 0.5 h at room temperature before setting up crystals. The crystals were generated by sitting drop vapor diffusion method at 20° C., by mixing equal volume reservoir solution with the sample. The detailed conditions are listed below: DMXAA-hSTING$^{group2}$: 2 M LiCl, 10% PEG6000, 0.01 M CaCl$_2$, 0.1 M Tris, pH 7.8; DMXAA-hSTING$^{G230I}$: 0.2 M Li$_2$SO$_4$, 20% PEG 3350, 0.015 mM CYMAL®-7, 0.1 M Tris, pH 8.1; DMXAA-hSTING$^{S162A/Q266I}$: 0.2 M Ca(Ac)$_2$, 15% PEG3000, 0.01 M L-Proline, 0.1 M NaAc, pH 5.1;

DMXAA-hSTING$^{S162A/G230I/Q266I}$: 0.2 M Ca(Ac)$_2$, 15% PEG3000, 0.1 M LiCl, 0.1 M NaAc, pH 5.1. All structures were solved using PHASER, COOT, PHENIX, and REFMAC programs.

Structure Determination

All the diffraction data sets (except mSTING$^{R231}$ with DMXAA) in the following Examples were collected at the Brookhaven National Laboratory, and were indexed, integrated and scaled using the HKL2000 program (Otwinowski and Minor, 1997). The data set for mSTING$^{R231}$, hSTING$^{group2}$, hSTING$^{G230I}$, hSTING$^{S162A/Q266I}$, and hSTING$^{S162A/G230I/Q266I}$ with DMXAA were collected at Argonne National Laboratory and was indexed, integrated and scaled using the RAPD online server. The structure of hSTING$^{H232}$ with c[G(2',5')pA(3',5')p] or c[G(2',5')pA(2',5')p] was solved using molecular replacement method in PHASER (McCoy et al., 2007) using the complex structure of hSTING$^{A230/R232}$ and c[di-GMP] (PDB: 4F5D) as the search model. For mSTING$^{R231}$ with c[G(2',5')pA(3',5')p], c[G(3',5')pA(3',5')p] and DMXAA, the structure of mSTING$^{R231}$ and CMA (PDB: 4JC5) was used as the search model. For the cGAMP-STING binary structures, two STING molecules in the STING dimer have equal probability to bind with either G or A moiety of the cGAMP isomers. The electron density also clearly indicated that the cGAMP isomers adopt two alternative conformations. We therefore assigned two conformations with 0.5 occupancy for bound cGAMP isomers.

The structures of DMXAA-hSTING$^{group2}$, DMXAA-hSTING$^{G230I}$, DMXAA-hSTING$^{S162A/Q266I}$, and DMXAA-hSTING$^{S162A/G230I/Q266I}$ were solved using molecular replacement method in PHASER (McCoy et al., 2007) using the structure of hSTING$^{H232}$ complex bound to c[G(2',5')pA(3',5')p] (PDB: 4LOH) as the search model.

The model building was conducted using the program COOT (Emsley et al., 2010) and structural refinement was conducted using the program REFMAC (Murshudov et al., 1997). The statistics of the data collection and refinement are shown in Table S1, S2, and S7.

Isothermal Titration Calorimetry

The dissociation constants (Kd) and thermodynamic parameters of binding reactions of hSTING$^{H232}$ (aa 140-379), hSTING$^{R232}$ (aa 140-379), hSTING$^{A230/R232}$ (aa 140-379), mSting$^{R231}$ (aa 139-378), mSting$^{A231}$ (aa 139-378), hSTING$^{H232}$ (aa 140-379), hSTING$^{group2}$ (aa 140-379), hSTING$^{G230I}$(aa 140-379), hSTING$^{S162A/Q266I}$ (aa 140-379), and hSTING$^{S162A/G230I/Q266I}$ (aa 140-379), mutants with different cGAMP isomers or DMXAA were measured in the following Examples by isothermal titration calorimetry using a MicroCal ITC200 calorimeter at 25° C. First, wild-type and mutant protein samples were dialyzed overnight against working buffer (100 mM NaCl, 30 mM HEPES, pH 7.5) at 4° C. Then, the protein samples were diluted with working buffer and the lyophilized cGAMP isomers or DMXAA were dissolved in working buffer. The titration was carried out with 16 successive injections of 2.4 µL cGAMP isomers or DMXAA, spaced 180 s apart, into the sample cell containing the protein solution. The data for mSting$^{R231}$ (aa 139-378) and hSTING$^{S162}$ (aa 140-379) mutants with DMXAA were collected using the same protocol as used for STING with cGAMP isomers. The detailed concentration for different titrations was listed in Table S3, S4 and S6. The data were fit using the program Origin 7.0 software.

We observe a mixture of exothermic and endothermic transitions for complex formation of hSTING/mSting complexes with c[G(3',5')pA(3',5')p] (green triangles, FIG. 4, and Table S3), primarily endothermic transitions for complex formation of hSTING/mSting complexes with c[G(2',5')pA(2',5')p] (red circles, FIG. 4, and Table S3), and exclusively endothermic transitions for hSTING/mSting complexes bound to c[G(2',5')pA(3',5')p] (black squares, FIG. 4, and Table S3). Endothermic binding events are not uncommon and may reflect ligand-induced conformational changes in STING that yield significant solvent reorganization/displacement, often resulting in 'melting' (an endothermic event) and release (an entropically favorable event) of 'restricted' (bound) solvent (Table S3). The distinct thermodynamic outcome (exothermic versus endothermic) could possibly relate to very subtle structural differences or alternately to the use of distinct folding pathways with defined energy parameters to arrive at the same or a distinct endpoint.

Mice

Female C57B/6 mice between 6 and 10 weeks of age were purchased from the Jackson Laboratory and were used for the preparation of bone marrow-derived macrophages in the following Examples. These mice were maintained in the animal facility at the Sloan-Kettering Cancer Institute. All procedures were performed in strict accordance with the recommendations in the Guide for the Care and Use of Laboratory Animals of the National Institutes of Health. The protocol was approved by the Committee on the Ethics of Animal Experiments of Sloan-Kettering Cancer Institute (protocol number 96-04-017). IRF3$^{-/-}$ and STING$^{Gt/Gt}$ mice were generated in the laboratories of Drs. Tadatsugu Taniguchi (University of Tokyo) and Russell Vance (University of California, Berkeley).

Generation of Bone-Marrow-Derived Macrophages

Female IRF3$^{-/-}$, STING$^{Gt/Gt}$ and WT C57B/6 mice were used for the preparation of bone marrow-derived macrophages in the following Examples. These mice were maintained in the animal facility at the Sloan-Kettering Cancer Institute. Bone marrow cells were cultured in complete medium (CM) in the presence of 5% of supernatant of L929 mouse fibroblasts as conditioned medium providing macrophage colony-stimulating factor (M-CSF) for 7 days. CM is RPMI 1640 medium supplemented with 10% heat-inactivated fetal bovine serum (FBS), 100 U/ml penicillin, 100 µg/ml streptomycin, 0.1 mM essential and nonessential amino acids, 2 mM L-glutamine, 1 mM sodium pyruvate, and 10 mM HEPES-KOH buffer. Cells were fed at day 4 by replacing 50% of the old medium with fresh medium. Cells were plated into 6-well plate (1 million cells per well) at day 7, the day before stimulation.

Generation of Bone Marrow-Derived Dendritic Cells

The protocol for generation of bone marrow-derived dendritic cells was described before (Dai et al., 2014). Bone marrow-derived dendritic cells were generated by culturing bone marrow cells from the tibia and femur of STING$^{Gt/Gt}$ mice in complete medium (CM) in the presence of GM-CSF (30 ng/ml, produced by the Monoclonal Antibody Core facility at the Sloan Kettering Institute) for 10 days. CM is RPMI 1640 medium supplemented with 10% heat-inactivated fetal bovine serum (FBS), 100 U/ml penicillin, 100 µg/ml streptomycin, 0.1 mM essential and nonessential amino acids, 2 mM L-glutamine, 1 mM sodium pyruvate, and 10 mM HEPES buffer. Cells were fed every 2-3 days by replacing 50% of the old medium with fresh medium. Cells were plated into 6-well plate (1×10$^6$ cells per well) at day 10, the day before retroviral infection. BMDCs (1×10$^6$ cells/well) were infected with retroviruses expressing hSTING (wt and various substitution mutants). 48 hours after retroviral infection, cells were stimulated with DMXAA.

Retroviruses Transduction and DMXAA Treatment hSTING cDNAs were cloned into pQCXIP-HA vector. In vitro packaging system was used to generate retroviruses according to protocol (Clontech). BMDCs ($1\times10^6$ cells/well) were seeded into 6-well plates and infected with retroviruses. 48 hours after retroviral infection, cells were stimulated with DMXAA at a final concentration of 50 μg/ml (Sigma). For real-time PCR analysis, cells were collected at 3 hours post DMXAA treatment. Supernatants were collected at 18 hours post DMXAA treatment. CXCL10 protein level was determined by ELISA.

THP1 Cell Culture

Human THP1 cells were cultured in RPMI1640 (Life Technologies) containing 10% FBS, 2 mM glutamine (Life Technologies), 1 mM sodium pyruvate (Life Technologies), and 100 U/ml penicillin/streptomycin (Life Technologies).

cGAMP Stimulation of Cells

Bone marrow derived murine macrophages and THP-1 cells were stimulated by incubation with cGAMP isomers at indicated concentrations for 18 hrs, or by Digitonin permeabilization (30 minutes) at indicated concentrations as described (Woodward et al., 2010). Cytokines in supernatants were determined after 18 hrs by ELISA. THP1 cells were plated at $8\times10^4$ cells per 96-well and treated as described above.

RT-PCR Analysis of THP1 Cells

For RT-PCR analyses in the following Examples, $5\times10^5$ THP1 cells were plated in 12-well dishes and incubated overnight. 12.5 μM of cGAMP isomers were applied to the media and cells were harvested at indicated times. RNA samples were isolated and cDNA libraries were generated. KOD Polymerase was used to PCR amplify regions of IFNB1 and CXCL10 and normalized against TUBA1B.

RNA Isolation and Real-Time PCR

Total RNA was extracted from whole-cell lystates with an RNeasy Mini kit (Qiagen) and reverse transcribed with the First Strand cDNA synthesis kit (Fermentas) in the following Examples. Quantitative real-time PCR was performed in triplicate with the Applied Biosystem 7500 Real-Time PCR Detection System (Life Technologies) using Fast SYBR Green Master Mix and gene-specific primers. Relative expression was normalized to the levels of glyceraldehyde-3-phosphate dehydrogenase (GADPH).

RT-PCR Analysis

RNA was extracted and isolated from each sample in the following Examples using TRIzol (Life Technologies), per manufacturer's instructions. Superscript III RT-PCR Kit (Life Technologies) was used for generating cDNA libraries, using oligo-dT primers, per manufacturer's instructions. The following primers were used for PCR:

```
IFNB1
                                     (SEQ ID NO.: 92)
5'-GGACCATAGTCAGAGTGGAAATCCTAAG-3'

(SEQ ID NO.: 93)
5'-CACTTAAACAGCATCTGCTGGTTGAAG-3'

(SEQ ID NO.: 81)
5'-TGGAGATGACGGAGAAGATG-3'

(SEQ ID NO.: 82)
5'-TTGGATGGCAAAGGCAGT-3'

TUBA1B
                                     (SEQ ID NO.: 94)
5'-ACCTTAACCGCCTTATTAGCCA-3'

(SEQ ID NO.: 95)
5'-ACATTCAGGGCTCCATCAAATC-3'

CXCL10
                                     (SEQ ID NO.: 96)
5'-GCTACCTACATACAATTCCAAACACATAC-3'

(SEQ ID NO.: 97)
5'-GTACTTAATTACATGTTATTCCATGTACACTGAAAAC-3'

(SEQ ID NO.: 83)
5'-GTCAGGTTGCCTCTGTCTCA-3'

(SEQ ID NO.: 84)
5'-TCAGGGAAGAGTCTGGAAAG-3'

CCL5
                                     (SEQ ID NO.: 85)
5'-GCCCACGTCAAGGAGTATTTCTA-3'

(SEQ ID NO.: 86)
5'-ACACACTTGGCGGTTCCTTC-3'

IL-6
                                     (SEQ ID NO.: 87)
5'-AGGCATAACGCACTAGGTTT-3'

(SEQ ID NO.: 88)
5'-AGCTGGAGTCACAGAAGGAG-3'

GAPDH
                                     (SEQ ID NO.: 89)
5'-ATCAAGAAGGTGGTGAAGCA-3'

(SEQ ID NO.: 90)
5'-AGACAACCTGGTCCTCAGTGT-3'
```

PCR was accomplished using KOD Hot Start DNA polymerase (EMD Millipore) according to manufacturer's instructions. ImageJ (v 1.47q) was used for quantitation of amplicons using TUBA1B for normalization.

Cell Culture 293T cells (Life Technologies, Carlsbad, Calif.) were grown in DMEM supplemented with 10% fetal bovine serum (FBS), 1 mM sodium pyruvate, 1×MEM nonessential amino acids and 100 U/ml Penicillin/Streptomycin (Life Technologies).

Luciferase Assay

HEK293T cells in the following Examples were reverse-transfected with STING expression plasmids and reporter constructs. 12 hrs later, DMXAA was added directly, while cGAMP isomers and c[di-GMP] were delivered with digitonin permeabilization. Luciferase expression was determined after another 12 hrs, or 30 hrs when transfected together with a cGAS-expression plasmid.

For cGAMP Luciferase Assays, $3\times10^4$ HEK293T cells (Life Technologies, Carlsbad, Calif.) per 96-well were reverse-transfected with a mix of pGL3-IFNB1-Gluc (50 ng), pLenti-EF1-Fluc (10 ng), pMAX-Flag-STING (5 ng) and 35 ng empty plasmid (pMAX-cloning; Amaxa, Cologne, Germany) using Trans-IT LT1 Reagent (MirusBio, Madison, Wis.). 12 h after transfection, cGAMP isomers (synthesized by Roger Jones) and c[di-GMP] (Invivogen, San Diego, Calif.) were delivered with digitonin permeabilization as described (Woodward et al., 2010). DMXAA (Sigma) was diluted in fresh medium added to transfected cells. Luciferase expression was determined after 12 h. For stimulation by cGAS, cells were transfected as described above, but instead of empty plasmid pLenti(p)-EF1-Flag-mm-cGAS (WT or non-functional E211A mutation) was used, and Luciferase expression was determined 30 h after transfection. In this setting, expression plasmid served as cGAS stimulus at the same time. Cells were lysed in Passive Lysis Buffer. Firefly and gaussia luciferase activities were determined on an EnVision reader (Perkin Elmer, Waltham, Mass.) using their respective substrates (D-Luciferin and coelenterazine, PJK GmbH, Kleinblittersdorf, Germany) according to standard protocols. IFNB1-Gluc values were normalized to constitutive firefly luciferase values and fold induction was calculated in relation to control-plasmid pMAX-GFP.

Luciferase assays for DMXAA experiments were performed as described above. Briefly, 3×10$^4$ 293T cells were reverse-transfected with STING constructs (5 ng per 96-well) and reporter constructs (50 ng pIFNβ-Gluc, 10 ng pLenti-EF1-Fluc for normalization, 35 ng pMAX-empty as stuffer, delivered with TransIT-LT1, MirusBio, Madison Wis.). 12 hours after transfection, medium was replaced with fresh Medium containing DMXAA. 12 hours after stimulation with STING-ligands, cells were resuspended in passive lysis buffer and luciferase activity was determined using the respective substrates Coelenterazine and D-Luciferin (PJK, Kleinblittersdorf, Germany). Gaussia Luciferase values were then normalized to constitutive Firefly Luciferase values (resulting in Relative Light Units, RLU).

ELISA

CXCL10 was measured using the BD Opteia human IP-10 ELISA Set according to manufacturer's recommendations. Murine IFN-α was determined by ELISA using antibody RMMA-1 for capture and rabbit-anti-murine IFN-α polyclonal antibody for detection (PBL Interferon Source, Piscataway, N.J.). Dose-response curves were fitted and EC$_{50}$ values were determined with Graphpad Prism (Graph Pad Software Inc., San Diego, Calif.).

Western Blot Analysis

BMDMs (1×10$^6$) were treated with cGAMP linkage isomers. At various times post-stimulation, the medium was removed and cells were collected. Whole-cell lysates were prepared at 2, 4, and 8 h post-treatment. Equal amounts of proteins were subjected to SDS-PAGE and transferred to a nitrocellulose membrane. Phosphorylation of IRF3 was determined using a rabbit polyclonal antibody specific for phosphoserine-396 of IRF3 (Cell signaling). The level of IRF3 was determined by using a rabbit polyclonal antibody against IRF3. Phosphorylation of TBK1 was determined using a rabbit monoclonal antibody specific for phosphoserine-172 of TBK1 (Cell Signaling). The level of TBK1 was determined by using a rabbit monoclonal antibody against TBK1 (Cell Signaling). Anti-glyceraldehyde-3-phosphate dehydrogenase (GADPH) was used as loading controls.

BMDCs (1×10$^6$ cells) were infected with retroviruses carrying WT hSTING and various hSTING mutants. Cells were collected at 2 days post retroviral infection. Whole-cell lysates were prepared by lysing cells in RIPA buffer. Equal amounts of proteins were subjected to SDS-PAGE and transferred to a nitrocellulose membrane. The levels of HA-hSTING in transduced cells were determined by using a mouse monoclonal antibody specific for HA tag (Covance). Anti-glyceraldehyde-3-phosphate dehydrogenase (GAPDH) was used as a loading control, and was detected using a polyclonal antibody against GAPDH (Cell Signaling).

Example 1: Crystal Structure of c[G(2',5')pA(3',5')p] Bound to hSTING$^{H232}$

The present Example presents the 2.25 Å crystal structure of an ~186 amino acid human STING polypeptide bound to c[G(2',5')pA(3',5')p].

The 2.25 Å crystal structure of c[G(2',5')pA(3',5')p] bound to the symmetrical dimer of human STING (G230/H232; aa 155-341; termed hSTING$^{H232}$) is shown in FIG. 1A (x-ray statistics in Table S1). The individual symmetry-related subunits of STING in a ribbon representation are color-coded in magenta and yellow, while the bound c[G(2',5')pA(3',5')p] is shown in a space-filling representation. The bound ligand is positioned in a deep U-shaped cleft between subunits, with the cyclic sugar-phosphate backbone at the base and the purine rings pointing upwards in a parallel alignment (expanded view in FIG. 1B). The bound U-shaped ligand is further anchored in place by an overhead cap element formed on complex formation by an anti-parallel four-stranded β-pleated sheet (FIG. 2A), such that the hSTING dimer completely envelops the bound ligand (FIG. 1C, D).

TABLE S1

X-ray Statistics for cGAMP Linkage Isomers with hSTING$^{H232}$
Data collection and refinement statistics of hSTING with Ligands

| Crystal | hSTING$^{H232}$ + c[G(2',5')pA(3',5')p] | hSTING$^{H232}$ + c[G(2',5')pA(2',5')p] |
|---|---|---|
| Beam line | NSLS-X29A | NSLS-X29A |
| Wavelength | 1.075 | 1.075 |
| Space group | P1 | P2$_1$2$_1$2 |
| Unit cell | | |
| a, b, c (Å) | 36.5, 59.2, 59.2 | 94.1, 116.7, 36.2 |
| α, β, γ (°) | 84.0, 85.8, 85.9 | 90.0, 90.0, 90.0 |
| Resolution (Å) | 50-2.3 (2.33-2.25)$^a$ | 50-1.9 (1.97-1.90)$^a$ |
| R$_{merge}$ | 0.026 (0.284) | 0.060 (0.382) |
| I/σ (I) | 45.4 (5.1) | 40.8 (5.8) |
| Completeness (%) | 97.9 (97.1) | 99.8 (100) |
| Redundancy | 3.9 (3.9) | 6.7 (6.5) |
| Number of unique reflections | 22653 | 32537 |
| Wilson B factors (Å$^2$) | 22.24 | 20.11 |
| R$_{work}$/R$_{free}$ (%) | 18.63/21.53 | 17.6/19.9 |
| Number of non-H atoms | | |
| Protein | 2960 | 2914 |
| Water | 127 | 227 |
| Ligands(molecule) | 1 | 1 |
| Average B factors (Å$^2$) | | |
| Protein | 36.09 | 31.42 |
| Water | 32.08 | 37.06 |
| ligands | 16.35 | 19.01 |
| R.m.s. deviations | | |
| Bond lengths (Å) | 0.020 | 0.018 |

$^a$Highest resolution shell (in Å) shown in parentheses.

Relates to FIGS. 1, 2 and 3.

The binding pocket is uncharged at its base, while both positive- and negative-charged residues line its walls. The bound c[G(2',5')pA(3',5')p] is anchored by its purine bases being bracketed on either side by Y167 (FIG. 1E) and by R238 (whose position is buttressed by Y240), with R238 aligned in the plane and hydrogen bonds to the N7 of one purine, while its guanidinium group stacks over the other purine of the bound cyclic dinucleotide (FIG. 1E, F, G). The bound ligand is further stabilized through a network of direct and water-mediated hydrogen bonds to the base edges from side chains of hSTING$^{H232}$ (FIG. 1F, G). Amino acids participating in this network and positioned above the bound ligand include N242, S241 and V239 which form water-mediated hydrogen bonds to the O6 of guanosine, while Y163, E260, and Y261 form water-mediated hydrogen bonds together with a direct hydrogen bond from T263 to the NH₂ group of guanosine (FIG. 1F). The edges of the adenosine base are not involved in hydrogen-bond formation (FIG. 1F).

The phosphate backbone and ribose hydroxyls of the cyclic dinucleotide ring system are additionally stabilized through hydrogen bonds. Amino acids participating in this network and positioned below the bound ligand include S162 and T267 (FIG. 1G), with the 3'-OH group of the guanosine hydrogen-bonded to the side chain hydroxyl of S162, while no hydrogen-bonding is observed to the 2'-OH of adenosine of c[G(2',5')pA(3',5')p] in the complex (FIG. 1G). The backbone phosphates of the bound cyclic dinucleotide are recognized by direct contacts from the guanidinium groups of R238 and through water-mediated hydrogen bonds from the hydroxyl groups of T267 and Y240 (FIG. 1G).

The four-stranded anti-parallel β-sheet that forms upon c[G(2',5')pA(3',5')p]-hSTING$^{H232}$ complex formation (FIG. 2A) caps the top of the binding pocket and restricts access to it (FIG. 1A). In addition to hydrogen-bonding between strands across the four-stranded β-pleated sheet, anchoring at either end of the sheet is achieved by salt bridges (FIG. 2A). It should be noted that G230 forms part of the outer β-strand of this four-stranded β-sheet (FIG. 2A).

Example 2: Comparison of Crystal Structures of c[G(2',5')pA(3',5')p] and c[di-GMP] Bound to hSTING$^{H232}$ The present Example describes the binding cleft of human STING and presents "open" and "closed" STING complex structure.

Figures 8C, 8D:
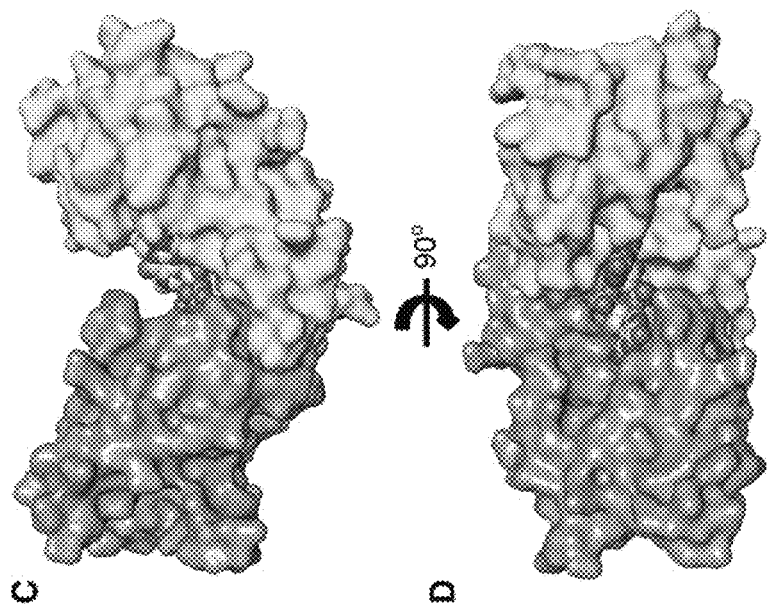
FIG. 8C depicts an exemplary surface representation of an exemplary structure of a complex of c[di-GMP] bound to human STING$^{H232}$ (aa 139-379) (PDB: 4EF4) with the same color-coding as in FIG. 1A.
FIG. 8D depicts an exemplary view in panel C rotated through 90°.
Figures 8A, 8B:
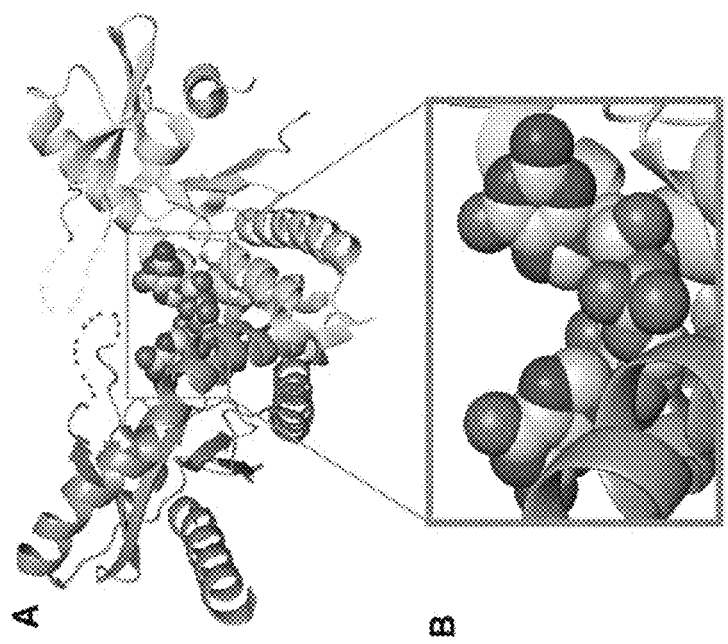
FIG. 8A depicts an exemplary 2.15 Å crystal structure of c[di-GMP] bound to hSTING$^{H232}$ (aa 139-379) (PDB: 4EF4). The representations and color codes are the same as used in FIG. 1A. Note that the two loops that protrude over the binding pocket are disordered for about half their lengths as one proceeds towards the tips of these loops.
FIG. 8B depicts an exemplary expanded view of the c[di-GMP] binding pocket in the complex.

An exemplary crystal structures of c[di-GMP] bound to the symmetrical dimer of hSTING$^{H232}$ (aa 139-379) (PDB: 4EF4; 2.15 Å resolution) is shown in FIG. 8A, with an expanded view of the ligand binding pocket shown in FIG. 8B. Note that the loops protruding over the binding pockets are disordered over half their lengths in the direction of their tips, while the symmetry-related α2-helices form a larger angle in the V-shaped c[di-GMP] complex (FIG. 8A), as compared to the U-shaped c[G(2',5')pA(3',5')p] complex (FIG. 1A) with hSTING$^{H232}$. Indeed, space filling views of the c[di-GMP] complex indicate that the hSTING$^{H232}$ dimer does not encapsulate the bound c[di-GMP] in its complex (FIG. 10C, D; termed the 'open' STING complex), as it does in space filling views of the c[G(2',5')pA(3',5')p] complex (FIG. 1C, D; termed the 'closed' STING complex) with hSTING$^{H232}$.

Figure 8E:
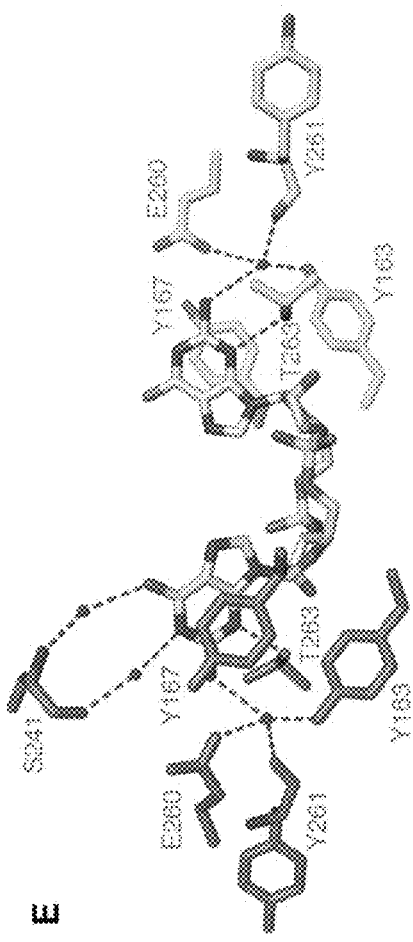
FIG. 8E and FIG. 8F depicts exemplary intermolecular contacts in the complex of c[di-GMP] bound to hSTING$^{H232}$. The bound cyclic c[di-GMP] is shown in biscuit color, with individual STING subunits in the symmetrical dimer shown in magenta and yellow. The intermolecular contacts to the base edges of the ligand by the magenta and yellow subunits of STING are shown in panel E, while the intermolecular contacts to the backbone phosphates of the ligand by STING are shown in panel F.
Figure 8F:
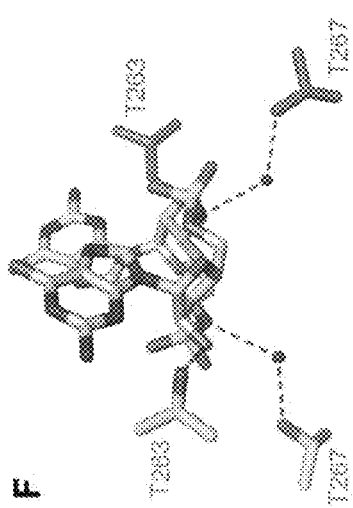

The intermolecular hydrogen bonds stabilizing complex formation in the exemplary structure of the complex of c[di-GMP] with hSTING$^{H232}$ (PDB: 4EF4) are shown in FIG. 8E, F. Notably, the side chains of R238 are disordered, unlike the key recognition role they play in the complex of c[G(2',5')pA(3',5')p] with hSTING$^{H232}$ (FIG. 1F, G).

The superposition of c[di-GMP] bound to the 'open' hSTING complex (both subunits in beige) with that for c[G(2',5')pA(3',5')p] bound to the 'closed' hSTING complex (both subunits in green) shows large conformational differences in STING between the two complexes (FIG. 2B; rmsd=3.11 Å). Indeed, the separation between the tips of the symmetry related α2-helices decreases from approx. 60 Å in the 'open' complex to approx. 38 Å in the 'closed' complex. Furthermore, superposition of the bound c[di-GMP] in beige with that of bound c[G(2',5')pA(3',5')p] in green establishes that the purine bases are further apart in the former complex compared to the latter complex (FIG. 2C), and presumably facilitate switching of the hSTING$^{H232}$ from an 'open' and more flexible (partly disordered loops positioned over the binding pocket) conformation in the c[di-GMP] complex (FIG. 8A) to a 'closed' and more compact (well defined four-stranded β-sheet cap over the binding pocket) conformation in the c[G(2',5')pA(3',5')p] complex (FIG. 1A). Furthermore, the bound c[G(2',5')pA(3',5')p] (in green) is positioned slightly deeper in the binding cleft than its bound c[di-GMP] counterpart (in beige) (FIG. 2C, top panel). Importantly, the conformational changes propagate to the surface of the STING protein as shown in a stereo view (FIG. 2D) highlighting the upper right segment of FIG. 2B.

Example 3: Similar 'Closed' Conformations Adopted by c[G(2',5')pA(3',5')p] Bound to mSting$^{R231}$ and hSTING$^{H232}$ The present Example describes the 1.77 Å crystal structure of an ~186 amino acid mouse STING polypeptide bound to c[G(2',5')pA(3',5')p].

Figure 3A:
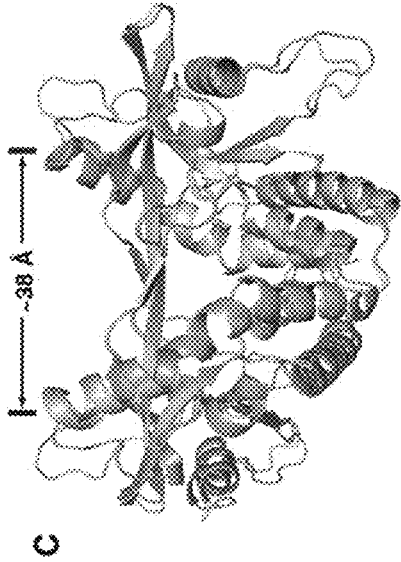
FIG. 3A depicts an exemplary 1.77 Å crystal structure of c[G(2',5')pA(3',5')p] bound to mSting$^{R231}$ (aa 154-340).

We have solved the 1.77 Å crystal structure of c[G(2',5')pA(3',5')p] bound to the symmetrical dimer of mSting$^{R231}$ (aa 154-340) (FIG. 3A and Table S2). The side chain of R231 of mSting$^{231}$ is shown in green in a stick representation (FIG. 3A). Given the high resolution of this complex, the network of hydrogen bonds are clearly visible; the 3'-OH of guanosine of bound c[G(2',5')pA(3',5')p] makes hydrogen bonds with the side chain of S161 and two water molecules (FIG. 3B). The guanidinium group of R231 interacts with the backbone phosphates of c[G(2',5')pA(3',5')p] through a bridging water molecule (FIG. 3B). Formation of the four-stranded anti-parallel β-pleated sheet acts as a cap over the bound ligand in the complex (FIG. 3A).

TABLE S2

X-ray Statistics for cGAMP Linkage Isomers and DMXAA with mSting$^{231}$
Data collection and refinement statistics of mSting with Ligands

| Crystal | mSting$^{R231}$ + c[G(2',5')pA(3',5')p] | mSting$^{R231}$ + c[G(3',5')pA(3',5')p] | mSting$^{R231}$ + DMXAA |
|---|---|---|---|
| Beam line | NSLS-X29A | NSLS-X29A | APS-24ID-E |
| Wavelength | 1.075 | 1.075 | 0.9792 |
| Space group | P2₁2₁2₁ | P2₁2₁2₁ | H3 |
| Unit cell | | | |
| a, b, c (Å) | 46.2, 46.5, 157.9 0. | 46.4, 47.4, 156.2 | 108.4, 108.4, 101.2 |
| α, β, γ (°) | 90.0, 90.0, 90.0 | 90.0, 90.0, 90.0 | 90.0, 90.0, 120.0 |
| Resolution (Å) | 50-1.8 (1.83-1.77)$^a$ | 50-2.1 (2.14-2.07)$^a$ | 50-2.4 (2.57-2.43)$^a$ |
| R$_{merge}$ | 0.050 (0.351) | 0.075 (0.542) | 0.046 (0.397) |
| I/σ (I) | 38.6 (4.5) | 29.8 (3.4) | 18.2 (3.4) |
| Completeness (%) | 96.5 (94.0) | 97.5 (94.3) | 99.5 (100) |

TABLE S2-continued

X-ray Statistics for cGAMP Linkage Isomers and DMXAA with mSting[231]
Data collection and refinement statistics of mSting with Ligands

| Crystal | mSting[R231] + c[G(2',5')pA(3',5')p] | mSting[R231] + c[G(3',5')pA(3',5')p] | mSting[R231] + DMXAA |
|---|---|---|---|
| Redundancy | 7.2 (7.2) | 8.0 (8.1) | 4.7 (4.8) |
| Number of unique reflections | 31300 | 20191 | 15773 |
| Wilson B factors (Å$^2$) | 17.73 | 28.34 | 49.02 |
| $R_{work}/R_{free}$ (%) | 19.1/21.2 | 17.7/23.6 | 16.1/18.9 |
| Number of non-H atoms | | | |
| Protein | 2889 | 2908 | 2870 |
| Water | 218 | 139 | 41 |
| Ligands (molecule) | 1 | 1 | 2 |
| Average B factors (Å$^2$) | | | |
| Protein | 24.94 | 42.95 | 63.36 |
| Water | 30.18 | 37.91 | 44.66 |
| ligands | 15.29 | 37.60 | 43.34 |
| R.m.s. deviations | | | |
| Bond lengths (Å) | 0.018 | 0.015 | 0.014 |
| Bond angles (°) | 2.005 | 1.843 | 1.741 |

[a] Highest resolution shell (in Å) shown in parentheses.

Relates to FIGS. 3 and 5.

Figure 3C:
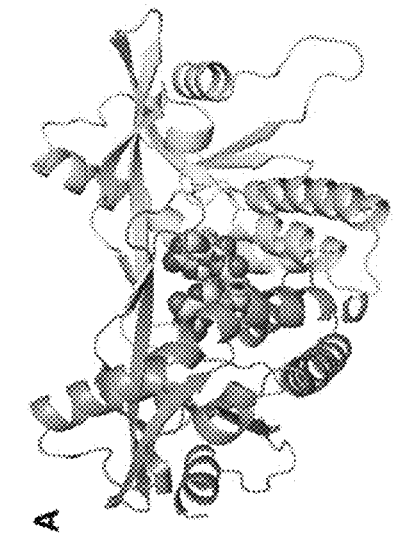
FIG. 3C depicts an exemplary superposition of the c[G(2',5')pA(3',5')p] bound structures of hSTING$^{H232}$ (both subunits in green) and mSTING$^{R231}$ (both subunits in magenta).
Figure 3B:
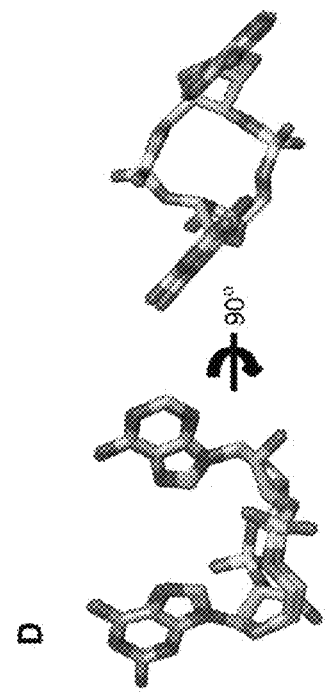
FIG. 3B depicts exemplary intermolecular contacts to the cyclic dinucleotide ring system of the ligand by the subunits of mSting$^{R231}$.
Figure 3D:
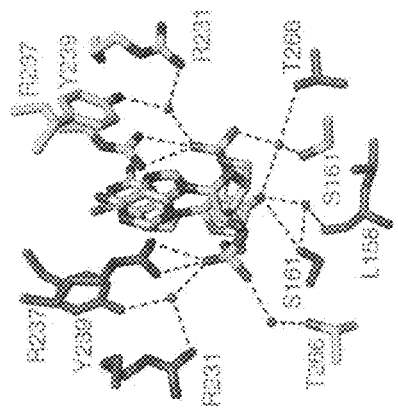
FIG. 3D depicts an exemplary superposition of the c[G(2',5')pA(3',5')p] in its complexes with hSTING$^{H232}$ in green and mSTING$^{R231}$ in magenta.

We observe excellent superposition of hSTING[H232] (both subunits in green) and mSting[R231] (both subunits in magenta) in its complexes with c[G(2',5')pA(3',5')p] as shown in FIG. 3C (rmsd=0.84 Å). The separation between the tips of symmetry related α2-helices are approx. 38 Å for both complexes (FIG. 3C). We also observe excellent superposition of the c[G(2',5')pA(3',5')p] dinucleotide in its complexes with hSTING[H232] and mSting[R231] (FIG. 3D). Thus, the same c[G(2',5')pA(3',5')p]-STING complex is observed whether a His or Arg occupies this key position. Indeed, the R238, S162 and T267 in hSTING[H232] (FIG. 1H) and their conserved counterparts R237, S161 and T266 in mSting[R231] (FIG. 3B) are involved in similar hydrogen-bonding interactions with the backbone phosphates and sugar hydroxyl groups in both complexes.

Example 4: c[G(2',5')pA(2',5')p]- and c[G(3',5')pA(3',5')p]-Bound STING Complexes Both Adopt 'Closed' Conformations The present Example describes the 1.9 Å crystal structure of an ~186 amino acid human STING polypeptide bound to c[G(2',5')pA(2',5')p]. The present Example also describes the 2.1 Å crystal structure of an ~186 amino acid mouse STING polypeptide bound to c[G(3',5')pA(3',5')p].

Figure 3E:
FIG. 3E depicts an exemplary 1.9 Å crystal structure of c[G(2',5')pA(2',5')p] bound to hSTING$^{H232}$ (aa 155-341).
Figure 3F:
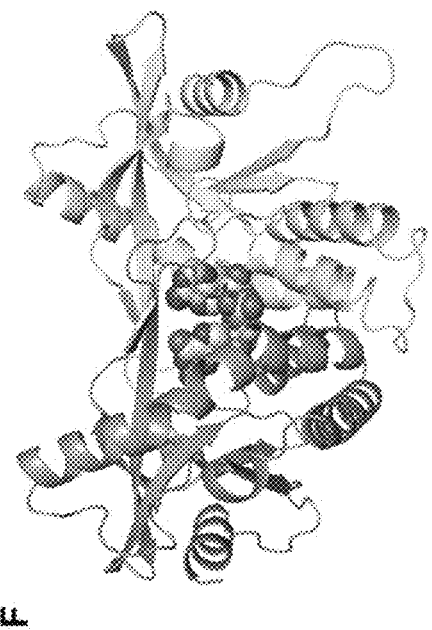
FIG. 3F depicts an exemplary 2.1 Å crystal structure of c[G(3',5')pA(3',5')p] bound to mSting$^{R231}$ (aa 154-340).

We also crystallized the two other cGAMP linkage isomers c[G(2',5')pA(2',5')p] and c[G(3',5')pA(3',5')p] with hSTING[H232] and mSting[R231], respectively. We solved a 1.9 Å crystal structure of c[G(2',5')pA(2',5')p] with hSTING[H232] (aa 155-341) (FIG. 3E and Table S1) and a 2.1 Å crystal structure of c[G(3',5')pA(3',5')p] with mSting[R231] (aa 154-340) (FIG. 3F and Table S2). The structures of both complexes adopt the 'closed' conformation as reflected by the positioning of the ligands in the binding pocket, the separation between the tips of the α2-helices by approx. 38 Å, and the formation of the four-stranded anti-parallel β-sheet cap over the bound ligands (FIG. 3E, F).

The crystal structures of c[G(2',5')pA(2',5')p] (in red) and c[G(2',5')pA(3',5')p] (in green) in their bound complexes with hSTING[H232] superimpose with an rmsd of 0.59 Å (FIG. 9A), with the 3'-OH groups of bound c[G(2',5')pA(2',5')p] forming water-mediated hydrogen bonds to the hydroxyls of S162 and T267 (FIG. 9B). The crystal structures of c[G(3', 5')pA(3',5')p] (in cyan) and c[G(2',5')pA(3',5')p] (in magenta) in their bound complexes with mSting[R321] superimpose with an rmsd of 0.25 Å (FIG. 9C), with the 2'-OH groups of bound c[G(3',5')pA(3',5')p] forming direct hydrogen bonds to the hydroxyls of T262 (FIG. 9D). The bound c[G(2',5')pA(2',5')p] (in red) is positioned somewhat deeper in the binding pocket than c[G(3',5')pA(3',5')p] (in cyan) (FIG. 9E).

Example 5: ITC Binding Studies of hSTING[H232] and its Mutants with Linkage Isomers of cGAMP The present Example describes isothermal titration calorimetric (ITC) binding curves for a human STING polypeptide bound with various linkage isomers of cGAMP including c[G(2',5')pA(2',5')p], c[G(3',5')pA(3',5')p], or c[G(2',5')pA(3',5')p].

Figure 4B:
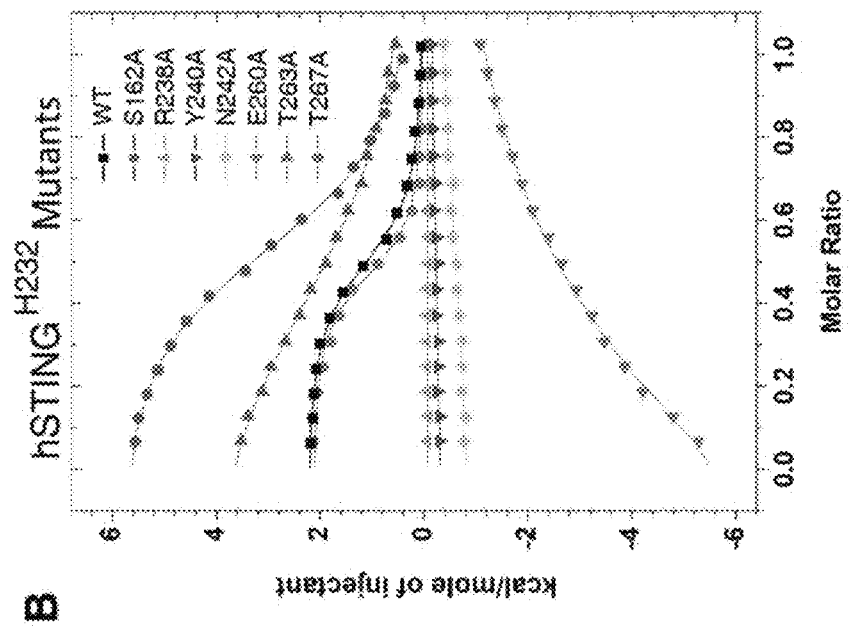
FIG. 4A and FIG. 4B depicts exemplary ITC binding curves for complex formation between cGAMP linkage isomers bound to hSTING$^{H232}$ (aa 140-379) (panel A) and binding of c[G(2',5')pA(3',5')p] to mutants of hSTING$^{H232}$ (panel B).
Figure 4A:
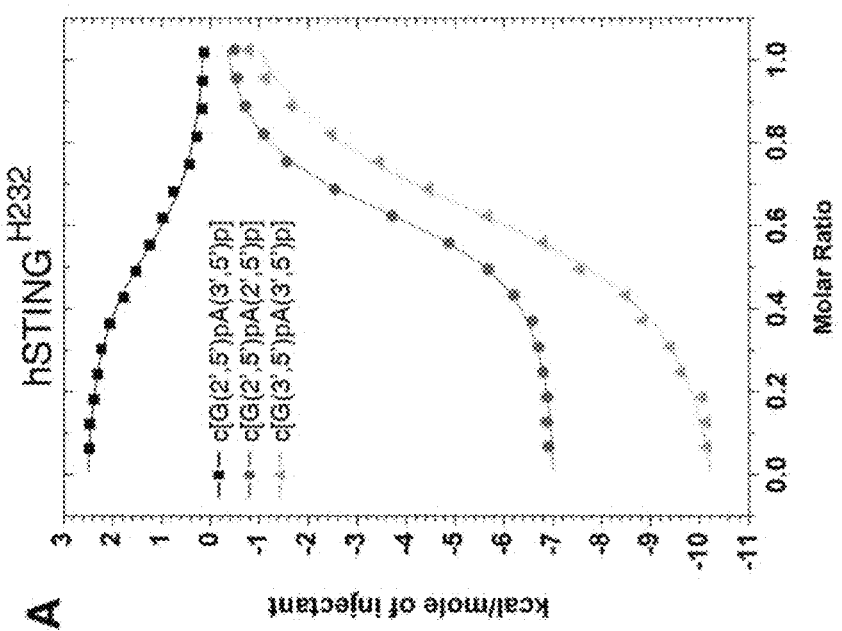
Figure 4D:
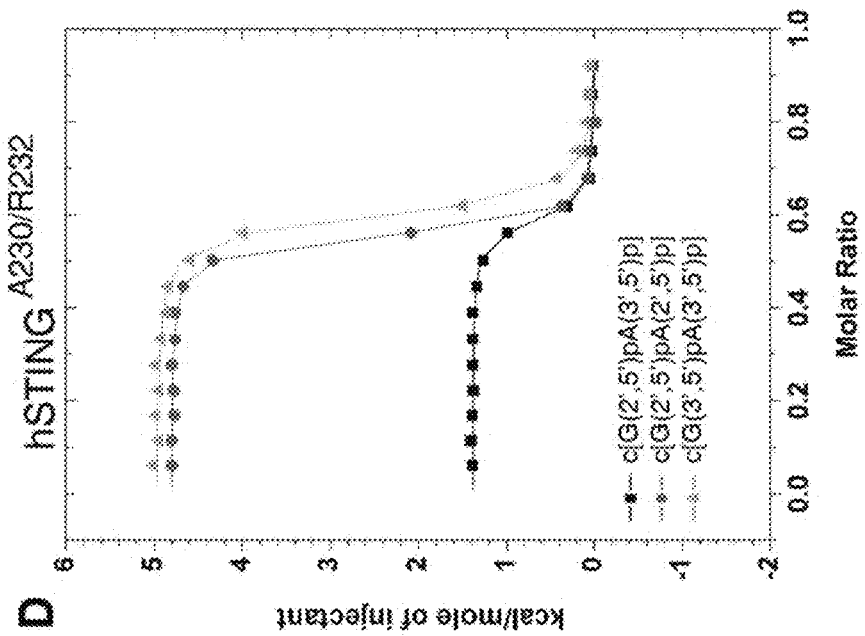
FIG. 4D depicts exemplary ITC binding curves for complex formation between cGAMP linkage isomers bound to hSTING$^{A230/R232}$ (aa 140-379).

We recorded the isothermal titration calorimetric (ITC) binding curves for hSTING[H232] (aa 140-379) with three linkage isomers of cGAMP as shown in FIG. 4A. The binding curves are exothermic for complex formation with c[G(2',5')pA(2',5')p] (red circles) and c[G(3',5')pA(3',5')p] (green triangles), and endothermic for complex formation with c[G(2',5')pA(3',5')p] (black squares; $K_D$=5.3 μM). The thermodynamic $K_D$, ΔG, ΔH and TΔS parameters for these complexes are listed in Table S3.

TABLE S3

ITC Parameters for Binding of cGAMP Linkage Isomers to hSTING and mSting Alleles

| | N | $K_D$ (μM) | ΔG (Kcal/mol) | ΔH (Kcal/mol) | TΔS (Kcal/mol) |
|---|---|---|---|---|---|
| hSTING[H232] with cGAMP Isomers Protein: 0.2 mM; Ligands: 1 mM; Buffer: 30 mM HEPES, 100 mM NaCl, pH 7.5; T: 25° C. | | | | | |
| c[G(3',5')pA(3',5')p] | 0.61 | 5.4 ± 0.1 | −7.01 | −10.62 | −3.61 |
| c[G(2',5')pA(2',5')p] | 0.62 | 2.5 ± 0.1 | −7.52 | −7.15 | +0.37 |
| c[G(2',5')pA(3',5')p] | 0.54 | 5.3 ± 0.5 | −7.19 | +2.62 | +9.81 |

TABLE S3-continued

ITC Parameters for Binding of cGAMP Linkage
Isomers to hSTING and mSting Alleles

| | N | $K_D$ (µM) | ΔG (Kcal/mol) | ΔH (Kcal/mol) | TΔS (Kcal/mol) |
|---|---|---|---|---|---|
| hSTING$^{R232}$ with cGAMP Isomers Protein: 0.2 mM; Ligands: 0.9 mM; Buffer: 30 mM HEPES, 100 mM NaCl, pH 7.5; T: 25° C. | | | | | |
| c[G(3',5')pA(3',5')p] | 0.61 | 1.4 ± 0.1 | −7.99 | −1.13 | +6.86 |
| c[G(2',5')pA(2',5')p] | 0.54 | 0.17 ± 0.02 | −9.25 | +5.63 | +14.88 |
| c[G(2',5')pA(3',5')p] | 0.52 | 0.11 ± 0.01 | −9.50 | +2.78 | +12.28 |
| hSTING$^{A230/R232}$ with cGAMP Isomers Protein: 0.2 mM; Ligands: 0.9 mM; Buffer: 30 mM HEPES, 100 mM NaCl, pH 7.5; T: 25° C. | | | | | |
| c[G(3',5')pA(3',5')p] | 0.57 | 0.16 ± 0.02 | −9.26 | +4.93 | +14.19 |
| c[G(2',5')pA(2',5')p] | 0.53 | 0.13 ± 0.02 | −9.39 | +4.74 | +14.13 |
| c[G(2',5')pA(3',5')p] | 0.56 | 0.16 ± 0.01 | −9.28 | +1.39 | +10.67 |
| mSting$^{R231}$ with cGAMP Isomers Protein: 0.2 mM; Ligands: 0.9 mM; Buffer: 30 mM HEPES, 100 mM NaCl, pH 7.5; T: 25° C. | | | | | |
| c[G(3',5')pA(3',5')p] | 0.55 | 0.26 ± 0.03 | −8.99 | +3.95 | +12.94 |
| c[G(2',5')pA(2',5')p] | 0.52 | 0.18 ± 0.02 | −9.20 | +3.92 | +13.12 |
| c[G(2',5')pA(3',5')p] | a | | | | |
| mSting$^{A231}$ with cGAMP Isomers Protein: 0.2 mM; Ligands: 1.0 mM; Buffer: 30 mM HEPES, 100 mM NaCl, pH 7.5; T: 25° C. | | | | | |
| c[G(3',5')pA(3',5')p] | 0.42 | 1.34 ± 0.14 | −8.01 | −7.36 | +0.65 |
| c[G(2',5')pA(2',5')p] | a | | | | |
| c[G(2',5')pA(3',5')p] | 0.41 | 0.34 ± 0.04 | −8.80 | +3.63 | +12.43 | a Values could not be measured due to precipitation of complex

Relates to FIG. 4.

We also recorded ITC binding curves for complex formation of c[G(2',5')pA(3',5')p] with mutants of hSTING$^{H232}$ that participate in intermolecular contacts on complex formation. For this linkage isomer, cGAMP binding is completely lost (FIG. 4B and Table S4) for the R238A mutant involved in cyclic dinucleotide base N7 and backbone phosphate recognition (FIG. 1E, F, G), as well as for the Y240A, N242A and E260A (significantly reduced) mutants involved in water-mediated guanosine base edge recognition (FIG. 1F). The impact of mutating the polar Thr and Ser residues involved in intermolecular hydrogen bond formation is more nuanced, with no effect on binding affinity for the T267A mutant, a modest reduction for the S162A mutant and a more pronounced reduction for the T263A mutant (FIG. 1B). The thermodynamic parameters are listed in Table S4.

TABLE S4

ITC Parameters for Binding of c[G(2',5')pA(3',5')p]
to hSTING$^{H232}$ Mutants
hSTING$^{H232}$ Mutants with c[G(2',5')pA(3',5')p]
Protein: 0.3 mM; Ligands: 1.5 mM; Buffer: 30 mM HEPES,
100 mM NaCl, pH 7.5, T: 25° C.

| | N | $K_D$ (µM) | ΔG (Kcal/mol) | ΔH (Kcal/mol) | TΔS (Kcal/mol) |
|---|---|---|---|---|---|
| T267A | 0.43 | 2.91 ± 0.35 | −7.59 | +2.25 | +9.84 |
| T263A | 0.52 | 41.67 ± 2.29 | −5.97 | +4.76 | +10.73 |
| E260A | UD | UD; >200 | | | |
| N242A | UD | UD; >200 | | | |
| Y240A | UD | UD; >200 | | | |
| R238A | UD | UD; >200 | | | |
| S162A | 0.55 | 10.66 ± 0.48 | −7.20 | +5.59 | +12.79 |
| WT | 0.47 | 4.39 ± 0.23 | −7.29 | +2.28 | +9.57 |

Relates to FIG. 4.

Figure 4C:
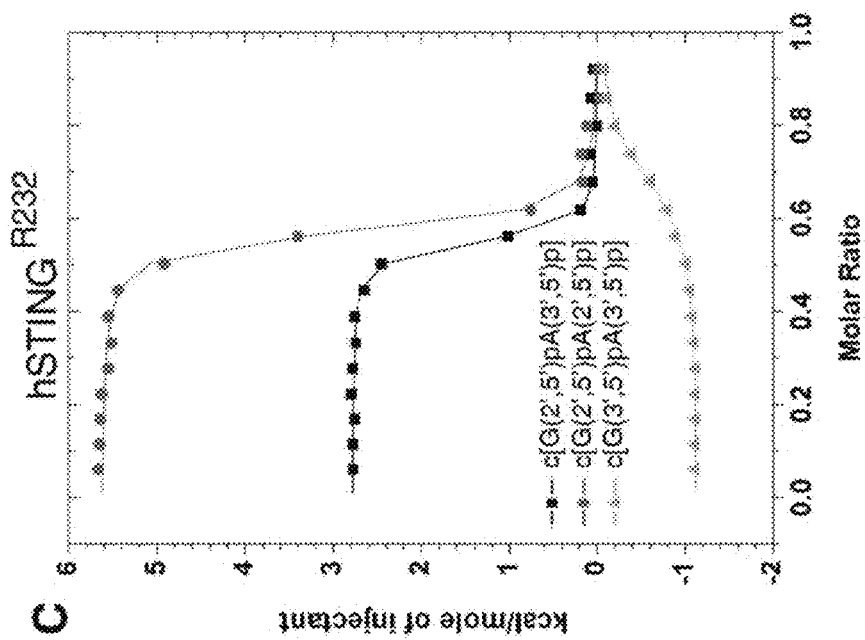
FIG. 4C depicts exemplary ITC binding curves for complex formation between cGAMP linkage isomers bound to hSTING$^{R232}$ (aa 140-379).
Figure 4F:
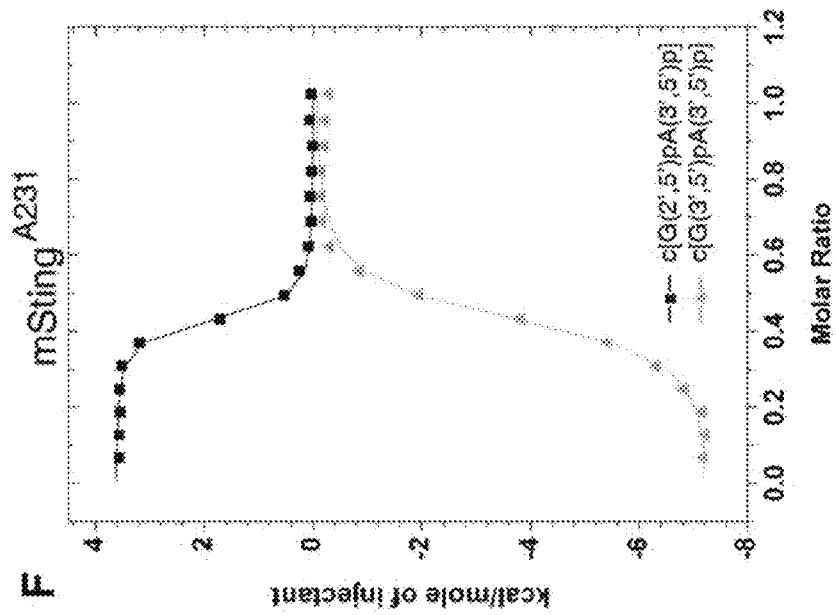
FIG. 4F depicts exemplary ITC binding curves for complex formation between cGAMP linkage isomers bound to mSting$^{A231}$ (aa 139-378).

ITC Binding Studies of hSTING$^{R232}$ and hSTING$^{A230/R232}$ with Linkage Isomers of cGAMP The corresponding ITC-based thermodynamic parameters were also recorded for complex formation of cGAMP linkage isomers with hSTING$^{R232}$ and hSTING$^{A230/R232}$ (aa 140-379) (FIG. 4C, D, respectively). The 2',5'-containing linkage isomers of cGAMP exhibited increased binding affinity by about an order of magnitude for STING variants with R232 compared to H232, while the corresponding binding affinity increase was about 4-fold for the all-3',5' linkage isomer of cGAMP (Table S3), with endothermic titration patterns observed for all binding curves, except for an exothermic titration pattern for c[G(3',5')pA(3',5')p] with hSTING$^{R232}$ (FIG. 4C). The dissociation constants for c[G(2',5')pA(3',5')p] bound to hSTING$^{R232}$ and hSTING$^{A230/R232}$ were $K_D$=0.11 µM and 0.16 µM, respectively (Table S3).

Figure 4E:
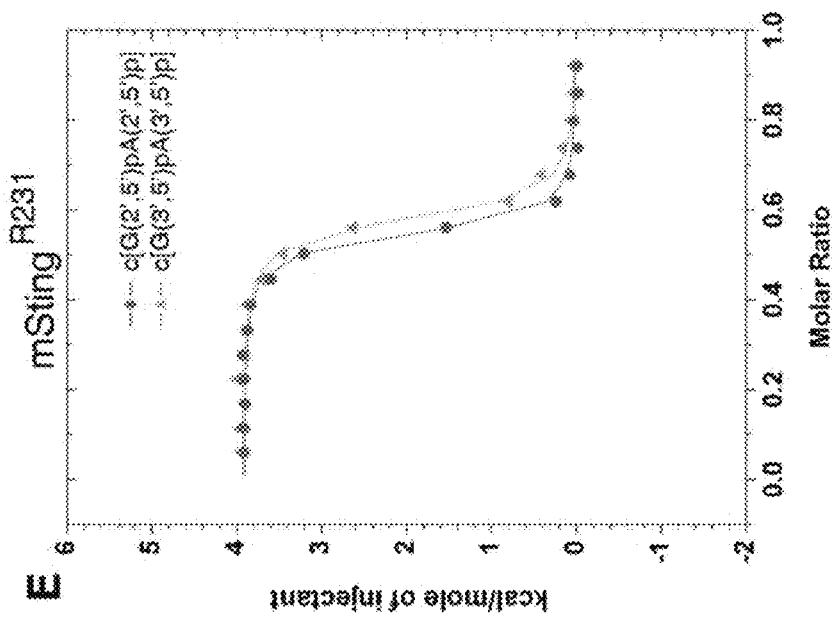
FIG. 4E depicts exemplary ITC binding curves for complex formation between cGAMP linkage isomers bound to mSting$^{R231}$ (aa 139-378).

ITC Binding Studies of mSting$^{R231}$ and mSting$^{A231}$ with Linkage Isomers of cGAMP The corresponding ITC-based thermodynamic parameters for complex formation of cGAMP linkage isomers with mouse Sting$^{R231}$ (I229/R231; aa 139-378) are plotted in FIG. 4E, with observed $K_D$ values similar to those observed for hSTING$^{A230/R232}$ (Table S3). The ITC titrations for mSting$^{A231}$ with the various cGAMP linkage isomers are plotted in FIG. 4F, with the observed $K_D$ values listed in Table S3. The dissociation constants for c[G(2',5')pA(3',5')p] bound to mSting$^{A231}$ was $K_D$=0.34 µM (Table S3).

Example 6: Crystal Structure of DMXAA Bound to mSting$^{R231}$

The present Example describes a 2.4 Å crystal structure of an ~186 amino acid mouse STING polypeptide bound to 5,6-dimethylxanthenone-4-acetic acid (DMXAA).

Reported antiviral small molecules reported to date that target mSting include 5,6-dimethylxanthenone-4-acetic acid (DMXAA) (FIG. 5A) (Conlon et al. 2013; Kim et al. 2013) and 10-carboxymethyl-9-acridine (CMA) (FIG. 10A) (Cavlar et al. 2013), with DMXAA and CMA showing species specificity for mouse but not human STING. The mode of binding of DMXAA and CMA to mSting is of interest for structure-based design of agonists and antagonists of hSTING with value as anti-cancer/anti-viral vaccine adjuvants and anti-inflammatory compounds, respectively.

Figure 5B:
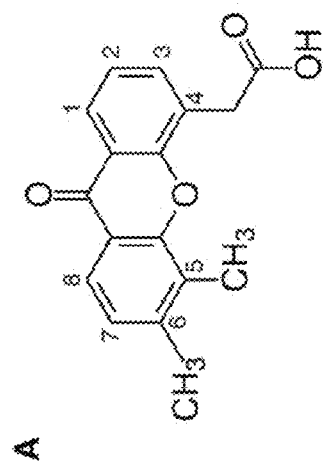
FIG. 5B depicts an exemplary 2.4 Å crystal structure of two molecules of DMXAA bound to mSting$^{R231}$ (aa 154-340).
Figure 5C:
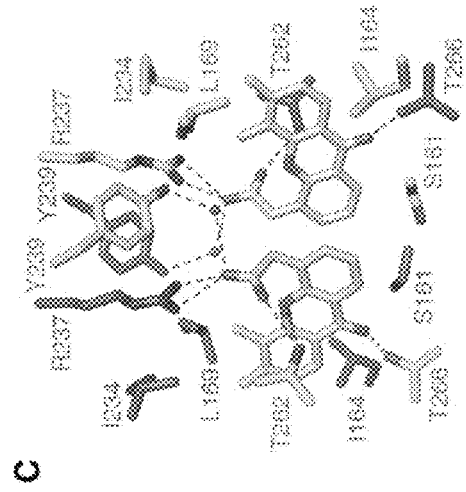
FIG. 5C depicts exemplary intermolecular contacts in the complex of DMXAA bound to mSting$^{R231}$. The two bound DMXAA molecules are shown in biscuit color, with individual mSting subunits in the symmetrical dimer shown in magenta and yellow. The intermolecular contacts to the polar and nonpolar edges of the DMXAA by the mSting subunits are shown in two alternate views.

We solved the 2.4 Å crystal structure of DMXAA bound to mSting$^{R231}$ (aa 154-340) (x-ray statistics in Table S2), with the complex containing two molecules of DMXAA per mSting$^{R231}$ dimer (FIG. 5B). The aromatic rings of the two DMXAA moieties are aligned in parallel but are not stacked on each other. The details of the intermolecular contacts in the complex are shown in FIG. 5C, with the ketone groups of DMXAA forming direct hydrogen bonds to the side chain of T266, while the carboxylate moieties of the ligand are anchored through direct hydrogen bonds to the side chains of R237 and T262. In addition, the adjacent aromatic methyl groups of DMXAA form a hydrophobic patch with side chains of L169 and I234 of mSting, while the non-substituted aromatic edges (positions 7 and 8) of DMXAA are positioned opposite I164 (FIG. 5C). A four-stranded antiparallel β-pleated sheet forms a cap over the binding pocket indicative of formation of a 'closed' conformation on complex formation, consistent also with DMXAA exposure leading to type I IFN pathway activation via mSting (Conlon et al. 2013; Kim et al. 2013).

Figure 5E:
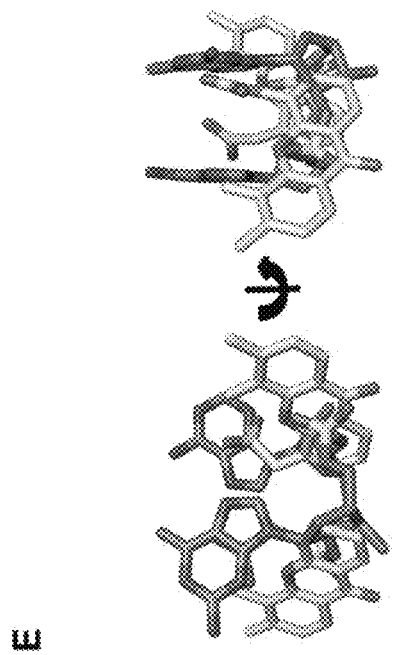
FIG. 5E depicts superposition of the mSting$^{R23'}$-bound DMXAA (in salmon) and c[G(2',5')pA(2',5')p] (in magenta) ligands.
Figure 5D:
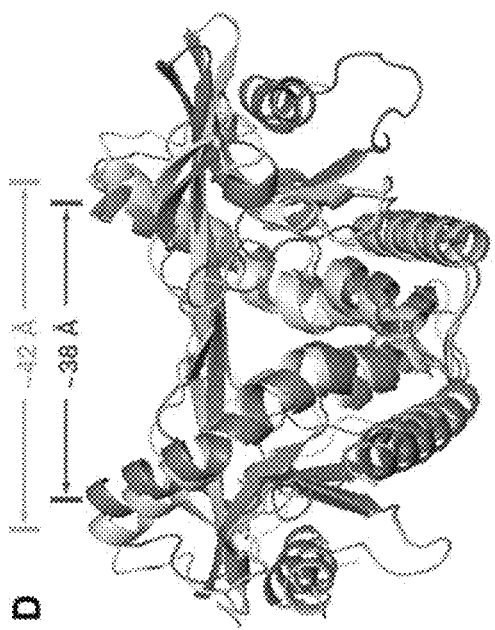
FIG. 5D depicts an exemplary superposition of the 2.4 Å DMXAA bound structure of mSting$^{R231}$ (both subunits in biscuit) and of the 1.77 Å structure of c[G(2',5')pA(3',5')p] of mSting$^{R231}$ (both subunits in magenta). For dose dependence: Data points were determined in triplicate and are depicted as means±SEM.
Figure 10A:
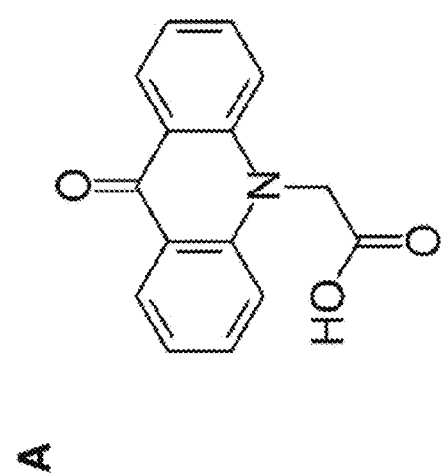
FIG. 10A depicts an exemplary chemical formula of 10-carboxymethyl-9-acridine (CMA).
Figure 10B:
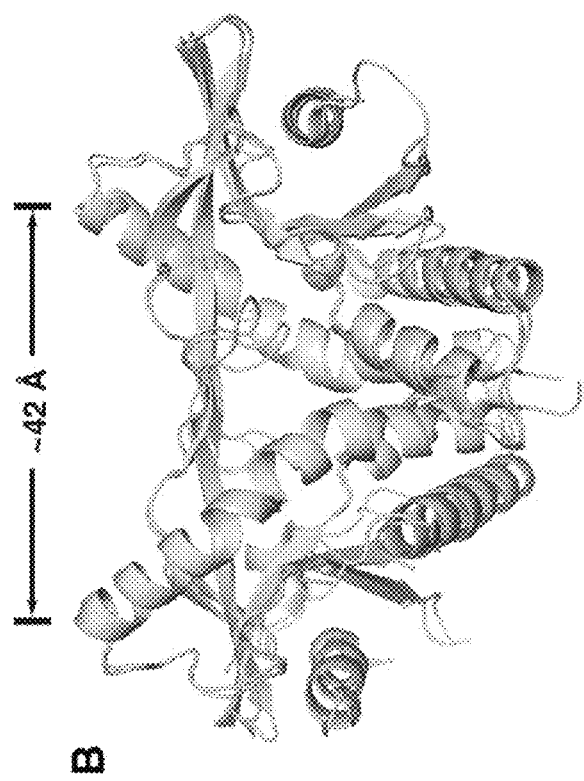
FIG. 10B depicts an exemplary superposition of the 2.90 Å DMXAA-bound structure of mSting$^{R231}$ (aa 154-340) with both subunits in biscuit and 2.75 Å CMA-bound structure of mSting$^{R231}$ (aa 149-348) with both subunits in yellow (PDB: 4JC5).

Finally, the mSting moieties bound to DMXAA (both subunits in biscuit) and to CMA (both subunits in yellow) (PDB: 4JC5) superpose well on each other (rmsd=0.75 Å) representing the 'closed' conformation for both complexes (FIG. 10B). By contrast, the mSting moieties bound to DMXAA (both subunits in biscuit) and to c[G(2',5')pA(3',5')p] (both subunits in magenta) show differences upon superposition despite both adopting the 'closed' conformation (rmsd=2.21 Å) with the separation between the tips of the α2-helices increasing from approx. 42 Å in the former complex to approx. 38 Å in the latter complex (FIG. 5D). Superposition of the mSting$^{R231}$-bound DMXAA (in salmon) and c[G(2',5')pA(2',5')p] (in magenta) ligands emphasize the different orientations adopted by these bound ligands within the same binding pocket (FIG. 5E).

Example 7: cGAMP Isomers Activate Type I IFN Pathway Through the STING/IRF3 Pathway The present Example describes a requirement for STING activation by cGAMP isomers to induce phosphorylation of Tbk1 and Irf3.

Figures 6A, 6B:
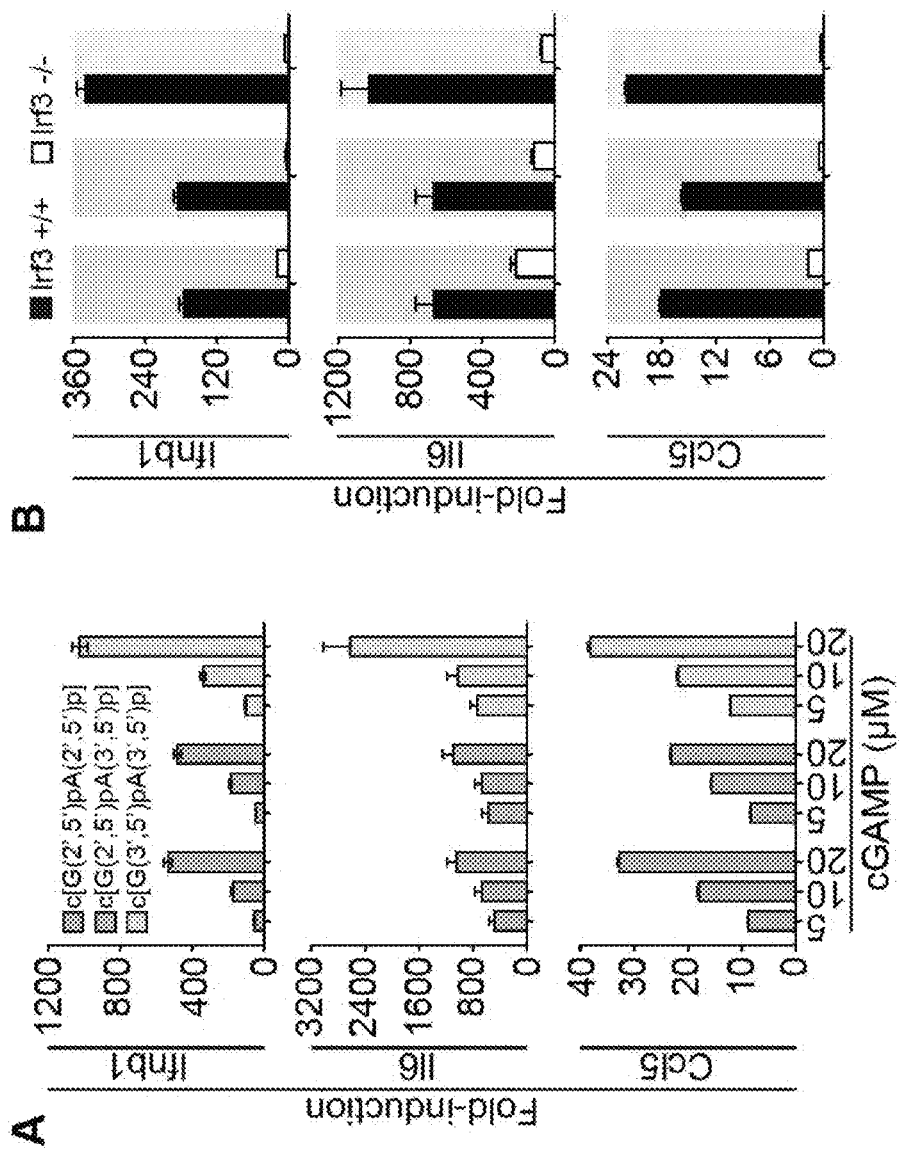
FIG. 6A depicts an exemplary result showing BMDMs (1×10$^6$) from C57B/6 mice were treated with increasing concentrations (5, 10 and 20 μM) of cGAMP linkage isomers, c[G(2',5')pA(2',5')p], c[G(2',5')pA(3',5')p] and c[G(3',5')pA(3',5')p], and cells were collected at 4 h post-treatment. cGAMP linkage isomers were provided by addition into media. Mock treatment control was included. qPCR analyses of Ifnb1, Il6 and Ccl5 mRNAs were performed.
FIG. 6B depicts an exemplary result showing BMDMs from IRF3$^{-/-}$ and age-matched wild-type control mice were generated. Cells (1×10$^6$) were treated with cGAMP linkage isomers, c[G(2',5')pA(2',5')p], c[G(2',5')pA(3',5')p] and c[G(3',5')pA(3',5')p] at a final concentration of 15 μM. cGAMP linkage isomers were provided by addition into media. qPCR analysis of Ifnb1, Il6 and Ccl5 mRNAs were performed.

To test whether cGAMP isomers elicit an innate immune response in murine macrophages, we recorded simple dose-response of cultured bone-marrow-derived macrophages (BMDMs) by addition of increasing concentrations of c[G(2',5')pA(2',5')p], c[G(2',5')pA(3',5')p] and c[G(3',5')pA(3',5')p] to the medium, and assaying 4 h post-treatment. Using real-time reverse transcription PCR (qPCR) analysis to monitor induction of Ifnb1, Il6, and Ccl5, we determined that exposure of BMDMs to 20 μM c[G(3',5')pA(3',5')p] elicited the strongest induction among the three isomers, with Ifnb1, Il6 and Ccl5 mRNA levels increased by 1024-, 2624-, and 38-fold, respectively, relative to mock-treatment (FIG. 6A). While c[G(3',5')pA(3',5')p] was the most potent compound, the differences between it and the other two isomers did not exceed three-fold. BMDMs isolated from Irf3$^{-/-}$ mice had reduced induction of Ifnb1, Il6, and Ccl5 upon exposure to cGAMP isomers, thereby indicating the involvement of Irf3-dependent type I IFN response pathway (FIG. 6B).

Figure 11:
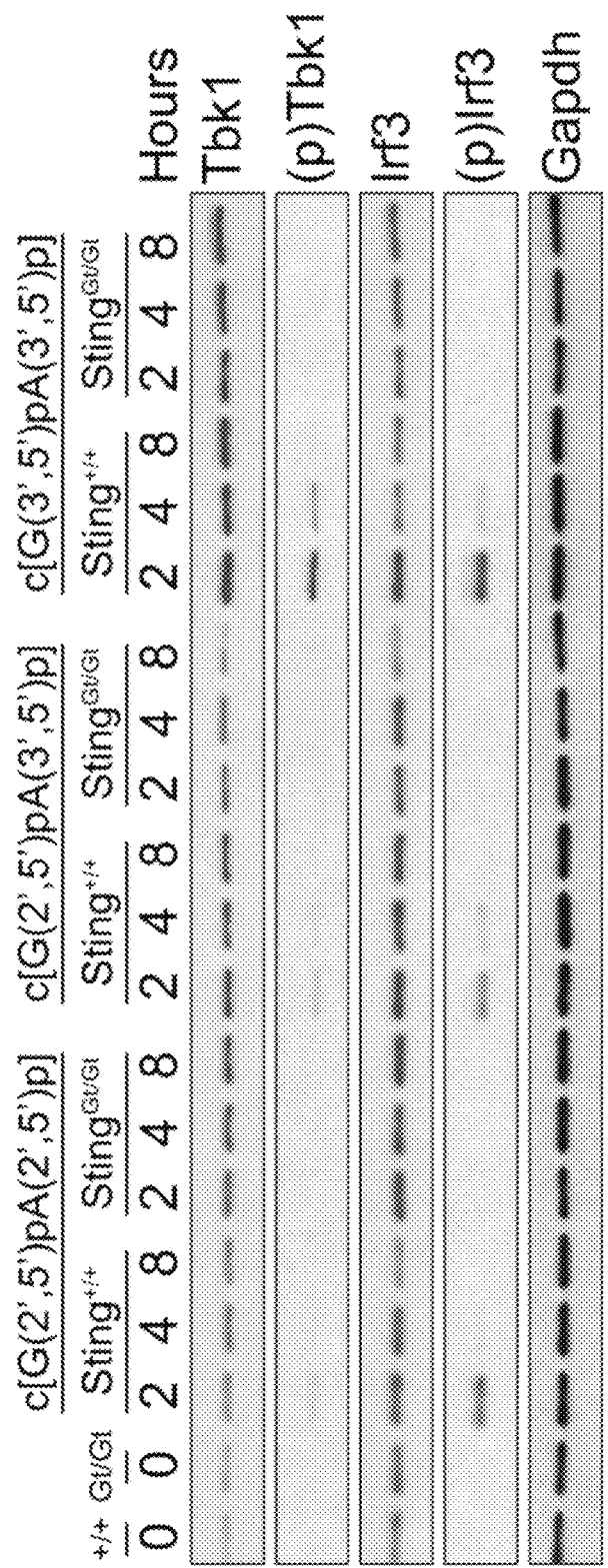
FIG. 11 depicts an exemplary experiment of cGAMP stimulation of BMDMs from wild-type and mutant STING mice. BMDMs from wild-type mice (Sting$^{+/+}$) and the N-ethyl-N-nitrosourea (ENU)-induced Goldenticket (Gt) mutant mice (Sting$^{Gt/Gt}$) were generated. Cells (1×10$^6$) were treated with cGAMP linkage isomers, c[G(2',5')pA(2',5')p], c[G(2',5')pA(3',5')p] and c[G(3',5')pA(3',5')p] at a final concentration of 15 µM. As before, cGAMP linkage isomers were provided by addition into media. Cells were collected at 2, 4, and 8 h post-treatment. Mock treatment controls were included (0 h). Western blot analysis was performed with anti-phosphoserine-396 of IRF3 or anti-IRF3, anti-phosphoserine-172 of TBK1 and anti-TBK1. Glyceraldehyde 3-phosphate dehydrogenase (Gapdh) was used as a loading control.
Figure 12A:
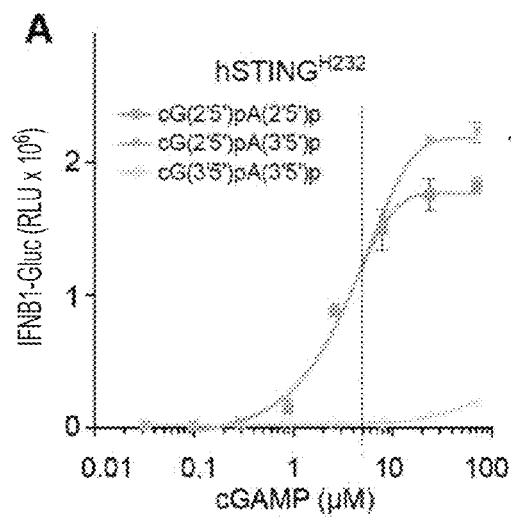
FIG. 12A, FIG. 12B, FIG. 12C, FIG. 12D, FIG. 12E, FIG. 12F and FIG. 12G depicts exemplary results showing HEK293T cells were transfected with human (panels A-F) or murine (panel G) STING variants for 12 h and cGAMP isomers delivered by Digitonin permeabilization (30 min) were titrated as indicated. Luciferase values were determined 12 h after stimulation.
Figure 12B:
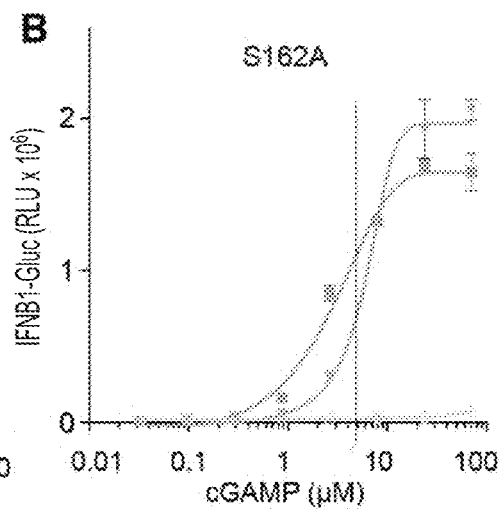
Figure 12C:
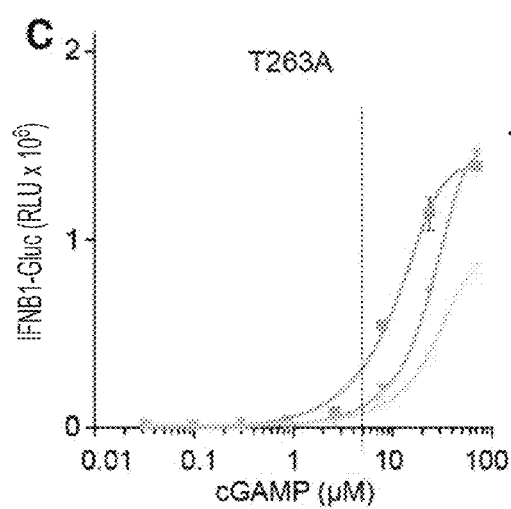
Figure 12D:
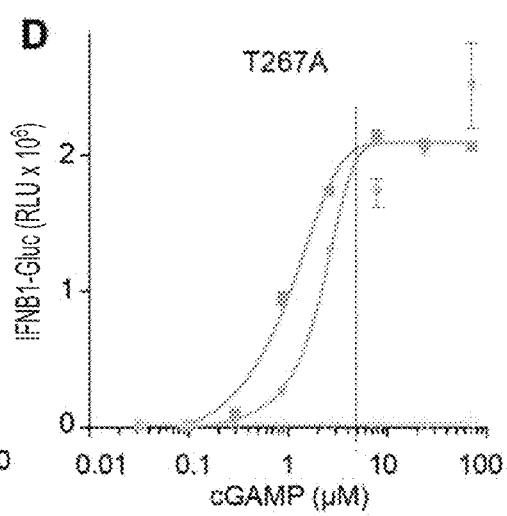
Figure 12E:
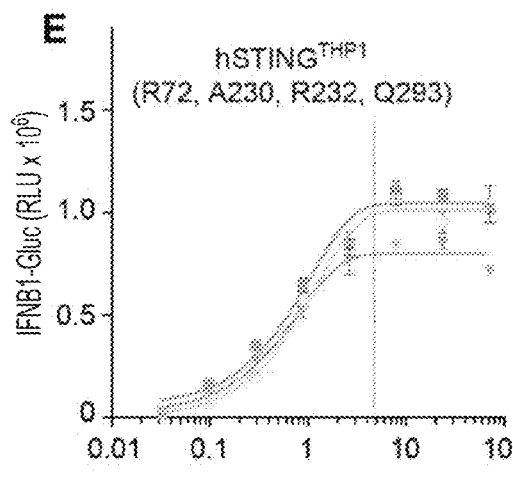
Figure 12F:
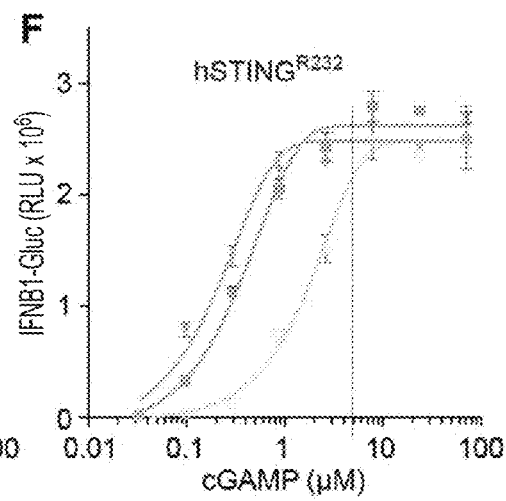
Figure 12G:
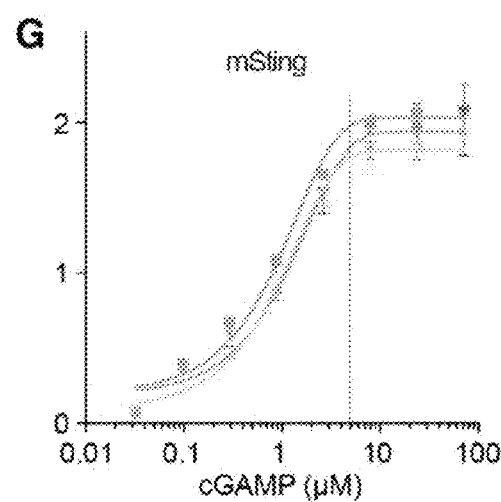

Western blot analysis further demonstrated that cGAMP isomers induced phosphorylation of Tbk1 and Irf3 at 2 and 4 h post-treatment of BMDMs (FIG. 11). Consistent with our qPCR results, incubation of BMDMs with c[G(3',5')pA(3',5')p] also showed the highest levels of Tbk1 and Irf3 protein phosphorylation compared to the two other isomers (FIG. 11). To test whether mSting is required for cGAMP-induced Tbk1 and Irf3 phosphorylation, we compared type I IFN response in BMDMs derived from wild-type and Goldenticket (Gt) mutant mice (Sting$^{Gt/Gt}$), which carry a I199R missense mutation in exon 6 of the mSting gene resulting in no detectable protein by Western blot analysis of BMDMs (Rasmussen et al. 2011). We observed that cGAMP-induced Tbk1 and Irf3 phosphorylation was absent from mSting-deficient cells (FIG. 11). We conclude that cGAMP treatment of BMDMs triggers type I IFN and pro-inflammatory cytokine/chemokine via the mSting/Irf3-dependent pathway. The strongest responses for mSting were seen for cGAMP derivatives comprising the non-metazoan all-3',5'-linkage isomer produced by bacteria, which was unexpected, considering the recent report suggesting that the natural c[G(2',5')pA(3',5')p] was the highest affinity ligand for hSTING (Zhang et al. 2013).

Figures 6C, 6D:
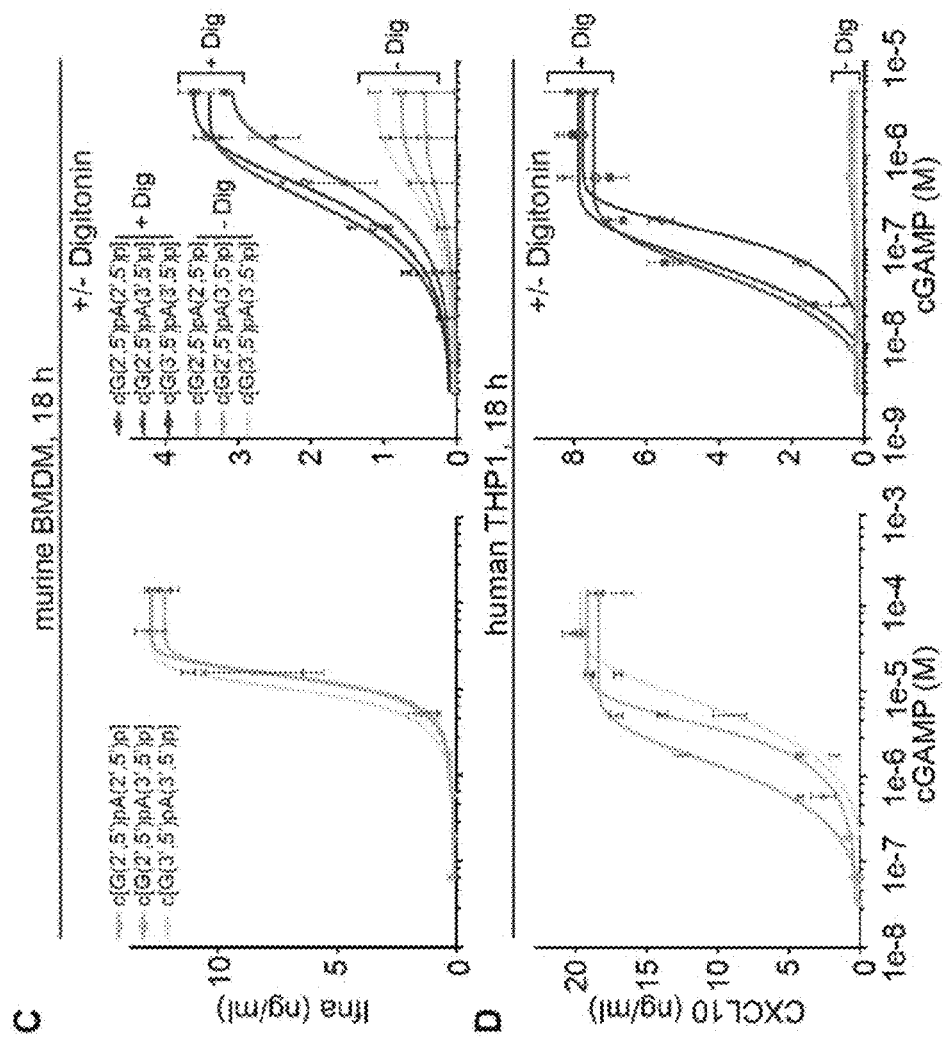
FIG. 6C depicts an exemplary result illustrating murine BMDMs were incubated in media supplemented with indicated concentrations of cGAMP isomers for 18 h (left panel), or for 30 min with and without Digitonin-mediated permeabilization (right panel). 18 h later, IFN-α concentrations in the supernatant were determined by ELISA.
FIG. 6D depicts an exemplary result showing THP1 cells were incubated in media supplemented with indicated concentrations of cGAMP linkage isomers for 18 h (left panel), or for 30 min with and without Digitonin-mediated permeabilization (right panel). CXCL10 concentrations were determined by ELISA after 18 h.
Figure 6E:
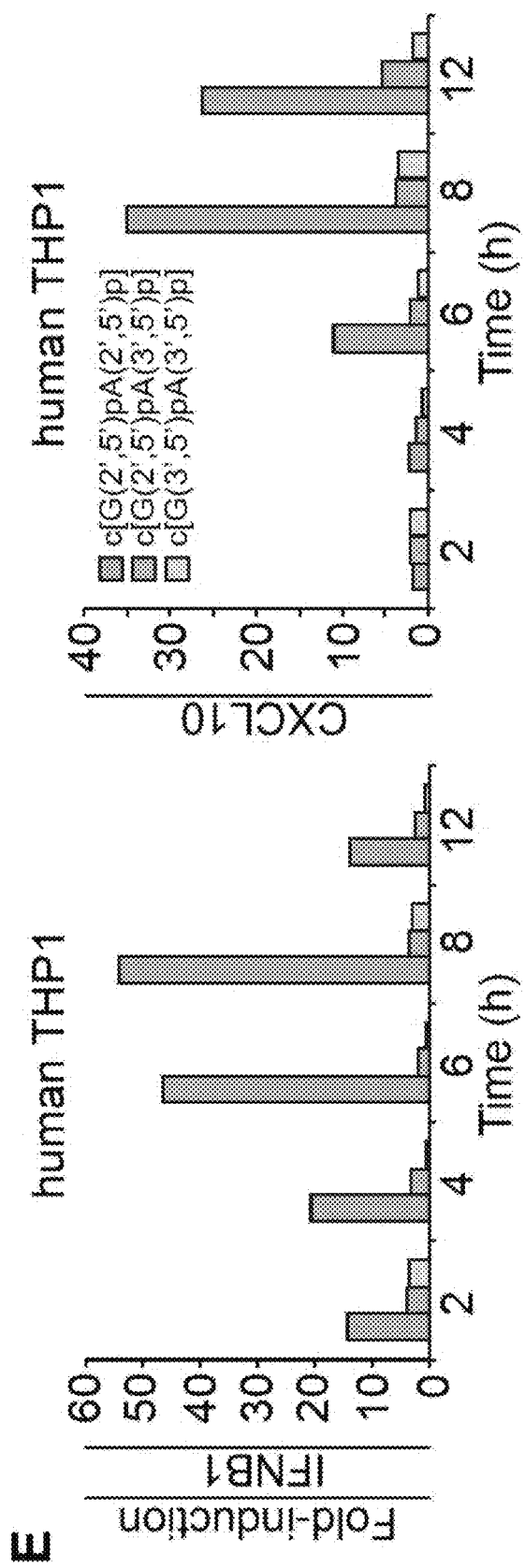
FIG. 6E depicts an exemplary time-course of STING-dependent IFN pathway activation by cGAMP linkage isomers. THP1 cells were incubated in media supplemented with cGAMP linkage isomers from 0 to 12 h without permeabilization. IFNB1 and CXCL10 transcriptional activation was measured by RT-PCR, normalized against TUBA1B and vehicle control. For bar graphs: Data points were determined in triplicate and are depicted as means±SEM.

Therefore, we also evaluated hSTING activation and its dependence on cGAMP isomer concentration. We assayed type I IFN and chemokine production in human THP1 cells by ELISA and RT-PCR analysis delivering cGAMP isomers by addition to the medium without or with Digitonin (Dig) permeabilization. In comparison to the murine system, which slightly favored the bacterial c[G(3',5')pA(3',5')p], the non-natural c[G(2',5')pA(2',5')p] stimulated THP1 cells 2.9- or 4.8-fold more effectively than the metazoan second messenger c[G(2',5')pA(3',5')p] or c[G(3',5')pA(3',5')p], respectively (FIGS. 6C and D, left panels, Table S5). Measuring transcriptional activation of hSTING-dependent IFN response genes by the various cGAMP linkage isomers (FIG. 6E) confirmed the ELISA results. As early as 2 h, we detected by RT-PCR that c[G(2',5')pA(2',5')p] stimulated expression of IFNB1 and CXCL10 the most. Digitonin-mediated cell permeabilization significantly increased and enhanced sensitivity to all cGAMP isomer in BMDM and THP1 cells (FIGS. 6C and D, right panels, Table S5). In THP1 cells, there was no difference in the EC$_{50}$ values obtained for c[G(2',5')pA(2',5')p] and c[G(2',5')pA(3',5')p] exposure.

TABLE S5

Effective concentration (EC$_{50}$) values of ELISA dose response curves for BMDM and THP1 stimulation with cGAMP linkage isomers

| | c[G(2',5')pA(2',5')p] | c[G(2',5')pA(3',5')p] | c[G(3',5')pA(3',5')p] |
|---|---|---|---|
| BMDM - Ifna, unpermeabilized (refers to FIG. 6C left panel) | | | |
| EC$_{50}$ (μM) | 12.5 | 12.5 | 8.4 |
| 95% CI (μM) | 9.7-16.2 | 10.1-15.2 | 7.7-9.2 |
| BMDM - Ifna, +Digitonin (refers to FIG. 6C right panel) | | | |
| EC$_{50}$ (μM) | 0.80 | 0.29 | 0.42 |
| 95% CI (μM) | 0.2-3.2 | 0.2-0.4 | 0.3-0.6 |
| THP1 - CXCL10, unpermeabilized (refers to FIG. 6D left panel) | | | |
| EC$_{50}$ (μM) | 1.2 | 3.4 | 5.7 |
| 95% CI (μM) | 1.0-1.4 | 2.9-3.8 | 5.0-6.4 |
| THP1 - CXCL10, +Digitonin (refers to FIG. 6D right panel) | | | |
| EC$_{50}$ (μM) | 0.12 | 0.14 | 0.33 |
| 95% CI (μM) | 0.09-0.16 | 0.12-0.16 | 0.28-0.39 |

Related to FIG. 6.

Example 8: Mutagenesis of hSTING and mSting Identified Amino Acids Important for its Ligand-Binding-Induced IFN Pathway Activation The present Example describes human STING amino acid residues important for ligand binding and IFN pathway activation.

Figures 7A, 7B:
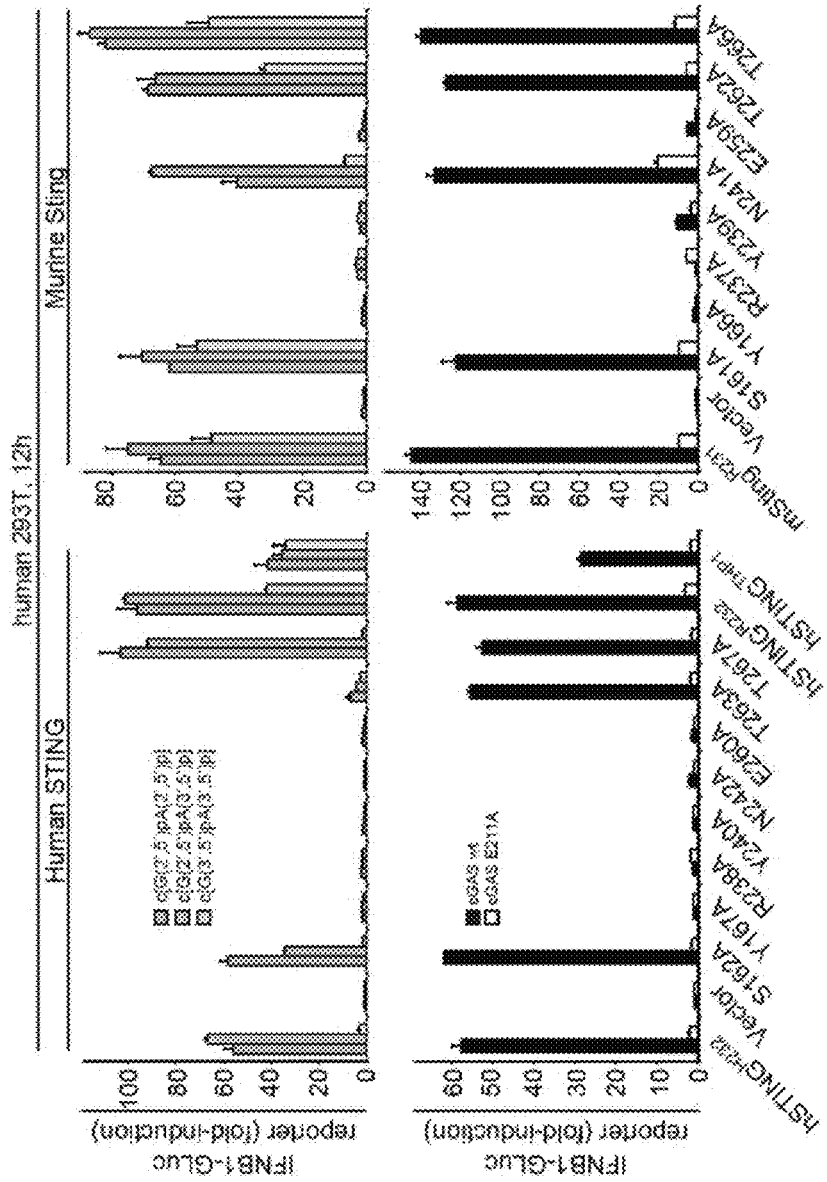
FIG. 7A depicts an exemplary experiment where HEK293T cells were transfected with reporter constructs and human or murine STING expression plasmids as indicated. After 12 h, cells were digitonin permeabilized to deliver cGAMP linkage isomers (5 μM concentration, 30 min permeabilization) and incubated for an additional 12 h, followed by luciferase-reporter assay.
FIG. 7B depicts an exemplary experiment where, to gauge STING mutant stimulation by murine cGAS compared to the inactive cGAS mutant E211A, plasmids containing the indicated human or murine STING variants were cotransfected with either cGAS form and luciferase reporter constructs. Luciferase induction was determined after 30 h. In this setting, the transfected plasmids provide the dsDNA stimulus for cGAS activation. Activation is expressed as fold induction in relation to control plasmid pMAX-GFP.
Figure 7G:
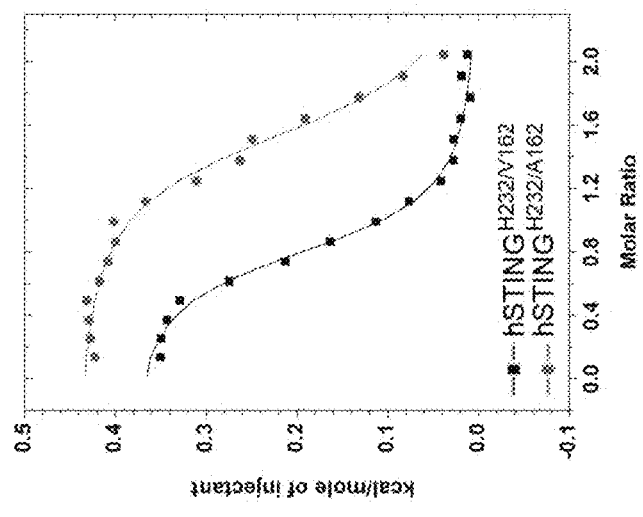
FIG. 7G depicts exemplary ITC binding curves for complex formation between DMAXX and hSTING$^{H232/A162}$ and hSTING$^{H232/V162}$.

To determine the functional importance of individual amino acids that interacted with c[G(2',5')pA(3',5')p] in the crystal structure, we generated Ala point mutants of specific residues within hSTING$^{H232}$, as well as of the corresponding mutations in mSting$^{R231}$, and tested their activities in human HEK293T cells using an IFN-sensitive luciferase reporter assay (Burdette et al. 2011; Gao et al. 2013). STING expression plasmids and IFNB1 luciferase reporter constructs were co-transfected followed by Dig-mediated delivery of cGAMP isomers (FIG. 7A), or co-transfected with wild-type or catalytic mutant (E211A) cGAS in the absence of exogenous cGAMP addition (FIG. 7B) (Gao et al. 2013). Human mutant STING variants with amino acid substitutions of either of Y167A, R238A, Y240A, or E260A, as well as their murine counterparts, were no longer able to stimulate the IFN-pathway. Notably, hSTING$^{H232/N242A}$ induced no measurable IFN reporter activity, whereas mSTING$^{R231/N241A}$ was only slightly impaired in its response. Mutants S162A and T267A of hSTING$^{H232}$ largely retained their normal function, whereas hSTING$^{H232/T263A}$ showed reduced activation (FIG. 7A). Dose-response studies of hSTING$^{H232}$ (FIG. 12) revealed no significant differences in stimulation between c[G(2',5')pA (2',5')p] and c[G(2',5')pA(3',5')p] and a lesser response to c[G(3',5')pA(3',5')p]. However, the hSTING$^{H232/T263A}$ mutant shows a gain in sensitivity to c[G(3',5')pA(3',5')p] compared to its response to 2',5' linkage isomers. The S162A and T267A hSTING$^{H232}$ mutants respond similarly to hSTING$^{H232}$, also showing a weaker response to c[G(3',5')pA (3',5')p].

Given the recent report of mSting and hSTING variants with distinct responsiveness (Diner et al. 2013), we sequenced hSTING DNAs derived from 8 Caucasians and our THP1 cells. All samples encoded R232 in both alleles; additionally hSTING$^{THP1}$ contained three additional point mutations (H72R, G230A, and R293Q) as reported before. We compared the cGAMP-dependent IFN-response for hSTING$^{H232}$, hSTING$^{R232}$, hSTING$^{THP1}$ and mSting$^{R231}$, and found that the prevalent hSTING$^{R232}$ was several-fold more responsive to all cGAMP isomers when compared to hSTING$^{H232}$, with the order of cGAMP isomer sensitivity remaining the same (FIGS. 7 and 12E, F). hSTING$^{THP1}$ and wild-type mSting$^{R231}$ displayed slightly reduced overall cGAMP sensitivity compared to hSTING$^{R232}$.

To complement our mutagenesis study of the cGAMP isomer response, we tested c[di-GMP] and DMXAA (FIGS. 7C and D). While both ligands stimulated mSting, nearly all hSTING variants were non-responsive except for hSTING$^{R232}$ and hSTING$^{THP-1}$, which showed a residual response to high concentrations of c-di-GMP) (FIGS. 7C and 12). Moreover, mSting mutants defective for recognition of all cGAMP isomers also failed to recognize c[di-GMP] and DMXAA. Mutants N241A and T262A of mSting were less responsive to c[di-GMP] and DMXAA compared to cGAMPs, whereas mSting (T266A) showed a moderately enhanced recognition of c[di-GMP] over DMXAA.

Example 9: S162A Mutant by hSTING is Activated by DMXAA

The present Example describes a point mutation in human STING that renders it sensitive to DMXAA.

Figure 13B:
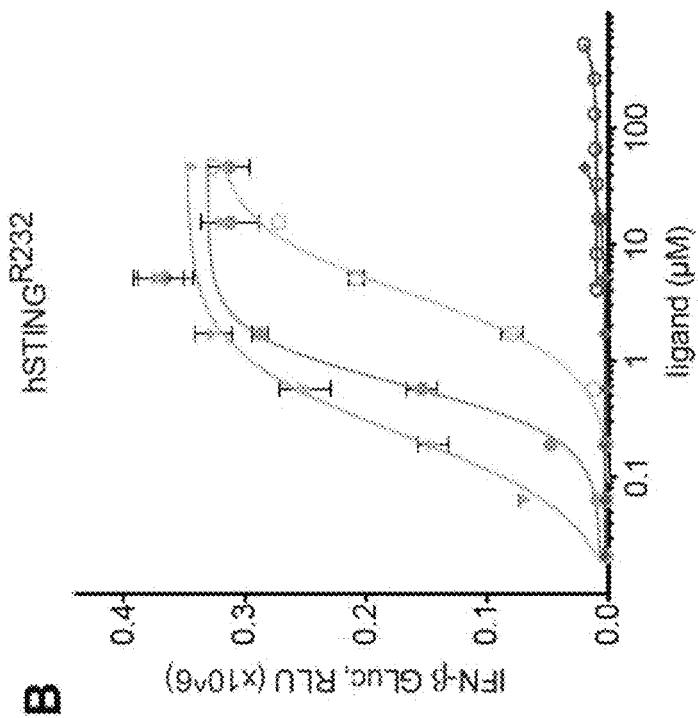
FIG. 13 depicts exemplary results showing that the S162A point mutation acquires DMXAA responsiveness in both hSTING$^{H232}$ and hSTING$^{R232}$ variants. HEK293T cells were transfected with human STING variants and murine STING as indicated, and 12 h later incubated with DMXAA without permeabilization or stimulated with c[di-GMP] and cGAMP isomers following digitonin permeabilization (30 min). Luciferase values were determined 12 h after stimulation. Panels A and B show human STING$^{H232}$ and STING$^{R232}$, panels C and D show the respective S162A mutants. In panel E responsiveness of murine Sting to DMXAA, c[di-GMP] and cGAMP isomers is shown for comparison. For dose dependence: Data points were determined in triplicate and are depicted as means±SEM.
Figure 13A:
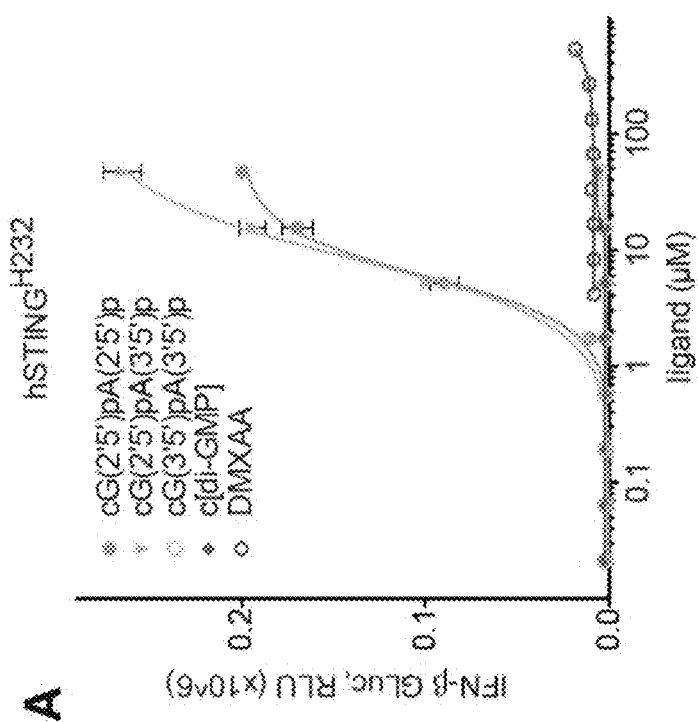
Figure 13D:
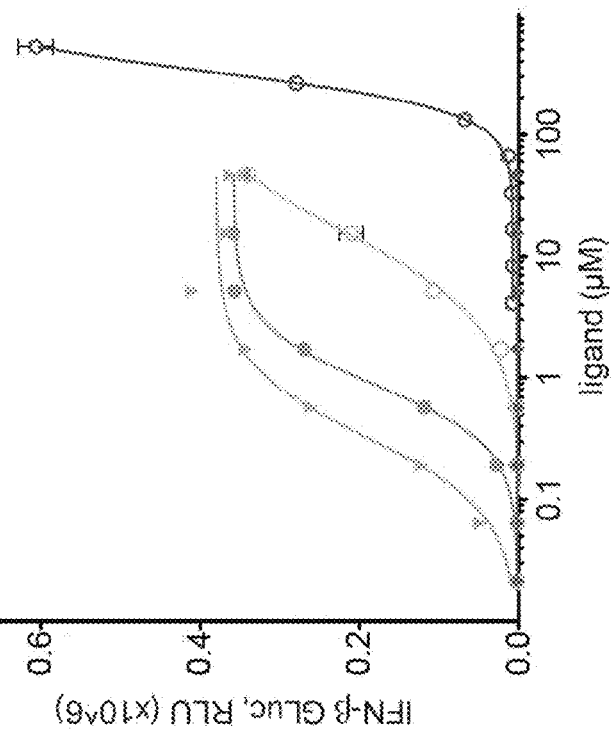
Figure 13C:
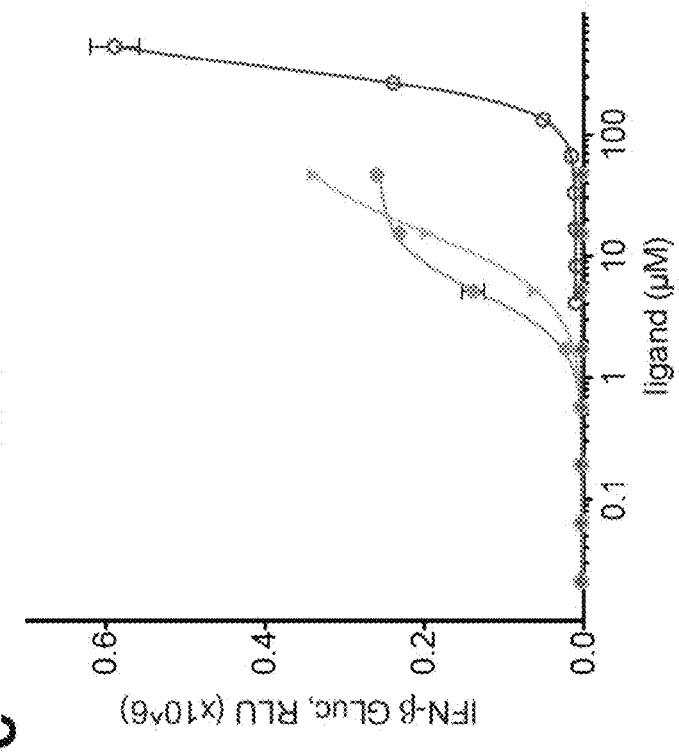
Figure 13E:
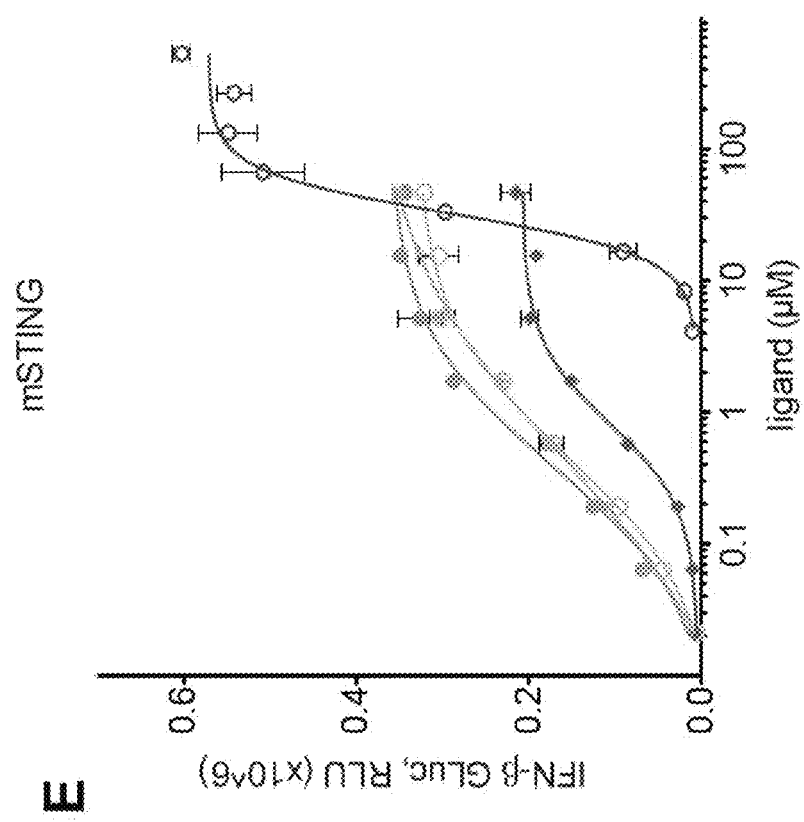
Figures 14A, 14B:
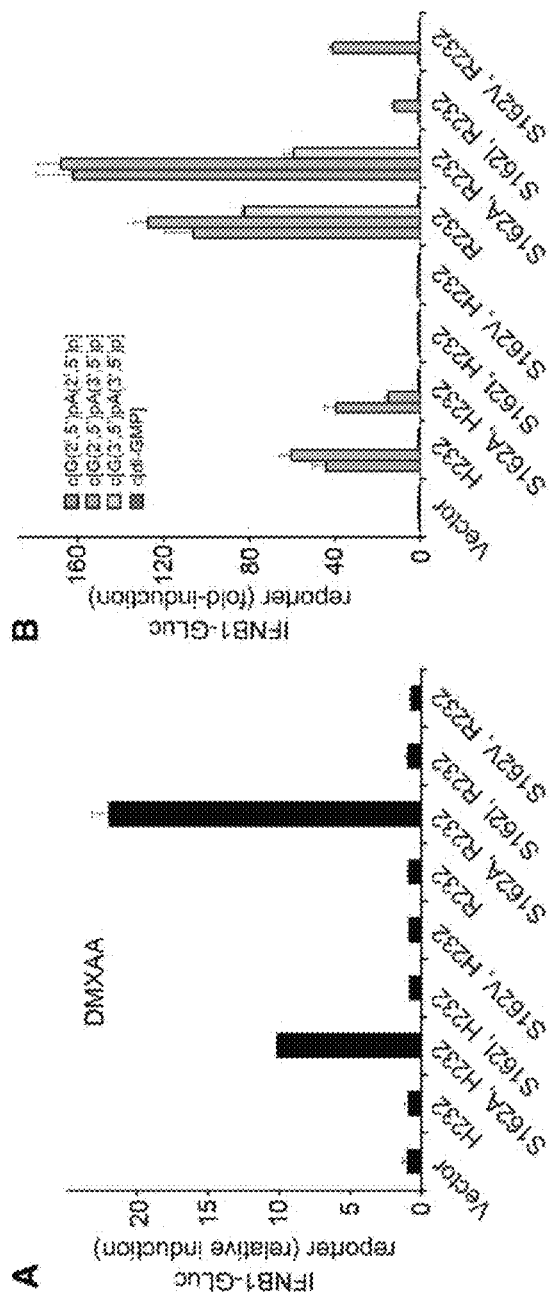
FIG. 14A depicts an exemplary result showing conversion of S162 to Ala in H232 or R232 hSTING background renders the protein sensitive to DMXAA stimulation. However, substitution by V162 or I162 does not yield similar results with DMXAA.
FIG. 14B depicts an exemplary result showing conversion of S162 to Ala in H232 or R232 hSTING background does not significantly affect the respective protein sensitivities to cGAMP linkage isomers or c-[di-GMP]. Substitution by V162 or I162 reduces/eliminates stimulation by any cyclic dinucleotide.

Strikingly, we found that the single point mutant S162A enabled recognition of DMXAA by human STING (FIG. 7D, left panel), while not restoring c[di-GMP] responsiveness (FIG. 7C, left panel). In both hSTING$^{H232}$ and hSTING$^{R232}$ background, the S162A mutation enabled DMXAA recognition with near-identical dose-responses (FIG. 13C, D). In contrast, the differences in recognition of cGAMP isomers and c[di-GMP] were only slightly altered or unchanged compared to the respective S162 variants (FIG. 14B). Noticeably, IFN induction was not observed in cellular assays for the S162V and S162I mutants of hSTING$^{H232}$ or hSTING$^{R132}$, which contain bulkier hydrophobic amino acids compared to Ala at position 162 (FIG. 14A).

Figure 7F:
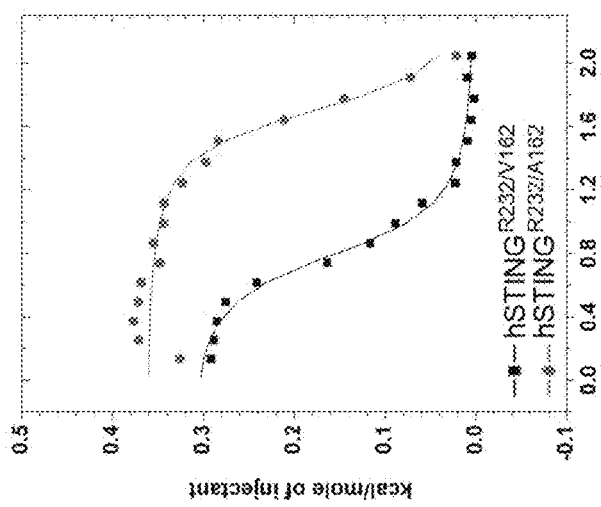
FIG. 7F depicts exemplary ITC binding curves for complex formation between DMAXX and hSTING$^{R232/A162}$ and hSTING$^{R232/V162}$.

ITC-based binding studies confirmed that mSting$^{R231}$ bound DMXAA as reported previously (FIG. 14E) (Kim et al., 2013), as did S162A (and S162V) mutants in a hSTING$^{R232}$ and hSTING$^{H232}$ context bound DMXAA (FIG. 7F, G).

TABLE S6

ITC Parameters for Binding of DMXAA to hSTING Containing S162A and S162V Mutants in a R232 and H232 context
hSTING and its S162 Mutants with DMXAA
Protein: 0.08 mM; Ligands: 0.8 mM; Buffer: 30 mM HEPES, 180 mM NaCl, pH 7.5; T: 25° C.

|  | N | $K_D$ (μM) | ΔG (Kcal/mol) | ΔH (Kcal/mol) | TΔS (Kcal/mol) |
|---|---|---|---|---|---|
| hSTING$^{R232/A162}$ | 1.49 | 0.86 ± 0.20 | −8.29 | +0.36 | +8.65 |
| hSTING$^{R232/V162}$ | 0.77 | 2.63 ± 0.45 | −7.61 | +0.32 | +7.93 |
| hSTING$^{H232/A162}$ | 1.52 | 2.88 ± 0.48 | −7.55 | +0.44 | +7.99 |
| hSTING$^{H232/V162}$ | 0.79 | 3.47 ± 0.39 | −7.45 | +0.39 | +7.84 |
| mSting$^{R231}$ | 1.23 | 0.49 ± 0.05 | −8.61 | −2.86 | +5.75 |

Figure 7E:
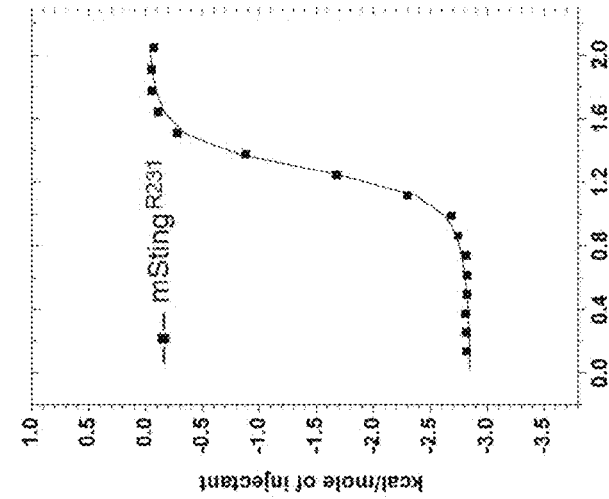
FIG. 7E depicts exemplary ITC binding curves for complex formation between DMAXX and mSting$^{R231}$.

Relates to FIGS. 7E, F and G.

Example 10: The Lid Region of the Ligand-Binding Pocket is Important for DMXAA Recognition Within STING, DMXAA (FIG. 15A) and c[G(2',5')pA(3', 5')p] share the same ligand binding pocket (Gao et al., 2013b), which in human and mouse proteins is composed of identical amino acids. Despite the fact that human and mouse STING C-terminal domains (CTD, aa 140-379) exhibit ~76% amino acid identity (FIG. 19), DMXAA only binds and activates mSTING and has no effect on hSTING (Conlon et al., 2013; Kim et al., 2013). Therefore, the non-conserved residues between the two species that are located outside the DMXAA-binding pocket must play a role for distinct DMXAA recognition. We subdivided the non-conserved residues located in the STING CTD into four groups (labeled as group1 to group4, hSTING$^{group1-4}$). We then substituted hSTING residues with their mSTING counterparts for each of the four groups (FIG. 19). These residues are located either along the dimer interface or within the regions that undergo large conformational changes during the 'open' to 'closed' transition associated with complex formation. We also generated a construct containing the combined substitution in all four groups (hSTING$^{group1234}$).

We performed isothermal titration calorimetry (ITC) experiments to measure the DMXAA-binding affinity of hSTING CTD (aa 140-379) containing various group substitutions. hSTING$^{group1234}$ showed a comparable exothermic binding curve and binding affinity ($K_D$: 0.69 μM) (FIG. 15B) to mSTING ($K_D$: 0.49 μM) (Gao et al., 2013b). Similar to wild-type (wt) hSTING protein, no detectable binding to DMXAA was observed for the isolated group1, group3, or group4 substitutions of hSTING (FIG. 20A). Only group2 substitutions of hSTING exhibited detectable endothermic binding with DMXAA ($K_D$: 3.12 µM; FIG. 15C).

To validate the binding results, we used an IFN-β luciferase reporter assay to further test the responsiveness of hSTING group substitutions to DMXAA stimulation in human 293T cells, which lack endogenous STING expression. Full-length hSTING (wt and substitutions) and mSTING (wt) constructs were used for this cellular assay, and were expressed at moderate levels allowing ligand-dependent activation of IFN-β promoter. We confirmed that mSTING-transfected 293T cells responded to DMXAA, while hSTING-transfected cells did not (FIG. 15D, left panel). Consistent with the ITC results among the individual group substitutions, only the hSTING$^{group2}$ substitutions showed responsiveness to DMXAA (FIG. 15D, middle panel). Inversely, removing the group2 substitutions from the combined group1234 substitutions (hSTING$^{group134}$) strongly diminished DMXAA activation, while loss of any of the other groups was tolerated (FIG. 15D, right panel). These results indicate that group2 residues from mSTING, which are located within the lid region of the binding pocket, play an a role in DMXAA recognition.

Example 11: Crystal Structure of DMXAA Bound to hSTING$^{group2}$

We proceeded to solve the crystal structure of DMXAA bound to hSTING$^{group2}$ (aa 155-341) at 1.88 Å resolution (x-ray statistics in Table S1) with the complex containing two molecules of DMXAA per hSTING$^{group2}$ dimer (FIG. 15E). The results were similar to what we observed for the complex of mSTING and DMXAA, described above. The four-stranded antiparallel β-pleated sheet formed a lid covering the binding pocket, indicative of formation of a 'closed' conformation of STING on complex formation, which is consistent with the conclusions drawn from our ITC (FIG. 15B, C) and IFN-β-dependent luciferase reporter (FIG. 15D) results. Rather than being stacked on each other, the aromatic rings of the two DMXAA moieties are aligned in parallel, with complex formation mediated by both intermolecular van der Waals contacts and hydrogen bond interactions. The details of the intermolecular contacts in the complex are shown in FIG. 15F, with the ketone and ether groups of DMXAA forming direct hydrogen bonds to the side chain of T267 and T263, respectively. The carboxylate moieties are anchored through direct hydrogen bonds to the side chains of R238 and T263 and through water-mediated hydrogen bonds to Y240. In addition, the adjacent aromatic methyl groups (positions 5 and 6) of DMXAA form a hydrophobic patch with side chains of L170 and I235, whereas the non-substituted aromatic edges (positions 7 and 8) of DMXAA are positioned opposite I165. We observed excellent superposition of hSTING$^{group2}$ and mSTING in their complexes with DMXAA as shown in FIG. 20B (rmsd: 0.95 Å).

To elucidate the molecular basis underlying DMXAA species selectivity, we compared the structure of the hSTING$^{group2}$-DMXAA complex with those of the hSTING-c[G(2',5')pA(3',5')p] (Gao et al., 2013a) and mSTING-DMXAA (Gao et al., 2013b) complexes. We found that in the hSTING$^{group2}$-DMXAA structure, the side chain of the substituted residue I230 (G230 in wt protein) is located in a hydrophobic pocket composed of residues from both the four-stranded antiparallel β-sheet region (R232, I235, R238, and Y240) and the adjacent long α-helix (L170 and I171) (FIG. 15G). The amino acids that form the hydrophobic pocket are identical between human and mouse proteins. This same structural feature was also found in the mSTING-DMXAA structure (FIG. 20C). In the structure of the hSTING-c[G(2',5')pA(3',5')p] complex, the corresponding position to I230 (or I229 in mSTING) is G230, which results in the loss of the hydrophobic interactions found in the other two structures. This isoleucine-mediated hydrophobic interaction may help stabilize the β-sheet and other parts of the protein, facilitating DMXAA-mediated formation of the 'closed' conformation by mSTING or hSTING$^{group2}$, thereby explaining the absence of complex formation by wt hSTING with a glycine at this position.

Example 12: G230 of hSTING and I229 of mSTING are Contributors to Differential DMXAA Recognition To support our conclusions based on our structural findings above, we generated the G230I single substitution in hSTING and tested its IFN-β induction activity using the luciferase assay. Indeed, hSTING$^{G230I}$ alone was sufficient to mimic the effects observed for hSTING$^{group2}$, resulting in almost identical IFN-β induction as hSTING$^{group2}$ (FIG. 16A). Using the same method, reverse substitutions on mSTING (I229G or I229A) were also generated and tested. As expected, mSTING$^{I229G}$ and mSTING$^{I229A}$ showed a significant decrease in DMXAA-mediated IFN-β induction (FIG. 16B).

Figure 21A:
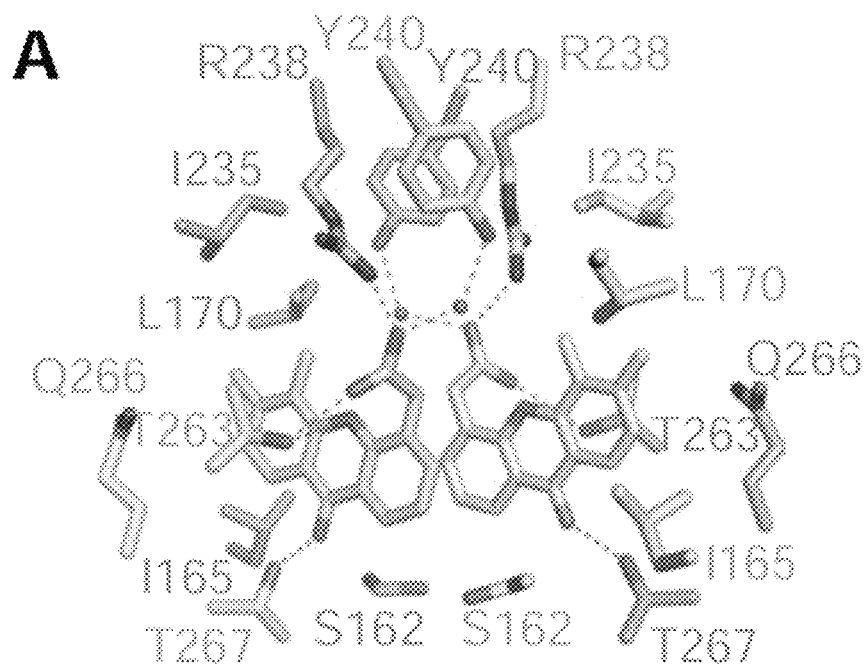
FIG. 21A depicts exemplary intermolecular contacts in the complex of DMXAA bound to hSTING$^{G230I}$ (aa 155-341). The bound DMXAA is shown with individual STING subunits in the symmetrical dimer.
Figure 21B:
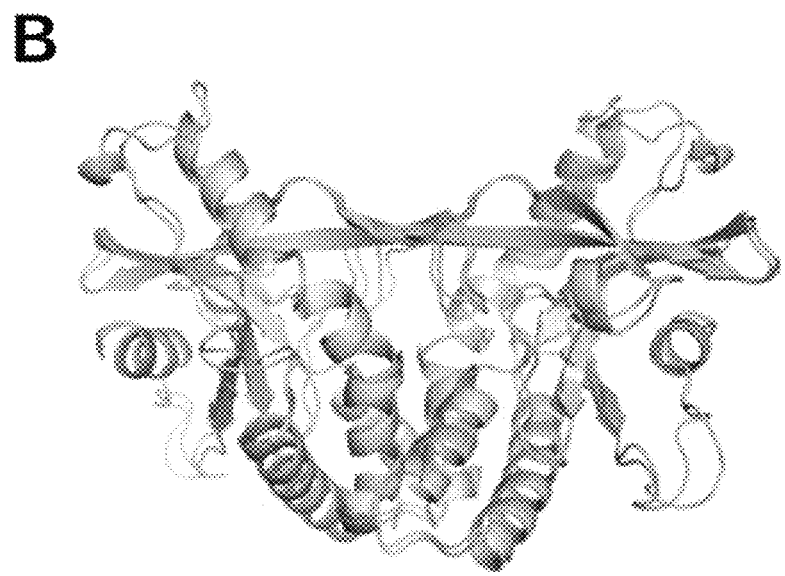
FIG. 21B depicts superposed structures of the complex of DMXAA bound with hSTING$^{G230I}$ (aa 155-341) and hSTING$^{group2}$ (aa 155-341).

We also solved the crystal structure of DMXAA bound to hSTING$^{G230I}$ (aa 155-341) at 2.51 Å resolution (x-ray statistics in Table S1), with hSTING$^{G230I}$ in the complex forming a 'closed' conformation (FIG. 16C). The detailed intermolecular contacts in the complex (FIG. 21A) are similar to those observed for the hSTING$^{group2}$-DMXAA structure (FIG. 15F). We observed excellent superposition of hSTING$^{G230I}$ and hSTING$^{group2}$ in their complexes with DMXAA, as shown in FIG. 21B (rmsd: 0.61 Å). The I230 residue, which is positioned within a hydrophobic pocket (FIG. 16D), forms the same intramolecular contacts as observed in the structures of the hSTING$^{group2}$-DMXAA (FIG. 15G) and mSTING-DMXAA (FIG. 20C) complexes. Taken together, our structural and functional data strongly demonstrate that the substitution of Gly with Ile at aa 230 results in the gain of function of hSTING for DMXAA recognition.

Example 13: hSTING$^{Q266I}$ is Activated by DMXAA

Examples 1-8 identify a point substitution (S162A) placed within the cyclic-dinucleotide-binding site of hSTING that confers partial sensitivity to the otherwise mouse-specific drug DMXAA (Gao et al., 2013b). Guided by the structures of complexes of hSTING substitutions with DMXAA, we next tested additional substitutions within the ligand-binding pocket to identify more constraints that would help in the design of future modifications on DMXAA. We generated five new substitutions (G166S, I235L, Q266I, Q266L, Q266V) in hSTING (FIG. 19) to either enhance the hydrophobic interaction or introduce additional hydrogen bonds with DMXAA. Initial IFN-β induction results showed that only the Q266I substitution in hSTING conferred DMXAA sensitivity at a level similar to that observed for the S162A substitution (FIG. 17A). Q266L resulted in a less pronounced gain of DMXAA-mediated IFN-β induction, while G166S, I235L and Q266V showed no effects (FIG. 17A). It should be noted that neither S162A nor Q266I substitutions alone were able to introduce IFN-β responsiveness to DMXAA at a level comparable to mSTING (FIG. 17B). We therefore tested whether the S162A/Q266I double substitution would augment DMXAA recognition, and indeed observed an enhanced DMXAA-induced IFN-β induction similar to mSTING (FIG. 17B). We further validated the luciferase reporter results by testing the binding affinity for hSTING$^{S162A}$, hSTING$^{Q266I}$ and hSTING$^{S162A/Q266I}$ (aa 140-379) with DMXAA using ITC. These results confirmed that hSTING$^{S162A/Q266I}$ binds to DMXAA with higher affinity ($K_D$: 1.99 µM) (FIG. 18C) when compared to either hSTING$^{S162A}$ (FIG. 21C) or hSTING$^{Q266I}$ (FIG. 21D).

Figures 17C, 17D:
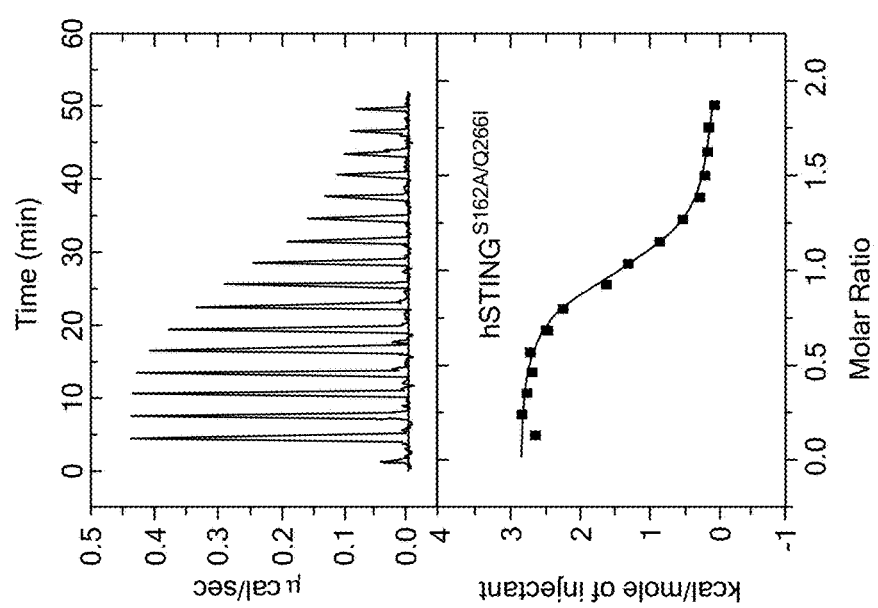
FIG. 17C depicts an ITC binding curve for complex formation between DMXAA bound to hSTINGS162A/Q266I (aa 140-379).
FIG. 17D depicts natural variants of hSTING (Yi et al., 2013). Five hSTING variants (shown in the left column) were studied in this work. The amino acid variations are shown in the right column.
Figure 17E:
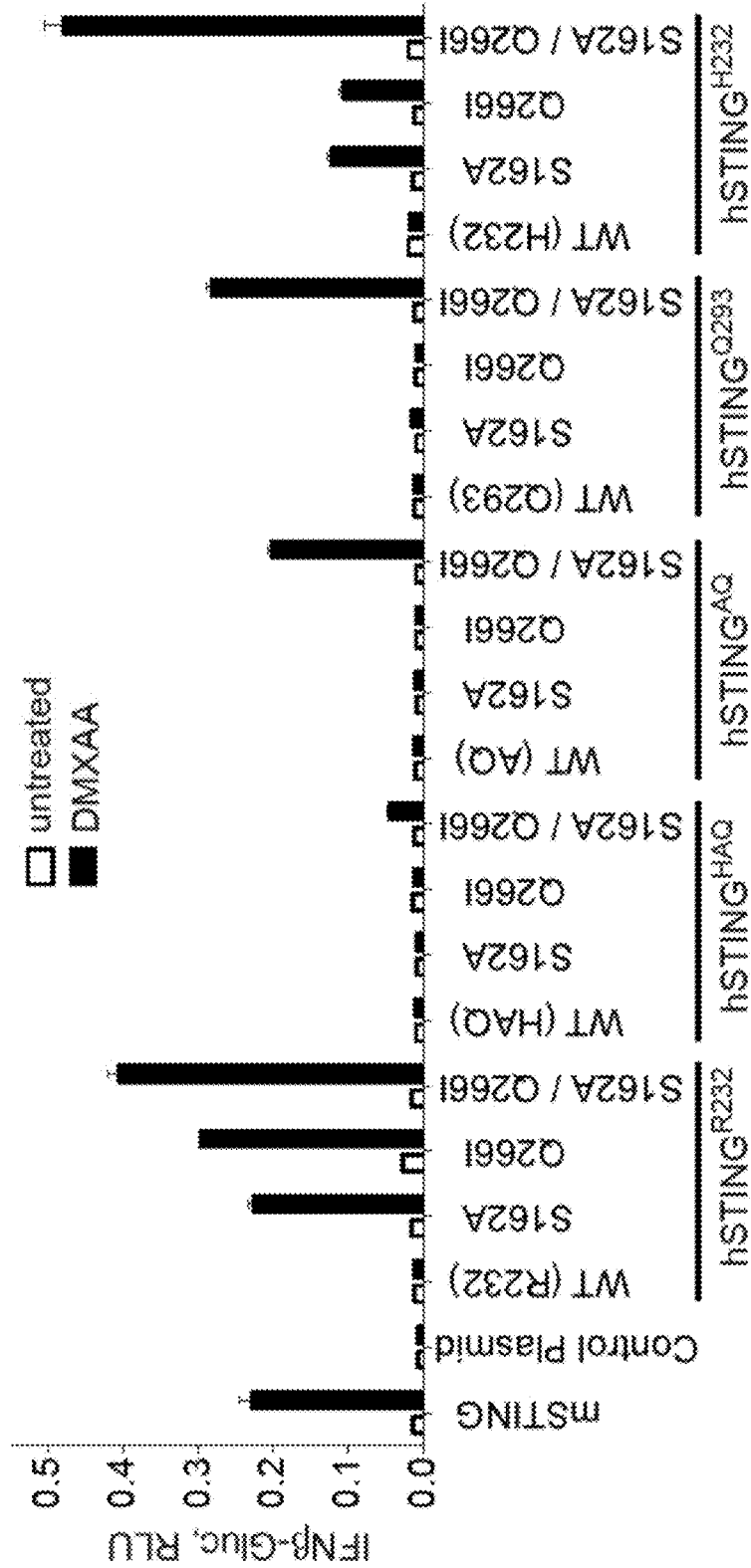
FIG. 17E depicts results where 293T cells were transfected and stimulated as in (A). Shown are S162A and Q266I mutants of major human STING alleles. WT denotes the respective allele in this context. Shown are the means of triplicates +SEM, representative of 3 independent experiments.

Besides the prevalent allelic hSTING variant (R71/G230/R232/R293, hSTING$^{R232}$), four major non-synonymous variants are found in high frequencies with R71H/G230A/R293Q (hSTING$^{HAQ}$) is present in 20.4%, R232H (hSTING$^{H232}$) in 13.7%, G230A/R293Q (hSTING$^{AQ}$) in 5.2%, and R293Q (hSTING$^{Q293}$) in 1.5% of the human population (Yi et al., 2013). To determine whether the S162A and Q266I substitutions were effective in all natural human STING variants, we generated the respective single and double substitutions for all major hSTING alleles (listed in FIG. 17D) and tested them for DMXAA recognition (FIG. 17E). The S162A/Q266I double substitution was able to induce DMXAA responsiveness in all hSTING alleles, whereas single substitutions were only effective in hSTING$^{R232}$ and hSTING$^{H232}$. This was further validated by titration of DMXAA concentrations (FIG. 17B for hSTING$^{R232}$, FIGS. 22A and 22B for other hSTING alleles), which showed a variable maximal IFN-β induction for different alleles, but clear sigmoidal dose-responses that diverges by less than one order of magnitude in their EC$_{50}$. Taken together, the Q266I substitution renders hSTING responsive to DMXAA. Further, hSTING containing Q266I and S162A substitutions led to a DMXAA-dependent IFN-β reporter response close to that observed for mSTING.

Example 14: Crystal Structure of DMXAA Bound to hSTING$^{S162A/Q266I}$

Figure 17F:
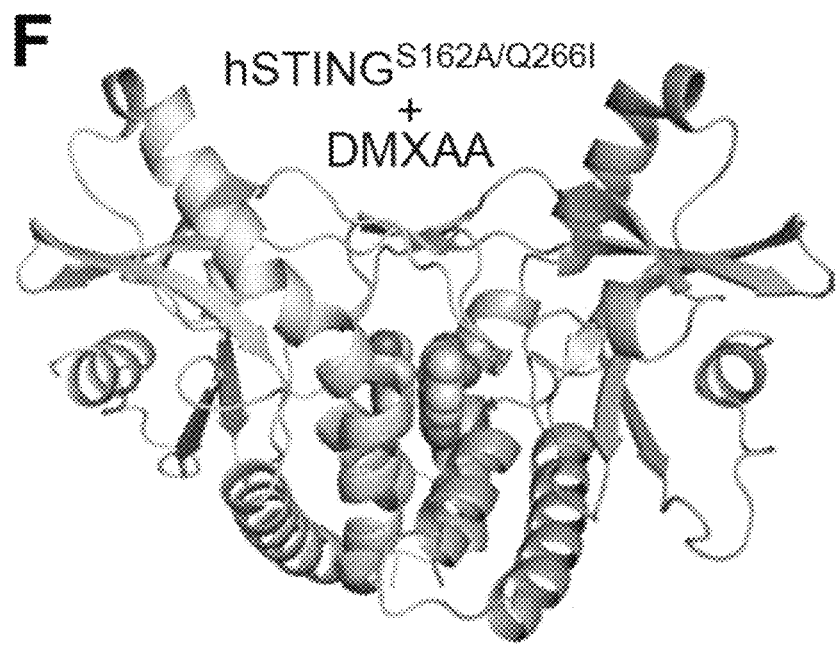
FIG. 17F depicts the 2.42 Å crystal structure of DMXAA bound to hSTINGS162A/Q266I (aa 155-341). The representations are the same as used in FIG. 15E.
Figure 17G:
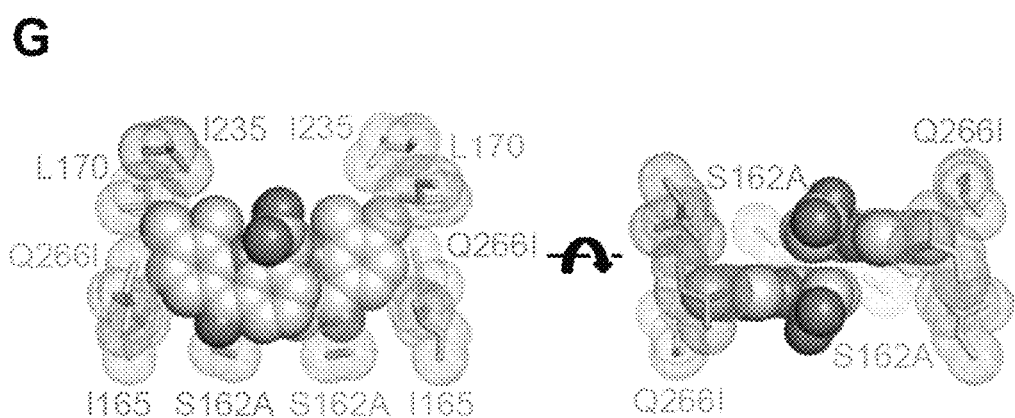
FIG. 17G depicts two alternate views of the hydrophobic interactions of DMXAA with hSTINGS162A/Q266I. The two bound DMXAA molecules are shown in space-filling representation, with surrounded hydrophobic side chains shown in stick and dot representations.
Figure 22D:
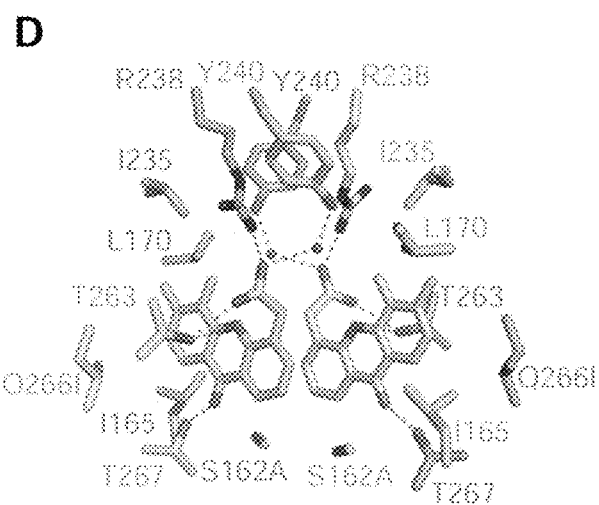
FIG. 22D depicts exemplary intermolecular contacts in the complex of DMXAA bound to hSTING$^{S162A/Q266I}$ (aa 155-341). The bound DMXAA is shown with individual STING subunits in the symmetrical dimer.

To better understand how S162A and Q266I substitutions facilitate the IFN induction of hSTING by DMXAA, we solved the co-crystal complex of DMXAA with hSTING$^{S162A/Q266I}$ (aa 155-341) at 2.42 Å resolution (x-ray statistics in Table S1). The complex adopts the 'closed' conformation as reflected by the positioning of two DMXAA in the binding pocket and the formation of the four-stranded antiparallel β-sheet lid over the bound ligands (FIG. 17F). The crystal structures of hSTING$^{S162A/Q266I}$ and hSTING$^{G230I}$ in their bound complexes with DMXAA superimpose with an rmsd of 0.70 Å (FIG. 22C). The details of the intermolecular contacts in the complex are shown in FIG. 22D, with the same intermolecular hydrogen bonding interaction network as observed in hSTING$^{group2}$-DMXAA (FIG. 15F) and hSTING$^{G230I}$-DMXAA (FIG. 21A) complexes. The substituted I266 side chain forms a hydrophobic patch together with the side chains of I165, L170 and I235, which fully covers the aromatic methyl groups (positions 5 and 6) and the non-substituted aromatic edges (positions 7 and 8) of DMXAA (FIG. 17G). The substituted A162 side chain is juxtaposed to the aromatic edges lining the other side (positions 1 and 2) of DMXAA, forming additional hydrophobic interactions (FIG. 17G). S162A and Q266I substitutions increase the binding affinity between hSTING and DMXAA and apparently assist hSTING to overcome the energy barrier from an 'open' to a 'closed' conformation. Based on the information on these two point substitutions in hSTING, it should be feasible to apply structure-guided approaches to design DMXAA analogs targeting hSTING.

Example 15: hSTING$^{S162A/G230I/Q266I}$ is More Sensitive to DMXAA than mSTING in IFN-β Induction We next tested whether combining the G230I substitution with the binding-pocket substitutions S162A/Q266I would further enhance hSTING sensitivity to DMXAA. We generated the triple mutant of hSTING and tested its binding to DMXAA by ITC, as well as IFN induction by DMXAA in transfected cells. The ITC titration for hSTING$^{S162A/G230I/Q266I}$ with added DMXAA is plotted in FIG. 18A, and showed a higher binding affinity ($K_D$: 0.99 µM) than that observed for hSTING$^{group2}$ ($K_D$: 3.12 µM) (FIG. 15C) or hSTING$^{S162A/Q266I}$ ($K_D$: 1.99 µM) (FIG. 17C), indicating that all three substitutions individually contribute to an increased DMXAA sensitivity. This increase in affinity translates to synergistic functional effects based on our luciferase reporter assays in which hSTING$^{S162A/G230I/Q266I}$ showed approximately two orders of magnitude higher sensitivity than hSTING$^{G230I}$, as well as an order of magnitude higher than either hSTING$^{S162A/Q266I}$ or mSTING for the IFN-β induction by DMXAA (FIG. 18B).

Figure 18C:
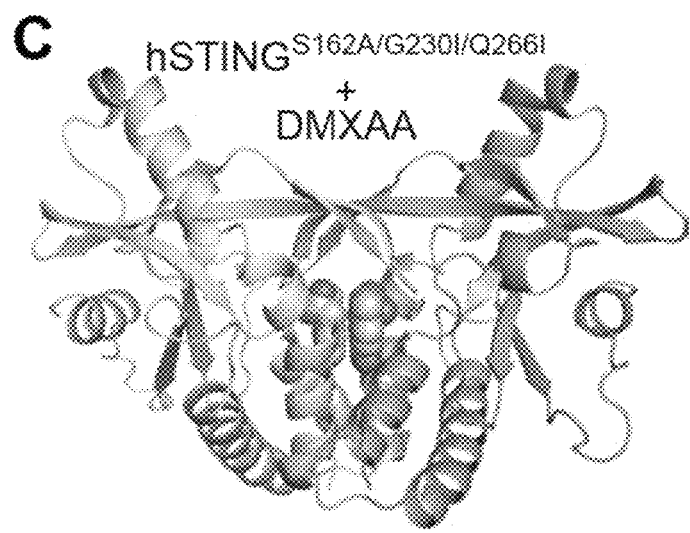
FIG. 18C depicts the 2.37 Å crystal structure of DMXAA bound to hSTING$^{S162A/G230I/Q266I}$ (aa 155-341). The representations are the same as used in FIG. 15E.
Figure 18D:
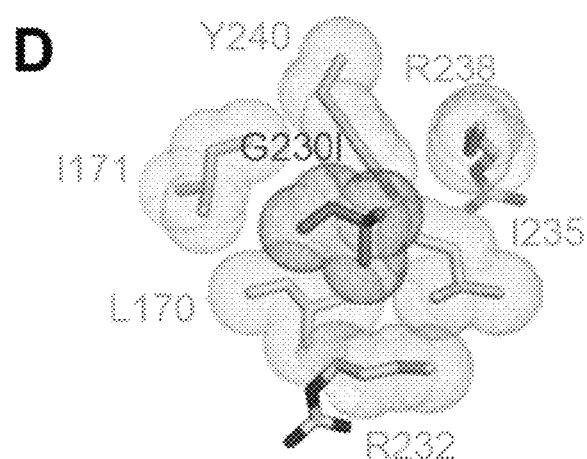
FIG. 18D depicts hydrophobic interactions of G230I substitution in the complex of DMXAA bound to hSTING$^{S162A/G230I/Q266I}$. The representations are the same as used in FIG. 15G.
Figure 18E:
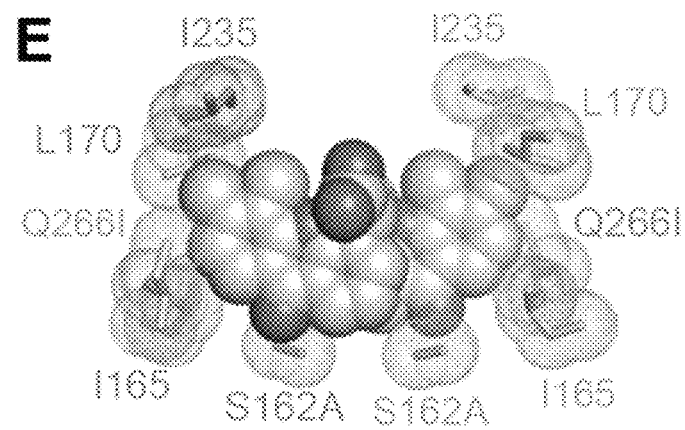
FIG. 18E depicts hydrophobic interactions of DMXAA in the ligand-binding pocket, with the same representations as FIG. 17G.
Figure 18F:
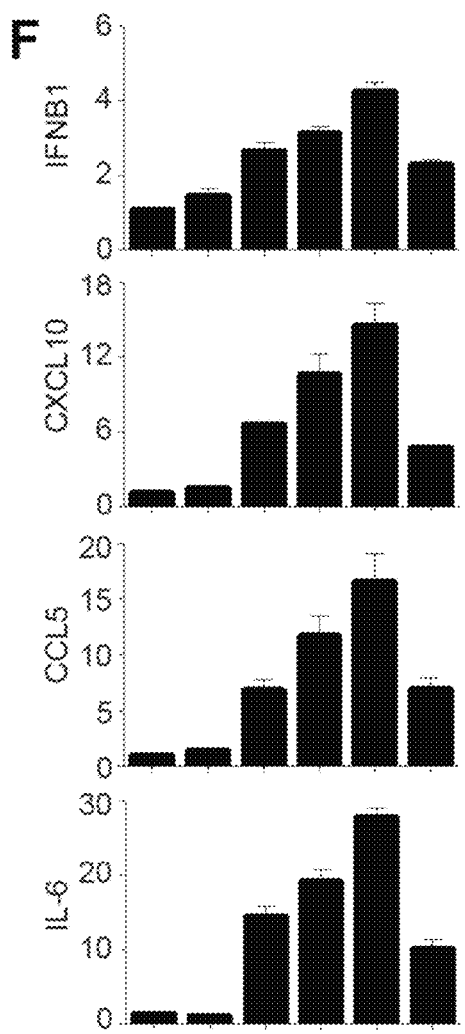
FIG. 18F depicts results where BMDCs (1×10$^6$) from STING$^{Gt/Gt}$ mouse were transduced with retroviruses expressing wt and various hSTING mutants. Two days afterviral infection, BMDCs were treated with 50 μg/ml of DMXAA for 3 hours and cells were collected for real-time PCR to measure IFN-β, CXCL10, CCL5 and IL-6 mRNA levels. Data shown are means±SEM (n=3), representative of two independent experiments.

We also solved the crystal structure of DMXAA bound to hSTING$^{S162A/G230I/Q266I}$ (aa 155-341) at 2.37 Å resolution (x-ray statistics in Table S1) in the 'closed' conformation (FIG. 18C). As expected, we observed both the hydrophobic pocket surrounding I230 (FIG. 18D), which is the same as in the hSTING$^{G230I}$-DMXAA complex (FIG. 16D), as well as the hydrophobic interactions within the DMXAA binding pocket (FIG. 18E), which is the same as in the hSTING$^{S162A/Q266I}$-DMXAA complex (FIG. 17G).

TABLE S7

| | X-ray Statistics for DMXAA with hSTING Mutants | | | |
|---|---|---|---|---|
| Crystal | hSTING$^{group2}$ + DMXAA | hSTING$^{G230I}$ + DMXAA | hSTING$^{S162A/Q266I}$ + DMXAA | hSTING$^{S162A/G230I/Q266I}$ + DMXAA |
| Beam line | APS-ID24C | APS-ID24C | APS-ID24C | APS-ID24C |
| Wavelength | 1.550 | 1.550 | 1.550 | 1.550 |
| Space group | P6$_1$22 | P2$_1$ | P6 | P6 |
| Unit cell | | | | |
| a, b, c (Å) | 62.9, 62.9, 196.1 | 36.6, 77.9, 79.6 | 148.0, 148.0, 36.1 | 148.6, 148.6, 36.2 |
| α, β, γ (°) | 90.0, 90.0, 120.0 | 90.0, 99.0, 90.0 | 90.0, 90.0, 120.0 | 90.0, 90.0, 120.0 |
| Resolution (Å) | 50-1.88 (1.92-1.88)$^a$ | 50-2.51 (2.61-2.51)$^a$ | 50-2.42 (2.55-2.42)$^a$ | 50-2.37 (2.50-2.37)$^a$ |
| R$_{merge}$ | 0.077 (0.785) | 0.102 (0.643) | 0.118 (1.017) | 0.115 (1.104) |
| I/σ (I) | 15.2 (2.4) | 12.1 (2.3) | 15.4 (2.3) | 25.9 (3.1) |

TABLE S7-continued

X-ray Statistics for DMXAA with hSTING Mutants

| Crystal | hSTING$^{group2}$ + DMXAA | hSTING$^{G230I}$ + DMXAA | hSTING$^{S162A/Q266I}$ + DMXAA | hSTING$^{S162A/G230I/Q266I}$ + DMXAA |
|---|---|---|---|---|
| Completeness (%) | 97.6 (93.7) | 94.6 (89.5) | 100.0 (100.0) | 100.0 (100.0) |
| Redundancy | 5.8 (6.0) | 3.8 (3.7) | 9.4 (9.0) | 9.1 (8.7) |
| Number of unique reflections | 19022 | 14320 | 17687 | 19048 |
| R$_{work}$/R$_{free}$ (%) | 17.4/21.8 | 19.7/23.9 | 18.2/22.8 | 18.7/23.1 |
| Number of non-H atoms | | | | |
| Protein | 1499 | 2932 | 2920 | 2928 |
| Water | 137 | 55 | 71 | 58 |
| Ligands(molecule) | 1 | 2 | 2 | 2 |
| Average B factors (Å$^2$) | | | | |
| Protein | 38.68 | 68.70 | 56.51 | 68.13 |
| Water | 45.73 | 44.55 | 51.55 | 63.79 |
| ligands | 21.53 | 49.91 | 28.21 | 38.75 |
| R.m.s. deviations | | | | |
| Bond lengths (Å) | 0.013 | 0.007 | 0.014 | 0.007 |
| Bond angles (°) | 1.580 | 1.262 | 1.613 | 1.203 |

$^a$Highest resolution shell (in Å) shown in parentheses.

Figure 18G:
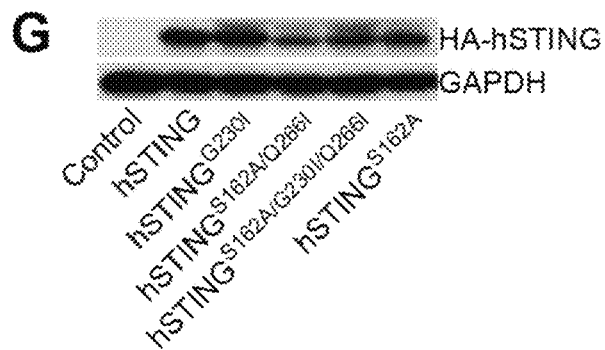
FIG. 18G depicts results where BMDCs were transfected with retroviruses expressing wt hSTING and various hSTING mutants. Cells were collected 2 days after retroviral infection, and the levels of hSTING were determined by Western blot analysis.

Example 16: DMXAA Activates Type I IFN and Proinflammatory Cytokine/Chemokine Production in mSTING-Deficient BMDCs Reconstituted with hSTING Substitutions Examples 1-8 show that c[G(2',5')pA(3',5')p] and its linkage analogs induce type I IFN and proinflammatory cytokine/chemokine production in a STING-dependent manner in bone marrow-derived macrophages. To test whether various hSTING substitutions can rescue the deficiency of type I IFN and proinflammatory cytokine/chemokine production in response to DMXAA in mSTING-deficient bone marrow-derived dendritic cells (BMDCs), we generated BMDCs from homozygous functional null STING mice (Goldenticket, STING$^{Gt/Gt}$) (Sauer et al., 2011). Retroviruses carrying wt hSTING or hSTING mutants (hSTING$^{G230I}$, hSTING$^{S162A/Q266I}$, hSTING$^{S162A/G230I/Q266I}$, hSTING$^{S162A}$) were used to transduce these BMDCs. Although wt hSTING did not induce the up-regulation of IFN-β mRNA after DMXAA treatment, we observed 2.6, 3.1, 4.2, and 2.2-fold increases in IFN-β mRNA levels in BMDCs expressing hSTING$^{G230I}$, hSTING$^{S162A/Q266I}$, hSTING$^{S162A/G230I/Q266I}$ and hSTING$^{S162A}$, respectively. Similar to the results obtained from the luciferase reporter assays, we found that STING$^{Gt/Gt}$-derived BMDCs expressing hSTING$^{S162A/G230I/Q266I}$ had the highest IFN-β mRNA induction after DMXAA treatment, corroborating that G230I substitution and the pocket substitutions S162A/Q226I lead to synergistic effects on hSTING sensitivity to DMXAA. We also observed up-regulation of CXCL10, CCL5 and IL-6 mRNAs in BMDCs expressing various hSTING mutants (FIG. 18F), with hSTING$^{S62A/G230I/Q266I}$ eliciting the strongest induction among the four mutants after DMXAA treatment. We also collected supernatants at 18 h post DMXAA treatment. At this time point, hSTING$^{S162A/G230I/Q266I}$ induced the highest level of CXCL10 production compared with the other hSTING substituents (FIG. 22E). We confirmed hSTING protein expression in transduced cells by Western blot analysis (FIG. 18G).

REFERENCES

1. Ablasser, A., Goldeck, M., Cavlar, T., Deimling, T., Witte, G., Rohl, I., Hopfner, K. P., Ludwig, J., and Hornung, V. (2013). cGAS produces a 2'-5'-linked cyclic dinucleotide second messenger that activates STING. Nature 498, 382-384.
2. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr. D Biol. Crystallogr. 66, 213-221.
3. Baguley, B. C., and Ching, L. M. (2002). DMXAA: an antivascular agent with multiple host responses. Int. J. Radiat. Oncol. Biol. Phys. 54, 1503-1511.
4. Burdette, D. L., and Vance, R. E. (2013). STING and the innate immune response to nucleic acids in the cytosol. Nat. Immunol. 14, 19-26.
5. Burdette, D. L., Monroe, K. M., Sotelo-Troha, K., Iwig, J. S., Eckert, B., Hyodo, M., Hayakawa, Y., and Vance, R. E. (2011). STING is a direct innate immune sensor of cyclic di-GMP. Nature 478, 515-518.
6. Cai, X., Chiu, Y. H., and Chen, Z. J. J. (2014). The cGAS-cGAMP-STING Pathway of Cytosolic DNA Sensing and Signaling. Mol. Cell 54, 289-296.
7. Cavlar, T., Deimling, T., Ablasser, A., Hopfner, K. P., and Hornung, V. (2013). Species-specific detection of the antiviral small-molecule compound CMA by STING. EMBO J. 32, 1440-1450.
8. Civril, F., Deimling, T., de Oliveira Mann, C. C., Ablasser, A., Moldt, M., Witte, G., Hornung, V., and Hopfner, K. P. (2013). Structural mechanism of cytosolic DNA sensing by cGAS. Nature 498, 332-337.
9. Conlon, J., Burdette, D. L., Sharma, S., Bhat, N., Thompson, M., Jiang, Z., Rathinam, V. A., Monks, B., Jin, T., Xiao, T. S., et al. (2013). Mouse, but not human STING, binds and signals in response to the vascular disrupting agent 5,6-Dimethylxanthenone-4-Acetic Acid. J. Immunol. 190, 5216-5225.
10. Dai, P., Wang, W., Cao, H., Avogadri, F., Dai, L., Drexler, I., Joyce, J. A., Li, X. D., Chen, Z., Merghoub, T., et al.

(2014). Modified vaccinia virus Ankara triggers type I IFN production in murine conventional dendritic cells via a cGAS/STING-mediated cytosolic DNA-sensing pathway. PLoS Pathog. 10, e1003989.

11. Danilchanka, O., and Mekalanos, J. J. (2013). Cyclic Dinucleotides and the Innate Immune Response. Cell 154, 962-970.

12. Diner, E. J., Burdette, D. L., Wilson, S. C., Monroe, K. M., Kellenberger, C. A., Hyodo, M., Hayakawa, Y., Hammond, M. C., and Vance, R. E. (2013). The innate immune DNA sensor cGAS produces a noncanonical cyclic dinucleotide that activates human STING. Cell reports 3, 1355-1361.

13. Emsley, P., Lohkamp, B., Scott, W. G., and Cowtan, K. (2010). Features and development of Coot. Acta Crystallogr. D Biol. Crystallogr. 66, 486-501.

14. Gall, A., Treuting, P., Elkon, K. B., Loo, Y. M., Gale, M., Jr., Barber, G. N., and Stetson, D. B. (2012). Autoimmunity initiates in nonhematopoietic cells and progresses via lymphocytes in an IFN-dependent autoimmune disease. Immunity 36, 120-131.

15. Gao, P., Ascano, M., Wu, Y., Barchet, W., Gaffney, B. L., Zillinger, T., Serganov, A. A., Liu, Y. Z., Jones, R. A., Hartmann, G., et al. (2013a). Cyclic [G(2',5') pA(3',5')p] Is the Metazoan Second Messenger Produced by DNA-Activated Cyclic GMP-AMP Synthase. Cell 153, 1094-1107.

16. Gao, P., Ascano, M., Zillinger, T., Wang, W. Y., Dai, P. H., Serganov, A. A., Gaffney, B. L., Shuman, S., Jones, R. A., Deng, L., et al. (2013b). Structure-Function Analysis of STING Activation by c[G(2',5') pA(3',5')p] and Targeting by Antiviral DMXAA. Cell 154, 748-762.

17. Gehrke, N., Mertens, C., Zillinger, T., Wenzel, J., Bald, T., Zahn, S., Tuting, T., Hartmann, G., and Barchet, W. (2013). Oxidative Damage of DNA Confers Resistance to Cytosolic Nuclease TREX1 Degradation and Potentiates STING-Dependent Immune Sensing. Immunity 39, 482-495.

18. Head, M., and Jameson, M. B. (2010). The development of the tumor vascular-disrupting agent ASA404 (vadimezan, DMXAA): current status and future opportunities. Expert Opin. Inv. Drug. 19, 295-304.

19. Huang, Y. H., Liu, X. Y., Du, X. X., Jiang, Z. F., and Su, X. D. (2012). The structural basis for the sensing and binding of cyclic di-GMP by STING. Nat. Struct. Mol. Bio. 19, 728-730.

20. Ishikawa, H., and Barber, G. N. (2008). STING is an endoplasmic reticulum adaptor that facilitates innate immune signalling. Nature 455, 674-678.

21. Ishikawa, H., Ma, Z., and Barber, G. N. (2009). STING regulates intracellular DNA-mediated, type I interferon-dependent innate immunity. Nature 461, 788-792.

22. Jin, L., Waterman, P. M., Jonscher, K. R., Short, C. M., Reisdorph, N. A., and Cambier, J. C. (2008). MPYS, a novel membrane tetraspanner, is associated with major histocompatibility complex class II and mediates transduction of apoptotic signals. Mol. Cell Biol. 28, 5014-5026.

23. Jin, L., Xu, L. G., Yang, I. V., Davidson, E. J., Schwartz, D. A., Wurfel, M. M., and Cambier, J. C. (2011). Identification and characterization of a loss-of-function human MPYS variant. Genes Immun. 12, 263-269.

24. Keating, S. E., Baran, M. and Bowie, A. G. (2011). Cytosolic DNA sensors regulating type I interferon induction. Trends in Immunol. 32, 574-581.

25. Kim, S., Li, L., Maliga, Z., Yin, Q., Wu, H., and Mitchison, T. J. (2013). Anticancer flavonoids are mouse-selective STING agonists. ACS Chem. Biol. 8, 1396-1401.

26. Lara, P. N., Jr., Douillard, J. Y., Nakagawa, K., von Pawel, J., McKeage, M. J., Albert, I., Losonczy, G., Reck, M., Heo, D. S., Fan, X., et al. (2011). Randomized phase III placebo-controlled trial of carboplatin and paclitaxel with or without the vascular disrupting agent vadimezan (ASA404) in advanced non-small-cell lung cancer. J. Clin. Oncol. 29, 2965-2971.

27. McCoy, A. J., Grosse-Kunstleve, R. W., Adams, P. D., Winn, M. D., Storoni, L. C., and Read, R. J. (2007). Phaser crystallographic software. J. Appl. Crystallogr. 40, 658-674.

28. Murshudov, G. N., Vagin, A. A., and Dodson, E. J. (1997). Refinement of macromolecular structures by the maximum-likelihood method. Acta Crystallogr. D Biol. Crystallogr. 53, 240-255.

29. O'Neill, L. A. J. (2013). Sensing the Dark Side of DNA. Science 339, 763-764.

30. Otwinowski, Z., and Minor, W. (1997). Processing of X-ray Diffraction Data Collected in Oscillation Mode. Methods in Enzymology 276, 307-326.

31. Ouyang, S., Song, X., Wang, Y., Ru, H., Shaw, N., Jiang, Y., Niu, F., Zhu, Y., Qiu, W., Parvatiyar, K., et al. (2012). Structural analysis of the STING adaptor protein reveals a hydrophobic dimer interface and mode of cyclic di-GMP binding. Immunity 36, 1073-1086.

32. Paludan, S. R. and Bowie, A. G. (2013). Immune sensing of DNA. Immunity 38, 870-880.

33. Prantner, D., Perkins, D. J., Lai, W., Williams, M. S., Sharma, S., Fitzgerald, K. A., and Vogel, S. N. (2012). 5,6-Dimethylxanthenone-4-acetic acid (DMXAA) activates stimulator of interferon gene (STING)-dependent innate immune pathways and is regulated by mitochondrial membrane potential. J. Biol. Chem. 287, 39776-39788.

34. Rasmussen, S. B., Horan, K. A., Holm, C. K., Stranks, A. J., Mettenleiter, T. C., Simon, A. K., Jensen, S. B., Rixon, F. J., He, B., and Paludan, S. R. (2011). Activation of autophagy by alpha-herpesviruses in myeloid cells is mediated by cytosolic viral DNA through a mechanism dependent on stimulator of IFN genes. J Immunol. 187, 5268-5276.

35. Roberts, Z. J., Ching, L. M., and Vogel, S. N. (2008). IFN-beta-dependent inhibition of tumor growth by the vascular disrupting agent 5,6-dimethylxanthenone-4-acetic acid (DMXAA). J. Interf. Cytok. Res. 28, 133-139.

36. Sauer, J. D., Sotelo-Troha, K., von Moltke, J., Monroe, K. M., Rae, C. S., Brubaker, S. W., Hyodo, M., Hayakawa, Y., Woodward, J. J., Portnoy, D. A., and Vance, R. E. (2011). The N-ethyl-N-nitrosourea-induced Goldenticket mouse mutant reveals an essential function of Sting in the in vivo interferon response to Listeria monocytogenes and cyclic dinucleotides. Infect. Immun. 79, 688-694.

37. Schoggins, J. W., Wilson, S. J., Panis, M., Murphy, M. Y., Jones, C. T., Bieniasz, P., and Rice, C. M. (2011). A diverse range of gene products are effectors of the type I interferon antiviral response. Nature 472, 481-485.

38. Shang, G., Zhu, D., Li, N., Zhang, J., Zhu, C., Lu, D., Liu, C., Yu, Q., Zhao, Y., Xu, S., et al. (2012). Crystal structures of STING protein reveal basis for recognition of cyclic di-GMP. Nat. Struct. Mol. Bio. 19, 725-727.

39. Shu, C., Yi, G., Watts, T., Kao, C. C., and Li, P. (2012). Structure of STING bound to cyclic di-GMP reveals the mechanism of cyclic dinucleotide recognition by the immune system. Nat. Struct. Mol. Bio. 19, 722-724.

40. Sun, L., Wu, J., Du, F., Chen, X., and Chen, Z. J. (2013). Cyclic GMP-AMP synthase is a cytosolic DNA sensor that activates the type I interferon pathway. Science 339, 786-791.

41. Sun, W., Li, Y., Chen, L., Chen, H., You, F., Zhou, X., Zhou, Y., Zhai, Z., Chen, D., and Jiang, Z. (2009). ERIS, an endoplasmic reticulum IFN stimulator, activates innate immune signaling through dimerization. Proc. Natl. Acad. Sci. USA 106, 8653-8658.

42. Woodward, J. J., Iavarone, A. T., and Portnoy, D. A. (2010). c-di-AMP secreted by intracellular *Listeria monocytogenes* activates a host type I interferon response. Science 328, 1703-1705.

43. Wu, J., Sun, L., Chen, X., Du, F., Shi, H., Chen, C., and Chen, Z. J. (2013). Cyclic GMP-AMP is an endogenous second messenger in innate immune signaling by cytosolic DNA. Science 339, 826-830.

44. Xiao, T. S., and Fitzgerald, K. A. (2013). The cGAS-STING Pathway for DNA Sensing. Mol. Cell 51, 135-139.

45. Yi, G. H., Brendel, V. P., Shu, C., Li, P. W., Palanathan, S., and Kao, C. C. (2013). Single Nucleotide Polymorphisms of Human STING Can Affect Innate Immune Response to Cyclic Dinucleotides. PLoS One 8, e77846.

46. Yin, Q., Tian, Y., Kabaleeswaran, V., Jiang, X., Tu, D., Eck, M. J., Chen, Z. J., and Wu, H. (2012). Cyclic di-GMP sensing via the innate immune signaling protein STING. Mol. Cell 46, 735-745.

47. Zhang, X., Shi, H. P., Wu, J. X., Zhang, X. W., Sun, L. J., Chen, C., and Chen, Z. J. (2013). Cyclic GMP-AMP Containing Mixed Phosphodiester Linkages Is An Endogenous High-Affinity Ligand for STING. Mol. Cell 51, 226-235.

48. Zhong, B., Yang, Y., Li, S., Wang, Y. Y., Li, Y., Diao, F., Lei, C., He, X., Zhang, L., Tien, P., et al. (2008). The adaptor protein MITA links virus-sensing receptors to IRF3 transcription factor activation. Immunity 29, 538-550.2.

TABLE 6

DMXAA-hSTING$^{group2}$ complex

| | | | |
|---|---|---|---|
| REMARK 3 | | | |
| REMARK 3 | REFINEMENT. | | |
| REMARK 3 | PROGRAM: PHENIX (phenix.refine: 1.8.2_1309) | | |
| REMARK 3 | AUTHORS: Adams, Afonine, Burnley, Chen, Davis, Echols, Gildea, | | |
| REMARK 3 | : Gopal, Gros, Grosse-Kunstleve, Headd, Hung, Immormino, | | |
| REMARK 3 | : Ioerger, McCoy, McKee, Moriarty, Pai, Read, Richardson, | | |
| REMARK 3 | : Richardson, Romo, Sacchettini, Sauter, Smith, Storoni, | | |
| REMARK 3 | : Terwilliger, Zwart | | |
| REMARK 3 | | | |
| REMARK 3 | REFINEMENT TARGET: ML | | |
| REMARK 3 | | | |
| REMARK 3 | DATA USED IN REFINEMENT. | | |
| REMARK 3 | RESOLUTION RANGE HIGH (ANGSTROMS): | 1.880 | |
| REMARK 3 | RESOLUTION RANGE LOW (ANGSTROMS): | 54.491 | |
| REMARK 3 | MIN(FOBS/SIGMA_FOBS): | 1.37 | |
| REMARK 3 | COMPLETENESS FOR RANGE (%): | 96.91 | |
| REMARK 3 | NUMBER OF REFLECTIONS: | 19022 | |
| REMARK 3 | NUMBER OF REFLECTIONS (NON-ANOMALOUS): | 19022 | |
| REMARK 3 | | | |
| REMARK 3 | FIT TO DATA USED IN REFINEMENT. | | |
| REMARK 3 | R VALUE (WORKING + TEST SET): 0.1765 | | |
| REMARK 3 | R VALUE (WORKING SET): 0.1743 | | |
| REMARK 3 | FREE R VALUE: 0.2185 | | |
| REMARK 3 | FREE R VALUE TEST SET SIZE (%): 5.14 | | |
| REMARK 3 | FREE R VALUE TEST SET COUNT: 977 | | |
| REMARK 3 | | | |
| REMARK 3 | FIT TO DATA USED IN REFINEMENT (IN BINS). | | |
| REMARK 3 | BIN  RESOLUTION RANGE  COMPL.  NWORK  NFREE  RWORK  RFREE | | |
| REMARK 3 | 1   54.5141-3.5962   0.98   2865   140   0.1574   0.1997 | | |
| REMARK 3 | 2   3.5962-2.8544    0.99   2698   112   0.1674   0.1953 | | |
| REMARK 3 | 3   2.8544-2.4936    0.98   2588   146   0.1813   0.2280 | | |
| REMARK 3 | 4   2.4936-2.2656    0.98   2537   160   0.1775   0.2272 | | |
| REMARK 3 | 5   2.2656-2.1032    0.97   2507   144   0.1899   0.2259 | | |
| REMARK 3 | 6   2.1032-1.9792    0.95   2455   131   0.2010   0.2427 | | |
| REMARK 3 | 7   1.9792-1.8801    0.93   2395   144   0.2943   0.3815 | | |
| REMARK 3 | | | |
| REMARK 3 | BULK SOLVENT MODELLING. | | |
| REMARK 3 | METHOD USED:   FLAT BULK SOLVENT MODEL | | |
| REMARK 3 | SOLVENT RADIUS:   1.11 | | |
| REMARK 3 | SHRINKAGE RADIUS: 0.90 | | |
| REMARK 3 | GRID STEP FACTOR: 4.00 | | |
| REMARK 3 | | | |
| REMARK 3 | ERROR ESTIMATES. | | |
| REMARK 3 | COORDINATE ERROR (MAXIMUM-LIKELIHOOD BASED): 0.22 | | |
| REMARK 3 | PHASE ERROR (DEGREES, MAXIMUM-LIKELIHOOD BASED): 20.66 | | |
| REMARK 3 | | | |
| REMARK 3 | STRUCTURE FACTORS CALCULATION ALGORITHM: FFT | | |
| REMARK 3 | | | |
| REMARK 3 | DEVIATIONS FROM IDEAL VALUES. | | |
| REMARK 3 |           RMSD    MAX    COUNT | | |
| REMARK 3 | BOND:    0.013   0.073   1551 | | |
| REMARK 3 | ANGLE:   1.580   11.179  2109 | | |

TABLE 6-continued

| DMXAA-hSTING$^{group2}$ complex | | | | |
|---|---|---|---|---|
| REMARK 3 | CHIRALITY: | 0.113 | 0.543 | 225 |
| REMARK 3 | PLANARITY: | 0.007 | 0.049 | 281 |
| REMARK 3 | DIHEDRAL: | 16.214 | 68.227 | 593 |
| REMARK 3 | MIN NONBONDED DISTANCE: 1.748 | | | |
| REMARK 3 | | | | |
| REMARK 3 | MOLPROBITY STATISTICS. | | | |
| REMARK 3 | ALL-ATOM CLASHSCORE: 4.68 | | | |
| REMARK 3 | RAMACHANDRAN PLOT: | | | |
| REMARK 3 | OUTLIERS: 0.00% | | | |
| REMARK 3 | ALLOWED: 4.35% | | | |
| REMARK 3 | FAVORED: 95.65% | | | |
| REMARK 3 | ROTAMER OUTLIERS: 3.07% | | | |
| REMARK 3 | CBETA DEVIATIONS: 1 | | | |
| REMARK 3 | | | | |
| REMARK 3 | ATOMIC DISPLACEMENT PARAMETERS. | | | |
| REMARK 3 | WILSON B: 31.20 | | | |
| REMARK 3 | RMS(B_ISO_OR_EQUIVALENT_BONDED): 6.85 | | | |
| REMARK 3 | ATOMS    NUMBER OF ATOMS | | | |
| REMARK 3 | ISO.   ANISO. | | | |
| REMARK 3 | ALL:       1650  1494 | | | |
| REMARK 3 | ALL (NO H):  1650  1494 | | | |
| REMARK 3 | SOLVENT:     135    0 | | | |
| REMARK 3 | NON-SOLVENT: 1515  1494 | | | |
| REMARK 3 | HYDROGENS:     0    0 | | | |
| REMARK 3 | | | | |
| REMARK 3 | TLS DETAILS. | | | |
| REMARK 3 | NUMBER OF TLS GROUPS: 7 | | | |
| REMARK 3 | ORIGIN: CENTER OF MASS | | | |
| REMARK 3 | TLS GROUP: 1 | | | |
| REMARK 3 | SELECTION: chain 'A' and (resid 154 through 167) | | | |
| REMARK 3 | ORIGIN FOR THE GROUP (A):   −13.4260   50.6427   4.3207 | | | |
| REMARK 3 | T TENSOR | | | |
| REMARK 3 | T11:   0.1683 T22:    0.1103 | | | |
| REMARK 3 | T33:   0.1207 T12:   −0.0135 | | | |
| REMARK 3 | T13:  −0.0096 T23:   −0.0277 | | | |
| REMARK 3 | L TENSOR | | | |
| REMARK 3 | L11:   4.8802 L22:    3.2007 | | | |
| REMARK 3 | L33:   6.2531 L12:    0.5545 | | | |
| REMARK 3 | L13:  −3.1583 L23:   −0.6229 | | | |
| REMARK 3 | S TENSOR | | | |
| REMARK 3 | S11:   0.0931 S12:   −0.6224 S13:    0.0424 | | | |
| REMARK 3 | S21:   0.2192 S22:   −0.0965 S23:   −0.1503 | | | |
| REMARK 3 | S31:  −0.0048 S32:    0.5314 S33:   −0.0194 | | | |
| REMARK 3 | TLS GROUP: 2 | | | |
| REMARK 3 | SELECTION: chain 'A' and (resid 168 through 185) | | | |
| REMARK 3 | ORIGIN FOR THE GROUP (A):   −32.7374   41.7922   9.1633 | | | |
| REMARK 3 | T TENSOR | | | |
| REMARK 3 | T11:   0.3021 T22:    0.2444 | | | |
| REMARK 3 | T33:   0.3426 T12:   −0.0595 | | | |
| REMARK 3 | T13:   0.0922 T23:   −0.0478 | | | |
| REMARK 3 | L TENSOR | | | |
| REMARK 3 | L11:   3.4374 L22:    2.9964 | | | |
| REMARK 3 | L33:   3.1918 L12:    2.4360 | | | |
| REMARK 3 | L13:   1.3854 L23:    2.0523 | | | |
| REMARK 3 | S TENSOR | | | |
| REMARK 3 | S11:   0.5743 S12:   −1.1553 S13:    0.5744 | | | |
| REMARK 3 | S21:   0.6347 S22:   −0.7613 S23:    0.8717 | | | |
| REMARK 3 | S31:   0.1473 S32:   −0.3896 S33:    0.0968 | | | |
| REMARK 3 | TLS GROUP: 3 | | | |
| REMARK 3 | SELECTION: chain 'A' and (resid 186 through 211) | | | |
| REMARK 3 | ORIGIN FOR THE GROUP (A):   −27.1904   34.9528   −0.7246 | | | |
| REMARK 3 | T TENSOR | | | |
| REMARK 3 | T11:   0.2543 T22:    0.1132 | | | |
| REMARK 3 | T33:   0.2799 T12:    0.0289 | | | |
| REMARK 3 | T13:   0.0152 T23:   −0.0043 | | | |
| REMARK 3 | L TENSOR | | | |
| REMARK 3 | L11:   9.8039 L22:    4.3916 | | | |
| REMARK 3 | L33:   2.9025 L12:    5.7740 | | | |
| REMARK 3 | L13:  −3.0538 L23:   −1.9563 | | | |
| REMARK 3 | S TENSOR | | | |
| REMARK 3 | S11:  −0.0078 S12:    0.1178 S13:    0.0817 | | | |
| REMARK 3 | S21:  −0.0786 S22:   −0.0580 S23:    0.0132 | | | |
| REMARK 3 | S31:   0.0919 S32:    0.0047 S33:   −0.0013 | | | |
| REMARK 3 | TLS GROUP: 4 | | | |
| REMARK 3 | SELECTION: chain 'A' and (resid 212 through 280) | | | |
| REMARK 3 | ORIGIN FOR THE GROUP (A):   −25.5020   42.8838   −4.1159 | | | |
| REMARK 3 | T TENSOR | | | |
| REMARK 3 | T11:   0.2173 T22:    0.1850 | | | |

TABLE 6-continued

| DMXAA-hSTING$^{group2}$ complex | | | | | | | | | |
|---|---|---|---|---|---|---|---|---|---|
| REMARK 3 | | T33: | 0.1792 | T12: | 0.0218 | | | | |
| REMARK 3 | | T13: | −0.0241 | T23: | −0.0111 | | | | |
| REMARK 3 | | L TENSOR | | | | | | | |
| REMARK 3 | | L11: | 2.6912 | L22: | 1.9708 | | | | |
| REMARK 3 | | L33: | 1.7012 | L12: | 0.7989 | | | | |
| REMARK 3 | | L13: | −0.5883 | L23: | −0.0806 | | | | |
| REMARK 3 | | S TENSOR | | | | | | | |
| REMARK 3 | | S11: | 0.0125 | S12: | 0.0312 | S13: | 0.0124 | | |
| REMARK 3 | | S21: | −0.0313 | S22: | −0.0579 | S23: | 0.1528 | | |
| REMARK 3 | | S31: | 0.0124 | S32: | −0.1562 | S33: | 0.0446 | | |
| REMARK 3 | TLS GROUP: 5 | | | | | | | | |
| REMARK 3 | SELECTION: chain 'A' and (resid 281 through 299) | | | | | | | | |
| REMARK 3 | | ORIGIN FOR THE GROUP (A): | | −7.1814 | | 43.5461 | | −1.4472 | |
| REMARK 3 | | T TENSOR | | | | | | | |
| REMARK 3 | | T11: | 0.1952 | T22: | 0.1940 | | | | |
| REMARK 3 | | T33: | 0.2378 | T12: | 0.0443 | | | | |
| REMARK 3 | | T13: | −0.0485 | T23: | −0.0102 | | | | |
| REMARK 3 | | L TENSOR | | | | | | | |
| REMARK 3 | | L11: | 9.1414 | L22: | 4.6808 | | | | |
| REMARK 3 | | L33: | 6.3324 | L12: | 1.0083 | | | | |
| REMARK 3 | | L13: | −6.9440 | L23: | −0.5677 | | | | |
| REMARK 3 | | S TENSOR | | | | | | | |
| REMARK 3 | | S11: | −0.1423 | S12: | −0.1738 | S13: | −0.4257 | | |
| REMARK 3 | | S21: | 0.0344 | S22: | 0.0534 | S23: | −0.4990 | | |
| REMARK 3 | | S31: | 0.5858 | S32: | 0.9638 | S33: | 0.2796 | | |
| REMARK 3 | TLS GROUP: 6 | | | | | | | | |
| REMARK 3 | SELECTION: chain 'A' and (resid 300 through 314) | | | | | | | | |
| REMARK 3 | | ORIGIN FOR THE GROUP (A): | | −18.7157 | | 39.1351 | | 8.9537 | |
| REMARK 3 | | T TENSOR | | | | | | | |
| REMARK 3 | | T11: | 0.4995 | T22: | 0.3964 | | | | |
| REMARK 3 | | T33: | 0.2781 | T12: | 0.0221 | | | | |
| REMARK 3 | | T13: | −0.0514 | T23: | 0.0212 | | | | |
| REMARK 3 | | L TENSOR | | | | | | | |
| REMARK 3 | | L11: | 4.8044 | L22: | 4.6243 | | | | |
| REMARK 3 | | L33: | 3.0810 | L12: | −0.7724 | | | | |
| REMARK 3 | | L13: | −1.9557 | L23: | 3.4708 | | | | |
| REMARK 3 | | S TENSOR | | | | | | | |
| REMARK 3 | | S11: | −0.0010 | S12: | −0.9497 | S13: | −0.1092 | | |
| REMARK 3 | | S21: | 1.1162 | S22: | 0.0813 | S23: | −0.3287 | | |
| REMARK 3 | | S31: | 0.4353 | S32: | −0.1031 | S33: | 0.1316 | | |
| REMARK 3 | TLS GROUP: 7 | | | | | | | | |
| REMARK 3 | SELECTION: chain 'A' and (resid 315 through 335) | | | | | | | | |
| REMARK 3 | | ORIGIN FOR THE GROUP (A): | | −16.9164 | | 28.0917 | | −5.8168 | |
| REMARK 3 | | T TENSOR | | | | | | | |
| REMARK 3 | | T11: | 0.3475 | T22: | 0.3288 | | | | |
| REMARK 3 | | T33: | 0.3348 | T12: | 0.0762 | | | | |
| REMARK 3 | | T13: | −0.0345 | T23: | 0.0252 | | | | |
| REMARK 3 | | L TENSOR | | | | | | | |
| REMARK 3 | | L11: | 3.4482 | L22: | 5.1152 | | | | |
| REMARK 3 | | L33: | 4.7731 | L12: | 2.2134 | | | | |
| REMARK 3 | | L13: | −4.0510 | L23: | −2.1278 | | | | |
| REMARK 3 | | S TENSOR | | | | | | | |
| REMARK 3 | | S11: | −0.2271 | S12: | −0.1756 | S13: | −0.6768 | | |
| REMARK 3 | | S21: | −0.3089 | S22: | −0.2971 | S23: | −0.3644 | | |
| REMARK 3 | | S31: | 1.0155 | S32: | 0.9738 | S33: | 0.4937 | | |
| REMARK 3 | | | | | | | | | |
| CRYST1 | 62.921 | 62.921 | 196.054 | 90.00 | 90.00 | 120.00 | P 61 2 2 | | |
| SCALE1 | 0.015893 | 0.009176 | 0.000000 | 0.00000 | | | | | |
| SCALE2 | 0.000000 | 0.018352 | 0.000000 | 0.00000 | | | | | |
| SCALE3 | 0.000000 | 0.000000 | 0.005101 | 0.00000 | | | | | |

| | | | | | | | | | | | | |
|---|---|---|---|---|---|---|---|---|---|---|---|---|
| ATOM | 1 | N | SER | A | 154 | −3.015 | 53.192 | 1.851 | 1.00 | 48.06 | | N |
| ANISOU | 1 | N | SER | A | 154 | 4854 | 7355 | 6050 | −705 | −138 | −354 | N |
| ATOM | 2 | CA | SER | A | 154 | −3.281 | 52.521 | 0.590 | 1.00 | 39.52 | | C |
| ANISOU | 2 | CA | SER | A | 154 | 3932 | 5969 | 5113 | −442 | −2 | −225 | C |
| ATOM | 3 | CB | SER | A | 154 | −2.946 | 51.028 | 0.690 | 1.00 | 43.14 | | C |
| ANISOU | 3 | CB | SER | A | 154 | 4273 | 6556 | 5563 | −73 | −34 | 16 | C |
| ATOM | 4 | OG | SER | A | 154 | −4.052 | 50.302 | 1.173 | 1.00 | 38.49 | | O |
| ANISOU | 4 | OG | SER | A | 154 | 3913 | 5780 | 4930 | 82 | −81 | 78 | O |
| ATOM | 5 | C | SER | A | 154 | −4.739 | 52.703 | 0.174 | 1.00 | 25.77 | | C |
| ANISOU | 5 | C | SER | A | 154 | 2572 | 3800 | 3418 | −416 | 56 | −282 | C |
| ATOM | 6 | O | SER | A | 154 | −5.618 | 52.958 | 0.989 | 1.00 | 26.82 | | O |
| ANISOU | 6 | O | SER | A | 154 | 2833 | 3874 | 3483 | −486 | −14 | −356 | O |
| ATOM | 7 | N | VAL | A | 155 | −4.997 | 52.549 | −1.127 | 1.00 | 23.93 | | N |
| ANISOU | 7 | N | VAL | A | 155 | 2502 | 3308 | 3283 | −308 | 189 | −240 | N |
| ATOM | 8 | CA | VAL | A | 155 | −6.369 | 52.608 | −1.607 | 1.00 | 21.08 | | C |
| ANISOU | 8 | CA | VAL | A | 155 | 2442 | 2628 | 2939 | −259 | 219 | −260 | C |
| ATOM | 9 | CB | VAL | A | 155 | −6.419 | 52.379 | −3.125 | 1.00 | 23.46 | | C |

TABLE 6-continued

DMXAA-hSTING$^{group2}$ complex

| | | | | | | | | | | | | |
|---|---|---|---|---|---|---|---|---|---|---|---|---|
| ANISOU | 9 | CB | VAL | A | 155 | 2874 | 2750 | 3291 | −158 | 351 | −209 | C |
| ATOM | 10 | CG1 | VAL | A | 155 | −7.832 | 52.019 | −3.525 | 1.00 | 23.12 | | C |
| ANISOU | 10 | CG1 | VAL | A | 155 | 3072 | 2495 | 3219 | −72 | 330 | −200 | C |
| ATOM | 11 | CG2 | VAL | A | 155 | −5.958 | 53.669 | −3.848 | 1.00 | 27.32 | | C |
| ANISOU | 11 | CG2 | VAL | A | 155 | 3375 | 3176 | 3828 | −342 | 478 | −263 | C |
| ATOM | 12 | C | VAL | A | 155 | −7.284 | 51.616 | −0.884 | 1.00 | 22.97 | | C |
| ANISOU | 12 | C | VAL | A | 155 | 2768 | 2836 | 3123 | −109 | 121 | −202 | C |
| ATOM | 13 | O | VAL | A | 155 | −8.384 | 51.959 | −0.434 | 1.00 | 22.48 | | O |
| ANISOU | 13 | O | VAL | A | 155 | 2846 | 2660 | 3037 | −163 | 83 | −260 | O |
| ATOM | 14 | N | ALA | A | 156 | −6.812 | 50.382 | −0.740 | 1.00 | 22.07 | | N |
| ANISOU | 14 | N | ALA | A | 156 | 2568 | 2817 | 3000 | 91 | 112 | −73 | N |
| ATOM | 15 | CA | ALA | A | 156 | −7.594 | 49.312 | −0.102 | 1.00 | 18.74 | | C |
| ANISOU | 15 | CA | ALA | A | 156 | 2251 | 2329 | 2539 | 237 | 69 | 10 | C |
| ATOM | 16 | CB | ALA | A | 156 | −6.768 | 48.036 | −0.063 | 1.00 | 24.84 | | C |
| ANISOU | 16 | CB | ALA | A | 156 | 2928 | 3179 | 3333 | 489 | 125 | 186 | C |
| ATOM | 17 | C | ALA | A | 156 | −7.988 | 49.642 | 1.329 | 1.00 | 29.73 | | C |
| ANISOU | 17 | C | ALA | A | 156 | 3598 | 3873 | 3826 | 142 | −58 | −15 | C |
| ATOM | 18 | O | ALA | A | 156 | −9.069 | 49.262 | 1.804 | 1.00 | 24.94 | | O |
| ANISOU | 18 | O | ALA | A | 156 | 3139 | 3149 | 3188 | 164 | −76 | −9 | O |
| ATOM | 19 | N | HIS | A | 157 | −7.057 | 50.249 | 2.054 | 1.00 | 23.60 | | N |
| ANISOU | 19 | N | HIS | A | 157 | 2597 | 3396 | 2973 | 29 | −138 | −43 | N |
| ATOM | 20 | C | HIS | A | 157 | −8.467 | 51.558 | 3.555 | 1.00 | 30.39 | | C |
| ANISOU | 20 | C | HIS | A | 157 | 3620 | 4236 | 3692 | −272 | −216 | −278 | C |
| ATOM | 21 | O | HIS | A | 157 | −9.351 | 51.389 | 4.384 | 1.00 | 28.20 | | O |
| ANISOU | 21 | O | HIS | A | 157 | 3443 | 3937 | 3334 | −269 | −245 | −286 | O |
| ATOM | 22 | CA | AHIS | A | 157 | −7.327 | 50.575 | 3.458 | 0.55 | 25.53 | | C |
| ANISOU | 22 | CA | AHIS | A | 157 | 2798 | 3839 | 3063 | −90 | −256 | −92 | C |
| ATOM | 23 | CB | AHIS | A | 157 | −6.100 | 51.149 | 4.148 | 0.55 | 28.32 | | C |
| ANISOU | 23 | CB | AHIS | A | 157 | 2859 | 4607 | 3296 | −250 | −357 | −138 | C |
| ATOM | 24 | CG | AHIS | A | 157 | −5.042 | 50.140 | 4.409 | 0.55 | 33.78 | | C |
| ANISOU | 24 | CG | AHIS | A | 157 | 3283 | 5620 | 3931 | −19 | −424 | 99 | C |
| ATOM | 25 | ND1 | AHIS | A | 157 | −3.714 | 50.355 | 4.105 | 0.55 | 49.79 | | N |
| ANISOU | 25 | ND1 | AHIS | A | 157 | 4999 | 7946 | 5973 | −53 | −440 | 126 | N |
| ATOM | 26 | CE1 | AHIS | A | 157 | −3.015 | 49.285 | 4.440 | 0.55 | 49.57 | | C |
| ANISOU | 26 | CE1 | AHIS | A | 157 | 4756 | 8181 | 5897 | 246 | −487 | 397 | C |
| ATOM | 27 | NE2 | AHIS | A | 157 | −3.838 | 48.387 | 4.945 | 0.55 | 40.13 | | N |
| ANISOU | 27 | NE2 | AHIS | A | 157 | 3761 | 6828 | 4660 | 459 | −486 | 544 | N |
| ATOM | 28 | CD2 | AHIS | A | 157 | −5.117 | 48.893 | 4.935 | 0.55 | 32.78 | | C |
| ANISOU | 28 | CD2 | AHIS | A | 157 | 3148 | 5560 | 3748 | 277 | −452 | 348 | C |
| ATOM | 29 | CA | BHIS | A | 157 | −7.288 | 50.581 | 3.457 | 0.45 | 26.09 | | C |
| ANISOU | 29 | CA | BHIS | A | 157 | 2862 | 3918 | 3134 | −91 | −257 | −92 | C |
| ATOM | 30 | CB | BHIS | A | 157 | −6.010 | 51.192 | 4.037 | 0.45 | 28.72 | | C |
| ANISOU | 30 | CB | BHIS | A | 157 | 2897 | 4654 | 3359 | −255 | −349 | −142 | C |
| ATOM | 31 | CG | BHIS | A | 157 | −5.912 | 51.095 | 5.521 | 0.45 | 32.23 | | C |
| ANISOU | 31 | CG | BHIS | A | 157 | 3220 | 5452 | 3574 | −313 | −500 | −123 | C |
| ATOM | 32 | ND1 | BHIS | A | 157 | −5.892 | 49.888 | 6.198 | 0.45 | 29.79 | | N |
| ANISOU | 32 | ND1 | BHIS | A | 157 | 2854 | 5303 | 3160 | −45 | −570 | 129 | N |
| ATOM | 33 | CE1 | BHIS | A | 157 | −5.776 | 50.119 | 7.495 | 0.45 | 33.98 | | C |
| ANISOU | 33 | CE1 | BHIS | A | 157 | 3274 | 6195 | 3440 | −169 | −710 | 105 | C |
| ATOM | 34 | NE2 | BHIS | A | 157 | −5.719 | 51.418 | 7.690 | 0.45 | 24.55 | | N |
| ANISOU | 34 | NE2 | BHIS | A | 157 | 2074 | 5065 | 2190 | −533 | −722 | −192 | N |
| ATOM | 35 | CD2 | BHIS | A | 157 | −5.794 | 52.058 | 6.476 | 0.45 | 47.22 | | C |
| ANISOU | 35 | CD2 | BHIS | A | 157 | 5053 | 7590 | 5297 | −619 | −579 | −325 | C |
| ATOM | 36 | N | GLY | A | 158 | −8.466 | 52.579 | 2.687 | 1.00 | 24.89 | | N |
| ANISOU | 36 | N | GLY | A | 158 | 2990 | 3364 | 3102 | −407 | −121 | −402 | N |
| ATOM | 37 | CA | GLY | A | 158 | −9.583 | 53.534 | 2.652 | 1.00 | 25.79 | | C |
| ANISOU | 37 | CA | GLY | A | 158 | 3307 | 3232 | 3260 | −509 | −41 | −530 | C |
| ATOM | 38 | C | GLY | A | 158 | −10.898 | 52.868 | 2.270 | 1.00 | 24.90 | | C |
| ANISOU | 38 | C | GLY | A | 158 | 3352 | 2916 | 3193 | −336 | −25 | −443 | C |
| ATOM | 39 | O | GLY | A | 158 | −11.920 | 53.116 | 2.899 | 1.00 | 23.56 | | O |
| ANISOU | 39 | O | GLY | A | 158 | 3276 | 2680 | 2997 | −355 | −11 | −492 | O |
| ATOM | 40 | N | LEU | A | 159 | −10.877 | 52.021 | 1.243 | 1.00 | 22.28 | | N |
| ANISOU | 40 | N | LEU | A | 159 | 3043 | 2501 | 2921 | −191 | −11 | −332 | N |
| ATOM | 41 | CA | LEU | A | 159 | −12.100 | 51.337 | 0.773 | 1.00 | 20.10 | | C |
| ANISOU | 41 | CA | LEU | A | 159 | 2897 | 2071 | 2670 | −90 | 1 | −280 | C |
| ATOM | 42 | CB | LEU | A | 159 | −11.835 | 50.527 | −0.496 | 1.00 | 21.10 | | C |
| ANISOU | 42 | CB | LEU | A | 159 | 3064 | 2118 | 2834 | 7 | 43 | −216 | C |
| ATOM | 43 | CG | LEU | A | 159 | −11.502 | 51.366 | −1.739 | 1.00 | 27.15 | | C |
| ANISOU | 43 | CG | LEU | A | 159 | 3856 | 2820 | 3641 | −28 | 109 | −239 | C |
| ATOM | 44 | CD1 | LEU | A | 159 | −11.225 | 50.461 | −2.926 | 1.00 | 24.38 | | C |
| ANISOU | 44 | CD1 | LEU | A | 159 | 3561 | 2419 | 3284 | 56 | 165 | −199 | C |
| ATOM | 45 | CD2 | LEU | A | 159 | −12.634 | 52.303 | −2.094 | 1.00 | 26.58 | | C |
| ANISOU | 45 | CD2 | LEU | A | 159 | 3805 | 2722 | 3571 | −49 | 94 | −235 | C |
| ATOM | 46 | C | LEU | A | 159 | −12.656 | 50.419 | 1.854 | 1.00 | 19.40 | | C |
| ANISOU | 46 | C | LEU | A | 159 | 2819 | 2038 | 2514 | −42 | −44 | −230 | C |
| ATOM | 47 | O | LEU | A | 159 | −13.868 | 50.344 | 2.060 | 1.00 | 19.64 | | O |
| ANISOU | 47 | O | LEU | A | 159 | 2927 | 1992 | 2545 | −52 | −33 | −245 | O |
| ATOM | 48 | N | ALA | A | 160 | −11.776 | 49.674 | 2.541 | 1.00 | 16.49 | | N |

TABLE 6-continued

| | | | | | | | | | | | | | |
|---|---|---|---|---|---|---|---|---|---|---|---|---|---|
| DMXAA-hSTING$^{group2}$ complex | | | | | | | | | | | | | |
| ANISOU | 48 | N | ALA | A | 160 | 2359 | 1823 | 2083 | 26 | −84 | −140 | | N |
| ATOM | 49 | CA | ALA | A | 160 | −12.257 | 48.750 | 3.579 | 1.00 | 19.37 | | | C |
| ANISOU | 49 | CA | ALA | A | 160 | 2758 | 2233 | 2370 | 93 | −102 | −44 | | C |
| ATOM | 50 | CB | ALA | A | 160 | −11.093 | 47.886 | 4.114 | 1.00 | 20.08 | | | C |
| ANISOU | 50 | CB | ALA | A | 160 | 2729 | 2506 | 2395 | 243 | −132 | 127 | | C |
| ATOM | 51 | C | ALA | A | 160 | −12.917 | 49.517 | 4.721 | 1.00 | 18.78 | | | C |
| ANISOU | 51 | C | ALA | A | 160 | 2691 | 2251 | 2195 | −30 | −133 | −136 | | C |
| ATOM | 52 | O | ALA | A | 160 | −13.970 | 49.109 | 5.244 | 1.00 | 19.81 | | | O |
| ANISOU | 52 | O | ALA | A | 160 | 2908 | 2320 | 2299 | −26 | −100 | −114 | | O |
| ATOM | 53 | N | TRP | A | 161 | −12.272 | 50.598 | 5.184 | 1.00 | 18.80 | | | N |
| ANISOU | 53 | N | TRP | A | 161 | 2605 | 2409 | 2128 | −162 | −174 | −254 | | N |
| ATOM | 54 | CA | TRP | A | 161 | −12.856 | 51.359 | 6.295 | 1.00 | 18.71 | | | C |
| ANISOU | 54 | CA | TRP | A | 161 | 2635 | 2471 | 2003 | −298 | −163 | −382 | | C |
| ATOM | 55 | CB | TRP | A | 161 | −11.852 | 52.340 | 6.892 | 1.00 | 20.35 | | | C |
| ANISOU | 55 | CB | TRP | A | 161 | 2740 | 2899 | 2094 | −491 | −207 | −532 | | C |
| ATOM | 56 | CG | TRP | A | 161 | −10.927 | 51.647 | 7.810 | 1.00 | 22.45 | | | C |
| ANISOU | 56 | CG | TRP | A | 161 | 2841 | 3531 | 2158 | −465 | −342 | −418 | | C |
| ATOM | 57 | CD1 | TRP | A | 161 | −9.643 | 51.258 | 7.534 | 1.00 | 22.96 | | | C |
| ANISOU | 57 | CD1 | TRP | A | 161 | 2699 | 3817 | 2206 | −406 | −432 | −306 | | C |
| ATOM | 58 | NE1 | TRP | A | 161 | −9.106 | 50.626 | 8.664 | 1.00 | 26.80 | | | N |
| ANISOU | 58 | NE1 | TRP | A | 161 | 3040 | 4687 | 2457 | −347 | −559 | −164 | | N |
| ATOM | 59 | CE2 | TRP | A | 161 | −10.067 | 50.558 | 9.637 | 1.00 | 20.31 | | | C |
| ANISOU | 59 | CE2 | TRP | A | 161 | 2364 | 3860 | 1493 | −378 | −540 | −188 | | C |
| ATOM | 60 | CD2 | TRP | A | 161 | −11.234 | 51.191 | 9.133 | 1.00 | 27.12 | | | C |
| ANISOU | 60 | CD2 | TRP | A | 161 | 3440 | 4341 | 2524 | −455 | −396 | −358 | | C |
| ATOM | 61 | CE3 | TRP | A | 161 | −12.374 | 51.245 | 9.948 | 1.00 | 29.02 | | | C |
| ANISOU | 61 | CE3 | TRP | A | 161 | 3833 | 4517 | 2675 | −488 | −324 | −411 | | C |
| ATOM | 62 | CZ3 | TRP | A | 161 | −12.312 | 50.688 | 11.239 | 1.00 | 30.61 | | | C |
| ANISOU | 62 | CZ3 | TRP | A | 161 | 4006 | 5022 | 2603 | −469 | −394 | −304 | | C |
| ATOM | 63 | CH2 | TRP | A | 161 | −11.137 | 50.066 | 11.706 | 1.00 | 29.95 | | | C |
| ANISOU | 63 | CH2 | TRP | A | 161 | 3724 | 5323 | 2333 | −386 | −553 | −115 | | C |
| ATOM | 64 | CZ2 | TRP | A | 161 | −10.011 | 49.986 | 10.931 | 1.00 | 22.60 | | | C |
| ANISOU | 64 | CZ2 | TRP | A | 161 | 2606 | 4479 | 1504 | −328 | −630 | −49 | | C |
| ATOM | 65 | C | TRP | A | 161 | −14.129 | 52.080 | 5.862 | 1.00 | 21.56 | | | C |
| ANISOU | 65 | C | TRP | A | 161 | 3126 | 2583 | 2482 | −323 | −51 | −481 | | C |
| ATOM | 66 | O | TRP | A | 161 | −15.098 | 52.169 | 6.601 | 1.00 | 21.19 | | | O |
| ANISOU | 66 | O | TRP | A | 161 | 3143 | 2520 | 2386 | −337 | 2 | −518 | | O |
| ATOM | 67 | N | SER | A | 162 | −14.160 | 52.585 | 4.639 | 1.00 | 16.81 | | | N |
| ANISOU | 67 | N | SER | A | 162 | 2551 | 1809 | 2028 | −304 | −4 | −498 | | N |
| ATOM | 68 | CA | SER | A | 162 | −15.357 | 53.322 | 4.246 | 1.00 | 19.51 | | | C |
| ANISOU | 68 | CA | SER | A | 162 | 2945 | 1996 | 2473 | −257 | 84 | −510 | | C |
| ATOM | 69 | CB | SER | A | 162 | −15.122 | 54.165 | 2.988 | 1.00 | 22.27 | | | C |
| ANISOU | 69 | CB | SER | A | 162 | 3270 | 2261 | 2932 | −211 | 109 | −462 | | C |
| ATOM | 70 | OG | SER | A | 162 | −14.791 | 53.302 | 1.937 | 1.00 | 29.53 | | | O |
| ANISOU | 70 | OG | SER | A | 162 | 4168 | 3172 | 3882 | −152 | 57 | −384 | | O |
| ATOM | 71 | C | SER | A | 162 | −16.536 | 52.367 | 4.057 | 1.00 | 19.48 | | | C |
| ANISOU | 71 | C | SER | A | 162 | 2962 | 1951 | 2490 | −170 | 79 | −425 | | C |
| ATOM | 72 | O | SER | A | 162 | −17.683 | 52.731 | 4.317 | 1.00 | 19.92 | | | O |
| ANISOU | 72 | O | SER | A | 162 | 3018 | 1978 | 2572 | −143 | 141 | −433 | | O |
| ATOM | 73 | N | TYR | A | 163 | −16.268 | 51.157 | 3.587 | 1.00 | 16.74 | | | N |
| ANISOU | 73 | N | TYR | A | 163 | 2621 | 1603 | 2137 | −130 | 24 | −339 | | N |
| ATOM | 74 | CA | TYR | A | 163 | −17.350 | 50.178 | 3.382 | 1.00 | 15.57 | | | C |
| ANISOU | 74 | CA | TYR | A | 163 | 2492 | 1416 | 2008 | −105 | 35 | −277 | | C |
| ATOM | 75 | CB | TYR | A | 163 | −16.787 | 49.009 | 2.570 | 1.00 | 19.52 | | | C |
| ANISOU | 75 | CB | TYR | A | 163 | 3026 | 1864 | 2527 | −71 | 15 | −209 | | C |
| ATOM | 76 | CG | TYR | A | 163 | −17.816 | 47.972 | 2.152 | 1.00 | 20.68 | | | C |
| ANISOU | 76 | CG | TYR | A | 163 | 3181 | 1980 | 2696 | −110 | 46 | −185 | | C |
| ATOM | 77 | CD1 | TYR | A | 163 | −18.877 | 48.315 | 1.297 | 1.00 | 20.58 | | | C |
| ANISOU | 77 | CD1 | TYR | A | 163 | 3118 | 1991 | 2711 | −158 | 29 | −227 | | C |
| ATOM | 78 | CE1 | TYR | A | 163 | −19.828 | 47.341 | 0.870 | 1.00 | 21.84 | | | C |
| ANISOU | 78 | CE1 | TYR | A | 163 | 3300 | 2133 | 2866 | −268 | 50 | −251 | | C |
| ATOM | 79 | CZ | TYR | A | 163 | −19.685 | 46.034 | 1.331 | 1.00 | 21.63 | | | C |
| ANISOU | 79 | CZ | TYR | A | 163 | 3343 | 2039 | 2836 | −300 | 121 | −217 | | C |
| ATOM | 80 | OH | TYR | A | 163 | −20.579 | 45.055 | 0.933 | 1.00 | 25.03 | | | O |
| ANISOU | 80 | OH | TYR | A | 163 | 3796 | 2449 | 3266 | −443 | 170 | −261 | | O |
| ATOM | 81 | CE2 | TYR | A | 163 | −18.625 | 45.678 | 2.173 | 1.00 | 26.54 | | | C |
| ANISOU | 81 | CE2 | TYR | A | 163 | 4032 | 2604 | 3447 | −199 | 158 | −135 | | C |
| ATOM | 82 | CD2 | TYR | A | 163 | −17.697 | 46.655 | 2.580 | 1.00 | 26.00 | | | C |
| ANISOU | 82 | CD2 | TYR | A | 163 | 3947 | 2575 | 3356 | −110 | 105 | −121 | | C |
| ATOM | 83 | C | TYR | A | 163 | −17.903 | 49.705 | 4.723 | 1.00 | 22.80 | | | C |
| ANISOU | 83 | C | TYR | A | 163 | 3420 | 2401 | 2843 | −131 | 67 | −257 | | C |
| ATOM | 84 | O | TYR | A | 163 | −19.100 | 49.451 | 4.884 | 1.00 | 22.77 | | | O |
| ANISOU | 84 | O | TYR | A | 163 | 3407 | 2385 | 2859 | −156 | 118 | −251 | | O |
| ATOM | 85 | N | TYR | A | 164 | −17.032 | 49.607 | 5.713 | 1.00 | 18.80 | | | N |
| ANISOU | 85 | N | TYR | A | 164 | 2912 | 2007 | 2223 | −133 | 39 | −237 | | N |
| ATOM | 86 | CA | TYR | A | 164 | −17.478 | 49.264 | 7.064 | 1.00 | 17.85 | | | C |
| ANISOU | 86 | CA | TYR | A | 164 | 2817 | 1990 | 1975 | −157 | 75 | −204 | | C |
| ATOM | 87 | CB | TYR | A | 164 | −16.284 | 48.963 | 7.957 | 1.00 | 18.02 | | | C |

TABLE 6-continued

DMXAA-hSTING[group2] complex

| | | | | | | | | | | | | |
|---|---|---|---|---|---|---|---|---|---|---|---|---|
| ANISOU | 87 | CB | TYR | A | 164 | 2810 | 2207 | 1829 | −133 | 0 | −129 | C |
| ATOM | 88 | CG | TYR | A | 164 | −16.714 | 48.809 | 9.406 | 1.00 | 23.37 | | C |
| ANISOU | 88 | CG | TYR | A | 164 | 3523 | 3040 | 2316 | −168 | 36 | −100 | C |
| ATOM | 89 | CD1 | TYR | A | 164 | −17.613 | 47.812 | 9.783 | 1.00 | 27.45 | | C |
| ANISOU | 89 | CD1 | TYR | A | 164 | 4115 | 3485 | 2829 | −134 | 128 | 27 | C |
| ATOM | 90 | CE1 | TYR | A | 164 | −18.018 | 47.704 | 11.122 | 1.00 | 33.52 | | C |
| ANISOU | 90 | CE1 | TYR | A | 164 | 4928 | 4408 | 3401 | −168 | 183 | 66 | C |
| ATOM | 91 | CZ | TYR | A | 164 | −17.504 | 48.597 | 12.056 | 1.00 | 39.32 | | C |
| ANISOU | 91 | CZ | TYR | A | 164 | 5635 | 5387 | 3919 | −246 | 130 | −50 | C |
| ATOM | 92 | OH | TYR | A | 164 | −17.860 | 48.519 | 13.362 | 1.00 | 39.13 | | O |
| ANISOU | 92 | OH | TYR | A | 164 | 5666 | 5548 | 3654 | −291 | 187 | −27 | O |
| ATOM | 93 | CE2 | TYR | A | 164 | −16.619 | 49.576 | 11.700 | 1.00 | 32.31 | | C |
| ANISOU | 93 | CE2 | TYR | A | 164 | 4674 | 4570 | 3034 | −314 | 36 | −208 | C |
| ATOM | 94 | CD2 | TYR | A | 164 | −16.234 | 49.680 | 10.371 | 1.00 | 28.56 | | C |
| ANISOU | 94 | CD2 | TYR | A | 164 | 4152 | 3919 | 2781 | −269 | −3 | −220 | C |
| ATOM | 95 | C | TYR | A | 164 | −18.288 | 50.438 | 7.662 | 1.00 | 18.86 | | C |
| ANISOU | 95 | C | TYR | A | 164 | 2950 | 2135 | 2080 | −223 | 155 | −347 | C |
| ATOM | 96 | O | TYR | A | 164 | −19.432 | 50.279 | 8.053 | 1.00 | 24.10 | | O |
| ANISOU | 96 | O | TYR | A | 164 | 3621 | 2783 | 2752 | −230 | 243 | −341 | O |
| ATOM | 97 | N | ILE | A | 165 | −17.698 | 51.623 | 7.673 | 1.00 | 18.20 | | N |
| ANISOU | 97 | N | ILE | A | 165 | 2866 | 2062 | 1987 | −277 | 157 | −481 | N |
| ATOM | 98 | CA | ILE | A | 165 | −18.314 | 52.796 | 8.311 | 1.00 | 18.05 | | C |
| ANISOU | 98 | CA | ILE | A | 165 | 2898 | 2010 | 1950 | −335 | 289 | −640 | C |
| ATOM | 99 | CB | ILE | A | 165 | −17.304 | 53.978 | 8.362 | 1.00 | 20.17 | | C |
| ANISOU | 99 | CB | ILE | A | 165 | 3160 | 2289 | 2213 | −426 | 285 | −760 | C |
| ATOM | 100 | CG1 | ILE | A | 165 | −16.109 | 53.611 | 9.240 | 1.00 | 24.29 | | C |
| ANISOU | 100 | CG1 | ILE | A | 165 | 3654 | 3068 | 2507 | −556 | 170 | −805 | C |
| ATOM | 101 | CD1 | ILE | A | 165 | −16.524 | 53.402 | 10.683 | 1.00 | 27.09 | | C |
| ANISOU | 101 | CD1 | ILE | A | 165 | 4048 | 3601 | 2642 | −612 | 202 | −840 | C |
| ATOM | 102 | CG2 | ILE | A | 165 | −17.941 | 55.281 | 8.938 | 1.00 | 22.09 | | C |
| ANISOU | 102 | CG2 | ILE | A | 165 | 3446 | 2450 | 2497 | −445 | 441 | −857 | C |
| ATOM | 103 | C | ILE | A | 165 | −19.561 | 53.238 | 7.533 | 1.00 | 21.76 | | C |
| ANISOU | 103 | C | ILE | A | 165 | 3353 | 2313 | 2603 | −234 | 396 | −623 | C |
| ATOM | 104 | O | ILE | A | 165 | −20.594 | 53.601 | 8.128 | 1.00 | 23.47 | | O |
| ANISOU | 104 | O | ILE | A | 165 | 3576 | 2516 | 2823 | −207 | 534 | −664 | O |
| ATOM | 105 | N | GLY | A | 166 | −19.460 | 53.210 | 6.215 | 1.00 | 20.23 | | N |
| ANISOU | 105 | N | GLY | A | 166 | 3117 | 2029 | 2540 | −167 | 337 | −549 | N |
| ATOM | 106 | CA | GLY | A | 166 | −20.499 | 53.788 | 5.360 | 1.00 | 19.98 | | C |
| ANISOU | 106 | CA | GLY | A | 166 | 3037 | 1904 | 2650 | −51 | 410 | −502 | C |
| ATOM | 107 | C | GLY | A | 166 | −21.514 | 52.776 | 4.821 | 1.00 | 24.12 | | C |
| ANISOU | 107 | C | GLY | A | 166 | 3447 | 2512 | 3206 | −17 | 351 | −387 | C |
| ATOM | 108 | O | GLY | A | 166 | −22.444 | 53.168 | 4.129 | 1.00 | 24.34 | | O |
| ANISOU | 108 | O | GLY | A | 166 | 3375 | 2554 | 3318 | 79 | 380 | −324 | O |
| ATOM | 109 | N | TYR | A | 167 | −21.397 | 51.504 | 5.175 | 1.00 | 23.68 | | N |
| ANISOU | 109 | N | TYR | A | 167 | 3396 | 2523 | 3077 | −101 | 287 | −352 | N |
| ATOM | 110 | CA | TYR | A | 167 | −22.426 | 50.533 | 4.765 | 1.00 | 19.81 | | C |
| ANISOU | 110 | CA | TYR | A | 167 | 2816 | 2096 | 2616 | −143 | 272 | −288 | C |
| ATOM | 111 | CB | TYR | A | 167 | −22.052 | 49.872 | 3.422 | 1.00 | 23.35 | | C |
| ANISOU | 111 | CB | TYR | A | 167 | 3267 | 2518 | 3086 | −176 | 164 | −258 | C |
| ATOM | 112 | CG | TYR | A | 167 | −23.121 | 48.879 | 2.961 | 1.00 | 23.88 | | C |
| ANISOU | 112 | CG | TYR | A | 167 | 3247 | 2666 | 3161 | −296 | 156 | −245 | C |
| ATOM | 113 | CD1 | TYR | A | 167 | −24.425 | 49.308 | 2.704 | 1.00 | 19.55 | | C |
| ANISOU | 113 | CD1 | TYR | A | 167 | 2505 | 2278 | 2646 | −287 | 165 | −226 | C |
| ATOM | 114 | CE1 | TYR | A | 167 | −25.424 | 48.411 | 2.321 | 1.00 | 22.32 | | C |
| ANISOU | 114 | CE1 | TYR | A | 167 | 2733 | 2762 | 2987 | −457 | 151 | −240 | C |
| ATOM | 115 | CZ | TYR | A | 167 | −25.105 | 47.061 | 2.165 | 1.00 | 24.77 | | C |
| ANISOU | 115 | CZ | TYR | A | 167 | 3178 | 2967 | 3267 | −649 | 163 | −292 | C |
| ATOM | 116 | OH | TYR | A | 167 | −26.079 | 46.168 | 1.785 | 1.00 | 20.89 | | O |
| ANISOU | 116 | OH | TYR | A | 167 | 2588 | 2587 | 2763 | −885 | 176 | −349 | O |
| ATOM | 117 | CE2 | TYR | A | 167 | −23.815 | 46.608 | 2.424 | 1.00 | 21.50 | | C |
| ANISOU | 117 | CE2 | TYR | A | 167 | 2991 | 2339 | 2840 | −605 | 186 | −285 | C |
| ATOM | 118 | CD2 | TYR | A | 167 | −22.832 | 47.524 | 2.818 | 1.00 | 22.85 | | C |
| ANISOU | 118 | CD2 | TYR | A | 167 | 3220 | 2456 | 3008 | −423 | 162 | −252 | C |
| ATOM | 119 | C | TYR | A | 167 | −22.700 | 49.471 | 5.808 | 1.00 | 26.51 | | C |
| ANISOU | 119 | C | TYR | A | 167 | 3702 | 2978 | 3391 | −236 | 325 | −262 | C |
| ATOM | 120 | O | TYR | A | 167 | −23.812 | 49.378 | 6.349 | 1.00 | 21.01 | | O |
| ANISOU | 120 | O | TYR | A | 167 | 2925 | 2356 | 2702 | −269 | 419 | −255 | O |
| ATOM | 121 | N | LEU | A | 168 | −21.682 | 48.664 | 6.117 | 1.00 | 20.15 | | N |
| ANISOU | 121 | N | LEU | A | 168 | 3350 | 1833 | 2474 | −240 | 126 | −203 | N |
| ATOM | 122 | CA | LEU | A | 168 | −21.900 | 47.511 | 7.002 | 1.00 | 19.16 | | C |
| ANISOU | 122 | CA | LEU | A | 168 | 3184 | 1907 | 2190 | −260 | 151 | −138 | C |
| ATOM | 123 | CB | LEU | A | 168 | −20.650 | 46.651 | 7.142 | 1.00 | 22.03 | | C |
| ANISOU | 123 | CB | LEU | A | 168 | 3570 | 2512 | 2289 | −278 | 21 | 1 | C |
| ATOM | 124 | CG | LEU | A | 168 | −20.227 | 46.018 | 5.808 | 1.00 | 24.77 | | C |
| ANISOU | 124 | CG | LEU | A | 168 | 3919 | 2788 | 2703 | −124 | −156 | 158 | C |
| ATOM | 125 | CD1 | LEU | A | 168 | −18.963 | 45.224 | 6.058 | 1.00 | 25.63 | | C |
| ANISOU | 125 | CD1 | LEU | A | 168 | 4007 | 3139 | 2591 | −127 | −287 | 228 | C |
| ATOM | 126 | CD2 | LEU | A | 168 | −21.337 | 45.096 | 5.188 | 1.00 | 22.93 | | C |

TABLE 6-continued

| | | | | | | | | | | | | |
|---|---|---|---|---|---|---|---|---|---|---|---|---|
| ANISOU | 126 | CD2 | LEU | A | 168 | 3673 | 2390 | 2650 | 27 | −217 | 288 | C |
| ATOM | 127 | C | LEU | A | 168 | −22.399 | 47.929 | 8.363 | 1.00 | 22.35 | | C |
| ANISOU | 127 | C | LEU | A | 168 | 3549 | 2418 | 2526 | −419 | 346 | −335 | C |
| ATOM | 128 | O | LEU | A | 168 | −23.295 | 47.323 | 8.944 | 1.00 | 25.48 | | O |
| ANISOU | 128 | O | LEU | A | 168 | 3902 | 2857 | 2922 | −451 | 424 | −349 | O |
| ATOM | 129 | N | ARG | A | 169 | −21.807 | 48.982 | 8.898 | 1.00 | 20.85 | | N |
| ANISOU | 129 | N | ARG | A | 169 | 3373 | 2291 | 2260 | −554 | 442 | −509 | N |
| ATOM | 130 | CA | ARG | A | 169 | −22.216 | 49.460 | 10.196 | 1.00 | 27.08 | | C |
| ANISOU | 130 | CA | ARG | A | 169 | 4117 | 3204 | 2969 | −735 | 648 | −741 | C |
| ATOM | 131 | CB | ARG | A | 169 | −21.316 | 50.632 | 10.607 | 1.00 | 31.16 | | C |
| ANISOU | 131 | CB | ARG | A | 169 | 4665 | 3783 | 3392 | −877 | 719 | −916 | C |
| ATOM | 132 | CG | ARG | A | 169 | −21.420 | 50.911 | 12.029 | 1.00 | 57.57 | | C |
| ANISOU | 132 | CG | ARG | A | 169 | 7975 | 7349 | 6550 | −1103 | 913 | −1129 | C |
| ATOM | 133 | CD | ARG | A | 169 | −20.118 | 51.483 | 12.519 | 1.00 | 58.51 | | C |
| ANISOU | 133 | CD | ARG | A | 169 | 8147 | 7661 | 6422 | −1265 | 913 | −1186 | C |
| ATOM | 134 | NE | ARG | A | 169 | −20.103 | 52.913 | 12.341 | 1.00 | 57.53 | | N |
| ANISOU | 134 | NE | ARG | A | 169 | 8006 | 7342 | 6512 | −1281 | 997 | −1396 | N |
| ATOM | 135 | CZ | ARG | A | 169 | −19.256 | 53.726 | 12.961 | 1.00 | 59.53 | | C |
| ANISOU | 135 | CZ | ARG | A | 169 | 8229 | 7721 | 6667 | −1415 | 1034 | −1459 | C |
| ATOM | 136 | NH1 | ARG | A | 169 | −18.340 | 53.230 | 13.791 | 1.00 | 52.23 | | N |
| ANISOU | 136 | NH1 | ARG | A | 169 | 7280 | 7099 | 5465 | −1536 | 981 | −1345 | N |
| ATOM | 137 | NH2 | ARG | A | 169 | −19.322 | 55.035 | 12.747 | 1.00 | 45.52 | | N |
| ANISOU | 137 | NH2 | ARG | A | 169 | 6446 | 5742 | 5109 | −1409 | 1091 | −1614 | N |
| ATOM | 138 | C | ARG | A | 169 | −23.674 | 49.912 | 10.190 | 1.00 | 32.27 | | C |
| ANISOU | 138 | C | ARG | A | 169 | 4672 | 3651 | 3938 | −679 | 782 | −940 | C |
| ATOM | 139 | O | ARG | A | 169 | −24.351 | 49.890 | 11.224 | 1.00 | 30.74 | | O |
| ANISOU | 139 | O | ARG | A | 169 | 4401 | 3589 | 3691 | −823 | 968 | −1129 | O |
| ATOM | 140 | N | LEU | A | 170 | −24.160 | 50.326 | 9.023 | 1.00 | 29.54 | | N |
| ANISOU | 140 | N | LEU | A | 170 | 4317 | 2989 | 3917 | −486 | 680 | −913 | N |
| ATOM | 141 | CA | LEU | A | 170 | −25.530 | 50.812 | 8.902 | 1.00 | 30.35 | | C |
| ANISOU | 141 | CA | LEU | A | 170 | 4297 | 2856 | 4379 | −390 | 756 | −1118 | C |
| ATOM | 142 | CB | LEU | A | 170 | −25.699 | 51.677 | 7.648 | 1.00 | 31.20 | | C |
| ANISOU | 142 | CB | LEU | A | 170 | 4430 | 2642 | 4781 | −201 | 558 | −1045 | C |
| ATOM | 143 | CG | LEU | A | 170 | −24.803 | 52.909 | 7.572 | 1.00 | 43.17 | | C |
| ANISOU | 143 | CG | LEU | A | 170 | 6037 | 4110 | 6257 | −266 | 508 | −1083 | C |
| ATOM | 144 | CD1 | LEU | A | 170 | −25.163 | 53.707 | 6.324 | 1.00 | 42.70 | | C |
| ANISOU | 144 | CD1 | LEU | A | 170 | 6043 | 3818 | 6363 | −103 | 255 | −927 | C |
| ATOM | 145 | CD2 | LEU | A | 170 | −24.964 | 53.755 | 8.811 | 1.00 | 45.81 | | C |
| ANISOU | 145 | CD2 | LEU | A | 170 | 6273 | 4542 | 6593 | −396 | 709 | −1381 | C |
| ATOM | 146 | C | LEU | A | 170 | −26.486 | 49.654 | 8.789 | 1.00 | 30.84 | | C |
| ANISOU | 146 | C | LEU | A | 170 | 4281 | 2952 | 4483 | −318 | 750 | −1015 | C |
| ATOM | 147 | O | LEU | A | 170 | −27.567 | 49.667 | 9.356 | 1.00 | 32.74 | | O |
| ANISOU | 147 | O | LEU | A | 170 | 4379 | 3206 | 4857 | −355 | 906 | −1234 | O |
| ATOM | 148 | N | ILE | A | 171 | −26.077 | 48.644 | 8.049 | 1.00 | 24.55 | | N |
| ANISOU | 148 | N | ILE | A | 171 | 3571 | 2181 | 3578 | −230 | 576 | −706 | N |
| ATOM | 149 | CA | ILE | A | 171 | −27.024 | 47.620 | 7.594 | 1.00 | 27.28 | | C |
| ANISOU | 149 | CA | ILE | A | 171 | 3860 | 2472 | 4034 | −123 | 523 | −585 | C |
| ATOM | 150 | CB | ILE | A | 171 | −26.692 | 47.227 | 6.136 | 1.00 | 23.98 | | C |
| ANISOU | 150 | CB | ILE | A | 171 | 3522 | 1881 | 3706 | 64 | 285 | −323 | C |
| ATOM | 151 | CG1 | ILE | A | 171 | −27.912 | 46.639 | 5.442 | 1.00 | 41.39 | | C |
| ANISOU | 151 | CG1 | ILE | A | 171 | 5641 | 3956 | 6129 | 204 | 216 | −269 | C |
| ATOM | 152 | CD1 | ILE | A | 171 | −28.780 | 47.742 | 4.831 | 1.00 | 42.71 | | C |
| ANISOU | 152 | CD1 | ILE | A | 171 | 5731 | 4079 | 6417 | 290 | 140 | −358 | C |
| ATOM | 153 | CG2 | ILE | A | 171 | −25.572 | 46.211 | 6.072 | 1.00 | 28.53 | | C |
| ANISOU | 153 | CG2 | ILE | A | 171 | 4204 | 2656 | 3982 | 35 | 173 | −82 | C |
| ATOM | 154 | C | ILE | A | 171 | −27.046 | 46.421 | 8.531 | 1.00 | 29.39 | | C |
| ANISOU | 154 | C | ILE | A | 171 | 4145 | 3018 | 4005 | −281 | 593 | −494 | C |
| ATOM | 155 | O | ILE | A | 171 | −28.076 | 45.781 | 8.758 | 1.00 | 27.90 | | O |
| ANISOU | 155 | O | ILE | A | 171 | 3878 | 2850 | 3872 | −310 | 668 | −525 | O |
| ATOM | 156 | N | LEU | A | 172 | −25.912 | 46.114 | 9.145 | 1.00 | 27.87 | | N |
| ANISOU | 156 | N | LEU | A | 172 | 4061 | 3046 | 3483 | −409 | 561 | −385 | N |
| ATOM | 157 | CA | LEU | A | 172 | −25.867 | 44.907 | 9.974 | 1.00 | 26.16 | | C |
| ANISOU | 157 | CA | LEU | A | 172 | 3910 | 3056 | 2976 | −563 | 555 | −241 | C |
| ATOM | 158 | CB | LEU | A | 172 | −24.426 | 44.468 | 10.243 | 1.00 | 22.14 | | C |
| ANISOU | 158 | CB | LEU | A | 172 | 3526 | 2717 | 2168 | −608 | 395 | −52 | C |
| ATOM | 159 | CG | LEU | A | 172 | −23.609 | 44.006 | 9.042 | 1.00 | 28.10 | | C |
| ANISOU | 159 | CG | LEU | A | 172 | 4321 | 3362 | 2993 | −386 | 156 | 157 | C |
| ATOM | 160 | CD1 | LEU | A | 172 | −22.179 | 43.700 | 9.507 | 1.00 | 25.83 | | C |
| ANISOU | 160 | CD1 | LEU | A | 172 | 4105 | 3279 | 2430 | −445 | 16 | 258 | C |
| ATOM | 161 | CD2 | LEU | A | 172 | −24.218 | 42.787 | 8.379 | 1.00 | 31.53 | | C |
| ANISOU | 161 | CD2 | LEU | A | 172 | 4768 | 3685 | 3527 | −258 | 30 | 350 | C |
| ATOM | 162 | C | LEU | A | 172 | −26.706 | 44.887 | 11.280 | 1.00 | 31.38 | | C |
| ANISOU | 162 | C | LEU | A | 172 | 4518 | 3905 | 3501 | −830 | 793 | −439 | C |
| ATOM | 163 | O | LEU | A | 172 | −27.306 | 43.832 | 11.605 | 1.00 | 30.65 | | O |
| ANISOU | 163 | O | LEU | A | 172 | 4456 | 3893 | 3297 | −934 | 797 | −327 | O |
| ATOM | 164 | N | PRO | A | 173 | −26.755 | 46.004 | 12.044 | 1.00 | 30.45 | | N |
| ANISOU | 164 | N | PRO | A | 173 | 4326 | 3868 | 3376 | −974 | 997 | −743 | N |
| ATOM | 165 | CA | PRO | A | 173 | −27.489 | 45.944 | 13.322 | 1.00 | 30.58 | | C |

TABLE 6-continued

DMXAA-hSTING$^{group2}$ complex

| | | | | | | | | | | | | |
|---|---|---|---|---|---|---|---|---|---|---|---|---|
| ANISOU | 165 | CA | PRO | A | 173 | 4285 | 4118 | 3216 | −1278 | 1246 | −963 | C |
| ATOM | 166 | CB | PRO | A | 173 | −27.504 | 47.400 | 13.792 | 1.00 | 34.05 | | C |
| ANISOU | 166 | CB | PRO | A | 173 | 4608 | 4557 | 3774 | −1341 | 1448 | −1346 | C |
| ATOM | 167 | CG | PRO | A | 173 | −26.195 | 47.937 | 13.299 | 1.00 | 36.01 | | C |
| ANISOU | 167 | CG | PRO | A | 173 | 4964 | 4726 | 3994 | −1214 | 1275 | −1213 | C |
| ATOM | 168 | CD | PRO | A | 173 | −26.014 | 47.266 | 11.913 | 1.00 | 28.01 | | C |
| ANISOU | 168 | CD | PRO | A | 173 | 4008 | 3488 | 3145 | −926 | 1012 | −893 | C |
| ATOM | 169 | C | PRO | A | 173 | −28.915 | 45.448 | 13.222 | 1.00 | 37.33 | | C |
| ANISOU | 169 | C | PRO | A | 173 | 5010 | 4928 | 4245 | −1293 | 1362 | −1062 | C |
| ATOM | 170 | O | PRO | A | 173 | −29.357 | 44.789 | 14.159 | 1.00 | 41.16 | | O |
| ANISOU | 170 | O | PRO | A | 173 | 5523 | 5650 | 4468 | −1584 | 1492 | −1084 | O |
| ATOM | 171 | N | GLU | A | 174 | −29.650 | 45.756 | 12.151 | 1.00 | 31.37 | | N |
| ANISOU | 171 | N | GLU | A | 174 | 4120 | 3892 | 3906 | −1020 | 1316 | −1129 | N |
| ATOM | 172 | CA | GLU | A | 174 | −31.053 | 45.322 | 12.137 | 1.00 | 35.66 | | C |
| ANISOU | 172 | CA | GLU | A | 174 | 4502 | 4425 | 4622 | −1053 | 1443 | −1275 | C |
| ATOM | 173 | CB | GLU | A | 174 | −32.016 | 46.487 | 11.920 | 1.00 | 47.44 | | C |
| ANISOU | 173 | CB | GLU | A | 174 | 5731 | 5744 | 6552 | −922 | 1585 | −1692 | C |
| ATOM | 174 | CG | GLU | A | 174 | −31.962 | 47.512 | 13.043 | 1.00 | 52.98 | | C |
| ANISOU | 174 | CG | GLU | A | 174 | 6333 | 6609 | 7187 | −1133 | 1840 | −2087 | C |
| ATOM | 175 | CD | GLU | A | 174 | −33.172 | 48.437 | 13.100 | 1.00 | 78.95 | | C |
| ANISOU | 175 | CD | GLU | A | 174 | 9307 | 9786 | 10904 | −1062 | 1944 | −2481 | C |
| ATOM | 176 | OE1 | GLU | A | 174 | −33.548 | 49.025 | 12.056 | 1.00 | 77.51 | | O |
| ANISOU | 176 | OE1 | GLU | A | 174 | 9026 | 9295 | 11130 | −744 | 1739 | −2438 | O |
| ATOM | 177 | OE2 | GLU | A | 174 | −33.748 | 48.583 | 14.208 | 1.00 | 96.52 | | O |
| ANISOU | 177 | OE2 | GLU | A | 174 | 11394 | 12249 | 13032 | −1344 | 2136 | −2736 | O |
| ATOM | 178 | C | GLU | A | 174 | −31.328 | 44.214 | 11.152 | 1.00 | 30.54 | | C |
| ANISOU | 178 | C | GLU | A | 174 | 3913 | 3634 | 4055 | −883 | 1239 | −960 | C |
| ATOM | 179 | O | GLU | A | 174 | −32.481 | 43.861 | 10.892 | 1.00 | 30.14 | | O |
| ANISOU | 179 | O | GLU | A | 174 | 3720 | 3533 | 4199 | −860 | 1304 | −1059 | O |
| ATOM | 180 | N | LEU | A | 175 | −30.260 | 43.653 | 10.597 | 1.00 | 26.19 | | N |
| ANISOU | 180 | N | LEU | A | 175 | 3556 | 3031 | 3364 | −766 | 993 | −608 | N |
| ATOM | 181 | CA | LEU | A | 175 | −30.424 | 42.636 | 9.557 | 1.00 | 23.01 | | C |
| ANISOU | 181 | CA | LEU | A | 175 | 3209 | 2474 | 3059 | −583 | 786 | −327 | C |
| ATOM | 182 | CB | LEU | A | 175 | −29.067 | 42.170 | 9.066 | 1.00 | 25.85 | | C |
| ANISOU | 182 | CB | LEU | A | 175 | 3753 | 2810 | 3260 | −468 | 537 | −18 | C |
| ATOM | 183 | CG | LEU | A | 175 | −29.171 | 41.063 | 8.012 | 1.00 | 33.37 | | C |
| ANISOU | 183 | CG | LEU | A | 175 | 4760 | 3616 | 4304 | −291 | 327 | 245 | C |
| ATOM | 184 | CD1 | LEU | A | 175 | −29.764 | 41.625 | 6.726 | 1.00 | 29.74 | | C |
| ANISOU | 184 | CD1 | LEU | A | 175 | 4179 | 2906 | 4216 | −45 | 276 | 176 | C |
| ATOM | 185 | CD2 | LEU | A | 175 | −27.795 | 40.514 | 7.759 | 1.00 | 35.69 | | C |
| ANISOU | 185 | CD2 | LEU | A | 175 | 5205 | 3940 | 4417 | −217 | 104 | 488 | C |
| ATOM | 186 | C | LEU | A | 175 | −31.176 | 41.428 | 10.074 | 1.00 | 27.04 | | C |
| ANISOU | 186 | C | LEU | A | 175 | 3751 | 3116 | 3407 | −785 | 843 | −241 | C |
| ATOM | 187 | O | LEU | A | 175 | −32.043 | 40.857 | 9.392 | 1.00 | 29.08 | | O |
| ANISOU | 187 | O | LEU | A | 175 | 3939 | 3253 | 3858 | −688 | 805 | −200 | O |
| ATOM | 188 | N | GLN | A | 176 | −30.817 | 40.996 | 11.276 | 1.00 | 32.36 | | N |
| ANISOU | 188 | N | GLN | A | 176 | 4555 | 4040 | 3702 | −1092 | 915 | −194 | N |
| ATOM | 189 | CA | GLN | A | 176 | −31.454 | 39.816 | 11.872 | 1.00 | 35.78 | | C |
| ANISOU | 189 | CA | GLN | A | 176 | 5076 | 4606 | 3914 | −1358 | 954 | −78 | C |
| ATOM | 190 | CB | GLN | A | 176 | −30.847 | 39.578 | 13.243 | 1.00 | 42.72 | | C |
| ANISOU | 190 | CB | GLN | A | 176 | 6135 | 5759 | 4336 | −1721 | 999 | −16 | C |
| ATOM | 191 | CG | GLN | A | 176 | −31.457 | 38.427 | 13.985 | 1.00 | 67.24 | | C |
| ANISOU | 191 | CG | GLN | A | 176 | 9381 | 9015 | 7153 | −2075 | 1034 | 116 | C |
| ATOM | 192 | CD | GLN | A | 176 | −30.502 | 37.853 | 15.002 | 1.00 | 74.59 | | C |
| ANISOU | 192 | CD | GLN | A | 176 | 10517 | 10063 | 7760 | −2195 | 791 | 308 | C |
| ATOM | 193 | OE1 | GLN | A | 176 | −30.917 | 37.196 | 15.953 | 1.00 | 73.42 | | O |
| ANISOU | 193 | OE1 | GLN | A | 176 | 10445 | 10043 | 7407 | −2464 | 781 | 310 | O |
| ATOM | 194 | NE2 | GLN | A | 176 | −29.205 | 38.093 | 14.802 | 1.00 | 83.07 | | N |
| ANISOU | 194 | NE2 | GLN | A | 176 | 11665 | 11082 | 8818 | −2001 | 587 | 451 | N |
| ATOM | 195 | C | GLN | A | 176 | −32.983 | 39.967 | 11.980 | 1.00 | 35.25 | | C |
| ANISOU | 195 | C | GLN | A | 176 | 4782 | 4576 | 4037 | −1472 | 1211 | −383 | C |
| ATOM | 196 | O | GLN | A | 176 | −33.768 | 39.034 | 11.713 | 1.00 | 36.10 | | O |
| ANISOU | 196 | O | GLN | A | 176 | 4889 | 4653 | 4174 | −1525 | 1195 | −289 | O |
| ATOM | 197 | N | ALA | A | 177 | −33.409 | 41.148 | 12.419 | 1.00 | 33.69 | | N |
| ANISOU | 197 | N | ALA | A | 177 | 4373 | 4453 | 3974 | −1521 | 1453 | −781 | N |
| ATOM | 198 | CA | ALA | A | 177 | −34.840 | 41.420 | 12.612 | 1.00 | 35.51 | | C |
| ANISOU | 198 | CA | ALA | A | 177 | 4327 | 4746 | 4418 | −1625 | 1715 | −1162 | C |
| ATOM | 199 | CB | ALA | A | 177 | −35.042 | 42.763 | 13.316 | 1.00 | 40.04 | | C |
| ANISOU | 199 | CB | ALA | A | 177 | 4690 | 5428 | 5096 | −1705 | 1974 | −1628 | C |
| ATOM | 200 | C | ALA | A | 177 | −35.577 | 41.396 | 11.264 | 1.00 | 36.04 | | C |
| ANISOU | 200 | C | ALA | A | 177 | 4230 | 4523 | 4940 | −1269 | 1584 | −1160 | C |
| ATOM | 201 | O | ALA | A | 177 | −36.722 | 40.937 | 11.165 | 1.00 | 32.93 | | O |
| ANISOU | 201 | O | ALA | A | 177 | 3678 | 4161 | 4673 | −1342 | 1688 | −1292 | O |
| ATOM | 202 | N | ARG | A | 178 | −34.922 | 41.903 | 10.226 | 1.00 | 33.09 | | N |
| ANISOU | 202 | N | ARG | A | 178 | 3894 | 3882 | 4795 | −912 | 1353 | −1018 | N |
| ATOM | 203 | CA | ARG | A | 178 | −35.522 | 41.929 | 8.895 | 1.00 | 31.30 | | C |
| ANISOU | 203 | CA | ARG | A | 178 | 3548 | 3376 | 4969 | −587 | 1189 | −984 | C |
| ATOM | 204 | CB | ARG | A | 178 | −34.660 | 42.750 | 7.917 | 1.00 | 24.32 | | C |

TABLE 6-continued

DMXAA-hSTING$^{group2}$ complex

| | | | | | | | | | | | | |
|---|---|---|---|---|---|---|---|---|---|---|---|---|
| ANISOU | 204 | CB | ARG | A | 178 | 2734 | 2235 | 4273 | −273 | 964 | −865 | C |
| ATOM | 205 | CG | ARG | A | 178 | −34.729 | 44.226 | 8.210 | 1.00 | 29.40 | | C |
| ANISOU | 205 | CG | ARG | A | 178 | 3226 | 2808 | 5136 | −216 | 1072 | −1210 | C |
| ATOM | 206 | CD | ARG | A | 178 | −33.594 | 44.968 | 7.492 | 1.00 | 36.68 | | C |
| ANISOU | 206 | CD | ARG | A | 178 | 4302 | 3535 | 6101 | −19 | 865 | −1043 | C |
| ATOM | 207 | NE | ARG | A | 178 | −33.780 | 44.953 | 6.045 | 1.00 | 32.58 | | N |
| ANISOU | 207 | NE | ARG | A | 178 | 3797 | 2827 | 5754 | 232 | 575 | −811 | N |
| ATOM | 208 | CZ | ARG | A | 178 | −32.785 | 44.927 | 5.164 | 1.00 | 32.73 | | C |
| ANISOU | 208 | CZ | ARG | A | 178 | 4012 | 2847 | 5577 | 323 | 340 | −503 | C |
| ATOM | 209 | NH1 | ARG | A | 178 | −31.534 | 44.928 | 5.602 | 1.00 | 31.02 | | N |
| ANISOU | 209 | NH1 | ARG | A | 178 | 3951 | 2630 | 5206 | 260 | 376 | −438 | N |
| ATOM | 210 | NH2 | ARG | A | 178 | −33.045 | 44.914 | 3.848 | 1.00 | 28.33 | | N |
| ANISOU | 210 | NH2 | ARG | A | 178 | 3507 | 2332 | 4927 | 427 | 123 | −318 | N |
| ATOM | 211 | C | ARG | A | 178 | −35.662 | 40.522 | 8.387 | 1.00 | 30.06 | | C |
| ANISOU | 211 | C | ARG | A | 178 | 3523 | 3198 | 4701 | −598 | 1045 | −659 | C |
| ATOM | 212 | O | ARG | A | 178 | −36.644 | 40.166 | 7.756 | 1.00 | 33.78 | | O |
| ANISOU | 212 | O | ARG | A | 178 | 3854 | 3576 | 5407 | −511 | 1026 | −707 | O |
| ATOM | 213 | N | ILE | A | 179 | −34.654 | 39.710 | 8.661 | 1.00 | 24.53 | | N |
| ANISOU | 213 | N | ILE | A | 179 | 3091 | 2575 | 3654 | −699 | 922 | −335 | N |
| ATOM | 214 | CA | ILE | A | 179 | −34.688 | 38.327 | 8.216 | 1.00 | 25.44 | | C |
| ANISOU | 214 | CA | ILE | A | 179 | 3356 | 2641 | 3668 | −707 | 758 | −23 | C |
| ATOM | 215 | CB | ILE | A | 179 | −33.300 | 37.686 | 8.390 | 1.00 | 29.09 | | C |
| ANISOU | 215 | CB | ILE | A | 179 | 4101 | 3124 | 3829 | −719 | 552 | 312 | C |
| ATOM | 216 | CG1 | ILE | A | 179 | −32.378 | 38.220 | 7.289 | 1.00 | 27.69 | | C |
| ANISOU | 216 | CG1 | ILE | A | 179 | 3936 | 2757 | 3828 | −381 | 349 | 408 | C |
| ATOM | 217 | CD1 | ILE | A | 179 | −30.955 | 37.759 | 7.426 | 1.00 | 29.97 | | C |
| ANISOU | 217 | CD1 | ILE | A | 179 | 4433 | 3081 | 3872 | −361 | 154 | 658 | C |
| ATOM | 218 | CG2 | ILE | A | 179 | −33.384 | 36.176 | 8.333 | 1.00 | 29.16 | | C |
| ANISOU | 218 | CG2 | ILE | A | 179 | 4286 | 3109 | 3682 | −817 | 407 | 598 | C |
| ATOM | 219 | C | ILE | A | 179 | −35.768 | 37.559 | 8.954 | 1.00 | 33.00 | | C |
| ANISOU | 219 | C | ILE | A | 179 | 4272 | 3772 | 4496 | −1030 | 945 | −113 | C |
| ATOM | 220 | O | ILE | A | 179 | −36.510 | 36.755 | 8.374 | 1.00 | 25.64 | | O |
| ANISOU | 220 | O | ILE | A | 179 | 3307 | 2758 | 3677 | −1004 | 893 | −36 | O |
| ATOM | 221 | N | ARG | A | 180 | −35.889 | 37.850 | 10.245 | 1.00 | 28.95 | | N |
| ANISOU | 221 | N | ARG | A | 180 | 3748 | 3516 | 3734 | −1365 | 1180 | −304 | N |
| ATOM | 222 | CA | ARG | A | 180 | −36.908 | 37.212 | 11.055 | 1.00 | 31.42 | | C |
| ANISOU | 222 | CA | ARG | A | 180 | 4020 | 4047 | 3872 | −1753 | 1401 | −431 | C |
| ATOM | 223 | CB | ARG | A | 180 | −36.792 | 37.742 | 12.471 | 1.00 | 34.30 | | C |
| ANISOU | 223 | CB | ARG | A | 180 | 4389 | 4716 | 3926 | −2127 | 1657 | −657 | C |
| ATOM | 224 | CG | ARG | A | 180 | −37.479 | 36.940 | 13.528 | 1.00 | 70.91 | | C |
| ANISOU | 224 | CG | ARG | A | 180 | 9115 | 9608 | 8220 | −2543 | 1773 | −696 | C |
| ATOM | 225 | CD | ARG | A | 180 | −36.682 | 37.111 | 14.819 | 1.00 | 77.83 | | C |
| ANISOU | 225 | CD | ARG | A | 180 | 10196 | 10686 | 8689 | −2768 | 1741 | −672 | C |
| ATOM | 226 | NE | ARG | A | 180 | −35.440 | 36.333 | 14.769 | 1.00 | 80.32 | | N |
| ANISOU | 226 | NE | ARG | A | 180 | 10839 | 10896 | 8783 | −2704 | 1411 | −205 | N |
| ATOM | 227 | CZ | ARG | A | 180 | −34.258 | 36.749 | 15.214 | 1.00 | 78.79 | | C |
| ANISOU | 227 | CZ | ARG | A | 180 | 10774 | 10734 | 8427 | −2671 | 1290 | −107 | C |
| ATOM | 228 | NH1 | ARG | A | 180 | −34.132 | 37.963 | 15.747 | 1.00 | 74.38 | | N |
| ANISOU | 228 | NH1 | ARG | A | 180 | 10072 | 10310 | 7878 | −2722 | 1489 | −424 | N |
| ATOM | 229 | NH2 | ARG | A | 180 | −33.201 | 35.942 | 15.121 | 1.00 | 78.07 | | N |
| ANISOU | 229 | NH2 | ARG | A | 180 | 10929 | 10527 | 8206 | −2559 | 950 | 277 | N |
| ATOM | 230 | C | ARG | A | 180 | −38.285 | 37.538 | 10.482 | 1.00 | 36.27 | | C |
| ANISOU | 230 | C | ARG | A | 180 | 4292 | 4608 | 4880 | −1646 | 1546 | −759 | C |
| ATOM | 231 | O | ARG | A | 180 | −39.166 | 36.679 | 10.371 | 1.00 | 33.43 | | O |
| ANISOU | 231 | O | ARG | A | 180 | 3896 | 4287 | 4520 | −1795 | 1592 | −745 | O |
| ATOM | 232 | N | THR | A | 181 | −38.469 | 38.806 | 10.116 | 1.00 | 32.13 | | N |
| ANISOU | 232 | N | THR | A | 181 | 3516 | 3982 | 4710 | −1387 | 1598 | −1064 | N |
| ATOM | 233 | CA | THR | A | 181 | −39.744 | 39.239 | 9.556 | 1.00 | 35.78 | | C |
| ANISOU | 233 | CA | THR | A | 181 | 3624 | 4365 | 5604 | −1237 | 1687 | −1404 | C |
| ATOM | 234 | CB | THR | A | 181 | −39.755 | 40.754 | 9.341 | 1.00 | 42.70 | | C |
| ANISOU | 234 | CB | THR | A | 181 | 4270 | 5103 | 6849 | −967 | 1707 | −1733 | C |
| ATOM | 235 | OG1 | THR | A | 181 | −39.657 | 41.397 | 10.618 | 1.00 | 39.05 | | O |
| ANISOU | 235 | OG1 | THR | A | 181 | 3741 | 4894 | 6200 | −1247 | 1987 | −2046 | O |
| ATOM | 236 | CG2 | THR | A | 181 | −41.032 | 41.173 | 8.650 | 1.00 | 41.92 | | C |
| ANISOU | 236 | CG2 | THR | A | 181 | 3810 | 4869 | 7250 | −755 | 1715 | −2055 | C |
| ATOM | 237 | C | THR | A | 181 | −39.999 | 38.515 | 8.224 | 1.00 | 34.84 | | C |
| ANISOU | 237 | C | THR | A | 181 | 3538 | 3999 | 5701 | −968 | 1426 | −1136 | C |
| ATOM | 238 | O | THR | A | 181 | −41.077 | 37.968 | 7.993 | 1.00 | 33.78 | | O |
| ANISOU | 238 | O | THR | A | 181 | 3242 | 3899 | 5696 | −1037 | 1491 | −1244 | O |
| ATOM | 239 | N | TYR | A | 182 | −38.983 | 38.485 | 7.376 | 1.00 | 28.75 | | N |
| ANISOU | 239 | N | TYR | A | 182 | 2972 | 3007 | 4943 | −694 | 1143 | −802 | N |
| ATOM | 240 | CA | TYR | A | 182 | −39.100 | 37.790 | 6.088 | 1.00 | 32.60 | | C |
| ANISOU | 240 | CA | TYR | A | 182 | 3512 | 3275 | 5597 | −458 | 892 | −545 | C |
| ATOM | 241 | CB | TYR | A | 182 | −37.766 | 37.890 | 5.372 | 1.00 | 27.90 | | C |
| ANISOU | 241 | CB | TYR | A | 182 | 3149 | 2507 | 4946 | −222 | 632 | −232 | C |
| ATOM | 242 | CG | TYR | A | 182 | −37.732 | 37.200 | 4.022 | 1.00 | 26.03 | | C |
| ANISOU | 242 | CG | TYR | A | 182 | 2981 | 2064 | 4845 | 4 | 377 | 21 | C |
| ATOM | 243 | CD1 | TYR | A | 182 | −38.106 | 37.899 | 2.868 | 1.00 | 34.42 | | C |

TABLE 6-continued

DMXAA-hSTING$^{group2}$ complex

| | | | | | | | | | | | | |
|---|---|---|---|---|---|---|---|---|---|---|---|---|
| ANISOU | 243 | CD1 | TYR | A | 182 | 3907 | 3020 | 6151 | 258 | 224 | −44 | C |
| ATOM | 244 | CE1 | TYR | A | 182 | −38.052 | 37.287 | 1.632 | 1.00 | 28.77 | | C |
| ANISOU | 244 | CE1 | TYR | A | 182 | 3300 | 2446 | 5185 | 322 | 10 | 131 | C |
| ATOM | 245 | CZ | TYR | A | 182 | −37.623 | 35.966 | 1.548 | 1.00 | 26.95 | | C |
| ANISOU | 245 | CZ | TYR | A | 182 | 3246 | 2262 | 4732 | 266 | −48 | 321 | C |
| ATOM | 246 | OH | TYR | A | 182 | −37.569 | 35.346 | 0.309 | 1.00 | 30.13 | | O |
| ANISOU | 246 | OH | TYR | A | 182 | 3725 | 2806 | 4919 | 308 | −162 | 363 | O |
| ATOM | 247 | CE2 | TYR | A | 182 | −37.249 | 35.254 | 2.681 | 1.00 | 26.36 | | C |
| ANISOU | 247 | CE2 | TYR | A | 182 | 3294 | 2093 | 4630 | 105 | 40 | 458 | C |
| ATOM | 248 | CD2 | TYR | A | 182 | −37.310 | 35.878 | 3.908 | 1.00 | 28.15 | | C |
| ANISOU | 248 | CD2 | TYR | A | 182 | 3466 | 2338 | 4889 | −76 | 262 | 321 | C |
| ATOM | 249 | C | TYR | A | 182 | −39.485 | 36.318 | 6.273 | 1.00 | 31.32 | | C |
| ANISOU | 249 | C | TYR | A | 182 | 3480 | 3209 | 5210 | −700 | 903 | −351 | C |
| ATOM | 250 | O | TYR | A | 182 | −40.404 | 35.777 | 5.626 | 1.00 | 28.21 | | O |
| ANISOU | 250 | O | TYR | A | 182 | 2964 | 2751 | 5002 | −658 | 872 | −374 | O |
| ATOM | 251 | N | ASN | A | 183 | −38.809 | 35.660 | 7.207 | 1.00 | 26.72 | | N |
| ANISOU | 251 | N | ASN | A | 183 | 3153 | 2779 | 4221 | −978 | 937 | −161 | N |
| ATOM | 252 | CA | ASN | A | 183 | −39.072 | 34.248 | 7.446 | 1.00 | 27.59 | | C |
| ANISOU | 252 | CA | ASN | A | 183 | 3447 | 2942 | 4094 | −1235 | 907 | 63 | C |
| ATOM | 253 | CB | ASN | A | 183 | −37.931 | 33.627 | 8.220 | 1.00 | 29.61 | | C |
| ANISOU | 253 | CB | ASN | A | 183 | 4050 | 3258 | 3943 | −1420 | 798 | 369 | C |
| ATOM | 254 | CG | ASN | A | 183 | −36.733 | 33.420 | 7.346 | 1.00 | 29.71 | | C |
| ANISOU | 254 | CG | ASN | A | 183 | 4233 | 3046 | 4009 | −1084 | 482 | 667 | C |
| ATOM | 255 | OD1 | ASN | A | 183 | −36.901 | 33.319 | 6.147 | 1.00 | 28.72 | | O |
| ANISOU | 255 | OD1 | ASN | A | 183 | 4027 | 2729 | 4158 | −799 | 344 | 710 | O |
| ATOM | 256 | ND2 | ASN | A | 183 | −35.528 | 33.372 | 7.916 | 1.00 | 27.65 | | N |
| ANISOU | 256 | ND2 | ASN | A | 183 | 4190 | 2823 | 3492 | −1123 | 366 | 849 | N |
| ATOM | 257 | C | ASN | A | 183 | −40.419 | 33.884 | 8.058 | 1.00 | 41.63 | | C |
| ANISOU | 257 | C | ASN | A | 183 | 5059 | 4924 | 5836 | −1582 | 1173 | −185 | C |
| ATOM | 258 | O | ASN | A | 183 | −40.760 | 32.687 | 8.225 | 1.00 | 33.33 | | O |
| ANISOU | 258 | O | ASN | A | 183 | 4166 | 3906 | 4591 | −1835 | 1153 | −4 | O |
| ATOM | 259 | N | GLN | A | 184 | −41.218 | 34.891 | 8.374 | 1.00 | 33.78 | | N |
| ANISOU | 259 | N | GLN | A | 184 | 3734 | 4060 | 5042 | −1607 | 1419 | −621 | N |
| ATOM | 260 | CA | GLN | A | 184 | −42.591 | 34.608 | 8.785 | 1.00 | 36.01 | | C |
| ANISOU | 260 | CA | GLN | A | 184 | 3776 | 4545 | 5359 | −1903 | 1681 | −931 | C |
| ATOM | 261 | CB | GLN | A | 184 | −43.284 | 35.867 | 9.291 | 1.00 | 58.73 | | C |
| ANISOU | 261 | CB | GLN | A | 184 | 6273 | 7583 | 8460 | −1910 | 1951 | −1472 | C |
| ATOM | 262 | CG | GLN | A | 184 | −42.728 | 36.349 | 10.615 | 1.00 | 60.83 | | C |
| ANISOU | 262 | CG | GLN | A | 184 | 6683 | 8078 | 8352 | −2147 | 2095 | −1570 | C |
| ATOM | 263 | CD | GLN | A | 184 | −43.342 | 37.664 | 11.059 | 1.00 | 84.00 | | C |
| ANISOU | 263 | CD | GLN | A | 184 | 9307 | 11098 | 11513 | −2056 | 2272 | −2104 | C |
| ATOM | 264 | OE1 | GLN | A | 184 | −44.275 | 38.172 | 10.428 | 1.00 | 89.57 | | O |
| ANISOU | 264 | OE1 | GLN | A | 184 | 9700 | 11690 | 12642 | −1817 | 2267 | −2403 | O |
| ATOM | 265 | NE2 | GLN | A | 184 | −42.815 | 38.230 | 12.150 | 1.00 | 85.62 | | N |
| ANISOU | 265 | NE2 | GLN | A | 184 | 9617 | 11472 | 11444 | −2240 | 2385 | −2226 | N |
| ATOM | 266 | C | GLN | A | 184 | −43.391 | 33.995 | 7.648 | 1.00 | 35.18 | | C |
| ANISOU | 266 | C | GLN | A | 184 | 3550 | 4272 | 5544 | −1720 | 1547 | −880 | C |
| ATOM | 267 | O | GLN | A | 184 | −44.429 | 33.365 | 7.853 | 1.00 | 39.10 | | O |
| ANISOU | 267 | O | GLN | A | 184 | 3925 | 4916 | 6016 | −1991 | 1706 | −1023 | O |
| ATOM | 268 | N | HIS | A | 185 | −42.918 | 34.165 | 6.426 | 1.00 | 34.54 | | N |
| ANISOU | 268 | N | HIS | A | 185 | 3503 | 3899 | 5720 | −1286 | 1258 | −683 | N |
| ATOM | 269 | CA | HIS | A | 185 | −43.628 | 33.576 | 5.312 | 1.00 | 38.32 | | C |
| ANISOU | 269 | CA | HIS | A | 185 | 3884 | 4224 | 6452 | −1120 | 1113 | −622 | C |
| ATOM | 270 | CB | HIS | A | 185 | −43.552 | 34.501 | 4.109 | 1.00 | 46.28 | | C |
| ANISOU | 270 | CB | HIS | A | 185 | 4729 | 4983 | 7873 | −650 | 901 | −670 | C |
| ATOM | 271 | CG | HIS | A | 185 | −44.340 | 35.745 | 4.301 | 1.00 | 61.63 | | C |
| ANISOU | 271 | CG | HIS | A | 185 | 6293 | 6976 | 10149 | −552 | 1046 | −1126 | C |
| ATOM | 272 | ND1 | HIS | A | 185 | −43.782 | 36.920 | 4.762 | 1.00 | 71.04 | | N |
| ANISOU | 272 | ND1 | HIS | A | 185 | 7448 | 8161 | 11385 | −457 | 1098 | −1282 | N |
| ATOM | 273 | CE1 | HIS | A | 185 | −44.727 | 37.836 | 4.875 | 1.00 | 65.56 | | C |
| ANISOU | 273 | CE1 | HIS | A | 185 | 6373 | 7492 | 11044 | −377 | 1217 | −1729 | C |
| ATOM | 274 | NE2 | HIS | A | 185 | −45.882 | 37.291 | 4.534 | 1.00 | 65.05 | | N |
| ANISOU | 274 | NE2 | HIS | A | 185 | 6125 | 7471 | 11120 | −423 | 1233 | −1862 | N |
| ATOM | 275 | CD2 | HIS | A | 185 | −45.671 | 35.975 | 4.189 | 1.00 | 63.20 | | C |
| ANISOU | 275 | CD2 | HIS | A | 185 | 6112 | 7240 | 10661 | −554 | 1159 | −1501 | C |
| ATOM | 276 | C | HIS | A | 185 | −43.087 | 32.218 | 4.955 | 1.00 | 39.55 | | C |
| ANISOU | 276 | C | HIS | A | 185 | 4384 | 4268 | 6377 | −1184 | 915 | −189 | C |
| ATOM | 277 | O | HIS | A | 185 | −43.547 | 31.588 | 3.992 | 1.00 | 37.89 | | O |
| ANISOU | 277 | O | HIS | A | 185 | 4142 | 3918 | 6335 | −1060 | 774 | −94 | O |
| ATOM | 278 | N | TYR | A | 186 | −42.103 | 31.772 | 5.730 | 1.00 | 29.89 | | N |
| ANISOU | 278 | N | TYR | A | 186 | 3484 | 2875 | 4999 | −392 | 741 | −719 | N |
| ATOM | 279 | CA | TYR | A | 186 | −41.445 | 30.502 | 5.470 | 1.00 | 27.72 | | C |
| ANISOU | 279 | CA | TYR | A | 186 | 3439 | 2716 | 4378 | −443 | 530 | −640 | C |
| ATOM | 280 | CB | TYR | A | 186 | −40.013 | 30.711 | 4.941 | 1.00 | 24.61 | | C |
| ANISOU | 280 | CB | TYR | A | 186 | 3168 | 2280 | 3902 | −352 | 436 | −574 | C |
| ATOM | 281 | CG | TYR | A | 186 | −40.085 | 31.397 | 3.601 | 1.00 | 35.70 | | C |
| ANISOU | 281 | CG | TYR | A | 186 | 4444 | 3650 | 5472 | −212 | 350 | −414 | C |
| ATOM | 282 | CD1 | TYR | A | 186 | −40.142 | 32.795 | 3.513 | 1.00 | 36.79 | | C |

TABLE 6-continued

DMXAA-hSTING$^{group2}$ complex

| | | | | | | | | | | | | |
|---|---|---|---|---|---|---|---|---|---|---|---|---|
| ANISOU | 282 | CD1 | TYR | A | 186 | 4395 | 3660 | 5923 | −105 | 462 | −380 | C |
| ATOM | 283 | CE1 | TYR | A | 186 | −40.266 | 33.422 | 2.277 | 1.00 | 41.78 | | C |
| ANISOU | 283 | CE1 | TYR | A | 186 | 4854 | 4294 | 6725 | −5 | 346 | −120 | C |
| ATOM | 284 | CZ | TYR | A | 186 | −40.357 | 32.643 | 1.127 | 1.00 | 35.61 | | C |
| ANISOU | 284 | CZ | TYR | A | 186 | 4111 | 3717 | 5704 | −81 | 124 | 48 | C |
| ATOM | 285 | OH | TYR | A | 186 | −40.492 | 33.220 | −0.110 | 1.00 | 35.86 | | O |
| ANISOU | 285 | OH | TYR | A | 186 | 3955 | 3862 | 5810 | −80 | −26 | 353 | O |
| ATOM | 286 | CE2 | TYR | A | 186 | −40.331 | 31.260 | 1.194 | 1.00 | 35.84 | | C |
| ANISOU | 286 | CE2 | TYR | A | 186 | 4348 | 3852 | 5417 | −213 | 74 | −85 | C |
| ATOM | 287 | CD2 | TYR | A | 186 | −40.198 | 30.642 | 2.432 | 1.00 | 28.35 | | C |
| ANISOU | 287 | CD2 | TYR | A | 186 | 3548 | 2827 | 4399 | −244 | 185 | −287 | C |
| ATOM | 288 | C | TYR | A | 186 | −41.478 | 29.609 | 6.706 | 1.00 | 35.09 | | C |
| ANISOU | 288 | C | TYR | A | 186 | 4500 | 3752 | 5081 | −645 | 574 | −743 | C |
| ATOM | 289 | O | TYR | A | 186 | −40.482 | 28.984 | 7.063 | 1.00 | 30.89 | | O |
| ANISOU | 289 | O | TYR | A | 186 | 4120 | 3263 | 4352 | −706 | 490 | −682 | O |
| ATOM | 290 | N | ASN | A | 187 | −42.643 | 29.527 | 7.337 | 1.00 | 27.12 | | N |
| ANISOU | 290 | N | ASN | A | 187 | 3389 | 2793 | 4123 | −760 | 699 | −845 | N |
| ATOM | 291 | CA | ASN | A | 187 | −42.794 | 28.596 | 8.443 | 1.00 | 32.10 | | C |
| ANISOU | 291 | CA | ASN | A | 187 | 4123 | 3570 | 4504 | −997 | 714 | −889 | C |
| ATOM | 292 | CB | ASN | A | 187 | −44.129 | 28.803 | 9.139 | 1.00 | 33.18 | | C |
| ANISOU | 292 | CB | ASN | A | 187 | 4113 | 3761 | 4734 | −1136 | 920 | −1062 | C |
| ATOM | 293 | CG | ASN | A | 187 | −44.186 | 30.076 | 9.900 | 1.00 | 44.34 | | C |
| ANISOU | 293 | CG | ASN | A | 187 | 5414 | 5135 | 6299 | −1233 | 1237 | −1340 | C |
| ATOM | 294 | OD1 | ASN | A | 187 | −43.181 | 30.537 | 10.448 | 1.00 | 46.16 | | O |
| ANISOU | 294 | OD1 | ASN | A | 187 | 5743 | 5420 | 6375 | −1358 | 1298 | −1441 | O |
| ATOM | 295 | ND2 | ASN | A | 187 | −45.368 | 30.680 | 9.949 | 1.00 | 42.48 | | N |
| ANISOU | 295 | ND2 | ASN | A | 187 | 4944 | 4791 | 6407 | −1203 | 1482 | −1480 | N |
| ATOM | 296 | C | ASN | A | 187 | −42.733 | 27.160 | 7.941 | 1.00 | 32.36 | | C |
| ANISOU | 296 | C | ASN | A | 187 | 4275 | 3605 | 4415 | −991 | 516 | −702 | C |
| ATOM | 297 | O | ASN | A | 187 | −42.530 | 26.226 | 8.716 | 1.00 | 35.90 | | O |
| ANISOU | 297 | O | ASN | A | 187 | 4813 | 4131 | 4698 | −1154 | 474 | −618 | O |
| ATOM | 298 | N | ASN | A | 188 | −42.969 | 26.969 | 6.644 | 1.00 | 28.11 | | N |
| ANISOU | 298 | N | ASN | A | 188 | 3715 | 2990 | 3974 | −851 | 418 | −629 | N |
| ATOM | 299 | CA | ASN | A | 188 | −42.731 | 25.654 | 6.064 | 1.00 | 25.78 | | C |
| ANISOU | 299 | CA | ASN | A | 188 | 3551 | 2642 | 3601 | −884 | 318 | −542 | C |
| ATOM | 300 | CB | ASN | A | 188 | −43.693 | 25.358 | 4.926 | 1.00 | 24.28 | | C |
| ANISOU | 300 | CB | ASN | A | 188 | 3295 | 2502 | 3427 | −919 | 268 | −548 | C |
| ATOM | 301 | CG | ASN | A | 188 | −43.418 | 24.021 | 4.254 | 1.00 | 25.69 | | C |
| ANISOU | 301 | CG | ASN | A | 188 | 3626 | 2594 | 3541 | −1023 | 259 | −566 | C |
| ATOM | 302 | OD1 | ASN | A | 188 | −42.536 | 23.233 | 4.657 | 1.00 | 25.99 | | O |
| ANISOU | 302 | OD1 | ASN | A | 188 | 3787 | 2461 | 3626 | −1015 | 306 | −531 | O |
| ATOM | 303 | ND2 | ASN | A | 188 | −44.182 | 23.740 | 3.175 | 1.00 | 25.74 | | N |
| ANISOU | 303 | ND2 | ASN | A | 188 | 3590 | 2717 | 3472 | −1159 | 223 | −608 | N |
| ATOM | 304 | C | ASN | A | 188 | −41.316 | 25.707 | 5.544 | 1.00 | 33.14 | | C |
| ANISOU | 304 | C | ASN | A | 188 | 4581 | 3462 | 4549 | −764 | 273 | −480 | C |
| ATOM | 305 | O | ASN | A | 188 | −41.037 | 26.402 | 4.564 | 1.00 | 30.13 | | O |
| ANISOU | 305 | O | ASN | A | 188 | 4165 | 3070 | 4212 | −654 | 243 | −490 | O |
| ATOM | 306 | N | LEU | A | 189 | −40.434 | 24.967 | 6.215 | 1.00 | 30.50 | | N |
| ANISOU | 306 | N | LEU | A | 189 | 4329 | 3059 | 4202 | −800 | 264 | −365 | N |
| ATOM | 307 | CA | LEU | A | 189 | −39.003 | 25.000 | 5.934 | 1.00 | 31.07 | | C |
| ANISOU | 307 | CA | LEU | A | 189 | 4444 | 3018 | 4343 | −685 | 240 | −264 | C |
| ATOM | 308 | CB | LEU | A | 189 | −38.266 | 24.108 | 6.923 | 1.00 | 35.06 | | C |
| ANISOU | 308 | CB | LEU | A | 189 | 4943 | 3482 | 4896 | −761 | 209 | −14 | C |
| ATOM | 309 | CG | LEU | A | 189 | −38.389 | 24.575 | 8.368 | 1.00 | 44.00 | | C |
| ANISOU | 309 | CG | LEU | A | 189 | 6019 | 4880 | 5818 | −959 | 164 | 65 | C |
| ATOM | 310 | CD1 | LEU | A | 189 | −37.542 | 23.658 | 9.241 | 1.00 | 50.94 | | C |
| ANISOU | 310 | CD1 | LEU | A | 189 | 6832 | 5783 | 6739 | −1074 | 68 | 457 | C |
| ATOM | 311 | CD2 | LEU | A | 189 | −37.967 | 26.036 | 8.508 | 1.00 | 40.10 | | C |
| ANISOU | 311 | CD2 | LEU | A | 189 | 5505 | 4522 | 5208 | −947 | 190 | −84 | C |
| ATOM | 312 | C | LEU | A | 189 | −38.709 | 24.500 | 4.541 | 1.00 | 29.90 | | C |
| ANISOU | 312 | C | LEU | A | 189 | 4355 | 2708 | 4296 | −612 | 282 | −334 | C |
| ATOM | 313 | O | LEU | A | 189 | −37.707 | 24.852 | 3.954 | 1.00 | 31.73 | | O |
| ANISOU | 313 | O | LEU | A | 189 | 4603 | 2870 | 4581 | −504 | 291 | −328 | O |
| ATOM | 314 | N | LEU | A | 190 | −39.576 | 23.640 | 4.025 | 1.00 | 25.63 | | N |
| ANISOU | 314 | N | LEU | A | 190 | 3849 | 2131 | 3758 | −727 | 336 | −430 | N |
| ATOM | 315 | CA | LEU | A | 190 | −39.349 | 23.098 | 2.701 | 1.00 | 27.45 | | C |
| ANISOU | 315 | CA | LEU | A | 190 | 4149 | 2257 | 4025 | −781 | 436 | −578 | C |
| ATOM | 316 | CB | LEU | A | 190 | −40.332 | 21.985 | 2.399 | 1.00 | 34.17 | | C |
| ANISOU | 316 | CB | LEU | A | 190 | 5045 | 3073 | 4864 | −995 | 531 | −707 | C |
| ATOM | 317 | CG | LEU | A | 190 | −40.206 | 20.736 | 3.260 | 1.00 | 35.46 | | C |
| ANISOU | 317 | CG | LEU | A | 190 | 5235 | 2973 | 5266 | −1022 | 640 | −606 | C |
| ATOM | 318 | CD1 | LEU | A | 190 | −41.180 | 19.706 | 2.762 | 1.00 | 32.07 | | C |
| ANISOU | 318 | CD1 | LEU | A | 190 | 4864 | 2493 | 4827 | −1268 | 773 | −797 | C |
| ATOM | 319 | CD2 | LEU | A | 190 | −38.796 | 20.135 | 3.206 | 1.00 | 38.04 | | C |
| ANISOU | 319 | CD2 | LEU | A | 190 | 5563 | 2952 | 5937 | −898 | 795 | −515 | C |
| ATOM | 320 | C | LEU | A | 190 | −39.455 | 24.188 | 1.621 | 1.00 | 31.04 | | C |
| ANISOU | 320 | C | LEU | A | 190 | 4563 | 2915 | 4317 | −777 | 359 | −646 | C |
| ATOM | 321 | O | LEU | A | 190 | −38.982 | 23.996 | 0.510 | 1.00 | 35.79 | | O |

TABLE 6-continued

| | | | | | | | | | | | | | |
|---|---|---|---|---|---|---|---|---|---|---|---|---|---|
| DMXAA-hSTING$^{group2}$ complex | | | | | | | | | | | | | |
| ANISOU | 321 | O | LEU | A | 190 | 5219 | 3502 | 4878 | −858 | 437 | −766 | O | |
| ATOM | 322 | V | ARG | A | 191 | −40.115 | 25.289 | 1.926 | 1.00 | 25.57 | | N | |
| ANISOU | 322 | N | ARG | A | 191 | 3748 | 2404 | 3565 | −719 | 237 | −563 | N | |
| ATOM | 323 | CA | ARG | A | 191 | −40.192 | 26.402 | 0.967 | 1.00 | 33.48 | | C | |
| ANISOU | 323 | CA | ARG | A | 191 | 4643 | 3571 | 4508 | −695 | 145 | −506 | C | |
| ATOM | 324 | CB | ARG | A | 191 | −41.468 | 27.225 | 1.148 | 1.00 | 35.97 | | C | |
| ANISOU | 324 | CB | ARG | A | 191 | 4746 | 4044 | 4876 | −693 | 61 | −387 | C | |
| ATOM | 325 | CG | ARG | A | 191 | −42.702 | 26.523 | 0.569 | 1.00 | 35.39 | | C | |
| ANISOU | 325 | CG | ARG | A | 191 | 4606 | 4163 | 4677 | −929 | 9 | −380 | C | |
| ATOM | 326 | CD | ARG | A | 191 | −43.983 | 27.372 | 0.580 | 1.00 | 41.69 | | C | |
| ANISOU | 326 | CD | ARG | A | 191 | 5103 | 5126 | 5609 | −919 | −83 | −174 | C | |
| ATOM | 327 | NE | ARG | A | 191 | −44.403 | 27.612 | 1.952 | 1.00 | 52.43 | | N | |
| ANISOU | 327 | NE | ARG | A | 191 | 6414 | 6340 | 7167 | −790 | 35 | −237 | N | |
| ATOM | 328 | CZ | ARG | A | 191 | −44.256 | 28.778 | 2.580 | 1.00 | 60.39 | | C | |
| ANISOU | 328 | CZ | ARG | A | 191 | 7293 | 7222 | 8431 | −606 | 127 | −213 | C | |
| ATOM | 329 | NH1 | ARG | A | 191 | −43.734 | 29.804 | 1.900 | 1.00 | 53.66 | | N | |
| ANISOU | 329 | NH1 | ARG | A | 191 | 6331 | 6343 | 7714 | −485 | 79 | −65 | N | |
| ATOM | 330 | NH2 | ARG | A | 191 | −44.631 | 28.918 | 3.878 | 1.00 | 41.67 | | N | |
| ANISOU | 330 | NH2 | ARG | A | 191 | 4900 | 4757 | 6176 | −593 | 297 | −358 | N | |
| ATOM | 331 | C | ARG | A | 191 | −38.954 | 27.308 | 0.972 | 1.00 | 41.40 | | C | |
| ANISOU | 331 | C | ARG | A | 191 | 5656 | 4494 | 5581 | −514 | 139 | −454 | C | |
| ATOM | 332 | O | ARG | A | 191 | −38.836 | 28.231 | 0.141 | 1.00 | 35.58 | | O | |
| ANISOU | 332 | O | ARG | A | 191 | 4829 | 3864 | 4824 | −491 | 67 | −369 | O | |
| ATOM | 333 | N | GLY | A | 192 | −38.037 | 27.058 | 1.906 | 1.00 | 36.92 | | N | |
| ANISOU | 333 | N | GLY | A | 192 | 5168 | 3768 | 5093 | −417 | 196 | −454 | N | |
| ATOM | 334 | CA | GLY | A | 192 | −36.747 | 27.728 | 1.907 | 1.00 | 32.93 | | C | |
| ANISOU | 334 | CA | GLY | A | 192 | 4677 | 3201 | 4635 | −287 | 196 | −408 | C | |
| ATOM | 335 | C | GLY | A | 192 | −36.715 | 29.055 | 2.625 | 1.00 | 33.35 | | C | |
| ANISOU | 335 | C | GLY | A | 192 | 4641 | 3300 | 4729 | −208 | 173 | −371 | C | |
| ATOM | 336 | O | GLY | A | 192 | −36.784 | 30.132 | 2.001 | 1.00 | 30.23 | | O | |
| ANISOU | 336 | O | GLY | A | 192 | 4157 | 2938 | 4389 | −146 | 148 | −338 | O | |
| ATOM | 337 | N | ALA | A | 193 | −36.606 | 28.991 | 3.958 | 1.00 | 29.09 | | N | |
| ANISOU | 337 | N | ALA | A | 193 | 4110 | 2770 | 4173 | −258 | 205 | −371 | N | |
| ATOM | 338 | CA | ALA | A | 193 | −36.398 | 30.179 | 4.784 | 1.00 | 27.07 | | C | |
| ANISOU | 338 | CA | ALA | A | 193 | 3796 | 2559 | 3930 | −278 | 265 | −429 | C | |
| ATOM | 339 | CB | ALA | A | 193 | −36.478 | 29.816 | 6.261 | 1.00 | 27.16 | | C | |
| ANISOU | 339 | CB | ALA | A | 193 | 3823 | 2690 | 3806 | −476 | 304 | −448 | C | |
| ATOM | 340 | C | ALA | A | 193 | −35.002 | 30.723 | 4.479 | 1.00 | 26.33 | | C | |
| ANISOU | 340 | C | ALA | A | 193 | 3732 | 2434 | 3840 | −200 | 237 | −374 | C | |
| ATOM | 341 | O | ALA | A | 193 | −34.071 | 29.947 | 4.192 | 1.00 | 29.22 | | O | |
| ANISOU | 341 | O | ALA | A | 193 | 4152 | 2760 | 4189 | −159 | 180 | −263 | O | |
| ATOM | 342 | N | VAL | A | 194 | −34.826 | 32.027 | 4.598 | 1.00 | 28.87 | | N | |
| ANISOU | 342 | N | VAL | A | 194 | 3995 | 2740 | 4234 | −186 | 313 | −454 | N | |
| ATOM | 343 | CA | VAL | A | 194 | −33.507 | 32.580 | 4.289 | 1.00 | 26.56 | | C | |
| ANISOU | 343 | CA | VAL | A | 194 | 3727 | 2430 | 3935 | −129 | 284 | −403 | C | |
| ATOM | 344 | CB | VAL | A | 194 | −33.595 | 34.032 | 3.772 | 1.00 | 26.20 | | C | |
| ANISOU | 344 | CB | VAL | A | 194 | 3592 | 2280 | 4082 | −50 | 371 | −458 | C | |
| ATOM | 345 | CG1 | VAL | A | 194 | −33.885 | 35.012 | 4.895 | 1.00 | 31.89 | | C | |
| ANISOU | 345 | CG1 | VAL | A | 194 | 4257 | 2972 | 4888 | −198 | 583 | −667 | C | |
| ATOM | 346 | CG2 | VAL | A | 194 | −32.296 | 34.413 | 3.085 | 1.00 | 29.79 | | C | |
| ANISOU | 346 | CG2 | VAL | A | 194 | 4080 | 2720 | 4518 | 30 | 308 | −370 | C | |
| ATOM | 347 | C | VAL | A | 194 | −32.559 | 32.436 | 5.478 | 1.00 | 31.50 | | C | |
| ANISOU | 347 | C | VAL | A | 194 | 4382 | 3195 | 4394 | −302 | 274 | −373 | C | |
| ATOM | 348 | O | VAL | A | 194 | −32.950 | 32.657 | 6.615 | 1.00 | 27.07 | | O | |
| ANISOU | 348 | O | VAL | A | 194 | 3806 | 2759 | 3719 | −522 | 358 | −485 | O | |
| ATOM | 349 | N | SER | A | 195 | −31.310 | 32.046 | 5.187 | 1.00 | 27.84 | | N | |
| ANISOU | 349 | N | SER | A | 195 | 3929 | 2739 | 3910 | −242 | 177 | −202 | N | |
| ATOM | 350 | CA | SER | A | 195 | −30.240 | 31.954 | 6.193 | 1.00 | 36.11 | | C | |
| ANISOU | 350 | CA | SER | A | 195 | 4935 | 3974 | 4811 | −422 | 111 | −50 | C | |
| ATOM | 351 | CB | SER | A | 195 | −28.925 | 31.482 | 5.552 | 1.00 | 34.33 | | C | |
| ANISOU | 351 | CB | SER | A | 195 | 4663 | 3678 | 4703 | −270 | 26 | 180 | C | |
| ATOM | 352 | OG | SER | A | 195 | −29.075 | 30.159 | 5.074 | 1.00 | 44.08 | | O | |
| ANISOU | 352 | OG | SER | A | 195 | 5886 | 4749 | 6113 | −136 | 18 | 310 | O | |
| ATOM | 353 | C | SER | A | 195 | −29.996 | 33.305 | 6.879 | 1.00 | 33.36 | | C | |
| ANISOU | 353 | C | SER | A | 195 | 4582 | 3759 | 4334 | −635 | 214 | −243 | C | |
| ATOM | 354 | O | SER | A | 195 | −30.309 | 34.356 | 6.327 | 1.00 | 25.85 | | O | |
| ANISOU | 354 | O | SER | A | 195 | 3643 | 2654 | 3526 | −543 | 345 | −444 | O | |
| ATOM | 355 | N | GLN | A | 196 | −29.375 | 33.260 | 8.052 | 1.00 | 30.11 | | N | |
| ANISOU | 355 | N | GLN | A | 196 | 4127 | 3644 | 3670 | −957 | 163 | −150 | N | |
| ATOM | 356 | CA | GLN | A | 196 | −29.196 | 34.455 | 8.896 | 1.00 | 30.39 | | C | |
| ANISOU | 356 | CA | GLN | A | 196 | 4170 | 3864 | 3511 | −1304 | 323 | −415 | C | |
| ATOM | 357 | CB | GLN | A | 196 | −28.852 | 34.034 | 10.322 | 1.00 | 39.79 | | C | |
| ANISOU | 357 | CB | GLN | A | 196 | 5301 | 5514 | 4301 | −1790 | 232 | −273 | C | |
| ATOM | 358 | CG | GLN | A | 196 | −29.887 | 33.163 | 10.929 | 1.00 | 53.31 | | C | |
| ANISOU | 358 | CG | GLN | A | 196 | 7015 | 7321 | 5920 | −1905 | 219 | −236 | C | |
| ATOM | 359 | CD | GLN | A | 196 | −31.135 | 33.950 | 11.222 | 1.00 | 62.60 | | C | |
| ANISOU | 359 | CD | GLN | A | 196 | 8262 | 8396 | 7126 | −2031 | 543 | −734 | C | |
| ATOM | 360 | OE1 | GLN | A | 196 | −31.083 | 35.178 | 11.359 | 1.00 | 71.86 | | O | |

TABLE 6-continued

DMXAA-hSTING$^{group2}$ complex

| | | | | | | | | | | | |
|---|---|---|---|---|---|---|---|---|---|---|---|
| ANISOU | 360 | OE1 | GLN | A | 196 | 9460 | 9517 | 8327 | −2185 | 806 | −1105 | O |
| ATOM | 361 | NE2 | GLN | A | 196 | −32.267 | 33.261 | 11.316 | 1.00 | 71.46 | | N |
| ANISOU | 361 | NE2 | GLN | A | 196 | 9394 | 9452 | 8306 | −1968 | 566 | −752 | N |
| ATOM | 362 | C | GLN | A | 196 | −28.135 | 35.468 | 8.510 | 1.00 | 43.01 | | C |
| ANISOU | 362 | C | GLN | A | 196 | 5763 | 5433 | 5144 | −1295 | 359 | −470 | C |
| ATOM | 363 | O | GLN | A | 196 | −28.114 | 36.566 | 9.069 | 1.00 | 61.02 | | O |
| ANISOU | 363 | O | GLN | A | 196 | 8067 | 7780 | 7340 | −1580 | 573 | −781 | O |
| ATOM | 364 | N | ARG | A | 197 | −27.181 | 35.131 | 7.662 | 1.00 | 32.24 | | N |
| ANISOU | 364 | N | ARG | A | 197 | 4363 | 3985 | 3901 | −1036 | 194 | −202 | N |
| ATOM | 365 | CA | ARG | A | 197 | −26.090 | 36.112 | 7.505 | 1.00 | 27.46 | | C |
| ANISOU | 365 | CA | ARG | A | 197 | 3741 | 3425 | 3267 | −1112 | 222 | −243 | C |
| ATOM | 366 | CB | ARG | A | 197 | −24.732 | 35.438 | 7.456 | 1.00 | 27.83 | | C |
| ANISOU | 366 | CB | ARG | A | 197 | 3666 | 3643 | 3265 | −1088 | −6 | 163 | C |
| ATOM | 367 | CG | ARG | A | 197 | −24.551 | 34.315 | 8.411 | 1.00 | 49.05 | | C |
| ANISOU | 367 | CG | ARG | A | 197 | 6223 | 6622 | 5792 | −1291 | −194 | 526 | C |
| ATOM | 368 | CD | ARG | A | 197 | −23.871 | 34.789 | 9.622 | 1.00 | 59.22 | | C |
| ANISOU | 368 | CD | ARG | A | 197 | 7421 | 8389 | 6690 | −1815 | −263 | 603 | C |
| ATOM | 369 | NE | ARG | A | 197 | −22.605 | 34.096 | 9.835 | 1.00 | 81.90 | | N |
| ANISOU | 369 | NE | ARG | A | 197 | 10048 | 11498 | 9571 | −1860 | −527 | 1171 | N |
| ATOM | 370 | CZ | ARG | A | 197 | −22.459 | 33.042 | 10.633 | 1.00 | 91.78 | | C |
| ANISOU | 370 | CZ | ARG | A | 197 | 11095 | 13025 | 10752 | −2040 | −746 | 1669 | C |
| ATOM | 371 | NH1 | ARG | A | 197 | −21.262 | 32.481 | 10.770 | 1.00 | 97.63 | | N |
| ANISOU | 371 | NH1 | ARG | A | 197 | 11538 | 13940 | 11616 | −2050 | −976 | 2263 | N |
| ATOM | 372 | NH2 | ARG | A | 197 | −23.505 | 32.555 | 11.293 | 1.00 | 89.88 | | N |
| ANISOU | 372 | NH2 | ARG | A | 197 | 10911 | 12882 | 10359 | −2213 | −733 | 1619 | N |
| ATOM | 373 | C | ARG | A | 197 | −26.211 | 36.922 | 6.225 | 1.00 | 28.26 | | C |
| ANISOU | 373 | C | ARG | A | 197 | 3889 | 3180 | 3667 | −792 | 330 | −381 | C |
| ATOM | 374 | O | ARG | A | 197 | −26.835 | 36.491 | 5.282 | 1.00 | 30.08 | | O |
| ANISOU | 374 | O | ARG | A | 197 | 4140 | 3200 | 4091 | −497 | 303 | −332 | O |
| ATOM | 375 | N | LEU | A | 198 | −25.559 | 38.075 | 6.203 | 1.00 | 25.54 | | N |
| ANISOU | 375 | N | LEU | A | 198 | 3546 | 2823 | 3334 | −906 | 439 | −521 | N |
| ATOM | 376 | CA | LEU | A | 198 | −25.313 | 38.757 | 4.933 | 1.00 | 23.51 | | C |
| ANISOU | 376 | CA | LEU | A | 198 | 3292 | 2300 | 3340 | −623 | 470 | −506 | C |
| ATOM | 377 | CB | LEU | A | 198 | −25.141 | 40.253 | 5.196 | 1.00 | 26.85 | | C |
| ANISOU | 377 | CB | LEU | A | 198 | 3718 | 2617 | 3869 | −811 | 711 | −774 | C |
| ATOM | 378 | CG | LEU | A | 198 | −24.763 | 41.039 | 3.944 | 1.00 | 32.54 | | C |
| ANISOU | 378 | CG | LEU | A | 198 | 4412 | 3092 | 4861 | −564 | 722 | −683 | C |
| ATOM | 379 | CD1 | LEU | A | 198 | −25.850 | 40.876 | 2.879 | 1.00 | 30.56 | | C |
| ANISOU | 379 | CD1 | LEU | A | 198 | 4122 | 2608 | 4883 | −252 | 692 | −559 | C |
| ATOM | 380 | CD2 | LEU | A | 198 | −24.580 | 42.502 | 4.286 | 1.00 | 27.59 | | C |
| ANISOU | 380 | CD2 | LEU | A | 198 | 3769 | 2298 | 4416 | −765 | 1005 | −945 | C |
| ATOM | 381 | C | LEU | A | 198 | −24.033 | 38.164 | 4.317 | 1.00 | 31.06 | | C |
| ANISOU | 381 | C | LEU | A | 198 | 4207 | 3353 | 4241 | −489 | 273 | −219 | C |
| ATOM | 382 | O | LEU | A | 198 | −22.965 | 38.222 | 4.922 | 1.00 | 25.07 | | O |
| ANISOU | 382 | O | LEU | A | 198 | 3391 | 2826 | 3310 | −692 | 203 | −119 | O |
| ATOM | 383 | N | TYR | A | 199 | −24.139 | 37.577 | 3.139 | 1.00 | 21.95 | | N |
| ANISOU | 383 | N | TYR | A | 199 | 3058 | 2049 | 3232 | −193 | 204 | −89 | N |
| ATOM | 384 | CA | TYR | A | 199 | −23.001 | 36.985 | 2.487 | 1.00 | 20.99 | | C |
| ANISOU | 384 | CA | TYR | A | 199 | 2879 | 1961 | 3134 | −71 | 111 | 116 | C |
| ATOM | 385 | CB | TYR | A | 199 | −23.357 | 35.639 | 1.862 | 1.00 | 26.01 | | C |
| ANISOU | 385 | CB | TYR | A | 199 | 3517 | 2495 | 3872 | 114 | 90 | 201 | C |
| ATOM | 386 | CG | TYR | A | 199 | −23.562 | 34.573 | 2.890 | 1.00 | 24.11 | | C |
| ANISOU | 386 | CG | TYR | A | 199 | 3220 | 2337 | 3605 | 38 | 27 | 336 | C |
| ATOM | 387 | CD1 | TYR | A | 199 | −24.772 | 34.392 | 3.477 | 1.00 | 27.07 | | C |
| ANISOU | 387 | CD1 | TYR | A | 199 | 3659 | 2722 | 3905 | −42 | 39 | 225 | C |
| ATOM | 388 | CE1 | TYR | A | 199 | −24.958 | 33.459 | 4.409 | 1.00 | 29.78 | | C |
| ANISOU | 388 | CE1 | TYR | A | 199 | 3941 | 3172 | 4202 | −150 | −33 | 388 | C |
| ATOM | 389 | CZ | TYR | A | 199 | −23.926 | 32.679 | 4.785 | 1.00 | 35.83 | | C |
| ANISOU | 389 | CZ | TYR | A | 199 | 4542 | 4022 | 5052 | −166 | −132 | 730 | C |
| ATOM | 390 | OH | TYR | A | 199 | −24.105 | 31.720 | 5.719 | 1.00 | 44.14 | | O |
| ANISOU | 390 | OH | TYR | A | 199 | 5481 | 5186 | 6104 | −285 | −230 | 1003 | O |
| ATOM | 391 | CE2 | TYR | A | 199 | −22.723 | 32.831 | 4.222 | 1.00 | 31.21 | | C |
| ANISOU | 391 | CE2 | TYR | A | 199 | 3858 | 3399 | 4602 | −60 | −132 | 858 | C |
| ATOM | 392 | CD2 | TYR | A | 199 | −22.542 | 33.786 | 3.287 | 1.00 | 30.62 | | C |
| ANISOU | 392 | CD2 | TYR | A | 199 | 3886 | 3237 | 4511 | 29 | −47 | 624 | C |
| ATOM | 393 | C | TYR | A | 199 | −22.489 | 37.949 | 1.447 | 1.00 | 24.55 | | C |
| ANISOU | 393 | C | TYR | A | 199 | 3345 | 2316 | 3668 | 13 | 159 | 76 | C |
| ATOM | 394 | O | TYR | A | 199 | −23.180 | 38.290 | 0.544 | 1.00 | 26.41 | | O |
| ANISOU | 394 | O | TYR | A | 199 | 3618 | 2414 | 4001 | 125 | 198 | 27 | O |
| ATOM | 395 | N | ILE | A | 200 | −21.259 | 38.372 | 1.626 | 1.00 | 20.52 | | N |
| ANISOU | 395 | N | ILE | A | 200 | 2774 | 1916 | 3106 | −78 | 137 | 148 | N |
| ATOM | 396 | CA | ILE | A | 200 | −20.647 | 39.356 | 0.769 | 1.00 | 21.56 | | C |
| ANISOU | 396 | CA | ILE | A | 200 | 2913 | 1977 | 3303 | −43 | 185 | 124 | C |
| ATOM | 397 | CB | ILE | A | 200 | −19.938 | 40.435 | 1.603 | 1.00 | 25.43 | | C |
| ANISOU | 397 | CB | ILE | A | 200 | 3373 | 2585 | 3702 | −292 | 223 | 61 | C |
| ATOM | 398 | CG1 | ILE | A | 200 | −20.923 | 41.148 | 2.490 | 1.00 | 31.11 | | C |
| ANISOU | 398 | CG1 | ILE | A | 200 | 4146 | 3294 | 4382 | −522 | 349 | −175 | C |
| ATOM | 399 | CD1 | ILE | A | 200 | −20.301 | 41.799 | 3.581 | 1.00 | 42.42 | | C |

TABLE 6-continued

| DMXAA-hSTING$^{group2}$ complex | | | | | | | | | | | |
|---|---|---|---|---|---|---|---|---|---|---|---|
| ANISOU | 399 | CD1 | ILE | A | 200 | 5616 | 4410 | 6091 | −434 | 529 | −338 | C |
| ATOM | 400 | CG2 | ILE | A | 200 | −19.276 | 41.450 | 0.733 | 1.00 | 24.16 | | C |
| ANISOU | 400 | CG2 | ILE | A | 200 | 3217 | 2311 | 3651 | −259 | 289 | 45 | C |
| ATOM | 401 | C | ILE | A | 200 | −19.654 | 38.723 | −0.190 | 1.00 | 24.76 | | C |
| ANISOU | 401 | C | ILE | A | 200 | 3259 | 2398 | 3750 | 103 | 153 | 270 | C |
| ATOM | 402 | O | ILE | A | 200 | −18.661 | 38.222 | 0.198 | 1.00 | 24.51 | | O |
| ANISOU | 402 | O | ILE | A | 200 | 3112 | 2475 | 3724 | 86 | 109 | 420 | O |
| ATOM | 408 | N | LEU | A | 201 | −19.960 | 38.810 | −1.461 | 1.00 | 24.18 | | N |
| ANISOU | 408 | N | LEU | A | 201 | 3231 | 2234 | 3722 | 209 | 194 | 244 | N |
| ATOM | 409 | CA | LEU | A | 201 | −19.136 | 38.263 | −2.490 | 1.00 | 20.54 | | C |
| ANISOU | 409 | CA | LEU | A | 201 | 2726 | 1791 | 3286 | 282 | 247 | 287 | C |
| ATOM | 410 | CB | LEU | A | 201 | −19.991 | 37.908 | −3.687 | 1.00 | 22.56 | | C |
| ANISOU | 410 | CB | LEU | A | 201 | 3056 | 2026 | 3489 | 293 | 293 | 213 | C |
| ATOM | 411 | CG | LEU | A | 201 | −21.179 | 36.989 | −3.468 | 1.00 | 28.77 | | C |
| ANISOU | 411 | CG | LEU | A | 201 | 3893 | 2761 | 4276 | 318 | 289 | 147 | C |
| ATOM | 412 | CD1 | LEU | A | 201 | −21.875 | 36.768 | −4.737 | 1.00 | 28.76 | | C |
| ANISOU | 412 | CD1 | LEU | A | 201 | 3945 | 2834 | 4148 | 230 | 324 | 86 | C |
| ATOM | 413 | CD2 | LEU | A | 201 | −20.706 | 35.732 | −2.910 | 1.00 | 30.85 | | C |
| ANISOU | 413 | CD2 | LEU | A | 201 | 4098 | 2950 | 4674 | 387 | 365 | 149 | C |
| ATOM | 414 | C | LEU | A | 201 | −18.001 | 39.197 | −2.902 | 1.00 | 19.94 | | C |
| ANISOU | 414 | C | LEU | A | 201 | 2604 | 1775 | 3197 | 230 | 257 | 338 | C |
| ATOM | 415 | O | LEU | A | 201 | −18.222 | 40.348 | −3.163 | 1.00 | 20.60 | | O |
| ANISOU | 415 | O | LEU | A | 201 | 2729 | 1834 | 3264 | 170 | 243 | 334 | O |
| ATOM | 416 | N | LEU | A | 202 | −16.801 | 38.646 | −2.937 | 1.00 | 20.66 | | N |
| ANISOU | 416 | N | LEU | A | 202 | 2572 | 1916 | 3360 | 259 | 301 | 419 | N |
| ATOM | 417 | CA | LEU | A | 202 | −15.604 | 39.345 | −3.285 | 1.00 | 21.42 | | C |
| ANISOU | 417 | CA | LEU | A | 202 | 2597 | 2090 | 3450 | 206 | 320 | 477 | C |
| ATOM | 418 | CB | LEU | A | 202 | −14.726 | 39.606 | −2.078 | 1.00 | 29.66 | | C |
| ANISOU | 418 | CB | LEU | A | 202 | 3504 | 3266 | 4498 | 108 | 227 | 626 | C |
| ATOM | 419 | CG | LEU | A | 202 | −15.343 | 40.555 | −1.091 | 1.00 | 29.99 | | C |
| ANISOU | 419 | CG | LEU | A | 202 | 3647 | 3346 | 4402 | −62 | 156 | 538 | C |
| ATOM | 420 | CD1 | LEU | A | 202 | −15.779 | 39.820 | 0.047 | 1.00 | 39.48 | | C |
| ANISOU | 420 | CD1 | LEU | A | 202 | 4777 | 4665 | 5560 | −140 | 67 | 635 | C |
| ATOM | 421 | CD2 | LEU | A | 202 | −14.366 | 41.537 | −0.682 | 1.00 | 39.38 | | C |
| ANISOU | 421 | CD2 | LEU | A | 202 | 4806 | 4646 | 5510 | −263 | 151 | 532 | C |
| ATOM | 422 | C | LEU | A | 202 | −14.789 | 38.652 | −4.371 | 1.00 | 22.57 | | C |
| ANISOU | 422 | C | LEU | A | 202 | 2661 | 2217 | 3698 | 272 | 484 | 453 | C |
| ATOM | 423 | O | LEU | A | 202 | −13.819 | 38.034 | −4.105 | 1.00 | 23.93 | | O |
| ANISOU | 423 | O | LEU | A | 202 | 2646 | 2375 | 4070 | 338 | 551 | 564 | O |
| ATOM | 424 | N | PRO | A | 203 | −15.242 | 38.786 | −5.601 | 1.00 | 26.16 | | N |
| ANISOU | 424 | N | PRO | A | 203 | 3222 | 2683 | 4034 | 218 | 569 | 322 | N |
| ATOM | 425 | CA | PRO | A | 203 | −14.472 | 38.328 | −6.761 | 1.00 | 24.39 | | C |
| ANISOU | 425 | CA | PRO | A | 203 | 2946 | 2491 | 3830 | 170 | 788 | 210 | C |
| ATOM | 426 | CB | PRO | A | 203 | −15.421 | 38.581 | −7.940 | 1.00 | 29.28 | | C |
| ANISOU | 426 | CB | PRO | A | 203 | 3713 | 3235 | 4179 | −6 | 793 | 105 | C |
| ATOM | 427 | CG | PRO | A | 203 | −16.291 | 39.798 | −7.482 | 1.00 | 23.44 | | C |
| ANISOU | 427 | CG | PRO | A | 203 | 3040 | 2510 | 3357 | −8 | 536 | 288 | C |
| ATOM | 428 | CD | PRO | A | 203 | −16.476 | 39.522 | −5.970 | 1.00 | 23.02 | | C |
| ANISOU | 428 | CD | PRO | A | 203 | 2963 | 2311 | 3472 | 144 | 461 | 313 | C |
| ATOM | 429 | C | PRO | A | 203 | −13.215 | 39.187 | −6.866 | 1.00 | 27.35 | | C |
| ANISOU | 429 | C | PRO | A | 203 | 3222 | 2956 | 4214 | 130 | 780 | 314 | C |
| ATOM | 430 | O | PRO | A | 203 | −13.289 | 40.403 | −6.946 | 1.00 | 28.27 | | O |
| ANISOU | 430 | O | PRO | A | 203 | 3403 | 3153 | 4185 | 42 | 643 | 397 | O |
| ATOM | 431 | N | LEU | A | 204 | −12.050 | 38.567 | −6.848 | 1.00 | 26.69 | | N |
| ANISOU | 431 | N | LEU | A | 204 | 2949 | 2830 | 4364 | 198 | 945 | 333 | N |
| ATOM | 432 | CA | LEU | A | 204 | −10.850 | 39.361 | −6.947 | 1.00 | 27.49 | | C |
| ANISOU | 432 | CA | LEU | A | 204 | 2936 | 3040 | 4468 | 145 | 934 | 441 | C |
| ATOM | 433 | CB | LEU | A | 204 | −9.647 | 38.626 | −6.377 | 1.00 | 36.36 | | C |
| ANISOU | 433 | CB | LEU | A | 204 | 3759 | 4103 | 5955 | 269 | 1035 | 603 | C |
| ATOM | 434 | CG | LEU | A | 204 | −9.808 | 38.250 | −4.913 | 1.00 | 45.00 | | C |
| ANISOU | 434 | CG | LEU | A | 204 | 4733 | 5188 | 7178 | 349 | 829 | 860 | C |
| ATOM | 435 | CD1 | LEU | A | 204 | −8.455 | 37.867 | −4.437 | 1.00 | 54.73 | | C |
| ANISOU | 435 | CD1 | LEU | A | 204 | 5600 | 6454 | 8742 | 410 | 856 | 1158 | C |
| ATOM | 436 | CD2 | LEU | A | 204 | −10.355 | 39.430 | −4.106 | 1.00 | 50.15 | | C |
| ANISOU | 436 | CD2 | LEU | A | 204 | 5555 | 6000 | 7501 | 198 | 550 | 900 | C |
| ATOM | 437 | C | LEU | A | 204 | −10.562 | 39.687 | −8.390 | 1.00 | 32.86 | | C |
| ANISOU | 437 | C | LEU | A | 204 | 3677 | 3826 | 4980 | −13 | 1107 | 280 | C |
| ATOM | 438 | O | LEU | A | 204 | −9.867 | 40.644 | −8.667 | 1.00 | 32.01 | | O |
| ANISOU | 438 | O | LEU | A | 204 | 3548 | 3842 | 4772 | −109 | 1057 | 363 | O |
| ATOM | 439 | N | ASP | A | 205 | −11.068 | 38.865 | −9.304 | 1.00 | 36.91 | | N |
| ANISOU | 439 | N | ASP | A | 205 | 4262 | 4323 | 5441 | −96 | 1329 | 40 | N |
| ATOM | 440 | CA | ASP | A | 205 | −10.725 | 39.039 | −10.708 | 1.00 | 48.20 | | C |
| ANISOU | 440 | CA | ASP | A | 205 | 5731 | 5935 | 6648 | −352 | 1538 | −144 | C |
| ATOM | 441 | CB | ASP | A | 205 | −11.003 | 37.760 | −11.486 | 1.00 | 52.93 | | C |
| ANISOU | 441 | CB | ASP | A | 205 | 6348 | 6476 | 7287 | −479 | 1914 | −505 | C |
| ATOM | 442 | CG | ASP | A | 205 | −10.152 | 36.586 | −10.987 | 1.00 | 64.85 | | C |
| ANISOU | 442 | CG | ASP | A | 205 | 7619 | 7655 | 9365 | −250 | 2244 | −599 | C |
| ATOM | 443 | OD1 | ASP | A | 205 | −8.914 | 36.771 | −10.836 | 1.00 | 74.14 | | O |

TABLE 6-continued

DMXAA-hSTING$^{group2}$ complex

| | | | | | | | | | | | | |
|---|---|---|---|---|---|---|---|---|---|---|---|---|
| ANISOU | 443 | OD1 | ASP | A | 205 | 8579 | 8785 | 10804 | −150 | 2337 | −486 | O |
| ATOM | 444 | OD2 | ASP | A | 205 | −10.734 | 35.511 | −10.715 | 1.00 | 49.64 | | O |
| ANISOU | 444 | OD2 | ASP | A | 205 | 5690 | 5505 | 7667 | −165 | 2397 | −730 | O |
| ATOM | 445 | C | ASP | A | 205 | −11.462 | 40.226 | −11.300 | 1.00 | 42.96 | | C |
| ANISOU | 445 | C | ASP | A | 205 | 5227 | 5511 | 5585 | −561 | 1284 | −1 | C |
| ATOM | 446 | O | ASP | A | 205 | −12.352 | 40.785 | −10.680 | 1.00 | 42.67 | | O |
| ANISOU | 446 | O | ASP | A | 205 | 5268 | 5428 | 5518 | −478 | 1013 | 182 | O |
| ATOM | 447 | N | CYS | A | 206 | −11.084 | 40.587 | −12.505 | 1.00 | 45.71 | | N |
| ANISOU | 447 | N | CYS | A | 206 | 5589 | 6111 | 5669 | −850 | 1398 | −63 | N |
| ATOM | 448 | CA | CYS | A | 206 | −11.534 | 41.829 | −13.103 | 1.00 | 54.14 | | C |
| ANISOU | 448 | CA | CYS | A | 206 | 6722 | 7413 | 6434 | −1058 | 1143 | 207 | C |
| ATOM | 449 | CB | CYS | A | 206 | −10.818 | 42.040 | −14.430 | 1.00 | 60.90 | | C |
| ANISOU | 449 | CB | CYS | A | 206 | 7554 | 8592 | 6992 | −1424 | 1323 | 125 | C |
| ATOM | 450 | SG | CYS | A | 206 | −11.670 | 41.292 | −15.822 | 1.00 | 140.36 | | S |
| ANISOU | 450 | SG | CYS | A | 206 | 17644 | 19019 | 16668 | −1770 | 1000 | 565 | S |
| ATOM | 451 | C | CYS | A | 206 | −13.040 | 41.871 | −13.333 | 1.00 | 57.09 | | C |
| ANISOU | 451 | C | CYS | A | 206 | 7192 | 7889 | 6610 | −1167 | 942 | 336 | C |
| ATOM | 452 | O | CYS | A | 206 | −13.612 | 40.965 | −13.954 | 1.00 | 53.89 | | O |
| ANISOU | 452 | O | CYS | A | 206 | 6844 | 7633 | 6000 | −1373 | 1084 | 119 | O |
| ATOM | 453 | N | GLY | A | 207 | −13.661 | 42.937 | −12.826 | 1.00 | 47.04 | | N |
| ANISOU | 453 | N | GLY | A | 207 | 5914 | 6521 | 5440 | −1051 | 647 | 678 | N |
| ATOM | 454 | CA | GLY | A | 207 | −15.061 | 43.185 | −13.105 | 1.00 | 47.98 | | C |
| ANISOU | 454 | CA | GLY | A | 207 | 6045 | 6737 | 5449 | −1150 | 435 | 915 | C |
| ATOM | 455 | C | GLY | A | 207 | −15.933 | 42.560 | −12.054 | 1.00 | 47.94 | | C |
| ANISOU | 455 | C | GLY | A | 207 | 6088 | 6473 | 5652 | −890 | 400 | 808 | C |
| ATOM | 456 | O | GLY | A | 207 | −15.551 | 41.590 | −11.382 | 1.00 | 44.85 | | O |
| ANISOU | 456 | O | GLY | A | 207 | 5734 | 5917 | 5391 | −720 | 566 | 516 | O |
| ATOM | 457 | N | VAL | A | 208 | −17.103 | 43.166 | −11.869 | 1.00 | 39.43 | | N |
| ANISOU | 457 | N | VAL | A | 208 | 4971 | 5343 | 4667 | −854 | 186 | 1095 | N |
| ATOM | 458 | CA | VAL | A | 208 | −18.143 | 42.577 | −11.057 | 1.00 | 40.20 | | C |
| ANISOU | 458 | CA | VAL | A | 208 | 5107 | 5266 | 4901 | −679 | 149 | 1011 | C |
| ATOM | 459 | CB | VAL | A | 208 | −18.262 | 43.189 | −9.619 | 1.00 | 53.25 | | C |
| ANISOU | 459 | CB | VAL | A | 208 | 6750 | 6544 | 6940 | −384 | 114 | 1028 | C |
| ATOM | 460 | CG1 | VAL | A | 208 | −17.191 | 44.251 | −9.384 | 1.00 | 48.83 | | C |
| ANISOU | 460 | CG1 | VAL | A | 208 | 6150 | 5876 | 6526 | −358 | 142 | 1100 | C |
| ATOM | 461 | CG2 | VAL | A | 208 | −19.648 | 43.744 | −9.362 | 1.00 | 44.97 | | C |
| ANISOU | 461 | CG2 | VAL | A | 208 | 5621 | 5365 | 6098 | −325 | −18 | 1268 | C |
| ATOM | 462 | C | VAL | A | 208 | −19.431 | 42.648 | −11.858 | 1.00 | 45.85 | | C |
| ANISOU | 462 | C | VAL | A | 208 | 5754 | 6221 | 5447 | −892 | −23 | 1284 | C |
| ATOM | 463 | O | VAL | A | 208 | −19.775 | 43.691 | −12.429 | 1.00 | 42.74 | | O |
| ANISOU | 463 | O | VAL | A | 208 | 5215 | 5930 | 5093 | −1010 | −200 | 1717 | O |
| ATOM | 464 | N | PRO | A | 209 | −20.098 | 41.497 | −11.975 | 1.00 | 48.01 | | N |
| ANISOU | 464 | N | PRO | A | 209 | 6099 | 6609 | 5535 | −980 | 33 | 1069 | N |
| ATOM | 465 | CA | PRO | A | 209 | −21.281 | 41.316 | −12.806 | 1.00 | 43.92 | | C |
| ANISOU | 465 | CA | PRO | A | 209 | 5510 | 6423 | 4752 | −1275 | −121 | 1286 | C |
| ATOM | 466 | CB | PRO | A | 209 | −21.732 | 39.900 | −12.456 | 1.00 | 41.75 | | C |
| ANISOU | 466 | CB | PRO | A | 209 | 5369 | 6102 | 4391 | −1263 | 38 | 877 | C |
| ATOM | 467 | CG | PRO | A | 209 | −20.497 | 39.211 | −12.109 | 1.00 | 45.60 | | C |
| ANISOU | 467 | CG | PRO | A | 209 | 5970 | 6395 | 4962 | −1134 | 328 | 461 | C |
| ATOM | 468 | CD | PRO | A | 209 | −19.697 | 40.234 | −11.333 | 1.00 | 48.95 | | C |
| ANISOU | 468 | CD | PRO | A | 209 | 6343 | 6553 | 5701 | −837 | 264 | 620 | C |
| ATOM | 469 | C | PRO | A | 209 | −22.347 | 42.277 | −12.375 | 1.00 | 44.75 | | C |
| ANISOU | 469 | C | PRO | A | 209 | 5440 | 6370 | 5193 | −1108 | −361 | 1744 | C |
| ATOM | 470 | O | PRO | A | 209 | −22.569 | 42.501 | −11.182 | 1.00 | 46.70 | | O |
| ANISOU | 470 | O | PRO | A | 209 | 5698 | 6209 | 5837 | −761 | −326 | 1672 | O |
| ATOM | 471 | N | ASP | A | 210 | −23.023 | 42.816 | −13.369 | 1.00 | 49.31 | | N |
| ANISOU | 471 | N | ASP | A | 210 | 5825 | 7293 | 5616 | −1403 | −585 | 2230 | N |
| ATOM | 472 | CA | ASP | A | 210 | −24.103 | 43.748 | −13.164 | 1.00 | 60.92 | | C |
| ANISOU | 472 | CA | ASP | A | 210 | 7031 | 8619 | 7497 | −1275 | −801 | 2778 | C |
| ATOM | 473 | CB | ASP | A | 210 | −24.569 | 44.201 | −14.531 | 1.00 | 86.00 | | C |
| ANISOU | 473 | CB | ASP | A | 210 | 9936 | 12294 | 10447 | −1654 | −1053 | 3211 | C |
| ATOM | 474 | CG | ASP | A | 210 | −24.805 | 43.028 | −15.465 | 1.00 | 104.03 | | C |
| ANISOU | 474 | CG | ASP | A | 210 | 12321 | 15155 | 12052 | −2143 | −1072 | 3002 | C |
| ATOM | 475 | OD2 | ASP | A | 210 | −25.935 | 42.899 | −15.990 | 1.00 | 114.81 | | O |
| ANISOU | 475 | OD2 | ASP | A | 210 | 13459 | 16819 | 13346 | −2360 | −1279 | 3232 | O |
| ATOM | 476 | OD1 | ASP | A | 210 | −23.869 | 42.211 | −15.628 | 1.00 | 107.27 | | O |
| ANISOU | 476 | OD1 | ASP | A | 210 | 13015 | 15694 | 12048 | −2326 | −825 | 2550 | O |
| ATOM | 477 | C | ASP | A | 210 | −25.248 | 43.022 | −12.496 | 1.00 | 60.74 | | C |
| ANISOU | 477 | C | ASP | A | 210 | 7019 | 8480 | 7578 | −1139 | −805 | 2644 | C |
| ATOM | 478 | O | ASP | A | 210 | −25.984 | 43.570 | −11.671 | 1.00 | 66.28 | | O |
| ANISOU | 478 | O | ASP | A | 210 | 7583 | 8810 | 8791 | −846 | −821 | 2813 | O |
| ATOM | 479 | N | ASN | A | 211 | −25.417 | 41.767 | −12.865 | 1.00 | 46.27 | | N |
| ANISOU | 479 | N | ASN | A | 211 | 5346 | 6955 | 5280 | −1383 | −747 | 2307 | N |
| ATOM | 480 | CA | ASN | A | 211 | −26.540 | 41.033 | −12.343 | 1.00 | 40.95 | | C |
| ANISOU | 480 | CA | ASN | A | 211 | 4676 | 6224 | 4658 | −1311 | −765 | 2204 | C |
| ATOM | 481 | CB | ASN | A | 211 | −27.502 | 40.675 | −13.456 | 1.00 | 51.39 | | C |
| ANISOU | 481 | CB | ASN | A | 211 | 5850 | 8121 | 5557 | −1790 | −975 | 2512 | C |
| ATOM | 482 | CG | ASN | A | 211 | −28.758 | 40.088 | −12.908 | 1.00 | 72.01 | | C |

TABLE 6-continued

DMXAA-hSTING$^{group2}$ complex

| | | | | | | | | | | | | |
|---|---|---|---|---|---|---|---|---|---|---|---|---|
| ANISOU | 482 | CG | ASN | A | 211 | 8413 | 10667 | 8283 | −1705 | −1027 | 2496 | C |
| ATOM | 483 | OD1 | ASN | A | 211 | −28.847 | 38.879 | −12.666 | 1.00 | 68.14 | | O |
| ANISOU | 483 | OD1 | ASN | A | 211 | 8146 | 10187 | 7560 | −1769 | −856 | 1997 | O |
| ATOM | 484 | ND2 | ASN | A | 211 | −29.736 | 40.951 | −12.639 | 1.00 | 86.37 | | N |
| ANISOU | 484 | ND2 | ASN | A | 211 | 9915 | 12351 | 10552 | −1530 | −1225 | 3044 | N |
| ATOM | 485 | C | ASN | A | 211 | −26.085 | 39.769 | −11.660 | 1.00 | 33.26 | | C |
| ANISOU | 485 | C | ASN | A | 211 | 3992 | 5067 | 3579 | −1190 | −501 | 1554 | C |
| ATOM | 486 | O | ASN | A | 211 | −25.713 | 38.820 | −12.314 | 1.00 | 34.24 | | O |
| ANISOU | 486 | O | ASN | A | 211 | 4258 | 5448 | 3303 | −1483 | −359 | 1231 | O |
| ATOM | 487 | N | LEU | A | 212 | −26.128 | 39.761 | −10.332 | 1.00 | 28.70 | | N |
| ANISOU | 487 | N | LEU | A | 212 | 3943 | 3682 | 3281 | 68 | −352 | −279 | N |
| ATOM | 488 | CA | LEU | A | 212 | −25.600 | 38.636 | −9.578 | 1.00 | 33.15 | | C |
| ANISOU | 488 | CA | LEU | A | 212 | 4526 | 4153 | 3916 | 53 | −278 | −314 | C |
| ATOM | 489 | CB | LEU | A | 212 | −25.863 | 38.877 | −8.090 | 1.00 | 30.76 | | C |
| ANISOU | 489 | CB | LEU | A | 212 | 4186 | 3815 | 3686 | 82 | −268 | −261 | C |
| ATOM | 490 | CG | LEU | A | 212 | −24.998 | 38.114 | −7.110 | 1.00 | 32.67 | | C |
| ANISOU | 490 | CG | LEU | A | 212 | 4451 | 3971 | 3990 | 92 | −206 | −238 | C |
| ATOM | 491 | CD1 | LEU | A | 212 | −25.093 | 38.792 | −5.756 | 1.00 | 32.43 | | C |
| ANISOU | 491 | CD1 | LEU | A | 212 | 4396 | 3948 | 3980 | 118 | −208 | −176 | C |
| ATOM | 492 | CD2 | LEU | A | 212 | −25.556 | 36.746 | −7.000 | 1.00 | 30.16 | | C |
| ANISOU | 492 | CD2 | LEU | A | 212 | 4133 | 3602 | 3724 | 33 | −174 | −285 | C |
| ATOM | 493 | C | LEU | A | 212 | −26.146 | 37.282 | −10.051 | 1.00 | 31.55 | | C |
| ANISOU | 493 | C | LEU | A | 212 | 4332 | 3934 | 3724 | −28 | −258 | −410 | C |
| ATOM | 494 | O | LEU | A | 212 | −25.398 | 36.333 | −10.245 | 1.00 | 33.54 | | O |
| ANISOU | 494 | O | LEU | A | 212 | 4629 | 4110 | 4006 | −44 | −188 | −461 | O |
| ATOM | 495 | N | SER | A | 213 | −27.456 | 37.192 | −10.292 | 1.00 | 30.03 | | N |
| ANISOU | 495 | N | SER | A | 213 | 4087 | 3808 | 3514 | −82 | −316 | −442 | N |
| ATOM | 496 | CA | SER | A | 213 | −28.034 | 35.904 | −10.657 | 1.00 | 32.73 | | C |
| ANISOU | 496 | CA | SER | A | 213 | 4432 | 4129 | 3875 | −179 | −295 | −545 | C |
| ATOM | 497 | CB | SER | A | 213 | −29.553 | 35.993 | −10.673 | 1.00 | 30.08 | | C |
| ANISOU | 497 | CB | SER | A | 213 | 4008 | 3883 | 3537 | −235 | −370 | −560 | C |
| ATOM | 498 | OG | SER | A | 213 | −29.950 | 36.788 | −11.747 | 1.00 | 42.22 | | O |
| ANISOU | 498 | OG | SER | A | 213 | 5521 | 5551 | 4968 | −238 | −465 | −551 | O |
| ATOM | 499 | C | SER | A | 213 | −27.516 | 35.415 | −12.018 | 1.00 | 35.75 | | C |
| ANISOU | 499 | C | SER | A | 213 | 4880 | 4532 | 4172 | −232 | −276 | −642 | C |
| ATOM | 500 | O | SER | A | 213 | −27.534 | 34.204 | −12.316 | 1.00 | 30.55 | | O |
| ANISOU | 500 | O | SER | A | 213 | 4254 | 3808 | 3544 | −309 | −217 | −751 | O |
| ATOM | 501 | N | MET | A | 214 | −27.046 | 36.346 | −12.859 | 1.00 | 26.97 | | N |
| ANISOU | 501 | N | MET | A | 214 | 3793 | 3505 | 2950 | −200 | −313 | −609 | N |
| ATOM | 502 | CA | MET | A | 214 | −26.566 | 35.934 | −14.188 | 1.00 | 31.51 | | C |
| ANISOU | 502 | CA | MET | A | 214 | 4436 | 4123 | 3415 | −263 | −285 | −707 | C |
| ATOM | 503 | CB | MET | A | 214 | −26.527 | 37.125 | −15.153 | 1.00 | 35.37 | | C |
| ANISOU | 503 | CB | MET | A | 214 | 4934 | 4753 | 3753 | −249 | −363 | −641 | C |
| ATOM | 504 | CG | MET | A | 214 | −27.866 | 37.465 | −15.775 | 1.00 | 43.29 | | C |
| ANISOU | 504 | CG | MET | A | 214 | 5880 | 5906 | 4664 | −308 | −496 | −631 | C |
| ATOM | 505 | SD | MET | A | 214 | −28.521 | 36.144 | −16.823 | 1.00 | 52.64 | | S |
| ANISOU | 505 | SD | MET | A | 214 | 7087 | 7161 | 5751 | −477 | −503 | −818 | S |
| ATOM | 506 | CE | MET | A | 214 | −27.746 | 36.529 | −18.385 | 1.00 | 47.91 | | C |
| ANISOU | 506 | CE | MET | A | 214 | 6584 | 6690 | 4928 | −524 | −500 | −845 | C |
| ATOM | 507 | C | MET | A | 214 | −25.153 | 35.337 | −14.091 | 1.00 | 28.72 | | C |
| ANISOU | 507 | C | MET | A | 214 | 4145 | 3646 | 3123 | −227 | −155 | −745 | C |
| ATOM | 508 | O | MET | A | 214 | −24.682 | 34.673 | −15.001 | 1.00 | 33.83 | | O |
| ANISOU | 508 | O | MET | A | 214 | 4850 | 4285 | 3720 | −281 | −86 | −860 | O |
| ATOM | 509 | N | ALA | A | 215 | −24.462 | 35.607 | −12.989 | 1.00 | 30.46 | | N |
| ANISOU | 509 | N | ALA | A | 215 | 4348 | 3776 | 3450 | −135 | −121 | −651 | N |
| ATOM | 510 | CA | ALA | A | 215 | −23.146 | 35.003 | −12.775 | 1.00 | 31.76 | | C |
| ANISOU | 510 | CA | ALA | A | 215 | 4544 | 3823 | 3702 | −89 | −10 | −668 | C |
| ATOM | 511 | CB | ALA | A | 215 | −22.561 | 35.502 | −11.466 | 1.00 | 28.46 | | C |
| ANISOU | 511 | CB | ALA | A | 215 | 4087 | 3350 | 3377 | 3 | −14 | −539 | C |
| ATOM | 512 | C | ALA | A | 215 | −23.172 | 33.472 | −12.803 | 1.00 | 33.12 | | C |
| ANISOU | 512 | C | ALA | A | 215 | 4740 | 3872 | 3972 | −138 | 78 | −781 | C |
| ATOM | 513 | O | ALA | A | 215 | −22.173 | 32.819 | −13.164 | 1.00 | 40.56 | | O |
| ANISOU | 513 | O | ALA | A | 215 | 5714 | 4726 | 4969 | −119 | 186 | −844 | O |
| ATOM | 514 | N | ASP | A | 216 | −24.301 | 32.872 | −12.432 | 1.00 | 29.15 | | N |
| ANISOU | 514 | N | ASP | A | 216 | 4217 | 3349 | 3508 | −203 | 46 | −811 | N |
| ATOM | 515 | CA | ASP | A | 216 | −24.357 | 31.408 | −12.295 | 1.00 | 33.61 | | C |
| ANISOU | 515 | CA | ASP | A | 216 | 4807 | 3764 | 4198 | −252 | 137 | −904 | C |
| ATOM | 516 | CB | ASP | A | 216 | −23.886 | 31.020 | −10.866 | 1.00 | 34.17 | | C |
| ANISOU | 516 | CB | ASP | A | 216 | 4854 | 3698 | 4431 | −171 | 173 | −780 | C |
| ATOM | 517 | CG | ASP | A | 216 | −23.770 | 29.485 | −10.645 | 1.00 | 45.87 | | C |
| ANISOU | 517 | CG | ASP | A | 216 | 6365 | 4985 | 6078 | −200 | 279 | −842 | C |
| ATOM | 518 | OD1 | ASP | A | 216 | −24.488 | 28.678 | −11.267 | 1.00 | 45.93 | | O |
| ANISOU | 518 | OD1 | ASP | A | 216 | 6401 | 4957 | 6093 | −309 | 311 | −980 | O |
| ATOM | 519 | OD2 | ASP | A | 216 | −22.929 | 29.093 | −9.812 | 1.00 | 47.89 | | O |
| ANISOU | 519 | OD2 | ASP | A | 216 | 6612 | 5119 | 6465 | −114 | 329 | −742 | O |
| ATOM | 520 | C | ASP | A | 216 | −25.800 | 30.968 | −12.504 | 1.00 | 26.10 | | C |
| ANISOU | 520 | C | ASP | A | 216 | 3839 | 2860 | 3219 | −373 | 84 | −983 | C |
| ATOM | 521 | O | ASP | A | 216 | −26.701 | 31.529 | −11.878 | 1.00 | 28.65 | | O |

TABLE 6-continued

| | | | | | | | | | | | | |
|---|---|---|---|---|---|---|---|---|---|---|---|---|
| | DMXAA-hSTING$^{group2}$ complex |
| ANISOU | 521 | O | ASP | A | 216 | 4102 | 3257 | 3528 | −376 | −3 | −902 | O |
| ATOM | 522 | N | PRO | A | 217 | −26.027 | 29.970 | −13.378 | 1.00 | 33.30 | | N |
| ANISOU | 522 | N | PRO | A | 217 | 4795 | 3729 | 4127 | −481 | 142 | −1152 | N |
| ATOM | 523 | CA | PRO | A | 217 | −27.404 | 29.511 | −13.623 | 1.00 | 35.75 | | C |
| ANISOU | 523 | CA | PRO | A | 217 | 5078 | 4094 | 4411 | −618 | 87 | −1241 | C |
| ATOM | 524 | CB | PRO | A | 217 | −27.262 | 28.468 | −14.733 | 1.00 | 39.27 | | C |
| ANISOU | 524 | CB | PRO | A | 217 | 5597 | 4486 | 4839 | −733 | 175 | −1453 | C |
| ATOM | 525 | CG | PRO | A | 217 | −25.840 | 28.489 | −15.169 | 1.00 | 39.99 | | C |
| ANISOU | 525 | CG | PRO | A | 217 | 5749 | 4513 | 4931 | −648 | 280 | −1476 | C |
| ATOM | 526 | CD | PRO | A | 217 | −25.033 | 29.157 | −14.099 | 1.00 | 37.33 | | C |
| ANISOU | 526 | CD | PRO | A | 217 | 5377 | 4129 | 4679 | −486 | 275 | −1279 | C |
| ATOM | 527 | C | PRO | A | 217 | −27.965 | 28.806 | −12.393 | 1.00 | 39.72 | | C |
| ANISOU | 527 | C | PRO | A | 217 | 5545 | 4467 | 5081 | −629 | 113 | −1181 | C |
| ATOM | 528 | O | PRO | A | 217 | −29.151 | 28.520 | −12.345 | 1.00 | 35.26 | | O |
| ANISOU | 528 | O | PRO | A | 217 | 4934 | 3946 | 4516 | −736 | 66 | −1224 | O |
| ATOM | 529 | N | ASN | A | 218 | −27.121 | 28.502 | −11.416 | 1.00 | 33.02 | | N |
| ANISOU | 529 | N | ASN | A | 218 | 4712 | 3465 | 4368 | −529 | 187 | −1076 | N |
| ATOM | 530 | CA | ASN | A | 218 | −27.651 | 27.869 | −10.208 | 1.00 | 29.26 | | C |
| ANISOU | 530 | CA | ASN | A | 218 | 4209 | 2878 | 4029 | −545 | 211 | −993 | C |
| ATOM | 531 | CB | ASN | A | 218 | −26.784 | 26.705 | −9.770 | 1.00 | 26.37 | | C |
| ANISOU | 531 | CB | ASN | A | 218 | 3898 | 2279 | 3845 | −507 | 337 | −979 | C |
| ATOM | 532 | CG | ASN | A | 218 | −26.863 | 25.557 | −10.718 | 1.00 | 36.13 | | C |
| ANISOU | 532 | CG | ASN | A | 218 | 5190 | 3392 | 5144 | −611 | 431 | −1174 | C |
| ATOM | 533 | OD1 | ASN | A | 218 | −27.948 | 25.115 | −11.093 | 1.00 | 39.63 | | O |
| ANISOU | 533 | OD1 | ASN | A | 218 | 5626 | 3862 | 5569 | −756 | 415 | −1288 | O |
| ATOM | 534 | ND2 | ASN | A | 218 | −25.703 | 25.059 | −11.142 | 1.00 | 40.30 | | N |
| ANISOU | 534 | ND2 | ASN | A | 218 | 5772 | 3789 | 5753 | −545 | 537 | −1227 | N |
| ATOM | 535 | C | ASN | A | 218 | −27.826 | 28.836 | −9.079 | 1.00 | 27.62 | | C |
| ANISOU | 535 | C | ASN | A | 218 | 3943 | 2753 | 3797 | −466 | 140 | −820 | C |
| ATOM | 536 | O | ASN | A | 218 | −28.078 | 28.433 | −7.945 | 1.00 | 29.65 | | O |
| ANISOU | 536 | O | ASN | A | 218 | 4185 | 2933 | 4148 | −464 | 166 | −723 | O |
| ATOM | 537 | N | ILE | A | 219 | −27.691 | 30.127 | −9.372 | 1.00 | 24.44 | | N |
| ANISOU | 537 | N | ILE | A | 219 | 3513 | 2505 | 3266 | −405 | 59 | −780 | N |
| ATOM | 538 | CA | ILE | A | 219 | −28.084 | 31.153 | −8.407 | 1.00 | 22.26 | | C |
| ANISOU | 538 | CA | ILE | A | 219 | 3177 | 2322 | 2958 | −349 | −7 | −651 | C |
| ATOM | 539 | CB | ILE | A | 219 | −26.950 | 32.168 | −8.194 | 1.00 | 24.06 | | C |
| ANISOU | 539 | CB | ILE | A | 219 | 3419 | 2581 | 3140 | −228 | −24 | −558 | C |
| ATOM | 540 | CG1 | ILE | A | 219 | −25.718 | 31.469 | −7.587 | 1.00 | 26.28 | | C |
| ANISOU | 540 | CG1 | ILE | A | 219 | 3742 | 2717 | 3526 | −164 | 55 | −497 | C |
| ATOM | 541 | CD1 | ILE | A | 219 | −24.535 | 32.420 | −7.342 | 1.00 | 30.86 | | C |
| ANISOU | 541 | CD1 | ILE | A | 219 | 4321 | 3334 | 4069 | −58 | 38 | −410 | C |
| ATOM | 542 | CG2 | ILE | A | 219 | −27.392 | 33.318 | −7.295 | 1.00 | 23.28 | | C |
| ANISOU | 542 | CG2 | ILE | A | 219 | 3265 | 2578 | 3002 | −182 | −84 | −457 | C |
| ATOM | 543 | C | ILE | A | 219 | −29.255 | 31.890 | −9.052 | 1.00 | 31.82 | | C |
| ANISOU | 543 | C | ILE | A | 219 | 4323 | 3697 | 4068 | −404 | −103 | −699 | C |
| ATOM | 544 | O | ILE | A | 219 | −29.120 | 32.367 | −10.185 | 1.00 | 33.03 | | O |
| ANISOU | 544 | O | ILE | A | 219 | 4490 | 3942 | 4119 | −408 | −150 | −756 | O |
| ATOM | 545 | N | ARG | A | 220 | −30.398 | 31.968 | −8.361 | 1.00 | 23.11 | | N |
| ANISOU | 545 | N | ARG | A | 220 | 3145 | 2640 | 2997 | −447 | −130 | −669 | N |
| ATOM | 546 | CA | ARG | A | 220 | −31.577 | 32.616 | −8.940 | 1.00 | 25.10 | | C |
| ANISOU | 546 | CA | ARG | A | 220 | 3307 | 3049 | 3181 | −491 | −226 | −704 | C |
| ATOM | 547 | CB | ARG | A | 220 | −32.723 | 31.653 | −9.178 | 1.00 | 28.33 | | C |
| ANISOU | 547 | CB | ARG | A | 220 | 3666 | 3464 | 3635 | −635 | −226 | −801 | C |
| ATOM | 548 | CG | ARG | A | 220 | −32.331 | 30.216 | −9.311 | 1.00 | 57.97 | | C |
| ANISOU | 548 | CG | ARG | A | 220 | 7500 | 7059 | 7466 | −719 | −131 | −889 | C |
| ATOM | 549 | CD | ARG | A | 220 | −31.909 | 29.918 | −10.719 | 1.00 | 67.27 | | C |
| ANISOU | 549 | CD | ARG | A | 220 | 8740 | 8257 | 8562 | −768 | −143 | −1021 | C |
| ATOM | 550 | NE | ARG | A | 220 | −32.940 | 30.284 | −11.683 | 1.00 | 82.63 | | N |
| ANISOU | 550 | NE | ARG | A | 220 | 10611 | 10384 | 10399 | −858 | −256 | −1097 | N |
| ATOM | 551 | CZ | ARG | A | 220 | −32.738 | 30.330 | −12.998 | 1.00 | 86.84 | | C |
| ANISOU | 551 | CZ | ARG | A | 220 | 11185 | 11006 | 10804 | −909 | −300 | −1199 | C |
| ATOM | 552 | NH1 | ARG | A | 220 | −33.730 | 30.671 | −13.822 | 1.00 | 77.68 | | N |
| ANISOU | 552 | NH1 | ARG | A | 220 | 9946 | 10032 | 9536 | −995 | −423 | −1246 | N |
| ATOM | 553 | NH2 | ARG | A | 220 | −31.536 | 30.039 | −13.487 | 1.00 | 78.97 | | N |
| ANISOU | 553 | NH2 | ARG | A | 220 | 10301 | 9922 | 9781 | −875 | −220 | −1249 | N |
| ATOM | 554 | C | ARG | A | 220 | −32.105 | 33.631 | −7.963 | 1.00 | 26.78 | | C |
| ANISOU | 554 | C | ARG | A | 220 | 3441 | 3327 | 3407 | −424 | −254 | −601 | C |
| ATOM | 555 | O | ARG | A | 220 | −32.290 | 33.328 | −6.779 | 1.00 | 24.58 | | O |
| ANISOU | 555 | O | ARG | A | 220 | 3149 | 2989 | 3200 | −428 | −193 | −550 | O |
| ATOM | 556 | N | PHE | A | 221 | −32.405 | 34.816 | −8.469 | 1.00 | 25.97 | | N |
| ANISOU | 556 | N | PHE | A | 221 | 3285 | 3346 | 3235 | −368 | −341 | −573 | N |
| ATOM | 557 | CA | PHE | A | 221 | −33.000 | 35.840 | −7.624 | 1.00 | 23.74 | | C |
| ANISOU | 557 | CA | PHE | A | 221 | 2919 | 3118 | 2983 | −301 | −357 | −497 | C |
| ATOM | 558 | CB | PHE | A | 221 | −33.112 | 37.123 | −8.424 | 1.00 | 32.34 | | C |
| ANISOU | 558 | CB | PHE | A | 221 | 3969 | 4311 | 4008 | −227 | −452 | −459 | C |
| ATOM | 559 | CG | PHE | A | 221 | −33.861 | 38.188 | −7.712 | 1.00 | 29.69 | | C |
| ANISOU | 559 | CG | PHE | A | 221 | 3533 | 4021 | 3727 | −156 | −465 | −398 | C |
| ATOM | 560 | CD1 | PHE | A | 221 | −33.302 | 38.805 | −6.613 | 1.00 | 28.32 | | C |

TABLE 6-continued

DMXAA-hSTING$^{group2}$ complex

| | | | | | | | | | | | | |
|---|---|---|---|---|---|---|---|---|---|---|---|---|
| ANISOU | 560 | CD1 | PHE | A | 221 | 3393 | 3786 | 3584 | −82 | −397 | −347 | C |
| ATOM | 561 | CE1 | PHE | A | 221 | −33.977 | 39.818 | −5.945 | 1.00 | 28.57 | | C |
| ANISOU | 561 | CE1 | PHE | A | 221 | 3337 | 3847 | 3672 | −18 | −388 | −314 | C |
| ATOM | 562 | CZ | PHE | A | 221 | −35.240 | 40.230 | −6.404 | 1.00 | 28.88 | | C |
| ANISOU | 562 | CZ | PHE | A | 221 | 3237 | 3977 | 3758 | −10 | −453 | −315 | C |
| ATOM | 563 | CE2 | PHE | A | 221 | −35.816 | 39.608 | −7.511 | 1.00 | 34.53 | | C |
| ANISOU | 563 | CE2 | PHE | A | 221 | 3905 | 4772 | 4441 | −83 | −542 | −348 | C |
| ATOM | 564 | CD2 | PHE | A | 221 | −35.118 | 38.578 | −8.162 | 1.00 | 32.07 | | C |
| ANISOU | 564 | CD2 | PHE | A | 221 | 3700 | 4433 | 4053 | −165 | −545 | −399 | C |
| ATOM | 565 | C | PHE | A | 221 | −34.399 | 35.395 | −7.227 | 1.00 | 27.59 | | C |
| ANISOU | 565 | C | PHE | A | 221 | 3293 | 3652 | 3539 | −384 | −355 | −529 | C |
| ATOM | 566 | O | PHE | A | 221 | −35.156 | 34.912 | −8.058 | 1.00 | 26.79 | | O |
| ANISOU | 566 | O | PHE | A | 221 | 3137 | 3615 | 3427 | −474 | −410 | −600 | O |
| ATOM | 567 | N | ARG | A | 222 | −34.753 | 35.575 | −5.963 | 1.00 | 23.13 | | N |
| ANISOU | 567 | N | ARG | A | 222 | 2687 | 3066 | 3035 | −365 | −290 | −483 | N |
| ATOM | 568 | CA | ARG | A | 222 | −36.108 | 35.250 | −5.540 | 1.00 | 22.96 | | C |
| ANISOU | 568 | CA | ARG | A | 222 | 2541 | 3098 | 3084 | −443 | −273 | −511 | C |
| ATOM | 569 | CB | ARG | A | 222 | −36.133 | 34.381 | −4.272 | 1.00 | 29.70 | | C |
| ANISOU | 569 | CB | ARG | A | 222 | 3427 | 3864 | 3994 | −506 | −154 | −490 | C |
| ATOM | 570 | CG | ARG | A | 222 | −37.547 | 34.394 | −3.681 | 1.00 | 33.28 | | C |
| ANISOU | 570 | CG | ARG | A | 222 | 3733 | 4393 | 4518 | −567 | −120 | −506 | C |
| ATOM | 571 | CD | ARG | A | 222 | −37.753 | 33.656 | −2.351 | 1.00 | 31.38 | | C |
| ANISOU | 571 | CD | ARG | A | 222 | 3511 | 4091 | 4320 | −640 | 7 | −471 | C |
| ATOM | 572 | NE | ARG | A | 222 | −37.248 | 32.289 | −2.247 | 1.00 | 35.04 | | N |
| ANISOU | 572 | NE | ARG | A | 222 | 4081 | 4426 | 4806 | −731 | 59 | −465 | N |
| ATOM | 573 | CZ | ARG | A | 222 | −37.030 | 31.705 | −1.068 | 1.00 | 39.92 | | C |
| ANISOU | 573 | CZ | ARG | A | 222 | 4759 | 4969 | 5438 | −770 | 162 | −391 | C |
| ATOM | 574 | NH1 | ARG | A | 222 | −37.249 | 32.395 | 0.062 | 1.00 | 30.38 | | N |
| ANISOU | 574 | NH1 | ARG | A | 222 | 3521 | 3823 | 4199 | −735 | 221 | −336 | N |
| ATOM | 575 | NH2 | ARG | A | 222 | −36.568 | 30.456 | −1.001 | 1.00 | 35.30 | | N |
| ANISOU | 575 | NH2 | ARG | A | 222 | 4269 | 4247 | 4897 | −841 | 208 | −368 | N |
| ATOM | 576 | C | ARG | A | 222 | −36.896 | 36.541 | −5.278 | 1.00 | 26.91 | | C |
| ANISOU | 576 | C | ARG | A | 222 | 2915 | 3698 | 3612 | −359 | −305 | −475 | C |
| ATOM | 577 | O | ARG | A | 222 | −37.895 | 36.814 | −5.940 | 1.00 | 29.21 | | O |
| ANISOU | 577 | O | ARG | A | 222 | 3078 | 4093 | 3927 | −375 | −384 | −497 | O |
| ATOM | 578 | N | ASP | A | 223 | −36.468 | 37.317 | −4.300 | 1.00 | 27.94 | | N |
| ANISOU | 578 | N | ASP | A | 223 | 3075 | 3796 | 3747 | −274 | −243 | −422 | N |
| ATOM | 579 | CA | ASP | A | 223 | −37.145 | 38.569 | −3.951 | 1.00 | 30.11 | | C |
| ANISOU | 579 | CA | ASP | A | 223 | 3239 | 4132 | 4069 | −185 | −245 | −401 | C |
| ATOM | 580 | CB | ASP | A | 223 | −38.558 | 38.336 | −3.413 | 1.00 | 36.93 | | C |
| ANISOU | 580 | CB | ASP | A | 223 | 3946 | 5062 | 5025 | −243 | −198 | −434 | C |
| ATOM | 581 | CG | ASP | A | 223 | −38.596 | 37.424 | −2.182 | 1.00 | 38.31 | | C |
| ANISOU | 581 | CG | ASP | A | 223 | 4162 | 5187 | 5208 | −337 | −68 | −442 | C |
| ATOM | 582 | OD1 | ASP | A | 223 | −37.523 | 36.987 | −1.690 | 1.00 | 32.66 | | O |
| ANISOU | 582 | OD1 | ASP | A | 223 | 3595 | 4387 | 4430 | −347 | −23 | −411 | O |
| ATOM | 583 | OD2 | ASP | A | 223 | −39.731 | 37.149 | −1.715 | 1.00 | 44.40 | | O |
| ANISOU | 583 | OD2 | ASP | A | 223 | 4807 | 6012 | 6052 | −402 | −11 | −471 | O |
| ATOM | 584 | C | ASP | A | 223 | −36.335 | 39.355 | −2.944 | 1.00 | 27.04 | | C |
| ANISOU | 584 | C | ASP | A | 223 | 2929 | 3685 | 3658 | −107 | −170 | −365 | C |
| ATOM | 585 | O | ASP | A | 223 | −35.176 | 39.056 | −2.724 | 1.00 | 29.55 | | O |
| ANISOU | 585 | O | ASP | A | 223 | 3379 | 3936 | 3913 | −108 | −150 | −342 | O |
| ATOM | 586 | N | MET | A | 224 | −36.940 | 40.382 | −2.343 | 1.00 | 26.04 | | N |
| ANISOU | 586 | N | MET | A | 224 | 2715 | 3587 | 3590 | −39 | −127 | −367 | N |
| ATOM | 587 | CA | MET | A | 224 | −36.206 | 41.229 | −1.410 | 1.00 | 27.28 | | C |
| ANISOU | 587 | CA | MET | A | 224 | 2948 | 3697 | 3722 | 22 | −54 | −357 | C |
| ATOM | 588 | CB | MET | A | 224 | −36.441 | 42.690 | −1.750 | 1.00 | 30.33 | | C |
| ANISOU | 588 | CB | MET | A | 224 | 3270 | 4083 | 4171 | 143 | −83 | −348 | C |
| ATOM | 589 | CG | MET | A | 224 | −36.508 | 42.920 | −3.231 | 1.00 | 48.94 | | C |
| ANISOU | 589 | CG | MET | A | 224 | 5593 | 6466 | 6534 | 187 | −219 | −305 | C |
| ATOM | 590 | SD | MET | A | 224 | −34.841 | 43.035 | −3.895 | 1.00 | 58.51 | | S |
| ANISOU | 590 | SD | MET | A | 224 | 6982 | 7614 | 7634 | 207 | −274 | −261 | S |
| ATOM | 591 | CE | MET | A | 224 | −34.623 | 44.790 | −3.628 | 1.00 | 71.47 | | C |
| ANISOU | 591 | CE | MET | A | 224 | 8618 | 9198 | 9339 | 334 | −249 | −233 | C |
| ATOM | 592 | C | MET | A | 224 | −36.625 | 41.043 | 0.033 | 1.00 | 29.38 | | C |
| ANISOU | 592 | C | MET | A | 224 | 3197 | 3973 | 3993 | −30 | 79 | −387 | C |
| ATOM | 593 | O | MET | A | 224 | −37.763 | 40.730 | 0.330 | 1.00 | 26.60 | | O |
| ANISOU | 593 | O | MET | A | 224 | 2728 | 3673 | 3705 | −76 | 129 | −418 | O |
| ATOM | 594 | N | LEU | A | 225 | −35.705 | 41.321 | 0.940 | 1.00 | 24.30 | | N |
| ANISOU | 594 | N | LEU | A | 225 | 2664 | 3293 | 3274 | −26 | 138 | −379 | N |
| ATOM | 595 | CA | LEU | A | 225 | −36.064 | 41.454 | 2.332 | 1.00 | 25.39 | | C |
| ANISOU | 595 | CA | LEU | A | 225 | 2794 | 3461 | 3392 | −69 | 268 | −413 | C |
| ATOM | 596 | CB | LEU | A | 225 | −34.796 | 41.685 | 3.159 | 1.00 | 25.55 | | C |
| ANISOU | 596 | CB | LEU | A | 225 | 2956 | 3454 | 3296 | −78 | 294 | −393 | C |
| ATOM | 597 | CG | LEU | A | 225 | −33.837 | 40.511 | 3.264 | 1.00 | 28.47 | | C |
| ANISOU | 597 | CG | LEU | A | 225 | 3438 | 3798 | 3581 | −144 | 256 | −315 | C |
| ATOM | 598 | CD1 | LEU | A | 225 | −32.759 | 40.931 | 4.279 | 1.00 | 28.78 | | C |
| ANISOU | 598 | CD1 | LEU | A | 225 | 3582 | 3845 | 3507 | −154 | 284 | −297 | C |
| ATOM | 599 | CD2 | LEU | A | 225 | −34.576 | 39.280 | 3.811 | 1.00 | 22.90 | | C |

TABLE 6-continued

| DMXAA-hSTING$^{group2}$ complex | | | | | | | | | | | | |
|---|---|---|---|---|---|---|---|---|---|---|---|---|
| ANISOU | 599 | CD2 | LEU | A | 225 | 2707 | 3118 | 2877 | −250 | 319 | −291 | C |
| ATOM | 600 | C | LEU | A | 225 | −36.962 | 42.681 | 2.465 | 1.00 | 30.12 | | C |
| ANISOU | 600 | C | LEU | A | 225 | 3272 | 4080 | 4091 | 11 | 322 | −478 | C |
| ATOM | 601 | O | LEU | A | 225 | −37.012 | 43.518 | 1.556 | 1.00 | 29.91 | | O |
| ANISOU | 601 | O | LEU | A | 225 | 3200 | 4027 | 4138 | 110 | 247 | −471 | O |
| ATOM | 602 | N | PRO | A | 226 | −37.650 | 42.819 | 3.610 | 1.00 | 35.06 | | N |
| ANISOU | 602 | N | PRO | A | 226 | 3848 | 4748 | 4724 | −30 | 461 | −537 | N |
| ATOM | 603 | CA | PRO | A | 226 | −38.235 | 44.144 | 3.895 | 1.00 | 30.32 | | C |
| ANISOU | 603 | CA | PRO | A | 226 | 3159 | 4138 | 4221 | 61 | 539 | −614 | C |
| ATOM | 604 | CB | PRO | A | 226 | −38.843 | 43.988 | 5.286 | 1.00 | 29.40 | | C |
| ANISOU | 604 | CB | PRO | A | 226 | 3018 | 4084 | 4070 | −22 | 714 | −687 | C |
| ATOM | 605 | CG | PRO | A | 226 | −38.260 | 42.708 | 5.865 | 1.00 | 41.96 | | C |
| ANISOU | 605 | CG | PRO | A | 226 | 4729 | 5708 | 5505 | −156 | 716 | −624 | C |
| ATOM | 606 | CD | PRO | A | 226 | −37.893 | 41.836 | 4.684 | 1.00 | 36.60 | | C |
| ANISOU | 606 | CD | PRO | A | 226 | 4072 | 4994 | 4841 | −158 | 563 | −535 | C |
| ATOM | 607 | C | PRO | A | 226 | −37.131 | 45.210 | 3.951 | 1.00 | 35.67 | | C |
| ANISOU | 607 | C | PRO | A | 226 | 3952 | 4744 | 4859 | 129 | 522 | −626 | C |
| ATOM | 608 | O | PRO | A | 226 | −35.966 | 44.912 | 4.288 | 1.00 | 29.81 | | O |
| ANISOU | 608 | O | PRO | A | 226 | 3355 | 3990 | 3983 | 77 | 496 | −596 | O |
| ATOM | 609 | N | GLN | A | 227 | −37.495 | 46.451 | 3.633 | 1.00 | 33.23 | | N |
| ANISOU | 609 | N | GLN | A | 227 | 3568 | 4379 | 4678 | 243 | 538 | −666 | N |
| ATOM | 610 | CA | GLN | A | 227 | −36.492 | 47.502 | 3.479 | 1.00 | 35.66 | | C |
| ANISOU | 610 | CA | GLN | A | 227 | 3975 | 4598 | 4976 | 307 | 512 | −671 | C |
| ATOM | 611 | CB | GLN | A | 227 | −37.093 | 48.716 | 2.805 | 1.00 | 47.86 | | C |
| ANISOU | 611 | CB | GLN | A | 227 | 5412 | 6065 | 6707 | 448 | 504 | −676 | C |
| ATOM | 612 | CG | GLN | A | 227 | −37.719 | 48.438 | 1.473 | 1.00 | 60.36 | | C |
| ANISOU | 612 | CG | GLN | A | 227 | 6883 | 7673 | 8380 | 511 | 367 | −576 | C |
| ATOM | 613 | CD | GLN | A | 227 | −38.448 | 49.663 | 0.955 | 1.00 | 65.60 | | C |
| ANISOU | 613 | CD | GLN | A | 227 | 7417 | 8265 | 9242 | 660 | 366 | −562 | C |
| ATOM | 614 | OE1 | GLN | A | 227 | −39.151 | 50.354 | 1.712 | 1.00 | 52.17 | | O |
| ANISOU | 614 | OE1 | GLN | A | 227 | 5630 | 6529 | 7663 | 708 | 505 | −651 | O |
| ATOM | 615 | NE2 | GLN | A | 227 | −38.258 | 49.964 | −0.332 | 1.00 | 68.20 | | N |
| ANISOU | 615 | NE2 | GLN | A | 227 | 7736 | 8569 | 9607 | 734 | 216 | −446 | N |
| ATOM | 616 | C | GLN | A | 227 | −35.945 | 47.953 | 4.811 | 1.00 | 39.65 | | C |
| ANISOU | 616 | C | GLN | A | 227 | 4580 | 5100 | 5387 | 246 | 640 | −768 | C |
| ATOM | 617 | O | GLN | A | 227 | −36.574 | 47.794 | 5.844 | 1.00 | 33.49 | | O |
| ANISOU | 617 | O | GLN | A | 227 | 3766 | 4378 | 4581 | 186 | 773 | −848 | O |
| ATOM | 618 | N | GLN | A | 228 | −34.772 | 48.578 | 4.763 | 1.00 | 35.35 | | N |
| ANISOU | 618 | N | GLN | A | 228 | 4154 | 4492 | 4786 | 256 | 601 | −766 | N |
| ATOM | 619 | CA | GLN | A | 228 | −34.188 | 49.174 | 5.941 | 1.00 | 30.17 | | C |
| ANISOU | 619 | CA | GLN | A | 228 | 3591 | 3834 | 4038 | 193 | 706 | −870 | C |
| ATOM | 620 | CB | GLN | A | 228 | −32.763 | 48.635 | 6.082 | 1.00 | 31.98 | | C |
| ANISOU | 620 | CB | GLN | A | 228 | 3960 | 4095 | 4095 | 111 | 615 | −806 | C |
| ATOM | 621 | CG | GLN | A | 228 | −31.923 | 49.342 | 7.144 | 1.00 | 28.30 | | C |
| ANISOU | 621 | CG | GLN | A | 228 | 3598 | 3635 | 3518 | 36 | 683 | −904 | C |
| ATOM | 622 | CD | GLN | A | 228 | −32.417 | 49.013 | 8.515 | 1.00 | 38.59 | | C |
| ANISOU | 622 | CD | GLN | A | 228 | 4913 | 5047 | 4703 | −71 | 813 | −990 | C |
| ATOM | 623 | OE1 | GLN | A | 228 | −32.424 | 47.845 | 8.900 | 1.00 | 45.26 | | O |
| ANISOU | 623 | OE1 | GLN | A | 228 | 5776 | 5990 | 5430 | −149 | 790 | −913 | O |
| ATOM | 624 | NE2 | GLN | A | 228 | −32.861 | 50.024 | 9.262 | 1.00 | 39.72 | | N |
| ANISOU | 624 | NE2 | GLN | A | 228 | 5046 | 5166 | 4880 | −78 | 962 | −1150 | N |
| ATOM | 625 | C | GLN | A | 228 | −34.149 | 50.699 | 5.749 | 1.00 | 32.10 | | C |
| ANISOU | 625 | C | GLN | A | 228 | 3825 | 3950 | 4422 | 288 | 756 | −946 | C |
| ATOM | 626 | O | GLN | A | 228 | −33.515 | 51.191 | 4.810 | 1.00 | 29.38 | | O |
| ANISOU | 626 | O | GLN | A | 228 | 3511 | 3519 | 4131 | 354 | 655 | −877 | O |
| ATOM | 627 | N | ASN | A | 229 | −34.820 | 51.429 | 6.631 | 1.00 | 32.30 | | N |
| ANISOU | 627 | N | ASN | A | 229 | 3810 | 3954 | 4509 | 291 | 921 | −1089 | N |
| ATOM | 628 | CA | ASN | A | 229 | −34.773 | 52.884 | 6.626 | 1.00 | 40.93 | | C |
| ANISOU | 628 | CA | ASN | A | 229 | 4905 | 4902 | 5746 | 371 | 999 | −1183 | C |
| ATOM | 629 | CB | ASN | A | 229 | −36.103 | 53.468 | 7.094 | 1.00 | 50.46 | | C |
| ANISOU | 629 | CB | ASN | A | 229 | 5978 | 6073 | 7123 | 438 | 1170 | −1302 | C |
| ATOM | 630 | CG | ASN | A | 229 | −37.184 | 53.342 | 6.034 | 1.00 | 69.56 | | C |
| ANISOU | 630 | CG | ASN | A | 229 | 8221 | 8471 | 9738 | 575 | 1102 | −1193 | C |
| ATOM | 631 | OD1 | ASN | A | 229 | −37.415 | 54.274 | 5.258 | 1.00 | 85.07 | | O |
| ANISOU | 631 | OD1 | ASN | A | 229 | 10121 | 10301 | 11901 | 713 | 1074 | −1153 | O |
| ATOM | 632 | ND2 | ASN | A | 229 | −37.831 | 52.178 | 5.973 | 1.00 | 71.20 | | N |
| ANISOU | 632 | ND2 | ASN | A | 229 | 8350 | 8812 | 9891 | 530 | 1065 | −1134 | N |
| ATOM | 633 | C | ASN | A | 229 | −33.639 | 53.364 | 7.518 | 1.00 | 45.38 | | C |
| ANISOU | 633 | C | ASN | A | 229 | 5620 | 5459 | 6162 | 261 | 1047 | −1287 | C |
| ATOM | 634 | O | ASN | A | 229 | −33.495 | 52.917 | 8.663 | 1.00 | 39.60 | | O |
| ANISOU | 634 | O | ASN | A | 229 | 4948 | 4844 | 5254 | 131 | 1124 | −1369 | O |
| ATOM | 635 | N | ILE | A | 230 | −32.832 | 54.270 | 6.985 | 1.00 | 35.87 | | N |
| ANISOU | 635 | N | ILE | A | 230 | 4477 | 4127 | 5025 | 303 | 999 | −1277 | N |
| ATOM | 636 | CA | ILE | A | 230 | −31.712 | 54.814 | 7.738 | 1.00 | 28.23 | | C |
| ANISOU | 636 | CA | ILE | A | 230 | 3642 | 3148 | 3934 | 191 | 1032 | −1380 | C |
| ATOM | 637 | CB | ILE | A | 230 | −30.396 | 54.600 | 7.004 | 1.00 | 31.07 | | C |
| ANISOU | 637 | CB | ILE | A | 230 | 4084 | 3504 | 4218 | 167 | 865 | −1252 | C |
| ATOM | 638 | CG1 | ILE | A | 230 | −30.119 | 53.114 | 6.857 | 1.00 | 34.74 | | C |

TABLE 6-continued

DMXAA-hSTING$^{group2}$ complex

| | | | | | | | | | | | |
|---|---|---|---|---|---|---|---|---|---|---|---|
| ANISOU | 638 | CG1 | ILE | A | 230 | 4553 | 4123 | 4523 | 115 | 744 | −1116 | C |
| ATOM | 639 | CD1 | ILE | A | 230 | −29.810 | 52.457 | 8.205 | 1.00 | 42.86 | | C |
| ANISOU | 639 | CD1 | ILE | A | 230 | 5646 | 5307 | 5332 | −35 | 789 | −1181 | C |
| ATOM | 640 | CG2 | ILE | A | 230 | −29.234 | 55.274 | 7.782 | 1.00 | 32.30 | | C |
| ANISOU | 640 | CG2 | ILE | A | 230 | 4358 | 3649 | 4263 | 44 | 897 | −1367 | C |
| ATOM | 641 | C | ILE | A | 230 | −31.911 | 56.298 | 7.931 | 1.00 | 39.52 | | C |
| ANISOU | 641 | C | ILE | A | 230 | 5074 | 4402 | 5540 | 244 | 1169 | −1529 | C |
| ATOM | 642 | O | ILE | A | 230 | −32.109 | 57.030 | 6.965 | 1.00 | 40.28 | | O |
| ANISOU | 642 | O | ILE | A | 230 | 5122 | 4340 | 5844 | 376 | 1140 | −1463 | O |
| ATOM | 643 | N | ASP | A | 231 | −31.871 | 56.734 | 9.191 | 1.00 | 38.78 | | N |
| ANISOU | 643 | N | ASP | A | 231 | 5039 | 4335 | 5361 | 135 | 1322 | −1729 | N |
| ATOM | 644 | CA | ASP | A | 231 | −31.930 | 58.145 | 9.521 | 1.00 | 38.69 | | C |
| ANISOU | 644 | CA | ASP | A | 231 | 5051 | 4145 | 5504 | 157 | 1474 | −1907 | C |
| ATOM | 645 | CB | ASP | A | 231 | −33.361 | 58.538 | 9.906 | 1.00 | 43.76 | | C |
| ANISOU | 645 | CB | ASP | A | 231 | 5574 | 4744 | 6308 | 243 | 1632 | −1990 | C |
| ATOM | 646 | CG | ASP | A | 231 | −33.661 | 59.998 | 9.592 | 1.00 | 76.54 | | C |
| ANISOU | 646 | CG | ASP | A | 231 | 9695 | 8673 | 10713 | 351 | 1690 | −2012 | C |
| ATOM | 647 | OD2 | ASP | A | 231 | −33.685 | 60.837 | 10.532 | 1.00 | 86.05 | | O |
| ANISOU | 647 | OD2 | ASP | A | 231 | 10945 | 9842 | 11908 | 275 | 1809 | −2160 | O |
| ATOM | 648 | OD1 | ASP | A | 231 | −33.874 | 60.301 | 8.395 | 1.00 | 88.58 | | O |
| ANISOU | 648 | OD1 | ASP | A | 231 | 11151 | 10063 | 12444 | 508 | 1611 | −1872 | O |
| ATOM | 649 | C | ASP | A | 231 | −30.962 | 58.462 | 10.669 | 1.00 | 54.88 | | C |
| ANISOU | 649 | C | ASP | A | 231 | 7238 | 6268 | 7344 | −35 | 1516 | −2056 | C |
| ATOM | 650 | O | ASP | A | 231 | −31.382 | 58.798 | 11.778 | 1.00 | 54.06 | | O |
| ANISOU | 650 | O | ASP | A | 231 | 7143 | 6220 | 7178 | −115 | 1635 | −2184 | O |
| ATOM | 651 | N | ARG | A | 232 | −29.666 | 58.360 | 10.385 | 1.00 | 50.25 | | N |
| ANISOU | 651 | N | ARG | A | 232 | 6745 | 5701 | 6647 | −112 | 1388 | −2001 | N |
| ATOM | 652 | CA | ARG | A | 232 | −28.629 | 58.666 | 11.356 | 1.00 | 50.55 | | C |
| ANISOU | 652 | CA | ARG | A | 232 | 6896 | 5823 | 6489 | −297 | 1385 | −2109 | C |
| ATOM | 653 | CB | ARG | A | 232 | −28.513 | 57.552 | 12.393 | 1.00 | 53.95 | | C |
| ANISOU | 653 | CB | ARG | A | 232 | 7362 | 6514 | 6625 | −442 | 1364 | −2117 | C |
| ATOM | 654 | CG | ARG | A | 232 | −27.882 | 56.281 | 11.846 | 1.00 | 52.47 | | C |
| ANISOU | 654 | CG | ARG | A | 232 | 7174 | 6457 | 6307 | −446 | 1173 | −1903 | C |
| ATOM | 655 | CD | ARG | A | 232 | −27.772 | 55.238 | 12.950 | 1.00 | 59.29 | | C |
| ANISOU | 655 | CD | ARG | A | 232 | 8077 | 7565 | 6887 | −591 | 1157 | −1893 | C |
| ATOM | 656 | NE | ARG | A | 232 | −27.302 | 53.946 | 12.452 | 1.00 | 63.91 | | N |
| ANISOU | 656 | NE | ARG | A | 232 | 8643 | 8256 | 7383 | −573 | 977 | −1658 | N |
| ATOM | 657 | CZ | ARG | A | 232 | −28.103 | 53.016 | 11.939 | 1.00 | 63.07 | | C |
| ANISOU | 657 | CZ | ARG | A | 232 | 8463 | 8166 | 7335 | −480 | 952 | −1524 | C |
| ATOM | 658 | NH1 | ARG | A | 232 | −29.412 | 53.247 | 11.854 | 1.00 | 60.46 | | N |
| ANISOU | 658 | NH1 | ARG | A | 232 | 8055 | 7768 | 7148 | −396 | 1084 | −1593 | N |
| ATOM | 659 | NH2 | ARG | A | 232 | −27.600 | 51.855 | 11.516 | 1.00 | 54.53 | | N |
| ANISOU | 659 | NH2 | ARG | A | 232 | 7375 | 7162 | 6180 | −474 | 800 | −1329 | N |
| ATOM | 660 | C | ARG | A | 232 | −27.309 | 58.791 | 10.610 | 1.00 | 49.47 | | C |
| ANISOU | 660 | C | ARG | A | 232 | 6820 | 5636 | 6340 | −325 | 1241 | −2022 | C |
| ATOM | 661 | O | ARG | A | 232 | −27.249 | 58.510 | 9.396 | 1.00 | 41.11 | | O |
| ANISOU | 661 | O | ARG | A | 232 | 5711 | 4514 | 5394 | −201 | 1120 | −1826 | O |
| ATOM | 662 | N | ALA | A | 233 | −26.255 | 59.173 | 11.342 | 1.00 | 48.73 | | N |
| ANISOU | 662 | N | ALA | A | 233 | 6811 | 5606 | 6098 | −489 | 1217 | −2109 | N |
| ATOM | 663 | CA | ALA | A | 233 | −24.918 | 59.411 | 10.776 | 1.00 | 52.66 | | C |
| ANISOU | 663 | CA | ALA | A | 233 | 7362 | 6063 | 6583 | −546 | 1098 | −2057 | C |
| ATOM | 664 | CB | ALA | A | 233 | −24.276 | 58.097 | 10.260 | 1.00 | 43.91 | | C |
| ANISOU | 664 | CB | ALA | A | 233 | 6226 | 5120 | 5337 | −537 | 898 | −1821 | C |
| ATOM | 665 | C | ALA | A | 233 | −24.964 | 60.438 | 9.651 | 1.00 | 44.36 | | C |
| ANISOU | 665 | C | ALA | A | 233 | 6294 | 4747 | 5816 | −416 | 1122 | −2016 | C |
| ATOM | 666 | O | ALA | A | 233 | −24.316 | 60.263 | 8.615 | 1.00 | 39.12 | | O |
| ANISOU | 666 | O | ALA | A | 233 | 5616 | 4048 | 5200 | −363 | 989 | −1837 | O |
| ATOM | 667 | N | GLY | A | 234 | −25.761 | 61.480 | 9.847 | 1.00 | 50.75 | | N |
| ANISOU | 667 | N | GLY | A | 234 | 7075 | 5404 | 6802 | −349 | 1254 | −2099 | N |
| ATOM | 668 | CA | GLY | A | 234 | −25.818 | 62.564 | 8.894 | 1.00 | 52.66 | | C |
| ANISOU | 668 | CA | GLY | A | 234 | 7304 | 5394 | 7310 | −233 | 1278 | −2045 | C |
| ATOM | 669 | C | GLY | A | 234 | −26.695 | 62.270 | 7.696 | 1.00 | 55.43 | | C |
| ANISOU | 669 | C | GLY | A | 234 | 7572 | 5640 | 7851 | −26 | 1252 | −1886 | C |
| ATOM | 670 | O | GLY | A | 234 | −27.012 | 63.172 | 6.925 | 1.00 | 58.34 | | O |
| ANISOU | 670 | O | GLY | A | 234 | 7911 | 5806 | 8449 | 95 | 1274 | −1812 | O |
| ATOM | 671 | N | ILE | A | 235 | −27.100 | 61.019 | 7.517 | 1.00 | 46.88 | | N |
| ANISOU | 671 | N | ILE | A | 235 | 6438 | 4717 | 6659 | 14 | 1178 | −1789 | N |
| ATOM | 672 | CA | ILE | A | 235 | −27.937 | 60.738 | 6.363 | 1.00 | 56.75 | | C |
| ANISOU | 672 | CA | ILE | A | 235 | 7588 | 5912 | 8064 | 200 | 1113 | −1597 | C |
| ATOM | 673 | CB | ILE | A | 235 | −27.490 | 59.504 | 5.548 | 1.00 | 62.57 | | C |
| ANISOU | 673 | CB | ILE | A | 235 | 8305 | 6810 | 8659 | 209 | 920 | −1381 | C |
| ATOM | 674 | CG1 | ILE | A | 235 | −27.630 | 58.225 | 6.340 | 1.00 | 54.36 | | C |
| ANISOU | 674 | CG1 | ILE | A | 235 | 7256 | 6002 | 7397 | 125 | 892 | −1398 | C |
| ATOM | 675 | CD1 | ILE | A | 235 | −26.913 | 57.078 | 5.675 | 1.00 | 60.49 | | C |
| ANISOU | 675 | CD1 | ILE | A | 235 | 8037 | 6912 | 8034 | 107 | 718 | −1217 | C |
| ATOM | 676 | CG2 | ILE | A | 235 | −26.040 | 59.676 | 5.099 | 1.00 | 61.11 | | C |
| ANISOU | 676 | CG2 | ILE | A | 235 | 8200 | 6613 | 8405 | 126 | 819 | −1314 | C |
| ATOM | 677 | C | ILE | A | 235 | −29.397 | 60.734 | 6.767 | 1.00 | 61.97 | | C |

TABLE 6-continued

DMXAA-hSTING[group2] complex

| | | | | | | | | | | | | |
|---|---|---|---|---|---|---|---|---|---|---|---|---|
| ANISOU | 677 | C | ILE | A | 235 | 8151 | 6559 | 8836 | 297 | 1241 | −1675 | C |
| ATOM | 678 | O | ILE | A | 235 | −29.803 | 60.244 | 7.835 | 1.00 | 56.45 | | O |
| ANISOU | 678 | O | ILE | A | 235 | 7449 | 5997 | 8002 | 216 | 1326 | −1808 | O |
| ATOM | 679 | N | LYS | A | 236 | −30.179 | 61.389 | 5.933 | 1.00 | 58.00 | | N |
| ANISOU | 679 | N | LYS | A | 236 | 7566 | 5879 | 8592 | 470 | 1265 | −1595 | N |
| ATOM | 680 | CA | LYS | A | 236 | −31.563 | 61.560 | 6.253 | 1.00 | 56.87 | | C |
| ANISOU | 680 | CA | LYS | A | 236 | 7306 | 5728 | 8575 | 569 | 1364 | −1633 | C |
| ATOM | 681 | CB | LYS | A | 236 | −31.974 | 63.015 | 6.093 | 1.00 | 56.19 | | C |
| ANISOU | 681 | CB | LYS | A | 236 | 7195 | 5435 | 8719 | 657 | 1437 | −1634 | C |
| ATOM | 682 | CG | LYS | A | 236 | −31.412 | 63.913 | 7.172 | 1.00 | 66.81 | | C |
| ANISOU | 682 | CG | LYS | A | 236 | 8641 | 6733 | 10010 | 516 | 1554 | −1825 | C |
| ATOM | 683 | CD | LYS | A | 236 | −32.445 | 64.920 | 7.609 | 1.00 | 70.51 | | C |
| ANISOU | 683 | CD | LYS | A | 236 | 9039 | 7080 | 10671 | 592 | 1698 | −1908 | C |
| ATOM | 684 | CE | LYS | A | 236 | −32.283 | 66.237 | 6.878 | 1.00 | 73.71 | | C |
| ANISOU | 684 | CE | LYS | A | 236 | 9457 | 7242 | 11306 | 682 | 1699 | −1830 | C |
| ATOM | 685 | NZ | LYS | A | 236 | −31.008 | 66.973 | 7.199 | 1.00 | 60.28 | | N |
| ANISOU | 685 | NZ | LYS | A | 236 | 7897 | 5465 | 9544 | 534 | 1715 | −1921 | N |
| ATOM | 686 | C | LYS | A | 236 | −32.347 | 60.673 | 5.320 | 1.00 | 51.03 | | C |
| ANISOU | 686 | C | LYS | A | 236 | 6441 | 5053 | 7894 | 702 | 1264 | −1462 | C |
| ATOM | 687 | O | LYS | A | 236 | −32.147 | 60.702 | 4.102 | 1.00 | 66.07 | | O |
| ANISOU | 687 | O | LYS | A | 236 | 8328 | 6909 | 9867 | 789 | 1122 | −1262 | O |
| ATOM | 688 | N | ASN | A | 237 | −33.181 | 59.844 | 5.925 | 1.00 | 43.83 | | N |
| ANISOU | 688 | N | ASN | A | 237 | 5451 | 4297 | 6903 | 684 | 1312 | −1515 | N |
| ATOM | 689 | CA | ASN | A | 237 | −34.173 | 59.071 | 5.221 | 1.00 | 50.87 | | C |
| ANISOU | 689 | CA | ASN | A | 237 | 6199 | 5278 | 7850 | 791 | 1226 | −1366 | C |
| ATOM | 690 | CB | ASN | A | 237 | −35.370 | 59.956 | 4.951 | 1.00 | 62.08 | | C |
| ANISOU | 690 | CB | ASN | A | 237 | 7474 | 6546 | 9569 | 964 | 1320 | −1370 | C |
| ATOM | 691 | CG | ASN | A | 237 | −35.874 | 60.609 | 6.213 | 1.00 | 76.21 | | C |
| ANISOU | 691 | CG | ASN | A | 237 | 9270 | 8322 | 11366 | 905 | 1503 | −1558 | C |
| ATOM | 692 | OD1 | ASN | A | 237 | −36.404 | 59.932 | 7.102 | 1.00 | 81.73 | | O |
| ANISOU | 692 | OD1 | ASN | A | 237 | 9933 | 9167 | 11954 | 830 | 1594 | −1667 | O |
| ATOM | 693 | ND2 | ASN | A | 237 | −35.673 | 61.923 | 6.330 | 1.00 | 77.96 | | N |
| ANISOU | 693 | ND2 | ASN | A | 237 | 9543 | 8369 | 11707 | 925 | 1564 | −1602 | N |
| ATOM | 694 | C | ASN | A | 237 | −33.667 | 58.433 | 3.944 | 1.00 | 48.25 | | C |
| ANISOU | 694 | C | ASN | A | 237 | 5877 | 5005 | 7451 | 817 | 1004 | −1135 | C |
| ATOM | 695 | O | ASN | A | 237 | −34.087 | 58.754 | 2.835 | 1.00 | 58.60 | | O |
| ANISOU | 695 | O | ASN | A | 237 | 7108 | 6238 | 8920 | 953 | 918 | −982 | O |
| ATOM | 696 | N | ARG | A | 238 | −32.727 | 57.533 | 4.101 | 1.00 | 29.46 | | N |
| ANISOU | 696 | N | ARG | A | 238 | 3599 | 2766 | 4829 | 683 | 916 | −1110 | N |
| ATOM | 697 | CA | ARG | A | 238 | −32.293 | 56.720 | 3.001 | 1.00 | 27.71 | | C |
| ANISOU | 697 | CA | ARG | A | 238 | 3383 | 2621 | 4525 | 694 | 728 | −918 | C |
| ATOM | 698 | CB | ARG | A | 238 | −30.811 | 56.514 | 3.080 | 1.00 | 31.28 | | C |
| ANISOU | 698 | CB | ARG | A | 238 | 3978 | 3100 | 4806 | 575 | 665 | −911 | C |
| ATOM | 699 | CG | ARG | A | 238 | −30.119 | 56.413 | 1.754 | 1.00 | 45.66 | | C |
| ANISOU | 699 | CG | ARG | A | 238 | 5823 | 4933 | 6593 | 603 | 504 | −729 | C |
| ATOM | 700 | CD | ARG | A | 238 | −28.621 | 56.449 | 1.919 | 1.00 | 35.81 | | C |
| ANISOU | 700 | CD | ARG | A | 238 | 4700 | 3689 | 5218 | 492 | 470 | −740 | C |
| ATOM | 701 | NE | ARG | A | 238 | −28.039 | 57.711 | 1.553 | 1.00 | 33.42 | | N |
| ANISOU | 701 | NE | ARG | A | 238 | 4448 | 3209 | 5042 | 517 | 505 | −745 | N |
| ATOM | 702 | CZ | ARG | A | 238 | −26.761 | 57.864 | 1.284 | 1.00 | 33.74 | | C |
| ANISOU | 702 | CZ | ARG | A | 238 | 4574 | 3234 | 5011 | 440 | 456 | −713 | C |
| ATOM | 703 | NH1 | ARG | A | 238 | −26.296 | 59.022 | 0.941 | 1.00 | 36.08 | | N |
| ANISOU | 703 | NH1 | ARG | A | 238 | 4917 | 3362 | 5430 | 451 | 491 | −707 | N |
| ATOM | 704 | NH2 | ARG | A | 238 | −25.959 | 56.855 | 1.380 | 1.00 | 24.24 | | N |
| ANISOU | 704 | NH2 | ARG | A | 238 | 3402 | 2182 | 3625 | 352 | 376 | −682 | N |
| ATOM | 705 | C | ARG | A | 238 | −32.979 | 55.392 | 3.149 | 1.00 | 32.56 | | C |
| ANISOU | 705 | C | ARG | A | 238 | 3925 | 3416 | 5031 | 660 | 692 | −891 | C |
| ATOM | 706 | O | ARG | A | 238 | −33.285 | 55.012 | 4.227 | 1.00 | 34.10 | | O |
| ANISOU | 706 | O | ARG | A | 238 | 4116 | 3692 | 5150 | 584 | 801 | −1016 | O |
| ATOM | 707 | N | VAL | A | 239 | −33.214 | 54.691 | 2.059 | 1.00 | 27.39 | | N |
| ANISOU | 707 | N | VAL | A | 239 | 3213 | 2825 | 4369 | 708 | 549 | −735 | N |
| ATOM | 708 | CA | VAL | A | 239 | −33.847 | 53.382 | 2.169 | 1.00 | 27.65 | | C |
| ANISOU | 708 | CA | VAL | A | 239 | 3180 | 3014 | 4311 | 662 | 515 | −713 | C |
| ATOM | 709 | CB | VAL | A | 239 | −35.220 | 53.338 | 1.521 | 1.00 | 36.43 | | C |
| ANISOU | 709 | CB | VAL | A | 239 | 4120 | 4141 | 5582 | 770 | 489 | −653 | C |
| ATOM | 710 | CG1 | VAL | A | 239 | −35.798 | 51.929 | 1.653 | 1.00 | 38.27 | | C |
| ANISOU | 710 | CG1 | VAL | A | 239 | 4293 | 4532 | 5715 | 695 | 458 | −640 | C |
| ATOM | 711 | CG2 | VAL | A | 239 | −36.140 | 54.349 | 2.152 | 1.00 | 33.68 | | C |
| ANISOU | 711 | CG2 | VAL | A | 239 | 3674 | 3698 | 5427 | 855 | 643 | −759 | C |
| ATOM | 712 | C | VAL | A | 239 | −32.944 | 52.388 | 1.482 | 1.00 | 28.59 | | C |
| ANISOU | 712 | C | VAL | A | 239 | 3378 | 3215 | 4272 | 598 | 372 | −603 | C |
| ATOM | 713 | O | VAL | A | 239 | −32.579 | 52.590 | 0.325 | 1.00 | 27.41 | | O |
| ANISOU | 713 | O | VAL | A | 239 | 3240 | 3027 | 4149 | 652 | 262 | −490 | O |
| ATOM | 714 | N | TYR | A | 240 | −32.538 | 51.330 | 2.207 | 1.00 | 22.82 | | N |
| ANISOU | 714 | N | TYR | A | 240 | 2703 | 2590 | 3376 | 482 | 380 | −633 | N |
| ATOM | 715 | CA | TYR | A | 240 | −31.687 | 50.296 | 1.614 | 1.00 | 23.45 | | C |
| ANISOU | 715 | CA | TYR | A | 240 | 2850 | 2734 | 3326 | 427 | 261 | −538 | C |
| ATOM | 716 | CB | TYR | A | 240 | −30.488 | 49.964 | 2.512 | 1.00 | 23.75 | | C |

TABLE 6-continued

| DMXAA-hSTING$^{group2}$ complex | | | | | | | | | | | |
|---|---|---|---|---|---|---|---|---|---|---|---|
| ANISOU | 716 | CB | TYR | A | 240 | 3005 | 2810 | 3210 | 319 | 279 | −573 | C |
| ATOM | 717 | CG | TYR | A | 240 | −29.448 | 51.069 | 2.615 | 1.00 | 25.40 | | C |
| ANISOU | 717 | CG | TYR | A | 240 | 3294 | 2933 | 3422 | 315 | 291 | −607 | C |
| ATOM | 718 | CD1 | TYR | A | 240 | −29.650 | 52.174 | 3.463 | 1.00 | 34.26 | | C |
| ANISOU | 718 | CD1 | TYR | A | 240 | 4425 | 3990 | 4601 | 311 | 409 | −733 | C |
| ATOM | 719 | CE1 | TYR | A | 240 | −28.689 | 53.181 | 3.548 | 1.00 | 34.44 | | C |
| ANISOU | 719 | CE1 | TYR | A | 240 | 4524 | 3926 | 4636 | 290 | 424 | −775 | C |
| ATOM | 720 | CZ | TYR | A | 240 | −27.524 | 53.079 | 2.760 | 1.00 | 28.77 | | C |
| ANISOU | 720 | CZ | TYR | A | 240 | 3862 | 3196 | 3873 | 277 | 318 | −678 | C |
| ATOM | 721 | OH | TYR | A | 240 | −26.537 | 54.046 | 2.799 | 1.00 | 29.68 | | O |
| ANISOU | 721 | OH | TYR | A | 240 | 4044 | 3228 | 4004 | 242 | 331 | −714 | O |
| ATOM | 722 | CE2 | TYR | A | 240 | −27.317 | 52.004 | 1.941 | 1.00 | 29.65 | | C |
| ANISOU | 722 | CE2 | TYR | A | 240 | 3961 | 3378 | 3927 | 289 | 212 | −557 | C |
| ATOM | 723 | CD2 | TYR | A | 240 | −28.284 | 50.998 | 1.872 | 1.00 | 24.89 | | C |
| ANISOU | 723 | CD2 | TYR | A | 240 | 3294 | 2852 | 3313 | 307 | 199 | −527 | C |
| ATOM | 724 | C | TYR | A | 240 | −32.477 | 49.011 | 1.412 | 1.00 | 26.68 | | C |
| ANISOU | 724 | C | TYR | A | 240 | 3189 | 3243 | 3707 | 398 | 225 | −499 | C |
| ATOM | 725 | O | TYR | A | 240 | −33.433 | 48.739 | 2.144 | 1.00 | 25.18 | | O |
| ANISOU | 725 | O | TYR | A | 240 | 2926 | 3100 | 3542 | 376 | 309 | −559 | O |
| ATOM | 726 | N | SER | A | 241 | −32.025 | 48.196 | 0.460 | 1.00 | 27.20 | | N |
| ANISOU | 726 | N | SER | A | 241 | 3281 | 3339 | 3716 | 385 | 112 | −409 | N |
| ATOM | 727 | CA | SER | A | 241 | −32.653 | 46.911 | 0.177 | 1.00 | 30.58 | | C |
| ANISOU | 727 | CA | SER | A | 241 | 3658 | 3846 | 4117 | 341 | 74 | −380 | C |
| ATOM | 728 | CB | SER | A | 241 | −33.281 | 46.920 | −1.212 | 1.00 | 31.87 | | C |
| ANISOU | 728 | CB | SER | A | 241 | 3740 | 4020 | 4350 | 403 | −28 | −316 | C |
| ATOM | 729 | OG | SER | A | 241 | −34.199 | 47.985 | −1.336 | 1.00 | 51.40 | | O |
| ANISOU | 729 | OG | SER | A | 241 | 6108 | 6462 | 6961 | 496 | −7 | −323 | O |
| ATOM | 730 | C | SER | A | 241 | −31.619 | 45.814 | 0.181 | 1.00 | 29.71 | | C |
| ANISOU | 730 | C | SER | A | 241 | 3645 | 3759 | 3884 | 264 | 31 | −341 | C |
| ATOM | 731 | O | SER | A | 241 | −30.433 | 46.081 | −0.060 | 1.00 | 26.33 | | O |
| ANISOU | 731 | O | SER | A | 241 | 3303 | 3294 | 3406 | 268 | −4 | −312 | O |
| ATOM | 732 | N | ASN | A | 242 | −32.060 | 44.570 | 0.404 | 1.00 | 21.69 | | N |
| ANISOU | 732 | N | ASN | A | 242 | 2610 | 2795 | 2837 | 196 | 38 | −335 | N |
| ATOM | 733 | CA | ASN | A | 242 | −31.138 | 43.438 | 0.208 | 1.00 | 20.43 | | C |
| ANISOU | 733 | CA | ASN | A | 242 | 2531 | 2634 | 2596 | 141 | −6 | −285 | C |
| ATOM | 734 | CB | ASN | A | 242 | −30.545 | 42.938 | 1.522 | 1.00 | 25.55 | | C |
| ANISOU | 734 | CB | ASN | A | 242 | 3247 | 3300 | 3161 | 70 | 53 | −279 | C |
| ATOM | 735 | CG | ASN | A | 242 | −29.729 | 43.996 | 2.224 | 1.00 | 34.55 | | C |
| ANISOU | 735 | CG | ASN | A | 242 | 4443 | 4431 | 4256 | 82 | 80 | −306 | C |
| ATOM | 736 | OD1 | ASN | A | 242 | −30.267 | 44.771 | 3.008 | 1.00 | 31.48 | | O |
| ANISOU | 736 | OD1 | ASN | A | 242 | 4028 | 4056 | 3875 | 79 | 157 | −374 | O |
| ATOM | 737 | ND2 | ASN | A | 242 | −28.420 | 44.060 | 1.920 | 1.00 | 25.65 | | N |
| ANISOU | 737 | ND2 | ASN | A | 242 | 3385 | 3277 | 3086 | 91 | 23 | −264 | N |
| ATOM | 738 | C | ASN | A | 242 | −31.906 | 42.336 | −0.462 | 1.00 | 26.18 | | C |
| ANISOU | 738 | C | ASN | A | 242 | 3206 | 3388 | 3353 | 103 | −40 | −275 | C |
| ATOM | 739 | O | ASN | A | 242 | −33.114 | 42.207 | −0.253 | 1.00 | 25.14 | | O |
| ANISOU | 739 | O | ASN | A | 242 | 2979 | 3296 | 3277 | 85 | −6 | −306 | O |
| ATOM | 740 | N | SER | A | 243 | −31.193 | 41.563 | −1.282 | 1.00 | 20.70 | | N |
| ANISOU | 740 | N | SER | A | 243 | 2568 | 2671 | 2627 | 87 | −100 | −241 | N |
| ATOM | 741 | CA | SER | A | 243 | −31.815 | 40.594 | −2.141 | 1.00 | 27.51 | | C |
| ANISOU | 741 | CA | SER | A | 243 | 3391 | 3549 | 3513 | 45 | −140 | −251 | C |
| ATOM | 742 | CB | SER | A | 243 | −31.215 | 40.694 | −3.538 | 1.00 | 29.13 | | C |
| ANISOU | 742 | CB | SER | A | 243 | 3632 | 3745 | 3691 | 77 | −222 | −240 | C |
| ATOM | 743 | OG | SER | A | 243 | −31.640 | 41.898 | −4.131 | 1.00 | 30.14 | | O |
| ANISOU | 743 | OG | SER | A | 243 | 3705 | 3903 | 3842147 | −270 | −229 | | O |
| ATOM | 744 | C | SER | A | 243 | −31.632 | 39.181 | −1.608 | 1.00 | 25.19 | | C |
| ANISOU | 744 | C | SER | A | 243 | 3141 | 3224 | 3206 | −39 | −98 | −240 | C |
| ATOM | 745 | O | SER | A | 243 | −30.565 | 38.827 | −1.132 | 1.00 | 20.41 | | O |
| ANISOU | 745 | O | SER | A | 243 | 2619 | 2574 | 2562 | −43 | −80 | −199 | O |
| ATOM | 746 | N | VAL | A | 244 | −32.672 | 38.363 | −1.796 | 1.00 | 21.22 | | N |
| ANISOU | 746 | N | VAL | A | 244 | 2574 | 2741 | 2747 | −107 | −90 | −270 | N |
| ATOM | 747 | CA | VAL | A | 244 | −32.644 | 36.958 | −1.403 | 1.00 | 22.25 | | C |
| ANISOU | 747 | CA | VAL | A | 244 | 2742 | 2820 | 2890 | −196 | −44 | −257 | C |
| ATOM | 748 | CB | VAL | A | 244 | −33.950 | 36.586 | −0.721 | 1.00 | 24.58 | | C |
| ANISOU | 748 | CB | VAL | A | 244 | 2949 | 3157 | 3232 | −272 | 17 | −278 | C |
| ATOM | 749 | CG1 | VAL | A | 244 | −33.926 | 35.109 | −0.342 | 1.00 | 23.73 | | C |
| ANISOU | 749 | CG1 | VAL | A | 244 | 2889 | 2979 | 3150 | −372 | 70 | −251 | C |
| ATOM | 750 | CG2 | VAL | A | 244 | −34.138 | 37.453 | 0.502 | 1.00 | 24.35 | | C |
| ANISOU | 750 | CG2 | VAL | A | 244 | 2901 | 3176 | 3177 | −245 | 86 | −264 | C |
| ATOM | 751 | C | VAL | A | 244 | −32.519 | 36.072 | −2.640 | 1.00 | 19.66 | | C |
| ANISOU | 751 | C | VAL | A | 244 | 2435 | 2453 | 2580 | −233 | −92 | −295 | C |
| ATOM | 752 | O | VAL | A | 244 | −33.279 | 36.219 | −3.595 | 1.00 | 21.30 | | O |
| ANISOU | 752 | O | VAL | A | 244 | 2574 | 2718 | 2801 | −249 | −149 | −348 | O |
| ATOM | 753 | N | TYR | A | 245 | −31.543 | 35.155 | −2.636 | 1.00 | 19.50 | | N |
| ANISOU | 753 | N | TYR | A | 245 | 2507 | 2339 | 2563 | −248 | −69 | −268 | N |
| ATOM | 754 | CA | TYR | A | 245 | −31.325 | 34.283 | −3.786 | 1.00 | 21.54 | | C |
| ANISOU | 754 | CA | TYR | A | 245 | 2798 | 2544 | 2841 | −287 | −90 | −327 | C |
| ATOM | 755 | CB | TYR | A | 245 | −29.903 | 34.467 | −4.296 | 1.00 | 22.35 | | C |

TABLE 6-continued

DMXAA-hSTING$^{group2}$ complex

| | | | | | | | | | | | |
|---|---|---|---|---|---|---|---|---|---|---|---|
| ANISOU | 755 | CB | TYR | A | 245 | 2982 | 2599 | 2910 | −213 | −105 | −308 | C |
| ATOM | 756 | CG | TYR | A | 245 | −29.661 | 35.834 | −4.853 | 1.00 | 20.09 | | C |
| ANISOU | 756 | CG | TYR | A | 245 | 2680 | 2396 | 2557 | −137 | −167 | −307 | C |
| ATOM | 757 | CD1 | TYR | A | 245 | −29.297 | 36.873 | −4.021 | 1.00 | 24.02 | | C |
| ANISOU | 757 | CD1 | TYR | A | 245 | 3175 | 2920 | 3030 | −72 | −165 | −246 | C |
| ATOM | 758 | CE1 | TYR | A | 245 | −29.087 | 38.121 | −4.512 | 1.00 | 23.57 | | C |
| ANISOU | 758 | CE1 | TYR | A | 245 | 3107 | 2913 | 2933 | −7 | −212 | −241 | C |
| ATOM | 759 | CZ | TYR | A | 245 | −29.243 | 38.363 | −5.876 | 1.00 | 27.94 | | C |
| ANISOU | 759 | CZ | TYR | A | 245 | 3653 | 3508 | 3454 | −2 | −270 | −276 | C |
| ATOM | 760 | OH | TYR | A | 245 | −29.016 | 39.636 | −6.356 | 1.00 | 30.92 | | O |
| ANISOU | 760 | OH | TYR | A | 245 | 4026 | 3926 | 3797 | 63 | −315 | −246 | O |
| ATOM | 761 | CE2 | TYR | A | 245 | −29.619 | 37.337 | −6.753 | 1.00 | 28.11 | | C |
| ANISOU | 761 | CE2 | TYR | A | 245 | 3677 | 3531 | 3474 | −74 | −282 | −340 | C |
| ATOM | 762 | CD2 | TYR | A | 245 | −29.845 | 36.088 | −6.224 | 1.00 | 22.22 | | C |
| ANISOU | 762 | CD2 | TYR | A | 245 | 2940 | 2719 | 2784 | −142 | −227 | −366 | C |
| ATOM | 763 | C | TYR | A | 245 | −31.476 | 32.827 | −3.383 | 1.00 | 23.87 | | C |
| ANISOU | 763 | C | TYR | A | 245 | 3124 | 2734 | 3210 | −376 | −22 | −325 | C |
| ATOM | 764 | O | TYR | A | 245 | −31.168 | 32.475 | −2.244 | 1.00 | 24.04 | | O |
| ANISOU | 764 | O | TYR | A | 245 | 3178 | 2704 | 3251 | −377 | 33 | −238 | O |
| ATOM | 765 | N | GLU | A | 246 | −31.907 | 31.984 | −4.328 | 1.00 | 22.81 | | N |
| ANISOU | 765 | N | GLU | A | 246 | 2986 | 2567 | 3114 | −457 | −26 | −417 | N |
| ATOM | 766 | CA | GLU | A | 246 | −31.921 | 30.529 | −4.156 | 1.00 | 22.71 | | C |
| ANISOU | 766 | CA | GLU | A | 246 | 3018 | 2415 | 3194 | −544 | 47 | −430 | C |
| ATOM | 767 | CB | GLU | A | 246 | −33.196 | 29.909 | −4.772 | 1.00 | 23.99 | | C |
| ANISOU | 767 | CB | GLU | A | 246 | 3115 | 2606 | 3396 | −679 | 41 | −541 | C |
| ATOM | 768 | CG | GLU | A | 246 | −34.442 | 30.468 | −4.113 | 1.00 | 3 | 1.00 | C |
| ANISOU | 768 | CG | GLU | A | 246 | 3887 | 3613 | 4280 | −715 | 30 | −519 | C |
| ATOM | 769 | CD | GLU | A | 246 | −35.755 | 29.880 | −4.614 | 1.00 | 49.61 | | C |
| ANISOU | 769 | CD | GLU | A | 246 | 6150 | 6014 | 6685 | −857 | 19 | −620 | C |
| ATOM | 770 | OE1 | GLU | A | 246 | −36.740 | 29.963 | −3.839 | 1.00 | 47.07 | | O |
| ANISOU | 770 | OE1 | GLU | A | 246 | 5735 | 5749 | 6401 | −907 | 52 | −592 | O |
| ATOM | 771 | OE2 | GLU | A | 246 | −35.800 | 29.347 | −5.750 | 1.00 | 51.49 | | O |
| ANISOU | 771 | OE2 | GLU | A | 246 | 6403 | 6239 | 6921 | −926 | −16 | −731 | O |
| ATOM | 772 | C | GLU | A | 246 | −30.689 | 29.934 | −4.807 | 1.00 | 28.55 | | C |
| ANISOU | 772 | C | GLU | A | 246 | 3851 | 3036 | 3961 | −504 | 71 | −452 | C |
| ATOM | 773 | O | GLU | A | 246 | −30.278 | 30.363 | −5.898 | 1.00 | 27.96 | | O |
| ANISOU | 773 | O | GLU | A | 246 | 3791 | 3007 | 3826 | −471 | 26 | −526 | O |
| ATOM | 774 | N | LEU | A | 247 | −30.102 | 28.930 | −4.149 | 1.00 | 23.76 | | N |
| ANISOU | 774 | N | LEU | A | 247 | 3304 | 2274 | 3450 | −505 | 146 | −384 | N |
| ATOM | 775 | CA | LEU | A | 247 | −28.939 | 28.242 | −4.686 | 1.00 | 24.67 | | C |
| ANISOU | 775 | CA | LEU | A | 247 | 3494 | 2249 | 3630 | −458 | 189 | −403 | C |
| ATOM | 776 | CB | LEU | A | 247 | −27.834 | 28.146 | −3.644 | 1.00 | 24.44 | | C |
| ANISOU | 776 | CB | LEU | A | 247 | 3500 | 2143 | 3643 | −360 | 214 | −241 | C |
| ATOM | 777 | CG | LEU | A | 247 | −27.530 | 29.467 | −2.968 | 1.00 | 32.33 | | C |
| ANISOU | 777 | CG | LEU | A | 247 | 4468 | 3289 | 4527 | −282 | 148 | −151 | C |
| ATOM | 778 | CD1 | LEU | A | 247 | −26.464 | 29.230 | −1.971 | 1.00 | 41.08 | | C |
| ANISOU | 778 | CD1 | LEU | A | 247 | 5605 | 4332 | 5671 | −209 | 161 | 4 | C |
| ATOM | 779 | CD2 | LEU | A | 247 | −27.029 | 30.420 | −4.025 | 1.00 | 35.98 | | C |
| ANISOU | 779 | CD2 | LEU | A | 247 | 4924 | 3839 | 4909 | −222 | 96 | −232 | C |
| ATOM | 780 | C | LEU | A | 247 | −29.392 | 26.842 | −5.050 | 1.00 | 32.38 | | C |
| ANISOU | 780 | C | LEU | A | 247 | 4501 | 3073 | 4729 | −569 | 265 | −489 | C |
| ATOM | 781 | O | LEU | A | 247 | −29.989 | 26.149 | −4.228 | 1.00 | 31.07 | | O |
| ANISOU | 781 | O | LEU | A | 247 | 4330 | 2834 | 4641 | −639 | 312 | −427 | O |
| ATOM | 782 | N | LEU | A | 248 | −29.106 | 26.418 | −6.286 | 1.00 | 25.92 | | N |
| ANISOU | 782 | N | LEU | A | 248 | 3719 | 2205 | 3925 | −597 | 287 | −638 | N |
| ATOM | 783 | CA | LEU | A | 248 | −29.552 | 25.102 | −6.744 | 1.00 | 27.72 | | C |
| ANISOU | 783 | CA | LEU | A | 248 | 3981 | 2280 | 4271 | −719 | 367 | −758 | C |
| ATOM | 784 | CB | LEU | A | 248 | −30.257 | 25.192 | −8.098 | 1.00 | 31.09 | | C |
| ANISOU | 784 | CB | LEU | A | 248 | 4391 | 2814 | 4607 | −831 | 326 | −962 | C |
| ATOM | 785 | CG | LEU | A | 248 | −31.263 | 26.318 | −8.311 | 1.00 | 47.71 | | C |
| ANISOU | 785 | CG | LEU | A | 248 | 6402 | 5163 | 6562 | −862 | 203 | −970 | C |
| ATOM | 786 | CD1 | LEU | A | 248 | −31.783 | 26.218 | −9.732 | 1.00 | 48.11 | | C |
| ANISOU | 786 | CD1 | LEU | A | 248 | 6447 | 5309 | 6525 | −976 | 158 | −1163 | C |
| ATOM | 787 | CD2 | LEU | A | 248 | −32.417 | 26.193 | −7.325 | 1.00 | 40.52 | | C |
| ANISOU | 787 | CD2 | LEU | A | 248 | 5415 | 4278 | 5701 | −937 | 199 | −900 | C |
| ATOM | 788 | C | LEU | A | 248 | −28.361 | 24.168 | −6.905 | 1.00 | 33.33 | | C |
| ANISOU | 788 | C | LEU | A | 248 | 4770 | 2770 | 5122 | −656 | 470 | −761 | C |
| ATOM | 789 | O | LEU | A | 248 | −27.233 | 24.605 | −7.187 | 1.00 | 36.91 | | O |
| ANISOU | 789 | O | LEU | A | 248 | 5242 | 3231 | 5549 | −535 | 468 | −739 | O |
| ATOM | 790 | N | GLU | A | 249 | −28.640 | 22.891 | −6.765 | 1.00 | 31.85 | | N |
| ANISOU | 790 | N | GLU | A | 249 | 4622 | 2383 | 5097 | −740 | 565 | −795 | N |
| ATOM | 791 | CA | GLU | A | 249 | −27.635 | 21.845 | −6.886 | 1.00 | 38.51 | | C |
| ANISOU | 791 | CA | GLU | A | 249 | 5534 | 2976 | 6124 | −683 | 682 | −801 | C |
| ATOM | 792 | CB | GLU | A | 249 | −27.110 | 21.539 | −5.496 | 1.00 | 37.38 | | C |
| ANISOU | 792 | CB | GLU | A | 249 | 5393 | 2716 | 6094 | −586 | 702 | −551 | C |
| ATOM | 793 | CG | GLU | A | 249 | −25.848 | 20.719 | −5.443 | 1.00 | 58.08 | | C |
| ANISOU | 793 | CG | GLU | A | 249 | 8057 | 5104 | 8908 | −467 | 796 | −489 | C |
| ATOM | 794 | CD | GLU | A | 249 | −25.417 | 20.442 | −4.002 | 1.00 | 68.73 | | C |

TABLE 6-continued

DMXAA-hSTING[group2] complex

| | | | | | | | | | | | | |
|---|---|---|---|---|---|---|---|---|---|---|---|---|
| ANISOU | 794 | CD | GLU | A | 249 | 9399 | 6366 | 10350 | −380 | 788 | −208 | C |
| ATOM | 795 | OE1 | GLU | A | 249 | −26.257 | 19.927 | −3.221 | 1.00 | 72.66 | | O |
| ANISOU | 795 | OE1 | GLU | A | 249 | 9907 | 6808 | 10891 | −475 | 804 | −116 | O |
| ATOM | 796 | OE2 | GLU | A | 249 | −24.253 | 20.764 | −3.650 | 1.00 | 65.39 | | O |
| ANISOU | 796 | OE2 | GLU | A | 249 | 8953 | 5948 | 9943 | −227 | 760 | −75 | O |
| ATOM | 797 | C | GLU | A | 249 | −28.379 | 20.644 | −7.440 | 1.00 | 45.56 | | C |
| ANISOU | 797 | C | GLU | A | 249 | 6466 | 3706 | 7137 | −847 | 775 | −973 | C |
| ATOM | 798 | O | GLU | A | 249 | −29.413 | 20.267 | −6.891 | 1.00 | 50.73 | | O |
| ANISOU | 798 | O | GLU | A | 249 | 7100 | 4346 | 7828 | −965 | 775 | −942 | O |
| ATOM | 799 | N | ASN | A | 250 | −27.881 | 20.058 | −8.539 | 1.00 | 45.94 | | N |
| ANISOU | 799 | N | ASN | A | 250 | 6570 | 3640 | 7244 | −867 | 861 | −1167 | N |
| ATOM | 800 | CA | ASN | A | 250 | −28.553 | 18.931 | −9.185 | 1.00 | 55.73 | | C |
| ANISOU | 800 | CA | ASN | A | 250 | 7843 | 4768 | 8563 | −1022 | 937 | −1346 | C |
| ATOM | 801 | CB | ASN | A | 250 | −28.425 | 17.654 | −8.343 | 1.00 | 62.11 | | C |
| ANISOU | 801 | CB | ASN | A | 250 | 8676 | 5331 | 9592 | −997 | 1029 | −1209 | C |
| ATOM | 802 | CG | ASN | A | 250 | −27.000 | 17.385 | −7.880 | 1.00 | 70.00 | | C |
| ANISOU | 802 | CG | ASN | A | 250 | 9694 | 6178 | 10725 | −795 | 1085 | −1051 | C |
| ATOM | 803 | OD1 | ASN | A | 250 | −26.028 | 17.772 | −8.536 | 1.00 | 71.45 | | O |
| ANISOU | 803 | OD1 | ASN | A | 250 | 9880 | 6399 | 10867 | −689 | 1097 | −1112 | O |
| ATOM | 804 | ND2 | ASN | A | 250 | −26.873 | 16.716 | −6.731 | 1.00 | 73.18 | | N |
| ANISOU | 804 | ND2 | ASN | A | 250 | 10101 | 6423 | 11282 | −745 | 1115 | −835 | N |
| ATOM | 805 | C | ASN | A | 250 | −30.042 | 19.183 | −9.435 | 1.00 | 56.24 | | C |
| ANISOU | 805 | C | ASN | A | 250 | 7859 | 4998 | 8510 | −1215 | 858 | −1455 | C |
| ATOM | 806 | O | ASN | A | 250 | −30.866 | 18.295 | −9.215 | 1.00 | 59.84 | | O |
| ANISOU | 806 | O | ASN | A | 250 | 8307 | 5377 | 9052 | −1334 | 892 | −1471 | O |
| ATOM | 807 | N | GLY | A | 251 | −30.381 | 20.402 | −9.844 | 1.00 | 52.77 | | N |
| ANISOU | 807 | N | GLY | A | 251 | 7365 | 4825 | 7861 | −1221 | 733 | −1488 | N |
| ATOM | 808 | CA | GLY | A | 251 | −31.746 | 20.723 | −10.222 | 1.00 | 53.96 | | C |
| ANISOU | 808 | CA | GLY | A | 251 | 7442 | 5173 | 7887 | −1384 | 635 | −1586 | C |
| ATOM | 809 | C | GLY | A | 251 | −32.710 | 21.053 | −9.092 | 1.00 | 66.52 | | C |
| ANISOU | 809 | C | GLY | A | 251 | 8942 | 6847 | 9484 | −1411 | 576 | −1422 | C |
| ATOM | 810 | O | GLY | A | 251 | −33.908 | 21.212 | −9.336 | 1.00 | 67.45 | | O |
| ANISOU | 810 | O | GLY | A | 251 | 8978 | 7114 | 9535 | −1550 | 507 | −1499 | O |
| ATOM | 811 | N | GLN | A | 252 | −32.213 | 21.154 | −7.857 | 1.00 | 60.21 | | N |
| ANISOU | 811 | N | GLN | A | 252 | 8151 | 5968 | 8760 | −1284 | 604 | −1198 | N |
| ATOM | 812 | CA | GLN | A | 252 | −33.083 | 21.373 | −6.694 | 1.00 | 48.70 | | C |
| ANISOU | 812 | CA | GLN | A | 252 | 6619 | 4575 | 7308 | −1318 | 579 | −1045 | C |
| ATOM | 813 | CB | GLN | A | 252 | −33.271 | 20.070 | −5.937 | 1.00 | 55.37 | | C |
| ANISOU | 813 | CB | GLN | A | 252 | 7512 | 5168 | 8358 | −1403 | 704 | −981 | C |
| ATOM | 814 | CG | GLN | A | 252 | −33.725 | 18.948 | −6.827 | 1.00 | 65.46 | | C |
| ANISOU | 814 | CG | GLN | A | 252 | 8828 | 6296 | 9749 | −1578 | 781 | −1198 | C |
| ATOM | 815 | CD | GLN | A | 252 | −34.827 | 18.177 | −6.198 | 1.00 | 86.42 | | C |
| ANISOU | 815 | CD | GLN | A | 252 | 11447 | 8873 | 12515 | −1748 | 838 | −1173 | C |
| ATOM | 816 | OE1 | GLN | A | 252 | −35.840 | 17.856 | −6.832 | 1.00 | 90.96 | | O |
| ANISOU | 816 | OE1 | GLN | A | 252 | 11964 | 9539 | 13057 | −1899 | 807 | −1323 | O |
| ATOM | 817 | NE2 | GLN | A | 252 | −34.652 | 17.874 | −4.924 | 1.00 | 96.23 | | N |
| ANISOU | 817 | NE2 | GLN | A | 252 | 12714 | 9993 | 13857 | −1699 | 900 | −948 | N |
| ATOM | 818 | C | GLN | A | 252 | −32.500 | 22.411 | −5.746 | 1.00 | 45.33 | | C |
| ANISOU | 818 | C | GLN | A | 252 | 6171 | 4254 | 6797 | −1147 | 523 | −836 | C |
| ATOM | 819 | O | GLN | A | 252 | −31.282 | 22.524 | −5.634 | 1.00 | 37.69 | | O |
| ANISOU | 819 | O | GLN | A | 252 | 5262 | 3213 | 5845 | −1004 | 540 | −758 | O |
| ATOM | 820 | N | ARG | A | 253 | −33.369 | 23.148 | −5.052 | 1.00 | 40.98 | | N |
| ANISOU | 820 | N | ARG | A | 253 | 5532 | 3874 | 6165 | −1167 | 465 | −755 | N |
| ATOM | 821 | CA | ARG | A | 253 | −32.894 | 24.207 | −4.172 | 1.00 | 41.24 | | C |
| ANISOU | 821 | CA | ARG | A | 253 | 5545 | 4021 | 6103 | −1024 | 415 | −588 | C |
| ATOM | 822 | CB | ARG | A | 253 | −34.024 | 25.098 | −3.664 | 1.00 | 35.88 | | C |
| ANISOU | 822 | CB | ARG | A | 253 | 4753 | 3546 | 5333 | −1061 | 359 | −560 | C |
| ATOM | 823 | CG | ARG | A | 253 | −33.483 | 26.346 | −2.958 | 1.00 | 31.49 | | C |
| ANISOU | 823 | CG | ARG | A | 253 | 4184 | 3117 | 4664 | −915 | 307 | −434 | C |
| ATOM | 824 | CD | ARG | A | 253 | −34.571 | 27.205 | −2.347 | 1.00 | 36.84 | | C |
| ANISOU | 824 | CD | ARG | A | 253 | 4751 | 3971 | 5276 | −941 | 281 | −411 | C |
| ATOM | 825 | NE | ARG | A | 253 | −35.447 | 26.375 | −1.544 | 1.00 | 45.19 | | N |
| ANISOU | 825 | NE | ARG | A | 253 | 5781 | 4974 | 6414 | −1069 | 366 | −370 | N |
| ATOM | 826 | CZ | ARG | A | 253 | −36.683 | 26.059 | −1.912 | 1.00 | 54.51 | | C |
| ANISOU | 826 | CZ | ARG | A | 253 | 6868 | 6204 | 7639 | −1206 | 372 | −472 | C |
| ATOM | 827 | NH1 | ARG | A | 253 | −37.180 | 26.538 | −3.051 | 1.00 | 50.43 | | N |
| ANISOU | 827 | NH1 | ARG | A | 253 | 6273 | 5805 | 7082 | −1223 | 281 | −609 | N |
| ATOM | 828 | NH2 | ARG | A | 253 | −37.418 | 25.271 | −1.145 | 1.00 | 56.92 | | N |
| ANISOU | 828 | NH2 | ARG | A | 253 | 7151 | 6449 | 8025 | −1331 | 463 | −427 | N |
| ATOM | 829 | C | ARG | A | 253 | −32.129 | 23.587 | −3.000 | 1.00 | 34.42 | | C |
| ANISOU | 829 | C | ARG | A | 253 | 4750 | 2991 | 5335 | −961 | 491 | −398 | C |
| ATOM | 830 | O | ARG | A | 253 | −32.591 | 22.638 | −2.368 | 1.00 | 39.52 | | O |
| ANISOU | 830 | O | ARG | A | 253 | 5414 | 3507 | 6094 | −1055 | 570 | −338 | O |
| ATOM | 831 | N | ALA | A | 254 | −30.947 | 24.103 | −2.740 | 1.00 | 34.10 | | N |
| ANISOU | 831 | N | ALA | A | 254 | 4746 | 2955 | 5254 | −809 | 462 | −297 | N |
| ATOM | 832 | CA | ALA | A | 254 | −30.088 | 23.540 | −1.708 | 1.00 | 41.66 | | C |
| ANISOU | 832 | CA | ALA | A | 254 | 5762 | 3772 | 6295 | −736 | 511 | −104 | C |
| ATOM | 833 | CB | ALA | A | 254 | −28.793 | 22.995 | −2.323 | 1.00 | 33.59 | | C |

TABLE 6-continued

DMXAA-hSTING$^{group2}$ complex

| | | | | | | | | | | | | |
|---|---|---|---|---|---|---|---|---|---|---|---|---|
| ANISOU | 833 | CB | ALA | A | 254 | 4800 | 2581 | 5380 | −635 | 544 | −120 | C |
| ATOM | 834 | C | ALA | A | 254 | −29.789 | 24.581 | −0.629 | 1.00 | 32.23 | | C |
| ANISOU | 834 | C | ALA | A | 254 | 4541 | 2737 | 4966 | −651 | 449 | 55 | C |
| ATOM | 835 | O | ALA | A | 254 | −29.318 | 24.257 | 0.449 | 1.00 | 31.77 | | O |
| ANISOU | 835 | O | ALA | A | 254 | 4516 | 2624 | 4932 | −616 | 468 | 239 | O |
| ATOM | 836 | N | GLY | A | 255 | −30.110 | 25.831 | −0.915 | 1.00 | 26.46 | | N |
| ANISOU | 836 | N | GLY | A | 255 | 3753 | 2208 | 4093 | −627 | 374 | −18 | N |
| ATOM | 837 | CA | GLY | A | 255 | −29.898 | 26.891 | 0.056 | 1.00 | 29.48 | | C |
| ANISOU | 837 | CA | GLY | A | 255 | 4112 | 2741 | 4347 | −561 | 327 | 94 | C |
| ATOM | 838 | C | GLY | A | 255 | −30.615 | 28.138 | −0.375 | 1.00 | 26.32 | | C |
| ANISOU | 838 | C | GLY | A | 255 | 3639 | 2530 | 3833 | −562 | 267 | −15 | C |
| ATOM | 839 | O | GLY | A | 255 | −31.012 | 28.283 | −1.535 | 1.00 | 25.81 | | O |
| ANISOU | 839 | O | GLY | A | 255 | 3543 | 2493 | 3770 | −585 | 237 | −158 | O |
| ATOM | 840 | N | THR | A | 256 | −30.772 | 29.064 | 0.573 | 1.00 | 23.65 | | N |
| ANISOU | 840 | N | THR | A | 256 | 3271 | 2322 | 3391 | −536 | 249 | 56 | N |
| ATOM | 841 | CA | THR | A | 256 | −31.410 | 30.344 | 0.301 | 1.00 | 22.76 | | C |
| ANISOU | 841 | CA | THR | A | 256 | 3084 | 2372 | 3191 | −516 | 202 | −29 | C |
| ATOM | 842 | CB | THR | A | 256 | −32.889 | 30.336 | 0.741 | 1.00 | 30.71 | | C |
| ANISOU | 842 | CB | THR | A | 256 | 4009 | 3455 | 4206 | −619 | 246 | −64 | C |
| ATOM | 843 | OG1 | THR | A | 256 | −33.585 | 29.233 | 0.152 | 1.00 | 33.73 | | O |
| ANISOU | 843 | OG1 | THR | A | 256 | 4375 | 3752 | 4690 | −727 | 279 | −129 | O |
| ATOM | 844 | CG2 | THR | A | 256 | −33.586 | 31.647 | 0.363 | 1.00 | 28.54 | | C |
| ANISOU | 844 | CG2 | THR | A | 256 | 3638 | 3332 | 3876 | −581 | 197 | −150 | C |
| ATOM | 845 | C | THR | A | 256 | −30.667 | 31.360 | 1.150 | 1.00 | 28.61 | | C |
| ANISOU | 845 | C | THR | A | 256 | 3844 | 3197 | 3831 | −432 | 176 | 52 | C |
| ATOM | 846 | O | THR | A | 256 | −30.492 | 31.139 | 2.357 | 1.00 | 27.63 | | O |
| ANISOU | 846 | O | THR | A | 256 | 3750 | 3077 | 3671 | −454 | 213 | 166 | O |
| ATOM | 847 | N | CYS | A | 257 | −30.229 | 32.465 | 0.554 | 1.00 | 23.84 | | N |
| ANISOU | 847 | N | CYS | A | 257 | 3225 | 2661 | 3172 | −349 | 114 | −1 | N |
| ATOM | 848 | CA | CYS | A | 257 | −29.446 | 33.420 | 1.335 | 1.00 | 21.24 | | C |
| ANISOU | 848 | CA | CYS | A | 257 | 2918 | 2400 | 2754 | −283 | 92 | 62 | C |
| ATOM | 849 | CB | CYS | A | 257 | −28.009 | 32.962 | 1.443 | 1.00 | 29.26 | | C |
| ANISOU | 849 | CB | CYS | A | 257 | 3998 | 3337 | 3781 | −228 | 70 | 152 | C |
| ATOM | 850 | SG | CYS | A | 257 | −27.290 | 32.878 | −0.152 | 1.00 | 47.49 | | S |
| ANISOU | 850 | SG | CYS | A | 257 | 6318 | 5576 | 6148 | −165 | 33 | 70 | S |
| ATOM | 851 | C | CYS | A | 257 | −29.497 | 34.828 | 0.785 | 1.00 | 26.04 | | C |
| ANISOU | 851 | C | CYS | A | 257 | 3486 | 3096 | 3313 | −220 | 44 | −16 | C |
| ATOM | 852 | O | CYS | A | 257 | −29.819 | 35.058 | −0.393 | 1.00 | 21.50 | | O |
| ANISOU | 852 | O | CYS | A | 257 | 2880 | 2525 | 2765 | −203 | 6 | −96 | O |
| ATOM | 853 | N | VAL | A | 258 | −29.160 | 35.764 | 1.659 | 1.00 | 20.23 | | N |
| ANISOU | 853 | N | VAL | A | 258 | 2757 | 2428 | 2500 | −192 | 45 | 14 | N |
| ATOM | 854 | CA | VAL | A | 258 | −28.966 | 37.158 | 1.272 | 1.00 | 23.24 | | C |
| ANISOU | 854 | CA | VAL | A | 258 | 3119 | 2865 | 2848 | −125 | 7 | −42 | C |
| ATOM | 855 | CB | VAL | A | 258 | −29.117 | 38.083 | 2.466 | 1.00 | 27.42 | | C |
| ANISOU | 855 | CB | VAL | A | 258 | 3643 | 3471 | 3304 | −134 | 45 | −44 | C |
| ATOM | 856 | CG1 | VAL | A | 258 | −29.060 | 39.550 | 2.003 | 1.00 | 28.03 | | C |
| ANISOU | 856 | CG1 | VAL | A | 258 | 3696 | 3576 | 3380 | −66 | 20 | −111 | C |
| ATOM | 857 | CG2 | VAL | A | 258 | −30.442 | 37.798 | 3.161 | 1.00 | 30.52 | | C |
| ANISOU | 857 | CG2 | VAL | A | 258 | 3985 | 3908 | 3705 | −204 | 121 | −67 | C |
| ATOM | 858 | C | VAL | A | 258 | −27.556 | 37.317 | 0.741 | 1.00 | 26.76 | | C |
| ANISOU | 858 | C | VAL | A | 258 | 3615 | 3271 | 3283 | −63 | −44 | −11 | C |
| ATOM | 859 | O | VAL | A | 258 | −26.611 | 37.090 | 1.464 | 1.00 | 24.60 | | O |
| ANISOU | 859 | O | VAL | A | 258 | 3381 | 2989 | 2977 | −60 | −48 | 64 | O |
| ATOM | 860 | N | LEU | A | 259 | −27.430 | 37.732 | −0.531 | 1.00 | 20.03 | | N |
| ANISOU | 860 | N | LEU | A | 259 | 2751 | 2406 | 2454 | −18 | −85 | −64 | N |
| ATOM | 861 | CA | LEU | A | 259 | −26.132 | 37.752 | −1.180 | 1.00 | 22.36 | | C |
| ANISOU | 861 | CA | LEU | A | 259 | 3087 | 2662 | 2749 | 31 | −116 | −44 | C |
| ATOM | 862 | CB | LEU | A | 259 | −26.194 | 36.757 | −2.345 | 1.00 | 24.21 | | C |
| ANISOU | 862 | CB | LEU | A | 259 | 3330 | 2835 | 3035 | 18 | −115 | −83 | C |
| ATOM | 863 | CG | LEU | A | 259 | −25.254 | 35.608 | −2.526 | 1.00 | 40.60 | | C |
| ANISOU | 863 | CG | LEU | A | 259 | 5445 | 4816 | 5164 | 25 | −91 | −51 | C |
| ATOM | 864 | CD1 | LEU | A | 259 | −24.920 | 34.948 | −1.220 | 1.00 | 37.34 | | C |
| ANISOU | 864 | CD1 | LEU | A | 259 | 5046 | 4369 | 4772 | 12 | −67 | 50 | C |
| ATOM | 865 | CD2 | LEU | A | 259 | −25.982 | 34.616 | −3.438 | 1.00 | 34.53 | | C |
| ANISOU | 865 | CD2 | LEU | A | 259 | 4678 | 3995 | 4447 | −28 | −69 | −129 | C |
| ATOM | 866 | C | LEU | A | 259 | −25.929 | 39.103 | −1.798 | 1.00 | 21.18 | | C |
| ANISOU | 866 | C | LEU | A | 259 | 2926 | 2550 | 2569 | 80 | −150 | −78 | C |
| ATOM | 867 | O | LEU | A | 259 | −26.867 | 39.673 | −2.367 | 1.00 | 22.04 | | O |
| ANISOU | 867 | O | LEU | A | 259 | 2996 | 2692 | 2685 | 87 | −166 | −125 | O |
| ATOM | 868 | N | GLU | A | 260 | −24.704 | 39.621 | −1.780 | 1.00 | 23.51 | | N |
| ANISOU | 868 | N | GLU | A | 260 | 3250 | 2840 | 2843 | 116 | −166 | −48 | N |
| ATOM | 869 | CA | GLU | A | 260 | −24.434 | 40.773 | −2.643 | 1.00 | 25.73 | | C |
| ANISOU | 869 | CA | GLU | A | 260 | 3531 | 3136 | 3111 | 157 | −192 | −73 | C |
| ATOM | 870 | CB | GLU | A | 260 | −25.032 | 42.055 | −2.061 | 1.00 | 25.76 | | C |
| ANISOU | 870 | CB | GLU | A | 260 | 3512 | 3172 | 3103 | 166 | −188 | −95 | C |
| ATOM | 871 | CG | GLU | A | 260 | −24.481 | 42.402 | −0.730 | 1.00 | 26.16 | | C |
| ANISOU | 871 | CG | GLU | A | 260 | 3579 | 3242 | 3118 | 143 | −167 | −80 | C |
| ATOM | 872 | CD | GLU | A | 260 | −25.329 | 43.511 | −0.074 | 1.00 | 46.27 | | C |

TABLE 6-continued

| DMXAA-hSTING$^{group2}$ complex | | | | | | | | | | | | |
|---|---|---|---|---|---|---|---|---|---|---|---|---|
| ANISOU | 872 | CD | GLU | A | 260 | 6104 | 5811 | 5666 | 141 | −133 | −133 | C |
| ATOM | 873 | OE1 | GLU | A | 260 | −26.576 | 43.404 | −0.112 | 1.00 | 39.73 | | O |
| ANISOU | 873 | OE1 | GLU | A | 260 | 5232 | 4994 | 4870 | 142 | −112 | −163 | O |
| ATOM | 874 | OE2 | GLU | A | 260 | −24.754 | 44.479 | 0.449 | 1.00 | 42.71 | | O |
| ANISOU | 874 | OE2 | GLU | A | 260 | 5673 | 5361 | 5193 | 137 | −123 | −153 | O |
| ATOM | 875 | C | GLU | A | 260 | −22.951 | 40.986 | −2.888 | 1.00 | 26.03 | | C |
| ANISOU | 875 | C | GLU | A | 260 | 3594 | 3155 | 3140 | 182 | −200 | −42 | C |
| ATOM | 876 | O | GLU | A | 260 | −22.122 | 40.583 | −2.102 | 1.00 | 22.38 | | O |
| ANISOU | 876 | O | GLU | A | 260 | 3137 | 2688 | 2679 | 175 | −197 | 4 | O |
| ATOM | 877 | N | TYR | A | 261 | −22.624 | 41.632 | −3.993 | 1.00 | 25.36 | | N |
| ANISOU | 877 | N | TYR | A | 261 | 3519 | 3071 | 3047 | 208 | −214 | −56 | N |
| ATOM | 878 | CA | TYR | A | 261 | −21.214 | 41.968 | −4.227 | 1.00 | 22.95 | | C |
| ANISOU | 878 | CA | TYR | A | 261 | 3226 | 2755 | 2739 | 224 | −210 | −29 | C |
| ATOM | 879 | CB | TYR | A | 261 | −20.993 | 42.352 | −5.678 | 1.00 | 20.10 | | C |
| ANISOU | 879 | CB | TYR | A | 261 | 2883 | 2396 | 2359 | 239 | −210 | −44 | C |
| ATOM | 880 | CG | TYR | A | 261 | −21.076 | 41.195 | −6.634 | 1.00 | 23.37 | | C |
| ANISOU | 880 | CG | TYR | A | 261 | 3309 | 2797 | 2773 | 231 | −190 | −79 | C |
| ATOM | 881 | CD1 | TYR | A | 261 | −20.113 | 40.202 | −6.623 | 1.00 | 24.12 | | C |
| ANISOU | 881 | CD1 | TYR | A | 261 | 3404 | 2851 | 2910 | 239 | −149 | −79 | C |
| ATOM | 882 | CE1 | TYR | A | 261 | −20.179 | 39.131 | −7.508 | 1.00 | 21.52 | | C |
| ANISOU | 882 | CE1 | TYR | A | 261 | 3092 | 2491 | 2592 | 226 | −112 | −134 | C |
| ATOM | 883 | CZ | TYR | A | 261 | −21.227 | 39.070 | −8.413 | 1.00 | 25.94 | | C |
| ANISOU | 883 | CZ | TYR | A | 261 | 3672 | 3086 | 3098 | 191 | −130 | −191 | C |
| ATOM | 884 | OH | TYR | A | 261 | −21.305 | 38.024 | −9.287 | 1.00 | 28.34 | | O |
| ANISOU | 884 | OH | TYR | A | 261 | 4001 | 3366 | 3401 | 159 | −90 | −269 | O |
| ATOM | 885 | CE2 | TYR | A | 261 | −22.197 | 40.039 | −8.445 | 1.00 | 27.78 | | C |
| ANISOU | 885 | CE2 | TYR | A | 261 | 3895 | 3378 | 3283 | 186 | −190 | −174 | C |
| ATOM | 886 | CD2 | TYR | A | 261 | −22.117 | 41.111 | −7.559 | 1.00 | 30.51 | | C |
| ANISOU | 886 | CD2 | TYR | A | 261 | 4221 | 3731 | 3640 | 214 | −212 | −117 | C |
| ATOM | 887 | C | TYR | A | 261 | −20.804 | 43.135 | −3.346 | 1.00 | 24.77 | | C |
| ANISOU | 887 | C | TYR | A | 261 | 3452 | 3003 | 2955 | 217 | −218 | −17 | C |
| ATOM | 888 | O | TYR | A | 261 | −21.569 | 44.050 | −3.102 | 1.00 | 22.54 | | O |
| ANISOU | 888 | O | TYR | A | 261 | 3169 | 2726 | 2668 | 217 | −219 | −41 | O |
| ATOM | 889 | N | ALA | A | 262 | −19.558 | 43.108 | −2.881 | 1.00 | 24.80 | | N |
| ANISOU | 889 | N | ALA | A | 262 | 3448 | 3015 | 2962 | 209 | −221 | 16 | N |
| ATOM | 890 | CA | ALA | A | 262 | −18.990 | 44.245 | −2.199 | 1.00 | 21.10 | | C |
| ANISOU | 890 | CA | ALA | A | 262 | 2976 | 2566 | 2474 | 183 | −230 | 13 | C |
| ATOM | 891 | CB | ALA | A | 262 | −17.694 | 43.849 | −1.540 | 1.00 | 22.62 | | C |
| ANISOU | 891 | CB | ALA | A | 262 | 3137 | 2790 | 2667 | 165 | −250 | 59 | C |
| ATOM | 892 | C | ALA | A | 262 | −18.756 | 45.394 | −3.183 | 1.00 | 26.11 | | C |
| ANISOU | 892 | C | ALA | A | 262 | 3626 | 3173 | 3121 | 194 | −219 | −1 | C |
| ATOM | 893 | O | ALA | A | 262 | −17.934 | 45.313 | −4.114 | 1.00 | 23.10 | | O |
| ANISOU | 893 | O | ALA | A | 262 | 3242 | 2784 | 2751 | 206 | −208 | 19 | O |
| ATOM | 894 | N | THR | A | 263 | −19.430 | 46.515 | −2.945 | 1.00 | 22.72 | | N |
| ANISOU | 894 | N | THR | A | 263 | 3212 | 2724 | 2695 | 189 | −212 | −33 | N |
| ATOM | 895 | CA | THR | A | 263 | −19.363 | 47.633 | −3.882 | 1.00 | 20.75 | | C |
| ANISOU | 895 | CA | THR | A | 263 | 2983 | 2429 | 2470 | 205 | −201 | −24 | C |
| ATOM | 896 | CB | THR | A | 263 | −20.320 | 48.754 | −3.439 | 1.00 | 20.95 | | C |
| ANISOU | 896 | CB | THR | A | 263 | 3018 | 2410 | 2531 | 215 | −186 | −60 | C |
| ATOM | 897 | OG1 | THR | A | 263 | −20.009 | 49.119 | −2.086 | 1.00 | 24.23 | | O |
| ANISOU | 897 | OG1 | THR | A | 263 | 3433 | 2836 | 2937 | 162 | −168 | −113 | O |
| ATOM | 898 | CG2 | THR | A | 263 | −21.780 | 48.259 | −3.504 | 1.00 | 23.24 | | C |
| ANISOU | 898 | CG2 | THR | A | 263 | 3287 | 2714 | 2830 | 254 | −194 | −70 | C |
| ATOM | 899 | C | THR | A | 263 | −17.986 | 48.257 | −4.137 | 1.00 | 20.82 | | C |
| ANISOU | 899 | C | THR | A | 263 | 2994 | 2428 | 2489 | 172 | −189 | −5 | C |
| ATOM | 900 | O | THR | A | 263 | −17.764 | 48.807 | −5.239 | 1.00 | 22.55 | | O |
| ANISOU | 900 | O | THR | A | 263 | 3234 | 2618 | 2717 | 184 | −175 | 29 | O |
| ATOM | 901 | N | PRO | A | 264 | −17.079 | 48.233 | −3.148 | 1.00 | 18.55 | | N |
| ANISOU | 901 | N | PRO | A | 264 | 2683 | 2172 | 2194 | 123 | −196 | −19 | N |
| ATOM | 902 | CA | PRO | A | 264 | −15.811 | 48.908 | −3.478 | 1.00 | 18.56 | | C |
| ANISOU | 902 | CA | PRO | A | 264 | 2671 | 2166 | 2217 | 84 | −183 | −3 | C |
| ATOM | 903 | CB | PRO | A | 264 | −15.021 | 48.852 | −2.174 | 1.00 | 21.66 | | C |
| ANISOU | 903 | CB | PRO | A | 264 | 3024 | 2616 | 2591 | 21 | −212 | −25 | C |
| ATOM | 904 | CG | PRO | A | 264 | −16.128 | 48.852 | −1.075 | 1.00 | 19.83 | | C |
| ANISOU | 904 | CG | PRO | A | 264 | 2819 | 2395 | 2321 | 12 | −220 | −75 | C |
| ATOM | 905 | CD | PRO | A | 264 | −17.192 | 47.966 | −1.690 | 1.00 | 20.43 | | C |
| ANISOU | 905 | CD | PRO | A | 264 | 2907 | 2456 | 2399 | 85 | −215 | −50 | C |
| ATOM | 906 | C | PRO | A | 264 | −15.024 | 48.214 | −4.584 | 1.00 | 21.01 | | C |
| ANISOU | 906 | C | PRO | A | 264 | 2958 | 2493 | 2532 | 108 | −166 | 43 | C |
| ATOM | 907 | O | PRO | A | 264 | −14.119 | 48.810 | −5.162 | 1.00 | 20.72 | | O |
| ANISOU | 907 | O | PRO | A | 264 | 2912 | 2446 | 2516 | 79 | −138 | 61 | O |
| ATOM | 908 | N | LEU | A | 265 | −15.358 | 46.976 | −4.887 | 1.00 | 19.28 | | N |
| ANISOU | 908 | N | LEU | A | 265 | 2731 | 2294 | 2300 | 152 | −171 | 53 | N |
| ATOM | 909 | CA | LEU | A | 265 | −14.728 | 46.348 | −6.054 | 1.00 | 20.19 | | C |
| ANISOU | 909 | CA | LEU | A | 265 | 2834 | 2416 | 2420 | 174 | −133 | 72 | C |
| ATOM | 910 | CB | LEU | A | 265 | −15.088 | 44.853 | −6.132 | 1.00 | 23.60 | | C |
| ANISOU | 910 | CB | LEU | A | 265 | 3257 | 2853 | 2857 | 215 | −131 | 63 | C |
| ATOM | 911 | CG | LEU | A | 265 | −14.629 | 44.051 | −4.909 | 1.00 | 28.28 | | C |

TABLE 6-continued

DMXAA-hSTING$^{group2}$ complex

| | | | | | | | | | | | | |
|---|---|---|---|---|---|---|---|---|---|---|---|---|
| ANISOU | 911 | CG | LEU | A | 265 | 3797 | 3463 | 3486 | 220 | −161 | 85 | C |
| ATOM | 912 | CD1 | LEU | A | 265 | −15.138 | 42.638 | −5.021 | 1.00 | 28.89 | | C |
| ANISOU | 912 | CD1 | LEU | A | 265 | 3878 | 3514 | 3585 | 258 | −150 | 82 | C |
| ATOM | 913 | CD2 | LEU | A | 265 | −13.110 | 43.994 | −4.758 | 1.00 | 32.78 | | C |
| ANISOU | 913 | CD2 | LEU | A | 265 | 4289 | 4058 | 4107 | 214 | −152 | 119 | C |
| ATOM | 914 | C | LEU | A | 265 | −15.103 | 47.054 | −7.342 | 1.00 | 24.01 | | C |
| ANISOU | 914 | C | LEU | A | 265 | 3371 | 2879 | 2871 | 176 | −105 | 83 | C |
| ATOM | 915 | O | LEU | A | 265 | −14.342 | 47.023 | −8.328 | 1.00 | 22.26 | | O |
| ANISOU | 915 | O | LEU | A | 265 | 3148 | 2671 | 2639 | 167 | −57 | 98 | O |
| ATOM | 916 | N | GLN | A | 266 | −16.293 | 47.668 | −7.396 | 1.00 | 18.89 | | N |
| ANISOU | 916 | N | GLN | A | 266 | 2766 | 2206 | 2207 | 190 | −132 | 85 | N |
| ATOM | 917 | CA | GLN | A | 266 | −16.656 | 48.442 | −8.587 | 1.00 | 19.73 | | C |
| ANISOU | 917 | CA | GLN | A | 266 | 2918 | 2297 | 2281 | 195 | −124 | 127 | C |
| ATOM | 918 | CB | GLN | A | 266 | −18.130 | 48.897 | −8.513 | 1.00 | 27.88 | | C |
| ANISOU | 918 | CB | GLN | A | 266 | 3970 | 3305 | 3317 | 231 | −169 | 135 | C |
| ATOM | 919 | CG | GLN | A | 266 | −19.079 | 47.726 | −8.335 | 1.00 | 31.19 | | C |
| ANISOU | 919 | CG | GLN | A | 266 | 4372 | 3765 | 3715 | 255 | −199 | 96 | C |
| ATOM | 920 | CD | GLN | A | 266 | −20.531 | 48.157 | −8.207 | 1.00 | 36.84 | | C |
| ANISOU | 920 | CD | GLN | A | 266 | 5080 | 4467 | 4450 | 290 | −240 | 102 | C |
| ATOM | 921 | OE1 | GLN | A | 266 | −20.989 | 49.073 | −8.886 | 1.00 | 39.49 | | O |
| ANISOU | 921 | OE1 | GLN | A | 266 | 5431 | 4783 | 4791 | 314 | −260 | 159 | O |
| ATOM | 922 | NE2 | GLN | A | 266 | −21.252 | 47.491 | −7.324 | 1.00 | 53.37 | | N |
| ANISOU | 922 | NE2 | GLN | A | 266 | 7143 | 6574 | 6563 | 296 | −251 | 55 | N |
| ATOM | 923 | C | GLN | A | 266 | −15.799 | 49.683 | −8.714 | 1.00 | 20.57 | | C |
| ANISOU | 923 | C | GLN | A | 266 | 3035 | 2363 | 2418 | 155 | −91 | 163 | C |
| ATOM | 924 | O | GLN | A | 266 | −15.507 | 50.169 | −9.822 | 1.00 | 20.87 | | O |
| ANISOU | 924 | O | GLN | A | 266 | 3106 | 2400 | 2423 | 141 | −62 | 217 | O |
| ATOM | 925 | N | THR | A | 267 | −15.422 | 50.238 | −7.579 | 1.00 | 19.79 | | N |
| ANISOU | 925 | N | THR | A | 267 | 2914 | 2233 | 2374 | 124 | −94 | 134 | N |
| ATOM | 926 | CA | THR | A | 267 | −14.516 | 51.374 | −7.587 | 1.00 | 18.48 | | C |
| ANISOU | 926 | CA | THR | A | 267 | 2751 | 2022 | 2250 | 66 | −59 | 152 | C |
| ATOM | 927 | CB | THR | A | 267 | −14.418 | 52.066 | −6.199 | 1.00 | 22.79 | | C |
| ANISOU | 927 | CB | THR | A | 267 | 3282 | 2531 | 2847 | 20 | −71 | 91 | C |
| ATOM | 928 | OG1 | THR | A | 267 | −15.681 | 52.681 | −5.921 | 1.00 | 20.99 | | O |
| ANISOU | 928 | OG1 | THR | A | 267 | 3095 | 2235 | 2645 | 58 | −80 | 76 | O |
| ATOM | 929 | CG2 | THR | A | 267 | −13.391 | 53.195 | −6.248 | 1.00 | 18.35 | | C |
| ANISOU | 929 | CG2 | THR | A | 267 | 2719 | 1918 | 2335 | −61 | −30 | 97 | C |
| ATOM | 930 | C | THR | A | 267 | −13.124 | 50.960 | −8.042 | 1.00 | 19.03 | | C |
| ANISOU | 930 | C | THR | A | 267 | 2774 | 2142 | 2313 | 27 | −18 | 164 | C |
| ATOM | 931 | O | THR | A | 267 | −12.509 | 51.639 | −8.887 | 1.00 | 22.68 | | O |
| ANISOU | 931 | O | THR | A | 267 | 3253 | 2586 | 2778 | −11 | 32 | 210 | O |
| ATOM | 932 | N | LEU | A | 268 | −12.611 | 49.854 | −7.525 | 1.00 | 17.28 | | N |
| ANISOU | 932 | N | LEU | A | 268 | 2490 | 1984 | 2093 | 38 | −31 | 134 | N |
| ATOM | 933 | CA | LEU | A | 268 | −11.289 | 49.389 | −8.016 | 1.00 | 17.76 | | C |
| ANISOU | 933 | CA | LEU | A | 268 | 2485 | 2091 | 2172 | 17 | 19 | 146 | C |
| ATOM | 934 | CB | LEU | A | 268 | −10.863 | 48.111 | −7.301 | 1.00 | 24.15 | | C |
| ANISOU | 934 | CB | LEU | A | 268 | 3217 | 2951 | 3010 | 52 | −7 | 126 | C |
| ATOM | 935 | CG | LEU | A | 268 | −10.521 | 48.300 | −5.828 | 1.00 | 25.93 | | C |
| ANISOU | 935 | CG | LEU | A | 268 | 3387 | 3201 | 3264 | 15 | −72 | 115 | C |
| ATOM | 936 | CD1 | LEU | A | 268 | −10.199 | 46.937 | −5.231 | 1.00 | 24.89 | | C |
| ANISOU | 936 | CD1 | LEU | A | 268 | 3184 | 3117 | 3158 | 63 | −105 | 131 | C |
| ATOM | 937 | CD2 | LEU | A | 268 | −9.289 | 49.192 | −5.715 | 1.00 | 29.21 | | C |
| ANISOU | 937 | CD2 | LEU | A | 268 | 3740 | 3635 | 3722 | −67 | −54 | 119 | C |
| ATOM | 938 | C | LEU | A | 268 | −11.307 | 49.127 | −9.522 | 1.00 | 20.11 | | C |
| ANISOU | 938 | C | LEU | A | 268 | 2823 | 2402 | 2417 | 35 | 83 | 171 | C |
| ATOM | 939 | O | LEU | A | 268 | −10.358 | 49.461 | −10.250 | 1.00 | 20.70 | | O |
| ANISOU | 939 | O | LEU | A | 268 | 2877 | 2491 | 2495 | −7 | 153 | 193 | O |
| ATOM | 940 | N | PHE | A | 269 | −12.383 | 48.537 | −9.998 | 1.00 | 18.55 | | N |
| ANISOU | 940 | N | PHE | A | 269 | 2680 | 2208 | 2161 | 83 | 63 | 163 | N |
| ATOM | 941 | CA | PHE | A | 269 | −12.519 | 48.282 | −11.440 | 1.00 | 21.81 | | C |
| ANISOU | 941 | CA | PHE | A | 269 | 3142 | 2654 | 2492 | 84 | 113 | 176 | C |
| ATOM | 942 | CB | PHE | A | 269 | −13.819 | 47.485 | −11.692 | 1.00 | 23.92 | | C |
| ANISOU | 942 | CB | PHE | A | 269 | 3453 | 2936 | 2700 | 128 | 65 | 148 | C |
| ATOM | 943 | CG | PHE | A | 269 | −14.066 | 47.254 | −13.165 | 1.00 | 35.27 | | C |
| ANISOU | 943 | CG | PHE | A | 269 | 4949 | 4428 | 4024 | 111 | 102 | 153 | C |
| ATOM | 944 | CD1 | PHE | A | 269 | −13.336 | 46.303 | −13.839 | 1.00 | 34.51 | | C |
| ANISOU | 944 | CD1 | PHE | A | 269 | 4838 | 4373 | 3902 | 100 | 186 | 94 | C |
| ATOM | 945 | CE1 | PHE | A | 269 | −13.544 | 46.071 | −15.211 | 1.00 | 39.02 | | C |
| ANISOU | 945 | CE1 | PHE | A | 269 | 5472 | 5012 | 4342 | 66 | 229 | 79 | C |
| ATOM | 946 | CZ | PHE | A | 269 | −14.470 | 46.823 | −15.892 | 1.00 | 35.95 | | C |
| ANISOU | 946 | CZ | PHE | A | 269 | 5154 | 4659 | 3847 | 47 | 167 | 151 | C |
| ATOM | 947 | CE2 | PHE | A | 269 | −15.208 | 47.801 | −15.223 | 1.00 | 50.29 | | C |
| ANISOU | 947 | CE2 | PHE | A | 269 | 6972 | 6421 | 5713 | 75 | 75 | 230 | C |
| ATOM | 948 | CD2 | PHE | A | 269 | −15.002 | 48.011 | −13.857 | 1.00 | 42.44 | | C |
| ANISOU | 948 | CD2 | PHE | A | 269 | 5921 | 5350 | 4853 | 105 | 53 | 218 | C |
| ATOM | 949 | C | PHE | A | 269 | −12.525 | 49.605 | −12.210 | 1.00 | 20.57 | | C |
| ANISOU | 949 | C | PHE | A | 269 | 3044 | 2475 | 2297 | 41 | 133 | 252 | C |
| ATOM | 950 | O | PHE | A | 269 | −11.804 | 49.793 | −13.214 | 1.00 | 19.82 | | O |

TABLE 6-continued

| | | | | | | | | | | | | |
|---|---|---|---|---|---|---|---|---|---|---|---|---|
| ANISOU | 950 | O | PHE | A | 269 | 2963 | 2414 | 2155 | −1 | 209 | 281 | O |
| ATOM | 951 | N | ALA | A | 270 | −13.319 | 50.562 | −11.779 | 1.00 | 21.86 | | N |
| ANISOU | 951 | N | ALA | A | 270 | 3244 | 2577 | 2486 | 49 | 77 | 291 | N |
| ATOM | 952 | CA | ALA | A | 270 | −13.330 | 51.861 | −12.475 | 1.00 | 22.59 | | C |
| ANISOU | 952 | CA | ALA | A | 270 | 3394 | 2622 | 2568 | 15 | 97 | 383 | C |
| ATOM | 953 | CB | ALA | A | 270 | −14.408 | 52.798 | −11.892 | 1.00 | 25.08 | | C |
| ANISOU | 953 | CB | ALA | A | 270 | 3741 | 2846 | 2944 | 50 | 35 | 415 | C |
| ATOM | 954 | C | ALA | A | 270 | −11.963 | 52.552 | −12.447 | 1.00 | 24.08 | | C |
| ANISOU | 954 | C | ALA | A | 270 | 3552 | 2786 | 2810 | −62 | 172 | 400 | C |
| ATOM | 955 | O | ALA | A | 270 | −11.532 | 53.125 | −13.440 | 1.00 | 25.67 | | O |
| ANISOU | 955 | O | ALA | A | 270 | 3792 | 2991 | 2970 | −108 | 230 | 474 | O |
| ATOM | 956 | N | MET | A | 271 | −11.269 | 52.526 | −11.308 | 1.00 | 21.47 | | N |
| ANISOU | 956 | N | MET | A | 271 | 3150 | 2442 | 2567 | −87 | 168 | 336 | N |
| ATOM | 957 | CA | MET | A | 271 | −9.940 | 53.165 | −11.249 | 1.00 | 24.68 | | C |
| ANISOU | 957 | CA | MET | A | 271 | 3507 | 2837 | 3032 | −174 | 233 | 344 | C |
| ATOM | 958 | CB | MET | A | 271 | −9.339 | 53.026 | −9.841 | 1.00 | 25.82 | | C |
| ANISOU | 958 | CB | MET | A | 271 | 3561 | 2991 | 3257 | −202 | 195 | 269 | C |
| ATOM | 959 | CG | MET | A | 271 | −10.162 | 53.827 | −8.799 | 1.00 | 28.30 | | C |
| ANISOU | 959 | CG | MET | A | 271 | 3918 | 3221 | 3613 | −206 | 135 | 237 | C |
| ATOM | 960 | SD | MET | A | 271 | −9.551 | 53.567 | −7.101 | 1.00 | 27.06 | | S |
| ANISOU | 960 | SD | MET | A | 271 | 3668 | 3114 | 3501 | −255 | 76 | 143 | S |
| ATOM | 961 | CE | MET | A | 271 | −7.959 | 54.385 | −7.235 | 1.00 | 25.30 | | C |
| ANISOU | 961 | CE | MET | A | 271 | 3373 | 2896 | 3346 | −383 | 134 | 149 | C |
| ATOM | 962 | C | MET | A | 271 | −9.008 | 52.520 | −12.265 | 1.00 | 21.88 | | C |
| ANISOU | 962 | C | MET | A | 271 | 3116 | 2567 | 2629 | −195 | 320 | 355 | C |
| ATOM | 963 | O | MET | A | 271 | −8.151 | 53.173 | −12.845 | 1.00 | 24.73 | | O |
| ANISOU | 963 | O | MET | A | 271 | 3469 | 2925 | 3001 | −269 | 398 | 398 | O |
| ATOM | 964 | N | SER | A | 272 | −9.151 | 51.222 | −12.502 | 1.00 | 23.19 | | N |
| ANISOU | 964 | N | SER | A | 272 | 3259 | 2803 | 2750 | −135 | 321 | 308 | N |
| ATOM | 965 | CA | SER | A | 272 | −8.237 | 50.583 | −13.459 | 1.00 | 27.82 | | C |
| ANISOU | 965 | CA | SER | A | 272 | 3806 | 3461 | 3301 | −152 | 427 | 294 | C |
| ATOM | 966 | CB | SER | A | 272 | −8.269 | 49.052 | −13.316 | 1.00 | 24.65 | | C |
| ANISOU | 966 | CB | SER | A | 272 | 3354 | 3106 | 2907 | −79 | 428 | 215 | C |
| ATOM | 967 | OG | SER | A | 272 | −9.504 | 48.520 | −13.763 | 1.00 | 30.73 | | O |
| ANISOU | 967 | OG | SER | A | 272 | 4212 | 3881 | 3583 | −33 | 386 | 200 | O |
| ATOM | 968 | C | SER | A | 272 | −8.551 | 51.032 | −14.911 | 1.00 | 35.47 | | C |
| ANISOU | 968 | C | SER | A | 272 | 4879 | 4455 | 4143 | −187 | 486 | 361 | C |
| ATOM | 969 | O | SER | A | 272 | −7.719 | 50.898 | −15.821 | 1.00 | 33.43 | | O |
| ANISOU | 969 | O | SER | A | 272 | 4606 | 4255 | 3840 | −234 | 599 | 363 | O |
| ATOM | 970 | N | GLN | A | 273 | −9.749 | 51.577 | −15.132 | 1.00 | 28.28 | | N |
| ANISOU | 970 | N | GLN | A | 273 | 4067 | 3508 | 3170 | −166 | 412 | 422 | N |
| ATOM | 971 | CA | GLN | A | 273 | −10.192 | 51.971 | −16.479 | 1.00 | 28.10 | | C |
| ANISOU | 971 | CA | GLN | A | 273 | 4144 | 3525 | 3007 | −194 | 437 | 509 | C |
| ATOM | 972 | CB | GLN | A | 273 | −11.718 | 51.842 | −16.621 | 1.00 | 33.47 | | C |
| ANISOU | 972 | CB | GLN | A | 273 | 4893 | 4207 | 3616 | −131 | 325 | 537 | C |
| ATOM | 973 | CG | GLN | A | 273 | −12.262 | 50.432 | −16.461 | 1.00 | 36.41 | | C |
| ANISOU | 973 | CG | GLN | A | 273 | 5242 | 4638 | 3955 | −77 | 291 | 425 | C |
| ATOM | 974 | CD | GLN | A | 273 | −11.631 | 49.481 | −17.473 | 1.00 | 55.46 | | C |
| ANISOU | 974 | CD | GLN | A | 273 | 7658 | 7150 | 6262 | −113 | 394 | 358 | C |
| ATOM | 975 | OE1 | GLN | A | 273 | −11.878 | 49.593 | −18.677 | 1.00 | 50.47 | | O |
| ANISOU | 975 | OE1 | GLN | A | 273 | 7104 | 6598 | 5475 | −156 | 418 | 402 | O |
| ATOM | 976 | NE2 | GLN | A | 273 | −10.781 | 48.569 | −16.994 | 1.00 | 60.68 | | N |
| ANISOU | 976 | NE2 | GLN | A | 273 | 8235 | 7810 | 7009 | −96 | 460 | 255 | N |
| ATOM | 977 | C | GLN | A | 273 | −9.837 | 53.413 | −16.776 | 1.00 | 33.75 | | C |
| ANISOU | 977 | C | GLN | A | 273 | 4903 | 4175 | 3747 | −262 | 471 | 631 | C |
| ATOM | 978 | O | GLN | A | 273 | −9.836 | 53.831 | −17.917 | 1.00 | 30.52 | | O |
| ANISOU | 978 | O | GLN | A | 273 | 4566 | 3804 | 3225 | −308 | 516 | 726 | O |
| ATOM | 979 | N | TYR | A | 274 | −9.617 | 54.201 | −15.728 | 1.00 | 27.34 | | N |
| ANISOU | 979 | N | TYR | A | 274 | 4054 | 3257 | 3078 | −275 | 444 | 630 | N |
| ATOM | 980 | CA | TYR | A | 274 | −9.406 | 55.641 | −15.883 | 1.00 | 36.32 | | C |
| ANISOU | 980 | CA | TYR | A | 274 | 5239 | 4292 | 4271 | −340 | 473 | 739 | C |
| ATOM | 981 | CB | TYR | A | 274 | −10.276 | 56.378 | −14.883 | 1.00 | 33.04 | | C |
| ANISOU | 981 | CB | TYR | A | 274 | 4843 | 3744 | 3966 | −295 | 384 | 741 | C |
| ATOM | 982 | CG | TYR | A | 274 | −11.732 | 56.134 | −15.112 | 1.00 | 31.18 | | C |
| ANISOU | 982 | CG | TYR | A | 274 | 4664 | 3515 | 3669 | −197 | 289 | 778 | C |
| ATOM | 983 | CD1 | TYR | A | 274 | −12.210 | 55.809 | −16.388 | 1.00 | 46.18 | | C |
| ANISOU | 983 | CD1 | TYR | A | 274 | 6625 | 5507 | 5416 | −182 | 280 | 864 | C |
| ATOM | 984 | CE1 | TYR | A | 274 | −13.554 | 55.615 | −16.611 | 1.00 | 40.99 | | C |
| ANISOU | 984 | CE1 | TYR | A | 274 | 6001 | 4868 | 4704 | −102 | 180 | 904 | C |
| ATOM | 985 | CZ | TYR | A | 274 | −14.417 | 55.736 | −15.531 | 1.00 | 51.08 | | C |
| ANISOU | 985 | CZ | TYR | A | 274 | 7250 | 6063 | 6096 | −28 | 105 | 853 | C |
| ATOM | 986 | OH | TYR | A | 274 | −15.758 | 55.552 | −15.712 | 1.00 | 71.32 | | O |
| ANISOU | 986 | OH | TYR | A | 274 | 9825 | 8648 | 8625 | 51 | 8 | 890 | O |
| ATOM | 987 | CE2 | TYR | A | 274 | −13.964 | 56.055 | −14.270 | 1.00 | 39.21 | | C |
| ANISOU | 987 | CE2 | TYR | A | 274 | 5698 | 4466 | 4734 | −43 | 127 | 762 | C |
| ATOM | 988 | CD2 | TYR | A | 274 | −12.635 | 56.256 | −14.070 | 1.00 | 40.83 | | C |
| ANISOU | 988 | CD2 | TYR | A | 274 | 5873 | 4662 | 4979 | −130 | 210 | 727 | C |
| ATOM | 989 | C | TYR | A | 274 | −7.954 | 56.008 | −15.653 | 1.00 | 35.57 | | C |

TABLE 6-continued

DMXAA-hSTING$^{group2}$ complex

| | | | | | | | | | | | | |
|---|---|---|---|---|---|---|---|---|---|---|---|---|
| ANISOU | 989 | C | TYR | A | 274 | 5067 | 4188 | 4261 | −441 | 571 | 713 | C |
| ATOM | 990 | O | TYR | A | 274 | −7.429 | 55.832 | −14.553 | 1.00 | 37.85 | | O |
| ANISOU | 990 | O | TYR | A | 274 | 5263 | 4464 | 4656 | −451 | 551 | 617 | O |
| ATOM | 991 | N | SER | A | 275 | −7.295 | 56.493 | −16.697 | 1.00 | 33.77 | | N |
| ANISOU | 991 | N | SER | A | 275 | 4871 | 3983 | 3976 | −523 | 674 | 802 | N |
| ATOM | 992 | CA | SER | A | 275 | −5.847 | 56.662 | −16.642 | 1.00 | 40.71 | | C |
| ANISOU | 992 | CA | SER | A | 275 | 5656 | 4886 | 4926 | −625 | 785 | 770 | C |
| ATOM | 993 | CB | SER | A | 275 | −5.257 | 56.889 | −18.035 | 1.00 | 46.55 | | C |
| ANISOU | 993 | CB | SER | A | 275 | 6440 | 5693 | 5554 | −707 | 917 | 865 | C |
| ATOM | 994 | OG | SER | A | 275 | −5.041 | 58.260 | −18.291 | 1.00 | 47.46 | | O |
| ANISOU | 994 | OG | SER | A | 275 | 6616 | 5697 | 5718 | −802 | 962 | 992 | O |
| ATOM | 995 | C | SER | A | 275 | −5.406 | 57.759 | −15.635 | 1.00 | 49.10 | | C |
| ANISOU | 995 | C | SER | A | 275 | 6682 | 5819 | 6157 | −699 | 772 | 762 | C |
| ATOM | 996 | O | SER | A | 275 | −4.282 | 57.737 | −15.114 | 1.00 | 44.36 | | O |
| ANISOU | 996 | O | SER | A | 275 | 5962 | 5245 | 5646 | −773 | 818 | 693 | O |
| ATOM | 997 | N | GLN | A | 276 | −6.287 | 58.707 | −15.330 | 1.00 | 42.88 | | N |
| ANISOU | 997 | N | GLN | A | 276 | 5985 | 4890 | 5418 | −682 | 710 | 822 | N |
| ATOM | 998 | CA | GLN | A | 276 | −5.909 | 59.695 | −14.327 | 1.00 | 51.79 | | C |
| ANISOU | 998 | CA | GLN | A | 276 | 7085 | 5888 | 6706 | −759 | 706 | 780 | C |
| ATOM | 999 | CB | GLN | A | 276 | −6.823 | 60.933 | −14.358 | 1.00 | 49.84 | | C |
| ANISOU | 999 | CB | GLN | A | 276 | 6960 | 5452 | 6525 | −748 | 684 | 877 | C |
| ATOM | 1000 | CG | GLN | A | 276 | −8.258 | 60.701 | −13.884 | 1.00 | 48.87 | | C |
| ANISOU | 1000 | CG | GLN | A | 276 | 6887 | 5288 | 6394 | −610 | 571 | 857 | C |
| ATOM | 1001 | CD | GLN | A | 276 | −9.008 | 62.021 | −13.631 | 1.00 | 68.61 | | C |
| ANISOU | 1001 | CD | GLN | A | 276 | 9474 | 7573 | 9023 | −599 | 563 | 923 | C |
| ATOM | 1002 | OE1 | GLN | A | 276 | −10.096 | 62.244 | −14.167 | 1.00 | 73.21 | | O |
| ANISOU | 1002 | OE1 | GLN | A | 276 | 10132 | 8103 | 9580 | −502 | 518 | 1036 | O |
| ATOM | 1003 | NE2 | GLN | A | 276 | −8.419 | 62.898 | −12.814 | 1.00 | 65.72 | | N |
| ANISOU | 1003 | NE2 | GLN | A | 276 | 9090 | 7078 | 8804 | −700 | 608 | 849 | N |
| ATOM | 1004 | C | GLN | A | 276 | −5.809 | 59.086 | −12.907 | 1.00 | 48.36 | | C |
| ANISOU | 1004 | C | GLN | A | 276 | 6549 | 5491 | 6335 | −733 | 624 | 621 | C |
| ATOM | 1005 | O | GLN | A | 276 | −5.309 | 59.743 | −11.983 | 1.00 | 46.50 | | O |
| ANISOU | 1005 | O | GLN | A | 276 | 6268 | 5189 | 6212 | −820 | 619 | 552 | O |
| ATOM | 1006 | N | ALA | A | 277 | −6.286 | 57.844 | −12.729 | 1.00 | 36.82 | | N |
| ANISOU | 1006 | N | ALA | A | 277 | 5056 | 4137 | 4796 | −625 | 559 | 564 | N |
| ATOM | 1007 | CA | ALA | A | 277 | −6.128 | 57.149 | −11.442 | 1.00 | 38.50 | | C |
| ANISOU | 1007 | CA | ALA | A | 277 | 5171 | 4405 | 5052 | −602 | 482 | 440 | C |
| ATOM | 1008 | CB | ALA | A | 277 | −7.175 | 56.061 | −11.272 | 1.00 | 34.08 | | C |
| ANISOU | 1008 | CB | ALA | A | 277 | 4635 | 3899 | 4416 | −470 | 402 | 410 | C |
| ATOM | 1009 | C | ALA | A | 277 | −4.707 | 56.580 | −11.194 | 1.00 | 52.09 | | C |
| ANISOU | 1009 | C | ALA | A | 277 | 6739 | 6240 | 6813 | −664 | 519 | 386 | C |
| ATOM | 1010 | O | ALA | A | 277 | −4.350 | 56.286 | −10.050 | 1.00 | 46.35 | | O |
| ANISOU | 1010 | O | ALA | A | 277 | 5918 | 5555 | 6136 | −679 | 451 | 304 | O |
| ATOM | 1011 | N | GLY | A | 278 | −3.916 | 56.410 | −12.259 | 1.00 | 47.00 | | N |
| ANISOU | 1011 | N | GLY | A | 278 | 6061 | 5656 | 6141 | −700 | 625 | 435 | N |
| ATOM | 1012 | CA | GLY | A | 278 | −2.535 | 55.944 | −12.142 | 1.00 | 50.39 | | C |
| ANISOU | 1012 | CA | GLY | A | 278 | 6326 | 6190 | 6632 | −755 | 679 | 394 | C |
| ATOM | 1013 | C | GLY | A | 278 | −2.407 | 54.518 | −11.617 | 1.00 | 52.27 | | C |
| ANISOU | 1013 | C | GLY | A | 278 | 6457 | 6533 | 6871 | −653 | 622 | 328 | C |
| ATOM | 1014 | O | GLY | A | 278 | −1.446 | 54.156 | −10.924 | 1.00 | 50.66 | | O |
| ANISOU | 1014 | O | GLY | A | 278 | 6095 | 6402 | 6751 | −679 | 602 | 285 | O |
| ATOM | 1015 | N | PHE | A | 279 | −3.372 | 53.685 | −11.987 | 1.00 | 39.00 | | N |
| ANISOU | 1015 | N | PHE | A | 279 | 4856 | 4860 | 5101 | −537 | 597 | 328 | N |
| ATOM | 1016 | CA | PHE | A | 279 | −3.610 | 52.432 | −11.303 | 1.00 | 35.20 | | C |
| ANISOU | 1016 | CA | PHE | A | 279 | 4313 | 4432 | 4627 | −433 | 522 | 273 | C |
| ATOM | 1017 | CB | PHE | A | 279 | −5.042 | 52.516 | −10.832 | 1.00 | 40.20 | | C |
| ANISOU | 1017 | CB | PHE | A | 279 | 5070 | 5000 | 5203 | −374 | 422 | 270 | C |
| ATOM | 1018 | CG | PHE | A | 279 | −5.363 | 51.673 | −9.664 | 1.00 | 29.70 | | C |
| ANISOU | 1018 | CG | PHE | A | 279 | 3689 | 3699 | 3895 | −308 | 318 | 222 | C |
| ATOM | 1019 | CD1 | PHE | A | 279 | −4.670 | 51.815 | −8.468 | 1.00 | 34.05 | | C |
| ANISOU | 1019 | CD1 | PHE | A | 279 | 4134 | 4285 | 4517 | −358 | 252 | 193 | C |
| ATOM | 1020 | CE1 | PHE | A | 279 | −5.017 | 51.071 | −7.353 | 1.00 | 30.63 | | C |
| ANISOU | 1020 | CE1 | PHE | A | 279 | 3666 | 3888 | 4083 | −305 | 150 | 168 | C |
| ATOM | 1021 | CZ | PHE | A | 279 | −6.079 | 50.179 | −7.423 | 1.00 | 29.15 | | C |
| ANISOU | 1021 | CZ | PHE | A | 279 | 3549 | 3684 | 3841 | −202 | 122 | 166 | C |
| ATOM | 1022 | CE2 | PHE | A | 279 | −6.803 | 50.043 | −8.627 | 1.00 | 28.00 | | C |
| ANISOU | 1022 | CE2 | PHE | A | 279 | 3504 | 3498 | 3635 | −155 | 186 | 180 | C |
| ATOM | 1023 | CD2 | PHE | A | 279 | −6.437 | 50.802 | −9.732 | 1.00 | 28.03 | | C |
| ANISOU | 1023 | CD2 | PHE | A | 279 | 3545 | 3483 | 3623 | −209 | 278 | 210 | C |
| ATOM | 1024 | C | PHE | A | 279 | −3.492 | 51.317 | −12.329 | 1.00 | 34.75 | | C |
| ANISOU | 1024 | C | PHE | A | 279 | 4246 | 4436 | 4523 | −361 | 610 | 263 | C |
| ATOM | 1025 | O | PHE | A | 279 | −4.336 | 51.199 | −13.208 | 1.00 | 45.87 | | O |
| ANISOU | 1025 | O | PHE | A | 279 | 5777 | 5828 | 5822 | −328 | 636 | 281 | O |
| ATOM | 1026 | N | SER | A | 280 | −2.463 | 50.478 | −12.222 | 1.00 | 31.76 | | N |
| ANISOU | 1026 | N | SER | A | 280 | 3715 | 4126 | 4227 | −336 | 657 | 230 | N |
| ATOM | 1027 | CA | SER | A | 280 | −2.288 | 49.395 | −13.195 | 1.00 | 26.67 | | C |
| ANISOU | 1027 | CA | SER | A | 280 | 3056 | 3523 | 3555 | −269 | 766 | 195 | C |
| ATOM | 1028 | CB | SER | A | 280 | −0.843 | 48.922 | −13.202 | 1.00 | 36.47 | | C |

TABLE 6-continued

DMXAA-hSTING$^{group2}$ complex

| | | | | | | | | | | | |
|---|---|---|---|---|---|---|---|---|---|---|---|
| ANISOU | 1028 | CB | SER | A | 280 | 4102 | 4828 | 4926 | −271 | 857 | 173 | C |
| ATOM | 1029 | OG | SER | A | 280 | −0.555 | 48.249 | −12.000 | 1.00 | 32.54 | | O |
| ANISOU | 1029 | OG | SER | A | 280 | 3475 | 4344 | 4544 | −205 | 751 | 166 | O |
| ATOM | 1030 | C | SER | A | 280 | −3.174 | 48.196 | −12.871 | 1.00 | 29.69 | | C |
| ANISOU | 1030 | C | SER | A | 280 | 3476 | 3887 | 3919 | −151 | 699 | 154 | C |
| ATOM | 1031 | O | SER | A | 280 | −3.796 | 48.128 | −11.830 | 1.00 | 28.25 | | O |
| ANISOU | 1031 | O | SER | A | 280 | 3308 | 3674 | 3751 | −118 | 570 | 161 | O |
| ATOM | 1032 | N | ARG | A | 281 | −3.222 | 47.210 | −13.768 | 1.00 | 31.32 | | N |
| ANISOU | 1032 | N | ARG | A | 281 | 3507 | 5175 | 3217 | 104 | 1232 | −276 | N |
| ATOM | 1033 | C | ARG | A | 281 | −3.418 | 45.225 | −12.314 | 1.00 | 30.70 | | C |
| ANISOU | 1033 | C | ARG | A | 281 | 3522 | 4747 | 3395 | 146 | 947 | −663 | C |
| ATOM | 1034 | O | ARG | A | 281 | −4.145 | 44.638 | −11.502 | 1.00 | 26.26 | | O |
| ANISOU | 1034 | O | ARG | A | 281 | 3035 | 4053 | 2889 | 137 | 750 | −706 | O |
| ATOM | 1035 | CA | AARG | A | 281 | −4.011 | 46.014 | −13.484 | 0.51 | 31.58 | | C |
| ANISOU | 1035 | CA | AARG | A | 281 | 3682 | 5189 | 3127 | 39 | 1013 | −490 | C |
| ATOM | 1036 | CB | AARG | A | 281 | −4.120 | 45.147 | −14.737 | 0.51 | 36.30 | | C |
| ANISOU | 1036 | CB | AARG | A | 281 | 4441 | 6023 | 3330 | −84 | 1150 | −739 | C |
| ATOM | 1037 | CG | AARG | A | 281 | −4.698 | 45.912 | −15.913 | 0.51 | 36.81 | | C |
| ANISOU | 1037 | CG | AARG | A | 281 | 4510 | 6566 | 2909 | −165 | 1180 | −504 | C |
| ATOM | 1038 | CD | AARG | A | 281 | −5.305 | 45.005 | −16.984 | 0.51 | 46.03 | | C |
| ANISOU | 1038 | CD | AARG | A | 281 | 5822 | 8136 | 3531 | −406 | 1185 | −799 | C |
| ATOM | 1039 | NE | AARG | A | 281 | −4.404 | 43.964 | −17.487 | 0.51 | 40.95 | | N |
| ANISOU | 1039 | NE | AARG | A | 281 | 5323 | 7329 | 2908 | −485 | 1495 | −1250 | N |
| ATOM | 1040 | CZ | AARG | A | 281 | −3.483 | 44.147 | −18.426 | 0.51 | 43.75 | | C |
| ANISOU | 1040 | CZ | AARG | A | 281 | 5711 | 7738 | 3173 | −446 | 1780 | −1260 | C |
| ATOM | 1041 | NH1 | AARG | A | 281 | −3.299 | 45.347 | −18.964 | 0.51 | 46.70 | | N |
| ANISOU | 1041 | NH1 | AARG | A | 281 | 5996 | 8353 | 3396 | −335 | 1834 | −859 | N |
| ATOM | 1042 | NH2 | AARG | A | 281 | −2.731 | 43.129 | −18.821 | 0.51 | 49.21 | | N |
| ANISOU | 1042 | NH2 | AARG | A | 281 | 6532 | 8162 | 4002 | −486 | 2042 | −1618 | N |
| ATOM | 1043 | CA | BARG | A | 281 | −4.019 | 46.022 | −13.485 | 0.49 | 31.54 | | C |
| ANISOU | 1043 | CA | BARG | A | 281 | 3677 | 5186 | 3121 | 39 | 1012 | −487 | C |
| ATOM | 1044 | CB | BARG | A | 281 | −4.154 | 45.161 | −14.745 | 0.49 | 35.97 | | C |
| ANISOU | 1044 | CB | BARG | A | 281 | 4399 | 5989 | 3278 | −87 | 1145 | −733 | C |
| ATOM | 1045 | CG | BARG | A | 281 | −4.775 | 45.900 | −15.939 | 0.49 | 36.87 | | C |
| ANISOU | 1045 | CG | BARG | A | 281 | 4522 | 6596 | 2891 | −174 | 1168 | −502 | C |
| ATOM | 1046 | CD | BARG | A | 281 | −6.094 | 46.605 | −15.575 | 0.49 | 33.65 | | C |
| ANISOU | 1046 | CD | BARG | A | 281 | 4034 | 6380 | 2370 | −179 | 894 | −150 | C |
| ATOM | 1047 | NE | BARG | A | 281 | −6.653 | 47.387 | −16.688 | 0.49 | 42.90 | | N |
| ANISOU | 1047 | NE | BARG | A | 281 | 5143 | 8091 | 3067 | −170 | 928 | 215 | N |
| ATOM | 1048 | CZ | BARG | A | 281 | −7.751 | 47.057 | −17.369 | 0.49 | 49.92 | | C |
| ANISOU | 1048 | CZ | BARG | A | 281 | 6014 | 9414 | 3537 | −311 | 696 | 223 | C |
| ATOM | 1049 | NH1 | BARG | A | 281 | −8.432 | 45.959 | −17.045 | 0.49 | 50.52 | | N |
| ANISOU | 1049 | NH1 | BARG | A | 281 | 6146 | 9496 | 3555 | −530 | 494 | −161 | N |
| ATOM | 1050 | NH2 | BARG | A | 281 | −8.179 | 47.834 | −18.366 | 0.49 | 45.31 | | N |
| ANISOU | 1050 | NH2 | BARG | A | 281 | 5329 | 9166 | 2719 | −225 | 670 | 602 | N |
| ATOM | 1051 | N | GLU | A | 282 | −2.095 | 45.214 | −12.221 | 1.00 | 28.82 | | N |
| ANISOU | 1051 | N | GLU | A | 282 | 3128 | 4411 | 3411 | 269 | 1126 | −724 | N |
| ATOM | 1052 | CA | GLU | A | 282 | −1.444 | 44.528 | −11.103 | 1.00 | 32.36 | | C |
| ANISOU | 1052 | CA | GLU | A | 282 | 3444 | 4666 | 4187 | 436 | 1054 | −782 | C |
| ATOM | 1053 | CB | GLU | A | 282 | 0.068 | 44.386 | −11.297 | 1.00 | 31.88 | | C |
| ANISOU | 1053 | CB | GLU | A | 282 | 3150 | 4595 | 4367 | 589 | 1293 | −841 | C |
| ATOM | 1054 | CG | GLU | A | 282 | 0.415 | 43.269 | −12.244 | 1.00 | 43.11 | | C |
| ANISOU | 1054 | CG | GLU | A | 282 | 4725 | 5902 | 5752 | 659 | 1605 | −1039 | C |
| ATOM | 1055 | CD | GLU | A | 282 | 1.914 | 43.029 | −12.359 | 1.00 | 63.96 | | C |
| ANISOU | 1055 | CD | GLU | A | 282 | 7099 | 8500 | 8705 | 864 | 1878 | −1060 | C |
| ATOM | 1056 | OE1 | GLU | A | 282 | 2.303 | 42.117 | −13.130 | 1.00 | 60.73 | | O |
| ANISOU | 1056 | OE1 | GLU | A | 282 | 6811 | 7934 | 8329 | 935 | 2231 | −1231 | O |
| ATOM | 1057 | OE2 | GLU | A | 282 | 2.690 | 43.748 | −11.679 | 1.00 | 73.40 | | O |
| ANISOU | 1057 | OE2 | GLU | A | 282 | 7944 | 9831 | 10115 | 927 | 1770 | −933 | O |
| ATOM | 1058 | C | GLU | A | 282 | −1.743 | 45.236 | −9.813 | 1.00 | 30.21 | | C |
| ANISOU | 1058 | C | GLU | A | 282 | 3041 | 4388 | 4050 | 415 | 793 | −630 | C |
| ATOM | 1059 | O | GLU | A | 282 | −2.002 | 44.580 | −8.807 | 1.00 | 31.89 | | O |
| ANISOU | 1059 | O | GLU | A | 282 | 3267 | 4497 | 4353 | 504 | 617 | −620 | O |
| ATOM | 1060 | N | ASP | A | 283 | −1.746 | 46.574 | −9.838 | 1.00 | 27.88 | | N |
| ANISOU | 1060 | N | ASP | A | 283 | 2644 | 4180 | 3770 | 285 | 829 | −513 | N |
| ATOM | 1061 | CA | ASP | A | 283 | −2.155 | 47.358 | −8.667 | 1.00 | 30.45 | | C |
| ANISOU | 1061 | CA | ASP | A | 283 | 2889 | 4471 | 4209 | 184 | 667 | −429 | C |
| ATOM | 1062 | CB | ASP | A | 283 | −2.114 | 48.863 | −8.932 | 1.00 | 33.61 | | C |
| ANISOU | 1062 | CB | ASP | A | 283 | 3211 | 4871 | 4688 | 27 | 892 | −322 | C |
| ATOM | 1063 | CG | ASP | A | 283 | −0.710 | 49.382 | −9.198 | 1.00 | 49.77 | | C |
| ANISOU | 1063 | CG | ASP | A | 283 | 5000 | 6983 | 6929 | −11 | 1147 | −435 | C |
| ATOM | 1064 | OD1 | ASP | A | 283 | 0.251 | 48.701 | −8.774 | 1.00 | 52.74 | | O |
| ANISOU | 1064 | OD1 | ASP | A | 283 | 5167 | 7462 | 7409 | 75 | 1057 | −587 | O |
| ATOM | 1065 | OD2 | ASP | A | 283 | −0.586 | 50.463 | −9.847 | 1.00 | 53.92 | | O |
| ANISOU | 1065 | OD2 | ASP | A | 283 | 5511 | 7456 | 7518 | −105 | 1472 | −337 | O |
| ATOM | 1066 | C | ASP | A | 283 | −3.578 | 47.030 | −8.259 | 1.00 | 30.85 | | C |
| ANISOU | 1066 | C | ASP | A | 283 | 3162 | 4433 | 4124 | 152 | 458 | −349 | C |
| ATOM | 1067 | O | ASP | A | 283 | −3.904 | 46.950 | −7.073 | 1.00 | 25.86 | | O |

TABLE 6-continued

| | | | | | | | | | | | | |
|---|---|---|---|---|---|---|---|---|---|---|---|---|
| ANISOU | 1067 | O | ASP | A | 283 | 2520 | 3732 | 3573 | 138 | 278 | −343 | O |
| ATOM | 1068 | N | ARG | A | 284 | −4.446 | 46.890 | −9.254 | 1.00 | 23.24 | | N |
| ANISOU | 1068 | N | ARG | A | 284 | 2374 | 3530 | 2925 | 119 | 489 | −286 | N |
| ATOM | 1069 | CA | ARG | A | 284 | −5.849 | 46.617 | −8.950 | 1.00 | 22.39 | | C |
| ANISOU | 1069 | CA | ARG | A | 284 | 2419 | 3392 | 2696 | 59 | 301 | −217 | C |
| ATOM | 1070 | CB | ARG | A | 284 | −6.679 | 46.520 | −10.237 | 1.00 | 22.88 | | C |
| ANISOU | 1070 | CB | ARG | A | 284 | 2575 | 3700 | 2419 | −12 | 325 | −159 | C |
| ATOM | 1071 | CG | ARG | A | 284 | −8.154 | 46.846 | −9.962 | 1.00 | 29.86 | | C |
| ANISOU | 1071 | CG | ARG | A | 284 | 3484 | 4646 | 3217 | −83 | 161 | 37 | C |
| ATOM | 1072 | CD | ARG | A | 284 | −9.144 | 45.712 | −10.189 | 1.00 | 37.19 | | C |
| ANISOU | 1072 | CD | ARG | A | 284 | 4521 | 5680 | 3928 | −202 | 5 | −153 | C |
| ATOM | 1073 | NE | ARG | A | 284 | −8.592 | 44.431 | −10.656 | 1.00 | 37.63 | | N |
| ANISOU | 1073 | NE | ARG | A | 284 | 4699 | 5698 | 3901 | −251 | 98 | −525 | N |
| ATOM | 1074 | CZ | ARG | A | 284 | −8.880 | 43.253 | −10.082 | 1.00 | 37.19 | | C |
| ANISOU | 1074 | CZ | ARG | A | 284 | 4778 | 5392 | 3962 | −294 | 89 | −776 | C |
| ATOM | 1075 | NH1 | ARG | A | 284 | −8.368 | 42.117 | −10.558 | 1.00 | 30.72 | | N |
| ANISOU | 1075 | NH1 | ARG | A | 284 | 4082 | 4463 | 3129 | −331 | 300 | −1106 | N |
| ATOM | 1076 | NH2 | ARG | A | 284 | −9.721 | 43.214 | −9.045 | 1.00 | 33.12 | | N |
| ANISOU | 1076 | NH2 | ARG | A | 284 | 4287 | 4697 | 3599 | −301 | −61 | −690 | N |
| ATOM | 1077 | C | ARG | A | 284 | −5.992 | 45.310 | −8.182 | 1.00 | 23.57 | | C |
| ANISOU | 1077 | C | ARG | A | 284 | 2669 | 3376 | 2910 | 123 | 163 | −384 | C |
| ATOM | 1078 | O | ARG | A | 284 | −6.709 | 45.226 | −7.178 | 1.00 | 24.32 | | O |
| ANISOU | 1078 | O | ARG | A | 284 | 2818 | 3344 | 3076 | 105 | 11 | −332 | O |
| ATOM | 1079 | N | LEU | A | 285 | −5.326 | 44.270 | −8.669 | 1.00 | 23.14 | | N |
| ANISOU | 1079 | N | LEU | A | 285 | 2658 | 3282 | 2854 | 212 | 287 | −567 | N |
| ATOM | 1080 | CA | LEU | A | 285 | −5.409 | 42.961 | −8.013 | 1.00 | 22.03 | | C |
| ANISOU | 1080 | CA | LEU | A | 285 | 2628 | 2907 | 2834 | 325 | 287 | −676 | C |
| ATOM | 1081 | CB | LEU | A | 285 | −4.683 | 41.899 | −8.840 | 1.00 | 25.04 | | C |
| ANISOU | 1081 | CB | LEU | A | 285 | 3074 | 3193 | 3248 | 409 | 576 | −884 | C |
| ATOM | 1082 | CG | LEU | A | 285 | −4.777 | 40.518 | −8.185 | 1.00 | 32.57 | | C |
| ANISOU | 1082 | CG | LEU | A | 285 | 4162 | 3807 | 4406 | 565 | 710 | −950 | C |
| ATOM | 1083 | CD1 | LEU | A | 285 | −6.212 | 40.009 | −8.165 | 1.00 | 39.55 | | C |
| ANISOU | 1083 | CD1 | LEU | A | 285 | 5279 | 4575 | 5172 | 344 | 674 | −1095 | C |
| ATOM | 1084 | CD2 | LEU | A | 285 | −3.883 | 39.577 | −8.965 | 1.00 | 40.85 | | C |
| ANISOU | 1084 | CD2 | LEU | A | 285 | 5250 | 4691 | 5580 | 682 | 1111 | −1131 | C |
| ATOM | 1085 | C | LEU | A | 285 | −4.821 | 42.996 | −6.590 | 1.00 | 26.28 | | C |
| ANISOU | 1085 | C | LEU | A | 285 | 3020 | 3376 | 3591 | 506 | 162 | −532 | C |
| ATOM | 1086 | O | LEU | A | 285 | −5.395 | 42.442 | −5.638 | 1.00 | 27.21 | | O |
| ANISOU | 1086 | O | LEU | A | 285 | 3236 | 3339 | 3763 | 567 | 64 | −473 | O |
| ATOM | 1087 | N | GLU | A | 286 | −3.673 | 43.641 | −6.453 | 1.00 | 24.82 | | N |
| ANISOU | 1087 | N | GLU | A | 286 | 2576 | 3357 | 3497 | 572 | 175 | −481 | N |
| ATOM | 1088 | CA | GLU | A | 286 | −2.997 | 43.764 | −5.155 | 1.00 | 28.42 | | C |
| ANISOU | 1088 | CA | GLU | A | 286 | 2802 | 3931 | 4064 | 692 | 22 | −372 | C |
| ATOM | 1089 | CB | GLU | A | 286 | −1.705 | 44.555 | −5.327 | 1.00 | 36.43 | | C |
| ANISOU | 1089 | CB | GLU | A | 286 | 3477 | 5203 | 5161 | 667 | 82 | −408 | C |
| ATOM | 1090 | CG | GLU | A | 286 | −0.926 | 44.728 | −4.045 | 1.00 | 51.92 | | C |
| ANISOU | 1090 | CG | GLU | A | 286 | 5108 | 7458 | 7160 | 725 | −105 | −345 | C |
| ATOM | 1091 | CD | GLU | A | 286 | 0.250 | 45.681 | −4.199 | 1.00 | 77.63 | | C |
| ANISOU | 1091 | CD | GLU | A | 286 | 7986 | 11011 | 10499 | 580 | −34 | −464 | C |
| ATOM | 1092 | OE1 | GLU | A | 286 | 0.885 | 45.690 | −5.280 | 1.00 | 76.40 | | O |
| ANISOU | 1092 | OE1 | GLU | A | 286 | 7770 | 10810 | 10447 | 625 | 197 | −521 | O |
| ATOM | 1093 | OE2 | GLU | A | 286 | 0.517 | 46.438 | −3.236 | 1.00 | 97.02 | | O |
| ANISOU | 1093 | OE2 | GLU | A | 286 | 10206 | 13749 | 12908 | 377 | −173 | −541 | O |
| ATOM | 1094 | C | GLU | A | 286 | −3.905 | 44.473 | −4.149 | 1.00 | 26.26 | | C |
| ANISOU | 1094 | C | GLU | A | 286 | 2593 | 3664 | 3720 | 517 | −175 | −313 | C |
| ATOM | 1095 | O | GLU | A | 286 | −4.055 | 44.041 | −2.995 | 1.00 | 24.26 | | O |
| ANISOU | 1095 | O | GLU | A | 286 | 2340 | 3419 | 3457 | 614 | −320 | −222 | O |
| ATOM | 1096 | N | GLN | A | 287 | −4.550 | 45.553 | −4.587 | 1.00 | 21.56 | | N |
| ANISOU | 1096 | N | GLN | A | 287 | 2060 | 3053 | 3076 | 283 | −134 | −329 | N |
| ATOM | 1097 | CA | GLN | A | 287 | −5.466 | 46.292 | −3.715 | 1.00 | 23.64 | | C |
| ANISOU | 1097 | CA | GLN | A | 287 | 2399 | 3253 | 3330 | 111 | −221 | −276 | C |
| ATOM | 1098 | CB | GLN | A | 287 | −5.783 | 47.691 | −4.278 | 1.00 | 23.23 | | C |
| ANISOU | 1098 | CB | GLN | A | 287 | 2323 | 3179 | 3324 | −89 | −40 | −234 | C |
| ATOM | 1099 | CG | GLN | A | 287 | −4.589 | 48.636 | −4.307 | 1.00 | 24.62 | | C |
| ANISOU | 1099 | CG | GLN | A | 287 | 2250 | 3489 | 3616 | −205 | 129 | −338 | C |
| ATOM | 1100 | CD | GLN | A | 287 | −3.913 | 48.810 | −2.942 | 1.00 | 31.58 | | C |
| ANISOU | 1100 | CD | GLN | A | 287 | 2933 | 4546 | 4519 | −323 | 15 | −494 | C |
| ATOM | 1101 | OE1 | GLN | A | 287 | −4.548 | 49.235 | −1.975 | 1.00 | 26.76 | | O |
| ANISOU | 1101 | OE1 | GLN | A | 287 | 2397 | 3873 | 3896 | −487 | −15 | −523 | O |
| ATOM | 1102 | NE2 | GLN | A | 287 | −2.616 | 48.440 | −2.837 | 1.00 | 27.30 | | N |
| ANISOU | 1102 | NE2 | GLN | A | 287 | 2107 | 4285 | 3980 | −243 | −51 | −592 | N |
| ATOM | 1103 | C | GLN | A | 287 | −6.777 | 45.542 | −3.438 | 1.00 | 23.58 | | C |
| ANISOU | 1103 | C | GLN | A | 287 | 2648 | 3042 | 3268 | 138 | −312 | −216 | C |
| ATOM | 1104 | O | GLN | A | 287 | −7.348 | 45.634 | −2.345 | 1.00 | 24.31 | | O |
| ANISOU | 1104 | O | GLN | A | 287 | 2807 | 3062 | 3366 | 88 | −405 | −173 | O |
| ATOM | 1105 | N | ALA | A | 288 | −7.295 | 44.833 | −4.431 | 1.00 | 21.19 | | N |
| ANISOU | 1105 | N | ALA | A | 288 | 2484 | 2668 | 2899 | 169 | −258 | −252 | N |
| ATOM | 1106 | CA | ALA | A | 288 | −8.462 | 43.974 | −4.186 | 1.00 | 19.98 | | C |

TABLE 6-continued

| | | | | | | | | | | | | |
|---|---|---|---|---|---|---|---|---|---|---|---|---|
| ANISOU | 1106 | CA | ALA | A | 288 | 2537 | 2331 | 2722 | 153 | −305 | −268 | C |
| ATOM | 1107 | CB | ALA | A | 288 | −8.871 | 43.253 | −5.462 | 1.00 | 21.80 | | C |
| ANISOU | 1107 | CB | ALA | A | 288 | 2865 | 2584 | 2833 | 87 | −205 | −419 | C |
| ATOM | 1108 | C | ALA | A | 288 | −8.122 | 42.939 | −3.085 | 1.00 | 22.48 | | C |
| ANISOU | 1108 | C | ALA | A | 288 | 2916 | 2492 | 3134 | 350 | −324 | −244 | C |
| ATOM | 1109 | O | ALA | A | 288 | −8.914 | 42.665 | −2.175 | 1.00 | 24.69 | | O |
| ANISOU | 1109 | O | ALA | A | 288 | 3326 | 2617 | 3440 | 342 | −378 | −181 | O |
| ATOM | 1110 | N | LYS | A | 289 | −6.957 | 42.319 | −3.193 | 1.00 | 19.61 | | N |
| ANISOU | 1110 | N | LYS | A | 289 | 2451 | 2168 | 2833 | 564 | −240 | −248 | N |
| ATOM | 1111 | CA | LYS | A | 289 | −6.564 | 41.332 | −2.162 | 1.00 | 21.60 | | C |
| ANISOU | 1111 | CA | LYS | A | 289 | 2714 | 2318 | 3175 | 846 | −220 | −100 | C |
| ATOM | 1112 | CB | LYS | A | 289 | −5.241 | 40.668 | −2.536 | 1.00 | 27.58 | | C |
| ANISOU | 1112 | CB | LYS | A | 289 | 3301 | 3129 | 4048 | 1130 | −61 | −53 | C |
| ATOM | 1113 | CG | LYS | A | 289 | −5.376 | 39.556 | −3.551 | 1.00 | 32.83 | | C |
| ANISOU | 1113 | CG | LYS | A | 289 | 4165 | 3468 | 4842 | 1181 | 278 | −213 | C |
| ATOM | 1114 | CD | LYS | A | 289 | −3.985 | 39.074 | −4.032 | 1.00 | 37.34 | | C |
| ANISOU | 1114 | CD | LYS | A | 289 | 4540 | 4076 | 5573 | 1459 | 502 | −166 | C |
| ATOM | 1115 | CE | LYS | A | 289 | −4.095 | 37.966 | −5.054 | 1.00 | 45.86 | | C |
| ANISOU | 1115 | CE | LYS | A | 289 | 5850 | 4779 | 6797 | 1460 | 945 | −395 | C |
| ATOM | 1116 | NZ | LYS | A | 289 | −2.752 | 37.600 | −5.643 | 1.00 | 45.51 | | N |
| ANISOU | 1116 | NZ | LYS | A | 289 | 5617 | 4738 | 6939 | 1711 | 1229 | −367 | N |
| ATOM | 1117 | C | LYS | A | 289 | −6.452 | 41.974 | −0.769 | 1.00 | 29.57 | | C |
| ANISOU | 1117 | C | LYS | A | 289 | 3603 | 3540 | 4092 | 847 | −441 | 57 | C |
| ATOM | 1118 | O | LYS | A | 289 | −6.889 | 41.426 | 0.255 | 1.00 | 27.87 | | O |
| ANISOU | 1118 | O | LYS | A | 289 | 3505 | 3228 | 3857 | 966 | −471 | 206 | O |
| ATOM | 1119 | N | LEU | A | 290 | −5.810 | 43.131 | −0.732 | 1.00 | 26.71 | | N |
| ANISOU | 1119 | N | LEU | A | 290 | 3003 | 3485 | 3662 | 691 | −549 | −1 | N |
| ATOM | 1120 | CA | LEU | A | 290 | −5.609 | 43.829 | 0.521 | 1.00 | 23.66 | | C |
| ANISOU | 1120 | CA | LEU | A | 290 | 2475 | 3373 | 3142 | 586 | −719 | 34 | C |
| ATOM | 1121 | CB | LEU | A | 290 | −4.632 | 44.993 | 0.316 | 1.00 | 28.24 | | C |
| ANISOU | 1121 | CB | LEU | A | 290 | 2744 | 4280 | 3708 | 378 | −731 | −123 | C |
| ATOM | 1122 | CG | LEU | A | 290 | −4.233 | 45.884 | 1.491 | 1.00 | 34.27 | | C |
| ANISOU | 1122 | CG | LEU | A | 290 | 3294 | 5417 | 4310 | 132 | −852 | −232 | C |
| ATOM | 1123 | CD1 | LEU | A | 290 | −3.648 | 45.054 | 2.647 | 1.00 | 39.60 | | C |
| ANISOU | 1123 | CD1 | LEU | A | 290 | 3788 | 6488 | 4769 | 380 | −1072 | −40 | C |
| ATOM | 1124 | CD2 | LEU | A | 290 | −3.151 | 46.875 | 1.00 | 8 | 1.00 | 36.66 | C |
| ANISOU | 1124 | CD2 | LEU | A | 290 | 3267 | 5982 | 4680 | −88 | −762 | −448 | C |
| ATOM | 1125 | C | LEU | A | 290 | −6.956 | 44.341 | 1.066 | 1.00 | 26.87 | | C |
| ANISOU | 1125 | C | LEU | A | 290 | 3128 | 3568 | 3515 | 352 | −726 | 5 | C |
| ATOM | 1126 | O | LEU | A | 290 | −7.141 | 44.412 | 2.282 | 1.00 | 24.10 | | O |
| ANISOU | 1126 | O | LEU | A | 290 | 2798 | 3327 | 3031 | 317 | −821 | 59 | O |
| ATOM | 1127 | N | PHE | A | 291 | −7.888 | 44.698 | 0.173 | 1.00 | 19.53 | | N |
| ANISOU | 1127 | N | PHE | A | 291 | 2355 | 2384 | 2682 | 202 | −617 | −58 | N |
| ATOM | 1128 | CA | PHE | A | 291 | −9.209 | 45.154 | 0.617 | 1.00 | 22.58 | | C |
| ANISOU | 1128 | CA | PHE | A | 291 | 2927 | 2560 | 3093 | 23 | −587 | −39 | C |
| ATOM | 1129 | CB | PHE | A | 291 | −10.063 | 45.543 | −0.594 | 1.00 | 25.93 | | C |
| ANISOU | 1129 | CB | PHE | A | 291 | 3402 | 2853 | 3598 | −82 | −488 | −36 | C |
| ATOM | 1130 | CG | PHE | A | 291 | −11.531 | 45.717 | −0.273 | 1.00 | 22.05 | | C |
| ANISOU | 1130 | CG | PHE | A | 291 | 3057 | 2150 | 3172 | −194 | −452 | 38 | C |
| ATOM | 1131 | CD1 | PHE | A | 291 | −11.981 | 46.887 | 0.308 | 1.00 | 19.19 | | C |
| ANISOU | 1131 | CD1 | PHE | A | 291 | 2672 | 1741 | 2877 | −347 | −328 | 83 | C |
| ATOM | 1132 | CE1 | PHE | A | 291 | −13.339 | 47.065 | 0.575 | 1.00 | 21.29 | | C |
| ANISOU | 1132 | CE1 | PHE | A | 291 | 2963 | 2017 | 3108 | −318 | −143 | 124 | C |
| ATOM | 1133 | CZ | PHE | A | 291 | −14.250 | 46.054 | 0.269 | 1.00 | 17.04 | | C |
| ANISOU | 1133 | CZ | PHE | A | 291 | 2460 | 1471 | 2542 | −256 | −182 | 131 | C |
| ATOM | 1134 | CE2 | PHE | A | 291 | −13.818 | 44.896 | −0.332 | 1.00 | 27.49 | | C |
| ANISOU | 1134 | CE2 | PHE | A | 291 | 3847 | 2742 | 3854 | −216 | −331 | 77 | C |
| ATOM | 1135 | CD2 | PHE | A | 291 | −12.454 | 44.723 | −0.601 | 1.00 | 29.77 | | C |
| ANISOU | 1135 | CD2 | PHE | A | 291 | 4165 | 2988 | 4160 | −161 | −468 | 30 | C |
| ATOM | 1136 | C | PHE | A | 291 | −9.873 | 44.041 | 1.394 | 1.00 | 24.77 | | C |
| ANISOU | 1136 | C | PHE | A | 291 | 3410 | 2648 | 3354 | 166 | −615 | 56 | C |
| ATOM | 1137 | O | PHE | A | 291 | −10.386 | 44.235 | 2.485 | 1.00 | 21.94 | | O |
| ANISOU | 1137 | O | PHE | A | 291 | 3148 | 2246 | 2941 | 93 | −634 | 100 | O |
| ATOM | 1138 | N | CYS | A | 292 | −9.809 | 42.838 | 0.831 | 1.00 | 21.83 | | N |
| ANISOU | 1138 | N | CYS | A | 292 | 3119 | 2135 | 3042 | 364 | −551 | 72 | N |
| ATOM | 1139 | C | CYS | A | 292 | −9.750 | 41.340 | 2.826 | 1.00 | 29.97 | | C |
| ANISOU | 1139 | C | CYS | A | 292 | 4326 | 3056 | 4003 | 750 | −532 | 387 | C |
| ATOM | 1140 | O | CYS | A | 292 | −10.453 | 41.060 | 3.812 | 1.00 | 28.68 | | O |
| ANISOU | 1140 | O | CYS | A | 292 | 4328 | 2769 | 3802 | 760 | −492 | 497 | O |
| ATOM | 1141 | CA | ACYS | A | 292 | −10.384 | 41.666 | 1.455 | 0.58 | 25.04 | | C |
| ANISOU | 1141 | CA | ACYS | A | 292 | 3737 | 2274 | 3503 | 520 | −462 | 165 | C |
| ATOM | 1142 | CB | ACYS | A | 292 | −10.210 | 40.480 | 0.515 | 0.58 | 29.34 | | C |
| ANISOU | 1142 | CB | ACYS | A | 292 | 4356 | 2611 | 4179 | 663 | −265 | 87 | C |
| ATOM | 1143 | SG | ACYS | A | 292 | −10.855 | 38.997 | 1.190 | 0.58 | 32.61 | | S |
| ANISOU | 1143 | SG | ACYS | A | 292 | 4866 | 2767 | 4755 | 723 | −15 | 161 | S |
| ATOM | 1144 | CA | BCYS | A | 292 | −10.370 | 41.649 | 1.473 | 0.42 | 25.91 | | C |
| ANISOU | 1144 | CA | BCYS | A | 292 | 3848 | 2385 | 3613 | 526 | −462 | 168 | C |
| ATOM | 1145 | CB | BCYS | A | 292 | −10.196 | 40.424 | 0.579 | 0.42 | 28.23 | | C |

TABLE 6-continued

DMXAA-hSTING$^{group2}$ complex

| | | | | | | | | | | | | |
|---|---|---|---|---|---|---|---|---|---|---|---|---|
| ANISOU | 1145 | CB | BCYS | A | 292 | 4222 | 2462 | 4042 | 679 | −260 | 99 | C |
| ATOM | 1146 | SG | BCYS | A | 292 | −11.302 | 40.449 | −0.818 | 0.42 | 36.65 | | S |
| ANISOU | 1146 | SG | BCYS | A | 292 | 5369 | 3413 | 5143 | 362 | −178 | −181 | S |
| ATOM | 1147 | N | ARG | A | 293 | −8.418 | 41.348 | 2.892 | 1.00 | 23.70 | | N |
| ANISOU | 1147 | N | ARG | A | 293 | 3276 | 2607 | 3122 | 935 | −622 | 474 | N |
| ATOM | 1148 | C | ARG | A | 293 | −8.050 | 42.153 | 5.231 | 1.00 | 23.90 | | C |
| ANISOU | 1148 | C | ARG | A | 293 | 3148 | 3253 | 2680 | 863 | −912 | 648 | C |
| ATOM | 1149 | O | ARG | A | 293 | −8.215 | 41.823 | 6.410 | 1.00 | 26.07 | | O |
| ANISOU | 1149 | O | ARG | A | 293 | 3493 | 3668 | 2744 | 972 | −960 | 844 | O |
| ATOM | 1150 | CA | AARG | A | 293 | −7.715 | 41.123 | 4.157 | 0.50 | 28.76 | | C |
| ANISOU | 1150 | CA | AARG | A | 293 | 3776 | 3601 | 3552 | 1158 | −749 | 727 | C |
| ATOM | 1151 | CB | AARG | A | 293 | −6.220 | 41.156 | 3.918 | 0.50 | 29.57 | | C |
| ANISOU | 1151 | CB | AARG | A | 293 | 3495 | 4140 | 3600 | 1345 | −850 | 798 | C |
| ATOM | 1152 | CG | AARG | A | 293 | −5.647 | 39.789 | 3.818 | 0.504 | 5.43 | | C |
| ANISOU | 1152 | CG | AARG | A | 293 | 5494 | 5984 | 5784 | 1686 | −641 | 1027 | C |
| ATOM | 1153 | CD | AARG | A | 293 | −4.313 | 39.750 | 4.500 | 0.505 | 6.11 | | C |
| ANISOU | 1153 | CD | AARG | A | 293 | 6486 | 7862 | 6972 | 1832 | −779 | 1208 | C |
| ATOM | 1154 | NE | AARG | A | 293 | −3.313 | 40.477 | 3.722 | 0.50 | 64.85 | | N |
| ANISOU | 1154 | NE | AARG | A | 293 | 7271 | 9263 | 8106 | 1744 | −871 | 1041 | N |
| ATOM | 1155 | CZ | AARG | A | 293 | −2.573 | 41.485 | 4.181 | 0.50 | 58.42 | | C |
| ANISOU | 1155 | CZ | AARG | A | 293 | 6145 | 8977 | 7075 | 1510 | −1094 | 912 | C |
| ATOM | 1156 | NH1 | AARG | A | 293 | −1.689 | 42.061 | 3.370 | 0.50 | 43.26 | | N |
| ANISOU | 1156 | NH1 | AARG | A | 293 | 3953 | 7233 | 5249 | 1410 | −1096 | 738 | N |
| ATOM | 1157 | NH2 | AARG | A | 293 | −2.706 | 41.916 | 5.434 | 0.504 | 8.44 | | N |
| ANISOU | 1157 | NH2 | AARG | A | 293 | 4852 | 8044 | 5507 | 1340 | −1263 | 916 | N |
| ATOM | 1158 | CA | BARG | A | 293 | −7.717 | 41.112 | 4.172 | 0.502 | 8.54 | | C |
| ANISOU | 1158 | CA | BARG | A | 293 | 3749 | 3572 | 3522 | 1162 | −749 | 731 | C |
| ATOM | 1159 | CB | BARG | A | 293 | −6.208 | 41.132 | 3.979 | 0.50 | 30.71 | | C |
| ANISOU | 1159 | CB | BARG | A | 293 | 3637 | 4297 | 3736 | 1357 | −854 | 813 | C |
| ATOM | 1160 | CG | BARG | A | 293 | −5.693 | 40.027 | 3.113 | 0.50 | 38.39 | | C |
| ANISOU | 1160 | CG | BARG | A | 293 | 4608 | 5003 | 4975 | 1634 | −611 | 899 | C |
| ATOM | 1161 | CD | BARG | A | 293 | −6.010 | 38.649 | 3.692 | 0.50 | 48.55 | | C |
| ANISOU | 1161 | CD | BARG | A | 293 | 6096 | 5980 | 6372 | 1834 | −379 | 1113 | C |
| ATOM | 1162 | NE | BARG | A | 293 | −5.060 | 37.673 | 3.176 | 0.50 | 61.22 | | N |
| ANISOU | 1162 | NE | BARG | A | 293 | 7586 | 7514 | 8160 | 2110 | −157 | 1231 | N |
| ATOM | 1163 | CZ | BARG | A | 293 | −5.336 | 36.394 | 2.934 | 0.50 | 65.64 | | C |
| ANISOU | 1163 | CZ | BARG | A | 293 | 8349 | 7653 | 8937 | 2240 | 199 | 1280 | C |
| ATOM | 1164 | NH1 | BARG | A | 293 | −4.386 | 35.590 | 2.471 | 0.50 | 58.47 | | N |
| ANISOU | 1164 | NH1 | BARG | A | 293 | 7326 | 6696 | 8196 | 2490 | 440 | 1404 | N |
| ATOM | 1165 | NH2 | BARG | A | 293 | −6.551 | 35.921 | 3.161 | 0.50 | 68.43 | | N |
| ANISOU | 1165 | NH2 | BARG | A | 293 | 8999 | 7655 | 9347 | 2088 | 345 | 1191 | N |
| ATOM | 1166 | N | THR | A | 294 | −8.104 | 43.397 | 4.820 | 1.00 | 23.14 | | N |
| ANISOU | 1166 | N | THR | A | 294 | 2965 | 3225 | 2601 | 494 | −939 | 369 | N |
| ATOM | 1167 | CA | THR | A | 294 | −8.306 | 44.526 | 5.720 | 1.00 | 23.71 | | C |
| ANISOU | 1167 | CA | THR | A | 294 | 3012 | 3509 | 2487 | 137 | −983 | 199 | C |
| ATOM | 1168 | CB | THR | A | 294 | −8.058 | 45.852 | 5.002 | 1.00 | 24.41 | | C |
| ANISOU | 1168 | CB | THR | A | 294 | 2954 | 3618 | 2702 | −208 | −892 | −85 | C |
| ATOM | 1169 | OG1 | THR | A | 294 | −6.707 | 45.837 | 4.495 | 1.00 | 27.60 | | O |
| ANISOU | 1169 | OG1 | THR | A | 294 | 3023 | 4383 | 3079 | −113 | −987 | −120 | O |
| ATOM | 1170 | CG2 | THR | A | 294 | −8.175 | 47.040 | 6.016 | 1.00 | 22.45 | | C |
| ANISOU | 1170 | CG2 | THR | A | 294 | 2683 | 3550 | 2297 | −634 | −820 | −333 | C |
| ATOM | 1171 | C | THR | A | 294 | −9.737 | 44.462 | 6.265 | 1.00 | 25.64 | | C |
| ANISOU | 1171 | C | THR | A | 294 | 3603 | 3353 | 2784 | 38 | −854 | 231 | C |
| ATOM | 1172 | O | THR | A | 294 | −9.985 | 44.618 | 7.459 | 1.00 | 23.05 | | O |
| ANISOU | 1172 | O | THR | A | 294 | 3359 | 3174 | 2226 | −64 | −872 | 245 | O |
| ATOM | 1173 | N | LEU | A | 295 | −10.668 | 44.186 | 5.380 | 1.00 | 19.55 | | N |
| ANISOU | 1173 | N | LEU | A | 295 | 3010 | 2125 | 2293 | 61 | −719 | 238 | N |
| ATOM | 1174 | CA | LEU | A | 295 | −12.070 | 44.118 | 5.782 | 1.00 | 27.49 | | C |
| ANISOU | 1174 | CA | LEU | A | 295 | 4286 | 2753 | 3406 | −39 | −580 | 264 | C |
| ATOM | 1175 | CB | LEU | A | 295 | −12.946 | 44.000 | 4.518 | 1.00 | 23.99 | | C |
| ANISOU | 1175 | CB | LEU | A | 295 | 3783 | 2118 | 3214 | −66 | −421 | 194 | C |
| ATOM | 1176 | CG | LEU | A | 295 | −14.439 | 44.027 | 4.824 | 1.00 | 26.60 | | C |
| ANISOU | 1176 | CG | LEU | A | 295 | 3980 | 2471 | 3654 | −120 | −156 | 160 | C |
| ATOM | 1177 | CD1 | LEU | A | 295 | −14.795 | 45.397 | 5.476 | 1.00 | 23.35 | | C |
| ANISOU | 1177 | CD1 | LEU | A | 295 | 3524 | 2093 | 3254 | −271 | −90 | 113 | C |
| ATOM | 1178 | CD2 | LEU | A | 295 | −15.279 | 43.771 | 3.546 | 1.00 | 25.45 | | C |
| ANISOU | 1178 | CD2 | LEU | A | 295 | 3748 | 2331 | 3591 | −132 | −100 | 118 | C |
| ATOM | 1179 | C | LEU | A | 295 | −12.327 | 42.936 | 6.742 | 1.00 | 26.13 | | C |
| ANISOU | 1179 | C | LEU | A | 295 | 4309 | 2489 | 3129 | 211 | −555 | 482 | C |
| ATOM | 1180 | O | LEU | A | 295 | −13.095 | 43.015 | 7.727 | 1.00 | 28.42 | | O |
| ANISOU | 1180 | O | LEU | A | 295 | 4792 | 2662 | 3346 | 119 | −468 | 522 | O |
| ATOM | 1181 | N | GLU | A | 296 | −11.705 | 41.808 | 6.434 | 1.00 | 23.16 | | N |
| ANISOU | 1181 | N | GLU | A | 296 | 3891 | 2125 | 2782 | 545 | −551 | 644 | N |
| ATOM | 1182 | CA | GLU | A | 296 | −11.740 | 40.659 | 7.318 | 1.00 | 25.88 | | C |
| ANISOU | 1182 | CA | GLU | A | 296 | 4254 | 2476 | 3104 | 772 | −413 | 873 | C |
| ATOM | 1183 | CB | GLU | A | 296 | −10.810 | 39.574 | 6.787 | 1.00 | 34.10 | | C |
| ANISOU | 1183 | CB | GLU | A | 296 | 5148 | 3539 | 4269 | 1054 | −361 | 1003 | C |
| ATOM | 1184 | CG | GLU | A | 296 | −11.558 | 38.389 | 6.269 | 1.00 | 64.30 | | C |

TABLE 6-continued

| DMXAA-hSTING$^{group2}$ complex | | | | | | | | | | | |
|---|---|---|---|---|---|---|---|---|---|---|---|
| ANISOU | 1184 | CG | GLU | A | 296 | 9052 | 6977 | 8403 | 1017 | −104 | 899 | C |
| ATOM | 1185 | CD | GLU | A | 296 | −10.662 | 37.329 | 5.640 | 1.00 | 92.01 | | C |
| ANISOU | 1185 | CD | GLU | A | 296 | 12513 | 10415 | 12030 | 1277 | 34 | 968 | C |
| ATOM | 1186 | OE1 | GLU | A | 296 | −9.438 | 37.569 | 5.472 | 1.00 | 96.61 | | O |
| ANISOU | 1186 | OE1 | GLU | A | 296 | 12926 | 11261 | 12521 | 1486 | −77 | 1096 | C |
| ATOM | 1187 | OE2 | GLU | A | 296 | −11.205 | 36.248 | 5.314 | 1.00 | 97.93 | | O |
| ANISOU | 1187 | OE2 | GLU | A | 296 | 13370 | 10877 | 12959 | 1262 | 285 | 882 | 0 |
| ATOM | 1188 | C | GLU | A | 296 | −11.304 | 41.045 | 8.723 | 1.00 | 33.80 | | C |
| ANISOU | 1188 | C | GLU | A | 296 | 5291 | 3878 | 3672 | 841 | −590 | 1063 | C |
| ATOM | 1189 | O | GLU | A | 296 | −11.938 | 40.680 | 9.731 | 1.00 | 31.61 | | O |
| ANISOU | 1189 | O | GLU | A | 296 | 5157 | 3531 | 3322 | 843 | −472 | 1181 | O |
| ATOM | 1190 | N | ASP | A | 297 | −10.197 | 41.771 | 8.802 | 1.00 | 32.22 | | N |
| ANISOU | 1190 | N | ASP | A | 297 | 4822 | 4229 | 3189 | 796 | −846 | 1009 | N |
| ATOM | 1191 | CA | ASP | A | 297 | −9.658 | 42.169 | 10.099 | 1.00 | 37.60 | | C |
| ANISOU | 1191 | CA | ASP | A | 297 | 5365 | 5539 | 3381 | 726 | −1027 | 1076 | C |
| ATOM | 1192 | CB | ASP | A | 297 | −8.272 | 42.775 | 9.944 | 1.00 | 44.36 | | C |
| ANISOU | 1192 | CB | ASP | A | 297 | 5780 | 7001 | 4073 | 616 | −1252 | 921 | C |
| ATOM | 1193 | CG | ASP | A | 297 | −7.233 | 41.739 | 9.555 | 1.00 | 66.67 | | C |
| ANISOU | 1193 | CG | ASP | A | 297 | 8385 | 9874 | 7073 | 1016 | −1250 | 1178 | C |
| ATOM | 1194 | OD1 | ASP | A | 297 | −7.503 | 40.534 | 9.776 | 1.00 | 70.41 | | O |
| ANISOU | 1194 | OD1 | ASP | A | 297 | 9017 | 10049 | 7688 | 1342 | −1080 | 1480 | O |
| ATOM | 1195 | OD2 | ASP | A | 297 | −6.158 | 42.129 | 9.028 | 1.00 | 73.49 | | O |
| ANISOU | 1195 | OD2 | ASP | A | 297 | 8917 | 11044 | 7961 | 972 | −1353 | 1051 | O |
| ATOM | 1196 | C | ASP | A | 297 | −10.557 | 43.156 | 10.830 | 1.00 | 33.25 | | C |
| ANISOU | 1196 | C | ASP | A | 297 | 5015 | 4913 | 2707 | 267 | −941 | 799 | C |
| ATOM | 1197 | O | ASP | A | 297 | −10.671 | 43.123 | 12.052 | 1.00 | 34.91 | | O |
| ANISOU | 1197 | O | ASP | A | 297 | 5309 | 5427 | 2528 | 232 | −967 | 896 | O |
| ATOM | 1198 | N | ILE | A | 298 | −11.150 | 44.071 | 10.084 | 1.00 | 28.81 | | N |
| ANISOU | 1198 | N | ILE | A | 298 | 4510 | 3979 | 2458 | −74 | −806 | 477 | N |
| ATOM | 1199 | CA | ILE | A | 298 | −12.064 | 45.027 | 10.713 | 1.00 | 28.98 | | C |
| ANISOU | 1199 | CA | ILE | A | 298 | 4725 | 3817 | 2469 | −483 | −614 | 237 | C |
| ATOM | 1200 | CB | ILE | A | 298 | −12.577 | 46.047 | 9.680 | 1.00 | 27.53 | | C |
| ANISOU | 1200 | CB | ILE | A | 298 | 4522 | 3234 | 2704 | −754 | −425 | −8 | C |
| ATOM | 1201 | CG1 | ILE | A | 298 | −11.447 | 46.978 | 9.281 | 1.00 | 31.04 | | C |
| ANISOU | 1201 | CG1 | ILE | A | 298 | 4656 | 4056 | 3083 | −975 | −492 | −260 | C |
| ATOM | 1202 | CD1 | ILE | A | 298 | −11.771 | 47.768 | 7.965 | 1.00 | 27.07 | | C |
| ANISOU | 1202 | CD1 | ILE | A | 298 | 4100 | 3166 | 3020 | −1079 | −299 | −352 | C |
| ATOM | 1203 | CG2 | ILE | A | 298 | −13.699 | 46.919 | 10.297 | 1.00 | 30.85 | | C |
| ANISOU | 1203 | CG2 | ILE | A | 298 | 5165 | 3320 | 3237 | −1095 | −113 | −172 | C |
| ATOM | 1204 | C | ILE | A | 298 | −13.257 | 44.295 | 11.319 | 1.00 | 29.64 | | C |
| ANISOU | 1204 | C | ILE | A | 298 | 5161 | 3480 | 2619 | −349 | −435 | 442 | C |
| ATOM | 1205 | O | ILE | A | 298 | −13.645 | 44.516 | 12.477 | 1.00 | 31.48 | | O |
| ANISOU | 1205 | O | ILE | A | 298 | 5562 | 3819 | 2579 | −510 | −343 | 416 | O |
| ATOM | 1206 | N | LEU | A | 299 | −13.834 | 43.388 | 10.538 | 1.00 | 28.35 | | N |
| ANISOU | 1206 | N | LEU | A | 299 | 5112 | 2850 | 2809 | −85 | −353 | 614 | N |
| ATOM | 1207 | CA | LEU | A | 299 | −15.025 | 42.662 | 10.982 | 1.00 | 32.92 | | C |
| ANISOU | 1207 | CA | LEU | A | 299 | 5823 | 3085 | 3601 | 6 | −112 | 680 | C |
| ATOM | 1208 | CB | LEU | A | 299 | −15.672 | 41.901 | 9.827 | 1.00 | 32.64 | | C |
| ANISOU | 1208 | CB | LEU | A | 299 | 5418 | 2943 | 4042 | 93 | −7 | 570 | C |
| ATOM | 1209 | CG | LEU | A | 299 | −16.196 | 42.848 | 8.772 | 1.00 | 33.61 | | C |
| ANISOU | 1209 | CG | LEU | A | 299 | 5250 | 3131 | 4390 | −85 | 2 | 354 | C |
| ATOM | 1210 | CD1 | LEU | A | 299 | −16.715 | 42.104 | 7.559 | 1.00 | 31.95 | | C |
| ANISOU | 1210 | CD1 | LEU | A | 299 | 4916 | 2871 | 4352 | −39 | 23 | 301 | C |
| ATOM | 1211 | CD2 | LEU | A | 299 | −17.313 | 43.679 | 9.394 | 1.00 | 40.66 | | C |
| ANISOU | 1211 | CD2 | LEU | A | 299 | 6172 | 4005 | 5271 | −231 | 109 | 259 | C |
| ATOM | 1212 | C | LEU | A | 299 | −14.793 | 41.726 | 12.149 | 1.00 | 38.69 | | C |
| ANISOU | 1212 | C | LEU | A | 299 | 6669 | 3986 | 4045 | 270 | −94 | 985 | C |
| ATOM | 1213 | O | LEU | A | 299 | −15.705 | 41.484 | 12.936 | 1.00 | 38.48 | | O |
| ANISOU | 1213 | O | LEU | A | 299 | 6751 | 3800 | 4071 | 227 | 93 | 983 | O |
| ATOM | 1214 | N | ALA | A | 300 | −13.581 | 41.191 | 12.271 | 1.00 | 40.24 | | N |
| ANISOU | 1214 | N | ALA | A | 300 | 6026 | 5491 | 3774 | 763 | −1795 | −692 | N |
| ATOM | 1215 | CA | ALA | A | 300 | −13.261 | 40.311 | 13.377 | 1.00 | 43.79 | | C |
| ANISOU | 1215 | CA | ALA | A | 300 | 6719 | 6087 | 3831 | 930 | −2090 | −539 | C |
| ATOM | 1216 | CB | ALA | A | 300 | −11.841 | 39.830 | 13.268 | 1.00 | 46.61 | | C |
| ANISOU | 1216 | CB | ALA | A | 300 | 6935 | 6377 | 4399 | 1113 | −2462 | −657 | C |
| ATOM | 1217 | C | ALA | A | 300 | −13.471 | 41.036 | 14.708 | 1.00 | 56.03 | | C |
| ANISOU | 1217 | C | ALA | A | 300 | 8381 | 7949 | 4961 | 975 | −2163 | −723 | C |
| ATOM | 1218 | O | ALA | A | 300 | −13.824 | 40.430 | 15.710 | 1.00 | 72.09 | | O |
| ANISOU | 1218 | O | ALA | A | 300 | 10734 | 10144 | 6513 | 1059 | −2245 | −509 | O |
| ATOM | 1219 | N | ASP | A | 301 | −13.254 | 42.347 | 14.697 | 1.00 | 54.94 | | N |
| ANISOU | 1219 | N | ASP | A | 301 | 7987 | 7878 | 5009 | 911 | −2101 | −1129 | N |
| ATOM | 1220 | CA | ASP | A | 301 | −13.354 | 43.184 | 15.884 | 1.00 | 59.31 | | C |
| ANISOU | 1220 | CA | ASP | A | 301 | 8566 | 8733 | 5237 | 936 | −2162 | −1410 | C |
| ATOM | 1221 | CB | ASP | A | 301 | −12.391 | 44.356 | 15.738 | 1.00 | 73.05 | | C |
| ANISOU | 1221 | CB | ASP | A | 301 | 9929 | 10474 | 7353 | 934 | −2239 | −1942 | C |
| ATOM | 1222 | CG | ASP | A | 301 | −10.962 | 44.004 | 16.101 | 1.00 | 89.11 | | C |
| ANISOU | 1222 | CG | ASP | A | 301 | 11823 | 12603 | 9432 | 1145 | −2689 | −2178 | C |
| ATOM | 1223 | OD1 | ASP | A | 301 | −10.618 | 42.802 | 16.176 | 1.00 | 89.10 | | O |

TABLE 6-continued

| | | | | | DMXAA-hSTING$^{group2}$ complex | | | | | | |
|---|---|---|---|---|---|---|---|---|---|---|---|
| ANISOU | 1223 | OD1 | ASP | A | 301 | 11996 | 12585 | 9273 | 1311 | −2947 | −1882 | O |
| ATOM | 1224 | OD2 | ASP | A | 301 | −10.178 | 44.957 | 16.315 | 1.00 | 97.29 | | O |
| ANISOU | 1224 | OD2 | ASP | A | 301 | 12548 | 13704 | 10713 | 1141 | −2745 | −2666 | O |
| ATOM | 1225 | C | ASP | A | 301 | −14.741 | 43.798 | 16.075 | 1.00 | 55.68 | | C |
| ANISOU | 1225 | C | ASP | A | 301 | 8205 | 8337 | 4614 | 756 | −1783 | −1368 | C |
| ATOM | 1226 | O | ASP | A | 301 | −15.158 | 44.107 | 17.194 | 1.00 | 54.35 | | O |
| ANISOU | 1226 | O | ASP | A | 301 | 8181 | 8438 | 4031 | 759 | −1786 | −1463 | O |
| ATOM | 1227 | N | ALA | A | 302 | −15.422 | 44.061 | 14.986 | 1.00 | 44.64 | | N |
| ANISOU | 1227 | N | ALA | A | 302 | 6706 | 6704 | 3551 | 614 | −1467 | −1265 | N |
| ATOM | 1228 | CA | ALA | A | 302 | −16.572 | 44.919 | 15.014 | 1.00 | 49.48 | | C |
| ANISOU | 1228 | CA | ALA | A | 302 | 7288 | 7346 | 4164 | 472 | −1127 | −1354 | C |
| ATOM | 1229 | CB | ALA | A | 302 | −16.998 | 45.269 | 13.638 | 1.00 | 41.37 | | C |
| ANISOU | 1229 | CB | ALA | A | 302 | 6111 | 6047 | 3561 | 394 | −867 | −1269 | C |
| ATOM | 1230 | C | ALA | A | 302 | −17.726 | 44.394 | 15.810 | 1.00 | 54.00 | | C |
| ANISOU | 1230 | C | ALA | A | 302 | 8150 | 8100 | 4268 | 407 | −984 | −1139 | C |
| ATOM | 1231 | O | ALA | A | 302 | −18.061 | 43.256 | 15.724 | 1.00 | 53.72 | | O |
| ANISOU | 1231 | O | ALA | A | 302 | 8331 | 8008 | 4070 | 402 | −962 | −784 | O |
| ATOM | 1232 | N | PRO | A | 303 | −18.327 | 45.276 | 16.582 | 1.00 | 52.89 | | N |
| ANISOU | 1232 | N | PRO | A | 303 | 8002 | 8152 | 3942 | 336 | −840 | −1380 | N |
| ATOM | 1233 | CA | PRO | A | 303 | −19.465 | 44.951 | 17.415 | 1.00 | 50.54 | | C |
| ANISOU | 1233 | CA | PRO | A | 303 | 7968 | 8041 | 3195 | 243 | −653 | −1246 | C |
| ATOM | 1234 | CB | PRO | A | 303 | −19.705 | 46.233 | 18.174 | 1.00 | 62.06 | | C |
| ANISOU | 1234 | CB | PRO | A | 303 | 9313 | 9715 | 4553 | 192 | −570 | −1658 | C |
| ATOM | 1235 | CG | PRO | A | 303 | −19.162 | 47.258 | 17.354 | 1.00 | 67.17 | | C |
| ANISOU | 1235 | CG | PRO | A | 303 | 9607 | 10168 | 5747 | 207 | −550 | −1943 | C |
| ATOM | 1236 | CD | PRO | A | 303 | −17.978 | 46.689 | 16.695 | 1.00 | 58.92 | | C |
| ANISOU | 1236 | CD | PRO | A | 303 | 8502 | 8954 | 4932 | 325 | −817 | −1828 | C |
| ATOM | 1237 | C | PRO | A | 303 | −20.685 | 44.565 | 16.619 | 1.00 | 53.93 | | C |
| ANISOU | 1237 | C | PRO | A | 303 | 8405 | 8318 | 3769 | 106 | −311 | −1039 | C |
| ATOM | 1238 | O | PRO | A | 303 | −21.444 | 43.768 | 17.109 | 1.00 | 60.62 | | O |
| ANISOU | 1238 | O | PRO | A | 303 | 9498 | 9253 | 4283 | 16 | −143 | −852 | O |
| ATOM | 1239 | N | GLU | A | 304 | −20.901 | 45.155 | 15.446 | 1.00 | 42.81 | | N |
| ANISOU | 1239 | N | GLU | A | 304 | 6744 | 6699 | 2823 | 95 | −193 | −1091 | N |
| ATOM | 1240 | CA | GLU | A | 304 | −22.109 | 44.852 | 14.678 | 1.00 | 60.92 | | C |
| ANISOU | 1240 | CA | GLU | A | 304 | 9003 | 8908 | 5235 | −3 | 99 | −965 | C |
| ATOM | 1241 | CB | GLU | A | 304 | −22.564 | 45.952 | 13.730 | 1.00 | 60.83 | | C |
| ANISOU | 1241 | CB | GLU | A | 304 | 8716 | 8776 | 5621 | 21 | 251 | −1161 | C |
| ATOM | 1242 | CG | GLU | A | 304 | −21.537 | 46.827 | 13.166 | 1.00 | 65.41 | | C |
| ANISOU | 1242 | CG | GLU | A | 304 | 9126 | 9176 | 6551 | 131 | 107 | −1270 | C |
| ATOM | 1243 | CD | GLU | A | 304 | −20.866 | 47.708 | 14.171 | 1.00 | 71.45 | | C |
| ANISOU | 1243 | CD | GLU | A | 304 | 9828 | 10036 | 7283 | 146 | 17 | −1599 | C |
| ATOM | 1244 | OE1 | GLU | A | 304 | −21.430 | 48.734 | 14.578 | 1.00 | 63.77 | | O |
| ANISOU | 1244 | OE1 | GLU | A | 304 | 8784 | 9152 | 6292 | 103 | 185 | −1845 | O |
| ATOM | 1245 | OE2 | GLU | A | 304 | −19.739 | 47.382 | 14.512 | 1.00 | 74.99 | | O |
| ANISOU | 1245 | OE2 | GLU | A | 304 | 10272 | 10479 | 7742 | 204 | −228 | −1646 | O |
| ATOM | 1246 | C | GLU | A | 304 | −22.184 | 43.470 | 14.059 | 1.00 | 61.21 | | C |
| ANISOU | 1246 | C | GLU | A | 304 | 9130 | 8796 | 5331 | −9 | 87 | −632 | C |
| ATOM | 1247 | O | GLU | A | 304 | −23.201 | 43.097 | 13.576 | 1.00 | 54.22 | | O |
| ANISOU | 1247 | O | GLU | A | 304 | 8172 | 7846 | 4583 | −79 | 298 | −565 | O |
| ATOM | 1248 | N | SER | A | 305 | −21.090 | 42.735 | 14.041 | 1.00 | 69.16 | | N |
| ANISOU | 1248 | N | SER | A | 305 | 10274 | 9757 | 6246 | 73 | −167 | −459 | N |
| ATOM | 1249 | CA | SER | A | 305 | −21.158 | 41.320 | 13.756 | 1.00 | 71.04 | | C |
| ANISOU | 1249 | CA | SER | A | 305 | 10644 | 9852 | 6495 | 58 | −162 | −140 | C |
| ATOM | 1250 | CB | SER | A | 305 | −20.544 | 41.117 | 12.405 | 1.00 | 59.16 | | C |
| ANISOU | 1250 | CB | SER | A | 305 | 8912 | 8138 | 5428 | 117 | −253 | −116 | C |
| ATOM | 1251 | OG | SER | A | 305 | −19.179 | 41.315 | 12.512 | 1.00 | 57.25 | | O |
| ANISOU | 1251 | OG | SER | A | 305 | 8655 | 7847 | 5252 | 249 | −570 | −141 | O |
| ATOM | 1252 | C | SER | A | 305 | −20.340 | 40.639 | 14.860 | 1.00 | 88.37 | | C |
| ANISOU | 1252 | C | SER | A | 305 | 13115 | 12092 | 8370 | 164 | −420 | 37 | C |
| ATOM | 1253 | O | SER | A | 305 | −19.185 | 40.967 | 14.956 | 1.00 | 103.54 | | O |
| ANISOU | 1253 | O | SER | A | 305 | 14946 | 13987 | 10408 | 310 | −730 | −44 | O |
| ATOM | 1254 | N | GLN | A | 306 | −20.792 | 39.670 | 15.657 | 1.00 | 91.87 | | N |
| ANISOU | 1254 | N | GLN | A | 306 | 13899 | 12590 | 8417 | 118 | −310 | 268 | N |
| ATOM | 1255 | CA | GLN | A | 306 | −22.160 | 39.115 | 15.826 | 1.00 | 86.51 | | C |
| ANISOU | 1255 | CA | GLN | A | 306 | 13372 | 11915 | 7582 | −81 | 97 | 375 | C |
| ATOM | 1256 | CB | GLN | A | 306 | −23.169 | 40.227 | 16.174 | 1.00 | 83.78 | | C |
| ANISOU | 1256 | CB | GLN | A | 306 | 12897 | 11760 | 7178 | −212 | 345 | 73 | C |
| ATOM | 1257 | CG | GLN | A | 306 | −22.810 | 40.988 | 17.422 | 1.00 | 81.90 | | C |
| ANISOU | 1257 | CG | GLN | A | 306 | 12788 | 11777 | 6555 | −155 | 215 | −99 | C |
| ATOM | 1258 | CD | GLN | A | 306 | −24.027 | 41.364 | 18.238 | 1.00 | 92.08 | | C |
| ANISOU | 1258 | CD | GLN | A | 306 | 14169 | 13244 | 7573 | −339 | 570 | −246 | C |
| ATOM | 1259 | OE1 | GLN | A | 306 | −25.110 | 41.576 | 17.690 | 1.00 | 98.93 | | O |
| ANISOU | 1259 | OE1 | GLN | A | 306 | 14846 | 14063 | 8681 | −486 | 872 | −366 | O |
| ATOM | 1260 | NE2 | GLN | A | 306 | −23.862 | 41.433 | 19.558 | 1.00 | 95.02 | | N |
| ANISOU | 1260 | NE2 | GLN | A | 306 | 14787 | 13838 | 7477 | −309 | 523 | −257 | N |
| ATOM | 1261 | C | GLN | A | 306 | −22.757 | 38.154 | 14.785 | 1.00 | 68.32 | | C |
| ANISOU | 1261 | C | GLN | A | 306 | 11024 | 9380 | 5553 | −195 | 326 | 562 | C |
| ATOM | 1262 | O | GLN | A | 306 | −23.966 | 38.190 | 14.551 | 1.00 | 63.46 | | O |

TABLE 6-continued

DMXAA-hSTING$^{group2}$ complex

| | | | | | | | | | | | | |
|---|---|---|---|---|---|---|---|---|---|---|---|---|
| ANISOU | 1262 | O | GLN | A | 306 | 10370 | 8778 | 4965 | −379 | 685 | 500 | O |
| ATOM | 1263 | N | ASN | A | 307 | −21.937 | 37.292 | 14.191 | 1.00 | 56.05 | | N |
| ANISOU | 1263 | N | ASN | A | 307 | 9461 | 7627 | 4209 | −92 | 130 | 751 | N |
| ATOM | 1264 | CA | ASN | A | 307 | −22.425 | 36.170 | 13.380 | 1.00 | 58.66 | | C |
| ANISOU | 1264 | CA | ASN | A | 307 | 9758 | 7736 | 4793 | −203 | 345 | 912 | C |
| ATOM | 1265 | CB | ASN | A | 307 | −23.004 | 35.045 | 14.237 | 1.00 | 68.96 | | C |
| ANISOU | 1265 | CB | ASN | A | 307 | 11451 | 8950 | 5800 | −312 | 617 | 1182 | C |
| ATOM | 1266 | CG | ASN | A | 307 | −22.011 | 33.941 | 14.480 | 1.00 | 81.43 | | C |
| ANISOU | 1266 | CG | ASN | A | 307 | 13307 | 10325 | 7308 | −153 | 405 | 1517 | C |
| ATOM | 1267 | OD1 | ASN | A | 307 | −21.976 | 32.949 | 13.745 | 1.00 | 92.50 | | O |
| ANISOU | 1267 | OD1 | ASN | A | 307 | 14667 | 11476 | 9003 | −193 | 492 | 1658 | O |
| ATOM | 1268 | ND2 | ASN | A | 307 | −21.178 | 34.111 | 15.500 | 1.00 | 80.70 | | N |
| ANISOU | 1268 | ND2 | ASN | A | 307 | 13479 | 10348 | 6836 | 48 | 106 | 1620 | N |
| ATOM | 1269 | C | ASN | A | 307 | −23.490 | 36.667 | 12.423 | 1.00 | 57.58 | | C |
| ANISOU | 1269 | C | ASN | A | 307 | 9288 | 7637 | 4951 | −342 | 597 | 675 | C |
| ATOM | 1270 | O | ASN | A | 307 | −24.595 | 36.113 | 12.339 | 1.00 | 55.42 | | O |
| ANISOU | 1270 | O | ASN | A | 307 | 9018 | 7334 | 4706 | −520 | 942 | 668 | O |
| ATOM | 1271 | N | ASN | A | 308 | −23.133 | 37.736 | 11.730 | 1.00 | 52.50 | | N |
| ANISOU | 1271 | N | ASN | A | 308 | 8364 | 7059 | 4525 | −246 | 427 | 464 | N |
| ATOM | 1272 | CA | ASN | A | 308 | −24.075 | 38.566 | 11.002 | 1.00 | 51.54 | | C |
| ANISOU | 1272 | CA | ASN | A | 308 | 7957 | 7026 | 4601 | −294 | 596 | 217 | C |
| ATOM | 1273 | CB | ASN | A | 308 | −23.983 | 39.972 | 11.566 | 1.00 | 44.59 | | C |
| ANISOU | 1273 | CB | ASN | A | 308 | 7029 | 6303 | 3611 | −227 | 520 | 5 | C |
| ATOM | 1274 | CG | ASN | A | 308 | −25.271 | 40.420 | 12.144 | 1.00 | 68.41 | | C |
| ANISOU | 1274 | CG | ASN | A | 308 | 10031 | 9476 | 6485 | −350 | 804 | −170 | C |
| ATOM | 1275 | OD1 | ASN | A | 308 | −26.299 | 39.775 | 11.944 | 1.00 | 78.84 | | O |
| ANISOU | 1275 | OD1 | ASN | A | 308 | 11317 | 10794 | 7844 | −485 | 1067 | −177 | O |
| ATOM | 1276 | ND2 | ASN | A | 308 | −25.240 | 41.524 | 12.884 | 1.00 | 71.94 | | N |
| ANISOU | 1276 | ND2 | ASN | A | 308 | 10478 | 10064 | 6793 | −319 | 773 | −360 | N |
| ATOM | 1277 | C | ASN | A | 308 | −23.700 | 38.671 | 9.546 | 1.00 | 38.43 | | C |
| ANISOU | 1277 | C | ASN | A | 308 | 6029 | 5263 | 3310 | −208 | 485 | 175 | C |
| ATOM | 1278 | O | ASN | A | 308 | −24.503 | 39.025 | 8.668 | 1.00 | 31.35 | | O |
| ANISOU | 1278 | O | ASN | A | 308 | 4901 | 4413 | 2596 | −213 | 612 | 26 | O |
| ATOM | 1279 | N | CYS | A | 309 | −22.436 | 38.403 | 9.299 | 1.00 | 32.05 | | N |
| ANISOU | 1279 | N | CYS | A | 309 | 5253 | 4329 | 2597 | −107 | 232 | 289 | N |
| ATOM | 1280 | CA | CYS | A | 309 | −21.873 | 38.739 | 8.016 | 1.00 | 30.24 | | C |
| ANISOU | 1280 | CA | CYS | A | 309 | 4798 | 4010 | 2684 | −20 | 121 | 223 | C |
| ATOM | 1281 | CB | CYS | A | 309 | −21.243 | 40.124 | 8.161 | 1.00 | 40.98 | | C |
| ANISOU | 1281 | CB | CYS | A | 309 | 6094 | 5408 | 4068 | 87 | −9 | 58 | C |
| ATOM | 1282 | SG | CYS | A | 309 | −20.620 | 40.771 | 6.675 | 1.00 | 43.61 | | S |
| ANISOU | 1282 | SG | CYS | A | 309 | 6210 | 5613 | 4749 | 183 | −59 | −25 | S |
| ATOM | 1283 | C | CYS | A | 309 | −20.802 | 37.714 | 7.700 | 1.00 | 33.97 | | C |
| ANISOU | 1283 | C | CYS | A | 309 | 5314 | 4306 | 3288 | 12 | −53 | 386 | C |
| ATOM | 1284 | O | CYS | A | 309 | −20.087 | 37.274 | 8.590 | 1.00 | 33.95 | | O |
| ANISOU | 1284 | O | CYS | A | 309 | 5503 | 4265 | 3130 | 56 | −213 | 506 | O |
| ATOM | 1285 | N | ARG | A | 310 | −20.682 | 37.332 | 6.437 | 1.00 | 27.49 | | N |
| ANISOU | 1285 | N | ARG | A | 310 | 4312 | 3388 | 2742 | 10 | −35 | 378 | N |
| ATOM | 1286 | CA | ARG | A | 310 | −19.639 | 36.403 | 6.028 | 1.00 | 27.36 | | C |
| ANISOU | 1286 | CA | ARG | A | 310 | 4292 | 3193 | 2912 | 37 | −190 | 488 | C |
| ATOM | 1287 | CB | ARG | A | 310 | −20.220 | 35.011 | 5.845 | 1.00 | 31.43 | | C |
| ANISOU | 1287 | CB | ARG | A | 310 | 4844 | 3614 | 3483 | −74 | −29 | 619 | C |
| ATOM | 1288 | CG | ARG | A | 310 | −19.161 | 33.962 | 5.568 | 1.00 | 47.33 | | C |
| ANISOU | 1288 | CG | ARG | A | 310 | 6871 | 5412 | 5699 | −37 | −183 | 742 | C |
| ATOM | 1289 | CD | ARG | A | 310 | −18.592 | 33.453 | 6.871 | 1.00 | 69.84 | | C |
| ANISOU | 1289 | CD | ARG | A | 310 | 10016 | 8185 | 8336 | 42 | −336 | 942 | C |
| ATOM | 1290 | NE | ARG | A | 310 | −17.935 | 32.159 | 6.714 | 1.00 | 89.65 | | N |
| ANISOU | 1290 | NE | ARG | A | 310 | 12580 | 10452 | 11032 | 74 | −414 | 1105 | N |
| ATOM | 1291 | CZ | ARG | A | 310 | −18.543 | 30.988 | 6.886 | 1.00 | 99.47 | | C |
| ANISOU | 1291 | CZ | ARG | A | 310 | 13965 | 11542 | 12287 | −23 | −196 | 1280 | C |
| ATOM | 1292 | NH1 | ARG | A | 310 | −17.866 | 29.854 | 6.726 | 1.00 | 100.90 | | N |
| ANISOU | 1292 | NH1 | ARG | A | 310 | 14193 | 11466 | 12680 | 29 | −272 | 1425 | N |
| ATOM | 1293 | NH2 | ARG | A | 310 | −19.829 | 30.951 | 7.224 | 1.00 | 101.33 | | N |
| ANISOU | 1293 | NH2 | ARG | A | 310 | 14286 | 11859 | 12355 | −178 | 124 | 1288 | N |
| ATOM | 1294 | C | ARG | A | 310 | −19.074 | 36.889 | 4.688 | 1.00 | 25.08 | | C |
| ANISOU | 1294 | C | ARG | A | 310 | 3776 | 2848 | 2905 | 87 | −236 | 363 | C |
| ATOM | 1295 | O | ARG | A | 310 | −19.835 | 37.176 | 3.778 | 1.00 | 26.01 | | O |
| ANISOU | 1295 | O | ARG | A | 310 | 3754 | 3040 | 3090 | 70 | −85 | 281 | O |
| ATOM | 1296 | N | LEU | A | 311 | −17.744 | 36.995 | 4.588 | 1.00 | 28.48 | | N |
| ANISOU | 1296 | N | LEU | A | 311 | 4175 | 3161 | 3486 | 158 | −439 | 331 | N |
| ATOM | 1297 | CA | LEU | A | 311 | −17.085 | 37.403 | 3.339 | 1.00 | 23.32 | | C |
| ANISOU | 1297 | CA | LEU | A | 311 | 3338 | 2421 | 3102 | 179 | −439 | 214 | C |
| ATOM | 1298 | CB | LEU | A | 311 | −15.748 | 38.080 | 3.637 | 1.00 | 28.59 | | C |
| ANISOU | 1298 | CB | LEU | A | 311 | 3973 | 3002 | 3886 | 247 | −619 | 82 | C |
| ATOM | 1299 | CG | LEU | A | 311 | −15.860 | 39.295 | 4.538 | 1.00 | 35.69 | | C |
| ANISOU | 1299 | CG | LEU | A | 311 | 4937 | 4006 | 4616 | 290 | −630 | −29 | C |
| ATOM | 1300 | CD1 | LEU | A | 311 | −14.510 | 40.015 | 4.593 | 1.00 | 37.69 | | C |
| ANISOU | 1300 | CD1 | LEU | A | 311 | 5085 | 4159 | 5074 | 333 | −760 | −246 | C |
| ATOM | 1301 | CD2 | LEU | A | 311 | −16.935 | 40.205 | 4.008 | 1.00 | 29.42 | | C |

TABLE 6-continued

| DMXAA-hSTING[group2] complex | | | | | | | | | | | |
|---|---|---|---|---|---|---|---|---|---|---|---|
| ANISOU | 1301 | CD2 | LEU | A | 311 | 4122 | 3293 | 3764 | 283 | −399 | −57 | C |
| ATOM | 1302 | C | LEU | A | 311 | −16.757 | 36.143 | 2.527 | 1.00 | 29.04 | | C |
| ANISOU | 1302 | C | LEU | A | 311 | 3971 | 3020 | 4043 | 129 | −445 | 273 | C |
| ATOM | 1303 | O | LEU | A | 311 | −16.204 | 35.180 | 3.075 | 1.00 | 30.33 | | O |
| ANISOU | 1303 | O | LEU | A | 311 | 4206 | 3072 | 4248 | 136 | −579 | 371 | O |
| ATOM | 1304 | N | ILE | A | 312 | −17.059 | 36.174 | 1.231 | 1.00 | 22.31 | | N |
| ANISOU | 1304 | N | ILE | A | 312 | 2970 | 2186 | 3322 | 98 | −308 | 204 | N |
| ATOM | 1305 | CA | ILE | A | 312 | −16.758 | 35.049 | 0.353 | 1.00 | 23.57 | | C |
| ANISOU | 1305 | CA | ILE | A | 312 | 3005 | 2245 | 3706 | 35 | −289 | 202 | C |
| ATOM | 1306 | CB | ILE | A | 312 | −18.021 | 34.471 | −0.217 | 1.00 | 25.02 | | C |
| ANISOU | 1306 | CB | ILE | A | 312 | 3110 | 2553 | 3843 | −35 | −103 | 194 | C |
| ATOM | 1307 | CG1 | ILE | A | 312 | −18.860 | 33.916 | 0.930 | 1.00 | 31.07 | | C |
| ANISOU | 1307 | CG1 | ILE | A | 312 | 4017 | 3344 | 4444 | −92 | −42 | 308 | C |
| ATOM | 1308 | CD1 | ILE | A | 312 | −20.200 | 33.372 | 0.495 | 1.00 | 32.02 | | C |
| ANISOU | 1308 | CD1 | ILE | A | 312 | 4025 | 3592 | 4549 | −186 | 178 | 230 | C |
| ATOM | 1309 | CG2 | ILE | A | 312 | −17.687 | 33.299 | −1.168 | 1.00 | 29.23 | | C |
| ANISOU | 1309 | CG2 | ILE | A | 312 | 3483 | 2987 | 4637 | −116 | −67 | 142 | C |
| ATOM | 1310 | C | ILE | A | 312 | −15.877 | 35.557 | −0.788 | 1.00 | 27.65 | | C |
| ANISOU | 1310 | C | ILE | A | 312 | 3390 | 2694 | 4422 | 51 | −281 | 69 | C |
| ATOM | 1311 | O | ILE | A | 312 | −16.356 | 36.148 | −1.761 | 1.00 | 24.50 | | O |
| ANISOU | 1311 | O | ILE | A | 312 | 2935 | 2395 | 3978 | 71 | −141 | 10 | O |
| ATOM | 1312 | N | ALA | A | 313 | −14.583 | 35.397 | −0.619 | 1.00 | 23.70 | | N |
| ANISOU | 1312 | N | ALA | A | 313 | 2854 | 2027 | 4125 | 60 | −428 | 13 | N |
| ATOM | 1313 | CA | ALA | A | 313 | −13.637 | 35.934 | −1.614 | 1.00 | 24.35 | | C |
| ANISOU | 1313 | CA | ALA | A | 313 | 2817 | 2013 | 4421 | 44 | −376 | −147 | C |
| ATOM | 1314 | CB | ALA | A | 313 | −12.417 | 36.462 | −0.967 | 1.00 | 28.54 | | C |
| ANISOU | 1314 | CB | ALA | A | 313 | 3332 | 2420 | 5092 | 80 | −526 | −272 | C |
| ATOM | 1315 | C | ALA | A | 313 | −13.276 | 34.766 | −2.529 | 1.00 | 28.76 | | C |
| ANISOU | 1315 | C | ALA | A | 313 | 3223 | 2487 | 5218 | −35 | −351 | −195 | C |
| ATOM | 1316 | O | ALA | A | 313 | −13.185 | 33.636 | −2.063 | 1.00 | 27.24 | | O |
| ANISOU | 1316 | O | ALA | A | 313 | 3015 | 2215 | 5120 | −50 | −461 | −128 | O |
| ATOM | 1317 | N | TYR | A | 314 | −13.083 | 35.038 | −3.828 | 1.00 | 24.14 | | N |
| ANISOU | 1317 | N | TYR | A | 314 | 2543 | 1908 | 4721 | −80 | −188 | −307 | N |
| ATOM | 1318 | CA | TYR | A | 314 | −12.761 | 33.964 | −4.788 | 1.00 | 21.36 | | C |
| ANISOU | 1318 | CA | TYR | A | 314 | 2022 | 1502 | 4593 | −172 | −138 | −400 | C |
| ATOM | 1319 | CB | TYR | A | 314 | −13.976 | 33.154 | −5.203 | 1.00 | 25.25 | | C |
| ANISOU | 1319 | CB | TYR | A | 314 | 2468 | 2156 | 4970 | −206 | −49 | −350 | C |
| ATOM | 1320 | CG | TYR | A | 314 | −15.095 | 34.008 | −5.714 | 1.00 | 22.95 | | C |
| ANISOU | 1320 | CG | TYR | A | 314 | 2243 | 2107 | 4370 | −136 | 83 | −324 | C |
| ATOM | 1321 | CD1 | TYR | A | 314 | −15.961 | 34.616 | −4.823 | 1.00 | 26.91 | | C |
| ANISOU | 1321 | CD1 | TYR | A | 314 | 2879 | 2711 | 4633 | −57 | 55 | −207 | C |
| ATOM | 1322 | CE1 | TYR | A | 314 | −16.994 | 35.388 | −5.258 | 1.00 | 28.70 | | C |
| ANISOU | 1322 | CE1 | TYR | A | 314 | 3146 | 3151 | 4606 | 40 | 149 | −201 | C |
| ATOM | 1323 | CZ | TYR | A | 314 | −17.171 | 35.604 | −6.616 | 1.00 | 28.95 | | C |
| ANISOU | 1323 | CZ | TYR | A | 314 | 3119 | 3314 | 4567 | 91 | 256 | −284 | C |
| ATOM | 1324 | OH | TYR | A | 314 | −18.218 | 36.401 | −6.993 | 1.00 | 31.00 | | O |
| ANISOU | 1324 | OH | TYR | A | 314 | 3432 | 3793 | 4553 | 248 | 305 | −267 | O |
| ATOM | 1325 | CE2 | TYR | A | 314 | −16.338 | 35.017 | −7.551 | 1.00 | 28.08 | | C |
| ANISOU | 1325 | CE2 | TYR | A | 314 | 2899 | 3129 | 4642 | 4 | 303 | −391 | C |
| ATOM | 1326 | CD2 | TYR | A | 314 | −15.266 | 34.229 | −7.084 | 1.00 | 26.73 | | C |
| ANISOU | 1326 | CD2 | TYR | A | 314 | 2656 | 2719 | 4783 | −125 | 225 | −424 | C |
| ATOM | 1327 | C | TYR | A | 314 | −12.033 | 34.510 | −5.984 | 1.00 | 32.30 | | C |
| ANISOU | 1327 | C | TYR | A | 314 | 3339 | 2875 | 6057 | −209 | 23 | −547 | C |
| ATOM | 1328 | O | TYR | A | 314 | −12.129 | 35.713 | −6.306 | 1.00 | 24.86 | | O |
| ANISOU | 1328 | O | TYR | A | 314 | 2510 | 1940 | 4997 | −173 | 155 | −550 | O |
| ATOM | 1329 | N | GLN | A | 315 | −11.193 | 33.657 | −6.539 | 1.00 | 31.12 | | N |
| ANISOU | 1329 | N | GLN | A | 315 | 2353 | 5936 | 3534 | 449 | −507 | 650 | N |
| ATOM | 1330 | CA | GLN | A | 315 | −10.335 | 34.001 | −7.654 | 1.00 | 29.17 | | C |
| ANISOU | 1330 | CA | GLN | A | 315 | 1998 | 5780 | 3306 | 571 | −354 | 631 | C |
| ATOM | 1331 | CB | GLN | A | 315 | −8.960 | 34.402 | −7.146 | 1.00 | 31.75 | | C |
| ANISOU | 1331 | CB | GLN | A | 315 | 1897 | 6571 | 3597 | 542 | −380 | 844 | C |
| ATOM | 1332 | CG | GLN | A | 315 | −8.030 | 34.958 | −8.189 | 1.00 | 41.08 | | C |
| ANISOU | 1332 | CG | GLN | A | 315 | 2938 | 7866 | 4804 | 604 | −206 | 814 | C |
| ATOM | 1333 | CD | GLN | A | 315 | −6.621 | 35.126 | −7.662 | 1.00 | 53.35 | | C |
| ANISOU | 1333 | CD | GLN | A | 315 | 4236 | 9687 | 6348 | 561 | −209 | 1016 | C |
| ATOM | 1334 | OE1 | GLN | A | 315 | −6.233 | 34.519 | −6.660 | 1.00 | 62.13 | | O |
| ANISOU | 1334 | OE1 | GLN | A | 315 | 5239 | 10917 | 7451 | 601 | −313 | 1238 | O |
| ATOM | 1335 | NE2 | GLN | A | 315 | −5.840 | 35.955 | −8.336 | 1.00 | 72.17 | | N |
| ANISOU | 1335 | NE2 | GLN | A | 315 | 6513 | 12184 | 8725 | 476 | −96 | 953 | N |
| ATOM | 1336 | C | GLN | A | 315 | −10.246 | 32.720 | −8.454 | 1.00 | 37.56 | | C |
| ANISOU | 1336 | C | GLN | A | 315 | 3249 | 6549 | 4474 | 959 | −169 | 672 | C |
| ATOM | 1337 | O | GLN | A | 315 | −10.024 | 31.651 | −7.890 | 1.00 | 35.66 | | O |
| ANISOU | 1337 | O | GLN | A | 315 | 2973 | 6268 | 4307 | 1202 | −138 | 872 | O |
| ATOM | 1338 | N | GLU | A | 316 | −10.457 | 32.833 | −9.758 | 1.00 | 34.53 | | N |
| ANISOU | 1338 | N | GLU | A | 316 | 3101 | 5939 | 4078 | 995 | −18 | 484 | N |
| ATOM | 1339 | CA | GLU | A | 316 | −10.470 | 31.691 | −10.660 | 1.00 | 37.57 | | C |
| ANISOU | 1339 | CA | GLU | A | 316 | 3774 | 5988 | 4513 | 1274 | 217 | 449 | C |
| ATOM | 1340 | CB | GLU | A | 316 | −11.659 | 31.805 | −11.602 | 1.00 | 43.39 | | C |

TABLE 6-continued

DMXAA-hSTING$^{group2}$ complex

| | | | | | | | | | | | | |
|---|---|---|---|---|---|---|---|---|---|---|---|---|
| ANISOU | 1340 | CB | GLU | A | 316 | 4922 | 6419 | 5147 | 1086 | 192 | 167 | C |
| ATOM | 1341 | CG | GLU | A | 316 | −12.939 | 32.260 | −10.968 | 1.00 | 53.58 | | C |
| ANISOU | 1341 | CG | GLU | A | 316 | 6279 | 7666 | 6413 | 799 | −68 | 71 | C |
| ATOM | 1342 | CD | GLU | A | 316 | −14.055 | 32.388 | −12.007 | 1.00 | 65.76 | | C |
| ANISOU | 1342 | CD | GLU | A | 316 | 8149 | 8974 | 7861 | 621 | −116 | −140 | C |
| ATOM | 1343 | OE1 | GLU | A | 316 | −14.122 | 31.508 | −12.909 | 1.00 | 62.88 | | O |
| ANISOU | 1343 | OE1 | GLU | A | 316 | 8087 | 8374 | 7430 | 713 | 36 | −236 | O |
| ATOM | 1344 | OE2 | GLU | A | 316 | −14.849 | 33.365 | −11.931 | 1.00 | 62.69 | | O |
| ANISOU | 1344 | OE2 | GLU | A | 316 | 7717 | 8643 | 7460 | 376 | −284 | −189 | O |
| ATOM | 1345 | C | GLU | A | 316 | −9.208 | 31.693 | −11.494 | 1.00 | 41.89 | | C |
| ANISOU | 1345 | C | GLU | A | 316 | 4180 | 6627 | 5109 | 1501 | 483 | 538 | C |
| ATOM | 1346 | O | GLU | A | 316 | −8.631 | 32.747 | −11.763 | 1.00 | 43.79 | | O |
| ANISOU | 1346 | O | GLU | A | 316 | 4205 | 7125 | 5310 | 1374 | 468 | 522 | O |
| ATOM | 1347 | N | PRO | A | 317 | −8.761 | 30.500 | −11.918 | 1.00 | 46.74 | | N |
| ANISOU | 1347 | N | PRO | A | 317 | 4934 | 6997 | 5829 | 1840 | 787 | 634 | N |
| ATOM | 1348 | CA | PRO | A | 317 | −7.609 | 30.417 | −12.813 | 1.00 | 48.15 | | C |
| ANISOU | 1348 | CA | PRO | A | 317 | 5026 | 7180 | 6088 | 2080 | 1128 | 715 | C |
| ATOM | 1349 | CB | PRO | A | 317 | −7.458 | 28.915 | −13.058 | 1.00 | 57.84 | | C |
| ANISOU | 1349 | CB | PRO | A | 317 | 6510 | 8017 | 7449 | 2438 | 1502 | 812 | C |
| ATOM | 1350 | CG | PRO | A | 317 | −8.408 | 28.239 | −12.100 | 1.00 | 59.58 | | C |
| ANISOU | 1350 | CG | PRO | A | 317 | 6865 | 8104 | 7668 | 2396 | 1313 | 828 | C |
| ATOM | 1351 | CD | PRO | A | 317 | −9.466 | 29.216 | −11.785 | 1.00 | 57.23 | | C |
| ANISOU | 1351 | CD | PRO | A | 317 | 6608 | 7940 | 7196 | 1974 | 897 | 608 | C |
| ATOM | 1352 | C | PRO | A | 317 | −7.951 | 31.083 | −14.144 | 1.00 | 40.30 | | C |
| ANISOU | 1352 | C | PRO | A | 317 | 4356 | 6035 | 4922 | 1878 | 1207 | 410 | C |
| ATOM | 1353 | O | PRO | A | 317 | −9.081 | 30.952 | −14.606 | 1.00 | 38.43 | | O |
| ANISOU | 1353 | O | PRO | A | 317 | 4529 | 5541 | 4533 | 1682 | 1120 | 170 | O |
| ATOM | 1354 | N | ALA | A | 318 | −6.988 | 31.770 | −14.751 | 1.00 | 44.03 | | N |
| ANISOU | 1354 | N | ALA | A | 318 | 4634 | 6683 | 5412 | 1917 | 1367 | 442 | N |
| ATOM | 1355 | CA | ALA | A | 318 | −7.240 | 32.476 | −16.005 | 1.00 | 44.94 | | C |
| ANISOU | 1355 | CA | ALA | A | 318 | 5049 | 6684 | 5344 | 1730 | 1447 | 189 | C |
| ATOM | 1356 | CB | ALA | A | 318 | −6.022 | 33.297 | −16.398 | 1.00 | 53.27 | | C |
| ANISOU | 1356 | CB | ALA | A | 318 | 5786 | 7990 | 6463 | 1785 | 1624 | 275 | C |
| ATOM | 1357 | C | ALA | A | 318 | −7.645 | 31.548 | −17.161 | 1.00 | 49.91 | | C |
| ANISOU | 1357 | C | ALA | A | 318 | 6253 | 6859 | 5852 | 1788 | 1737 | −1 | C |
| ATOM | 1358 | O | ALA | A | 318 | −8.307 | 31.986 | −18.105 | 1.00 | 43.64 | | O |
| ANISOU | 1358 | O | ALA | A | 318 | 5809 | 5951 | 4822 | 1547 | 1685 | −229 | O |
| ATOM | 1359 | N | ASP | A | 319 | −7.232 | 30.279 | −17.093 | 1.00 | 44.29 | | N |
| ANISOU | 1359 | N | ASP | A | 319 | 5646 | 5893 | 5289 | 2091 | 2064 | 110 | N |
| ATOM | 1360 | CA | ASP | A | 319 | −7.416 | 29.347 | −18.194 | 1.00 | 47.04 | | C |
| ANISOU | 1360 | CA | ASP | A | 319 | 6573 | 5778 | 5522 | 2132 | 2459 | −79 | C |
| ATOM | 1361 | CB | ASP | A | 319 | −6.128 | 28.541 | −18.421 | 1.00 | 55.85 | | C |
| ANISOU | 1361 | CB | ASP | A | 319 | 7609 | 6717 | 6893 | 2562 | 3031 | 133 | C |
| ATOM | 1362 | CG | ASP | A | 319 | −5.830 | 27.561 | −17.274 | 1.00 | 70.31 | | C |
| ANISOU | 1362 | CG | ASP | A | 319 | 9168 | 8528 | 9020 | 2888 | 3093 | 453 | C |
| ATOM | 1363 | OD1 | ASP | A | 319 | −6.160 | 27.860 | −16.100 | 1.00 | 70.90 | | O |
| ANISOU | 1363 | OD1 | ASP | A | 319 | 8881 | 8913 | 9143 | 2844 | 2675 | 596 | O |
| ATOM | 1364 | OD2 | ASP | A | 319 | −5.268 | 26.481 | −17.558 | 1.00 | 88.04 | | O |
| ANISOU | 1364 | OD2 | ASP | A | 319 | 11585 | 10444 | 11423 | 3058 | 3457 | 577 | O |
| ATOM | 1365 | C | ASP | A | 319 | −8.564 | 28.361 | −17.997 | 1.00 | 46.87 | | C |
| ANISOU | 1365 | C | ASP | A | 319 | 6963 | 5443 | 5404 | 2013 | 2394 | −225 | C |
| ATOM | 1366 | O | ASP | A | 319 | −8.716 | 27.420 | −18.776 | 1.00 | 58.24 | | O |
| ANISOU | 1366 | O | ASP | A | 319 | 8915 | 6469 | 6745 | 2017 | 2765 | −387 | O |
| ATOM | 1367 | N | ASP | A | 320 | −9.350 | 28.535 | −16.953 | 1.00 | 46.14 | | N |
| ANISOU | 1367 | N | ASP | A | 320 | 6675 | 5518 | 5340 | 1886 | 1973 | −179 | N |
| ATOM | 1368 | CA | ASP | A | 320 | −10.400 | 27.559 | −16.690 | 1.00 | 61.81 | | C |
| ANISOU | 1368 | CA | ASP | A | 320 | 9013 | 7202 | 7269 | 1782 | 1936 | −303 | C |
| ATOM | 1369 | CB | ASP | A | 320 | −9.979 | 26.608 | −15.560 | 1.00 | 71.44 | | C |
| ANISOU | 1369 | CB | ASP | A | 320 | 10024 | 8352 | 8767 | 2132 | 2088 | −28 | C |
| ATOM | 1370 | CG | ASP | A | 320 | −10.789 | 25.314 | −15.541 | 1.00 | 85.13 | | C |
| ANISOU | 1370 | CG | ASP | A | 320 | 12237 | 9637 | 10472 | 2102 | 2284 | −165 | C |
| ATOM | 1371 | OD1 | ASP | A | 320 | −11.965 | 25.325 | −15.971 | 1.00 | 90.43 | | O |
| ANISOU | 1371 | OD1 | ASP | A | 320 | 13266 | 10181 | 10912 | 1717 | 2086 | −459 | O |
| ATOM | 1372 | OD2 | ASP | A | 320 | −10.235 | 24.285 | −15.080 | 1.00 | 91.79 | | O |
| ANISOU | 1372 | OD2 | ASP | A | 320 | 13076 | 10263 | 11536 | 2464 | 2649 | 48 | O |
| ATOM | 1373 | C | ASP | A | 320 | −11.666 | 28.303 | −16.327 | 1.00 | 53.37 | | C |
| ANISOU | 1373 | C | ASP | A | 320 | 7908 | 6309 | 6062 | 1409 | 1417 | −427 | C |
| ATOM | 1374 | O | ASP | A | 320 | −11.617 | 29.373 | −15.716 | 1.00 | 58.58 | | O |
| ANISOU | 1374 | O | ASP | A | 320 | 8167 | 7318 | 6775 | 1342 | 1110 | −319 | O |
| ATOM | 1375 | N | SER | A | 321 | −12.806 | 27.750 | −16.720 | 1.00 | 45.18 | | N |
| ANISOU | 1375 | N | SER | A | 321 | 7292 | 5023 | 4853 | 1146 | 1348 | −651 | N |
| ATOM | 1376 | CA | SER | A | 321 | −14.077 | 28.398 | −16.414 | 1.00 | 51.69 | | C |
| ANISOU | 1376 | CA | SER | A | 321 | 8055 | 5995 | 5588 | 808 | 884 | −730 | C |
| ATOM | 1377 | CB | SER | A | 321 | −14.758 | 28.873 | −17.706 | 1.00 | 48.40 | | C |
| ANISOU | 1377 | CB | SER | A | 321 | 7942 | 5584 | 4865 | 461 | 759 | −933 | C |
| ATOM | 1378 | OG | SER | A | 321 | −14.893 | 27.794 | −18.619 | 1.00 | 63.20 | | O |
| ANISOU | 1378 | OG | SER | A | 321 | 10355 | 7122 | 6538 | 352 | 1051 | −1142 | O |
| ATOM | 1379 | C | SER | A | 321 | −14.990 | 27.442 | −15.642 | 1.00 | 53.39 | | C |

TABLE 6-continued

DMXAA-hSTING[group2] complex

| | | | | | | | | | | | |
|---|---|---|---|---|---|---|---|---|---|---|---|
| ANISOU | 1379 | C | SER | A | 321 | 8411 | 5995 | 5879 | 745 | 820 | −768 | C |
| ATOM | 1380 | O | SER | A | 321 | −16.213 | 27.513 | −15.748 | 1.00 | 65.39 | | O |
| ANISOU | 1380 | O | SER | A | 321 | 10067 | 7489 | 7291 | 422 | 554 | −902 | O |
| ATOM | 1381 | N | SER | A | 322 | −14.391 | 26.538 | −14.872 | 1.00 | 51.56 | | N |
| ANISOU | 1381 | N | SER | A | 322 | 8130 | 5614 | 5847 | 1063 | 1077 | −620 | N |
| ATOM | 1382 | CA | SER | A | 322 | −15.164 | 25.517 | −14.179 | 1.00 | 46.87 | | C |
| ANISOU | 1382 | CA | SER | A | 322 | 7724 | 4758 | 5327 | 1036 | 1103 | −655 | C |
| ATOM | 1383 | CB | SER | A | 322 | −14.372 | 24.223 | −14.094 | 1.00 | 58.70 | | C |
| ANISOU | 1383 | CB | SER | A | 322 | 9422 | 5922 | 6959 | 1394 | 1618 | −558 | C |
| ATOM | 1384 | OG | SER | A | 322 | −13.158 | 24.461 | −13.414 | 1.00 | 66.40 | | O |
| ANISOU | 1384 | OG | SER | A | 322 | 9952 | 7129 | 8148 | 1792 | 1699 | −218 | O |
| ATOM | 1385 | C | SER | A | 322 | −15.577 | 25.939 | −12.779 | 1.00 | 43.31 | | C |
| ANISOU | 1385 | C | SER | A | 322 | 6900 | 4517 | 5037 | 1041 | 774 | −486 | C |
| ATOM | 1386 | O | SER | A | 322 | −16.247 | 25.189 | −12.063 | 1.00 | 39.55 | | O |
| ANISOU | 1386 | O | SER | A | 322 | 6541 | 3845 | 4639 | 1019 | 772 | −493 | O |
| ATOM | 1387 | N | PHE | A | 323 | −15.191 | 27.137 | −12.360 | 1.00 | 34.26 | | N |
| ANISOU | 1387 | N | PHE | A | 323 | 5340 | 3747 | 3930 | 1041 | 529 | −347 | N |
| ATOM | 1388 | CA | PHE | A | 323 | −15.562 | 27.540 | −11.008 | 1.00 | 31.45 | | C |
| ANISOU | 1388 | CA | PHE | A | 323 | 4692 | 3566 | 3692 | 999 | 268 | −207 | C |
| ATOM | 1389 | CB | PHE | A | 323 | −14.832 | 28.827 | −10.649 | 1.00 | 29.78 | | C |
| ANISOU | 1389 | CB | PHE | A | 323 | 4061 | 3760 | 3492 | 995 | 108 | −64 | C |
| ATOM | 1390 | CG | PHE | A | 323 | −15.370 | 29.501 | −9.416 | 1.00 | 28.30 | | C |
| ANISOU | 1390 | CG | PHE | A | 323 | 3648 | 3746 | 3360 | 820 | −155 | 10 | C |
| ATOM | 1391 | CD1 | PHE | A | 323 | −15.035 | 29.021 | −8.159 | 1.00 | 31.41 | | C |
| ANISOU | 1391 | CD1 | PHE | A | 323 | 3893 | 4210 | 3833 | 959 | −163 | 211 | C |
| ATOM | 1392 | CE1 | PHE | A | 323 | −15.508 | 29.639 | −7.005 | 1.00 | 27.35 | | C |
| ANISOU | 1392 | CE1 | PHE | A | 323 | 3227 | 3836 | 3328 | 756 | −368 | 260 | C |
| ATOM | 1393 | CZ | PHE | A | 323 | −16.326 | 30.757 | −7.125 | 1.00 | 25.45 | | C |
| ANISOU | 1393 | CZ | PHE | A | 323 | 2973 | 3629 | 3069 | 443 | −514 | 114 | C |
| ATOM | 1394 | CE2 | PHE | A | 323 | −16.674 | 31.257 | −8.406 | 1.00 | 30.63 | | C |
| ANISOU | 1394 | CE2 | PHE | A | 323 | 3732 | 4224 | 3683 | 348 | −509 | −43 | C |
| ATOM | 1395 | CD2 | PHE | A | 323 | −16.198 | 30.620 | −9.534 | 1.00 | 33.68 | | C |
| ANISOU | 1395 | CD2 | PHE | A | 323 | 4281 | 4507 | 4008 | 519 | −356 | −100 | C |
| ATOM | 1396 | C | PHE | A | 323 | −17.079 | 27.726 | −10.920 | 1.00 | 37.58 | | C |
| ANISOU | 1396 | C | PHE | A | 323 | 5608 | 4236 | 4436 | 653 | 19 | −378 | C |
| ATOM | 1397 | O | PHE | A | 323 | −17.685 | 28.373 | −11.776 | 1.00 | 38.32 | | O |
| ANISOU | 1397 | O | PHE | A | 323 | 5769 | 4375 | 4415 | 406 | −125 | −516 | O |
| ATOM | 1398 | N | SER | A | 324 | −17.689 | 27.163 | −9.878 | 1.00 | 34.34 | | N |
| ANISOU | 1398 | N | SER | A | 324 | 5218 | 3694 | 4136 | 644 | −24 | −334 | N |
| ATOM | 1399 | CA | SER | A | 324 | −19.121 | 27.351 | −9.636 | 1.00 | 31.00 | | C |
| ANISOU | 1399 | CA | SER | A | 324 | 4861 | 3176 | 3742 | 332 | −240 | −454 | C |
| ATOM | 1400 | CB | SER | A | 324 | −19.806 | 26.004 | −9.447 | 1.00 | 38.51 | | C |
| ANISOU | 1400 | CB | SER | A | 324 | 6136 | 3765 | 4731 | 311 | −94 | −556 | C |
| ATOM | 1401 | OG | SER | A | 324 | −21.013 | 26.174 | −8.726 | 1.00 | 35.52 | | O |
| ANISOU | 1401 | OG | SER | A | 324 | 5710 | 3328 | 4458 | 80 | −283 | −587 | O |
| ATOM | 1402 | C | SER | A | 324 | −19.379 | 28.228 | −8.407 | 1.00 | 25.05 | | C |
| ANISOU | 1402 | C | SER | A | 324 | 3806 | 2608 | 3102 | 257 | −430 | −321 | C |
| ATOM | 1403 | O | SER | A | 324 | −19.102 | 27.848 | −7.288 | 1.00 | 26.21 | | O |
| ANISOU | 1403 | O | SER | A | 324 | 3885 | 2753 | 3321 | 386 | −388 | −185 | O |
| ATOM | 1404 | N | LEU | A | 325 | −19.947 | 29.406 | −8.625 | 1.00 | 25.52 | | N |
| ANISOU | 1404 | N | LEU | A | 325 | 3714 | 2815 | 3169 | 31 | −613 | −350 | N |
| ATOM | 1405 | CA | LEU | A | 325 | −20.181 | 30.339 | −7.530 | 1.00 | 26.25 | | C |
| ANISOU | 1405 | CA | LEU | A | 325 | 3574 | 3039 | 3361 | −79 | −710 | −250 | C |
| ATOM | 1406 | CB | LEU | A | 325 | −20.634 | 31.693 | −8.084 | 1.00 | 25.17 | | C |
| ANISOU | 1406 | CB | LEU | A | 325 | 3290 | 3033 | 3241 | −275 | −813 | −262 | C |
| ATOM | 1407 | CG | LEU | A | 325 | −20.838 | 32.775 | −7.030 | 1.00 | 25.13 | | C |
| ANISOU | 1407 | CG | LEU | A | 325 | 3093 | 3117 | 3339 | −418 | −816 | −179 | C |
| ATOM | 1408 | CD1 | LEU | A | 325 | −19.565 | 32.966 | −6.204 | 1.00 | 24.63 | | C |
| ANISOU | 1408 | CD1 | LEU | A | 325 | 2898 | 3280 | 3179 | −328 | −754 | −91 | C |
| ATOM | 1409 | CD2 | LEU | A | 325 | −21.197 | 34.069 | −7.765 | 1.00 | 32.63 | | C |
| ANISOU | 1409 | CD2 | LEU | A | 325 | 3921 | 4153 | 4324 | −553 | −838 | −162 | C |
| ATOM | 1410 | C | LEU | A | 325 | −21.231 | 29.782 | −6.557 | 1.00 | 24.51 | | C |
| ANISOU | 1410 | C | LEU | A | 325 | 3448 | 2590 | 3277 | −184 | −728 | −261 | C |
| ATOM | 1411 | O | LEU | A | 325 | −21.118 | 29.948 | −5.330 | 1.00 | 26.39 | | O |
| ANISOU | 1411 | O | LEU | A | 325 | 3599 | 2867 | 3560 | −190 | −715 | −162 | O |
| ATOM | 1412 | N | SER | A | 326 | −22.235 | 29.104 | −7.091 | 1.00 | 27.07 | | N |
| ANISOU | 1412 | N | SER | A | 326 | 3961 | 2682 | 3641 | −298 | −750 | −383 | N |
| ATOM | 1413 | CA | SER | A | 326 | −23.239 | 28.519 | −6.217 | 1.00 | 26.94 | | C |
| ANISOU | 1413 | CA | SER | A | 326 | 4037 | 2427 | 3771 | −402 | −737 | −404 | C |
| ATOM | 1414 | CB | SER | A | 326 | −24.389 | 27.888 | −7.005 | 1.00 | 27.11 | | C |
| ANISOU | 1414 | CB | SER | A | 326 | 4229 | 2249 | 3824 | −605 | −792 | −553 | C |
| ATOM | 1415 | OG | SER | A | 326 | −23.925 | 26.883 | −7.894 | 1.00 | 33.76 | | O |
| ANISOU | 1415 | OG | SER | A | 326 | 5339 | 2988 | 4499 | −527 | −679 | −676 | O |
| ATOM | 1416 | C | SER | A | 326 | −22.599 | 27.475 | −5.299 | 1.00 | 29.26 | | C |
| ANISOU | 1416 | C | SER | A | 326 | 4462 | 2607 | 4049 | −176 | −578 | −333 | C |
| ATOM | 1417 | O | SER | A | 326 | −22.928 | 27.388 | −4.116 | 1.00 | 28.35 | | O |
| ANISOU | 1417 | O | SER | A | 326 | 4338 | 2413 | 4021 | −205 | −555 | −262 | O |
| ATOM | 1418 | N | GLN | A | 327 | −21.699 | 26.655 | −5.841 | 1.00 | 25.32 | | N |

TABLE 6-continued

DMXAA-hSTING$^{group2}$ complex

| | | | | | | | | | | | |
|---|---|---|---|---|---|---|---|---|---|---|---|
| ANISOU | 1418 | N | GLN | A | 327 | 4098 | 2077 | 3445 | 58 | −434 | −329 | N |
| ATOM | 1419 | CA | GLN | A | 327 | −21.010 | 25.678 | −4.986 | 1.00 | 27.04 | | C |
| ANISOU | 1419 | CA | GLN | A | 327 | 4398 | 2202 | 3674 | 335 | −255 | −178 | C |
| ATOM | 1420 | CB | GLN | A | 327 | −20.126 | 24.744 | −5.811 | 1.00 | 31.11 | | C |
| ANISOU | 1420 | CB | GLN | A | 327 | 5086 | 2609 | 4126 | 606 | −11 | −171 | C |
| ATOM | 1421 | CG | GLN | A | 327 | −20.915 | 23.655 | −6.525 | 1.00 | 39.92 | | C |
| ANISOU | 1421 | CG | GLN | A | 327 | 6596 | 3330 | 5241 | 498 | 171 | −398 | C |
| ATOM | 1422 | CD | GLN | A | 327 | −21.653 | 22.761 | −5.532 | 1.00 | 45.24 | | C |
| ANISOU | 1422 | CD | GLN | A | 327 | 7449 | 3709 | 6032 | 485 | 278 | −389 | C |
| ATOM | 1423 | OE1 | GLN | A | 327 | −21.034 | 22.145 | −4.662 | 1.00 | 46.97 | | O |
| ANISOU | 1423 | OE1 | GLN | A | 327 | 7673 | 3871 | 6303 | 780 | 445 | −172 | O |
| ATOM | 1424 | NE2 | GLN | A | 327 | −22.987 | 22.701 | −5.641 | 1.00 | 40.65 | | N |
| ANISOU | 1424 | NE2 | GLN | A | 327 | 6989 | 2957 | 5499 | 143 | 180 | −595 | N |
| ATOM | 1425 | C | GLN | A | 327 | −20.161 | 26.365 | −3.906 | 1.00 | 28.99 | | C |
| ANISOU | 1425 | C | GLN | A | 327 | 4363 | 2765 | 3887 | 432 | −340 | 57 | C |
| ATOM | 1426 | O | GLN | A | 327 | −20.047 | 25.904 | −2.772 | 1.00 | 29.42 | | O |
| ANISOU | 1426 | O | GLN | A | 327 | 4429 | 2794 | 3956 | 524 | −303 | 215 | O |
| ATOM | 1427 | N | GLU | A | 328 | −19.533 | 27.468 | −4.278 | 1.00 | 25.60 | | N |
| ANISOU | 1427 | N | GLU | A | 328 | 3693 | 2651 | 3384 | 384 | −452 | 85 | N |
| ATOM | 1428 | CA | GLU | A | 328 | −18.671 | 28.161 | −3.332 | 1.00 | 32.77 | | C |
| ANISOU | 1428 | CA | GLU | A | 328 | 4336 | 3902 | 4213 | 395 | −537 | 282 | C |
| ATOM | 1429 | CB | GLU | A | 328 | −17.942 | 29.292 | −4.046 | 1.00 | 30.51 | | C |
| ANISOU | 1429 | CB | GLU | A | 328 | 3824 | 3920 | 3850 | 337 | −602 | 265 | C |
| ATOM | 1430 | CG | GLU | A | 328 | −16.852 | 29.890 | −3.206 | 1.00 | 38.72 | | C |
| ANISOU | 1430 | CG | GLU | A | 328 | 4580 | 5356 | 4774 | 329 | −675 | 465 | C |
| ATOM | 1431 | CD | GLU | A | 328 | −15.697 | 28.907 | −2.952 | 1.00 | 42.08 | | C |
| ANISOU | 1431 | CD | GLU | A | 328 | 4893 | 5921 | 5175 | 683 | −606 | 737 | C |
| ATOM | 1432 | OE1 | GLU | A | 328 | −14.875 | 29.237 | −2.093 | 1.00 | 43.17 | | O |
| ANISOU | 1432 | OE1 | GLU | A | 328 | 4777 | 6424 | 5203 | 654 | −711 | 954 | O |
| ATOM | 1433 | OE2 | GLU | A | 328 | −15.593 | 27.836 | −3.618 | 1.00 | 47.49 | | O |
| ANISOU | 1433 | OE2 | GLU | A | 328 | 5736 | 6359 | 5948 | 974 | −426 | 750 | O |
| ATOM | 1434 | C | GLU | A | 328 | −19.508 | 28.720 | −2.157 | 1.00 | 27.77 | | C |
| ANISOU | 1434 | C | GLU | A | 328 | 3706 | 3240 | 3605 | 118 | −621 | 269 | C |
| ATOM | 1435 | O | GLU | A | 328 | −19.134 | 28.627 | −0.980 | 1.00 | 30.45 | | O |
| ANISOU | 1435 | O | GLU | A | 328 | 3994 | 3712 | 3863 | 116 | −647 | 436 | O |
| ATOM | 1436 | N | VAL | A | 329 | −20.667 | 29.266 | −2.489 | 1.00 | 27.93 | | N |
| ANISOU | 1436 | N | VAL | A | 329 | 3794 | 3081 | 3737 | −121 | −647 | 92 | N |
| ATOM | 1437 | CA | VAL | A | 329 | −21.541 | 29.833 | −1.451 | 1.00 | 28.45 | | C |
| ANISOU | 1437 | CA | VAL | A | 329 | 3881 | 3051 | 3876 | −381 | −645 | 73 | C |
| ATOM | 1438 | CB | VAL | A | 329 | −22.671 | 30.696 | −2.074 | 1.00 | 29.21 | | C |
| ANISOU | 1438 | CB | VAL | A | 329 | 3944 | 3012 | 4143 | −603 | −653 | −59 | C |
| ATOM | 1439 | CG1 | VAL | A | 329 | −23.641 | 31.135 | −0.998 | 1.00 | 35.10 | | C |
| ANISOU | 1439 | CG1 | VAL | A | 329 | 4738 | 3574 | 5026 | −836 | −563 | −63 | C |
| ATOM | 1440 | CG2 | VAL | A | 329 | −22.068 | 31.919 | −2.727 | 1.00 | 25.08 | | C |
| ANISOU | 1440 | CG2 | VAL | A | 329 | 3229 | 2749 | 3551 | −660 | −685 | −55 | C |
| ATOM | 1441 | C | VAL | A | 329 | −22.141 | 28.726 | −0.603 | 1.00 | 28.84 | | C |
| ANISOU | 1441 | C | VAL | A | 329 | 4142 | 2824 | 3990 | −335 | −568 | 99 | C |
| ATOM | 1442 | O | VAL | A | 329 | −22.217 | 28.824 | 0.622 | 1.00 | 33.19 | | O |
| ANISOU | 1442 | O | VAL | A | 329 | 4734 | 3382 | 4495 | −441 | −541 | 181 | O |
| ATOM | 1443 | N | LEU | A | 330 | −22.520 | 27.627 | −1.250 | 1.00 | 28.62 | | N |
| ANISOU | 1443 | N | LEU | A | 330 | 4287 | 2547 | 4041 | −194 | −507 | 23 | N |
| ATOM | 1444 | CA | LEU | A | 330 | −23.097 | 26.505 | −0.513 | 1.00 | 28.99 | | C |
| ANISOU | 1444 | CA | LEU | A | 330 | 4566 | 2289 | 4160 | −144 | −386 | 35 | C |
| ATOM | 1445 | CB | LEU | A | 330 | −23.568 | 25.404 | −1.462 | 1.00 | 33.47 | | C |
| ANISOU | 1445 | CB | LEU | A | 330 | 5350 | 2565 | 4804 | −69 | −283 | −111 | C |
| ATOM | 1446 | CG | LEU | A | 330 | −24.898 | 25.699 | −2.148 | 1.00 | 33.79 | | C |
| ANISOU | 1446 | CG | LEU | A | 330 | 5389 | 2462 | 4987 | −357 | −342 | −311 | C |
| ATOM | 1447 | CD1 | LEU | A | 330 | −25.147 | 24.664 | −3.247 | 1.00 | 32.28 | | C |
| ANISOU | 1447 | CD1 | LEU | A | 330 | 5358 | 2136 | 4772 | −339 | −242 | −464 | C |
| ATOM | 1448 | CD2 | LEU | A | 330 | −26.029 | 25.637 | −1.100 | 1.00 | 33.43 | | C |
| ANISOU | 1448 | CD2 | LEU | A | 330 | 5203 | 2429 | 5069 | −476 | −174 | −307 | C |
| ATOM | 1449 | C | LEU | A | 330 | −22.106 | 25.926 | 0.509 | 1.00 | 40.33 | | C |
| ANISOU | 1449 | C | LEU | A | 330 | 6015 | 3854 | 5457 | 82 | −339 | 280 | C |
| ATOM | 1450 | O | LEU | A | 330 | −22.501 | 25.497 | 1.603 | 1.00 | 38.52 | | O |
| ANISOU | 1450 | O | LEU | A | 330 | 5923 | 3476 | 5234 | 47 | −273 | 353 | O |
| ATOM | 1451 | N | ARG | A | 331 | −20.829 | 25.890 | 0.138 | 1.00 | 34.46 | | N |
| ANISOU | 1451 | N | ARG | A | 331 | 5114 | 3391 | 4591 | 318 | −368 | 435 | N |
| ATOM | 1452 | CA | ARG | A | 331 | −19.789 | 25.511 | 1.088 | 1.00 | 43.92 | | C |
| ANISOU | 1452 | CA | ARG | A | 331 | 6213 | 4825 | 5649 | 526 | −378 | 750 | C |
| ATOM | 1453 | CB | ARG | A | 331 | −18.427 | 25.754 | 0.488 | 1.00 | 48.86 | | C |
| ANISOU | 1453 | CB | ARG | A | 331 | 6566 | 5811 | 6188 | 739 | −427 | 914 | C |
| ATOM | 1454 | CG | ARG | A | 331 | −17.656 | 24.541 | 0.224 | 1.00 | 66.08 | | C |
| ANISOU | 1454 | CG | ARG | A | 331 | 8778 | 7910 | 8420 | 1170 | −240 | 1135 | C |
| ATOM | 1455 | CD | ARG | A | 331 | −16.339 | 24.980 | −0.310 | 1.00 | 72.85 | | C |
| ANISOU | 1455 | CD | ARG | A | 331 | 9306 | 9155 | 9219 | 1338 | −290 | 1306 | C |
| ATOM | 1456 | NE | ARG | A | 331 | −16.178 | 24.508 | −1.670 | 1.00 | 79.52 | | N |
| ANISOU | 1456 | NE | ARG | A | 331 | 10270 | 9768 | 10177 | 1538 | −72 | 1171 | N |
| ATOM | 1457 | CZ | ARG | A | 331 | −15.371 | 23.507 | −1.997 | 1.00 | 87.77 | | C |

TABLE 6-continued

| DMXAA-hSTING$^{group2}$ complex | | | | | | | | | | | |
|---|---|---|---|---|---|---|---|---|---|---|---|
| ANISOU | 1457 | CZ | ARG | A | 331 | 11325 | 10712 | 11312 | 1951 | 192 | 1392 | C |
| ATOM | 1458 | NH1 | ARG | A | 331 | −14.649 | 22.919 | −1.050 | 1.00 | 82.48 | | N |
| ANISOU | 1458 | NH1 | ARG | A | 331 | 10488 | 10201 | 10648 | 2237 | 224 | 1809 | N |
| ATOM | 1459 | NH2 | ARG | A | 331 | −15.269 | 23.110 | −3.263 | 1.00 | 94.50 | | N |
| ANISOU | 1459 | NH2 | ARG | A | 331 | 12356 | 11309 | 12241 | 2075 | 442 | 1223 | N |
| ATOM | 1460 | C | ARG | A | 331 | −19.869 | 26.326 | 2.382 | 1.00 | 50.48 | | C |
| ANISOU | 1460 | C | ARG | A | 331 | 6971 | 5871 | 6336 | 245 | −510 | 832 | C |
| ATOM | 1461 | O | ARG | A | 331 | −19.793 | 25.779 | 3.483 | 1.00 | 50.95 | | O |
| ANISOU | 1461 | O | ARG | A | 331 | 7122 | 5932 | 6307 | 290 | −494 | 1026 | O |
| ATOM | 1462 | N | HIS | A | 332 | −20.003 | 27.640 | 2.247 | 1.00 | 47.45 | | N |
| ANISOU | 1462 | N | HIS | A | 332 | 6455 | 5661 | 5914 | −59 | −608 | 691 | N |
| ATOM | 1463 | CA | HIS | A | 332 | −20.064 | 28.505 | 3.422 | 1.00 | 48.11 | | C |
| ANISOU | 1463 | CA | HIS | A | 332 | 6525 | 5919 | 5835 | −394 | −667 | 724 | C |
| ATOM | 1464 | CB | HIS | A | 332 | −19.932 | 29.970 | 3.030 | 1.00 | 39.01 | | C |
| ANISOU | 1464 | CB | HIS | A | 332 | 5209 | 4969 | 4643 | −677 | −709 | 581 | C |
| ATOM | 1465 | CG | HIS | A | 332 | −18.555 | 30.363 | 2.662 | 1.00 | 43.71 | | C |
| ANISOU | 1465 | CG | HIS | A | 332 | 5519 | 6021 | 5067 | −596 | −836 | 716 | C |
| ATOM | 1466 | ND1 | HIS | A | 332 | −17.677 | 30.932 | 3.573 | 1.00 | 43.01 | | N |
| ANISOU | 1466 | ND1 | HIS | A | 332 | 5287 | 6358 | 4698 | −816 | −951 | 867 | N |
| ATOM | 1467 | CE1 | HIS | A | 332 | −16.535 | 31.187 | 2.964 | 1.00 | 46.31 | | C |
| ANISOU | 1467 | CE1 | HIS | A | 332 | 5413 | 7140 | 5041 | −698 | −1047 | 972 | C |
| ATOM | 1468 | NE2 | HIS | A | 332 | −16.623 | 30.797 | 1.705 | 1.00 | 42.72 | | N |
| ANISOU | 1468 | NE2 | HIS | A | 332 | 4945 | 6487 | 4801 | −396 | −975 | 892 | N |
| ATOM | 1469 | CD2 | HIS | A | 332 | −17.882 | 30.271 | 1.489 | 1.00 | 43.95 | | C |
| ANISOU | 1469 | CD2 | HIS | A | 332 | 5377 | 6163 | 5158 | −349 | −858 | 727 | C |
| ATOM | 1470 | C | HIS | A | 332 | −21.368 | 28.329 | 4.173 | 1.00 | 48.81 | | C |
| ANISOU | 1470 | C | HIS | A | 332 | 6891 | 5617 | 6040 | −588 | −535 | 603 | C |
| ATOM | 1471 | O | HIS | A | 332 | −21.416 | 28.396 | 5.398 | 1.00 | 51.44 | | O |
| ANISOU | 1471 | O | HIS | A | 332 | 7339 | 5992 | 6214 | −767 | −522 | 694 | O |
| ATOM | 1472 | N | LEU | A | 333 | −22.438 | 28.126 | 3.426 | 1.00 | 39.92 | | N |
| ANISOU | 1472 | N | LEU | A | 333 | 5866 | 4123 | 5179 | −582 | −437 | 404 | N |
| ATOM | 1473 | CA | LEU | A | 333 | −23.730 | 27.960 | 4.049 | 1.00 | 44.01 | | C |
| ANISOU | 1473 | CA | LEU | A | 333 | 6600 | 4258 | 5866 | −761 | −290 | 295 | C |
| ATOM | 1474 | CB | LEU | A | 333 | −24.798 | 27.797 | 2.990 | 1.00 | 43.50 | | C |
| ANISOU | 1474 | CB | LEU | A | 333 | 6496 | 3947 | 6084 | −737 | −223 | 99 | C |
| ATOM | 1475 | CG | LEU | A | 333 | −25.796 | 28.932 | 2.854 | 1.00 | 51.50 | | C |
| ANISOU | 1475 | CG | LEU | A | 333 | 7177 | 5114 | 7278 | −810 | −73 | −40 | C |
| ATOM | 1476 | CD1 | LEU | A | 333 | −25.136 | 30.243 | 3.047 | 1.00 | 62.55 | | C |
| ANISOU | 1476 | CD1 | LEU | A | 333 | 8501 | 6724 | 8542 | −953 | −116 | −7 | C |
| ATOM | 1477 | CD2 | LEU | A | 333 | −26.388 | 28.887 | 1.480 | 1.00 | 46.78 | | C |
| ANISOU | 1477 | CD2 | LEU | A | 333 | 6480 | 4543 | 6752 | −755 | −29 | −153 | C |
| ATOM | 1478 | C | LEU | A | 333 | −23.711 | 26.723 | 4.919 | 1.00 | 52.19 | | C |
| ANISOU | 1478 | C | LEU | A | 333 | 7853 | 5136 | 6839 | −599 | −214 | 435 | C |
| ATOM | 1479 | O | LEU | A | 333 | −24.203 | 26.722 | 6.042 | 1.00 | 59.27 | | O |
| ANISOU | 1479 | O | LEU | A | 333 | 8930 | 5895 | 7697 | −774 | −117 | 459 | O |
| ATOM | 1480 | N | ARG | A | 334 | −23.131 | 25.663 | 4.382 | 1.00 | 50.19 | | N |
| ANISOU | 1480 | N | ARG | A | 334 | 7610 | 4879 | 6580 | −255 | −215 | 537 | N |
| ATOM | 1481 | CA | ARG | A | 334 | −23.110 | 24.374 | 5.047 | 1.00 | 63.41 | | C |
| ANISOU | 1481 | CA | ARG | A | 334 | 9504 | 6352 | 8237 | −33 | −85 | 696 | C |
| ATOM | 1482 | CB | ARG | A | 334 | −22.873 | 23.277 | 4.019 | 1.00 | 58.91 | | C |
| ANISOU | 1482 | CB | ARG | A | 334 | 8999 | 5600 | 7785 | 299 | 33 | 686 | C |
| ATOM | 1483 | CG | ARG | A | 334 | −24.070 | 23.092 | 3.119 | 1.00 | 54.79 | | C |
| ANISOU | 1483 | CG | ARG | A | 334 | 8612 | 4709 | 7496 | 142 | 128 | 364 | C |
| ATOM | 1484 | CD | ARG | A | 334 | −23.716 | 22.301 | 1.879 | 1.00 | 58.47 | | C |
| ANISOU | 1484 | CD | ARG | A | 334 | 9137 | 5073 | 8006 | 363 | 230 | 292 | C |
| ATOM | 1485 | NE | ARG | A | 334 | −24.907 | 21.997 | 1.090 | 1.00 | 53.37 | | N |
| ANISOU | 1485 | NE | ARG | A | 334 | 8380 | 4386 | 7511 | 127 | 233 | −9 | N |
| ATOM | 1486 | CZ | ARG | A | 334 | −24.871 | 21.562 | −0.164 | 1.00 | 56.33 | | C |
| ANISOU | 1486 | CZ | ARG | A | 334 | 8807 | 4709 | 7888 | 148 | 278 | −152 | C |
| ATOM | 1487 | NH1 | ARG | A | 334 | −23.695 | 21.404 | −0.775 | 1.00 | 48.14 | | N |
| ANISOU | 1487 | NH1 | ARG | A | 334 | 7901 | 3643 | 6748 | 417 | 372 | −56 | N |
| ATOM | 1488 | NH2 | ARG | A | 334 | −26.007 | 21.292 | −0.808 | 1.00 | 47.87 | | N |
| ANISOU | 1488 | NH2 | ARG | A | 334 | 7650 | 3629 | 6908 | −76 | 229 | −359 | N |
| ATOM | 1489 | C | ARG | A | 334 | −22.075 | 24.282 | 6.164 | 1.00 | 75.37 | | C |
| ANISOU | 1489 | C | ARG | A | 334 | 10961 | 8210 | 9465 | 59 | −179 | 1037 | C |
| ATOM | 1490 | O | ARG | A | 334 | −21.314 | 23.310 | 6.226 | 1.00 | 73.23 | | O |
| ANISOU | 1490 | O | ARG | A | 334 | 10684 | 7996 | 9143 | 418 | −138 | 1304 | O |
| ATOM | 1491 | N | GLN | A | 335 | −22.066 | 25.287 | 7.043 | 1.00 | 82.10 | | N |
| ANISOU | 1491 | N | GLN | A | 335 | 11779 | 9287 | 10129 | −282 | −281 | 1045 | N |
| ATOM | 1492 | CA | GLN | A | 335 | −21.179 | 25.311 | 8.207 | 1.00 | 87.81 | | C |
| ANISOU | 1492 | CA | GLN | A | 335 | 12461 | 10394 | 10508 | −322 | −415 | 1361 | C |
| ATOM | 1493 | CB | GLN | A | 335 | −19.723 | 25.282 | 7.761 | 1.00 | 87.61 | | C |
| ANISOU | 1493 | CB | GLN | A | 335 | 12085 | 10862 | 10339 | −64 | −609 | 1637 | C |
| ATOM | 1494 | CG | GLN | A | 335 | −19.219 | 26.618 | 7.293 | 1.00 | 87.85 | | C |
| ANISOU | 1494 | CG | GLN | A | 335 | 11852 | 11255 | 10271 | −330 | −765 | 1507 | C |
| ATOM | 1495 | CD | GLN | A | 335 | −17.801 | 26.526 | 6.793 | 1.00 | 100.41 | | C |
| ANISOU | 1495 | CD | GLN | A | 335 | 13072 | 13311 | 11768 | −59 | −928 | 1783 | C |
| ATOM | 1496 | OE1 | GLN | A | 335 | −17.369 | 27.322 | 5.953 | 1.00 | 97.19 | | O |

TABLE 6-continued

| | | | | | | | | | | | | |
|---|---|---|---|---|---|---|---|---|---|---|---|---|
| ANISOU | 1496 | OE1 | GLN | A | 335 | 12442 | 13096 | 11390 | −124 | −990 | 1657 | O |
| ATOM | 1497 | NE2 | GLN | A | 335 | −17.058 | 25.540 | 7.302 | 1.00 | 106.17 | | N |
| ANISOU | 1497 | NE2 | GLN | A | 335 | 13716 | 14216 | 12405 | 270 | −971 | 2194 | N |
| ATOM | 1498 | C | GLN | A | 335 | −21.395 | 26.541 | 9.093 | 1.00 | 86.69 | | C |
| ANISOU | 1498 | C | GLN | A | 335 | 12375 | 10417 | 10147 | −832 | −462 | 1256 | C |
| ATOM | 1499 | O | GLN | A | 335 | −22.446 | 27.182 | 9.066 | 1.00 | 84.41 | | O |
| ANISOU | 1499 | O | GLN | A | 335 | 12232 | 9813 | 10028 | −1111 | −302 | 969 | O |
| TER | 1500 | | GLN | A | 335 | | | | | | | |
| HETATM | 1501 | OAD | DRG | B | 1 | −16.913 | 52.085 | −3.644 | 1.00 | 2.187 | | O |
| HETATM | 1502 | CAQ | DRG | B | 1 | −18.087 | 52.173 | −3.207 | 1.00 | 18.29 | | C |
| HETATM | 1503 | CAS | DRG | B | 1 | −19.156 | 52.069 | −4.081 | 1.00 | 18.47 | | C |
| HETATM | 1504 | CAJ | DRG | B | 1 | −18.968 | 51.880 | −5.449 | 1.00 | 19.15 | | C |
| HETATM | 1505 | CAH | DRG | B | 1 | −20.089 | 51.757 | −6.304 | 1.00 | 16.84 | | C |
| HETATM | 1506 | CAN | DRG | B | 1 | −21.395 | 51.829 | −5.799 | 1.00 | 19.67 | | C |
| HETATM | 1507 | CAA | DRG | B | 1 | −22.520 | 51.711 | −6.653 | 1.00 | 25.26 | | C |
| HETATM | 1508 | CAO | DRG | B | 1 | −21.592 | 52.036 | −4.427 | 1.00 | 22.20 | | C |
| HETATM | 1509 | CAB | DRG | B | 1 | −22.866 | 52.116 | −3.794 | 1.00 | 19.46 | | C |
| HETATM | 1510 | CAT | DRG | B | 1 | −20.465 | 52.177 | −3.620 | 1.00 | 21.40 | | C |
| HETATM | 1511 | OAL | DRG | B | 1 | −20.706 | 52.339 | −2.325 | 1.00 | 22.41 | | O |
| HETATM | 1512 | CAU | DRG | B | 1 | −19.692 | 52.388 | −1.437 | 1.00 | 22.13 | | C |
| HETATM | 1513 | CAR | DRG | B | 1 | −18.353 | 52.319 | −1.857 | 1.00 | 15.64 | | C |
| HETATM | 1514 | CAI | DRG | B | 1 | −17.334 | 52.372 | −0.879 | 1.00 | 22.69 | | C |
| HETATM | 1515 | CAF | DRG | B | 1 | −17.712 | 52.519 | 0.460 | 1.00 | 18.38 | | C |
| HETATM | 1516 | CAG | DRG | B | 1 | −19.054 | 52.618 | 0.841 | 1.00 | 21.40 | | C |
| HETATM | 1517 | CAP | DRG | B | 1 | −20.066 | 52.548 | −0.115 | 1.00 | 21.65 | | C |
| HETATM | 1518 | CAK | DRG | B | 1 | −21.433 | 52.639 | 0.231 | 1.00 | 25.61 | | C |
| HETATM | 1519 | CAM | DRG | B | 1 | −22.368 | 51.413 | −0.084 | 1.00 | 32.80 | | C |
| HETATM | 1520 | OAE | DRG | B | 1 | −21.857 | 50.326 | −0.472 | 1.00 | 22.31 | | O |
| HETATM | 1521 | OAC | DRG | B | 1 | −23.600 | 51.605 | 0.140 | 1.00 | 24.49 | | O |
| HETATM | 1523 | O | HOH | S | 1 | −28.626 | 34.785 | 4.215 | 1.00 | 27.03 | | O |
| HETATM | 1524 | O | HOH | S | 2 | −47.650 | 29.425 | 8.056 | 1.00 | 26.56 | | O |
| HETATM | 1525 | O | HOH | S | 3 | −24.245 | 53.450 | 2.078 | 1.00 | 23.35 | | O |
| HETATM | 1526 | O | HOH | S | 4 | −12.178 | 44.652 | −8.731 | 1.00 | 28.37 | | O |
| HETATM | 1527 | O | HOH | S | 5 | −24.927 | 42.673 | −5.489 | 1.00 | 28.51 | | O |
| HETATM | 1528 | O | HOH | S | 6 | −23.646 | 48.402 | −0.574 | 1.00 | 26.00 | | O |
| HETATM | 1529 | O | HOH | S | 7 | −22.287 | 45.745 | −0.729 | 1.00 | 29.09 | | O |
| HETATM | 1530 | O | HOH | S | 8 | −31.590 | 54.969 | 11.707 | 1.00 | 29.64 | | O |
| HETATM | 1531 | O | HOH | S | 9 | −28.418 | 41.765 | −0.998 | 1.00 | 31.77 | | O |
| HETATM | 1532 | O | HOH | S | 10 | −30.530 | 45.924 | 8.039 | 1.00 | 29.84 | | O |
| HETATM | 1533 | O | HOH | S | 11 | −33.319 | 26.230 | 0.957 | 1.00 | 29.84 | | O |
| HETATM | 1534 | O | HOH | S | 12 | −35.646 | 26.330 | 5.040 | 1.00 | 34.11 | | O |
| HETATM | 1535 | O | HOH | S | 13 | −34.846 | 44.984 | 0.897 | 1.00 | 29.86 | | O |
| HETATM | 1536 | O | HOH | S | 14 | −27.499 | 41.332 | −4.679 | 1.00 | 28.34 | | O |
| HETATM | 1537 | O | HOH | S | 15 | −45.238 | 30.820 | 6.608 | 1.00 | 43.53 | | O |
| HETATM | 1538 | O | HOH | S | 16 | −28.702 | 41.986 | 12.955 | 1.00 | 37.06 | | O |
| HETATM | 1539 | O | HOH | S | 17 | −31.558 | 42.751 | 14.241 | 1.00 | 35.37 | | O |
| HETATM | 1540 | O | HOH | S | 18 | −24.593 | 24.298 | −7.345 | 1.00 | 34.03 | | O |
| HETATM | 1541 | O | HOH | S | 19 | −8.656 | 59.398 | −16.700 | 1.00 | 36.28 | | O |
| HETATM | 1542 | O | HOH | S | 20 | −13.395 | 34.463 | 1.907 | 1.00 | 44.34 | | O |
| HETATM | 1543 | O | HOH | S | 21 | −40.903 | 35.861 | 0.075 | 1.00 | 42.86 | | O |
| HETATM | 1544 | O | HOH | S | 22 | −30.129 | 28.153 | 3.170 | 1.00 | 34.09 | | O |
| HETATM | 1545 | O | HOH | S | 23 | −12.878 | 28.829 | −13.442 | 1.00 | 47.21 | | O |
| HETATM | 1546 | O | HOH | S | 24 | −41.253 | 37.066 | 3.047 | 1.00 | 36.72 | | O |
| HETATM | 1547 | O | HOH | S | 25 | 1.987 | 48.116 | −11.341 | 1.00 | 46.52 | | O |
| HETATM | 1548 | O | HOH | S | 26 | −9.801 | 45.800 | −13.365 | 1.00 | 49.67 | | O |
| HETATM | 1549 | O | HOH | S | 27 | −20.039 | 30.304 | −11.343 | 1.00 | 46.35 | | O |
| HETATM | 1550 | O | HOH | S | 28 | −0.095 | 44.565 | −0.710 | 1.00 | 39.19 | | O |
| HETATM | 1551 | O | HOH | S | 29 | −0.804 | 42.091 | −8.287 | 1.00 | 33.98 | | O |
| HETATM | 1552 | O | HOH | S | 30 | −13.241 | 42.472 | −8.951 | 1.00 | 33.71 | | O |
| HETATM | 1553 | O | HOH | S | 31 | −41.235 | 40.094 | 3.813 | 1.00 | 48.03 | | O |
| HETATM | 1554 | O | HOH | S | 33 | −16.015 | 36.319 | 7.016 | 1.00 | 41.21 | | O |
| HETATM | 1555 | O | HOH | S | 34 | −20.404 | 23.105 | −2.297 | 1.00 | 47.69 | | O |
| HETATM | 1556 | O | HOH | S | 35 | −2.053 | 42.697 | −1.666 | 1.00 | 34.78 | | O |
| HETATM | 1557 | O | HOH | S | 36 | −39.542 | 41.578 | −3.465 | 1.00 | 35.79 | | O |
| HETATM | 1558 | O | HOH | S | 37 | −17.528 | 50.479 | −11.644 | 1.00 | 45.34 | | O |
| HETATM | 1559 | O | HOH | S | 38 | −2.790 | 36.224 | −7.911 | 1.00 | 42.91 | | O |
| HETATM | 1560 | O | HOH | S | 39 | −40.194 | 28.680 | −2.146 | 1.00 | 39.59 | | O |
| HETATM | 1561 | O | HOH | S | 40 | −38.407 | 41.038 | 13.382 | 1.00 | 42.80 | | O |
| HETATM | 1562 | O | HOH | S | 41 | −22.915 | 26.393 | −10.704 | 1.00 | 51.77 | | O |
| HETATM | 1563 | O | HOH | S | 42 | −38.845 | 41.788 | −5.971 | 1.00 | 49.03 | | O |
| HETATM | 1564 | O | HOH | S | 43 | −36.099 | 50.115 | 9.037 | 1.00 | 41.25 | | O |
| HETATM | 1565 | O | HOH | S | 44 | −17.355 | 45.376 | −13.697 | 1.00 | 44.10 | | O |
| HETATM | 1566 | O | HOH | S | 45 | −1.162 | 40.678 | −6.005 | 1.00 | 39.09 | | O |
| HETATM | 1567 | O | HOH | S | 46 | −28.753 | 22.369 | −10.777 | 1.00 | 55.50 | | O |
| HETATM | 1568 | O | HOH | S | 47 | −0.975 | 52.746 | −7.990 | 1.00 | 46.39 | | O |
| HETATM | 1569 | O | HOH | S | 48 | −0.894 | 40.925 | −3.330 | 1.00 | 51.81 | | O |
| HETATM | 1570 | O | HOH | S | 49 | −38.793 | 44.872 | 0.338 | 1.00 | 48.00 | | O |
| HETATM | 1571 | O | HOH | S | 50 | −4.562 | 44.866 | 5.976 | 1.00 | 44.49 | | O |

TABLE 6-continued

| | | | | | | | | | | | |
|---|---|---|---|---|---|---|---|---|---|---|---|
| HETATM | 1572 | O | HOH | S | 51 | −8.838 | 52.510 | −19.877 | 1.00 | 48.90 | O |
| HETATM | 1573 | O | HOH | S | 52 | −3.172 | 41.183 | 0.843 | 1.00 | 32.89 | O |
| HETATM | 1574 | O | HOH | S | 53 | −39.600 | 39.040 | −6.706 | 1.00 | 44.50 | O |
| HETATM | 1575 | O | HOH | S | 54 | −25.008 | 47.181 | −2.438 | 1.00 | 54.96 | O |
| HETATM | 1576 | O | HOH | S | 55 | −41.565 | 36.148 | −3.772 | 1.00 | 49.33 | O |
| HETATM | 1577 | O | HOH | S | 56 | −16.996 | 30.410 | −13.718 | 1.00 | 49.44 | O |
| HETATM | 1578 | O | HOH | S | 57 | −0.606 | 40.376 | −10.330 | 1.00 | 47.80 | O |
| HETATM | 1579 | O | HOH | S | 58 | −34.434 | 26.234 | 7.374 | 1.00 | 53.47 | O |
| HETATM | 1580 | O | HOH | S | 59 | −35.799 | 24.448 | 0.839 | 1.00 | 54.83 | O |
| HETATM | 1581 | O | HOH | S | 60 | −4.278 | 32.309 | −13.316 | 1.00 | 54.95 | O |
| HETATM | 1582 | O | HOH | S | 61 | −32.854 | 27.376 | 3.585 | 1.00 | 57.52 | O |
| HETATM | 1583 | O | HOH | S | 62 | −29.653 | 39.466 | −9.483 | 1.00 | 30.72 | O |
| HETATM | 1584 | O | HOH | S | 63 | −38.448 | 44.245 | 9.663 | 1.00 | 41.03 | O |
| HETATM | 1585 | O | HOH | S | 64 | −12.664 | 36.441 | −9.105 | 1.00 | 34.86 | O |
| HETATM | 1586 | O | HOH | S | 65 | −26.130 | 31.681 | 7.764 | 1.00 | 52.31 | O |
| HETATM | 1587 | O | HOH | S | 66 | −7.106 | 38.900 | 6.887 | 1.00 | 53.76 | O |
| HETATM | 1588 | O | HOH | S | 67 | −5.686 | 44.678 | 8.679 | 1.00 | 53.91 | O |
| HETATM | 1589 | O | HOH | S | 68 | −5.310 | 50.083 | −15.622 | 1.00 | 48.56 | O |
| HETATM | 1590 | O | HOH | S | 69 | −12.151 | 44.755 | −11.201 | 1.00 | 52.71 | O |
| HETATM | 1591 | O | HOH | S | 70 | −32.153 | 39.882 | −10.835 | 1.00 | 52.92 | O |
| HETATM | 1592 | O | HOH | S | 71 | −40.912 | 45.254 | 8.515 | 1.00 | 57.89 | O |
| HETATM | 1593 | O | HOH | S | 72 | −2.684 | 33.749 | −15.633 | 1.00 | 73.29 | O |
| HETATM | 1594 | O | HOH | S | 73 | −36.012 | 52.047 | 11.245 | 1.00 | 52.92 | O |
| HETATM | 1595 | O | HOH | S | 74 | −0.858 | 48.085 | −5.158 | 1.00 | 40.90 | O |
| HETATM | 1596 | O | HOH | S | 75 | −21.507 | 55.180 | 10.249 | 1.00 | 38.22 | O |
| HETATM | 1597 | O | HOH | S | 76 | −29.020 | 37.926 | 11.432 | 1.00 | 58.69 | O |
| HETATM | 1598 | O | HOH | S | 77 | −36.997 | 40.484 | 15.741 | 1.00 | 54.77 | O |
| HETATM | 1599 | O | HOH | S | 78 | −7.288 | 40.043 | −12.107 | 1.00 | 46.19 | O |
| HETATM | 1600 | O | HOH | S | 79 | −39.134 | 51.613 | 3.883 | 1.00 | 60.09 | O |
| HETATM | 1601 | O | HOH | S | 80 | −29.823 | 60.093 | 1.452 | 1.00 | 41.05 | O |
| HETATM | 1602 | O | HOH | S | 81 | −6.828 | 60.448 | −9.582 | 1.00 | 38.94 | O |
| HETATM | 1603 | O | HOH | S | 82 | −20.347 | 50.897 | −10.447 | 1.00 | 41.52 | O |
| HETATM | 1604 | O | HOH | S | 83 | −20.453 | 38.061 | 11.698 | 1.00 | 52.10 | O |
| HETATM | 1605 | O | HOH | S | 84 | −9.000 | 38.961 | −14.050 | 1.00 | 55.93 | O |
| HETATM | 1606 | O | HOH | S | 85 | −13.476 | 38.546 | 10.079 | 1.00 | 45.40 | O |
| HETATM | 1607 | O | HOH | S | 86 | −1.261 | 50.399 | −5.536 | 1.00 | 51.75 | O |
| HETATM | 1608 | O | HOH | S | 87 | −29.289 | 25.588 | 3.450 | 1.00 | 58.12 | O |
| HETATM | 1609 | O | HOH | S | 88 | −27.435 | 36.764 | 12.898 | 1.00 | 54.77 | O |
| HETATM | 1610 | O | HOH | S | 89 | −39.441 | 47.478 | 6.524 | 1.00 | 52.37 | O |
| HETATM | 1611 | O | HOH | S | 90 | −28.782 | 30.517 | 9.098 | 1.00 | 60.43 | O |
| HETATM | 1612 | O | HOH | S | 91 | −25.426 | 31.438 | 10.148 | 1.00 | 61.49 | O |
| HETATM | 1613 | O | HOH | S | 92 | −33.527 | 37.427 | −12.120 | 1.00 | 49.18 | O |
| HETATM | 1614 | O | HOH | S | 93 | −6.868 | 50.707 | −18.505 | 1.00 | 50.15 | O |
| HETATM | 1615 | O | HOH | S | 94 | −35.352 | 21.726 | −2.285 | 1.00 | 61.43 | O |
| HETATM | 1616 | O | HOH | S | 95 | −15.812 | 25.105 | 4.715 | 1.00 | 63.37 | O |
| HETATM | 1617 | O | HOH | S | 96 | −29.866 | 61.685 | 9.944 | 1.00 | 65.49 | O |
| HETATM | 1618 | O | HOH | S | 97 | −27.164 | 42.367 | −8.980 | 1.00 | 48.83 | O |
| HETATM | 1619 | O | HOH | S | 98 | −18.982 | 36.563 | −9.603 | 1.00 | 29.51 | O |
| HETATM | 1620 | O | HOH | S | 99 | −11.189 | 32.358 | −16.167 | 1.00 | 32.70 | O |
| HETATM | 1621 | O | HOH | S | 100 | −10.913 | 22.271 | −12.926 | 1.00 | 68.19 | O |
| HETATM | 1622 | O | HOH | S | 101 | −28.185 | 47.430 | 0.578 | 1.00 | 38.10 | O |
| HETATM | 1623 | O | HOH | S | 102 | −35.456 | 47.332 | 10.106 | 1.00 | 56.92 | O |
| HETATM | 1624 | O | HOH | S | 103 | −17.914 | 47.101 | −11.833 | 1.00 | 43.20 | O |
| HETATM | 1625 | O | HOH | S | 104 | −0.497 | 48.708 | −0.679 | 1.00 | 42.44 | O |
| HETATM | 1626 | O | HOH | S | 105 | −3.385 | 38.402 | 0.448 | 1.00 | 46.11 | O |
| HETATM | 1627 | O | HOH | S | 106 | −5.480 | 37.289 | −0.956 | 1.00 | 56.81 | O |
| HETATM | 1628 | O | HOH | S | 107 | −39.368 | 34.378 | 11.707 | 1.00 | 45.98 | O |
| HETATM | 1629 | O | HOH | S | 108 | −7.993 | 44.416 | −14.099 | 1.00 | 57.03 | O |
| HETATM | 1630 | O | HOH | S | 109 | −26.188 | 21.362 | −10.628 | 1.00 | 50.15 | O |
| HETATM | 1631 | O | HOH | S | 110 | −7.070 | 53.352 | −21.857 | 1.00 | 51.73 | O |
| HETATM | 1632 | O | HOH | S | 111 | −27.759 | 45.038 | −2.135 | 1.00 | 52.15 | O |
| HETATM | 1633 | O | HOH | S | 112 | −45.575 | 33.318 | 11.373 | 1.00 | 54.88 | O |
| HETATM | 1634 | O | HOH | S | 113 | −40.213 | 41.041 | 1.415 | 1.00 | 56.13 | O |
| HETATM | 1635 | O | HOH | S | 114 | −24.062 | 22.286 | −9.305 | 1.00 | 56.30 | O |
| HETATM | 1636 | O | HOH | S | 115 | −29.751 | 62.184 | 3.214 | 1.00 | 59.44 | O |
| HETATM | 1637 | O | HOH | S | 116 | −36.144 | 21.864 | −4.757 | 1.00 | 66.85 | O |
| HETATM | 1638 | O | HOH | S | 117 | −14.039 | 32.204 | 0.301 | 1.00 | 53.76 | O |
| HETATM | 1639 | O | HOH | S | 118 | −4.451 | 41.510 | −15.804 | 1.00 | 56.62 | O |
| HETATM | 1640 | O | HOH | S | 119 | −40.947 | 31.934 | −2.395 | 1.00 | 51.83 | O |
| HETATM | 1641 | O | HOH | S | 120 | −2.530 | 52.445 | −3.131 | 1.00 | 32.81 | O |
| HETATM | 1643 | O | HOH | S | 122 | −18.008 | 51.050 | 14.806 | 1.00 | 46.96 | O |
| HETATM | 1644 | O | HOH | S | 123 | −29.579 | 48.175 | 10.569 | 1.00 | 36.92 | O |
| HETATM | 1645 | O | HOH | S | 124 | −30.555 | 50.195 | 12.051 | 1.00 | 43.32 | O |
| HETATM | 1646 | O | HOH | S | 125 | −35.450 | 33.626 | 11.031 | 1.00 | 35.19 | O |
| HETATM | 1647 | O | HOH | S | 126 | −33.049 | 36.196 | 11.934 | 1.00 | 54.98 | O |
| HETATM | 1648 | O | HOH | S | 127 | −42.986 | 29.868 | −1.137 | 1.00 | 53.56 | O |
| HETATM | 1649 | O | HOH | S | 128 | −32.867 | 34.876 | −11.501 | 1.00 | 34.67 | O |
| HETATM | 1650 | O | HOH | S | 129 | −29.358 | 32.427 | −13.212 | 1.00 | 34.76 | O |

TABLE 6-continued

DMXAA-hSTING$^{group2}$ complex

| HETATM | 1651 | O | HOH | S | 130 | −40.317 | 46.851 | 2.832 | 1.00 | 48.74 | O |
|---|---|---|---|---|---|---|---|---|---|---|---|
| HETATM | 1653 | O | HOH | S | 132 | −23.707 | 45.060 | −4.522 | 1.00 | 44.38 | O |
| HETATM | 1654 | O | HOH | S | 133 | −5.646 | 53.727 | −14.252 | 1.00 | 35.34 | O |
| HETATM | 1655 | O | HOH | S | 135 | −9.150 | 37.201 | 1.775 | 1.00 | 50.25 | O |
| HETATM | 1656 | O | HOH | S | 136 | −22.113 | 30.881 | 7.444 | 1.00 | 58.42 | O |
| HETATM | 1659 | O | HOH | S | 138 | −7.204 | 46.240 | 9.573 | 1.00 | 30.00 | O |
| HETATM | 1660 | O | HOH | S | 139 | −38.441 | 50.149 | 7.696 | 1.00 | 30.00 | O |
| END | | | | | | | | | | | |

TABLE 7

DMXAA-hSTING$^{G230I}$ complex

```
REMARK 3
REMARK 3  REFINEMENT.
REMARK 3    PROGRAM:   PHENIX (phenix.refine: 1.8.2 1309)
REMARK 3    AUTHORS:   Adams, Afonine, Burnley, Chen, Davis, Echols, Gildea,
REMARK 3         :     Gopal, Gros, Grosse-Kunstleve, Headd, Hung, Immormino,
REMARK 3         :     Ioerger, McCoy, McKee, Moriarty, Pai, Read, Richardson,
REMARK 3         :     Richardson, Romo, Sacchettini, Sauter, Smith, Storoni,
REMARK 3         :     Terwilliger, Zwart
REMARK 3
REMARK 3  REFINEMENT TARGET: ML
REMARK 3
REMARK 3  DATA USED IN REFINEMENT.
REMARK 3    RESOLUTION RANGE HIGH (ANGSTROMS):    2.510
REMARK 3    RESOLUTION RANGE LOW  (ANGSTROMS):   78.660
REMARK 3    MIN(FOBS/SIGMA_FOBS):                 1.39
REMARK 3    COMPLETENESS FOR RANGE (%):          94.13
REMARK 3    NUMBER OF REFLECTIONS:               14320
REMARK 3    NUMBER OF REFLECTIONS (NON-ANOMALOUS): 14320
REMARK 3
REMARK 3  FIT TO DATA USED IN REFINEMENT.
REMARK 3    R VALUE (WORKING + TEST SET): 0.1995
REMARK 3    R VALUE (WORKING SET):        0.1975
REMARK 3    FREE R VALUE :                0.2391
REMARK 3    FREE R VALUE TEST SET SIZE (%): 5.03
REMARK 3    FREE R VALUE TEST SET COUNT:   720
REMARK 3
REMARK 3    FIT TO DATA USED IN REFINEMENT (IN BINS).
REMARK 3    BIN   RESOLUTION RANGE  COMPL.  NWORK  NFREE  RWORK   RFREE
REMARK 3     1    78.6985-4.2921     0.95    2803    147   0.1705  0.1929
REMARK 3     2     4.2921-3.4068     0.95    2763    123   0.1804  0.2261
REMARK 3     3     3.4068-2.9761     0.93    2678    149   0.2266  0.2915
REMARK 3     4     2.9761-2.7040     0.94    2706    156   0.2615  0.3201
REMARK 3     5     2.7040-2.5102     0.92    2650    145   0.2906  0.3356
REMARK 3
REMARK 3  BULK SOLVENT MODELLING.
REMARK 3    METHOD USED:      FLAT BULK SOLVENT MODEL
REMARK 3    SOLVENT RADIUS:   1.11
REMARK 3    SHRINKAGE RADIUS: 0.90
REMARK 3    GRID STEP FACTOR: 4.00
REMARK 3
REMARK 3  ERROR ESTIMATES.
REMARK 3    COORDINATE ERROR (MAXIMUM-LIKELIHOOD BASED):          0.38
REMARK 3    PHASE ERROR (DEGREES, MAXIMUM-LIKELIHOOD BASED):     28.36
REMARK 3
REMARK 3  STRUCTURE FACTORS CALCULATION ALGORITHM: FFT
REMARK 3
REMARK 3  DEVIATIONS FROM IDEAL VALUES.
REMARK 3                 RMSD     MAX    COUNT
REMARK 3    BOND:        0.007    0.050   3034
REMARK 3    ANGLE:       1.262   16.566   4120
REMARK 3    CHIRALITY:   0.081    0.389    446
REMARK 3    PLANARITY:   0.005    0.043    544
REMARK 3    DIHEDRAL:   20.446   89.486   1142
REMARK 3    MIN NONBONDED DISTANCE: 2.017
REMARK 3
REMARK 3  MOLPROBITY STATISTICS.
REMARK 3    ALL-ATOM CLASHSCORE: 14.50
REMARK 3    RAMACHANDRAN PLOT:
REMARK 3      OUTLIERS:  0.56%
REMARK 3      ALLOWED:   3.89%
REMARK 3      FAVORED:  95.56%
REMARK 3    ROTAMER OUTLIERS: 14.15%
```

TABLE 7-continued

| DMXAA-hSTING$^{G230I}$ complex | | | | | | |
|---|---|---|---|---|---|---|
| REMARK 3 | CBETA DEVIATIONS: 3 | | | | | |
| REMARK 3 | | | | | | |
| REMARK 3 | ATOMIC DISPLACEMENT PARAMETERS. | | | | | |
| REMARK 3 | WILSON B: None | | | | | |
| REMARK 3 | RMS(B_ISO_OR_EQUIVALENT_BONDED): 8.54 | | | | | |
| REMARK 3 | ATOMS | NUMBER OF ATOMS | | | | |
| REMARK 3 | | ISO. | ANISO. | | | |
| REMARK 3 | ALL: | 3020 | 2932 | | | |
| REMARK 3 | ALL (NO H): | 3020 | 2932 | | | |
| REMARK 3 | SOLVENT: | 46 | 0 | | | |
| REMARK 3 | NON-SOLVENT: | 2974 | 2932 | | | |
| REMARK 3 | HYDROGENS: | 0 | 0 | | | |
| REMARK 3 | | | | | | |
| REMARK 3 | TLS DETAILS. | | | | | |
| REMARK 3 | NUMBER OF TLS GROUPS: 13 | | | | | |
| REMARK 3 | ORIGIN: CENTER OF MASS | | | | | |
| REMARK 3 | TLS GROUP: 1 | | | | | |
| REMARK 3 | SELECTION: chain 'A' and (resid 154 through 184) | | | | | |
| REMARK 3 | ORIGIN FOR THE GROUP (A): | | 18.5649 | −84.9417 | −65.0832 | |
| REMARK 3 | T TENSOR | | | | | |
| REMARK 3 | T11: | 0.4393 | T22: | 0.3018 | | |
| REMARK 3 | T33: | 0.4398 | T12: | 0.0825 | | |
| REMARK 3 | T13: | −0.0564 | T23: | −0.0648 | | |
| REMARK 3 | L TENSOR | | | | | |
| REMARK 3 | L11: | 0.5884 | L22: | 3.2436 | | |
| REMARK 3 | L33: | 1.0127 | L12: | −0.3808 | | |
| REMARK 3 | L13: | 0.0492 | L23: | 1.3981 | | |
| REMARK 3 | S TENSOR | | | | | |
| REMARK 3 | S11: | −0.0732 | S12: | −0.1629 | S13: | 0.0759 |
| REMARK 3 | S21: | −0.2078 | S22: | 0.5745 | S23: | −0.8923 |
| REMARK 3 | S31: | 0.5100 | S32: | 0.4198 | S33: | −0.2551 |
| REMARK 3 | TLS GROUP: 2 | | | | | |
| REMARK 3 | : chain 'A' and (resid 185 through 203) | | | | | |
| REMARK 3 | ORIGIN FOR THE GROUP (A): | | 15.0533 | −97.1915 | −72.8326 | |
| REMARK 3 | T TENSOR | | | | | |
| REMARK 3 | T11: | 0.4444 | T22: | 0.4429 | | |
| REMARK 3 | T33: | 0.7942 | T12: | 0.0775 | | |
| REMARK 3 | T13: | 0.1063 | T23: | −0.1346 | | |
| REMARK 3 | L TENSOR | | | | | |
| REMARK 3 | L11: | 1.3482 | L22: | 3.5737 | | |
| REMARK 3 | L33: | 1.1882 | L12: | −0.3929 | | |
| REMARK 3 | L13: | 0.5508 | L23: | 0.1118 | | |
| REMARK 3 | S TENSOR | | | | | |
| REMARK 3 | S11: | −0.1754 | S12: | 0.1904 | S13: | −0.9845 |
| REMARK 3 | S21: | −0.1476 | S22: | −0.0773 | S23: | −0.9503 |
| REMARK 3 | S31: | 0.5475 | S32: | −0.1593 | S33: | 0.2662 |
| REMARK 3 | TLS GROUP: 3 | | | | | |
| REMARK 3 | SELECTION: chain 'A' and (resid 204 through 218) | | | | | |
| REMARK 3 | ORIGIN FOR THE GROUP (A): | | −0.0262 | −86.6210 | −74.0738 | |
| REMARK 3 | T TENSOR | | | | | |
| REMARK 3 | T11: | 0.4134 | T22: | 0.5352 | | |
| REMARK 3 | T33: | 1.1526 | T12: | 0.0870 | | |
| REMARK 3 | T13: | 0.0015 | T23: | 0.0352 | | |
| REMARK 3 | L TENSOR | | | | | |
| REMARK 3 | L11: | 0.3197 | L22: | 2.3847 | | |
| REMARK 3 | L33: | 1.9616 | L12: | −0.7523 | | |
| REMARK 3 | L13: | −0.2715 | L23: | 1.7058 | | |
| REMARK 3 | S TENSOR | | | | | |
| REMARK 3 | S11: | −0.1620 | S12: | 0.0679 | S13: | −1.4908 |
| REMARK 3 | S21: | −0.4128 | S22: | −0.4686 | S23: | 2.4070 |
| REMARK 3 | S31: | 0.1596 | S32: | −0.0763 | S33: | 0.3138 |
| REMARK 3 | TLS GROUP: 4 | | | | | |
| REMARK 3 | SELECTION: chain 'A' and (resid 219 through 247) | | | | | |
| REMARK 3 | ORIGIN FOR THE GROUP (A): | | 12.4963 | −92.7353 | −62.3817 | |
| REMARK 3 | T TENSOR | | | | | |
| REMARK 3 | T11: | 0.6214 | T22: | 0.4812 | | |
| REMARK 3 | T33: | 0.6515 | T12: | 0.0930 | | |
| REMARK 3 | T13: | 0.0352 | T23: | 0.0210 | | |
| REMARK 3 | L TENSOR | | | | | |
| REMARK 3 | L11: | 2.3340 | L22: | 4.1461 | | |
| REMARK 3 | L33: | 4.4152 | L12: | −1.2271 | | |
| REMARK 3 | L13: | −1.0413 | L23: | 0.0238 | | |
| REMARK 3 | S TENSOR | | | | | |
| REMARK 3 | S11: | −0.1280 | S12: | −0.6561 | S13: | −0.2175 |
| REMARK 3 | S21: | 1.0992 | S22: | 0.2608 | S23: | −0.2951 |
| REMARK 3 | S31: | 0.3088 | S32: | −0.4641 | S33: | 0.1404 |
| REMARK 3 | TLS GROUP: 5 | | | | | |
| REMARK 3 | SELECTION: chain 'A' and (resid 248 through 262) | | | | | |

TABLE 7-continued

| DMXAA-hSTING$^{G230I}$ complex |
|---|

| | | | | | | |
|---|---|---|---|---|---|---|
| REMARK 3 | ORIGIN FOR THE GROUP (A): | | 8.4387 | −94.2521 | −79.3077 | |
| REMARK 3 | T TENSOR | | | | | |
| REMARK 3 | T11: | 0.6585 | T22: | 0.4111 | | |
| REMARK 3 | T33: | 0.6599 | T12: | 0.1126 | | |
| REMARK 3 | T13: | −0.0693 | T23: | −0.1355 | | |
| REMARK 3 | L TENSOR | | | | | |
| REMARK 3 | L11: | 2.0873 | L22: | 1.5403 | | |
| REMARK 3 | L33: | 0.4325 | L12: | 0.6038 | | |
| REMARK 3 | L13: | 0.5988 | L23: | −0.0328 | | |
| REMARK 3 | S TENSOR | | | | | |
| REMARK 3 | S11: | 0.1274 | S12: | 0.2224 | S13: | −0.5200 |
| REMARK 3 | S21: | −0.6720 | S22: | −0.2759 | S23: | 0.6116 |
| REMARK 3 | S31: | 0.0107 | S32: | 0.0571 | S33: | −0.0481 |
| REMARK 3 | TLS GROUP: 6 | | | | | |
| REMARK 3 | SELECTION: chain 'A' and (resid 263 through 280) | | | | | |
| REMARK 3 | ORIGIN FOR THE GROUP (A): | | −0.0640 | −71.1490 | −64.7673 | |
| REMARK 3 | T TENSOR | | | | | |
| REMARK 3 | T11: | 0.2561 | T22: | 0.3183 | | |
| REMARK 3 | T33: | 0.4491 | T12: | −0.0366 | | |
| REMARK 3 | T13: | 0.0507 | T23: | −0.0720 | | |
| REMARK 3 | L TENSOR | | | | | |
| REMARK 3 | L11: | 3.8910 | L22: | 3.4313 | | |
| REMARK 3 | L33: | 2.8197 | L12: | −2.0277 | | |
| REMARK 3 | L13: | −0.9236 | L23: | 0.2563 | | |
| REMARK 3 | S TENSOR | | | | | |
| REMARK 3 | S11: | −0.1066 | S12: | 0.1651 | S13: | 0.0430 |
| REMARK 3 | S21: | 0.1833 | S22: | −0.0732 | S23: | 0.6659 |
| REMARK 3 | S31: | 0.3945 | S32: | −0.8557 | S33: | 0.0402 |
| REMARK 3 | TLS GROUP: 7 | | | | | |
| REMARK 3 | SELECTION: chain 'A' and (resid 281 through 301) | | | | | |
| REMARK 3 | ORIGIN FOR THE GROUP (A): | | 11.2863 | −70.6978 | −72.9476 | |
| REMARK 3 | T TENSOR | | | | | |
| REMARK 3 | T11: | 0.3233 | T22: | 0.2157 | | |
| REMARK 3 | T33: | 0.3495 | T12: | 0.0468 | | |
| REMARK 3 | T13: | 0.0400 | T23: | 0.0147 | | |
| REMARK 3 | L TENSOR | | | | | |
| REMARK 3 | L11: | 8.5718 | L22: | 4.6285 | | |
| REMARK 3 | L33: | 3.2871 | L12: | −2.7268 | | |
| REMARK 3 | L13: | 1.2567 | L23: | 0.1583 | | |
| REMARK 3 | S TENSOR | | | | | |
| REMARK 3 | S11: | 0.4866 | S12: | 0.3128 | S13: | 1.2110 |
| REMARK 3 | S21: | −0.5846 | S22: | −0.2970 | S23: | −0.6743 |
| REMARK 3 | S31: | −0.0057 | S32: | 0.0562 | S33: | −0.0866 |
| REMARK 3 | TLS GROUP: 8 | | | | | |
| REMARK 3 | SELECTION: chain 'A' and (resid 302 through 314) | | | | | |
| REMARK 3 | ORIGIN FOR THE GROUP (A): | | 19.5103 | −82.4342 | −73.4070 | |
| REMARK 3 | T TENSOR | | | | | |
| REMARK 3 | T11: | 0.4366 | T22: | 0.4324 | | |
| REMARK 3 | T33: | 0.9085 | T12: | −0.0064 | | |
| REMARK 3 | T13: | −0.0121 | T23: | −0.1791 | | |
| REMARK 3 | L TENSOR | | | | | |
| REMARK 3 | L11: | 5.0079 | L22: | 1.4371 | | |
| REMARK 3 | L33: | 2.3589 | L12: | 0.3981 | | |
| REMARK 3 | L13: | 1.8094 | L23: | 0.5328 | | |
| REMARK 3 | S TENSOR | | | | | |
| REMARK 3 | S11: | −0.2832 | S12: | −0.0864 | S13: | 1.3536 |
| REMARK 3 | S21: | −0.2094 | S22: | 0.2364 | S23: | −1.3952 |
| REMARK 3 | S31: | −0.0630 | S32: | 0.4603 | S33: | −0.1243 |
| REMARK 3 | TLS GROUP: 9 | | | | | |
| REMARK 3 | SELECTION: chain 'A' and (resid 315 through 335) | | | | | |
| REMARK 3 | ORIGIN FOR THE GROUP (A): | | 5.9841 | −84.6983 | −84.8320 | |
| REMARK 3 | T TENSOR | | | | | |
| REMARK 3 | T11: | 0.8254 | T22: | 0.4773 | | |
| REMARK 3 | T33: | 0.7360 | T12: | 0.0892 | | |
| REMARK 3 | T13: | −0.2281 | T23: | −0.1026 | | |
| REMARK 3 | L TENSOR | | | | | |
| REMARK 3 | L11: | 0.5859 | L22: | 3.6900 | | |
| REMARK 3 | L33: | 3.4392 | L12: | 0.8135 | | |
| REMARK 3 | L13: | −1.0849 | L23: | 0.4363 | | |
| REMARK 3 | S TENSOR | | | | | |
| REMARK 3 | S11: | 0.1659 | S12: | 0.6695 | S13: | 0.4312 |
| REMARK 3 | S21: | −1.8859 | S22: | 0.0194 | S23: | 0.7650 |
| REMARK 3 | S31: | −1.3287 | S32: | −0.1047 | S33: | 0.1265 |
| REMARK 3 | TLS GROUP: 10 | | | | | |
| REMARK 3 | SELECTION: chain 'B' and (resid 154 through 184) | | | | | |
| REMARK 3 | ORIGIN FOR THE GROUP (A): | | 2.6989 | −79.4016 | −49.5127 | |
| REMARK 3 | T TENSOR | | | | | |
| REMARK 3 | T11: | 0.4055 | T22: | 0.5218 | | |

TABLE 7-continued

| DMXAA-hSTING$^{G230I}$ complex | | | | | | | | | |
|---|---|---|---|---|---|---|---|---|---|
| REMARK 3 | | T33: | 0.4268 T12: | −0.0439 | | | | | |
| REMARK 3 | | T13: | 0.0964 T23: | 0.1163 | | | | | |
| REMARK 3 | | L TENSOR | | | | | | | |
| REMARK 3 | | L11: | 0.8467 L22: | 1.0167 | | | | | |
| REMARK 3 | | L33: | 1.5333 L12: | 0.1082 | | | | | |
| REMARK 3 | | L13: | 0.4092 L23: | −0.9415 | | | | | |
| REMARK 3 | | S TENSOR | | | | | | | |
| REMARK 3 | | S11: | −0.3737 S12: | −0.2406 S13: | −0.4167 | | | | |
| REMARK 3 | | S21: | −0.1505 S22: | 0.5597 S23: | −0.1553 | | | | |
| REMARK 3 | | S31: | 0.3988 S32: | −0.8521 S33: | −0.0941 | | | | |
| REMARK 3 | TLS GROUP: 11 | | | | | | | | |
| REMARK 3 | | SELECTION: chain 'B' and (resid 185 through 197) | | | | | | | |
| REMARK 3 | | ORIGIN FOR THE GROUP (A): | | 4.3298 | −89.0654 | −31.6612 | | | |
| REMARK 3 | | T TENSOR | | | | | | | |
| REMARK 3 | | T11: | 0.8391 T22: | 0.9093 | | | | | |
| REMARK 3 | | T33: | 0.9086 T12: | −0.0131 | | | | | |
| REMARK 3 | | T13: | 0.1673 T23: | 0.1257 | | | | | |
| REMARK 3 | | L TENSOR | | | | | | | |
| REMARK 3 | | L11: | 0.3021 L22: | 2.2105 | | | | | |
| REMARK 3 | | L33: | 0.2378 L12: | 0.5587 | | | | | |
| REMARK 3 | | L13: | 0.0275 L23: | 0.7643 | | | | | |
| REMARK 3 | | S TENSOR | | | | | | | |
| REMARK 3 | | S11: | −0.3698 S12: | −0.2731 S13: | −0.2713 | | | | |
| REMARK 3 | | S21: | 1.3272 S22: | 0.5413 S23: | −0.7772 | | | | |
| REMARK 3 | | S31: | −0.2905 S32: | −0.6279 S33: | −0.0887 | | | | |
| REMARK 3 | TLS GROUP: 12 | | | | | | | | |
| REMARK 3 | | SELECTION: chain 'B' and (resid 198 through 252) | | | | | | | |
| REMARK 3 | | ORIGIN FOR THE GROUP (A): | | 12.7528 | −81.7477 | −42.9709 | | | |
| REMARK 3 | | T TENSOR | | | | | | | |
| REMARK 3 | | T11: | 0.6197 T22: | 0.7199 | | | | | |
| REMARK 3 | | T33: | 0.5747 T12: | 0.0259 | | | | | |
| REMARK 3 | | T13: | −0.0478 T23: | 0.1385 | | | | | |
| REMARK 3 | | L TENSOR | | | | | | | |
| REMARK 3 | | L11: | 1.7783 L22: | 3.4469 | | | | | |
| REMARK 3 | | L33: | 1.9528 L12: | 0.4436 | | | | | |
| REMARK 3 | | L13: | −0.9387 L23: | −1.2119 | | | | | |
| REMARK 3 | | S TENSOR | | | | | | | |
| REMARK 3 | | S11: | 0.0497 S12: | −0.4807 S13: | −0.8641 | | | | |
| REMARK 3 | | S21: | 0.2895 S22: | −0.1031 S23: | −0.6763 | | | | |
| REMARK 3 | | S31: | 0.5541 S32: | 0.3894 S33: | 0.0559 | | | | |
| REMARK 3 | TLS GROUP: 13 | | | | | | | | |
| REMARK 3 | | SELECTION: chain 'B' and (resid 253 through 335) | | | | | | | |
| REMARK 3 | | ORIGIN FOR THE GROUP (A): | | 12.4991 | −68.6162 | −46.0924 | | | |
| REMARK 3 | | T TENSOR | | | | | | | |
| REMARK 3 | | T11: | 0.3619 T22: | 0.5606 | | | | | |
| REMARK 3 | | T33: | 0.3032 T12: | 0.0043 | | | | | |
| REMARK 3 | | T13: | −0.0138 T23: | −0.0069 | | | | | |
| REMARK 3 | | L TENSOR | | | | | | | |
| REMARK 3 | | L11: | 2.2900 L22: | 3.5956 | | | | | |
| REMARK 3 | | L33: | 3.1007 L12: | 0.4476 | | | | | |
| REMARK 3 | | L13: | −0.6791 L23: | −1.4882 | | | | | |
| REMARK 3 | | S TENSOR | | | | | | | |
| REMARK 3 | | S11: | 0.1403 S12: | −0.7469 S13: | 0.0186 | | | | |
| REMARK 3 | | S21: | 0.7529 S22: | −0.0615 S23: | 0.0205 | | | | |
| REMARK 3 | | S31: | −0.3571 S32: | 0.0704 S33: | −0.0094 | | | | |
| REMARK 3 | | | | | | | | | |
| CRYST1 | 36.570 | 77.919 | 79.634 | 90.00 98.97 90.00 | | P 1 21 1 | | | |
| SCALE1 | 0.027345 | 0.000000 | 0.004317 | 0.00000 | | | | | |
| SCALE2 | 0.000000 | 0.012834 | 0.000000 | 0.00000 | | | | | |
| SCALE3 | 0.000000 | 0.000000 | 0.012713 | 0.00000 | | | | | |

| ATOM | 1 | N | SER | A | 154 | 12.290 | −62.777 | −65.163 | 1.00 | 38.38 | | | N |
|---|---|---|---|---|---|---|---|---|---|---|---|---|---|
| ANISOU | 1 | N | SER | A | 154 | 4119 | 4350 | 6113 | −935 | 208 | −285 | | N |
| ATOM | 2 | CA | SER | A | 154 | 11.396 | −63.506 | −66.054 | 1.00 | 25.17 | | | C |
| ANISOU | 2 | CA | SER | A | 154 | 2763 | 2582 | 4220 | −991 | 161 | −112 | | C |
| ATOM | 3 | CB | SER | A | 154 | 12.123 | −63.829 | −67.354 | 1.00 | 30.71 | | | C |
| ANISOU | 3 | CB | SER | A | 154 | 3671 | 3116 | 4882 | −1071 | 398 | −137 | | C |
| ATOM | 4 | OG | SER | A | 154 | 11.332 | −64.604 | −68.222 | 1.00 | 38.95 | | | O |
| ANISOU | 4 | OG | SER | A | 154 | 5026 | 4061 | 5710 | −1111 | 343 | 16 | | O |
| ATOM | 5 | C | SER | A | 154 | 10.920 | −64.795 | −65.403 | 1.00 | 36.48 | | | C |
| ANISOU | 5 | C | SER | A | 154 | 4192 | 4114 | 5553 | −883 | −20 | −45 | | C |
| ATOM | 6 | O | SER | A | 154 | 11.686 | −65.464 | −64.707 | 1.00 | 40.92 | | | O |
| ANISOU | 6 | O | SER | A | 154 | 4592 | 4763 | 6193 | −768 | −27 | −147 | | O |
| ATOM | 7 | N | VAL | A | 155 | 9.654 | −65.141 | −65.634 | 1.00 | 38.95 | | | N |
| ANISOU | 7 | N | VAL | A | 155 | 4692 | 4404 | 5704 | −917 | −168 | 118 | | N |
| ATOM | 8 | CA | VAL | A | 155 | 9.066 | −66.362 | −65.094 | 1.00 | 30.23 | | | C |
| ANISOU | 8 | CA | VAL | A | 155 | 3619 | 3370 | 4498 | −838 | −323 | 197 | | C |
| ATOM | 9 | CB | VAL | A | 155 | 7.565 | −66.467 | −65.416 | 1.00 | 34.83 | | | C |

TABLE 7-continued

| DMXAA-hSTING$^{G230I}$ complex | | | | | | | | | | | |
|---|---|---|---|---|---|---|---|---|---|---|---|
| ANISOU | 9 | CB | VAL | A | 155 | 4383 | 3908 | 4945 | −903 | −477 | 357 | C |
| ATOM | 10 | CG1 | VAL | A | 155 | 7.082 | −67.913 | −65.299 | 1.00 | 26.15 | | C |
| ANISOU | 10 | CG1 | VAL | A | 155 | 3391 | 2817 | 3729 | −855 | −571 | 439 | C |
| ATOM | 11 | CG2 | VAL | A | 155 | 6.765 | −65.560 | −64.508 | 1.00 | 17.05 | | C |
| ANISOU | 11 | CG2 | VAL | A | 155 | 1968 | 1754 | 2755 | −901 | −610 | 369 | C |
| ATOM | 12 | C | VAL | A | 155 | 9.781 | −67.590 | −65.652 | 1.00 | 22.80 | | C |
| ANISOU | 12 | C | VAL | A | 155 | 2793 | 2367 | 3502 | −802 | −230 | 175 | C |
| ATOM | 13 | O | VAL | A | 155 | 10.131 | −68.517 | −64.919 | 1.00 | 35.79 | | O |
| ANISOU | 13 | O | VAL | A | 155 | 4350 | 4095 | 5154 | −688 | −288 | 139 | O |
| ATOM | 14 | N | ALA | A | 156 | 9.997 | −67.576 | −66.960 | 1.00 | 21.75 | | N |
| ANISOU | 14 | N | ALA | A | 156 | 2877 | 2081 | 3307 | −895 | −85 | 196 | N |
| ATOM | 15 | CA | ALA | A | 156 | 10.641 | −68.677 | −67.665 | 1.00 | 30.61 | | C |
| ANISOU | 15 | CA | ALA | A | 156 | 4137 | 3123 | 4369 | −877 | 24 | 176 | C |
| ATOM | 16 | CB | ALA | A | 156 | 10.571 | −68.456 | −69.164 | 1.00 | 42.97 | | C |
| ANISOU | 16 | CB | ALA | A | 156 | 5999 | 4500 | 5826 | −1001 | 167 | 229 | C |
| ATOM | 17 | C | ALA | A | 156 | 12.095 | −68.868 | −67.247 | 1.00 | 39.65 | | C |
| ANISOU | 17 | C | ALA | A | 156 | 5066 | 4319 | 5682 | −792 | 159 | −10 | C |
| ATOM | 18 | O | ALA | A | 156 | 12.624 | −69.982 | −67.245 | 1.00 | 48.24 | | O |
| ANISOU | 18 | O | ALA | A | 156 | 6166 | 5406 | 6756 | −714 | 173 | −50 | O |
| ATOM | 19 | N | HIS | A | 157 | 12.751 | −67.764 | −66.923 | 1.00 | 33.82 | | N |
| ANISOU | 19 | N | HIS | A | 157 | 4124 | 3612 | 5116 | −806 | 256 | −135 | N |
| ATOM | 20 | CA | HIS | A | 157 | 14.158 | −67.781 | −66.578 | 1.00 | 30.84 | | C |
| ANISOU | 20 | CA | HIS | A | 157 | 3512 | 3266 | 4941 | −733 | 390 | −345 | C |
| ATOM | 21 | CB | HIS | A | 157 | 14.680 | −66.351 | −66.440 | 1.00 | 44.66 | | C |
| ANISOU | 21 | CB | HIS | A | 157 | 5077 | 5016 | 6877 | −792 | 513 | −466 | C |
| ATOM | 22 | CG | HIS | A | 157 | 16.159 | −66.254 | −66.244 | 1.00 | 41.24 | | C |
| ANISOU | 22 | CG | HIS | A | 157 | 4392 | 4586 | 6690 | −740 | 679 | −708 | C |
| ATOM | 23 | ND1 | HIS | A | 157 | 17.059 | −66.776 | −67.134 | 1.00 | 43.00 | | N |
| ANISOU | 23 | ND1 | HIS | A | 157 | 4684 | 4694 | 6960 | −775 | 905 | −806 | N |
| ATOM | 24 | CE1 | HIS | A | 157 | 18.292 | −66.536 | −66.707 | 1.00 | 40.67 | | C |
| ANISOU | 24 | CE1 | HIS | A | 157 | 4095 | 4426 | 6932 | −715 | 1012 | −1047 | C |
| ATOM | 25 | NE2 | HIS | A | 157 | 18.214 | −65.881 | −65.569 | 1.00 | 35.86 | | N |
| ANISOU | 25 | NE2 | HIS | A | 157 | 3242 | 3945 | 6436 | −637 | 849 | −1103 | N |
| ATOM | 26 | CD2 | HIS | A | 157 | 16.885 | −65.684 | −65.256 | 1.00 | 34.62 | | C |
| ANISOU | 26 | CD2 | HIS | A | 157 | 3227 | 3848 | 6080 | −654 | 648 | −889 | C |
| ATOM | 27 | C | HIS | A | 157 | 14.386 | −68.557 | −65.279 | 1.00 | 33.45 | | C |
| ANISOU | 27 | C | HIS | A | 157 | 3643 | 3745 | 5322 | −555 | 203 | −407 | C |
| ATOM | 28 | O | HIS | A | 157 | 15.263 | −69.426 | −65.196 | 1.00 | 36.54 | | O |
| ANISOU | 28 | O | HIS | A | 157 | 3971 | 4136 | 5776 | −459 | 237 | −520 | O |
| ATOM | 29 | N | GLY | A | 158 | 13.584 | −68.249 | −64.266 | 1.00 | 30.30 | | N |
| ANISOU | 29 | N | GLY | A | 158 | 3164 | 3462 | 4888 | −508 | 4 | −334 | N |
| ATOM | 30 | CA | GLY | A | 158 | 13.659 | −68.964 | −63.006 | 1.00 | 25.57 | | C |
| ANISOU | 30 | CA | GLY | A | 158 | 2434 | 2991 | 4292 | −341 | −184 | −367 | C |
| ATOM | 31 | C | GLY | A | 158 | 13.309 | −70.431 | −63.176 | 1.00 | 30.72 | | C |
| ANISOU | 31 | C | GLY | A | 158 | 3285 | 3621 | 4766 | −292 | −277 | −248 | C |
| ATOM | 32 | O | GLY | A | 158 | 13.948 | −71.304 | −62.589 | 1.00 | 42.20 | | O |
| ANISOU | 32 | O | GLY | A | 158 | 4680 | 5128 | 6227 | −144 | −372 | −310 | O |
| ATOM | 33 | N | LEU | A | 159 | 12.288 | −70.700 | −63.984 | 1.00 | 24.37 | | N |
| ANISOU | 33 | N | LEU | A | 159 | 2729 | 2727 | 3804 | −411 | −260 | −83 | N |
| ATOM | 34 | CA | LEU | A | 159 | 11.844 | −72.068 | −64.235 | 1.00 | 25.17 | | C |
| ANISOU | 34 | CA | LEU | A | 159 | 3030 | 2791 | 3741 | −385 | −342 | 35 | C |
| ATOM | 35 | CB | LEU | A | 159 | 10.560 | −72.069 | −65.067 | 1.00 | 36.37 | | C |
| ANISOU | 35 | CB | LEU | A | 159 | 4689 | 4120 | 5010 | −524 | −364 | 211 | C |
| ATOM | 36 | CG | LEU | A | 159 | 9.251 | −72.243 | −64.293 | 1.00 | 35.53 | | C |
| ANISOU | 36 | CG | LEU | A | 159 | 4631 | 4067 | 4802 | −530 | −546 | 352 | C |
| ATOM | 37 | CD2 | LEU | A | 159 | 8.069 | −71.768 | −65.123 | 1.00 | 18.32 | | C |
| ANISOU | 37 | CD2 | LEU | A | 159 | 2607 | 1802 | 2554 | −672 | −565 | 466 | C |
| ATOM | 38 | CD1 | LEU | A | 159 | 9.310 | −71.503 | −62.965 | 1.00 | 38.67 | | C |
| ANISOU | 38 | CD1 | LEU | A | 159 | 4804 | 4608 | 5280 | −452 | −641 | 305 | C |
| ATOM | 39 | C | LEU | A | 159 | 12.917 | −72.905 | −64.928 | 1.00 | 29.35 | | C |
| ANISOU | 39 | C | LEU | A | 159 | 3607 | 3247 | 4297 | −333 | −227 | −61 | C |
| ATOM | 40 | O | LEU | A | 159 | 13.122 | −74.070 | −64.587 | 1.00 | 35.64 | | O |
| ANISOU | 40 | O | LEU | A | 159 | 4431 | 4062 | 5047 | −220 | −312 | −66 | O |
| ATOM | 41 | N | ALA | A | 160 | 13.598 | −72.306 | −65.900 | 1.00 | 37.83 | | N |
| ANISOU | 41 | N | ALA | A | 160 | 4701 | 4226 | 5446 | −420 | −23 | −142 | N |
| ATOM | 42 | CA | ALA | A | 160 | 14.657 | −72.996 | −66.627 | 1.00 | 31.63 | | C |
| ANISOU | 42 | CA | ALA | A | 160 | 3943 | 3361 | 4715 | −388 | 128 | −260 | C |
| ATOM | 43 | CB | ALA | A | 160 | 15.168 | −72.131 | −67.769 | 1.00 | 25.03 | | C |
| ANISOU | 43 | CB | ALA | A | 160 | 3171 | 2401 | 3937 | −526 | 387 | −322 | C |
| ATOM | 44 | C | ALA | A | 160 | 15.795 | −73.362 | −65.683 | 1.00 | 34.97 | | C |
| ANISOU | 44 | C | ALA | A | 160 | 4105 | 3868 | 5315 | −217 | 89 | −457 | C |
| ATOM | 45 | O | ALA | A | 160 | 16.364 | −74.450 | −65.764 | 1.00 | 30.64 | | O |
| ANISOU | 45 | O | ALA | A | 160 | 3585 | 3304 | 4754 | −112 | 53 | −506 | O |
| ATOM | 46 | N | TRP | A | 161 | 16.115 | −72.437 | −64.785 | 1.00 | 33.35 | | N |
| ANISOU | 46 | N | TRP | A | 161 | 3645 | 3743 | 5283 | −183 | 84 | −584 | N |
| ATOM | 47 | CA | TRP | A | 161 | 17.152 | −72.645 | −63.787 | 1.00 | 26.02 | | C |
| ANISOU | 47 | CA | TRP | A | 161 | 2457 | 2894 | 4534 | −5 | 4 | −787 | C |
| ATOM | 48 | CB | TRP | A | 161 | 17.634 | −71.318 | −63.223 | 1.00 | 35.89 | | C |

TABLE 7-continued

DMXAA-hSTING$^{G230I}$ complex

| ANISOU | 48 | CB | TRP | A | 161 | 3436 | 4209 | 5993 | −6 | 36 | −935 | C |
|---|---|---|---|---|---|---|---|---|---|---|---|---|
| ATOM | 49 | CG | TRP | A | 161 | 18.635 | −70.691 | −64.132 | 1.00 | 43.81 | | C |
| ANISOU | 49 | CG | TRP | A | 161 | 4337 | 5114 | 7193 | −105 | 312 | −1104 | C |
| ATOM | 50 | CD1 | TRP | A | 161 | 18.423 | −69.712 | −65.065 | 1.00 | 27.79 | | C |
| ANISOU | 50 | CD1 | TRP | A | 161 | 2394 | 2998 | 5168 | −294 | 522 | −1056 | C |
| ATOM | 51 | NE1 | TRP | A | 161 | 19.588 | −69.438 | −65.731 | 1.00 | 51.15 | | N |
| ANISOU | 51 | NE1 | TRP | A | 161 | 5238 | 5863 | 8333 | −345 | 782 | −1256 | N |
| ATOM | 52 | CE2 | TRP | A | 161 | 20.580 | −70.245 | −65.240 | 1.00 | 44.33 | | C |
| ANISOU | 52 | CE2 | TRP | A | 161 | 4188 | 5031 | 7625 | −183 | 731 | −1451 | C |
| ATOM | 53 | CD2 | TRP | A | 161 | 20.008 | −71.056 | −64.239 | 1.00 | 38.97 | | C |
| ANISOU | 53 | CD2 | TRP | A | 161 | 3539 | 4463 | 6806 | −22 | 425 | −1354 | C |
| ATOM | 54 | CE3 | TRP | A | 161 | 20.819 | −71.988 | −63.576 | 1.00 | 38.53 | | C |
| ANISOU | 54 | CE3 | TRP | A | 161 | 3342 | 4444 | 6853 | 177 | 294 | −1516 | C |
| ATOM | 55 | CZ3 | TRP | A | 161 | 22.153 | −72.074 | −63.924 | 1.00 | 32.78 | | C |
| ANISOU | 55 | CZ3 | TRP | A | 161 | 2415 | 3651 | 6388 | 212 | 460 | −1783 | C |
| ATOM | 56 | CH2 | TRP | A | 161 | 22.696 | −71.249 | −64.926 | 1.00 | 48.47 | | C |
| ANISOU | 56 | CH2 | TRP | A | 161 | 4352 | 5533 | 8531 | 36 | 788 | −1884 | C |
| ATOM | 57 | CZ2 | TRP | A | 161 | 21.928 | −70.333 | −65.593 | 1.00 | 45.55 | | C |
| ANISOU | 57 | CZ2 | TRP | A | 161 | 4152 | 5116 | 8039 | −163 | 932 | −1714 | C |
| ATOM | 58 | C | TRP | A | 161 | 16.763 | −73.609 | −62.669 | 1.00 | 34.15 | | C |
| ANISOU | 58 | C | TRP | A | 161 | 3517 | 4010 | 5448 | 163 | −254 | −725 | C |
| ATOM | 59 | O | TRP | A | 161 | 17.583 | −74.406 | −62.219 | 1.00 | 36.07 | | O |
| ANISOU | 59 | O | TRP | A | 161 | 3682 | 4262 | 5762 | 324 | −327 | −858 | O |
| ATOM | 60 | N | SER | A | 162 | 15.518 | −73.543 | −62.214 | 1.00 | 39.41 | | N |
| ANISOU | 60 | N | SER | A | 162 | 4305 | 4727 | 5941 | 128 | −389 | −532 | N |
| ATOM | 61 | CA | SER | A | 162 | 15.095 | −74.397 | −61.114 | 1.00 | 29.89 | | C |
| ANISOU | 61 | CA | SER | A | 162 | 3153 | 3589 | 4613 | 271 | −605 | −465 | C |
| ATOM | 62 | C | SER | A | 162 | 14.876 | −75.814 | −61.623 | 1.00 | 23.85 | | C |
| ANISOU | 62 | C | SER | A | 162 | 2623 | 2742 | 3696 | 288 | −621 | −366 | C |
| ATOM | 63 | O | SER | A | 162 | 15.062 | −76.783 | −60.892 | 1.00 | 28.93 | | O |
| ANISOU | 63 | O | SER | A | 162 | 3309 | 3402 | 4282 | 441 | −761 | −379 | O |
| ATOM | 64 | CB | SER | A | 162 | 13.837 | −73.867 | −60.426 | 1.00 | 40.44 | | C |
| ANISOU | 64 | CB | SER | A | 162 | 4532 | 5000 | 5833 | 220 | −717 | −307 | C |
| ATOM | 65 | OG | SER | A | 162 | 12.692 | −74.127 | −61.207 | 1.00 | 54.79 | | O |
| ANISOU | 65 | OG | SER | A | 162 | 6572 | 6752 | 7492 | 71 | −685 | −110 | O |
| ATOM | 66 | N | TYR | A | 163 | 14.484 | −75.931 | −62.886 | 1.00 | 23.57 | | N |
| ANISOU | 66 | N | TYR | A | 163 | 2759 | 2608 | 3590 | 134 | −484 | −269 | N |
| ATOM | 67 | CA | TYR | A | 163 | 14.335 | −77.235 | −63.506 | 1.00 | 28.48 | | C |
| ANISOU | 67 | CA | TYR | A | 163 | 3601 | 3140 | 4082 | 139 | −483 | −189 | C |
| ATOM | 68 | CB | TYR | A | 163 | 13.719 | −77.119 | −64.892 | 1.00 | 34.72 | | C |
| ANISOU | 68 | CB | TYR | A | 163 | 4592 | 3821 | 4779 | −44 | −348 | −71 | C |
| ATOM | 69 | CG | TYR | A | 163 | 13.306 | −78.446 | −65.478 | 1.00 | 37.27 | | C |
| ANISOU | 69 | CG | TYR | A | 163 | 5162 | 4053 | 4945 | −49 | −378 | 39 | C |
| ATOM | 70 | CD1 | TYR | A | 163 | 12.506 | −79.328 | −64.749 | 1.00 | 39.18 | | C |
| ANISOU | 70 | CD1 | TYR | A | 163 | 5509 | 4321 | 5057 | 9 | −548 | 163 | C |
| ATOM | 71 | CE1 | TYR | A | 163 | 12.115 | −80.546 | −65.283 | 1.00 | 38.93 | | C |
| ANISOU | 71 | CE1 | TYR | A | 163 | 5701 | 4198 | 4894 | 0 | −574 | 259 | C |
| ATOM | 72 | CZ | TYR | A | 163 | 12.524 | −80.891 | −66.564 | 1.00 | 35.64 | | C |
| ANISOU | 72 | CZ | TYR | A | 163 | 5409 | 3669 | 4463 | −61 | −438 | 232 | C |
| ATOM | 73 | OH | TYR | A | 163 | 12.129 | −82.103 | −67.081 | 1.00 | 42.87 | | O |
| ANISOU | 73 | OH | TYR | A | 163 | 6546 | 4493 | 5251 | −66 | −474 | 322 | O |
| ATOM | 74 | CE2 | TYR | A | 163 | 13.322 | −80.029 | −67.308 | 1.00 | 32.75 | | C |
| ANISOU | 74 | CE2 | TYR | A | 163 | 4957 | 3275 | 4211 | −120 | −257 | 111 | C |
| ATOM | 75 | CD2 | TYR | A | 163 | 13.707 | −78.820 | −66.762 | 1.00 | 37.16 | | C |
| ANISOU | 75 | CD2 | TYR | A | 163 | 5288 | 3919 | 4911 | −117 | −223 | 16 | C |
| ATOM | 76 | C | TYR | A | 163 | 15.697 | −77.905 | −63.614 | 1.00 | 25.39 | | C |
| ANISOU | 76 | C | TYR | A | 163 | 3120 | 2712 | 3814 | 269 | −435 | −381 | C |
| ATOM | 77 | O | TYR | A | 163 | 15.836 | −79.114 | −63.453 | 1.00 | 36.60 | | O |
| ANISOU | 77 | O | TYR | A | 163 | 4646 | 4099 | 5159 | 374 | −522 | −369 | O |
| ATOM | 78 | N | TYR | A | 164 | 16.707 | −77.098 | −63.892 | 1.00 | 50.12 | | N |
| ANISOU | 78 | N | TYR | A | 164 | 6049 | 5843 | 7153 | 259 | −291 | −569 | N |
| ATOM | 79 | CA | TYR | A | 164 | 18.058 | −77.593 | −64.022 | 1.00 | 28.03 | | C |
| ANISOU | 79 | CA | TYR | A | 164 | 3119 | 3007 | 4525 | 373 | −226 | −791 | C |
| ATOM | 80 | CB | TYR | A | 164 | 18.911 | −76.586 | −64.779 | 1.00 | 29.02 | | C |
| ANISOU | 80 | CB | TYR | A | 164 | 3078 | 3087 | 4860 | 270 | 23 | −960 | C |
| ATOM | 81 | CG | TYR | A | 164 | 20.391 | −76.807 | −64.635 | 1.00 | 47.79 | | C |
| ANISOU | 81 | CG | TYR | A | 164 | 5214 | 5448 | 7495 | 401 | 81 | −1248 | C |
| ATOM | 82 | CD1 | TYR | A | 164 | 20.987 | −77.963 | −65.128 | 1.00 | 57.40 | | C |
| ANISOU | 82 | CD1 | TYR | A | 164 | 6504 | 6586 | 8719 | 472 | 118 | −1323 | C |
| ATOM | 83 | CE1 | TYR | A | 164 | 22.342 | −78.174 | −65.003 | 1.00 | 59.14 | | C |
| ANISOU | 83 | CE1 | TYR | A | 164 | 6485 | 6786 | 9202 | 597 | 164 | −1609 | C |
| ATOM | 84 | CZ | TYR | A | 164 | 23.128 | −77.219 | −64.385 | 1.00 | 58.63 | | C |
| ANISOU | 84 | CZ | TYR | A | 164 | 6096 | 6777 | 9404 | 651 | 173 | −1831 | C |
| ATOM | 85 | OH | TYR | A | 164 | 24.481 | −77.436 | −64.264 | 1.00 | 64.14 | | O |
| ANISOU | 85 | OH | TYR | A | 164 | 6531 | 7445 | 10395 | 780 | 209 | −2143 | O |
| ATOM | 86 | CE2 | TYR | A | 164 | 22.563 | −76.054 | −63.889 | 1.00 | 51.96 | | C |
| ANISOU | 86 | CE2 | TYR | A | 164 | 5181 | 6012 | 8550 | 579 | 139 | −1755 | C |
| ATOM | 87 | CD2 | TYR | A | 164 | 21.198 | −75.860 | −64.012 | 1.00 | 39.99 | | C |

TABLE 7-continued

| | | | | | | | | | | | | |
|---|---|---|---|---|---|---|---|---|---|---|---|---|
| DMXAA-hSTING$^{G230I}$ complex | | | | | | | | | | | | |
| ANISOU | 87 | CD2 | TYR | A | 164 | 3913 | 4519 | 6762 | 456 | 93 | −1462 | C |
| ATOM | 88 | C | TYR | A | 164 | 18.678 | −77.923 | −62.655 | 1.00 | 42.04 | | C |
| ANISOU | 88 | C | TYR | A | 164 | 4715 | 4866 | 6392 | 604 | −440 | −932 | C |
| ATOM | 89 | O | TYR | A | 164 | 19.248 | −78.997 | −62.456 | 1.00 | 41.43 | | O |
| ANISOU | 89 | O | TYR | A | 164 | 4664 | 4757 | 6321 | 753 | −528 | −1012 | O |
| ATOM | 90 | N | ILE | A | 165 | 18.548 | −77.000 | −61.711 | 1.00 | 34.21 | | N |
| ANISOU | 90 | N | ILE | A | 165 | 3560 | 3975 | 5463 | 641 | −537 | −964 | N |
| ATOM | 91 | CA | ILE | A | 165 | 19.126 | −77.164 | −60.385 | 1.00 | 29.13 | | C |
| ANISOU | 91 | CA | ILE | A | 165 | 2761 | 3407 | 4900 | 865 | −753 | −1106 | C |
| ATOM | 92 | CB | ILE | A | 165 | 19.170 | −75.821 | −59.620 | 1.00 | 28.86 | | C |
| ANISOU | 92 | CB | ILE | A | 165 | 2500 | 3471 | 4994 | 868 | −791 | −1188 | C |
| ATOM | 93 | CG1 | ILE | A | 165 | 20.057 | −74.816 | −60.346 | 1.00 | 29.74 | | C |
| ANISOU | 93 | CG1 | ILE | A | 165 | 2376 | 3551 | 5372 | 769 | −568 | −1381 | C |
| ATOM | 94 | CD1 | ILE | A | 165 | 21.515 | −75.304 | −60.487 | 1.00 | 31.91 | | C |
| ANISOU | 94 | CD1 | ILE | A | 165 | 2462 | 3773 | 5891 | 903 | −531 | −1665 | C |
| ATOM | 95 | CG2 | ILE | A | 165 | 19.674 | −76.008 | −58.192 | 1.00 | 29.77 | | C |
| ANISOU | 95 | CG2 | ILE | A | 165 | 2493 | 3659 | 5158 | 1115 | −1046 | −1325 | C |
| ATOM | 96 | C | ILE | A | 165 | 18.376 | −78.203 | −59.545 | 1.00 | 41.79 | | C |
| ANISOU | 96 | C | ILE | A | 165 | 4585 | 5029 | 6265 | 982 | −975 | −944 | C |
| ATOM | 97 | O | ILE | A | 165 | 18.973 | −78.957 | −58.772 | 1.00 | 38.50 | | O |
| ANISOU | 97 | O | ILE | A | 165 | 4157 | 4613 | 5860 | 1192 | −1149 | −1050 | O |
| ATOM | 98 | N | GLY | A | 166 | 17.058 | −78.239 | −59.691 | 1.00 | 42.72 | | N |
| ANISOU | 98 | N | GLY | A | 166 | 4911 | 5151 | 6171 | 845 | −969 | −694 | N |
| ATOM | 99 | CA | GLY | A | 166 | 16.215 | −79.045 | −58.830 | 1.00 | 43.82 | | C |
| ANISOU | 99 | CA | GLY | A | 166 | 5253 | 5305 | 6091 | 922 | −1145 | −532 | C |
| ATOM | 100 | C | GLY | A | 166 | 15.796 | −80.370 | −59.423 | 1.00 | 58.76 | | C |
| ANISOU | 100 | C | GLY | A | 166 | 7407 | 7099 | 7819 | 897 | −1137 | −396 | C |
| ATOM | 101 | O | GLY | A | 166 | 15.092 | −81.162 | −58.791 | 1.00 | 62.85 | | O |
| ANISOU | 101 | O | GLY | A | 166 | 8120 | 7606 | 8155 | 948 | −1257 | −258 | O |
| ATOM | 102 | N | TYR | A | 167 | 16.224 | −80.621 | −60.650 | 1.00 | 55.21 | | N |
| ANISOU | 102 | N | TYR | A | 167 | 6976 | 6568 | 7433 | 814 | −982 | −438 | N |
| ATOM | 103 | CA | TYR | A | 167 | 15.887 | −81.878 | −61.286 | 1.00 | 49.20 | | C |
| ANISOU | 103 | CA | TYR | A | 167 | 6459 | 5708 | 6528 | 792 | −973 | −324 | C |
| ATOM | 104 | CB | TYR | A | 167 | 14.620 | −81.744 | −62.120 | 1.00 | 25.58 | | C |
| ANISOU | 104 | CB | TYR | A | 167 | 3646 | 2676 | 3397 | 576 | −881 | −109 | C |
| ATOM | 105 | CG | TYR | A | 167 | 14.215 | −83.061 | −62.711 | 1.00 | 35.84 | | C |
| ANISOU | 105 | CG | TYR | A | 167 | 5198 | 3870 | 4550 | 557 | −890 | 6 | C |
| ATOM | 106 | CD1 | TYR | A | 167 | 13.920 | −84.139 | −61.874 | 1.00 | 49.68 | | C |
| ANISOU | 106 | CD1 | TYR | A | 167 | 7095 | 5606 | 6174 | 676 | −1044 | 79 | C |
| ATOM | 107 | CE1 | TYR | A | 167 | 13.564 | −85.366 | −62.379 | 1.00 | 46.91 | | C |
| ANISOU | 107 | CE1 | TYR | A | 167 | 6973 | 5152 | 5700 | 661 | −1055 | 178 | C |
| ATOM | 108 | CZ | TYR | A | 167 | 13.495 | −85.541 | −63.750 | 1.00 | 51.83 | | C |
| ANISOU | 108 | CZ | TYR | A | 167 | 7683 | 5690 | 6319 | 533 | −920 | 203 | C |
| ATOM | 109 | OH | TYR | A | 167 | 13.130 | −86.773 | −64.236 | 1.00 | 67.21 | | O |
| ANISOU | 109 | OH | TYR | A | 167 | 9857 | 7533 | 8147 | 522 | −941 | 297 | O |
| ATOM | 110 | CE2 | TYR | A | 167 | 13.790 | −84.490 | −64.620 | 1.00 | 44.14 | | C |
| ANISOU | 110 | CE2 | TYR | A | 167 | 6591 | 4727 | 5454 | 417 | −764 | 134 | C |
| ATOM | 111 | CD2 | TYR | A | 167 | 14.156 | −83.253 | −64.090 | 1.00 | 25.70 | | C |
| ANISOU | 111 | CD2 | TYR | A | 167 | 4024 | 2492 | 3249 | 427 | −744 | 37 | C |
| ATOM | 112 | C | TYR | A | 167 | 16.995 | −82.452 | −62.152 | 1.00 | 46.60 | | C |
| ANISOU | 112 | C | TYR | A | 167 | 6095 | 5295 | 6317 | 838 | −872 | −482 | C |
| ATOM | 113 | O | TYR | A | 167 | 17.515 | −83.537 | −61.874 | 1.00 | 51.43 | | O |
| ANISOU | 113 | O | TYR | A | 167 | 6770 | 5860 | 6910 | 995 | −976 | −543 | O |
| ATOM | 114 | N | LEU | A | 168 | 17.346 | −81.733 | −63.211 | 1.00 | 43.65 | | N |
| ANISOU | 114 | N | LEU | A | 168 | 5634 | 4890 | 6060 | 701 | −663 | −551 | N |
| ATOM | 115 | CA | LEU | A | 168 | 18.150 | −82.314 | −64.279 | 1.00 | 33.98 | | C |
| ANISOU | 115 | CA | LEU | A | 168 | 4437 | 3565 | 4910 | 690 | −513 | −660 | C |
| ATOM | 116 | CB | LEU | A | 168 | 18.264 | −81.365 | −65.470 | 1.00 | 30.00 | | C |
| ANISOU | 116 | CB | LEU | A | 168 | 3900 | 3016 | 4483 | 497 | −254 | −687 | C |
| ATOM | 117 | CG | LEU | A | 168 | 17.030 | −81.352 | −66.369 | 1.00 | 36.41 | | C |
| ANISOU | 117 | CG | LEU | A | 168 | 4980 | 3767 | 5086 | 307 | −191 | −450 | C |
| ATOM | 118 | CD1 | LEU | A | 168 | 17.256 | −80.423 | −67.544 | 1.00 | 31.34 | | C |
| ANISOU | 118 | CD1 | LEU | A | 168 | 4342 | 3059 | 4507 | 137 | 62 | −491 | C |
| ATOM | 119 | CD2 | LEU | A | 168 | 16.681 | −82.770 | −66.851 | 1.00 | 28.35 | | C |
| ANISOU | 119 | CD2 | LEU | A | 168 | 4213 | 2657 | 3903 | 329 | −242 | −346 | C |
| ATOM | 120 | C | LEU | A | 168 | 19.526 | −82.789 | −63.834 | 1.00 | 44.16 | | C |
| ANISOU | 120 | C | LEU | A | 168 | 5539 | 4849 | 6390 | 895 | −570 | −916 | C |
| ATOM | 121 | O | LEU | A | 168 | 19.971 | −83.868 | −64.215 | 1.00 | 45.07 | | O |
| ANISOU | 121 | O | LEU | A | 168 | 5746 | 4885 | 6493 | 972 | −575 | −966 | O |
| ATOM | 122 | N | ARG | A | 169 | 20.125 | −81.982 | −62.989 | 1.00 | 46.34 | | N |
| ANISOU | 122 | N | ARG | A | 169 | 5549 | 5204 | 6852 | 995 | −628 | −1092 | N |
| ATOM | 123 | CA | ARG | A | 169 | 21.377 | −82.228 | −62.347 | 1.00 | 62.71 | | C |
| ANISOU | 123 | CA | ARG | A | 169 | 7419 | 7265 | 9143 | 1199 | −701 | −1369 | C |
| ATOM | 124 | CB | ARG | A | 169 | 21.669 | −81.068 | −61.445 | 1.00 | 63.72 | | C |
| ANISOU | 124 | CB | ARG | A | 169 | 7208 | 7451 | 9553 | 1217 | −635 | −1604 | C |
| ATOM | 125 | CG | ARG | A | 169 | 22.895 | −80.329 | −61.807 | 1.00 | 55.08 | | C |
| ANISOU | 125 | CG | ARG | A | 169 | 6014 | 6468 | 8446 | 1314 | −843 | −1593 | C |
| ATOM | 126 | CD | ARG | A | 169 | 22.684 | −78.898 | −61.490 | 1.00 | 55.94 | | C |

TABLE 7-continued

DMXAA-hSTING$^{G230I}$ complex

| | | | | | | | | | | | | |
|---|---|---|---|---|---|---|---|---|---|---|---|---|
| ANISOU | 126 | CD | ARG | A | 169 | 5827 | 6620 | 8808 | 1243 | −707 | −1768 | C |
| ATOM | 127 | NE | ARG | A | 169 | 22.761 | −78.639 | −60.078 | 1.00 | 70.61 | | N |
| ANISOU | 127 | NE | ARG | A | 169 | 7521 | 8579 | 10731 | 1388 | −921 | −1853 | N |
| ATOM | 128 | CZ | ARG | A | 169 | 23.694 | −77.870 | −59.549 | 1.00 | 67.93 | | C |
| ANISOU | 128 | CZ | ARG | A | 169 | 6950 | 8281 | 10580 | 1357 | −891 | −2043 | C |
| ATOM | 129 | NH1 | ARG | A | 169 | 24.611 | −77.350 | −60.327 | 1.00 | 60.38 | | N |
| ANISOU | 129 | NH1 | ARG | A | 169 | 5836 | 7266 | 9841 | 1251 | −668 | −2212 | N |
| ATOM | 130 | NH2 | ARG | A | 169 | 23.710 | −77.624 | −58.262 | 1.00 | 68.38 | | N |
| ANISOU | 130 | NH2 | ARG | A | 169 | 6991 | 8423 | 10568 | 1392 | −1066 | −2041 | N |
| ATOM | 131 | C | ARG | A | 169 | 21.331 | −83.404 | −61.453 | 1.00 | 65.45 | | C |
| ANISOU | 131 | C | ARG | A | 169 | 7861 | 7631 | 9376 | 1428 | −1003 | −1347 | C |
| ATOM | 132 | O | ARG | A | 169 | 22.301 | −84.093 | −61.318 | 1.00 | 73.90 | | O |
| ANISOU | 132 | O | ARG | A | 169 | 8813 | 8677 | 10587 | 1637 | −1131 | −1560 | O |
| ATOM | 133 | N | LEU | A | 170 | 20.244 | −83.552 | −60.735 | 1.00 | 64.80 | | N |
| ANISOU | 133 | N | LEU | A | 170 | 8001 | 7580 | 9039 | 1391 | −1117 | −1095 | N |
| ATOM | 134 | CA | LEU | A | 170 | 20.068 | −84.719 | −59.939 | 1.00 | 77.52 | | C |
| ANISOU | 134 | CA | LEU | A | 170 | 9794 | 9175 | 10487 | 1577 | −1364 | −1028 | C |
| ATOM | 135 | CB | LEU | A | 170 | 18.816 | −84.557 | −59.104 | 1.00 | 77.11 | | C |
| ANISOU | 135 | CB | LEU | A | 170 | 9910 | 9181 | 10207 | 1518 | −1455 | −787 | C |
| ATOM | 136 | CG | LEU | A | 170 | 18.590 | −83.230 | −58.395 | 1.00 | 76.46 | | C |
| ANISOU | 136 | CG | LEU | A | 170 | 9645 | 9214 | 10191 | 1503 | −1485 | −819 | C |
| ATOM | 137 | CD1 | LEU | A | 170 | 17.531 | −83.409 | −57.331 | 1.00 | 75.73 | | C |
| ANISOU | 137 | CD1 | LEU | A | 170 | 9757 | 9158 | 9859 | 1492 | −1601 | −600 | C |
| ATOM | 138 | CD2 | LEU | A | 170 | 19.888 | −82.769 | −57.789 | 1.00 | 74.45 | | C |
| ANISOU | 138 | CD2 | LEU | A | 170 | 9141 | 8996 | 10150 | 1724 | −1622 | −1101 | C |
| ATOM | 139 | C | LEU | A | 170 | 19.932 | −85.961 | −60.796 | 1.00 | 78.96 | | C |
| ANISOU | 139 | C | LEU | A | 170 | 10203 | 9243 | 10555 | 1571 | −1335 | −950 | C |
| ATOM | 140 | O | LEU | A | 170 | 20.548 | −86.963 | −60.545 | 1.00 | 84.49 | | O |
| ANISOU | 140 | O | LEU | A | 170 | 10994 | 9886 | 11221 | 1765 | −1503 | −1011 | O |
| ATOM | 141 | N | ILE | A | 171 | 19.101 | −85.893 | −61.809 | 1.00 | 66.03 | | N |
| ANISOU | 141 | N | ILE | A | 171 | 8668 | 7563 | 8858 | 1354 | −1129 | −822 | N |
| ATOM | 142 | CA | ILE | A | 171 | 18.858 | −87.025 | −62.660 | 1.00 | 55.20 | | C |
| ANISOU | 142 | CA | ILE | A | 171 | 7555 | 6085 | 7332 | 1316 | −1108 | −695 | C |
| ATOM | 143 | CB | ILE | A | 171 | 17.487 | −86.897 | −63.326 | 1.00 | 61.34 | | C |
| ANISOU | 143 | CB | ILE | A | 171 | 8543 | 6854 | 7908 | 1095 | −1029 | −421 | C |
| ATOM | 144 | CG1 | ILE | A | 171 | 16.828 | −88.256 | −63.493 | 1.00 | 72.80 | | C |
| ANISOU | 144 | CG1 | ILE | A | 171 | 10208 | 8304 | 9150 | 1150 | −1212 | −234 | C |
| ATOM | 145 | CD1 | ILE | A | 171 | 15.944 | −88.669 | −62.340 | 1.00 | 59.38 | | C |
| ANISOU | 145 | CD1 | ILE | A | 171 | 8790 | 6488 | 7285 | 1115 | −1224 | −89 | C |
| ATOM | 146 | CG2 | ILE | A | 171 | 17.589 | −86.242 | −64.677 | 1.00 | 67.08 | | C |
| ANISOU | 146 | CG2 | ILE | A | 171 | 9421 | 7477 | 8591 | 959 | −864 | −368 | C |
| ATOM | 147 | C | ILE | A | 171 | 19.940 | −87.480 | −63.636 | 1.00 | 58.92 | | C |
| ANISOU | 147 | C | ILE | A | 171 | 7971 | 6470 | 7945 | 1317 | −956 | −861 | C |
| ATOM | 148 | O | ILE | A | 171 | 20.138 | −88.650 | −63.801 | 1.00 | 54.29 | | O |
| ANISOU | 148 | O | ILE | A | 171 | 7531 | 5797 | 7301 | 1409 | −1017 | −867 | O |
| ATOM | 149 | N | LEU | A | 172 | 20.557 | −86.515 | −64.312 | 1.00 | 53.72 | | N |
| ANISOU | 149 | N | LEU | A | 172 | 7108 | 5827 | 7477 | 1216 | −749 | −1004 | N |
| ATOM | 150 | CA | LEU | A | 172 | 21.427 | −86.756 | −65.464 | 1.00 | 56.08 | | C |
| ANISOU | 150 | CA | LEU | A | 172 | 7363 | 6036 | 7910 | 1184 | −551 | −1162 | C |
| ATOM | 151 | CB | LEU | A | 172 | 21.790 | −85.427 | −66.135 | 1.00 | 35.51 | | C |
| ANISOU | 151 | CB | LEU | A | 172 | 4615 | 3435 | 5442 | 996 | −269 | −1235 | C |
| ATOM | 152 | CG | LEU | A | 172 | 20.721 | −84.809 | −67.038 | 1.00 | 47.25 | | C |
| ANISOU | 152 | CG | LEU | A | 172 | 6311 | 4912 | 6729 | 762 | −154 | −983 | C |
| ATOM | 153 | CD1 | LEU | A | 172 | 21.355 | −83.886 | −68.068 | 1.00 | 45.09 | | C |
| ANISOU | 153 | CD1 | LEU | A | 172 | 5960 | 4596 | 6575 | 589 | 148 | −1072 | C |
| ATOM | 154 | CD2 | LEU | A | 172 | 19.899 | −85.893 | −67.718 | 1.00 | 52.67 | | C |
| ANISOU | 154 | CD2 | LEU | A | 172 | 7323 | 5514 | 7176 | 710 | −190 | −782 | C |
| ATOM | 155 | C | LEU | A | 172 | 22.698 | −87.558 | −65.198 | 1.00 | 66.82 | | C |
| ANISOU | 155 | C | LEU | A | 172 | 8564 | 7354 | 9470 | 1409 | −632 | −1436 | C |
| ATOM | 156 | O | LEU | A | 172 | 23.085 | −88.395 | −66.024 | 1.00 | 68.79 | | O |
| ANISOU | 156 | O | LEU | A | 172 | 8895 | 7506 | 9735 | 1413 | −536 | −1497 | O |
| ATOM | 157 | N | PRO | A | 173 | 23.348 | −87.342 | −64.074 | 1.00 | 68.01 | | N |
| ANISOU | 157 | N | PRO | A | 173 | 8492 | 7571 | 9779 | 1601 | −813 | −1614 | N |
| ATOM | 158 | CA | PRO | A | 173 | 24.640 | −87.967 | −63.826 | 1.00 | 56.26 | | C |
| ANISOU | 158 | CA | PRO | A | 173 | 6838 | 6030 | 8510 | 1820 | −902 | −1903 | C |
| ATOM | 159 | CB | PRO | A | 173 | 24.972 | −87.501 | −62.420 | 1.00 | 57.62 | | C |
| ANISOU | 159 | CB | PRO | A | 173 | 6808 | 6284 | 8800 | 2021 | −1150 | −2046 | C |
| ATOM | 160 | CG | PRO | A | 173 | 24.282 | −86.209 | −62.270 | 1.00 | 62.84 | | C |
| ANISOU | 160 | CG | PRO | A | 173 | 7395 | 7044 | 9437 | 1853 | −1052 | −1934 | C |
| ATOM | 161 | CD | PRO | A | 173 | 23.117 | −86.184 | −63.203 | 1.00 | 66.33 | | C |
| ANISOU | 161 | CD | PRO | A | 173 | 8143 | 7471 | 9589 | 1631 | −935 | −1602 | C |
| ATOM | 162 | C | PRO | A | 173 | 24.563 | −89.461 | −63.819 | 1.00 | 48.33 | | C |
| ANISOU | 162 | C | PRO | A | 173 | 6079 | 4934 | 7351 | 1951 | −1056 | −1837 | C |
| ATOM | 163 | O | PRO | A | 173 | 25.404 | −90.100 | −64.359 | 1.00 | 55.00 | | O |
| ANISOU | 163 | O | PRO | A | 173 | 6867 | 5696 | 8336 | 2017 | −988 | −2017 | O |
| ATOM | 164 | N | GLU | A | 174 | 23.542 | −90.003 | −63.214 | 1.00 | 41.45 | | N |
| ANISOU | 164 | N | GLU | A | 174 | 5476 | 4071 | 6203 | 1982 | −1247 | −1588 | N |
| ATOM | 165 | CA | GLU | A | 174 | 23.377 | −91.446 | −63.088 | 1.00 | 46.26 | | C |

TABLE 7-continued

DMXAA-hSTING$^{G230I}$ complex

| ANISOU | 165 | CA | GLU | A | 174 | 6341 | 4583 | 6652 | 2111 | −1408 | −1511 | C |
|---|---|---|---|---|---|---|---|---|---|---|---|---|
| ATOM | 166 | CB | GLU | A | 174 | 22.772 | −91.793 | −61.725 | 1.00 | 46.65 | | C |
| ANISOU | 166 | CB | GLU | A | 174 | 6545 | 4652 | 6528 | 2284 | −1710 | −1403 | C |
| ATOM | 167 | CG | GLU | A | 174 | 23.793 | −91.922 | −60.607 | 1.00 | 67.59 | | C |
| ANISOU | 167 | CG | GLU | A | 174 | 9002 | 7342 | 9337 | 2520 | −1924 | −1649 | C |
| ATOM | 168 | CD | GLU | A | 174 | 24.975 | −92.789 | −60.994 | 1.00 | 91.29 | | C |
| ANISOU | 168 | CD | GLU | A | 174 | 11961 | 10285 | 12441 | 2612 | −1953 | −1820 | C |
| ATOM | 169 | OE1 | GLU | A | 174 | 24.866 | −94.028 | −60.884 | 1.00 | 95.75 | | O |
| ANISOU | 169 | OE1 | GLU | A | 174 | 12796 | 10769 | 12816 | 2682 | −2074 | −1704 | O |
| ATOM | 170 | OE2 | GLU | A | 174 | 26.013 | −92.231 | −61.409 | 1.00 | 99.33 | | O |
| ANISOU | 170 | OE2 | GLU | A | 174 | 12676 | 11336 | 13730 | 2597 | −1841 | −2063 | O |
| ATOM | 171 | C | GLU | A | 174 | 22.550 | −92.092 | −64.201 | 1.00 | 50.45 | | C |
| ANISOU | 171 | C | GLU | A | 174 | 7157 | 5044 | 6967 | 1916 | −1263 | −1269 | C |
| ATOM | 172 | O | GLU | A | 174 | 22.392 | −93.313 | −64.221 | 1.00 | 43.46 | | O |
| ANISOU | 172 | O | GLU | A | 174 | 6525 | 4079 | 5910 | 1986 | −1391 | −1149 | O |
| ATOM | 173 | N | LEU | A | 175 | 22.010 | −91.290 | −65.115 | 1.00 | 48.09 | | N |
| ANISOU | 173 | N | LEU | A | 175 | 6832 | 4764 | 6677 | 1677 | −1006 | −1201 | N |
| ATOM | 174 | CA | LEU | A | 175 | 21.102 | −91.830 | −66.098 | 1.00 | 50.79 | | C |
| ANISOU | 174 | CA | LEU | A | 175 | 7452 | 5040 | 6807 | 1489 | −892 | −967 | C |
| ATOM | 175 | CB | LEU | A | 175 | 20.475 | −90.690 | −66.885 | 1.00 | 49.50 | | C |
| ANISOU | 175 | CB | LEU | A | 175 | 7266 | 4915 | 6626 | 1240 | −666 | −870 | C |
| ATOM | 176 | CG | LEU | A | 175 | 19.413 | −91.054 | −67.896 | 1.00 | 45.73 | | C |
| ANISOU | 176 | CG | LEU | A | 175 | 7081 | 4363 | 5931 | 1055 | −579 | −637 | C |
| ATOM | 177 | CD1 | LEU | A | 175 | 18.072 | −91.160 | −67.244 | 1.00 | 52.78 | | C |
| ANISOU | 177 | CD1 | LEU | A | 175 | 8141 | 5293 | 6620 | 1003 | −736 | −384 | C |
| ATOM | 178 | CD2 | LEU | A | 175 | 19.389 | −90.058 | −69.004 | 1.00 | 40.45 | | C |
| ANISOU | 178 | CD2 | LEU | A | 175 | 6389 | 3679 | 5300 | 850 | −315 | −644 | C |
| ATOM | 179 | C | LEU | A | 175 | 21.642 | −92.863 | −67.066 | 1.00 | 52.09 | | C |
| ANISOU | 179 | C | LEU | A | 175 | 7728 | 5083 | 6983 | 1517 | −814 | −1041 | C |
| ATOM | 180 | O | LEU | A | 175 | 21.090 | −93.911 | −67.175 | 1.00 | 57.07 | | O |
| ANISOU | 180 | O | LEU | A | 175 | 8622 | 5638 | 7426 | 1520 | −900 | −882 | O |
| ATOM | 181 | N | GLN | A | 176 | 22.768 | −92.609 | −67.700 | 1.00 | 58.12 | | N |
| ANISOU | 181 | N | GLN | A | 176 | 8291 | 5820 | 7974 | 1529 | −638 | −1288 | N |
| ATOM | 182 | CA | GLN | A | 176 | 23.321 | −93.575 | −68.645 | 1.00 | 50.45 | | C |
| ANISOU | 182 | CA | GLN | A | 176 | 7403 | 4731 | 7033 | 1553 | −537 | −1387 | C |
| ATOM | 183 | CB | GLN | A | 176 | 24.651 | −93.085 | −69.228 | 1.00 | 60.10 | | C |
| ANISOU | 183 | CB | GLN | A | 176 | 8340 | 5936 | 8557 | 1566 | −318 | −1701 | C |
| ATOM | 184 | CG | GLN | A | 176 | 24.683 | −91.597 | −69.528 | 1.00 | 72.92 | | C |
| ANISOU | 184 | CG | GLN | A | 176 | 9788 | 7629 | 10290 | 1392 | −93 | −1736 | C |
| ATOM | 185 | CD | GLN | A | 176 | 25.022 | −91.287 | −70.975 | 1.00 | 79.12 | | C |
| ANISOU | 185 | CD | GLN | A | 176 | 10599 | 8332 | 11131 | 1209 | 265 | −1809 | C |
| ATOM | 186 | OE1 | GLN | A | 176 | 24.610 | −92.001 | −71.889 | 1.00 | 83.90 | | O |
| ANISOU | 186 | OE1 | GLN | A | 176 | 11467 | 8846 | 11566 | 1129 | 349 | −1693 | O |
| ATOM | 187 | NE2 | GLN | A | 176 | 25.785 | −90.219 | −71.189 | 1.00 | 85.31 | | N |
| ANISOU | 187 | NE2 | GLN | A | 176 | 11123 | 9138 | 12152 | 1142 | 486 | −2007 | N |
| ATOM | 188 | C | GLN | A | 176 | 23.531 | −94.909 | −67.946 | 1.00 | 52.03 | | C |
| ANISOU | 188 | C | GLN | A | 176 | 7714 | 4873 | 7182 | 1780 | −802 | −1407 | C |
| ATOM | 189 | O | GLN | A | 176 | 23.275 | −95.977 | −68.509 | 1.00 | 62.01 | | O |
| ANISOU | 189 | O | GLN | A | 176 | 9205 | 6037 | 8319 | 1777 | −809 | −1325 | O |
| ATOM | 190 | N | ALA | A | 177 | 23.982 | −94.836 | −66.699 | 1.00 | 52.81 | | N |
| ANISOU | 190 | N | ALA | A | 177 | 7671 | 5025 | 7371 | 1983 | −1031 | −1514 | N |
| ATOM | 191 | CA | ALA | A | 177 | 24.251 | −96.024 | −65.895 | 1.00 | 46.56 | | C |
| ANISOU | 191 | CA | ALA | A | 177 | 6994 | 4168 | 6529 | 2229 | −1312 | −1548 | C |
| ATOM | 192 | CB | ALA | A | 177 | 24.894 | −95.638 | −64.578 | 1.00 | 45.50 | | C |
| ANISOU | 192 | CB | ALA | A | 177 | 6662 | 4097 | 6530 | 2452 | −1544 | −1714 | C |
| ATOM | 193 | C | ALA | A | 177 | 22.987 | −96.839 | −65.644 | 1.00 | 51.22 | | C |
| ANISOU | 193 | C | ALA | A | 177 | 7950 | 4711 | 6801 | 2180 | −1434 | −1233 | C |
| ATOM | 194 | O | ALA | A | 177 | 22.985 | −98.066 | −65.785 | 1.00 | 63.05 | | O |
| ANISOU | 194 | O | ALA | A | 177 | 9651 | 6100 | 8206 | 2269 | −1528 | −1201 | O |
| ATOM | 195 | N | ARG | A | 178 | 21.914 | −96.159 | −65.260 | 1.00 | 50.29 | | N |
| ANISOU | 195 | N | ARG | A | 178 | 7910 | 4670 | 6529 | 2039 | −1429 | −1012 | N |
| ATOM | 196 | CA | ARG | A | 178 | 20.647 | −96.825 | −64.973 | 1.00 | 52.59 | | C |
| ANISOU | 196 | CA | ARG | A | 178 | 8521 | 4917 | 6544 | 1971 | −1521 | −723 | C |
| ATOM | 197 | CB | ARG | A | 178 | 19.618 | −95.828 | −64.440 | 1.00 | 59.25 | | C |
| ANISOU | 197 | CB | ARG | A | 178 | 9363 | 5863 | 7284 | 1827 | −1505 | −540 | C |
| ATOM | 198 | CG | ARG | A | 178 | 19.826 | −95.466 | −62.986 | 1.00 | 50.64 | | C |
| ANISOU | 198 | CG | ARG | A | 178 | 8195 | 4842 | 6203 | 2000 | −1705 | −586 | C |
| ATOM | 199 | CD | ARG | A | 178 | 19.115 | −94.178 | −62.637 | 1.00 | 54.80 | | C |
| ANISOU | 199 | CD | ARG | A | 178 | 8617 | 5492 | 6711 | 1853 | −1637 | −485 | C |
| ATOM | 200 | NE | ARG | A | 178 | 17.667 | −94.322 | −62.492 | 1.00 | 51.78 | | N |
| ANISOU | 200 | NE | ARG | A | 178 | 8469 | 5099 | 6104 | 1694 | −1628 | −203 | N |
| ATOM | 201 | CZ | ARG | A | 178 | 16.779 | −93.470 | −62.998 | 1.00 | 59.71 | | C |
| ANISOU | 201 | CZ | ARG | A | 178 | 9446 | 6161 | 7080 | 1466 | −1480 | −73 | C |
| ATOM | 202 | NH1 | ARG | A | 178 | 17.194 | −92.423 | −63.697 | 1.00 | 59.37 | | N |
| ANISOU | 202 | NH1 | ARG | A | 178 | 9182 | 6184 | 7193 | 1369 | −1323 | −182 | N |
| ATOM | 203 | NH2 | ARG | A | 178 | 15.480 | −93.665 | −62.813 | 1.00 | 63.18 | | N |
| ANISOU | 203 | NH2 | ARG | A | 178 | 10080 | 6581 | 7343 | 1337 | −1486 | 156 | N |
| ATOM | 204 | C | ARG | A | 178 | 20.099 | −97.524 | −66.207 | 1.00 | 57.11 | | C |

TABLE 7-continued

DMXAA-hSTING$^{G230I}$ complex

| | | | | | | | | | | | | |
|---|---|---|---|---|---|---|---|---|---|---|---|---|
| ANISOU | 204 | C | ARG | A | 178 | 9298 | 5393 | 7008 | 1812 | −1379 | −600 | C |
| ATOM | 205 | O | ARG | A | 178 | 19.438 | −98.561 | −66.123 | 1.00 | 60.12 | | O |
| ANISOU | 205 | O | ARG | A | 178 | 9947 | 5684 | 7213 | 1820 | −1475 | −441 | O |
| ATOM | 206 | N | ILE | A | 179 | 20.387 | −96.936 | −67.357 | 1.00 | 50.50 | | N |
| ANISOU | 206 | N | ILE | A | 179 | 8345 | 4566 | 6277 | 1669 | −1146 | −681 | N |
| ATOM | 207 | CA | ILE | A | 179 | 19.951 | −97.456 | −68.636 | 1.00 | 47.01 | | C |
| ANISOU | 207 | CA | ILE | A | 179 | 8090 | 4032 | 5740 | 1518 | −996 | −590 | C |
| ATOM | 208 | CB | ILE | A | 179 | 20.028 | −96.343 | −69.692 | 1.00 | 47.63 | | C |
| ANISOU | 208 | CB | ILE | A | 179 | 8052 | 4149 | 5898 | 1325 | −730 | −636 | C |
| ATOM | 209 | CG1 | ILE | A | 179 | 18.853 | −95.376 | −69.503 | 1.00 | 42.06 | | C |
| ANISOU | 209 | CG1 | ILE | A | 179 | 7383 | 3521 | 5076 | 1149 | −715 | −429 | C |
| ATOM | 210 | CD1 | ILE | A | 179 | 18.911 | −94.151 | −70.393 | 1.00 | 36.23 | | C |
| ANISOU | 210 | CD1 | ILE | A | 179 | 6541 | 2818 | 4407 | 973 | −478 | −468 | C |
| ATOM | 211 | CG2 | ILE | A | 179 | 20.079 | −96.914 | −71.097 | 1.00 | 39.24 | | C |
| ANISOU | 211 | CG2 | ILE | A | 179 | 7147 | 2973 | 4790 | 1227 | −560 | −644 | C |
| ATOM | 212 | C | ILE | A | 179 | 20.764 | −98.693 | −69.048 | 1.00 | 53.99 | | C |
| ANISOU | 212 | C | ILE | A | 179 | 9041 | 4799 | 6674 | 1663 | −1029 | −731 | C |
| ATOM | 213 | O | ILE | A | 179 | 20.220 | −99.668 | −69.578 | 1.00 | 53.06 | | O |
| ANISOU | 213 | O | ILE | A | 179 | 9173 | 4579 | 6410 | 1620 | −1044 | −606 | O |
| ATOM | 214 | N | ARG | A | 180 | 22.067 | −98.649 | −68.785 | 1.00 | 57.47 | | N |
| ANISOU | 214 | N | ARG | A | 180 | 9248 | 5251 | 7336 | 1839 | −1048 | −1002 | N |
| ATOM | 215 | CA | ARG | A | 180 | 22.937 | −99.800 | −69.000 | 1.00 | 67.50 | | C |
| ANISOU | 215 | CA | ARG | A | 180 | 10546 | 6415 | 8687 | 2014 | −1114 | −1171 | C |
| ATOM | 216 | CB | ARG | A | 180 | 24.378 | −99.465 | −68.630 | 1.00 | 75.66 | | C |
| ANISOU | 216 | CB | ARG | A | 180 | 11251 | 7480 | 10018 | 2201 | −1134 | −1505 | C |
| ATOM | 217 | CG | ARG | A | 180 | 25.321 | −99.335 | −69.808 | 1.00 | 85.75 | | C |
| ANISOU | 217 | CG | ARG | A | 180 | 12363 | 8714 | 11502 | 2147 | −868 | −1739 | C |
| ATOM | 218 | CD | ARG | A | 180 | 26.223 | −98.120 | −69.643 | 1.00 | 102.62 | | C |
| ANISOU | 218 | CD | ARG | A | 180 | 14129 | 10940 | 13921 | 2153 | −742 | −1983 | C |
| ATOM | 219 | NE | ARG | A | 180 | 26.758 | −98.000 | −68.289 | 1.00 | 115.10 | | N |
| ANISOU | 219 | NE | ARG | A | 180 | 15526 | 12580 | 15629 | 2381 | −1012 | −2116 | N |
| ATOM | 220 | CZ | ARG | A | 180 | 27.389 | −96.924 | −67.824 | 1.00 | 115.40 | | C |
| ANISOU | 220 | CZ | ARG | A | 180 | 15238 | 12734 | 15875 | 2376 | −968 | −2269 | C |
| ATOM | 221 | NH1 | ARG | A | 180 | 27.567 | −95.867 | −68.604 | 1.00 | 110.30 | | N |
| ANISOU | 221 | NH1 | ARG | A | 180 | 14434 | 12099 | 15375 | 2215 | −673 | −2370 | N |
| ATOM | 222 | NH2 | ARG | A | 180 | 27.841 | −96.903 | −66.575 | 1.00 | 118.89 | | N |
| ANISOU | 222 | NH2 | ARG | A | 180 | 15530 | 13278 | 16366 | 2520 | −1218 | −2316 | N |
| ATOM | 223 | C | ARG | A | 180 | 22.461 | −100.947 | −68.134 | 1.00 | 65.71 | | C |
| ANISOU | 223 | C | ARG | A | 180 | 10565 | 6117 | 8286 | 2160 | −1387 | −1032 | C |
| ATOM | 224 | O | ARG | A | 180 | 22.390 | −102.098 | −68.575 | 1.00 | 63.24 | | O |
| ANISOU | 224 | O | ARG | A | 180 | 10454 | 5686 | 7889 | 2197 | −1425 | −996 | O |
| ATOM | 225 | N | THR | A | 181 | 22.155 | −100.615 | −66.885 | 1.00 | 66.20 | | N |
| ANISOU | 225 | N | THR | A | 181 | 10618 | 6244 | 8292 | 2244 | −1570 | −959 | N |
| ATOM | 226 | CA | THR | A | 181 | 21.571 | −101.564 | −65.960 | 1.00 | 74.70 | | C |
| ANISOU | 226 | CA | THR | A | 181 | 11946 | 7267 | 9168 | 2341 | −1798 | −793 | C |
| ATOM | 227 | CB | THR | A | 181 | 21.175 | −100.898 | −64.641 | 1.00 | 84.72 | | C |
| ANISOU | 227 | CB | THR | A | 181 | 13172 | 8655 | 10364 | 2364 | −1925 | −708 | C |
| ATOM | 228 | OG1 | THR | A | 181 | 22.351 | −100.429 | −63.972 | 1.00 | 90.29 | | O |
| ANISOU | 228 | OG1 | THR | A | 181 | 13600 | 9441 | 11266 | 2542 | −2025 | −959 | O |
| ATOM | 229 | CG2 | THR | A | 181 | 20.442 | −101.889 | −63.747 | 1.00 | 84.99 | | C |
| ANISOU | 229 | CG2 | THR | A | 181 | 13445 | 8701 | 10146 | 2342 | −2058 | −523 | C |
| ATOM | 230 | C | THR | A | 181 | 20.337 | −102.168 | −66.601 | 1.00 | 73.84 | | C |
| ANISOU | 230 | C | THR | A | 181 | 12126 | 7088 | 8842 | 2145 | −1720 | −531 | C |
| ATOM | 231 | O | THR | A | 181 | 20.229 | −103.378 | −66.744 | 1.00 | 65.69 | | O |
| ANISOU | 231 | O | THR | A | 181 | 11256 | 5999 | 7704 | 2155 | −1773 | −478 | O |
| ATOM | 232 | N | TYR | A | 182 | 19.424 | −101.314 | −67.037 | 1.00 | 74.70 | | N |
| ANISOU | 232 | N | TYR | A | 182 | 12245 | 7246 | 8890 | 1926 | −1573 | −379 | N |
| ATOM | 233 | CA | TYR | A | 182 | 18.179 | −101.800 | −67.602 | 1.00 | 62.64 | | C |
| ANISOU | 233 | CA | TYR | A | 182 | 10959 | 5665 | 7175 | 1729 | −1513 | −142 | C |
| ATOM | 234 | CB | TYR | A | 182 | 17.217 | −100.669 | −67.916 | 1.00 | 58.98 | | C |
| ANISOU | 234 | CB | TYR | A | 182 | 10461 | 5278 | 6672 | 1504 | −1384 | 1 | C |
| ATOM | 235 | CG | TYR | A | 182 | 15.879 | −101.195 | −68.361 | 1.00 | 61.74 | | C |
| ANISOU | 235 | CG | TYR | A | 182 | 10951 | 5654 | 6853 | 1271 | −1323 | 198 | C |
| ATOM | 236 | CD1 | TYR | A | 182 | 14.905 | −101.540 | −67.428 | 1.00 | 58.52 | | C |
| ANISOU | 236 | CD1 | TYR | A | 182 | 10537 | 5354 | 6343 | 1175 | −1364 | 308 | C |
| ATOM | 237 | CE1 | TYR | A | 182 | 13.684 | −102.030 | −67.827 | 1.00 | 59.84 | | C |
| ANISOU | 237 | CE1 | TYR | A | 182 | 10743 | 5557 | 6437 | 968 | −1284 | 414 | C |
| ATOM | 238 | CZ | TYR | A | 182 | 13.431 | −102.193 | −69.177 | 1.00 | 65.30 | | C |
| ANISOU | 238 | CZ | TYR | A | 182 | 11495 | 6197 | 7117 | 857 | −1195 | 426 | C |
| ATOM | 239 | OH | TYR | A | 182 | 12.217 | −102.683 | −69.592 | 1.00 | 71.77 | | O |
| ANISOU | 239 | OH | TYR | A | 182 | 12322 | 7054 | 7895 | 677 | −1141 | 498 | O |
| ATOM | 240 | CE2 | TYR | A | 182 | 14.383 | −101.862 | −70.124 | 1.00 | 65.98 | | C |
| ANISOU | 240 | CE2 | TYR | A | 182 | 11632 | 6183 | 7256 | 933 | −1151 | 346 | C |
| ATOM | 241 | CD2 | TYR | A | 182 | 15.599 | −101.380 | −69.713 | 1.00 | 63.55 | | C |
| ANISOU | 241 | CD2 | TYR | A | 182 | 11273 | 5815 | 7057 | 1137 | −1198 | 224 | C |
| ATOM | 242 | C | TYR | A | 182 | 18.346 | −102.693 | −68.831 | 1.00 | 65.69 | | C |
| ANISOU | 242 | C | TYR | A | 182 | 11475 | 5934 | 7552 | 1691 | −1426 | −173 | C |
| ATOM | 243 | O | TYR | A | 182 | 17.645 | −103.693 | −68.987 | 1.00 | 65.11 | | O |

TABLE 7-continued

DMXAA-hSTING[G230I] complex

| | | | | | | | | | | | |
|---|---|---|---|---|---|---|---|---|---|---|---|
| ANISOU | 243 | O | TYR | A | 182 | 11555 | 5854 | 7331 | 1596 | −1446 | −44 O |
| ATOM | 244 | N | ASN | A | 183 | 19.252 | −102.325 | −69.722 | 1.00 | 68.48 | N |
| ANISOU | 244 | N | ASN | A | 183 | 11672 | 6286 | 8060 | 1696 | −1274 | −366 N |
| ATOM | 245 | CA | ASN | A | 183 | 19.447 | −103.124 | −70.921 | 1.00 | 66.45 | C |
| ANISOU | 245 | CA | ASN | A | 183 | 11542 | 5917 | 7790 | 1659 | −1172 | −409 C |
| ATOM | 246 | CB | ASN | A | 183 | 20.246 | −102.360 | −71.970 | 1.00 | 49.23 | C |
| ANISOU | 246 | CB | ASN | A | 183 | 9175 | 3769 | 5763 | 1587 | −927 | −595 C |
| ATOM | 247 | CG | ASN | A | 183 | 19.437 | −101.253 | −72.611 | 1.00 | 55.28 | C |
| ANISOU | 247 | CG | ASN | A | 183 | 9949 | 4595 | 6460 | 1347 | −757 | −466 C |
| ATOM | 248 | OD1 | ASN | A | 183 | 18.205 | −101.284 | −72.589 | 1.00 | 53.34 | O |
| ANISOU | 248 | OD1 | ASN | A | 183 | 9882 | 4339 | 6046 | 1219 | −814 | −239 O |
| ATOM | 249 | ND2 | ASN | A | 183 | 20.121 | −100.265 | −73.183 | 1.00 | 54.63 | N |
| ANISOU | 249 | ND2 | ASN | A | 183 | 9675 | 4566 | 6518 | 1286 | −548 | −619 N |
| ATOM | 250 | C | ASN | A | 183 | 20.063 | −104.485 | −70.629 | 1.00 | 75.19 | C |
| ANISOU | 250 | C | ASN | A | 183 | 12745 | 6918 | 8906 | 1864 | −1329 | −498 C |
| ATOM | 251 | O | ASN | A | 183 | 19.620 | −105.500 | −71.166 | 1.00 | 78.02 | O |
| ANISOU | 251 | O | ASN | A | 183 | 13281 | 7220 | 9143 | 1798 | −1332 | −399 O |
| ATOM | 252 | N | GLN | A | 184 | 21.133 | −104.524 | −69.856 | 1.00 | 80.73 | N |
| ANISOU | 252 | N | GLN | A | 184 | 13264 | 7663 | 9747 | 2075 | −1454 | −680 N |
| ATOM | 253 | CA | GLN | A | 184 | 21.670 | −105.801 | −69.444 | 1.00 | 91.89 | C |
| ANISOU | 253 | CA | GLN | A | 184 | 14695 | 9048 | 11170 | 2244 | −1610 | −767 C |
| ATOM | 254 | CB | GLN | A | 184 | 23.058 | −105.634 | −68.847 | 1.00 | 100.74 | C |
| ANISOU | 254 | CB | GLN | A | 184 | 15525 | 10227 | 12525 | 2453 | −1686 | −1048 C |
| ATOM | 255 | CG | GLN | A | 184 | 24.053 | −104.976 | −69.772 | 1.00 | 107.62 | C |
| ANISOU | 255 | CG | GLN | A | 184 | 16153 | 11093 | 13644 | 2446 | −1471 | −1306 C |
| ATOM | 256 | CD | GLN | A | 184 | 25.196 | −104.357 | −69.015 | 1.00 | 112.72 | C |
| ANISOU | 256 | CD | GLN | A | 184 | 16451 | 11843 | 14536 | 2597 | −1536 | −1557 C |
| ATOM | 257 | OE1 | GLN | A | 184 | 25.187 | −104.318 | −67.791 | 1.00 | 116.08 | O |
| ANISOU | 257 | OE1 | GLN | A | 184 | 16843 | 12341 | 14921 | 2712 | −1759 | −1525 O |
| ATOM | 258 | NE2 | GLN | A | 184 | 26.187 | −103.873 | −69.734 | 1.00 | 112.69 | N |
| ANISOU | 258 | NE2 | GLN | A | 184 | 16185 | 11851 | 14781 | 2581 | −1328 | −1808 N |
| ATOM | 259 | C | GLN | A | 184 | 20.809 | −106.581 | −68.473 | 1.00 | 94.56 | C |
| ANISOU | 259 | C | GLN | A | 184 | 15215 | 9417 | 11295 | 2246 | −1797 | −568 C |
| ATOM | 260 | O | GLN | A | 184 | 20.570 | −107.743 | −68.667 | 1.00 | 97.43 | O |
| ANISOU | 260 | O | GLN | A | 184 | 15759 | 9723 | 11537 | 2222 | −1839 | −487 O |
| ATOM | 261 | N | HIS | A | 185 | 20.265 | −105.961 | −67.445 | 1.00 | 108.20 | N |
| ANISOU | 261 | N | HIS | A | 185 | 12282 | 9713 | 19115 | 1301 | 496 | −276 N |
| ATOM | 262 | C | HIS | A | 185 | 18.122 | −107.285 | −66.815 | 1.00 | 116.07 | C |
| ANISOU | 262 | C | HIS | A | 185 | 13619 | 10627 | 19856 | 1058 | 449 | −161 C |
| ATOM | 263 | O | HIS | A | 185 | 17.560 | −108.043 | −66.050 | 1.00 | 113.01 | O |
| ANISOU | 263 | O | HIS | A | 185 | 13385 | 10120 | 19433 | 984 | 344 | −2 O |
| ATOM | 264 | CA | HIS | A | 185 | 19.486 | −106.707 | −66.448 | 1.00 | 113.33 | C |
| ANISOU | 264 | CA | HIS | A | 185 | 13108 | 10222 | 19731 | 1250 | 299 | −62 C |
| ATOM | 265 | CB | HIS | A | 185 | 19.352 | −105.927 | −65.167 | 1.00 | 119.64 | C |
| ANISOU | 265 | CB | HIS | A | 185 | 13998 | 11228 | 20233 | 1259 | 31 | 166 C |
| ATOM | 266 | CG | HIS | A | 185 | 20.518 | −106.076 | −64.251 | 1.00 | 127.12 | C |
| ANISOU | 266 | CG | HIS | A | 185 | 14970 | 11991 | 21338 | 1368 | −268 | 422 C |
| ATOM | 267 | ND1 | HIS | A | 185 | 21.809 | −106.209 | −64.711 | 1.00 | 132.10 | N |
| ANISOU | 267 | ND1 | HIS | A | 185 | 15466 | 12534 | 22191 | 1435 | −308 | 413 N |
| ATOM | 268 | CE1 | HIS | A | 185 | 22.629 | −106.314 | −63.682 | 1.00 | 134.29 | C |
| ANISOU | 268 | CE1 | HIS | A | 185 | 15827 | 12752 | 22443 | 1483 | −594 | 633 C |
| ATOM | 269 | NE2 | HIS | A | 185 | 21.916 | −106.234 | −62.571 | 1.00 | 131.80 | N |
| ANISOU | 269 | NE2 | HIS | A | 185 | 15716 | 12492 | 21871 | 1451 | −735 | 794 N |
| ATOM | 270 | CD2 | HIS | A | 185 | 20.594 | −106.083 | −62.900 | 1.00 | 127.82 | C |
| ANISOU | 270 | CD2 | HIS | A | 185 | 15234 | 12072 | 21259 | 1378 | −537 | 676 C |
| ATOM | 271 | O | TYR | A | 186 | 17.692 | −107.513 | −70.296 | 1.00 | 131.41 | O |
| ANISOU | 271 | O | TYR | A | 186 | 15518 | 12941 | 21472 | 828 | 1210 | −1011 O |
| ATOM | 272 | N | TYR | A | 186 | 17.551 | −106.872 | −67.930 | 1.00 | 122.21 | N |
| ANISOU | 272 | N | TYR | A | 186 | 14368 | 11595 | 20470 | 974 | 689 | −420 N |
| ATOM | 273 | CA | TYR | A | 186 | 16.276 | −107.410 | −68.391 | 1.00 | 126.62 | C |
| ANISOU | 273 | CA | TYR | A | 186 | 15060 | 12219 | 20832 | 789 | 818 | −538 C |
| ATOM | 274 | C | TYR | A | 186 | 16.776 | −108.044 | −69.692 | 1.00 | 130.67 | C |
| ANISOU | 274 | C | TYR | A | 186 | 15514 | 12670 | 21466 | 773 | 1094 | −857 C |
| ATOM | 275 | CB | TYR | A | 186 | 15.179 | −106.337 | −68.236 | 1.00 | 124.50 | C |
| ANISOU | 275 | CB | TYR | A | 186 | 14870 | 12344 | 20091 | 670 | 778 | −522 C |
| ATOM | 276 | CG | TYR | A | 186 | 15.431 | −105.545 | −66.977 | 1.00 | 119.70 | C |
| ANISOU | 276 | CG | TYR | A | 186 | 14302 | 11897 | 19280 | 722 | 535 | −265 C |
| ATOM | 277 | CD2 | TYR | A | 186 | 14.842 | −105.879 | −65.786 | 1.00 | 112.09 | C |
| ANISOU | 277 | CD2 | TYR | A | 186 | 13496 | 10964 | 18128 | 629 | 413 | −66 C |
| ATOM | 278 | CD1 | TYR | A | 186 | 16.328 | −104.509 | −66.971 | 1.00 | 122.36 | C |
| ANISOU | 278 | CD1 | TYR | A | 186 | 14531 | 12369 | 19593 | 856 | 440 | −233 C |
| ATOM | 279 | CE2 | TYR | A | 186 | 15.110 | −105.182 | −64.649 | 1.00 | 109.74 | C |
| ANISOU | 279 | CE2 | TYR | A | 186 | 13261 | 10821 | 17613 | 687 | 197 | 153 C |
| ATOM | 280 | CE1 | TYR | A | 186 | 16.594 | −103.809 | −65.836 | 1.00 | 118.54 | C |
| ANISOU | 280 | CE1 | TYR | A | 186 | 14097 | 12028 | 18915 | 908 | 205 | −19 C |
| ATOM | 281 | CZ | TYR | A | 186 | 15.987 | −104.147 | −64.683 | 1.00 | 113.64 | C |
| ANISOU | 281 | CZ | TYR | A | 186 | 13649 | 11436 | 18093 | 831 | 83 | 168 C |
| ATOM | 282 | OH | TYR | A | 186 | 16.268 | −103.428 | −63.556 | 1.00 | 114.20 | O |

TABLE 7-continued

| DMXAA-hSTING$^{G230I}$ complex | | | | | | | | | | | |
|---|---|---|---|---|---|---|---|---|---|---|---|
| ANISOU | 282 | OH | TYR | A | 186 | 13791 | 11648 | 17951 | 899 | −149 | 368 | O |
| ATOM | 283 | O | ASN | A | 187 | 15.356 | −110.153 | −67.321 | 1.00 | 112.92 | | O |
| ANISOU | 283 | O | ASN | A | 187 | 13708 | 10078 | 19117 | 297 | 984 | −574 | O |
| ATOM | 284 | N | ASN | A | 187 | 16.341 | −109.247 | −70.046 | 1.00 | 128.71 | | N |
| ANISOU | 284 | N | ASN | A | 187 | 15332 | 12168 | 21404 | 701 | 1202 | −961 | N |
| ATOM | 285 | CA | ASN | A | 187 | 15.120 | −109.938 | −69.671 | 1.00 | 123.40 | | C |
| ANISOU | 285 | CA | ASN | A | 187 | 14790 | 11282 | 20816 | 601 | 1098 | −798 | C |
| ATOM | 286 | C | ASN | A | 187 | 14.702 | −109.714 | −68.258 | 1.00 | 122.38 | | C |
| ANISOU | 286 | C | ASN | A | 187 | 14790 | 11412 | 20299 | 410 | 1041 | −714 | C |
| ATOM | 287 | CB | ASN | A | 187 | 15.753 | −111.299 | −69.623 | 1.00 | 125.83 | | C |
| ANISOU | 287 | CB | ASN | A | 187 | 15076 | 11274 | 21458 | 742 | 907 | −544 | C |
| ATOM | 288 | CG | ASN | A | 187 | 17.049 | −111.272 | −68.863 | 1.00 | 133.97 | | C |
| ANISOU | 288 | CG | ASN | A | 187 | 16134 | 11892 | 22878 | 753 | 968 | −594 | C |
| ATOM | 289 | OD1 | ASN | A | 187 | 17.435 | −112.234 | −68.206 | 1.00 | 140.04 | | O |
| ANISOU | 289 | OD1 | ASN | A | 187 | 16910 | 12592 | 23706 | 688 | 1172 | −850 | O |
| ATOM | 290 | ND2 | ASN | A | 187 | 17.731 | −110.144 | −68.937 | 1.00 | 136.34 | | N |
| ANISOU | 290 | ND2 | ASN | A | 187 | 16464 | 11981 | 23356 | 826 | 765 | −346 | N |
| ATOM | 291 | O | ASN | A | 188 | 13.481 | −106.429 | −69.712 | 1.00 | 137.31 | | O |
| ANISOU | 291 | O | ASN | A | 188 | 16554 | 13697 | 21921 | 422 | 1393 | −1280 | O |
| ATOM | 292 | N | ASN | A | 188 | 13.542 | −109.092 | −68.123 | 1.00 | 130.97 | | N |
| ANISOU | 292 | N | ASN | A | 188 | 15845 | 12870 | 21047 | 393 | 1051 | −778 | N |
| ATOM | 293 | CA | ASN | A | 188 | 12.752 | −108.698 | −69.297 | 1.00 | 132.44 | | C |
| ANISOU | 293 | CA | ASN | A | 188 | 16081 | 13338 | 20901 | 223 | 1149 | −944 | C |
| ATOM | 294 | C | ASN | A | 188 | 13.358 | −107.566 | −70.145 | 1.00 | 130.85 | | C |
| ANISOU | 294 | C | ASN | A | 188 | 15824 | 13056 | 20835 | 261 | 1346 | −1247 | C |
| ATOM | 295 | CB | ASN | A | 188 | 11.295 | −108.364 | −68.869 | 1.00 | 130.18 | | C |
| ANISOU | 295 | CB | ASN | A | 188 | 15771 | 13455 | 20238 | 234 | 1072 | −907 | C |
| ATOM | 296 | CG | ASN | A | 188 | 11.072 | −106.888 | −68.574 | 1.00 | 87.73 | | C |
| ANISOU | 296 | CG | ASN | A | 188 | 10286 | 8220 | 14829 | 358 | 1154 | −1080 | C |
| ATOM | 297 | OD1 | ASN | A | 188 | 10.563 | −106.151 | −69.415 | 1.00 | 95.34 | | O |
| ANISOU | 297 | OD1 | ASN | A | 188 | 11236 | 9184 | 15804 | 337 | 1333 | −1343 | O |
| ATOM | 298 | ND2 | ASN | A | 188 | 11.425 | −106.457 | −67.362 | 1.00 | 66.22 | | N |
| ANISOU | 298 | ND2 | ASN | A | 188 | 7498 | 5624 | 12036 | 482 | 1017 | −927 | N |
| ATOM | 299 | O | LEU | A | 189 | 15.291 | −108.371 | −73.265 | 1.00 | 110.59 | | O |
| ANISOU | 299 | O | LEU | A | 189 | 13161 | 10540 | 18319 | 411 | 1754 | −1836 | O |
| ATOM | 300 | N | LEU | A | 189 | 13.651 | −107.852 | −71.399 | 1.00 | 124.07 | | N |
| ANISOU | 300 | N | LEU | A | 189 | 15016 | 12363 | 19764 | 123 | 1457 | −1472 | N |
| ATOM | 301 | CA | LEU | A | 189 | 13.405 | −109.124 | −72.033 | 1.00 | 121.52 | | C |
| ANISOU | 301 | CA | LEU | A | 189 | 14716 | 11891 | 19564 | 97 | 1639 | −1767 | C |
| ATOM | 302 | C | LEU | A | 189 | 14.470 | −109.263 | −73.079 | 1.00 | 113.32 | | C |
| ANISOU | 302 | C | LEU | A | 189 | 13596 | 10729 | 18730 | 285 | 1770 | −1896 | C |
| ATOM | 303 | CB | LEU | A | 189 | 12.016 | −109.176 | −72.676 | 1.00 | 125.08 | | C |
| ANISOU | 303 | CB | LEU | A | 189 | 15228 | 12615 | 19680 | −58 | 1696 | −1989 | C |
| ATOM | 304 | CG | LEU | A | 189 | 10.756 | −108.647 | −71.964 | 1.00 | 127.32 | | C |
| ANISOU | 304 | CG | LEU | A | 189 | 15519 | 13229 | 19627 | −170 | 1562 | −1847 | C |
| ATOM | 305 | CD1 | LEU | A | 189 | 9.742 | −108.113 | −72.961 | 1.00 | 126.49 | | C |
| ANISOU | 305 | CD1 | LEU | A | 189 | 15458 | 13351 | 19252 | −307 | 1616 | −2103 | C |
| ATOM | 306 | CD2 | LEU | A | 189 | 10.083 | −109.681 | −71.086 | 1.00 | 74.54 | | C |
| ANISOU | 306 | CD2 | LEU | A | 189 | 8872 | 6457 | 12993 | −279 | 1447 | −1584 | C |
| ATOM | 307 | N | LEU | A | 190 | 14.457 | −110.396 | −73.749 | 1.00 | 104.26 | | N |
| ANISOU | 307 | N | LEU | A | 190 | 12479 | 9290 | 17846 | 303 | 1909 | −2077 | N |
| ATOM | 308 | CA | LEU | A | 190 | 15.388 | −110.668 | −74.798 | 1.00 | 68.03 | | C |
| ANISOU | 308 | CA | LEU | A | 190 | 7820 | 4558 | 13472 | 476 | 2083 | −2233 | C |
| ATOM | 309 | CB | LEU | A | 190 | 15.224 | −112.066 | −75.325 | 1.00 | 86.22 | | C |
| ANISOU | 309 | CB | LEU | A | 190 | 10187 | 6536 | 16036 | 468 | 2203 | −2408 | C |
| ATOM | 310 | CG | LEU | A | 190 | 15.519 | −113.176 | −74.350 | 1.00 | 72.84 | | C |
| ANISOU | 310 | CG | LEU | A | 190 | 8517 | 4533 | 14627 | 422 | 2063 | −2213 | C |
| ATOM | 311 | CD2 | LEU | A | 190 | 16.779 | −112.852 | −73.600 | 1.00 | 74.17 | | C |
| ANISOU | 311 | CD2 | LEU | A | 190 | 8557 | 4616 | 15010 | 579 | 1925 | −1920 | C |
| ATOM | 312 | CD1 | LEU | A | 190 | 15.676 | −114.429 | −75.158 | 1.00 | 76.01 | | C |
| ANISOU | 312 | CD1 | LEU | A | 190 | 8985 | 4720 | 15174 | 394 | 2140 | −2358 | C |
| ATOM | 313 | C | LEU | A | 190 | 15.166 | −109.722 | −75.900 | 1.00 | 75.09 | | C |
| ANISOU | 313 | C | LEU | A | 190 | 8729 | 5745 | 14058 | 489 | 2221 | −2447 | C |
| ATOM | 314 | O | LEU | A | 190 | 16.008 | −109.613 | −76.735 | 1.00 | 73.82 | | O |
| ANISOU | 314 | O | LEU | A | 190 | 8528 | 5572 | 13950 | 604 | 2379 | −2565 | O |
| ATOM | 315 | N | ARG | A | 191 | 14.021 | −109.063 | −75.948 | 1.00 | 82.50 | | N |
| ANISOU | 315 | N | ARG | A | 191 | 9731 | 7004 | 14610 | 353 | 2136 | −2457 | N |
| ATOM | 316 | CA | ARG | A | 191 | 13.870 | −107.966 | −76.905 | 1.00 | 78.40 | | C |
| ANISOU | 316 | CA | ARG | A | 191 | 9251 | 6783 | 13757 | 351 | 2228 | −2643 | C |
| ATOM | 317 | CB | ARG | A | 191 | 12.721 | −108.193 | −77.851 | 1.00 | 73.01 | | C |
| ANISOU | 317 | CB | ARG | A | 191 | 8716 | 6199 | 12826 | 177 | 2242 | −2875 | C |
| ATOM | 318 | CG | ARG | A | 191 | 12.137 | −109.591 | −77.842 | 1.00 | 84.33 | | C |
| ANISOU | 318 | CG | ARG | A | 191 | 10222 | 7343 | 14476 | 65 | 2237 | −2946 | C |
| ATOM | 319 | CD | ARG | A | 191 | 13.170 | −110.689 | −77.957 | 1.00 | 96.27 | | C |
| ANISOU | 319 | CD | ARG | A | 191 | 11747 | 8494 | 16336 | 185 | 2409 | −3086 | C |
| ATOM | 320 | NE | ARG | A | 191 | 12.594 | −111.811 | −78.648 | 1.00 | 104.48 | | N |
| ANISOU | 320 | NE | ARG | A | 191 | 12917 | 9383 | 17398 | 66 | 2434 | −3284 | N |
| ATOM | 321 | CZ | ARG | A | 191 | 11.832 | −112.709 | −78.068 | 1.00 | 112.51 | | C |

TABLE 7-continued

DMXAA-hSTING$^{G230I}$ complex

| | | | | | | | | | | | | |
|---|---|---|---|---|---|---|---|---|---|---|---|---|
| ANISOU | 321 | CZ | ARG | A | 191 | 13968 | 10191 | 18592 | −76 | 2342 | −3244 | C |
| ATOM | 322 | NH1 | ARG | A | 191 | 11.598 | −112.635 | −76.778 | 1.00 | 112.22 | | N |
| ANISOU | 322 | NH1 | ARG | A | 191 | 13852 | 10166 | 18620 | −125 | 2184 | −2931 | N |
| ATOM | 323 | NH2 | ARG | A | 191 | 11.336 | −113.695 | −78.774 | 1.00 | 123.75 | | N |
| ANISOU | 323 | NH2 | ARG | A | 191 | 15503 | 11492 | 20022 | −177 | 2355 | −3432 | N |
| ATOM | 324 | C | ARG | A | 191 | 13.791 | −106.573 | −76.267 | 1.00 | 77.81 | | C |
| ANISOU | 324 | C | ARG | A | 191 | 9103 | 7025 | 13435 | 371 | 2081 | −2443 | C |
| ATOM | 325 | O | ARG | A | 191 | 12.924 | −106.312 | −75.466 | 1.00 | 76.08 | | O |
| ANISOU | 325 | O | ARG | A | 191 | 8909 | 6977 | 13022 | 256 | 1915 | −2317 | O |
| ATOM | 326 | N | GLY | A | 192 | 14.718 | −105.704 | −76.652 | 1.00 | 59.28 | | N |
| ANISOU | 326 | N | GLY | A | 192 | 6666 | 4746 | 11113 | 519 | 2151 | −2418 | N |
| ATOM | 327 | CA | GLY | A | 192 | 14.932 | −104.394 | −76.064 | 1.00 | 83.82 | | C |
| ANISOU | 327 | CA | GLY | A | 192 | 9701 | 8121 | 14024 | 558 | 2011 | −2236 | C |
| ATOM | 328 | C | GLY | A | 192 | 14.800 | −103.329 | −77.113 | 1.00 | 75.54 | | C |
| ANISOU | 328 | C | GLY | A | 192 | 8697 | 7330 | 12675 | 570 | 2128 | −2415 | C |
| ATOM | 329 | O | GLY | A | 192 | 13.950 | −103.488 | −77.952 | 1.00 | 68.42 | | O |
| ANISOU | 329 | O | GLY | A | 192 | 7930 | 6516 | 11549 | 470 | 2204 | −2642 | O |
| ATOM | 330 | N | ALA | A | 193 | 15.641 | −102.290 | −77.141 | 1.00 | 69.65 | | N |
| ANISOU | 330 | N | ALA | A | 193 | 7852 | 6696 | 11917 | 684 | 2134 | −2320 | N |
| ATOM | 331 | CA | ALA | A | 193 | 16.566 | −101.835 | −76.107 | 1.00 | 61.52 | | C |
| ANISOU | 331 | CA | ALA | A | 193 | 6658 | 5588 | 11127 | 798 | 1997 | −2050 | C |
| ATOM | 332 | CB | ALA | A | 193 | 17.937 | −102.384 | −76.357 | 1.00 | 60.58 | | C |
| ANISOU | 332 | CB | ALA | A | 193 | 6411 | 5173 | 11432 | 944 | 2166 | −2065 | C |
| ATOM | 333 | C | ALA | A | 193 | 16.625 | −100.303 | −76.117 | 1.00 | 63.09 | | C |
| ANISOU | 333 | C | ALA | A | 193 | 6822 | 6084 | 11065 | 827 | 1914 | −1975 | C |
| ATOM | 334 | O | ALA | A | 193 | 16.621 | −99.703 | −77.150 | 1.00 | 59.63 | | O |
| ANISOU | 334 | O | ALA | A | 193 | 6439 | 5799 | 10417 | 825 | 2063 | −2141 | O |
| ATOM | 335 | N | VAL | A | 194 | 16.703 | −99.697 | −74.949 | 1.00 | 50.17 | | N |
| ANISOU | 335 | N | VAL | A | 194 | 5113 | 4518 | 9432 | 859 | 1672 | −1727 | N |
| ATOM | 336 | CA | VAL | A | 194 | 16.514 | −98.258 | −74.765 | 1.00 | 55.43 | | C |
| ANISOU | 336 | CA | VAL | A | 194 | 5783 | 5489 | 9791 | 857 | 1542 | −1658 | C |
| ATOM | 337 | CB | VAL | A | 194 | 16.109 | −97.925 | −73.316 | 1.00 | 61.87 | | C |
| ANISOU | 337 | CB | VAL | A | 194 | 6604 | 6400 | 10505 | 837 | 1244 | −1419 | C |
| ATOM | 338 | CG1 | VAL | A | 194 | 15.228 | −99.007 | −72.759 | 1.00 | 58.98 | | C |
| ANISOU | 338 | CG1 | VAL | A | 194 | 6323 | 5921 | 10166 | 738 | 1197 | −1395 | C |
| ATOM | 339 | CG2 | VAL | A | 194 | 17.313 | −97.777 | −72.426 | 1.00 | 67.41 | | C |
| ANISOU | 339 | CG2 | VAL | A | 194 | 7166 | 6950 | 11499 | 973 | 1097 | −1193 | C |
| ATOM | 340 | C | VAL | A | 194 | 17.624 | −97.312 | −75.219 | 1.00 | 57.36 | | C |
| ANISOU | 340 | C | VAL | A | 194 | 5898 | 5743 | 10153 | 979 | 1615 | −1623 | C |
| ATOM | 341 | O | VAL | A | 194 | 18.776 | −97.606 | −75.061 | 1.00 | 60.20 | | O |
| ANISOU | 341 | O | VAL | A | 194 | 6114 | 5859 | 10900 | 1089 | 1689 | −1562 | O |
| ATOM | 342 | N | SER | A | 195 | 17.254 | −96.152 | −75.728 | 1.00 | 47.46 | | N |
| ANISOU | 342 | N | SER | A | 195 | 4689 | 4763 | 8581 | 959 | 1594 | −1660 | N |
| ATOM | 343 | CA | SER | A | 195 | 18.226 | −95.156 | −76.114 | 1.00 | 51.50 | | C |
| ANISOU | 343 | CA | SER | A | 195 | 5087 | 5304 | 9176 | 1055 | 1658 | −1613 | C |
| ATOM | 344 | CB | SER | A | 195 | 17.607 | −94.112 | −77.000 | 1.00 | 57.14 | | C |
| ANISOU | 344 | CB | SER | A | 195 | 5918 | 6307 | 9484 | 1002 | 1713 | −1738 | C |
| ATOM | 345 | OG | SER | A | 195 | 17.317 | −94.673 | −78.245 | 1.00 | 67.53 | | O |
| ANISOU | 345 | OG | SER | A | 195 | 7372 | 7623 | 10664 | 948 | 1964 | −1991 | O |
| ATOM | 346 | C | SER | A | 195 | 18.886 | −94.536 | −74.905 | 1.00 | 49.50 | | C |
| ANISOU | 346 | C | SER | A | 195 | 4692 | 5018 | 9099 | 1137 | 1392 | −1348 | C |
| ATOM | 347 | O | SER | A | 195 | 18.451 | −94.742 | −73.810 | 1.00 | 50.41 | | O |
| ANISOU | 347 | O | SER | A | 195 | 4842 | 5148 | 9163 | 1115 | 1150 | −1209 | O |
| ATOM | 348 | N | GLN | A | 196 | 19.997 | −93.851 | −75.108 | 1.00 | 59.41 | | N |
| ANISOU | 348 | N | GLN | A | 196 | 5796 | 6223 | 10556 | 1231 | 1436 | −1277 | N |
| ATOM | 349 | CA | GLN | A | 196 | 20.854 | −93.405 | −74.008 | 1.00 | 64.26 | | C |
| ANISOU | 349 | CA | GLN | A | 196 | 6247 | 6731 | 11438 | 1327 | 1187 | −1037 | C |
| ATOM | 350 | CB | GLN | A | 196 | 22.314 | −93.372 | −74.452 | 1.00 | 55.36 | | C |
| ANISOU | 350 | CB | GLN | A | 196 | 4998 | 5459 | 10577 | 1350 | 1287 | −961 | C |
| ATOM | 351 | CG | GLN | A | 196 | 22.888 | −94.734 | −74.727 | 1.00 | 76.79 | | C |
| ANISOU | 351 | CG | GLN | A | 196 | 7686 | 7928 | 13564 | 1346 | 1450 | −1011 | C |
| ATOM | 352 | CD | GLN | A | 196 | 22.736 | −95.666 | −73.538 | 1.00 | 97.02 | | C |
| ANISOU | 352 | CD | GLN | A | 196 | 10235 | 10306 | 16323 | 1377 | 1248 | −905 | C |
| ATOM | 353 | OE1 | GLN | A | 196 | 22.997 | −95.283 | −72.396 | 1.00 | 99.29 | | O |
| ANISOU | 353 | OE1 | GLN | A | 196 | 10473 | 10568 | 16686 | 1419 | 952 | −707 | O |
| ATOM | 354 | NE2 | GLN | A | 196 | 22.296 | −96.893 | −73.801 | 1.00 | 104.02 | | N |
| ANISOU | 354 | NE2 | GLN | A | 196 | 11193 | 11060 | 17271 | 1350 | 1394 | −1034 | N |
| ATOM | 355 | C | GLN | A | 196 | 20.494 | −92.059 | −73.388 | 1.00 | 60.44 | | C |
| ANISOU | 355 | C | GLN | A | 196 | 5796 | 6486 | 10684 | 1322 | 913 | −906 | C |
| ATOM | 356 | O | GLN | A | 196 | 21.037 | −91.690 | −72.347 | 1.00 | 61.96 | | O |
| ANISOU | 356 | O | GLN | A | 196 | 5894 | 6601 | 11045 | 1395 | 651 | −707 | O |
| ATOM | 357 | N | ARG | A | 197 | 19.650 | −91.294 | −74.050 | 1.00 | 54.71 | | N |
| ANISOU | 357 | N | ARG | A | 197 | 5209 | 6035 | 9543 | 1244 | 958 | −1022 | N |
| ATOM | 358 | CA | ARG | A | 197 | 19.252 | −89.991 | −73.570 | 1.00 | 52.91 | | C |
| ANISOU | 358 | CA | ARG | A | 197 | 5011 | 6031 | 9060 | 1248 | 720 | −919 | C |
| ATOM | 359 | CB | ARG | A | 197 | 19.297 | −88.979 | −74.686 | 1.00 | 52.63 | | C |
| ANISOU | 359 | CB | ARG | A | 197 | 5008 | 6164 | 8827 | 1225 | 887 | −1034 | C |
| ATOM | 360 | CG | ARG | A | 197 | 20.442 | −89.155 | −75.621 | 1.00 | 48.63 | | C |

TABLE 7-continued

| | | | | | | | | | | | | |
|---|---|---|---|---|---|---|---|---|---|---|---|---|
| DMXAA-hSTING$^{G230I}$ complex | | | | | | | | | | | | |
| ANISOU | 360 | CG | ARG | A | 197 | 4354 | 5479 | 8644 | 1280 | 1160 | −1068 | C |
| ATOM | 361 | CD | ARG | A | 197 | 20.454 | −88.029 | −76.617 | 1.00 | 68.47 | | C |
| ANISOU | 361 | CD | ARG | A | 197 | 6930 | 8178 | 10908 | 1253 | 1288 | −1143 | C |
| ATOM | 362 | NE | ARG | A | 197 | 21.664 | −88.006 | −77.426 | 1.00 | 82.41 | | N |
| ANISOU | 362 | NE | ARG | A | 197 | 8614 | 9810 | 12890 | 1267 | 1533 | −1128 | N |
| ATOM | 363 | CZ | ARG | A | 197 | 22.350 | −86.910 | −77.707 | 1.00 | 88.41 | | C |
| ANISOU | 363 | CZ | ARG | A | 197 | 9287 | 10592 | 13713 | 1286 | 1513 | −1013 | C |
| ATOM | 364 | NH1 | ARG | A | 197 | 23.428 | −86.984 | −78.443 | 1.00 | 80.56 | | N |
| ANISOU | 364 | NH1 | ARG | A | 197 | 8238 | 9479 | 12891 | 1273 | 1741 | −995 | N |
| ATOM | 365 | NH2 | ARG | A | 197 | 21.958 | −85.735 | −77.255 | 1.00 | 92.14 | | N |
| ANISOU | 365 | NH2 | ARG | A | 197 | 9724 | 11202 | 14084 | 1314 | 1259 | −921 | N |
| ATOM | 366 | C | ARG | A | 197 | 17.893 | −89.926 | −72.906 | 1.00 | 52.07 | | C |
| ANISOU | 366 | C | ARG | A | 197 | 5072 | 6134 | 8577 | 1177 | 517 | −911 | C |
| ATOM | 367 | O | ARG | A | 197 | 17.079 | −90.807 | −73.038 | 1.00 | 46.29 | | O |
| ANISOU | 367 | O | ARG | A | 197 | 4447 | 5418 | 7722 | 1096 | 601 | −1018 | O |
| ATOM | 368 | N | LEU | A | 198 | 17.678 | −88.822 | −72.200 | 1.00 | 36.02 | | N |
| ANISOU | 368 | N | LEU | A | 198 | 3057 | 4257 | 6373 | 1208 | 255 | −785 | N |
| ATOM | 369 | CA | LEU | A | 198 | 16.403 | −88.550 | −71.578 | 1.00 | 37.30 | | C |
| ANISOU | 369 | CA | LEU | A | 198 | 3370 | 4656 | 6146 | 1152 | 83 | −788 | C |
| ATOM | 370 | CB | LEU | A | 198 | 16.594 | −87.940 | −70.191 | 1.00 | 38.99 | | C |
| ANISOU | 370 | CB | LEU | A | 198 | 3579 | 4903 | 6334 | 1231 | −251 | −582 | C |
| ATOM | 371 | CG | LEU | A | 198 | 15.318 | −87.612 | −69.413 | 1.00 | 39.89 | | C |
| ANISOU | 371 | CG | LEU | A | 198 | 3827 | 5128 | 6199 | 1203 | −428 | −517 | C |
| ATOM | 372 | CD1 | LEU | A | 198 | 15.654 | −87.013 | −68.056 | 1.00 | 33.43 | | C |
| ANISOU | 372 | CD1 | LEU | A | 198 | 3062 | 4481 | 5159 | 1267 | −714 | −405 | C |
| ATOM | 373 | CD2 | LEU | A | 198 | 14.427 | −86.673 | −70.212 | 1.00 | 32.49 | | C |
| ANISOU | 373 | CD2 | LEU | A | 198 | 3000 | 4357 | 4987 | 1079 | −267 | −692 | C |
| ATOM | 374 | C | LEU | A | 198 | 15.754 | −87.549 | −72.515 | 1.00 | 35.15 | | C |
| ANISOU | 374 | C | LEU | A | 198 | 3186 | 4640 | 5529 | 1095 | 167 | −945 | C |
| ATOM | 375 | O | LEU | A | 198 | 16.266 | −86.450 | −72.727 | 1.00 | 44.16 | | O |
| ANISOU | 375 | O | LEU | A | 198 | 4289 | 5851 | 6640 | 1137 | 129 | −917 | O |
| ATOM | 376 | N | TYR | A | 199 | 14.625 | −87.948 | −73.079 | 1.00 | 42.52 | | N |
| ANISOU | 376 | N | TYR | A | 199 | 4239 | 5703 | 6213 | 997 | 269 | −1108 | N |
| ATOM | 377 | CA | TYR | A | 199 | 13.914 | −87.150 | −74.025 | 1.00 | 48.62 | | C |
| ANISOU | 377 | CA | TYR | A | 199 | 5113 | 6714 | 6646 | 946 | 313 | −1261 | C |
| ATOM | 378 | CB | TYR | A | 199 | 13.350 | −88.023 | −75.116 | 1.00 | 43.25 | | C |
| ANISOU | 378 | CB | TYR | A | 199 | 4519 | 6028 | 5887 | 854 | 558 | −1488 | C |
| ATOM | 379 | CG | TYR | A | 199 | 14.409 | −88.469 | −76.040 | 1.00 | 43.73 | | C |
| ANISOU | 379 | CG | TYR | A | 199 | 4523 | 5886 | 6208 | 887 | 819 | −1549 | C |
| ATOM | 380 | CD1 | TYR | A | 199 | 15.221 | −89.522 | −75.723 | 1.00 | 51.53 | | C |
| ANISOU | 380 | CD1 | TYR | A | 199 | 5403 | 6600 | 7576 | 925 | 913 | −1484 | C |
| ATOM | 381 | CE1 | TYR | A | 199 | 16.208 | −89.931 | −76.567 | 1.00 | 49.04 | | C |
| ANISOU | 381 | CE1 | TYR | A | 199 | 5019 | 6095 | 7520 | 968 | 1168 | −1545 | C |
| ATOM | 382 | CZ | TYR | A | 199 | 16.398 | −89.274 | −77.726 | 1.00 | 48.01 | | C |
| ANISOU | 382 | CZ | TYR | A | 199 | 4945 | 6049 | 7248 | 968 | 1349 | −1660 | C |
| ATOM | 383 | OH | TYR | A | 199 | 17.376 | −89.659 | −78.573 | 1.00 | 57.63 | | O |
| ANISOU | 383 | OH | TYR | A | 199 | 6100 | 7079 | 8718 | 1015 | 1637 | −1721 | O |
| ATOM | 384 | CE2 | TYR | A | 199 | 15.604 | −88.221 | −78.064 | 1.00 | 51.17 | | C |
| ANISOU | 384 | CE2 | TYR | A | 199 | 5472 | 6714 | 7256 | 926 | 1248 | −1714 | C |
| ATOM | 385 | CD2 | TYR | A | 199 | 14.625 | −87.818 | −77.215 | 1.00 | 46.97 | | C |
| ANISOU | 385 | CD2 | TYR | A | 199 | 4989 | 6366 | 6489 | 890 | 976 | −1661 | C |
| ATOM | 386 | C | TYR | A | 199 | 12.858 | −86.362 | −73.294 | 1.00 | 46.31 | | C |
| ANISOU | 386 | C | TYR | A | 199 | 4899 | 6667 | 6030 | 933 | 69 | −1222 | C |
| ATOM | 387 | O | TYR | A | 199 | 12.030 | −86.881 | −72.623 | 1.00 | 37.25 | | O |
| ANISOU | 387 | O | TYR | A | 199 | 3797 | 5571 | 4785 | 884 | 4 | −1220 | O |
| ATOM | 388 | N | ILE | A | 200 | 12.963 | −85.066 | −73.425 | 1.00 | 46.68 | | N |
| ANISOU | 388 | N | ILE | A | 200 | 4954 | 6854 | 5928 | 983 | −59 | −1182 | N |
| ATOM | 389 | CA | ILE | A | 200 | 12.113 | −84.154 | −72.701 | 1.00 | 45.80 | | C |
| ANISOU | 389 | CA | ILE | A | 200 | 4906 | 6963 | 5533 | 1000 | −305 | −1134 | C |
| ATOM | 390 | CB | ILE | A | 200 | 12.931 | −83.100 | −71.989 | 1.00 | 34.87 | | C |
| ANISOU | 390 | CB | ILE | A | 200 | 3465 | 5556 | 4228 | 1107 | −523 | −954 | C |
| ATOM | 391 | CG1 | ILE | A | 200 | 13.804 | −83.775 | −70.937 | 1.00 | 32.54 | | C |
| ANISOU | 391 | CG1 | ILE | A | 200 | 3080 | 5025 | 4257 | 1168 | −599 | −777 | C |
| ATOM | 392 | CD1 | ILE | A | 200 | 14.642 | −82.817 | −70.148 | 1.00 | 29.05 | | C |
| ANISOU | 392 | CD1 | ILE | A | 200 | 2581 | 4530 | 3924 | 1276 | −850 | −598 | C |
| ATOM | 393 | CG2 | ILE | A | 200 | 12.015 | −82.071 | −71.347 | 1.00 | 37.87 | | C |
| ANISOU | 393 | CG2 | ILE | A | 200 | 3931 | 6174 | 4284 | 1136 | −769 | −931 | C |
| ATOM | 394 | C | ILE | A | 200 | 11.143 | −83.497 | −73.653 | 1.00 | 41.34 | | C |
| ANISOU | 394 | C | ILE | A | 200 | 4446 | 6631 | 4630 | 945 | −279 | −1310 | C |
| ATOM | 395 | O | ILE | A | 200 | 11.538 | −82.887 | −74.641 | 1.00 | 63.22 | | O |
| ANISOU | 395 | O | ILE | A | 200 | 7239 | 9424 | 7357 | 951 | −195 | −1374 | O |
| ATOM | 396 | N | LEU | A | 201 | 9.865 | −83.649 | −73.358 | 1.00 | 33.16 | | N |
| ANISOU | 396 | N | LEU | A | 201 | 3474 | 5762 | 3365 | 890 | −349 | −1387 | N |
| ATOM | 397 | CA | LEU | A | 201 | 8.831 | −83.119 | −74.214 | 1.00 | 36.22 | | C |
| ANISOU | 397 | CA | LEU | A | 201 | 3949 | 6318 | 3495 | 820 | −346 | −1513 | C |
| ATOM | 398 | CB | LEU | A | 201 | 7.568 | −83.962 | −74.105 | 1.00 | 34.09 | | C |
| ANISOU | 398 | CB | LEU | A | 201 | 3699 | 6049 | 3203 | 701 | −302 | −1545 | C |
| ATOM | 399 | CG | LEU | A | 201 | 7.658 | −85.302 | −74.816 | 1.00 | 40.99 | | C |

TABLE 7-continued

DMXAA-hSTING[G230I] complex

| | | | | | | | | | | | | |
|---|---|---|---|---|---|---|---|---|---|---|---|---|
| ANISOU | 399 | CG | LEU | A | 201 | 4586 | 6836 | 4154 | 636 | −90 | −1747 | C |
| ATOM | 400 | CD1 | LEU | A | 201 | 6.421 | −86.121 | −74.500 | 1.00 | 51.18 | | C |
| ANISOU | 400 | CD1 | LEU | A | 201 | 5876 | 8155 | 5413 | 528 | −88 | −1788 | C |
| ATOM | 401 | CD2 | LEU | A | 201 | 7.783 | −85.059 | −76.308 | 1.00 | 47.57 | | C |
| ANISOU | 401 | CD2 | LEU | A | 201 | 5509 | 7584 | 4982 | 571 | 20 | −1780 | C |
| ATOM | 402 | C | LEU | A | 201 | 8.542 | −81.681 | −73.829 | 1.00 | 37.07 | | C |
| ANISOU | 402 | C | LEU | A | 201 | 4076 | 6421 | 3588 | 840 | −490 | −1294 | C |
| ATOM | 403 | O | LEU | A | 201 | 8.344 | −81.363 | −72.650 | 1.00 | 29.14 | | O |
| ANISOU | 403 | O | LEU | A | 201 | 3074 | 5387 | 2610 | 877 | −585 | −1154 | O |
| ATOM | 404 | N | LEU | A | 202 | 8.519 | −80.814 | −74.829 | 1.00 | 34.29 | | N |
| ANISOU | 404 | N | LEU | A | 202 | 3777 | 6031 | 3221 | 801 | −452 | −1264 | N |
| ATOM | 405 | CA | LEU | A | 202 | 8.213 | −79.416 | −74.603 | 1.00 | 40.08 | | C |
| ANISOU | 405 | CA | LEU | A | 202 | 4561 | 6690 | 3978 | 799 | −512 | −1097 | C |
| ATOM | 406 | CB | LEU | A | 202 | 9.460 | −78.569 | −74.788 | 1.00 | 31.05 | | C |
| ANISOU | 406 | CB | LEU | A | 202 | 3404 | 5543 | 2851 | 885 | −554 | −1071 | C |
| ATOM | 407 | CG | LEU | A | 202 | 10.540 | −78.866 | −73.762 | 1.00 | 36.65 | | C |
| ANISOU | 407 | CG | LEU | A | 202 | 4042 | 6260 | 3623 | 1002 | −656 | −1052 | C |
| ATOM | 408 | CD1 | LEU | A | 202 | 11.919 | −78.657 | −74.376 | 1.00 | 46.89 | | C |
| ANISOU | 408 | CD1 | LEU | A | 202 | 5252 | 7623 | 4942 | 1104 | −701 | −1123 | C |
| ATOM | 409 | CD2 | LEU | A | 202 | 10.344 | −77.972 | −72.554 | 1.00 | 30.81 | | C |
| ANISOU | 409 | CD2 | LEU | A | 202 | 3393 | 5357 | 2958 | 962 | −723 | −853 | C |
| ATOM | 410 | C | LEU | A | 202 | 7.102 | −78.924 | −75.515 | 1.00 | 44.85 | | C |
| ANISOU | 410 | C | LEU | A | 202 | 5251 | 7236 | 4556 | 688 | −470 | −1073 | C |
| ATOM | 411 | O | LEU | A | 202 | 7.366 | −78.236 | −76.506 | 1.00 | 36.94 | | O |
| ANISOU | 411 | O | LEU | A | 202 | 4292 | 6224 | 3518 | 681 | −454 | −1083 | O |
| ATOM | 412 | N | PRO | A | 203 | 5.855 | −79.310 | −75.198 | 1.00 | 45.03 | | N |
| ANISOU | 412 | N | PRO | A | 203 | 5238 | 7305 | 4567 | 663 | −469 | −1097 | N |
| ATOM | 413 | CA | PRO | A | 203 | 4.694 | −78.745 | −75.887 | 1.00 | 39.17 | | C |
| ANISOU | 413 | CA | PRO | A | 203 | 4470 | 6630 | 3783 | 662 | −474 | −1140 | C |
| ATOM | 414 | CB | PRO | A | 203 | 3.507 | −79.484 | −75.261 | 1.00 | 34.94 | | C |
| ANISOU | 414 | CB | PRO | A | 203 | 3880 | 6149 | 3246 | 629 | −469 | −1175 | C |
| ATOM | 415 | CG | PRO | A | 203 | 4.016 | −79.980 | −73.920 | 1.00 | 41.04 | | C |
| ANISOU | 415 | CG | PRO | A | 203 | 4651 | 6889 | 4055 | 648 | −479 | −1108 | C |
| ATOM | 416 | CD | PRO | A | 203 | 5.465 | −80.327 | −74.210 | 1.00 | 42.10 | | C |
| ANISOU | 416 | CD | PRO | A | 203 | 4851 | 6935 | 4211 | 633 | −467 | −1096 | C |
| ATOM | 417 | C | PRO | A | 203 | 4.575 | −77.263 | −75.576 | 1.00 | 33.03 | | C |
| ANISOU | 417 | C | PRO | A | 203 | 3663 | 5871 | 3017 | 762 | −521 | −1078 | C |
| ATOM | 418 | O | PRO | A | 203 | 4.496 | −76.884 | −74.404 | 1.00 | 29.27 | | O |
| ANISOU | 418 | O | PRO | A | 203 | 3157 | 5392 | 2572 | 827 | −542 | −1023 | O |
| ATOM | 419 | N | LEU | A | 204 | 4.550 | −76.439 | −76.616 | 1.00 | 34.53 | | N |
| ANISOU | 419 | N | LEU | A | 204 | 4868 | 5402 | 2849 | 967 | −1660 | 593 | N |
| ATOM | 420 | CA | LEU | A | 204 | 4.412 | −75.002 | −76.445 | 1.00 | 44.90 | | C |
| ANISOU | 420 | CA | LEU | A | 204 | 6331 | 6766 | 3965 | 763 | −1569 | 611 | C |
| ATOM | 421 | CB | LEU | A | 204 | 4.730 | −74.268 | −77.743 | 1.00 | 39.38 | | C |
| ANISOU | 421 | CB | LEU | A | 204 | 5789 | 6036 | 3137 | 554 | −1615 | 386 | C |
| ATOM | 422 | CG | LEU | A | 204 | 6.178 | −74.408 | −78.192 | 1.00 | 41.48 | | C |
| ANISOU | 422 | CG | LEU | A | 204 | 6112 | 6441 | 3209 | 287 | −1336 | 442 | C |
| ATOM | 423 | CD1 | LEU | A | 204 | 6.389 | −73.632 | −79.468 | 1.00 | 37.62 | | C |
| ANISOU | 423 | CD1 | LEU | A | 204 | 5844 | 5843 | 2607 | 375 | −1443 | 197 | C |
| ATOM | 424 | CD2 | LEU | A | 204 | 7.122 | −73.920 | −77.101 | 1.00 | 30.08 | | C |
| ANISOU | 424 | CD2 | LEU | A | 204 | 4768 | 4979 | 1683 | 105 | −1007 | 597 | C |
| ATOM | 425 | C | LEU | A | 204 | 3.026 | −74.601 | −75.932 | 1.00 | 53.13 | | C |
| ANISOU | 425 | C | LEU | A | 204 | 7149 | 7660 | 5379 | 993 | −1806 | 552 | C |
| ATOM | 426 | O | LEU | A | 204 | 2.873 | −73.560 | −75.297 | 1.00 | 58.32 | | O |
| ANISOU | 426 | O | LEU | A | 204 | 7870 | 8434 | 5857 | 914 | −1652 | 687 | O |
| ATOM | 427 | N | ASP | A | 205 | 2.013 | −75.416 | −76.210 | 1.00 | 50.93 | | N |
| ANISOU | 427 | N | ASP | A | 205 | 6480 | 7001 | 5869 | 1062 | −1977 | 313 | N |
| ATOM | 428 | CA | ASP | A | 205 | 0.672 | −75.116 | −75.716 | 1.00 | 55.17 | | C |
| ANISOU | 428 | CA | ASP | A | 205 | 6646 | 7285 | 7031 | 1099 | −2013 | 207 | C |
| ATOM | 429 | CB | ASP | A | 205 | −0.422 | −75.845 | −76.516 | 1.00 | 52.86 | | C |
| ANISOU | 429 | CB | ASP | A | 205 | 6034 | 6567 | 7484 | 1199 | −2403 | −206 | C |
| ATOM | 430 | CG | ASP | A | 205 | −0.287 | −77.370 | −76.471 | 1.00 | 62.05 | | C |
| ANISOU | 430 | CG | ASP | A | 205 | 6881 | 7556 | 9138 | 1164 | −2186 | −191 | C |
| ATOM | 431 | OD2 | ASP | A | 205 | −0.667 | −78.010 | −77.476 | 1.00 | 75.31 | | O |
| ANISOU | 431 | OD2 | ASP | A | 205 | 8489 | 8979 | 11146 | 1244 | −2568 | −529 | O |
| ATOM | 432 | OD1 | ASP | A | 205 | 0.197 | −77.923 | −75.453 | 1.00 | 45.81 | | O |
| ANISOU | 432 | OD1 | ASP | A | 205 | 4669 | 5611 | 7126 | 1067 | −1649 | 149 | O |
| ATOM | 433 | C | ASP | A | 205 | 0.566 | −75.434 | −74.215 | 1.00 | 57.84 | | C |
| ANISOU | 433 | C | ASP | A | 205 | 6622 | 7668 | 7688 | 1005 | −1407 | 556 | C |
| ATOM | 434 | O | ASP | A | 205 | −0.477 | −75.211 | −73.589 | 1.00 | 57.84 | | O |
| ANISOU | 434 | O | ASP | A | 205 | 6284 | 7487 | 8205 | 1009 | −1322 | 525 | O |
| ATOM | 435 | N | CYS | A | 206 | 1.647 | −75.980 | −73.662 | 1.00 | 42.18 | | N |
| ANISOU | 435 | N | CYS | A | 206 | 4715 | 5916 | 5396 | 931 | −992 | 871 | N |
| ATOM | 436 | CA | CYS | A | 206 | 1.754 | −76.299 | −72.237 | 1.00 | 45.96 | | C |
| ANISOU | 436 | CA | CYS | A | 206 | 4940 | 6470 | 6052 | 858 | −397 | 1236 | C |
| ATOM | 437 | CB | CYS | A | 206 | 1.669 | −75.033 | −71.378 | 1.00 | 43.88 | | C |
| ANISOU | 437 | CB | CYS | A | 206 | 4782 | 6426 | 5465 | 825 | −225 | 1444 | C |
| ATOM | 438 | SG | CYS | A | 206 | 3.051 | −73.897 | −71.628 | 1.00 | 51.52 | | S |

TABLE 7-continued

DMXAA-hSTING$^{G230I}$ complex

| | | | | | | | | | | | | |
|---|---|---|---|---|---|---|---|---|---|---|---|---|
| ANISOU | 438 | SG | CYS | A | 206 | 6362 | 7888 | 5326 | 788 | −285 | 1600 | S |
| ATOM | 439 | C | CYS | A | 206 | 0.723 | −77.325 | −71.778 | 1.00 | 53.16 | | C |
| ANISOU | 439 | C | CYS | A | 206 | 5323 | 6993 | 7884 | 854 | −206 | 1170 | C |
| ATOM | 440 | O | CYS | A | 206 | 0.384 | −77.396 | −70.595 | 1.00 | 51.86 | | O |
| ANISOU | 440 | O | CYS | A | 206 | 4904 | 6796 | 8005 | 804 | 236 | 1406 | O |
| ATOM | 441 | N | GLY | A | 207 | 0.219 | −78.108 | −72.725 | 1.00 | 57.04 | | N |
| ANISOU | 441 | N | GLY | A | 207 | 5657 | 7181 | 8835 | 902 | −536 | 837 | N |
| ATOM | 442 | CA | GLY | A | 207 | −0.716 | −79.171 | −72.422 | 1.00 | 45.53 | | C |
| ANISOU | 442 | CA | GLY | A | 207 | 3704 | 5334 | 8262 | 883 | −372 | 730 | C |
| ATOM | 443 | C | GLY | A | 207 | 0.010 | −80.436 | −72.013 | 1.00 | 45.38 | | C |
| ANISOU | 443 | C | GLY | A | 207 | 3619 | 5306 | 8315 | 842 | 31 | 955 | C |
| ATOM | 444 | O | GLY | A | 207 | 0.657 | −81.093 | −72.829 | 1.00 | 45.28 | | O |
| ANISOU | 444 | O | GLY | A | 207 | 3769 | 5310 | 8126 | 876 | −155 | 858 | O |
| ATOM | 445 | N | VAL | A | 208 | −0.102 | −80.773 | −70.735 | 1.00 | 55.32 | | N |
| ANISOU | 445 | N | VAL | A | 208 | 4658 | 6534 | 9826 | 778 | 586 | 1257 | N |
| ATOM | 446 | CA | VAL | A | 208 | 0.537 | −81.952 | −70.178 | 1.00 | 49.52 | | C |
| ANISOU | 446 | CA | VAL | A | 208 | 3873 | 5774 | 9167 | 755 | 1021 | 1502 | C |
| ATOM | 447 | CB | VAL | A | 208 | 1.398 | −81.585 | −68.971 | 1.00 | 49.49 | | C |
| ANISOU | 447 | CB | VAL | A | 208 | 4054 | 6105 | 8644 | 737 | 1511 | 1954 | C |
| ATOM | 448 | CG1 | VAL | A | 208 | 2.171 | −82.810 | −68.476 | 1.00 | 42.72 | | C |
| ANISOU | 448 | CG1 | VAL | A | 208 | 3207 | 5240 | 7785 | 751 | 1915 | 2194 | C |
| ATOM | 449 | CG2 | VAL | A | 208 | 2.335 | −80.438 | −69.336 | 1.00 | 42.90 | | C |
| ANISOU | 449 | CG2 | VAL | A | 208 | 3657 | 5713 | 6932 | 763 | 1279 | 2016 | C |
| ATOM | 450 | C | VAL | A | 208 | −0.520 | −82.949 | −69.732 | 1.00 | 54.82 | | C |
| ANISOU | 450 | C | VAL | A | 208 | 4076 | 5998 | 10757 | 703 | 1276 | 1420 | C |
| ATOM | 451 | O | VAL | A | 208 | −1.303 | −82.656 | −68.829 | 1.00 | 67.74 | | O |
| ANISOU | 451 | O | VAL | A | 208 | 5460 | 7512 | 12765 | 648 | 1566 | 1509 | O |
| ATOM | 452 | N | PRO | A | 209 | −0.544 | −84.129 | −70.319 | 1.00 | 59.87 | | N |
| ANISOU | 452 | N | PRO | A | 209 | 4596 | 6384 | 11767 | 712 | 1180 | 1239 | N |
| ATOM | 453 | CA | PRO | A | 209 | −1.500 | −85.151 | −69.928 | 1.00 | 66.95 | | C |
| ANISOU | 453 | CA | PRO | A | 209 | 5044 | 6826 | 13567 | 644 | 1412 | 1120 | C |
| ATOM | 454 | CB | PRO | A | 209 | −1.468 | −86.114 | −71.088 | 1.00 | 56.90 | | C |
| ANISOU | 454 | CB | PRO | A | 209 | 3736 | 5339 | 12546 | 681 | 1063 | 810 | C |
| ATOM | 455 | CG | PRO | A | 209 | −1.048 | −85.296 | −72.218 | 1.00 | 79.05 | | C |
| ANISOU | 455 | CG | PRO | A | 209 | 6956 | 8469 | 14609 | 775 | 565 | 708 | C |
| ATOM | 456 | CD | PRO | A | 209 | −0.012 | −84.401 | −71.645 | 1.00 | 69.42 | | C |
| ANISOU | 456 | CD | PRO | A | 209 | 6065 | 7689 | 12622 | 779 | 820 | 1092 | C |
| ATOM | 457 | C | PRO | A | 209 | −1.161 | −85.876 | −68.658 | 1.00 | 67.95 | | C |
| ANISOU | 457 | C | PRO | A | 209 | 5304 | 6905 | 13610 | 560 | 2004 | 1478 | C |
| ATOM | 458 | O | PRO | A | 209 | −0.031 | −85.933 | −68.258 | 1.00 | 70.33 | | O |
| ANISOU | 458 | O | PRO | A | 209 | 5919 | 7494 | 13307 | 611 | 2209 | 1785 | O |
| ATOM | 459 | N | ASP | A | 210 | −2.184 | −86.426 | −68.032 | 1.00 | 77.10 | | N |
| ANISOU | 459 | N | ASP | A | 210 | 6319 | 7680 | 15296 | 451 | 2202 | 1397 | N |
| ATOM | 460 | CA | ASP | A | 210 | −2.050 | −87.226 | −66.834 | 1.00 | 85.13 | | C |
| ANISOU | 460 | CA | ASP | A | 210 | 7534 | 8542 | 16270 | 429 | 2646 | 1652 | C |
| ATOM | 461 | CB | ASP | A | 210 | −3.451 | −87.651 | −66.364 | 1.00 | 95.97 | | C |
| ANISOU | 461 | CB | ASP | A | 210 | 8669 | 9456 | 18340 | 333 | 2782 | 1469 | C |
| ATOM | 462 | CG | ASP | A | 210 | −3.567 | −87.738 | −64.853 | 1.00 | 99.87 | | C |
| ANISOU | 462 | CG | ASP | A | 210 | 9401 | 9895 | 18649 | 369 | 3146 | 1710 | C |
| ATOM | 463 | OD2 | ASP | A | 210 | −3.522 | −88.871 | −64.318 | 1.00 | 102.43 | | O |
| ANISOU | 463 | OD2 | ASP | A | 210 | 9807 | 10003 | 19107 | 409 | 3427 | 1813 | O |
| ATOM | 464 | OD1 | ASP | A | 210 | −3.703 | −86.678 | −64.203 | 1.00 | 84.79 | | O |
| ANISOU | 464 | OD1 | ASP | A | 210 | 7590 | 8161 | 16466 | 379 | 3121 | 1772 | O |
| ATOM | 465 | C | ASP | A | 210 | −1.241 | −88.438 | −67.193 | 1.00 | 86.00 | | C |
| ANISOU | 465 | C | ASP | A | 210 | 7701 | 8602 | 16374 | 475 | 2746 | 1727 | C |
| ATOM | 466 | O | ASP | A | 210 | −0.401 | −88.882 | −66.447 | 1.00 | 82.91 | | O |
| ANISOU | 466 | O | ASP | A | 210 | 7620 | 8312 | 15570 | 551 | 3002 | 2000 | O |
| ATOM | 467 | N | ASN | A | 211 | −1.562 | −88.957 | −68.361 | 1.00 | 87.26 | | N |
| ANISOU | 467 | N | ASN | A | 211 | 7565 | 8604 | 16985 | 463 | 2467 | 1429 | N |
| ATOM | 468 | CA | ASN | A | 211 | −1.023 | −90.153 | −68.900 | 1.00 | 73.27 | | C |
| ANISOU | 468 | CA | ASN | A | 211 | 5763 | 6706 | 15370 | 502 | 2516 | 1416 | C |
| ATOM | 469 | CB | ASN | A | 211 | −2.201 | −91.082 | −69.108 | 1.00 | 83.13 | | C |
| ANISOU | 469 | CB | ASN | A | 211 | 6699 | 7425 | 17461 | 390 | 2541 | 1133 | C |
| ATOM | 470 | CG | ASN | A | 211 | −1.810 | −92.473 | −69.497 | 1.00 | 106.96 | | C |
| ANISOU | 470 | CG | ASN | A | 211 | 9721 | 10237 | 20681 | 408 | 2735 | 1185 | C |
| ATOM | 471 | OD1 | ASN | A | 211 | −1.291 | −92.708 | −70.580 | 1.00 | 110.81 | | O |
| ANISOU | 471 | OD1 | ASN | A | 211 | 10025 | 10618 | 21460 | 446 | 2429 | 911 | O |
| ATOM | 472 | ND2 | ASN | A | 211 | −2.125 | −93.420 | −68.646 | 1.00 | 119.38 | | N |
| ANISOU | 472 | ND2 | ASN | A | 211 | 11544 | 11741 | 22072 | 427 | 3195 | 1509 | N |
| ATOM | 473 | C | ASN | A | 211 | −0.435 | −89.819 | −70.238 | 1.00 | 73.45 | | C |
| ANISOU | 473 | C | ASN | A | 211 | 5743 | 6969 | 15196 | 645 | 2056 | 1231 | C |
| ATOM | 474 | O | ASN | A | 211 | −1.135 | −89.445 | −71.143 | 1.00 | 85.46 | | O |
| ANISOU | 474 | O | ASN | A | 211 | 7141 | 8397 | 16934 | 647 | 1566 | 860 | O |
| ATOM | 475 | N | LEU | A | 212 | 0.854 | −90.013 | −70.380 | 1.00 | 67.52 | | N |
| ANISOU | 475 | N | LEU | A | 212 | 5355 | 6528 | 13770 | 734 | 2081 | 1443 | N |
| ATOM | 476 | CA | LEU | A | 212 | 1.511 | −89.867 | −71.655 | 1.00 | 68.19 | | C |
| ANISOU | 476 | CA | LEU | A | 212 | 5692 | 6818 | 13400 | 815 | 1542 | 1226 | C |
| ATOM | 477 | CB | LEU | A | 212 | 3.009 | −89.882 | −71.446 | 1.00 | 63.81 | | C |

TABLE 7-continued

DMXAA-hSTING$^{G230I}$ complex

| | | | | | | | | | | | |
|---|---|---|---|---|---|---|---|---|---|---|---|
| ANISOU | 477 | CB | LEU | A | 212 | 5547 | 6700 | 11999 | 900 | 1668 | 1525 C |
| ATOM | 478 | CG | LEU | A | 212 | 3.920 | −89.921 | −72.654 | 1.00 | 67.58 | C |
| ANISOU | 478 | CG | LEU | A | 212 | 6323 | 7406 | 11950 | 982 | 1223 | 1355 C |
| ATOM | 479 | CD1 | LEU | A | 212 | 3.256 | −89.250 | −73.828 | 1.00 | 75.08 | C |
| ANISOU | 479 | CD1 | LEU | A | 212 | 7292 | 8342 | 12894 | 980 | 629 | 983 C |
| ATOM | 480 | CD2 | LEU | A | 212 | 5.229 | −89.251 | −72.287 | 1.00 | 47.46 | C |
| ANISOU | 480 | CD2 | LEU | A | 212 | 4146 | 5360 | 8525 | 1039 | 1382 | 1655 C |
| ATOM | 481 | C | LEU | A | 212 | 1.114 | −90.933 | −72.641 | 1.00 | 79.56 | C |
| ANISOU | 481 | C | LEU | A | 212 | 6953 | 7887 | 15389 | 819 | 1309 | 908 C |
| ATOM | 482 | O | LEU | A | 212 | 0.964 | −90.683 | −73.807 | 1.00 | 80.85 | O |
| ANISOU | 482 | O | LEU | A | 212 | 7131 | 8009 | 15580 | 855 | 767 | 554 O |
| ATOM | 483 | N | SER | A | 213 | 0.991 | −92.149 | −72.159 | 1.00 | 86.18 | N |
| ANISOU | 483 | N | SER | A | 213 | 7639 | 8443 | 16661 | 786 | 1725 | 1033 N |
| ATOM | 484 | CA | SER | A | 213 | 0.613 | −93.255 | −73.004 | 1.00 | 96.17 | C |
| ANISOU | 484 | CA | SER | A | 213 | 8738 | 9341 | 18461 | 780 | 1578 | 766 C |
| ATOM | 485 | CB | SER | A | 213 | 0.726 | −94.540 | −72.224 | 1.00 | 97.60 | C |
| ANISOU | 485 | CB | SER | A | 213 | 8778 | 9212 | 19093 | 727 | 2166 | 983 C |
| ATOM | 486 | OG | SER | A | 213 | 0.238 | −95.598 | −73.001 | 1.00 | 96.24 | O |
| ANISOU | 486 | OG | SER | A | 213 | 8738 | 9239 | 18591 | 728 | 2676 | 1408 O |
| ATOM | 487 | C | SER | A | 213 | −0.785 | −93.166 | −73.593 | 1.00 | 105.94 | C |
| ANISOU | 487 | C | SER | A | 213 | 9639 | 10262 | 20350 | 727 | 1151 | 299 C |
| ATOM | 488 | O | SER | A | 213 | −0.983 | −93.458 | −74.760 | 1.00 | 111.89 | O |
| ANISOU | 488 | O | SER | A | 213 | 10365 | 10864 | 21283 | 768 | 739 | −24 O |
| ATOM | 489 | N | MET | A | 214 | −1.748 | −92.797 | −72.759 | 1.00 | 103.52 | N |
| ANISOU | 489 | N | MET | A | 214 | 9076 | 9859 | 20399 | 646 | 1236 | 247 N |
| ATOM | 490 | CA | MET | A | 214 | −3.137 | −92.766 | −73.175 | 1.00 | 107.12 | C |
| ANISOU | 490 | CA | MET | A | 214 | 9241 | 10089 | 21369 | 628 | 764 | −218 C |
| ATOM | 491 | CB | MET | A | 214 | −4.041 | −92.384 | −72.002 | 1.00 | 112.52 | C |
| ANISOU | 491 | CB | MET | A | 214 | 9590 | 10354 | 22808 | 416 | 1024 | −361 C |
| ATOM | 492 | CG | MET | A | 214 | −5.212 | −93.329 | −71.788 | 1.00 | 119.93 | C |
| ANISOU | 492 | CG | MET | A | 214 | 10266 | 10958 | 24342 | 370 | 549 | −897 C |
| ATOM | 493 | SD | MET | A | 214 | −6.666 | −92.865 | −72.748 | 1.00 | 179.49 | S |
| ANISOU | 493 | SD | MET | A | 214 | 17963 | 18728 | 31506 | 561 | −300 | −1277 S |
| ATOM | 494 | CE | MET | A | 214 | −6.734 | −94.209 | −73.930 | 1.00 | 80.71 | C |
| ANISOU | 494 | CE | MET | A | 214 | 5281 | 5856 | 19531 | 542 | −695 | −1742 C |
| ATOM | 495 | C | MET | A | 214 | −3.290 | −91.764 | −74.303 | 1.00 | 112.71 | C |
| ANISOU | 495 | C | MET | A | 214 | 10105 | 11106 | 21612 | 686 | 399 | −283 C |
| ATOM | 496 | O | MET | A | 214 | −4.050 | −91.981 | −75.246 | 1.00 | 115.31 | O |
| ANISOU | 496 | O | MET | A | 214 | 10493 | 11641 | 21677 | 655 | 682 | −10 O |
| ATOM | 497 | N | ALA | A | 215 | −2.567 | −90.656 | −74.192 | 1.00 | 117.16 | N |
| ANISOU | 497 | N | ALA | A | 215 | 10732 | 11662 | 22120 | 774 | −236 | −667 N |
| ATOM | 498 | CA | ALA | A | 215 | −2.729 | −89.573 | −75.116 | 1.00 | 118.83 | C |
| ANISOU | 498 | CA | ALA | A | 215 | 11145 | 12109 | 21896 | 861 | −733 | −836 C |
| ATOM | 499 | CB | ALA | A | 215 | −1.915 | −88.381 | −74.673 | 1.00 | 114.08 | C |
| ANISOU | 499 | CB | ALA | A | 215 | 10838 | 11922 | 20585 | 857 | −497 | −454 C |
| ATOM | 500 | C | ALA | A | 215 | −2.407 | −89.940 | −76.555 | 1.00 | 116.17 | C |
| ANISOU | 500 | C | ALA | A | 215 | 11128 | 11872 | 21141 | 976 | −1228 | −1030 C |
| ATOM | 501 | O | ALA | A | 215 | −3.025 | −89.413 | −77.456 | 1.00 | 116.67 | O |
| ANISOU | 501 | O | ALA | A | 215 | 11388 | 12041 | 20902 | 1073 | −1759 | −1279 O |
| ATOM | 502 | N | ASP | A | 216 | −1.403 | −90.778 | −76.793 | 1.00 | 102.02 | N |
| ANISOU | 502 | N | ASP | A | 216 | 9410 | 10043 | 19309 | 971 | −1032 | −903 N |
| ATOM | 503 | CA | ASP | A | 216 | −0.988 | −91.053 | −78.164 | 1.00 | 81.17 | C |
| ANISOU | 503 | CA | ASP | A | 216 | 6993 | 7411 | 16438 | 1070 | −1460 | −1122 C |
| ATOM | 504 | CB | ASP | A | 216 | 0.430 | −90.546 | −78.449 | 1.00 | 68.17 | C |
| ANISOU | 504 | CB | ASP | A | 216 | 5853 | 6219 | 13831 | 1127 | −1437 | −842 C |
| ATOM | 505 | CG | ASP | A | 216 | 0.872 | −90.780 | −79.881 | 1.00 | 75.45 | C |
| ANISOU | 505 | CG | ASP | A | 216 | 7062 | 7194 | 14411 | 1238 | −1976 | −1116 C |
| ATOM | 506 | OD1 | ASP | A | 216 | 0.801 | −91.903 | −80.361 | 1.00 | 87.85 | O |
| ANISOU | 506 | OD1 | ASP | A | 216 | 8516 | 8516 | 16347 | 1264 | −2073 | −1291 O |
| ATOM | 507 | OD2 | ASP | A | 216 | 1.311 | −89.857 | −80.550 | 1.00 | 70.57 | O |
| ANISOU | 507 | OD2 | ASP | A | 216 | 6802 | 6860 | 13153 | 1298 | −2290 | −1156 O |
| ATOM | 508 | C | ASP | A | 216 | −1.106 | −92.517 | −78.408 | 1.00 | 85.47 | C |
| ANISOU | 508 | C | ASP | A | 216 | 7279 | 7605 | 17592 | 1028 | −1259 | −1186 C |
| ATOM | 509 | O | ASP | A | 216 | −0.919 | −93.307 | −77.500 | 1.00 | 94.35 | O |
| ANISOU | 509 | O | ASP | A | 216 | 8316 | 8685 | 18848 | 950 | −696 | −869 O |
| ATOM | 510 | N | PRO | A | 217 | −1.499 | −92.866 | −79.704 | 1.00 | 83.09 | N |
| ANISOU | 510 | N | PRO | A | 217 | 6865 | 7037 | 17668 | 1086 | −1712 | −1600 N |
| ATOM | 511 | CA | PRO | A | 217 | −1.630 | −94.312 | −79.897 | 1.00 | 81.29 | C |
| ANISOU | 511 | CA | PRO | A | 217 | 6412 | 6473 | 18003 | 1042 | −1521 | −1664 C |
| ATOM | 512 | CB | PRO | A | 217 | −2.714 | −94.438 | −80.978 | 1.00 | 89.92 | C |
| ANISOU | 512 | CB | PRO | A | 217 | 7250 | 7246 | 19670 | 1029 | −2027 | −2197 C |
| ATOM | 513 | CG | PRO | A | 217 | −2.869 | −93.094 | −81.605 | 1.00 | 92.23 | C |
| ANISOU | 513 | CG | PRO | A | 217 | 7702 | 7726 | 19616 | 1114 | −2532 | −2410 C |
| ATOM | 514 | CD | PRO | A | 217 | −1.785 | −92.233 | −81.080 | 1.00 | 85.60 | C |
| ANISOU | 514 | CD | PRO | A | 217 | 7242 | 7313 | 17967 | 1197 | −2395 | −2034 C |
| ATOM | 515 | C | PRO | A | 217 | −0.343 | −94.984 | −80.347 | 1.00 | 72.50 | C |
| ANISOU | 515 | C | PRO | A | 217 | 5664 | 5552 | 16332 | 1119 | −1524 | −1504 C |
| ATOM | 516 | O | PRO | A | 217 | −0.236 | −96.180 | −80.307 | 1.00 | 74.21 | O |

TABLE 7-continued

| DMXAA-hSTING$^{G230I}$ complex | | | | | | | | | | | |
|---|---|---|---|---|---|---|---|---|---|---|---|
| ANISOU | 516 | O | PRO | A | 217 | 5775 | 5545 | 16878 | 1095 | −1312 | −1480 O |
| ATOM | 517 | N | ASN | A | 218 | 0.628 | −94.196 | −80.761 | 1.00 | 84.13 | N |
| ANISOU | 517 | N | ASN | A | 218 | 7567 | 7436 | 16963 | 1208 | −1755 | −1405 N |
| ATOM | 518 | CA | ASN | A | 218 | 1.910 | −94.711 | −81.164 | 1.00 | 80.88 | C |
| ANISOU | 518 | CA | ASN | A | 218 | 7510 | 7257 | 15966 | 1281 | −1748 | −1256 C |
| ATOM | 519 | CB | ASN | A | 218 | 2.374 | −94.042 | −82.429 | 1.00 | 65.84 | C |
| ANISOU | 519 | CB | ASN | A | 218 | 5956 | 5557 | 13503 | 1396 | −2337 | −1498 C |
| ATOM | 520 | CG | ASN | A | 218 | 1.551 | −94.437 | −83.607 | 1.00 | 69.10 | C |
| ANISOU | 520 | CG | ASN | A | 218 | 6205 | 5617 | 14433 | 1460 | −2869 | −1984 C |
| ATOM | 521 | OD1 | ASN | A | 218 | 1.218 | −95.581 | −83.755 | 1.00 | 71.77 | O |
| ANISOU | 521 | OD1 | ASN | A | 218 | 6308 | 5633 | 15328 | 1451 | −2833 | −2121 O |
| ATOM | 522 | ND2 | ASN | A | 218 | 1.216 | −93.493 | −84.444 | 1.00 | 69.06 | N |
| ANISOU | 522 | ND2 | ASN | A | 218 | 6335 | 5661 | 14242 | 1536 | −3375 | −2258 N |
| ATOM | 523 | C | ASN | A | 218 | 2.938 | −94.558 | −80.076 | 1.00 | 76.59 | C |
| ANISOU | 523 | C | ASN | A | 218 | 7193 | 7078 | 14829 | 1259 | −1240 | −771 C |
| ATOM | 524 | O | ASN | A | 218 | 4.107 | −94.714 | −80.319 | 1.00 | 72.42 | O |
| ANISOU | 524 | O | ASN | A | 218 | 6993 | 6838 | 13685 | 1326 | −1238 | −633 O |
| ATOM | 525 | N | ILE | A | 219 | 2.496 | −94.208 | −78.881 | 1.00 | 66.32 | N |
| ANISOU | 525 | N | ILE | A | 219 | 6081 | 9555 | 9561 | −94 | 952 | −404 N |
| ATOM | 526 | CA | ILE | A | 219 | 3.393 | −94.166 | −77.738 | 1.00 | 65.72 | C |
| ANISOU | 526 | CA | ILE | A | 219 | 6212 | 9181 | 9579 | −72 | 1048 | −310 C |
| ATOM | 527 | CB | ILE | A | 219 | 3.620 | −92.745 | −77.206 | 1.00 | 64.88 | C |
| ANISOU | 527 | CB | ILE | A | 219 | 6116 | 9124 | 9411 | 274 | 1156 | −241 C |
| ATOM | 528 | CG1 | ILE | A | 219 | 4.273 | −91.873 | −78.271 | 1.00 | 59.25 | C |
| ANISOU | 528 | CG1 | ILE | A | 219 | 5506 | 8318 | 8690 | 570 | 1152 | −300 C |
| ATOM | 529 | CD1 | ILE | A | 219 | 4.549 | −90.458 | −77.806 | 1.00 | 57.36 | C |
| ANISOU | 529 | CD1 | ILE | A | 219 | 5316 | 8071 | 8409 | 892 | 1271 | −246 C |
| ATOM | 530 | CG2 | ILE | A | 219 | 4.496 | −92.778 | −75.962 | 1.00 | 57.46 | C |
| ANISOU | 530 | CG2 | ILE | A | 219 | 5381 | 7903 | 8550 | 264 | 1212 | −167 C |
| ATOM | 531 | C | ILE | A | 219 | 2.808 | −95.035 | −76.641 | 1.00 | 58.39 | C |
| ANISOU | 531 | C | ILE | A | 219 | 5219 | 8293 | 8675 | −380 | 1094 | −229 C |
| ATOM | 532 | O | ILE | A | 219 | 1.721 | −94.769 | −76.135 | 1.00 | 64.43 | O |
| ANISOU | 532 | O | ILE | A | 219 | 5734 | 9391 | 9357 | −415 | 1164 | −170 O |
| ATOM | 533 | N | ARG | A | 220 | 3.532 | −96.084 | −76.286 | 1.00 | 54.92 | N |
| ANISOU | 533 | N | ARG | A | 220 | 5009 | 7508 | 8349 | −588 | 1075 | −216 N |
| ATOM | 534 | CA | ARG | A | 220 | 3.020 | −97.081 | −75.372 | 1.00 | 60.48 | C |
| ANISOU | 534 | CA | ARG | A | 220 | 5708 | 8192 | 9078 | −908 | 1133 | −133 C |
| ATOM | 535 | CB | ARG | A | 220 | 2.793 | −98.388 | −76.118 | 1.00 | 65.47 | C |
| ANISOU | 535 | CB | ARG | A | 220 | 6374 | 8710 | 9791 | −1252 | 1048 | −229 C |
| ATOM | 536 | CG | ARG | A | 220 | 2.451 | −99.550 | −75.230 | 1.00 | 81.76 | C |
| ANISOU | 536 | CG | ARG | A | 220 | 8513 | 10642 | 11912 | −1608 | 1130 | −137 C |
| ATOM | 537 | CD | ARG | A | 220 | 2.623 | −100.853 | −75.977 | 1.00 | 92.84 | C |
| ANISOU | 537 | CD | ARG | A | 220 | 10080 | 11777 | 13417 | −1910 | 1047 | −246 C |
| ATOM | 538 | NE | ARG | A | 220 | 1.405 | −101.301 | −76.631 | 1.00 | 104.97 | N |
| ANISOU | 538 | NE | ARG | A | 220 | 11345 | 13587 | 14950 | −2224 | 994 | −357 N |
| ATOM | 539 | CZ | ARG | A | 220 | 0.412 | −101.905 | −75.990 | 1.00 | 108.81 | C |
| ANISOU | 539 | CZ | ARG | A | 220 | 11665 | 14209 | 15470 | −2570 | 1095 | −290 C |
| ATOM | 540 | NH1 | ARG | A | 220 | −0.673 | −102.298 | −76.645 | 1.00 | 108.87 | N |
| ANISOU | 540 | NH1 | ARG | A | 220 | 11384 | 14481 | 15499 | −2875 | 1022 | −416 N |
| ATOM | 541 | NH2 | ARG | A | 220 | 0.508 | −102.109 | −74.683 | 1.00 | 111.49 | N |
| ANISOU | 541 | NH2 | ARG | A | 220 | 12124 | 14423 | 15815 | −2611 | 1271 | −98 N |
| ATOM | 542 | C | ARG | A | 220 | 3.998 | −97.283 | −74.227 | 1.00 | 64.38 | C |
| ANISOU | 542 | C | ARG | A | 220 | 6483 | 8363 | 9614 | −860 | 1184 | −22 C |
| ATOM | 543 | O | ARG | A | 220 | 5.192 | −97.494 | −74.448 | 1.00 | 69.74 | O |
| ANISOU | 543 | O | ARG | A | 220 | 7400 | 8711 | 10387 | −767 | 1117 | −53 O |
| ATOM | 544 | N | PHE | A | 221 | 3.494 | −97.200 | −73.002 | 1.00 | 68.57 | N |
| ANISOU | 544 | N | PHE | A | 221 | 6979 | 9009 | 10066 | −900 | 1304 | 109 N |
| ATOM | 545 | CA | PHE | A | 221 | 4.340 | −97.367 | −71.836 | 1.00 | 61.90 | C |
| ANISOU | 545 | CA | PHE | A | 221 | 6408 | 7898 | 9214 | −834 | 1333 | 218 C |
| ATOM | 546 | CB | PHE | A | 221 | 3.572 | −97.065 | −70.555 | 1.00 | 51.11 | C |
| ANISOU | 546 | CB | PHE | A | 221 | 4981 | 6740 | 7699 | −834 | 1490 | 356 C |
| ATOM | 547 | CG | PHE | A | 221 | 4.291 | −97.479 | −69.311 | 1.00 | 53.73 | C |
| ANISOU | 547 | CG | PHE | A | 221 | 5621 | 6812 | 7982 | −811 | 1512 | 479 C |
| ATOM | 548 | CD1 | PHE | A | 221 | 5.260 | −96.656 | −68.751 | 1.00 | 50.85 | C |
| ANISOU | 548 | CD1 | PHE | A | 221 | 5425 | 6327 | 7567 | −516 | 1440 | 471 C |
| ATOM | 549 | CE1 | PHE | A | 221 | 5.933 | −97.033 | −67.600 | 1.00 | 47.34 | C |
| ANISOU | 549 | CE1 | PHE | A | 221 | 5264 | 5670 | 7052 | −473 | 1420 | 575 C |
| ATOM | 550 | CZ | PHE | A | 221 | 5.637 | −98.259 | −66.996 | 1.00 | 49.71 | C |
| ANISOU | 550 | CZ | PHE | A | 221 | 5714 | 5851 | 7323 | −709 | 1505 | 716 C |
| ATOM | 551 | CE2 | PHE | A | 221 | 4.670 | −99.094 | −67.552 | 1.00 | 51.54 | C |
| ANISOU | 551 | CE2 | PHE | A | 221 | 5792 | 6166 | 7625 | −1029 | 1612 | 732 C |
| ATOM | 552 | CD2 | PHE | A | 221 | 4.007 | −98.700 | −68.701 | 1.00 | 60.21 | C |
| ANISOU | 552 | CD2 | PHE | A | 221 | 6575 | 7499 | 8801 | −1087 | 1599 | 602 C |
| ATOM | 553 | C | PHE | A | 221 | 4.877 | −98.786 | −71.799 | 1.00 | 66.05 | C |
| ANISOU | 553 | C | PHE | A | 221 | 7175 | 8073 | 9846 | −1074 | 1294 | 245 C |
| ATOM | 554 | O | PHE | A | 221 | 4.125 | −99.755 | −71.951 | 1.00 | 69.47 | O |
| ANISOU | 554 | O | PHE | A | 221 | 7557 | 8526 | 10310 | −1395 | 1343 | 257 O |
| ATOM | 555 | N | LEU | A | 222 | 6.182 | −98.915 | −71.604 | 1.00 | 57.16 | N |

TABLE 7-continued

DMXAA-hSTING$^{G230I}$ complex

| | | | | | | | | | | | | |
|---|---|---|---|---|---|---|---|---|---|---|---|---|
| ANISOU | 555 | N | LEU | A | 222 | 6308 | 6620 | 8788 | −921 | 1209 | 252 | N |
| ATOM | 556 | CA | LEU | A | 222 | 6.797 | −100.226 | −71.524 | 1.00 | 58.48 | | C |
| ANISOU | 556 | CA | LEU | A | 222 | 6739 | 6428 | 9051 | −1080 | 1177 | 293 | C |
| ATOM | 557 | CB | LEU | A | 222 | 8.097 | −100.261 | −72.318 | 1.00 | 68.01 | | C |
| ANISOU | 557 | CB | LEU | A | 222 | 8082 | 7360 | 10400 | −902 | 1052 | 196 | C |
| ATOM | 558 | CG | LEU | A | 222 | 8.011 | −100.741 | −73.758 | 1.00 | 67.43 | | C |
| ANISOU | 558 | CG | LEU | A | 222 | 7975 | 7227 | 10420 | −1017 | 1013 | 50 | C |
| ATOM | 559 | CD2 | LEU | A | 222 | 7.111 | −101.961 | −73.861 | 1.00 | 61.70 | | C |
| ANISOU | 559 | CD2 | LEU | A | 222 | 7286 | 6462 | 9693 | −1394 | 1066 | 57 | C |
| ATOM | 560 | CD1 | LEU | A | 222 | 9.409 | −101.051 | −74.244 | 1.00 | 60.29 | | C |
| ANISOU | 560 | CD1 | LEU | A | 222 | 7274 | 5978 | 9655 | −845 | 938 | 4 | C |
| ATOM | 561 | C | LEU | A | 222 | 7.092 | −100.595 | −70.088 | 1.00 | 56.21 | | C |
| ANISOU | 561 | C | LEU | A | 222 | 6675 | 6000 | 8680 | −1060 | 1226 | 466 | C |
| ATOM | 562 | O | LEU | A | 222 | 6.644 | −101.627 | −69.587 | 1.00 | 54.92 | | O |
| ANISOU | 562 | O | LEU | A | 222 | 6641 | 5730 | 8495 | −1301 | 1321 | 576 | O |
| ATOM | 563 | N | ASP | A | 223 | 7.851 | −99.740 | −69.422 | 1.00 | 55.33 | | N |
| ANISOU | 563 | N | ASP | A | 223 | 6627 | 5882 | 8514 | −772 | 1160 | 487 | N |
| ATOM | 564 | CA | ASP | A | 223 | 8.398 | −100.110 | −68.138 | 1.00 | 55.70 | | C |
| ANISOU | 564 | CA | ASP | A | 223 | 6935 | 5759 | 8469 | −695 | 1147 | 631 | C |
| ATOM | 565 | CB | ASP | A | 223 | 9.437 | −101.219 | −68.336 | 1.00 | 63.37 | | C |
| ANISOU | 565 | CB | ASP | A | 223 | 8159 | 6343 | 9575 | −702 | 1050 | 656 | C |
| ATOM | 566 | CG | ASP | A | 223 | 9.612 | −102.085 | −67.108 | 1.00 | 79.65 | | C |
| ANISOU | 566 | CG | ASP | A | 223 | 10524 | 8218 | 11521 | −722 | 1083 | 848 | C |
| ATOM | 567 | OD1 | ASP | A | 223 | 8.656 | −102.172 | −66.305 | 1.00 | 92.81 | | O |
| ANISOU | 567 | OD1 | ASP | A | 223 | 12208 | 10034 | 13023 | −854 | 1239 | 970 | O |
| ATOM | 568 | OD2 | ASP | A | 223 | 10.703 | −102.673 | −66.952 | 1.00 | 79.79 | | O |
| ANISOU | 568 | OD2 | ASP | A | 223 | 10763 | 7945 | 11608 | −587 | 964 | 888 | O |
| ATOM | 569 | C | ASP | A | 223 | 9.042 | −98.920 | −67.452 | 1.00 | 58.61 | | C |
| ANISOU | 569 | C | ASP | A | 223 | 7311 | 6205 | 8753 | −391 | 1055 | 606 | C |
| ATOM | 570 | O | ASP | A | 223 | 9.082 | −97.813 | −67.990 | 1.00 | 57.58 | | O |
| ANISOU | 570 | O | ASP | A | 223 | 6994 | 6227 | 8655 | −251 | 1026 | 483 | O |
| ATOM | 571 | N | LYS | A | 224 | 9.553 | −99.165 | −66.255 | 1.00 | 56.49 | | N |
| ANISOU | 571 | N | LYS | A | 224 | 7283 | 5817 | 8366 | −289 | 1006 | 721 | N |
| ATOM | 572 | CA | LYS | A | 224 | 10.285 | −98.164 | −65.513 | 1.00 | 57.81 | | C |
| ANISOU | 572 | CA | LYS | A | 224 | 7501 | 6018 | 8447 | −20 | 876 | 680 | C |
| ATOM | 573 | CB | LYS | A | 224 | 9.728 | −98.051 | −64.105 | 1.00 | 52.80 | | C |
| ANISOU | 573 | CB | LYS | A | 224 | 7028 | 5506 | 7528 | 17 | 964 | 813 | C |
| ATOM | 574 | CG | LYS | A | 224 | 8.361 | −97.472 | −64.055 | 1.00 | 60.84 | | C |
| ANISOU | 574 | CG | LYS | A | 224 | 7864 | 6837 | 8417 | −68 | 1183 | 828 | C |
| ATOM | 575 | CD | LYS | A | 224 | 8.252 | −96.576 | −62.852 | 1.00 | 72.80 | | C |
| ANISOU | 575 | CD | LYS | A | 224 | 9494 | 8494 | 9670 | 134 | 1203 | 850 | C |
| ATOM | 576 | CE | LYS | A | 224 | 6.871 | −96.013 | −62.766 | 1.00 | 80.98 | | C |
| ANISOU | 576 | CE | LYS | A | 224 | 10342 | 9852 | 10575 | 83 | 1452 | 880 | C |
| ATOM | 577 | NZ | LYS | A | 224 | 5.905 | −96.904 | −63.482 | 1.00 | 86.45 | | N |
| ANISOU | 577 | NZ | LYS | A | 224 | 10843 | 10620 | 11384 | −217 | 1618 | 949 | N |
| ATOM | 578 | C | LYS | A | 224 | 11.758 | −98.513 | −65.435 | 1.00 | 62.08 | | C |
| ANISOU | 578 | C | LYS | A | 224 | 8190 | 6281 | 9115 | 136 | 658 | 659 | C |
| ATOM | 579 | O | LYS | A | 224 | 12.138 | −99.685 | −65.452 | 1.00 | 64.62 | | O |
| ANISOU | 579 | O | LYS | A | 224 | 8681 | 6373 | 9501 | 73 | 633 | 750 | O |
| ATOM | 580 | N | LEU | A | 225 | 12.586 | −97.481 | −65.349 | 1.00 | 61.28 | | N |
| ANISOU | 580 | N | LEU | A | 225 | 8020 | 6200 | 9064 | 343 | 506 | 537 | N |
| ATOM | 581 | CA | LEU | A | 225 | 14.001 | −97.653 | −65.072 | 1.00 | 60.96 | | C |
| ANISOU | 581 | CA | LEU | A | 225 | 8073 | 5954 | 9135 | 514 | 276 | 512 | C |
| ATOM | 582 | CB | LEU | A | 225 | 14.741 | −96.349 | −65.340 | 1.00 | 63.08 | | C |
| ANISOU | 582 | CB | LEU | A | 225 | 8165 | 6271 | 9529 | 664 | 156 | 332 | C |
| ATOM | 583 | CG | LEU | A | 225 | 15.092 | −96.002 | −66.780 | 1.00 | 63.22 | | C |
| ANISOU | 583 | CG | LEU | A | 225 | 7960 | 6235 | 9824 | 646 | 202 | 206 | C |
| ATOM | 584 | CD1 | LEU | A | 225 | 15.547 | −94.564 | −66.830 | 1.00 | 62.08 | | C |
| ANISOU | 584 | CD1 | LEU | A | 225 | 7679 | 6160 | 9749 | 766 | 146 | 51 | C |
| ATOM | 585 | CD2 | LEU | A | 225 | 16.190 | −96.920 | −67.288 | 1.00 | 58.08 | | C |
| ANISOU | 585 | CD2 | LEU | A | 225 | 7327 | 5338 | 9403 | 688 | 99 | 219 | C |
| ATOM | 586 | C | LEU | A | 225 | 14.151 | −98.022 | −63.605 | 1.00 | 74.14 | | C |
| ANISOU | 586 | C | LEU | A | 225 | 10011 | 7601 | 10559 | 610 | 182 | 645 | C |
| ATOM | 587 | O | LEU | A | 225 | 13.228 | −97.771 | −62.813 | 1.00 | 81.92 | | O |
| ANISOU | 587 | O | LEU | A | 225 | 11087 | 8754 | 11286 | 575 | 306 | 718 | O |
| ATOM | 588 | N | PRO | A | 226 | 15.306 | −98.602 | −63.227 | 1.00 | 72.48 | | N |
| ANISOU | 588 | N | PRO | A | 226 | 9932 | 7198 | 10411 | 757 | −29 | 682 | N |
| ATOM | 589 | CA | PRO | A | 226 | 15.532 | −98.814 | −61.798 | 1.00 | 72.91 | | C |
| ANISOU | 589 | CA | PRO | A | 226 | 10256 | 7253 | 10193 | 901 | −159 | 796 | C |
| ATOM | 590 | CB | PRO | A | 226 | 16.926 | −99.447 | −61.745 | 1.00 | 64.66 | | C |
| ANISOU | 590 | CB | PRO | A | 226 | 9267 | 5999 | 9301 | 1083 | −415 | 811 | C |
| ATOM | 591 | CG | PRO | A | 226 | 17.583 | −99.030 | −63.029 | 1.00 | 61.65 | | C |
| ANISOU | 591 | CG | PRO | A | 226 | 8577 | 5565 | 9282 | 1069 | −446 | 640 | C |
| ATOM | 592 | CD | PRO | A | 226 | 16.464 | −99.019 | −64.032 | 1.00 | 62.04 | | C |
| ANISOU | 592 | CD | PRO | A | 226 | 8513 | 5672 | 9386 | 835 | −162 | 623 | C |
| ATOM | 593 | C | PRO | A | 226 | 15.533 | −97.483 | −61.051 | 1.00 | 82.38 | | C |
| ANISOU | 593 | C | PRO | A | 226 | 11427 | 8651 | 11222 | 1020 | −260 | 671 | C |
| ATOM | 594 | O | PRO | A | 226 | 15.944 | −96.452 | −61.596 | 1.00 | 80.06 | | O |

TABLE 7-continued

DMXAA-hSTING$^{G230I}$ complex

| | | | | | | | | | | | |
|---|---|---|---|---|---|---|---|---|---|---|---|
| ANISOU | 594 | O | PRO | A | 226 | 10906 | 8411 | 11102 | 1052 | −333 | 479 | O |
| ATOM | 595 | N | GLN | A | 227 | 15.063 | −97.511 | −59.811 | 1.00 | 82.90 | | N |
| ANISOU | 595 | N | GLN | A | 227 | 11751 | 8807 | 10941 | 1084 | −243 | 779 | N |
| ATOM | 596 | CA | GLN | A | 227 | 14.912 | −96.295 | −59.037 | 1.00 | 73.01 | | C |
| ANISOU | 596 | CA | GLN | A | 227 | 10533 | 7735 | 9474 | 1194 | −305 | 660 | C |
| ATOM | 597 | CB | GLN | A | 227 | 14.103 | −96.565 | −57.774 | 1.00 | 76.63 | | C |
| ANISOU | 597 | CB | GLN | A | 227 | 11313 | 8290 | 9514 | 1237 | −178 | 830 | C |
| ATOM | 598 | CG | GLN | A | 227 | 12.631 | −96.757 | −58.045 | 1.00 | 78.01 | | C |
| ANISOU | 598 | CG | GLN | A | 227 | 11437 | 8589 | 9614 | 1038 | 208 | 950 | C |
| ATOM | 599 | CD | GLN | A | 227 | 11.925 | −97.465 | −56.914 | 1.00 | 85.04 | | C |
| ANISOU | 599 | CD | GLN | A | 227 | 12655 | 9505 | 10151 | 1044 | 383 | 1186 | C |
| ATOM | 600 | OE1 | GLN | A | 227 | 12.523 | −98.279 | −56.208 | 1.00 | 90.72 | | O |
| ANISOU | 600 | OE1 | GLN | A | 227 | 13660 | 10074 | 10737 | 1154 | 248 | 1321 | O |
| ATOM | 601 | NE2 | GLN | A | 227 | 10.647 | −97.155 | −56.729 | 1.00 | 83.42 | | N |
| ANISOU | 601 | NE2 | GLN | A | 227 | 12412 | 9496 | 9787 | 943 | 700 | 1249 | N |
| ATOM | 602 | C | GLN | A | 227 | 16.246 | −95.652 | −58.695 | 1.00 | 70.38 | | C |
| ANISOU | 602 | C | GLN | A | 227 | 10167 | 7359 | 9217 | 1379 | −668 | 485 | C |
| ATOM | 603 | O | GLN | A | 227 | 17.304 | −96.285 | −58.747 | 1.00 | 73.10 | | O |
| ANISOU | 603 | O | GLN | A | 227 | 10505 | 7557 | 9711 | 1469 | −894 | 503 | O |
| ATOM | 604 | N | GLN | A | 228 | 16.181 | −94.376 | −58.354 | 1.00 | 72.46 | | N |
| ANISOU | 604 | N | GLN | A | 228 | 10398 | 7750 | 9385 | 1433 | −718 | 308 | N |
| ATOM | 605 | CA | GLN | A | 228 | 17.353 | −93.619 | −57.983 | 1.00 | 76.24 | | C |
| ANISOU | 605 | CA | GLN | A | 228 | 10832 | 8202 | 9934 | 1562 | −1060 | 104 | C |
| ATOM | 606 | CB | GLN | A | 228 | 17.630 | −92.547 | −59.036 | 1.00 | 75.48 | | C |
| ANISOU | 606 | CB | GLN | A | 228 | 10419 | 8090 | 10171 | 1477 | −1024 | −111 | C |
| ATOM | 607 | CG | GLN | A | 228 | 18.600 | −91.464 | −58.613 | 1.00 | 80.08 | | C |
| ANISOU | 607 | CG | GLN | A | 228 | 10950 | 8661 | 10815 | 1552 | −1315 | −359 | C |
| ATOM | 608 | CD | GLN | A | 228 | 19.823 | −91.389 | −59.504 | 1.00 | 83.98 | | C |
| ANISOU | 608 | CD | GLN | A | 228 | 11126 | 9024 | 11758 | 1516 | −1475 | −480 | C |
| ATOM | 609 | OE1 | GLN | A | 228 | 19.787 | −91.793 | −60.667 | 1.00 | 80.28 | | O |
| ANISOU | 609 | OE1 | GLN | A | 228 | 10459 | 8479 | 11564 | 1430 | −1295 | −417 | O |
| ATOM | 610 | NE2 | GLN | A | 228 | 20.920 | −90.871 | −58.960 | 1.00 | 89.67 | | N |
| ANISOU | 610 | NE2 | GLN | A | 228 | 11792 | 9724 | 12553 | 1581 | −1814 | −660 | N |
| ATOM | 611 | C | GLN | A | 228 | 17.097 | −92.998 | −56.619 | 1.00 | 79.11 | | C |
| ANISOU | 611 | C | GLN | A | 228 | 11488 | 8690 | 9882 | 1694 | −1157 | 57 | C |
| ATOM | 612 | O | GLN | A | 228 | 15.951 | −92.758 | −56.242 | 1.00 | 81.95 | | O |
| ANISOU | 612 | O | GLN | A | 228 | 11996 | 9170 | 9971 | 1674 | −894 | 130 | O |
| ATOM | 613 | N | THR | A | 229 | 18.163 | −92.757 | −55.869 | 1.00 | 80.30 | | N |
| ANISOU | 613 | N | THR | A | 229 | 11717 | 8820 | 9973 | 1838 | −1536 | −68 | N |
| ATOM | 614 | CA | THR | A | 229 | 18.037 | −92.144 | −54.563 | 1.00 | 79.90 | | C |
| ANISOU | 614 | CA | THR | A | 229 | 11975 | 8877 | 9505 | 1980 | −1676 | −149 | C |
| ATOM | 615 | CB | THR | A | 229 | 18.344 | −93.156 | −53.457 | 1.00 | 79.87 | | C |
| ANISOU | 615 | CB | THR | A | 229 | 12300 | 8873 | 9172 | 2163 | −1875 | 32 | C |
| ATOM | 616 | OG1 | THR | A | 229 | 17.451 | −94.266 | −53.584 | 1.00 | 79.72 | | O |
| ANISOU | 616 | OG1 | THR | A | 229 | 12409 | 8825 | 9056 | 2107 | −1546 | 334 | O |
| ATOM | 617 | CG2 | THR | A | 229 | 18.171 | −92.535 | −52.077 | 1.00 | 80.85 | | C |
| ANISOU | 617 | CG2 | THR | A | 229 | 12794 | 9118 | 8807 | 2330 | −2013 | −51 | C |
| ATOM | 618 | C | THR | A | 229 | 18.940 | −90.923 | −54.485 | 1.00 | 87.92 | | C |
| ANISOU | 618 | C | THR | A | 229 | 12861 | 9884 | 10659 | 1994 | −1974 | −472 | C |
| ATOM | 619 | O | THR | A | 229 | 19.990 | −90.871 | −55.126 | 1.00 | 88.12 | | O |
| ANISOU | 619 | O | THR | A | 229 | 12592 | 9820 | 11070 | 1947 | −2183 | −590 | O |
| ATOM | 620 | N | ILE | A | 230 | 18.523 | −89.935 | −53.704 | 1.00 | 97.10 | | N |
| ANISOU | 620 | N | ILE | A | 230 | 14246 | 11131 | 11516 | 2051 | −1974 | −619 | N |
| ATOM | 621 | CA | ILE | A | 230 | 19.181 | −88.645 | −53.709 | 1.00 | 103.59 | | C |
| ANISOU | 621 | CA | ILE | A | 230 | 14967 | 11916 | 12478 | 2015 | −2183 | −947 | C |
| ATOM | 622 | C | ILE | A | 230 | 19.863 | −88.320 | −52.399 | 1.00 | 113.84 | | C |
| ANISOU | 622 | C | ILE | A | 230 | 16534 | 13262 | 13458 | 2162 | −2601 | −1118 | C |
| ATOM | 623 | O | ILE | A | 230 | 19.295 | −88.510 | −51.324 | 1.00 | 121.58 | | O |
| ANISOU | 623 | O | ILE | A | 230 | 17907 | 14339 | 13949 | 2317 | −2584 | −1029 | O |
| ATOM | 624 | CB | ILE | A | 230 | 18.179 | −87.538 | −53.982 | 1.00 | 105.04 | | C |
| ANISOU | 624 | CB | ILE | A | 230 | 15193 | 12122 | 12595 | 1958 | −1845 | −1041 | C |
| ATOM | 625 | CG1 | ILE | A | 230 | 17.152 | −88.005 | −55.010 | 1.00 | 104.55 | | C |
| ANISOU | 625 | CG1 | ILE | A | 230 | 14959 | 12086 | 12678 | 1863 | −1408 | −819 | C |
| ATOM | 626 | CG2 | ILE | A | 230 | 18.903 | −86.301 | −54.458 | 1.00 | 105.54 | | C |
| ANISOU | 626 | CG2 | ILE | A | 230 | 15063 | 12070 | 12969 | 1856 | −1977 | −1352 | C |
| ATOM | 627 | CD1 | ILE | A | 230 | 17.745 | −88.229 | −56.383 | 1.00 | 104.69 | | C |
| ANISOU | 627 | CD1 | ILE | A | 230 | 14579 | 11987 | 13209 | 1717 | −1392 | −826 | C |
| ATOM | 628 | N | ASP | A | 231 | 21.086 | −87.838 | −52.482 | 1.00 | 115.91 | | N |
| ANISOU | 628 | N | ASP | A | 231 | 16583 | 13462 | 13997 | 2110 | −2974 | −1372 | N |
| ATOM | 629 | CA | ASP | A | 231 | 21.641 | −87.140 | −51.355 | 1.00 | 120.15 | | C |
| ANISOU | 629 | CA | ASP | A | 231 | 17336 | 14052 | 14261 | 2219 | −3418 | −1602 | C |
| ATOM | 630 | CB | ASP | A | 231 | 22.261 | −88.073 | −50.356 | 1.00 | 123.58 | | C |
| ANISOU | 630 | CB | ASP | A | 231 | 17760 | 14547 | 14647 | 2373 | −3831 | −1503 | C |
| ATOM | 631 | CG | ASP | A | 231 | 21.380 | −88.242 | −49.187 | 1.00 | 128.77 | | C |
| ANISOU | 631 | CG | ASP | A | 231 | 18883 | 15309 | 14735 | 2606 | −3803 | −1258 | C |
| ATOM | 632 | OD1 | ASP | A | 231 | 20.737 | −89.295 | −49.084 | 1.00 | 126.27 | | O |
| ANISOU | 632 | OD1 | ASP | A | 231 | 18942 | 15052 | 13982 | 2675 | −3670 | −1305 | O |
| ATOM | 633 | OD2 | ASP | A | 231 | 21.278 | −87.276 | −48.411 | 1.00 | 134.04 | | O |

TABLE 7-continued

DMXAA-hSTING^{G230I} complex

| | | | | | | | | | | | |
|---|---|---|---|---|---|---|---|---|---|---|---|
| ANISOU | 633 | OD2 | ASP | A | 231 | 19559 | 15984 | 15387 | 2731 | −3885 | −1010 O |
| ATOM | 634 | C | ASP | A | 231 | 22.444 | −85.889 | −51.637 | 1.00 | 125.72 | C |
| ANISOU | 634 | C | ASP | A | 231 | 17842 | 14665 | 15262 | 2056 | −3605 | −1975 C |
| ATOM | 635 | O | ASP | A | 231 | 23.430 | −85.578 | −50.971 | 1.00 | 130.82 | O |
| ANISOU | 635 | O | ASP | A | 231 | 18489 | 15333 | 15883 | 2074 | −4069 | −2215 O |
| ATOM | 636 | N | ARG | A | 232 | 21.995 | −85.170 | −52.642 | 1.00 | 126.23 | N |
| ANISOU | 636 | N | ARG | A | 232 | 17735 | 14620 | 15606 | 1893 | −3243 | −2024 N |
| ATOM | 637 | CA | ARG | A | 232 | 22.454 | −83.831 | −52.862 | 1.00 | 134.44 | C |
| ANISOU | 637 | CA | ARG | A | 232 | 18668 | 15529 | 16885 | 1731 | −3322 | −2364 C |
| ATOM | 638 | CB | ARG | A | 232 | 22.190 | −83.405 | −54.301 | 1.00 | 129.88 | C |
| ANISOU | 638 | CB | ARG | A | 232 | 17785 | 14814 | 16749 | 1563 | −2921 | −2323 C |
| ATOM | 639 | CG | ARG | A | 232 | 22.414 | −84.525 | −55.308 | 1.00 | 126.61 | C |
| ANISOU | 639 | CG | ARG | A | 232 | 17023 | 14405 | 16678 | 1532 | −2808 | −2070 C |
| ATOM | 640 | CD | ARG | A | 232 | 23.728 | −84.381 | −56.055 | 1.00 | 128.51 | C |
| ANISOU | 640 | CD | ARG | A | 232 | 16828 | 14531 | 17471 | 1374 | −3003 | −2217 C |
| ATOM | 641 | NE | ARG | A | 232 | 23.583 | −83.816 | −57.393 | 1.00 | 128.05 | N |
| ANISOU | 641 | NE | ARG | A | 232 | 16541 | 14324 | 17789 | 1222 | −2636 | −2228 N |
| ATOM | 642 | CZ | ARG | A | 232 | 24.433 | −84.032 | −58.394 | 1.00 | 126.77 | C |
| ANISOU | 642 | CZ | ARG | A | 232 | 15985 | 14070 | 18113 | 1112 | −2596 | −2206 C |
| ATOM | 643 | NH1 | ARG | A | 232 | 24.232 | −83.474 | −59.579 | 1.00 | 122.76 | N |
| ANISOU | 643 | NH1 | ARG | A | 232 | 15332 | 13425 | 17886 | 1000 | −2241 | −2206 N |
| ATOM | 644 | NH2 | ARG | A | 232 | 25.489 | −84.807 | −58.209 | 1.00 | 127.58 | N |
| ANISOU | 644 | NH2 | ARG | A | 232 | 15849 | 14219 | 18408 | 1141 | −2899 | −2176 N |
| ATOM | 645 | C | ARG | A | 232 | 21.706 | −82.977 | −51.836 | 1.00 | 142.51 | C |
| ANISOU | 645 | C | ARG | A | 232 | 20155 | 16571 | 17423 | 1824 | −3281 | −2523 C |
| ATOM | 646 | O | ARG | A | 232 | 20.819 | −83.484 | −51.140 | 1.00 | 144.75 | O |
| ANISOU | 646 | O | ARG | A | 232 | 20784 | 16981 | 17234 | 2009 | −3143 | −2342 O |
| ATOM | 647 | N | ALA | A | 233 | 22.108 | −81.716 | −51.686 | 1.00 | 143.11 | N |
| ANISOU | 647 | N | ALA | A | 233 | 20255 | 16505 | 17614 | 1696 | −3381 | −2861 N |
| ATOM | 648 | CA | ALA | A | 233 | 21.492 | −80.842 | −50.695 | 1.00 | 138.64 | C |
| ANISOU | 648 | CA | ALA | A | 233 | 20161 | 15926 | 16589 | 1791 | −3377 | −3062 C |
| ATOM | 649 | CB | ALA | A | 233 | 22.207 | −79.516 | −50.625 | 1.00 | 139.58 | C |
| ANISOU | 649 | CB | ALA | A | 233 | 20248 | 15843 | 16945 | 1594 | −3582 | −3476 C |
| ATOM | 650 | C | ALA | A | 233 | 20.032 | −80.612 | −50.987 | 1.00 | 130.68 | C |
| ANISOU | 650 | C | ALA | A | 233 | 19385 | 14939 | 15328 | 1911 | −2826 | −2876 C |
| ATOM | 651 | O | ALA | A | 233 | 19.631 | −80.498 | −52.133 | 1.00 | 123.83 | O |
| ANISOU | 651 | O | ALA | A | 233 | 18270 | 14018 | 14763 | 1838 | −2447 | −2725 O |
| ATOM | 652 | N | GLY | A | 234 | 19.248 | −80.601 | −49.919 | 1.00 | 129.16 | N |
| ANISOU | 652 | N | GLY | A | 234 | 19667 | 14839 | 14568 | 2113 | −2787 | −2890 N |
| ATOM | 653 | CA | GLY | A | 234 | 17.868 | −80.190 | −49.930 | 1.00 | 121.13 | C |
| ANISOU | 653 | CA | GLY | A | 234 | 18884 | 13862 | 13278 | 2253 | −2280 | −2750 C |
| ATOM | 654 | C | GLY | A | 234 | 16.980 | −81.324 | −50.323 | 1.00 | 115.06 | C |
| ANISOU | 654 | C | GLY | A | 234 | 18018 | 13277 | 12421 | 2346 | −1955 | −2335 C |
| ATOM | 655 | O | GLY | A | 234 | 15.779 | −81.266 | −50.165 | 1.00 | 112.28 | O |
| ANISOU | 655 | O | GLY | A | 234 | 17846 | 13024 | 11790 | 2485 | −1551 | −2175 O |
| ATOM | 656 | N | ILE | A | 235 | 17.585 | −82.392 | −50.807 | 1.00 | 118.14 | N |
| ANISOU | 656 | N | ILE | A | 235 | 18116 | 13712 | 13061 | 2265 | −2126 | −2162 N |
| ATOM | 657 | CA | ILE | A | 235 | 16.837 | −83.594 | −51.079 | 1.00 | 116.53 | C |
| ANISOU | 657 | CA | ILE | A | 235 | 17814 | 13643 | 12818 | 2307 | −1838 | −1784 C |
| ATOM | 658 | CB | ILE | A | 235 | 16.631 | −83.752 | −52.586 | 1.00 | 101.63 | C |
| ANISOU | 658 | CB | ILE | A | 235 | 15504 | 11702 | 11411 | 2149 | −1532 | −1668 C |
| ATOM | 659 | CG1 | ILE | A | 235 | 16.041 | −85.107 | −52.909 | 1.00 | 102.57 | C |
| ANISOU | 659 | CG1 | ILE | A | 235 | 15486 | 11937 | 11548 | 2141 | −1318 | −1311 C |
| ATOM | 660 | CD1 | ILE | A | 235 | 15.510 | −85.210 | −54.320 | 1.00 | 101.97 | C |
| ANISOU | 660 | CD1 | ILE | A | 235 | 15053 | 11840 | 11850 | 2011 | −992 | −1204 C |
| ATOM | 661 | CG2 | ILE | A | 235 | 17.931 | −83.537 | −53.315 | 1.00 | 92.37 | C |
| ANISOU | 661 | CG2 | ILE | A | 235 | 13989 | 10357 | 10749 | 1967 | −1798 | −1865 C |
| ATOM | 662 | C | ILE | A | 235 | 17.544 | −84.794 | −50.449 | 1.00 | 125.11 | C |
| ANISOU | 662 | C | ILE | A | 235 | 18914 | 14799 | 13821 | 2357 | −2152 | −1626 C |
| ATOM | 663 | O | ILE | A | 235 | 18.695 | −85.089 | −50.748 | 1.00 | 129.27 | O |
| ANISOU | 663 | O | ILE | A | 235 | 19162 | 15258 | 14699 | 2258 | −2463 | −1682 O |
| ATOM | 664 | N | LYS | A | 236 | 16.859 | −85.458 | −49.540 | 1.00 | 123.27 | N |
| ANISOU | 664 | N | LYS | A | 236 | 19029 | 14699 | 13109 | 2532 | −2052 | −1423 N |
| ATOM | 665 | CA | LYS | A | 236 | 17.371 | −86.669 | −48.951 | 1.00 | 114.92 | C |
| ANISOU | 665 | CA | LYS | A | 236 | 18078 | 13699 | 11888 | 2630 | −2295 | −1230 C |
| ATOM | 666 | CB | LYS | A | 236 | 17.898 | −86.421 | −47.532 | 1.00 | 113.45 | C |
| ANISOU | 666 | CB | LYS | A | 236 | 18312 | 13564 | 11228 | 2825 | −2700 | −1398 C |
| ATOM | 667 | CG | LYS | A | 236 | 17.834 | −84.968 | −47.042 | 1.00 | 111.53 | C |
| ANISOU | 667 | CG | LYS | A | 236 | 18275 | 13281 | 10820 | 2839 | −2776 | −1760 C |
| ATOM | 668 | CD | LYS | A | 236 | 16.484 | −84.624 | −46.406 | 1.00 | 105.27 | C |
| ANISOU | 668 | CD | LYS | A | 236 | 17892 | 12574 | 9531 | 3002 | −2360 | −1675 C |
| ATOM | 669 | CE | LYS | A | 236 | 15.824 | −83.402 | −47.022 | 1.00 | 96.12 | C |
| ANISOU | 669 | CE | LYS | A | 236 | 16631 | 11335 | 8557 | 2914 | −2029 | −1841 C |
| ATOM | 670 | NZ | LYS | A | 236 | 14.653 | −83.764 | −47.859 | 1.00 | 89.20 | N |
| ANISOU | 670 | NZ | LYS | A | 236 | 15528 | 10526 | 7838 | 2867 | −1480 | −1542 N |
| ATOM | 671 | C | LYS | A | 236 | 16.249 | −87.674 | −48.930 | 1.00 | 109.77 | C |
| ANISOU | 671 | C | LYS | A | 236 | 17539 | 13141 | 11027 | 2679 | −1867 | −852 C |
| ATOM | 672 | O | LYS | A | 236 | 15.233 | −87.479 | −48.277 | 1.00 | 102.98 | O |

TABLE 7-continued

DMXAA-hSTING$^{G230I}$ complex

| | | | | | | | | | | | |
|---|---|---|---|---|---|---|---|---|---|---|---|
| ANISOU | 672 | O | LYS | A | 236 | 16975 | 12377 | 9775 | 2790 | −1565 | −779 O |
| ATOM | 673 | N | ASP | A | 237 | 16.466 | −88.792 | −49.587 | 1.00 | 110.51 | N |
| ANISOU | 673 | N | ASP | A | 237 | 17388 | 13197 | 11406 | 2586 | −1825 | −621 N |
| ATOM | 674 | CA | ASP | A | 237 | 15.513 | −89.845 | −49.453 | 1.00 | 109.66 | C |
| ANISOU | 674 | CA | ASP | A | 237 | 17362 | 13143 | 11160 | 2582 | −1453 | −260 C |
| ATOM | 675 | CB | ASP | A | 237 | 15.250 | −90.027 | −47.980 | 1.00 | 114.61 | C |
| ANISOU | 675 | CB | ASP | A | 237 | 18502 | 13861 | 11186 | 2803 | −1437 | −107 C |
| ATOM | 676 | CG | ASP | A | 237 | 16.439 | −90.614 | −47.285 | 1.00 | 120.20 | C |
| ANISOU | 676 | CG | ASP | A | 237 | 19399 | 14525 | 11747 | 2960 | −1900 | −83 C |
| ATOM | 677 | OD2 | ASP | A | 237 | 16.700 | −91.804 | −47.497 | 1.00 | 127.13 | O |
| ANISOU | 677 | OD2 | ASP | A | 237 | 20476 | 15390 | 12438 | 3037 | −1803 | 224 O |
| ATOM | 678 | OD1 | ASP | A | 237 | 17.149 | −89.895 | −46.570 | 1.00 | 119.09 | O |
| ANISOU | 678 | OD1 | ASP | A | 237 | 19201 | 14361 | 11686 | 3005 | −2357 | −367 O |
| ATOM | 679 | C | ASP | A | 237 | 14.254 | −89.705 | −50.273 | 1.00 | 102.04 | C |
| ANISOU | 679 | C | ASP | A | 237 | 16189 | 12237 | 10347 | 2439 | −947 | −162 C |
| ATOM | 680 | O | ASP | A | 237 | 13.234 | −90.305 | −49.986 | 1.00 | 102.84 | O |
| ANISOU | 680 | O | ASP | A | 237 | 16412 | 12426 | 10236 | 2442 | −589 | 94 O |
| ATOM | 681 | N | ARG | A | 238 | 14.347 | −88.889 | −51.300 | 1.00 | 86.07 | N |
| ANISOU | 681 | N | ARG | A | 238 | 13848 | 10170 | 8686 | 2319 | −912 | −359 N |
| ATOM | 682 | CA | ARG | A | 238 | 13.368 | −88.855 | −52.333 | 1.00 | 68.71 | C |
| ANISOU | 682 | CA | ARG | A | 238 | 11364 | 8022 | 6720 | 2178 | −502 | −247 C |
| ATOM | 683 | CB | ARG | A | 238 | 13.647 | −87.688 | −53.201 | 1.00 | 64.35 | C |
| ANISOU | 683 | CB | ARG | A | 238 | 10582 | 7425 | 6442 | 2125 | −467 | −495 C |
| ATOM | 684 | CG | ARG | A | 238 | 12.534 | −86.809 | −53.351 | 1.00 | 80.76 | C |
| ANISOU | 684 | CG | ARG | A | 238 | 12705 | 9636 | 8344 | 2194 | −74 | −492 C |
| ATOM | 685 | CD | ARG | A | 238 | 13.089 | −85.485 | −53.158 | 1.00 | 82.55 | C |
| ANISOU | 685 | CD | ARG | A | 238 | 13158 | 9808 | 8401 | 2328 | −185 | −781 C |
| ATOM | 686 | NE | ARG | A | 238 | 12.328 | −84.515 | −53.878 | 1.00 | 75.31 | N |
| ANISOU | 686 | NE | ARG | A | 238 | 12048 | 8868 | 7697 | 2313 | 45 | −895 N |
| ATOM | 687 | CZ | ARG | A | 238 | 11.618 | −83.563 | −53.330 | 1.00 | 85.25 | C |
| ANISOU | 687 | CZ | ARG | A | 238 | 13495 | 10183 | 8714 | 2471 | 276 | −981 C |
| ATOM | 688 | NH1 | ARG | A | 238 | 11.037 | −82.744 | −54.147 | 1.00 | 68.92 | N |
| ANISOU | 688 | NH1 | ARG | A | 238 | 11813 | 8200 | 6173 | 2650 | 324 | −978 N |
| ATOM | 689 | NH2 | ARG | A | 238 | 11.244 | −83.615 | −52.068 | 1.00 | 92.77 | N |
| ANISOU | 689 | NH2 | ARG | A | 238 | 14266 | 11098 | 9883 | 2476 | 477 | −1061 N |
| ATOM | 690 | C | ARG | A | 238 | 13.680 | −90.055 | −53.152 | 1.00 | 67.66 | C |
| ANISOU | 690 | C | ARG | A | 238 | 10977 | 7805 | 6924 | 2025 | −530 | −73 C |
| ATOM | 691 | O | ARG | A | 238 | 14.825 | −90.420 | −53.255 | 1.00 | 66.89 | O |
| ANISOU | 691 | O | ARG | A | 238 | 10808 | 7585 | 7023 | 2021 | −874 | −141 O |
| ATOM | 692 | N | VAL | A | 239 | 12.675 | −90.651 | −53.757 | 1.00 | 62.98 | N |
| ANISOU | 692 | N | VAL | A | 239 | 10250 | 7281 | 6398 | 1903 | −174 | 144 N |
| ATOM | 693 | CA | VAL | A | 239 | 12.877 | −91.768 | −54.633 | 1.00 | 61.13 | C |
| ANISOU | 693 | CA | VAL | A | 239 | 9796 | 6947 | 6483 | 1742 | −166 | 291 C |
| ATOM | 694 | CB | VAL | A | 239 | 12.141 | −92.992 | −54.166 | 1.00 | 67.70 | C |
| ANISOU | 694 | CB | VAL | A | 239 | 10808 | 7802 | 7113 | 1693 | 51 | 596 C |
| ATOM | 695 | CG1 | VAL | A | 239 | 12.298 | −94.081 | −55.154 | 1.00 | 61.52 | C |
| ANISOU | 695 | CG1 | VAL | A | 239 | 9805 | 6891 | 6680 | 1502 | 94 | 720 C |
| ATOM | 696 | CG2 | VAL | A | 239 | 12.667 | −93.440 | −52.841 | 1.00 | 66.47 | C |
| ANISOU | 696 | CG2 | VAL | A | 239 | 11066 | 7606 | 6586 | 1883 | −159 | 679 C |
| ATOM | 697 | C | VAL | A | 239 | 12.354 | −91.369 | −55.966 | 1.00 | 71.40 | C |
| ANISOU | 697 | C | VAL | A | 239 | 10722 | 8277 | 8130 | 1582 | 50 | 245 C |
| ATOM | 698 | O | VAL | A | 239 | 11.300 | −90.834 | −56.061 | 1.00 | 75.06 | O |
| ANISOU | 698 | O | VAL | A | 239 | 11115 | 8899 | 8507 | 1546 | 371 | 304 O |
| ATOM | 699 | N | TYR | A | 240 | 13.108 | −91.620 | −57.012 | 1.00 | 72.90 | N |
| ANISOU | 699 | N | TYR | A | 240 | 10667 | 8328 | 8703 | 1505 | −124 | 142 N |
| ATOM | 700 | CA | TYR | A | 240 | 12.701 | −91.220 | −58.340 | 1.00 | 73.01 | C |
| ANISOU | 700 | CA | TYR | A | 240 | 10354 | 8359 | 9027 | 1378 | 57 | 94 C |
| ATOM | 701 | CB | TYR | A | 240 | 13.734 | −90.307 | −58.944 | 1.00 | 58.93 | C |
| ANISOU | 701 | CB | TYR | A | 240 | 8405 | 6462 | 7525 | 1405 | −133 | −145 C |
| ATOM | 702 | CG | TYR | A | 240 | 13.712 | −88.916 | −58.444 | 1.00 | 54.44 | C |
| ANISOU | 702 | CG | TYR | A | 240 | 7957 | 5939 | 6790 | 1525 | −151 | −332 C |
| ATOM | 703 | CD2 | TYR | A | 240 | 13.063 | −87.934 | −59.138 | 1.00 | 52.37 | C |
| ANISOU | 703 | CD2 | TYR | A | 240 | 7573 | 5744 | 6583 | 1536 | 83 | −409 C |
| ATOM | 704 | CE2 | TYR | A | 240 | 13.052 | −86.669 | −58.701 | 1.00 | 52.09 | C |
| ANISOU | 704 | CE2 | TYR | A | 240 | 7687 | 5712 | 6393 | 1658 | 87 | −584 C |
| ATOM | 705 | CZ | TYR | A | 240 | 13.709 | −86.364 | −57.565 | 1.00 | 72.81 | C |
| ANISOU | 705 | CZ | TYR | A | 240 | 10584 | 8284 | 8797 | 1748 | −166 | −704 C |
| ATOM | 706 | OH | TYR | A | 240 | 13.712 | −85.101 | −57.105 | 1.00 | 72.59 | O |
| ANISOU | 706 | OH | TYR | A | 240 | 10745 | 8232 | 8604 | 1859 | −167 | −903 O |
| ATOM | 707 | CE1 | TYR | A | 240 | 14.370 | −87.320 | −56.860 | 1.00 | 74.81 | C |
| ANISOU | 707 | CE1 | TYR | A | 240 | 10945 | 8501 | 8977 | 1744 | −427 | −632 C |
| ATOM | 708 | CD1 | TYR | A | 240 | 14.372 | −88.573 | −57.297 | 1.00 | 62.68 | C |
| ANISOU | 708 | CD1 | TYR | A | 240 | 9262 | 6952 | 7603 | 1644 | −408 | −436 C |
| ATOM | 709 | C | TYR | A | 240 | 12.606 | −92.382 | −59.262 | 1.00 | 79.47 | C |
| ANISOU | 709 | C | TYR | A | 240 | 11021 | 9109 | 10066 | 1213 | 142 | 250 C |
| ATOM | 710 | O | TYR | A | 240 | 13.258 | −93.372 | −59.087 | 1.00 | 78.87 | O |
| ANISOU | 710 | O | TYR | A | 240 | 11034 | 8889 | 10043 | 1207 | −24 | 335 O |
| ATOM | 711 | N | SER | A | 241 | 11.791 | −92.245 | −60.275 | 1.00 | 79.90 | N |

TABLE 7-continued

| | | | | | | | | | | | |
|---|---|---|---|---|---|---|---|---|---|---|---|
| DMXAA-hSTING$^{G230I}$ complex | | | | | | | | | | | |
| ANISOU | 711 | N | SER | A | 241 | 10855 | 9264 | 10238 | 1092 | 395 | 282 | N |
| ATOM | 712 | CA | SER | A | 241 | 11.721 | −93.257 | −61.304 | 1.00 | 79.70 | | C |
| ANISOU | 712 | CA | SER | A | 241 | 10667 | 9161 | 10453 | 919 | 458 | 370 | C |
| ATOM | 713 | CB | SER | A | 241 | 10.567 | −94.228 | −61.051 | 1.00 | 72.20 | | C |
| ANISOU | 713 | CB | SER | A | 241 | 9773 | 8310 | 9349 | 769 | 699 | 579 | C |
| ATOM | 714 | OG | SER | A | 241 | 9.320 | −93.568 | −61.151 | 1.00 | 61.03 | | O |
| ANISOU | 714 | OG | SER | A | 241 | 8221 | 7146 | 7820 | 747 | 953 | 583 | O |
| ATOM | 715 | C | SER | A | 241 | 11.537 | −92.543 | −62.635 | 1.00 | 66.75 | | C |
| ANISOU | 715 | C | SER | A | 241 | 8740 | 7566 | 9055 | 879 | 546 | 244 | C |
| ATOM | 716 | O | SER | A | 241 | 11.049 | −91.414 | −62.683 | 1.00 | 57.48 | | O |
| ANISOU | 716 | O | SER | A | 241 | 7501 | 6529 | 7811 | 965 | 648 | 154 | O |
| ATOM | 717 | N | ASN | A | 242 | 11.949 | −93.201 | −63.709 | 1.00 | 57.03 | | N |
| ANISOU | 717 | N | ASN | A | 242 | 7369 | 6207 | 8091 | 773 | 514 | 243 | N |
| ATOM | 718 | CA | ASN | A | 242 | 11.715 | −92.701 | −65.045 | 1.00 | 46.44 | | C |
| ANISOU | 718 | CA | ASN | A | 242 | 5787 | 4909 | 6949 | 737 | 613 | 152 | C |
| ATOM | 719 | CB | ASN | A | 242 | 13.020 | −92.279 | −65.702 | 1.00 | 51.82 | | C |
| ANISOU | 719 | CB | ASN | A | 242 | 6391 | 5396 | 7900 | 812 | 451 | 12 | C |
| ATOM | 720 | CG | ASN | A | 242 | 13.734 | −91.197 | −64.936 | 1.00 | 53.93 | | C |
| ANISOU | 720 | CG | ASN | A | 242 | 6736 | 5627 | 8130 | 959 | 310 | −114 | C |
| ATOM | 721 | OD1 | ASN | A | 242 | 14.380 | −91.464 | −63.925 | 1.00 | 64.35 | | O |
| ANISOU | 721 | OD1 | ASN | A | 242 | 8213 | 6875 | 9363 | 1012 | 121 | −107 | O |
| ATOM | 722 | ND2 | ASN | A | 242 | 13.608 | −89.958 | −65.405 | 1.00 | 57.51 | | N |
| ANISOU | 722 | ND2 | ASN | A | 242 | 7096 | 6121 | 8634 | 1028 | 395 | −237 | N |
| ATOM | 723 | C | ASN | A | 242 | 11.060 | −93.789 | −65.861 | 1.00 | 50.51 | | C |
| ANISOU | 723 | C | ASN | A | 242 | 6208 | 5441 | 7541 | 544 | 733 | 248 | C |
| ATOM | 724 | O | ASN | A | 242 | 11.251 | −94.977 | −65.592 | 1.00 | 51.19 | | O |
| ANISOU | 724 | O | ASN | A | 242 | 6420 | 5397 | 7633 | 442 | 693 | 355 | O |
| ATOM | 725 | N | SER | A | 243 | 10.303 | −93.386 | −66.869 | 1.00 | 51.20 | | N |
| ANISOU | 725 | N | SER | A | 243 | 6092 | 5679 | 7683 | 502 | 870 | 203 | N |
| ATOM | 726 | CA | SER | A | 243 | 9.513 | −94.343 | −67.618 | 1.00 | 61.98 | | C |
| ANISOU | 726 | CA | SER | A | 243 | 7354 | 7105 | 9093 | 296 | 972 | 266 | C |
| ATOM | 727 | CB | SER | A | 243 | 8.031 | −93.970 | −67.572 | 1.00 | 56.65 | | C |
| ANISOU | 727 | CB | SER | A | 243 | 6516 | 6753 | 8254 | 245 | 1164 | 310 | C |
| ATOM | 728 | OG | SER | A | 243 | 7.543 | −94.042 | −66.250 | 1.00 | 44.33 | | O |
| ANISOU | 728 | OG | SER | A | 243 | 5081 | 5286 | 6475 | 248 | 1245 | 423 | O |
| ATOM | 729 | C | SER | A | 243 | 9.984 | −94.510 | −69.050 | 1.00 | 46.82 | | C |
| ANISOU | 729 | C | SER | A | 243 | 5320 | 5070 | 7399 | 268 | 930 | 171 | C |
| ATOM | 730 | O | SER | A | 243 | 10.370 | −93.549 | −69.712 | 1.00 | 45.92 | | O |
| ANISOU | 730 | O | SER | A | 243 | 5115 | 4959 | 7373 | 411 | 920 | 65 | O |
| ATOM | 731 | N | ILE | A | 244 | 9.922 | −95.747 | −69.518 | 1.00 | 45.57 | | N |
| ANISOU | 731 | N | ILE | A | 244 | 5197 | 4797 | 7320 | 82 | 928 | 214 | N |
| ATOM | 732 | CA | ILE | A | 244 | 10.367 | −96.107 | −70.850 | 1.00 | 50.86 | | C |
| ANISOU | 732 | CA | ILE | A | 244 | 5815 | 5334 | 8176 | 49 | 896 | 128 | C |
| ATOM | 733 | CB | ILE | A | 244 | 11.176 | −97.394 | −70.813 | 1.00 | 40.31 | | C |
| ANISOU | 733 | CB | ILE | A | 244 | 4665 | 3694 | 6956 | −32 | 818 | 174 | C |
| ATOM | 734 | CG1 | ILE | A | 244 | 12.437 | −97.174 | −69.992 | 1.00 | 40.12 | | C |
| ANISOU | 734 | CG1 | ILE | A | 244 | 4764 | 3493 | 6988 | 156 | 682 | 191 | C |
| ATOM | 735 | CD1 | ILE | A | 244 | 12.776 | −98.327 | −69.103 | 1.00 | 61.33 | | C |
| ANISOU | 735 | CD1 | ILE | A | 244 | 7677 | 5991 | 9635 | 106 | 622 | 321 | C |
| ATOM | 736 | CG2 | ILE | A | 244 | 11.525 | −97.844 | −72.214 | 1.00 | 43.76 | | C |
| ANISOU | 736 | CG2 | ILE | A | 244 | 5074 | 3995 | 7556 | −68 | 815 | 80 | C |
| ATOM | 737 | C | ILE | A | 244 | 9.170 | −96.318 | −71.745 | 1.00 | 45.97 | | C |
| ANISOU | 737 | C | ILE | A | 244 | 5030 | 4923 | 7513 | −112 | 992 | 100 | C |
| ATOM | 738 | O | ILE | A | 244 | 8.204 | −96.977 | −71.362 | 1.00 | 43.32 | | O |
| ANISOU | 738 | O | ILE | A | 244 | 4671 | 4707 | 7083 | −316 | 1064 | 176 | O |
| ATOM | 739 | N | TYR | A | 245 | 9.235 | −95.767 | −72.947 | 1.00 | 42.32 | | N |
| ANISOU | 739 | N | TYR | A | 245 | 4450 | 4510 | 7118 | −24 | 994 | −8 | N |
| ATOM | 740 | CA | TYR | A | 245 | 8.122 | −95.871 | −73.861 | 1.00 | 45.39 | | C |
| ANISOU | 740 | CA | TYR | A | 245 | 4667 | 5132 | 7446 | −142 | 1043 | −55 | C |
| ATOM | 741 | CB | TYR | A | 245 | 7.534 | −94.497 | −74.140 | 1.00 | 44.07 | | C |
| ANISOU | 741 | CB | TYR | A | 245 | 4319 | 5248 | 7178 | 59 | 1104 | −89 | C |
| ATOM | 742 | CG | TYR | A | 245 | 6.857 | −93.926 | −72.929 | 1.00 | 51.54 | | C |
| ANISOU | 742 | CG | TYR | A | 245 | 5208 | 6396 | 7978 | 104 | 1183 | −2 | C |
| ATOM | 743 | CD1 | TYR | A | 245 | 7.597 | −93.313 | −71.917 | 1.00 | 55.10 | | C |
| ANISOU | 743 | CD1 | TYR | A | 245 | 5802 | 6720 | 8414 | 259 | 1173 | 26 | C |
| ATOM | 744 | CE1 | TYR | A | 245 | 6.981 | −92.802 | −70.799 | 1.00 | 51.82 | | C |
| ANISOU | 744 | CE1 | TYR | A | 245 | 5380 | 6478 | 7833 | 317 | 1255 | 96 | C |
| ATOM | 745 | CZ | TYR | A | 245 | 5.601 | −92.907 | −70.679 | 1.00 | 57.80 | | C |
| ANISOU | 745 | CZ | TYR | A | 245 | 5950 | 7551 | 8459 | 222 | 1374 | 157 | C |
| ATOM | 746 | OH | TYR | A | 245 | 4.968 | −92.399 | −69.568 | 1.00 | 62.60 | | O |
| ANISOU | 746 | OH | TYR | A | 245 | 6555 | 8339 | 8893 | 302 | 1493 | 235 | O |
| ATOM | 747 | CE2 | TYR | A | 245 | 4.847 | −93.517 | −71.668 | 1.00 | 64.11 | | C |
| ANISOU | 747 | CE2 | TYR | A | 245 | 6558 | 8501 | 9301 | 48 | 1375 | 132 | C |
| ATOM | 748 | CD2 | TYR | A | 245 | 5.478 | −94.025 | −72.778 | 1.00 | 62.26 | | C |
| ANISOU | 748 | CD2 | TYR | A | 245 | 6367 | 8079 | 9210 | −14 | 1267 | 45 | C |
| ATOM | 749 | C | TYR | A | 245 | 8.498 | −96.575 | −75.147 | 1.00 | 54.37 | | C |
| ANISOU | 749 | C | TYR | A | 245 | 5856 | 6110 | 8693 | −212 | 993 | −149 | C |
| ATOM | 750 | O | TYR | A | 245 | 9.658 | −96.594 | −75.556 | 1.00 | 56.14 | | O |

TABLE 7-continued

DMXAA-hSTING$^{G230I}$ complex

| | | | | | | | | | | | | |
|---|---|---|---|---|---|---|---|---|---|---|---|---|
| ANISOU | 750 | O | TYR | A | 245 | 6204 | 6078 | 9050 | −87 | 958 | −190 | O |
| ATOM | 751 | N | GLU | A | 246 | | 7.492 | −97.170 | −75.765 | 1.00 | 56.22 | N |
| ANISOU | 751 | N | GLU | A | 246 | 5987 | 6504 | 8871 | −420 | 994 | −191 | N |
| ATOM | 752 | CA | GLU | A | 246 | | 7.652 | −97.872 | −77.011 | 1.00 | 49.56 | C |
| ANISOU | 752 | CA | GLU | A | 246 | 5209 | 5540 | 8084 | −508 | 940 | −304 | C |
| ATOM | 753 | CB | GLU | A | 246 | | 6.878 | −99.179 | −76.942 | 1.00 | 68.75 | C |
| ANISOU | 753 | CB | GLU | A | 246 | 7660 | 7954 | 10507 | −869 | 925 | −309 | C |
| ATOM | 754 | CG | GLU | A | 246 | | 6.783 | −99.964 | −78.227 | 1.00 | 89.25 | C |
| ANISOU | 754 | CG | GLU | A | 246 | 10325 | 10461 | 13123 | −1013 | 855 | −457 | C |
| ATOM | 755 | CD | GLU | A | 246 | | 5.777 | −101.091 | −78.101 | 1.00 | 101.26 | C |
| ANISOU | 755 | CD | GLU | A | 246 | 11815 | 12024 | 14635 | −1416 | 844 | −478 | C |
| ATOM | 756 | OE1 | GLU | A | 246 | | 5.414 | −101.693 | −79.133 | 1.00 | 101.76 | O |
| ANISOU | 756 | OE1 | GLU | A | 246 | 11895 | 12086 | 14686 | −1586 | 766 | −629 | O |
| ATOM | 757 | OE2 | GLU | A | 246 | | 5.356 | −101.362 | −76.960 | 1.00 | 103.92 | O |
| ANISOU | 757 | OE2 | GLU | A | 246 | 12122 | 12391 | 14973 | −1569 | 921 | −347 | O |
| ATOM | 758 | C | GLU | A | 246 | | 7.062 | −96.962 | −78.063 | 1.00 | 52.61 | C |
| ANISOU | 758 | C | GLU | A | 246 | 5411 | 6208 | 8371 | −364 | 933 | −393 | C |
| ATOM | 759 | O | GLU | A | 246 | | 6.003 | −96.373 | −77.857 | 1.00 | 54.05 | O |
| ANISOU | 759 | O | GLU | A | 246 | 5370 | 6734 | 8433 | −359 | 956 | −369 | O |
| ATOM | 760 | N | LEU | A | 247 | | 7.753 | −96.813 | −79.182 | 1.00 | 62.85 | N |
| ANISOU | 760 | N | LEU | A | 247 | 6808 | 7369 | 9705 | −213 | 915 | −483 | N |
| ATOM | 761 | CA | LEU | A | 247 | | 7.251 | −95.977 | −80.257 | 1.00 | 65.99 | C |
| ANISOU | 761 | CA | LEU | A | 247 | 7082 | 8013 | 9980 | −40 | 910 | −555 | C |
| ATOM | 762 | CB | LEU | A | 247 | | 8.272 | −94.914 | −80.637 | 1.00 | 59.12 | C |
| ANISOU | 762 | CB | LEU | A | 247 | 6299 | 7001 | 9161 | 288 | 994 | −545 | C |
| ATOM | 763 | CG | LEU | A | 247 | | 8.763 | −93.951 | −79.566 | 1.00 | 51.92 | C |
| ANISOU | 763 | CG | LEU | A | 247 | 5368 | 6045 | 8314 | 445 | 1069 | −450 | C |
| ATOM | 764 | CD1 | LEU | A | 247 | | 9.570 | −92.884 | −80.260 | 1.00 | 59.21 | C |
| ANISOU | 764 | CD1 | LEU | A | 247 | 6355 | 6858 | 9285 | 731 | 1164 | −467 | C |
| ATOM | 765 | CD2 | LEU | A | 247 | | 7.607 | −93.333 | −78.806 | 1.00 | 37.80 | C |
| ANISOU | 765 | CD2 | LEU | A | 247 | 3387 | 4591 | 6383 | 447 | 1086 | −390 | C |
| ATOM | 766 | C | LEU | A | 247 | | 6.959 | −96.825 | −81.473 | 1.00 | 71.10 | C |
| ANISOU | 766 | C | LEU | A | 247 | 7789 | 8653 | 10574 | −178 | 822 | −690 | C |
| ATOM | 767 | O | LEU | A | 247 | | 7.789 | −97.632 | −81.888 | 1.00 | 75.37 | O |
| ANISOU | 767 | O | LEU | A | 247 | 8555 | 8876 | 11208 | −229 | 817 | −743 | O |
| ATOM | 768 | N | LEU | A | 248 | | 5.786 | −96.636 | −82.057 | 1.00 | 50.61 | N |
| ANISOU | 768 | N | LEU | A | 248 | 7284 | 4303 | 7644 | 1327 | −1322 | −1910 | N |
| ATOM | 769 | CA | LEU | A | 248 | | 5.417 | −97.407 | −83.225 | 1.00 | 63.20 | C |
| ANISOU | 769 | CA | LEU | A | 248 | 8970 | 5788 | 9254 | 1408 | −1506 | −2095 | C |
| ATOM | 770 | CB | LEU | A | 248 | | 4.080 | −98.126 | −83.030 | 1.00 | 53.38 | C |
| ANISOU | 770 | CB | LEU | A | 248 | 7561 | 4367 | 8355 | 1396 | −1666 | −2195 | C |
| ATOM | 771 | CG | LEU | A | 248 | | 3.995 | −99.081 | −81.841 | 1.00 | 70.24 | C |
| ANISOU | 771 | CG | LEU | A | 248 | 9460 | 6444 | 10785 | 1325 | −1542 | −2118 | C |
| ATOM | 772 | CD1 | LEU | A | 248 | | 3.466 | −98.353 | −80.611 | 1.00 | 74.77 | C |
| ANISOU | 772 | CD1 | LEU | A | 248 | 9866 | 7062 | 11481 | 1228 | −1454 | −1983 | C |
| ATOM | 773 | CD2 | LEU | A | 248 | | 3.126 | −100.277 | −82.170 | 1.00 | 59.29 | C |
| ANISOU | 773 | CD2 | LEU | A | 248 | 7977 | 4870 | 9680 | 1350 | −1709 | −2263 | C |
| ATOM | 774 | C | LEU | A | 248 | | 5.374 | −96.533 | −84.460 | 1.00 | 66.39 | C |
| ANISOU | 774 | C | LEU | A | 248 | 9601 | 6239 | 9384 | 1468 | −1657 | −2170 | C |
| ATOM | 775 | O | LEU | A | 248 | | 5.017 | −95.353 | −84.403 | 1.00 | 56.00 | O |
| ANISOU | 775 | O | LEU | A | 248 | 8321 | 4967 | 7989 | 1445 | −1709 | −2109 | O |
| ATOM | 776 | N | GLU | A | 249 | | 5.763 | −97.123 | −85.578 | 1.00 | 54.63 | N |
| ANISOU | 776 | N | GLU | A | 249 | 8266 | 4743 | 7749 | 1540 | −1727 | −2303 | N |
| ATOM | 777 | CA | GLU | A | 249 | | 5.634 | −96.486 | −86.861 | 1.00 | 62.70 | C |
| ANISOU | 777 | CA | GLU | A | 249 | 9508 | 5802 | 8514 | 1590 | −1898 | −2391 | C |
| ATOM | 778 | CB | GLU | A | 249 | | 6.985 | −95.985 | −87.347 | 1.00 | 66.32 | C |
| ANISOU | 778 | CB | GLU | A | 249 | 10151 | 6441 | 8607 | 1609 | −1751 | −2322 | C |
| ATOM | 779 | CG | GLU | A | 249 | | 6.928 | −95.243 | −88.664 | 1.00 | 78.31 | C |
| ANISOU | 779 | CG | GLU | A | 249 | 11908 | 8025 | 9822 | 1644 | −1917 | −2385 | C |
| ATOM | 780 | CD | GLU | A | 249 | | 8.275 | −94.679 | −89.066 | 1.00 | 80.93 | C |
| ANISOU | 780 | CD | GLU | A | 249 | 12407 | 8548 | 9796 | 1649 | −1753 | −2293 | C |
| ATOM | 781 | OE1 | GLU | A | 249 | | 8.895 | −95.232 | −90.005 | 1.00 | 81.21 | O |
| ANISOU | 781 | OE1 | GLU | A | 249 | 12583 | 8641 | 9633 | 1699 | −1738 | −2407 | O |
| ATOM | 782 | OE2 | GLU | A | 249 | | 8.710 | −93.692 | −88.430 | 1.00 | 71.64 | O |
| ANISOU | 782 | OE2 | GLU | A | 249 | 11215 | 7464 | 8543 | 1601 | −1636 | −2113 | O |
| ATOM | 783 | C | GLU | A | 249 | | 5.113 | −97.566 | −87.775 | 1.00 | 62.38 | C |
| ANISOU | 783 | C | GLU | A | 249 | 9507 | 5637 | 8559 | 1651 | −2077 | −2604 | C |
| ATOM | 784 | O | GLU | A | 249 | | 5.775 | −98.583 | −87.952 | 1.00 | 66.38 | O |
| ANISOU | 784 | O | GLU | A | 249 | 10018 | 6135 | 9070 | 1686 | −1987 | −2679 | O |
| ATOM | 785 | N | ASN | A | 250 | | 3.917 | −97.366 | −88.322 | 1.00 | 68.95 | N |
| ANISOU | 785 | N | ASN | A | 250 | 10356 | 6361 | 9480 | 1662 | −2333 | −2705 | N |
| ATOM | 786 | CA | ASN | A | 250 | | 3.277 | −98.359 | −89.181 | 1.00 | 61.19 | C |
| ANISOU | 786 | CA | ASN | A | 250 | 9405 | 5244 | 8601 | 1714 | −2535 | −2916 | C |
| ATOM | 787 | CB | ASN | A | 250 | | 4.117 | −98.620 | −90.431 | 1.00 | 83.15 | C |
| ANISOU | 787 | CB | ASN | A | 250 | 12422 | 8120 | 11050 | 1776 | −2544 | −3038 | C |
| ATOM | 788 | CG | ASN | A | 250 | | 4.124 | −97.448 | −91.382 | 1.00 | 86.63 | C |
| ANISOU | 788 | CG | ASN | A | 250 | 13086 | 8675 | 11153 | 1779 | −2670 | −3017 | C |
| ATOM | 789 | OD1 | ASN | A | 250 | | 3.082 | −96.863 | −91.657 | 1.00 | 92.92 | O |

TABLE 7-continued

DMXAA-hSTING$^{G230I}$ complex

| | | | | | | | | | | | |
|---|---|---|---|---|---|---|---|---|---|---|---|
| ANISOU | 789 | OD1 | ASN | A | 250 | 13894 | 9400 | 12014 | 1765 | −2895 | −3029 O |
| ATOM | 790 | ND2 | ASN | A | 250 | 5.304 | −97.086 | −91.878 | 1.00 | 87.05 | N |
| ANISOU | 790 | ND2 | ASN | A | 250 | 13313 | 8907 | 10856 | 1792 | −2527 | −2975 N |
| ATOM | 791 | C | ASN | A | 250 | 2.972 | −99.672 | −88.461 | 1.00 | 61.23 | C |
| ANISOU | 791 | C | ASN | A | 250 | 9195 | 5102 | 8968 | 1706 | −2492 | −2968 C |
| ATOM | 792 | O | ASN | A | 250 | 3.009 | −100.744 | −89.063 | 1.00 | 62.74 | O |
| ANISOU | 792 | O | ASN | A | 250 | 9413 | 5211 | 9213 | 1756 | −2560 | −3133 O |
| ATOM | 793 | N | GLY | A | 251 | 2.673 | −99.573 | −87.168 | 1.00 | 66.76 | N |
| ANISOU | 793 | N | GLY | A | 251 | 9679 | 5772 | 9913 | 1639 | −2379 | −2825 N |
| ATOM | 794 | CA | GLY | A | 251 | 2.377 | −100.730 | −86.346 | 1.00 | 64.09 | C |
| ANISOU | 794 | CA | GLY | A | 251 | 9119 | 5306 | 9925 | 1611 | −2329 | −2831 C |
| ATOM | 795 | C | GLY | A | 251 | 3.636 | −101.509 | −86.021 | 1.00 | 67.33 | C |
| ANISOU | 795 | C | GLY | A | 251 | 9515 | 5773 | 10293 | 1619 | −2108 | −2786 C |
| ATOM | 796 | O | GLY | A | 251 | 3.580 | −102.656 | −85.578 | 1.00 | 59.53 | O |
| ANISOU | 796 | O | GLY | A | 251 | 8376 | 4671 | 9571 | 1609 | −2080 | −2812 O |
| ATOM | 797 | N | GLN | A | 252 | 4.777 | −100.865 | −86.180 | 1.00 | 65.92 | N |
| ANISOU | 797 | N | GLN | A | 252 | 9486 | 5767 | 9794 | 1633 | −1953 | −2710 N |
| ATOM | 798 | CA | GLN | A | 252 | 6.064 | −101.531 | −86.188 | 1.00 | 65.93 | C |
| ANISOU | 798 | CA | GLN | A | 252 | 9510 | 5826 | 9713 | 1660 | −1765 | −2699 C |
| ATOM | 799 | CB | GLN | A | 252 | 6.737 | −101.346 | −87.536 | 1.00 | 69.09 | C |
| ANISOU | 799 | CB | GLN | A | 252 | 10162 | 6317 | 9773 | 1741 | −1799 | −2838 C |
| ATOM | 800 | CG | GLN | A | 252 | 6.625 | −102.478 | −88.537 | 1.00 | 67.68 | C |
| ANISOU | 800 | CG | GLN | A | 252 | 10027 | 6021 | 9669 | 1816 | −1920 | −3079 C |
| ATOM | 801 | CD | GLN | A | 252 | 5.384 | −103.310 | −88.378 | 1.00 | 87.92 | C |
| ANISOU | 801 | CD | GLN | A | 252 | 12457 | 8377 | 12570 | 1809 | −2141 | −3187 C |
| ATOM | 802 | OE1 | GLN | A | 252 | 5.322 | −104.179 | −87.540 | 1.00 | 97.73 | O |
| ANISOU | 802 | OE1 | GLN | A | 252 | 13490 | 9495 | 14148 | 1776 | −2103 | −3148 O |
| ATOM | 803 | NE2 | GLN | A | 252 | 4.398 | −103.058 | −89.199 | 1.00 | 88.08 | N |
| ANISOU | 803 | NE2 | GLN | A | 252 | 12597 | 8360 | 12510 | 1834 | −2380 | −3315 N |
| ATOM | 804 | C | GLN | A | 252 | 7.020 | −101.031 | −85.137 | 1.00 | 65.63 | C |
| ANISOU | 804 | C | GLN | A | 252 | 9409 | 5925 | 9604 | 1599 | −1508 | −2474 C |
| ATOM | 805 | O | GLN | A | 252 | 6.782 | −100.044 | −84.498 | 1.00 | 54.80 | O |
| ANISOU | 805 | O | GLN | A | 252 | 8018 | 4635 | 8168 | 1541 | −1464 | −2332 O |
| ATOM | 806 | N | ARG | A | 253 | 8.057 | −101.820 | −84.901 | 1.00 | 70.21 | N |
| ANISOU | 806 | N | ARG | A | 253 | 9946 | 6515 | 10215 | 1612 | −1348 | −2452 N |
| ATOM | 807 | CA | ARG | A | 253 | 9.374 | −101.358 | −84.511 | 1.00 | 68.31 | C |
| ANISOU | 807 | CA | ARG | A | 253 | 9743 | 6435 | 9778 | 1591 | −1114 | −2293 C |
| ATOM | 808 | CB | ARG | A | 253 | 10.072 | −100.715 | −85.693 | 1.00 | 80.53 | C |
| ANISOU | 808 | CB | ARG | A | 253 | 11539 | 8109 | 10951 | 1665 | −1113 | −2384 C |
| ATOM | 809 | CG | ARG | A | 253 | 11.452 | −101.249 | −85.953 | 1.00 | 85.88 | C |
| ANISOU | 809 | CG | ARG | A | 253 | 12258 | 8865 | 11508 | 1703 | −922 | −2378 C |
| ATOM | 810 | CD | ARG | A | 253 | 12.140 | −100.483 | −87.045 | 1.00 | 90.46 | C |
| ANISOU | 810 | CD | ARG | A | 253 | 13078 | 9605 | 11688 | 1752 | −902 | −2428 C |
| ATOM | 811 | NE | ARG | A | 253 | 11.212 | −100.203 | −88.116 | 1.00 | 103.68 | N |
| ANISOU | 811 | NE | ARG | A | 253 | 14899 | 11248 | 13247 | 1790 | −1133 | −2594 N |
| ATOM | 812 | CZ | ARG | A | 253 | 11.335 | −99.208 | −88.985 | 1.00 | 112.47 | C |
| ANISOU | 812 | CZ | ARG | A | 253 | 16200 | 12488 | 14044 | 1790 | −1193 | −2575 C |
| ATOM | 813 | NH1 | ARG | A | 253 | 10.435 | −99.032 | −89.942 | 1.00 | 116.05 | N |
| ANISOU | 813 | NH1 | ARG | A | 253 | 16715 | 13105 | 14273 | 1757 | −1031 | −2400 N |
| ATOM | 814 | NH2 | ARG | A | 253 | 12.370 | −98.400 | −88.907 | 1.00 | 111.39 | N |
| ANISOU | 814 | NH2 | ARG | A | 253 | 16189 | 12311 | 13823 | 1818 | −1424 | −2721 N |
| ATOM | 815 | C | ARG | A | 253 | 9.225 | −100.540 | −83.242 | 1.00 | 68.11 | C |
| ANISOU | 815 | C | ARG | A | 253 | 9601 | 6490 | 9787 | 1489 | −999 | −2062 C |
| ATOM | 816 | O | ARG | A | 253 | 8.715 | −101.110 | −82.295 | 1.00 | 77.18 | O |
| ANISOU | 816 | O | ARG | A | 253 | 10549 | 7559 | 11218 | 1422 | −968 | −1983 O |
| ATOM | 817 | N | ALA | A | 254 | 9.558 | −99.248 | −83.174 | 1.00 | 60.53 | N |
| ANISOU | 817 | N | ALA | A | 254 | 8745 | 5680 | 8572 | 1464 | −933 | −1950 N |
| ATOM | 818 | CA | ALA | A | 254 | 10.476 | −98.491 | −83.983 | 1.00 | 51.67 | C |
| ANISOU | 818 | CA | ALA | A | 254 | 7844 | 4702 | 7088 | 1512 | −896 | −1956 C |
| ATOM | 819 | CB | ALA | A | 254 | 9.738 | −97.522 | −84.860 | 1.00 | 52.21 | C |
| ANISOU | 819 | CB | ALA | A | 254 | 8049 | 4782 | 7008 | 1530 | −1086 | −2021 C |
| ATOM | 820 | C | ALA | A | 254 | 11.462 | −97.776 | −83.143 | 1.00 | 49.89 | C |
| ANISOU | 820 | C | ALA | A | 254 | 7594 | 4622 | 6742 | 1451 | −679 | −1742 C |
| ATOM | 821 | O | ALA | A | 254 | 12.436 | −97.296 | −83.637 | 1.00 | 75.75 | O |
| ANISOU | 821 | O | ALA | A | 254 | 11010 | 8027 | 11475 | 1475 | −580 | −1698 O |
| ATOM | 822 | N | GLY | A | 255 | 11.158 | −97.669 | −81.866 | 1.00 | 52.73 | N |
| ANISOU | 822 | N | GLY | A | 255 | 7768 | 4960 | 7307 | 1364 | −607 | −1607 N |
| ATOM | 823 | CA | GLY | A | 255 | 12.022 | −97.059 | −80.899 | 1.00 | 49.18 | C |
| ANISOU | 823 | CA | GLY | A | 255 | 7274 | 4640 | 6774 | 1291 | −413 | −1401 C |
| ATOM | 824 | C | GLY | A | 255 | 11.620 | −97.436 | −79.506 | 1.00 | 49.13 | C |
| ANISOU | 824 | C | GLY | A | 255 | 7043 | 4592 | 7033 | 1191 | −345 | −1283 C |
| ATOM | 825 | O | GLY | A | 255 | 10.499 | −97.792 | −79.263 | 1.00 | 46.52 | O |
| ANISOU | 825 | O | GLY | A | 255 | 6596 | 4150 | 6929 | 1168 | −460 | −1345 O |
| ATOM | 826 | N | THR | A | 256 | 12.559 | −97.318 | −78.594 | 1.00 | 48.50 | N |
| ANISOU | 826 | N | THR | A | 256 | 6901 | 4610 | 6919 | 1126 | −156 | −1106 N |
| ATOM | 827 | CA | THR | A | 256 | 12.338 | −97.524 | −77.181 | 1.00 | 47.91 | C |
| ANISOU | 827 | CA | THR | A | 256 | 6626 | 4536 | 7040 | 1011 | −67 | −963 C |
| ATOM | 828 | CB | THR | A | 256 | 12.829 | −98.910 | −76.737 | 1.00 | 59.52 | C |

TABLE 7-continued

DMXAA-hSTING$^{G230I}$ complex

| | | | | | | | | | | | |
|---|---|---|---|---|---|---|---|---|---|---|---|
| ANISOU | 828 | CB | THR | A | 256 | 7965 | 5933 | 8718 | 992 | 1 | −916 C |
| ATOM | 829 | OG1 | THR | A | 256 | 12.020 | −99.934 | −77.332 | 1.00 | 78.80 | O |
| ANISOU | 829 | OG1 | THR | A | 256 | 10364 | 8208 | 11369 | 1049 | −152 | −1083 O |
| ATOM | 830 | CG2 | THR | A | 256 | 12.765 | −99.038 | −75.241 | 1.00 | 52.86 | C |
| ANISOU | 830 | CG2 | THR | A | 256 | 6929 | 5123 | 8030 | 855 | 108 | −731 C |
| ATOM | 831 | C | THR | A | 256 | 13.165 | −96.444 | −76.499 | 1.00 | 50.47 | C |
| ANISOU | 831 | C | THR | A | 256 | 6983 | 5025 | 7167 | 946 | 87 | −788 C |
| ATOM | 832 | O | THR | A | 256 | 14.373 | −96.349 | −76.726 | 1.00 | 56.24 | O |
| ANISOU | 832 | O | THR | A | 256 | 7800 | 5838 | 7728 | 969 | 197 | −719 O |
| ATOM | 833 | N | CYS | A | 257 | 12.531 | −95.604 | −75.692 | 1.00 | 45.32 | N |
| ANISOU | 833 | N | CYS | A | 257 | 6261 | 4420 | 6538 | 866 | 96 | −727 N |
| ATOM | 834 | CA | CYS | A | 257 | 13.264 | −94.498 | −75.098 | 1.00 | 40.42 | C |
| ANISOU | 834 | CA | CYS | A | 257 | 5682 | 3950 | 5728 | 806 | 226 | −581 C |
| ATOM | 835 | CB | CYS | A | 257 | 13.315 | −93.305 | −76.062 | 1.00 | 40.41 | C |
| ANISOU | 835 | CB | CYS | A | 257 | 5872 | 3997 | 5486 | 876 | 151 | −642 C |
| ATOM | 836 | SG | CYS | A | 257 | 11.737 | −92.410 | −76.245 | 1.00 | 72.72 | S |
| ANISOU | 836 | SG | CYS | A | 257 | 9955 | 8021 | 9656 | 882 | −30 | −767 S |
| ATOM | 837 | C | CYS | A | 257 | 12.694 | −94.067 | −73.756 | 1.00 | 47.88 | C |
| ANISOU | 837 | C | CYS | A | 257 | 6469 | 4941 | 6781 | 683 | 289 | −489 C |
| ATOM | 838 | O | CYS | A | 257 | 11.531 | −94.324 | −73.444 | 1.00 | 58.45 | O |
| ANISOU | 838 | O | CYS | A | 257 | 7690 | 6201 | 8316 | 654 | 210 | −560 O |
| ATOM | 839 | N | VAL | A | 258 | 13.534 | −93.413 | −72.961 | 1.00 | 38.95 | N |
| ANISOU | 839 | N | VAL | A | 258 | 5335 | 3943 | 5520 | 607 | 435 | −333 N |
| ATOM | 840 | CA | VAL | A | 258 | 13.090 | −92.801 | −71.721 | 1.00 | 37.87 | C |
| ANISOU | 840 | CA | VAL | A | 258 | 5075 | 3881 | 5433 | 488 | 507 | −256 C |
| ATOM | 841 | CB | VAL | A | 258 | 14.215 | −92.703 | −70.696 | 1.00 | 49.08 | C |
| ANISOU | 841 | CB | VAL | A | 258 | 6453 | 5432 | 6763 | 386 | 683 | −59 C |
| ATOM | 842 | CG2 | VAL | A | 258 | 14.720 | −94.092 | −70.335 | 1.00 | 42.74 | C |
| ANISOU | 842 | CG2 | VAL | A | 258 | 5549 | 4589 | 6101 | 352 | 738 | 31 C |
| ATOM | 843 | CG1 | VAL | A | 258 | 13.737 | −91.958 | −69.458 | 1.00 | 41.05 | C |
| ANISOU | 843 | CG1 | VAL | A | 258 | 5325 | 4508 | 5764 | 261 | 757 | −3 C |
| ATOM | 844 | C | VAL | A | 258 | 12.575 | −91.413 | −72.041 | 1.00 | 37.64 | C |
| ANISOU | 844 | C | VAL | A | 258 | 5133 | 3878 | 5289 | 516 | 438 | −332 C |
| ATOM | 845 | O | VAL | A | 258 | 13.303 | −90.582 | −72.590 | 1.00 | 37.22 | O |
| ANISOU | 845 | O | VAL | A | 258 | 5230 | 3886 | 5026 | 561 | 446 | −305 O |
| ATOM | 846 | N | LEU | A | 259 | 11.320 | −91.164 | −71.680 | 1.00 | 52.37 | N |
| ANISOU | 846 | N | LEU | A | 259 | 6893 | 5696 | 7309 | 486 | 369 | −422 N |
| ATOM | 847 | CA | LEU | A | 259 | 10.568 | −90.044 | −72.223 | 1.00 | 38.24 | C |
| ANISOU | 847 | CA | LEU | A | 259 | 5173 | 3874 | 5482 | 538 | 248 | −536 C |
| ATOM | 848 | CB | LEU | A | 259 | 9.706 | −90.554 | −73.378 | 1.00 | 39.42 | C |
| ANISOU | 848 | CB | LEU | A | 259 | 5368 | 3875 | 5735 | 643 | 54 | −697 C |
| ATOM | 849 | CG | LEU | A | 259 | 8.977 | −89.616 | −74.331 | 1.00 | 53.35 | C |
| ANISOU | 849 | CG | LEU | A | 259 | 7238 | 5572 | 7460 | 724 | −126 | −821 C |
| ATOM | 850 | CD1 | LEU | A | 259 | 9.952 | −88.891 | −75.223 | 1.00 | 56.32 | C |
| ANISOU | 850 | CD1 | LEU | A | 259 | 7825 | 6009 | 7564 | 786 | −142 | −777 C |
| ATOM | 851 | CD2 | LEU | A | 259 | 8.019 | −90.435 | −75.175 | 1.00 | 49.92 | C |
| ANISOU | 851 | CD2 | LEU | A | 259 | 6795 | 4988 | 7186 | 796 | −305 | −969 C |
| ATOM | 852 | C | LEU | A | 259 | 9.683 | −89.405 | −71.159 | 1.00 | 42.59 | C |
| ANISOU | 852 | C | LEU | A | 259 | 5572 | 4457 | 6154 | 448 | 286 | −557 C |
| ATOM | 853 | O | LEU | A | 259 | 8.977 | −90.102 | −70.437 | 1.00 | 50.93 | O |
| ANISOU | 853 | O | LEU | A | 259 | 6459 | 5487 | 7404 | 380 | 315 | −570 O |
| ATOM | 854 | N | GLU | A | 260 | 9.708 | −88.082 | −71.058 | 1.00 | 37.71 | N |
| ANISOU | 854 | N | GLU | A | 260 | 5007 | 3893 | 5429 | 443 | 288 | −563 N |
| ATOM | 855 | CA | GLU | A | 260 | 8.866 | −87.404 | −70.083 | 1.00 | 57.14 | C |
| ANISOU | 855 | CA | GLU | A | 260 | 7322 | 6384 | 8006 | 364 | 328 | −610 C |
| ATOM | 856 | CB | GLU | A | 260 | 9.445 | −87.537 | −68.673 | 1.00 | 37.08 | C |
| ANISOU | 856 | CB | GLU | A | 260 | 4670 | 3987 | 5432 | 225 | 533 | −477 C |
| ATOM | 857 | CG | GLU | A | 260 | 10.743 | −86.792 | −68.432 | 1.00 | 49.66 | C |
| ANISOU | 857 | CG | GLU | A | 260 | 6373 | 5703 | 6791 | 196 | 639 | −346 C |
| ATOM | 858 | CD | GLU | A | 260 | 11.408 | −87.203 | −67.124 | 1.00 | 69.53 | C |
| ANISOU | 858 | CD | GLU | A | 260 | 8788 | 8356 | 9274 | 56 | 825 | −196 C |
| ATOM | 859 | OE1 | GLU | A | 260 | 11.289 | −88.393 | −66.741 | 1.00 | 69.55 | O |
| ANISOU | 859 | OE1 | GLU | A | 260 | 8687 | 8347 | 9392 | 7 | 864 | −147 O |
| ATOM | 860 | OE2 | GLU | A | 260 | 12.031 | −86.331 | −66.479 | 1.00 | 78.26 | O |
| ANISOU | 860 | OE2 | GLU | A | 260 | 9915 | 9576 | 10243 | −9 | 921 | −126 O |
| ATOM | 861 | C | GLU | A | 260 | 8.607 | −85.938 | −70.419 | 1.00 | 49.86 | C |
| ANISOU | 861 | C | GLU | A | 260 | 6475 | 5451 | 7018 | 405 | 247 | −678 C |
| ATOM | 862 | O | GLU | A | 260 | 9.412 | −85.282 | −71.081 | 1.00 | 53.54 | O |
| ANISOU | 862 | O | GLU | A | 260 | 7107 | 5941 | 7294 | 457 | 216 | −627 O |
| ATOM | 863 | N | TYR | A | 261 | 7.465 | −85.440 | −69.962 | 1.00 | 40.46 | N |
| ANISOU | 863 | N | TYR | A | 261 | 5152 | 4220 | 6001 | 380 | 211 | −793 N |
| ATOM | 864 | CA | TYR | A | 261 | 7.144 | −84.027 | −70.083 | 1.00 | 41.00 | C |
| ANISOU | 864 | CA | TYR | A | 261 | 5253 | 4270 | 6054 | 407 | 142 | −863 C |
| ATOM | 865 | CB | TYR | A | 261 | 5.662 | −83.785 | −69.851 | 1.00 | 39.58 | C |
| ANISOU | 865 | CB | TYR | A | 261 | 4912 | 3997 | 6132 | 408 | 60 | −1026 C |
| ATOM | 866 | CG | TYR | A | 261 | 4.799 | −84.140 | −71.026 | 1.00 | 67.12 | C |
| ANISOU | 866 | CG | TYR | A | 261 | 8437 | 7318 | 9747 | 514 | −161 | −1135 C |
| ATOM | 867 | CD1 | TYR | A | 261 | 4.609 | −83.233 | −72.064 | 1.00 | 41.08 | C |

TABLE 7-continued

DMXAA-hSTING$^{G230I}$ complex

| | | | | | | | | | | | | |
|---|---|---|---|---|---|---|---|---|---|---|---|---|
| ANISOU | 867 | CD1 | TYR | A | 261 | 5267 | 3927 | 6413 | 607 | −351 | −1188 | C |
| ATOM | 868 | CE1 | TYR | A | 261 | 3.826 | −83.546 | −73.147 | 1.00 | 46.60 | | C |
| ANISOU | 868 | CE1 | TYR | A | 261 | 6009 | 4481 | 7217 | 696 | −566 | −1282 | C |
| ATOM | 869 | CZ | TYR | A | 261 | 3.220 | −84.791 | −73.209 | 1.00 | 47.70 | | C |
| ANISOU | 869 | CZ | TYR | A | 261 | 6059 | 4558 | 7509 | 698 | −592 | −1334 | C |
| ATOM | 870 | OH | TYR | A | 261 | 2.435 | −85.114 | −74.289 | 1.00 | 47.41 | | O |
| ANISOU | 870 | OH | TYR | A | 261 | 6065 | 4373 | 7577 | 783 | −817 | −1433 | O |
| ATOM | 871 | CE2 | TYR | A | 261 | 3.402 | −85.717 | −72.192 | 1.00 | 51.22 | | C |
| ANISOU | 871 | CE2 | TYR | A | 261 | 6370 | 5085 | 8005 | 609 | −405 | −1279 | C |
| ATOM | 872 | CD2 | TYR | A | 261 | 4.184 | −85.386 | −71.111 | 1.00 | 41.20 | | C |
| ANISOU | 872 | CD2 | TYR | A | 261 | 5063 | 3969 | 6622 | 515 | −193 | −1176 | C |
| ATOM | 873 | C | TYR | A | 261 | 7.929 | −83.193 | −69.090 | 1.00 | 37.67 | | C |
| ANISOU | 873 | C | TYR | A | 261 | 4821 | 3991 | 5500 | 318 | 306 | −775 | C |
| ATOM | 874 | O | TYR | A | 261 | 8.149 | −83.610 | −67.954 | 1.00 | 41.68 | | O |
| ANISOU | 874 | O | TYR | A | 261 | 5213 | 4608 | 6014 | 208 | 477 | −713 | O |
| ATOM | 875 | N | ALA | A | 262 | 8.338 | −82.004 | −69.517 | 1.00 | 43.51 | | N |
| ANISOU | 875 | N | ALA | A | 262 | 5680 | 4729 | 6122 | 359 | 246 | −765 | N |
| ATOM | 876 | CA | ALA | A | 262 | 8.974 | −81.065 | −68.614 | 1.00 | 37.57 | | C |
| ANISOU | 876 | CA | ALA | A | 262 | 4916 | 4093 | 5267 | 280 | 377 | −707 | C |
| ATOM | 877 | CB | ALA | A | 262 | 9.635 | −79.928 | −69.378 | 1.00 | 36.69 | | C |
| ANISOU | 877 | CB | ALA | A | 262 | 4975 | 3961 | 5003 | 341 | 284 | −661 | C |
| ATOM | 878 | C | ALA | A | 262 | 7.918 | −80.527 | −67.660 | 1.00 | 46.72 | | C |
| ANISOU | 878 | C | ALA | A | 262 | 5887 | 5251 | 6613 | 221 | 418 | −845 | C |
| ATOM | 879 | O | ALA | A | 262 | 6.958 | −79.880 | −68.079 | 1.00 | 38.37 | | O |
| ANISOU | 879 | O | ALA | A | 262 | 4794 | 4076 | 5709 | 282 | 278 | −983 | O |
| ATOM | 880 | N | THR | A | 263 | 8.105 | −80.801 | −66.374 | 1.00 | 35.15 | | N |
| ANISOU | 880 | N | THR | A | 263 | 5895 | 2823 | 4636 | −587 | 750 | −531 | N |
| ATOM | 881 | CA | THR | A | 263 | 7.187 | −80.360 | −65.329 | 1.00 | 32.79 | | C |
| ANISOU | 881 | CA | THR | A | 263 | 5520 | 2526 | 4413 | −679 | 858 | −542 | C |
| ATOM | 882 | CB | THR | A | 263 | 7.637 | −80.873 | −63.949 | 1.00 | 40.95 | | C |
| ANISOU | 882 | CB | THR | A | 263 | 6718 | 3485 | 5357 | −581 | 995 | −424 | C |
| ATOM | 883 | OG1 | THR | A | 263 | 8.964 | −80.417 | −63.674 | 1.00 | 50.25 | | O |
| ANISOU | 883 | OG1 | THR | A | 263 | 7938 | 4709 | 6446 | −336 | 891 | −336 | O |
| ATOM | 884 | CG2 | THR | A | 263 | 7.627 | −82.387 | −63.945 | 1.00 | 26.95 | | C |
| ANISOU | 884 | CG2 | THR | A | 263 | 5102 | 1599 | 3538 | −666 | 1112 | −400 | C |
| ATOM | 885 | C | THR | A | 263 | 6.883 | −78.853 | −65.249 | 1.00 | 35.95 | | C |
| ANISOU | 885 | C | THR | A | 263 | 5671 | 3107 | 4881 | −593 | 751 | −542 | C |
| ATOM | 886 | O | THR | A | 263 | 5.768 | −78.488 | −64.874 | 1.00 | 53.48 | | O |
| ANISOU | 886 | O | THR | A | 263 | 7716 | 5425 | 7180 | −696 | 795 | −584 | O |
| ATOM | 887 | N | PRO | A | 264 | 7.862 | −77.972 | −65.570 | 1.00 | 35.75 | | N |
| ANISOU | 887 | N | PRO | A | 264 | 5606 | 3131 | 4845 | −396 | 623 | −483 | N |
| ATOM | 888 | CA | PRO | A | 264 | 7.516 | −76.556 | −65.415 | 1.00 | 25.13 | | C |
| ANISOU | 888 | CA | PRO | A | 264 | 4021 | 1933 | 3596 | −315 | 540 | −477 | C |
| ATOM | 889 | CB | PRO | A | 264 | 8.826 | −75.841 | −65.726 | 1.00 | 34.16 | | C |
| ANISOU | 889 | CB | PRO | A | 264 | 5168 | 3055 | 4757 | −116 | 437 | −400 | C |
| ATOM | 890 | CG | PRO | A | 264 | 9.877 | −76.821 | −65.342 | 1.00 | 32.72 | | C |
| ANISOU | 890 | CG | PRO | A | 264 | 5238 | 2725 | 4471 | −60 | 492 | −362 | C |
| ATOM | 891 | CD | PRO | A | 264 | 9.314 | −78.139 | −65.771 | 1.00 | 30.82 | | C |
| ANISOU | 891 | CD | PRO | A | 264 | 5140 | 2415 | 4156 | −228 | 581 | −409 | C |
| ATOM | 892 | C | PRO | A | 264 | 6.433 | −76.066 | −66.372 | 1.00 | 28.16 | | C |
| ANISOU | 892 | C | PRO | A | 264 | 4169 | 2480 | 4052 | −403 | 462 | −535 | C |
| ATOM | 893 | O | PRO | A | 264 | 5.874 | −74.988 | −66.165 | 1.00 | 37.68 | | O |
| ANISOU | 893 | O | PRO | A | 264 | 5171 | 3800 | 5346 | −353 | 424 | −533 | O |
| ATOM | 894 | N | LEU | A | 265 | 6.159 | −76.822 | −67.425 | 1.00 | 35.30 | | N |
| ANISOU | 894 | N | LEU | A | 265 | 5100 | 3401 | 4910 | −509 | 425 | −596 | N |
| ATOM | 895 | CA | LEU | A | 265 | 5.080 | −76.452 | −68.332 | 1.00 | 46.00 | | C |
| ANISOU | 895 | CA | LEU | A | 265 | 6226 | 4945 | 6307 | −580 | 326 | −673 | C |
| ATOM | 896 | CB | LEU | A | 265 | 5.082 | −77.311 | −69.588 | 1.00 | 36.83 | | C |
| ANISOU | 896 | CB | LEU | A | 265 | 5139 | 3802 | 5053 | −647 | 248 | −764 | C |
| ATOM | 897 | CG | LEU | A | 265 | 6.321 | −77.225 | −70.467 | 1.00 | 41.47 | | C |
| ANISOU | 897 | CG | LEU | A | 265 | 5865 | 4364 | 5529 | −459 | 184 | −678 | C |
| ATOM | 898 | CD1 | LEU | A | 265 | 6.036 | −77.958 | −71.741 | 1.00 | 51.11 | | C |
| ANISOU | 898 | CD1 | LEU | A | 265 | 7124 | 5658 | 6636 | −514 | 91 | −806 | C |
| ATOM | 899 | CD2 | LEU | A | 265 | 6.727 | −75.780 | −70.770 | 1.00 | 25.97 | | C |
| ANISOU | 899 | CD2 | LEU | A | 265 | 3749 | 2510 | 3607 | −243 | 114 | −533 | C |
| ATOM | 900 | C | LEU | A | 265 | 3.740 | −76.575 | −67.609 | 1.00 | 43.44 | | C |
| ANISOU | 900 | C | LEU | A | 265 | 5748 | 4678 | 6079 | −756 | 411 | −756 | C |
| ATOM | 901 | O | LEU | A | 265 | 2.800 | −75.829 | −67.887 | 1.00 | 47.75 | | O |
| ANISOU | 901 | O | LEU | A | 265 | 6037 | 5407 | 6699 | −759 | 341 | −791 | O |
| ATOM | 902 | N | GLN | A | 266 | 3.653 | −77.533 | −66.691 | 1.00 | 38.33 | | N |
| ANISOU | 902 | N | GLN | A | 266 | 5255 | 3873 | 5434 | −889 | 579 | −770 | N |
| ATOM | 903 | CA | GLN | A | 266 | 2.468 | −77.680 | −65.849 | 1.00 | 41.70 | | C |
| ANISOU | 903 | CA | GLN | A | 266 | 5549 | 4332 | 5963 | −1047 | 719 | −813 | C |
| ATOM | 904 | C | GLN | A | 266 | 2.248 | −76.399 | −65.077 | 1.00 | 50.69 | | C |
| ANISOU | 904 | C | GLN | A | 266 | 6533 | 5587 | 7141 | −893 | 725 | −751 | C |
| ATOM | 905 | O | GLN | A | 266 | 1.128 | −75.893 | −64.974 | 1.00 | 45.72 | | O |
| ANISOU | 905 | O | GLN | A | 266 | 5651 | 5107 | 6612 | −948 | 738 | −798 | O |
| ATOM | 906 | CB | GLN | A | 266 | 2.617 | −78.825 | −64.853 | 1.00 | 32.58 | | C |

TABLE 7-continued

DMXAA-hSTING$^{G230I}$ complex

| | | | | | | | | | | | |
|---|---|---|---|---|---|---|---|---|---|---|---|
| ANISOU | 906 | CB | GLN | A | 266 | 4631 | 2961 | 4785 | −1154 | 943 | −776 C |
| ATOM | 907 | CG | GLN | A | 266 | 2.163 | −80.177 | −65.355 | 1.00 | 46.50 | C |
| ANISOU | 907 | CG | GLN | A | 266 | 6465 | 4594 | 6611 | −1406 | 1013 | −879 C |
| ATOM | 908 | CD | GLN | A | 266 | 2.512 | −81.291 | −64.382 | 1.00 | 56.89 | C |
| ANISOU | 908 | CD | GLN | A | 266 | 8067 | 5649 | 7899 | −1464 | 1259 | −793 C |
| ATOM | 909 | OE1 | GLN | A | 266 | 1.787 | −81.532 | −63.421 | 1.00 | 59.31 | O |
| ANISOU | 909 | OE1 | GLN | A | 266 | 8626 | 5804 | 8106 | −1393 | 1253 | −753 O |
| ATOM | 910 | NE2 | GLN | A | 266 | 3.615 | −81.994 | −64.644 | 1.00 | 50.56 | N |
| ANISOU | 910 | NE2 | GLN | A | 266 | 7217 | 4827 | 7166 | −1544 | 1479 | −733 N |
| ATOM | 911 | N | THR | A | 267 | 3.341 | −75.889 | −64.524 | 1.00 | 36.15 | N |
| ANISOU | 911 | N | THR | A | 267 | 4838 | 3669 | 5230 | −695 | 712 | −663 N |
| ATOM | 912 | CA | THR | A | 267 | 3.303 | −74.644 | −63.789 | 1.00 | 33.16 | C |
| ANISOU | 912 | CA | THR | A | 267 | 4342 | 3365 | 4891 | −532 | 700 | −635 C |
| ATOM | 913 | CB | THR | A | 267 | 4.624 | −74.358 | −63.088 | 1.00 | 27.38 | C |
| ANISOU | 913 | CB | THR | A | 267 | 3802 | 2517 | 4085 | −345 | 681 | −577 C |
| ATOM | 914 | OG1 | THR | A | 267 | 4.835 | −75.338 | −62.072 | 1.00 | 28.48 | O |
| ANISOU | 914 | OG1 | THR | A | 267 | 4168 | 2544 | 4108 | −376 | 838 | −553 O |
| ATOM | 915 | CG2 | THR | A | 267 | 4.601 | −72.954 | −62.467 | 1.00 | 22.52 | C |
| ANISOU | 915 | CG2 | THR | A | 267 | 3046 | 1967 | 3542 | −176 | 632 | −593 C |
| ATOM | 916 | C | THR | A | 267 | 2.894 | −73.465 | −64.677 | 1.00 | 24.06 | C |
| ANISOU | 916 | C | THR | A | 267 | 2932 | 2371 | 3839 | −448 | 547 | −643 C |
| ATOM | 917 | O | THR | A | 267 | 2.053 | −72.659 | −64.291 | 1.00 | 35.64 | O |
| ANISOU | 917 | O | THR | A | 267 | 4202 | 3949 | 5390 | −412 | 568 | −666 O |
| ATOM | 918 | N | LEU | A | 268 | 3.485 | −73.368 | −65.864 | 1.00 | 27.55 | N |
| ANISOU | 918 | N | LEU | A | 268 | 3384 | 2823 | 4262 | −395 | 410 | −611 N |
| ATOM | 919 | CA | LEU | A | 268 | 3.108 | −72.323 | −66.814 | 1.00 | 30.13 | C |
| ANISOU | 919 | CA | LEU | A | 268 | 3491 | 3300 | 4659 | −289 | 280 | −584 C |
| ATOM | 920 | CB | LEU | A | 268 | 3.935 | −72.390 | −68.107 | 1.00 | 22.85 | C |
| ANISOU | 920 | CB | LEU | A | 268 | 2642 | 2375 | 3667 | −206 | 168 | −519 C |
| ATOM | 921 | CG | LEU | A | 268 | 5.362 | −71.851 | −68.073 | 1.00 | 32.15 | C |
| ANISOU | 921 | CG | LEU | A | 268 | 3939 | 3412 | 4864 | −37 | 156 | −405 C |
| ATOM | 922 | CD1 | LEU | A | 268 | 6.010 | −71.993 | −69.439 | 1.00 | 25.64 | C |
| ANISOU | 922 | CD1 | LEU | A | 268 | 3169 | 2616 | 3959 | 44 | 82 | −327 C |
| ATOM | 923 | CD2 | LEU | A | 268 | 5.408 | −70.385 | −67.643 | 1.00 | 20.92 | C |
| ANISOU | 923 | CD2 | LEU | A | 268 | 2367 | 1980 | 3602 | 117 | 143 | −346 C |
| ATOM | 924 | C | LEU | A | 268 | 1.611 | −72.387 | −67.138 | 1.00 | 41.27 | C |
| ANISOU | 924 | C | LEU | A | 268 | 4661 | 4901 | 6119 | −409 | 266 | −670 C |
| ATOM | 925 | O | LEU | A | 268 | 0.943 | −71.358 | −67.274 | 1.00 | 44.67 | O |
| ANISOU | 925 | O | LEU | A | 268 | 4868 | 5468 | 6636 | −306 | 217 | −653 O |
| ATOM | 926 | N | PHE | A | 269 | 1.086 | −73.601 | −67.255 | 1.00 | 34.51 | N |
| ANISOU | 926 | N | PHE | A | 269 | 3839 | 4043 | 5229 | −625 | 311 | −769 N |
| ATOM | 927 | CA | PHE | A | 269 | −0.334 | −73.774 | −67.535 | 1.00 | 33.62 | C |
| ANISOU | 927 | CA | PHE | A | 269 | 3465 | 4110 | 5198 | −772 | 293 | −879 C |
| ATOM | 928 | CB | PHE | A | 269 | −0.671 | −75.211 | −67.913 | 1.00 | 30.59 | C |
| ANISOU | 928 | CB | PHE | A | 269 | 3144 | 3676 | 4801 | −1028 | 313 | −1010 C |
| ATOM | 929 | CG | PHE | A | 269 | −2.055 | −75.365 | −68.455 | 1.00 | 42.66 | C |
| ANISOU | 929 | CG | PHE | A | 269 | 4362 | 5412 | 6432 | −1181 | 237 | −1158 C |
| ATOM | 930 | CD1 | PHE | A | 269 | −2.317 | −75.054 | −69.782 | 1.00 | 37.97 | C |
| ANISOU | 930 | CD1 | PHE | A | 269 | 3620 | 5029 | 5778 | −1100 | 2 | −1225 C |
| ATOM | 931 | CE1 | PHE | A | 269 | −3.597 | −75.163 | −70.300 | 1.00 | 42.36 | C |
| ANISOU | 931 | CE1 | PHE | A | 269 | 3859 | 5812 | 6424 | −1221 | −107 | −1383 C |
| ATOM | 932 | CZ | PHE | A | 269 | −4.651 | −75.585 | −69.475 | 1.00 | 49.01 | C |
| ANISOU | 932 | CZ | PHE | A | 269 | 4506 | 6656 | 7462 | −1452 | 45 | −1469 C |
| ATOM | 933 | CE2 | PHE | A | 269 | −4.405 | −75.889 | −68.135 | 1.00 | 41.41 | C |
| ANISOU | 933 | CE2 | PHE | A | 269 | 3702 | 5469 | 6564 | −1533 | 319 | −1375 C |
| ATOM | 934 | CD2 | PHE | A | 269 | −3.107 | −75.768 | −67.634 | 1.00 | 35.26 | C |
| ANISOU | 934 | CD2 | PHE | A | 269 | 3262 | 4483 | 5653 | −1383 | 400 | −1223 C |
| ATOM | 935 | C | PHE | A | 269 | −1.207 | −73.343 | −66.352 | 1.00 | 45.00 | C |
| ANISOU | 935 | C | PHE | A | 269 | 4751 | 5594 | 6753 | −796 | 444 | −882 C |
| ATOM | 936 | O | PHE | A | 269 | −2.189 | −72.610 | −66.518 | 1.00 | 44.41 | O |
| ANISOU | 936 | O | PHE | A | 269 | 4393 | 5710 | 6770 | −753 | 398 | −908 O |
| ATOM | 937 | N | ALA | A | 270 | −0.842 | −73.809 | −65.162 | 1.00 | 29.37 | N |
| ANISOU | 937 | N | ALA | A | 270 | 2963 | 3447 | 4748 | −839 | 631 | −848 N |
| ATOM | 938 | CA | ALA | A | 270 | −1.561 | −73.462 | −63.944 | 1.00 | 33.76 | C |
| ANISOU | 938 | CA | ALA | A | 270 | 3422 | 4037 | 5368 | −831 | 809 | −840 C |
| ATOM | 939 | CB | ALA | A | 270 | −0.896 | −74.060 | −62.726 | 1.00 | 29.89 | C |
| ANISOU | 939 | CB | ALA | A | 270 | 3218 | 3359 | 4778 | −826 | 997 | −782 C |
| ATOM | 940 | C | ALA | A | 270 | −1.659 | −71.952 | −63.795 | 1.00 | 39.87 | C |
| ANISOU | 940 | C | ALA | A | 270 | 4041 | 4918 | 6191 | −595 | 735 | −807 C |
| ATOM | 941 | O | ALA | A | 270 | −2.739 | −71.413 | −63.559 | 1.00 | 31.21 | O |
| ANISOU | 941 | O | ALA | A | 270 | 2691 | 3973 | 5193 | −582 | 783 | −838 O |
| ATOM | 942 | N | MET | A | 271 | −0.515 | −71.285 | −63.938 | 1.00 | 27.67 | N |
| ANISOU | 942 | N | MET | A | 271 | 2640 | 3277 | 4597 | −409 | 629 | −746 N |
| ATOM | 943 | CA | MET | A | 271 | −0.426 | −69.837 | −63.818 | 1.00 | 37.35 | C |
| ANISOU | 943 | CA | MET | A | 271 | 3754 | 4536 | 5901 | −184 | 564 | −716 C |
| ATOM | 944 | CB | MET | A | 271 | 0.997 | −69.357 | −64.075 | 1.00 | 25.21 | C |
| ANISOU | 944 | CB | MET | A | 271 | 2389 | 2845 | 4345 | −38 | 459 | −652 C |
| ATOM | 945 | CG | MET | A | 271 | 1.999 | −69.856 | −63.055 | 1.00 | 41.28 | C |

TABLE 7-continued

DMXAA-hSTING$^{G230I}$ complex

| | | | | | | | | | | | |
|---|---|---|---|---|---|---|---|---|---|---|---|
| ANISOU | 945 | CG | MET | A | 271 | 4689 | 4714 | 6283 | −29 | 532 | −663 | C |
| ATOM | 946 | SD | MET | A | 271 | 3.679 | −69.322 | −63.408 | 1.00 | 38.90 | | S |
| ANISOU | 946 | SD | MET | A | 271 | 4528 | 4245 | 6007 | 122 | 400 | −603 | S |
| ATOM | 947 | CE | MET | A | 271 | 3.540 | −67.565 | −63.054 | 1.00 | 24.01 | | C |
| ANISOU | 947 | CE | MET | A | 271 | 2466 | 2346 | 4312 | 322 | 356 | −628 | C |
| ATOM | 948 | C | MET | A | 271 | −1.400 | −69.136 | −64.757 | 1.00 | 28.37 | | C |
| ANISOU | 948 | C | MET | A | 271 | 2319 | 3596 | 4865 | −135 | 460 | −715 | C |
| ATOM | 949 | O | MET | A | 271 | −1.980 | −68.109 | −64.417 | 1.00 | 33.88 | | O |
| ANISOU | 949 | O | MET | A | 271 | 2847 | 4367 | 5661 | 5 | 479 | −714 | O |
| ATOM | 950 | N | SER | A | 272 | −1.574 | −69.695 | −65.947 | 1.00 | 34.24 | | N |
| ANISOU | 950 | N | SER | A | 272 | 3006 | 4433 | 5572 | −226 | 342 | −722 | N |
| ATOM | 951 | CA | SER | A | 272 | −2.434 | −69.087 | −66.946 | 1.00 | 30.27 | | C |
| ANISOU | 951 | CA | SER | A | 272 | 2231 | 4150 | 5122 | −146 | 209 | −718 | C |
| ATOM | 952 | CB | SER | A | 272 | −2.214 | −69.725 | −68.324 | 1.00 | 36.09 | | C |
| ANISOU | 952 | CB | SER | A | 272 | 2998 | 4965 | 5749 | −198 | 46 | −729 | C |
| ATOM | 953 | OG | SER | A | 272 | −2.716 | −71.050 | −68.375 | 1.00 | 31.80 | | O |
| ANISOU | 953 | OG | SER | A | 272 | 2453 | 4451 | 5180 | −464 | 70 | −866 | O |
| ATOM | 954 | C | SER | A | 272 | −3.903 | −69.215 | −66.546 | 1.00 | 32.65 | | C |
| ANISOU | 954 | C | SER | A | 272 | 2252 | 4634 | 5519 | −254 | 281 | −812 | C |
| ATOM | 955 | O | SER | A | 272 | −4.752 | −68.492 | −67.055 | 1.00 | 39.74 | | O |
| ANISOU | 955 | O | SER | A | 272 | 2880 | 5732 | 6487 | −141 | 194 | −809 | O |
| ATOM | 956 | N | GLN | A | 273 | −4.215 | −70.115 | −65.642 | 1.00 | 35.83 | | N |
| ANISOU | 956 | N | GLN | A | 273 | 2710 | 4971 | 5933 | −461 | 455 | −881 | N |
| ATOM | 957 | CA | GLN | A | 273 | −5.577 | −70.399 | −65.279 | 1.00 | 35.92 | | C |
| ANISOU | 957 | CA | GLN | A | 273 | 2441 | 5143 | 6063 | −610 | 560 | −966 | C |
| ATOM | 958 | CB | GLN | A | 273 | −5.818 | −71.889 | −65.233 | 1.00 | 37.14 | | C |
| ANISOU | 958 | CB | GLN | A | 273 | 2652 | 5231 | 6229 | −926 | 653 | −1054 | C |
| ATOM | 959 | CG | GLN | A | 273 | −5.391 | −72.620 | −66.466 | 1.00 | 61.16 | | C |
| ANISOU | 959 | CG | GLN | A | 273 | 5766 | 8273 | 9199 | −1028 | 454 | −1122 | C |
| ATOM | 960 | CD | GLN | A | 273 | −6.433 | −72.667 | −67.531 | 1.00 | 62.36 | | C |
| ANISOU | 960 | CD | GLN | A | 273 | 5566 | 8699 | 9428 | −1081 | 264 | −1246 | C |
| ATOM | 961 | OE1 | GLN | A | 273 | −6.305 | −72.045 | −68.567 | 1.00 | 69.29 | | O |
| ANISOU | 961 | OE1 | GLN | A | 273 | 6211 | 9662 | 10453 | −1313 | 328 | −1371 | C |
| ATOM | 962 | NE2 | GLN | A | 273 | −7.470 | −73.429 | −67.286 | 1.00 | 52.67 | | N |
| ANISOU | 962 | NE2 | GLN | A | 273 | 4284 | 7619 | 8108 | −857 | 34 | −1207 | N |
| ATOM | 963 | C | GLN | A | 273 | −5.968 | −69.850 | −63.961 | 1.00 | 36.39 | | C |
| ANISOU | 963 | C | GLN | A | 273 | 2455 | 5191 | 6183 | −514 | 770 | −939 | C |
| ATOM | 964 | O | GLN | A | 273 | −7.099 | −69.851 | −63.653 | 1.00 | 41.14 | | O |
| ANISOU | 964 | O | GLN | A | 273 | 2782 | 5948 | 6900 | −575 | 876 | −985 | O |
| ATOM | 965 | N | TYR | A | 274 | −5.024 | −69.388 | −63.177 | 1.00 | 37.13 | | N |
| ANISOU | 965 | N | TYR | A | 274 | 2806 | 5107 | 6194 | −359 | 830 | −879 | N |
| ATOM | 966 | CA | TYR | A | 274 | −5.325 | −68.740 | −61.907 | 1.00 | 35.08 | | C |
| ANISOU | 966 | CA | TYR | A | 274 | 2537 | 4839 | 5952 | −224 | 1009 | −879 | C |
| ATOM | 967 | CB | TYR | A | 274 | −4.444 | −69.261 | −60.781 | 1.00 | 34.04 | | C |
| ANISOU | 967 | CB | TYR | A | 274 | 2741 | 4516 | 5678 | −228 | 1156 | −862 | C |
| ATOM | 968 | CG | TYR | A | 274 | −4.632 | −70.717 | −60.499 | 1.00 | 53.48 | | C |
| ANISOU | 968 | CG | TYR | A | 274 | 5302 | 6925 | 8094 | −482 | 1319 | −853 | C |
| ATOM | 969 | CD1 | TYR | A | 274 | −5.865 | −71.205 | −60.091 | 1.00 | 61.20 | | C |
| ANISOU | 969 | CD1 | TYR | A | 274 | 6070 | 8014 | 9168 | −635 | 1524 | −869 | C |
| ATOM | 970 | CE1 | TYR | A | 274 | −6.050 | −72.544 | −59.832 | 1.00 | 66.25 | | C |
| ANISOU | 970 | CE1 | TYR | A | 274 | 6799 | 8564 | 9810 | −883 | 1705 | −849 | C |
| ATOM | 971 | CZ | TYR | A | 274 | −4.986 | −73.418 | −59.985 | 1.00 | 60.65 | | C |
| ANISOU | 971 | CZ | TYR | A | 274 | 6409 | 7653 | 8982 | −959 | 1670 | −815 | C |
| ATOM | 972 | OH | TYR | A | 274 | −5.150 | −74.757 | −59.733 | 1.00 | 63.90 | | O |
| ANISOU | 972 | OH | TYR | A | 274 | 6930 | 7935 | 9416 | −1196 | 1866 | −784 | O |
| ATOM | 973 | CE2 | TYR | A | 274 | −3.750 | −72.958 | −60.391 | 1.00 | 54.23 | | C |
| ANISOU | 973 | CE2 | TYR | A | 274 | 5799 | 6753 | 8052 | −794 | 1456 | −803 | C |
| ATOM | 974 | CD2 | TYR | A | 274 | −3.580 | −71.616 | −60.643 | 1.00 | 55.22 | | C |
| ANISOU | 974 | CD2 | TYR | A | 274 | 5817 | 6966 | 8198 | −569 | 1288 | −821 | C |
| ATOM | 975 | C | TYR | A | 274 | −5.178 | −67.233 | −62.001 | 1.00 | 41.43 | | C |
| ANISOU | 975 | C | TYR | A | 274 | 3266 | 5659 | 6819 | 60 | 905 | −859 | C |
| ATOM | 976 | O | TYR | A | 274 | −4.122 | −66.722 | −62.405 | 1.00 | 35.34 | | O |
| ANISOU | 976 | O | TYR | A | 274 | 2653 | 4752 | 6023 | 181 | 767 | −816 | O |
| ATOM | 977 | N | SER | A | 275 | −6.204 | −66.525 | −61.578 | 1.00 | 36.49 | | N |
| ANISOU | 977 | N | SER | A | 275 | 2392 | 5179 | 6294 | 168 | 992 | −885 | N |
| ATOM | 978 | CA | SER | A | 275 | −6.271 | −65.073 | −61.646 | 1.00 | 39.77 | | C |
| ANISOU | 978 | CA | SER | A | 275 | 2710 | 5599 | 6803 | 448 | 920 | −870 | C |
| ATOM | 979 | CB | SER | A | 275 | −7.688 | −64.597 | −61.343 | 1.00 | 39.32 | | C |
| ANISOU | 979 | CB | SER | A | 275 | 2337 | 5746 | 6859 | 536 | 1040 | −903 | C |
| ATOM | 980 | OG | SER | A | 275 | −8.067 | −64.994 | −60.077 | 1.00 | 40.50 | | O |
| ANISOU | 980 | OG | SER | A | 275 | 2529 | 5907 | 6952 | 459 | 1290 | −953 | O |
| ATOM | 981 | C | SER | A | 275 | −5.216 | −64.398 | −60.787 | 1.00 | 35.19 | | C |
| ANISOU | 981 | C | SER | A | 275 | 2403 | 4793 | 6174 | 609 | 948 | −897 | C |
| ATOM | 982 | O | SER | A | 275 | −4.810 | −63.313 | −61.047 | 1.00 | 47.30 | | O |
| ANISOU | 982 | O | SER | A | 275 | 3947 | 6225 | 7802 | 808 | 848 | −882 | O |
| ATOM | 983 | N | GLN | A | 276 | −4.830 | −65.075 | −59.739 | 1.00 | 42.25 | | N |
| ANISOU | 983 | N | GLN | A | 276 | 3514 | 5608 | 6932 | 530 | 1088 | −942 | N |
| ATOM | 984 | CA | GLN | A | 276 | −3.760 | −64.673 | −58.863 | 1.00 | 42.55 | | C |

TABLE 7-continued

DMXAA-hSTING$^{G230I}$ complex

| | | | | | | | | | | | |
|---|---|---|---|---|---|---|---|---|---|---|---|
| ANISOU | 984 | CA | GLN | A | 276 | 3805 | 5467 | 6895 | 683 | 1093 | −1007 | C |
| ATOM | 985 | CB | GLN | A | 276 | −3.732 | −65.543 | −57.653 | 1.00 | 34.61 | | C |
| ANISOU | 985 | CB | GLN | A | 276 | 2998 | 4456 | 5696 | 622 | 1283 | −1042 | C |
| ATOM | 986 | CG | GLN | A | 276 | −4.081 | −64.747 | −56.456 | 1.00 | 60.34 | | C |
| ANISOU | 986 | CG | GLN | A | 276 | 6277 | 7748 | 8903 | 833 | 1426 | −1142 | C |
| ATOM | 987 | CD | GLN | A | 276 | −3.112 | −64.904 | −55.350 | 1.00 | 65.48 | | C |
| ANISOU | 987 | CD | GLN | A | 276 | 7248 | 8273 | 9357 | 942 | 1426 | −1224 | C |
| ATOM | 988 | OE1 | GLN | A | 276 | −2.957 | −65.974 | −54.819 | 1.00 | 74.85 | | O |
| ANISOU | 988 | OE1 | GLN | A | 276 | 8618 | 9471 | 10350 | 859 | 1557 | −1180 | O |
| ATOM | 989 | NE2 | GLN | A | 276 | −2.489 | −63.825 | −54.962 | 1.00 | 65.53 | | N |
| ANISOU | 989 | NE2 | GLN | A | 276 | 7323 | 8153 | 9422 | 1135 | 1275 | −1345 | N |
| ATOM | 990 | C | GLN | A | 276 | −2.363 | −64.578 | −59.457 | 1.00 | 35.73 | | C |
| ANISOU | 990 | C | GLN | A | 276 | 3124 | 4415 | 6039 | 692 | 901 | −976 | C |
| ATOM | 991 | O | GLN | A | 276 | −1.577 | −63.792 | −59.024 | 1.00 | 39.31 | | O |
| ANISOU | 991 | O | GLN | A | 276 | 3690 | 4713 | 6532 | 849 | 834 | −1041 | O |
| ATOM | 992 | N | ALA | A | 277 | −2.062 | −65.441 | −60.396 | 1.00 | 34.12 | | N |
| ANISOU | 992 | N | ALA | A | 277 | 2938 | 4220 | 5806 | 522 | 818 | −891 | N |
| ATOM | 993 | CA | ALA | A | 277 | −0.841 | −65.389 | −61.124 | 1.00 | 28.62 | | C |
| ANISOU | 993 | CA | ALA | A | 277 | 2401 | 3363 | 5112 | 527 | 665 | −841 | C |
| ATOM | 994 | CB | ALA | A | 277 | −0.651 | −66.633 | −61.947 | 1.00 | 33.53 | | C |
| ANISOU | 994 | CB | ALA | A | 277 | 3099 | 4009 | 5631 | 320 | 634 | −777 | C |
| ATOM | 995 | C | ALA | A | 277 | −0.739 | −64.163 | −61.981 | 1.00 | 48.08 | | C |
| ANISOU | 995 | C | ALA | A | 277 | 4728 | 5784 | 7755 | 680 | 537 | −777 | C |
| ATOM | 996 | O | ALA | A | 277 | 0.345 | −63.802 | −62.357 | 1.00 | 48.44 | | O |
| ANISOU | 996 | O | ALA | A | 277 | 4881 | 5665 | 7858 | 734 | 439 | −732 | O |
| ATOM | 997 | N | GLY | A | 278 | −1.852 | −63.546 | −62.328 | 1.00 | 36.07 | | N |
| ANISOU | 997 | N | GLY | A | 278 | 2961 | 4411 | 6333 | 758 | 551 | −755 | N |
| ATOM | 998 | CA | GLY | A | 278 | −1.853 | −62.397 | −63.219 | 1.00 | 30.45 | | C |
| ANISOU | 998 | CA | GLY | A | 278 | 2117 | 3668 | 5786 | 936 | 455 | −660 | C |
| ATOM | 999 | C | GLY | A | 278 | −1.139 | −62.697 | −64.521 | 1.00 | 41.10 | | C |
| ANISOU | 999 | C | GLY | A | 278 | 3517 | 4992 | 7108 | 896 | 331 | −524 | C |
| ATOM | 1000 | O | GLY | A | 278 | −0.367 | −61.887 | −65.030 | 1.00 | 57.64 | | O |
| ANISOU | 1000 | O | GLY | A | 278 | 5676 | 6937 | 9286 | 1010 | 272 | −420 | O |
| ATOM | 1001 | N | PHE | A | 279 | −1.405 | −63.875 | −65.062 | 1.00 | 30.09 | | N |
| ANISOU | 1001 | N | PHE | A | 279 | 2125 | 3745 | 5564 | 717 | 302 | −518 | N |
| ATOM | 1002 | CA | PHE | A | 279 | −0.601 | −64.445 | −66.123 | 1.00 | 36.68 | | C |
| ANISOU | 1002 | CA | PHE | A | 279 | 3073 | 4552 | 6311 | 658 | 204 | −427 | C |
| ATOM | 1003 | CB | PHE | A | 279 | 0.062 | −65.696 | −65.570 | 1.00 | 39.04 | | C |
| ANISOU | 1003 | CB | PHE | A | 279 | 3595 | 4765 | 6472 | 462 | 249 | −500 | C |
| ATOM | 1004 | CG | PHE | A | 279 | 1.154 | −66.257 | −66.424 | 1.00 | 25.35 | | C |
| ANISOU | 1004 | CG | PHE | A | 279 | 2028 | 2948 | 4654 | 425 | 174 | −422 | C |
| ATOM | 1005 | CD1 | PHE | A | 279 | 2.365 | −65.578 | −66.567 | 1.00 | 31.27 | | C |
| ANISOU | 1005 | CD1 | PHE | A | 279 | 2880 | 3510 | 5492 | 551 | 147 | −335 | C |
| ATOM | 1006 | CE1 | PHE | A | 279 | 3.414 | −66.114 | −67.341 | 1.00 | 23.25 | | C |
| ANISOU | 1006 | CE1 | PHE | A | 279 | 2010 | 2424 | 4402 | 530 | 104 | −252 | C |
| ATOM | 1007 | CZ | PHE | A | 279 | 3.240 | −67.355 | −67.971 | 1.00 | 30.38 | | C |
| ANISOU | 1007 | CZ | PHE | A | 279 | 2985 | 3438 | 5121 | 391 | 75 | −275 | C |
| ATOM | 1008 | CE2 | PHE | A | 279 | 2.014 | −68.051 | −67.811 | 1.00 | 40.84 | | C |
| ANISOU | 1008 | CE2 | PHE | A | 279 | 4215 | 4930 | 6374 | 245 | 88 | −386 | C |
| ATOM | 1009 | CD2 | PHE | A | 279 | 0.994 | −67.490 | −67.035 | 1.00 | 25.44 | | C |
| ANISOU | 1009 | CD2 | PHE | A | 279 | 2094 | 3054 | 4518 | 260 | 144 | −449 | C |
| ATOM | 1010 | C | PHE | A | 279 | −1.519 | −64.819 | −67.271 | 1.00 | 43.93 | | C |
| ANISOU | 1010 | C | PHE | A | 279 | 3812 | 5722 | 7156 | 629 | 112 | −393 | C |
| ATOM | 1011 | O | PHE | A | 279 | −2.354 | −65.709 | −67.124 | 1.00 | 44.45 | | O |
| ANISOU | 1011 | O | PHE | A | 279 | 3792 | 5943 | 7156 | 456 | 131 | −497 | O |
| ATOM | 1012 | N | SER | A | 280 | −1.391 | −64.144 | −68.407 | 1.00 | 29.85 | | N |
| ANISOU | 1012 | N | SER | A | 280 | 1963 | 3988 | 5390 | 804 | 14 | −252 | N |
| ATOM | 1013 | CA | SER | A | 280 | −2.302 | −64.403 | −69.511 | 1.00 | 34.02 | | C |
| ANISOU | 1013 | CA | SER | A | 280 | 2308 | 4797 | 5821 | 826 | −107 | −236 | C |
| ATOM | 1014 | CB | SER | A | 280 | −2.506 | −63.162 | −70.385 | 1.00 | 35.78 | | C |
| ANISOU | 1014 | CB | SER | A | 280 | 2400 | 5088 | 6106 | 1125 | −169 | −58 | C |
| ATOM | 1015 | OG | SER | A | 280 | −1.302 | −62.815 | −71.036 | 1.00 | 57.27 | | O |
| ANISOU | 1015 | OG | SER | A | 280 | 5303 | 7638 | 8818 | 1241 | −170 | 112 | O |
| ATOM | 1016 | C | SER | A | 280 | −1.837 | −65.577 | −70.364 | 1.00 | 36.98 | | C |
| ANISOU | 1016 | C | SER | A | 280 | 2817 | 5227 | 6005 | 685 | −197 | −262 | C |
| ATOM | 1017 | O | SER | A | 280 | −0.692 | −66.025 | −70.266 | 1.00 | 44.22 | | O |
| ANISOU | 1017 | O | SER | A | 280 | 3974 | 5953 | 6875 | 620 | −159 | −237 | O |
| ATOM | 1018 | N | ARG | A | 281 | −2.734 | −66.061 | −71.215 | 1.00 | 46.62 | | N |
| ANISOU | 1018 | N | ARG | A | 281 | 5219 | 6006 | 6489 | 895 | −525 | −580 | N |
| ATOM | 1019 | CA | ARG | A | 281 | −2.451 | −67.205 | −72.066 | 1.00 | 41.03 | | C |
| ANISOU | 1019 | CA | ARG | A | 281 | 4752 | 5356 | 5482 | 820 | −618 | −360 | C |
| ATOM | 1020 | CB | ARG | A | 281 | −3.716 | −67.664 | −72.783 | 1.00 | 33.20 | | C |
| ANISOU | 1020 | CB | ARG | A | 281 | 3729 | 4550 | 4335 | 888 | −819 | −278 | C |
| ATOM | 1021 | CG | ARG | A | 281 | −3.662 | −69.087 | −73.250 | 1.00 | 54.60 | | C |
| ANISOU | 1021 | CG | ARG | A | 281 | 6606 | 7383 | 6756 | 751 | −981 | −206 | C |
| ATOM | 1022 | CD | ARG | A | 281 | −4.263 | −69.236 | −74.634 | 1.00 | 84.05 | | C |
| ANISOU | 1022 | CD | ARG | A | 281 | 10451 | 11138 | 10347 | 955 | −1184 | −65 | C |
| ATOM | 1023 | NE | ARG | A | 281 | −4.000 | −70.562 | −75.185 | 1.00 | 96.97 | | N |

TABLE 7-continued

DMXAA-hSTING$^{G230I}$ complex

| | | | | | | | | | | | |
|---|---|---|---|---|---|---|---|---|---|---|---|
| ANISOU | 1023 | NE | ARG | A | 281 | 12281 | 12830 | 11735 | 866 | −1361 | −56 | N |
| ATOM | 1024 | CZ | ARG | A | 281 | −4.766 | −71.627 | −74.973 | 1.00 | 104.06 | | C |
| ANISOU | 1024 | CZ | ARG | A | 281 | 13075 | 13868 | 12593 | 678 | −1580 | −163 | C |
| ATOM | 1025 | NH1 | ARG | A | 281 | −4.438 | −72.796 | −75.510 | 1.00 | 111.91 | | N |
| ANISOU | 1025 | NH1 | ARG | A | 281 | 14255 | 14839 | 13427 | 619 | −1764 | −188 | N |
| ATOM | 1026 | NH2 | ARG | A | 281 | −5.857 | −71.527 | −74.226 | 1.00 | 99.41 | | N |
| ANISOU | 1026 | NH2 | ARG | A | 281 | 12177 | 13434 | 12162 | 554 | −1610 | −246 | N |
| ATOM | 1027 | C | ARG | A | 281 | −1.373 | −66.849 | −73.087 | 1.00 | 45.00 | | C |
| ANISOU | 1027 | C | ARG | A | 281 | 5480 | 5578 | 6040 | 949 | −522 | −115 | C |
| ATOM | 1028 | O | ARG | A | 281 | −0.584 | −67.700 | −73.514 | 1.00 | 48.57 | | O |
| ANISOU | 1028 | O | ARG | A | 281 | 6134 | 6038 | 6282 | 884 | −523 | −7 | O |
| ATOM | 1029 | N | GLU | A | 282 | −1.352 | −65.581 | −73.479 | 1.00 | 41.06 | | N |
| ANISOU | 1029 | N | GLU | A | 282 | 4925 | 4827 | 5849 | 1146 | −427 | −7 | N |
| ATOM | 1030 | CA | GLU | A | 282 | −0.326 | −65.060 | −74.373 | 1.00 | 40.60 | | C |
| ANISOU | 1030 | CA | GLU | A | 282 | 5019 | 4491 | 5917 | 1269 | −272 | 295 | C |
| ATOM | 1031 | CB | GLU | A | 282 | −0.702 | −63.666 | −74.875 | 1.00 | 50.25 | | C |
| ANISOU | 1031 | CB | GLU | A | 282 | 6147 | 5438 | 7509 | 1509 | −210 | 484 | C |
| ATOM | 1032 | CG | GLU | A | 282 | −2.110 | −63.577 | −75.439 | 1.00 | 65.32 | | C |
| ANISOU | 1032 | CG | GLU | A | 282 | 8021 | 7523 | 9275 | 1707 | −397 | 546 | C |
| ATOM | 1033 | CD | GLU | A | 282 | −3.163 | −63.389 | −74.354 | 1.00 | 90.16 | | C |
| ANISOU | 1033 | CD | GLU | A | 282 | 10897 | 10804 | 12557 | 1648 | −503 | 168 | C |
| ATOM | 1034 | OE1 | GLU | A | 282 | −4.143 | −64.167 | −74.322 | 1.00 | 93.93 | | O |
| ANISOU | 1034 | OE1 | GLU | A | 282 | 11324 | 11610 | 12755 | 1608 | −678 | 63 | O |
| ATOM | 1035 | OE2 | GLU | A | 282 | −3.005 | −62.461 | −73.531 | 1.00 | 102.42 | | O |
| ANISOU | 1035 | OE2 | GLU | A | 282 | 12264 | 12137 | 14515 | 1649 | −412 | −40 | O |
| ATOM | 1036 | C | GLU | A | 282 | 1.021 | −65.017 | −73.662 | 1.00 | 39.51 | | C |
| ANISOU | 1036 | C | GLU | A | 282 | 4859 | 4181 | 5974 | 1097 | −114 | 187 | C |
| ATOM | 1037 | O | GLU | A | 282 | 2.054 | −65.384 | −74.232 | 1.00 | 50.21 | | O |
| ANISOU | 1037 | O | GLU | A | 282 | 6367 | 5471 | 7241 | 1086 | −6 | 387 | O |
| ATOM | 1038 | N | ASP | A | 283 | 1.002 | −64.566 | −72.411 | 1.00 | 36.25 | | N |
| ANISOU | 1038 | N | ASP | A | 283 | 4234 | 3727 | 5813 | 989 | −113 | −157 | N |
| ATOM | 1039 | CA | ASP | A | 283 | 2.185 | −64.585 | −71.555 | 1.00 | 36.68 | | C |
| ANISOU | 1039 | CA | ASP | A | 283 | 4228 | 3678 | 6030 | 827 | −33 | −354 | C |
| ATOM | 1040 | CB | ASP | A | 283 | 1.851 | −64.123 | −70.136 | 1.00 | 48.57 | | C |
| ANISOU | 1040 | CB | ASP | A | 283 | 5494 | 5261 | 7701 | 774 | −93 | −808 | C |
| ATOM | 1041 | CG | ASP | A | 283 | 1.656 | −62.635 | −70.031 | 1.00 | 55.19 | | C |
| ANISOU | 1041 | CG | ASP | A | 283 | 6135 | 5749 | 9085 | 925 | −60 | −932 | C |
| ATOM | 1042 | OD1 | ASP | A | 283 | 2.042 | −61.920 | −70.979 | 1.00 | 56.74 | | O |
| ANISOU | 1042 | OD1 | ASP | A | 283 | 6374 | 5573 | 9614 | 1024 | 40 | −615 | O |
| ATOM | 1043 | OD2 | ASP | A | 283 | 1.125 | −62.188 | −68.991 | 1.00 | 63.03 | | O |
| ANISOU | 1043 | OD2 | ASP | A | 283 | 6924 | 6845 | 10179 | 959 | −130 | −1341 | O |
| ATOM | 1044 | C | ASP | A | 283 | 2.741 | −65.994 | −71.476 | 1.00 | 45.58 | | C |
| ANISOU | 1044 | C | ASP | A | 283 | 5523 | 5048 | 6747 | 671 | −74 | −332 | C |
| ATOM | 1045 | O | ASP | A | 283 | 3.952 | −66.207 | −71.499 | 1.00 | 40.22 | | O |
| ANISOU | 1045 | O | ASP | A | 283 | 4897 | 4256 | 6130 | 601 | 14 | −285 | O |
| ATOM | 1046 | N | ARG | A | 284 | 1.869 | −66.959 | −71.371 | 1.00 | 33.93 | | N |
| ANISOU | 1046 | N | ARG | A | 284 | 4102 | 3886 | 4903 | 617 | −218 | −366 | N |
| ATOM | 1047 | CA | ARG | A | 284 | 2.248 | −68.323 | −71.256 | 1.00 | 32.75 | | C |
| ANISOU | 1047 | CA | ARG | A | 284 | 4097 | 3928 | 4419 | 467 | −296 | −352 | C |
| ATOM | 1048 | CB | ARG | A | 284 | 0.998 | −69.163 | −71.086 | 1.00 | 32.00 | | C |
| ANISOU | 1048 | CB | ARG | A | 284 | 3983 | 4119 | 4059 | 390 | −465 | −385 | C |
| ATOM | 1049 | CG | ARG | A | 284 | 1.284 | −70.549 | −70.615 | 1.00 | 31.12 | | C |
| ANISOU | 1049 | CG | ARG | A | 284 | 3976 | 4150 | 3696 | 207 | −562 | −380 | C |
| ATOM | 1050 | CD | ARG | A | 284 | 0.092 | −71.437 | −70.703 | 1.00 | 40.90 | | C |
| ANISOU | 1050 | CD | ARG | A | 284 | 5166 | 5597 | 4778 | 114 | −729 | −354 | C |
| ATOM | 1051 | NE | ARG | A | 284 | −0.469 | −71.521 | −72.026 | 1.00 | 38.29 | | N |
| ANISOU | 1051 | NE | ARG | A | 284 | 4958 | 5209 | 4379 | 252 | −858 | −231 | N |
| ATOM | 1052 | CZ | ARG | A | 284 | −1.676 | −71.979 | −72.260 | 1.00 | 36.50 | | C |
| ANISOU | 1052 | CZ | ARG | A | 284 | 4641 | 5119 | 4109 | 230 | −1031 | −229 | C |
| ATOM | 1053 | NH1 | ARG | A | 284 | −2.145 | −72.040 | −73.466 | 1.00 | 33.52 | | N |
| ANISOU | 1053 | NH1 | ARG | A | 284 | 4384 | 4710 | 3642 | 395 | −1187 | −157 | N |
| ATOM | 1054 | NH2 | ARG | A | 284 | −2.416 | −72.357 | −71.272 | 1.00 | 40.25 | | N |
| ANISOU | 1054 | NH2 | ARG | A | 284 | 4882 | 5791 | 4621 | 56 | −1048 | −298 | N |
| ATOM | 1055 | C | ARG | A | 284 | 2.991 | −68.830 | −72.452 | 1.00 | 41.12 | | C |
| ANISOU | 1055 | C | ARG | A | 284 | 5389 | 4882 | 5352 | 548 | −254 | −95 | C |
| ATOM | 1056 | O | ARG | A | 284 | 3.931 | −69.559 | −72.320 | 1.00 | 46.30 | | O |
| ANISOU | 1056 | O | ARG | A | 284 | 6132 | 5532 | 5927 | 464 | −230 | −102 | O |
| ATOM | 1057 | N | LEU | A | 285 | 2.526 | −68.480 | −73.629 | 1.00 | 45.30 | | N |
| ANISOU | 1057 | N | LEU | A | 285 | 6012 | 5366 | 5836 | 745 | −248 | 130 | N |
| ATOM | 1058 | CA | LEU | A | 285 | 3.174 | −68.906 | −74.832 | 1.00 | 44.40 | | C |
| ANISOU | 1058 | CA | LEU | A | 285 | 6118 | 5243 | 5510 | 886 | −198 | 369 | C |
| ATOM | 1059 | CB | LEU | A | 285 | 2.326 | −68.659 | −76.062 | 1.00 | 36.97 | | C |
| ANISOU | 1059 | CB | LEU | A | 285 | 5281 | 4384 | 4381 | 1138 | −274 | 577 | C |
| ATOM | 1060 | CG | LEU | A | 285 | 2.967 | −69.206 | −77.328 | 1.00 | 44.36 | | C |
| ANISOU | 1060 | CG | LEU | A | 285 | 6453 | 5404 | 4997 | 1346 | −226 | 796 | C |
| ATOM | 1061 | CD1 | LEU | A | 285 | 3.658 | −70.527 | −77.133 | 1.00 | 35.41 | | C |
| ANISOU | 1061 | CD1 | LEU | A | 285 | 5451 | 4394 | 3609 | 1230 | −367 | 599 | C |
| ATOM | 1062 | CD2 | LEU | A | 285 | 2.013 | −69.309 | −78.475 | 1.00 | 30.95 | | C |

TABLE 7-continued

DMXAA-hSTING$^{G230I}$ complex

| | | | | | | | | | | | |
|---|---|---|---|---|---|---|---|---|---|---|---|
| ANISOU | 1062 | CD2 | LEU | A | 285 | 4863 | 3868 | 3028 | 1632 | −359 | 960 | C |
| ATOM | 1063 | C | LEU | A | 285 | 4.524 | −68.300 | −74.982 | 1.00 | 35.89 | | C |
| ANISOU | 1063 | C | LEU | A | 285 | 5014 | 3936 | 4685 | 922 | 62 | 526 | C |
| ATOM | 1064 | O | LEU | A | 285 | 5.399 | −68.920 | −75.472 | 1.00 | 40.10 | | O |
| ANISOU | 1064 | O | LEU | A | 285 | 5670 | 4496 | 5069 | 948 | 140 | 615 | O |
| ATOM | 1065 | N | GLU | A | 286 | 4.661 | −67.051 | −74.615 | 1.00 | 29.21 | | N |
| ANISOU | 1065 | N | GLU | A | 286 | 3980 | 2848 | 4272 | 924 | 192 | 545 | N |
| ATOM | 1066 | CA | GLU | A | 286 | 5.924 | −66.377 | −74.715 | 1.00 | 31.14 | | C |
| ANISOU | 1066 | CA | GLU | A | 286 | 4124 | 2812 | 4896 | 914 | 431 | 691 | C |
| ATOM | 1067 | CB | GLU | A | 286 | 5.706 | −64.872 | −74.513 | 1.00 | 49.55 | | C |
| ANISOU | 1067 | CB | GLU | A | 286 | 6233 | 4813 | 7782 | 938 | 508 | 696 | C |
| ATOM | 1068 | CG | GLU | A | 286 | 6.776 | −64.110 | −73.740 | 1.00 | 62.59 | | C |
| ANISOU | 1068 | CG | GLU | A | 286 | 7655 | 6146 | 9980 | 791 | 626 | 559 | C |
| ATOM | 1069 | CD | GLU | A | 286 | 6.272 | −62.922 | −72.952 | 1.00 | 76.20 | | C |
| ANISOU | 1069 | CD | GLU | A | 286 | 9137 | 7589 | 12228 | 775 | 560 | 298 | C |
| ATOM | 1070 | OE1 | GLU | A | 286 | 5.630 | −63.087 | −71.901 | 1.00 | 69.51 | | O |
| ANISOU | 1070 | OE1 | GLU | A | 286 | 8232 | 6938 | 11240 | 725 | 371 | −106 | O |
| ATOM | 1071 | OE2 | GLU | A | 286 | 6.570 | −61.795 | −73.373 | 1.00 | 84.20 | | O |
| ANISOU | 1071 | OE2 | GLU | A | 286 | 10008 | 8224 | 13761 | 811 | 695 | 499 | O |
| ATOM | 1072 | C | GLU | A | 286 | 6.975 | −66.948 | −73.784 | 1.00 | 35.15 | | C |
| ANISOU | 1072 | C | GLU | A | 286 | 4566 | 3337 | 5453 | 711 | 419 | 433 | C |
| ATOM | 1073 | O | GLU | A | 286 | 8.086 | −67.122 | −74.148 | 1.00 | 35.76 | | O |
| ANISOU | 1073 | O | GLU | A | 286 | 4654 | 3349 | 5586 | 712 | 572 | 571 | O |
| ATOM | 1074 | N | GLN | A | 287 | 6.575 | −67.204 | −72.566 | 1.00 | 40.86 | | N |
| ANISOU | 1074 | N | GLN | A | 287 | 5208 | 4190 | 6127 | 561 | 240 | 77 | N |
| ATOM | 1075 | CA | GLN | A | 287 | 7.382 | −67.796 | −71.541 | 1.00 | 39.48 | | C |
| ANISOU | 1075 | CA | GLN | A | 287 | 4964 | 4075 | 5962 | 397 | 186 | −175 | C |
| ATOM | 1076 | CB | GLN | A | 287 | 6.702 | −67.668 | −70.190 | 1.00 | 27.45 | | C |
| ANISOU | 1076 | CB | GLN | A | 287 | 3295 | 2703 | 4432 | 292 | 31 | −538 | C |
| ATOM | 1077 | CG | GLN | A | 287 | 6.583 | −66.272 | −69.667 | 1.00 | 26.25 | | C |
| ANISOU | 1077 | CG | GLN | A | 287 | 2905 | 2332 | 4738 | 327 | 66 | −740 | C |
| ATOM | 1078 | CD | GLN | A | 287 | 7.887 | −65.527 | −69.587 | 1.00 | 50.78 | | C |
| ANISOU | 1078 | CD | GLN | A | 287 | 5848 | 5110 | 8335 | 290 | 170 | −788 | C |
| ATOM | 1079 | OE1 | GLN | A | 287 | 8.705 | −65.835 | −68.776 | 1.00 | 39.68 | | O |
| ANISOU | 1079 | OE1 | GLN | A | 287 | 4370 | 3774 | 6932 | 190 | 106 | −1002 | O |
| ATOM | 1080 | NE2 | GLN | A | 287 | 8.052 | −64.518 | −70.401 | 1.00 | 30.37 | | N |
| ANISOU | 1080 | NE2 | GLN | A | 287 | 3183 | 2156 | 6198 | 371 | 324 | −561 | N |
| ATOM | 1081 | C | GLN | A | 287 | 7.713 | −69.233 | −71.838 | 1.00 | 43.35 | | C |
| ANISOU | 1081 | C | GLN | A | 287 | 5661 | 4769 | 6043 | 373 | 112 | −110 | C |
| ATOM | 1082 | O | GLN | A | 287 | 8.672 | −69.730 | −71.372 | 1.00 | 32.72 | | O |
| ANISOU | 1082 | O | GLN | A | 287 | 4291 | 3422 | 4721 | 300 | 116 | −191 | O |
| ATOM | 1083 | N | ALA | A | 288 | 6.852 | −69.923 | −72.543 | 1.00 | 39.44 | | N |
| ANISOU | 1083 | N | ALA | A | 288 | 5350 | 4430 | 5204 | 446 | 10 | 5 | N |
| ATOM | 1084 | CA | ALA | A | 288 | 7.118 | −71.318 | −72.840 | 1.00 | 37.04 | | C |
| ANISOU | 1084 | CA | ALA | A | 288 | 5236 | 4264 | 4572 | 438 | −105 | 20 | C |
| ATOM | 1085 | CB | ALA | A | 288 | 5.871 | −72.015 | −73.376 | 1.00 | 28.57 | | C |
| ANISOU | 1085 | CB | ALA | A | 288 | 4303 | 3344 | 3206 | 479 | −298 | 43 | C |
| ATOM | 1086 | C | ALA | A | 288 | 8.259 | −71.390 | −73.844 | 1.00 | 39.20 | | C |
| ANISOU | 1086 | C | ALA | A | 288 | 5600 | 4458 | 4836 | 590 | 71 | 207 | C |
| ATOM | 1087 | O | ALA | A | 288 | 9.172 | −72.209 | −73.716 | 1.00 | 36.28 | | O |
| ANISOU | 1087 | O | ALA | A | 288 | 5279 | 4109 | 4396 | 569 | 56 | 154 | O |
| ATOM | 1088 | N | LYS | A | 289 | 8.210 | −70.522 | −74.845 | 1.00 | 37.58 | | N |
| ANISOU | 1088 | N | LYS | A | 289 | 5401 | 4178 | 4700 | 766 | 250 | 454 | N |
| ATOM | 1089 | CA | LYS | A | 289 | 9.275 | −70.463 | −75.833 | 1.00 | 34.60 | | C |
| ANISOU | 1089 | CA | LYS | A | 289 | 5070 | 3775 | 4300 | 937 | 485 | 698 | C |
| ATOM | 1090 | CB | LYS | A | 289 | 8.956 | −69.438 | −76.902 | 1.00 | 28.34 | | C |
| ANISOU | 1090 | CB | LYS | A | 289 | 4284 | 2936 | 3548 | 1144 | 680 | 1048 | C |
| ATOM | 1091 | CG | LYS | A | 289 | 7.756 | −69.756 | −77.731 | 1.00 | 49.65 | | C |
| ANISOU | 1091 | CG | LYS | A | 289 | 7183 | 5839 | 5842 | 1331 | 508 | 1102 | C |
| ATOM | 1092 | CD | LYS | A | 289 | 7.327 | −68.497 | −78.430 | 1.00 | 47.13 | | C |
| ANISOU | 1092 | CD | LYS | A | 289 | 6813 | 5427 | 5669 | 1502 | 672 | 1446 | C |
| ATOM | 1093 | CE | LYS | A | 289 | 6.463 | −68.774 | −79.624 | 1.00 | 58.72 | | C |
| ANISOU | 1093 | CE | LYS | A | 289 | 8494 | 7159 | 6660 | 1797 | 555 | 1594 | C |
| ATOM | 1094 | NZ | LYS | A | 289 | 6.671 | −67.664 | −80.589 | 1.00 | 76.11 | | N |
| ANISOU | 1094 | NZ | LYS | A | 289 | 10629 | 9329 | 8961 | 1971 | 824 | 2003 | N |
| ATOM | 1095 | C | LYS | A | 289 | 10.565 | −70.066 | −75.154 | 1.00 | 39.80 | | C |
| ANISOU | 1095 | C | LYS | A | 289 | 5511 | 4257 | 5355 | 805 | 648 | 656 | C |
| ATOM | 1096 | O | LYS | A | 289 | 11.626 | −70.656 | −75.384 | 1.00 | 47.29 | | O |
| ANISOU | 1096 | O | LYS | A | 289 | 6470 | 5248 | 6249 | 849 | 739 | 680 | O |
| ATOM | 1097 | N | LEU | A | 290 | 10.465 | −69.057 | −74.302 | 1.00 | 39.17 | | N |
| ANISOU | 1097 | N | LEU | A | 290 | 5211 | 3978 | 5696 | 659 | 661 | 551 | N |
| ATOM | 1098 | CA | LEU | A | 290 | 11.622 | −68.516 | −73.609 | 1.00 | 27.14 | | C |
| ANISOU | 1098 | CA | LEU | A | 290 | 3428 | 2250 | 4634 | 528 | 767 | 455 | C |
| ATOM | 1099 | CB | LEU | A | 290 | 11.245 | −67.247 | −72.854 | 1.00 | 35.91 | | C |
| ANISOU | 1099 | CB | LEU | A | 290 | 4308 | 3114 | 6220 | 425 | 744 | 306 | C |
| ATOM | 1100 | CG | LEU | A | 290 | 12.348 | −66.570 | −72.048 | 1.00 | 41.42 | | C |
| ANISOU | 1100 | CG | LEU | A | 290 | 4693 | 3562 | 7481 | 281 | 782 | 114 | C |
| ATOM | 1101 | CD1 | LEU | A | 290 | 13.412 | −65.994 | −72.970 | 1.00 | 47.28 | | C |

TABLE 7-continued

DMXAA-hSTING$^{G230I}$ complex

| | | | | | | | | | | | | |
|---|---|---|---|---|---|---|---|---|---|---|---|---|
| ANISOU | 1101 | CD1 | LEU | A | 290 | 5287 | 4065 | 8610 | 323 | 1096 | 488 | C |
| ATOM | 1102 | CD2 | LEU | A | 290 | 11.719 | −65.480 | −71.213 | 1.00 | 31.06 | | C |
| ANISOU | 1102 | CD2 | LEU | A | 290 | 3196 | 2051 | 6553 | 217 | 667 | −160 | C |
| ATOM | 1103 | C | LEU | A | 290 | 12.210 | −69.542 | −72.644 | 1.00 | 30.60 | | C |
| ANISOU | 1103 | C | LEU | A | 290 | 3862 | 2825 | 4940 | 406 | 583 | 156 | C |
| ATOM | 1104 | O | LEU | A | 290 | 13.424 | −69.618 | −72.464 | 1.00 | 33.02 | | O |
| ANISOU | 1104 | O | LEU | A | 290 | 4023 | 3062 | 5460 | 371 | 666 | 128 | O |
| ATOM | 1105 | N | PHE | A | 291 | 11.333 | −70.321 | −72.025 | 1.00 | 23.18 | | N |
| ANISOU | 1105 | N | PHE | A | 291 | 3059 | 2079 | 3669 | 347 | 336 | −36 | N |
| ATOM | 1106 | CA | PHE | A | 291 | 11.753 | −71.416 | −71.170 | 1.00 | 33.49 | | C |
| ANISOU | 1106 | CA | PHE | A | 291 | 4400 | 3531 | 4793 | 257 | 150 | −234 | C |
| ATOM | 1107 | CB | PHE | A | 291 | 10.535 | −72.132 | −70.586 | 1.00 | 32.68 | | C |
| ANISOU | 1107 | CB | PHE | A | 291 | 4426 | 3624 | 4366 | 182 | −78 | −337 | C |
| ATOM | 1108 | CG | PHE | A | 291 | 10.868 | −73.384 | −69.840 | 1.00 | 19.36 | | C |
| ANISOU | 1108 | CG | PHE | A | 291 | 2810 | 2074 | 2471 | 107 | −265 | −431 | C |
| ATOM | 1109 | CD1 | PHE | A | 291 | 11.378 | −73.325 | −68.546 | 1.00 | 19.60 | | C |
| ANISOU | 1109 | CD1 | PHE | A | 291 | 2683 | 2181 | 2582 | 11 | −355 | −627 | C |
| ATOM | 1110 | CE1 | PHE | A | 291 | 11.688 | −74.485 | −67.844 | 1.00 | 19.29 | | C |
| ANISOU | 1110 | CE1 | PHE | A | 291 | 2714 | 2274 | 2340 | −34 | −531 | −649 | C |
| ATOM | 1111 | CZ | PHE | A | 291 | 11.499 | −75.732 | −68.459 | 1.00 | 18.74 | | C |
| ANISOU | 1111 | CZ | PHE | A | 291 | 2867 | 2191 | 2062 | −4 | −624 | −495 | C |
| ATOM | 1112 | CE2 | PHE | A | 291 | 10.988 | −75.795 | −69.769 | 1.00 | 18.54 | | C |
| ANISOU | 1112 | CE2 | PHE | A | 291 | 2993 | 2076 | 1975 | 90 | −557 | −372 | C |
| ATOM | 1113 | CD2 | PHE | A | 291 | 10.679 | −74.623 | −70.438 | 1.00 | 26.49 | | C |
| ANISOU | 1113 | CD2 | PHE | A | 291 | 3935 | 3021 | 3109 | 154 | −375 | −330 | C |
| ATOM | 1114 | C | PHE | A | 291 | 12.613 | −72.419 | −71.944 | 1.00 | 33.35 | | C |
| ANISOU | 1114 | C | PHE | A | 291 | 4521 | 3558 | 4594 | 372 | 197 | −110 | C |
| ATOM | 1115 | O | PHE | A | 291 | 13.635 | −72.897 | −71.452 | 1.00 | 33.02 | | O |
| ANISOU | 1115 | O | PHE | A | 291 | 4398 | 3518 | 4628 | 343 | 161 | −211 | O |
| ATOM | 1116 | N | CYS | A | 292 | 12.187 | −72.735 | −73.161 | 1.00 | 31.32 | | N |
| ANISOU | 1116 | N | CYS | A | 292 | 4462 | 3356 | 4082 | 537 | 259 | 81 | N |
| ATOM | 1117 | CA | CYS | A | 292 | 12.887 | −73.704 | −73.990 | 1.00 | 34.89 | | C |
| ANISOU | 1117 | CA | CYS | A | 292 | 5059 | 3886 | 4309 | 707 | 292 | 146 | C |
| ATOM | 1118 | CB | CYS | A | 292 | 12.064 | −74.067 | −75.228 | 1.00 | 31.63 | | C |
| ANISOU | 1118 | CB | CYS | A | 292 | 4890 | 3596 | 3534 | 910 | 266 | 264 | C |
| ATOM | 1119 | SG | CYS | A | 292 | 10.588 | −75.049 | −74.872 | 1.00 | 46.81 | | S |
| ANISOU | 1119 | SG | CYS | A | 292 | 7000 | 5595 | 5192 | 808 | −118 | 85 | S |
| ATOM | 1120 | C | CYS | A | 292 | 14.261 | −73.190 | −74.405 | 1.00 | 39.97 | | C |
| ANISOU | 1120 | C | CYS | A | 292 | 5519 | 4457 | 5210 | 793 | 585 | 283 | C |
| ATOM | 1121 | O | CYS | A | 292 | 15.255 | −73.913 | −74.362 | 1.00 | 43.56 | | O |
| ANISOU | 1121 | O | CYS | A | 292 | 5948 | 4948 | 5655 | 849 | 587 | 216 | O |
| ATOM | 1122 | N | ARG | A | 293 | 14.332 | −71.950 | −74.824 | 1.00 | 38.08 | | N |
| ANISOU | 1122 | N | ARG | A | 293 | 5128 | 4100 | 5243 | 806 | 836 | 500 | N |
| ATOM | 1123 | CA | ARG | A | 293 | 15.569 | −71.334 | −75.222 | 1.00 | 32.59 | | C |
| ANISOU | 1123 | CA | ARG | A | 293 | 4194 | 3303 | 4886 | 853 | 1158 | 706 | C |
| ATOM | 1124 | CB | ARG | A | 293 | 15.294 | −69.934 | −75.705 | 1.00 | 31.49 | | C |
| ANISOU | 1124 | CB | ARG | A | 293 | 3907 | 2972 | 5084 | 845 | 1399 | 1000 | C |
| ATOM | 1125 | CG | ARG | A | 293 | 14.937 | −69.836 | −77.145 | 1.00 | 60.24 | | C |
| ANISOU | 1125 | CG | ARG | A | 293 | 7691 | 6753 | 8444 | 1114 | 1659 | 1413 | C |
| ATOM | 1126 | CD | ARG | A | 293 | 14.643 | −68.403 | −77.523 | 1.00 | 79.46 | | C |
| ANISOU | 1126 | CD | ARG | A | 293 | 9982 | 8945 | 11264 | 1085 | 1846 | 1725 | C |
| ATOM | 1127 | NE | ARG | A | 293 | 13.263 | −68.025 | −77.228 | 1.00 | 91.40 | | N |
| ANISOU | 1127 | NE | ARG | A | 293 | 11655 | 10449 | 12622 | 1068 | 1597 | 1600 | N |
| ATOM | 1128 | CZ | ARG | A | 293 | 12.805 | −66.786 | −77.160 | 1.00 | 81.75 | | C |
| ANISOU | 1128 | CZ | ARG | A | 293 | 10328 | 8986 | 11745 | 1033 | 1644 | 1752 | C |
| ATOM | 1129 | NH1 | ARG | A | 293 | 11.543 | −66.584 | −76.881 | 1.00 | 71.09 | | N |
| ANISOU | 1129 | NH1 | ARG | A | 293 | 9116 | 7682 | 10214 | 1046 | 1406 | 1607 | N |
| ATOM | 1130 | NH2 | ARG | A | 293 | 13.595 | −65.761 | −77.387 | 1.00 | 76.60 | | N |
| ANISOU | 1130 | NH2 | ARG | A | 293 | 9407 | 8024 | 11672 | 984 | 1923 | 2049 | N |
| ATOM | 1131 | C | ARG | A | 293 | 16.548 | −71.218 | −74.100 | 1.00 | 42.13 | | C |
| ANISOU | 1131 | C | ARG | A | 293 | 5131 | 4387 | 6489 | 667 | 1085 | 469 | C |
| ATOM | 1132 | O | ARG | A | 293 | 17.702 | −71.448 | −74.269 | 1.00 | 39.07 | | O |
| ANISOU | 1132 | O | ARG | A | 293 | 4602 | 4024 | 6217 | 724 | 1213 | 498 | O |
| ATOM | 1133 | N | THR | A | 294 | 16.067 | −70.816 | −72.950 | 1.00 | 33.02 | | N |
| ANISOU | 1133 | N | THR | A | 294 | 3883 | 3129 | 5532 | 471 | 874 | 218 | N |
| ATOM | 1134 | CA | THR | A | 294 | 16.905 | −70.664 | −71.776 | 1.00 | 31.76 | | C |
| ANISOU | 1134 | CA | THR | A | 294 | 3458 | 2886 | 5724 | 315 | 746 | −63 | C |
| ATOM | 1135 | CB | THR | A | 294 | 16.141 | −70.023 | −70.626 | 1.00 | 32.28 | | C |
| ANISOU | 1135 | CB | THR | A | 294 | 3445 | 2895 | 5927 | 163 | 530 | −349 | C |
| ATOM | 1136 | OG1 | THR | A | 294 | 15.627 | −68.762 | −71.055 | 1.00 | 40.41 | | O |
| ANISOU | 1136 | OG1 | THR | A | 294 | 4377 | 3697 | 7280 | 150 | 692 | −207 | O |
| ATOM | 1137 | CG2 | THR | A | 294 | 17.058 | −69.820 | −69.429 | 1.00 | 28.64 | | C |
| ANISOU | 1137 | CG2 | THR | A | 294 | 2696 | 2388 | 5799 | 47 | 366 | −687 | C |
| ATOM | 1138 | C | THR | A | 294 | 17.471 | −72.006 | −71.336 | 1.00 | 35.30 | | C |
| ANISOU | 1138 | C | THR | A | 294 | 4000 | 3520 | 5890 | 354 | 554 | −226 | C |
| ATOM | 1139 | O | THR | A | 294 | 18.638 | −72.117 | −70.957 | 1.00 | 41.67 | | O |
| ANISOU | 1139 | O | THR | A | 294 | 4586 | 4299 | 6949 | 337 | 553 | −327 | O |
| ATOM | 1140 | N | LEU | A | 295 | 16.645 | −73.038 | −71.408 | 1.00 | 30.04 | | N |

TABLE 7-continued

| DMXAA-hSTING$^{G230I}$ complex | | | | | | | | | | |
|---|---|---|---|---|---|---|---|---|---|---|
| ANISOU | 1140 | N | LEU | A | 295 | 3646 | 3020 | 4746 | 411 | 376 | −242 | N |
| ATOM | 1141 | CA | LEU | A | 295 | 17.078 | −74.354 | −70.975 | 1.00 | 31.77 | | C |
| ANISOU | 1141 | CA | LEU | A | 295 | 3973 | 3360 | 4737 | 451 | 165 | −365 | C |
| ATOM | 1142 | CB | LEU | A | 295 | 15.898 | −75.304 | −70.846 | 1.00 | 24.18 | | C |
| ANISOU | 1142 | CB | LEU | A | 295 | 3314 | 2507 | 3369 | 439 | −68 | −381 | C |
| ATOM | 1143 | CG | LEU | A | 295 | 16.274 | −76.627 | −70.191 | 1.00 | 27.31 | | C |
| ANISOU | 1143 | CG | LEU | A | 295 | 3803 | 2966 | 3609 | 448 | −322 | −478 | C |
| ATOM | 1144 | CD1 | LEU | A | 295 | 16.761 | −76.378 | −68.764 | 1.00 | 30.25 | | C |
| ANISOU | 1144 | CD1 | LEU | A | 295 | 3965 | 3393 | 4135 | 323 | −468 | −648 | C |
| ATOM | 1145 | CD2 | LEU | A | 295 | 15.089 | −77.570 | −70.202 | 1.00 | 39.74 | | C |
| ANISOU | 1145 | CD2 | LEU | A | 295 | 5644 | 4581 | 4875 | 414 | −530 | −438 | C |
| ATOM | 1146 | C | LEU | A | 295 | 18.111 | −74.937 | −71.942 | 1.00 | 42.33 | | C |
| ANISOU | 1146 | C | LEU | A | 295 | 5314 | 4717 | 6051 | 651 | 334 | −248 | C |
| ATOM | 1147 | O | LEU | A | 295 | 19.084 | −75.571 | −71.524 | 1.00 | 45.99 | | O |
| ANISOU | 1147 | O | LEU | A | 295 | 5680 | 5205 | 6590 | 690 | 245 | −359 | O |
| ATOM | 1148 | N | GLU | A | 296 | 17.876 | −74.734 | −73.235 | 1.00 | 39.62 | | N |
| ANISOU | 1148 | N | GLU | A | 296 | 5081 | 4404 | 5570 | 811 | 572 | −26 | N |
| ATOM | 1149 | CA | GLU | A | 296 | 18.799 | −75.167 | −74.278 | 1.00 | 38.91 | | C |
| ANISOU | 1149 | CA | GLU | A | 296 | 4981 | 4404 | 5399 | 1056 | 795 | 97 | C |
| ATOM | 1150 | CB | GLU | A | 296 | 18.336 | −74.648 | −75.638 | 1.00 | 56.51 | | C |
| ANISOU | 1150 | CB | GLU | A | 296 | 7322 | 6721 | 7429 | 1239 | 1076 | 382 | C |
| ATOM | 1151 | CG | GLU | A | 296 | 17.911 | −75.707 | −76.622 | 1.00 | 72.87 | | C |
| ANISOU | 1151 | CG | GLU | A | 296 | 9719 | 8988 | 8981 | 1517 | 995 | 348 | C |
| ATOM | 1152 | CD | GLU | A | 296 | 17.130 | −75.126 | −77.792 | 1.00 | 82.94 | | C |
| ANISOU | 1152 | CD | GLU | A | 296 | 11140 | 10393 | 9982 | 1691 | 1177 | 598 | C |
| ATOM | 1153 | OE1 | GLU | A | 296 | 17.325 | −73.932 | −78.113 | 1.00 | 76.19 | | O |
| ANISOU | 1153 | OE1 | GLU | A | 296 | 10096 | 9491 | 9362 | 1667 | 1494 | 906 | O |
| ATOM | 1154 | OE2 | GLU | A | 296 | 16.311 | −75.865 | −78.377 | 1.00 | 87.35 | | O |
| ANISOU | 1154 | OE2 | GLU | A | 296 | 11990 | 11083 | 10118 | 1856 | 978 | 489 | O |
| ATOM | 1155 | C | GLU | A | 296 | 20.185 | −74.615 | −73.978 | 1.00 | 51.23 | | C |
| ANISOU | 1155 | C | GLU | A | 296 | 6154 | 5888 | 7425 | 1008 | 987 | 117 | C |
| ATOM | 1156 | O | GLU | A | 296 | 21.195 | −75.337 | −74.007 | 1.00 | 49.44 | | O |
| ANISOU | 1156 | O | GLU | A | 296 | 5837 | 5730 | 7218 | 1132 | 991 | 39 | O |
| ATOM | 1157 | N | ASP | A | 297 | 20.220 | −73.321 | −73.670 | 1.00 | 43.34 | | N |
| ANISOU | 1157 | N | ASP | A | 297 | 4897 | 4720 | 6851 | 827 | 1125 | 200 | N |
| ATOM | 1158 | CA | ASP | A | 297 | 21.464 | −72.616 | −73.372 | 1.00 | 34.60 | | C |
| ANISOU | 1158 | CA | ASP | A | 297 | 3355 | 3478 | 6312 | 733 | 1293 | 213 | C |
| ATOM | 1159 | CB | ASP | A | 297 | 21.217 | −71.120 | −73.197 | 1.00 | 49.13 | | C |
| ANISOU | 1159 | CB | ASP | A | 297 | 4958 | 5059 | 8651 | 538 | 1424 | 317 | C |
| ATOM | 1160 | CG | ASP | A | 297 | 20.822 | −70.442 | −74.477 | 1.00 | 64.44 | | C |
| ANISOU | 1160 | CG | ASP | A | 297 | 6959 | 6974 | 10551 | 652 | 1793 | 760 | C |
| ATOM | 1161 | OD1 | ASP | A | 297 | 21.065 | −71.025 | −75.552 | 1.00 | 64.82 | | O |
| ANISOU | 1161 | OD1 | ASP | A | 297 | 7143 | 7246 | 10239 | 898 | 2016 | 994 | O |
| ATOM | 1162 | OD2 | ASP | A | 297 | 20.271 | −69.324 | −74.408 | 1.00 | 84.97 | | O |
| ANISOU | 1162 | OD2 | ASP | A | 297 | 9471 | 9344 | 13469 | 526 | 1851 | 869 | O |
| ATOM | 1163 | C | ASP | A | 297 | 22.155 | −73.148 | −72.129 | 1.00 | 39.94 | | C |
| ANISOU | 1163 | C | ASP | A | 297 | 3876 | 4157 | 7141 | 638 | 979 | −137 | C |
| ATOM | 1164 | O | ASP | A | 297 | 23.379 | −73.300 | −72.103 | 1.00 | 56.63 | | O |
| ANISOU | 1164 | O | ASP | A | 297 | 5709 | 6280 | 9530 | 684 | 1060 | −165 | O |
| ATOM | 1165 | N | ILE | A | 298 | 21.376 | −73.405 | −71.088 | 1.00 | 31.56 | | N |
| ANISOU | 1165 | N | ILE | A | 298 | 2975 | 3118 | 5898 | 523 | 627 | −383 | N |
| ATOM | 1166 | CA | ILE | A | 298 | 21.936 | −73.891 | −69.842 | 1.00 | 32.53 | | C |
| ANISOU | 1166 | CA | ILE | A | 298 | 2975 | 3296 | 6087 | 463 | 305 | −685 | C |
| ATOM | 1167 | CB | ILE | A | 298 | 20.870 | −74.035 | −68.763 | 1.00 | 35.43 | | C |
| ANISOU | 1167 | CB | ILE | A | 298 | 3533 | 3746 | 6183 | 351 | −16 | −875 | C |
| ATOM | 1168 | CG1 | ILE | A | 298 | 20.304 | −72.674 | −68.385 | 1.00 | 38.63 | | C |
| ANISOU | 1168 | CG1 | ILE | A | 298 | 3781 | 4020 | 6876 | 192 | 21 | −970 | C |
| ATOM | 1169 | CD1 | ILE | A | 298 | 19.221 | −72.759 | −67.326 | 1.00 | 39.89 | | C |
| ANISOU | 1169 | CD1 | ILE | A | 298 | 4096 | 4328 | 6733 | 115 | −252 | −1166 | C |
| ATOM | 1170 | CG2 | ILE | A | 298 | 21.451 | −74.694 | −67.525 | 1.00 | 38.88 | | C |
| ANISOU | 1170 | CG2 | ILE | A | 298 | 3886 | 4317 | 6569 | 351 | −350 | −1124 | C |
| ATOM | 1171 | C | ILE | A | 298 | 22.574 | −75.255 | −70.065 | 1.00 | 39.86 | | C |
| ANISOU | 1171 | C | ILE | A | 298 | 4025 | 4358 | 6760 | 657 | 220 | −685 | C |
| ATOM | 1172 | O | ILE | A | 298 | 23.686 | −75.532 | −69.602 | 1.00 | 43.02 | | O |
| ANISOU | 1172 | O | ILE | A | 298 | 4180 | 4781 | 7383 | 697 | 132 | −817 | O |
| ATOM | 1173 | N | LEU | A | 299 | 21.858 | −76.102 | −70.793 | 1.00 | 38.83 | | N |
| ANISOU | 1173 | N | LEU | A | 299 | 4259 | 4302 | 6195 | 793 | 223 | −563 | N |
| ATOM | 1174 | CA | LEU | A | 299 | 22.257 | −77.488 | −70.971 | 1.00 | 40.23 | | C |
| ANISOU | 1174 | CA | LEU | A | 299 | 4603 | 4555 | 6127 | 991 | 79 | −609 | C |
| ATOM | 1175 | CB | LEU | A | 299 | 21.113 | −78.307 | −71.563 | 1.00 | 38.88 | | C |
| ANISOU | 1175 | CB | LEU | A | 299 | 4848 | 4407 | 5518 | 1075 | −20 | −548 | C |
| ATOM | 1176 | CG | LEU | A | 299 | 19.925 | −78.424 | −70.620 | 1.00 | 56.16 | | C |
| ANISOU | 1176 | CG | LEU | A | 299 | 7211 | 6584 | 7541 | 871 | −299 | −594 | C |
| ATOM | 1177 | CD1 | LEU | A | 299 | 18.853 | −79.317 | −71.219 | 1.00 | 63.09 | | C |
| ANISOU | 1177 | CD1 | LEU | A | 299 | 8445 | 7449 | 8077 | 936 | −425 | −544 | C |
| ATOM | 1178 | CD2 | LEU | A | 299 | 20.394 | −78.954 | −69.273 | 1.00 | 54.97 | | C |
| ANISOU | 1178 | CD2 | LEU | A | 299 | 6971 | 6463 | 7450 | 803 | −595 | −723 | C |
| ATOM | 1179 | C | LEU | A | 299 | 23.485 | −77.595 | −71.852 | 1.00 | 41.10 | | C |

TABLE 7-continued

DMXAA-hSTING$^{G230I}$ complex

| | | | | | | | | | | | |
|---|---|---|---|---|---|---|---|---|---|---|---|
| ANISOU | 1179 | C | LEU | A | 299 | 4507 | 4707 | 6404 | 1204 | 353 | −540 C |
| ATOM | 1180 | O | LEU | A | 299 | 24.356 | −78.429 | −71.612 | 1.00 | 59.31 | O |
| ANISOU | 1180 | O | LEU | A | 299 | 6736 | 7048 | 8751 | 1344 | 226 | −657 O |
| ATOM | 1181 | N | ALA | A | 300 | 23.547 | −76.745 | −72.872 | 1.00 | 48.26 | N |
| ANISOU | 1181 | N | ALA | A | 300 | 5309 | 5624 | 7403 | 1246 | 743 | −321 N |
| ATOM | 1182 | CA | ALA | A | 300 | 24.686 | −76.711 | −73.780 | 1.00 | 52.76 | C |
| ANISOU | 1182 | CA | ALA | A | 300 | 5636 | 6290 | 8122 | 1454 | 1094 | −187 C |
| ATOM | 1183 | CB | ALA | A | 300 | 24.570 | −75.543 | −74.727 | 1.00 | 39.76 | C |
| ANISOU | 1183 | CB | ALA | A | 300 | 3858 | 4643 | 6605 | 1439 | 1534 | 147 C |
| ATOM | 1184 | C | ALA | A | 300 | 26.010 | −76.634 | −73.031 | 1.00 | 55.46 | C |
| ANISOU | 1184 | C | ALA | A | 300 | 5548 | 6592 | 8932 | 1400 | 1047 | −325 C |
| ATOM | 1185 | O | ALA | A | 300 | 27.012 | −77.207 | −73.451 | 1.00 | 59.73 | O |
| ANISOU | 1185 | O | ALA | A | 300 | 5930 | 7246 | 9519 | 1621 | 1168 | −338 O |
| ATOM | 1186 | N | ASP | A | 301 | 26.002 | −75.930 | −71.908 | 1.00 | 65.09 | N |
| ANISOU | 1186 | N | ASP | A | 301 | 6564 | 7671 | 10495 | 1129 | 849 | −467 N |
| ATOM | 1187 | CA | ASP | A | 301 | 27.227 | −75.630 | −71.179 | 1.00 | 62.82 | C |
| ANISOU | 1187 | CA | ASP | A | 301 | 5808 | 7337 | 10724 | 1052 | 780 | −627 C |
| ATOM | 1188 | CB | ASP | A | 301 | 27.296 | −74.133 | −70.878 | 1.00 | 64.32 | C |
| ANISOU | 1188 | CB | ASP | A | 301 | 5643 | 7324 | 11473 | 778 | 905 | −602 C |
| ATOM | 1189 | CG | ASP | A | 301 | 28.156 | −73.381 | −71.866 | 1.00 | 84.37 | C |
| ANISOU | 1189 | CG | ASP | A | 301 | 7787 | 9799 | 14469 | 791 | 1395 | −298 C |
| ATOM | 1190 | OD1 | ASP | A | 301 | 27.634 | −73.001 | −72.936 | 1.00 | 83.28 | O |
| ANISOU | 1190 | OD1 | ASP | A | 301 | 7800 | 9672 | 14171 | 850 | 1754 | 51 O |
| ATOM | 1191 | OD2 | ASP | A | 301 | 29.355 | −73.182 | −71.569 | 1.00 | 99.13 | O |
| ANISOU | 1191 | OD2 | ASP | A | 301 | 9307 | 11640 | 16719 | 714 | 1370 | −375 O |
| ATOM | 1192 | C | ASP | A | 301 | 27.410 | −76.414 | −69.881 | 1.00 | 55.33 | C |
| ANISOU | 1192 | C | ASP | A | 301 | 4899 | 6435 | 9687 | 1047 | 288 | −942 C |
| ATOM | 1193 | O | ASP | A | 301 | 28.436 | −76.281 | −69.214 | 1.00 | 57.65 | O |
| ANISOU | 1193 | O | ASP | A | 301 | 4812 | 6728 | 10364 | 1021 | 156 | −1121 O |
| ATOM | 1194 | N | ALA | A | 302 | 26.423 | −77.218 | −69.504 | 1.00 | 69.57 | N |
| ANISOU | 1194 | N | ALA | A | 302 | 4806 | 6124 | 15501 | −233 | −1237 | −3085 N |
| ATOM | 1195 | CA | ALA | A | 302 | 26.471 | −77.857 | −68.192 | 1.00 | 73.72 | C |
| ANISOU | 1195 | CA | ALA | A | 302 | 5393 | 6890 | 15730 | 3 | −1488 | −3415 C |
| ATOM | 1196 | CB | ALA | A | 302 | 25.071 | −78.095 | −67.648 | 1.00 | 63.73 | C |
| ANISOU | 1196 | CB | ALA | A | 302 | 4422 | 5807 | 13984 | 129 | −1635 | −3524 C |
| ATOM | 1197 | C | ALA | A | 302 | 27.271 | −79.153 | −68.215 | 1.00 | 75.63 | C |
| ANISOU | 1197 | C | ALA | A | 302 | 5551 | 7340 | 15845 | 52 | −1407 | −3423 C |
| ATOM | 1198 | O | ALA | A | 302 | 27.071 | −79.982 | −69.109 | 1.00 | 70.93 | O |
| ANISOU | 1198 | O | ALA | A | 302 | 5038 | 6845 | 15065 | 1 | −1165 | −3205 O |
| ATOM | 1199 | N | PRO | A | 303 | 28.167 | −79.336 | −67.229 | 1.00 | 77.08 | N |
| ANISOU | 1199 | N | PRO | A | 303 | 5631 | 7597 | 16059 | 189 | −1586 | −3645 N |
| ATOM | 1200 | CA | PRO | A | 303 | 28.966 | −80.563 | −67.195 | 1.00 | 74.85 | C |
| ANISOU | 1200 | CA | PRO | A | 303 | 5274 | 7504 | 15662 | 271 | −1541 | −3651 C |
| ATOM | 1201 | CB | PRO | A | 303 | 29.811 | −80.404 | −65.924 | 1.00 | 72.35 | C |
| ANISOU | 1201 | CB | PRO | A | 303 | 4879 | 7215 | 15397 | 399 | −1798 | −3917 C |
| ATOM | 1202 | CG | PRO | A | 303 | 29.051 | −79.424 | −65.075 | 1.00 | 73.64 | C |
| ANISOU | 1202 | CG | PRO | A | 303 | 5161 | 7326 | 15491 | 457 | −2000 | −4090 C |
| ATOM | 1203 | CD | PRO | A | 303 | 28.400 | −78.485 | −66.053 | 1.00 | 69.99 | C |
| ANISOU | 1203 | CD | PRO | A | 303 | 4698 | 6635 | 15262 | 298 | −1844 | −3908 C |
| ATOM | 1204 | C | PRO | A | 303 | 28.072 | −81.797 | −67.084 | 1.00 | 78.23 | C |
| ANISOU | 1204 | C | PRO | A | 303 | 5941 | 8201 | 15583 | 394 | −1582 | −3631 C |
| ATOM | 1205 | O | PRO | A | 303 | 28.353 | −82.837 | −67.694 | 1.00 | 73.46 | O |
| ANISOU | 1205 | O | PRO | A | 303 | 5373 | 7702 | 14837 | 445 | −1396 | −3477 O |
| ATOM | 1206 | N | GLU | A | 304 | 26.987 | −81.662 | −66.328 | 1.00 | 73.82 | N |
| ANISOU | 1206 | N | GLU | A | 304 | 5627 | 7749 | 14673 | 467 | −1782 | −3745 N |
| ATOM | 1207 | CA | GLU | A | 304 | 26.070 | −82.766 | −66.065 | 1.00 | 68.05 | C |
| ANISOU | 1207 | CA | GLU | A | 304 | 5157 | 7290 | 13408 | 572 | −1868 | −3723 C |
| ATOM | 1208 | CB | GLU | A | 304 | 25.025 | −82.358 | −65.017 | 1.00 | 65.55 | C |
| ANISOU | 1208 | CB | GLU | A | 304 | 5084 | 7116 | 12707 | 656 | −2072 | −3862 C |
| ATOM | 1209 | CG | GLU | A | 304 | 25.549 | −82.274 | −63.592 | 1.00 | 68.63 | C |
| ANISOU | 1209 | CG | GLU | A | 304 | 5448 | 7637 | 12992 | 806 | −2291 | −4066 C |
| ATOM | 1210 | CD | GLU | A | 304 | 25.981 | −80.870 | −63.195 | 1.00 | 91.01 | C |
| ANISOU | 1210 | CD | GLU | A | 304 | 8101 | 10263 | 16214 | 797 | −2337 | −4236 C |
| ATOM | 1211 | OE1 | GLU | A | 304 | 26.159 | −80.622 | −61.982 | 1.00 | 97.21 | O |
| ANISOU | 1211 | OE1 | GLU | A | 304 | 8879 | 11175 | 16882 | 918 | −2509 | −4429 O |
| ATOM | 1212 | OE2 | GLU | A | 304 | 26.136 | −80.014 | −64.091 | 1.00 | 97.88 | O |
| ANISOU | 1212 | OE2 | GLU | A | 304 | 8834 | 10849 | 17509 | 665 | −2202 | −4161 O |
| ATOM | 1213 | C | GLU | A | 304 | 25.352 | −83.268 | −67.318 | 1.00 | 65.33 | C |
| ANISOU | 1213 | C | GLU | A | 304 | 5140 | 6919 | 12762 | 511 | −1515 | −3371 C |
| ATOM | 1214 | O | GLU | A | 304 | 24.963 | −84.432 | −67.407 | 1.00 | 66.79 | O |
| ANISOU | 1214 | O | GLU | A | 304 | 5599 | 7274 | 12504 | 603 | −1465 | −3244 O |
| ATOM | 1215 | N | SER | A | 305 | 25.185 | −82.383 | −68.290 | 1.00 | 69.48 | N |
| ANISOU | 1215 | N | SER | A | 305 | 5632 | 7227 | 13539 | 349 | −1289 | −3207 N |
| ATOM | 1216 | CA | SER | A | 305 | 24.188 | −82.588 | −69.331 | 1.00 | 71.53 | C |
| ANISOU | 1216 | CA | SER | A | 305 | 6224 | 7483 | 13473 | 279 | −1019 | −2913 C |
| ATOM | 1217 | CB | SER | A | 305 | 23.281 | −81.367 | −69.399 | 1.00 | 82.68 | C |
| ANISOU | 1217 | CB | SER | A | 305 | 7670 | 8740 | 15004 | 172 | −1081 | −2926 C |
| ATOM | 1218 | OG | SER | A | 305 | 23.949 | −80.322 | −70.084 | 1.00 | 92.08 | O |

TABLE 7-continued

| DMXAA-hSTING$^{G230I}$ complex | | | | | | | | | | | |
|---|---|---|---|---|---|---|---|---|---|---|---|
| ANISOU | 1218 | OG | SER | A | 305 | 8593 | 9651 | 16742 | 1 | −955 | −2824 O |
| ATOM | 1219 | C | SER | A | 305 | 24.763 | −82.781 | −70.718 | 1.00 | 71.52 | C |
| ANISOU | 1219 | C | SER | A | 305 | 6186 | 7391 | 13595 | 172 | −630 | −2618 C |
| ATOM | 1220 | O | SER | A | 305 | 24.209 | −82.259 | −71.687 | 1.00 | 68.46 | O |
| ANISOU | 1220 | O | SER | A | 305 | 5909 | 6898 | 13204 | 32 | −412 | −2381 O |
| ATOM | 1221 | N | GLN | A | 306 | 25.863 | −83.512 | −70.832 | 1.00 | 71.66 | N |
| ANISOU | 1221 | N | GLN | A | 306 | 6038 | 7471 | 13718 | 239 | −546 | −2634 N |
| ATOM | 1222 | CA | GLN | A | 306 | 26.501 | −83.664 | −72.129 | 1.00 | 68.61 | C |
| ANISOU | 1222 | CA | GLN | A | 306 | 5559 | 7054 | 13457 | 140 | −169 | −2397 C |
| ATOM | 1223 | CB | GLN | A | 306 | 28.007 | −83.438 | −72.006 | 1.00 | 85.92 | C |
| ANISOU | 1223 | CB | GLN | A | 306 | 7306 | 9193 | 16146 | 121 | −167 | −2516 C |
| ATOM | 1224 | CG | GLN | A | 306 | 28.359 | −82.185 | −71.204 | 1.00 | 93.36 | C |
| ANISOU | 1224 | CG | GLN | A | 306 | 7950 | 9954 | 17570 | 32 | −430 | −2707 C |
| ATOM | 1225 | CD | GLN | A | 306 | 28.188 | −80.892 | −71.995 | 1.00 | 95.94 | C |
| ANISOU | 1225 | CD | GLN | A | 306 | 8171 | 10053 | 18229 | −222 | −278 | −2501 C |
| ATOM | 1226 | OE1 | GLN | A | 306 | 28.299 | −80.882 | −73.222 | 1.00 | 91.63 | O |
| ANISOU | 1226 | OE1 | GLN | A | 306 | 7634 | 9511 | 17672 | −362 | 68 | −2201 O |
| ATOM | 1227 | NE2 | GLN | A | 306 | 27.924 | −79.795 | −71.292 | 1.00 | 100.57 | N |
| ANISOU | 1227 | NE2 | GLN | A | 306 | 8647 | 10447 | 19119 | −282 | −554 | −2665 N |
| ATOM | 1228 | C | GLN | A | 306 | 26.178 | −85.017 | −72.773 | 1.00 | 67.93 | C |
| ANISOU | 1228 | C | GLN | A | 306 | 5767 | 7143 | 12900 | 249 | 32 | −2259 C |
| ATOM | 1229 | O | GLN | A | 306 | 26.569 | −86.069 | −72.261 | 1.00 | 61.54 | O |
| ANISOU | 1229 | O | GLN | A | 306 | 4982 | 6447 | 11953 | 427 | −87 | −2389 O |
| ATOM | 1230 | N | ASN | A | 307 | 25.434 | −84.960 | −73.878 | 1.00 | 75.55 | N |
| ANISOU | 1230 | N | ASN | A | 307 | 6956 | 8117 | 13633 | 141 | 310 | −1998 N |
| ATOM | 1231 | CA | ASN | A | 307 | 25.054 | −86.128 | −74.686 | 1.00 | 76.62 | C |
| ANISOU | 1231 | CA | ASN | A | 307 | 7372 | 8405 | 13336 | 216 | 535 | −1860 C |
| ATOM | 1232 | CB | ASN | A | 307 | 26.280 | −86.935 | −75.126 | 1.00 | 85.31 | C |
| ANISOU | 1232 | CB | ASN | A | 307 | 8255 | 9592 | 14568 | 307 | 704 | −1915 C |
| ATOM | 1233 | CG | ASN | A | 307 | 27.046 | −86.269 | −76.241 | 1.00 | 101.69 | C |
| ANISOU | 1233 | CG | ASN | A | 307 | 10041 | 11662 | 16933 | 128 | 1045 | −1756 C |
| ATOM | 1234 | OD1 | ASN | A | 307 | 26.741 | −86.462 | −77.418 | 1.00 | 108.66 | O |
| ANISOU | 1234 | OD1 | ASN | A | 307 | 11046 | 12647 | 17592 | 48 | 1362 | −1549 O |
| ATOM | 1235 | ND2 | ASN | A | 307 | 28.041 | −85.466 | −75.880 | 1.00 | 102.27 | N |
| ANISOU | 1235 | ND2 | ASN | A | 307 | 9719 | 11640 | 17499 | 47 | 977 | −1844 N |
| ATOM | 1236 | C | ASN | A | 307 | 24.006 | −87.070 | −74.090 | 1.00 | 69.24 | C |
| ANISOU | 1236 | C | ASN | A | 307 | 6822 | 7574 | 11913 | 359 | 342 | −1908 C |
| ATOM | 1237 | O | ASN | A | 307 | 23.724 | −88.126 | −74.656 | 1.00 | 63.30 | O |
| ANISOU | 1237 | O | ASN | A | 307 | 6299 | 6923 | 10828 | 435 | 480 | −1825 O |
| ATOM | 1238 | N | ASN | A | 308 | 23.419 | −86.693 | −72.962 | 1.00 | 71.89 | N |
| ANISOU | 1238 | N | ASN | A | 308 | 7216 | 7898 | 12199 | 388 | 22 | −2046 N |
| ATOM | 1239 | CA | ASN | A | 308 | 22.476 | −87.580 | −72.290 | 1.00 | 67.52 | C |
| ANISOU | 1239 | CA | ASN | A | 308 | 6989 | 7484 | 11181 | 500 | −180 | −2082 C |
| ATOM | 1240 | CB | ASN | A | 308 | 23.009 | −87.952 | −70.913 | 1.00 | 69.39 | C |
| ANISOU | 1240 | CB | ASN | A | 308 | 7092 | 7788 | 11486 | 637 | −536 | −2318 C |
| ATOM | 1241 | CG | ASN | A | 308 | 23.457 | −86.742 | −70.126 | 1.00 | 71.01 | C |
| ANISOU | 1241 | CG | ASN | A | 308 | 6981 | 7913 | 12087 | 589 | −731 | −2519 C |
| ATOM | 1242 | OD1 | ASN | A | 308 | 23.284 | −85.603 | −70.569 | 1.00 | 72.61 | O |
| ANISOU | 1242 | OD1 | ASN | A | 308 | 7082 | 7980 | 12527 | 451 | −624 | −2477 O |
| ATOM | 1243 | ND2 | ASN | A | 308 | 24.039 | −86.978 | −68.954 | 1.00 | 67.54 | N |
| ANISOU | 1243 | ND2 | ASN | A | 308 | 6378 | 7550 | 11735 | 700 | −1038 | −2737 N |
| ATOM | 1244 | C | ASN | A | 308 | 21.075 | −87.012 | −72.132 | 1.00 | 54.62 | C |
| ANISOU | 1244 | C | ASN | A | 308 | 5594 | 5880 | 9278 | 423 | −253 | −2027 C |
| ATOM | 1245 | O | ASN | A | 308 | 20.317 | −87.467 | −71.281 | 1.00 | 43.18 | O |
| ANISOU | 1245 | O | ASN | A | 308 | 4336 | 4572 | 7499 | 492 | −486 | −2102 O |
| ATOM | 1246 | N | CYS | A | 309 | 20.738 | −86.021 | −72.949 | 1.00 | 51.60 | N |
| ANISOU | 1246 | N | CYS | A | 309 | 5188 | 5379 | 9038 | 276 | −63 | −1886 N |
| ATOM | 1247 | CA | CYS | A | 309 | 19.468 | −85.320 | −72.824 | 1.00 | 49.91 | C |
| ANISOU | 1247 | CA | CYS | A | 309 | 5149 | 5163 | 8650 | 211 | −145 | −1857 C |
| ATOM | 1248 | CB | CYS | A | 309 | 19.565 | −84.256 | −71.733 | 1.00 | 45.05 | C |
| ANISOU | 1248 | CB | CYS | A | 309 | 4296 | 4471 | 8348 | 215 | −444 | −2114 C |
| ATOM | 1249 | SG | CYS | A | 309 | 17.995 | −83.510 | −71.263 | 1.00 | 68.53 | S |
| ANISOU | 1249 | SG | CYS | A | 309 | 7450 | 7496 | 11091 | 199 | −629 | −2194 S |
| ATOM | 1250 | C | CYS | A | 309 | 19.096 | −84.664 | −74.148 | 1.00 | 53.87 | C |
| ANISOU | 1250 | C | CYS | A | 309 | 5710 | 5547 | 9210 | 55 | 148 | −1588 C |
| ATOM | 1251 | O | CYS | A | 309 | 19.948 | −84.083 | −74.817 | 1.00 | 67.10 | O |
| ANISOU | 1251 | O | CYS | A | 309 | 7150 | 7087 | 11260 | −49 | 323 | −1488 O |
| ATOM | 1252 | N | ARG | A | 310 | 17.828 | −84.744 | −74.532 | 1.00 | 44.79 | N |
| ANISOU | 1252 | N | ARG | A | 310 | 4862 | 4468 | 7688 | 26 | 197 | −1455 N |
| ATOM | 1253 | CA | ARG | A | 310 | 17.393 | −84.127 | −75.778 | 1.00 | 51.21 | C |
| ANISOU | 1253 | CA | ARG | A | 310 | 5747 | 5188 | 8522 | −122 | 450 | −1178 C |
| ATOM | 1254 | CB | ARG | A | 310 | 17.333 | −85.146 | −76.916 | 1.00 | 40.81 | C |
| ANISOU | 1254 | CB | ARG | A | 310 | 4638 | 4006 | 6862 | −133 | 758 | −960 C |
| ATOM | 1255 | CG | ARG | A | 310 | 17.206 | −84.504 | −78.287 | 1.00 | 71.63 | C |
| ANISOU | 1255 | CG | ARG | A | 310 | 8543 | 7848 | 10826 | −304 | 1050 | −653 C |
| ATOM | 1256 | CD | ARG | A | 310 | 18.432 | −83.658 | −78.602 | 1.00 | 86.94 | C |
| ANISOU | 1256 | CD | ARG | A | 310 | 10110 | 9635 | 13289 | −423 | 1153 | −594 C |
| ATOM | 1257 | NE | ARG | A | 310 | 18.067 | −82.363 | −79.169 | 1.00 | 97.63 | N |

TABLE 7-continued

| | | | | | | | | | | | | |
|---|---|---|---|---|---|---|---|---|---|---|---|---|
| ANISOU | 1257 | NE | ARG | A | 310 | 11397 | 10810 | 14887 | −604 | 1189 | −370 | N |
| ATOM | 1258 | CZ | ARG | A | 310 | 18.057 | −81.219 | −78.489 | 1.00 | 93.75 | | C |
| ANISOU | 1258 | CZ | ARG | A | 310 | 10728 | 10085 | 14808 | −647 | 943 | −470 | C |
| ATOM | 1259 | NH1 | ARG | A | 310 | 18.412 | −81.198 | −77.212 | 1.00 | 88.06 | | N |
| ANISOU | 1259 | NH1 | ARG | A | 310 | 9866 | 9321 | 14271 | −523 | 660 | −807 | N |
| ATOM | 1260 | NH2 | ARG | A | 310 | 17.704 | −80.091 | −79.092 | 1.00 | 90.92 | | N |
| ANISOU | 1260 | NH2 | ARG | A | 310 | 10325 | 9533 | 14688 | −813 | 965 | −236 | N |
| ATOM | 1261 | C | ARG | A | 310 | 16.047 | −83.433 | −75.613 | 1.00 | 49.00 | | C |
| ANISOU | 1261 | C | ARG | A | 310 | 5636 | 4887 | 8096 | −152 | 317 | −1164 | C |
| ATOM | 1262 | O | ARG | A | 310 | 15.107 | −84.003 | −75.066 | 1.00 | 49.14 | | O |
| ANISOU | 1262 | O | ARG | A | 310 | 5883 | 5076 | 7713 | −66 | 182 | −1254 | O |
| ATOM | 1263 | N | LEU | A | 311 | 15.963 | −82.201 | −76.102 | 1.00 | 46.61 | | N |
| ANISOU | 1263 | N | LEU | A | 311 | 5207 | 4373 | 8130 | −279 | 348 | −1044 | N |
| ATOM | 1264 | CA | LEU | A | 311 | 14.762 | −81.396 | −75.967 | 1.00 | 41.12 | | C |
| ANISOU | 1264 | CA | LEU | A | 311 | 4621 | 3612 | 7390 | −295 | 199 | −1053 | C |
| ATOM | 1265 | CB | LEU | A | 311 | 15.122 | −79.942 | −75.684 | 1.00 | 43.85 | | C |
| ANISOU | 1265 | CB | LEU | A | 311 | 4673 | 3657 | 8331 | −365 | 27 | −1138 | C |
| ATOM | 1266 | CG | LEU | A | 311 | 15.935 | −79.703 | −74.419 | 1.00 | 45.22 | | C |
| ANISOU | 1266 | CG | LEU | A | 311 | 4567 | 3786 | 8828 | −276 | −238 | −1502 | C |
| ATOM | 1267 | CD1 | LEU | A | 311 | 16.209 | −78.220 | −74.230 | 1.00 | 48.19 | | C |
| ANISOU | 1267 | CD1 | LEU | A | 311 | 4660 | 3827 | 9821 | −356 | −420 | −1589 | C |
| ATOM | 1268 | CD2 | LEU | A | 311 | 15.205 | −80.268 | −73.216 | 1.00 | 55.42 | | C |
| ANISOU | 1268 | CD2 | LEU | A | 311 | 5984 | 5333 | 9739 | −105 | −486 | −1815 | C |
| ATOM | 1269 | C | LEU | A | 311 | 13.915 | −81.479 | −77.218 | 1.00 | 40.12 | | C |
| ANISOU | 1269 | C | LEU | A | 311 | 4747 | 3521 | 6975 | −389 | 437 | −718 | C |
| ATOM | 1270 | O | LEU | A | 311 | 14.387 | −81.228 | −78.325 | 1.00 | 52.01 | | O |
| ANISOU | 1270 | O | LEU | A | 311 | 6197 | 4942 | 8621 | −527 | 685 | −433 | O |
| ATOM | 1271 | N | ILE | A | 312 | 12.650 | −81.827 | −77.032 | 1.00 | 39.73 | | N |
| ANISOU | 1271 | N | ILE | A | 312 | 4963 | 3628 | 6504 | −324 | 356 | −752 | N |
| ATOM | 1272 | CA | ILE | A | 312 | 11.711 | −81.950 | −78.132 | 1.00 | 40.98 | | C |
| ANISOU | 1272 | CA | ILE | A | 312 | 5378 | 3849 | 6344 | −398 | 546 | −463 | C |
| ATOM | 1273 | CB | ILE | A | 312 | 11.097 | −83.346 | −78.166 | 1.00 | 42.85 | | C |
| ANISOU | 1273 | CB | ILE | A | 312 | 5916 | 4373 | 5992 | −323 | 621 | −464 | C |
| ATOM | 1274 | CG1 | ILE | A | 312 | 12.200 | −84.400 | −78.173 | 1.00 | 42.28 | | C |
| ANISOU | 1274 | CG1 | ILE | A | 312 | 5799 | 4383 | 5885 | −280 | 747 | −501 | C |
| ATOM | 1275 | CD1 | ILE | A | 312 | 11.700 | −85.811 | −78.345 | 1.00 | 43.53 | | C |
| ANISOU | 1275 | CD1 | ILE | A | 312 | 6248 | 4766 | 5524 | −219 | 822 | −476 | C |
| ATOM | 1276 | CG2 | ILE | A | 312 | 10.204 | −83.509 | −79.382 | 1.00 | 49.83 | | C |
| ANISOU | 1276 | CG2 | ILE | A | 312 | 7053 | 5333 | 6548 | −406 | 830 | −171 | C |
| ATOM | 1277 | C | ILE | A | 312 | 10.613 | −80.893 | −78.015 | 1.00 | 36.75 | | C |
| ANISOU | 1277 | C | ILE | A | 312 | 4870 | 3196 | 5896 | −407 | 364 | −477 | C |
| ATOM | 1278 | O | ILE | A | 312 | 9.618 | −81.089 | −77.325 | 1.00 | 34.99 | | O |
| ANISOU | 1278 | O | ILE | A | 312 | 4779 | 3126 | 5391 | −307 | 187 | −663 | O |
| ATOM | 1279 | N | ALA | A | 313 | 10.819 | −79.761 | −78.678 | 1.00 | 42.89 | | N |
| ANISOU | 1279 | N | ALA | A | 313 | 5505 | 3706 | 7087 | −531 | 397 | −278 | N |
| ATOM | 1280 | CA | ALA | A | 313 | 9.888 | −78.646 | −78.601 | 1.00 | 48.70 | | C |
| ANISOU | 1280 | CA | ALA | A | 313 | 6229 | 4262 | 8016 | −531 | 193 | −293 | C |
| ATOM | 1281 | CB | ALA | A | 313 | 10.636 | −77.323 | −78.512 | 1.00 | 43.37 | | C |
| ANISOU | 1281 | CB | ALA | A | 313 | 5238 | 3208 | 8031 | −616 | 56 | −293 | C |
| ATOM | 1282 | C | ALA | A | 313 | 8.966 | −78.652 | −79.806 | 1.00 | 46.31 | | C |
| ANISOU | 1282 | C | ALA | A | 313 | 6165 | 4004 | 7426 | −619 | 366 | 64 | C |
| ATOM | 1283 | O | ALA | A | 313 | 9.409 | −78.861 | −80.936 | 1.00 | 54.57 | | O |
| ANISOU | 1283 | O | ALA | A | 313 | 7254 | 5065 | 8415 | −757 | 643 | 406 | O |
| ATOM | 1284 | N | TYR | A | 314 | 7.688 | −78.465 | −79.564 | 1.00 | 44.11 | | N |
| ANISOU | 1284 | N | TYR | A | 314 | 6026 | 3776 | 6959 | −539 | 201 | −25 | N |
| ATOM | 1285 | CA | TYR | A | 314 | 6.729 | −78.469 | −80.639 | 1.00 | 51.97 | | C |
| ANISOU | 1285 | CA | TYR | A | 314 | 7257 | 4843 | 7645 | −607 | 340 | 293 | C |
| ATOM | 1286 | CB | TYR | A | 314 | 6.349 | −79.905 | −80.989 | 1.00 | 47.50 | | C |
| ANISOU | 1286 | CB | TYR | A | 314 | 6967 | 4636 | 6445 | −587 | 559 | 352 | C |
| ATOM | 1287 | CG | TYR | A | 314 | 5.843 | −80.707 | −79.831 | 1.00 | 46.11 | | C |
| ANISOU | 1287 | CG | TYR | A | 314 | 6879 | 4707 | 5933 | −435 | 398 | −2 | C |
| ATOM | 1288 | CD1 | TYR | A | 314 | 6.712 | −81.297 | −78.958 | 1.00 | 37.13 | | C |
| ANISOU | 1288 | CD1 | TYR | A | 314 | 5639 | 3647 | 4820 | −370 | 359 | −235 | C |
| ATOM | 1289 | CE1 | TYR | A | 314 | 6.258 | −82.024 | −77.900 | 1.00 | 40.74 | | C |
| ANISOU | 1289 | CE1 | TYR | A | 314 | 6173 | 4353 | 4953 | −256 | 200 | −513 | C |
| ATOM | 1290 | CZ | TYR | A | 314 | 4.933 | −82.164 | −77.718 | 1.00 | 44.45 | | C |
| ANISOU | 1290 | CZ | TYR | A | 314 | 6810 | 5015 | 5063 | −211 | 94 | −575 | C |
| ATOM | 1291 | OH | TYR | A | 314 | 4.501 | −82.879 | −76.688 | 1.00 | 40.93 | | O |
| ANISOU | 1291 | OH | TYR | A | 314 | 6422 | 4852 | 4275 | −129 | −58 | −817 | O |
| ATOM | 1292 | CE2 | TYR | A | 314 | 4.038 | −81.598 | −78.565 | 1.00 | 35.48 | | C |
| ANISOU | 1292 | CE2 | TYR | A | 314 | 5770 | 3806 | 3904 | −259 | 136 | −378 | C |
| ATOM | 1293 | CD2 | TYR | A | 314 | 4.494 | −80.876 | −79.621 | 1.00 | 36.48 | | C |
| ANISOU | 1293 | CD2 | TYR | A | 314 | 5833 | 3665 | 4363 | −367 | 279 | −86 | C |
| ATOM | 1294 | C | TYR | A | 314 | 5.477 | −77.671 | −80.361 | 1.00 | 52.57 | | C |
| ANISOU | 1294 | C | TYR | A | 314 | 7377 | 4854 | 7742 | −524 | 91 | 184 | C |
| ATOM | 1295 | O | TYR | A | 314 | 5.102 | −77.476 | −79.246 | 1.00 | 58.84 | | O |
| ANISOU | 1295 | O | TYR | A | 314 | 8084 | 5687 | 8584 | −378 | −167 | −205 | O |
| ATOM | 1296 | N | GLN | A | 315 | 4.813 | −77.242 | −81.416 | 1.00 | 78.48 | | N |

TABLE 7-continued

DMXAA-hSTING$^{G230I}$ complex

| | | | | | | | | | | | |
|---|---|---|---|---|---|---|---|---|---|---|---|
| ANISOU | 1296 | N | GLN | A | 315 | 12340 | 6281 | 11200 | 1199 | −1498 | −400 | N |
| ATOM | 1297 | CA | GLN | A | 315 | 3.437 | −76.773 | −81.353 | 1.00 | 82.66 | | C |
| ANISOU | 1297 | CA | GLN | A | 315 | 12853 | 6562 | 11992 | 1625 | −1833 | −279 | C |
| ATOM | 1298 | CB | GLN | A | 315 | 3.315 | −75.315 | −81.780 | 1.00 | 83.38 | | C |
| ANISOU | 1298 | CB | GLN | A | 315 | 13620 | 6228 | 11830 | 1723 | −1757 | −56 | C |
| ATOM | 1299 | CG | GLN | A | 315 | 4.312 | −74.862 | −82.822 | 1.00 | 92.81 | | C |
| ANISOU | 1299 | CG | GLN | A | 315 | 15444 | 7359 | 12459 | 1471 | −1586 | 29 | C |
| ATOM | 1300 | CD | GLN | A | 315 | 3.692 | −74.009 | −83.911 | 1.00 | 100.51 | | C |
| ANISOU | 1300 | CD | GLN | A | 315 | 17125 | 7915 | 13148 | 1707 | −1728 | 281 | C |
| ATOM | 1301 | OE1 | GLN | A | 315 | 2.573 | −74.252 | −84.334 | 1.00 | 104.15 | | O |
| ANISOU | 1301 | OE1 | GLN | A | 315 | 17605 | 8249 | 13719 | 2135 | −2186 | 407 | O |
| ATOM | 1302 | NE2 | GLN | A | 315 | 4.434 | −73.016 | −84.385 | 1.00 | 100.46 | | N |
| ANISOU | 1302 | NE2 | GLN | A | 315 | 17708 | 7693 | 12771 | 1427 | −1336 | 353 | N |
| ATOM | 1303 | C | GLN | A | 315 | 2.566 | −77.648 | −82.250 | 1.00 | 92.39 | | C |
| ANISOU | 1303 | C | GLN | A | 315 | 13930 | 7932 | 13242 | 1924 | −2368 | −262 | C |
| ATOM | 1304 | O | GLN | A | 315 | 2.979 | −77.990 | −83.337 | 1.00 | 99.61 | | O |
| ANISOU | 1304 | O | GLN | A | 315 | 15145 | 8925 | 13778 | 1857 | −2492 | −223 | O |
| ATOM | 1305 | N | GLU | A | 316 | 1.380 | −78.034 | −81.796 | 1.00 | 90.84 | | N |
| ANISOU | 1305 | N | GLU | A | 316 | 13264 | 7769 | 13483 | 2228 | −2668 | −305 | N |
| ATOM | 1306 | CA | GLU | A | 316 | 0.488 | −78.789 | −82.653 | 1.00 | 86.85 | | C |
| ANISOU | 1306 | CA | GLU | A | 316 | 12586 | 7385 | 13027 | 2517 | −3204 | −291 | C |
| ATOM | 1307 | CB | GLU | A | 316 | −0.433 | −79.685 | −81.856 | 1.00 | 81.04 | | C |
| ANISOU | 1307 | CB | GLU | A | 316 | 11087 | 6995 | 12709 | 2531 | −3240 | −459 | C |
| ATOM | 1308 | CG | GLU | A | 316 | 0.226 | −80.498 | −80.781 | 1.00 | 76.25 | | C |
| ANISOU | 1308 | CG | GLU | A | 316 | 10098 | 6686 | 12187 | 2314 | −3180 | −685 | C |
| ATOM | 1309 | CD | GLU | A | 316 | −0.679 | −81.571 | −80.240 | 1.00 | 81.39 | | C |
| ANISOU | 1309 | CD | GLU | A | 316 | 10104 | 7675 | 13145 | 2186 | −3040 | −844 | C |
| ATOM | 1310 | OE1 | GLU | A | 316 | −1.681 | −81.883 | −80.893 | 1.00 | 82.49 | | O |
| ANISOU | 1310 | OE1 | GLU | A | 316 | 10041 | 7941 | 13360 | 2291 | −3228 | −829 | O |
| ATOM | 1311 | OE2 | GLU | A | 316 | −0.386 | −82.111 | −79.167 | 1.00 | 84.72 | | O |
| ANISOU | 1311 | OE2 | GLU | A | 316 | 10278 | 8213 | 13698 | 1952 | −2720 | −982 | O |
| ATOM | 1312 | C | GLU | A | 316 | −0.366 | −77.791 | −83.360 | 1.00 | 92.02 | | C |
| ANISOU | 1312 | C | GLU | A | 316 | 13622 | 7805 | 13535 | 2825 | −3480 | −54 | C |
| ATOM | 1313 | O | GLU | A | 316 | −1.096 | −77.062 | −82.733 | 1.00 | 95.16 | | O |
| ANISOU | 1313 | O | GLU | A | 316 | 13834 | 8162 | 14160 | 2954 | −3383 | 8 | O |
| ATOM | 1314 | N | PRO | A | 317 | −0.289 | −77.772 | −84.674 | 1.00 | 99.97 | | N |
| ANISOU | 1314 | N | PRO | A | 317 | 15164 | 8694 | 14125 | 2909 | −3774 | 81 | N |
| ATOM | 1315 | CA | PRO | A | 317 | −0.969 | −76.740 | −85.454 | 1.00 | 110.29 | | C |
| ANISOU | 1315 | CA | PRO | A | 317 | 16878 | 9797 | 15230 | 3149 | −3965 | 312 | C |
| ATOM | 1316 | CB | PRO | A | 317 | −0.519 | −77.025 | −86.886 | 1.00 | 112.90 | | C |
| ANISOU | 1316 | CB | PRO | A | 317 | 17808 | 10049 | 15039 | 3138 | −4246 | 416 | C |
| ATOM | 1317 | CG | PRO | A | 317 | −0.242 | −78.494 | −86.899 | 1.00 | 110.25 | | C |
| ANISOU | 1317 | CG | PRO | A | 317 | 17070 | 10076 | 14746 | 2955 | −4326 | 208 | C |
| ATOM | 1318 | CD | PRO | A | 317 | 0.342 | −78.786 | −85.534 | 1.00 | 103.75 | | C |
| ANISOU | 1318 | CD | PRO | A | 317 | 15752 | 9415 | 14254 | 2693 | −3853 | 4 | C |
| ATOM | 1319 | C | PRO | A | 317 | −2.477 | −76.882 | −85.353 | 1.00 | 115.18 | | C |
| ANISOU | 1319 | C | PRO | A | 317 | 16957 | 10648 | 16158 | 3381 | −4236 | 303 | C |
| ATOM | 1320 | O | PRO | A | 317 | −3.004 | −77.992 | −85.440 | 1.00 | 114.75 | | O |
| ANISOU | 1320 | O | PRO | A | 317 | 16448 | 10917 | 16233 | 3357 | −4463 | 159 | O |
| ATOM | 1321 | N | ALA | A | 318 | −3.162 | −75.762 | −85.149 | 1.00 | 119.53 | | N |
| ANISOU | 1321 | N | ALA | A | 318 | 17573 | 11021 | 16821 | 3581 | −4170 | 451 | N |
| ATOM | 1322 | CA | ALA | A | 318 | −4.611 | −75.752 | −85.183 | 1.00 | 119.96 | | C |
| ANISOU | 1322 | CA | ALA | A | 318 | 17214 | 11238 | 17127 | 3819 | −4414 | 478 | C |
| ATOM | 1323 | CB | ALA | A | 318 | −5.144 | −74.414 | −84.712 | 1.00 | 111.78 | | C |
| ANISOU | 1323 | CB | ALA | A | 318 | 16268 | 9955 | 16250 | 4024 | −4215 | 642 | C |
| ATOM | 1324 | C | ALA | A | 318 | −5.050 | −76.031 | −86.614 | 1.00 | 132.46 | | C |
| ANISOU | 1324 | C | ALA | A | 318 | 19062 | 12866 | 18403 | 3957 | −4900 | 570 | C |
| ATOM | 1325 | O | ALA | A | 318 | −6.016 | −76.756 | −86.854 | 1.00 | 138.36 | | O |
| ANISOU | 1325 | O | ALA | A | 318 | 19398 | 13877 | 19296 | 4023 | −5182 | 494 | O |
| ATOM | 1326 | N | ASP | A | 319 | −4.316 | −75.458 | −87.562 | 1.00 | 139.08 | | N |
| ANISOU | 1326 | N | ASP | A | 319 | 20628 | 13433 | 18783 | 3964 | −4963 | 730 | N |
| ATOM | 1327 | CA | ASP | A | 319 | −4.604 | −75.619 | −88.981 | 1.00 | 147.58 | | C |
| ANISOU | 1327 | CA | ASP | A | 319 | 22080 | 14508 | 19485 | 4067 | −5395 | 834 | C |
| ATOM | 1328 | CB | ASP | A | 319 | −3.747 | −74.655 | −89.808 | 1.00 | 149.84 | | C |
| ANISOU | 1328 | CB | ASP | A | 319 | 23260 | 14420 | 19252 | 4051 | −5315 | 1034 | C |
| ATOM | 1329 | CG | ASP | A | 319 | −4.309 | −74.412 | −91.195 | 1.00 | 157.47 | | C |
| ANISOU | 1329 | CG | ASP | A | 319 | 24644 | 15322 | 19867 | 4227 | −5737 | 1190 | C |
| ATOM | 1330 | OD2 | ASP | A | 319 | −3.516 | −74.147 | −92.124 | 1.00 | 155.33 | | O |
| ANISOU | 1330 | OD2 | ASP | A | 319 | 25108 | 14841 | 19068 | 4118 | −5734 | 1292 | O |
| ATOM | 1331 | OD1 | ASP | A | 319 | −5.547 | −74.480 | −91.357 | 1.00 | 164.57 | | O |
| ANISOU | 1331 | OD1 | ASP | A | 319 | 25149 | 16373 | 21005 | 4457 | −6050 | 1209 | O |
| ATOM | 1332 | C | ASP | A | 319 | −4.368 | −77.052 | −89.456 | 1.00 | 152.05 | | C |
| ANISOU | 1332 | C | ASP | A | 319 | 22482 | 15356 | 19934 | 3883 | −5615 | 665 | C |
| ATOM | 1333 | O | ASP | A | 319 | −3.304 | −77.628 | −89.216 | 1.00 | 152.57 | | O |
| ANISOU | 1333 | O | ASP | A | 319 | 22637 | 15443 | 19891 | 3648 | −5418 | 560 | O |
| ATOM | 1334 | N | ASP | A | 320 | −5.376 | −77.619 | −90.117 | 1.00 | 153.32 | | N |
| ANISOU | 1334 | N | ASP | A | 320 | 22404 | 15724 | 20126 | 3988 | −6005 | 641 | N |
| ATOM | 1335 | CA | ASP | A | 320 | −5.254 | −78.896 | −90.823 | 1.00 | 146.21 | | C |

TABLE 7-continued

| DMXAA-hSTING$^{G230I}$ complex | | | | | | | | | | | |
|---|---|---|---|---|---|---|---|---|---|---|---|
| ANISOU | 1335 | CA | ASP | A | 320 | 21461 | 15053 | 19040 | 3825 | −6248 | 510 | C |
| ATOM | 1336 | CB | ASP | A | 320 | −4.260 | −78.773 | −91.990 | 1.00 | 147.85 | | C |
| ANISOU | 1336 | CB | ASP | A | 320 | 22484 | 15053 | 18638 | 3729 | −6334 | 629 | C |
| ATOM | 1337 | CG | ASP | A | 320 | −4.875 | −78.151 | −93.230 | 1.00 | 152.59 | | C |
| ANISOU | 1337 | CG | ASP | A | 320 | 23549 | 15507 | 18922 | 3915 | −6686 | 819 | C |
| ATOM | 1338 | OD2 | ASP | A | 320 | −4.107 | −77.783 | −94.143 | 1.00 | 153.12 | | O |
| ANISOU | 1338 | OD2 | ASP | A | 320 | 24366 | 15345 | 18468 | 3840 | −6690 | 945 | O |
| ATOM | 1339 | OD1 | ASP | A | 320 | −6.118 | −78.047 | −93.300 | 1.00 | 156.73 | | O |
| ANISOU | 1339 | OD1 | ASP | A | 320 | 23701 | 16144 | 19704 | 4122 | −6940 | 843 | O |
| ATOM | 1340 | C | ASP | A | 320 | −4.759 | −79.929 | −89.813 | 1.00 | 132.77 | | C |
| ANISOU | 1340 | C | ASP | A | 320 | 19246 | 13616 | 17583 | 3584 | −6042 | 259 | C |
| ATOM | 1341 | O | ASP | A | 320 | −5.434 | −80.246 | −88.830 | 1.00 | 123.63 | | O |
| ANISOU | 1341 | O | ASP | A | 320 | 17438 | 12703 | 16831 | 3565 | −5998 | 107 | O |
| ATOM | 1342 | N | SER | A | 321 | −3.571 | −80.434 | −90.063 | 1.00 | 130.82 | | N |
| ANISOU | 1342 | N | SER | A | 321 | 19344 | 13304 | 17059 | 3391 | −5889 | 227 | N |
| ATOM | 1343 | CA | SER | A | 321 | −3.034 | −81.747 | −89.714 | 1.00 | 128.83 | | C |
| ANISOU | 1343 | CA | SER | A | 321 | 18757 | 13306 | 16887 | 3161 | −5789 | 8 | C |
| ATOM | 1344 | CB | SER | A | 321 | −1.514 | −81.762 | −89.887 | 1.00 | 120.53 | | C |
| ANISOU | 1344 | CB | SER | A | 321 | 18232 | 12090 | 15472 | 3001 | −5595 | 51 | C |
| ATOM | 1345 | OG | SER | A | 321 | −0.960 | −82.971 | −89.394 | 1.00 | 110.50 | | O |
| ANISOU | 1345 | OG | SER | A | 321 | 16582 | 11082 | 14319 | 2792 | −5451 | −165 | O |
| ATOM | 1346 | C | SER | A | 321 | −3.379 | −82.273 | −88.325 | 1.00 | 127.96 | | C |
| ANISOU | 1346 | C | SER | A | 321 | 17888 | 13424 | 17306 | 3077 | −5524 | −200 | C |
| ATOM | 1347 | O | SER | A | 321 | −3.604 | −81.510 | −87.382 | 1.00 | 125.70 | | O |
| ANISOU | 1347 | O | SER | A | 321 | 17394 | 13052 | 17315 | 3145 | −5290 | −174 | O |
| ATOM | 1348 | N | SER | A | 322 | −3.416 | −83.597 | −88.224 | 1.00 | 127.79 | | N |
| ANISOU | 1348 | N | SER | A | 322 | 17502 | 13686 | 17368 | 2902 | −5526 | −403 | N |
| ATOM | 1349 | CA | SER | A | 322 | −3.370 | −84.265 | −86.937 | 1.00 | 125.23 | | C |
| ANISOU | 1349 | CA | SER | A | 322 | 16592 | 13562 | 17427 | 2736 | −5193 | −613 | C |
| ATOM | 1350 | CB | SER | A | 322 | −4.329 | −85.449 | −86.871 | 1.00 | 128.30 | | C |
| ANISOU | 1350 | CB | SER | A | 322 | 16528 | 14228 | 17990 | 2634 | −5236 | −781 | C |
| ATOM | 1351 | OG | SER | A | 322 | −5.262 | −85.264 | −85.819 | 1.00 | 130.27 | | O |
| ANISOU | 1351 | OG | SER | A | 322 | 16328 | 14544 | 18623 | 2644 | −5043 | −836 | O |
| ATOM | 1352 | C | SER | A | 322 | −1.928 | −84.692 | −86.697 | 1.00 | 114.89 | | C |
| ANISOU | 1352 | C | SER | A | 322 | 15414 | 12253 | 15984 | 2572 | −4992 | −687 | C |
| ATOM | 1353 | O | SER | A | 322 | −1.412 | −85.622 | −87.320 | 1.00 | 114.32 | | O |
| ANISOU | 1353 | O | SER | A | 322 | 15461 | 12308 | 15666 | 2456 | −5089 | −760 | O |
| ATOM | 1354 | N | PHE | A | 323 | −1.299 | −83.965 | −85.788 | 1.00 | 104.42 | | N |
| ANISOU | 1354 | N | PHE | A | 323 | 14075 | 10778 | 14821 | 2565 | −4693 | −662 | N |
| ATOM | 1355 | CA | PHE | A | 323 | 0.123 | −84.024 | −85.526 | 1.00 | 92.32 | | C |
| ANISOU | 1355 | CA | PHE | A | 323 | 12725 | 9228 | 13124 | 2328 | −4312 | −707 | C |
| ATOM | 1356 | CB | PHE | A | 323 | 0.442 | −82.860 | −84.583 | 1.00 | 86.87 | | C |
| ANISOU | 1356 | CB | PHE | A | 323 | 12071 | 8324 | 12612 | 2307 | −3944 | −643 | C |
| ATOM | 1357 | CG | PHE | A | 323 | 1.744 | −82.973 | −83.863 | 1.00 | 84.24 | | C |
| ANISOU | 1357 | CG | PHE | A | 323 | 11684 | 8096 | 12228 | 1945 | −3391 | −759 | C |
| ATOM | 1358 | CD1 | PHE | A | 323 | 2.919 | −82.534 | −84.453 | 1.00 | 81.08 | | C |
| ANISOU | 1358 | CD1 | PHE | A | 323 | 11794 | 7624 | 11388 | 1697 | −3085 | −687 | C |
| ATOM | 1359 | CE1 | PHE | A | 323 | 4.123 | −82.615 | −83.774 | 1.00 | 67.68 | | C |
| ANISOU | 1359 | CE1 | PHE | A | 323 | 10004 | 6048 | 9665 | 1362 | −2588 | −796 | C |
| ATOM | 1360 | CZ | PHE | A | 323 | 4.154 | −83.130 | −82.481 | 1.00 | 70.89 | | C |
| ANISOU | 1360 | CZ | PHE | A | 323 | 9836 | 6632 | 10467 | 1283 | −2411 | −967 | C |
| ATOM | 1361 | CE2 | PHE | A | 323 | 2.978 | −83.558 | −81.879 | 1.00 | 74.76 | | C |
| ANISOU | 1361 | CE2 | PHE | A | 323 | 9862 | 7166 | 11377 | 1525 | −2698 | −1036 | C |
| ATOM | 1362 | CD2 | PHE | A | 323 | 1.786 | −83.474 | −82.569 | 1.00 | 78.37 | | C |
| ANISOU | 1362 | CD2 | PHE | A | 323 | 10384 | 7515 | 11878 | 1849 | −3174 | −938 | C |
| ATOM | 1363 | C | PHE | A | 323 | 0.519 | −85.375 | −84.940 | 1.00 | 85.93 | | C |
| ANISOU | 1363 | C | PHE | A | 323 | 11443 | 8743 | 12464 | 2111 | −4135 | −952 | C |
| ATOM | 1364 | O | PHE | A | 323 | −0.255 | −85.999 | −84.218 | 1.00 | 94.92 | | O |
| ANISOU | 1364 | O | PHE | A | 323 | 12062 | 10045 | 13958 | 2138 | −4179 | −1092 | O |
| ATOM | 1365 | N | SER | A | 324 | 1.712 | −85.845 | −85.280 | 1.00 | 67.43 | | N |
| ANISOU | 1365 | N | SER | A | 324 | 9311 | 6518 | 9791 | 1822 | −3826 | −1010 | N |
| ATOM | 1366 | CA | SER | A | 324 | 2.182 | −87.103 | −84.731 | 1.00 | 59.71 | | C |
| ANISOU | 1366 | CA | SER | A | 324 | 7925 | 5829 | 8933 | 1631 | −3631 | −1229 | C |
| ATOM | 1367 | CB | SER | A | 324 | 2.670 | −88.044 | −85.824 | 1.00 | 57.13 | | C |
| ANISOU | 1367 | CB | SER | A | 324 | 7854 | 5644 | 8210 | 1499 | −3686 | −1273 | C |
| ATOM | 1368 | OG | SER | A | 324 | 2.801 | −89.359 | −85.318 | 1.00 | 61.93 | | O |
| ANISOU | 1368 | OG | SER | A | 324 | 8032 | 6516 | 8984 | 1395 | −3599 | −1483 | O |
| ATOM | 1369 | C | SER | A | 324 | 3.291 | −86.853 | −83.732 | 1.00 | 68.42 | | C |
| ANISOU | 1369 | C | SER | A | 324 | 8901 | 6975 | 10118 | 1389 | −3102 | −1296 | C |
| ATOM | 1370 | O | SER | A | 324 | 4.389 | −86.437 | −84.100 | 1.00 | 78.78 | | O |
| ANISOU | 1370 | O | SER | A | 324 | 10574 | 8248 | 11112 | 1183 | −2791 | −1240 | O |
| ATOM | 1371 | N | LEU | A | 325 | 2.993 | −87.103 | −82.464 | 1.00 | 72.69 | | N |
| ANISOU | 1371 | N | LEU | A | 325 | 8932 | 7600 | 11087 | 1401 | −3002 | −1422 | N |
| ATOM | 1372 | CA | LEU | A | 325 | 3.979 | −86.960 | −81.410 | 1.00 | 68.75 | | C |
| ANISOU | 1372 | CA | LEU | A | 325 | 8262 | 7169 | 10691 | 1168 | −2541 | −1500 | C |
| ATOM | 1373 | CB | LEU | A | 325 | 3.331 | −87.207 | −80.050 | 1.00 | 58.12 | | C |
| ANISOU | 1373 | CB | LEU | A | 325 | 6381 | 5868 | 9833 | 1235 | −2527 | −1626 | C |
| ATOM | 1374 | CG | LEU | A | 325 | 4.100 | −86.672 | −78.850 | 1.00 | 58.26 | | C |

TABLE 7-continued

DMXAA-hSTING$^{G230I}$ complex

| | | | | | | | | | | | | |
|---|---|---|---|---|---|---|---|---|---|---|---|---|
| ANISOU | 1374 | CG | LEU | A | 325 | 6273 | 5869 | 9994 | 1036 | −2108 | −1663 | C |
| ATOM | 1375 | CD1 | LEU | A | 325 | 4.480 | −85.235 | −79.126 | 1.00 | 53.01 | | C |
| ANISOU | 1375 | CD1 | LEU | A | 325 | 6057 | 4951 | 9135 | 994 | −1956 | −1486 | C |
| ATOM | 1376 | CD2 | LEU | A | 325 | 3.250 | −86.769 | −77.596 | 1.00 | 55.50 | | C |
| ANISOU | 1376 | CD2 | LEU | A | 325 | 5593 | 5558 | 9937 | 997 | −2039 | −1715 | C |
| ATOM | 1377 | C | LEU | A | 325 | 5.078 | −87.981 | −81.669 | 1.00 | 61.37 | | C |
| ANISOU | 1377 | C | LEU | A | 325 | 7308 | 6481 | 9528 | 935 | −2312 | −1615 | C |
| ATOM | 1378 | O | LEU | A | 325 | 6.270 | −87.706 | −81.527 | 1.00 | 57.75 | | O |
| ANISOU | 1378 | O | LEU | A | 325 | 6975 | 6065 | 8901 | 702 | −1936 | −1614 | O |
| ATOM | 1379 | N | SER | A | 326 | 4.675 | −89.168 | −82.055 | 1.00 | 57.01 | | N |
| ANISOU | 1379 | N | SER | A | 326 | 6597 | 6089 | 8974 | 1004 | −2541 | −1717 | N |
| ATOM | 1380 | CA | SER | A | 326 | 5.605 | −90.218 | −82.325 | 1.00 | 58.67 | | C |
| ANISOU | 1380 | CA | SER | A | 326 | 6789 | 6521 | 8981 | 831 | −2353 | −1831 | C |
| ATOM | 1381 | CB | SER | A | 326 | 4.863 | −91.496 | −82.546 | 1.00 | 63.95 | | C |
| ANISOU | 1381 | CB | SER | A | 326 | 7302 | 7311 | 9685 | 946 | −2675 | −1937 | C |
| ATOM | 1382 | OG | SER | A | 326 | 4.079 | −91.363 | −83.677 | 1.00 | 78.93 | | O |
| ANISOU | 1382 | OG | SER | A | 326 | 8856 | 9234 | 11900 | 999 | −2516 | −1957 | O |
| ATOM | 1383 | C | SER | A | 326 | 6.537 | −89.917 | −83.473 | 1.00 | 59.11 | | C |
| ANISOU | 1383 | C | SER | A | 326 | 7350 | 6533 | 8578 | 681 | −2172 | −1734 | C |
| ATOM | 1384 | O | SER | A | 326 | 7.683 | −90.242 | −83.390 | 1.00 | 55.11 | | O |
| ANISOU | 1384 | O | SER | A | 326 | 6830 | 6163 | 7947 | 473 | −1805 | −1796 | O |
| ATOM | 1385 | N | GLN | A | 327 | 6.068 | −89.296 | −84.541 | 1.00 | 61.56 | | N |
| ANISOU | 1385 | N | GLN | A | 327 | 8105 | 6652 | 8635 | 789 | −2430 | −1585 | N |
| ATOM | 1386 | CA | GLN | A | 327 | 6.942 | −88.928 | −85.642 | 1.00 | 58.07 | | C |
| ANISOU | 1386 | CA | GLN | A | 327 | 8208 | 6130 | 7727 | 641 | −2262 | −1489 | C |
| ATOM | 1387 | CB | GLN | A | 327 | 6.142 | −88.368 | −86.818 | 1.00 | 60.68 | | C |
| ANISOU | 1387 | CB | GLN | A | 327 | 9025 | 6236 | 7793 | 810 | −2653 | −1323 | C |
| ATOM | 1388 | CG | GLN | A | 327 | 5.491 | −89.452 | −87.653 | 1.00 | 56.58 | | C |
| ANISOU | 1388 | CG | GLN | A | 327 | 8536 | 5816 | 7147 | 904 | −3015 | −1380 | C |
| ATOM | 1389 | CD | GLN | A | 327 | 6.488 | −90.527 | −88.072 | 1.00 | 61.98 | | C |
| ANISOU | 1389 | CD | GLN | A | 327 | 9272 | 6687 | 7591 | 691 | −2731 | −1510 | C |
| ATOM | 1390 | OE1 | GLN | A | 327 | 7.400 | −90.268 | −88.859 | 1.00 | 74.76 | | O |
| ANISOU | 1390 | OE1 | GLN | A | 327 | 11335 | 8241 | 8827 | 525 | −2482 | −1455 | O |
| ATOM | 1391 | NE2 | GLN | A | 327 | 6.327 | −91.736 | −87.533 | 1.00 | 55.10 | | N |
| ANISOU | 1391 | NE2 | GLN | A | 327 | 7954 | 6036 | 6947 | 696 | −2742 | −1686 | N |
| ATOM | 1392 | C | GLN | A | 327 | 7.970 | −87.917 | −85.169 | 1.00 | 56.30 | | C |
| ANISOU | 1392 | C | GLN | A | 327 | 8105 | 5832 | 7456 | 443 | −1833 | −1435 | C |
| ATOM | 1393 | O | GLN | A | 327 | 9.128 | −87.939 | −85.582 | 1.00 | 56.11 | | O |
| ANISOU | 1393 | O | GLN | A | 327 | 8297 | 5865 | 7156 | 217 | −1491 | −1450 | O |
| ATOM | 1394 | N | GLU | A | 328 | 7.530 | −87.042 | −84.276 | 1.00 | 47.72 | | N |
| ANISOU | 1394 | N | GLU | A | 328 | 6865 | 4618 | 6649 | 519 | −1841 | −1384 | N |
| ATOM | 1395 | CA | GLU | A | 328 | 8.375 | −85.995 | −83.731 | 1.00 | 65.69 | | C |
| ANISOU | 1395 | CA | GLU | A | 328 | 9256 | 6801 | 8903 | 323 | −1458 | −1334 | C |
| ATOM | 1396 | CB | GLU | A | 328 | 7.537 | −85.047 | −82.880 | 1.00 | 53.31 | | C |
| ANISOU | 1396 | CB | GLU | A | 328 | 7575 | 5035 | 7646 | 478 | −1566 | −1262 | C |
| ATOM | 1397 | CG | GLU | A | 328 | 8.225 | −83.757 | −82.563 | 1.00 | 62.79 | | C |
| ANISOU | 1397 | CG | GLU | A | 328 | 9056 | 6054 | 8749 | 296 | −1228 | −1172 | C |
| ATOM | 1398 | CD | GLU | A | 328 | 8.302 | −82.845 | −83.767 | 1.00 | 85.08 | | C |
| ANISOU | 1398 | CD | GLU | A | 328 | 12553 | 8611 | 11163 | 310 | −1268 | −991 | C |
| ATOM | 1399 | OE1 | GLU | A | 328 | 9.137 | −81.911 | −83.750 | 1.00 | 85.59 | | O |
| ANISOU | 1399 | OE1 | GLU | A | 328 | 12936 | 8549 | 11035 | 83 | −921 | −934 | O |
| ATOM | 1400 | OE2 | GLU | A | 328 | 7.525 | −83.063 | −84.728 | 1.00 | 95.00 | | O |
| ANISOU | 1400 | OE2 | GLU | A | 328 | 14035 | 9783 | 12278 | 535 | −1648 | −909 | O |
| ATOM | 1401 | C | GLU | A | 328 | 9.492 | −86.593 | −82.879 | 1.00 | 63.08 | | C |
| ANISOU | 1401 | C | GLU | A | 328 | 8547 | 6737 | 8684 | 75 | −1064 | −1491 | C |
| ATOM | 1402 | O | GLU | A | 328 | 10.668 | −86.241 | −83.013 | 1.00 | 59.40 | | O |
| ANISOU | 1402 | O | GLU | A | 328 | 8252 | 6311 | 8006 | −181 | −695 | −1490 | O |
| ATOM | 1403 | N | VAL | A | 329 | 9.108 | −87.498 | −81.990 | 1.00 | 54.87 | | N |
| ANISOU | 1403 | N | VAL | A | 329 | 6988 | 5879 | 7981 | 153 | −1150 | −1627 | N |
| ATOM | 1404 | CA | VAL | A | 329 | 10.066 | −88.135 | −81.111 | 1.00 | 53.12 | | C |
| ANISOU | 1404 | CA | VAL | A | 329 | 6382 | 5912 | 7889 | −38 | −833 | −1769 | C |
| ATOM | 1405 | CB | VAL | A | 329 | 9.380 | −89.004 | −80.063 | 1.00 | 54.00 | | C |
| ANISOU | 1405 | CB | VAL | A | 329 | 5972 | 6153 | 8391 | 90 | −981 | −1900 | C |
| ATOM | 1406 | CG1 | VAL | A | 329 | 10.420 | −89.658 | −79.161 | 1.00 | 32.72 | | C |
| ANISOU | 1406 | CG1 | VAL | A | 329 | 2914 | 3716 | 5803 | −96 | −668 | −2032 | C |
| ATOM | 1407 | CG2 | VAL | A | 329 | 8.426 | −88.164 | −79.248 | 1.00 | 35.27 | | C |
| ANISOU | 1407 | CG2 | VAL | A | 329 | 3498 | 3587 | 6317 | 213 | −1116 | −1850 | C |
| ATOM | 1408 | C | VAL | A | 329 | 11.014 | −88.986 | −81.930 | 1.00 | 52.84 | | C |
| ANISOU | 1408 | C | VAL | A | 329 | 6447 | 6060 | 7568 | −162 | −663 | −1829 | C |
| ATOM | 1409 | O | VAL | A | 329 | 12.223 | −89.004 | −81.694 | 1.00 | 62.39 | | O |
| ANISOU | 1409 | O | VAL | A | 329 | 7584 | 7419 | 8702 | −386 | −300 | −1878 | O |
| ATOM | 1410 | N | LEU | A | 330 | 10.478 | −89.670 | −82.909 | 1.00 | 49.00 | | N |
| ANISOU | 1410 | N | LEU | A | 330 | 6132 | 5563 | 6924 | −19 | −925 | −1828 | N |
| ATOM | 1411 | CA | LEU | A | 330 | 11.275 | −90.514 | −83.735 | 1.00 | 54.01 | | C |
| ANISOU | 1411 | CA | LEU | A | 330 | 6893 | 6344 | 7284 | −114 | −771 | −1891 | C |
| ATOM | 1412 | CB | LEU | A | 330 | 10.408 | −91.383 | −84.626 | 1.00 | 54.45 | | C |
| ANISOU | 1412 | CB | LEU | A | 330 | 7089 | 6373 | 7225 | 66 | −1136 | −1905 | C |
| ATOM | 1413 | CG | LEU | A | 330 | 9.927 | −92.679 | −84.014 | 1.00 | 47.37 | | C |

TABLE 7-continued

DMXAA-hSTING$^{G230I}$ complex

| | | | | | | | | | | | | |
|---|---|---|---|---|---|---|---|---|---|---|---|---|
| ANISOU | 1413 | CG | LEU | A | 330 | 5736 | 5657 | 6604 | 180 | −1278 | −2058 | C |
| ATOM | 1414 | CD1 | LEU | A | 330 | 8.817 | −93.282 | −84.823 | 1.00 | 40.73 | | C |
| ANISOU | 1414 | CD1 | LEU | A | 330 | 5047 | 4751 | 5676 | 351 | −1704 | −2058 | C |
| ATOM | 1415 | CD2 | LEU | A | 330 | 11.042 | −93.658 | −83.827 | 1.00 | 37.71 | | C |
| ANISOU | 1415 | CD2 | LEU | A | 330 | 4344 | 4664 | 5321 | 48 | −930 | −2184 | C |
| ATOM | 1416 | C | LEU | A | 330 | 12.286 | −89.772 | −84.546 | 1.00 | 60.61 | | C |
| ANISOU | 1416 | C | LEU | A | 330 | 8188 | 7093 | 7749 | −318 | −478 | −1805 | C |
| ATOM | 1417 | O | LEU | A | 330 | 13.396 | −90.220 | −84.696 | 1.00 | 57.78 | | O |
| ANISOU | 1417 | O | LEU | A | 330 | 7807 | 6896 | 7251 | −494 | −140 | −1877 | O |
| ATOM | 1418 | N | ARG | A | 331 | 11.901 | −88.630 | −85.074 | 1.00 | 60.96 | | N |
| ANISOU | 1418 | N | ARG | A | 331 | 8657 | 6870 | 7636 | −289 | −600 | −1651 | N |
| ATOM | 1419 | CA | ARG | A | 331 | 12.796 | −87.887 | −85.913 | 1.00 | 56.55 | | C |
| ANISOU | 1419 | CA | ARG | A | 331 | 8602 | 6178 | 6708 | −492 | −323 | −1561 | C |
| ATOM | 1420 | CB | ARG | A | 331 | 12.078 | −86.673 | −86.468 | 1.00 | 67.64 | | C |
| ANISOU | 1420 | CB | ARG | A | 331 | 10456 | 7250 | 7993 | −389 | −540 | −1379 | C |
| ATOM | 1421 | CG | ARG | A | 331 | 12.956 | −85.480 | −86.800 | 1.00 | 81.49 | | C |
| ANISOU | 1421 | CG | ARG | A | 331 | 12809 | 8814 | 9338 | −599 | −263 | −1275 | C |
| ATOM | 1422 | CD | ARG | A | 331 | 12.123 | −84.291 | −87.225 | 1.00 | 85.89 | | C |
| ANISOU | 1422 | CD | ARG | A | 331 | 13751 | 9036 | 9848 | −489 | −434 | −1096 | C |
| ATOM | 1423 | NE | ARG | A | 331 | 12.252 | −83.133 | −86.353 | 1.00 | 86.24 | | N |
| ANISOU | 1423 | NE | ARG | A | 331 | 13631 | 9046 | 10091 | −641 | −151 | −1097 | N |
| ATOM | 1424 | CZ | ARG | A | 331 | 13.405 | −82.620 | −85.942 | 1.00 | 88.99 | | C |
| ANISOU | 1424 | CZ | ARG | A | 331 | 14228 | 9350 | 10233 | −955 | 286 | −1091 | C |
| ATOM | 1425 | NH1 | ARG | A | 331 | 14.552 | −83.174 | −86.290 | 1.00 | 95.44 | | N |
| ANISOU | 1425 | NH1 | ARG | A | 331 | 15459 | 10150 | 10655 | −1139 | 505 | −1087 | N |
| ATOM | 1426 | NH2 | ARG | A | 331 | 13.409 | −81.554 | −85.160 | 1.00 | 77.36 | | N |
| ANISOU | 1426 | NH2 | ARG | A | 331 | 12601 | 7849 | 8944 | −1105 | 518 | −1099 | N |
| ATOM | 1427 | C | ARG | A | 331 | 13.998 | −87.503 | −85.080 | 1.00 | 69.23 | | C |
| ANISOU | 1427 | C | ARG | A | 331 | 9979 | 7930 | 8395 | −768 | 147 | −1628 | C |
| ATOM | 1428 | O | ARG | A | 331 | 15.111 | −87.606 | −85.529 | 1.00 | 76.31 | | O |
| ANISOU | 1428 | O | ARG | A | 331 | 11007 | 8924 | 9062 | −987 | 497 | −1671 | O |
| ATOM | 1429 | N | HIS | A | 332 | 13.775 | −87.057 | −83.857 | 1.00 | 66.23 | | N |
| ANISOU | 1429 | N | HIS | A | 332 | 9246 | 7572 | 8346 | −766 | 157 | −1643 | N |
| ATOM | 1430 | CA | HIS | A | 332 | 14.851 | −86.724 | −82.964 | 1.00 | 59.31 | | C |
| ANISOU | 1430 | CA | HIS | A | 332 | 8107 | 6854 | 7574 | −1034 | 553 | −1712 | C |
| ATOM | 1431 | CB | HIS | A | 332 | 14.317 | −86.150 | −81.685 | 1.00 | 42.49 | | C |
| ANISOU | 1431 | CB | HIS | A | 332 | 5715 | 4657 | 5772 | −1008 | 490 | −1699 | C |
| ATOM | 1432 | CG | HIS | A | 332 | 13.906 | −84.728 | −81.793 | 1.00 | 60.89 | | C |
| ANISOU | 1432 | CG | HIS | A | 332 | 8476 | 6649 | 8008 | −991 | 431 | −1547 | C |
| ATOM | 1433 | ND1 | HIS | A | 332 | 12.862 | −84.315 | −82.580 | 1.00 | 70.24 | | N |
| ANISOU | 1433 | ND1 | HIS | A | 332 | 9994 | 7582 | 9113 | −727 | 74 | −1425 | N |
| ATOM | 1434 | CE1 | HIS | A | 332 | 12.730 | −83.012 | −82.485 | 1.00 | 67.36 | | C |
| ANISOU | 1434 | CE1 | HIS | A | 332 | 9987 | 6931 | 8677 | −748 | 112 | −1295 | C |
| ATOM | 1435 | NE2 | HIS | A | 332 | 13.652 | −82.567 | −81.662 | 1.00 | 62.85 | | N |
| ANISOU | 1435 | NE2 | HIS | A | 332 | 9338 | 6416 | 8125 | −1045 | 494 | −1339 | N |
| ATOM | 1436 | CD2 | HIS | A | 332 | 14.397 | −83.620 | −81.210 | 1.00 | 54.31 | | C |
| ANISOU | 1436 | CD2 | HIS | A | 332 | 7810 | 5682 | 7143 | −1203 | 685 | −1495 | C |
| ATOM | 1437 | C | HIS | A | 332 | 15.620 | −87.942 | −82.617 | 1.00 | 65.45 | | C |
| ANISOU | 1437 | C | HIS | A | 332 | 8431 | 7973 | 8463 | −1092 | 724 | −1869 | C |
| ATOM | 1438 | O | HIS | A | 332 | 16.810 | −87.905 | −82.478 | 1.00 | 67.77 | | O |
| ANISOU | 1438 | O | HIS | A | 332 | 8631 | 8437 | 8682 | −1335 | 1093 | −1928 | O |
| ATOM | 1439 | N | LEU | A | 333 | 14.897 | −89.026 | −82.413 | 1.00 | 74.14 | | N |
| ANISOU | 1439 | N | LEU | A | 333 | 9248 | 9171 | 9751 | −863 | 453 | −1938 | N |
| ATOM | 1440 | CA | LEU | A | 333 | 15.481 | −90.283 | −81.956 | 1.00 | 72.04 | | C |
| ANISOU | 1440 | CA | LEU | A | 333 | 8543 | 9204 | 9626 | −862 | 573 | −2082 | C |
| ATOM | 1441 | CB | LEU | A | 333 | 14.388 | −91.334 | −81.756 | 1.00 | 77.23 | | C |
| ANISOU | 1441 | CB | LEU | A | 333 | 8982 | 9884 | 10476 | −595 | 220 | −2142 | C |
| ATOM | 1442 | CG | LEU | A | 333 | 14.047 | −91.758 | −80.332 | 1.00 | 75.86 | | C |
| ANISOU | 1442 | CG | LEU | A | 333 | 8299 | 9832 | 10694 | −523 | 144 | −2229 | C |
| ATOM | 1443 | CD1 | LEU | A | 333 | 13.263 | −93.058 | −80.359 | 1.00 | 68.32 | | C |
| ANISOU | 1443 | CD1 | LEU | A | 333 | 7162 | 8941 | 9854 | −309 | −108 | −2321 | C |
| ATOM | 1444 | CD2 | LEU | A | 333 | 15.314 | −91.918 | −79.519 | 1.00 | 78.69 | | C |
| ANISOU | 1444 | CD2 | LEU | A | 333 | 8326 | 10434 | 11141 | −712 | 488 | −2305 | C |
| ATOM | 1445 | C | LEU | A | 333 | 16.506 | −90.842 | −82.930 | 1.00 | 71.32 | | C |
| ANISOU | 1445 | C | LEU | A | 333 | 8613 | 9236 | 9251 | −976 | 845 | −2126 | C |
| ATOM | 1446 | O | LEU | A | 333 | 17.533 | −91.392 | −82.531 | 1.00 | 72.07 | | O |
| ANISOU | 1446 | O | LEU | A | 333 | 8388 | 9580 | 9415 | −1085 | 1126 | −2222 | O |
| ATOM | 1447 | N | ARG | A | 334 | 16.208 | −90.712 | −84.215 | 1.00 | 68.75 | | N |
| ANISOU | 1447 | N | ARG | A | 334 | 8787 | 8728 | 8605 | −941 | 756 | −2054 | N |
| ATOM | 1448 | CA | ARG | A | 334 | 16.986 | −91.378 | −85.244 | 1.00 | 64.04 | | C |
| ANISOU | 1448 | CA | ARG | A | 334 | 8394 | 8211 | 7727 | −1017 | 984 | −2103 | C |
| ATOM | 1449 | CB | ARG | A | 334 | 16.163 | −91.522 | −86.524 | 1.00 | 49.46 | | C |
| ANISOU | 1449 | CB | ARG | A | 334 | 7065 | 6146 | 5580 | −891 | 710 | −2031 | C |
| ATOM | 1450 | CG | ARG | A | 334 | 15.062 | −92.561 | −86.366 | 1.00 | 54.21 | | C |
| ANISOU | 1450 | CG | ARG | A | 334 | 7465 | 6781 | 6349 | −634 | 316 | −2083 | C |
| ATOM | 1451 | CD | ARG | A | 334 | 13.975 | −92.462 | −87.424 | 1.00 | 57.75 | | C |
| ANISOU | 1451 | CD | ARG | A | 334 | 8382 | 7000 | 6560 | −498 | −73 | −1991 | C |
| ATOM | 1452 | NE | ARG | A | 334 | 13.199 | −93.699 | −87.494 | 1.00 | 56.49 | | N |

TABLE 7-continued

DMXAA-hSTING$^{G230I}$ complex

| | | | | | | | | | | |
|---|---|---|---|---|---|---|---|---|---|---|
| ANISOU | 1452 | NE | ARG | A | 334 | 8054 | 6921 | 6489 | −320 | −356 | −2080 | N |
| ATOM | 1453 | CZ | ARG | A | 334 | 11.980 | −93.808 | −88.014 | 1.00 | 59.56 | | C |
| ANISOU | 1453 | CZ | ARG | A | 334 | 8637 | 7174 | 6819 | −158 | −802 | −2031 | C |
| ATOM | 1454 | NH1 | ARG | A | 334 | 11.366 | −92.741 | −88.513 | 1.00 | 65.55 | | N |
| ANISOU | 1454 | NH1 | ARG | A | 334 | 9767 | 7703 | 7438 | −114 | −1041 | −1878 | N |
| ATOM | 1455 | NH2 | ARG | A | 334 | 11.369 | −94.987 | −88.030 | 1.00 | 54.39 | | N |
| ANISOU | 1455 | NH2 | ARG | A | 334 | 7806 | 6614 | 6245 | −40 | −1014 | −2137 | N |
| ATOM | 1456 | C | ARG | A | 334 | 18.330 | −90.702 | −85.487 | 1.00 | 85.34 | | C |
| ANISOU | 1456 | C | ARG | A | 334 | 11215 | 10962 | 10248 | −1313 | 1449 | −2104 | C |
| ATOM | 1457 | O | ARG | A | 334 | 18.599 | −90.201 | −86.578 | 1.00 | 87.32 | | O |
| ANISOU | 1457 | O | ARG | A | 334 | 11979 | 11049 | 10152 | −1431 | 1581 | −2042 | O |
| ATOM | 1458 | N | GLN | A | 335 | 19.149 | −90.681 | −84.433 | 1.00 | 99.41 | | N |
| ANISOU | 1458 | N | GLN | A | 335 | 12525 | 12975 | 12272 | −1441 | 1688 | −2178 | N |
| ATOM | 1459 | CA | GLN | A | 335 | 20.533 | −90.204 | −84.463 | 1.00 | 101.72 | | C |
| ANISOU | 1459 | CA | GLN | A | 335 | 12776 | 13402 | 12471 | −1740 | 2148 | −2216 | C |
| ATOM | 1460 | CB | GLN | A | 335 | 20.625 | −88.732 | −84.877 | 1.00 | 96.70 | | C |
| ANISOU | 1460 | CB | GLN | A | 335 | 12614 | 12522 | 11606 | −1959 | 2269 | −2109 | C |
| ATOM | 1461 | CG | GLN | A | 335 | 19.533 | −87.844 | −84.316 | 1.00 | 92.69 | | C |
| ANISOU | 1461 | CG | GLN | A | 335 | 12220 | 11781 | 11215 | −1861 | 1949 | −1999 | C |
| ATOM | 1462 | CD | GLN | A | 335 | 18.812 | −87.082 | −85.410 | 1.00 | 97.37 | | C |
| ANISOU | 1462 | CD | GLN | A | 335 | 13490 | 12016 | 11489 | −1807 | 1783 | −1858 | C |
| ATOM | 1463 | OE1 | GLN | A | 335 | 18.806 | −85.853 | −85.425 | 1.00 | 97.60 | | O |
| ANISOU | 1463 | OE1 | GLN | A | 335 | 13843 | 11834 | 11405 | −1946 | 1862 | −1764 | O |
| ATOM | 1464 | NE2 | GLN | A | 335 | 18.211 | −87.812 | −86.346 | 1.00 | 99.42 | | N |
| ANISOU | 1464 | NE2 | GLN | A | 335 | 13991 | 12199 | 11584 | −1609 | 1552 | −1840 | N |
| ATOM | 1465 | C | GLN | A | 335 | 21.198 | −90.404 | −83.104 | 1.00 | 101.48 | | C |
| ANISOU | 1465 | C | GLN | A | 335 | 12117 | 13664 | 12776 | −1815 | 2281 | −2304 | C |
| ATOM | 1466 | O | GLN | A | 335 | 21.642 | −91.502 | −82.776 | 1.00 | 100.12 | | O |
| ANISOU | 1466 | O | GLN | A | 335 | 11547 | 13741 | 12754 | −1722 | 2346 | −2404 | O |
| TER | 1467 | | GLN | A | 335 | | | | | | | |
| HETATM | 1468 | OAD | DRG | C | 1 | 7.647 | −76.692 | −62.085 | 1.00 | 44.74 | | O |
| HETATM | 1469 | CAQ | DRG | C | 1 | 8.003 | −77.711 | −61.497 | 1.00 | 55.27 | | C |
| HETATM | 1470 | CAS | DRG | C | 1 | 7.089 | −78.705 | −61.199 | 1.00 | 51.55 | | C |
| HETATM | 1471 | CAJ | DRG | C | 1 | 5.760 | −78.535 | −61.568 | 1.00 | 51.37 | | C |
| HETATM | 1472 | CAH | DRG | C | 1 | 4.840 | −79.541 | −61.279 | 1.00 | 56.00 | | C |
| HETATM | 1473 | CAN | DRG | C | 1 | 5.237 | −80.711 | −60.627 | 1.00 | 46.44 | | C |
| HETATM | 1474 | CAA | DRG | C | 1 | 4.300 | −81.703 | −60.347 | 1.00 | 26.68 | | C |
| HETATM | 1475 | CAO | DRG | C | 1 | 6.574 | −80.882 | −60.258 | 1.00 | 45.72 | | C |
| HETATM | 1476 | CAB | DRG | C | 1 | 6.990 | −82.043 | −59.604 | 1.00 | 30.41 | | C |
| HETATM | 1477 | CAT | DRG | C | 1 | 7.483 | −79.863 | −60.537 | 1.00 | 43.76 | | C |
| HETATM | 1478 | OAL | DRG | C | 1 | 8.781 | −80.059 | −60.194 | 1.00 | 36.28 | | O |
| HETATM | 1479 | CAU | DRG | C | 1 | 9.705 | −79.109 | −60.509 | 1.00 | 47.85 | | C |
| HETATM | 1480 | CAR | DRG | C | 1 | 9.328 | −77.933 | −61.155 | 1.00 | 57.72 | | C |
| HETATM | 1481 | CAI | DRG | C | 1 | 10.309 | −76.990 | −61.463 | 1.00 | 52.34 | | C |
| HETATM | 1482 | CAF | DRG | C | 1 | 11.633 | −77.232 | −61.107 | 1.00 | 41.69 | | C |
| HETATM | 1483 | CAG | DRG | C | 1 | 11.999 | −78.407 | −60.453 | 1.00 | 34.93 | | C |
| HETATM | 1484 | CAP | DRG | C | 1 | 11.022 | −79.346 | −60.145 | 1.00 | 47.31 | | C |
| HETATM | 1485 | CAK | DRG | C | 1 | 11.361 | −80.525 | −59.495 | 1.00 | 48.85 | | C |
| HETATM | 1486 | CAM | DRG | C | 1 | 11.257 | −81.740 | −60.416 | 1.00 | 49.85 | | C |
| HETATM | 1487 | OAE | DRG | C | 1 | 10.890 | −81.531 | −61.601 | 1.00 | 37.91 | | O |
| HETATM | 1488 | OAC | DRG | C | 1 | 11.567 | −82.840 | −59.898 | 1.00 | 44.52 | | O |
| ATOM | 1490 | N | SER | B | 154 | 8.907 | −62.145 | −63.562 | 1.00 | 35.71 | | N |
| ANISOU | 1490 | N | SER | B | 154 | 4521 | 4617 | 4430 | −347 | 455 | −551 | N |
| ATOM | 1491 | CA | SER | B | 154 | 9.833 | −62.192 | −62.435 | 1.00 | 31.79 | | C |
| ANISOU | 1491 | CA | SER | B | 154 | 4035 | 3980 | 4063 | −129 | 429 | −586 | C |
| ATOM | 1492 | CB | SER | B | 154 | 9.235 | −61.519 | −61.198 | 1.00 | 35.80 | | C |
| ANISOU | 1492 | CB | SER | B | 154 | 4487 | 4624 | 4491 | 140 | 301 | −507 | C |
| ATOM | 1493 | OG | SER | B | 154 | 9.521 | −62.261 | −60.029 | 1.00 | 31.17 | | O |
| ANISOU | 1493 | OG | SER | B | 154 | 3897 | 3982 | 3964 | 270 | 328 | −489 | O |
| ATOM | 1494 | C | SER | B | 154 | 10.256 | −63.615 | −62.083 | 1.00 | 39.11 | | C |
| ANISOU | 1494 | C | SER | B | 154 | 4993 | 4785 | 5082 | −197 | 562 | −605 | C |
| ATOM | 1495 | O | SER | B | 154 | 9.475 | −64.561 | −62.177 | 1.00 | 39.55 | | O |
| ANISOU | 1495 | O | SER | B | 154 | 5044 | 4922 | 5062 | −334 | 640 | −550 | O |
| ATOM | 1496 | N | VAL | B | 155 | 11.502 | −63.749 | −61.653 | 1.00 | 45.14 | | N |
| ANISOU | 1496 | N | VAL | B | 155 | 5788 | 5352 | 6013 | −99 | 579 | −674 | N |
| ATOM | 1497 | CA | VAL | B | 155 | 12.072 | −65.036 | −61.294 | 1.00 | 34.34 | | C |
| ANISOU | 1497 | CA | VAL | B | 155 | 4451 | 3838 | 4756 | −138 | 702 | −697 | C |
| ATOM | 1498 | CB | VAL | B | 155 | 13.593 | −64.913 | −61.080 | 1.00 | 30.21 | | C |
| ANISOU | 1498 | CB | VAL | B | 155 | 3954 | 3094 | 4431 | −39 | 710 | −777 | C |
| ATOM | 1499 | CG1 | VAL | B | 155 | 14.130 | −66.040 | −60.217 | 1.00 | 23.59 | | C |
| ANISOU | 1499 | CG1 | VAL | B | 155 | 3126 | 2129 | 3708 | 22 | 788 | −771 | C |
| ATOM | 1500 | CG2 | VAL | B | 155 | 14.289 | −64.898 | −62.412 | 1.00 | 23.39 | | C |
| ANISOU | 1500 | CG2 | VAL | B | 155 | 3138 | 2116 | 3634 | −221 | 800 | −865 | C |
| ATOM | 1501 | C | VAL | B | 155 | 11.395 | −65.600 | −60.054 | 1.00 | 35.98 | | C |
| ANISOU | 1501 | C | VAL | B | 155 | 4617 | 4144 | 4908 | −14 | 680 | −604 | C |
| ATOM | 1502 | O | VAL | B | 155 | 11.068 | −66.786 | −59.981 | 1.00 | 30.48 | | O |
| ANISOU | 1502 | O | VAL | B | 155 | 3936 | 3439 | 4206 | −128 | 781 | −573 | O |
| ATOM | 1503 | N | ALA | B | 156 | 11.189 | −64.729 | −59.076 | 1.00 | 37.45 | | N |

TABLE 7-continued

DMXAA-hSTING$^{G230I}$ complex

| | | | | | | | | | | | |
|---|---|---|---|---|---|---|---|---|---|---|---|
| ANISOU | 1503 | N | ALA | B | 156 | 4757 | 4422 | 5048 | 222 | 545 | −557 | N |
| ATOM | 1504 | CA | ALA | B | 156 | 10.560 | −65.103 | −57.820 | 1.00 | 27.62 | | C |
| ANISOU | 1504 | CA | ALA | B | 156 | 3467 | 3290 | 3737 | 373 | 513 | −463 | C |
| ATOM | 1505 | CB | ALA | B | 156 | 10.539 | −63.933 | −56.889 | 1.00 | 33.50 | | C |
| ANISOU | 1505 | CB | ALA | B | 156 | 4188 | 4105 | 4437 | 645 | 359 | −441 | C |
| ATOM | 1506 | C | ALA | B | 156 | 9.138 | −65.589 | −58.050 | 1.00 | 38.88 | | C |
| ANISOU | 1506 | C | ALA | B | 156 | 4847 | 4930 | 4995 | 244 | 551 | −360 | C |
| ATOM | 1507 | O | ALA | B | 156 | 8.670 | −66.551 | −57.434 | 1.00 | 43.76 | | O |
| ANISOU | 1507 | O | ALA | B | 156 | 5441 | 5600 | 5585 | 227 | 602 | −285 | O |
| ATOM | 1508 | N | HIS | B | 157 | 8.448 | −64.880 | −58.927 | 1.00 | 37.71 | | N |
| ANISOU | 1508 | N | HIS | B | 157 | 4680 | 4911 | 4735 | 153 | 515 | −346 | N |
| ATOM | 1509 | CA | HIS | B | 157 | 7.055 | −65.140 | −59.219 | 1.00 | 28.64 | | C |
| ANISOU | 1509 | CA | HIS | B | 157 | 3473 | 3990 | 3418 | 31 | 528 | −234 | C |
| ATOM | 1510 | CB | HIS | B | 157 | 6.568 | −64.137 | −60.258 | 1.00 | 41.84 | | C |
| ANISOU | 1510 | CB | HIS | B | 157 | 5132 | 5768 | 4998 | −49 | 472 | −237 | C |
| ATOM | 1511 | CG | HIS | B | 157 | 5.092 | −64.144 | −60.475 | 1.00 | 46.26 | | C |
| ANISOU | 1511 | CG | HIS | B | 157 | 5611 | 6591 | 5376 | −132 | 456 | −102 | C |
| ATOM | 1512 | ND1 | HIS | B | 157 | 4.196 | −63.819 | −59.488 | 1.00 | 47.33 | | N |
| ANISOU | 1512 | ND1 | HIS | B | 157 | 5655 | 6934 | 5395 | 65 | 389 | 20 | N |
| ATOM | 1513 | CE1 | HIS | B | 157 | 2.965 | −63.908 | −59.967 | 1.00 | 44.73 | | C |
| ANISOU | 1513 | CE1 | HIS | B | 157 | 5252 | 6823 | 4919 | −69 | 391 | 139 | C |
| ATOM | 1514 | NE2 | HIS | B | 157 | 3.036 | −64.268 | −61.228 | 1.00 | 40.72 | | N |
| ANISOU | 1514 | NE2 | HIS | B | 157 | 4795 | 6251 | 4425 | −352 | 448 | 94 | N |
| ATOM | 1515 | CD2 | HIS | B | 157 | 4.357 | −64.425 | −61.576 | 1.00 | 44.55 | | C |
| ANISOU | 1515 | CD2 | HIS | B | 157 | 5387 | 6470 | 5071 | −393 | 496 | −61 | C |
| ATOM | 1516 | C | HIS | B | 157 | 6.889 | −66.560 | −59.754 | 1.00 | 36.70 | | C |
| ANISOU | 1516 | C | HIS | B | 157 | 4531 | 4956 | 4456 | −233 | 661 | −224 | C |
| ATOM | 1517 | O | HIS | B | 157 | 5.980 | −67.295 | −59.357 | 1.00 | 40.73 | | O |
| ANISOU | 1517 | O | HIS | B | 157 | 4996 | 5604 | 4878 | −287 | 685 | −111 | O |
| ATOM | 1518 | N | GLY | B | 158 | 7.784 | −66.943 | −60.655 | 1.00 | 32.57 | | N |
| ANISOU | 1518 | N | GLY | B | 158 | 4097 | 4229 | 4047 | −395 | 746 | −340 | N |
| ATOM | 1519 | CA | GLY | B | 158 | 7.754 | −68.262 | −61.250 | 1.00 | 34.69 | | C |
| ANISOU | 1519 | CA | GLY | B | 158 | 4434 | 4407 | 4340 | −644 | 875 | −355 | C |
| ATOM | 1520 | C | GLY | B | 158 | 8.177 | −69.341 | −60.268 | 1.00 | 39.59 | | C |
| ANISOU | 1520 | C | GLY | B | 158 | 5071 | 4911 | 5060 | −575 | 933 | −340 | C |
| ATOM | 1521 | O | GLY | B | 158 | 7.650 | −70.458 | −60.277 | 1.00 | 40.37 | | O |
| ANISOU | 1521 | O | GLY | B | 158 | 5191 | 5023 | 5124 | −730 | 1000 | −284 | O |
| ATOM | 1522 | N | LEU | B | 159 | 9.130 | −69.003 | −59.407 | 1.00 | 32.14 | | N |
| ANISOU | 1522 | N | LEU | B | 159 | 4119 | 3852 | 4240 | −347 | 897 | −384 | N |
| ATOM | 1523 | CA | LEU | B | 159 | 9.626 | −69.934 | −58.403 | 1.00 | 36.27 | | C |
| ANISOU | 1523 | CA | LEU | B | 159 | 4652 | 4259 | 4870 | −258 | 940 | −367 | C |
| ATOM | 1524 | CB | LEU | B | 159 | 10.875 | −69.386 | −57.715 | 1.00 | 25.56 | | C |
| ANISOU | 1524 | CB | LEU | B | 159 | 3297 | 2750 | 3666 | −31 | 894 | −435 | C |
| ATOM | 1525 | CG | LEU | B | 159 | 12.218 | −70.011 | −58.082 | 1.00 | 45.33 | | C |
| ANISOU | 1525 | CG | LEU | B | 159 | 5876 | 4982 | 6367 | −84 | 999 | −542 | C |
| ATOM | 1526 | CD2 | LEU | B | 159 | 13.321 | −68.998 | −57.832 | 1.00 | 24.84 | | C |
| ANISOU | 1526 | CD2 | LEU | B | 159 | 3267 | 2285 | 3886 | 99 | 921 | −606 | C |
| ATOM | 1527 | CD1 | LEU | B | 159 | 12.248 | −70.468 | −59.532 | 1.00 | 33.73 | | C |
| ANISOU | 1527 | CD1 | LEU | B | 159 | 4485 | 3436 | 4895 | −347 | 1116 | −617 | C |
| ATOM | 1528 | C | LEU | B | 159 | 8.558 | −70.248 | −57.353 | 1.00 | 41.54 | | C |
| ANISOU | 1528 | C | LEU | B | 159 | 5239 | 5126 | 5417 | −176 | 891 | −219 | C |
| ATOM | 1529 | O | LEU | B | 159 | 8.406 | −71.387 | −56.903 | 1.00 | 42.78 | | O |
| ANISOU | 1529 | O | LEU | B | 159 | 5408 | 5248 | 5598 | −238 | 952 | −165 | O |
| ATOM | 1530 | N | ALA | B | 160 | 7.827 | −69.220 | −56.947 | 1.00 | 36.79 | | N |
| ANISOU | 1530 | N | ALA | B | 160 | 4557 | 4736 | 4687 | −26 | 781 | −150 | N |
| ATOM | 1531 | CA | ALA | B | 160 | 6.806 | −69.365 | −55.918 | 1.00 | 26.97 | | C |
| ANISOU | 1531 | CA | ALA | B | 160 | 3223 | 3708 | 3315 | 85 | 733 | −2 | C |
| ATOM | 1532 | CB | ALA | B | 160 | 6.332 | −68.008 | −55.444 | 1.00 | 32.89 | | C |
| ANISOU | 1532 | CB | ALA | B | 160 | 3904 | 4641 | 3951 | 315 | 611 | 37 | C |
| ATOM | 1533 | C | ALA | B | 160 | 5.633 | −70.179 | −56.448 | 1.00 | 48.40 | | C |
| ANISOU | 1533 | C | ALA | B | 160 | 5909 | 6572 | 5908 | −157 | 785 | 106 | C |
| ATOM | 1534 | O | ALA | B | 160 | 5.121 | −71.084 | −55.787 | 1.00 | 28.64 | | O |
| ANISOU | 1534 | O | ALA | B | 160 | 3373 | 4137 | 3372 | −184 | 811 | 213 | O |
| ATOM | 1535 | N | TRP | B | 161 | 5.197 | −69.834 | −57.650 | 1.00 | 27.98 | | N |
| ANISOU | 1535 | N | TRP | B | 161 | 3337 | 4042 | 3251 | −340 | 792 | 86 | N |
| ATOM | 1536 | CA | TRP | B | 161 | 4.117 | −70.555 | −58.299 | 1.00 | 33.96 | | C |
| ANISOU | 1536 | CA | TRP | B | 161 | 4079 | 4932 | 3893 | −601 | 829 | 185 | C |
| ATOM | 1537 | CB | TRP | B | 161 | 3.675 | −69.847 | −59.572 | 1.00 | 28.89 | | C |
| ANISOU | 1537 | CB | TRP | B | 161 | 3442 | 4372 | 3163 | −757 | 808 | 162 | C |
| ATOM | 1538 | CG | TRP | B | 161 | 2.635 | −68.829 | −59.259 | 1.00 | 35.12 | | C |
| ANISOU | 1538 | CG | TRP | B | 161 | 4103 | 5443 | 3797 | −617 | 707 | 283 | C |
| ATOM | 1539 | CD1 | TRP | B | 161 | 2.806 | −67.485 | −59.104 | 1.00 | 28.21 | | C |
| ANISOU | 1539 | CD1 | TRP | B | 161 | 3193 | 4620 | 2905 | −397 | 621 | 247 | C |
| ATOM | 1540 | NE1 | TRP | B | 161 | 1.612 | −66.889 | −58.772 | 1.00 | 60.28 | | N |
| ANISOU | 1540 | NE1 | TRP | B | 161 | 7133 | 8966 | 6806 | −300 | 551 | 394 | N |
| ATOM | 1541 | CE2 | TRP | B | 161 | 0.644 | −67.856 | −58.693 | 1.00 | 45.91 | | C |
| ANISOU | 1541 | CE2 | TRP | B | 161 | 5252 | 7294 | 4896 | −464 | 589 | 540 | C |
| ATOM | 1542 | CD2 | TRP | B | 161 | 1.258 | −69.094 | −58.977 | 1.00 | 44.34 | | C |

TABLE 7-continued

DMXAA-hSTING$^{G230I}$ complex

| ANISOU | 1542 | CD2 | TRP | B | 161 | 5158 | 6884 | 4807 | −669 | 681 | 473 | C |
|---|---|---|---|---|---|---|---|---|---|---|---|---|
| ATOM | 1543 | CE3 | TRP | B | 161 | 0.477 | −70.258 | −58.960 | 1.00 | 31.05 | | C |
| ANISOU | 1543 | CE3 | TRP | B | 161 | 3450 | 5286 | 3062 | −875 | 723 | 600 | C |
| ATOM | 1544 | CZ3 | TRP | B | 161 | −0.870 | −70.153 | −58.657 | 1.00 | 57.74 | | C |
| ANISOU | 1544 | CZ3 | TRP | B | 161 | 6689 | 8972 | 6278 | −874 | 674 | 798 | C |
| ATOM | 1545 | CH2 | TRP | B | 161 | −1.454 | −68.902 | −58.377 | 1.00 | 56.94 | | C |
| ANISOU | 1545 | CH2 | TRP | B | 161 | 6473 | 9089 | 6071 | −654 | 594 | 865 | C |
| ATOM | 1546 | CZ2 | TRP | B | 161 | −0.717 | −67.748 | −58.393 | 1.00 | 45.93 | | C |
| ANISOU | 1546 | CZ2 | TRP | B | 161 | 5117 | 7603 | 4733 | −446 | 550 | 733 | C |
| ATOM | 1547 | C | TRP | B | 161 | 4.474 | −72.012 | −58.559 | 1.00 | 37.56 | | C |
| ANISOU | 1547 | C | TRP | B | 161 | 4632 | 5201 | 4437 | −816 | 936 | 156 | C |
| ATOM | 1548 | O | TRP | B | 161 | 3.636 | −72.905 | −58.428 | 1.00 | 31.88 | | O |
| ANISOU | 1548 | O | TRP | B | 161 | 3891 | 4581 | 3642 | −963 | 954 | 276 | O |
| ATOM | 1549 | N | SER | B | 162 | 5.733 | −72.238 | −58.914 | 1.00 | 46.87 | | N |
| ANISOU | 1549 | N | SER | B | 162 | 5921 | 6110 | 5779 | −827 | 1004 | 1 | N |
| ATOM | 1550 | CA | SER | B | 162 | 6.244 | −73.578 | −59.175 | 1.00 | 36.68 | | C |
| ANISOU | 1550 | CA | SER | B | 162 | 4743 | 4602 | 4591 | −999 | 1114 | −50 | C |
| ATOM | 1551 | C | SER | B | 162 | 6.380 | −74.406 | −57.889 | 1.00 | 36.66 | | C |
| ANISOU | 1551 | C | SER | B | 162 | 4714 | 4561 | 4655 | −877 | 1122 | 24 | C |
| ATOM | 1552 | O | SER | B | 162 | 6.220 | −75.633 | −57.888 | 1.00 | 40.62 | | O |
| ANISOU | 1552 | O | SER | B | 162 | 5274 | 4981 | 5178 | −1038 | 1185 | 61 | O |
| ATOM | 1553 | CB | SER | B | 162 | 7.588 | −73.494 | −59.892 | 1.00 | 37.53 | | C |
| ANISOU | 1553 | CB | SER | B | 162 | 4960 | 4445 | 4856 | −1012 | 1191 | −230 | C |
| ATOM | 1554 | OG | SER | B | 162 | 8.282 | −74.718 | −59.823 | 1.00 | 51.15 | | O |
| ANISOU | 1554 | OG | SER | B | 162 | 6784 | 5939 | 6710 | −1086 | 1297 | −283 | O |
| ATOM | 1555 | N | TYR | B | 163 | 6.690 | −73.729 | −56.793 | 1.00 | 29.49 | | N |
| ANISOU | 1555 | N | TYR | B | 163 | 3725 | 3702 | 3776 | −595 | 1052 | 47 | N |
| ATOM | 1556 | CA | TYR | B | 163 | 6.818 | −74.380 | −55.503 | 1.00 | 29.78 | | C |
| ANISOU | 1556 | CA | TYR | B | 163 | 3727 | 3723 | 3864 | −457 | 1046 | 124 | C |
| ATOM | 1557 | CB | TYR | B | 163 | 7.460 | −73.443 | −54.498 | 1.00 | 37.41 | | C |
| ANISOU | 1557 | CB | TYR | B | 163 | 4639 | 4691 | 4882 | −143 | 967 | 100 | C |
| ATOM | 1558 | CG | TYR | B | 163 | 7.878 | −74.119 | −53.226 | 1.00 | 29.13 | | C |
| ANISOU | 1558 | CG | TYR | B | 163 | 3575 | 3574 | 3917 | 1 | 968 | 152 | C |
| ATOM | 1559 | CD1 | TYR | B | 163 | 8.658 | −75.280 | −53.259 | 1.00 | 29.55 | | C |
| ANISOU | 1559 | CD1 | TYR | B | 163 | 3712 | 3388 | 4129 | −96 | 1060 | 107 | C |
| ATOM | 1560 | CE1 | TYR | B | 163 | 9.052 | −75.909 | −52.099 | 1.00 | 29.83 | | C |
| ANISOU | 1560 | CE1 | TYR | B | 163 | 3731 | 3357 | 4246 | 31 | 1056 | 162 | C |
| ATOM | 1561 | CZ | TYR | B | 163 | 8.672 | −75.369 | −50.880 | 1.00 | 59.91 | | C |
| ANISOU | 1561 | CZ | TYR | B | 163 | 7445 | 7348 | 7971 | 257 | 960 | 261 | C |
| ATOM | 1562 | OH | TYR | B | 163 | 9.077 | −76.005 | −49.732 | 1.00 | 49.72 | | O |
| ANISOU | 1562 | OH | TYR | B | 163 | 6140 | 5992 | 6757 | 376 | 954 | 319 | O |
| ATOM | 1563 | CE2 | TYR | B | 163 | 7.900 | −74.206 | −50.819 | 1.00 | 29.30 | | C |
| ANISOU | 1563 | CE2 | TYR | B | 163 | 3493 | 3709 | 3929 | 367 | 874 | 299 | C |
| ATOM | 1564 | CD2 | TYR | B | 163 | 7.512 | −73.596 | −51.990 | 1.00 | 29.02 | | C |
| ANISOU | 1564 | CD2 | TYR | B | 163 | 3471 | 3732 | 3824 | 240 | 878 | 247 | C |
| ATOM | 1565 | C | TYR | B | 163 | 5.448 | −74.798 | −54.988 | 1.00 | 44.33 | | C |
| ANISOU | 1565 | C | TYR | B | 163 | 5479 | 5820 | 5546 | −512 | 1010 | 311 | C |
| ATOM | 1566 | O | TYR | B | 163 | 5.297 | −75.824 | −54.320 | 1.00 | 44.16 | | O |
| ANISOU | 1566 | O | TYR | B | 163 | 5455 | 5776 | 5548 | −546 | 1036 | 396 | O |
| ATOM | 1567 | N | TYR | B | 164 | 4.448 | −73.982 | −55.290 | 1.00 | 30.68 | | N |
| ANISOU | 1567 | N | TYR | B | 164 | 3665 | 4338 | 3653 | −518 | 946 | 385 | N |
| ATOM | 1568 | CA | TYR | B | 164 | 3.095 | −74.292 | −54.900 | 1.00 | 48.01 | | C |
| ANISOU | 1568 | CA | TYR | B | 164 | 5754 | 6802 | 5686 | −576 | 912 | 578 | C |
| ATOM | 1569 | CB | TYR | B | 164 | 2.203 | −73.063 | −55.002 | 1.00 | 45.20 | | C |
| ANISOU | 1569 | CB | TYR | B | 164 | 5286 | 6720 | 5169 | −472 | 831 | 649 | C |
| ATOM | 1570 | CG | TYR | B | 164 | 0.746 | −73.407 | −54.918 | 1.00 | 32.61 | | C |
| ANISOU | 1570 | CG | TYR | B | 164 | 3577 | 5411 | 3402 | −590 | 808 | 855 | C |
| ATOM | 1571 | CD1 | TYR | B | 164 | 0.229 | −74.030 | −53.785 | 1.00 | 37.39 | | C |
| ANISOU | 1571 | CD1 | TYR | B | 164 | 4098 | 6149 | 3961 | −511 | 801 | 1012 | C |
| ATOM | 1572 | CE1 | TYR | B | 164 | −1.103 | −74.363 | −53.700 | 1.00 | 37.07 | | C |
| ANISOU | 1572 | CE1 | TYR | B | 164 | 3939 | 6383 | 3765 | −625 | 780 | 1219 | C |
| ATOM | 1573 | CZ | TYR | B | 164 | −1.944 | −74.070 | −54.758 | 1.00 | 49.56 | | C |
| ANISOU | 1573 | CZ | TYR | B | 164 | 5486 | 8108 | 5236 | −822 | 761 | 1273 | C |
| ATOM | 1574 | OH | TYR | B | 164 | −3.277 | −74.397 | −54.671 | 1.00 | 61.70 | | O |
| ANISOU | 1574 | OH | TYR | B | 164 | 6891 | 9931 | 6621 | −941 | 734 | 1497 | O |
| ATOM | 1575 | CE2 | TYR | B | 164 | −1.455 | −73.449 | −55.901 | 1.00 | 44.78 | | C |
| ANISOU | 1575 | CE2 | TYR | B | 164 | 4970 | 7371 | 4672 | −905 | 765 | 1114 | C |
| ATOM | 1576 | CD2 | TYR | B | 164 | −0.112 | −73.128 | −55.972 | 1.00 | 34.26 | | C |
| ANISOU | 1576 | CD2 | TYR | B | 164 | 3756 | 5765 | 3495 | −788 | 792 | 907 | C |
| ATOM | 1577 | C | TYR | B | 164 | 2.521 | −75.445 | −55.732 | 1.00 | 54.50 | | C |
| ANISOU | 1577 | C | TYR | B | 164 | 6635 | 7597 | 6475 | −919 | 969 | 631 | C |
| ATOM | 1578 | O | TYR | B | 164 | 1.954 | −76.396 | −55.195 | 1.00 | 56.97 | | O |
| ANISOU | 1578 | O | TYR | B | 164 | 6917 | 7974 | 6754 | −1003 | 976 | 765 | O |
| ATOM | 1579 | N | ILE | B | 165 | 2.685 | −75.363 | −57.046 | 1.00 | 57.40 | | N |
| ANISOU | 1579 | N | ILE | B | 165 | 7095 | 7864 | 6851 | −1123 | 1005 | 526 | N |
| ATOM | 1580 | CA | ILE | B | 165 | 2.143 | −76.365 | −57.959 | 1.00 | 44.53 | | C |
| ANISOU | 1580 | CA | ILE | B | 165 | 5546 | 6200 | 5175 | −1463 | 1049 | 560 | C |
| ATOM | 1581 | CB | ILE | B | 165 | 2.130 | −75.866 | −59.428 | 1.00 | 33.68 | | C |

TABLE 7-continued

| | | | | | | | | | | | |
|---|---|---|---|---|---|---|---|---|---|---|---|
| DMXAA-hSTING$^{G230I}$ complex | | | | | | | | | | | |
| ANISOU | 1581 | CB | ILE | B | 165 | 4246 | 4795 | 3757 | −1651 | 1063 | 458 | C |
| ATOM | 1582 | CG1 | ILE | B | 165 | 1.361 | −74.551 | −59.560 | 1.00 | 36.68 | | C |
| ANISOU | 1582 | CG1 | ILE | B | 165 | 4490 | 5446 | 4000 | −1550 | 974 | 530 | C |
| ATOM | 1583 | CD1 | ILE | B | 165 | −0.100 | −74.644 | −59.088 | 1.00 | 38.43 | | C |
| ANISOU | 1583 | CD1 | ILE | B | 165 | 4561 | 5989 | 4052 | −1588 | 906 | 763 | C |
| ATOM | 1584 | CG2 | ILE | B | 165 | 1.545 | −76.924 | −60.351 | 1.00 | 35.04 | | C |
| ANISOU | 1584 | CG2 | ILE | B | 165 | 4518 | 4928 | 3867 | −2011 | 1099 | 494 | C |
| ATOM | 1585 | C | ILE | B | 165 | 2.932 | −77.670 | −57.892 | 1.00 | 49.39 | | C |
| ANISOU | 1585 | C | ILE | B | 165 | 6302 | 6530 | 5936 | −1568 | 1137 | 488 | C |
| ATOM | 1586 | O | ILE | B | 165 | 2.366 | −78.759 | −58.002 | 1.00 | 63.30 | | O |
| ANISOU | 1586 | O | ILE | B | 165 | 8107 | 8285 | 7660 | −1787 | 1154 | 577 | O |
| ATOM | 1587 | N | GLY | B | 166 | 4.240 | −77.569 | −57.736 | 1.00 | 45.47 | | N |
| ANISOU | 1587 | N | GLY | B | 166 | 5876 | 5793 | 5606 | −1412 | 1189 | 333 | N |
| ATOM | 1588 | CA | GLY | B | 166 | 5.113 | −78.712 | −57.832 | 1.00 | 40.49 | | C |
| ANISOU | 1588 | CA | GLY | B | 166 | 5395 | 4862 | 5128 | −1509 | 1287 | 235 | C |
| ATOM | 1589 | C | GLY | B | 166 | 5.567 | −79.380 | −56.570 | 1.00 | 50.71 | | C |
| ANISOU | 1589 | C | GLY | B | 166 | 6666 | 6068 | 6533 | −1347 | 1295 | 286 | C |
| ATOM | 1590 | O | GLY | B | 166 | 6.226 | −80.367 | −56.617 | 1.00 | 53.81 | | O |
| ANISOU | 1590 | O | GLY | B | 166 | 7177 | 6204 | 7066 | −1401 | 1376 | 214 | O |
| ATOM | 1591 | N | TYR | B | 167 | 5.229 | −78.815 | −55.437 | 1.00 | 49.00 | | N |
| ANISOU | 1591 | N | TYR | B | 167 | 6301 | 6062 | 6254 | −1143 | 1212 | 413 | N |
| ATOM | 1592 | CA | TYR | B | 167 | 5.491 | −79.458 | −54.180 | 1.00 | 43.43 | | C |
| ANISOU | 1592 | CA | TYR | B | 167 | 5566 | 5301 | 5635 | −995 | 1209 | 481 | C |
| ATOM | 1593 | CB | TYR | B | 167 | 6.755 | −78.908 | −53.568 | 1.00 | 33.03 | | C |
| ANISOU | 1593 | CB | TYR | B | 167 | 4253 | 3822 | 4473 | −731 | 1215 | 361 | C |
| ATOM | 1594 | CG | TYR | B | 167 | 7.127 | −79.517 | −52.263 | 1.00 | 49.16 | | C |
| ANISOU | 1594 | CG | TYR | B | 167 | 6261 | 5816 | 6603 | −571 | 1202 | 437 | C |
| ATOM | 1595 | CD1 | TYR | B | 167 | 7.430 | −80.839 | −52.161 | 1.00 | 40.45 | | C |
| ANISOU | 1595 | CD1 | TYR | B | 167 | 5246 | 4514 | 5609 | −694 | 1270 | 450 | C |
| ATOM | 1596 | CE1 | TYR | B | 167 | 7.777 | −81.386 | −50.966 | 1.00 | 36.31 | | C |
| ANISOU | 1596 | CE1 | TYR | B | 167 | 4686 | 3945 | 5165 | −555 | 1255 | 527 | C |
| ATOM | 1597 | CZ | TYR | B | 167 | 7.827 | −80.621 | −49.875 | 1.00 | 39.10 | | C |
| ANISOU | 1597 | CZ | TYR | B | 167 | 4921 | 4456 | 5479 | −290 | 1171 | 588 | C |
| ATOM | 1598 | OH | TYR | B | 167 | 8.176 | −81.142 | −48.687 | 1.00 | 45.50 | | O |
| ANISOU | 1598 | OH | TYR | B | 167 | 5700 | 5226 | 6363 | −157 | 1152 | 669 | O |
| ATOM | 1599 | CE2 | TYR | B | 167 | 7.531 | −79.306 | −49.944 | 1.00 | 32.94 | | C |
| ANISOU | 1599 | CE2 | TYR | B | 167 | 4064 | 3867 | 4584 | −157 | 1104 | 568 | C |
| ATOM | 1600 | CD2 | TYR | B | 167 | 7.189 | −78.756 | −51.134 | 1.00 | 32.64 | | C |
| ANISOU | 1600 | CD2 | TYR | B | 167 | 4056 | 3871 | 4476 | −297 | 1119 | 496 | C |
| ATOM | 1601 | C | TYR | B | 167 | 4.329 | −79.357 | −53.204 | 1.00 | 48.10 | | C |
| ANISOU | 1601 | C | TYR | B | 167 | 6003 | 6192 | 6081 | −904 | 1126 | 685 | C |
| ATOM | 1602 | O | TYR | B | 167 | 3.822 | −80.344 | −52.760 | 1.00 | 55.34 | | O |
| ANISOU | 1602 | O | TYR | B | 167 | 6907 | 7143 | 6975 | −1005 | 1127 | 817 | O |
| ATOM | 1603 | N | LEU | B | 168 | 3.946 | −78.152 | −52.833 | 1.00 | 42.29 | | N |
| ANISOU | 1603 | N | LEU | B | 168 | 5151 | 5676 | 5241 | −711 | 1053 | 716 | N |
| ATOM | 1604 | CA | LEU | B | 168 | 3.056 | −77.956 | −51.722 | 1.00 | 42.28 | | C |
| ANISOU | 1604 | CA | LEU | B | 168 | 5000 | 5958 | 5107 | −559 | 983 | 898 | C |
| ATOM | 1605 | CB | LEU | B | 168 | 2.952 | −76.480 | −51.413 | 1.00 | 33.21 | | C |
| ANISOU | 1605 | CB | LEU | B | 168 | 3762 | 4984 | 3874 | −297 | 912 | 879 | C |
| ATOM | 1606 | CG | LEU | B | 168 | 4.163 | −75.971 | −50.672 | 1.00 | 35.57 | | C |
| ANISOU | 1606 | CG | LEU | B | 168 | 4093 | 5120 | 4302 | −25 | 894 | 761 | C |
| ATOM | 1607 | CD1 | LEU | B | 168 | 4.005 | −74.554 | −50.241 | 1.00 | 37.53 | | C |
| ANISOU | 1607 | CD1 | LEU | B | 168 | 4264 | 5551 | 4446 | 234 | 809 | 759 | C |
| ATOM | 1608 | CD2 | LEU | B | 168 | 4.462 | −76.820 | −49.480 | 1.00 | 34.97 | | C |
| ANISOU | 1608 | CD2 | LEU | B | 168 | 4002 | 4993 | 4291 | 66 | 901 | 842 | C |
| ATOM | 1609 | C | LEU | B | 168 | 1.672 | −78.546 | −51.914 | 1.00 | 53.61 | | C |
| ANISOU | 1609 | C | LEU | B | 168 | 6364 | 7620 | 6387 | −778 | 968 | 1090 | C |
| ATOM | 1610 | O | LEU | B | 168 | 1.157 | −79.205 | −51.059 | 1.00 | 36.39 | | O |
| ANISOU | 1610 | O | LEU | B | 168 | 4109 | 5556 | 4162 | −762 | 951 | 1252 | O |
| ATOM | 1611 | N | ARG | B | 169 | 1.100 | −78.342 | −53.076 | 1.00 | 50.76 | | N |
| ANISOU | 1611 | N | ARG | B | 169 | 6019 | 7326 | 5940 | −990 | 969 | 1084 | N |
| ATOM | 1612 | CA | ARG | B | 169 | −0.270 | −78.792 | −53.279 | 1.00 | 60.81 | | C |
| ANISOU | 1612 | CA | ARG | B | 169 | 7208 | 8842 | 7055 | −1200 | 938 | 1282 | C |
| ATOM | 1613 | CB | ARG | B | 169 | −0.957 | −78.010 | −54.392 | 1.00 | 51.65 | | C |
| ANISOU | 1613 | CB | ARG | B | 169 | 6019 | 7832 | 5774 | −1325 | 909 | 1281 | C |
| ATOM | 1614 | CG | ARG | B | 169 | −0.830 | −78.591 | −55.776 | 1.00 | 54.22 | | C |
| ANISOU | 1614 | CG | ARG | B | 169 | 6497 | 7975 | 6131 | −1654 | 952 | 1185 | C |
| ATOM | 1615 | CD | ARG | B | 169 | −1.611 | −77.701 | −56.714 | 1.00 | 60.70 | | C |
| ANISOU | 1615 | CD | ARG | B | 169 | 7257 | 8994 | 6813 | −1746 | 908 | 1215 | C |
| ATOM | 1616 | NE | ARG | B | 169 | −1.643 | −78.152 | −58.097 | 1.00 | 74.02 | | N |
| ANISOU | 1616 | NE | ARG | B | 169 | 9082 | 10549 | 8492 | −2073 | 936 | 1138 | N |
| ATOM | 1617 | CZ | ARG | B | 169 | −2.516 | −77.696 | −58.988 | 1.00 | 70.95 | | C |
| ANISOU | 1617 | CZ | ARG | B | 169 | 8653 | 10322 | 7983 | −2209 | 878 | 1188 | C |
| ATOM | 1618 | NH1 | ARG | B | 169 | −3.412 | −76.797 | −58.611 | 1.00 | 71.31 | | N |
| ANISOU | 1618 | NH1 | ARG | B | 169 | 8517 | 10667 | 7909 | −2054 | 801 | 1323 | N |
| ATOM | 1619 | NH2 | ARG | B | 169 | −2.502 | −78.136 | −60.241 | 1.00 | 62.31 | | N |
| ANISOU | 1619 | NH2 | ARG | B | 169 | 7707 | 9053 | 6913 | −2413 | 866 | 1069 | N |
| ATOM | 1620 | C | ARG | B | 169 | −0.345 | −80.302 | −53.518 | 1.00 | 66.92 | | C |

TABLE 7-continued

| DMXAA-hSTING$^{G230I}$ complex | | | | | | | | | | | |
|---|---|---|---|---|---|---|---|---|---|---|---|
| ATOM | 1620 | C | ARG | B | 169 | 8085 | 9460 | 7882 | −1486 | 977 | 1330 | C |
| ANISOU | 1621 | O | ARG | B | 169 | −1.426 | −80.881 | −53.657 | 1.00 | 71.65 | | O |
| ATOM | 1621 | O | ARG | B | 169 | 8630 | 10230 | 8366 | −1697 | 945 | 1507 | O |
| ANISOU | 1622 | N | LEU | B | 170 | 0.820 | −80.935 | −53.548 | 1.00 | 66.93 | | N |
| ATOM | 1622 | N | LEU | B | 170 | 8235 | 9134 | 8061 | −1488 | 1042 | 1179 | N |
| ANISOU | 1623 | CA | LEU | B | 170 | 0.913 | −82.372 | −53.725 | 1.00 | 74.46 | | C |
| ATOM | 1623 | CA | LEU | B | 170 | 9313 | 9892 | 9087 | −1728 | 1083 | 1200 | C |
| ANISOU | 1624 | CB | LEU | B | 170 | 1.978 | −82.698 | −54.774 | 1.00 | 80.00 | | C |
| ATOM | 1624 | CB | LEU | B | 170 | 10220 | 10248 | 9930 | −1846 | 1169 | 973 | C |
| ANISOU | 1625 | CG | LEU | B | 170 | 1.810 | −81.921 | −56.083 | 1.00 | 86.52 | | C |
| ATOM | 1625 | CG | LEU | B | 170 | 11086 | 11107 | 10680 | −1967 | 1174 | 871 | C |
| ANISOU | 1626 | CD1 | LEU | B | 170 | 3.155 | −81.663 | −56.726 | 1.00 | 84.69 | | C |
| ATOM | 1626 | CD1 | LEU | B | 170 | 10993 | 10585 | 10602 | −1901 | 1258 | 630 | C |
| ANISOU | 1627 | CD2 | LEU | B | 170 | 0.892 | −82.658 | −57.052 | 1.00 | 86.63 | | C |
| ATOM | 1627 | CD2 | LEU | B | 170 | 11177 | 11156 | 10583 | −2332 | 1163 | 944 | C |
| ANISOU | 1628 | C | LEU | B | 170 | 1.250 | −83.025 | −52.387 | 1.00 | 65.89 | | C |
| ATOM | 1628 | C | LEU | B | 170 | 8189 | 8760 | 8085 | −1573 | 1082 | 1282 | C |
| ANISOU | 1629 | O | LEU | B | 170 | 0.874 | −84.167 | −52.118 | 1.00 | 67.30 | | O |
| ATOM | 1629 | O | LEU | B | 170 | 8396 | 8905 | 8268 | −1740 | 1079 | 1401 | O |
| ANISOU | 1630 | N | ILE | B | 171 | 1.943 | −82.270 | −51.544 | 1.00 | 56.51 | | N |
| ATOM | 1630 | N | ILE | B | 171 | 6938 | 7574 | 6958 | −1258 | 1074 | 1224 | N |
| ANISOU | 1631 | CA | ILE | B | 171 | 2.448 | −82.770 | −50.275 | 1.00 | 57.34 | | C |
| ATOM | 1631 | CA | ILE | B | 171 | 7017 | 7613 | 7156 | −1083 | 1072 | 1276 | C |
| ANISOU | 1632 | CB | ILE | B | 171 | 3.904 | −82.277 | −50.027 | 1.00 | 60.02 | | C |
| ATOM | 1632 | CB | ILE | B | 171 | 7421 | 7715 | 7670 | −847 | 1106 | 1085 | C |
| ANISOU | 1633 | CG1 | ILE | B | 171 | 4.906 | −83.417 | −50.235 | 1.00 | 58.39 | | C |
| ATOM | 1633 | CG1 | ILE | B | 171 | 7372 | 7154 | 7660 | −951 | 1184 | 987 | C |
| ANISOU | 1634 | CD1 | ILE | B | 171 | 5.310 | −84.128 | −48.938 | 1.00 | 54.50 | | C |
| ATOM | 1634 | CD1 | ILE | B | 171 | 6850 | 6595 | 7261 | −817 | 1174 | 1075 | C |
| ANISOU | 1635 | CG2 | ILE | B | 171 | 4.057 | −81.657 | −48.630 | 1.00 | 55.88 | | C |
| ATOM | 1635 | CG2 | ILE | B | 171 | 6774 | 7332 | 7127 | −528 | 1048 | 1152 | C |
| ANISOU | 1636 | C | ILE | B | 171 | 1.529 | −82.406 | −49.098 | 1.00 | 54.34 | | C |
| ATOM | 1636 | C | ILE | B | 171 | 6449 | 7570 | 6628 | −916 | 1000 | 1483 | C |
| ANISOU | 1637 | O | ILE | B | 171 | 1.309 | −83.212 | −48.187 | 1.00 | 62.23 | | O |
| ATOM | 1637 | O | ILE | B | 171 | 7406 | 8607 | 7633 | −913 | 987 | 1625 | O |
| ANISOU | 1638 | N | LEU | B | 172 | 0.985 | −81.194 | −49.124 | 1.00 | 40.73 | | N |
| ATOM | 1638 | N | LEU | B | 172 | 4614 | 6093 | 4769 | −775 | 956 | 1503 | N |
| ANISOU | 1639 | CA | LEU | B | 172 | 0.141 | −80.713 | −48.030 | 1.00 | 49.61 | | C |
| ATOM | 1639 | CA | LEU | B | 172 | 5562 | 7547 | 5741 | −579 | 899 | 1685 | C |
| ANISOU | 1640 | CB | LEU | B | 172 | −0.139 | −79.212 | −48.149 | 1.00 | 48.51 | | C |
| ATOM | 1640 | CB | LEU | B | 172 | 5340 | 7603 | 5487 | −373 | 860 | 1644 | C |
| ANISOU | 1641 | CG | LEU | B | 172 | 1.020 | −78.271 | −47.828 | 1.00 | 41.26 | | C |
| ATOM | 1641 | CG | LEU | B | 172 | 4478 | 6529 | 4668 | −95 | 851 | 1456 | C |
| ANISOU | 1642 | CD1 | LEU | B | 172 | 0.544 | −76.843 | −47.895 | 1.00 | 39.83 | | C |
| ATOM | 1642 | CD1 | LEU | B | 172 | 4214 | 6569 | 4351 | 95 | 800 | 1448 | C |
| ANISOU | 1643 | CD2 | LEU | B | 172 | 1.584 | −78.564 | −46.447 | 1.00 | 48.72 | | C |
| ATOM | 1643 | CD2 | LEU | B | 172 | 5407 | 7428 | 5674 | 122 | 838 | 1491 | C |
| ANISOU | 1644 | C | LEU | B | 172 | −1.170 | −81.477 | −47.787 | 1.00 | 63.57 | | C |
| ATOM | 1644 | C | LEU | B | 172 | 7220 | 9565 | 7369 | −760 | 875 | 1939 | C |
| ANISOU | 1645 | O | LEU | B | 172 | −1.561 | −81.651 | −46.625 | 1.00 | 68.56 | | O |
| ATOM | 1645 | O | LEU | B | 172 | 7739 | 10374 | 7937 | −620 | 850 | 2098 | O |
| ANISOU | 1646 | N | PRO | B | 173 | −1.871 | −81.903 | −48.864 | 1.00 | 58.72 | | N |
| ATOM | 1646 | N | PRO | B | 173 | 6633 | 8980 | 6700 | −1070 | 876 | 1987 | N |
| ANISOU | 1647 | CA | PRO | B | 173 | −3.172 | −82.549 | −48.642 | 1.00 | 64.63 | | C |
| ATOM | 1647 | CA | PRO | B | 173 | 7259 | 9991 | 7306 | −1249 | 839 | 2250 | C |
| ANISOU | 1648 | CB | PRO | B | 173 | −3.577 | −83.004 | −50.042 | 1.00 | 57.76 | | C |
| ATOM | 1648 | CB | PRO | B | 173 | 6485 | 9044 | 6420 | −1611 | 841 | 2230 | C |
| ANISOU | 1649 | CG | PRO | B | 173 | −2.985 | −81.972 | −50.927 | 1.00 | 58.83 | | C |
| ATOM | 1649 | CG | PRO | B | 173 | 6693 | 9073 | 6589 | −1535 | 864 | 2012 | C |
| ANISOU | 1650 | CD | PRO | B | 173 | −1.650 | −81.652 | −50.301 | 1.00 | 46.16 | | C |
| ATOM | 1650 | CD | PRO | B | 173 | 5160 | 7240 | 5139 | −1258 | 901 | 1829 | C |
| ANISOU | 1651 | C | PRO | B | 173 | −3.153 | −83.747 | −47.692 | 1.00 | 64.28 | | C |
| ATOM | 1651 | C | PRO | B | 173 | 7210 | 9898 | 7313 | −1295 | 837 | 2386 | C |
| ANISOU | 1652 | O | PRO | B | 173 | −4.082 | −83.891 | −46.896 | 1.00 | 65.21 | | O |
| ATOM | 1652 | O | PRO | B | 173 | 7167 | 10307 | 7304 | −1261 | 801 | 2619 | O |
| ANISOU | 1653 | N | GLU | B | 174 | −2.124 | −84.586 | −47.774 | 1.00 | 62.33 | | N |
| ATOM | 1653 | N | GLU | B | 174 | 7133 | 9300 | 7250 | −1367 | 878 | 2253 | N |
| ANISOU | 1654 | CA | GLU | B | 174 | −2.043 | −85.763 | −46.914 | 1.00 | 51.04 | | C |
| ATOM | 1654 | CA | GLU | B | 174 | 5714 | 7794 | 5885 | −1420 | 873 | 2377 | C |
| ANISOU | 1655 | CB | GLU | B | 174 | −1.623 | −86.998 | −47.708 | 1.00 | 52.82 | | C |
| ATOM | 1655 | CB | GLU | B | 174 | 6138 | 7689 | 6243 | −1725 | 904 | 2303 | C |
| ANISOU | 1656 | CG | GLU | B | 174 | −2.767 | −87.699 | −48.405 | 1.00 | 75.76 | | C |
| ATOM | 1656 | CG | GLU | B | 174 | 9040 | 10710 | 9034 | −2079 | 862 | 2467 | C |
| ANISOU | 1657 | CD | GLU | B | 174 | −3.715 | −88.372 | −47.427 | 1.00 | 99.46 | | C |
| ATOM | 1657 | CD | GLU | B | 174 | 11912 | 13921 | 11955 | −2084 | 785 | 2694 | C |
| ANISOU | 1658 | OE1 | GLU | B | 174 | −4.920 | −88.043 | −47.447 | 1.00 | 107.31 | | O |
| ATOM | 1658 | OE1 | GLU | B | 174 | 12772 | 15198 | 12804 | −2075 | 702 | 2784 | O |
| ANISOU | 1659 | OE2 | GLU | B | 174 | −3.253 | −89.229 | −46.643 | 1.00 | 109.14 | | O |

TABLE 7-continued

| | | | | | | | | | | | | |
|---|---|---|---|---|---|---|---|---|---|---|---|---|
| ANISOU | 1659 | OE2 | GLU | B | 174 | 13172 | 15018 | 13278 | −2084 | 799 | 2766 | O |
| ATOM | 1660 | C | GLU | B | 174 | −1.098 | −85.588 | −45.730 | 1.00 | 49.22 | | C |
| ANISOU | 1660 | C | GLU | B | 174 | 5473 | 7471 | 5756 | −1110 | 886 | 2318 | C |
| ATOM | 1661 | O | GLU | B | 174 | −0.711 | −86.567 | −45.100 | 1.00 | 52.18 | | O |
| ANISOU | 1661 | O | GLU | B | 174 | 5895 | 7699 | 6233 | −1140 | 892 | 2369 | O |
| ATOM | 1662 | N | LEU | B | 175 | −0.721 | −84.351 | −45.428 | 1.00 | 42.59 | | N |
| ANISOU | 1662 | N | LEU | B | 175 | 4580 | 6710 | 4891 | −817 | 883 | 2215 | N |
| ATOM | 1663 | CA | LEU | B | 175 | 0.287 | −84.119 | −44.400 | 1.00 | 51.79 | | C |
| ANISOU | 1663 | CA | LEU | B | 175 | 5759 | 7759 | 6160 | −532 | 887 | 2136 | C |
| ATOM | 1664 | CB | LEU | B | 175 | 0.852 | −82.698 | −44.468 | 1.00 | 56.18 | | C |
| ANISOU | 1664 | CB | LEU | B | 175 | 6312 | 8324 | 6711 | −267 | 879 | 1966 | C |
| ATOM | 1665 | CG | LEU | B | 175 | 2.121 | −82.507 | −43.635 | 1.00 | 51.60 | | C |
| ANISOU | 1665 | CG | LEU | B | 175 | 5787 | 7543 | 6274 | −16 | 879 | 1845 | C |
| ATOM | 1666 | CD1 | LEU | B | 175 | 3.278 | −83.296 | −44.236 | 1.00 | 48.68 | | C |
| ANISOU | 1666 | CD1 | LEU | B | 175 | 5585 | 6780 | 6132 | −151 | 935 | 1687 | C |
| ATOM | 1667 | CD2 | LEU | B | 175 | 2.483 | −81.036 | −43.519 | 1.00 | 43.28 | | C |
| ANISOU | 1667 | CD2 | LEU | B | 175 | 4711 | 6557 | 5176 | 257 | 846 | 1721 | C |
| ATOM | 1668 | C | LEU | B | 175 | −0.233 | −84.397 | −42.993 | 1.00 | 49.48 | | C |
| ANISOU | 1668 | C | LEU | B | 175 | 5329 | 7694 | 5776 | −392 | 849 | 2349 | C |
| ATOM | 1669 | O | LEU | B | 175 | 0.381 | −85.137 | −42.221 | 1.00 | 60.46 | | O |
| ANISOU | 1669 | O | LEU | B | 175 | 6759 | 8934 | 7279 | −349 | 853 | 2370 | O |
| ATOM | 1670 | N | GLN | B | 176 | −1.368 | −83.794 | −42.669 | 1.00 | 62.04 | | N |
| ANISOU | 1670 | N | GLN | B | 176 | 6755 | 9655 | 7161 | −317 | 817 | 2513 | N |
| ATOM | 1671 | CA | GLN | B | 176 | −1.961 | −83.906 | −41.344 | 1.00 | 55.13 | | C |
| ANISOU | 1671 | CA | GLN | B | 176 | 5733 | 9047 | 6165 | −159 | 788 | 2723 | C |
| ATOM | 1672 | CB | GLN | B | 176 | −3.194 | −83.018 | −41.244 | 1.00 | 61.77 | | C |
| ANISOU | 1672 | CB | GLN | B | 176 | 6399 | 10298 | 6775 | −60 | 767 | 2870 | C |
| ATOM | 1673 | CG | GLN | B | 176 | −3.112 | −82.000 | −40.142 | 1.00 | 76.66 | | C |
| ANISOU | 1673 | CG | GLN | B | 176 | 8203 | 12368 | 8558 | 323 | 752 | 2870 | C |
| ATOM | 1674 | CD | GLN | B | 176 | −3.742 | −80.680 | −40.531 | 1.00 | 92.34 | | C |
| ANISOU | 1674 | CD | GLN | B | 176 | 10108 | 14589 | 10387 | 472 | 743 | 2848 | C |
| ATOM | 1675 | OE1 | GLN | B | 176 | −4.062 | −80.451 | −41.700 | 1.00 | 96.95 | | O |
| ANISOU | 1675 | OE1 | GLN | B | 176 | 10710 | 15160 | 10966 | 295 | 748 | 2799 | O |
| ATOM | 1676 | NE2 | GLN | B | 176 | −3.923 | −79.800 | −39.552 | 1.00 | 96.28 | | N |
| ANISOU | 1676 | NE2 | GLN | B | 176 | 10526 | 15302 | 10755 | 803 | 729 | 2883 | N |
| ATOM | 1677 | C | GLN | B | 176 | −2.328 | −85.347 | −41.010 | 1.00 | 59.33 | | C |
| ANISOU | 1677 | C | GLN | B | 176 | 6256 | 9558 | 6730 | −392 | 782 | 2911 | C |
| ATOM | 1678 | O | GLN | B | 176 | −2.211 | −85.784 | −39.862 | 1.00 | 46.35 | | O |
| ANISOU | 1678 | O | GLN | B | 176 | 4562 | 7959 | 5089 | −276 | 768 | 3023 | O |
| ATOM | 1679 | N | ALA | B | 177 | −2.772 | −86.078 | −42.025 | 1.00 | 56.68 | | N |
| ANISOU | 1679 | N | ALA | B | 177 | 5975 | 9148 | 6414 | −727 | 786 | 2947 | N |
| ATOM | 1680 | CA | ALA | B | 177 | −3.102 | −87.485 | −41.870 | 1.00 | 58.53 | | C |
| ANISOU | 1680 | CA | ALA | B | 177 | 6229 | 9321 | 6689 | −988 | 770 | 3113 | C |
| ATOM | 1681 | CB | ALA | B | 177 | −3.701 | −88.031 | −43.148 | 1.00 | 48.93 | | C |
| ANISOU | 1681 | CB | ALA | B | 177 | 5080 | 8053 | 5459 | −1354 | 763 | 3136 | C |
| ATOM | 1682 | C | ALA | B | 177 | −1.851 | −88.269 | −41.505 | 1.00 | 63.19 | | C |
| ANISOU | 1682 | C | ALA | B | 177 | 6972 | 9540 | 7496 | −964 | 794 | 2991 | C |
| ATOM | 1683 | O | ALA | B | 177 | −1.878 | −89.170 | −40.660 | 1.00 | 71.04 | | O |
| ANISOU | 1683 | O | ALA | B | 177 | 7944 | 10525 | 8523 | −994 | 774 | 3138 | O |
| ATOM | 1684 | N | ARG | B | 178 | −0.748 | −87.934 | −42.163 | 1.00 | 58.22 | | N |
| ANISOU | 1684 | N | ARG | B | 178 | 6495 | 8608 | 7017 | −911 | 837 | 2728 | N |
| ATOM | 1685 | CA | ARG | B | 178 | 0.502 | −88.655 | −41.972 | 1.00 | 56.34 | | C |
| ANISOU | 1685 | CA | ARG | B | 178 | 6407 | 7999 | 7001 | −893 | 868 | 2600 | C |
| ATOM | 1686 | CB | ARG | B | 178 | 1.488 | −88.318 | −43.081 | 1.00 | 55.24 | | C |
| ANISOU | 1686 | CB | ARG | B | 178 | 6432 | 7553 | 7004 | −915 | 925 | 2326 | C |
| ATOM | 1687 | CG | ARG | B | 178 | 1.178 | −89.005 | −44.389 | 1.00 | 59.72 | | C |
| ANISOU | 1687 | CG | ARG | B | 178 | 7127 | 7972 | 7591 | −1254 | 951 | 2286 | C |
| ATOM | 1688 | CD | ARG | B | 178 | 2.037 | −88.439 | −45.499 | 1.00 | 62.22 | | C |
| ANISOU | 1688 | CD | ARG | B | 178 | 7578 | 8054 | 8007 | −1246 | 1011 | 2022 | C |
| ATOM | 1689 | NE | ARG | B | 178 | 3.460 | −88.642 | −45.250 | 1.00 | 70.66 | | N |
| ANISOU | 1689 | NE | ARG | B | 178 | 8757 | 8800 | 9290 | −1097 | 1062 | 1857 | N |
| ATOM | 1690 | CZ | ARG | B | 178 | 4.393 | −87.702 | −45.385 | 1.00 | 74.13 | | C |
| ANISOU | 1690 | CZ | ARG | B | 178 | 9216 | 9145 | 9807 | −886 | 1090 | 1673 | C |
| ATOM | 1691 | NH1 | ARG | B | 178 | 4.050 | −86.480 | −45.767 | 1.00 | 62.98 | | N |
| ANISOU | 1691 | NH1 | ARG | B | 178 | 7731 | 7924 | 8273 | −795 | 1070 | 1620 | N |
| ATOM | 1692 | NH2 | ARG | B | 178 | 5.668 | −87.982 | −45.140 | 1.00 | 80.72 | | N |
| ANISOU | 1692 | NH2 | ARG | B | 178 | 10138 | 9690 | 10841 | −767 | 1133 | 1549 | N |
| ATOM | 1693 | C | ARG | B | 178 | 1.114 | −88.352 | −40.617 | 1.00 | 63.40 | | C |
| ANISOU | 1693 | C | ARG | B | 178 | 7235 | 8925 | 7927 | −582 | 851 | 2618 | C |
| ATOM | 1694 | O | ARG | B | 178 | 1.718 | −89.219 | −39.978 | 1.00 | 68.21 | | O |
| ANISOU | 1694 | O | ARG | B | 178 | 7897 | 9353 | 8668 | −579 | 852 | 2649 | O |
| ATOM | 1695 | N | ILE | B | 179 | 0.953 | −87.111 | −40.182 | 1.00 | 55.37 | | N |
| ANISOU | 1695 | N | ILE | B | 179 | 6112 | 8139 | 6787 | −322 | 832 | 2598 | N |
| ATOM | 1696 | CA | ILE | B | 179 | 1.448 | −86.687 | −38.887 | 1.00 | 52.15 | | C |
| ANISOU | 1696 | CA | ILE | B | 179 | 5645 | 7794 | 6375 | −17 | 805 | 2616 | C |
| ATOM | 1697 | CB | ILE | B | 179 | 1.314 | −85.176 | −38.715 | 1.00 | 54.36 | | C |
| ANISOU | 1697 | CB | ILE | B | 179 | 5851 | 8283 | 6519 | 254 | 786 | 2542 | C |
| ATOM | 1698 | CG1 | ILE | B | 179 | 2.300 | −84.469 | −39.642 | 1.00 | 58.58 | | C |

TABLE 7-continued

DMXAA-hSTING$^{G230I}$ complex

| | | | | | | | | | | | |
|---|---|---|---|---|---|---|---|---|---|---|---|
| ANISOU | 1698 | CG1 | ILE | B | 179 | 6512 | 8563 | 7184 | 295 | 810 | 2276 | C |
| ATOM | 1699 | CD1 | ILE | B | 179 | 2.559 | −83.029 | −39.294 | 1.00 | 51.49 | | C |
| ANISOU | 1699 | CD1 | ILE | B | 179 | 5582 | 7776 | 6207 | 598 | 777 | 2172 | C |
| ATOM | 1700 | CG2 | ILE | B | 179 | 1.532 | −84.786 | −37.266 | 1.00 | 43.34 | | C |
| ANISOU | 1700 | CG2 | ILE | B | 179 | 4383 | 7022 | 5062 | 554 | 746 | 2609 | C |
| ATOM | 1701 | C | ILE | B | 179 | 0.721 | −87.398 | −37.752 | 1.00 | 60.84 | | C |
| ANISOU | 1701 | C | ILE | B | 179 | 6625 | 9113 | 7377 | −20 | 771 | 2877 | C |
| ATOM | 1702 | O | ILE | B | 179 | 1.346 | −87.886 | −36.803 | 1.00 | 59.33 | | O |
| ANISOU | 1702 | O | ILE | B | 179 | 6449 | 8818 | 7275 | 83 | 757 | 2912 | O |
| ATOM | 1703 | N | ARG | B | 180 | −0.587 | −87.455 | −37.813 | 1.00 | 65.85 | | N |
| ANISOU | 1703 | N | ARG | B | 180 | 7132 | 10058 | 7827 | −144 | 756 | 3073 | N |
| ATOM | 1704 | CA | ARG | B | 180 | −1.335 | −88.132 | −36.792 | 1.00 | 73.03 | | C |
| ANISOU | 1704 | CA | ARG | B | 180 | 7909 | 11214 | 8626 | −153 | 725 | 3344 | C |
| ATOM | 1705 | CB | ARG | B | 180 | −2.821 | −87.834 | −36.887 | 1.00 | 83.96 | | C |
| ANISOU | 1705 | CB | ARG | B | 180 | 9119 | 13006 | 9776 | −228 | 712 | 3553 | C |
| ATOM | 1706 | CG | ARG | B | 180 | −3.552 | −88.462 | −38.043 | 1.00 | 93.72 | | C |
| ANISOU | 1706 | CG | ARG | B | 180 | 10384 | 14215 | 11011 | −588 | 711 | 3604 | C |
| ATOM | 1707 | CD | ARG | B | 180 | −5.020 | −88.080 | −37.976 | 1.00 | 98.78 | | C |
| ANISOU | 1707 | CD | ARG | B | 180 | 10854 | 15197 | 11481 | −594 | 635 | 3681 | C |
| ATOM | 1708 | NE | ARG | B | 180 | −5.282 | −86.739 | −38.466 | 1.00 | 103.55 | | N |
| ANISOU | 1708 | NE | ARG | B | 180 | 11399 | 15966 | 11978 | −407 | 648 | 3578 | N |
| ATOM | 1709 | CZ | ARG | B | 180 | −5.854 | −86.490 | −39.635 | 1.00 | 107.42 | | C |
| ANISOU | 1709 | CZ | ARG | B | 180 | 11896 | 16484 | 12436 | −553 | 628 | 3506 | C |
| ATOM | 1710 | NH1 | ARG | B | 180 | −6.050 | −85.239 | −40.031 | 1.00 | 111.09 | | N |
| ANISOU | 1710 | NH1 | ARG | B | 180 | 12431 | 16823 | 12954 | −885 | 593 | 3519 | N |
| ATOM | 1711 | NH2 | ARG | B | 180 | −6.221 | −87.509 | −40.406 | 1.00 | 101.12 | | N |
| ANISOU | 1711 | NH2 | ARG | B | 180 | 11043 | 15828 | 11548 | −365 | 636 | 3417 | N |
| ATOM | 1712 | C | ARG | B | 180 | −1.045 | −89.600 | −36.777 | 1.00 | 72.29 | | C |
| ANISOU | 1712 | C | ARG | B | 180 | 7903 | 10879 | 8687 | −402 | 719 | 3421 | C |
| ATOM | 1713 | O | ARG | B | 180 | −1.005 | −90.205 | −35.743 | 1.00 | 70.11 | | O |
| ANISOU | 1713 | O | ARG | B | 180 | 7577 | 10644 | 8417 | −349 | 695 | 3569 | O |
| ATOM | 1714 | N | THR | B | 181 | −0.871 | −90.171 | −37.948 | 1.00 | 69.60 | | N |
| ANISOU | 1714 | N | THR | B | 181 | 7703 | 10273 | 8469 | −666 | 742 | 3313 | N |
| ATOM | 1715 | CA | THR | B | 181 | −0.544 | −91.586 | −38.062 | 1.00 | 60.87 | | C |
| ANISOU | 1715 | CA | THR | B | 181 | 6716 | 8891 | 7521 | −907 | 738 | 3357 | C |
| ATOM | 1716 | CB | THR | B | 181 | −0.437 | −92.000 | −39.525 | 1.00 | 56.51 | | C |
| ANISOU | 1716 | CB | THR | B | 181 | 6328 | 8085 | 7059 | −1188 | 768 | 3218 | C |
| ATOM | 1717 | OG1 | THR | B | 181 | −1.530 | −91.439 | −40.257 | 1.00 | 63.53 | | O |
| ANISOU | 1717 | OG1 | THR | B | 181 | 7132 | 9239 | 7769 | −1308 | 754 | 3281 | O |
| ATOM | 1718 | CG2 | THR | B | 181 | −0.465 | −93.506 | −39.661 | 1.00 | 53.47 | | C |
| ANISOU | 1718 | CG2 | THR | B | 181 | 6054 | 7481 | 6782 | −1476 | 751 | 3316 | C |
| ATOM | 1719 | C | THR | B | 181 | 0.778 | −91.857 | −37.363 | 1.00 | 60.09 | | C |
| ANISOU | 1719 | C | THR | B | 181 | 6708 | 8509 | 7614 | −728 | 753 | 3243 | C |
| ATOM | 1720 | O | THR | B | 181 | 0.945 | −92.857 | −36.666 | 1.00 | 69.84 | | O |
| ANISOU | 1720 | O | THR | B | 181 | 7956 | 9652 | 8928 | −785 | 730 | 3367 | O |
| ATOM | 1721 | N | TYR | B | 182 | 1.720 | −90.946 | −37.554 | 1.00 | 59.94 | | N |
| ANISOU | 1721 | N | TYR | B | 182 | 6747 | 8355 | 7673 | −514 | 785 | 3014 | N |
| ATOM | 1722 | CA | TYR | B | 182 | 3.000 | −91.015 | −36.877 | 1.00 | 59.17 | | C |
| ANISOU | 1722 | CA | TYR | B | 182 | 6716 | 8017 | 7749 | −317 | 792 | 2906 | C |
| ATOM | 1723 | CB | TYR | B | 182 | 3.946 | −89.962 | −37.446 | 1.00 | 63.09 | | C |
| ANISOU | 1723 | CB | TYR | B | 182 | 7287 | 8360 | 8327 | −145 | 826 | 2643 | C |
| ATOM | 1724 | CG | TYR | B | 182 | 5.285 | −89.953 | −36.769 | 1.00 | 59.41 | | C |
| ANISOU | 1724 | CG | TYR | B | 182 | 6876 | 7657 | 8039 | 60 | 825 | 2539 | C |
| ATOM | 1725 | CD2 | TYR | B | 182 | 6.331 | −90.736 | −37.253 | 1.00 | 66.67 | | C |
| ANISOU | 1725 | CD2 | TYR | B | 182 | 7944 | 8191 | 9199 | −33 | 873 | 2417 | C |
| ATOM | 1726 | CE2 | TYR | B | 182 | 7.562 | −90.739 | −36.631 | 1.00 | 53.00 | | C |
| ANISOU | 1726 | CE2 | TYR | B | 182 | 6250 | 6251 | 7638 | 153 | 870 | 2339 | C |
| ATOM | 1727 | CZ | TYR | B | 182 | 7.751 | −89.956 | −35.506 | 1.00 | 51.54 | | C |
| ANISOU | 1727 | CZ | TYR | B | 182 | 5968 | 6239 | 7377 | 422 | 809 | 2379 | C |
| ATOM | 1728 | OH | TYR | B | 182 | 8.969 | −89.949 | −34.874 | 1.00 | 56.88 | | O |
| ANISOU | 1728 | OH | TYR | B | 182 | 6677 | 6715 | 8219 | 596 | 793 | 2313 | O |
| ATOM | 1729 | CE1 | TYR | B | 182 | 6.726 | −89.173 | −35.006 | 1.00 | 58.48 | | C |
| ANISOU | 1729 | CE1 | TYR | B | 182 | 6719 | 7492 | 8010 | 522 | 763 | 2487 | C |
| ATOM | 1730 | CD1 | TYR | B | 182 | 5.506 | −89.174 | −35.638 | 1.00 | 49.54 | | C |
| ANISOU | 1730 | CD1 | TYR | B | 182 | 5537 | 6570 | 6716 | 347 | 776 | 2568 | C |
| ATOM | 1731 | C | TYR | B | 182 | 2.814 | −90.809 | −35.372 | 1.00 | 62.27 | | C |
| ANISOU | 1731 | C | TYR | B | 182 | 6971 | 8652 | 8039 | −89 | 741 | 3070 | C |
| ATOM | 1732 | O | TYR | B | 182 | 3.416 | −91.509 | −34.552 | 1.00 | 65.18 | | O |
| ANISOU | 1732 | O | TYR | B | 182 | 7361 | 8882 | 8521 | −42 | 723 | 3128 | O |
| ATOM | 1733 | N | ASN | B | 183 | 1.978 | −89.836 | −35.022 | 1.00 | 63.75 | | N |
| ANISOU | 1733 | N | ASN | B | 183 | 7018 | 9199 | 8004 | 57 | 719 | 3146 | N |
| ATOM | 1734 | CA | ASN | B | 183 | 1.655 | −89.529 | −33.630 | 1.00 | 59.44 | | C |
| ANISOU | 1734 | CA | ASN | B | 183 | 6339 | 8929 | 7315 | 284 | 678 | 3305 | C |
| ATOM | 1735 | CB | ASN | B | 183 | 0.732 | −88.315 | −33.549 | 1.00 | 62.04 | | C |
| ANISOU | 1735 | CB | ASN | B | 183 | 6539 | 9634 | 7400 | 446 | 673 | 3344 | C |
| ATOM | 1736 | CG | ASN | B | 183 | 1.486 | −87.005 | −33.558 | 1.00 | 62.65 | | C |
| ANISOU | 1736 | CG | ASN | B | 183 | 6665 | 9657 | 7483 | 722 | 670 | 3123 | C |
| ATOM | 1737 | OD1 | ASN | B | 183 | 2.706 | −86.974 | −33.385 | 1.00 | 62.90 | | O |

TABLE 7-continued

| DMXAA-hSTING$^{G230I}$ complex | | | | | | | | | | | |
|---|---|---|---|---|---|---|---|---|---|---|---|
| ANISOU | 1737 | OD1 | ASN | B | 183 | 6804 | 9409 | 7687 | 825 | 663 | 2968 | O |
| ATOM | 1738 | ND2 | ASN | B | 183 | 0.760 | −85.907 | −33.750 | 1.00 | 61.78 | | N |
| ANISOU | 1738 | ND2 | ASN | B | 183 | 6474 | 9816 | 7184 | 845 | 671 | 3116 | N |
| ATOM | 1739 | C | ASN | B | 183 | 0.997 | −90.675 | −32.877 | 1.00 | 56.75 | | C |
| ANISOU | 1739 | C | ASN | B | 183 | 5919 | 8712 | 6933 | 143 | 650 | 3574 | C |
| ATOM | 1740 | O | ASN | B | 183 | 1.208 | −90.846 | −31.675 | 1.00 | 60.03 | | O |
| ANISOU | 1740 | O | ASN | B | 183 | 6281 | 9199 | 7328 | 298 | 619 | 3680 | O |
| ATOM | 1741 | N | GLN | B | 184 | 0.152 | −91.398 | −33.578 | 1.00 | 59.61 | | N |
| ANISOU | 1741 | N | GLN | B | 184 | 6272 | 9106 | 7271 | −159 | 654 | 3693 | N |
| ATOM | 1742 | CA | GLN | B | 184 | −0.516 | −92.551 | −33.047 | 1.00 | 68.99 | | C |
| ANISOU | 1742 | CA | GLN | B | 184 | 7382 | 10418 | 8413 | −332 | 618 | 3966 | C |
| ATOM | 1743 | CB | GLN | B | 184 | −1.605 | −93.021 | −33.993 | 1.00 | 82.55 | | C |
| ANISOU | 1743 | CB | GLN | B | 184 | 9066 | 12255 | 10044 | −651 | 611 | 4097 | C |
| ATOM | 1744 | CG | GLN | B | 184 | −2.840 | −92.143 | −34.049 | 1.00 | 94.76 | | C |
| ANISOU | 1744 | CG | GLN | B | 184 | 10450 | 14197 | 11358 | −582 | 602 | 4154 | C |
| ATOM | 1745 | CD | GLN | B | 184 | −3.620 | −92.416 | −35.311 | 1.00 | 111.99 | | C |
| ANISOU | 1745 | CD | GLN | B | 184 | 12664 | 16362 | 13526 | −875 | 574 | 4106 | C |
| ATOM | 1746 | OE1 | GLN | B | 184 | −3.508 | −93.492 | −35.884 | 1.00 | 118.95 | | O |
| ANISOU | 1746 | OE1 | GLN | B | 184 | 13670 | 16998 | 14529 | −1153 | 555 | 4105 | O |
| ATOM | 1747 | NE2 | GLN | B | 184 | −4.391 | −91.441 | −35.766 | 1.00 | 116.17 | | N |
| ANISOU | 1747 | NE2 | GLN | B | 184 | 13094 | 17136 | 13909 | −807 | 564 | 4056 | N |
| ATOM | 1748 | C | GLN | B | 184 | 0.387 | −93.705 | −32.714 | 1.00 | 59.54 | | C |
| ANISOU | 1748 | C | GLN | B | 184 | 6312 | 8866 | 7442 | −434 | 607 | 3956 | C |
| ATOM | 1749 | O | GLN | B | 184 | 0.184 | −94.354 | −31.723 | 1.00 | 59.88 | | O |
| ANISOU | 1749 | O | GLN | B | 184 | 6291 | 8988 | 7473 | −440 | 569 | 4156 | O |
| ATOM | 1750 | N | HIS | B | 185 | 1.423 | −93.911 | −33.512 | 1.00 | 73.31 | | N |
| ANISOU | 1750 | N | HIS | B | 185 | 7831 | 10418 | 9606 | −826 | 2814 | 1752 | N |
| ATOM | 1751 | C | HIS | B | 185 | 2.578 | −95.731 | −32.338 | 1.00 | 85.65 | | C |
| ANISOU | 1751 | C | HIS | B | 185 | 9529 | 11590 | 11424 | −909 | 2458 | 1760 | C |
| ATOM | 1752 | O | HIS | B | 185 | 2.990 | −95.013 | −31.467 | 1.00 | 69.94 | | O |
| ANISOU | 1752 | O | HIS | B | 185 | 7860 | 9395 | 9321 | −717 | 2189 | 1713 | O |
| ATOM | 1753 | CA | HIS | B | 185 | 2.090 | −95.186 | −33.646 | 1.00 | 76.96 | | C |
| ANISOU | 1753 | CA | HIS | B | 185 | 8123 | 10728 | 10391 | −1025 | 2719 | 1721 | C |
| ATOM | 1754 | CB | HIS | B | 185 | 3.269 | −95.078 | −34.603 | 1.00 | 68.76 | | C |
| ANISOU | 1754 | CB | HIS | B | 185 | 6809 | 9502 | 9814 | −1233 | 2580 | 1525 | C |
| ATOM | 1755 | CG | HIS | B | 185 | 3.783 | −96.399 | −35.083 | 1.00 | 76.80 | | C |
| ANISOU | 1755 | CG | HIS | B | 185 | 7554 | 10435 | 11193 | −1483 | 2578 | 1493 | C |
| ATOM | 1756 | ND1 | HIS | B | 185 | 4.688 | −97.151 | −34.375 | 1.00 | 73.05 | | N |
| ANISOU | 1756 | ND1 | HIS | B | 185 | 7172 | 9659 | 10925 | −1491 | 2282 | 1437 | N |
| ATOM | 1757 | CE1 | HIS | B | 185 | 4.944 | −98.260 | −35.036 | 1.00 | 66.97 | | C |
| ANISOU | 1757 | CE1 | HIS | B | 185 | 6101 | 8879 | 10465 | −1733 | 2360 | 1418 | C |
| ATOM | 1758 | NE2 | HIS | B | 185 | 4.240 | −98.256 | −36.146 | 1.00 | 72.19 | | N |
| ANISOU | 1758 | NE2 | HIS | B | 185 | 6484 | 9827 | 11118 | −1886 | 2698 | 1462 | N |
| ATOM | 1759 | CD2 | HIS | B | 185 | 3.504 | −97.105 | −36.198 | 1.00 | 79.32 | | C |
| ANISOU | 1759 | CD2 | HIS | B | 185 | 7511 | 10925 | 11699 | −1731 | 2834 | 1511 | C |
| ATOM | 1760 | N | TYR | B | 186 | 2.568 | −97.042 | −32.213 | 1.00 | 86.34 | | N |
| ANISOU | 1760 | N | TYR | B | 186 | 9525 | 11705 | 11576 | −1030 | 2538 | 1848 | N |
| ATOM | 1761 | CA | TYR | B | 186 | 2.961 | −97.669 | −30.972 | 1.00 | 89.54 | | C |
| ANISOU | 1761 | CA | TYR | B | 186 | 10224 | 11898 | 11899 | −938 | 2311 | 1906 | C |
| ATOM | 1762 | CB | TYR | B | 186 | 2.702 | −99.168 | −31.000 | 1.00 | 87.32 | | C |
| ANISOU | 1762 | CB | TYR | B | 186 | 9777 | 11695 | 11705 | −1107 | 2463 | 2011 | C |
| ATOM | 1763 | CG | TYR | B | 186 | 3.574 | −100.021 | −31.883 | 1.00 | 79.14 | | C |
| ANISOU | 1763 | CG | TYR | B | 186 | 8387 | 10502 | 11180 | −1367 | 2359 | 1889 | C |
| ATOM | 1764 | CD1 | TYR | B | 186 | 4.815 | −100.416 | −31.491 | 1.00 | 72.30 | | C |
| ANISOU | 1764 | CD1 | TYR | B | 186 | 7613 | 9272 | 10584 | −1382 | 1980 | 1792 | C |
| ATOM | 1765 | CE1 | TYR | B | 186 | 5.584 | −101.220 | −32.293 | 1.00 | 74.95 | | C |
| ANISOU | 1765 | CE1 | TYR | B | 186 | 7615 | 9457 | 11408 | −1620 | 1893 | 1667 | C |
| ATOM | 1766 | CZ | TYR | B | 186 | 5.108 | −101.650 | −33.485 | 1.00 | 73.04 | | C |
| ANISOU | 1766 | CZ | TYR | B | 186 | 6953 | 9432 | 11368 | −1856 | 2198 | 1646 | C |
| ATOM | 1767 | OH | TYR | B | 186 | 5.842 | −102.452 | −34.297 | 1.00 | 66.80 | | O |
| ANISOU | 1767 | OH | TYR | B | 186 | 5828 | 8488 | 11065 | −2104 | 2131 | 1516 | O |
| ATOM | 1768 | CE2 | TYR | B | 186 | 3.870 | −101.288 | −33.884 | 1.00 | 72.22 | | C |
| ANISOU | 1768 | CE2 | TYR | B | 186 | 6764 | 9689 | 10988 | −1847 | 2565 | 1750 | C |
| ATOM | 1769 | CD2 | TYR | B | 186 | 3.106 | −100.491 | −33.077 | 1.00 | 80.13 | | C |
| ANISOU | 1769 | CD2 | TYR | B | 186 | 8087 | 10835 | 11523 | −1601 | 2640 | 1868 | C |
| ATOM | 1770 | C | TYR | B | 186 | 4.382 | −97.411 | −30.588 | 1.00 | 96.22 | | C |
| ANISOU | 1770 | C | TYR | B | 186 | 11152 | 12355 | 13051 | −931 | 1883 | 1739 | C |
| ATOM | 1771 | O | TYR | B | 186 | 4.669 | −97.153 | −29.444 | 1.00 | 73.39 | | O |
| ANISOU | 1771 | O | TYR | B | 186 | 8635 | 9249 | 9998 | −743 | 1606 | 1744 | O |
| ATOM | 1772 | O | ASN | B | 187 | 8.035 | −95.640 | −30.296 | 1.00 | 113.96 | | O |
| ANISOU | 1772 | O | ASN | B | 187 | 13116 | 13919 | 16262 | −1049 | 1187 | 1129 | O |
| ATOM | 1773 | N | ASN | B | 187 | 5.267 | −97.474 | −31.568 | 1.00 | 101.84 | | N |
| ANISOU | 1773 | N | ASN | B | 187 | 11515 | 12968 | 14212 | −1141 | 1830 | 1581 | N |
| ATOM | 1774 | CA | ASN | B | 187 | 6.697 | −97.312 | −31.354 | 1.00 | 108.32 | | C |
| ANISOU | 1774 | CA | ASN | B | 187 | 12356 | 13410 | 15389 | −1160 | 1436 | 1398 | C |
| ATOM | 1775 | C | ASN | B | 187 | 7.021 | −95.908 | −30.920 | 1.00 | 108.58 | | C |
| ANISOU | 1775 | C | ASN | B | 187 | 12608 | 13355 | 15292 | −970 | 1277 | 1307 | C |
| ATOM | 1776 | CB | ASN | B | 187 | 7.482 | −97.724 | −32.587 | 1.00 | 105.16 | | C |

TABLE 7-continued

| | | | | | | | | | | | |
|---|---|---|---|---|---|---|---|---|---|---|---|
| DMXAA-hSTING$^{G230I}$ complex | | | | | | | | | | | |
| ANISOU | 1776 | CB | ASN | B | 187 | 11515 | 12922 | 15517 | −1449 | 1449 | 1239 | C |
| ATOM | 1777 | CG | ASN | B | 187 | 8.374 | −98.917 | −32.329 | 1.00 | 105.41 | | C |
| ANISOU | 1777 | CG | ASN | B | 187 | 11532 | 12592 | 15926 | −1522 | 1102 | 1132 | C |
| ATOM | 1778 | OD1 | ASN | B | 187 | 8.919 | −99.059 | −31.244 | 1.00 | 107.70 | | O |
| ANISOU | 1778 | OD1 | ASN | B | 187 | 12145 | 12625 | 16153 | −1344 | 761 | 1111 | O |
| ATOM | 1779 | ND2 | ASN | B | 187 | 8.543 | −99.776 | −33.335 | 1.00 | 102.24 | | N |
| ANISOU | 1779 | ND2 | ASN | B | 187 | 10757 | 12164 | 15927 | −1787 | 1183 | 1060 | N |
| ATOM | 1780 | O | ASN | B | 188 | 4.913 | −92.779 | −29.418 | 1.00 | 107.10 | | O |
| ANISOU | 1780 | O | ASN | B | 188 | 12717 | 13368 | 14609 | −625 | 1374 | 1249 | O |
| ATOM | 1781 | N | ASN | B | 188 | 6.137 | −95.003 | −31.270 | 1.00 | 106.51 | | N |
| ANISOU | 1781 | N | ASN | B | 188 | 12732 | 13163 | 14575 | −723 | 1273 | 1435 | N |
| ATOM | 1782 | CA | ASN | B | 188 | 6.395 | −93.613 | −31.063 | 1.00 | 108.75 | | C |
| ANISOU | 1782 | CA | ASN | B | 188 | 13360 | 13280 | 14681 | −488 | 1021 | 1375 | C |
| ATOM | 1783 | C | ASN | B | 188 | 6.018 | −93.219 | −29.684 | 1.00 | 111.68 | | C |
| ANISOU | 1783 | C | ASN | B | 188 | 13640 | 13759 | 15034 | −450 | 1121 | 1280 | C |
| ATOM | 1784 | CB | ASN | B | 188 | 5.613 | −92.794 | −32.056 | 1.00 | 132.65 | | C |
| ANISOU | 1784 | CB | ASN | B | 188 | 16555 | 15887 | 17959 | −453 | 556 | 1260 | C |
| ATOM | 1785 | CG | ASN | B | 188 | 6.375 | −92.563 | −33.324 | 1.00 | 131.08 | | C |
| ANISOU | 1785 | CG | ASN | B | 188 | 15988 | 15475 | 18340 | −682 | 407 | 1060 | C |
| ATOM | 1786 | OD1 | ASN | B | 188 | 7.111 | −91.620 | −33.412 | 1.00 | 129.45 | | O |
| ANISOU | 1786 | OD1 | ASN | B | 188 | 15749 | 15035 | 18401 | −765 | 182 | 1022 | O |
| ATOM | 1787 | ND2 | ASN | B | 188 | 6.201 | −93.422 | −34.304 | 1.00 | 131.47 | | N |
| ANISOU | 1787 | ND2 | ASN | B | 188 | 15765 | 15597 | 18590 | −791 | 534 | 930 | N |
| ATOM | 1788 | O | LEU | B | 189 | 6.333 | −90.882 | −27.862 | 1.00 | 132.56 | | O |
| ANISOU | 1788 | O | LEU | B | 189 | 17206 | 16594 | 16568 | 227 | 1145 | 1452 | O |
| ATOM | 1789 | N | LEU | B | 189 | 7.025 | −93.249 | −28.837 | 1.00 | 120.16 | | N |
| ANISOU | 1789 | N | LEU | B | 189 | 15034 | 14733 | 15888 | −222 | 945 | 1246 | N |
| ATOM | 1790 | CA | LEU | B | 189 | 6.879 | −93.144 | −27.412 | 1.00 | 123.95 | | C |
| ANISOU | 1790 | CA | LEU | B | 189 | 15968 | 15037 | 16091 | 3 | 693 | 1310 | C |
| ATOM | 1791 | C | LEU | B | 189 | 6.162 | −91.852 | −27.137 | 1.00 | 130.79 | | C |
| ANISOU | 1791 | C | LEU | B | 189 | 17116 | 16137 | 16440 | 217 | 901 | 1451 | C |
| ATOM | 1792 | CB | LEU | B | 189 | 8.261 | −93.088 | −26.777 | 1.00 | 115.83 | | C |
| ANISOU | 1792 | CB | LEU | B | 189 | 15091 | 13633 | 15287 | 85 | 257 | 1127 | C |
| ATOM | 1793 | CG | LEU | B | 189 | 9.465 | −92.799 | −27.677 | 1.00 | 104.58 | | C |
| ANISOU | 1793 | CG | LEU | B | 189 | 13395 | 11923 | 14417 | −116 | 11 | 955 | C |
| ATOM | 1794 | CD1 | LEU | B | 189 | 9.234 | −91.662 | −28.654 | 1.00 | 98.03 | | C |
| ANISOU | 1794 | CD1 | LEU | B | 189 | 12193 | 11097 | 13956 | −284 | 89 | 772 | C |
| ATOM | 1795 | CD2 | LEU | B | 189 | 10.704 | −92.560 | −26.835 | 1.00 | 100.47 | | C |
| ANISOU | 1795 | CD2 | LEU | B | 189 | 13155 | 11001 | 14018 | −3 | −467 | 870 | C |
| ATOM | 1796 | N | LEU | B | 190 | 5.364 | −91.839 | −26.081 | 1.00 | 132.03 | | N |
| ANISOU | 1796 | N | LEU | B | 190 | 17671 | 16230 | 16266 | 384 | 809 | 1567 | N |
| ATOM | 1797 | CA | LEU | B | 190 | 4.355 | −90.823 | −25.900 | 1.00 | 133.05 | | C |
| ANISOU | 1797 | CA | LEU | B | 190 | 18111 | 16521 | 15919 | 606 | 959 | 1667 | C |
| ATOM | 1798 | CB | LEU | B | 190 | 3.666 | −90.980 | −24.560 | 1.00 | 129.40 | | C |
| ANISOU | 1798 | CB | LEU | B | 190 | 18091 | 15972 | 15104 | 747 | 876 | 1800 | C |
| ATOM | 1799 | CG | LEU | B | 190 | 3.474 | −92.408 | −24.081 | 1.00 | 126.80 | | C |
| ANISOU | 1799 | CG | LEU | B | 190 | 17929 | 15941 | 14307 | 857 | 1246 | 1969 | C |
| ATOM | 1800 | CD1 | LEU | B | 190 | 4.498 | −92.755 | −23.006 | 1.00 | 122.80 | | C |
| ANISOU | 1800 | CD1 | LEU | B | 190 | 17113 | 15761 | 13786 | 825 | 1598 | 1968 | C |
| ATOM | 1801 | CD2 | LEU | B | 190 | 2.042 | −92.603 | −23.587 | 1.00 | 124.67 | | C |
| ANISOU | 1801 | CD2 | LEU | B | 190 | 17676 | 15748 | 13944 | 757 | 1406 | 2115 | C |
| ATOM | 1802 | C | LEU | B | 190 | 5.044 | −89.489 | −25.941 | 1.00 | 139.48 | | C |
| ANISOU | 1802 | C | LEU | B | 190 | 19043 | 17179 | 16774 | 740 | 731 | 1520 | C |
| ATOM | 1803 | O | LEU | B | 190 | 4.454 | −88.485 | −26.336 | 1.00 | 141.79 | | O |
| ANISOU | 1803 | O | LEU | B | 190 | 19434 | 17632 | 16807 | 880 | 882 | 1539 | O |
| ATOM | 1804 | N | ARG | B | 191 | 6.310 | −89.477 | −25.562 | 1.00 | 137.25 | | N |
| ANISOU | 1804 | N | ARG | B | 191 | 18728 | 16575 | 16844 | 688 | 368 | 1364 | N |
| ATOM | 1805 | CA | ARG | B | 191 | 7.045 | −88.249 | −25.599 | 1.00 | 131.45 | | C |
| ANISOU | 1805 | CA | ARG | B | 191 | 18049 | 15658 | 16238 | 778 | 131 | 1196 | C |
| ATOM | 1806 | CB | ARG | B | 191 | 8.484 | −88.488 | −25.176 | 1.00 | 129.64 | | C |
| ANISOU | 1806 | CB | ARG | B | 191 | 17870 | 15025 | 16363 | 746 | −318 | 1046 | C |
| ATOM | 1807 | CG | ARG | B | 191 | 8.663 | −88.557 | −23.677 | 1.00 | 133.40 | | C |
| ANISOU | 1807 | CG | ARG | B | 191 | 18845 | 15262 | 16580 | 961 | −640 | 1085 | C |
| ATOM | 1808 | CD | ARG | B | 191 | 7.557 | −89.380 | −23.032 | 1.00 | 135.60 | | C |
| ANISOU | 1808 | CD | ARG | B | 191 | 19362 | 15666 | 16494 | 1003 | −489 | 1297 | C |
| ATOM | 1809 | NE | ARG | B | 191 | 7.279 | −88.980 | −21.661 | 1.00 | 135.46 | | N |
| ANISOU | 1809 | NE | ARG | B | 191 | 19859 | 15592 | 16020 | 1249 | −590 | 1378 | N |
| ATOM | 1810 | CZ | ARG | B | 191 | 6.552 | −89.697 | −20.822 | 1.00 | 131.20 | | C |
| ANISOU | 1810 | CZ | ARG | B | 191 | 19611 | 15154 | 15083 | 1321 | −446 | 1556 | C |
| ATOM | 1811 | NH1 | ARG | B | 191 | 6.343 | −89.261 | −19.587 | 1.00 | 133.13 | | N |
| ANISOU | 1811 | NH1 | ARG | B | 191 | 20334 | 15328 | 14921 | 1536 | −539 | 1612 | N |
| ATOM | 1812 | NH2 | ARG | B | 191 | 6.041 | −90.849 | −21.222 | 1.00 | 123.52 | | N |
| ANISOU | 1812 | NH2 | ARG | B | 191 | 18461 | 14352 | 14120 | 1172 | −199 | 1674 | N |
| ATOM | 1813 | C | ARG | B | 191 | 7.010 | −87.715 | −27.000 | 1.00 | 122.20 | | C |
| ANISOU | 1813 | C | ARG | B | 191 | 16487 | 14652 | 15291 | 643 | 341 | 1099 | C |
| ATOM | 1814 | O | ARG | B | 191 | 7.106 | −88.454 | −27.969 | 1.00 | 118.48 | | O |
| ANISOU | 1814 | O | ARG | B | 191 | 15643 | 14297 | 15075 | 418 | 525 | 1093 | O |
| ATOM | 1815 | N | GLY | B | 192 | 6.829 | −86.411 | −27.089 | 1.00 | 116.92 | | N |

TABLE 7-continued

| DMXAA-hSTING$^{G230I}$ complex | | | | | | | | | | | |
|---|---|---|---|---|---|---|---|---|---|---|---|
| ANISOU | 1815 | N | GLY | B | 192 | 15922 | 13990 | 14513 | 779 | 313 | 1025 | N |
| ATOM | 1816 | CA | GLY | B | 192 | 6.946 | −85.727 | −28.351 | 1.00 | 114.99 | | C |
| ANISOU | 1816 | CA | GLY | B | 192 | 15367 | 13833 | 14491 | 665 | 440 | 906 | C |
| ATOM | 1817 | C | GLY | B | 192 | 5.923 | −85.769 | −29.453 | 1.00 | 110.83 | | C |
| ANISOU | 1817 | C | GLY | B | 192 | 14533 | 13662 | 13915 | 524 | 857 | 1004 | C |
| ATOM | 1818 | O | GLY | B | 192 | 6.217 | −86.221 | −30.557 | 1.00 | 111.63 | | O |
| ANISOU | 1818 | O | GLY | B | 192 | 14285 | 13798 | 14330 | 282 | 960 | 965 | O |
| ATOM | 1819 | N | ALA | B | 193 | 4.705 | −85.344 | −29.145 | 1.00 | 102.03 | | N |
| ANISOU | 1819 | N | ALA | B | 193 | 13548 | 12805 | 12415 | 673 | 1094 | 1124 | N |
| ATOM | 1820 | CA | ALA | B | 193 | 3.734 | −85.141 | −30.195 | 1.00 | 96.07 | | C |
| ANISOU | 1820 | CA | ALA | B | 193 | 12512 | 12381 | 11607 | 565 | 1469 | 1202 | C |
| ATOM | 1821 | CB | ALA | B | 193 | 2.379 | −84.863 | −29.592 | 1.00 | 73.06 | | C |
| ANISOU | 1821 | CB | ALA | B | 193 | 9795 | 9725 | 8240 | 746 | 1711 | 1375 | C |
| ATOM | 1822 | C | ALA | B | 193 | 4.118 | −84.024 | −31.150 | 1.00 | 89.86 | | C |
| ANISOU | 1822 | C | ALA | B | 193 | 11563 | 11602 | 10978 | 518 | 1482 | 1068 | C |
| ATOM | 1823 | O | ALA | B | 193 | 4.195 | −82.886 | −30.754 | 1.00 | 92.05 | | O |
| ANISOU | 1823 | O | ALA | B | 193 | 12054 | 11837 | 11085 | 704 | 1392 | 1025 | O |
| ATOM | 1824 | N | VAL | B | 194 | 4.332 | −84.369 | −32.412 | 1.00 | 75.71 | | N |
| ANISOU | 1824 | N | VAL | B | 194 | 9404 | 9856 | 9505 | 265 | 1596 | 999 | N |
| ATOM | 1825 | CA | VAL | B | 194 | 4.730 | −83.404 | −33.410 | 1.00 | 69.96 | | C |
| ANISOU | 1825 | CA | VAL | B | 194 | 8530 | 9098 | 8952 | 189 | 1596 | 857 | C |
| ATOM | 1826 | CB | VAL | B | 194 | 5.381 | −84.066 | −34.659 | 1.00 | 79.58 | | C |
| ANISOU | 1826 | CB | VAL | B | 194 | 9371 | 10256 | 10611 | −130 | 1642 | 742 | C |
| ATOM | 1827 | CG1 | VAL | B | 194 | 6.018 | −85.383 | −34.302 | 1.00 | 77.25 | | C |
| ANISOU | 1827 | CG1 | VAL | B | 194 | 9006 | 9803 | 10543 | −247 | 1517 | 738 | C |
| ATOM | 1828 | CG2 | VAL | B | 194 | 4.423 | −84.256 | −35.809 | 1.00 | 64.73 | | C |
| ANISOU | 1828 | CG2 | VAL | B | 194 | 7221 | 8685 | 8689 | −286 | 1990 | 829 | C |
| ATOM | 1829 | C | VAL | B | 194 | 3.598 | −82.463 | −33.758 | 1.00 | 73.60 | | C |
| ANISOU | 1829 | C | VAL | B | 194 | 8998 | 9847 | 9120 | 288 | 1851 | 946 | C |
| ATOM | 1830 | O | VAL | B | 194 | 2.460 | −82.850 | −33.750 | 1.00 | 76.48 | | O |
| ANISOU | 1830 | O | VAL | B | 194 | 9314 | 10481 | 9265 | 306 | 2108 | 1105 | O |
| ATOM | 1831 | N | SER | B | 195 | 3.927 | −81.228 | −34.077 | 1.00 | 67.11 | | N |
| ANISOU | 1831 | N | SER | B | 195 | 8238 | 8956 | 8303 | 357 | 1772 | 837 | N |
| ATOM | 1832 | CA | SER | B | 195 | 2.920 | −80.254 | −34.464 | 1.00 | 68.83 | | C |
| ANISOU | 1832 | CA | SER | B | 195 | 8478 | 9410 | 8263 | 463 | 1971 | 903 | C |
| ATOM | 1833 | CB | SER | B | 195 | 3.498 | −78.845 | −34.429 | 1.00 | 69.50 | | C |
| ANISOU | 1833 | CB | SER | B | 195 | 8724 | 9339 | 8342 | 587 | 1796 | 770 | C |
| ATOM | 1834 | OG | SER | B | 195 | 3.980 | −78.570 | −33.132 | 1.00 | 75.38 | | O |
| ANISOU | 1834 | OG | SER | B | 195 | 9792 | 9884 | 8964 | 802 | 1543 | 745 | O |
| ATOM | 1835 | C | SER | B | 195 | 2.359 | −80.582 | −35.835 | 1.00 | 67.58 | | C |
| ANISOU | 1835 | C | SER | B | 195 | 7980 | 9472 | 8225 | 233 | 2242 | 936 | C |
| ATOM | 1836 | O | SER | B | 195 | 2.993 | −81.280 | −36.625 | 1.00 | 69.16 | | O |
| ANISOU | 1836 | O | SER | B | 195 | 7932 | 9597 | 8750 | −22 | 2247 | 859 | O |
| ATOM | 1837 | N | GLN | B | 196 | 1.173 | −80.061 | −36.119 | 1.00 | 73.42 | | N |
| ANISOU | 1837 | N | GLN | B | 196 | 8712 | 10477 | 8709 | 323 | 2462 | 1044 | N |
| ATOM | 1838 | CA | GLN | B | 196 | 0.407 | −80.502 | −37.276 | 1.00 | 79.39 | | C |
| ANISOU | 1838 | CA | GLN | B | 196 | 9169 | 11476 | 9518 | 131 | 2733 | 1114 | C |
| ATOM | 1839 | CB | GLN | B | 196 | −1.081 | −80.536 | −36.925 | 1.00 | 80.62 | | C |
| ANISOU | 1839 | CB | GLN | B | 196 | 9371 | 11924 | 9337 | 289 | 2964 | 1292 | C |
| ATOM | 1840 | CG | GLN | B | 196 | −1.388 | −81.324 | −35.658 | 1.00 | 92.59 | | C |
| ANISOU | 1840 | CG | GLN | B | 196 | 11064 | 13445 | 10672 | 427 | 2957 | 1397 | C |
| ATOM | 1841 | CD | GLN | B | 196 | −1.864 | −82.739 | −35.945 | 1.00 | 96.38 | | C |
| ANISOU | 1841 | CD | GLN | B | 196 | 11319 | 14075 | 11228 | 251 | 3151 | 1500 | C |
| ATOM | 1842 | OE1 | GLN | B | 196 | −2.392 | −83.019 | −37.023 | 1.00 | 95.20 | | O |
| ANISOU | 1842 | OE1 | GLN | B | 196 | 10893 | 14110 | 11168 | 81 | 3353 | 1533 | O |
| ATOM | 1843 | NE2 | GLN | B | 196 | −1.680 | −83.638 | −34.980 | 1.00 | 96.65 | | N |
| ANISOU | 1843 | NE2 | GLN | B | 196 | 11480 | 14024 | 11220 | 290 | 3085 | 1552 | N |
| ATOM | 1844 | C | GLN | B | 196 | 0.633 | −79.679 | −38.550 | 1.00 | 82.00 | | C |
| ANISOU | 1844 | C | GLN | B | 196 | 9349 | 11809 | 9999 | −13 | 2770 | 1011 | C |
| ATOM | 1845 | O | GLN | B | 196 | 0.001 | −79.940 | −39.570 | 1.00 | 85.40 | | O |
| ANISOU | 1845 | O | GLN | B | 196 | 9550 | 12434 | 10465 | −174 | 2981 | 1063 | O |
| ATOM | 1846 | N | ARG | B | 197 | 1.525 | −78.693 | −38.496 | 1.00 | 70.77 | | N |
| ANISOU | 1846 | N | ARG | B | 197 | 8064 | 10167 | 8659 | 41 | 2565 | 865 | N |
| ATOM | 1847 | CA | ARG | B | 197 | 1.804 | −77.872 | −39.672 | 1.00 | 65.26 | | C |
| ANISOU | 1847 | CA | ARG | B | 197 | 7256 | 9444 | 8095 | −100 | 2592 | 758 | C |
| ATOM | 1848 | CB | ARG | B | 197 | 1.687 | −76.378 | −39.353 | 1.00 | 62.00 | | C |
| ANISOU | 1848 | CB | ARG | B | 197 | 7083 | 8995 | 7477 | 132 | 2495 | 722 | C |
| ATOM | 1849 | CG | ARG | B | 197 | 1.138 | −76.053 | −37.982 | 1.00 | 67.41 | | C |
| ANISOU | 1849 | CG | ARG | B | 197 | 8047 | 9721 | 7844 | 453 | 2433 | 817 | C |
| ATOM | 1850 | CD | ARG | B | 197 | −0.095 | −75.161 | −38.082 | 1.00 | 71.93 | | C |
| ANISOU | 1850 | CD | ARG | B | 197 | 8688 | 10526 | 8116 | 629 | 2585 | 920 | C |
| ATOM | 1851 | NE | ARG | B | 197 | 0.103 | −74.009 | −38.956 | 1.00 | 65.71 | | N |
| ANISOU | 1851 | NE | ARG | B | 197 | 7890 | 9699 | 7377 | 591 | 2559 | 826 | N |
| ATOM | 1852 | CZ | ARG | B | 197 | −0.814 | −73.070 | −39.175 | 1.00 | 76.21 | | C |
| ANISOU | 1852 | CZ | ARG | B | 197 | 9278 | 11189 | 8490 | 731 | 2653 | 886 | C |
| ATOM | 1853 | NH1 | ARG | B | 197 | −0.556 | −72.052 | −39.991 | 1.00 | 79.34 | | N |
| ANISOU | 1853 | NH1 | ARG | B | 197 | 9676 | 11526 | 8941 | 681 | 2613 | 796 | N |
| ATOM | 1854 | NH2 | ARG | B | 197 | −1.993 | −73.148 | −38.573 | 1.00 | 79.11 | | N |

TABLE 7-continued

DMXAA-hSTING$^{G230I}$ complex

| | | | | | | | | | | | | |
|---|---|---|---|---|---|---|---|---|---|---|---|---|
| ANISOU | 1854 | NH2 | ARG | B | 197 | 9701 | 11766 | 8589 | 918 | 2788 | 1031 | N |
| ATOM | 1855 | C | ARG | B | 197 | 3.182 | −78.158 | −40.259 | 1.00 | 70.72 | | C |
| ANISOU | 1855 | C | ARG | B | 197 | 7815 | 9873 | 9183 | −347 | 2463 | 571 | C |
| ATOM | 1856 | O | ARG | B | 197 | 4.055 | −78.713 | −39.589 | 1.00 | 71.06 | | O |
| ANISOU | 1856 | O | ARG | B | 197 | 7902 | 9707 | 9391 | −350 | 2284 | 501 | O |
| ATOM | 1857 | N | LEU | B | 198 | 3.369 | −77.769 | −41.516 | 1.00 | 59.90 | | N |
| ANISOU | 1857 | N | LEU | B | 198 | 8054 | 8945 | 5763 | −704 | 156 | 1396 | N |
| ATOM | 1858 | CA | LEU | B | 198 | 4.670 | −77.840 | −42.169 | 1.00 | 66.08 | | C |
| ANISOU | 1858 | CA | LEU | B | 198 | 8764 | 9710 | 6634 | −607 | 66 | 1263 | C |
| ATOM | 1859 | CB | LEU | B | 198 | 4.522 | −78.011 | −43.678 | 1.00 | 40.58 | | C |
| ANISOU | 1859 | CB | LEU | B | 198 | 5472 | 6400 | 3547 | −603 | 108 | 1100 | C |
| ATOM | 1860 | CG | LEU | B | 198 | 5.517 | −78.918 | −44.409 | 1.00 | 54.88 | | C |
| ANISOU | 1860 | CG | LEU | B | 198 | 7251 | 8063 | 5540 | −502 | 39 | 1021 | C |
| ATOM | 1861 | CD1 | LEU | B | 198 | 5.577 | −78.543 | −45.884 | 1.00 | 48.83 | | C |
| ANISOU | 1861 | CD1 | LEU | B | 198 | 6444 | 7286 | 4824 | −500 | 109 | 816 | C |
| ATOM | 1862 | CD2 | LEU | B | 198 | 6.913 | −78.891 | −43.790 | 1.00 | 45.42 | | C |
| ANISOU | 1862 | CD2 | LEU | B | 198 | 6001 | 6902 | 4354 | −390 | −57 | 1055 | C |
| ATOM | 1863 | C | LEU | B | 198 | 5.402 | −76.538 | −41.906 | 1.00 | 62.97 | | C |
| ANISOU | 1863 | C | LEU | B | 198 | 8343 | 9493 | 6090 | −595 | 73 | 1176 | C |
| ATOM | 1864 | O | LEU | B | 198 | 4.926 | −75.466 | −42.283 | 1.00 | 57.55 | | O |
| ANISOU | 1864 | O | LEU | B | 198 | 7645 | 8908 | 5315 | −644 | 189 | 1084 | O |
| ATOM | 1865 | N | TYR | B | 199 | 6.562 | −76.621 | −41.271 | 1.00 | 58.59 | | N |
| ANISOU | 1865 | N | TYR | B | 199 | 7775 | 8972 | 5515 | −534 | −55 | 1213 | N |
| ATOM | 1866 | CA | TYR | B | 199 | 7.344 | −75.427 | −41.028 | 1.00 | 56.04 | | C |
| ANISOU | 1866 | CA | TYR | B | 199 | 7422 | 8807 | 5062 | −543 | −71 | 1125 | C |
| ATOM | 1867 | CB | TYR | B | 199 | 7.931 | −75.430 | −39.626 | 1.00 | 68.63 | | C |
| ANISOU | 1867 | CB | TYR | B | 199 | 9089 | 10476 | 6510 | −560 | −209 | 1265 | C |
| ATOM | 1868 | CG | TYR | B | 199 | 6.870 | −75.257 | −38.573 | 1.00 | 78.54 | | C |
| ANISOU | 1868 | CG | TYR | B | 199 | 10516 | 11765 | 7560 | −653 | −132 | 1390 | C |
| ATOM | 1869 | CD1 | TYR | B | 199 | 6.082 | −76.333 | −38.170 | 1.00 | 79.03 | | C |
| ANISOU | 1869 | CD1 | TYR | B | 199 | 10649 | 11710 | 7668 | −654 | −122 | 1556 | C |
| ATOM | 1870 | CE1 | TYR | B | 199 | 5.100 | −76.179 | −37.216 | 1.00 | 80.21 | | C |
| ANISOU | 1870 | CE1 | TYR | B | 199 | 10952 | 11882 | 7640 | −733 | −22 | 1682 | C |
| ATOM | 1871 | CZ | TYR | B | 199 | 4.890 | −74.933 | −36.655 | 1.00 | 83.73 | | C |
| ANISOU | 1871 | CZ | TYR | B | 199 | 11501 | 12461 | 7851 | −808 | 80 | 1632 | C |
| ATOM | 1872 | OH | TYR | B | 199 | 3.911 | −74.780 | −35.702 | 1.00 | 91.29 | | O |
| ANISOU | 1872 | OH | TYR | B | 199 | 12627 | 13425 | 8633 | −876 | 216 | 1759 | O |
| ATOM | 1873 | CE2 | TYR | B | 199 | 5.653 | −73.845 | −37.045 | 1.00 | 80.33 | | C |
| ANISOU | 1873 | CE2 | TYR | B | 199 | 11015 | 12139 | 7368 | −815 | 67 | 1458 | C |
| ATOM | 1874 | CD2 | TYR | B | 199 | 6.633 | −74.012 | −38.003 | 1.00 | 79.60 | | C |
| ANISOU | 1874 | CD2 | TYR | B | 199 | 10750 | 12031 | 7462 | −740 | −43 | 1343 | C |
| ATOM | 1875 | C | TYR | B | 199 | 8.408 | −75.269 | −42.094 | 1.00 | 49.32 | | C |
| ANISOU | 1875 | C | TYR | B | 199 | 6428 | 7946 | 4364 | −460 | −94 | 969 | C |
| ATOM | 1876 | O | TYR | B | 199 | 9.326 | −76.075 | −42.204 | 1.00 | 41.86 | | O |
| ANISOU | 1876 | O | TYR | B | 199 | 5407 | 6920 | 3577 | −366 | −202 | 1003 | O |
| ATOM | 1877 | N | ILE | B | 200 | 8.245 | −74.232 | −42.901 | 1.00 | 39.04 | | N |
| ANISOU | 1877 | N | ILE | B | 200 | 5091 | 6717 | 3026 | −488 | 27 | 811 | N |
| ATOM | 1878 | CA | ILE | B | 200 | 9.087 | −74.019 | −44.055 | 1.00 | 50.96 | | C |
| ANISOU | 1878 | CA | ILE | B | 200 | 6480 | 8209 | 4673 | −415 | 53 | 655 | C |
| ATOM | 1879 | CB | ILE | B | 200 | 8.240 | −73.709 | −45.275 | 1.00 | 45.61 | | C |
| ANISOU | 1879 | CB | ILE | B | 200 | 5809 | 7504 | 4015 | −439 | 201 | 533 | C |
| ATOM | 1880 | CG1 | ILE | B | 200 | 7.323 | −74.891 | −45.562 | 1.00 | 47.06 | | C |
| ANISOU | 1880 | CG1 | ILE | B | 200 | 6052 | 7542 | 4286 | −451 | 198 | 601 | C |
| ATOM | 1881 | CD1 | ILE | B | 200 | 6.407 | −74.669 | −46.736 | 1.00 | 45.30 | | C |
| ANISOU | 1881 | CD1 | ILE | B | 200 | 5840 | 7299 | 4071 | −499 | 305 | 504 | C |
| ATOM | 1882 | CG2 | ILE | B | 200 | 9.124 | −73.414 | −46.475 | 1.00 | 36.49 | | C |
| ANISOU | 1882 | CG2 | ILE | B | 200 | 4558 | 6335 | 2972 | −365 | 251 | 369 | C |
| ATOM | 1883 | C | ILE | B | 200 | 10.073 | −72.896 | −43.788 | 1.00 | 57.28 | | C |
| ANISOU | 1883 | C | ILE | B | 200 | 7215 | 9149 | 5401 | −427 | 27 | 583 | C |
| ATOM | 1884 | O | ILE | B | 200 | 9.686 | −71.747 | −43.573 | 1.00 | 48.74 | | O |
| ANISOU | 1884 | O | ILE | B | 200 | 6184 | 8177 | 4157 | −509 | 113 | 529 | O |
| ATOM | 1885 | N | LEU | B | 201 | 11.351 | −73.247 | −43.784 | 1.00 | 39.60 | | N |
| ANISOU | 1885 | N | LEU | B | 201 | 4857 | 6894 | 3296 | −347 | −87 | 591 | N |
| ATOM | 1886 | CA | LEU | B | 201 | 12.382 | −72.276 | −43.481 | 1.00 | 58.20 | | C |
| ANISOU | 1886 | CA | LEU | B | 201 | 7126 | 9378 | 5611 | −373 | −144 | 540 | C |
| ATOM | 1887 | CB | LEU | B | 201 | 13.637 | −72.957 | −42.942 | 1.00 | 54.35 | | C |
| ANISOU | 1887 | CB | LEU | B | 201 | 6512 | 8879 | 5260 | −300 | −339 | 656 | C |
| ATOM | 1888 | CG | LEU | B | 201 | 13.450 | −73.647 | −41.594 | 1.00 | 57.73 | | C |
| ANISOU | 1888 | CG | LEU | B | 201 | 7034 | 9315 | 5585 | −332 | −509 | 859 | C |
| ATOM | 1889 | CD1 | LEU | B | 201 | 14.664 | −74.489 | −41.268 | 1.00 | 46.05 | | C |
| ANISOU | 1889 | CD1 | LEU | B | 201 | 5401 | 7800 | 4295 | −228 | −698 | 997 | C |
| ATOM | 1890 | CD2 | LEU | B | 201 | 13.226 | −72.613 | −40.509 | 1.00 | 64.44 | | C |
| ANISOU | 1890 | CD2 | LEU | B | 201 | 8011 | 10323 | 6151 | −484 | −558 | 871 | C |
| ATOM | 1891 | C | LEU | B | 201 | 12.697 | −71.443 | −44.714 | 1.00 | 50.57 | | C |
| ANISOU | 1891 | C | LEU | B | 201 | 6071 | 8428 | 4714 | −350 | 4 | 355 | C |
| ATOM | 1892 | O | LEU | B | 201 | 12.817 | −71.967 | −45.821 | 1.00 | 38.34 | | O |
| ANISOU | 1892 | O | LEU | B | 201 | 4466 | 6772 | 3328 | −257 | 84 | 285 | O |
| ATOM | 1893 | N | LEU | B | 202 | 12.809 | −70.137 | −44.510 | 1.00 | 52.60 | | N |

TABLE 7-continued

DMXAA-hSTING$^{G230I}$ complex

| | | | | | | | | | | | | |
|---|---|---|---|---|---|---|---|---|---|---|---|---|
| ANISOU | 1893 | N | LEU | B | 202 | 6341 | 8810 | 4836 | −439 | 53 | 275 | N |
| ATOM | 1894 | CA | LEU | B | 202 | 13.062 | −69.214 | −45.600 | 1.00 | 51.98 | | C |
| ANISOU | 1894 | CA | LEU | B | 202 | 6192 | 8755 | 4802 | −428 | 207 | 112 | C |
| ATOM | 1895 | CB | LEU | B | 202 | 11.796 | −68.437 | −45.944 | 1.00 | 52.06 | | C |
| ANISOU | 1895 | CB | LEU | B | 202 | 6328 | 8791 | 4661 | −492 | 383 | 52 | C |
| ATOM | 1896 | CG | LEU | B | 202 | 10.672 | −69.242 | −46.577 | 1.00 | 45.95 | | C |
| ANISOU | 1896 | CG | LEU | B | 202 | 5620 | 7922 | 3918 | −457 | 448 | 80 | C |
| ATOM | 1897 | CD1 | LEU | B | 202 | 9.365 | −68.509 | −46.408 | 1.00 | 51.03 | | C |
| ANISOU | 1897 | CD1 | LEU | B | 202 | 6375 | 8615 | 4400 | −538 | 573 | 96 | C |
| ATOM | 1898 | CD2 | LEU | B | 202 | 10.965 | −69.457 | −48.043 | 1.00 | 45.46 | | C |
| ANISOU | 1898 | CD2 | LEU | B | 202 | 5487 | 7786 | 4000 | −373 | 537 | −35 | C |
| ATOM | 1899 | C | LEU | B | 202 | 14.173 | −68.245 | −45.249 | 1.00 | 44.28 | | C |
| ANISOU | 1899 | C | LEU | B | 202 | 5121 | 7885 | 3819 | −481 | 153 | 62 | C |
| ATOM | 1900 | O | LEU | B | 202 | 13.905 | −67.084 | −44.915 | 1.00 | 43.72 | | O |
| ANISOU | 1900 | O | LEU | B | 202 | 5128 | 7900 | 3584 | −590 | 221 | 1 | O |
| ATOM | 1901 | N | PRO | B | 203 | 15.423 | −68.725 | −45.304 | 1.00 | 44.72 | | N |
| ANISOU | 1901 | N | PRO | B | 203 | 5002 | 7924 | 4066 | −410 | 35 | 97 | N |
| ATOM | 1902 | CA | PRO | B | 203 | 16.555 | −67.809 | −45.150 | 1.00 | 45.86 | | C |
| ANISOU | 1902 | CA | PRO | B | 203 | 5011 | 8163 | 4250 | −466 | −16 | 46 | C |
| ATOM | 1903 | CB | PRO | B | 203 | 17.771 | −68.736 | −45.162 | 1.00 | 41.96 | | C |
| ANISOU | 1903 | CB | PRO | B | 203 | 4306 | 7626 | 4011 | −354 | −161 | 146 | C |
| ATOM | 1904 | CG | PRO | B | 203 | 17.289 | −69.992 | −45.866 | 1.00 | 47.92 | | C |
| ANISOU | 1904 | CG | PRO | B | 203 | 5091 | 8223 | 4893 | −206 | −83 | 176 | C |
| ATOM | 1905 | CD | PRO | B | 203 | 15.853 | −70.123 | −45.458 | 1.00 | 42.28 | | C |
| ANISOU | 1905 | CD | PRO | B | 203 | 4605 | 7502 | 3960 | −276 | −53 | 198 | C |
| ATOM | 1906 | C | PRO | B | 203 | 16.616 | −66.851 | −46.334 | 1.00 | 46.13 | | C |
| ANISOU | 1906 | C | PRO | B | 203 | 5004 | 8195 | 4328 | −456 | 205 | −122 | C |
| ATOM | 1907 | O | PRO | B | 203 | 16.713 | −67.282 | −47.486 | 1.00 | 39.94 | | O |
| ANISOU | 1907 | O | PRO | B | 203 | 4158 | 7319 | 3700 | −336 | 332 | −178 | O |
| ATOM | 1908 | N | LEU | B | 204 | 16.553 | −65.557 | −46.049 | 1.00 | 51.09 | | N |
| ANISOU | 1908 | N | LEU | B | 204 | 5689 | 8913 | 4809 | −585 | 261 | −202 | N |
| ATOM | 1909 | CA | LEU | B | 204 | 16.578 | −64.553 | −47.097 | 1.00 | 51.59 | | C |
| ANISOU | 1909 | CA | LEU | B | 204 | 5728 | 8975 | 4900 | −582 | 477 | −346 | C |
| ATOM | 1910 | CB | LEU | B | 204 | 16.164 | −63.192 | −46.558 | 1.00 | 58.39 | | C |
| ANISOU | 1910 | CB | LEU | B | 204 | 6720 | 9912 | 5553 | −735 | 551 | −413 | C |
| ATOM | 1911 | CG | LEU | B | 204 | 14.708 | −63.113 | −46.138 | 1.00 | 59.56 | | C |
| ANISOU | 1911 | CG | LEU | B | 204 | 7087 | 10053 | 5489 | −772 | 629 | −381 | C |
| ATOM | 1912 | CD1 | LEU | B | 204 | 14.376 | −61.695 | −45.750 | 1.00 | 66.56 | | C |
| ANISOU | 1912 | CD1 | LEU | B | 204 | 8102 | 10987 | 6201 | −901 | 757 | −460 | C |
| ATOM | 1913 | CD2 | LEU | B | 204 | 13.812 | −63.580 | −47.279 | 1.00 | 53.69 | | C |
| ANISOU | 1913 | CD2 | LEU | B | 204 | 6363 | 9236 | 4799 | −657 | 780 | −393 | C |
| ATOM | 1914 | C | LEU | B | 204 | 17.940 | −64.449 | −47.774 | 1.00 | 55.69 | | C |
| ANISOU | 1914 | C | LEU | B | 204 | 6018 | 9484 | 5658 | −522 | 489 | −390 | C |
| ATOM | 1915 | O | LEU | B | 204 | 18.037 | −64.001 | −48.917 | 1.00 | 57.20 | | O |
| ANISOU | 1915 | O | LEU | B | 204 | 6169 | 9638 | 5927 | −465 | 687 | −492 | O |
| ATOM | 1916 | N | ASP | B | 205 | 18.995 | −64.850 | −47.071 | 1.00 | 57.66 | | N |
| ANISOU | 1916 | N | ASP | B | 205 | 6112 | 9770 | 6028 | −534 | 282 | −297 | N |
| ATOM | 1917 | CA | ASP | B | 205 | 20.325 | −64.859 | −47.668 | 1.00 | 41.42 | | C |
| ANISOU | 1917 | CA | ASP | B | 205 | 3799 | 7697 | 4242 | −463 | 293 | −306 | C |
| ATOM | 1918 | CB | ASP | B | 205 | 21.419 | −64.855 | −46.599 | 1.00 | 43.92 | | C |
| ANISOU | 1918 | CB | ASP | B | 205 | 3946 | 8106 | 4636 | −551 | 24 | −194 | C |
| ATOM | 1919 | CG | ASP | B | 205 | 21.443 | −66.130 | −45.773 | 1.00 | 81.55 | | C |
| ANISOU | 1919 | CG | ASP | B | 205 | 8698 | 12857 | 9429 | −490 | −203 | −15 | C |
| ATOM | 1920 | OD1 | ASP | B | 205 | 20.459 | −66.904 | −45.816 | 1.00 | 78.72 | | O |
| ANISOU | 1920 | OD1 | ASP | B | 205 | 8505 | 12424 | 8980 | −418 | −160 | 13 | O |
| ATOM | 1921 | OD2 | ASP | B | 205 | 22.453 | −66.346 | −45.071 | 1.00 | 85.58 | | O |
| ANISOU | 1921 | OD2 | ASP | B | 205 | 9024 | 13432 | 10059 | −520 | −433 | 109 | O |
| ATOM | 1922 | C | ASP | B | 205 | 20.463 | −66.065 | −48.604 | 1.00 | 48.66 | | C |
| ANISOU | 1922 | C | ASP | B | 205 | 4640 | 8481 | 5368 | −260 | 381 | −276 | C |
| ATOM | 1923 | O | ASP | B | 205 | 21.492 | −66.250 | −49.266 | 1.00 | 60.16 | | O |
| ANISOU | 1923 | O | ASP | B | 205 | 5892 | 9889 | 7076 | −158 | 446 | −277 | O |
| ATOM | 1924 | N | CYS | B | 206 | 19.412 | −66.885 | −48.627 | 1.00 | 53.14 | | N |
| ANISOU | 1924 | N | CYS | B | 206 | 5382 | 8978 | 5832 | −208 | 392 | −248 | N |
| ATOM | 1925 | CA | CYS | B | 206 | 19.302 | −68.069 | −49.484 | 1.00 | 48.49 | | C |
| ANISOU | 1925 | CA | CYS | B | 206 | 4795 | 8239 | 5390 | −41 | 483 | −239 | C |
| ATOM | 1926 | CB | CYS | B | 206 | 19.382 | −67.688 | −50.966 | 1.00 | 45.91 | | C |
| ANISOU | 1926 | CB | CYS | B | 206 | 4468 | 7844 | 5132 | 35 | 747 | −386 | C |
| ATOM | 1927 | SG | CYS | B | 206 | 18.035 | −66.634 | −51.515 | 1.00 | 53.11 | | S |
| ANISOU | 1927 | SG | CYS | B | 206 | 5603 | 8807 | 5770 | −67 | 912 | −514 | S |
| ATOM | 1928 | C | CYS | B | 206 | 20.320 | −69.155 | −49.161 | 1.00 | 42.93 | | C |
| ANISOU | 1928 | C | CYS | B | 206 | 3906 | 7469 | 4937 | 78 | 350 | −100 | C |
| ATOM | 1929 | O | CYS | B | 206 | 20.613 | −70.004 | −49.998 | 1.00 | 48.50 | | O |
| ANISOU | 1929 | O | CYS | B | 206 | 4568 | 8030 | 5829 | 233 | 469 | −109 | O |
| ATOM | 1930 | N | GLY | B | 207 | 20.871 | −69.117 | −47.953 | 1.00 | 53.82 | | N |
| ANISOU | 1930 | N | GLY | B | 207 | 5182 | 8948 | 6319 | 5 | 109 | 32 | N |
| ATOM | 1931 | CA | GLY | B | 207 | 21.794 | −70.145 | −47.505 | 1.00 | 51.71 | | C |
| ANISOU | 1931 | CA | GLY | B | 207 | 4726 | 8633 | 6288 | 116 | −50 | 206 | C |
| ATOM | 1932 | C | GLY | B | 207 | 21.070 | −71.383 | −46.996 | 1.00 | 60.15 | | C |

TABLE 7-continued

DMXAA-hSTING$^{G230I}$ complex

| | | | | | | | | | | | |
|---|---|---|---|---|---|---|---|---|---|---|---|
| ANISOU | 1932 | C | GLY | B | 207 | 5936 | 9611 | 7308 | 175 | −146 | 325 | C |
| ATOM | 1933 | O | GLY | B | 207 | 20.353 | −71.342 | −45.993 | 1.00 | 55.02 | | O |
| ANISOU | 1933 | O | GLY | B | 207 | 5436 | 9036 | 6431 | 60 | −296 | 390 | O |
| ATOM | 1934 | N | VAL | B | 208 | 21.263 | −72.495 | −47.694 | 1.00 | 62.08 | | N |
| ANISOU | 1934 | N | VAL | B | 208 | 6143 | 9677 | 7768 | 354 | −39 | 354 | N |
| ATOM | 1935 | CA | VAL | B | 208 | 20.581 | −73.740 | −47.369 | 1.00 | 61.34 | | C |
| ANISOU | 1935 | CA | VAL | B | 208 | 6189 | 9458 | 7661 | 418 | −94 | 455 | C |
| ATOM | 1936 | CB | VAL | B | 208 | 19.648 | −74.156 | −48.508 | 1.00 | 55.52 | | C |
| ANISOU | 1936 | CB | VAL | B | 208 | 5650 | 8564 | 6881 | 466 | 138 | 304 | C |
| ATOM | 1937 | CG1 | VAL | B | 208 | 18.960 | −75.468 | −48.172 | 1.00 | 60.75 | | C |
| ANISOU | 1937 | CG1 | VAL | B | 208 | 6453 | 9080 | 7550 | 516 | 82 | 408 | C |
| ATOM | 1938 | CG2 | VAL | B | 208 | 18.634 | −73.060 | −48.787 | 1.00 | 44.02 | | C |
| ANISOU | 1938 | CG2 | VAL | B | 208 | 4360 | 7216 | 5148 | 314 | 224 | 149 | C |
| ATOM | 1939 | C | VAL | B | 208 | 21.569 | −74.877 | −47.136 | 1.00 | 71.47 | | C |
| ANISOU | 1939 | C | VAL | B | 208 | 7282 | 10627 | 9246 | 590 | −178 | 641 | C |
| ATOM | 1940 | O | VAL | B | 208 | 22.240 | −75.307 | −48.079 | 1.00 | 73.14 | | O |
| ANISOU | 1940 | O | VAL | B | 208 | 7379 | 10697 | 9714 | 750 | −1 | 604 | O |
| ATOM | 1941 | N | PRO | B | 209 | 21.674 | −75.369 | −45.892 | 1.00 | 76.75 | | N |
| ANISOU | 1941 | N | PRO | B | 209 | 7921 | 11351 | 9890 | 566 | −434 | 850 | N |
| ATOM | 1942 | CA | PRO | B | 209 | 22.599 | −76.484 | −45.683 | 1.00 | 74.40 | | C |
| ANISOU | 1942 | CA | PRO | B | 209 | 7432 | 10936 | 9902 | 748 | −510 | 1055 | C |
| ATOM | 1943 | CB | PRO | B | 209 | 22.866 | −76.460 | −44.173 | 1.00 | 67.01 | | C |
| ANISOU | 1943 | CB | PRO | B | 209 | 6433 | 10164 | 8865 | 653 | −849 | 1279 | C |
| ATOM | 1944 | CG | PRO | B | 209 | 22.309 | −75.152 | −43.677 | 1.00 | 67.57 | | C |
| ANISOU | 1944 | CG | PRO | B | 209 | 6637 | 10444 | 8594 | 417 | −926 | 1159 | C |
| ATOM | 1945 | CD | PRO | B | 209 | 21.194 | −74.813 | −44.622 | 1.00 | 75.22 | | C |
| ANISOU | 1945 | CD | PRO | B | 209 | 7831 | 11340 | 9410 | 381 | −662 | 924 | C |
| ATOM | 1946 | C | PRO | B | 209 | 22.011 | −77.839 | −46.067 | 1.00 | 81.19 | | C |
| ANISOU | 1946 | C | PRO | B | 209 | 8446 | 11551 | 10853 | 884 | −388 | 1083 | C |
| ATOM | 1947 | O | PRO | B | 209 | 20.804 | −78.063 | −45.959 | 1.00 | 74.82 | | O |
| ANISOU | 1947 | O | PRO | B | 209 | 7894 | 10707 | 9828 | 799 | −368 | 1027 | O |
| ATOM | 1948 | N | ASP | B | 210 | 22.886 | −78.736 | −46.506 | 1.00 | 98.88 | | N |
| ANISOU | 1948 | N | ASP | B | 210 | 10522 | 13614 | 13433 | 1093 | −300 | 1177 | N |
| ATOM | 1949 | CA | ASP | B | 210 | 22.538 | −80.125 | −46.751 | 1.00 | 105.98 | | C |
| ANISOU | 1949 | CA | ASP | B | 210 | 11545 | 14254 | 14468 | 1237 | −198 | 1238 | C |
| ATOM | 1950 | CB | ASP | B | 210 | 23.759 | −80.852 | −47.304 | 1.00 | 116.33 | | C |
| ANISOU | 1950 | CB | ASP | B | 210 | 12625 | 15383 | 16190 | 1482 | −62 | 1333 | C |
| ATOM | 1951 | CG | ASP | B | 210 | 25.039 | −80.065 | −47.091 | 1.00 | 113.98 | | C |
| ANISOU | 1951 | CG | ASP | B | 210 | 11981 | 15260 | 16066 | 1504 | −160 | 1426 | C |
| ATOM | 1952 | OD1 | ASP | B | 210 | 25.440 | −79.884 | −45.919 | 1.00 | 113.95 | | O |
| ANISOU | 1952 | OD1 | ASP | B | 210 | 11825 | 15434 | 16039 | 1440 | −465 | 1637 | O |
| ATOM | 1953 | OD2 | ASP | B | 210 | 25.635 | −79.618 | −48.094 | 1.00 | 107.48 | | O |
| ANISOU | 1953 | OD2 | ASP | B | 210 | 11045 | 14398 | 15394 | 1573 | 64 | 1290 | O |
| ATOM | 1954 | C | ASP | B | 210 | 22.112 | −80.772 | −45.445 | 1.00 | 103.09 | | C |
| ANISOU | 1954 | C | ASP | B | 210 | 11251 | 13918 | 14002 | 1194 | −451 | 1465 | C |
| ATOM | 1955 | O | ASP | B | 210 | 21.257 | −81.657 | −45.418 | 1.00 | 102.62 | | O |
| ANISOU | 1955 | O | ASP | B | 210 | 11402 | 13697 | 13893 | 1206 | −404 | 1479 | O |
| ATOM | 1956 | N | ASN | B | 211 | 22.723 | −80.330 | −44.354 | 1.00 | 101.38 | | N |
| ANISOU | 1956 | N | ASN | B | 211 | 10862 | 13907 | 13751 | 1134 | −724 | 1649 | N |
| ATOM | 1957 | CA | ASN | B | 211 | 22.332 | −80.813 | −43.041 | 1.00 | 96.37 | | C |
| ANISOU | 1957 | CA | ASN | B | 211 | 10314 | 13331 | 12970 | 1074 | −978 | 1871 | C |
| ATOM | 1958 | CB | ASN | B | 211 | 23.459 | −81.586 | −42.374 | 1.00 | 103.55 | | C |
| ANISOU | 1958 | CB | ASN | B | 211 | 10969 | 14213 | 14163 | 1233 | −1163 | 2181 | C |
| ATOM | 1959 | CG | ASN | B | 211 | 23.017 | −82.950 | −41.924 | 1.00 | 104.56 | | C |
| ANISOU | 1959 | CG | ASN | B | 211 | 11226 | 14144 | 14360 | 1342 | −1184 | 2370 | C |
| ATOM | 1960 | OD1 | ASN | B | 211 | 22.190 | −83.079 | −41.028 | 1.00 | 106.42 | | O |
| ANISOU | 1960 | OD1 | ASN | B | 211 | 11661 | 14442 | 14333 | 1220 | −1328 | 2451 | O |
| ATOM | 1961 | ND2 | ASN | B | 211 | 23.534 | −83.984 | −42.577 | 1.00 | 103.81 | | N |
| ANISOU | 1961 | ND2 | ASN | B | 211 | 11035 | 13788 | 14620 | 1574 | −1010 | 2436 | N |
| ATOM | 1962 | C | ASN | B | 211 | 21.826 | −79.711 | −42.131 | 1.00 | 85.61 | | C |
| ANISOU | 1962 | C | ASN | B | 211 | 9058 | 12235 | 11236 | 832 | −1171 | 1841 | C |
| ATOM | 1963 | O | ASN | B | 211 | 22.604 | −78.920 | −41.598 | 1.00 | 82.44 | | O |
| ANISOU | 1963 | O | ASN | B | 211 | 8484 | 12033 | 10805 | 754 | −1357 | 1900 | O |
| ATOM | 1964 | N | LEU | B | 212 | 20.508 | −79.666 | −41.967 | 1.00 | 78.49 | | N |
| ANISOU | 1964 | N | LEU | B | 212 | 8443 | 11324 | 10056 | 709 | −1116 | 1749 | N |
| ATOM | 1965 | CA | LEU | B | 212 | 19.887 | −78.660 | −41.125 | 1.00 | 76.93 | | C |
| ANISOU | 1965 | CA | LEU | B | 212 | 8390 | 11344 | 9495 | 490 | −1243 | 1711 | C |
| ATOM | 1966 | CB | LEU | B | 212 | 18.364 | −78.700 | −41.257 | 1.00 | 75.74 | | C |
| ANISOU | 1966 | CB | LEU | B | 212 | 8532 | 11134 | 9113 | 393 | −1096 | 1593 | C |
| ATOM | 1967 | CG | LEU | B | 212 | 17.512 | −78.064 | −40.154 | 1.00 | 72.30 | | C |
| ANISOU | 1967 | CG | LEU | B | 212 | 8299 | 10862 | 8311 | 200 | −1206 | 1626 | C |
| ATOM | 1968 | CD1 | LEU | B | 212 | 17.952 | −76.639 | −39.810 | 1.00 | 76.19 | | C |
| ANISOU | 1968 | CD1 | LEU | B | 212 | 8744 | 11581 | 8622 | 52 | −1291 | 1534 | C |
| ATOM | 1969 | CD2 | LEU | B | 212 | 16.058 | −78.062 | −40.593 | 1.00 | 57.26 | | C |
| ANISOU | 1969 | CD2 | LEU | B | 212 | 6619 | 8877 | 6260 | 131 | −1005 | 1494 | C |
| ATOM | 1970 | C | LEU | B | 212 | 20.290 | −78.872 | −39.679 | 1.00 | 87.24 | | C |
| ANISOU | 1970 | C | LEU | B | 212 | 9668 | 12776 | 10703 | 443 | −1553 | 1976 | C |
| ATOM | 1971 | O | LEU | B | 212 | 20.689 | −77.926 | −38.996 | 1.00 | 88.34 | | O |

TABLE 7-continued

DMXAA-hSTING$^{G230I}$ complex

| | | | | | | | | | | | |
|---|---|---|---|---|---|---|---|---|---|---|---|
| ANISOU | 1971 | O | LEU | B | 212 | 9767 | 13128 | 10668 | 299 | −1732 | 1987 | O |
| ATOM | 1972 | N | SER | B | 213 | 20.194 | −80.116 | −39.219 | 1.00 | 95.53 | | N |
| ANISOU | 1972 | N | SER | B | 213 | 10752 | 13688 | 11857 | 556 | −1620 | 2192 | N |
| ATOM | 1973 | CA | SER | B | 213 | 20.435 | −80.437 | −37.814 | 1.00 | 99.86 | | C |
| ANISOU | 1973 | CA | SER | B | 213 | 11318 | 14343 | 12280 | 514 | −1915 | 2469 | C |
| ATOM | 1974 | CB | SER | B | 213 | 20.388 | −81.949 | −37.578 | 1.00 | 98.55 | | C |
| ANISOU | 1974 | CB | SER | B | 213 | 11165 | 13968 | 12312 | 689 | −1928 | 2705 | C |
| ATOM | 1975 | OG | SER | B | 213 | 20.275 | −82.654 | −38.802 | 1.00 | 98.47 | | O |
| ANISOU | 1975 | OG | SER | B | 213 | 11126 | 13704 | 12585 | 849 | −1657 | 2587 | O |
| ATOM | 1976 | C | SER | B | 213 | 21.757 | −79.856 | −37.325 | 1.00 | 106.65 | | C |
| ANISOU | 1976 | C | SER | B | 213 | 11918 | 15398 | 13208 | 488 | −2173 | 2586 | C |
| ATOM | 1977 | O | SER | B | 213 | 21.910 | −79.529 | −36.151 | 1.00 | 111.35 | | O |
| ANISOU | 1977 | O | SER | B | 213 | 12565 | 16174 | 13569 | 355 | −2444 | 2732 | O |
| ATOM | 1978 | N | MET | B | 214 | 22.699 | −79.699 | −38.247 | 1.00 | 111.66 | | N |
| ANISOU | 1978 | N | MET | B | 214 | 12279 | 15992 | 14153 | 604 | −2083 | 2516 | N |
| ATOM | 1979 | CA | MET | B | 214 | 24.029 | −79.195 | −37.930 | 1.00 | 116.13 | | C |
| ANISOU | 1979 | CA | MET | B | 214 | 12541 | 16724 | 14859 | 590 | −2312 | 2634 | C |
| ATOM | 1980 | CB | MET | B | 214 | 25.026 | −79.653 | −38.995 | 1.00 | 118.92 | | C |
| ANISOU | 1980 | CB | MET | B | 214 | 12578 | 16926 | 15679 | 820 | −2152 | 2648 | C |
| ATOM | 1981 | CG | MET | B | 214 | 25.832 | −80.881 | −38.605 | 1.00 | 124.68 | | C |
| ANISOU | 1981 | CG | MET | B | 214 | 13093 | 17546 | 16732 | 1034 | −2289 | 2984 | C |
| ATOM | 1982 | SD | MET | B | 214 | 24.996 | −81.995 | −37.456 | 1.00 | 203.20 | | S |
| ANISOU | 1982 | SD | MET | B | 214 | 23302 | 27421 | 26484 | 1045 | −2447 | 3233 | S |
| ATOM | 1983 | CE | MET | B | 214 | 23.737 | −82.718 | −38.496 | 1.00 | 102.87 | | C |
| ANISOU | 1983 | CE | MET | B | 214 | 10881 | 14410 | 13793 | 1136 | −2041 | 3008 | C |
| ATOM | 1984 | C | MET | B | 214 | 24.070 | −77.679 | −37.801 | 1.00 | 111.16 | | C |
| ANISOU | 1984 | C | MET | B | 214 | 11941 | 16320 | 13975 | 353 | −2371 | 2439 | C |
| ATOM | 1985 | O | MET | B | 214 | 24.795 | −77.143 | −36.960 | 1.00 | 109.07 | | O |
| ANISOU | 1985 | O | MET | B | 214 | 11562 | 16255 | 13626 | 226 | −2666 | 2559 | O |
| ATOM | 1986 | N | ALA | B | 215 | 23.291 | −76.996 | −38.638 | 1.00 | 108.50 | | N |
| ANISOU | 1986 | N | ALA | B | 215 | 11763 | 15945 | 13517 | 289 | −2097 | 2145 | N |
| ATOM | 1987 | CA | ALA | B | 215 | 23.247 | −75.533 | −38.640 | 1.00 | 106.46 | | C |
| ANISOU | 1987 | CA | ALA | B | 215 | 11553 | 15863 | 13033 | 78 | −2095 | 1939 | C |
| ATOM | 1988 | CB | ALA | B | 215 | 22.180 | −75.030 | −39.599 | 1.00 | 99.85 | | C |
| ANISOU | 1988 | CB | ALA | B | 215 | 10919 | 14943 | 12077 | 50 | −1765 | 1655 | C |
| ATOM | 1989 | C | ALA | B | 215 | 23.010 | −74.983 | −37.239 | 1.00 | 113.63 | | C |
| ANISOU | 1989 | C | ALA | B | 215 | 12643 | 16967 | 13564 | −146 | −2368 | 2022 | C |
| ATOM | 1990 | O | ALA | B | 215 | 23.570 | −73.954 | −36.859 | 1.00 | 119.67 | | O |
| ANISOU | 1990 | O | ALA | B | 215 | 13349 | 17907 | 14215 | −320 | −2518 | 1971 | O |
| ATOM | 1991 | N | ASP | B | 216 | 22.187 | −75.684 | −36.470 | 1.00 | 109.50 | | N |
| ANISOU | 1991 | N | ASP | B | 216 | 12357 | 16404 | 12846 | −150 | −2423 | 2149 | N |
| ATOM | 1992 | CA | ASP | B | 216 | 21.976 | −75.336 | −35.075 | 1.00 | 100.68 | | C |
| ANISOU | 1992 | CA | ASP | B | 216 | 11443 | 15452 | 11360 | −345 | −2677 | 2259 | C |
| ATOM | 1993 | CB | ASP | B | 216 | 20.602 | −74.698 | −34.886 | 1.00 | 86.77 | | C |
| ANISOU | 1993 | CB | ASP | B | 216 | 10044 | 13696 | 9229 | −491 | −2485 | 2074 | C |
| ATOM | 1994 | CG | ASP | B | 216 | 20.473 | −73.963 | −33.562 | 1.00 | 85.74 | | C |
| ANISOU | 1994 | CG | ASP | B | 216 | 10145 | 13749 | 8685 | −729 | −2696 | 2112 | C |
| ATOM | 1995 | OD1 | ASP | B | 216 | 21.070 | −74.404 | −32.555 | 1.00 | 81.84 | | O |
| ANISOU | 1995 | OD1 | ASP | B | 216 | 9628 | 13346 | 8122 | −762 | −3010 | 2351 | O |
| ATOM | 1996 | OD2 | ASP | B | 216 | 19.773 | −72.930 | −33.537 | 1.00 | 86.19 | | O |
| ANISOU | 1996 | OD2 | ASP | B | 216 | 10418 | 13852 | 8477 | −884 | −2541 | 1904 | O |
| ATOM | 1997 | C | ASP | B | 216 | 22.099 | −76.547 | −34.206 | 1.00 | 103.64 | | C |
| ANISOU | 1997 | C | ASP | B | 216 | 11826 | 15787 | 11767 | −245 | −2889 | 2578 | C |
| ATOM | 1998 | O | ASP | B | 216 | 21.372 | −77.552 | −34.423 | 1.00 | 112.65 | | O |
| ANISOU | 1998 | O | ASP | B | 216 | 13072 | 16750 | 12979 | −109 | −2734 | 2634 | O |
| ATOM | 1999 | N | PRO | B | 217 | 23.005 | −76.550 | −33.217 | 1.00 | 102.82 | | N |
| ANISOU | 1999 | N | PRO | B | 217 | 11614 | 15844 | 11607 | −322 | −3252 | 2797 | N |
| ATOM | 2000 | CA | PRO | B | 217 | 23.112 | −77.683 | −32.297 | 1.00 | 105.41 | | C |
| ANISOU | 2000 | CA | PRO | B | 217 | 11969 | 16150 | 11933 | −236 | −3474 | 3127 | C |
| ATOM | 2001 | CB | PRO | B | 217 | 24.246 | −77.266 | −31.358 | 1.00 | 108.70 | | C |
| ANISOU | 2001 | CB | PRO | B | 217 | 12232 | 16797 | 12272 | −374 | −3896 | 3313 | C |
| ATOM | 2002 | CG | PRO | B | 217 | 24.243 | −75.769 | −31.418 | 1.00 | 106.06 | | C |
| ANISOU | 2002 | CG | PRO | B | 217 | 11982 | 16616 | 11699 | −620 | −3878 | 3036 | C |
| ATOM | 2003 | CD | PRO | B | 217 | 23.918 | −75.460 | −32.848 | 1.00 | 101.90 | | C |
| ANISOU | 2003 | CD | PRO | B | 217 | 11371 | 15944 | 11405 | −514 | −3488 | 2757 | C |
| ATOM | 2004 | C | PRO | B | 217 | 21.824 | −77.866 | −31.501 | 1.00 | 102.07 | | C |
| ANISOU | 2004 | C | PRO | B | 217 | 11957 | 15705 | 11119 | −332 | −3412 | 3140 | C |
| ATOM | 2005 | O | PRO | B | 217 | 21.486 | −78.987 | −31.116 | 1.00 | 101.06 | | O |
| ANISOU | 2005 | O | PRO | B | 217 | 11904 | 15463 | 11032 | −209 | −3431 | 3355 | O |
| ATOM | 2006 | N | ASN | B | 218 | 21.111 | −76.768 | −31.265 | 1.00 | 101.95 | | N |
| ANISOU | 2006 | N | ASN | B | 218 | 12205 | 15788 | 10744 | −544 | −3317 | 2917 | N |
| ATOM | 2007 | CA | ASN | B | 218 | 19.824 | −76.817 | −30.578 | 1.00 | 103.23 | | C |
| ANISOU | 2007 | CA | ASN | B | 218 | 12756 | 15922 | 10543 | −636 | −3198 | 2906 | C |
| ATOM | 2008 | CB | ASN | B | 218 | 19.442 | −75.444 | −30.025 | 1.00 | 99.42 | | C |
| ANISOU | 2008 | CB | ASN | B | 218 | 12534 | 15599 | 9644 | −898 | −3189 | 2711 | C |
| ATOM | 2009 | CG | ASN | B | 218 | 20.028 | −75.176 | −28.658 | 1.00 | 99.11 | | C |
| ANISOU | 2009 | CG | ASN | B | 218 | 12622 | 15644 | 9390 | −1032 | −3442 | 2779 | C |
| ATOM | 2010 | OD1 | ASN | B | 218 | 20.559 | −76.076 | −28.006 | 1.00 | 96.31 | | O |

TABLE 7-continued

| | | | | | | | | | | | | |
|---|---|---|---|---|---|---|---|---|---|---|---|---|
| DMXAA-hSTING$^{G230I}$ complex | | | | | | | | | | | | |
| ANISOU | 2010 | OD1 | ASN | B | 218 | 12200 | 15274 | 9121 | −946 | −3655 | 3022 | O |
| ATOM | 2011 | ND2 | ASN | B | 218 | 19.919 | −73.932 | −28.206 | 1.00 | 97.11 | | N |
| ANISOU | 2011 | ND2 | ASN | B | 218 | 12567 | 15457 | 8871 | −1234 | −3393 | 2550 | N |
| ATOM | 2012 | C | ASN | B | 218 | 18.698 | −77.336 | −31.468 | 1.00 | 99.24 | | C |
| ANISOU | 2012 | C | ASN | B | 218 | 12333 | 15202 | 10171 | −505 | −2830 | 2785 | C |
| ATOM | 2013 | O | ASN | B | 218 | 17.532 | −77.322 | −31.078 | 1.00 | 99.62 | | O |
| ANISOU | 2013 | O | ASN | B | 218 | 12673 | 15211 | 9968 | −574 | −2674 | 2754 | O |
| ATOM | 2014 | N | ILE | B | 219 | 19.045 | −77.773 | −32.671 | 1.00 | 91.90 | | N |
| ANISOU | 2014 | N | ILE | B | 219 | 11149 | 14132 | 9636 | −325 | −2687 | 2718 | N |
| ATOM | 2015 | CA | ILE | B | 219 | 18.074 | −78.369 | −33.572 | 1.00 | 84.84 | | C |
| ANISOU | 2015 | CA | ILE | B | 219 | 10319 | 13027 | 8889 | −208 | −2374 | 2613 | C |
| ATOM | 2016 | CB | ILE | B | 219 | 17.821 | −77.503 | −34.803 | 1.00 | 80.55 | | C |
| ANISOU | 2016 | CB | ILE | B | 219 | 9718 | 12462 | 8424 | −227 | −2117 | 2301 | C |
| ATOM | 2017 | CG1 | ILE | B | 219 | 17.124 | −76.210 | −34.395 | 1.00 | 82.56 | | C |
| ANISOU | 2017 | CG1 | ILE | B | 219 | 10199 | 12859 | 8310 | −441 | −2046 | 2128 | C |
| ATOM | 2018 | CD1 | ILE | B | 219 | 16.530 | −75.441 | −35.549 | 1.00 | 80.61 | | C |
| ANISOU | 2018 | CD1 | ILE | B | 219 | 9956 | 12569 | 8105 | −455 | −1754 | 1848 | C |
| ATOM | 2019 | CG2 | ILE | B | 219 | 16.970 | −78.258 | −35.816 | 1.00 | 73.92 | | C |
| ANISOU | 2019 | CG2 | ILE | B | 219 | 8912 | 11401 | 7775 | −100 | −1840 | 2216 | C |
| ATOM | 2020 | C | ILE | B | 219 | 18.564 | −79.726 | −34.018 | 1.00 | 91.93 | | C |
| ANISOU | 2020 | C | ILE | B | 219 | 11024 | 13737 | 10167 | 23 | −2383 | 2788 | C |
| ATOM | 2021 | O | ILE | B | 219 | 19.578 | −79.835 | −34.703 | 1.00 | 99.18 | | O |
| ANISOU | 2021 | O | ILE | B | 219 | 11661 | 14626 | 11396 | 145 | −2409 | 2783 | O |
| ATOM | 2022 | N | ARG | B | 220 | 17.847 | −80.767 | −33.621 | 1.00 | 91.03 | | N |
| ANISOU | 2022 | N | ARG | B | 220 | 11066 | 13483 | 10040 | 86 | −2343 | 2949 | N |
| ATOM | 2023 | CA | ARG | B | 220 | 18.286 | −82.121 | −33.900 | 1.00 | 87.09 | | C |
| ANISOU | 2023 | CA | ARG | B | 220 | 10420 | 12782 | 9887 | 303 | −2352 | 3141 | C |
| ATOM | 2024 | CB | ARG | B | 220 | 18.643 | −82.844 | −32.603 | 1.00 | 99.40 | | C |
| ANISOU | 2024 | CB | ARG | B | 220 | 12018 | 14386 | 11365 | 327 | −2628 | 3493 | C |
| ATOM | 2025 | CG | ARG | B | 220 | 20.120 | −82.856 | −32.282 | 1.00 | 107.39 | | C |
| ANISOU | 2025 | CG | ARG | B | 220 | 12740 | 15515 | 12548 | 399 | −2921 | 3686 | C |
| ATOM | 2026 | CD | ARG | B | 220 | 20.465 | −84.098 | −31.477 | 1.00 | 119.55 | | C |
| ANISOU | 2026 | CD | ARG | B | 220 | 14254 | 16972 | 14199 | 538 | −3107 | 4064 | C |
| ATOM | 2027 | NE | ARG | B | 220 | 21.508 | −84.894 | −32.118 | 1.00 | 126.77 | | N |
| ANISOU | 2027 | NE | ARG | B | 220 | 14839 | 17741 | 15588 | 782 | −3113 | 4200 | N |
| ATOM | 2028 | CZ | ARG | B | 220 | 21.759 | −86.169 | −31.837 | 1.00 | 129.76 | | C |
| ANISOU | 2028 | CZ | ARG | B | 220 | 15159 | 17946 | 16198 | 974 | −3161 | 4497 | C |
| ATOM | 2029 | NH1 | ARG | B | 220 | 22.732 | −86.813 | −32.470 | 1.00 | 129.01 | | N |
| ANISOU | 2029 | NH1 | ARG | B | 220 | 14757 | 17707 | 16552 | 1206 | −3131 | 4609 | N |
| ATOM | 2030 | NH2 | ARG | B | 220 | 21.036 | −86.807 | −30.927 | 1.00 | 132.27 | | N |
| ANISOU | 2030 | NH2 | ARG | B | 220 | 15728 | 18220 | 16309 | 942 | −3217 | 4691 | N |
| ATOM | 2031 | C | ARG | B | 220 | 17.238 | −82.915 | −34.647 | 1.00 | 73.27 | | C |
| ANISOU | 2031 | C | ARG | B | 220 | 8797 | 10782 | 8259 | 378 | −2068 | 3054 | C |
| ATOM | 2032 | O | ARG | B | 220 | 16.046 | −82.821 | −34.362 | 1.00 | 72.31 | | O |
| ANISOU | 2032 | O | ARG | B | 220 | 8920 | 10648 | 7906 | 264 | −1954 | 3002 | O |
| ATOM | 2033 | N | PHE | B | 221 | 17.702 | −83.706 | −35.604 | 1.00 | 76.14 | | N |
| ANISOU | 2033 | N | PHE | B | 221 | 8992 | 10941 | 8995 | 566 | −1952 | 3041 | N |
| ATOM | 2034 | CA | PHE | B | 221 | 16.843 | −84.614 | −36.337 | 1.00 | 76.47 | | C |
| ANISOU | 2034 | CA | PHE | B | 221 | 9151 | 10719 | 9186 | 637 | −1710 | 2973 | C |
| ATOM | 2035 | CB | PHE | B | 221 | 17.611 | −85.244 | −37.489 | 1.00 | 71.19 | | C |
| ANISOU | 2035 | CB | PHE | B | 221 | 8284 | 9845 | 8918 | 838 | −1576 | 2914 | C |
| ATOM | 2036 | CG | PHE | B | 221 | 16.893 | −86.382 | −38.147 | 1.00 | 72.78 | | C |
| ANISOU | 2036 | CG | PHE | B | 221 | 8615 | 9740 | 9297 | 919 | −1361 | 2881 | C |
| ATOM | 2037 | CD1 | PHE | B | 221 | 15.934 | −86.141 | −39.120 | 1.00 | 76.27 | | C |
| ANISOU | 2037 | CD1 | PHE | B | 221 | 9194 | 10100 | 9683 | 829 | −1135 | 2607 | C |
| ATOM | 2038 | CE1 | PHE | B | 221 | 15.273 | −87.189 | −39.737 | 1.00 | 76.02 | | C |
| ANISOU | 2038 | CE1 | PHE | B | 221 | 9293 | 9785 | 9807 | 874 | −958 | 2567 | C |
| ATOM | 2039 | CZ | PHE | B | 221 | 15.573 | −88.499 | −39.379 | 1.00 | 76.06 | | C |
| ANISOU | 2039 | CZ | PHE | B | 221 | 9299 | 9565 | 10036 | 1023 | −979 | 2799 | C |
| ATOM | 2040 | CE2 | PHE | B | 221 | 16.531 | −88.751 | −38.407 | 1.00 | 73.04 | | C |
| ANISOU | 2040 | CE2 | PHE | B | 221 | 8772 | 9259 | 9722 | 1136 | −1190 | 3089 | C |
| ATOM | 2041 | CD2 | PHE | B | 221 | 17.184 | −87.695 | −37.801 | 1.00 | 74.16 | | C |
| ANISOU | 2041 | CD2 | PHE | B | 221 | 8776 | 9703 | 9697 | 1078 | −1392 | 3131 | C |
| ATOM | 2042 | C | PHE | B | 221 | 16.310 | −85.682 | −35.402 | 1.00 | 84.19 | | C |
| ANISOU | 2042 | C | PHE | B | 221 | 10288 | 11583 | 10118 | 661 | −1776 | 3239 | C |
| ATOM | 2043 | O | PHE | B | 221 | 17.066 | −86.343 | −34.683 | 1.00 | 98.40 | | O |
| ANISOU | 2043 | O | PHE | B | 221 | 11997 | 13370 | 12022 | 770 | −1965 | 3519 | O |
| ATOM | 2044 | N | LEU | B | 222 | 14.997 | −85.853 | −35.416 | 1.00 | 81.21 | | N |
| ANISOU | 2044 | N | LEU | B | 222 | 10139 | 11121 | 9597 | 558 | −1618 | 3166 | N |
| ATOM | 2045 | CA | LEU | B | 222 | 14.344 | −86.789 | −34.525 | 1.00 | 80.21 | | C |
| ANISOU | 2045 | CA | LEU | B | 222 | 10186 | 10885 | 9403 | 554 | −1648 | 3407 | C |
| ATOM | 2046 | CB | LEU | B | 222 | 13.034 | −86.192 | −34.028 | 1.00 | 74.82 | | C |
| ANISOU | 2046 | CB | LEU | B | 222 | 9743 | 10304 | 8383 | 354 | −1564 | 3337 | C |
| ATOM | 2047 | CG | LEU | B | 222 | 12.665 | −86.447 | −32.571 | 1.00 | 85.34 | | C |
| ANISOU | 2047 | CG | LEU | B | 222 | 11259 | 11708 | 9457 | 287 | −1693 | 3608 | C |
| ATOM | 2048 | CD2 | LEU | B | 222 | 11.926 | −87.767 | −32.426 | 1.00 | 90.23 | | C |
| ANISOU | 2048 | CD2 | LEU | B | 222 | 11999 | 12070 | 10214 | 341 | −1586 | 3778 | C |
| ATOM | 2049 | CD1 | LEU | B | 222 | 11.809 | −85.305 | −32.083 | 1.00 | 83.99 | | C |

TABLE 7-continued

DMXAA-hSTING$^{G230I}$ complex

| | | | | | | | | | | | | |
|---|---|---|---|---|---|---|---|---|---|---|---|---|
| ANISOU | 2049 | CD1 | LEU | B | 222 | 11266 | 11733 | 8912 | 88 | −1634 | 3490 | C |
| ATOM | 2050 | C | LEU | B | 222 | 14.074 | −88.082 | −35.268 | 1.00 | 68.40 | | C |
| ANISOU | 2050 | C | LEU | B | 222 | 8702 | 9061 | 8227 | 684 | −1477 | 3423 | C |
| ATOM | 2051 | O | LEU | B | 222 | 14.440 | −89.169 | −34.817 | 1.00 | 90.57 | | O |
| ANISOU | 2051 | O | LEU | B | 222 | 11495 | 11712 | 11205 | 816 | −1543 | 3676 | O |
| ATOM | 2052 | N | ASP | B | 223 | 13.449 | −87.950 | −36.428 | 1.00 | 66.05 | | N |
| ANISOU | 2052 | N | ASP | B | 223 | 8437 | 8652 | 8007 | 641 | −1258 | 3151 | N |
| ATOM | 2053 | CA | ASP | B | 223 | 12.876 | −89.092 | −37.104 | 1.00 | 68.40 | | C |
| ANISOU | 2053 | CA | ASP | B | 223 | 8820 | 8636 | 8531 | 693 | −1080 | 3127 | C |
| ATOM | 2054 | CB | ASP | B | 223 | 11.741 | −89.643 | −36.253 | 1.00 | 69.52 | | C |
| ANISOU | 2054 | CB | ASP | B | 223 | 9170 | 8714 | 8530 | 587 | −1066 | 3292 | C |
| ATOM | 2055 | CG | ASP | B | 223 | 11.650 | −91.139 | −36.301 | 1.00 | 74.01 | | C |
| ANISOU | 2055 | CG | ASP | B | 223 | 9800 | 8957 | 9364 | 698 | −997 | 3453 | C |
| ATOM | 2056 | OD1 | ASP | B | 223 | 11.716 | −91.698 | −37.418 | 1.00 | 77.66 | | O |
| ANISOU | 2056 | OD1 | ASP | B | 223 | 10244 | 9186 | 10079 | 764 | −844 | 3295 | O |
| ATOM | 2057 | OD2 | ASP | B | 223 | 11.524 | −91.749 | −35.218 | 1.00 | 85.74 | | O |
| ANISOU | 2057 | OD2 | ASP | B | 223 | 11369 | 10412 | 10797 | 716 | −1089 | 3738 | O |
| ATOM | 2058 | C | ASP | B | 223 | 12.328 | −88.681 | −38.459 | 1.00 | 70.87 | | C |
| ANISOU | 2058 | C | ASP | B | 223 | 9155 | 8890 | 8883 | 621 | −880 | 2795 | C |
| ATOM | 2059 | O | ASP | B | 223 | 12.285 | −87.497 | −38.791 | 1.00 | 73.99 | | O |
| ANISOU | 2059 | O | ASP | B | 223 | 9505 | 9492 | 9115 | 530 | −871 | 2606 | O |
| ATOM | 2060 | N | LYS | B | 224 | 11.895 | −89.665 | −39.235 | 1.00 | 70.99 | | N |
| ANISOU | 2060 | N | LYS | B | 224 | 9252 | 8616 | 9106 | 652 | −723 | 2729 | N |
| ATOM | 2061 | CA | LYS | B | 224 | 11.299 | −89.410 | −40.534 | 1.00 | 71.08 | | C |
| ANISOU | 2061 | CA | LYS | B | 224 | 9316 | 8551 | 9141 | 567 | −549 | 2428 | C |
| ATOM | 2062 | CB | LYS | B | 224 | 11.991 | −90.243 | −41.612 | 1.00 | 78.77 | | C |
| ANISOU | 2062 | CB | LYS | B | 224 | 10257 | 9247 | 10425 | 723 | −417 | 2327 | C |
| ATOM | 2063 | CG | LYS | B | 224 | 13.242 | −89.615 | −42.199 | 1.00 | 85.97 | | C |
| ANISOU | 2063 | CG | LYS | B | 224 | 10977 | 10252 | 11434 | 859 | −410 | 2221 | C |
| ATOM | 2064 | CD | LYS | B | 224 | 12.896 | −88.333 | −42.931 | 1.00 | 91.59 | | C |
| ANISOU | 2064 | CD | LYS | B | 224 | 11677 | 11171 | 11951 | 726 | −359 | 1952 | C |
| ATOM | 2065 | CE | LYS | B | 224 | 13.744 | −88.137 | −44.181 | 1.00 | 91.82 | | C |
| ANISOU | 2065 | CE | LYS | B | 224 | 11616 | 11127 | 12146 | 840 | −218 | 1744 | C |
| ATOM | 2066 | NZ | LYS | B | 224 | 13.362 | −86.877 | −44.907 | 1.00 | 78.39 | | N |
| ANISOU | 2066 | NZ | LYS | B | 224 | 9915 | 9625 | 10244 | 708 | −164 | 1495 | N |
| ATOM | 2067 | C | LYS | B | 224 | 9.821 | −89.748 | −40.489 | 1.00 | 66.39 | | C |
| ANISOU | 2067 | C | LYS | B | 224 | 8904 | 7870 | 8451 | 389 | −472 | 2413 | C |
| ATOM | 2068 | O | LYS | B | 224 | 9.417 | −90.699 | −39.823 | 1.00 | 72.47 | | O |
| ANISOU | 2068 | O | LYS | B | 224 | 9771 | 8484 | 9280 | 390 | −484 | 2614 | O |
| ATOM | 2069 | N | LEU | B | 225 | 9.010 | −88.961 | −41.189 | 1.00 | 64.95 | | N |
| ANISOU | 2069 | N | LEU | B | 225 | 8757 | 7788 | 8132 | 237 | −393 | 2192 | N |
| ATOM | 2070 | CA | LEU | B | 225 | 7.598 | −89.274 | −41.350 | 1.00 | 69.97 | | C |
| ANISOU | 2070 | CA | LEU | B | 225 | 9530 | 8334 | 8720 | 61 | −314 | 2162 | C |
| ATOM | 2071 | CB | LEU | B | 225 | 6.863 | −88.104 | −41.998 | 1.00 | 60.51 | | C |
| ANISOU | 2071 | CB | LEU | B | 225 | 8319 | 7329 | 7344 | −89 | −262 | 1951 | C |
| ATOM | 2072 | CG | LEU | B | 225 | 6.184 | −87.069 | −41.103 | 1.00 | 68.75 | | C |
| ANISOU | 2072 | CG | LEU | B | 225 | 9360 | 8637 | 8126 | −203 | −296 | 2031 | C |
| ATOM | 2073 | CD1 | LEU | B | 225 | 5.432 | −86.076 | −41.971 | 1.00 | 52.06 | | C |
| ANISOU | 2073 | CD1 | LEU | B | 225 | 7226 | 6654 | 5903 | −332 | −216 | 1820 | C |
| ATOM | 2074 | CD2 | LEU | B | 225 | 5.239 | −87.737 | −40.117 | 1.00 | 79.39 | | C |
| ANISOU | 2074 | CD2 | LEU | B | 225 | 10814 | 9911 | 9442 | −287 | −293 | 2256 | C |
| ATOM | 2075 | C | LEU | B | 225 | 7.500 | −90.495 | −42.247 | 1.00 | 90.96 | | C |
| ANISOU | 2075 | C | LEU | B | 225 | 12279 | 10654 | 11628 | 85 | −212 | 2084 | C |
| ATOM | 2076 | O | LEU | B | 225 | 8.450 | −90.790 | −42.984 | 1.00 | 96.21 | | O |
| ANISOU | 2076 | O | LEU | B | 225 | 12903 | 11193 | 12461 | 226 | −164 | 1981 | O |
| ATOM | 2077 | N | PRO | B | 226 | 6.367 | −91.216 | −42.201 | 1.00 | 95.47 | | N |
| ANISOU | 2077 | N | PRO | B | 226 | 12979 | 11064 | 12232 | −57 | −165 | 2132 | N |
| ATOM | 2078 | CA | PRO | B | 226 | 6.280 | −92.330 | −43.146 | 1.00 | 97.42 | | C |
| ANISOU | 2078 | CA | PRO | B | 226 | 13337 | 10976 | 12702 | −60 | −66 | 2020 | C |
| ATOM | 2079 | CB | PRO | B | 226 | 4.971 | −93.030 | −42.757 | 1.00 | 97.09 | | C |
| ANISOU | 2079 | CB | PRO | B | 226 | 13415 | 10801 | 12674 | −241 | −49 | 2135 | C |
| ATOM | 2080 | CG | PRO | B | 226 | 4.172 | −91.983 | −42.048 | 1.00 | 93.34 | | C |
| ANISOU | 2080 | CG | PRO | B | 226 | 12878 | 10630 | 11957 | −367 | −101 | 2210 | C |
| ATOM | 2081 | CD | PRO | B | 226 | 5.177 | −91.119 | −41.342 | 1.00 | 92.08 | | C |
| ANISOU | 2081 | CD | PRO | B | 226 | 12604 | 10719 | 11663 | −216 | −184 | 2285 | C |
| ATOM | 2082 | C | PRO | B | 226 | 6.223 | −91.820 | −44.585 | 1.00 | 91.99 | | C |
| ANISOU | 2082 | C | PRO | B | 226 | 12663 | 10298 | 11992 | −125 | 8 | 1704 | C |
| ATOM | 2083 | O | PRO | B | 226 | 5.623 | −90.775 | −44.853 | 1.00 | 83.24 | | O |
| ANISOU | 2083 | O | PRO | B | 226 | 11509 | 9421 | 10696 | −252 | −12 | 1594 | O |
| ATOM | 2084 | N | GLN | B | 227 | 6.869 | −92.550 | −45.488 | 1.00 | 90.49 | | N |
| ANISOU | 2084 | N | GLN | B | 227 | 12543 | 9851 | 11989 | −27 | 104 | 1570 | N |
| ATOM | 2085 | CA | GLN | B | 227 | 6.978 | −92.157 | −46.885 | 1.00 | 84.23 | | C |
| ANISOU | 2085 | CA | GLN | B | 227 | 11794 | 9040 | 11170 | −65 | 188 | 1272 | C |
| ATOM | 2086 | CB | GLN | B | 227 | 7.701 | −93.240 | −47.677 | 1.00 | 78.72 | | C |
| ANISOU | 2086 | CB | GLN | B | 227 | 11219 | 7987 | 10703 | 60 | 327 | 1169 | C |
| ATOM | 2087 | CG | GLN | B | 227 | 9.147 | −93.415 | −47.305 | 1.00 | 80.79 | | C |
| ANISOU | 2087 | CG | GLN | B | 227 | 11355 | 8208 | 11133 | 341 | 361 | 1287 | C |
| ATOM | 2088 | CD | GLN | B | 227 | 9.696 | −94.739 | −47.786 | 1.00 | 95.49 | | C |

TABLE 7-continued

DMXAA-hSTING^{G230I} complex

| | | | | | | | | | | |
|---|---|---|---|---|---|---|---|---|---|---|
| ANISOU | 2088 | CD | GLN | B | 227 | 13353 | 9661 | 13269 | 475 | 519 | 1268 C |
| ATOM | 2089 | OE1 | GLN | B | 227 | 9.152 | −95.801 | −47.471 | 1.00 | 96.72 | O |
| ANISOU | 2089 | OE1 | GLN | B | 227 | 13646 | 9565 | 13536 | 417 | 537 | 1370 O |
| ATOM | 2090 | NE2 | GLN | B | 227 | 10.772 | −94.687 | −48.560 | 1.00 | 100.70 | N |
| ANISOU | 2090 | NE2 | GLN | B | 227 | 13980 | 10234 | 14048 | 654 | 656 | 1138 N |
| ATOM | 2091 | C | GLN | B | 227 | 5.624 | −91.905 | −47.527 | 1.00 | 89.11 | C |
| ANISOU | 2091 | C | GLN | B | 227 | 12506 | 9696 | 11655 | −329 | 176 | 1129 C |
| ATOM | 2092 | O | GLN | B | 227 | 4.626 | −92.522 | −47.157 | 1.00 | 88.83 | O |
| ANISOU | 2092 | O | GLN | B | 227 | 12549 | 9557 | 11646 | −482 | 146 | 1231 O |
| ATOM | 2093 | N | GLN | B | 228 | 5.596 | −90.993 | −48.492 | 1.00 | 94.73 | N |
| ANISOU | 2093 | N | GLN | B | 228 | 13198 | 10560 | 12233 | −384 | 195 | 910 N |
| ATOM | 2094 | CA | GLN | B | 228 | 4.401 | −90.798 | −49.297 | 1.00 | 93.52 | C |
| ANISOU | 2094 | CA | GLN | B | 228 | 13132 | 10429 | 11970 | −627 | 174 | 765 C |
| ATOM | 2095 | CB | GLN | B | 228 | 3.826 | −89.398 | −49.126 | 1.00 | 85.12 | C |
| ANISOU | 2095 | CB | GLN | B | 228 | 11926 | 9723 | 10693 | −715 | 106 | 773 C |
| ATOM | 2096 | CG | GLN | B | 228 | 2.385 | −89.323 | −49.573 | 1.00 | 78.85 | C |
| ANISOU | 2096 | CG | GLN | B | 228 | 11176 | 8961 | 9824 | −974 | 53 | 736 C |
| ATOM | 2097 | CD | GLN | B | 228 | 1.948 | −87.920 | −49.899 | 1.00 | 80.65 | C |
| ANISOU | 2097 | CD | GLN | B | 228 | 11286 | 9498 | 9858 | −1041 | 24 | 673 C |
| ATOM | 2098 | OE1 | GLN | B | 228 | 2.002 | −87.029 | −49.051 | 1.00 | 80.98 | O |
| ANISOU | 2098 | OE1 | GLN | B | 228 | 11189 | 9772 | 9807 | −980 | 14 | 796 O |
| ATOM | 2099 | NE2 | GLN | B | 228 | 1.521 | −87.706 | −51.139 | 1.00 | 84.72 | N |
| ANISOU | 2099 | NE2 | GLN | B | 228 | 11872 | 10014 | 10305 | −1170 | 14 | 481 N |
| ATOM | 2100 | C | GLN | B | 228 | 4.677 | −91.064 | −50.769 | 1.00 | 90.83 | C |
| ANISOU | 2100 | C | GLN | B | 228 | 12948 | 9915 | 11647 | −650 | 264 | 487 C |
| ATOM | 2101 | O | GLN | B | 228 | 5.680 | −90.609 | −51.322 | 1.00 | 93.30 | O |
| ANISOU | 2101 | O | GLN | B | 228 | 13232 | 10268 | 11950 | −496 | 344 | 360 O |
| ATOM | 2102 | N | THR | B | 229 | 3.774 | −91.805 | −51.395 | 1.00 | 84.09 | N |
| ANISOU | 2102 | N | THR | B | 229 | 12268 | 8866 | 10816 | −855 | 253 | 396 N |
| ATOM | 2103 | CA | THR | B | 229 | 3.910 | −92.155 | −52.796 | 1.00 | 81.57 | C |
| ANISOU | 2103 | CA | THR | B | 229 | 12154 | 8357 | 10481 | −917 | 331 | 124 C |
| ATOM | 2104 | CB | THR | B | 229 | 3.653 | −93.650 | −53.020 | 1.00 | 89.58 | C |
| ANISOU | 2104 | CB | THR | B | 229 | 13402 | 8970 | 11665 | −1004 | 382 | 91 C |
| ATOM | 2105 | OG1 | THR | B | 229 | 4.468 | −94.405 | −52.119 | 1.00 | 93.66 | O |
| ANISOU | 2105 | OG1 | THR | B | 229 | 13885 | 9310 | 12391 | −785 | 460 | 270 O |
| ATOM | 2106 | CG2 | THR | B | 229 | 3.988 | −94.051 | −54.451 | 1.00 | 92.26 | C |
| ANISOU | 2106 | CG2 | THR | B | 229 | 13998 | 9081 | 11978 | −1041 | 497 | −207 C |
| ATOM | 2107 | C | THR | B | 229 | 2.949 | −91.301 | −53.606 | 1.00 | 74.13 | C |
| ANISOU | 2107 | C | THR | B | 229 | 11214 | 7625 | 9327 | −1141 | 237 | −7 C |
| ATOM | 2108 | O | THR | B | 229 | 1.940 | −90.828 | −53.088 | 1.00 | 68.42 | O |
| ANISOU | 2108 | O | THR | B | 229 | 10366 | 7098 | 8533 | −1288 | 117 | 127 O |
| ATOM | 2109 | N | ILE | B | 230 | 3.284 | −91.080 | −54.870 | 1.00 | 86.55 | N |
| ANISOU | 2109 | N | ILE | B | 230 | 12925 | 9160 | 10801 | −1155 | 301 | −256 N |
| ATOM | 2110 | CA | ILE | B | 230 | 2.616 | −90.068 | −55.666 | 1.00 | 97.11 | C |
| ANISOU | 2110 | CA | ILE | B | 230 | 14237 | 10741 | 11919 | −1313 | 216 | −368 C |
| ATOM | 2111 | C | ILE | B | 230 | 1.945 | −90.697 | −56.854 | 1.00 | 103.87 | C |
| ANISOU | 2111 | C | ILE | B | 230 | 15354 | 11408 | 12705 | −1552 | 177 | −569 C |
| ATOM | 2112 | O | ILE | B | 230 | 2.503 | −91.586 | −57.496 | 1.00 | 103.69 | O |
| ANISOU | 2112 | O | ILE | B | 230 | 15572 | 11081 | 12743 | −1519 | 295 | −733 O |
| ATOM | 2113 | CB | ILE | B | 230 | 3.614 | −89.040 | −56.212 | 1.00 | 101.03 | C |
| ANISOU | 2113 | CB | ILE | B | 230 | 14673 | 11407 | 12307 | −1132 | 317 | −491 C |
| ATOM | 2114 | CG1 | ILE | B | 230 | 4.762 | −88.848 | −55.229 | 1.00 | 100.37 | C |
| ANISOU | 2114 | CG1 | ILE | B | 230 | 14412 | 11370 | 12352 | −855 | 401 | −352 C |
| ATOM | 2115 | CG2 | ILE | B | 230 | 2.916 | −87.721 | −56.492 | 1.00 | 99.24 | C |
| ANISOU | 2115 | CG2 | ILE | B | 230 | 14313 | 11518 | 11875 | −1244 | 217 | −490 C |
| ATOM | 2116 | CD1 | ILE | B | 230 | 4.298 | −88.390 | −53.865 | 1.00 | 100.15 | C |
| ANISOU | 2116 | CD1 | ILE | B | 230 | 14163 | 11556 | 12332 | −857 | 289 | −96 C |
| ATOM | 2117 | N | ASP | B | 231 | 0.749 | −90.222 | −57.159 | 1.00 | 110.22 | N |
| ANISOU | 2117 | N | ASP | B | 231 | 16112 | 12388 | 13377 | −1797 | 13 | −552 N |
| ATOM | 2118 | CA | ASP | B | 231 | 0.047 | −90.694 | −58.331 | 1.00 | 119.46 | C |
| ANISOU | 2118 | CA | ASP | B | 231 | 17521 | 13426 | 14444 | −2060 | −71 | −737 C |
| ATOM | 2119 | CB | ASP | B | 231 | −1.428 | −90.904 | −58.011 | 1.00 | 117.13 | C |
| ANISOU | 2119 | CB | ASP | B | 231 | 17140 | 13189 | 14176 | −2348 | −273 | −589 C |
| ATOM | 2120 | CG | ASP | B | 231 | −2.062 | −91.964 | −58.879 | 1.00 | 119.36 | C |
| ANISOU | 2120 | CG | ASP | B | 231 | 17703 | 13198 | 14450 | −2632 | −360 | −746 C |
| ATOM | 2121 | OD2 | ASP | B | 231 | −2.060 | −93.142 | −58.463 | 1.00 | 123.34 | O |
| ANISOU | 2121 | OD2 | ASP | B | 231 | 18328 | 13400 | 15135 | −2666 | −316 | −719 O |
| ATOM | 2122 | OD1 | ASP | B | 231 | −2.553 | −91.624 | −59.977 | 1.00 | 116.74 | O |
| ANISOU | 2122 | OD1 | ASP | B | 231 | 17481 | 12949 | 13927 | −2827 | −476 | −894 O |
| ATOM | 2123 | C | ASP | B | 231 | 0.180 | −89.661 | −59.429 | 1.00 | 124.08 | C |
| ANISOU | 2123 | C | ASP | B | 231 | 18139 | 14215 | 14791 | −2074 | −80 | −903 C |
| ATOM | 2124 | O | ASP | B | 231 | 0.368 | −90.005 | −60.598 | 1.00 | 124.61 | O |
| ANISOU | 2124 | O | ASP | B | 231 | 18480 | 14125 | 14741 | −2157 | −44 | −1138 O |
| ATOM | 2125 | N | ARG | B | 232 | 0.110 | −88.395 | −59.020 | 1.00 | 123.32 | N |
| ANISOU | 2125 | N | ARG | B | 232 | 17780 | 14457 | 14621 | −1985 | −111 | −777 N |
| ATOM | 2126 | CA | ARG | B | 232 | −0.134 | −87.270 | −59.921 | 1.00 | 120.75 | C |
| ANISOU | 2126 | CA | ARG | B | 232 | 17426 | 14381 | 14071 | −2045 | −165 | −862 C |
| ATOM | 2127 | CB | ARG | B | 232 | 0.000 | −85.937 | −59.181 | 1.00 | 111.88 | C |

TABLE 7-continued

| | | | | | | | | | | | |
|---|---|---|---|---|---|---|---|---|---|---|---|
| DMXAA-hSTING$^{G230I}$ complex | | | | | | | | | | | |
| ANISOU | 2127 | CB | ARG | B | 232 | 16001 | 13585 | 12925 | −1887 | −143 | −697 | C |
| ATOM | 2128 | CG | ARG | B | 232 | −0.742 | −85.877 | −57.864 | 1.00 | 106.07 | | C |
| ANISOU | 2128 | CG | ARG | B | 232 | 15031 | 12955 | 12316 | −1917 | −220 | −432 | C |
| ATOM | 2129 | CD | ARG | B | 232 | −2.209 | −85.469 | −58.008 | 1.00 | 105.07 | | C |
| ANISOU | 2129 | CD | ARG | B | 232 | 14786 | 13004 | 12131 | −2161 | −397 | −311 | C |
| ATOM | 2130 | NE | ARG | B | 232 | −2.598 | −84.446 | −57.033 | 1.00 | 102.74 | | N |
| ANISOU | 2130 | NE | ARG | B | 232 | 14211 | 12973 | 11852 | −2086 | −388 | −91 | N |
| ATOM | 2131 | CZ | ARG | B | 232 | −2.495 | −84.563 | −55.707 | 1.00 | 103.39 | | C |
| ANISOU | 2131 | CZ | ARG | B | 232 | 14166 | 13057 | 12060 | −1978 | −329 | 88 | C |
| ATOM | 2132 | NH1 | ARG | B | 232 | −2.010 | −85.668 | −55.153 | 1.00 | 106.19 | | N |
| ANISOU | 2132 | NH1 | ARG | B | 232 | 14622 | 13172 | 12555 | −1922 | −285 | 97 | N |
| ATOM | 2133 | NH2 | ARG | B | 232 | −2.880 | −83.564 | −54.922 | 1.00 | 97.17 | | N |
| ANISOU | 2133 | NH2 | ARG | B | 232 | 13161 | 12505 | 11252 | −1924 | −304 | 264 | N |
| ATOM | 2134 | C | ARG | B | 232 | 0.720 | −87.255 | −61.183 | 1.00 | 123.82 | | C |
| ANISOU | 2134 | C | ARG | B | 232 | 18068 | 14661 | 14315 | −1982 | −40 | −1130 | C |
| ATOM | 2135 | O | ARG | B | 232 | 1.802 | −87.840 | −61.236 | 1.00 | 127.43 | | O |
| ANISOU | 2135 | O | ARG | B | 232 | 18660 | 14895 | 14864 | −1803 | 145 | −1238 | O |
| ATOM | 2136 | N | ALA | B | 233 | 0.206 | −86.564 | −62.193 | 1.00 | 120.79 | | N |
| ANISOU | 2136 | N | ALA | B | 233 | 17744 | 14441 | 13709 | −2128 | −136 | −1220 | N |
| ATOM | 2137 | CA | ALA | B | 233 | 0.765 | −86.589 | −63.536 | 1.00 | 116.54 | | C |
| ANISOU | 2137 | CA | ALA | B | 233 | 17497 | 13801 | 12983 | −2134 | −43 | −1479 | C |
| ATOM | 2138 | CB | ALA | B | 233 | −0.140 | −85.839 | −64.479 | 1.00 | 107.16 | | C |
| ANISOU | 2138 | CB | ALA | B | 233 | 16337 | 12833 | 11546 | −2350 | −225 | −1507 | C |
| ATOM | 2139 | C | ALA | B | 233 | 2.178 | −86.031 | −63.620 | 1.00 | 121.46 | | C |
| ANISOU | 2139 | C | ALA | B | 233 | 18098 | 14440 | 13613 | −1826 | 209 | −1559 | C |
| ATOM | 2140 | O | ALA | B | 233 | 2.563 | −85.150 | −62.850 | 1.00 | 114.68 | | O |
| ANISOU | 2140 | O | ALA | B | 233 | 16960 | 13791 | 12823 | −1646 | 255 | −1414 | O |
| ATOM | 2141 | N | GLY | B | 234 | 2.941 | −86.548 | −64.579 | 1.00 | 131.81 | | N |
| ANISOU | 2141 | N | GLY | B | 234 | 19712 | 15519 | 14852 | −1777 | 377 | −1794 | N |
| ATOM | 2142 | CA | GLY | B | 234 | 4.302 | −86.103 | −64.805 | 1.00 | 135.87 | | C |
| ANISOU | 2142 | CA | GLY | B | 234 | 20222 | 16017 | 15387 | −1495 | 639 | −1881 | C |
| ATOM | 2143 | C | GLY | B | 234 | 5.242 | −86.488 | −63.680 | 1.00 | 145.69 | | C |
| ANISOU | 2143 | C | GLY | B | 234 | 21283 | 17151 | 16921 | −1239 | 781 | −1761 | C |
| ATOM | 2144 | O | GLY | B | 234 | 6.353 | −85.964 | −63.591 | 1.00 | 144.33 | | O |
| ANISOU | 2144 | O | GLY | B | 234 | 20997 | 17026 | 16817 | −994 | 965 | −1764 | O |
| ATOM | 2145 | N | ILE | B | 235 | 4.800 | −87.415 | −62.832 | 1.00 | 155.51 | | N |
| ANISOU | 2145 | N | ILE | B | 235 | 22497 | 18248 | 18342 | −1301 | 691 | −1644 | N |
| ATOM | 2146 | CA | ILE | B | 235 | 5.556 | −87.799 | −61.636 | 1.00 | 151.99 | | C |
| ANISOU | 2146 | CA | ILE | B | 235 | 21860 | 17721 | 18167 | −1076 | 779 | −1482 | C |
| ATOM | 2147 | CB | ILE | B | 235 | 5.568 | −86.633 | −60.600 | 1.00 | 138.87 | | C |
| ANISOU | 2147 | CB | ILE | B | 235 | 19830 | 16407 | 16528 | −976 | 694 | −1265 | C |
| ATOM | 2148 | CG1 | ILE | B | 235 | 6.451 | −86.947 | −59.398 | 1.00 | 133.39 | | C |
| ANISOU | 2148 | CG1 | ILE | B | 235 | 18946 | 15655 | 16081 | −744 | 768 | −1098 | C |
| ATOM | 2149 | CD1 | ILE | B | 235 | 6.095 | −86.150 | −58.163 | 1.00 | 130.97 | | C |
| ANISOU | 2149 | CD1 | ILE | B | 235 | 18341 | 15632 | 15789 | −731 | 630 | −864 | C |
| ATOM | 2150 | CG2 | ILE | B | 235 | 4.155 | −86.247 | −60.171 | 1.00 | 138.70 | | C |
| ANISOU | 2150 | CG2 | ILE | B | 235 | 19690 | 16594 | 16418 | −1204 | 457 | −1123 | C |
| ATOM | 2151 | C | ILE | B | 235 | 5.438 | −89.236 | −61.087 | 1.00 | 142.70 | | C |
| ANISOU | 2151 | C | ILE | B | 235 | 20772 | 16287 | 17161 | −1179 | 708 | −1404 | C |
| ATOM | 2152 | O | ILE | B | 235 | 5.874 | −89.548 | −59.976 | 1.00 | 140.03 | | O |
| ANISOU | 2152 | O | ILE | B | 235 | 20222 | 16016 | 16969 | −1147 | 617 | −1182 | O |
| ATOM | 2153 | N | LYS | B | 236 | 4.812 | −90.119 | −61.856 | 1.00 | 134.69 | | N |
| ANISOU | 2153 | N | LYS | B | 236 | 20092 | 14965 | 16120 | −1310 | 759 | −1589 | N |
| ATOM | 2154 | CA | LYS | B | 236 | 4.291 | −91.359 | −61.308 | 1.00 | 125.94 | | C |
| ANISOU | 2154 | CA | LYS | B | 236 | 19078 | 13600 | 15174 | −1431 | 693 | −1518 | C |
| ATOM | 2155 | CB | LYS | B | 236 | 3.765 | −92.287 | −62.409 | 1.00 | 123.68 | | C |
| ANISOU | 2155 | CB | LYS | B | 236 | 19193 | 13022 | 14779 | −1680 | 688 | −1754 | C |
| ATOM | 2156 | CG | LYS | B | 236 | 4.774 | −93.247 | −62.975 | 1.00 | 118.98 | | C |
| ANISOU | 2156 | CG | LYS | B | 236 | 18898 | 12028 | 14280 | −1530 | 968 | −1943 | C |
| ATOM | 2157 | CD | LYS | B | 236 | 4.067 | −94.332 | −63.757 | 1.00 | 112.62 | | C |
| ANISOU | 2157 | CD | LYS | B | 236 | 18491 | 10902 | 13397 | −1819 | 930 | −2138 | C |
| ATOM | 2158 | CE | LYS | B | 236 | 4.027 | −94.031 | −65.238 | 1.00 | 104.95 | | C |
| ANISOU | 2158 | CE | LYS | B | 236 | 17842 | 9922 | 12115 | −1963 | 964 | −2425 | C |
| ATOM | 2159 | NZ | LYS | B | 236 | 3.192 | −95.049 | −65.931 | 1.00 | 104.61 | | N |
| ANISOU | 2159 | NZ | LYS | B | 236 | 18184 | 9594 | 11969 | −2301 | 868 | −2607 | N |
| ATOM | 2160 | C | LYS | B | 236 | 5.300 | −92.055 | −60.400 | 1.00 | 119.11 | | C |
| ANISOU | 2160 | C | LYS | B | 236 | 18129 | 12531 | 14598 | −1157 | 862 | −1394 | C |
| ATOM | 2161 | O | LYS | B | 236 | 6.496 | −92.105 | −60.695 | 1.00 | 119.34 | | O |
| ANISOU | 2161 | O | LYS | B | 236 | 18197 | 12439 | 14707 | −913 | 1088 | −1475 | O |
| ATOM | 2162 | N | ASP | B | 237 | 4.804 | −92.535 | −59.266 | 1.00 | 115.87 | | N |
| ANISOU | 2162 | N | ASP | B | 237 | 17577 | 12100 | 14348 | −1191 | 748 | −1174 | N |
| ATOM | 2163 | CA | ASP | B | 237 | 5.586 | −93.357 | −58.351 | 1.00 | 113.72 | | C |
| ANISOU | 2163 | CA | ASP | B | 237 | 17244 | 11612 | 14352 | −966 | 869 | −1023 | C |
| ATOM | 2164 | CB | ASP | B | 237 | 5.972 | −94.673 | −59.022 | 1.00 | 116.41 | | C |
| ANISOU | 2164 | CB | ASP | B | 237 | 17924 | 11493 | 14814 | −954 | 1059 | −1194 | C |
| ATOM | 2165 | CG | ASP | B | 237 | 4.978 | −95.769 | −58.750 | 1.00 | 117.04 | | C |
| ANISOU | 2165 | CG | ASP | B | 237 | 18161 | 11333 | 14975 | −1189 | 957 | −1152 | C |
| ATOM | 2166 | OD1 | ASP | B | 237 | 3.867 | −95.718 | −59.316 | 1.00 | 117.48 | | O |

TABLE 7-continued

DMXAA-hSTING$^{G230I}$ complex

| | | | | | | | | | | | | |
|---|---|---|---|---|---|---|---|---|---|---|---|---|
| ANISOU | 2166 | OD1 | ASP | B | 237 | 18343 | 11438 | 14856 | −1503 | 793 | −1255 | O |
| ATOM | 2167 | OD2 | ASP | B | 237 | 5.302 | −96.674 | −57.953 | 1.00 | 113.38 | | O |
| ANISOU | 2167 | OD2 | ASP | B | 237 | 17683 | 10636 | 14759 | −1063 | 1033 | −999 | O |
| ATOM | 2168 | C | ASP | B | 237 | 6.823 | −92.692 | −57.752 | 1.00 | 104.16 | | C |
| ANISOU | 2168 | C | ASP | B | 237 | 15774 | 10559 | 13243 | −643 | 975 | −901 | C |
| ATOM | 2169 | O | ASP | B | 237 | 7.798 | −93.371 | −57.423 | 1.00 | 109.02 | | O |
| ANISOU | 2169 | O | ASP | B | 237 | 16388 | 10953 | 14083 | −414 | 1134 | −842 | O |
| ATOM | 2170 | N | ARG | B | 238 | 6.796 | −91.372 | −57.609 | 1.00 | 85.47 | | N |
| ANISOU | 2170 | N | ARG | B | 238 | 13183 | 8566 | 10726 | −627 | 885 | −856 | N |
| ATOM | 2171 | CA | ARG | B | 238 | 7.854 | −90.710 | −56.872 | 1.00 | 75.40 | | C |
| ANISOU | 2171 | CA | ARG | B | 238 | 11637 | 7464 | 9546 | −364 | 937 | −713 | C |
| ATOM | 2172 | CB | ARG | B | 238 | 7.801 | −89.201 | −57.072 | 1.00 | 59.15 | | C |
| ANISOU | 2172 | CB | ARG | B | 238 | 9408 | 5782 | 7285 | −383 | 873 | −741 | C |
| ATOM | 2173 | CG | ARG | B | 238 | 9.123 | −88.509 | −56.843 | 1.00 | 75.14 | | C |
| ANISOU | 2173 | CG | ARG | B | 238 | 11230 | 7928 | 9391 | −122 | 985 | −700 | C |
| ATOM | 2174 | CD | ARG | B | 238 | 9.622 | −87.841 | −58.116 | 1.00 | 74.99 | | C |
| ANISOU | 2174 | CD | ARG | B | 238 | 11301 | 7949 | 9243 | −87 | 1134 | −927 | C |
| ATOM | 2175 | NE | ARG | B | 238 | 9.274 | −86.424 | −58.164 | 1.00 | 71.44 | | N |
| ANISOU | 2175 | NE | ARG | B | 238 | 10698 | 7854 | 8590 | −161 | 1038 | −924 | N |
| ATOM | 2176 | CZ | ARG | B | 238 | 9.582 | −85.605 | −59.165 | 1.00 | 72.13 | | C |
| ANISOU | 2176 | CZ | ARG | B | 238 | 10829 | 8044 | 8534 | −148 | 1139 | −1087 | C |
| ATOM | 2177 | NH1 | ARG | B | 238 | 10.257 | −86.064 | −60.211 | 1.00 | 73.10 | | N |
| ANISOU | 2177 | NH1 | ARG | B | 238 | 11154 | 7943 | 8679 | −66 | 1348 | −1274 | N |
| ATOM | 2178 | NH2 | ARG | B | 238 | 9.218 | −84.329 | −59.123 | 1.00 | 74.26 | | N |
| ANISOU | 2178 | NH2 | ARG | B | 238 | 10953 | 8624 | 8636 | −213 | 1051 | −1059 | N |
| ATOM | 2179 | C | ARG | B | 238 | 7.633 | −91.057 | −55.409 | 1.00 | 80.76 | | C |
| ANISOU | 2179 | C | ARG | B | 238 | 12141 | 8179 | 10367 | −330 | 815 | −430 | C |
| ATOM | 2180 | O | ARG | B | 238 | 6.511 | −91.365 | −55.010 | 1.00 | 88.18 | | O |
| ANISOU | 2180 | O | ARG | B | 238 | 13114 | 9123 | 11268 | −531 | 675 | −347 | O |
| ATOM | 2181 | N | VAL | B | 239 | 8.685 | −91.044 | −54.603 | 1.00 | 61.80 | | N |
| ANISOU | 2181 | N | VAL | B | 239 | 9553 | 5796 | 8130 | −83 | 863 | −269 | N |
| ATOM | 2182 | CA | VAL | B | 239 | 8.494 | −91.237 | −53.173 | 1.00 | 68.99 | | C |
| ANISOU | 2182 | CA | VAL | B | 239 | 10301 | 6784 | 9129 | −54 | 730 | 12 | C |
| ATOM | 2183 | CB | VAL | B | 239 | 9.048 | −92.578 | −52.653 | 1.00 | 71.55 | | C |
| ANISOU | 2183 | CB | VAL | B | 239 | 10684 | 6779 | 9724 | 98 | 811 | 149 | C |
| ATOM | 2184 | CG1 | VAL | B | 239 | 8.890 | −92.661 | −51.144 | 1.00 | 70.00 | | C |
| ANISOU | 2184 | CG1 | VAL | B | 239 | 10316 | 6699 | 9580 | 133 | 663 | 457 | C |
| ATOM | 2185 | CG2 | VAL | B | 239 | 8.342 | −93.746 | −53.324 | 1.00 | 66.73 | | C |
| ANISOU | 2185 | CG2 | VAL | B | 239 | 10371 | 5819 | 9166 | −59 | 879 | 19 | C |
| ATOM | 2186 | C | VAL | B | 239 | 9.087 | −90.084 | −52.385 | 1.00 | 64.72 | | C |
| ANISOU | 2186 | C | VAL | B | 239 | 9482 | 6579 | 8531 | 69 | 653 | 148 | C |
| ATOM | 2187 | O | VAL | B | 239 | 10.280 | −89.810 | −52.465 | 1.00 | 59.43 | | O |
| ANISOU | 2187 | O | VAL | B | 239 | 8696 | 5928 | 7957 | 276 | 742 | 145 | O |
| ATOM | 2188 | N | TYR | B | 240 | 8.230 | −89.400 | −51.637 | 1.00 | 67.75 | | N |
| ANISOU | 2188 | N | TYR | B | 240 | 9763 | 7217 | 8761 | −68 | 496 | 267 | N |
| ATOM | 2189 | CA | TYR | B | 240 | 8.658 | −88.287 | −50.811 | 1.00 | 65.26 | | C |
| ANISOU | 2189 | CA | TYR | B | 240 | 9220 | 7215 | 8360 | 10 | 414 | 391 | C |
| ATOM | 2190 | CB | TYR | B | 240 | 7.656 | −87.153 | −50.891 | 1.00 | 52.70 | | C |
| ANISOU | 2190 | CB | TYR | B | 240 | 7591 | 5902 | 6530 | −175 | 334 | 345 | C |
| ATOM | 2191 | CG | TYR | B | 240 | 7.664 | −86.410 | −52.188 | 1.00 | 74.23 | | C |
| ANISOU | 2191 | CG | TYR | B | 240 | 10365 | 8702 | 9136 | −222 | 410 | 106 | C |
| ATOM | 2192 | CD2 | TYR | B | 240 | 8.281 | −85.175 | −52.299 | 1.00 | 61.95 | | C |
| ANISOU | 2192 | CD2 | TYR | B | 240 | 8667 | 7384 | 7486 | −145 | 433 | 57 | C |
| ATOM | 2193 | CE2 | TYR | B | 240 | 8.276 | −84.488 | −53.489 | 1.00 | 58.98 | | C |
| ANISOU | 2193 | CE2 | TYR | B | 240 | 8343 | 7073 | 6994 | −185 | 512 | −147 | C |
| ATOM | 2194 | CZ | TYR | B | 240 | 7.650 | −85.036 | −54.593 | 1.00 | 73.55 | | C |
| ANISOU | 2194 | CZ | TYR | B | 240 | 10398 | 8755 | 8795 | −311 | 552 | −310 | C |
| ATOM | 2195 | OH | TYR | B | 240 | 7.640 | −84.358 | −55.788 | 1.00 | 68.54 | | O |
| ANISOU | 2195 | OH | TYR | B | 240 | 9835 | 8189 | 8018 | −355 | 622 | −503 | O |
| ATOM | 2196 | CE1 | TYR | B | 240 | 7.028 | −86.262 | −54.504 | 1.00 | 82.85 | | C |
| ANISOU | 2196 | CE1 | TYR | B | 240 | 11725 | 9696 | 10060 | −406 | 515 | −277 | C |
| ATOM | 2197 | CD1 | TYR | B | 240 | 7.046 | −86.938 | −53.307 | 1.00 | 78.22 | | C |
| ANISOU | 2197 | CD1 | TYR | B | 240 | 11073 | 9037 | 9611 | −356 | 455 | −69 | C |
| ATOM | 2198 | C | TYR | B | 240 | 8.757 | −88.702 | −49.364 | 1.00 | 70.75 | | C |
| ANISOU | 2198 | C | TYR | B | 240 | 9821 | 7925 | 9135 | 74 | 311 | 669 | C |
| ATOM | 2199 | O | TYR | B | 240 | 8.005 | −89.556 | −48.894 | 1.00 | 71.35 | | O |
| ANISOU | 2199 | O | TYR | B | 240 | 9993 | 7856 | 9259 | −15 | 271 | 782 | O |
| ATOM | 2200 | N | SER | B | 241 | 9.675 | −88.075 | −48.649 | 1.00 | 73.13 | | N |
| ANISOU | 2200 | N | SER | B | 241 | 9938 | 8407 | 9441 | 217 | 259 | 784 | N |
| ATOM | 2201 | CA | SER | B | 241 | 9.734 | −88.242 | −47.215 | 1.00 | 74.30 | | C |
| ANISOU | 2201 | CA | SER | B | 241 | 10000 | 8633 | 9596 | 255 | 131 | 1053 | C |
| ATOM | 2202 | CB | SER | B | 241 | 10.872 | −89.179 | −46.813 | 1.00 | 70.03 | | C |
| ANISOU | 2202 | CB | SER | B | 241 | 9402 | 7902 | 9304 | 474 | 144 | 1206 | C |
| ATOM | 2203 | OG | SER | B | 241 | 12.097 | −88.479 | −46.758 | 1.00 | 76.28 | | O |
| ANISOU | 2203 | OG | SER | B | 241 | 10001 | 8845 | 10137 | 627 | 128 | 1215 | O |
| ATOM | 2204 | C | SER | B | 241 | 9.921 | −86.870 | −46.586 | 1.00 | 69.65 | | C |
| ANISOU | 2204 | C | SER | B | 241 | 9258 | 8389 | 8816 | 236 | 34 | 1094 | C |
| ATOM | 2205 | O | SER | B | 241 | 10.463 | −85.956 | −47.209 | 1.00 | 61.40 | | O |

TABLE 7-continued

DMXAA-hSTING<sup>G230I</sup> complex

| | | | | | | | | | | | |
|---|---|---|---|---|---|---|---|---|---|---|---|
| ANISOU | 2205 | O | SER | B | 241 | 8128 | 7480 | 7720 | 269 | 78 | 945 | O |
| ATOM | 2206 | N | ASN | B | 242 | 9.454 | −86.732 | −45.354 | 1.00 | 70.57 | | N |
| ANISOU | 2206 | N | ASN | B | 242 | 9359 | 8634 | 8819 | 174 | −83 | 1293 | N |
| ATOM | 2207 | CA | ASN | B | 242 | 9.621 | −85.505 | −44.603 | 1.00 | 52.13 | | C |
| ANISOU | 2207 | CA | ASN | B | 242 | 6916 | 6601 | 6288 | 145 | −173 | 1345 | C |
| ATOM | 2208 | CB | ASN | B | 242 | 8.276 | −84.819 | −44.395 | 1.00 | 60.04 | | C |
| ANISOU | 2208 | CB | ASN | B | 242 | 7990 | 7750 | 7073 | −47 | −167 | 1325 | C |
| ATOM | 2209 | CG | ASN | B | 242 | 7.598 | −84.466 | −45.700 | 1.00 | 59.03 | | C |
| ANISOU | 2209 | CG | ASN | B | 242 | 7909 | 7604 | 6916 | −148 | −62 | 1098 | C |
| ATOM | 2210 | OD1 | ASN | B | 242 | 6.952 | −85.311 | −46.322 | 1.00 | 58.02 | | O |
| ANISOU | 2210 | OD1 | ASN | B | 242 | 7889 | 7279 | 6877 | −214 | −15 | 1047 | O |
| ATOM | 2211 | ND2 | ASN | B | 242 | 7.762 | −83.217 | −46.138 | 1.00 | 53.49 | | N |
| ANISOU | 2211 | ND2 | ASN | B | 242 | 7135 | 7103 | 6086 | −168 | −32 | 962 | N |
| ATOM | 2212 | C | ASN | B | 242 | 10.268 | −85.802 | −43.267 | 1.00 | 57.66 | | C |
| ANISOU | 2212 | C | ASN | B | 242 | 7555 | 7349 | 7005 | 236 | −311 | 1601 | C |
| ATOM | 2213 | O | ASN | B | 242 | 10.037 | −86.858 | −42.681 | 1.00 | 55.55 | | O |
| ANISOU | 2213 | O | ASN | B | 242 | 7361 | 6918 | 6829 | 261 | −342 | 1778 | O |
| ATOM | 2214 | N | SER | B | 243 | 11.069 | −84.863 | −42.781 | 1.00 | 55.40 | | N |
| ANISOU | 2214 | N | SER | B | 243 | 7141 | 7285 | 6625 | 275 | −402 | 1628 | N |
| ATOM | 2215 | CA | SER | B | 243 | 11.867 | −85.090 | −41.589 | 1.00 | 57.61 | | C |
| ANISOU | 2215 | CA | SER | B | 243 | 7346 | 7628 | 6916 | 362 | −567 | 1868 | C |
| ATOM | 2216 | CB | SER | B | 243 | 13.307 | −84.661 | −41.827 | 1.00 | 63.12 | | C |
| ANISOU | 2216 | CB | SER | B | 243 | 7842 | 8405 | 7736 | 496 | −620 | 1842 | C |
| ATOM | 2217 | OG | SER | B | 243 | 13.840 | −85.318 | −42.955 | 1.00 | 80.80 | | O |
| ANISOU | 2217 | OG | SER | B | 243 | 10033 | 10425 | 10241 | 630 | −482 | 1733 | O |
| ATOM | 2218 | C | SER | B | 243 | 11.320 | −84.377 | −40.367 | 1.00 | 64.20 | | C |
| ANISOU | 2218 | C | SER | B | 243 | 8245 | 8683 | 7465 | 232 | −676 | 1988 | C |
| ATOM | 2219 | O | SER | B | 243 | 10.816 | −83.258 | −40.456 | 1.00 | 64.72 | | O |
| ANISOU | 2219 | O | SER | B | 243 | 8335 | 8926 | 7328 | 111 | −634 | 1858 | O |
| ATOM | 2220 | N | ILE | B | 244 | 11.450 | −85.032 | −39.219 | 1.00 | 63.60 | | N |
| ANISOU | 2220 | N | ILE | B | 244 | 8209 | 8586 | 7370 | 265 | −803 | 2245 | N |
| ATOM | 2221 | CA | ILE | B | 244 | 10.965 | −84.496 | −37.958 | 1.00 | 70.32 | | C |
| ANISOU | 2221 | CA | ILE | B | 244 | 9162 | 9621 | 7935 | 149 | −899 | 2383 | C |
| ATOM | 2222 | CB | ILE | B | 244 | 10.158 | −85.544 | −37.200 | 1.00 | 69.84 | | C |
| ANISOU | 2222 | CB | ILE | B | 244 | 9254 | 9415 | 7867 | 127 | −893 | 2598 | C |
| ATOM | 2223 | CG1 | ILE | B | 244 | 9.018 | −86.055 | −38.068 | 1.00 | 65.43 | | C |
| ANISOU | 2223 | CG1 | ILE | B | 244 | 8778 | 8668 | 7413 | 60 | −708 | 2479 | C |
| ATOM | 2224 | CD1 | ILE | B | 244 | 8.306 | −87.231 | −37.472 | 1.00 | 61.07 | | C |
| ANISOU | 2224 | CD1 | ILE | B | 244 | 8355 | 7926 | 6923 | 46 | −687 | 2687 | C |
| ATOM | 2225 | CG2 | ILE | B | 244 | 9.621 | −84.972 | −35.901 | 1.00 | 69.56 | | C |
| ANISOU | 2225 | CG2 | ILE | B | 244 | 9354 | 9562 | 7512 | 6 | −958 | 2737 | C |
| ATOM | 2226 | C | ILE | B | 244 | 12.135 | −84.060 | −37.093 | 1.00 | 71.63 | | C |
| ANISOU | 2226 | C | ILE | B | 244 | 9228 | 9966 | 8023 | 197 | −1109 | 2515 | C |
| ATOM | 2227 | O | ILE | B | 244 | 13.123 | −84.779 | −36.970 | 1.00 | 78.15 | | O |
| ANISOU | 2227 | O | ILE | B | 244 | 9935 | 10711 | 9049 | 343 | −1221 | 2660 | O |
| ATOM | 2228 | N | TYR | B | 245 | 12.022 | −82.886 | −36.487 | 1.00 | 68.99 | | N |
| ANISOU | 2228 | N | TYR | B | 245 | 8942 | 9867 | 7403 | 70 | −1165 | 2472 | N |
| ATOM | 2229 | CA | TYR | B | 245 | 13.115 | −82.332 | −35.708 | 1.00 | 72.23 | | C |
| ANISOU | 2229 | CA | TYR | B | 245 | 9267 | 10466 | 7710 | 73 | −1385 | 2567 | C |
| ATOM | 2230 | CB | TYR | B | 245 | 13.679 | −81.097 | −36.398 | 1.00 | 64.00 | | C |
| ANISOU | 2230 | CB | TYR | B | 245 | 8094 | 9572 | 6649 | 33 | −1360 | 2334 | C |
| ATOM | 2231 | CG | TYR | B | 245 | 14.442 | −81.406 | −37.660 | 1.00 | 65.21 | | C |
| ANISOU | 2231 | CG | TYR | B | 245 | 8040 | 9603 | 7134 | 178 | −1284 | 2215 | C |
| ATOM | 2232 | CD1 | TYR | B | 245 | 13.778 | −81.569 | −38.876 | 1.00 | 54.88 | | C |
| ANISOU | 2232 | CD1 | TYR | B | 245 | 6758 | 8147 | 5946 | 196 | −1057 | 2021 | C |
| ATOM | 2233 | CE1 | TYR | B | 245 | 14.472 | −81.854 | −40.029 | 1.00 | 54.85 | | C |
| ANISOU | 2233 | CE1 | TYR | B | 245 | 6604 | 8020 | 6216 | 326 | −965 | 1905 | C |
| ATOM | 2234 | CZ | TYR | B | 245 | 15.857 | −81.982 | −39.979 | 1.00 | 68.45 | | C |
| ANISOU | 2234 | CZ | TYR | B | 245 | 8113 | 9761 | 8133 | 456 | −1084 | 1995 | C |
| ATOM | 2235 | OH | TYR | B | 245 | 16.572 | −82.265 | −41.122 | 1.00 | 56.99 | | O |
| ANISOU | 2235 | OH | TYR | B | 245 | 6515 | 8174 | 6964 | 599 | −956 | 1886 | O |
| ATOM | 2236 | CE2 | TYR | B | 245 | 16.538 | −81.824 | −38.782 | 1.00 | 60.73 | | C |
| ANISOU | 2236 | CE2 | TYR | B | 245 | 7070 | 8940 | 7067 | 439 | −1330 | 2204 | C |
| ATOM | 2237 | CD2 | TYR | B | 245 | 15.829 | −81.538 | −37.637 | 1.00 | 62.09 | | C |
| ANISOU | 2237 | CD2 | TYR | B | 245 | 7425 | 9238 | 6929 | 294 | −1436 | 2305 | C |
| ATOM | 2238 | C | TYR | B | 245 | 12.680 | −81.971 | −34.301 | 1.00 | 83.23 | | C |
| ANISOU | 2238 | C | TYR | B | 245 | 10854 | 12009 | 8759 | −58 | −1493 | 2719 | C |
| ATOM | 2239 | O | TYR | B | 245 | 11.529 | −81.603 | −34.075 | 1.00 | 91.08 | | O |
| ANISOU | 2239 | O | TYR | B | 245 | 12031 | 13023 | 9552 | −176 | −1350 | 2666 | O |
| ATOM | 2240 | N | GLU | B | 246 | 13.596 | −82.083 | −33.348 | 1.00 | 81.90 | | N |
| ANISOU | 2240 | N | GLU | B | 246 | 10650 | 11947 | 8522 | −37 | −1745 | 2920 | N |
| ATOM | 2241 | CA | GLU | B | 246 | 13.318 | −81.576 | −32.018 | 1.00 | 86.01 | | C |
| ANISOU | 2241 | CA | GLU | B | 246 | 11379 | 12635 | 8666 | −181 | −1862 | 3037 | C |
| ATOM | 2242 | CB | GLU | B | 246 | 13.632 | −82.606 | −30.927 | 1.00 | 96.92 | | C |
| ANISOU | 2242 | CB | GLU | B | 246 | 12823 | 13982 | 10019 | −120 | −2064 | 3373 | C |
| ATOM | 2243 | CG | GLU | B | 246 | 15.082 | −82.672 | −30.488 | 1.00 | 108.60 | | C |
| ANISOU | 2243 | CG | GLU | B | 246 | 14118 | 15577 | 11567 | −58 | −2379 | 3537 | C |
| ATOM | 2244 | CD | GLU | B | 246 | 15.432 | −84.013 | −29.872 | 1.00 | 123.05 | | C |

TABLE 7-continued

| DMXAA-hSTING$^{G230I}$ complex | | | | | | | | | | | | |
|---|---|---|---|---|---|---|---|---|---|---|---|---|
| ANISOU | 2244 | CD | GLU | B | 246 | 15927 | 17289 | 13536 | 82 | −2530 | 3876 | C |
| ATOM | 2245 | OE1 | GLU | B | 246 | 15.051 | −84.262 | −28.705 | 1.00 | 123.49 | | O |
| ANISOU | 2245 | OE1 | GLU | B | 246 | 16203 | 17395 | 13321 | 13 | −2630 | 4085 | O |
| ATOM | 2246 | OE2 | GLU | B | 246 | 16.076 | −84.827 | −30.566 | 1.00 | 130.20 | | O |
| ANISOU | 2246 | OE2 | GLU | B | 246 | 16606 | 18037 | 14825 | 269 | −2528 | 3938 | O |
| ATOM | 2247 | C | GLU | B | 246 | 14.092 | −80.290 | −31.806 | 1.00 | 84.01 | | C |
| ANISOU | 2247 | C | GLU | B | 246 | 11073 | 12613 | 8235 | −290 | −2001 | 2917 | C |
| ATOM | 2248 | O | GLU | B | 246 | 15.216 | −80.127 | −32.291 | 1.00 | 79.50 | | O |
| ANISOU | 2248 | O | GLU | B | 246 | 10260 | 12086 | 7862 | −222 | −2124 | 2880 | O |
| ATOM | 2249 | N | LEU | B | 247 | 13.462 | −79.370 | −31.091 | 1.00 | 90.72 | | N |
| ANISOU | 2249 | N | LEU | B | 247 | 12154 | 13596 | 8720 | −463 | −1958 | 2852 | N |
| ATOM | 2250 | CA | LEU | B | 247 | 14.046 | −78.076 | −30.811 | 1.00 | 95.56 | | C |
| ANISOU | 2250 | CA | LEU | B | 247 | 12776 | 14414 | 9120 | −603 | −2065 | 2718 | C |
| ATOM | 2251 | CB | LEU | B | 247 | 13.072 | −76.983 | −31.208 | 1.00 | 87.34 | | C |
| ANISOU | 2251 | CB | LEU | B | 247 | 11875 | 13397 | 7914 | −718 | −1790 | 2466 | C |
| ATOM | 2252 | CG | LEU | B | 247 | 12.490 | −77.211 | −32.592 | 1.00 | 81.32 | | C |
| ANISOU | 2252 | CG | LEU | B | 247 | 10978 | 12481 | 7440 | −614 | −1537 | 2308 | C |
| ATOM | 2253 | CD1 | LEU | B | 247 | 11.454 | −76.169 | −32.813 | 1.00 | 82.23 | | C |
| ANISOU | 2253 | CD1 | LEU | B | 247 | 11241 | 12629 | 7372 | −726 | −1284 | 2116 | C |
| ATOM | 2254 | CD2 | LEU | B | 247 | 13.584 | −77.114 | −33.638 | 1.00 | 75.08 | | C |
| ANISOU | 2254 | CD2 | LEU | B | 247 | 9894 | 11687 | 6947 | −517 | −1600 | 2194 | C |
| ATOM | 2255 | C | LEU | B | 247 | 14.319 | −77.990 | −29.330 | 1.00 | 99.21 | | C |
| ANISOU | 2255 | C | LEU | B | 247 | 13437 | 15018 | 9241 | −720 | −2306 | 2914 | C |
| ATOM | 2256 | O | LEU | B | 247 | 13.601 | −78.584 | −28.525 | 1.00 | 101.58 | | O |
| ANISOU | 2256 | O | LEU | B | 247 | 13950 | 15240 | 9404 | −719 | −2252 | 3052 | O |
| ATOM | 2257 | N | LEU | B | 248 | 15.337 | −77.259 | −28.929 | 1.00 | 97.94 | | N |
| ANISOU | 2257 | N | LEU | B | 248 | 13204 | 15014 | 8995 | −808 | −2533 | 2872 | N |
| ATOM | 2258 | CA | LEU | B | 248 | 15.681 | −77.234 | −27.525 | 1.00 | 102.92 | | C |
| ANISOU | 2258 | CA | LEU | B | 248 | 13989 | 15685 | 9431 | −871 | −2718 | 2957 | C |
| ATOM | 2259 | CB | LEU | B | 248 | 17.048 | −77.859 | −27.315 | 1.00 | 99.32 | | C |
| ANISOU | 2259 | CB | LEU | B | 248 | 13268 | 15289 | 9182 | −786 | −3067 | 3174 | C |
| ATOM | 2260 | CG | LEU | B | 248 | 17.505 | −78.935 | −28.285 | 1.00 | 89.53 | | C |
| ANISOU | 2260 | CG | LEU | B | 248 | 11732 | 13958 | 8327 | −574 | −3135 | 3398 | C |
| ATOM | 2261 | CD1 | LEU | B | 248 | 18.782 | −79.583 | −27.795 | 1.00 | 79.76 | | C |
| ANISOU | 2261 | CD1 | LEU | B | 248 | 10273 | 12766 | 7264 | −494 | −3462 | 3619 | C |
| ATOM | 2262 | CD2 | LEU | B | 248 | 16.441 | −79.989 | −28.464 | 1.00 | 86.34 | | C |
| ANISOU | 2262 | CD2 | LEU | B | 248 | 11471 | 13373 | 7962 | −465 | −2956 | 3547 | C |
| ATOM | 2263 | C | LEU | B | 248 | 15.661 | −75.850 | −26.900 | 1.00 | 110.24 | | C |
| ANISOU | 2263 | C | LEU | B | 248 | 15107 | 16704 | 10077 | −1056 | −2680 | 2719 | C |
| ATOM | 2264 | O | LEU | B | 248 | 16.100 | −74.882 | −27.510 | 1.00 | 111.08 | | O |
| ANISOU | 2264 | O | LEU | B | 248 | 15104 | 16889 | 10211 | −1136 | −2663 | 2524 | O |
| ATOM | 2265 | N | GLU | B | 249 | 15.133 | −75.757 | −25.685 | 1.00 | 107.55 | | N |
| ANISOU | 2265 | N | GLU | B | 249 | 15057 | 16340 | 9469 | −1115 | −2653 | 2742 | N |
| ATOM | 2266 | CA | GLU | B | 249 | 15.349 | −74.591 | −24.850 | 1.00 | 107.14 | | C |
| ANISOU | 2266 | CA | GLU | B | 249 | 15188 | 16371 | 9148 | −1280 | −2695 | 2581 | C |
| ATOM | 2267 | CB | GLU | B | 249 | 14.046 | −73.874 | −24.516 | 1.00 | 104.50 | | C |
| ANISOU | 2267 | CB | GLU | B | 249 | 15161 | 15953 | 8592 | −1335 | −2345 | 2400 | C |
| ATOM | 2268 | CG | GLU | B | 249 | 14.199 | −72.367 | −24.602 | 1.00 | 112.35 | | C |
| ANISOU | 2268 | CG | GLU | B | 249 | 16190 | 16986 | 9514 | −1464 | −2220 | 2115 | C |
| ATOM | 2269 | CD | GLU | B | 249 | 12.937 | −71.598 | −24.308 | 1.00 | 116.37 | | C |
| ANISOU | 2269 | CD | GLU | B | 249 | 16973 | 17393 | 9850 | −1486 | −1858 | 1956 | C |
| ATOM | 2270 | OE1 | GLU | B | 249 | 12.294 | −71.123 | −25.256 | 1.00 | 114.53 | | O |
| ANISOU | 2270 | OE1 | GLU | B | 249 | 16688 | 17090 | 9737 | −1447 | −1588 | 1818 | O |
| ATOM | 2271 | OE2 | GLU | B | 249 | 12.599 | −71.444 | −23.129 | 1.00 | 118.74 | | O |
| ANISOU | 2271 | OE2 | GLU | B | 249 | 17527 | 17685 | 9903 | −1535 | −1841 | 1979 | O |
| ATOM | 2272 | C | GLU | B | 249 | 16.060 | −75.028 | −23.586 | 1.00 | 112.53 | | C |
| ANISOU | 2272 | C | GLU | B | 249 | 15940 | 17113 | 9703 | −1295 | −2986 | 2781 | C |
| ATOM | 2273 | O | GLU | B | 249 | 15.608 | −75.930 | −22.908 | 1.00 | 121.73 | | O |
| ANISOU | 2273 | O | GLU | B | 249 | 17245 | 18207 | 10801 | −1213 | −2959 | 2961 | O |
| ATOM | 2274 | N | ASN | B | 250 | 17.176 | −74.399 | −23.262 | 1.00 | 109.84 | | N |
| ANISOU | 2274 | N | ASN | B | 250 | 15489 | 16903 | 9341 | −1402 | −3266 | 2758 | N |
| ATOM | 2275 | CA | ASN | B | 250 | 17.925 | −74.807 | −22.090 | 1.00 | 120.61 | | C |
| ANISOU | 2275 | CA | ASN | B | 250 | 16880 | 18349 | 10596 | −1432 | −3585 | 2949 | C |
| ATOM | 2276 | CB | ASN | B | 250 | 17.037 | −74.702 | −20.868 | 1.00 | 129.25 | | C |
| ANISOU | 2276 | CB | ASN | B | 250 | 18374 | 19422 | 11314 | −1509 | −3484 | 2933 | C |
| ATOM | 2277 | CG | ASN | B | 250 | 16.461 | −73.322 | −20.696 | 1.00 | 131.19 | | C |
| ANISOU | 2277 | CG | ASN | B | 250 | 18854 | 19662 | 11329 | −1665 | −3254 | 2636 | C |
| ATOM | 2278 | OD1 | ASN | B | 250 | 17.194 | −72.338 | −20.649 | 1.00 | 136.26 | | O |
| ANISOU | 2278 | OD1 | ASN | B | 250 | 19487 | 20399 | 11888 | −1826 | −3399 | 2501 | O |
| ATOM | 2279 | ND2 | ASN | B | 250 | 15.145 | −73.237 | −20.596 | 1.00 | 125.70 | | N |
| ANISOU | 2279 | ND2 | ASN | B | 250 | 18357 | 18845 | 10557 | −1615 | −2884 | 2540 | N |
| ATOM | 2280 | C | ASN | B | 250 | 18.472 | −76.226 | −22.190 | 1.00 | 117.49 | | C |
| ANISOU | 2280 | C | ASN | B | 250 | 16252 | 17930 | 10458 | −1252 | −3789 | 3263 | C |
| ATOM | 2281 | O | ASN | B | 250 | 18.643 | −76.908 | −21.198 | 1.00 | 115.12 | | O |
| ANISOU | 2281 | O | ASN | B | 250 | 16056 | 17641 | 10045 | −1222 | −3947 | 3465 | O |
| ATOM | 2282 | N | GLY | B | 251 | 18.753 | −76.666 | −23.399 | 1.00 | 114.76 | | N |
| ANISOU | 2282 | N | GLY | B | 251 | 15594 | 17546 | 10465 | −1123 | −3773 | 3307 | N |
| ATOM | 2283 | CA | GLY | B | 251 | 19.474 | −77.898 | −23.590 | 1.00 | 114.27 | | C |

TABLE 7-continued

| DMXAA-hSTING$^{G230I}$ complex | | | | | | | | | | | |
|---|---|---|---|---|---|---|---|---|---|---|---|
| ANISOU | 2283 | CA | GLY | B | 251 | 15272 | 17440 | 10708 | −934 | −3950 | 3600 | C |
| ATOM | 2284 | C | GLY | B | 251 | 18.570 | −79.078 | −23.477 | 1.00 | 117.08 | | C |
| ANISOU | 2284 | C | GLY | B | 251 | 15777 | 17634 | 11072 | −792 | −3773 | 3761 | C |
| ATOM | 2285 | O | GLY | B | 251 | 19.023 | −80.206 | −23.568 | 1.00 | 120.17 | | O |
| ANISOU | 2285 | O | GLY | B | 251 | 15997 | 17947 | 11714 | −619 | −3876 | 4017 | O |
| ATOM | 2286 | N | GLN | B | 252 | 17.283 | −78.811 | −23.313 | 1.00 | 117.47 | | N |
| ANISOU | 2286 | N | GLN | B | 252 | 16142 | 17620 | 10870 | −860 | −3490 | 3617 | N |
| ATOM | 2287 | CA | GLN | B | 252 | 16.277 | −79.854 | −23.204 | 1.00 | 119.13 | | C |
| ANISOU | 2287 | CA | GLN | B | 252 | 16504 | 17669 | 11090 | −748 | −3281 | 3747 | C |
| ATOM | 2288 | CB | GLN | B | 252 | 15.707 | −79.884 | −21.791 | 1.00 | 131.29 | | C |
| ANISOU | 2288 | CB | GLN | B | 252 | 18387 | 19205 | 12292 | −800 | −3256 | 3816 | C |
| ATOM | 2289 | CG | GLN | B | 252 | 14.357 | −80.573 | −21.648 | 1.00 | 137.67 | | C |
| ANISOU | 2289 | CG | GLN | B | 252 | 19424 | 19854 | 13030 | −744 | −2935 | 3850 | C |
| ATOM | 2290 | CD | GLN | B | 252 | 14.341 | −81.963 | −22.230 | 1.00 | 142.83 | | C |
| ANISOU | 2290 | CD | GLN | B | 252 | 19942 | 20349 | 13976 | −568 | −2922 | 4101 | C |
| ATOM | 2291 | OE1 | GLN | B | 252 | 15.237 | −82.340 | −22.975 | 1.00 | 145.38 | | O |
| ANISOU | 2291 | OE1 | GLN | B | 252 | 19974 | 20662 | 14603 | −463 | −3103 | 4226 | O |
| ATOM | 2292 | NE2 | GLN | B | 252 | 13.313 | −82.731 | −21.903 | 1.00 | 143.70 | | N |
| ANISOU | 2292 | NE2 | GLN | B | 252 | 20262 | 20321 | 14018 | −529 | −2687 | 4179 | N |
| ATOM | 2293 | C | GLN | B | 252 | 15.171 | −79.620 | −24.209 | 1.00 | 108.97 | | C |
| ANISOU | 2293 | C | GLN | B | 252 | 15261 | 16285 | 9856 | −749 | −2939 | 3567 | C |
| ATOM | 2294 | O | GLN | B | 252 | 14.888 | −78.498 | −24.572 | 1.00 | 101.43 | | O |
| ANISOU | 2294 | O | GLN | B | 252 | 14387 | 15385 | 8765 | −870 | −2790 | 3308 | O |
| ATOM | 2295 | N | ARG | B | 253 | 14.539 | −80.701 | −24.640 | 1.00 | 112.48 | | N |
| ANISOU | 2295 | N | ARG | B | 253 | 15778 | 18102 | 8859 | −576 | −1105 | 2972 | N |
| ATOM | 2296 | CA | ARG | B | 253 | 13.600 | −80.650 | −25.738 | 1.00 | 106.03 | | C |
| ANISOU | 2296 | CA | ARG | B | 253 | 14840 | 17175 | 8273 | −515 | −806 | 2892 | C |
| ATOM | 2297 | CB | ARG | B | 253 | 13.054 | −82.041 | −26.039 | 1.00 | 104.27 | | C |
| ANISOU | 2297 | CB | ARG | B | 253 | 14450 | 16845 | 8323 | −417 | −672 | 3195 | C |
| ATOM | 2298 | CG | ARG | B | 253 | 11.713 | −82.084 | −26.750 | 1.00 | 104.17 | | C |
| ANISOU | 2298 | CG | ARG | B | 253 | 14318 | 16730 | 8534 | −366 | −351 | 3144 | C |
| ATOM | 2299 | CD | ARG | B | 253 | 11.300 | −83.510 | −27.032 | 1.00 | 106.79 | | C |
| ANISOU | 2299 | CD | ARG | B | 253 | 14518 | 16937 | 9121 | −299 | −232 | 3446 | C |
| ATOM | 2300 | NE | ARG | B | 253 | 12.413 | −84.313 | −27.519 | 1.00 | 109.44 | | N |
| ANISOU | 2300 | NE | ARG | B | 253 | 14665 | 17183 | 9734 | −239 | −489 | 3644 | N |
| ATOM | 2301 | CZ | ARG | B | 253 | 12.302 | −85.576 | −27.902 | 1.00 | 109.01 | | C |
| ANISOU | 2301 | CZ | ARG | B | 253 | 14495 | 16976 | 9947 | −174 | −435 | 3903 | C |
| ATOM | 2302 | NH1 | ARG | B | 253 | 11.131 | −86.170 | −27.856 | 1.00 | 110.67 | | N |
| ANISOU | 2302 | NH1 | ARG | B | 253 | 14746 | 17118 | 10187 | −184 | −153 | 3999 | N |
| ATOM | 2303 | NH2 | ARG | B | 253 | 13.358 | −86.246 | −28.328 | 1.00 | 104.40 | | N |
| ANISOU | 2303 | NH2 | ARG | B | 253 | 13757 | 16293 | 9616 | −98 | −647 | 4062 | N |
| ATOM | 2304 | C | ARG | B | 253 | 12.501 | −79.736 | −25.337 | 1.00 | 101.97 | | C |
| ANISOU | 2304 | C | ARG | B | 253 | 14578 | 16686 | 7481 | −543 | −481 | 2660 | C |
| ATOM | 2305 | O | ARG | B | 253 | 11.990 | −79.831 | −24.251 | 1.00 | 100.27 | | O |
| ANISOU | 2305 | O | ARG | B | 253 | 14606 | 16517 | 6975 | −551 | −312 | 2719 | O |
| ATOM | 2306 | N | ALA | B | 254 | 12.131 | −78.847 | −26.237 | 1.00 | 98.19 | | N |
| ANISOU | 2306 | N | ALA | B | 254 | 14040 | 16165 | 7102 | −544 | −373 | 2403 | N |
| ATOM | 2307 | CA | ALA | B | 254 | 11.086 | −77.879 | −25.945 | 1.00 | 89.90 | | C |
| ANISOU | 2307 | CA | ALA | B | 254 | 13209 | 15115 | 5833 | −545 | −45 | 2158 | C |
| ATOM | 2308 | CB | ALA | B | 254 | 11.694 | −76.511 | −25.678 | 1.00 | 91.63 | | C |
| ANISOU | 2308 | CB | ALA | B | 254 | 13645 | 15367 | 5806 | −634 | −177 | 1837 | C |
| ATOM | 2309 | C | ALA | B | 254 | 10.088 | −77.798 | −27.091 | 1.00 | 85.63 | | C |
| ANISOU | 2309 | C | ALA | B | 254 | 12443 | 14488 | 5604 | −459 | 231 | 2110 | C |
| ATOM | 2310 | O | ALA | B | 254 | 9.178 | −76.971 | −27.074 | 1.00 | 80.87 | | O |
| ANISOU | 2310 | O | ALA | B | 254 | 11950 | 13867 | 4910 | −428 | 530 | 1908 | O |
| ATOM | 2311 | N | GLY | B | 255 | 10.274 | −78.649 | −28.095 | 1.00 | 90.59 | | N |
| ANISOU | 2311 | N | GLY | B | 255 | 12757 | 15052 | 6612 | −407 | 134 | 2296 | N |
| ATOM | 2312 | CA | GLY | B | 255 | 9.376 | −78.691 | −29.232 | 1.00 | 65.34 | | C |
| ANISOU | 2312 | CA | GLY | B | 255 | 9327 | 11770 | 3731 | −325 | 359 | 2284 | C |
| ATOM | 2313 | C | GLY | B | 255 | 9.712 | −79.780 | −30.233 | 1.00 | 73.76 | | C |
| ANISOU | 2313 | C | GLY | B | 255 | 10101 | 12696 | 5228 | −275 | 217 | 2489 | C |
| ATOM | 2314 | O | GLY | B | 255 | 10.854 | −80.232 | −30.327 | 1.00 | 74.38 | | O |
| ANISOU | 2314 | O | GLY | B | 255 | 10116 | 12793 | 5352 | −290 | −83 | 2614 | O |
| ATOM | 2315 | N | THR | B | 256 | 8.704 | −80.201 | −30.988 | 1.00 | 73.09 | | N |
| ANISOU | 2315 | N | THR | B | 256 | 9840 | 12457 | 5474 | −214 | 439 | 2520 | N |
| ATOM | 2316 | CA | THR | B | 256 | 8.885 | −81.197 | −32.031 | 1.00 | 67.31 | | C |
| ANISOU | 2316 | CA | THR | B | 256 | 8869 | 11542 | 5165 | −175 | 342 | 2666 | C |
| ATOM | 2317 | CB | THR | B | 256 | 8.457 | −82.589 | −31.551 | 1.00 | 69.95 | | C |
| ANISOU | 2317 | CB | THR | B | 256 | 9190 | 11857 | 5530 | −180 | 425 | 3012 | C |
| ATOM | 2318 | OG1 | THR | B | 256 | 9.159 | −82.928 | −30.352 | 1.00 | 73.64 | | O |
| ANISOU | 2318 | OG1 | THR | B | 256 | 9836 | 12484 | 5660 | −211 | 284 | 3190 | O |
| ATOM | 2319 | CG2 | THR | B | 256 | 8.745 | −83.623 | −32.618 | 1.00 | 58.75 | | C |
| ANISOU | 2319 | CG2 | THR | B | 256 | 7572 | 10218 | 4534 | −145 | 318 | 3144 | C |
| ATOM | 2320 | C | THR | B | 256 | 8.060 | −80.807 | −33.256 | 1.00 | 67.67 | | C |
| ANISOU | 2320 | C | THR | B | 256 | 8734 | 11415 | 5561 | −136 | 497 | 2483 | C |
| ATOM | 2321 | O | THR | B | 256 | 6.867 | −80.541 | −33.138 | 1.00 | 77.30 | | O |
| ANISOU | 2321 | O | THR | B | 256 | 9947 | 12642 | 6780 | −128 | 770 | 2443 | O |
| ATOM | 2322 | N | CYS | B | 257 | 8.685 | −80.771 | −34.430 | 1.00 | 66.39 | | N |

TABLE 7-continued

DMXAA-hSTING$^{G230I}$ complex

| | | | | | | | | | | | |
|---|---|---|---|---|---|---|---|---|---|---|---|
| ANISOU | 2322 | N | CYS | B | 257 | 8421 | 11107 | 5696 | −109 | 329 | 2387 | N |
| ATOM | 2323 | CA | CYS | B | 257 | 7.982 | −80.309 | −35.623 | 1.00 | 70.95 | | C |
| ANISOU | 2323 | CA | CYS | B | 257 | 8847 | 11538 | 6574 | −81 | 440 | 2207 | C |
| ATOM | 2324 | CB | CYS | B | 257 | 7.947 | −78.777 | −35.656 | 1.00 | 76.14 | | C |
| ANISOU | 2324 | CB | CYS | B | 257 | 9580 | 12253 | 7098 | −66 | 488 | 1909 | C |
| ATOM | 2325 | SG | CYS | B | 257 | 9.560 | −78.008 | −35.989 | 1.00 | 123.88 | | S |
| ANISOU | 2325 | SG | CYS | B | 257 | 15664 | 18308 | 13097 | −83 | 178 | 1735 | S |
| ATOM | 2326 | C | CYS | B | 257 | 8.569 | −80.827 | −36.938 | 1.00 | 65.27 | | C |
| ANISOU | 2326 | C | CYS | B | 257 | 7965 | 10627 | 6209 | −57 | 276 | 2206 | C |
| ATOM | 2327 | O | CYS | B | 257 | 9.745 | −81.184 | −37.014 | 1.00 | 67.68 | | O |
| ANISOU | 2327 | O | CYS | B | 257 | 8268 | 10918 | 6530 | −40 | 63 | 2272 | O |
| ATOM | 2328 | N | VAL | B | 258 | 7.731 | −80.849 | −37.972 | 1.00 | 53.60 | | N |
| ANISOU | 2328 | N | VAL | B | 258 | 6351 | 9008 | 5008 | −55 | 383 | 2136 | N |
| ATOM | 2329 | CA | VAL | B | 258 | 8.169 | −81.139 | −39.332 | 1.00 | 49.06 | | C |
| ANISOU | 2329 | CA | VAL | B | 258 | 5656 | 8244 | 4741 | −38 | 260 | 2078 | C |
| ATOM | 2330 | CB | VAL | B | 258 | 7.025 | −81.674 | −40.202 | 1.00 | 54.71 | | C |
| ANISOU | 2330 | CB | VAL | B | 258 | 6248 | 8814 | 5724 | −80 | 380 | 2111 | C |
| ATOM | 2331 | CG2 | VAL | B | 258 | 6.482 | −82.959 | −39.620 | 1.00 | 67.44 | | C |
| ANISOU | 2331 | CG2 | VAL | B | 258 | 7871 | 10397 | 7357 | −137 | 461 | 2378 | C |
| ATOM | 2332 | CG1 | VAL | B | 258 | 7.489 | −81.886 | −41.642 | 1.00 | 49.40 | | C |
| ANISOU | 2332 | CG1 | VAL | B | 258 | 5499 | 7947 | 5324 | −70 | 255 | 2019 | C |
| ATOM | 2333 | C | VAL | B | 258 | 8.720 | −79.860 | −39.949 | 1.00 | 53.21 | | C |
| ANISOU | 2333 | C | VAL | B | 258 | 6173 | 8777 | 5269 | −4 | 179 | 1815 | C |
| ATOM | 2334 | O | VAL | B | 258 | 8.020 | −78.855 | −40.052 | 1.00 | 53.18 | | O |
| ANISOU | 2334 | O | VAL | B | 258 | 6167 | 8810 | 5231 | 3 | 301 | 1650 | O |
| ATOM | 2335 | N | LEU | B | 259 | 9.975 | −79.907 | −40.374 | 1.00 | 58.54 | | N |
| ANISOU | 2335 | N | LEU | B | 259 | 6834 | 9406 | 6001 | 23 | −13 | 1792 | N |
| ATOM | 2336 | CA | LEU | B | 259 | 10.723 | −78.699 | −40.658 | 1.00 | 53.14 | | C |
| ANISOU | 2336 | CA | LEU | B | 259 | 6165 | 8764 | 5263 | 34 | −111 | 1579 | C |
| ATOM | 2337 | CB | LEU | B | 259 | 11.633 | −78.403 | −39.470 | 1.00 | 53.17 | | C |
| ANISOU | 2337 | CB | LEU | B | 259 | 6283 | 8947 | 4974 | 5 | −241 | 1618 | C |
| ATOM | 2338 | CG | LEU | B | 259 | 12.281 | −77.038 | −39.290 | 1.00 | 62.54 | | C |
| ANISOU | 2338 | CG | LEU | B | 259 | 7544 | 10221 | 5999 | −34 | −331 | 1401 | C |
| ATOM | 2339 | CD1 | LEU | B | 259 | 11.268 | −76.035 | −38.779 | 1.00 | 59.33 | | C |
| ANISOU | 2339 | CD1 | LEU | B | 259 | 7267 | 9869 | 5405 | −52 | −137 | 1232 | C |
| ATOM | 2340 | CD2 | LEU | B | 259 | 13.426 | −77.176 | −38.310 | 1.00 | 73.41 | | C |
| ANISOU | 2340 | CD2 | LEU | B | 259 | 8986 | 11756 | 7150 | −86 | −542 | 1513 | C |
| ATOM | 2341 | C | LEU | B | 259 | 11.571 | −78.904 | −41.899 | 1.00 | 61.07 | | C |
| ANISOU | 2341 | C | LEU | B | 259 | 7067 | 9618 | 6521 | 73 | −235 | 1541 | C |
| ATOM | 2342 | O | LEU | B | 259 | 12.289 | −79.897 | −41.996 | 1.00 | 70.70 | | O |
| ANISOU | 2342 | O | LEU | B | 259 | 8250 | 10777 | 7836 | 105 | −329 | 1705 | O |
| ATOM | 2343 | N | GLU | B | 260 | 11.501 | −77.972 | −42.846 | 1.00 | 58.63 | | N |
| ANISOU | 2343 | N | GLU | B | 260 | 6717 | 9242 | 6319 | 81 | −221 | 1335 | N |
| ATOM | 2344 | CA | GLU | B | 260 | 12.359 | −78.051 | −44.021 | 1.00 | 58.16 | | C |
| ANISOU | 2344 | CA | GLU | B | 260 | 6578 | 9052 | 6470 | 118 | −319 | 1288 | C |
| ATOM | 2345 | CB | GLU | B | 260 | 11.824 | −79.078 | −45.020 | 1.00 | 50.41 | | C |
| ANISOU | 2345 | CB | GLU | B | 260 | 5546 | 7884 | 5724 | 134 | −259 | 1358 | C |
| ATOM | 2346 | CG | GLU | B | 260 | 10.596 | −78.650 | −45.780 | 1.00 | 55.43 | | C |
| ANISOU | 2346 | CG | GLU | B | 260 | 6155 | 8455 | 6452 | 103 | −147 | 1241 | C |
| ATOM | 2347 | CD | GLU | B | 260 | 9.917 | −79.823 | −46.470 | 1.00 | 65.19 | | C |
| ANISOU | 2347 | CD | GLU | B | 260 | 7369 | 9533 | 7869 | 69 | −105 | 1343 | C |
| ATOM | 2348 | OE1 | GLU | B | 260 | 10.023 | −80.956 | −45.948 | 1.00 | 75.25 | | O |
| ANISOU | 2348 | OE1 | GLU | B | 260 | 8672 | 10771 | 9147 | 61 | −106 | 1523 | O |
| ATOM | 2349 | OE2 | GLU | B | 260 | 9.294 | −79.609 | −47.531 | 1.00 | 48.80 | | O |
| ANISOU | 2349 | OE2 | GLU | B | 260 | 5257 | 7362 | 5922 | 40 | −81 | 1248 | O |
| ATOM | 2350 | C | GLU | B | 260 | 12.609 | −76.709 | −44.704 | 1.00 | 54.88 | | C |
| ANISOU | 2350 | C | GLU | B | 260 | 6152 | 8624 | 6077 | 115 | −335 | 1061 | C |
| ATOM | 2351 | O | GLU | B | 260 | 11.821 | −75.769 | −44.577 | 1.00 | 57.42 | | O |
| ANISOU | 2351 | O | GLU | B | 260 | 6516 | 8982 | 6320 | 98 | −237 | 927 | O |
| ATOM | 2352 | N | TYR | B | 261 | 13.730 | −76.639 | −45.419 | 1.00 | 54.81 | | N |
| ANISOU | 2352 | N | TYR | B | 261 | 6083 | 8556 | 6187 | 142 | −443 | 1037 | N |
| ATOM | 2353 | CA | TYR | B | 261 | 14.097 | −75.467 | −46.197 | 1.00 | 49.69 | | C |
| ANISOU | 2353 | CA | TYR | B | 261 | 5417 | 7871 | 5591 | 134 | −461 | 848 | C |
| ATOM | 2354 | CB | TYR | B | 261 | 15.597 | −75.452 | −46.472 | 1.00 | 52.50 | | C |
| ANISOU | 2354 | CB | TYR | B | 261 | 5696 | 8233 | 6018 | 147 | −599 | 881 | C |
| ATOM | 2355 | CG | TYR | B | 261 | 16.446 | −74.967 | −45.325 | 1.00 | 55.29 | | C |
| ANISOU | 2355 | CG | TYR | B | 261 | 6068 | 8763 | 6179 | 81 | −740 | 905 | C |
| ATOM | 2356 | CD1 | TYR | B | 261 | 16.571 | −73.605 | −45.053 | 1.00 | 44.20 | | C |
| ANISOU | 2356 | CD1 | TYR | B | 261 | 4732 | 7421 | 4643 | −4 | −770 | 724 | C |
| ATOM | 2357 | CE1 | TYR | B | 261 | 17.347 | −73.156 | −44.004 | 1.00 | 48.79 | | C |
| ANISOU | 2357 | CE1 | TYR | B | 261 | 5353 | 8159 | 5024 | −101 | −923 | 733 | C |
| ATOM | 2358 | CZ | TYR | B | 261 | 18.020 | −74.078 | −43.213 | 1.00 | 62.25 | | C |
| ANISOU | 2358 | CZ | TYR | B | 261 | 7005 | 9985 | 6662 | −101 | −1060 | 949 | C |
| ATOM | 2359 | OH | TYR | B | 261 | 18.801 | −73.647 | −42.164 | 1.00 | 60.64 | | O |
| ANISOU | 2359 | OH | TYR | B | 261 | 6842 | 9959 | 6241 | −219 | −1247 | 972 | O |
| ATOM | 2360 | CE2 | TYR | B | 261 | 17.913 | −75.438 | −43.469 | 1.00 | 60.16 | | C |
| ANISOU | 2360 | CE2 | TYR | B | 261 | 6659 | 9655 | 6544 | 9 | −1018 | 1149 | C |
| ATOM | 2361 | CD2 | TYR | B | 261 | 17.131 | −75.871 | −44.519 | 1.00 | 58.55 | | C |

TABLE 7-continued

DMXAA-hSTING$^{G230I}$ complex

| | | | | | | | | | | | | |
|---|---|---|---|---|---|---|---|---|---|---|---|---|
| ANISOU | 2361 | CD2 | TYR | B | 261 | 6439 | 9270 | 6536 | 93 | −853 | 1114 | C |
| ATOM | 2362 | C | TYR | B | 261 | 13.366 | −75.457 | −47.528 | 1.00 | 41.40 | | C |
| ANISOU | 2362 | C | TYR | B | 261 | 4337 | 6665 | 4727 | 162 | −368 | 770 | C |
| ATOM | 2363 | O | TYR | B | 261 | 13.243 | −76.491 | −48.185 | 1.00 | 37.07 | | O |
| ANISOU | 2363 | O | TYR | B | 261 | 3763 | 6001 | 4323 | 190 | −350 | 859 | O |
| ATOM | 2364 | N | ALA | B | 262 | 12.901 | −74.283 | −47.936 | 1.00 | 31.44 | | N |
| ANISOU | 2364 | N | ALA | B | 262 | 3097 | 5392 | 3458 | 151 | −315 | 606 | N |
| ATOM | 2365 | CA | ALA | B | 262 | 12.297 | −74.126 | −49.247 | 1.00 | 28.20 | | C |
| ANISOU | 2365 | CA | ALA | B | 262 | 2656 | 4852 | 3207 | 172 | −259 | 537 | C |
| ATOM | 2366 | CB | ALA | B | 262 | 11.648 | −72.769 | −49.381 | 1.00 | 36.77 | | C |
| ANISOU | 2366 | CB | ALA | B | 262 | 3768 | 5948 | 4256 | 174 | −189 | 390 | C |
| ATOM | 2367 | C | ALA | B | 262 | 13.349 | −74.314 | −50.329 | 1.00 | 45.59 | | C |
| ANISOU | 2367 | C | ALA | B | 262 | 4826 | 6949 | 5546 | 197 | −322 | 525 | C |
| ATOM | 2368 | O | ALA | B | 262 | 14.293 | −73.528 | −50.435 | 1.00 | 50.76 | | O |
| ANISOU | 2368 | O | ALA | B | 262 | 5470 | 7625 | 6192 | 194 | −373 | 453 | O |
| ATOM | 2369 | N | THR | B | 263 | 13.176 | −75.356 | −51.136 | 1.00 | 46.93 | | N |
| ANISOU | 2369 | N | THR | B | 263 | 4992 | 6998 | 5841 | 215 | −305 | 593 | N |
| ATOM | 2370 | CA | THR | B | 263 | 14.098 | −75.662 | −52.232 | 1.00 | 45.40 | | C |
| ANISOU | 2370 | CA | THR | B | 263 | 4793 | 6684 | 5772 | 257 | −320 | 584 | C |
| ATOM | 2371 | CB | THR | B | 263 | 13.665 | −76.930 | −53.001 | 1.00 | 45.13 | | C |
| ANISOU | 2371 | CB | THR | B | 263 | 4812 | 6495 | 5842 | 260 | −281 | 648 | C |
| ATOM | 2372 | OG1 | THR | B | 263 | 12.305 | −76.803 | −53.422 | 1.00 | 51.16 | | O |
| ANISOU | 2372 | OG1 | THR | B | 263 | 5600 | 7234 | 6606 | 195 | −254 | 603 | O |
| ATOM | 2373 | CG2 | THR | B | 263 | 13.804 | −78.148 | −52.116 | 1.00 | 27.84 | | C |
| ANISOU | 2373 | CG2 | THR | B | 263 | 2624 | 4305 | 3648 | 276 | −287 | 811 | C |
| ATOM | 2374 | C | THR | B | 263 | 14.404 | −74.528 | −53.234 | 1.00 | 39.46 | | C |
| ANISOU | 2374 | C | THR | B | 263 | 4042 | 5890 | 5060 | 260 | −310 | 445 | C |
| ATOM | 2375 | O | THR | B | 263 | 15.538 | −74.428 | −53.704 | 1.00 | 41.27 | | O |
| ANISOU | 2375 | O | THR | B | 263 | 4243 | 6087 | 5352 | 295 | −323 | 442 | O |
| ATOM | 2376 | N | PRO | B | 264 | 13.401 | −73.689 | −53.583 | 1.00 | 28.90 | | N |
| ANISOU | 2376 | N | PRO | B | 264 | 2726 | 4553 | 3700 | 232 | −278 | 352 | N |
| ATOM | 2377 | CA | PRO | B | 264 | 13.715 | −72.660 | −54.584 | 1.00 | 29.23 | | C |
| ANISOU | 2377 | CA | PRO | B | 264 | 2781 | 4539 | 3784 | 240 | −267 | 245 | C |
| ATOM | 2378 | CB | PRO | B | 264 | 12.387 | −71.930 | −54.778 | 1.00 | 23.87 | | C |
| ANISOU | 2378 | CB | PRO | B | 264 | 2114 | 3870 | 3087 | 227 | −232 | 191 | C |
| ATOM | 2379 | CG | PRO | B | 264 | 11.347 | −72.934 | −54.421 | 1.00 | 43.54 | | C |
| ANISOU | 2379 | CG | PRO | B | 264 | 4588 | 6377 | 5578 | 202 | −222 | 282 | C |
| ATOM | 2380 | CD | PRO | B | 264 | 11.952 | −73.734 | −53.302 | 1.00 | 39.45 | | C |
| ANISOU | 2380 | CD | PRO | B | 264 | 4063 | 5921 | 5007 | 203 | −239 | 366 | C |
| ATOM | 2381 | C | PRO | B | 264 | 14.782 | −71.654 | −54.158 | 1.00 | 30.34 | | C |
| ANISOU | 2381 | C | PRO | B | 264 | 2897 | 4741 | 3891 | 232 | −298 | 188 | C |
| ATOM | 2382 | O | PRO | B | 264 | 15.325 | −70.970 | −55.018 | 1.00 | 35.93 | | O |
| ANISOU | 2382 | O | PRO | B | 264 | 3609 | 5389 | 4655 | 236 | −285 | 127 | O |
| ATOM | 2383 | N | LEU | B | 265 | 15.051 | −71.537 | −52.861 | 1.00 | 25.26 | | N |
| ANISOU | 2383 | N | LEU | B | 265 | 2238 | 4214 | 3146 | 204 | −342 | 209 | N |
| ATOM | 2384 | CA | LEU | B | 265 | 16.114 | −70.660 | −52.390 | 1.00 | 25.91 | | C |
| ANISOU | 2384 | CA | LEU | B | 265 | 2300 | 4359 | 3186 | 157 | −405 | 160 | C |
| ATOM | 2385 | CB | LEU | B | 265 | 16.068 | −70.511 | −50.873 | 1.00 | 29.44 | | C |
| ANISOU | 2385 | CB | LEU | B | 265 | 2779 | 4943 | 3464 | 104 | −459 | 168 | C |
| ATOM | 2386 | CG | LEU | B | 265 | 14.828 | −69.860 | −50.275 | 1.00 | 42.21 | | C |
| ANISOU | 2386 | CG | LEU | B | 265 | 4494 | 6582 | 4962 | 98 | −377 | 80 | C |
| ATOM | 2387 | CD1 | LEU | B | 265 | 15.017 | −69.705 | −48.790 | 1.00 | 47.27 | | C |
| ANISOU | 2387 | CD1 | LEU | B | 265 | 5202 | 7357 | 5402 | 36 | −427 | 78 | C |
| ATOM | 2388 | CD2 | LEU | B | 265 | 14.544 | −68.502 | −50.911 | 1.00 | 27.69 | | C |
| ANISOU | 2388 | CD2 | LEU | B | 265 | 2710 | 4654 | 3157 | 96 | −314 | −66 | C |
| ATOM | 2389 | C | LEU | B | 265 | 17.475 | −71.206 | −52.827 | 1.00 | 42.92 | | C |
| ANISOU | 2389 | C | LEU | B | 265 | 4359 | 6499 | 5448 | 178 | −452 | 247 | C |
| ATOM | 2390 | O | LEU | B | 265 | 18.435 | −70.457 | −53.015 | 1.00 | 38.56 | | O |
| ANISOU | 2390 | O | LEU | B | 265 | 3758 | 5960 | 4933 | 138 | −489 | 213 | O |
| ATOM | 2391 | N | GLN | B | 266 | 17.558 | −72.526 | −52.962 | 1.00 | 37.72 | | N |
| ANISOU | 2391 | N | GLN | B | 266 | 3672 | 5808 | 4853 | 243 | −439 | 370 | N |
| ATOM | 2392 | CA | GLN | B | 266 | 18.759 | −73.163 | −53.484 | 1.00 | 40.02 | | C |
| ANISOU | 2392 | CA | GLN | B | 266 | 3873 | 6058 | 5274 | 304 | −437 | 467 | C |
| ATOM | 2393 | C | GLN | B | 266 | 18.989 | −72.722 | −54.915 | 1.00 | 35.27 | | C |
| ANISOU | 2393 | C | GLN | B | 266 | 3293 | 5334 | 4775 | 330 | −347 | 390 | C |
| ATOM | 2394 | O | GLN | B | 266 | 20.116 | −72.453 | −55.333 | 1.00 | 31.24 | | O |
| ANISOU | 2394 | O | GLN | B | 266 | 2692 | 4821 | 4355 | 347 | −337 | 418 | O |
| ATOM | 2395 | CB | GLN | B | 266 | 18.624 | −74.676 | −53.457 | 1.00 | 33.31 | | C |
| ANISOU | 2395 | CB | GLN | B | 266 | 3035 | 5144 | 4479 | 384 | −402 | 600 | C |
| ATOM | 2396 | CG | GLN | B | 266 | 19.182 | −75.333 | −52.231 | 1.00 | 30.58 | | C |
| ANISOU | 2396 | CG | GLN | B | 266 | 2609 | 4913 | 4095 | 399 | −493 | 758 | C |
| ATOM | 2397 | CD | GLN | B | 266 | 18.959 | −76.826 | −52.252 | 1.00 | 48.22 | | C |
| ANISOU | 2397 | CD | GLN | B | 266 | 4880 | 7046 | 6397 | 484 | −439 | 893 | C |
| ATOM | 2398 | OE1 | GLN | B | 266 | 19.738 | −77.566 | −52.851 | 1.00 | 52.55 | | O |
| ANISOU | 2398 | OE1 | GLN | B | 266 | 5502 | 7601 | 6864 | 452 | −438 | 923 | O |
| ATOM | 2399 | NE2 | GLN | B | 266 | 17.907 | −77.285 | −51.569 | 1.00 | 54.98 | | N |
| ANISOU | 2399 | NE2 | GLN | B | 266 | 5691 | 7788 | 7410 | 594 | −371 | 978 | N |
| ATOM | 2400 | N | THR | B | 267 | 17.903 | −72.669 | −55.671 | 1.00 | 28.45 | | N |

TABLE 7-continued

DMXAA-hSTING$^{G230I}$ complex

| ANISOU | 2400 | N   | THR | B | 267 | 2541   | 4376    | 3894    | 330  | -284 | 310  | N |
| ------ | ---- | --- | --- | - | --- | ------ | ------- | ------- | ---- | ---- | ---- | - |
| ATOM   | 2401 | CA  | THR | B | 267 | 17.976 | -72.242 | -57.053 | 1.00 | 33.19 |      | C |
| ANISOU | 2401 | CA  | THR | B | 267 | 3194   | 4864    | 4552    | 346  | -207 | 240  | C |
| ATOM   | 2402 | CB  | THR | B | 267 | 16.653 | -72.474 | -57.785 | 1.00 | 23.69 |      | C |
| ANISOU | 2402 | CB  | THR | B | 267 | 2112   | 3576    | 3314    | 336  | -177 | 189  | C |
| ATOM   | 2403 | OG1 | THR | B | 267 | 16.428 | -73.875 | -57.901 | 1.00 | 35.41 |      | O |
| ANISOU | 2403 | OG1 | THR | B | 267 | 3646   | 4986    | 4823    | 366  | -154 | 259  | O |
| ATOM   | 2404 | CG2 | THR | B | 267 | 16.682 | -71.856 | -59.182 | 1.00 | 23.29 |      | C |
| ANISOU | 2404 | CG2 | THR | B | 267 | 2135   | 3431    | 3283    | 338  | -118 | 120  | C |
| ATOM   | 2405 | C   | THR | B | 267 | 18.414 | -70.781 | -57.144 | 1.00 | 33.42 |      | C |
| ANISOU | 2405 | C   | THR | B | 267 | 3192   | 4931    | 4575    | 292  | -221 | 160  | C |
| ATOM   | 2406 | O   | THR | B | 267 | 19.252 | -70.419 | -57.965 | 1.00 | 33.85 |      | O |
| ANISOU | 2406 | O   | THR | B | 267 | 3220   | 4937    | 4705    | 305  | -168 | 157  | O |
| ATOM   | 2407 | N   | LEU | B | 268 | 17.848 | -69.945 | -56.284 | 1.00 | 39.86 |      | N |
| ANISOU | 2407 | N   | LEU | B | 268 | 4022   | 5820    | 5301    | 230  | -277 | 96   | N |
| ATOM   | 2408 | CA  | LEU | B | 268 | 18.213 | -68.534 | -56.241 | 1.00 | 45.74 |      | C |
| ANISOU | 2408 | CA  | LEU | B | 268 | 4769   | 6574    | 6035    | 163  | -290 | 9    | C |
| ATOM   | 2409 | CB  | LEU | B | 268 | 17.344 | -67.789 | -55.237 | 1.00 | 37.50 |      | C |
| ANISOU | 2409 | CB  | LEU | B | 268 | 3792   | 5583    | 4874    | 118  | -318 | -72  | C |
| ATOM   | 2410 | CG  | LEU | B | 268 | 15.940 | -67.513 | -55.733 | 1.00 | 35.81 |      | C |
| ANISOU | 2410 | CG  | LEU | B | 268 | 3658   | 5303    | 4645    | 165  | -248 | -117 | C |
| ATOM   | 2411 | CD1 | LEU | B | 268 | 15.191 | -66.758 | -54.663 | 1.00 | 40.90 |      | C |
| ANISOU | 2411 | CD1 | LEU | B | 268 | 4361   | 5994    | 5186    | 145  | -236 | -190 | C |
| ATOM   | 2412 | CD2 | LEU | B | 268 | 15.991 | -66.713 | -57.035 | 1.00 | 31.24 |      | C |
| ANISOU | 2412 | CD2 | LEU | B | 268 | 3118   | 4613    | 4141    | 178  | -196 | -158 | C |
| ATOM   | 2413 | C   | LEU | B | 268 | 19.674 | -68.359 | -55.864 | 1.00 | 34.11 |      | C |
| ANISOU | 2413 | C   | LEU | B | 268 | 3177   | 5168    | 4613    | 113  | -350 | 59   | C |
| ATOM   | 2414 | O   | LEU | B | 268 | 20.355 | -67.455 | -56.334 | 1.00 | 33.73 |      | O |
| ANISOU | 2414 | O   | LEU | B | 268 | 3104   | 5090    | 4623    | 60   | -336 | 23   | O |
| ATOM   | 2415 | N   | PHE | B | 269 | 20.148 | -69.225 | -54.988 | 1.00 | 26.46 |      | N |
| ANISOU | 2415 | N   | PHE | B | 269 | 2124   | 4299    | 3630    | 121  | -424 | 160  | N |
| ATOM   | 2416 | CA  | PHE | B | 269 | 21.533 | -69.164 | -54.593 | 1.00 | 27.89 |      | C |
| ANISOU | 2416 | CA  | PHE | B | 269 | 2153   | 4570    | 3874    | 73   | -506 | 245  | C |
| ATOM   | 2417 | CB  | PHE | B | 269 | 21.799 | -70.087 | -53.427 | 1.00 | 28.96 |      | C |
| ANISOU | 2417 | CB  | PHE | B | 269 | 2215   | 4833    | 3956    | 83   | -615 | 370  | C |
| ATOM   | 2418 | CG  | PHE | B | 269 | 23.194 | -70.009 | -52.931 | 1.00 | 40.48 |      | C |
| ANISOU | 2418 | CG  | PHE | B | 269 | 3488   | 6414    | 5477    | 24   | -736 | 485  | C |
| ATOM   | 2419 | CD1 | PHE | B | 269 | 23.563 | -69.010 | -52.042 | 1.00 | 38.58 |      | C |
| ANISOU | 2419 | CD1 | PHE | B | 269 | 3243   | 6285    | 5131    | -145 | -884 | 426  | C |
| ATOM   | 2420 | CE1 | PHE | B | 269 | 24.861 | -68.911 | -51.586 | 1.00 | 47.05 |      | C |
| ANISOU | 2420 | CE1 | PHE | B | 269 | 4123   | 7489    | 6265    | -232 | -1031| 546  | C |
| ATOM   | 2421 | CZ  | PHE | B | 269 | 25.821 | -69.816 | -52.039 | 1.00 | 49.71 |      | C |
| ANISOU | 2421 | CZ  | PHE | B | 269 | 4242   | 7849    | 6797    | -116 | -1003| 746  | C |
| ATOM   | 2422 | CE2 | PHE | B | 269 | 25.463 | -70.813 | -52.945 | 1.00 | 45.06 |      | C |
| ANISOU | 2422 | CE2 | PHE | B | 269 | 3679   | 7125    | 6316    | 80   | -818 | 795  | C |
| ATOM   | 2423 | CD2 | PHE | B | 269 | 24.158 | -70.898 | -53.389 | 1.00 | 34.56 |      | C |
| ANISOU | 2423 | CD2 | PHE | B | 269 | 2569   | 5663    | 4901    | 132  | -698 | 656  | C |
| ATOM   | 2424 | C   | PHE | B | 269 | 22.430 | -69.543 | -55.771 | 1.00 | 40.31 |      | C |
| ANISOU | 2424 | C   | PHE | B | 269 | 3629   | 6068    | 5620    | 153  | -405 | 325  | C |
| ATOM   | 2425 | O   | PHE | B | 269 | 23.424 | -68.874 | -56.072 | 1.00 | 32.89 |      | O |
| ANISOU | 2425 | O   | PHE | B | 269 | 2580   | 5146    | 4769    | 97   | -409 | 344  | O |
| ATOM   | 2426 | N   | ALA | B | 270 | 22.062 | -70.619 | -56.451 | 1.00 | 33.97 |      | N |
| ANISOU | 2426 | N   | ALA | B | 270 | 2876   | 5171    | 4861    | 278  | -300 | 371  | N |
| ATOM   | 2427 | CA  | ALA | B | 270 | 22.816 | -71.085 | -57.604 | 1.00 | 29.48 |      | C |
| ANISOU | 2427 | CA  | ALA | B | 270 | 2263   | 4508    | 4431    | 376  | -162 | 434  | C |
| ATOM   | 2428 | CB  | ALA | B | 270 | 22.225 | -72.375 | -58.140 | 1.00 | 28.83 |      | C |
| ANISOU | 2428 | CB  | ALA | B | 270 | 2297   | 4305    | 4352    | 493  | -63  | 459  | C |
| ATOM   | 2429 | C   | ALA | B | 270 | 22.862 | -70.028 | -58.702 | 1.00 | 33.02 |      | C |
| ANISOU | 2429 | C   | ALA | B | 270 | 2770   | 4876    | 4899    | 336  | -73  | 339  | C |
| ATOM   | 2430 | O   | ALA | B | 270 | 23.913 | -69.779 | -59.299 | 1.00 | 44.38 |      | O |
| ANISOU | 2430 | O   | ALA | B | 270 | 4103   | 6305    | 6454    | 351  | 5    | 396  | O |
| ATOM   | 2431 | N   | MET | B | 271 | 21.721 | -69.416 | -58.984 | 1.00 | 30.23 |      | N |
| ANISOU | 2431 | N   | MET | B | 271 | 2576   | 4468    | 4442    | 293  | -76  | 216  | N |
| ATOM   | 2432 | CA  | MET | B | 271 | 21.670 | -68.408 | -60.028 | 1.00 | 37.61 |      | C |
| ANISOU | 2432 | CA  | MET | B | 271 | 3584   | 5320    | 5385    | 263  | 2    | 144  | C |
| ATOM   | 2433 | CB  | MET | B | 271 | 20.249 | -67.895 | -60.225 | 1.00 | 34.47 |      | C |
| ANISOU | 2433 | CB  | MET | B | 271 | 3347   | 4872    | 4880    | 242  | -18  | 42   | C |
| ATOM   | 2434 | CG  | MET | B | 271 | 19.271 | -68.970 | -60.646 | 1.00 | 36.44 |      | C |
| ANISOU | 2434 | CG  | MET | B | 271 | 3702   | 5066    | 5076    | 308  | 4    | 46   | C |
| ATOM   | 2435 | SD  | MET | B | 271 | 17.587 | -68.349 | -60.699 | 1.00 | 35.84 |      | S |
| ANISOU | 2435 | SD  | MET | B | 271 | 3740   | 4974    | 4903    | 279  | -46  | -32  | S |
| ATOM   | 2436 | CE  | MET | B | 271 | 17.595 | -67.547 | -62.290 | 1.00 | 31.60 |      | C |
| ANISOU | 2436 | CE  | MET | B | 271 | 3310   | 4330    | 4368    | 284  | 33   | -57  | C |
| ATOM   | 2437 | C   | MET | B | 271 | 22.630 | -67.269 | -59.723 | 1.00 | 36.85 |      | C |
| ANISOU | 2437 | C   | MET | B | 271 | 3373   | 5279    | 5351    | 157  | -37  | 145  | C |
| ATOM   | 2438 | O   | MET | B | 271 | 23.251 | -66.704 | -60.623 | 1.00 | 41.85 |      | O |
| ANISOU | 2438 | O   | MET | B | 271 | 3988   | 5856    | 6058    | 145  | 58   | 158  | O |
| ATOM   | 2439 | N   | SER | B | 272 | 22.776 | -66.938 | -58.447 | 1.00 | 33.01 |      | N |

TABLE 7-continued

DMXAA-hSTING$^{G230I}$ complex

| | | | | | | | | | | | |
|---|---|---|---|---|---|---|---|---|---|---|---|
| ANISOU | 2439 | N | SER | B | 272 | 2816 | 4900 | 4824 | 65 | −179 | 136 | N |
| ATOM | 2440 | CA | SER | B | 272 | 23.716 | −65.895 | −58.050 | 1.00 | 30.97 | | C |
| ANISOU | 2440 | CA | SER | B | 272 | 2456 | 4695 | 4616 | −76 | −249 | 132 | C |
| ATOM | 2441 | CB | SER | B | 272 | 23.505 | −65.507 | −56.580 | 1.00 | 29.22 | | C |
| ANISOU | 2441 | CB | SER | B | 272 | 2250 | 4577 | 4275 | −194 | −418 | 74 | C |
| ATOM | 2442 | OG | SER | B | 272 | 23.991 | −66.508 | −55.705 | 1.00 | 31.03 | | O |
| ANISOU | 2442 | OG | SER | B | 272 | 2350 | 4942 | 4500 | −172 | −520 | 192 | O |
| ATOM | 2443 | C | SER | B | 272 | 25.172 | −66.344 | −58.274 | 1.00 | 35.53 | | C |
| ANISOU | 2443 | C | SER | B | 272 | 2807 | 5338 | 5356 | −62 | −227 | 287 | C |
| ATOM | 2444 | O | SER | B | 272 | 26.091 | −65.521 | −58.312 | 1.00 | 38.97 | | O |
| ANISOU | 2444 | O | SER | B | 272 | 3124 | 5802 | 5879 | −181 | −253 | 314 | O |
| ATOM | 2445 | N | GLN | B | 273 | 25.384 | −67.652 | −58.401 | 1.00 | 38.03 | | N |
| ANISOU | 2445 | N | GLN | B | 273 | 3052 | 5671 | 5725 | 82 | −172 | 399 | N |
| ATOM | 2446 | CA | GLN | B | 273 | 26.738 | −68.213 | −58.476 | 1.00 | 36.20 | | C |
| ANISOU | 2446 | CA | GLN | B | 273 | 2577 | 5510 | 5666 | 134 | −139 | 577 | C |
| ATOM | 2447 | CB | GLN | B | 273 | 26.870 | −69.427 | −57.559 | 1.00 | 40.53 | | C |
| ANISOU | 2447 | CB | GLN | B | 273 | 3030 | 6151 | 6218 | 220 | −227 | 701 | C |
| ATOM | 2448 | CG | GLN | B | 273 | 26.559 | −69.142 | −56.110 | 1.00 | 49.91 | | C |
| ANISOU | 2448 | CG | GLN | B | 273 | 4221 | 7476 | 7267 | 87 | −458 | 672 | C |
| ATOM | 2449 | CD | GLN | B | 273 | 27.785 | −68.733 | −55.316 | 1.00 | 67.27 | | C |
| ANISOU | 2449 | CD | GLN | B | 273 | 6174 | 9846 | 9538 | −45 | −631 | 793 | C |
| ATOM | 2450 | OE1 | GLN | B | 273 | 28.719 | −69.519 | −55.155 | 1.00 | 66.78 | | O |
| ANISOU | 2450 | OE1 | GLN | B | 273 | 5886 | 9872 | 9618 | 39 | −647 | 994 | O |
| ATOM | 2451 | NE2 | GLN | B | 273 | 27.789 | −67.498 | −54.816 | 1.00 | 74.28 | | N |
| ANISOU | 2451 | NE2 | GLN | B | 273 | 7107 | 10780 | 10338 | −256 | −763 | 678 | N |
| ATOM | 2452 | C | GLN | B | 273 | 27.174 | −68.620 | −59.877 | 1.00 | 34.65 | | C |
| ANISOU | 2452 | C | GLN | B | 273 | 2379 | 5198 | 5588 | 273 | 100 | 632 | C |
| ATOM | 2453 | O | GLN | B | 273 | 28.325 | −68.989 | −60.084 | 1.00 | 44.07 | | O |
| ANISOU | 2453 | O | GLN | B | 273 | 3360 | 6435 | 6949 | 336 | 177 | 786 | O |
| ATOM | 2454 | N | TYR | B | 274 | 26.254 | −68.586 | −60.830 | 1.00 | 34.70 | | N |
| ANISOU | 2454 | N | TYR | B | 274 | 2621 | 5063 | 5502 | 325 | 220 | 516 | N |
| ATOM | 2455 | CA | TYR | B | 274 | 26.584 | −68.936 | −62.203 | 1.00 | 33.36 | | C |
| ANISOU | 2455 | CA | TYR | B | 274 | 2511 | 4773 | 5391 | 444 | 454 | 545 | C |
| ATOM | 2456 | CB | TYR | B | 274 | 25.696 | −70.069 | −62.711 | 1.00 | 30.27 | | C |
| ANISOU | 2456 | CB | TYR | B | 274 | 2334 | 4262 | 4903 | 573 | 539 | 496 | C |
| ATOM | 2457 | CG | TYR | B | 274 | 25.938 | −71.361 | −61.993 | 1.00 | 50.54 | | C |
| ANISOU | 2457 | CG | TYR | B | 274 | 4814 | 6857 | 7530 | 682 | 517 | 599 | C |
| ATOM | 2458 | CD1 | TYR | B | 274 | 27.239 | −71.849 | −61.819 | 1.00 | 57.48 | | C |
| ANISOU | 2458 | CD1 | TYR | B | 274 | 5455 | 7791 | 8593 | 777 | 591 | 771 | C |
| ATOM | 2459 | CE1 | TYR | B | 274 | 27.468 | −73.038 | −61.148 | 1.00 | 60.64 | | C |
| ANISOU | 2459 | CE1 | TYR | B | 274 | 5773 | 8206 | 9059 | 895 | 571 | 892 | C |
| ATOM | 2460 | CZ | TYR | B | 274 | 26.395 | −73.740 | −60.629 | 1.00 | 63.95 | | C |
| ANISOU | 2460 | CZ | TYR | B | 274 | 6361 | 8584 | 9355 | 898 | 479 | 831 | C |
| ATOM | 2461 | OH | TYR | B | 274 | 26.615 | −74.933 | −59.963 | 1.00 | 69.82 | | O |
| ANISOU | 2461 | OH | TYR | B | 274 | 7037 | 9324 | 10167 | 1016 | 466 | 966 | O |
| ATOM | 2462 | CE2 | TYR | B | 274 | 25.102 | −73.282 | −60.782 | 1.00 | 47.12 | | C |
| ANISOU | 2462 | CE2 | TYR | B | 274 | 4449 | 6408 | 7046 | 791 | 407 | 660 | C |
| ATOM | 2463 | CD2 | TYR | B | 274 | 24.877 | −72.095 | −61.458 | 1.00 | 40.02 | | C |
| ANISOU | 2463 | CD2 | TYR | B | 274 | 3618 | 5499 | 6088 | 692 | 423 | 548 | C |
| ATOM | 2464 | C | TYR | B | 274 | 26.472 | −67.724 | −63.106 | 1.00 | 40.80 | | C |
| ANISOU | 2464 | C | TYR | B | 274 | 3553 | 5648 | 6302 | 358 | 527 | 468 | C |
| ATOM | 2465 | O | TYR | B | 274 | 25.477 | −67.000 | −63.062 | 1.00 | 35.56 | | O |
| ANISOU | 2465 | O | TYR | B | 274 | 3049 | 4949 | 5515 | 277 | 443 | 347 | O |
| ATOM | 2466 | N | SER | B | 275 | 27.510 | −67.516 | −63.914 | 1.00 | 35.66 | | N |
| ANISOU | 2466 | N | SER | B | 275 | 2796 | 4977 | 5775 | 386 | 698 | 559 | N |
| ATOM | 2467 | CA | SER | B | 275 | 27.631 | −66.352 | −64.782 | 1.00 | 37.42 | | C |
| ANISOU | 2467 | CA | SER | B | 275 | 3084 | 5139 | 5993 | 301 | 788 | 527 | C |
| ATOM | 2468 | CB | SER | B | 275 | 28.962 | −66.377 | −65.522 | 1.00 | 34.81 | | C |
| ANISOU | 2468 | CB | SER | B | 275 | 2579 | 4816 | 5832 | 351 | 1002 | 672 | C |
| ATOM | 2469 | OG | SER | B | 275 | 30.033 | −66.339 | −64.612 | 1.00 | 48.21 | | O |
| ANISOU | 2469 | OG | SER | B | 275 | 3952 | 6656 | 7711 | 289 | 907 | 803 | O |
| ATOM | 2470 | C | SER | B | 275 | 26.512 | −66.314 | −65.792 | 1.00 | 31.32 | | C |
| ANISOU | 2470 | C | SER | B | 275 | 2618 | 4235 | 5047 | 347 | 864 | 415 | C |
| ATOM | 2471 | O | SER | B | 275 | 26.025 | −65.250 | −66.155 | 1.00 | 37.98 | | O |
| ANISOU | 2471 | O | SER | B | 275 | 3577 | 5030 | 5825 | 257 | 839 | 352 | O |
| ATOM | 2472 | N | GLN | B | 276 | 26.132 | −67.492 | −66.266 | 1.00 | 38.37 | | N |
| ANISOU | 2472 | N | GLN | B | 276 | 3646 | 5064 | 5870 | 485 | 956 | 402 | N |
| ATOM | 2473 | CA | GLN | B | 276 | 25.134 | −67.619 | −67.315 | 1.00 | 36.83 | | C |
| ANISOU | 2473 | CA | GLN | B | 276 | 3744 | 4752 | 5497 | 517 | 1017 | 311 | C |
| ATOM | 2474 | CB | GLN | B | 276 | 25.037 | −69.063 | −67.771 | 1.00 | 40.27 | | C |
| ANISOU | 2474 | CB | GLN | B | 276 | 4309 | 5108 | 5885 | 655 | 1136 | 307 | C |
| ATOM | 2475 | CG | GLN | B | 276 | 25.096 | −69.221 | −69.265 | 1.00 | 55.59 | | C |
| ANISOU | 2475 | CG | GLN | B | 276 | 6480 | 6927 | 7715 | 716 | 1352 | 286 | C |
| ATOM | 2476 | CD | GLN | B | 276 | 24.170 | −70.302 | −69.764 | 1.00 | 62.07 | | C |
| ANISOU | 2476 | CD | GLN | B | 276 | 7578 | 7639 | 8368 | 762 | 1354 | 195 | C |
| ATOM | 2477 | OE1 | GLN | B | 276 | 24.314 | −71.473 | −69.407 | 1.00 | 67.46 | | O |
| ANISOU | 2477 | OE1 | GLN | B | 276 | 8258 | 8277 | 9095 | 852 | 1394 | 205 | O |
| ATOM | 2478 | NE2 | GLN | B | 276 | 23.195 | −69.913 | −70.578 | 1.00 | 60.22 | | N |

TABLE 7-continued

| | | | | | | | | | | | | |
|---|---|---|---|---|---|---|---|---|---|---|---|---|
| DMXAA-hSTING$^{G230I}$ complex | | | | | | | | | | | | |
| ANISOU | 2478 | NE2 | GLN | B | 276 | 7583 | 7356 | 7941 | 690 | 1297 | 115 | N |
| ATOM | 2479 | C | GLN | B | 276 | 23.745 | −67.115 | −66.897 | 1.00 | 28.53 | | C |
| ANISOU | 2479 | C | GLN | B | 276 | 2817 | 3705 | 4317 | 433 | 815 | 206 | C |
| ATOM | 2480 | O | GLN | B | 276 | 22.935 | −66.726 | −67.737 | 1.00 | 32.88 | | O |
| ANISOU | 2480 | O | GLN | B | 276 | 3566 | 4188 | 4740 | 416 | 821 | 153 | O |
| ATOM | 2481 | N | ALA | B | 277 | 23.472 | −67.133 | −65.599 | 1.00 | 27.77 | | N |
| ANISOU | 2481 | N | ALA | B | 277 | 2603 | 3697 | 4253 | 386 | 643 | 190 | N |
| ATOM | 2482 | CA | ALA | B | 277 | 22.157 | −66.754 | −65.094 | 1.00 | 35.65 | | C |
| ANISOU | 2482 | CA | ALA | B | 277 | 3697 | 4703 | 5145 | 331 | 483 | 103 | C |
| ATOM | 2483 | CB | ALA | B | 277 | 21.918 | −67.308 | −63.689 | 1.00 | 25.90 | | C |
| ANISOU | 2483 | CB | ALA | B | 277 | 2356 | 3563 | 3924 | 321 | 343 | 100 | C |
| ATOM | 2484 | C | ALA | B | 277 | 21.988 | −65.237 | −65.116 | 1.00 | 37.93 | | C |
| ANISOU | 2484 | C | ALA | B | 277 | 3998 | 4978 | 5434 | 236 | 444 | 67 | C |
| ATOM | 2485 | O | ALA | B | 277 | 20.865 | −64.723 | −65.039 | 1.00 | 34.68 | | O |
| ANISOU | 2485 | O | ALA | B | 277 | 3692 | 4543 | 4943 | 216 | 363 | 8 | O |
| ATOM | 2486 | N | GLY | B | 278 | 23.110 | −64.528 | −65.207 | 1.00 | 37.18 | | N |
| ANISOU | 2486 | N | GLY | B | 278 | 3789 | 4890 | 5448 | 178 | 508 | 117 | N |
| ATOM | 2487 | CA | GLY | B | 278 | 23.100 | −63.077 | −65.243 | 1.00 | 27.77 | | C |
| ANISOU | 2487 | CA | GLY | B | 278 | 2621 | 3654 | 4277 | 74 | 488 | 90 | C |
| ATOM | 2488 | C | GLY | B | 278 | 22.449 | −62.525 | −63.994 | 1.00 | 35.28 | | C |
| ANISOU | 2488 | C | GLY | B | 278 | 3566 | 4639 | 5200 | 3 | 328 | 6 | C |
| ATOM | 2489 | O | GLY | B | 278 | 21.693 | −61.551 | −64.025 | 1.00 | 48.27 | | O |
| ANISOU | 2489 | O | GLY | B | 278 | 5325 | 6211 | 6803 | −27 | 302 | −52 | O |
| ATOM | 2490 | N | PHE | B | 279 | 22.755 | −63.163 | −62.877 | 1.00 | 30.97 | | N |
| ANISOU | 2490 | N | PHE | B | 279 | 2895 | 4201 | 4673 | −14 | 231 | 8 | N |
| ATOM | 2491 | CA | PHE | B | 279 | 22.033 | −62.945 | −61.647 | 1.00 | 37.34 | | C |
| ANISOU | 2491 | CA | PHE | B | 279 | 3727 | 5054 | 5409 | −58 | 96 | −74 | C |
| ATOM | 2492 | CB | PHE | B | 279 | 21.358 | −64.250 | −61.279 | 1.00 | 41.73 | | C |
| ANISOU | 2492 | CB | PHE | B | 279 | 4288 | 5670 | 5896 | 40 | 58 | −61 | C |
| ATOM | 2493 | CG | PHE | B | 279 | 20.146 | −64.096 | −60.435 | 1.00 | 32.44 | | C |
| ANISOU | 2493 | CG | PHE | B | 279 | 3194 | 4512 | 4619 | 41 | −23 | −139 | C |
| ATOM | 2494 | CD1 | PHE | B | 279 | 19.054 | −63.370 | −60.896 | 1.00 | 38.73 | | C |
| ANISOU | 2494 | CD1 | PHE | B | 279 | 4121 | 5224 | 5371 | 69 | 6 | −192 | C |
| ATOM | 2495 | CE1 | PHE | B | 279 | 17.906 | −63.232 | −60.116 | 1.00 | 43.92 | | C |
| ANISOU | 2495 | CE1 | PHE | B | 279 | 4831 | 5901 | 5955 | 91 | −37 | −246 | C |
| ATOM | 2496 | CZ | PHE | B | 279 | 17.853 | −63.839 | −58.855 | 1.00 | 41.75 | | C |
| ANISOU | 2496 | CZ | PHE | B | 279 | 4504 | 5732 | 5626 | 73 | −108 | −258 | C |
| ATOM | 2497 | CE2 | PHE | B | 279 | 18.951 | −64.581 | −58.392 | 1.00 | 46.69 | | C |
| ANISOU | 2497 | CE2 | PHE | B | 279 | 5016 | 6445 | 6278 | 35 | −158 | −202 | C |
| ATOM | 2498 | CD2 | PHE | B | 279 | 20.084 | −64.700 | −59.187 | 1.00 | 32.06 | | C |
| ANISOU | 2498 | CD2 | PHE | B | 279 | 3087 | 4571 | 4523 | 26 | −117 | −139 | C |
| ATOM | 2499 | C | PHE | B | 279 | 22.997 | −62.525 | −60.556 | 1.00 | 41.74 | | C |
| ANISOU | 2499 | C | PHE | B | 279 | 4148 | 5694 | 6017 | −195 | −7 | −73 | C |
| ATOM | 2500 | O | PHE | B | 279 | 23.904 | −63.282 | −60.203 | 1.00 | 52.23 | | O |
| ANISOU | 2500 | O | PHE | B | 279 | 5309 | 7127 | 7410 | −197 | −40 | 16 | O |
| ATOM | 2501 | N | SER | B | 280 | 22.821 | −61.316 | −60.032 | 1.00 | 41.01 | | N |
| ANISOU | 2501 | N | SER | B | 280 | 4132 | 5551 | 5897 | −313 | −59 | −166 | N |
| ATOM | 2502 | CA | SER | B | 280 | 23.709 | −60.805 | −59.004 | 1.00 | 30.32 | | C |
| ANISOU | 2502 | CA | SER | B | 280 | 2687 | 4267 | 4566 | −486 | −182 | −185 | C |
| ATOM | 2503 | CB | SER | B | 280 | 23.894 | −59.300 | −59.149 | 1.00 | 45.50 | | C |
| ANISOU | 2503 | CB | SER | B | 280 | 4707 | 6058 | 6524 | −630 | −164 | −261 | C |
| ATOM | 2504 | OG | SER | B | 280 | 22.746 | −58.625 | −58.682 | 1.00 | 47.58 | | O |
| ANISOU | 2504 | OG | SER | B | 280 | 5179 | 6225 | 6676 | −613 | −164 | −396 | O |
| ATOM | 2505 | C | SER | B | 280 | 23.188 | −61.107 | −57.607 | 1.00 | 40.62 | | C |
| ANISOU | 2505 | C | SER | B | 280 | 4033 | 5666 | 5734 | −512 | −314 | −256 | C |
| ATOM | 2506 | O | SER | B | 280 | 22.039 | −61.528 | −57.410 | 1.00 | 34.68 | | O |
| ANISOU | 2506 | O | SER | B | 280 | 3388 | 4906 | 4883 | −398 | −291 | −300 | O |
| ATOM | 2507 | N | ARG | B | 281 | 24.048 | −60.867 | −56.629 | 1.00 | 38.99 | | N |
| ANISOU | 2507 | N | ARG | B | 281 | 3740 | 5556 | 5518 | −677 | −457 | −257 | N |
| ATOM | 2508 | CA | ARG | B | 281 | 23.722 | −61.144 | −55.245 | 1.00 | 50.02 | | C |
| ANISOU | 2508 | CA | ARG | B | 281 | 5186 | 7061 | 6757 | −725 | −593 | −313 | C |
| ATOM | 2509 | CB | ARG | B | 281 | 24.964 | −60.966 | −54.399 | 1.00 | 53.59 | | C |
| ANISOU | 2509 | CB | ARG | B | 281 | 5498 | 7644 | 7219 | −929 | −777 | −268 | C |
| ATOM | 2510 | CG | ARG | B | 281 | 24.740 | −61.191 | −52.947 | 1.00 | 77.79 | | C |
| ANISOU | 2510 | CG | ARG | B | 281 | 8635 | 10834 | 10089 | −1006 | −936 | −320 | C |
| ATOM | 2511 | CD | ARG | B | 281 | 25.802 | −60.458 | −52.169 | 1.00 | 92.12 | | C |
| ANISOU | 2511 | CD | ARG | B | 281 | 10402 | 12723 | 11876 | −1278 | −1133 | −340 | C |
| ATOM | 2512 | NE | ARG | B | 281 | 25.752 | −60.757 | −50.769 | 1.00 | 101.63 | | N |
| ANISOU | 2512 | NE | ARG | B | 281 | 11668 | 14077 | 12868 | −1371 | −1312 | −366 | N |
| ATOM | 2513 | CZ | ARG | B | 281 | 26.155 | −61.904 | −50.239 | 1.00 | 108.82 | | C |
| ANISOU | 2513 | CZ | ARG | B | 281 | 12403 | 15184 | 13761 | −1319 | −1431 | −199 | C |
| ATOM | 2514 | NH1 | ARG | B | 281 | 26.081 | −62.101 | −48.916 | 1.00 | 115.47 | | N |
| ANISOU | 2514 | NH1 | ARG | B | 281 | 13333 | 16166 | 14375 | −1418 | −1602 | −221 | N |
| ATOM | 2515 | NH2 | ARG | B | 281 | 26.631 | −62.866 | −51.011 | 1.00 | 106.78 | | N |
| ANISOU | 2515 | NH2 | ARG | B | 281 | 11898 | 14973 | 13699 | −1162 | −1370 | −6 | N |
| ATOM | 2516 | C | ARG | B | 281 | 22.618 | −60.215 | −54.741 | 1.00 | 54.56 | | C |
| ANISOU | 2516 | C | ARG | B | 281 | 6015 | 7523 | 7192 | −744 | −557 | −491 | C |
| ATOM | 2517 | O | ARG | B | 281 | 21.763 | −60.603 | −53.940 | 1.00 | 48.05 | | O |

TABLE 7-continued

| DMXAA-hSTING$^{G230I}$ complex | | | | | | | | | | |
|---|---|---|---|---|---|---|---|---|---|---|
| ANISOU | 2517 | O | ARG | B | 281 | 5286 | 6748 | 6224 | −682 | −570 | −541 | O |
| ATOM | 2518 | N | GLU | B | 282 | 22.659 | −58.977 | −55.219 | 1.00 | 52.67 | | N |
| ANISOU | 2518 | N | GLU | B | 282 | 5885 | 7121 | 7005 | −823 | −493 | −574 | N |
| ATOM | 2519 | CA | GLU | B | 282 | 21.651 | −57.975 | −54.897 | 1.00 | 50.47 | | C |
| ANISOU | 2519 | CA | GLU | B | 282 | 5855 | 6690 | 6633 | −814 | −418 | −734 | C |
| ATOM | 2520 | CB | GLU | B | 282 | 22.046 | −56.610 | −55.473 | 1.00 | 59.30 | | C |
| ANISOU | 2520 | CB | GLU | B | 282 | 7069 | 7615 | 7848 | −932 | −361 | −793 | C |
| ATOM | 2521 | CG | GLU | B | 282 | 23.300 | −55.981 | −54.852 | 1.00 | 66.14 | | C |
| ANISOU | 2521 | CG | GLU | B | 282 | 7905 | 8502 | 8725 | −1212 | −509 | −831 | C |
| ATOM | 2522 | CD | GLU | B | 282 | 24.589 | −56.761 | −55.130 | 1.00 | 75.64 | | C |
| ANISOU | 2522 | CD | GLU | B | 282 | 8808 | 9882 | 10049 | −1286 | −614 | −657 | C |
| ATOM | 2523 | OE1 | GLU | B | 282 | 25.470 | −56.781 | −54.242 | 1.00 | 83.50 | | O |
| ANISOU | 2523 | OE1 | GLU | B | 282 | 9716 | 11004 | 11006 | −1485 | −799 | −651 | O |
| ATOM | 2524 | OE2 | GLU | B | 282 | 24.723 | −57.347 | −56.230 | 1.00 | 71.09 | | O |
| ANISOU | 2524 | OE2 | GLU | B | 282 | 8088 | 9319 | 9604 | −1143 | −510 | −522 | O |
| ATOM | 2525 | C | GLU | B | 282 | 20.318 | −58.421 | −55.475 | 1.00 | 42.93 | | C |
| ANISOU | 2525 | C | GLU | B | 282 | 4952 | 5690 | 5669 | −581 | −283 | −712 | C |
| ATOM | 2526 | O | GLU | B | 282 | 19.278 | −58.366 | −54.808 | 1.00 | 48.03 | | O |
| ANISOU | 2526 | O | GLU | B | 282 | 5724 | 6324 | 6201 | −505 | −240 | −790 | O |
| ATOM | 2527 | N | ASP | B | 283 | 20.357 | −58.861 | −56.728 | 1.00 | 39.35 | | N |
| ANISOU | 2527 | N | ASP | B | 283 | 4401 | 5217 | 5335 | −476 | −212 | −599 | N |
| ATOM | 2528 | CA | ASP | B | 283 | 19.184 | −59.412 | −57.397 | 1.00 | 43.06 | | C |
| ANISOU | 2528 | CA | ASP | B | 283 | 4895 | 5667 | 5800 | −286 | −123 | −555 | C |
| ATOM | 2529 | CB | ASP | B | 283 | 19.554 | −59.987 | −58.765 | 1.00 | 58.00 | | C |
| ANISOU | 2529 | CB | ASP | B | 283 | 6691 | 7553 | 7793 | −218 | −72 | −434 | C |
| ATOM | 2530 | CG | ASP | B | 283 | 19.794 | −58.922 | −59.810 | 1.00 | 68.52 | | C |
| ANISOU | 2530 | CG | ASP | B | 283 | 8089 | 8734 | 9213 | −243 | 14 | −424 | C |
| ATOM | 2531 | OD1 | ASP | B | 283 | 19.360 | −57.772 | −59.591 | 1.00 | 77.38 | | O |
| ANISOU | 2531 | OD1 | ASP | B | 283 | 9343 | 9729 | 10328 | −271 | 48 | −506 | O |
| ATOM | 2532 | OD2 | ASP | B | 283 | 20.410 | −59.245 | −60.851 | 1.00 | 67.51 | | O |
| ANISOU | 2532 | OD2 | ASP | B | 283 | 7892 | 8603 | 9155 | −227 | 64 | −331 | O |
| ATOM | 2533 | C | ASP | B | 283 | 18.577 | −60.520 | −56.559 | 1.00 | 46.48 | | C |
| ANISOU | 2533 | C | ASP | B | 283 | 5290 | 6240 | 6132 | −217 | −171 | −539 | C |
| ATOM | 2534 | O | ASP | B | 283 | 17.361 | −60.580 | −56.356 | 1.00 | 51.52 | | O |
| ANISOU | 2534 | O | ASP | B | 283 | 6000 | 6863 | 6714 | −113 | −116 | −565 | O |
| ATOM | 2535 | N | ARG | B | 284 | 19.453 | −61.391 | −56.073 | 1.00 | 39.50 | | N |
| ANISOU | 2535 | N | ARG | B | 284 | 4279 | 5492 | 5239 | −274 | −269 | −476 | N |
| ATOM | 2536 | CA | ARG | B | 284 | 19.053 | −62.591 | −55.364 | 1.00 | 33.67 | | C |
| ANISOU | 2536 | CA | ARG | B | 284 | 3490 | 4883 | 4420 | −212 | −317 | −425 | C |
| ATOM | 2537 | CB | ARG | B | 284 | 20.272 | −63.428 | −54.987 | 1.00 | 28.15 | | C |
| ANISOU | 2537 | CB | ARG | B | 284 | 2630 | 4315 | 3750 | −271 | −426 | −322 | C |
| ATOM | 2538 | CG | ARG | B | 284 | 19.912 | −64.691 | −54.250 | 1.00 | 27.84 | | C |
| ANISOU | 2538 | CG | ARG | B | 284 | 2548 | 4395 | 3635 | −205 | −473 | −247 | C |
| ATOM | 2539 | CD | ARG | B | 284 | 21.133 | −65.407 | −53.748 | 1.00 | 28.92 | | C |
| ANISOU | 2539 | CD | ARG | B | 284 | 2523 | 4662 | 3804 | −256 | −591 | −127 | C |
| ATOM | 2540 | NE | ARG | B | 284 | 21.669 | −64.773 | −52.553 | 1.00 | 33.95 | | N |
| ANISOU | 2540 | NE | ARG | B | 284 | 3179 | 5395 | 4327 | −418 | −734 | −176 | N |
| ATOM | 2541 | CZ | ARG | B | 284 | 22.957 | −64.737 | −52.232 | 1.00 | 41.87 | | C |
| ANISOU | 2541 | CZ | ARG | B | 284 | 4031 | 6497 | 5379 | −534 | −868 | −96 | C |
| ATOM | 2542 | NH1 | ARG | B | 284 | 23.338 | −64.132 | −51.113 | 1.00 | 40.81 | | N |
| ANISOU | 2542 | NH1 | ARG | B | 284 | 3948 | 6452 | 5106 | −711 | −1022 | −155 | N |
| ATOM | 2543 | NH2 | ARG | B | 284 | 23.860 | −65.305 | −53.030 | 1.00 | 36.38 | | N |
| ANISOU | 2543 | NH2 | ARG | B | 284 | 3139 | 5814 | 4869 | −477 | −845 | 47 | N |
| ATOM | 2544 | C | ARG | B | 284 | 18.241 | −62.282 | −54.115 | 1.00 | 38.55 | | C |
| ANISOU | 2544 | C | ARG | B | 284 | 4231 | 5533 | 4882 | −227 | −326 | −520 | C |
| ATOM | 2545 | O | ARG | B | 284 | 17.240 | −62.947 | −53.833 | 1.00 | 43.50 | | O |
| ANISOU | 2545 | O | ARG | B | 284 | 4873 | 6204 | 5452 | −128 | −285 | −495 | O |
| ATOM | 2546 | N | LEU | B | 285 | 18.674 | −61.282 | −53.356 | 1.00 | 33.79 | | N |
| ANISOU | 2546 | N | LEU | B | 285 | 3726 | 4907 | 4205 | −362 | −371 | −631 | N |
| ATOM | 2547 | CA | LEU | B | 285 | 17.985 | −60.910 | −52.124 | 1.00 | 34.65 | | C |
| ANISOU | 2547 | CA | LEU | B | 285 | 3996 | 5033 | 4135 | −384 | −356 | −743 | C |
| ATOM | 2548 | CB | LEU | B | 285 | 18.823 | −59.925 | −51.299 | 1.00 | 36.43 | | C |
| ANISOU | 2548 | CB | LEU | B | 285 | 4339 | 5240 | 4264 | −587 | −449 | −866 | C |
| ATOM | 2549 | CG | LEU | B | 285 | 18.129 | −59.286 | −50.088 | 1.00 | 48.66 | | C |
| ANISOU | 2549 | CG | LEU | B | 285 | 6128 | 6758 | 5601 | −620 | −398 | −1025 | C |
| ATOM | 2550 | CD1 | LEU | B | 285 | 17.621 | −60.344 | −49.105 | 1.00 | 42.16 | | C |
| ANISOU | 2550 | CD1 | LEU | B | 285 | 5294 | 6110 | 4614 | −562 | −421 | −969 | C |
| ATOM | 2551 | CD2 | LEU | B | 285 | 19.065 | −58.307 | −49.385 | 1.00 | 37.47 | | C |
| ANISOU | 2551 | CD2 | LEU | B | 285 | 4853 | 5303 | 4081 | −863 | −515 | −1160 | C |
| ATOM | 2552 | C | LEU | B | 285 | 16.598 | −60.319 | −52.403 | 1.00 | 39.78 | | C |
| ANISOU | 2552 | C | LEU | B | 285 | 4769 | 5554 | 4791 | −242 | −182 | −807 | C |
| ATOM | 2553 | O | LEU | B | 285 | 15.622 | −60.620 | −51.710 | 1.00 | 45.18 | | O |
| ANISOU | 2553 | O | LEU | B | 285 | 5508 | 6285 | 5374 | −158 | −113 | −821 | O |
| ATOM | 2554 | N | GLU | B | 286 | 16.510 | −59.470 | −53.418 | 1.00 | 38.57 | | N |
| ANISOU | 2554 | N | GLU | B | 286 | 4647 | 5243 | 4766 | −209 | −104 | −826 | N |
| ATOM | 2555 | CA | GLU | B | 286 | 15.245 | −58.823 | −53.738 | 1.00 | 36.15 | | C |
| ANISOU | 2555 | CA | GLU | B | 286 | 4434 | 4809 | 4491 | −63 | 53 | −857 | C |
| ATOM | 2556 | CB | GLU | B | 286 | 15.451 | −57.655 | −54.716 | 1.00 | 33.14 | | C |

TABLE 7-continued

DMXAA-hSTING$^{G230I}$ complex

| | | | | | | | | | | | |
|---|---|---|---|---|---|---|---|---|---|---|---|
| ANISOU | 2556 | CB | GLU | B | 286 | 4120 | 4235 | 4237 | −68 | 114 | −882 C |
| ATOM | 2557 | CG | GLU | B | 286 | 14.712 | −57.756 | −56.037 | 1.00 | 55.45 | C |
| ANISOU | 2557 | CG | GLU | B | 286 | 6870 | 7007 | 7191 | 84 | 180 | −764 C |
| ATOM | 2558 | CD | GLU | B | 286 | 15.366 | −56.918 | −57.124 | 1.00 | 85.14 | C |
| ANISOU | 2558 | CD | GLU | B | 286 | 10659 | 10623 | 11067 | 37 | 195 | −742 C |
| ATOM | 2559 | OE1 | GLU | B | 286 | 15.889 | −55.828 | −56.803 | 1.00 | 89.53 | O |
| ANISOU | 2559 | OE1 | GLU | B | 286 | 11345 | 11044 | 11628 | −66 | 220 | −843 O |
| ATOM | 2560 | OE2 | GLU | B | 286 | 15.380 | −57.361 | −58.294 | 1.00 | 98.84 | O |
| ANISOU | 2560 | OE2 | GLU | B | 286 | 12304 | 12375 | 12878 | 89 | 183 | −625 O |
| ATOM | 2561 | C | GLU | B | 286 | 14.256 | −59.870 | −54.268 | 1.00 | 39.59 | C |
| ANISOU | 2561 | C | GLU | B | 286 | 4739 | 5327 | 4975 | 91 | 85 | −727 C |
| ATOM | 2562 | O | GLU | B | 286 | 13.061 | −59.818 | −53.980 | 1.00 | 34.72 | O |
| ANISOU | 2562 | O | GLU | B | 286 | 4148 | 4705 | 4338 | 210 | 188 | −723 O |
| ATOM | 2563 | N | GLN | B | 287 | 14.776 | −60.843 | −55.012 | 1.00 | 44.75 | N |
| ANISOU | 2563 | N | GLN | B | 287 | 5254 | 6054 | 5694 | 80 | 1 | −618 N |
| ATOM | 2564 | CA | GLN | B | 287 | 13.964 | −61.939 | −55.535 | 1.00 | 41.43 | C |
| ANISOU | 2564 | CA | GLN | B | 287 | 4732 | 5702 | 5309 | 182 | 4 | −503 C |
| ATOM | 2565 | CB | GLN | B | 287 | 14.714 | −62.720 | −56.617 | 1.00 | 40.76 | C |
| ANISOU | 2565 | CB | GLN | B | 287 | 4555 | 5628 | 5304 | 163 | −58 | −414 C |
| ATOM | 2566 | CG | GLN | B | 287 | 14.775 | −62.028 | −57.972 | 1.00 | 29.92 | C |
| ANISOU | 2566 | CG | GLN | B | 287 | 3211 | 4134 | 4024 | 189 | −16 | −395 C |
| ATOM | 2567 | CD | GLN | B | 287 | 13.396 | −61.570 | −58.451 | 1.00 | 31.93 | C |
| ANISOU | 2567 | CD | GLN | B | 287 | 3497 | 4330 | 4305 | 299 | 46 | −367 C |
| ATOM | 2568 | OE1 | GLN | B | 287 | 12.576 | −62.378 | −58.900 | 1.00 | 39.66 | O |
| ANISOU | 2568 | OE1 | GLN | B | 287 | 4418 | 5358 | 5291 | 355 | 25 | −286 O |
| ATOM | 2569 | NE2 | GLN | B | 287 | 13.131 | −60.272 | −58.333 | 1.00 | 27.71 | N |
| ANISOU | 2569 | NE2 | GLN | B | 287 | 3051 | 3684 | 3794 | 325 | 120 | −426 N |
| ATOM | 2570 | C | GLN | B | 287 | 13.545 | −62.899 | −54.427 | 1.00 | 39.65 | C |
| ANISOU | 2570 | C | GLN | B | 287 | 4473 | 5613 | 4981 | 188 | −16 | −478 C |
| ATOM | 2571 | O | GLN | B | 287 | 12.519 | −63.563 | −54.519 | 1.00 | 41.19 | O |
| ANISOU | 2571 | O | GLN | B | 287 | 4612 | 5850 | 5188 | 268 | 19 | −404 O |
| ATOM | 2572 | N | ALA | B | 288 | 14.355 | −62.991 | −53.381 | 1.00 | 33.95 | N |
| ANISOU | 2572 | N | ALA | B | 288 | 3781 | 4967 | 4153 | 90 | −83 | −523 N |
| ATOM | 2573 | CA | ALA | B | 288 | 14.047 | −63.891 | −52.279 | 1.00 | 36.31 | C |
| ANISOU | 2573 | CA | ALA | B | 288 | 4064 | 5399 | 4332 | 89 | −105 | −483 C |
| ATOM | 2574 | CB | ALA | B | 288 | 15.283 | −64.149 | −51.418 | 1.00 | 31.44 | C |
| ANISOU | 2574 | CB | ALA | B | 288 | 3445 | 4882 | 3618 | −37 | −237 | −488 C |
| ATOM | 2575 | C | ALA | B | 288 | 12.908 | −63.316 | −51.436 | 1.00 | 39.30 | C |
| ANISOU | 2575 | C | ALA | B | 288 | 4551 | 5770 | 4610 | 150 | 25 | −553 C |
| ATOM | 2576 | O | ALA | B | 288 | 12.043 | −64.044 | −50.945 | 1.00 | 45.30 | O |
| ANISOU | 2576 | O | ALA | B | 288 | 5274 | 6612 | 5325 | 210 | 77 | −485 O |
| ATOM | 2577 | O | LYS | B | 289 | 9.476 | −61.562 | −50.849 | 1.00 | 39.69 | O |
| ANISOU | 2577 | O | LYS | B | 289 | 4734 | 5668 | 4677 | 487 | 508 | −625 O |
| ATOM | 2578 | N | LYS | B | 289 | 12.924 | −62.001 | −51.261 | 1.00 | 41.72 | N |
| ANISOU | 2578 | N | LYS | B | 289 | 4998 | 5966 | 4889 | 135 | 96 | −686 N |
| ATOM | 2579 | CA | LYS | B | 289 | 11.853 | −61.317 | −50.557 | 1.00 | 42.18 | C |
| ANISOU | 2579 | CA | LYS | B | 289 | 5178 | 5978 | 4870 | 223 | 265 | −761 C |
| ATOM | 2580 | C | LYS | B | 289 | 10.570 | −61.385 | −51.379 | 1.00 | 34.77 | C |
| ANISOU | 2580 | C | LYS | B | 289 | 4130 | 4999 | 4083 | 387 | 381 | −663 C |
| ATOM | 2581 | CB | LYS | B | 289 | 12.231 | −59.865 | −50.288 | 1.00 | 43.09 | C |
| ANISOU | 2581 | CB | LYS | B | 289 | 5495 | 5939 | 4937 | 169 | 323 | −933 C |
| ATOM | 2582 | CG | LYS | B | 289 | 13.396 | −59.703 | −49.335 | 1.00 | 36.93 | C |
| ANISOU | 2582 | CG | LYS | B | 289 | 4839 | 5210 | 3982 | −25 | 194 | −1039 C |
| ATOM | 2583 | CD | LYS | B | 289 | 13.807 | −58.250 | −49.216 | 1.00 | 38.40 | C |
| ANISOU | 2583 | CD | LYS | B | 289 | 5238 | 5211 | 4141 | −111 | 237 | −1214 C |
| ATOM | 2584 | CE | LYS | B | 289 | 14.775 | −58.046 | −48.066 | 1.00 | 42.13 | C |
| ANISOU | 2584 | CE | LYS | B | 289 | 5866 | 5745 | 4395 | −328 | 103 | −1334 C |
| ATOM | 2585 | NZ | LYS | B | 289 | 15.258 | −56.640 | −48.000 | 1.00 | 48.68 | N |
| ANISOU | 2585 | NZ | LYS | B | 289 | 6918 | 6373 | 5204 | −455 | 124 | −1514 N |
| ATOM | 2586 | N | LEU | B | 290 | 10.716 | −61.248 | −52.689 | 1.00 | 35.65 | N |
| ANISOU | 2586 | N | LEU | B | 290 | 4161 | 5033 | 4351 | 408 | 331 | −606 N |
| ATOM | 2587 | CA | LEU | B | 290 | 9.582 | −61.303 | −53.598 | 1.00 | 33.78 | C |
| ANISOU | 2587 | CA | LEU | B | 290 | 3811 | 4771 | 4254 | 539 | 391 | −494 C |
| ATOM | 2588 | CB | LEU | B | 290 | 9.995 | −60.865 | −55.003 | 1.00 | 27.96 | C |
| ANISOU | 2588 | CB | LEU | B | 290 | 3054 | 3927 | 3641 | 535 | 329 | −462 C |
| ATOM | 2589 | CG | LEU | B | 290 | 8.893 | −60.718 | −56.051 | 1.00 | 39.48 | C |
| ANISOU | 2589 | CG | LEU | B | 290 | 4415 | 5352 | 5232 | 655 | 360 | −340 C |
| ATOM | 2590 | CD1 | LEU | B | 290 | 7.794 | −59.783 | −55.558 | 1.00 | 29.63 | C |
| ANISOU | 2590 | CD1 | LEU | B | 290 | 3192 | 4042 | 4023 | 803 | 532 | −345 C |
| ATOM | 2591 | CD2 | LEU | B | 290 | 9.483 | −60.197 | −57.344 | 1.00 | 39.77 | C |
| ANISOU | 2591 | CD2 | LEU | B | 290 | 4482 | 5282 | 5345 | 633 | 301 | −320 C |
| ATOM | 2592 | C | LEU | B | 290 | 9.002 | −62.717 | −53.631 | 1.00 | 36.63 | C |
| ANISOU | 2592 | C | LEU | B | 290 | 4019 | 5274 | 4627 | 544 | 336 | −359 C |
| ATOM | 2593 | O | LEU | B | 290 | 7.807 | −62.918 | −53.846 | 1.00 | 36.44 | O |
| ANISOU | 2593 | O | LEU | B | 290 | 3888 | 5280 | 4676 | 636 | 398 | −260 O |
| ATOM | 2594 | N | PHE | B | 291 | 9.870 | −63.698 | −53.433 | 1.00 | 33.79 | N |
| ANISOU | 2594 | N | PHE | B | 291 | 3639 | 4994 | 4207 | 441 | 217 | −342 N |
| ATOM | 2595 | CA | PHE | B | 291 | 9.461 | −65.087 | −53.417 | 1.00 | 35.66 | C |

TABLE 7-continued

DMXAA-hSTING$^{G230I}$ complex

| | | | | | | | | | | | |
|---|---|---|---|---|---|---|---|---|---|---|---|
| ANISOU | 2595 | CA | PHE | B | 291 | 3763 | 5334 | 4453 | 428 | 165 | −222 | C |
| ATOM | 2596 | CB | PHE | B | 291 | 10.687 | −65.996 | −53.407 | 1.00 | 38.41 | | C |
| ANISOU | 2596 | CB | PHE | B | 291 | 4106 | 5720 | 4765 | 333 | 38 | −205 | C |
| ATOM | 2597 | CG | PHE | B | 291 | 10.380 | −67.418 | −53.073 | 1.00 | 33.19 | | C |
| ANISOU | 2597 | CG | PHE | B | 291 | 3373 | 5146 | 4090 | 314 | 2 | −92 | C |
| ATOM | 2598 | CD1 | PHE | B | 291 | 9.874 | −68.273 | −54.041 | 1.00 | 31.66 | | C |
| ANISOU | 2598 | CD1 | PHE | B | 291 | 3106 | 4926 | 3997 | 316 | −36 | 0 | C |
| ATOM | 2599 | CE1 | PHE | B | 291 | 9.585 | −69.598 | −53.739 | 1.00 | 24.91 | | C |
| ANISOU | 2599 | CE1 | PHE | B | 291 | 2204 | 4122 | 3139 | 283 | −65 | 103 | C |
| ATOM | 2600 | CZ | PHE | B | 291 | 9.794 | −70.071 | −52.441 | 1.00 | 29.79 | | C |
| ANISOU | 2600 | CZ | PHE | B | 291 | 2839 | 4830 | 3651 | 264 | −50 | 133 | C |
| ATOM | 2601 | CE2 | PHE | B | 291 | 10.294 | −69.212 | −51.461 | 1.00 | 28.65 | | C |
| ANISOU | 2601 | CE2 | PHE | B | 291 | 2767 | 4734 | 3382 | 265 | −21 | 46 | C |
| ATOM | 2602 | CD2 | PHE | B | 291 | 10.579 | −67.899 | −51.783 | 1.00 | 30.67 | | C |
| ANISOU | 2602 | CD2 | PHE | B | 291 | 3082 | 4928 | 3645 | 282 | 3 | −76 | C |
| ATOM | 2603 | C | PHE | B | 291 | 8.598 | −65.352 | −52.188 | 1.00 | 34.67 | | C |
| ANISOU | 2603 | C | PHE | B | 291 | 3632 | 5304 | 4238 | 464 | 270 | −197 | C |
| ATOM | 2604 | O | PHE | B | 291 | 7.539 | −65.978 | −52.274 | 1.00 | 40.53 | | O |
| ANISOU | 2604 | O | PHE | B | 291 | 4260 | 6100 | 5040 | 504 | 308 | −84 | O |
| ATOM | 2605 | N | CYS | B | 292 | 9.067 | −64.875 | −51.039 | 1.00 | 28.81 | | N |
| ANISOU | 2605 | N | CYS | B | 292 | 3018 | 4585 | 3343 | 435 | 314 | −298 | N |
| ATOM | 2606 | CA | CYS | B | 292 | 8.345 | −65.044 | −49.784 | 1.00 | 37.29 | | C |
| ANISOU | 2606 | CA | CYS | B | 292 | 4130 | 5750 | 4290 | 468 | 439 | −289 | C |
| ATOM | 2607 | CB | CYS | B | 292 | 9.150 | −64.507 | −48.597 | 1.00 | 37.22 | | C |
| ANISOU | 2607 | CB | CYS | B | 292 | 4314 | 5761 | 4067 | 394 | 442 | −424 | C |
| ATOM | 2608 | SG | CYS | B | 292 | 10.529 | −65.576 | −48.103 | 1.00 | 57.95 | | S |
| ANISOU | 2608 | SG | CYS | B | 292 | 6935 | 8504 | 6579 | 245 | 224 | −375 | S |
| ATOM | 2609 | C | CYS | B | 292 | 6.973 | −64.377 | −49.820 | 1.00 | 41.57 | | C |
| ANISOU | 2609 | C | CYS | B | 292 | 4632 | 6255 | 4909 | 609 | 633 | −268 | C |
| ATOM | 2610 | O | CYS | B | 292 | 5.978 | −64.929 | −49.347 | 1.00 | 51.19 | | O |
| ANISOU | 2610 | O | CYS | B | 292 | 5759 | 7561 | 6129 | 660 | 737 | −164 | O |
| ATOM | 2611 | N | ARG | B | 293 | 6.932 | −63.176 | −50.379 | 1.00 | 34.57 | | N |
| ANISOU | 2611 | N | ARG | B | 293 | 3802 | 5234 | 4099 | 675 | 691 | −349 | N |
| ATOM | 2612 | CA | ARG | B | 293 | 5.693 | −62.428 | −50.480 | 1.00 | 43.87 | | C |
| ANISOU | 2612 | CA | ARG | B | 293 | 4932 | 6359 | 5379 | 838 | 883 | −314 | C |
| ATOM | 2613 | CB | ARG | B | 293 | 5.943 | −61.038 | −51.024 | 1.00 | 33.54 | | C |
| ANISOU | 2613 | CB | ARG | B | 293 | 3737 | 4869 | 4135 | 899 | 935 | −419 | C |
| ATOM | 2614 | CG | ARG | B | 293 | 4.782 | −60.115 | −50.788 | 1.00 | 56.13 | | C |
| ANISOU | 2614 | CG | ARG | B | 293 | 6601 | 7653 | 7072 | 1093 | 1180 | −405 | C |
| ATOM | 2615 | CD | ARG | B | 293 | 5.002 | −58.831 | −51.517 | 1.00 | 64.41 | | C |
| ANISOU | 2615 | CD | ARG | B | 293 | 7748 | 8502 | 8222 | 1160 | 1215 | −472 | C |
| ATOM | 2616 | NE | ARG | B | 293 | 4.456 | −58.852 | −52.864 | 1.00 | 88.04 | | N |
| ANISOU | 2616 | NE | ARG | B | 293 | 10543 | 11483 | 11425 | 1232 | 1135 | −304 | N |
| ATOM | 2617 | CZ | ARG | B | 293 | 4.550 | −57.840 | −53.718 | 1.00 | 99.42 | | C |
| ANISOU | 2617 | CZ | ARG | B | 293 | 12033 | 12762 | 12981 | 1300 | 1144 | −306 | C |
| ATOM | 2618 | NH1 | ARG | B | 293 | 4.020 | −57.937 | −54.929 | 1.00 | 95.00 | | N |
| ANISOU | 2618 | NH1 | ARG | B | 293 | 11294 | 12218 | 12582 | 1356 | 1050 | −133 | N |
| ATOM | 2619 | NH2 | ARG | B | 293 | 5.179 | −56.728 | −53.356 | 1.00 | 110.97 | | N |
| ANISOU | 2619 | NH2 | ARG | B | 293 | 13735 | 14041 | 14386 | 1297 | 1239 | −475 | N |
| ATOM | 2620 | C | ARG | B | 293 | 4.682 | −63.129 | −51.383 | 1.00 | 55.14 | | C |
| ANISOU | 2620 | C | ARG | B | 293 | 6110 | 7849 | 6990 | 889 | 844 | −119 | C |
| ATOM | 2621 | O | ARG | B | 293 | 3.496 | −63.269 | −51.048 | 1.00 | 33.81 | | O |
| ANISOU | 2621 | O | ARG | B | 293 | 3282 | 5215 | 4350 | 987 | 984 | −10 | O |
| ATOM | 2622 | N | THR | B | 294 | 5.159 | −63.554 | −52.546 | 1.00 | 35.91 | | N |
| ANISOU | 2622 | N | THR | B | 294 | 3610 | 5393 | 4642 | 813 | 655 | −72 | N |
| ATOM | 2623 | CA | THR | B | 294 | 4.299 | −64.206 | −53.517 | 1.00 | 33.96 | | C |
| ANISOU | 2623 | CA | THR | B | 294 | 3163 | 5196 | 4545 | 820 | 574 | 96 | C |
| ATOM | 2624 | CB | THR | B | 294 | 5.002 | −64.397 | −54.856 | 1.00 | 34.59 | | C |
| ANISOU | 2624 | CB | THR | B | 294 | 3252 | 5213 | 4676 | 740 | 387 | 100 | C |
| ATOM | 2625 | OG1 | THR | B | 294 | 5.428 | −63.126 | −55.348 | 1.00 | 42.60 | | O |
| ANISOU | 2625 | OG1 | THR | B | 294 | 4370 | 6098 | 5720 | 801 | 420 | 17 | O |
| ATOM | 2626 | CG2 | THR | B | 294 | 4.058 | −65.035 | −55.861 | 1.00 | 36.75 | | C |
| ANISOU | 2626 | CG2 | THR | B | 294 | 3353 | 5538 | 5074 | 723 | 286 | 263 | C |
| ATOM | 2627 | C | THR | B | 294 | 3.757 | −65.532 | −52.980 | 1.00 | 41.59 | | C |
| ANISOU | 2627 | C | THR | B | 294 | 4011 | 6298 | 5492 | 754 | 557 | 210 | C |
| ATOM | 2628 | O | THR | B | 294 | 2.570 | −65.842 | −53.122 | 1.00 | 43.13 | | O |
| ANISOU | 2628 | O | THR | B | 294 | 4024 | 6564 | 5800 | 792 | 597 | 357 | O |
| ATOM | 2629 | N | LEU | B | 295 | 4.625 | −66.300 | −52.336 | 1.00 | 34.03 | | N |
| ANISOU | 2629 | N | LEU | B | 295 | 3147 | 5380 | 4403 | 652 | 498 | 160 | N |
| ATOM | 2630 | CA | LEU | B | 295 | 4.220 | −67.570 | −51.755 | 1.00 | 31.60 | | C |
| ANISOU | 2630 | CA | LEU | B | 295 | 2758 | 5181 | 4069 | 584 | 490 | 272 | C |
| ATOM | 2631 | CB | LEU | B | 295 | 5.423 | −68.324 | −51.191 | 1.00 | 36.27 | | C |
| ANISOU | 2631 | CB | LEU | B | 295 | 3470 | 5789 | 4522 | 484 | 397 | 221 | C |
| ATOM | 2632 | CG | LEU | B | 295 | 5.126 | −69.743 | −50.718 | 1.00 | 42.93 | | C |
| ANISOU | 2632 | CG | LEU | B | 295 | 4247 | 6713 | 5350 | 407 | 370 | 354 | C |
| ATOM | 2633 | CD1 | LEU | B | 295 | 4.521 | −70.570 | −51.840 | 1.00 | 38.47 | | C |
| ANISOU | 2633 | CD1 | LEU | B | 295 | 3551 | 6120 | 4945 | 344 | 265 | 469 | C |
| ATOM | 2634 | CD2 | LEU | B | 295 | 6.399 | −70.394 | −50.217 | 1.00 | 39.81 | | C |

TABLE 7-continued

| DMXAA-hSTING$^{G230I}$ complex | | | | | | | | | | | | |
|---|---|---|---|---|---|---|---|---|---|---|---|---|
| ANISOU | 2634 | CD2 | LEU | B | 295 | 3966 | 6325 | 4834 | 336 | 272 | 324 | C |
| ATOM | 2635 | C | LEU | B | 295 | 3.156 | −67.374 | −50.668 | 1.00 | 38.30 | | C |
| ANISOU | 2635 | C | LEU | B | 295 | 3548 | 6116 | 4890 | 671 | 701 | 330 | C |
| ATOM | 2636 | O | LEU | B | 295 | 2.194 | −68.138 | −50.572 | 1.00 | 41.36 | | O |
| ANISOU | 2636 | O | LEU | B | 295 | 3772 | 6588 | 5356 | 652 | 733 | 484 | O |
| ATOM | 2637 | N | GLU | B | 296 | 3.335 | −66.338 | −49.855 | 1.00 | 43.48 | | N |
| ANISOU | 2637 | N | GLU | B | 296 | 4347 | 6742 | 5432 | 758 | 856 | 204 | N |
| ATOM | 2638 | CA | GLU | B | 296 | 2.371 | −66.014 | −48.810 | 1.00 | 40.89 | | C |
| ANISOU | 2638 | CA | GLU | B | 296 | 4003 | 6476 | 5057 | 867 | 1105 | 237 | C |
| ATOM | 2639 | CB | GLU | B | 296 | 2.831 | −64.813 | −47.997 | 1.00 | 56.06 | | C |
| ANISOU | 2639 | CB | GLU | B | 296 | 6167 | 8320 | 6815 | 940 | 1256 | 46 | C |
| ATOM | 2640 | CG | GLU | B | 296 | 3.488 | −65.183 | −46.695 | 1.00 | 74.55 | | C |
| ANISOU | 2640 | CG | GLU | B | 296 | 8700 | 10735 | 8890 | 855 | 1277 | −34 | C |
| ATOM | 2641 | CD | GLU | B | 296 | 3.062 | −64.281 | −45.560 | 1.00 | 88.96 | | C |
| ANISOU | 2641 | CD | GLU | B | 296 | 10707 | 12542 | 10552 | 963 | 1552 | −142 | C |
| ATOM | 2642 | OE1 | GLU | B | 296 | 3.334 | −63.067 | −45.641 | 1.00 | 94.34 | | O |
| ANISOU | 2642 | OE1 | GLU | B | 296 | 11550 | 13082 | 11213 | 1024 | 1623 | −303 | O |
| ATOM | 2643 | OE2 | GLU | B | 296 | 2.444 | −64.784 | −44.598 | 1.00 | 94.25 | | O |
| ANISOU | 2643 | OE2 | GLU | B | 296 | 11373 | 13325 | 11112 | 987 | 1712 | −66 | O |
| ATOM | 2644 | C | GLU | B | 296 | 0.987 | −65.739 | −49.385 | 1.00 | 45.46 | | C |
| ANISOU | 2644 | C | GLU | B | 296 | 4346 | 7072 | 5855 | 987 | 1212 | 388 | C |
| ATOM | 2645 | O | GLU | B | 296 | −0.016 | −66.282 | −48.907 | 1.00 | 46.46 | | O |
| ANISOU | 2645 | O | GLU | B | 296 | 4312 | 7308 | 6033 | 1013 | 1335 | 538 | O |
| ATOM | 2646 | N | ASP | B | 297 | 0.937 | −64.887 | −50.407 | 1.00 | 44.94 | | N |
| ANISOU | 2646 | N | ASP | B | 297 | 4246 | 6903 | 5925 | 1059 | 1164 | 369 | N |
| ATOM | 2647 | CA | ASP | B | 297 | −0.320 | −64.536 | −51.066 | 1.00 | 43.98 | | C |
| ANISOU | 2647 | CA | ASP | B | 297 | 3882 | 6801 | 6027 | 1180 | 1230 | 536 | C |
| ATOM | 2648 | CB | ASP | B | 297 | −0.100 | −63.544 | −52.206 | 1.00 | 55.26 | | C |
| ANISOU | 2648 | CB | ASP | B | 297 | 5333 | 8099 | 7565 | 1249 | 1147 | 501 | C |
| ATOM | 2649 | CG | ASP | B | 297 | 0.364 | −62.195 | −51.730 | 1.00 | 55.60 | | C |
| ANISOU | 2649 | CG | ASP | B | 297 | 5603 | 7991 | 7530 | 1377 | 1322 | 323 | C |
| ATOM | 2650 | OD1 | ASP | B | 297 | 0.296 | −61.941 | −50.512 | 1.00 | 59.05 | | O |
| ANISOU | 2650 | OD1 | ASP | B | 297 | 6168 | 8432 | 7838 | 1437 | 1536 | 235 | O |
| ATOM | 2651 | OD2 | ASP | B | 297 | 0.795 | −61.395 | −52.587 | 1.00 | 65.99 | | O |
| ANISOU | 2651 | OD2 | ASP | B | 297 | 6990 | 9177 | 8906 | 1406 | 1247 | 273 | O |
| ATOM | 2652 | C | ASP | B | 297 | −1.041 | −65.762 | −51.612 | 1.00 | 38.33 | | C |
| ANISOU | 2652 | C | ASP | B | 297 | 2914 | 6210 | 5440 | 1064 | 1083 | 740 | C |
| ATOM | 2653 | O | ASP | B | 297 | −2.264 | −65.860 | −51.532 | 1.00 | 42.92 | | O |
| ANISOU | 2653 | O | ASP | B | 297 | 3255 | 6885 | 6169 | 1132 | 1188 | 920 | O |
| ATOM | 2654 | N | ILE | B | 298 | −0.278 | −66.691 | −52.176 | 1.00 | 35.77 | | N |
| ANISOU | 2654 | N | ILE | B | 298 | 2645 | 5879 | 5068 | 884 | 845 | 717 | N |
| ATOM | 2655 | CA | ILE | B | 298 | −0.846 | −67.912 | −52.735 | 1.00 | 40.37 | | C |
| ANISOU | 2655 | CA | ILE | B | 298 | 3045 | 6542 | 5751 | 737 | 685 | 881 | C |
| ATOM | 2656 | CB | ILE | B | 298 | 0.202 | −68.768 | −53.461 | 1.00 | 46.53 | | C |
| ANISOU | 2656 | CB | ILE | B | 298 | 3961 | 7257 | 6463 | 566 | 446 | 809 | C |
| ATOM | 2657 | CG1 | ILE | B | 298 | 0.770 | −68.028 | −54.658 | 1.00 | 36.57 | | C |
| ANISOU | 2657 | CG1 | ILE | B | 298 | 2779 | 5889 | 5225 | 589 | 320 | 727 | C |
| ATOM | 2658 | CD1 | ILE | B | 298 | 1.810 | −68.840 | −55.397 | 1.00 | 41.99 | | C |
| ANISOU | 2658 | CD1 | ILE | B | 298 | 3605 | 6504 | 5844 | 444 | 127 | 657 | C |
| ATOM | 2659 | CG2 | ILE | B | 298 | −0.414 | −70.075 | −53.955 | 1.00 | 54.61 | | C |
| ANISOU | 2659 | CG2 | ILE | B | 298 | 4841 | 8335 | 7574 | 397 | 297 | 961 | C |
| ATOM | 2660 | C | ILE | B | 298 | −1.461 | −68.766 | −51.642 | 1.00 | 40.22 | | C |
| ANISOU | 2660 | C | ILE | B | 298 | 2935 | 6641 | 5708 | 696 | 814 | 990 | C |
| ATOM | 2661 | O | ILE | B | 298 | −2.615 | −69.194 | −51.738 | 1.00 | 53.46 | | O |
| ANISOU | 2661 | O | ILE | B | 298 | 4363 | 8414 | 7535 | 672 | 837 | 1181 | O |
| ATOM | 2662 | N | LEU | B | 299 | −0.684 | −69.014 | −50.596 | 1.00 | 38.66 | | N |
| ANISOU | 2662 | N | LEU | B | 299 | 2930 | 6441 | 5319 | 678 | 892 | 883 | N |
| ATOM | 2663 | CA | LEU | B | 299 | −1.113 | −69.917 | −49.538 | 1.00 | 46.92 | | C |
| ANISOU | 2663 | CA | LEU | B | 299 | 3929 | 7592 | 6306 | 624 | 1004 | 989 | C |
| ATOM | 2664 | CB | LEU | B | 299 | 0.058 | −70.313 | −48.638 | 1.00 | 40.37 | | C |
| ANISOU | 2664 | CB | LEU | B | 299 | 3349 | 6748 | 5241 | 568 | 992 | 869 | C |
| ATOM | 2665 | CG | LEU | B | 299 | 1.242 | −71.008 | −49.298 | 1.00 | 47.07 | | C |
| ANISOU | 2665 | CG | LEU | B | 299 | 4317 | 7514 | 6054 | 439 | 743 | 802 | C |
| ATOM | 2666 | CD1 | LEU | B | 299 | 2.249 | −71.378 | −48.227 | 1.00 | 34.26 | | C |
| ANISOU | 2666 | CD1 | LEU | B | 299 | 2889 | 5913 | 4214 | 406 | 751 | 735 | C |
| ATOM | 2667 | CD2 | LEU | B | 299 | 0.786 | −72.245 | −50.063 | 1.00 | 56.46 | | C |
| ANISOU | 2667 | CD2 | LEU | B | 299 | 5367 | 8698 | 7387 | 294 | 593 | 949 | C |
| ATOM | 2668 | C | LEU | B | 299 | −2.200 | −69.268 | −48.702 | 1.00 | 53.70 | | C |
| ANISOU | 2668 | C | LEU | B | 299 | 4669 | 8535 | 7199 | 782 | 1299 | 1069 | C |
| ATOM | 2669 | O | LEU | B | 299 | −2.954 | −69.947 | −48.008 | 1.00 | 57.94 | | O |
| ANISOU | 2669 | O | LEU | B | 299 | 5079 | 9180 | 7755 | 752 | 1424 | 1220 | O |
| ATOM | 2670 | N | ALA | B | 300 | −2.267 | −67.946 | −48.767 | 1.00 | 63.18 | | N |
| ANISOU | 2670 | N | ALA | B | 300 | 5919 | 9672 | 8414 | 958 | 1429 | 972 | N |
| ATOM | 2671 | CA | ALA | B | 300 | −3.282 | −67.204 | −48.040 | 1.00 | 59.85 | | C |
| ANISOU | 2671 | CA | ALA | B | 300 | 5401 | 9299 | 8039 | 1150 | 1747 | 1037 | C |
| ATOM | 2672 | CB | ALA | B | 300 | −3.050 | −65.706 | −48.178 | 1.00 | 60.38 | | C |
| ANISOU | 2672 | CB | ALA | B | 300 | 5611 | 9233 | 8097 | 1337 | 1868 | 881 | C |
| ATOM | 2673 | C | ALA | B | 300 | −4.695 | −67.582 | −48.493 | 1.00 | 57.08 | | C |

TABLE 7-continued

| DMXAA-hSTING$^{G230I}$ complex | | | | | | | | | | | |
|---|---|---|---|---|---|---|---|---|---|---|---|
| ANISOU | 2673 | C | ALA | B | 300 | 4669 | 9062 | 7957 | 1165 | 1780 | 1306 | C |
| ATOM | 2674 | O | ALA | B | 300 | −5.610 | −67.662 | −47.677 | 1.00 | 66.06 | | O |
| ANISOU | 2674 | O | ALA | B | 300 | 5712 | 10267 | 9119 | 1226 | 2000 | 1412 | O |
| ATOM | 2675 | N | ASP | B | 301 | −4.886 | −67.815 | −49.788 | 1.00 | 65.21 | | N |
| ANISOU | 2675 | N | ASP | B | 301 | 5528 | 10083 | 9166 | 1075 | 1521 | 1398 | N |
| ATOM | 2676 | CA | ASP | B | 301 | −6.214 | −68.201 | −50.283 | 1.00 | 67.76 | | C |
| ANISOU | 2676 | CA | ASP | B | 301 | 5586 | 10456 | 9703 | 1011 | 1440 | 1610 | C |
| ATOM | 2677 | CB | ASP | B | 301 | −6.868 | −67.074 | −51.115 | 1.00 | 81.90 | | C |
| ANISOU | 2677 | CB | ASP | B | 301 | 7289 | 12176 | 11655 | 1153 | 1416 | 1647 | C |
| ATOM | 2678 | CG | ASP | B | 301 | −5.877 | −66.324 | −52.000 | 1.00 | 89.10 | | C |
| ANISOU | 2678 | CG | ASP | B | 301 | 8343 | 12981 | 12531 | 1204 | 1283 | 1505 | C |
| ATOM | 2679 | OD2 | ASP | B | 301 | −5.328 | −65.298 | −51.536 | 1.00 | 88.15 | | O |
| ANISOU | 2679 | OD2 | ASP | B | 301 | 8401 | 12769 | 12323 | 1381 | 1473 | 1352 | O |
| ATOM | 2680 | OD1 | ASP | B | 301 | −5.663 | −66.743 | −53.161 | 1.00 | 90.10 | | O |
| ANISOU | 2680 | OD1 | ASP | B | 301 | 8421 | 13104 | 12710 | 1060 | 995 | 1542 | O |
| ATOM | 2681 | C | ASP | B | 301 | −6.288 | −69.545 | −51.025 | 1.00 | 56.04 | | C |
| ANISOU | 2681 | C | ASP | B | 301 | 3986 | 9021 | 8286 | 745 | 1149 | 1724 | C |
| ATOM | 2682 | O | ASP | B | 301 | −7.196 | −69.770 | −51.820 | 1.00 | 56.45 | | O |
| ANISOU | 2682 | O | ASP | B | 301 | 3860 | 9089 | 8499 | 659 | 991 | 1865 | O |
| ATOM | 2683 | N | ALA | B | 302 | −5.345 | −70.439 | −50.748 | 1.00 | 57.46 | | N |
| ANISOU | 2683 | N | ALA | B | 302 | 4278 | 9220 | 8334 | 611 | 1081 | 1668 | N |
| ATOM | 2684 | CA | ALA | B | 302 | −5.311 | −71.733 | −51.428 | 1.00 | 56.84 | | C |
| ANISOU | 2684 | CA | ALA | B | 302 | 4155 | 9138 | 8303 | 351 | 814 | 1745 | C |
| ATOM | 2685 | CB | ALA | B | 302 | −3.879 | −72.149 | −51.719 | 1.00 | 45.83 | | C |
| ANISOU | 2685 | CB | ALA | B | 302 | 3079 | 7607 | 6728 | 257 | 640 | 1543 | C |
| ATOM | 2686 | C | ALA | B | 302 | −6.028 | −72.827 | −50.645 | 1.00 | 71.42 | | C |
| ANISOU | 2686 | C | ALA | B | 302 | 5889 | 11064 | 10181 | 221 | 894 | 1908 | C |
| ATOM | 2687 | O | ALA | B | 302 | −5.816 | −72.955 | −49.431 | 1.00 | 74.27 | | O |
| ANISOU | 2687 | O | ALA | B | 302 | 6326 | 11478 | 10417 | 283 | 1119 | 1901 | O |
| ATOM | 2688 | N | PRO | B | 303 | −6.855 | −73.631 | −51.336 | 1.00 | 72.68 | | N |
| ANISOU | 2688 | N | PRO | B | 303 | 5904 | 11225 | 10487 | 28 | 703 | 2047 | N |
| ATOM | 2689 | CA | PRO | B | 303 | −7.617 | −74.701 | −50.690 | 1.00 | 74.37 | | C |
| ANISOU | 2689 | CA | PRO | B | 303 | 6012 | 11491 | 10754 | −118 | 758 | 2211 | C |
| ATOM | 2690 | CB | PRO | B | 303 | −8.429 | −75.305 | −51.839 | 1.00 | 73.83 | | C |
| ANISOU | 2690 | CB | PRO | B | 303 | 5805 | 11401 | 10846 | −328 | 484 | 2322 | C |
| ATOM | 2691 | CG | PRO | B | 303 | −7.663 | −74.932 | −53.083 | 1.00 | 71.49 | | C |
| ANISOU | 2691 | CG | PRO | B | 303 | 5624 | 11023 | 10516 | −351 | 247 | 2187 | C |
| ATOM | 2692 | CD | PRO | B | 303 | −7.105 | −73.574 | −52.781 | 1.00 | 66.21 | | C |
| ANISOU | 2692 | CD | PRO | B | 303 | 5031 | 10355 | 9771 | −75 | 420 | 2058 | C |
| ATOM | 2693 | C | PRO | B | 303 | −6.731 | −75.775 | −50.063 | 1.00 | 73.91 | | C |
| ANISOU | 2693 | C | PRO | B | 303 | 6098 | 11416 | 10568 | −251 | 769 | 2197 | C |
| ATOM | 2694 | O | PRO | B | 303 | −7.024 | −76.250 | −48.963 | 1.00 | 77.94 | | O |
| ANISOU | 2694 | O | PRO | B | 303 | 6599 | 11982 | 11032 | −255 | 960 | 2290 | O |
| ATOM | 2695 | N | GLU | B | 304 | −5.661 | −76.151 | −50.754 | 1.00 | 69.48 | | N |
| ANISOU | 2695 | N | GLU | B | 304 | 5728 | 10742 | 9929 | −347 | 561 | 2066 | N |
| ATOM | 2696 | CA | GLU | B | 304 | −4.767 | −77.200 | −50.281 | 1.00 | 68.27 | | C |
| ANISOU | 2696 | CA | GLU | B | 304 | 5821 | 10486 | 9634 | −454 | 525 | 2008 | C |
| ATOM | 2697 | CB | GLU | B | 304 | −3.688 | −77.501 | −51.328 | 1.00 | 73.82 | | C |
| ANISOU | 2697 | CB | GLU | B | 304 | 6759 | 11016 | 10274 | −531 | 277 | 1836 | C |
| ATOM | 2698 | CG | GLU | B | 304 | −4.210 | −78.117 | −52.613 | 1.00 | 87.50 | | C |
| ANISOU | 2698 | CG | GLU | B | 304 | 8408 | 12687 | 12152 | −748 | 29 | 1895 | C |
| ATOM | 2699 | CD | GLU | B | 304 | −4.517 | −77.086 | −53.689 | 1.00 | 96.38 | | C |
| ANISOU | 2699 | CD | GLU | B | 304 | 9428 | 13848 | 13345 | −684 | −86 | 1853 | C |
| ATOM | 2700 | OE1 | GLU | B | 304 | −4.824 | −77.498 | −54.830 | 1.00 | 98.39 | | O |
| ANISOU | 2700 | OE1 | GLU | B | 304 | 9657 | 14053 | 13673 | −864 | −319 | 1877 | O |
| ATOM | 2701 | OE2 | GLU | B | 304 | −4.445 | −75.871 | −53.398 | 1.00 | 99.97 | | O |
| ANISOU | 2701 | OE2 | GLU | B | 304 | 9844 | 14369 | 13770 | −459 | 53 | 1798 | O |
| ATOM | 2702 | C | GLU | B | 304 | −4.079 | −76.849 | −48.966 | 1.00 | 72.34 | | C |
| ANISOU | 2702 | C | GLU | B | 304 | 6514 | 11032 | 9939 | −286 | 747 | 1927 | C |
| ATOM | 2703 | O | GLU | B | 304 | −3.619 | −77.731 | −48.239 | 1.00 | 68.39 | | O |
| ANISOU | 2703 | O | GLU | B | 304 | 6152 | 10500 | 9333 | −356 | 777 | 1959 | O |
| ATOM | 2704 | N | SER | B | 305 | −4.003 | −75.559 | −48.660 | 1.00 | 81.91 | | N |
| ANISOU | 2704 | N | SER | B | 305 | 7740 | 12297 | 11084 | −73 | 896 | 1825 | N |
| ATOM | 2705 | CA | SER | B | 305 | −3.018 | −75.088 | −47.694 | 1.00 | 81.25 | | C |
| ANISOU | 2705 | CA | SER | B | 305 | 7910 | 12203 | 10758 | 60 | 1021 | 1672 | C |
| ATOM | 2706 | CB | SER | B | 305 | −1.918 | −74.309 | −48.420 | 1.00 | 90.03 | | C |
| ANISOU | 2706 | CB | SER | B | 305 | 9204 | 13206 | 11798 | 132 | 876 | 1450 | C |
| ATOM | 2707 | OG | SER | B | 305 | −2.281 | −72.947 | −48.558 | 1.00 | 95.84 | | O |
| ANISOU | 2707 | OG | SER | B | 305 | 9881 | 13966 | 12568 | 304 | 994 | 1381 | O |
| ATOM | 2708 | C | SER | B | 305 | −3.557 | −74.213 | −46.568 | 1.00 | 68.97 | | C |
| ANISOU | 2708 | C | SER | B | 305 | 6326 | 10763 | 9115 | 240 | 1333 | 1685 | C |
| ATOM | 2709 | O | SER | B | 305 | −2.983 | −73.166 | −46.268 | 1.00 | 60.24 | | O |
| ANISOU | 2709 | O | SER | B | 305 | 5386 | 9633 | 7868 | 391 | 1416 | 1510 | O |
| ATOM | 2710 | N | GLN | B | 306 | −4.645 | −74.633 | −45.936 | 1.00 | 61.47 | | N |
| ANISOU | 2710 | N | GLN | B | 306 | 5182 | 9929 | 8245 | 220 | 1520 | 1888 | N |
| ATOM | 2711 | CA | GLN | B | 306 | −5.167 | −73.874 | −44.810 | 1.00 | 71.71 | | C |
| ANISOU | 2711 | CA | GLN | B | 306 | 6477 | 11330 | 9440 | 401 | 1862 | 1904 | C |
| ATOM | 2712 | CB | GLN | B | 306 | −6.651 | −73.553 | −44.986 | 1.00 | 79.97 | | C |

TABLE 7-continued

DMXAA-hSTING$^{G230I}$ complex

| | | | | | | | | | | |
|---|---|---|---|---|---|---|---|---|---|---|
| ANISOU | 2712 | CB | GLN | B | 306 | 7229 | 12429 | 10725 | 462 | 1993 | 2060 | C |
| ATOM | 2713 | CG | GLN | B | 306 | −6.918 | −72.103 | −45.367 | 1.00 | 82.70 | | C |
| ANISOU | 2713 | CG | GLN | B | 306 | 7564 | 12723 | 11135 | 676 | 2073 | 1941 | C |
| ATOM | 2714 | CD | GLN | B | 306 | −7.004 | −71.895 | −46.871 | 1.00 | 84.65 | | C |
| ANISOU | 2714 | CD | GLN | B | 306 | 7669 | 12905 | 11589 | 625 | 1793 | 1943 | C |
| ATOM | 2715 | OE1 | GLN | B | 306 | −7.975 | −72.313 | −47.504 | 1.00 | 89.64 | | O |
| ANISOU | 2715 | OE1 | GLN | B | 306 | 8084 | 13547 | 12428 | 524 | 1664 | 2096 | O |
| ATOM | 2716 | NE2 | GLN | B | 306 | −5.986 | −71.250 | −47.452 | 1.00 | 66.88 | | N |
| ANISOU | 2716 | NE2 | GLN | B | 306 | 5553 | 10590 | 9267 | 685 | 1690 | 1774 | N |
| ATOM | 2717 | C | GLN | B | 306 | −4.918 | −74.564 | −43.471 | 1.00 | 77.44 | | C |
| ANISOU | 2717 | C | GLN | B | 306 | 7367 | 12119 | 9938 | 361 | 2015 | 1958 | C |
| ATOM | 2718 | O | GLN | B | 306 | −5.391 | −75.679 | −43.241 | 1.00 | 68.72 | | O |
| ANISOU | 2718 | O | GLN | B | 306 | 6146 | 11059 | 8904 | 213 | 2014 | 2157 | O |
| ATOM | 2719 | N | ASN | B | 307 | −4.164 | −73.880 | −42.608 | 1.00 | 85.87 | | N |
| ANISOU | 2719 | N | ASN | B | 307 | 8718 | 13183 | 10724 | 480 | 2133 | 1782 | N |
| ATOM | 2720 | CA | ASN | B | 307 | −3.852 | −74.336 | −41.251 | 1.00 | 89.27 | | C |
| ANISOU | 2720 | CA | ASN | B | 307 | 9355 | 13690 | 10875 | 463 | 2282 | 1814 | C |
| ATOM | 2721 | CB | ASN | B | 307 | −5.124 | −74.653 | −40.455 | 1.00 | 97.75 | | C |
| ANISOU | 2721 | CB | ASN | B | 307 | 10244 | 14899 | 11997 | 490 | 2602 | 2043 | C |
| ATOM | 2722 | CG | ASN | B | 307 | −5.812 | −73.412 | −39.938 | 1.00 | 109.38 | | C |
| ANISOU | 2722 | CG | ASN | B | 307 | 11753 | 16370 | 13437 | 700 | 2886 | 1936 | C |
| ATOM | 2723 | OD1 | ASN | B | 307 | −5.588 | −72.993 | −38.803 | 1.00 | 113.80 | | O |
| ANISOU | 2723 | OD1 | ASN | B | 307 | 12569 | 16962 | 13708 | 785 | 3096 | 1839 | O |
| ATOM | 2724 | ND2 | ASN | B | 307 | −6.647 | −72.805 | −40.776 | 1.00 | 112.34 | | N |
| ANISOU | 2724 | ND2 | ASN | B | 307 | 11900 | 16687 | 14098 | 776 | 2872 | 1944 | N |
| ATOM | 2725 | C | ASN | B | 307 | −2.870 | −75.502 | −41.150 | 1.00 | 91.34 | | C |
| ANISOU | 2725 | C | ASN | B | 307 | 9769 | 13907 | 11029 | 293 | 2040 | 1845 | C |
| ATOM | 2726 | O | ASN | B | 307 | −2.672 | −76.062 | −40.072 | 1.00 | 99.67 | | O |
| ANISOU | 2726 | O | ASN | B | 307 | 10967 | 15032 | 11872 | 259 | 2134 | 1926 | O |
| ATOM | 2727 | N | ASN | B | 308 | −2.248 | −75.871 | −42.261 | 1.00 | 85.11 | | N |
| ANISOU | 2727 | N | ASN | B | 308 | 8959 | 12997 | 10380 | 200 | 1741 | 1790 | N |
| ATOM | 2728 | CA | ASN | B | 308 | −1.301 | −76.979 | −42.251 | 1.00 | 75.53 | | C |
| ANISOU | 2728 | CA | ASN | B | 308 | 7882 | 11716 | 9100 | 67 | 1527 | 1827 | C |
| ATOM | 2729 | CB | ASN | B | 308 | −1.801 | −78.114 | −43.143 | 1.00 | 75.11 | | C |
| ANISOU | 2729 | CB | ASN | B | 308 | 7645 | 11583 | 9312 | −98 | 1383 | 1987 | C |
| ATOM | 2730 | CG | ASN | B | 308 | −2.246 | −77.625 | −44.508 | 1.00 | 73.38 | | C |
| ANISOU | 2730 | CG | ASN | B | 308 | 7246 | 11300 | 9333 | −106 | 1263 | 1923 | C |
| ATOM | 2731 | OD1 | ASN | B | 308 | −2.113 | −76.441 | −44.824 | 1.00 | 84.42 | | O |
| ANISOU | 2731 | OD1 | ASN | B | 308 | 8657 | 12703 | 10714 | 28 | 1285 | 1766 | O |
| ATOM | 2732 | ND2 | ASN | B | 308 | −2.776 | −78.531 | −45.326 | 1.00 | 64.61 | | N |
| ANISOU | 2732 | ND2 | ASN | B | 308 | 5984 | 10124 | 8439 | −272 | 1127 | 2049 | N |
| ATOM | 2733 | C | ASN | B | 308 | 0.105 | −76.575 | −42.679 | 1.00 | 70.87 | | C |
| ANISOU | 2733 | C | ASN | B | 308 | 7487 | 11032 | 8408 | 94 | 1308 | 1619 | C |
| ATOM | 2734 | O | ASN | B | 308 | 0.948 | −77.427 | −42.962 | 1.00 | 67.49 | | O |
| ANISOU | 2734 | O | ASN | B | 308 | 7137 | 10521 | 7986 | 8 | 1112 | 1642 | O |
| ATOM | 2735 | N | CYS | B | 309 | 0.362 | −75.275 | −42.722 | 1.00 | 65.83 | | N |
| ANISOU | 2735 | N | CYS | B | 309 | 6925 | 10399 | 7689 | 216 | 1357 | 1426 | N |
| ATOM | 2736 | CA | CYS | B | 309 | 1.624 | −74.785 | −43.246 | 1.00 | 66.74 | | C |
| ANISOU | 2736 | CA | CYS | B | 309 | 7186 | 10425 | 7746 | 229 | 1155 | 1236 | C |
| ATOM | 2737 | CB | CYS | B | 309 | 1.482 | −74.528 | −44.745 | 1.00 | 65.90 | | C |
| ANISOU | 2737 | CB | CYS | B | 309 | 6938 | 10208 | 7892 | 221 | 1017 | 1181 | C |
| ATOM | 2738 | SG | CYS | B | 309 | 3.012 | −74.649 | −45.686 | 1.00 | 83.51 | | S |
| ANISOU | 2738 | SG | CYS | B | 309 | 9288 | 12305 | 10135 | 176 | 734 | 1046 | S |
| ATOM | 2739 | C | CYS | B | 309 | 2.053 | −73.505 | −42.537 | 1.00 | 72.59 | | C |
| ANISOU | 2739 | C | CYS | B | 309 | 8114 | 11205 | 8261 | 334 | 1261 | 1048 | C |
| ATOM | 2740 | O | CYS | B | 309 | 1.223 | −72.648 | −42.247 | 1.00 | 89.26 | | O |
| ANISOU | 2740 | O | CYS | B | 309 | 10198 | 13353 | 10365 | 439 | 1484 | 1009 | O |
| ATOM | 2741 | N | ARG | B | 310 | 3.346 | −73.374 | −42.262 | 1.00 | 64.25 | | N |
| ANISOU | 2741 | N | ARG | B | 310 | 7248 | 10135 | 7030 | 303 | 1105 | 935 | N |
| ATOM | 2742 | CA | ARG | B | 310 | 3.873 | −72.173 | −41.621 | 1.00 | 65.46 | | C |
| ANISOU | 2742 | CA | ARG | B | 310 | 7609 | 10307 | 6954 | 358 | 1163 | 738 | C |
| ATOM | 2743 | CB | ARG | B | 310 | 4.147 | −72.420 | −40.136 | 1.00 | 71.32 | | C |
| ANISOU | 2743 | CB | ARG | B | 310 | 8553 | 11178 | 7369 | 325 | 1235 | 773 | C |
| ATOM | 2744 | CG | ARG | B | 310 | 3.201 | −71.715 | −39.172 | 1.00 | 76.79 | | C |
| ANISOU | 2744 | CG | ARG | B | 310 | 9347 | 11941 | 7889 | 416 | 1555 | 735 | C |
| ATOM | 2745 | CD | ARG | B | 310 | 3.302 | −70.200 | −39.288 | 1.00 | 85.28 | | C |
| ANISOU | 2745 | CD | ARG | B | 310 | 10560 | 12934 | 8909 | 502 | 1644 | 486 | C |
| ATOM | 2746 | NE | ARG | B | 310 | 2.225 | −69.649 | −40.104 | 1.00 | 98.75 | | N |
| ANISOU | 2746 | NE | ARG | B | 310 | 12068 | 14564 | 10890 | 628 | 1813 | 493 | N |
| ATOM | 2747 | CZ | ARG | B | 310 | 1.021 | −69.330 | −39.637 | 1.00 | 98.10 | | C |
| ANISOU | 2747 | CZ | ARG | B | 310 | 11932 | 14522 | 10820 | 751 | 2135 | 549 | C |
| ATOM | 2748 | NH1 | ARG | B | 310 | 0.101 | −68.839 | −40.457 | 1.00 | 100.92 | | N |
| ANISOU | 2748 | NH1 | ARG | B | 310 | 12070 | 14816 | 11457 | 870 | 2254 | 584 | N |
| ATOM | 2749 | NH2 | ARG | B | 310 | 0.736 | −69.504 | −38.352 | 1.00 | 93.93 | | N |
| ANISOU | 2749 | NH2 | ARG | B | 310 | 11564 | 14104 | 10023 | 761 | 2343 | 586 | N |
| ATOM | 2750 | C | ARG | B | 310 | 5.157 | −71.710 | −42.296 | 1.00 | 56.07 | | C |
| ANISOU | 2750 | C | ARG | B | 310 | 6493 | 9031 | 5780 | 322 | 928 | 585 | C |
| ATOM | 2751 | O | ARG | B | 310 | 6.097 | −72.485 | −42.452 | 1.00 | 46.80 | | O |

TABLE 7-continued

DMXAA-hSTING$^{G230I}$ complex

| | | | | | | | | | | |
|---|---|---|---|---|---|---|---|---|---|---|
| ANISOU | 2751 | O | ARG | B | 310 | 5322 | 7851 | 4609 | 244 | 723 | 644 | O |
| ATOM | 2752 | N | LEU | B | 311 | 5.201 | −70.440 | −42.681 | 1.00 | 55.08 | | N |
| ANISOU | 2752 | N | LEU | B | 311 | 6423 | 8829 | 5675 | 385 | 974 | 403 | N |
| ATOM | 2753 | CA | LEU | B | 311 | 6.395 | −69.888 | −43.306 | 1.00 | 47.77 | | C |
| ANISOU | 2753 | CA | LEU | B | 311 | 5563 | 7821 | 4768 | 342 | 775 | 260 | C |
| ATOM | 2754 | CB | LEU | B | 311 | 6.038 | −68.967 | −44.469 | 1.00 | 41.67 | | C |
| ANISOU | 2754 | CB | LEU | B | 311 | 4706 | 6920 | 4208 | 417 | 807 | 165 | C |
| ATOM | 2755 | CG | LEU | B | 311 | 5.259 | −69.562 | −45.632 | 1.00 | 47.31 | | C |
| ANISOU | 2755 | CG | LEU | B | 311 | 5188 | 7590 | 5198 | 441 | 785 | 296 | C |
| ATOM | 2756 | CD1 | LEU | B | 311 | 5.151 | −68.525 | −46.734 | 1.00 | 39.47 | | C |
| ANISOU | 2756 | CD1 | LEU | B | 311 | 4153 | 6478 | 4365 | 507 | 780 | 196 | C |
| ATOM | 2757 | CD2 | LEU | B | 311 | 5.937 | −70.826 | −46.136 | 1.00 | 56.26 | | C |
| ANISOU | 2757 | CD2 | LEU | B | 311 | 6254 | 8717 | 6406 | 343 | 581 | 404 | C |
| ATOM | 2758 | C | LEU | B | 311 | 7.222 | −69.107 | −42.310 | 1.00 | 49.00 | | C |
| ANISOU | 2758 | C | LEU | B | 311 | 5965 | 8014 | 4637 | 295 | 755 | 105 | C |
| ATOM | 2759 | O | LEU | B | 311 | 6.756 | −68.125 | −41.731 | 1.00 | 53.93 | | O |
| ANISOU | 2759 | O | LEU | B | 311 | 6738 | 8624 | 5128 | 351 | 941 | −24 | O |
| ATOM | 2760 | N | ILE | B | 312 | 8.460 | −69.539 | −42.127 | 1.00 | 50.10 | | N |
| ANISOU | 2760 | N | ILE | B | 312 | 6151 | 8196 | 4687 | 190 | 527 | 120 | N |
| ATOM | 2761 | CA | ILE | B | 312 | 9.385 | −68.840 | −41.260 | 1.00 | 56.88 | | C |
| ANISOU | 2761 | CA | ILE | B | 312 | 7229 | 9103 | 5279 | 102 | 440 | −17 | C |
| ATOM | 2762 | CB | ILE | B | 312 | 9.977 | −69.777 | −40.214 | 1.00 | 57.55 | | C |
| ANISOU | 2762 | CB | ILE | B | 312 | 7378 | 9346 | 5143 | 14 | 312 | 121 | C |
| ATOM | 2763 | CG1 | ILE | B | 312 | 8.854 | −70.395 | −39.383 | 1.00 | 58.06 | | C |
| ANISOU | 2763 | CG1 | ILE | B | 312 | 7470 | 9499 | 5091 | 69 | 525 | 249 | C |
| ATOM | 2764 | CD1 | ILE | B | 312 | 9.348 | −71.173 | −38.184 | 1.00 | 66.92 | | C |
| ANISOU | 2764 | CD1 | ILE | B | 312 | 8708 | 10783 | 5936 | −14 | 429 | 383 | C |
| ATOM | 2765 | CG2 | ILE | B | 312 | 10.946 | −69.028 | −39.314 | 1.00 | 62.34 | | C |
| ANISOU | 2765 | CG2 | ILE | B | 312 | 8215 | 10021 | 5453 | −109 | 183 | −18 | C |
| ATOM | 2766 | C | ILE | B | 312 | 10.488 | −68.203 | −42.094 | 1.00 | 58.72 | | C |
| ANISOU | 2766 | C | ILE | B | 312 | 7442 | 9245 | 5626 | 42 | 251 | −132 | C |
| ATOM | 2767 | O | ILE | B | 312 | 11.409 | −68.883 | −42.548 | 1.00 | 58.08 | | O |
| ANISOU | 2767 | O | ILE | B | 312 | 7241 | 9181 | 5645 | −11 | 47 | −37 | O |
| ATOM | 2768 | N | ALA | B | 313 | 10.368 | −66.897 | −42.314 | 1.00 | 49.35 | | N |
| ANISOU | 2768 | N | ALA | B | 313 | 6367 | 7946 | 4437 | 60 | 341 | −327 | N |
| ATOM | 2769 | CA | ALA | B | 313 | 11.343 | −66.146 | −43.085 | 1.00 | 56.06 | | C |
| ANISOU | 2769 | CA | ALA | B | 313 | 7212 | 8694 | 5393 | −6 | 193 | −442 | C |
| ATOM | 2770 | CB | ALA | B | 313 | 10.643 | −65.213 | −44.061 | 1.00 | 52.60 | | C |
| ANISOU | 2770 | CB | ALA | B | 313 | 6745 | 8087 | 5154 | 102 | 346 | −539 | C |
| ATOM | 2771 | C | ALA | B | 313 | 12.248 | −65.352 | −42.150 | 1.00 | 61.09 | | C |
| ANISOU | 2771 | C | ALA | B | 313 | 8081 | 9365 | 5764 | −156 | 88 | −596 | C |
| ATOM | 2772 | O | ALA | B | 313 | 11.772 | −64.751 | −41.185 | 1.00 | 68.71 | | O |
| ANISOU | 2772 | O | ALA | B | 313 | 9278 | 10337 | 6491 | −161 | 231 | −716 | O |
| ATOM | 2773 | N | TYR | B | 314 | 13.550 | −65.334 | −42.429 | 1.00 | 47.83 | | N |
| ANISOU | 2773 | N | TYR | B | 314 | 6346 | 7705 | 4122 | −285 | −157 | −593 | N |
| ATOM | 2774 | CA | TYR | B | 314 | 14.497 | −64.704 | −41.515 | 1.00 | 44.44 | | C |
| ANISOU | 2774 | CA | TYR | B | 314 | 6111 | 7336 | 3437 | −471 | −314 | −711 | C |
| ATOM | 2775 | CB | TYR | B | 314 | 14.834 | −65.652 | −40.365 | 1.00 | 52.33 | | C |
| ANISOU | 2775 | CB | TYR | B | 314 | 7144 | 8547 | 4191 | −546 | −448 | −571 | C |
| ATOM | 2776 | CG | TYR | B | 314 | 15.399 | −66.985 | −40.809 | 1.00 | 54.74 | | C |
| ANISOU | 2776 | CG | TYR | B | 314 | 7175 | 8948 | 4676 | −514 | −610 | −319 | C |
| ATOM | 2777 | CD1 | TYR | B | 314 | 14.552 | −68.036 | −41.168 | 1.00 | 45.98 | | C |
| ANISOU | 2777 | CD1 | TYR | B | 314 | 5924 | 7835 | 3711 | −361 | −480 | −157 | C |
| ATOM | 2778 | CE1 | TYR | B | 314 | 15.057 | −69.256 | −41.575 | 1.00 | 51.00 | | C |
| ANISOU | 2778 | CE1 | TYR | B | 314 | 6348 | 8520 | 4510 | −326 | −605 | 61 | C |
| ATOM | 2779 | CZ | TYR | B | 314 | 16.431 | −69.438 | −41.630 | 1.00 | 53.70 | | C |
| ANISOU | 2779 | CZ | TYR | B | 314 | 6586 | 8930 | 4888 | −417 | −852 | 138 | C |
| ATOM | 2780 | OH | TYR | B | 314 | 16.939 | −70.650 | −42.029 | 1.00 | 57.45 | | O |
| ANISOU | 2780 | OH | TYR | B | 314 | 6860 | 9432 | 5538 | −353 | −944 | 359 | O |
| ATOM | 2781 | CE2 | TYR | B | 314 | 17.299 | −68.412 | −41.274 | 1.00 | 49.58 | | C |
| ANISOU | 2781 | CE2 | TYR | B | 314 | 6160 | 8442 | 4235 | −576 | −1000 | 1 | C |
| ATOM | 2782 | CD2 | TYR | B | 314 | 16.779 | −67.196 | −40.869 | 1.00 | 50.19 | | C |
| ANISOU | 2782 | CD2 | TYR | B | 314 | 6479 | 8455 | 4135 | −636 | −886 | −235 | C |
| ATOM | 2783 | C | TYR | B | 314 | 15.790 | −64.197 | −42.149 | 1.00 | 53.73 | | C |
| ANISOU | 2783 | C | TYR | B | 314 | 7207 | 8468 | 4741 | −608 | −532 | −753 | C |
| ATOM | 2784 | O | TYR | B | 314 | 16.194 | −64.631 | −43.229 | 1.00 | 57.40 | | O |
| ANISOU | 2784 | O | TYR | B | 314 | 7435 | 8897 | 5476 | −559 | −595 | −643 | O |
| ATOM | 2785 | N | GLN | B | 315 | 16.430 | −63.265 | −41.449 | 1.00 | 63.40 | | N |
| ANISOU | 2785 | N | GLN | B | 315 | 8643 | 9690 | 5755 | −793 | −636 | −916 | N |
| ATOM | 2786 | CA | GLN | B | 315 | 17.754 | −62.769 | −41.784 | 1.00 | 58.19 | | C |
| ANISOU | 2786 | CA | GLN | B | 315 | 7915 | 9023 | 5170 | −978 | −872 | −945 | C |
| ATOM | 2787 | CB | GLN | B | 315 | 17.682 | −61.320 | −42.249 | 1.00 | 63.88 | | C |
| ANISOU | 2787 | CB | GLN | B | 315 | 8803 | 9520 | 5950 | −1030 | −768 | −1173 | C |
| ATOM | 2788 | CG | GLN | B | 315 | 17.232 | −61.139 | −43.684 | 1.00 | 76.11 | | C |
| ANISOU | 2788 | CG | GLN | B | 315 | 10187 | 10898 | 7834 | −859 | −611 | −1148 | C |
| ATOM | 2789 | CD | GLN | B | 315 | 16.845 | −59.703 | −43.998 | 1.00 | 78.59 | | C |
| ANISOU | 2789 | CD | GLN | B | 315 | 10712 | 10970 | 8179 | −863 | −446 | −1363 | C |
| ATOM | 2790 | OE1 | GLN | B | 315 | 16.212 | −59.028 | −43.182 | 1.00 | 79.14 | | O |

TABLE 7-continued

DMXAA-hSTING$^{G230I}$ complex

| | | | | | | | | | | | | |
|---|---|---|---|---|---|---|---|---|---|---|---|---|
| ANISOU | 2790 | OE1 | GLN | B | 315 | 11067 | 10965 | 8038 | −863 | −301 | −1531 | O |
| ATOM | 2791 | NE2 | GLN | B | 315 | 17.233 | −59.226 | −45.179 | 1.00 | 72.97 | | N |
| ANISOU | 2791 | NE2 | GLN | B | 315 | 9876 | 10124 | 7726 | −858 | −453 | −1355 | N |
| ATOM | 2792 | C | GLN | B | 315 | 18.601 | −62.846 | −40.517 | 1.00 | 76.95 | | C |
| ANISOU | 2792 | C | GLN | B | 315 | 10416 | 11586 | 7237 | −1200 | −1119 | −940 | C |
| ATOM | 2793 | O | GLN | B | 315 | 18.141 | −62.471 | −39.446 | 1.00 | 89.39 | | O |
| ANISOU | 2793 | O | GLN | B | 315 | 12286 | 13186 | 8493 | −1260 | −1055 | −1070 | O |
| ATOM | 2794 | N | GLU | B | 316 | 19.829 | −63.340 | −40.641 | 1.00 | 91.32 | | N |
| ANISOU | 2794 | N | GLU | B | 316 | 12012 | 13541 | 9145 | −1317 | −1396 | −780 | N |
| ATOM | 2795 | CA | GLU | B | 316 | 20.745 | −63.371 | −39.512 | 1.00 | 103.82 | | C |
| ANISOU | 2795 | CA | GLU | B | 316 | 13675 | 15319 | 10452 | −1552 | −1684 | −747 | C |
| ATOM | 2796 | CB | GLU | B | 316 | 21.678 | −64.576 | −39.595 | 1.00 | 104.60 | | C |
| ANISOU | 2796 | CB | GLU | B | 316 | 13440 | 15618 | 10684 | −1540 | −1918 | −441 | C |
| ATOM | 2797 | CG | GLU | B | 316 | 20.938 | −65.885 | −39.352 | 1.00 | 107.98 | | C |
| ANISOU | 2797 | CG | GLU | B | 316 | 13801 | 16131 | 11094 | −1329 | −1806 | −248 | C |
| ATOM | 2798 | CD | GLU | B | 316 | 21.616 | −67.105 | −39.941 | 1.00 | 108.58 | | C |
| ANISOU | 2798 | CD | GLU | B | 316 | 13521 | 16292 | 11443 | −1215 | −1916 | 46 | C |
| ATOM | 2799 | OE1 | GLU | B | 316 | 21.908 | −67.099 | −41.155 | 1.00 | 110.89 | | O |
| ANISOU | 2799 | OE1 | GLU | B | 316 | 13604 | 16465 | 12064 | −1130 | −1858 | 71 | O |
| ATOM | 2800 | OE2 | GLU | B | 316 | 21.844 | −68.076 | −39.186 | 1.00 | 107.84 | | O |
| ANISOU | 2800 | OE2 | GLU | B | 316 | 13373 | 16374 | 11226 | −1202 | −2045 | 257 | O |
| ATOM | 2801 | C | GLU | B | 316 | 21.498 | −62.044 | −39.454 | 1.00 | 106.74 | | C |
| ANISOU | 2801 | C | GLU | B | 316 | 14194 | 15602 | 10762 | −1812 | −1819 | −953 | C |
| ATOM | 2802 | O | GLU | B | 316 | 21.997 | −61.573 | −40.481 | 1.00 | 93.77 | | O |
| ANISOU | 2802 | O | GLU | B | 316 | 12385 | 13837 | 9404 | −1831 | −1827 | −967 | O |
| ATOM | 2803 | N | PRO | B | 317 | 21.567 | −61.425 | −38.261 | 1.00 | 122.71 | | N |
| ANISOU | 2803 | N | PRO | B | 317 | 16548 | 17673 | 12402 | −2024 | −1916 | −1118 | N |
| ATOM | 2804 | CA | PRO | B | 317 | 21.948 | −60.013 | −38.191 | 1.00 | 132.63 | | C |
| ANISOU | 2804 | CA | PRO | B | 317 | 18048 | 18767 | 13576 | −2260 | −1962 | −1380 | C |
| ATOM | 2805 | CB | PRO | B | 317 | 21.568 | −59.613 | −36.766 | 1.00 | 135.12 | | C |
| ANISOU | 2805 | CB | PRO | B | 317 | 18755 | 19068 | 13515 | −2318 | −1917 | −1530 | C |
| ATOM | 2806 | CG | PRO | B | 317 | 21.634 | −60.870 | −35.987 | 1.00 | 134.36 | | C |
| ANISOU | 2806 | CG | PRO | B | 317 | 18545 | 19228 | 13276 | −2251 | −2038 | −1289 | C |
| ATOM | 2807 | CD | PRO | B | 317 | 21.250 | −61.978 | −36.937 | 1.00 | 127.50 | | C |
| ANISOU | 2807 | CD | PRO | B | 317 | 17354 | 18461 | 12629 | −2051 | −1964 | −1076 | C |
| ATOM | 2808 | C | PRO | B | 317 | 23.423 | −59.711 | −38.449 | 1.00 | 136.31 | | C |
| ANISOU | 2808 | C | PRO | B | 317 | 18280 | 19257 | 14254 | −2455 | −2252 | −1283 | C |
| ATOM | 2809 | O | PRO | B | 317 | 24.275 | −60.600 | −38.460 | 1.00 | 137.99 | | O |
| ANISOU | 2809 | O | PRO | B | 317 | 18171 | 19659 | 14602 | −2449 | −2462 | −1018 | O |
| ATOM | 2810 | N | ALA | B | 318 | 23.698 | −58.425 | −38.644 | 1.00 | 134.68 | | N |
| ANISOU | 2810 | N | ALA | B | 318 | 18244 | 18839 | 14088 | −2615 | −2233 | −1496 | N |
| ATOM | 2811 | CA | ALA | B | 318 | 25.045 | −57.927 | −38.868 | 1.00 | 134.75 | | C |
| ANISOU | 2811 | CA | ALA | B | 318 | 18067 | 18844 | 14287 | −2827 | −2473 | −1435 | C |
| ATOM | 2812 | CB | ALA | B | 318 | 24.989 | −56.513 | −39.418 | 1.00 | 130.58 | | C |
| ANISOU | 2812 | CB | ALA | B | 318 | 17740 | 18024 | 13849 | −2946 | −2352 | −1682 | C |
| ATOM | 2813 | C | ALA | B | 318 | 25.845 | −57.962 | −37.571 | 1.00 | 142.07 | | C |
| ANISOU | 2813 | C | ALA | B | 318 | 19063 | 19921 | 14997 | −3003 | −2729 | −1385 | C |
| ATOM | 2814 | O | ALA | B | 318 | 27.007 | −58.367 | −37.557 | 1.00 | 141.03 | | O |
| ANISOU | 2814 | O | ALA | B | 318 | 18626 | 19946 | 15012 | −3096 | −2977 | −1173 | O |
| ATOM | 2815 | N | ASP | B | 319 | 25.212 | −57.527 | −36.485 | 1.00 | 148.14 | | N |
| ANISOU | 2815 | N | ASP | B | 319 | 20234 | 20636 | 15417 | −3041 | −2650 | −1580 | N |
| ATOM | 2816 | CA | ASP | B | 319 | 25.834 | −57.534 | −35.164 | 1.00 | 154.39 | | C |
| ANISOU | 2816 | CA | ASP | B | 319 | 21149 | 21569 | 15944 | −3215 | −2879 | −1558 | C |
| ATOM | 2817 | CB | ASP | B | 319 | 24.908 | −56.862 | −34.135 | 1.00 | 155.73 | | C |
| ANISOU | 2817 | CB | ASP | B | 319 | 21823 | 21614 | 15735 | −3226 | −2698 | −1831 | C |
| ATOM | 2818 | CG | ASP | B | 319 | 25.460 | −56.892 | −32.705 | 1.00 | 156.17 | | C |
| ANISOU | 2818 | CG | ASP | B | 319 | 22047 | 21824 | 15468 | −3409 | −2927 | −1821 | C |
| ATOM | 2819 | OD2 | ASP | B | 319 | 24.720 | −56.475 | −31.790 | 1.00 | 154.31 | | O |
| ANISOU | 2819 | OD2 | ASP | B | 319 | 22214 | 21512 | 14904 | −3402 | −2775 | −2019 | O |
| ATOM | 2820 | OD1 | ASP | B | 319 | 26.617 | −57.306 | −32.482 | 1.00 | 157.72 | | O |
| ANISOU | 2820 | OD1 | ASP | B | 319 | 21981 | 22212 | 15735 | −3553 | −3243 | −1617 | O |
| ATOM | 2821 | C | ASP | B | 319 | 26.207 | −58.955 | −34.734 | 1.00 | 158.08 | | C |
| ANISOU | 2821 | C | ASP | B | 319 | 21342 | 22330 | 16393 | −3121 | −3053 | −1246 | C |
| ATOM | 2822 | O | ASP | B | 319 | 27.335 | −59.199 | −34.309 | 1.00 | 158.92 | | O |
| ANISOU | 2822 | O | ASP | B | 319 | 21258 | 22595 | 16530 | −3265 | −3338 | −1080 | O |
| ATOM | 2823 | N | ASP | B | 320 | 25.280 | −59.899 | −34.853 | 1.00 | 162.03 | | N |
| ANISOU | 2823 | N | ASP | B | 320 | 21812 | 22895 | 16857 | −2878 | −2880 | −1152 | N |
| ATOM | 2824 | CA | ASP | B | 320 | 25.534 | −61.216 | −34.276 | 1.00 | 165.55 | | C |
| ANISOU | 2824 | CA | ASP | B | 320 | 22067 | 23590 | 17246 | −2785 | −3022 | −867 | C |
| ATOM | 2825 | CB | ASP | B | 320 | 24.931 | −61.301 | −32.866 | 1.00 | 166.08 | | C |
| ANISOU | 2825 | CB | ASP | B | 320 | 22495 | 23724 | 16883 | −2800 | −2989 | −950 | C |
| ATOM | 2826 | CG | ASP | B | 320 | 23.511 | −60.766 | −32.801 | 1.00 | 159.31 | | C |
| ANISOU | 2826 | CG | ASP | B | 320 | 22006 | 22693 | 15833 | −2684 | −2638 | −1210 | C |
| ATOM | 2827 | OD1 | ASP | B | 320 | 23.335 | −59.533 | −32.894 | 1.00 | 160.32 | | O |
| ANISOU | 2827 | OD1 | ASP | B | 320 | 22385 | 22609 | 15921 | −2786 | −2530 | −1486 | O |
| ATOM | 2828 | OD2 | ASP | B | 320 | 22.572 | −61.577 | −32.650 | 1.00 | 151.47 | | O |
| ANISOU | 2828 | OD2 | ASP | B | 320 | 21046 | 21765 | 14740 | −2484 | −2455 | −1130 | O |
| ATOM | 2829 | C | ASP | B | 320 | 25.139 | −62.449 | −35.096 | 1.00 | 160.85 | | C |

TABLE 7-continued

DMXAA-hSTING$^{G230I}$ complex

| | | | | | | | | | | | |
|---|---|---|---|---|---|---|---|---|---|---|---|
| ANISOU | 2829 | C | ASP | B | 320 | 21166 | 23073 | 16876 | −2528 | −2918 | −632 | C |
| ATOM | 2830 | O | ASP | B | 320 | 24.187 | −62.435 | −35.871 | 1.00 | 153.36 | | O |
| ANISOU | 2830 | O | ASP | B | 320 | 20252 | 22015 | 16005 | −2380 | −2672 | −718 | O |
| ATOM | 2831 | N | SER | B | 321 | 25.906 | −63.518 | −34.914 | 1.00 | 160.92 | | N |
| ANISOU | 2831 | N | SER | B | 321 | 20877 | 23269 | 16997 | −2477 | −3108 | −329 | N |
| ATOM | 2832 | CA | SER | B | 321 | 25.512 | −64.834 | −35.387 | 1.00 | 151.93 | | C |
| ANISOU | 2832 | CA | SER | B | 321 | 19501 | 22211 | 16013 | −2229 | −3015 | −86 | C |
| ATOM | 2833 | CB | SER | B | 321 | 26.713 | −65.606 | −35.929 | 1.00 | 146.23 | | C |
| ANISOU | 2833 | CB | SER | B | 321 | 18341 | 21583 | 15637 | −2176 | −3187 | 212 | C |
| ATOM | 2834 | OG | SER | B | 321 | 27.142 | −65.068 | −37.169 | 1.00 | 139.13 | | O |
| ANISOU | 2834 | OG | SER | B | 321 | 17238 | 20565 | 15059 | −2188 | −3145 | 166 | O |
| ATOM | 2835 | C | SER | B | 321 | 24.888 | −65.553 | −34.201 | 1.00 | 151.24 | | C |
| ANISOU | 2835 | C | SER | B | 321 | 19618 | 22246 | 15599 | −2165 | −2993 | −13 | C |
| ATOM | 2836 | O | SER | B | 321 | 24.579 | −66.745 | −34.263 | 1.00 | 149.88 | | O |
| ANISOU | 2836 | O | SER | B | 321 | 19295 | 22158 | 15493 | −1979 | −2940 | 214 | O |
| ATOM | 2837 | N | SER | B | 322 | 24.703 | −64.796 | −33.120 | 1.00 | 148.53 | | N |
| ANISOU | 2837 | N | SER | B | 322 | 19634 | 21897 | 14905 | −2322 | −3019 | −211 | N |
| ATOM | 2838 | CA | SER | B | 322 | 24.074 | −65.282 | −31.896 | 1.00 | 139.82 | | C |
| ANISOU | 2838 | CA | SER | B | 322 | 18789 | 20897 | 13441 | −2284 | −2975 | −183 | C |
| ATOM | 2839 | CB | SER | B | 322 | 24.248 | −64.263 | −30.769 | 1.00 | 136.69 | | C |
| ANISOU | 2839 | CB | SER | B | 322 | 18757 | 20484 | 12695 | −2503 | −3061 | −412 | C |
| ATOM | 2840 | OG | SER | B | 322 | 23.663 | −64.732 | −29.567 | 1.00 | 135.33 | | O |
| ANISOU | 2840 | OG | SER | B | 322 | 18841 | 20418 | 12161 | −2461 | −3009 | −380 | O |
| ATOM | 2841 | C | SER | B | 322 | 22.594 | −65.528 | −32.130 | 1.00 | 131.96 | | C |
| ANISOU | 2841 | C | SER | B | 322 | 17957 | 19828 | 12355 | −2092 | −2633 | −263 | C |
| ATOM | 2842 | O | SER | B | 322 | 21.897 | −66.087 | −31.280 | 1.00 | 124.96 | | O |
| ANISOU | 2842 | O | SER | B | 322 | 17249 | 19021 | 11209 | −2011 | −2529 | −207 | O |
| ATOM | 2843 | N | PHE | B | 323 | 22.124 | −65.067 | −33.282 | 1.00 | 131.11 | | N |
| ANISOU | 2843 | N | PHE | B | 323 | 17787 | 19571 | 12458 | −2026 | −2453 | −394 | N |
| ATOM | 2844 | CA | PHE | B | 323 | 20.783 | −65.336 | −33.756 | 1.00 | 125.36 | | C |
| ANISOU | 2844 | CA | PHE | B | 323 | 17128 | 18784 | 11719 | −1837 | −2131 | −441 | C |
| ATOM | 2845 | CB | PHE | B | 323 | 20.672 | −64.887 | −35.206 | 1.00 | 115.89 | | C |
| ANISOU | 2845 | CB | PHE | B | 323 | 15754 | 17449 | 10831 | −1794 | −2031 | −533 | C |
| ATOM | 2846 | CG | PHE | B | 323 | 19.483 | −65.432 | −35.919 | 1.00 | 103.25 | | C |
| ANISOU | 2846 | CG | PHE | B | 323 | 14067 | 15762 | 9402 | −1530 | −1712 | −493 | C |
| ATOM | 2847 | CD2 | PHE | B | 323 | 18.332 | −64.680 | −36.026 | 1.00 | 98.48 | | C |
| ANISOU | 2847 | CD2 | PHE | B | 323 | 13693 | 14968 | 8757 | −1426 | −1379 | −722 | C |
| ATOM | 2848 | CE2 | PHE | B | 323 | 17.246 | −65.176 | −36.682 | 1.00 | 91.99 | | C |
| ANISOU | 2848 | CE2 | PHE | B | 323 | 12749 | 14045 | 8158 | −1171 | −1092 | −659 | C |
| ATOM | 2849 | CZ | PHE | B | 323 | 17.285 | −66.447 | −37.242 | 1.00 | 89.11 | | C |
| ANISOU | 2849 | CZ | PHE | B | 323 | 12068 | 13746 | 8044 | −1030 | −1128 | −389 | C |
| ATOM | 2850 | CE1 | PHE | B | 323 | 18.427 | −67.206 | −37.140 | 1.00 | 90.71 | | C |
| ANISOU | 2850 | CE1 | PHE | B | 323 | 12070 | 14108 | 8286 | −1114 | −1429 | −174 | C |
| ATOM | 2851 | CD1 | PHE | B | 323 | 19.516 | −66.698 | −36.490 | 1.00 | 96.20 | | C |
| ANISOU | 2851 | CD1 | PHE | B | 323 | 12848 | 14925 | 8778 | −1352 | −1719 | −213 | C |
| ATOM | 2852 | C | PHE | B | 323 | 20.493 | −66.827 | −33.655 | 1.00 | 118.50 | | C |
| ANISOU | 2852 | C | PHE | B | 323 | 16065 | 18067 | 10893 | −1665 | −2116 | −131 | C |
| ATOM | 2853 | O | PHE | B | 323 | 21.286 | −67.654 | −34.106 | 1.00 | 114.91 | | O |
| ANISOU | 2853 | O | PHE | B | 323 | 15277 | 17687 | 10698 | −1619 | −2294 | 120 | O |
| ATOM | 2854 | N | SER | B | 324 | 19.344 | −67.169 | −33.084 | 1.00 | 109.51 | | N |
| ANISOU | 2854 | N | SER | B | 324 | 15132 | 16955 | 9522 | −1558 | −1876 | −141 | N |
| ATOM | 2855 | CA | SER | B | 324 | 18.992 | −68.567 | −32.937 | 1.00 | 103.68 | | C |
| ANISOU | 2855 | CA | SER | B | 324 | 14236 | 16340 | 8817 | −1404 | −1840 | 156 | C |
| ATOM | 2856 | CB | SER | B | 324 | 18.778 | −68.928 | −31.470 | 1.00 | 106.53 | | C |
| ANISOU | 2856 | CB | SER | B | 324 | 14848 | 16804 | 8823 | −1428 | −1842 | 222 | C |
| ATOM | 2857 | OG | SER | B | 324 | 19.087 | −70.292 | −31.240 | 1.00 | 107.49 | | O |
| ANISOU | 2857 | OG | SER | B | 324 | 14763 | 17046 | 9034 | −1339 | −1960 | 562 | O |
| ATOM | 2858 | C | SER | B | 324 | 17.758 | −68.907 | −33.752 | 1.00 | 97.37 | | C |
| ANISOU | 2858 | C | SER | B | 324 | 13358 | 15440 | 8196 | −1195 | −1505 | 155 | C |
| ATOM | 2859 | O | SER | B | 324 | 16.683 | −68.338 | −33.549 | 1.00 | 89.22 | | O |
| ANISOU | 2859 | O | SER | B | 324 | 12553 | 14306 | 7040 | −1133 | −1208 | −35 | O |
| ATOM | 2860 | N | LEU | B | 325 | 17.936 | −69.831 | −34.689 | 1.00 | 92.59 | | N |
| ANISOU | 2860 | N | LEU | B | 325 | 12414 | 14792 | 7974 | −1050 | −1523 | 364 | N |
| ATOM | 2861 | CA | LEU | B | 325 | 16.844 | −70.345 | −35.487 | 1.00 | 77.71 | | C |
| ANISOU | 2861 | CA | LEU | B | 325 | 10408 | 12755 | 6362 | −833 | −1227 | 400 | C |
| ATOM | 2862 | CB | LEU | B | 325 | 17.380 | −71.355 | −36.490 | 1.00 | 67.08 | | C |
| ANISOU | 2862 | CB | LEU | B | 325 | 8717 | 11366 | 5403 | −723 | −1323 | 625 | C |
| ATOM | 2863 | CG | LEU | B | 325 | 16.495 | −71.622 | −37.698 | 1.00 | 58.36 | | C |
| ANISOU | 2863 | CG | LEU | B | 325 | 7468 | 10063 | 4644 | −547 | −1077 | 602 | C |
| ATOM | 2864 | CD1 | LEU | B | 325 | 16.414 | −70.353 | −38.494 | 1.00 | 59.41 | | C |
| ANISOU | 2864 | CD1 | LEU | B | 325 | 7634 | 10047 | 4894 | −569 | −999 | 337 | C |
| ATOM | 2865 | CD2 | LEU | B | 325 | 17.079 | −72.746 | −38.530 | 1.00 | 52.74 | | C |
| ANISOU | 2865 | CD2 | LEU | B | 325 | 6476 | 9311 | 4253 | −449 | −1172 | 830 | C |
| ATOM | 2866 | C | LEU | B | 325 | 15.881 | −71.044 | −34.550 | 1.00 | 78.74 | | C |
| ANISOU | 2866 | C | LEU | B | 325 | 10687 | 12974 | 6257 | −767 | −1051 | 517 | C |
| ATOM | 2867 | O | LEU | B | 325 | 14.665 | −70.868 | −34.639 | 1.00 | 80.00 | | O |
| ANISOU | 2867 | O | LEU | B | 325 | 10929 | 13037 | 6432 | −659 | −742 | 426 | O |
| ATOM | 2868 | N | SER | B | 326 | 16.454 | −71.842 | −33.651 | 1.00 | 79.29 | | N |

TABLE 7-continued

| | | | | | | | | | | | |
|---|---|---|---|---|---|---|---|---|---|---|---|
| ANISOU | 2868 | N | SER | B | 326 | 10773 | 13235 | 6119 | −832 | −1251 | 743 | N |
| ATOM | 2869 | CA | SER | B | 326 | 15.705 | −72.604 | −32.657 | 1.00 | 82.66 | | C |
| ANISOU | 2869 | CA | SER | B | 326 | 11344 | 13772 | 6291 | −790 | −1118 | 903 | C |
| ATOM | 2870 | CB | SER | B | 326 | 16.638 | −73.137 | −31.575 | 1.00 | 82.97 | | C |
| ANISOU | 2870 | CB | SER | B | 326 | 11446 | 14000 | 6080 | −901 | −1408 | 1102 | C |
| ATOM | 2871 | OG | SER | B | 326 | 17.338 | −74.275 | −32.027 | 1.00 | 84.18 | | O |
| ANISOU | 2871 | OG | SER | B | 326 | 11301 | 14158 | 6527 | −820 | −1580 | 1394 | O |
| ATOM | 2872 | C | SER | B | 326 | 14.607 | −71.785 | −32.006 | 1.00 | 89.06 | | C |
| ANISOU | 2872 | C | SER | B | 326 | 12468 | 14558 | 6812 | −795 | −821 | 678 | C |
| ATOM | 2873 | O | SER | B | 326 | 13.459 | −72.218 | −31.932 | 1.00 | 91.15 | | O |
| ANISOU | 2873 | O | SER | B | 326 | 12744 | 14781 | 7108 | −668 | −527 | 737 | O |
| ATOM | 2874 | N | GLN | B | 327 | 14.968 | −70.598 | −31.533 | 1.00 | 94.43 | | N |
| ANISOU | 2874 | N | GLN | B | 327 | 13405 | 15257 | 7219 | −945 | −889 | 422 | N |
| ATOM | 2875 | CA | GLN | B | 327 | 14.006 | −69.728 | −30.870 | 1.00 | 100.82 | | C |
| ANISOU | 2875 | CA | GLN | B | 327 | 14554 | 16022 | 7729 | −942 | −589 | 185 | C |
| ATOM | 2876 | CB | GLN | B | 327 | 14.705 | −68.571 | −30.154 | 1.00 | 100.96 | | C |
| ANISOU | 2876 | CB | GLN | B | 327 | 14876 | 16005 | 7480 | −1115 | −741 | −70 | C |
| ATOM | 2877 | CG | GLN | B | 327 | 15.542 | −69.003 | −28.964 | 1.00 | 93.11 | | C |
| ANISOU | 2877 | CG | GLN | B | 327 | 13988 | 15136 | 6254 | −1218 | −1017 | 65 | C |
| ATOM | 2878 | CD | GLN | B | 327 | 14.704 | −69.601 | −27.846 | 1.00 | 92.22 | | C |
| ANISOU | 2878 | CD | GLN | B | 327 | 14083 | 15104 | 5853 | −1132 | −806 | 179 | C |
| ATOM | 2879 | OE1 | GLN | B | 327 | 14.798 | −70.796 | −27.554 | 1.00 | 94.63 | | O |
| ANISOU | 2879 | OE1 | GLN | B | 327 | 14252 | 15521 | 6182 | −1086 | −889 | 478 | O |
| ATOM | 2880 | NE2 | GLN | B | 327 | 13.886 | −68.770 | −27.207 | 1.00 | 94.87 | | N |
| ANISOU | 2880 | NE2 | GLN | B | 327 | 14748 | 15369 | 5928 | −1097 | −516 | −53 | N |
| ATOM | 2881 | C | GLN | B | 327 | 12.977 | −69.201 | −31.857 | 1.00 | 96.35 | | C |
| ANISOU | 2881 | C | GLN | B | 327 | 13891 | 15230 | 7487 | −768 | −256 | 28 | C |
| ATOM | 2882 | O | GLN | B | 327 | 11.796 | −69.087 | −31.530 | 1.00 | 99.40 | | O |
| ANISOU | 2882 | O | GLN | B | 327 | 14400 | 15577 | 7790 | −652 | 90 | −18 | O |
| ATOM | 2883 | N | GLU | B | 328 | 13.424 | −68.883 | −33.067 | 1.00 | 88.48 | | N |
| ANISOU | 2883 | N | GLU | B | 328 | 12664 | 14094 | 6862 | −746 | −359 | −35 | N |
| ATOM | 2884 | CA | GLU | B | 328 | 12.514 | −68.406 | −34.097 | 1.00 | 90.78 | | C |
| ANISOU | 2884 | CA | GLU | B | 328 | 12838 | 14180 | 7475 | −585 | −88 | −153 | C |
| ATOM | 2885 | CB | GLU | B | 328 | 13.255 | −68.096 | −35.383 | 1.00 | 98.28 | | C |
| ANISOU | 2885 | CB | GLU | B | 328 | 13555 | 15004 | 8785 | −596 | −262 | −200 | C |
| ATOM | 2886 | CG | GLU | B | 328 | 12.697 | −66.895 | −36.085 | 1.00 | 108.87 | | C |
| ANISOU | 2886 | CG | GLU | B | 328 | 14955 | 16138 | 10272 | −527 | −56 | −445 | C |
| ATOM | 2887 | CD | GLU | B | 328 | 13.614 | −65.709 | −35.959 | 1.00 | 117.73 | | C |
| ANISOU | 2887 | CD | GLU | B | 328 | 16269 | 17203 | 11260 | −702 | −218 | −676 | C |
| ATOM | 2888 | OE1 | GLU | B | 328 | 13.467 | −64.924 | −34.994 | 1.00 | 123.80 | | O |
| ANISOU | 2888 | OE1 | GLU | B | 328 | 17383 | 17974 | 11682 | −788 | −134 | −864 | O |
| ATOM | 2889 | OE2 | GLU | B | 328 | 14.484 | −65.578 | −36.826 | 1.00 | 117.61 | | O |
| ANISOU | 2889 | OE2 | GLU | B | 328 | 16069 | 17136 | 11482 | −760 | −421 | −667 | O |
| ATOM | 2890 | C | GLU | B | 328 | 11.466 | −69.457 | −34.393 | 1.00 | 94.75 | | C |
| ANISOU | 2890 | C | GLU | B | 328 | 13139 | 14679 | 8182 | −414 | 124 | 61 | C |
| ATOM | 2891 | O | GLU | B | 328 | 10.273 | −69.160 | −34.489 | 1.00 | 104.29 | | O |
| ANISOU | 2891 | O | GLU | B | 328 | 14372 | 15807 | 9448 | −285 | 445 | −1 | O |
| ATOM | 2892 | N | VAL | B | 329 | 11.922 | −70.692 | −34.547 | 1.00 | 87.98 | | N |
| ANISOU | 2892 | N | VAL | B | 329 | 12074 | 13904 | 7450 | −415 | −57 | 323 | N |
| ATOM | 2893 | CA | VAL | B | 329 | 11.021 | −71.789 | −34.843 | 1.00 | 76.45 | | C |
| ANISOU | 2893 | CA | VAL | B | 329 | 10427 | 12428 | 6194 | −289 | 108 | 539 | C |
| ATOM | 2894 | CB | VAL | B | 329 | 11.776 | −73.066 | −35.218 | 1.00 | 63.80 | | C |
| ANISOU | 2894 | CB | VAL | B | 329 | 8603 | 10858 | 4780 | −296 | −128 | 800 | C |
| ATOM | 2895 | CG1 | VAL | B | 329 | 10.790 | −74.173 | −35.534 | 1.00 | 55.84 | | C |
| ANISOU | 2895 | CG1 | VAL | B | 329 | 7434 | 9800 | 3982 | −192 | 50 | 1004 | C |
| ATOM | 2896 | CG2 | VAL | B | 329 | 12.669 | −72.807 | −36.413 | 1.00 | 53.65 | | C |
| ANISOU | 2896 | CG2 | VAL | B | 329 | 7130 | 9460 | 3794 | −301 | −320 | 732 | C |
| ATOM | 2897 | C | VAL | B | 329 | 10.123 | −72.062 | −33.654 | 1.00 | 77.23 | | C |
| ANISOU | 2897 | C | VAL | B | 329 | 10716 | 12641 | 5989 | −270 | 339 | 614 | C |
| ATOM | 2898 | O | VAL | B | 329 | 8.917 | −72.254 | −33.806 | 1.00 | 81.90 | | O |
| ANISOU | 2898 | O | VAL | B | 329 | 11236 | 13182 | 6700 | −158 | 627 | 659 | O |
| ATOM | 2899 | N | LEU | B | 330 | 10.720 | −72.072 | −32.467 | 1.00 | 85.03 | | N |
| ANISOU | 2899 | N | LEU | B | 330 | 11940 | 13791 | 6576 | −387 | 210 | 640 | N |
| ATOM | 2900 | CA | LEU | B | 330 | 9.979 | −72.305 | −31.232 | 1.00 | 87.54 | | C |
| ANISOU | 2900 | CA | LEU | B | 330 | 12487 | 14236 | 6537 | −383 | 426 | 712 | C |
| ATOM | 2901 | CB | LEU | B | 330 | 10.918 | −72.294 | −30.031 | 1.00 | 86.76 | | C |
| ANISOU | 2901 | CB | LEU | B | 330 | 12655 | 14329 | 5981 | −548 | 185 | 740 | C |
| ATOM | 2902 | CG | LEU | B | 330 | 11.548 | −73.642 | −29.702 | 1.00 | 86.00 | | C |
| ANISOU | 2902 | CG | LEU | B | 330 | 12431 | 14371 | 5876 | −583 | −58 | 1083 | C |
| ATOM | 2903 | CD1 | LEU | B | 330 | 12.777 | −73.452 | −28.833 | 1.00 | 89.09 | | C |
| ANISOU | 2903 | CD1 | LEU | B | 330 | 12998 | 14849 | 6001 | −733 | −401 | 1072 | C |
| ATOM | 2904 | CD2 | LEU | B | 330 | 10.523 | −74.525 | −29.009 | 1.00 | 82.24 | | C |
| ANISOU | 2904 | CD2 | LEU | B | 330 | 12003 | 13964 | 5282 | −509 | 208 | 1303 | C |
| ATOM | 2905 | C | LEU | B | 330 | 8.916 | −71.244 | −31.044 | 1.00 | 83.28 | | C |
| ANISOU | 2905 | C | LEU | B | 330 | 12128 | 13614 | 5899 | −303 | 794 | 476 | C |
| ATOM | 2906 | O | LEU | B | 330 | 7.772 | −71.545 | −30.702 | 1.00 | 69.29 | | O |
| ANISOU | 2906 | O | LEU | B | 330 | 10360 | 11860 | 4109 | −199 | 1116 | 565 | O |
| ATOM | 2907 | N | ARG | B | 331 | 9.323 | −69.998 | −31.256 | 1.00 | 89.37 | | N |

TABLE 7-continued

DMXAA-hSTING$^{G230I}$ complex

| | | | | | | | | | | | | |
|---|---|---|---|---|---|---|---|---|---|---|---|---|
| ANISOU | 2907 | N | ARG | B | 331 | 13049 | 14292 | 6618 | −350 | 752 | 188 | N |
| ATOM | 2908 | CA | ARG | B | 331 | 8.427 | −68.857 | −31.161 | 1.00 | 99.06 | | C |
| ANISOU | 2908 | CA | ARG | B | 331 | 14462 | 15399 | 7778 | −256 | 1098 | −59 | C |
| ATOM | 2909 | CB | ARG | B | 331 | 9.116 | −67.599 | −31.675 | 1.00 | 101.32 | | C |
| ANISOU | 2909 | CB | ARG | B | 331 | 14854 | 15538 | 8105 | −326 | 969 | −348 | C |
| ATOM | 2910 | CG | ARG | B | 331 | 8.181 | −66.445 | −31.847 | 1.00 | 100.55 | | C |
| ANISOU | 2910 | CG | ARG | B | 331 | 14892 | 15262 | 8051 | −189 | 1331 | −581 | C |
| ATOM | 2911 | CD | ARG | B | 331 | 8.909 | −65.180 | −32.265 | 1.00 | 102.02 | | C |
| ANISOU | 2911 | CD | ARG | B | 331 | 15229 | 15284 | 8249 | −280 | 1203 | −866 | C |
| ATOM | 2912 | NE | ARG | B | 331 | 8.630 | −64.744 | −33.637 | 1.00 | 100.43 | | N |
| ANISOU | 2912 | NE | ARG | B | 331 | 14763 | 14893 | 8504 | −153 | 1255 | −906 | N |
| ATOM | 2913 | CZ | ARG | B | 331 | 7.418 | −64.585 | −34.172 | 1.00 | 100.26 | | C |
| ANISOU | 2913 | CZ | ARG | B | 331 | 14591 | 14765 | 8738 | 65 | 1582 | −876 | C |
| ATOM | 2914 | NH1 | ARG | B | 331 | 6.315 | −64.840 | −33.479 | 1.00 | 105.24 | | N |
| ANISOU | 2914 | NH1 | ARG | B | 331 | 15280 | 15458 | 9249 | 197 | 1919 | −801 | N |
| ATOM | 2915 | NH2 | ARG | B | 331 | 7.307 | −64.168 | −35.426 | 1.00 | 96.48 | | N |
| ANISOU | 2915 | NH2 | ARG | B | 331 | 13888 | 14127 | 8643 | 152 | 1569 | −904 | N |
| ATOM | 2916 | C | ARG | B | 331 | 7.147 | −69.115 | −31.945 | 1.00 | 98.93 | | C |
| ANISOU | 2916 | C | ARG | B | 331 | 14170 | 15281 | 8140 | −56 | 1405 | 36 | C |
| ATOM | 2917 | O | ARG | B | 331 | 6.054 | −69.081 | −31.383 | 1.00 | 99.18 | | O |
| ANISOU | 2917 | O | ARG | B | 331 | 14280 | 15336 | 8067 | 53 | 1759 | 64 | O |
| ATOM | 2918 | N | HIS | B | 332 | 7.291 | −69.397 | −33.238 | 1.00 | 96.73 | | N |
| ANISOU | 2918 | N | HIS | B | 332 | 13562 | 14899 | 8292 | −15 | 1265 | 100 | N |
| ATOM | 2919 | CA | HIS | B | 332 | 6.155 | −69.778 | −34.076 | 1.00 | 90.75 | | C |
| ANISOU | 2919 | CA | HIS | B | 332 | 12508 | 14064 | 7909 | 138 | 1479 | 223 | C |
| ATOM | 2920 | CB | HIS | B | 332 | 6.599 | −70.048 | −35.513 | 1.00 | 80.89 | | C |
| ANISOU | 2920 | CB | HIS | B | 332 | 10961 | 12703 | 7070 | 138 | 1249 | 262 | C |
| ATOM | 2921 | CG | HIS | B | 332 | 7.070 | −68.842 | −36.254 | 1.00 | 82.31 | | C |
| ANISOU | 2921 | CG | HIS | B | 332 | 11183 | 12737 | 7355 | 141 | 1178 | 18 | C |
| ATOM | 2922 | ND1 | HIS | B | 332 | 8.304 | −68.271 | −36.036 | 1.00 | 93.69 | | N |
| ANISOU | 2922 | ND1 | HIS | B | 332 | 12801 | 14178 | 8618 | 6 | 936 | −133 | N |
| ATOM | 2923 | CE1 | HIS | B | 332 | 8.453 | −67.233 | −36.838 | 1.00 | 90.28 | | C |
| ANISOU | 2923 | CE1 | HIS | B | 332 | 12366 | 13587 | 8349 | 32 | 936 | −322 | C |
| ATOM | 2924 | NE2 | HIS | B | 332 | 7.363 | −67.112 | −37.572 | 1.00 | 78.63 | | N |
| ANISOU | 2924 | NE2 | HIS | B | 332 | 10717 | 12015 | 7143 | 191 | 1161 | −291 | N |
| ATOM | 2925 | CD2 | HIS | B | 332 | 6.484 | −68.109 | −37.226 | 1.00 | 76.20 | | C |
| ANISOU | 2925 | CD2 | HIS | B | 332 | 10287 | 11810 | 6855 | 254 | 1308 | −80 | C |
| ATOM | 2926 | C | HIS | B | 332 | 5.508 | −71.052 | −33.563 | 1.00 | 93.35 | | C |
| ANISOU | 2926 | C | HIS | B | 332 | 12730 | 14519 | 8220 | 153 | 1585 | 509 | C |
| ATOM | 2927 | O | HIS | B | 332 | 4.306 | −71.252 | −33.702 | 1.00 | 95.85 | | O |
| ANISOU | 2927 | O | HIS | B | 332 | 12899 | 14821 | 8699 | 264 | 1866 | 608 | O |
| ATOM | 2928 | N | LEU | B | 333 | 6.321 | −71.936 | −33.000 | 1.00 | 97.34 | | N |
| ANISOU | 2928 | N | LEU | B | 333 | 13290 | 15146 | 8550 | 37 | 1350 | 663 | N |
| ATOM | 2929 | CA | LEU | B | 333 | 5.851 | −73.270 | −32.662 | 1.00 | 92.43 | | C |
| ANISOU | 2929 | CA | LEU | B | 333 | 12544 | 14613 | 7963 | 38 | 1403 | 965 | C |
| ATOM | 2930 | CB | LEU | B | 333 | 7.021 | −74.184 | −32.310 | 1.00 | 86.42 | | C |
| ANISOU | 2930 | CB | LEU | B | 333 | 11808 | 13945 | 7081 | −78 | 1066 | 1134 | C |
| ATOM | 2931 | CG | LEU | B | 333 | 7.060 | −75.490 | −33.095 | 1.00 | 79.82 | | C |
| ANISOU | 2931 | CG | LEU | B | 333 | 10685 | 13047 | 6598 | −69 | 941 | 1385 | C |
| ATOM | 2932 | CD1 | LEU | B | 333 | 8.087 | −76.405 | −32.494 | 1.00 | 75.19 | | C |
| ANISOU | 2932 | CD1 | LEU | B | 333 | 10155 | 12564 | 5851 | −151 | 675 | 1589 | C |
| ATOM | 2933 | CD2 | LEU | B | 333 | 5.701 | −76.139 | −33.059 | 1.00 | 77.71 | | C |
| ANISOU | 2933 | CD2 | LEU | B | 333 | 10289 | 12768 | 6470 | −10 | 1236 | 1557 | C |
| ATOM | 2934 | C | LEU | B | 333 | 4.846 | −73.249 | −31.521 | 1.00 | 93.42 | | C |
| ANISOU | 2934 | C | LEU | B | 333 | 12842 | 14845 | 7807 | 85 | 1755 | 1022 | C |
| ATOM | 2935 | O | LEU | B | 333 | 3.900 | −74.035 | −31.499 | 1.00 | 96.59 | | O |
| ANISOU | 2935 | O | LEU | B | 333 | 13077 | 15270 | 8351 | 134 | 1953 | 1235 | O |
| ATOM | 2936 | N | ARG | B | 334 | 5.057 | −72.344 | −30.575 | 1.00 | 94.55 | | N |
| ANISOU | 2936 | N | ARG | B | 334 | 13332 | 15050 | 7545 | 59 | 1841 | 829 | N |
| ATOM | 2937 | CA | ARG | B | 334 | 4.224 | −72.275 | −29.384 | 1.00 | 99.20 | | C |
| ANISOU | 2937 | CA | ARG | B | 334 | 14150 | 15748 | 7795 | 102 | 2190 | 864 | C |
| ATOM | 2938 | CB | ARG | B | 334 | 5.045 | −71.778 | −28.201 | 1.00 | 100.52 | | C |
| ANISOU | 2938 | CB | ARG | B | 334 | 14750 | 16013 | 7428 | −23 | 2078 | 721 | C |
| ATOM | 2939 | CG | ARG | B | 334 | 6.370 | −72.466 | −28.025 | 1.00 | 100.08 | | C |
| ANISOU | 2939 | CG | ARG | B | 334 | 14710 | 16058 | 7257 | −185 | 1622 | 845 | C |
| ATOM | 2940 | CD | ARG | B | 334 | 7.260 | −71.668 | −27.100 | 1.00 | 96.93 | | C |
| ANISOU | 2940 | CD | ARG | B | 334 | 14713 | 15656 | 6460 | −304 | 1440 | 631 | C |
| ATOM | 2941 | NE | ARG | B | 334 | 8.211 | −72.527 | −26.405 | 1.00 | 93.55 | | N |
| ANISOU | 2941 | NE | ARG | B | 334 | 14344 | 15333 | 5867 | −417 | 1097 | 832 | N |
| ATOM | 2942 | CZ | ARG | B | 334 | 9.371 | −72.112 | −25.911 | 1.00 | 90.12 | | C |
| ANISOU | 2942 | CZ | ARG | B | 334 | 14093 | 14932 | 5216 | −538 | 760 | 725 | C |
| ATOM | 2943 | NH1 | ARG | B | 334 | 9.731 | −70.843 | −26.044 | 1.00 | 92.11 | | N |
| ANISOU | 2943 | NH1 | ARG | B | 334 | 14500 | 15107 | 5389 | −581 | 715 | 408 | N |
| ATOM | 2944 | NH2 | ARG | B | 334 | 10.173 | −72.966 | −25.290 | 1.00 | 87.05 | | N |
| ANISOU | 2944 | NH2 | ARG | B | 334 | 13710 | 14647 | 4718 | −616 | 463 | 943 | N |
| ATOM | 2945 | C | ARG | B | 334 | 3.051 | −71.329 | −29.574 | 1.00 | 105.20 | | C |
| ANISOU | 2945 | C | ARG | B | 334 | 14899 | 16407 | 8666 | 270 | 2606 | 711 | C |
| ATOM | 2946 | O | ARG | B | 334 | 2.972 | −70.311 | −28.891 | 1.00 | 106.41 | | O |

TABLE 7-continued

DMXAA-hSTING$^{G230I}$ complex

| | | | | | | | | | | | |
|---|---|---|---|---|---|---|---|---|---|---|---|
| ANISOU | 2946 | O | ARG | B | 334 | 15366 | 16513 | 8551 | 275 | 2774 | 471 | O |
| ATOM | 2947 | N | GLN | B | 335 | 2.151 | −71.656 | −30.499 | 1.00 | 110.13 | | N |
| ANISOU | 2947 | N | GLN | B | 335 | 15156 | 16954 | 9735 | 377 | 2740 | 839 | N |
| ATOM | 2948 | CA | GLN | B | 335 | 0.966 | −70.834 | −30.755 | 1.00 | 117.76 | | C |
| ANISOU | 2948 | CA | GLN | B | 335 | 16035 | 17825 | 10885 | 551 | 3122 | 746 | C |
| ATOM | 2949 | CB | GLN | B | 335 | 1.361 | −69.420 | −31.188 | 1.00 | 120.81 | | C |
| ANISOU | 2949 | CB | GLN | B | 335 | 16579 | 18065 | 11257 | 612 | 3111 | 422 | C |
| ATOM | 2950 | CG | GLN | B | 335 | 2.490 | −69.384 | −32.185 | 1.00 | 120.50 | | C |
| ANISOU | 2950 | CG | GLN | B | 335 | 16437 | 17937 | 11411 | 503 | 2674 | 339 | C |
| ATOM | 2951 | CD | GLN | B | 335 | 3.390 | −68.182 | −32.004 | 1.00 | 124.25 | | C |
| ANISOU | 2951 | CD | GLN | B | 335 | 17237 | 18322 | 11651 | 445 | 2558 | 23 | C |
| ATOM | 2952 | OE1 | GLN | B | 335 | 3.520 | −67.352 | −32.902 | 1.00 | 120.49 | | O |
| ANISOU | 2952 | OE1 | GLN | B | 335 | 16690 | 17685 | 11405 | 495 | 2512 | −138 | O |
| ATOM | 2953 | NE2 | GLN | B | 335 | 4.030 | −68.088 | −30.840 | 1.00 | 126.10 | | N |
| ANISOU | 2953 | NE2 | GLN | B | 335 | 17837 | 18660 | 11416 | 321 | 2496 | −60 | N |
| ATOM | 2954 | C | GLN | B | 335 | 0.043 | −71.446 | −31.797 | 1.00 | 114.50 | | C |
| ANISOU | 2954 | C | GLN | B | 335 | 15167 | 17378 | 10959 | 630 | 3193 | 961 | C |
| ATOM | 2955 | O | GLN | B | 335 | −1.171 | −71.477 | −31.614 | 1.00 | 115.60 | | O |
| ANISOU | 2955 | O | GLN | B | 335 | 15158 | 17485 | 11278 | 704 | 3477 | 1044 | O |
| TER | 2956 | | GLN | B | 335 | | | | | | | |
| HETATM | 2957 | OAD | DRG | D | 1 | 13.814 | −74.811 | −57.156 | 1.00 | 41.47 | | O |
| HETATM | 2958 | CAQ | DRG | D | 1 | 13.450 | −75.957 | −56.917 | 1.00 | 45.68 | | C |
| HETATM | 2959 | CAS | DRG | D | 1 | 14.342 | −76.902 | −56.447 | 1.00 | 42.75 | | C |
| HETATM | 2960 | CAJ | DRG | D | 1 | 15.671 | −76.550 | −56.238 | 1.00 | 42.35 | | C |
| HETATM | 2961 | CAH | DRG | D | 1 | 16.562 | −77.506 | −55.749 | 1.00 | 49.36 | | C |
| HETATM | 2962 | CAN | DRG | D | 1 | 16.123 | −78.806 | −55.462 | 1.00 | 48.99 | | C |
| HETATM | 2963 | CAA | DRG | D | 1 | 17.016 | −79.758 | −54.970 | 1.00 | 26.42 | | C |
| HETATM | 2964 | CAO | DRG | D | 1 | 14.786 | −79.154 | −55.664 | 1.00 | 51.59 | | C |
| HETATM | 2965 | CAB | DRG | D | 1 | 14.292 | −80.436 | −55.390 | 1.00 | 28.74 | | C |
| HETATM | 2966 | CAT | DRG | D | 1 | 13.929 | −78.201 | −56.179 | 1.00 | 49.39 | | C |
| HETATM | 2967 | OAL | DRG | D | 1 | 12.621 | −78.571 | −56.317 | 1.00 | 46.58 | | O |
| HETATM | 2968 | CAU | DRG | D | 1 | 11.725 | −77.635 | −56.724 | 1.00 | 40.76 | | C |
| HETATM | 2969 | CAR | DRG | D | 1 | 12.132 | −76.337 | −57.038 | 1.00 | 46.46 | | C |
| HETATM | 2970 | CAI | DRG | D | 1 | 11.168 | −75.414 | −57.440 | 1.00 | 47.74 | | C |
| HETATM | 2971 | CAP | DRG | D | 1 | 9.841 | −75.826 | −57.549 | 1.00 | 48.69 | | C |
| HETATM | 2972 | CAG | DRG | D | 1 | 9.444 | −77.132 | −57.259 | 1.00 | 36.91 | | C |
| HETATM | 2973 | CAP | DRG | D | 1 | 10.407 | −78.046 | −56.856 | 1.00 | 38.74 | | C |
| HETATM | 2974 | CAK | DRG | D | 1 | 10.054 | −79.341 | −56.541 | 1.00 | 42.21 | | C |
| HETATM | 2975 | CAM | DRG | D | 1 | 10.081 | −79.604 | −55.033 | 1.00 | 54.65 | | C |
| HETATM | 2976 | OAE | DRG | D | 1 | 10.594 | −78.735 | −54.276 | 1.00 | 48.95 | | O |
| HETATM | 2977 | OAC | DRG | D | 1 | 9.595 | −80.706 | −54.692 | 1.00 | 41.30 | | O |
| HETATM | 2979 | O | HOH | S | 1 | 2.217 | −85.573 | −47.183 | 1.00 | 50.78 | | O |
| HETATM | 2980 | O | HOH | S | 2 | −3.594 | −65.733 | −64.471 | 1.00 | 36.73 | | O |
| HETATM | 2981 | O | HOH | S | 3 | 24.930 | −64.725 | −61.859 | 1.00 | 40.78 | | O |
| HETATM | 2982 | O | HOH | S | 4 | 1.176 | −71.805 | −74.402 | 1.00 | 34.49 | | O |
| HETATM | 2983 | O | HOH | S | 5 | 11.022 | −83.611 | −62.726 | 1.00 | 42.43 | | O |
| HETATM | 2984 | O | HOH | S | 6 | 4.883 | −80.212 | −37.724 | 1.00 | 46.39 | | O |
| HETATM | 2985 | O | HOH | S | 7 | 25.621 | −92.276 | −66.048 | 1.00 | 45.02 | | O |
| HETATM | 2986 | O | HOH | S | 8 | 10.194 | −83.572 | −65.584 | 1.00 | 47.90 | | O |
| HETATM | 2987 | O | HOH | S | 9 | 19.849 | −63.512 | −50.865 | 1.00 | 51.16 | | O |
| HETATM | 2988 | O | HOH | S | 10 | 16.036 | −66.137 | −69.887 | 1.00 | 35.95 | | O |
| HETATM | 2989 | O | HOH | S | 11 | 7.939 | −62.990 | −66.847 | 1.00 | 41.65 | | O |
| HETATM | 2990 | O | HOH | S | 12 | 13.158 | −79.013 | −80.095 | 1.00 | 44.90 | | O |
| HETATM | 2991 | O | HOH | S | 13 | 20.377 | −68.249 | −68.348 | 1.00 | 42.43 | | O |
| HETATM | 2992 | O | HOH | S | 14 | 16.858 | −56.224 | −46.295 | 1.00 | 56.08 | | O |
| HETATM | 2994 | O | HOH | S | 16 | 7.586 | −92.781 | −64.034 | 1.00 | 61.96 | | O |
| HETATM | 2995 | O | HOH | S | 17 | 19.381 | −83.199 | −40.815 | 1.00 | 55.77 | | O |
| HETATM | 2997 | O | HOH | S | 19 | 15.164 | −97.419 | −79.818 | 1.00 | 54.74 | | O |
| HETATM | 2998 | O | HOH | S | 20 | 10.123 | −101.470 | −79.963 | 1.00 | 56.73 | | O |
| HETATM | 2999 | O | HOH | S | 21 | 4.593 | −92.925 | −86.083 | 1.00 | 55.37 | | O |
| HETATM | 3000 | O | HOH | S | 22 | 7.192 | −104.777 | −84.427 | 1.00 | 53.62 | | O |
| HETATM | 3001 | O | HOH | S | 23 | 24.377 | −66.599 | −48.416 | 1.00 | 59.98 | | O |
| HETATM | 3002 | O | HOH | S | 24 | 1.900 | −83.547 | −75.937 | 1.00 | 42.46 | | O |
| HETATM | 3003 | O | HOH | S | 25 | −3.652 | −60.328 | −73.024 | 1.00 | 60.61 | | O |
| HETATM | 3004 | O | HOH | S | 26 | 26.176 | −95.792 | −60.275 | 1.00 | 56.47 | | O |
| HETATM | 3006 | O | HOH | S | 28 | 19.316 | −67.824 | −72.914 | 1.00 | 50.53 | | O |
| HETATM | 3008 | O | HOH | S | 30 | −7.004 | −64.935 | −74.273 | 1.00 | 62.07 | | O |
| HETATM | 3009 | O | HOH | S | 31 | 31.241 | −83.404 | −68.030 | 1.00 | 65.30 | | O |
| HETATM | 3010 | O | HOH | S | 32 | −4.763 | −63.171 | −65.860 | 1.00 | 52.40 | | O |
| HETATM | 3011 | O | HOH | S | 33 | 21.227 | −63.566 | −42.503 | 1.00 | 61.42 | | O |
| HETATM | 3012 | O | HOH | S | 34 | 24.930 | −58.511 | −50.005 | 1.00 | 66.31 | | O |
| HETATM | 3013 | O | HOH | S | 35 | 14.612 | −64.157 | −69.006 | 1.00 | 41.03 | | O |
| HETATM | 3014 | O | HOH | S | 36 | −6.479 | −67.372 | −58.316 | 1.00 | 51.27 | | O |
| HETATM | 3015 | O | HOH | S | 37 | 9.493 | −65.519 | −76.010 | 1.00 | 32.12 | | O |
| HETATM | 3016 | O | HOH | S | 38 | 9.375 | −89.110 | −64.986 | 1.00 | 52.41 | | O |
| HETATM | 3017 | O | HOH | S | 39 | 9.158 | −100.778 | −90.878 | 1.00 | 65.90 | | O |
| HETATM | 3018 | O | HOH | S | 40 | 28.647 | −92.308 | −65.349 | 1.00 | 69.87 | | O |
| HETATM | 3019 | O | HOH | S | 41 | 15.091 | −104.360 | −71.265 | 1.00 | 52.22 | | O |

TABLE 7-continued

DMXAA-hSTING$^{G230I}$ complex

| HETATM | 3020 | O | HOH | S | 42 | 2.782 | −68.546 | −42.680 | 1.00 | 57.16 | O |
|---|---|---|---|---|---|---|---|---|---|---|---|
| HETATM | 3021 | O | HOH | S | 43 | −3.943 | −83.815 | −83.396 | 1.00 | 70.15 | O |
| HETATM | 3022 | O | HOH | S | 44 | −1.599 | −90.833 | −42.798 | 1.00 | 64.86 | O |
| HETATM | 3023 | O | HOH | S | 45 | 19.552 | −84.988 | −42.859 | 1.00 | 75.26 | O |
| HETATM | 3024 | O | HOH | S | 46 | 20.052 | −87.144 | −34.562 | 1.00 | 69.51 | O |
| HETATM | 3026 | O | HOH | S | 47 | 12.863 | −82.710 | −57.870 | 1.00 | 30.00 | O |
| HETATM | 3027 | O | HOH | S | 48 | 8.400 | −82.027 | −55.979 | 1.00 | 30.00 | O |
| HETATM | 3028 | O | HOH | S | 49 | 10.621 | −79.597 | −52.004 | 1.00 | 30.00 | O |
| HETATM | 3029 | O | HOH | S | 50 | 11.112 | −77.252 | −49.600 | 1.00 | 30.00 | O |
| HETATM | 3030 | O | HOH | S | 51 | 12.196 | −95.589 | −62.162 | 1.00 | 30.00 | O |
| HETATM | 3031 | O | HOH | S | 52 | 3.183 | −85.455 | −66.846 | 1.00 | 30.00 | O |
| HETATM | 3032 | O | HOH | S | 53 | 10.175 | −63.155 | −74.823 | 1.00 | 30.00 | O |
| HETATM | 3034 | O | HOH | S | 55 | 0.703 | −90.850 | −62.879 | 1.00 | 30.00 | O |
| END | | | | | | | | | | | |

TABLE 8

DMXAA-hSTING$^{S162A/Q266I}$ complex

REMARK 3
REMARK 3 REFINEMENT.
REMARK 3 PROGRAM: PHENIX (phenix.refine: 1.8.2_1309)
REMARK 3 AUTHORS: Adams, Afonine, Burnley, Chen, Davis, Echols, Gildea,
REMARK 3: Gopal, Gros, Grosse-Kunstleve, Headd, Hung, Immormino,
REMARK 3: Ioerger, McCoy, McKee, Moriarty, Pai, Read, Richardson,
REMARK 3: Richardson, Romo, Sacchettini, Sauter, Smith, Storoni,
EMARK 3: Terwilliger, Zwart
REMARK 3
REMARK 3 REFINEMENT TARGET: ML
REMARK 3
REMARK 3 DATA USED IN REFINEMENT.
REMARK 3 RESOLUTION RANGE HIGH (ANGSTROMS): 2.420
REMARK 3 RESOLUTION RANGE LOW (ANGSTROMS): 128.132
REMARK 3 MIN(FOBS/SIGMA_FOBS): 1.37
REMARK 3 COMPLETENESS FOR RANGE (%): 99.92
REMARK 3 NUMBER OF REFLECTIONS: 17687
REMARK 3 NUMBER OF REFLECTIONS (NON-ANOMALOUS): 17687
REMARK 3
REMARK 3 FIT TO DATA USED IN REFINEMENT.
REMARK 3 R VALUE (WORKING + TEST SET): 0.1849
REMARK 3 R VALUE (WORKING SET): 0.1826
REMARK 3 FREE R VALUE: 0.2288
REMARK 3 FREE R VALUE TEST SET SIZE (%): 5.09
REMARK 3 FREE R VALUE TEST SET COUNT: 900
REMARK 3
REMARK 3 FIT TO DATA USED IN REFINEMENT (IN BINS).
REMARK 3 BIN RESOLUTION RANGE COMPL. NWORK NFREE RWORK RFREE
REMARK 3 1 128.3118-4.3975 1.00 2916 153 0.1666 0.2093
REMARK 3 2 4.3975-3.4904 1.00 2807 157 0.1516 0.1892
REMARK 3 3 3.4904-3.0491 1.00 2768 152 0.1784 0.2393
REMARK 3 4 3.0491-2.7703 1.00 2762 163 0.2125 0.2572
REMARK 3 5 2.7703-2.5717 1.00 2785 124 0.2508 0.2956
REMARK 3 6 2.5717-2.4201 1.00 2749 151 0.3209 0.3813
REMARK 3
REMARK 3 BULK SOLVENT MODELLING.
REMARK 3 METHOD USED: FLAT BULK SOLVENT MODEL
REMARK 3 SOLVENT RADIUS: 1.11
REMARK 3 SHRINKAGE RADIUS: 0.90
REMARK 3 GRID STEP FACTOR: 4.00
REMARK 3
REMARK 3 ERROR ESTHRATES.
REMARK 3 COORDINATE ERROR (MAXIMUM-LIKELIHOOD BASED): 0.36
REMARK 3 PHASE ERROR (DEGREES, MAXIMUM-LIKELIHOOD BASED): 23.15
REMARK 3
REMARK 3 STRUCTURE FACTORS CALCULATION ALGORITHM: FFT
REMARK 3
REMARK 3 DEVIATIONS FROM IDEAL VALUES.
REMARK 3 RMSD MAX COUNT
REMARK 3 BOND: 0.014 0.122 3030
REMARK 3 T33: 0.2519 TI2: 0.0735
REMARK 3 T13: 0.0755 T23: 0.0818
REMARK 3 L TENSOR
REMARK 3 L11: 5.9722 L22: 1.3349
REMARK 3 L33: 1.7568 L12: −1.1178
REMARK 3 L13: −0.3822 L23: 0.2016
REMARK 3 S TENSOR
REMARK 3 S11: 0.2128 S12: 0.9436 S13: −0.0733
REMARK 3 S21: −0.3067 S22: −0.3874 S23: −0.1726
REMARK 3 S31: −0.0468 S32: 0.1617 S33: 0.1883
REMARK 3 TLS GROUP: 2
REMARK 3 SELECTION: chain 'A' and (resid 186 through 197)
REMARK 3 ORIGIN FOR THE GROUP (A): 190.7984 42.0205 −3.5854
REMARK 3 T TENSOR
REMARK 3 T11: 0.3433 T22: 0.7278
REMARK 3 T33: 0.9942 T12: 0.0625
REMARK 3 T13: 0.0145 T23: −0.1884
REMARK 3 L TENSOR
REMARK 3 L11: 0.6328 L22: 1.4550
REMARK 3 L33: 1.9966 L12: 0.9561
REMARK 3 L13: −1.1238 L23: −1.7024
REMARK 3 S TENSOR
REMARK 3 S11: 0.2236 S12: 2.5099 S13: 0.4877
REMARK 3 S21: 0.3243 S22: 0.4937 S23: −0.6010
REMARK 3 S31: 0.4014 S32: 0.9611 S33: −0.3780
REMARK 3 TLS GROUP: 3
REMARK 3 SELECTION: chain 'A' and (resid 198 through 211)
REMARK 3 ORIGIN FOR THE GROUP (A): 170.7088 39.7653 7.4402
REMARK 3 T TENSOR
REMARK 3 T11: 0.2740 T22: 0.4544
REMARK 3 T33: 0.4040 T12: 0.0404
REMARK 3 T13: −0.0470 T23: 0.0714
REMARK 3 L TENSOR
REMARK 3 L11: 5.7895 L22: 3.3168
REMARK 3 L33: 4.0196 L12: 1.5375
REMARK 3 L13: −1.1285 L23: −0.3983
REMARK 3 S TENSOR
REMARK 3 S11: 0.2141 S12: −1.2485 S13: −0.3878
REMARK 3 S21: 0.4935 S22: 0.0 H 6 S23: −0.0676
REMARK 3 S31: 0.0221 S32: 0.3522 S33: −0.0548
REMARK 3 TLS GROUP: 4
REMARK 3 SELECTION: chain 'A' and (resid 212 through 224)
REMARK 3 ORIGIN FOR THE GROUP (A): 183.4756 40.9208 10.1738
REMARK 3 T TENSOR
REMARK 3 T11: 0.4807 T22: 0.3883
REMARK 3 T33: 0.4005 T12: −0.0833
REMARK 3 T13: 0.0009 T23: −0.0042
REMARK 3 L TENSOR
REMARK 3 L11: 1.4467 L22: 7.9564
REMARK 3 L33: 2.3372 L12: 0.3458
REMARK 3 L13: 0.8944 L23: −3.1919
REMARK 3 S TENSOR
REMARK 3 S11: −0.2837 S12: −0.0988 S13: 0.1904
REMARK 3 S21: 0.6346 S22: 0.1878 S23: −0.8066
REMARK 3 S31: −0.6748 S32: 0.1563 S33: −0.0333
REMARK 3 TLS GROUP: 5

TABLE 8-continued

DMXAA-hSTING$^{S162A/Q266I}$ complex

| | |
|---|---|
| REMARK 3 ANGLE: 1.613 32.388 4116 | REMARK 3 SELECTION: chain 'A' and (resid 225 through 280) |
| REMARK 3 CHIRALITY: 0.094 0.461 444 | REMARK 3 ORIGIN FOR THE GROUP (A): 172.8424 46.4350 4.7085 |
| REMARK 3 PLANARITY: 0.006 0.049 542 | REMARK 3 T TENSOR |
| REMARK 3 DIHEDRAL: 19.567 88.200 1134 | REMARK 3 T11: 0.2443 T22: 0.2704 |
| REMARK 3 MIN NONBONDED DISTANCE: 1.815 | REMARK 3 T33: 0.3434 T12: −0.0185 |
| REMARK 3 | REMARK 3 T13: −0.0020 T23: 0.0299 |
| REMARK 3 MOLPROBITY STATISTICS. | REMARK 3 L TENSOR |
| REMARK 3 ALL-ATOM CLASHSCORE: 7.69 | REMARK 3 L11: 2.4041 L22: 1.1461 |
| REMARK 3 RAMACHANDRAN PLOT: | REMARK 3 L33: 1.2070 L12: −1.6704 |
| REMARK 3 OUTLIERS: 0.00% | REMARK 3 L13: −0.6579 L23: 0.4071 |
| REMARK 3 ALLOWED: 2.50% | REMARK 3 S TENSOR |
| REMARK 3 FAVORED: 97.50% | REMARK 3 S11: −0.0871 S12: 0.2281 S13: 0.3173 |
| REMARK 3 ROTAMER OUTLIERS: 11.78 % | REMARK 3 S21: −0.0231 S22: −0.0117 S23: −0.3709 |
| REMARK 3 CBETA DEVIATIONS: 1 | REMARK 3 S31: −0.0217 S32: 0.0440 S33: 0.0348 |
| REMARK 3 | REMARK 3 TLS GROUP: 6 |
| REMARK 3 ATOMIC DISPLACEMENT PARAMETERS. | REMARK 3 SELECTION: chain 'A' and (resid 281 through 300) |
| REMARK 3 WILSON B: 51.93 | REMARK 3 ORIGIN FOR THE GROUP (A): 158.8087 37.1274 2.4555 |
| REMARK 3 RMS(B_ISO_OR_EQUIVALENT_BONDED): 5.80 | REMARK 3 T TENSOR |
| REMARK 3 ATOMS NUMBER OF ATOMS | REMARK 3 T11: 0.3605 T22: 0.3488 |
| REMARK 3 ISO. ANISO. | REMARK 3 T33: 0.2887 T12: −0.0224 |
| REMARK 3 ALL: 3043 2920 | REMARK 3 T13: −0.0733 T23: −0.0596 |
| REMARK 3 ALL (NO H): 3043 2920 | REMARK 3 L TENSOR |
| REMARK 3 SOLVENT: 71 0 | REMARK 3 L11: 4.6775 L22: 2.9261 |
| REMARK 3 NON-SOLVENT: 2972 2920 | REMARK 3 L33: 2.9523 L12: 0.9648 |
| REMARK 3 HYDROGENS: 0 0 | REMARK 3 L13: −3.4362 L23: −1.5127 |
| REMARK 3 | REMARK 3 S TENSOR |
| REMARK 3 TLS DETAILS. | REMARK 3 S11: −0.3680 S12: 0.2443 S13: −0.471 |
| REMARK 3 NUMBER OF TLS GROUPS: 12 | REMARK 3 S21: 0.1364 S22: −0.0570 S23: −0.3094 |
| REMARK 3 ORIGIN: CENTER OF MASS | REMARK 3 S31: 0.9835 S32: −0.6684 S33: 0.3625 |
| REMARK 3 TLS GROUP: 1 | REMARK 3 TLS GROUP: 7 |
| REMARK 3 SELECTION: chain 'A' and (resid 154 through 185) | REMARK 3 SELECTION: chain 'A' and (resid 301 through 314) |
| REMARK 3 ORIGIN FOR THE GROUP (A): 172.7210 47.3865 −5.8660 | REMARK 3 ORIGIN FOR THE GROUP (A): 170.2562 38.6578 −7.1494 |
| REMARK 3 T TENSOR | REMARK 3 T TENSOR |
| REMARK 3 T11: 0.2534 T22: 0.3103 | REMARK 3 T11: 0.5190 T22: 0.6208 |
| REMARK 3 T33: 0.4400 T12: 0.0640 | ATOM 1 N SER A 154 149.794 43.875 0.944 1.00 53.87 N |
| REMARK 3 T13: −0.0926 T23: −0.0604 | ANISOU 1 N SER A 154 5844 6672 7950 −33 79 −1372 N |
| REMARK 3 L TENSOR | ATOM 2 CA SER A 154 150.705 43.059 1.743 1.00 52.37 C |
| REMARK 3 L11: 5.8148 L22: 3.1473 | ANISOU 2 CA SER A 154 5691 6277 7929 −137 192 −1196 C |
| REMARK 3 L33: 7.2083 L12: −0.5064 | ATOM 3 CB SER A 154 151.126 41.817 0.973 1.00 55.15 C |
| REMARK 3 L13: 0.3236 L23: −1.4244 | ANISOU 3 CB SER A 154 5970 6490 8496 −178 196 −1360 C |
| REMARK 3 S TENSOR | ATOM 4 OG SER A 154 152.145 41.132 1.673 1.00 59.93 O |
| REMARK 3 S11: 0.5128 S12: 1.6665 S13: −0.3026 | ANISOU 4 OG SER A 154 6624 6898 9249 −245 301 −1157 O |
| REMARK 3 S21: −0.7158 S22: 0.0837 S23: 0.1667 | ATOM 5 C SER A 154 151.949 43.871 2.055 1.00 51.68 C |
| REMARK 3 S31: 0.4492 S32: −0.0973 S33: −0.3437 | ANISOU 5 C SER A 154 5794 6199 7644 −71 204 −980 C |
| REMARK 3 TLS GROUP: 8 | ATOM 6 O SER A 154 152.510 44.522 1.157 1.00 47.64 O |
| REMARK 3 SELECTION: chain 'A' and (resid 315 through 324) | ANISOU 6 O SER A 154 5377 5774 6951 40 133 −1015 O |
| REMARK 3 ORIGIN FOR THE GROUP (A): 170.6276 27.3415 14.5534 | ATOM 7 N VAL A 155 152.406 43.846 3.308 1.00 48.39 N |
| REMARK 3 T TENSOR | ANISOU 7 N VAL A 155 5417 5714 7255 −135 295 −752 N |
| REMARK 3 T11: 1.2692 T22: 0.6924 | ATOM 8 CA VAL A 155 153.546 44.697 3.647 1.00 43.68 C |
| REMARK 3 T33: 1.1103 T12: −0.0744 | ANISOU 8 CA VAL A 155 4976 5143 6476 −79 293 −583 C |
| REMARK 3 T13: 0.1042 T23: 0.2604 | ATOM 9 CB VAL A 155 153.717 44.980 5.193 1.00 39.56 C |
| REMARK 3 L TENSOR | ANISOU 9 CB VAL A 155 4466 4651 5915 −126 368 −376 C |
| REMARK 3 L11: 7.5278 L22: 1.6870 | ATOM 10 CG2 VAL A 155 154.740 44.043 5.841 1.00 38.37 C |
| REMARK 3 L33: 9.8141 L12: −3.5637 | ANISOU 10 CG2 VAL A 155 4315 4390 5872 −189 457 −186 C |
| REMARK 3 L13: −3.7198 L23: 1.7498 | ATOM 11 CG1 VAL A 155 152.386 44.893 5.884 1.00 36.13 C |
| REMARK 3 S TENSOR | ANISOU 11 CG1 VAL A 155 3904 4291 5535 −173 406 −403 C |
| REMARK 3 S11: 0.0458 S12: −2.0270 S13: −1.4329 | ATOM 12 C VAL A 155 154.828 44.185 2.989 1.00 38.14 C |
| REMARK 3 S21: 1.3370 S22: −0.0239 S23: 1.7906 | ANISOU 12 C VAL A 155 4342 4347 5801 −60 297 −559 C |
| REMARK 3 S31: 2.4361 S32: 0.3927 S33: −0.1444 | ATOM 13 O VAL A 155 155.671 44.973 2.577 1.00 36.68 O |
| REMARK 3 TLS GROUP: 9 | ANISOU 13 O VAL A 155 4270 4211 5455 16 259 −509 O |
| REMARK 3 SELECTION: chain 'A' and (resid 325 through 335) | ATOM 14 N ALA A 156 154.974 42.865 2.888 1.00 33.51 N |
| REMARK 3 ORIGIN FOR THE GROUP (A): 178.5034 29.5117 2.0047 | ANISOU 14 N ALA A 156 3672 3616 5444 −127 351 −593 N |
| REMARK 3 T TENSOR | ATOM 15 CA ALA A 156 156.171 42.292 2.276 1.00 37.55 C |
| REMARK 3 T11: 0.4443 T22: 0.4647 | ANISOU 15 CA ALA A 156 4229 4036 6003 −99 361 −593 C |
| REMARK 3 T33: 0.6744 T12: −0.0140 | ATOM 16 CB ALA A 156 156.183 40.810 2.404 1.00 40.72 C |
| REMARK 3 T13: −0.0648 T23: −0.0400 | ANISOU 16 CB ALA A 156 4514 4232 6727 −180 435 −621 C |
| REMARK 3 L TENSOR | ATOM 17 C ALA A 156 156.284 42.665 0.802 1.00 37.36 C |
| REMARK 3 L11: 9.0488 L22: 3.3618 | ANISOU 17 C ALA A 156 4232 4129 5833 10 269 −797 C |
| REMARK 3 L33: 3.4168 L12: −0.0452 | ATOM 18 O ALA A 156 157.343 43.033 0.317 1.00 41.01 O |
| REMARK 3 L13: 2.0494 L23: −2.3999 | ANISOU 18 O ALA A 156 4786 4633 6161 81 258 −738 O |
| REMARK 3 S TENSOR | ATOM 19 N HIS A 157 155.194 42.518 0.085 1.00 33.78 N |
| REMARK 3 S11: 0.2304 S12: 0.9520 S13: −0.9120 | ANISOU 19 N HIS A 157 3678 3753 5403 26 208 −1032 N |
| REMARK 3 S21: −0.7421 S22: −0.4966 S23: 1.9928 | ATOM 20 CA HIS A 157 155.146 42.901 −1.309 1.00 34.99 C |
| REMARK 3 S31: 1.4968 S32: −0.7976 S33: −0.1278 | ANISOU 20 CA HIS A 157 3829 4094 5373 151 114 −1223 C |
| REMARK 3 TLS GROUP: 10 | ATOM 21 CB HIS A 157 153.685 42.840 −1.739 1.00 40.24 C |
| REMARK 3 SELECTION: chain 'B' and (resid 154 through 224) | ANISOU 21 CB HIS A 157 4357 4871 6063 155 42 −1459 C |
| REMARK 3 ORIGIN FOR THE GROUP (A): 164.5783 68.6137 5.2563 | ATOM 22 CG HIS A 157 153.477 43.052 −3.196 1.00 44.01 C |
| REMARK 3 T TENSOR | ANISOU 22 CG HIS A 157 4783 5591 6347 295 −63 −1688 C |

TABLE 8-continued

DMXAA-hSTING$^{S162A/Q266I}$ complex

| | |
|---|---|
| REMARK 3 T11: 0.3109 T22: 0.2744 | ATOM 23 ND1 HIS A 157 153.921 42.155 −4.136 1.00 41.61 N |
| REMARK 3 T33: 0.2894 T12: −0.0050 | ANISOU 23 ND1 HIS A 157 4403 5312 6094 330 −83 −1922 N |
| REMARK 3 T13: −0.0342 T23: −0.0250 | ATOM 24 CE1 HIS A 157 153.587 42.593 −5.347 1.00 44.82 C |
| REMARK 3 L TENSOR | ANISOU 24 CE1 HIS A 157 4757 6023 6250 479 −185 −2094 C |
| REMARK 3 L11: 1.1815 L22: 5.4982 | ATOM 25 NE2 HIS A 157 152.970 43.752 −5.214 1.00 46.42 N |
| REMARK 3 L33: 1.2885 L12: 1.2374 | ANISOU 25 NE2 HIS A 157 5007 6366 6264 543 −226 −1945 N |
| REMARK 3 L13: −0.9898 L23: −2.2745 | ATOM 26 CD2 HIS A 157 152.900 44.078 −3.875 1.00 45.40 C |
| REMARK 3 S TENSOR | ANISOU 26 CD2 HIS A 157 4962 6024 6265 428 −152 −1709 C |
| REMARK 3 S11: 0.1075 S12: −0.0459 S13: 0.1579 | ATOM 27 C HIS A 157 155.713 44.334 −1.492 1.00 42.87 C |
| REMARK 3 S21: 0.2770 S22: −0.1307 S23: −0.1873 | ANISOU 27 C HIS A 157 4970 5236 6082 259 83 −1039 C |
| REMARK 3 S31: −0.2585 S32: 0.1217 S33: 0.0429 | ATOM 28 O HIS A 157 156.633 44.602 −2.313 1.00 35.34 O |
| REMARK 3 TLS GROUP: 11 | ANISOU 28 O HIS A 157 4076 4369 4982 353 71 −1010 O |
| REMARK 3 SELECTION: chain 'B' and (resid 225 through 300) | ATOM 29 N GLY A 158 155.176 45.257 −0.697 1.00 35.52 N |
| REMARK 3 ORIGIN FOR THE GROUP (A): 159.7422 61.6690 0.7515 | ANISOU 29 N GLY A 158 4082 4322 5094 245 80 −911 N |
| REMARK 3 T TENSOR | ATOM 30 CA GLY A 158 155.554 46.652 −0.813 1.00 35.14 C |
| REMARK 3 T11: 0.2675 T22: 0.3443 | ANISOU 30 CA GLY A 158 4143 4360 4848 337 53 −755 C |
| REMARK 3 T33: 0.2681 T12: 0.0012 | ATOM 31 C GLY A 158 157.011 46.873 −0.399 1.00 36.27 C |
| REMARK 3 T13: −0.0309 T23: 0.0041 | ANISOU 31 C GLY A 158 4396 4409 4978 314 110 −555 C |
| REMARK 3 L TENSOR | ATOM 32 O GLY A 158 157.714 47.705 −0.954 1.00 39.18 O |
| REMARK 3 L11: 1.5753 L22: 4.4695 | ANISOU 32 O GLY A 158 4835 4836 5217 395 97 −449 O |
| REMARK 3 L33: 0.9759 L12: 0.3661 | ATOM 33 N LEU A 159 157.477 46.16 0.587 1.00 30.24 N |
| REMARK 3 L13: −0.3170 L23: −0.1073 | ANISOU 33 N LEU A 159 3628 3506 4356 207 178 −485 N |
| REMARK 3 S TENSOR | ATOM 34 CA LEU A 159 158.833 46.303 1.112 1.00 26.40 C |
| REMARK 3 S11: 0.0602 S12: −0.2372 S13: 0.0459 | ANISOU 34 CA LEU A 159 3222 2952 3857 183 224 −302 C |
| REMARK 3 S21: 0.2045 S22: −0.0996 S23: −0.3266 | ATOM 35 CB LEU A 159 158.998 45.51 2.409 1.00 32.92 C |
| REMARK 3 S31: 0.0274 S32: −0.0058 S33: 0.0686 | ANISOU 35 CB LEU A 159 4012 3671 4823 77 293 −208 C |
| REMARK 3 TLS GROUP: 12 | ATOM 36 CG LEU A 159 159.098 46.193 3.779 1.00 34.21 C |
| REMARK 3 SELECTION: chain 'B' and (resid 301 through 335) | ANISOU 36 CG LEU A 159 4202 3856 4939 32 312 −67 C |
| REMARK 3 ORIGIN FOR THE GROUP (A): 153.1948 71.0160 3.2560 | ATOM 37 CD2 LEU A 159 158.598 45.229 4.850 1.00 31.07 C |
| REMARK 3 T TENSOR | ANISOU 37 CD2 LEU A 159 3714 3423 4669 −49 380 −7 C |
| REMARK 3 T11: 0.3016 T22: 0.2782 | ATOM 38 CD1 LEU A 159 158.333 47.454 3.849 1.00 31.46 C |
| REMARK 3 T33: 0.3329 T12: 0.0023 | ANISOU 38 CD1 LEU A 159 3878 3590 4485 73 258 −120 C |
| REMARK 3 T13: −0.0231 T23: −0.0370 | ATOM 39 C LEU A 159 159.844 45.791 0.077 1.00 27.87 C |
| REMARK 3 L TENSOR | ANISOU 39 C LEU A 159 3419 3149 4023 237 235 −324 C |
| REMARK 3 L11: 3.5463 L22: 6.1072 | ATOM 40 O LEU A 159 160.921 46.347 −0.093 1.00 31.32 O |
| REMARK 3 L33: 2.9035 L12: 0.1756 | ANISOU 40 O LEU A 159 3922 3602 4378 269 249 −195 O |
| REMARK 3 L13: −0.6982 L23: −1.5250 | ATOM 41 N ALA A 160 159.510 44.686 −0.591 1.00 23.62 N |
| REMARK 3 S TENSOR | ANISOU 41 N ALA A 160 2796 2599 3578 244 233 −507 N |
| REMARK 3 S11: −0.0905 S12: −0.1850 S13: 0.2165 | ATOM 42 CA ALA A 160 160.416 44.064 −1.572 1.00 25.96 C |
| REMARK 3 S21: 0.2176 S22: 0.0114 S23: 0.391 | ANISOU 42 CA ALA A 160 3077 2922 3863 308 246 −582 C |
| REMARK 3 S31: −0.4021 S32: −0.2621 S33: 0.0931 | ATOM 43 CB ALA A 160 159.885 42.732 −2.032 1.00 24.05 C |
| REMARK 3 | ANISOU 43 CB ALA A 160 2715 2620 3805 291 244 −837 C |
| CRYST1 147.954 147.954 36.122 90.00 90.00 120.00 P 6 | ATOM 44 C ALA A 160 160.610 45.022 −2.760 1.00 28.93 C |
| SCALE1 0.006759 0.003902 0.000000 0.00000 | ANISOU 44 C ALA A 160 3487 3516 3989 441 199 −581 C |
| SCALE2 0.000000 0.007804 0.000000 0.00000 | ATOM 45 O ALA A 160 161.749 45.312 −3.172 1.00 31.42 O |
| SCALE3 0.000000 0.000000 0.027684 0.00000 | ANISOU 45 O ALA A 160 3848 3881 4210 492 231 −463 O |
| ATOM 46 N TRP A 161 159.499 45.546 −3.256 1.00 20.34 N | ATOM 91 CB ILE A 165 161.958 50.940 −6.474 1.00 33.92 C |
| ANISOU 46 N TRP A 161 2366 2566 2797 499 132 −679 N | ANISOU 91 CB ILE A 165 4263 4871 3753 999 193 330 C |
| ATOM 47 CA TRP A 161 159.517 46.595 −4.293 1.00 30.15 C | ATOM 92 CG1 ILE A 165 161.379 50.305 −7.719 1.00 39.43 C |
| ANISOU 47 CA TRP A 161 3629 4030 3796 642 91 −613 C | ANISOU 92 CG1 ILE A 165 4863 5889 4230 1148 146 149 C |
| ATOM 48 CB TRP A 161 158.093 46.980 −4.788 1.00 28.13 C | ATOM 93 CD1 ILE A 165 160.073 49.723 −7.443 1.00 52.65 C |
| ANISOU 48 CB TRP A 161 3304 3937 3447 716 6 −746 C | ANISOU 93 CD1 ILE A 165 6491 7562 5951 1121 61 −123 C |
| ATOM 49 CG TRP A 161 157.609 45.937 −5.725 1.00 31.55 C | ATOM 94 CG2 ILE A 165 161.754 52.452 −6.554 1.00 28.16 C |
| ANISOU 49 CG TRP A 161 3606 4520 3861 767 −43 −1056 C | ANISOU 94 CG2 ILE A 165 3561 4107 3033 1061 199 596 C |
| ATOM 50 CD1 TRP A 161 156.851 44.827 −5.427 1.00 29.05 C | ATOM 95 C ILE A 165 164.280 51.582 −5.641 1.00 31.65 C |
| ANISOU 50 CD1 TRP A 161 3186 4101 3751 671 −60 −1312 C | ANISOU 95 C ILE A 165 4055 4314 3655 850 327 671 C |
| ATOM 51 NE1 TRP A 161 156.689 44.070 −6.561 1.00 36.95 N | ATOM 96 O ILE A 165 164.821 52.451 −6.296 1.00 35.24 O |
| ANISOU 51 NE1 TRP A 161 4060 5285 4693 754 −112 −1609 N | ANISOU 96 O ILE A 165 4497 4837 4054 921 378 908 O |
| ATOM 52 CE2 TRP A 161 157.352 44.658 −7.600 1.00 32.48 C | ATOM 97 N GLY A 166 164.398 51.479 −4.339 1.00 28.43 N |
| ANISOU 52 CE2 TRP A 161 3517 4983 3840 916 −124 −1532 C | ANISOU 97 N GLY A 166 3694 3674 3434 700 320 622 N |
| ATOM 53 CD2 TRP A 161 157.965 45.830 −7.110 1.00 32.64 C | ATOM 98 CA GLY A 166 165.135 52.428 −3.565 1.00 29.34 C |
| ANISOU 53 CD2 TRP A 161 3682 4940 3779 921 −72 −1160 C | ANISOU 98 CA GLY A 166 1841 1601 1702 612 349 795 C |
| ATOM 54 CE3 TRP A 161 158.691 46.639 −7.987 1.00 37.14 C | ATOM 99 C GLY A 166 166.485 52.015 −3.062 1.00 39.98 C |
| ANISOU 54 CE3 TRP A 161 4287 5733 4093 1069 −56 −972 C | ANISOU 99 C GLY A 166 5187 4876 5128 514 401 844 C |
| ATOM 55 CZ3 TRP A 161 158.834 46.226 −9.347 1.00 37.87 C | ATOM 100 O GLY A 166 167.061 52.698 −2.274 1.00 41.51 O |
| ANISOU 55 CZ3 TRP A 161 4268 6160 3959 1226 −90 −1155 C | ANISOU 100 O GLY A 166 5390 4918 5466 416 410 922 O |
| ATOM 56 CH2 TRP A 161 158.217 45.058 −9.810 1.00 33.52 C | ATOM 101 N TYR A 167 166.959 50.858 −3.456 1.00 35.42 N |
| ANISOU 56 CH2 TRP A 161 3573 5700 3463 1229 −155 −1569 C | ANISOU 101 N TYR A 167 4581 4409 4469 544 430 770 N |
| ATOM 57 CZ2 TRP A 161 157.469 44.268 −8.964 1.00 36.44 C | ATOM 102 CA TYR A 167 168.307 50.457 −3.134 1.00 32.58 C |
| ANISOU 57 CZ2 TRP A 161 3904 5803 4137 1068 −173 −1766 C | ANISOU 102 CA TYR A 167 4202 4001 4176 477 482 833 C |
| ATOM 58 C TRP A 161 160.280 47.820 −3.842 1.00 30.40 C | ATOM 103 CB TYR A 167 168.405 49.791 −1.781 1.00 28.78 C |
| ANISOU 58 C TRP A 161 3766 4004 3779 639 127 −324 C | ANISOU 103 CB TYR A 167 3734 3386 3817 365 455 727 C |
| ATOM 59 O TRP A 161 161.075 48.391 −4.592 1.00 29.27 O | ATOM 104 CG TYR A 167 169.792 49.482 −1.418 1.00 27.18 C |
| ANISOU 59 O TRP A 161 3647 3970 3504 726 150 −185 O | ANISOU 104 CG TYR A 167 3496 3159 3673 315 500 812 C |
| ATOM 60 N ALA A 162 160.040 48.230 −2.602 1.00 23.38 N | ATOM 105 CD1 TYR A 167 170.636 50.467 −1.032 1.00 31.38 C |
| ANISOU 60 N ALA A 162 2923 2951 3008 538 137 −241 N | ANISOU 105 CD1 TYR A 167 4010 3634 4279 249 517 959 C |
| ATOM 61 CA ALA A 162 160.770 49.382 −2.101 1.00 21.94 C | ATOM 106 CE1 TYR A 167 171.916 50.193 −0.681 1.00 30.78 C |
| ANISOU 61 CA ALA A 162 2820 2692 2825 522 162 −21 C | ANISOU 106 CE1 TYR A 167 3880 3556 4259 199 551 1029 C |

TABLE 8-continued

DMXAA-hSTING$^{S162A/Q266I}$ complex

| | |
|---|---|
| ATOM 62 CB ALA A 162 160.207 49.871 −0.765 1.00 17.98 C | ATOM 107 CZ TYR A 167 172.360 48.934 −0.724 1.00 32.41 C |
| ANISOU 62 CB ALA A 162 2339 2066 2425 434 152 −8 C | ANISOU 107 CZ TYR A 167 4060 3809 4446 235 575 969 C |
| ATOM 63 C ALA A 162 162.289 49.105 −2.025 1.00 25.44 C | ATOM 108 OH TYR A 167 173.627 48.700 −0.374 1.00 38.67 O |
| ANISOU 63 C ALA A 162 3292 3080 3294 483 225 97 C | ANISOU 108 OH TYR A 167 4788 4612 5291 203 606 1047 O |
| ATOM 64 O ALA A 162 163.126 49.951 −2.332 1.00 31.86 O | ATOM 109 CE2 TYR A 167 171.543 47.931 −1.105 1.00 27.35 C |
| ANISOU 64 O ALA A 162 4137 3903 4065 514 251 267 O | ANISOU 109 CE2 TYR A 167 3441 3190 3763 302 566 824 C |
| ATOM 65 N TYR A 163 162.657 47.900 −1.634 1.00 26.08 N | ATOM 110 CD2 TYR A 167 170.263 48.208 −1.448 1.00 29.95 C |
| ANISOU 65 N TYR A 163 3346 3095 3466 420 255 19 N | ANISOU 110 CD2 TYR A 167 3814 3529 4036 334 526 736 C |
| ATOM 66 CA TYR A 163 164.076 47.618 −1.441 1.00 27.22 C | ATOM 111 C TYR A 167 169.024 49.655 −4.189 1.00 30.36 C |
| ANISOU 66 CA TYR A 163 3506 3188 3647 388 311 133 C | ANISOU 111 C TYR A 167 3869 3890 3776 569 536 812 C |
| ATOM 67 CB TYR A 163 164.215 46.291 −0.698 1.00 24.76 C | ATOM 112 O TYR A 167 170.019 50.053 −4.661 1.00 35.83 O |
| ANISOU 67 CB TYR A 163 3157 2764 3486 315 342 67 C | ANISOU 112 O TYR A 167 4525 4669 4421 606 602 978 O |
| ATOM 68 CG TYR A 163 165.644 45.909 −0.383 1.00 24.16 C | ATOM 113 N LEU A 168 168.522 48.485 −4.488 1.00 30.68 N |
| ANISOU 68 CG TYR A 163 3082 2637 3460 292 395 187 C | ANISOU 113 N LEU A 168 3890 3981 3785 609 513 595 N |
| ATOM 69 CD1 TYR A 163 166.475 46.777 0.322 1.00 22.18 C | ATOM 114 CA LEU A 168 169.219 47.559 −5.325 1.00 33.92 C |
| ANISOU 69 CD1 TYR A 163 2866 2370 3191 246 403 356 C | ANISOU 114 CA LEU A 168 4236 4543 4111 702 560 509 C |
| ATOM 70 CE1 TYR A 163 167.780 46.432 0.631 1.00 25.57 C | ATOM 115 CB LEU A 168 168.456 46.253 −5.378 1.00 30.70 C |
| ANISOU 70 CE1 TYR A 163 3276 2777 3663 228 444 461 C | ANISOU 115 CB LEU A 168 3794 4120 3748 725 521 217 C |
| ATOM 71 CZ TYR A 163 168.266 45.202 0.210 1.00 33.88 C | ATOM 116 CG LEU A 168 168.440 45.444 −4.102 1.00 34.18 C |
| ANISOU 71 CZ TYR A 163 4283 3808 4783 269 486 409 C | ANISOU 116 CG LEU A 168 4254 4314 4418 602 512 172 C |
| ATOM 72 OH TYR A 163 169.562 44.813 0.501 1.00 37.79 O | ATOM 117 CD1 LEU A 168 167.773 44.124 −4.324 1.00 30.65 C |
| ANISOU 72 OH TYR A 163 4745 4286 5325 268 527 517 O | ANISOU 117 CD1 LEU A 168 3751 3815 4079 619 490 −97 C |
| ATOM 73 CE2 TYR A 163 167.457 44.331 −0.517 1.00 31.48 C | ATOM 118 CD2 LEU A 168 169.830 45.226 −3.591 1.00 38.43 C |
| ANISOU 73 CE2 TYR A 163 3946 3495 4520 317 482 225 C | ANISOU 118 CD2 LEU A 168 4779 4779 5042 564 572 312 C |
| ATOM 74 CD2 TYR A 163 166.160 44.687 −0.798 1.00 28.59 C | ATOM 119 C LEU A 168 169.451 48.086 −6.719 1.00 35.00 C |
| ANISOU 74 CD2 TYR A 163 3592 3168 4105 322 434 110 C | ANISOU 119 C LEU A 168 4323 4955 4022 847 602 607 C |
| ATOM 75 C TYR A 163 164.768 47.551 −2.814 1.00 32.43 C | ATOM 120 O LEU A 168 170.502 47.958 −7.260 1.00 38.69 O |
| ANISOU 75 C TYR A 163 4144 3997 4181 499 335 140 C | ANISOU 120 O LEU A 168 4737 5541 4421 898 677 700 O |
| ATOM 76 O TYR A 163 165.939 47.881 −2.965 1.00 40.06 O | ATOM 121 N ARG A 169 168.454 48.710 −7.285 1.00 35.80 N |
| ANISOU 76 O TYR A 163 5122 4975 5123 506 381 288 O | ANISOU 121 N ARG A 169 4429 5179 3997 924 558 608 N |
| ATOM 77 N TYR A 164 164.026 47.114 −3.828 1.00 30.44 N | ATOM 122 CA ARG A 169 168.514 49.140 −8.678 1.00 39.62 C |
| ANISOU 77 N TYR A 164 3839 3890 3837 592 302 −32 N | ANISOU 122 CA ARG A 169 4845 5985 4225 1094 594 705 C |
| ATOM 78 CA TYR A 164 164.548 47.078 −5.207 1.00 31.03 C | ATOM 123 CB ARG A 169 167.112 49.354 −9.258 1.00 33.68 C |
| ANISOU 78 CA TYR A 164 3869 4186 3733 726 320 −48 C | ANISOU 123 CB ARG A 169 4076 5397 3325 1198 513 599 C |
| ATOM 79 CB TYR A 164 163.669 46.203 −6.080 1.00 25.75 C | ATOM 124 CG ARG A 169 166.696 50.771 −9.344 1.00 38.48 C |
| ANISOU 79 CB TYR A 164 3111 3672 3001 809 268 −341 C | ANISOU 124 CG ARG A 169 4711 5996 3911 1230 515 884 C |
| ATOM 80 CG TYR A 164 163.938 46.379 −7.528 1.00 33.74 C | ATOM 125 CD ARG A 169 165.282 50.892 −9.866 1.00 48.06 C |
| ANISOU 80 CG TYR A 164 4060 5002 3758 979 270 −368 C | ANISOU 125 CD ARG A 169 5895 7385 4980 1345 426 765 C |
| ATOM 81 CD1 TYR A 164 165.139 45.971 −8.086 1.00 44.41 C | ATOM 126 NE ARG A 169 164.676 52.176 −9.500 1.00 50.64 N |
| ANISOU 81 CD1 TYR A 164 5381 6448 5047 1036 336 −349 C | ANISOU 126 NE ARG A 169 6270 7572 5401 1336 409 993 N |
| ATOM 82 CE1 TYR A 164 165.383 46.121 −9.427 1.00 51.28 C | ATOM 127 CZ ARG A 169 163.626 52.719 −10.114 1.00 50.15 C |
| ANISOU 82 CE1 TYR A 164 6174 7666 5645 1208 347 −371 C | ANISOU 127 CZ ARG A 169 6169 7689 5197 1475 355 1036 C |
| ATOM 83 CZ TYR A 164 164.409 46.678 −10.241 1.00 58.05 C | ATOM 128 NH1 ARG A 169 163.043 52.073 −11.123 1.00 44.14 N |
| ANISOU 83 CZ TYR A 164 6982 8792 6281 1334 283 −399 C | ANISOU 128 NH1 ARG A 169 5313 7290 4167 1629 301 844 N |
| ATOM 84 OH TYR A 164 164.639 46.827 −11.588 1.00 69.06 O | ATOM 129 NH2 ARG A 169 163.166 53.909 −9.719 1.00 48.29 N |
| ANISOU 84 OH TYR A 164 8281 10597 7361 1528 295 −401 O | ANISOU 129 NH2 ARG A 169 5973 7278 5098 1469 350 1254 N |
| ATOM 85 CE2 TYR A 164 163.206 47.078 −9.715 1.00 49.42 C | ATOM 130 C ARG A 169 169.358 50.404 −8.767 1.00 41.21 C |
| ANISOU 85 CE2 TYR A 164 5921 7594 5264 1281 208 −421 C | ANISOU 130 C ARG A 169 5048 6166 4442 1080 677 1079 C |
| ATOM 86 CD2 TYR A 164 162.980 46.912 −8.354 1.00 42.91 C | ATOM 131 O ARG A 169 169.744 50.820 −9.843 1.00 51.32 O |
| ANISOU 86 CD2 TYR A 164 5175 6407 4723 1099 206 −415 C | ANISOU 131 O ARG A 169 6259 7707 5532 1211 744 1255 O |
| ATOM 87 C TYR A 164 164.629 48.474 −5.831 1.00 32.16 C | ATOM 132 N LEU A 170 169.653 50.994 −7.616 1.00 41.79 N |
| ANISOU 87 C TYR A 164 4038 4468 3715 814 325 174 C | ANISOU 132 N LEU A 170 5184 5939 4755 922 675 1193 N |
| ATOM 88 O TYR A 164 165.632 48.876 −6.382 1.00 39.33 O | ATOM 133 CA LEU A 170 170.588 52.121 −7.530 1.00 49.74 C |
| ANISOU 88 O TYR A 164 4939 5467 4538 866 385 344 O | ANISOU 133 CA LEU A 170 6173 6856 5869 868 755 1507 C |
| ATOM 89 N ILE A 165 163.575 49.229 −5.672 1.00 24.47 N | ATOM 134 CB LEU A 170 170.197 53.091 −6.406 1.00 52.23 C |
| ANISOU 89 N ILE A 165 3081 3487 2728 826 271 195 N | ANISOU 134 CB LEU A 170 6550 6867 6427 734 708 1567 C |
| ATOM 90 CA ILE A 165 163.454 50.522 −6.332 1.00 30.88 C | ATOM 135 CG LEU A 170 168.710 53.443 −6.325 1.00 58.79 C |
| ANISOU 90 CA ILE A 165 3899 4416 3419 932 275 412 C | ANISOU 135 CG LEU A 170 7430 7669 7237 780 624 1479 C |
| ATOM 136 CD1 LEU A 170 168.420 54.284 −5.108 1.00 56.58 C | ATOM 181 CA GLN A 176 181.055 45.127 −10.476 1.00 59.62 C |
| ANISOU 136 CD1 LEU A 170 7199 7095 7206 649 580 1481 C | ANISOU 181 CA GLN A 176 6588 9245 6820 1347 1432 1122 C |
| ATOM 137 CD2 LEU A 170 168.233 54.157 −7.595 1.00 61.54 C | ATOM 182 CB GLN A 176 180.661 44.404 −11.748 1.00 69.15 C |
| ANISOU 137 CD2 LEU A 170 7734 8231 7416 953 655 1680 C | ANISOU 182 CB GLN A 176 7752 10731 7793 1529 1414 845 C |
| ATOM 138 C LEU A 170 172.022 51.631 −7.291 1.00 51.30 C | ATOM 183 CG GLN A 176 179.248 43.921 −11.722 1.00 84.31 C |
| ANISOU 138 C LEU A 170 6325 7032 6135 801 824 1540 C | ANISOU 183 CG GLN A 176 9737 12605 9692 1578 1337 572 C |
| ATOM 139 O LEU A 170 172.978 52.226 −7.755 1.00 58.75 O | ATOM 184 CD GLN A 176 179.136 42.455 −12.086 1.00 97.37 C |
| ANISOU 139 O LEU A 170 7202 8040 7081 810 919 1783 O | ANISOU 184 CD GLN A 176 11337 14269 11391 1690 1298 145 C |
| ATOM 140 N ILE A 171 172.183 50.540 −6.562 1.00 45.53 N | ATOM 185 OE1 GLN A 176 178.572 42.101 −13.129 1.00 102.93 O |
| ANISOU 140 N ILE A 171 5616 6211 5474 737 784 1316 N | ANISOU 185 OE1 GLN A 176 12011 15190 11909 1790 1240 −100 O |
| ATOM 141 CA ILE A 171 173.528 50.113 −6.177 1.00 38.25 C | ATOM 186 NE2 GLN A 176 179.685 41.586 −11.232 1.00 100.03 N |
| ANISOU 141 CA ILE A 171 4645 5247 4642 673 839 1356 C | ANISOU 186 NE2 GLN A 176 11658 14345 12006 1659 1311 56 N |
| ATOM 142 CB ILE A 171 173.558 49.581 −4.693 1.00 54.60 C | ATOM 187 C GLN A 176 182.234 46.050 −10.777 1.00 58.38 C |
| ANISOU 142 CB ILE A 171 6760 7082 6903 536 773 1224 C | ANISOU 187 C GLN A 176 6366 9163 6651 1281 1475 1420 C |
| ATOM 143 CG1 ILE A 171 174.905 49.836 −4.068 1.00 54.95 C | ATOM 188 O GLN A 176 183.389 45.691 −10.557 1.00 62.58 O |
| ANISOU 143 CG1 ILE A 171 6747 7053 7078 439 813 1356 C | ANISOU 188 O GLN A 176 6817 9683 7276 1266 1514 1443 O |
| ATOM 144 CD1 ILE A 171 175.067 51.316 −3.748 1.00 59.62 C | ATOM 189 N ALA A 177 181.931 47.239 −11.283 1.00 53.99 N |
| ANISOU 144 CD1 ILE A 171 7331 7529 7794 342 817 1539 C | ANISOU 189 N ALA A 177 5833 8667 6014 1250 1461 1640 N |
| ATOM 145 CG2 ILE A 171 173.276 48.107 −4.588 1.00 55.70 C | ATOM 190 CA ALA A 177 182.965 48.208 −11.613 1.00 51.61 C |
| ANISOU 145 CG2 ILE A 171 6901 7231 7031 579 746 988 C | ANISOU 190 CA ALA A 177 5452 8398 5759 1194 1497 1914 C |

TABLE 8-continued

DMXAA-hSTING$^{S162A/Q266I}$ complex

| | |
|---|---|
| ATOM 146 C ILE A 171 174.107 49.068 −7.143 1.00 35.71 C | ATOM 191 CB ALA A 177 182.385 49.410 −12.334 1.00 41.97 C |
| ANISOU 146 C ILE A 171 4247 5162 4159 805 898 1256 C | ANISOU 191 CB ALA A 177 4237 7246 4464 1212 1482 2120 C |
| ATOM 147 O ILE A 171 175.289 49.068 −7.451 1.00 48.25 O | ATOM 192 C ALA A 177 183.647 48.632 −10.331 1.00 54.09 C |
| ANISOU 147 O ILE A 171 5758 6840 5736 819 983 1380 O | ANISOU 192 C ALA A 177 5772 8412 6369 1002 1474 2017 C |
| ATOM 148 N LEU A 172 173.279 48.165 −7.633 1.00 38.21 N | ATOM 193 O ALA A 177 184.864 48.741 −10.281 1.00 59.93 O |
| ANISOU 148 N LEU A 172 4568 5587 4362 903 853 1006 N | ANISOU 193 O ALA A 177 6414 9165 7190 962 1511 2111 O |
| ATOM 149 CA LEU A 172 173.772 47.037 −8.415 1.00 44.51 C | ATOM 194 N ARG A 178 182.867 48.847 −9.275 1.00 48.28 N |
| ANISOU 149 CA LEU A 172 5283 6576 5051 1025 893 824 C | ANISOU 194 N ARG A 178 5139 7421 5784 885 1403 1977 N |
| ATOM 150 CB LEU A 172 172.658 46.005 −8.629 1.00 47.45 C | ATOM 195 CA ARG A 178 183.472 49.247 −8.018 1.00 47.16 C |
| ANISOU 150 CB LEU A 172 5661 6966 5403 1085 814 479 C | ANISOU 195 CA ARG A 178 4994 7025 5902 708 1352 2026 C |
| ATOM 151 CG LEU A 172 172.259 45.226 −7.375 1.00 48.68 C | ATOM 196 CB ARG A 178 182.410 49.647 −7.008 1.00 42.63 C |
| ANISOU 151 CG LEU A 172 5874 6801 5822 957 753 335 C | ANISOU 196 CB ARG A 178 4540 6207 5451 594 1258 1970 C |
| ATOM 152 CD1 LEU A 172 171.335 44.085 −7.733 1.00 51.07 C | ATOM 197 CG ARG A 178 181.715 50.932 −7.412 1.00 37.36 C |
| ANISOU 152 CD1 LEU A 172 6139 7113 6151 1017 699 −13 C | ANISOU 197 CG ARG A 178 3913 5483 4798 562 1227 2079 C |
| ATOM 153 CD2 LEU A 172 173.490 44.698 −6.612 1.00 42.38 C | ATOM 198 CD ARG A 178 180.454 51.157 −6.528 1.00 42.44 C |
| ANISOU 153 CD2 LEU A 172 5054 5849 5199 893 803 409 C | ANISOU 198 CD ARG A 178 4686 5923 5518 485 1135 1976 C |
| ATOM 154 C LEU A 172 174.415 47.406 −9.765 1.00 51.61 C | ATOM 199 NE ARG A 178 180.816 51.341 −5.120 1.00 40.41 N |
| ANISOU 154 C LEU A 172 6082 7828 5701 1177 990 960 C | ANISOU 199 NE ARG A 178 4434 5452 5468 327 1058 1911 N |
| ATOM 155 O LEU A 172 175.421 46.807 −10.142 1.00 57.40 O | ATOM 200 CZ ARG A 178 180.109 50.884 −4.094 1.00 44.12 C |
| ANISOU 155 O LEU A 172 6731 8684 6397 1238 1062 924 O | ANISOU 200 CZ ARG A 178 4987 5796 5981 276 986 1778 C |
| ATOM 156 N PRO A 173 173.819 48.353 −10.518 1.00 50.56 N | ATOM 201 NH1 ARG A 178 178.997 50.213 −4.326 1.00 44.59 N |
| ANISOU 156 N PRO A 173 5942 7881 5385 1256 998 1123 N | ANISOU 201 NH1 ARG A 178 5136 5887 5920 359 990 1701 N |
| ATOM 157 CA PRO A 173 174.427 48.673 −11.822 1.00 57.61 C | ATOM 202 NH2 ARG A 178 180.519 51.082 −2.842 1.00 45.29 N |
| ANISOU 157 CA PRO A 173 6718 9161 6009 1420 1105 1291 C | ANISOU 202 NH2 ARG A 178 5114 5811 6282 150 915 1726 N |
| ATOM 158 CB PRO A 173 173.648 49.907 −12.277 1.00 57.66 C | ATOM 203 C ARG A 178 184.386 48.174 −7.464 1.00 47.72 C |
| ANISOU 158 CB PRO A 173 6741 9236 5930 1459 1081 1534 C | ANISOU 203 C ARG A 178 4994 7106 6032 721 1377 1934 C |
| ATOM 159 CG PRO A 173 172.249 49.662 −11.693 1.00 55.73 C | ATOM 204 O ARG A 178 185.439 48.475 −6.911 1.00 47.05 C |
| ANISOU 159 CG PRO A 173 6596 8840 5739 1424 960 1305 C | ANISOU 204 O ARG A 178 4831 6954 6090 626 1364 2010 O |
| ATOM 160 CD PRO A 173 172.509 49.013 −10.349 1.00 52.05 C | ATOM 205 N ILE A 179 183.958 46.926 −7.634 1.00 48.20 N |
| ANISOU 160 CD PRO A 173 6207 7997 5572 1240 913 1138 C | ANISOU 205 N ILE A 179 5066 7251 5995 852 1412 1750 N |
| ATOM 161 C PRO A 173 175.928 48.981 −11.773 1.00 59.73 C | ATOM 206 CA ILE A 179 184.694 45.760 −7.193 1.00 48.50 C |
| ANISOU 161 C PRO A 173 6920 9399 6375 1361 1202 1522 C | ANISOU 206 CA ILE A 179 5025 7286 6115 910 1439 1634 C |
| ATOM 162 O PRO A 173 176.638 48.581 −12.685 1.00 61.49 O | ATOM 207 CB ILE A 179 183.815 44.516 −7.290 1.00 51.23 C |
| ANISOU 162 O PRO A 173 7041 9870 6451 1470 1235 1483 O | ANISOU 207 CB ILE A 179 5430 7600 6437 1037 1413 1356 C |
| ATOM 163 N GLU A 174 176.411 49.662 −10.738 1.00 56.89 N | ATOM 208 CG1 ILE A 179 182.643 44.624 −6.342 1.00 60.80 C |
| ANISOU 163 N GLU A 174 6606 8720 6288 1178 1205 1708 N | ANISOU 208 CG1 ILE A 179 6794 8553 7754 925 1289 1294 C |
| ATOM 164 CA GLU A 174 177.823 50.037 −10.719 1.00 54.95 C | ATOM 209 CD1 ILE A 179 183.063 44.561 −4.944 1.00 62.50 C |
| ANISOU 164 CA GLU A 174 6278 8426 6174 1107 1253 1877 C | ANISOU 209 CD1 ILE A 179 7012 8566 8169 802 1223 1362 C |
| ATOM 165 CB GLU A 174 178.022 51.509 −10.342 1.00 57.70 C | ATOM 210 CG2 ILE A 179 184.581 43.302 −6.871 1.00 50.72 C |
| ANISOU 165 CB GLU A 174 6626 8541 6756 969 1227 2109 C | ANISOU 210 CG2 ILE A 179 5289 7472 6509 1109 1417 1232 C |
| ATOM 166 CG GLU A 174 177.490 52.511 −11.355 1.00 67.68 C | ATOM 211 C ILE A 179 185.942 45.532 −8.055 1.00 51.38 C |
| ANISOU 166 CG GLU A 174 7846 9937 7930 1062 1234 2282 C | ANISOU 211 C ILE A 179 5265 7862 6394 999 1508 1661 C |
| ATOM 167 CD GLU A 174 178.155 52.387 −12.725 1.00 80.62 C | ATOM 212 O ILE A 179 187.017 45.249 −7.538 1.00 50.58 O |
| ANISOU 167 CD GLU A 174 9352 11927 9351 1225 1306 2387 C | ANISOU 212 O ILE A 179 5076 7729 6412 969 1513 1697 O |
| ATOM 168 OE1 GLU A 174 179.293 51.839 −12.802 1.00 84.29 O | ATOM 213 N ARG A 180 185.771 45.628 −9.372 1.00 52.67 N |
| ANISOU 168 OE1 GLU A 174 9751 12469 9807 1223 1357 2372 O | ANISOU 213 N ARG A 180 5415 8263 6336 1117 1554 1639 N |
| ATOM 169 OE2 GLU A 174 177.522 52.844 −13.714 1.00 83.96 O | ATOM 214 CA ARG A 180 186.860 45.449 −10.326 1.00 60.20 C |
| ANISOU 169 OE2 GLU A 174 9728 12564 9610 1361 1309 2485 O | ANISOU 214 CA ARG A 180 6249 9456 7170 1212 1624 1662 C |
| ATOM 170 C GLU A 174 178.634 49.172 −9.779 1.00 48.63 C | ATOM 215 CB ARG A 180 186.346 45.651 −11.753 1.00 69.09 C |
| ANISOU 170 C GLU A 174 5472 7486 5521 1023 1279 1768 C | ANISOU 215 CB ARG A 180 7373 10861 8017 1345 1651 1638 C |
| ATOM 171 O GLU A 174 179.766 49.496 −9.461 1.00 51.76 O | ATOM 216 CG ARG A 180 186.513 44.452 −12.661 1.00 77.82 C |
| ANISOU 171 O GLU A 174 5808 7792 6067 933 1297 1887 O | ANISOU 216 CG ARG A 180 8412 12202 8954 1535 1683 1356 C |
| ATOM 172 N LEU A 175 178.077 48.067 −9.327 1.00 45.45 N | ATOM 217 CD ARG A 180 185.184 44.024 −13.309 1.00 83.31 C |
| ANISOU 172 N LEU A 175 5120 7024 5125 1047 1236 1495 N | ANISOU 217 CD ARG A 180 9174 13008 9474 1649 1632 1109 C |
| ATOM 173 CA LEU A 175 178.783 47.309 −8.305 1.00 47.79 C | ATOM 218 NE ARG A 180 185.152 44.261 −14.760 1.00 90.87 N |
| ANISOU 173 CA LEU A 175 5414 7115 5629 957 1211 1394 C | ANISOU 218 NE ARG A 180 10069 14328 10130 1783 1647 1114 N |
| ATOM 174 CB LEU A 175 177.864 46.317 −7.610 1.00 44.51 C | ATOM 219 CZ ARG A 180 185.845 43.559 −15.666 1.00 93.66 C |
| ANISOU 174 CB LEU A 175 5086 6510 5314 938 1104 1111 C | ANISOU 219 CZ ARG A 180 10312 14935 10339 1920 1685 951 C |
| ATOM 175 CG LEU A 175 178.599 45.713 −6.426 1.00 46.88 C | ATOM 220 NH1 ARG A 180 186.643 42.567 −15.276 1.00 95.47 N |
| ANISOU 175 CG LEU A 175 5378 6598 5836 844 1083 1096 C | ANISOU 220 NH1 ARG A 180 10486 15066 10723 1941 1717 765 N |
| ATOM 176 CD1 LEU A 175 178.824 46.798 −5.403 1.00 43.61 C | ATOM 221 NH2 ARG A 180 185.745 43.846 −16.965 1.00 89.93 N |
| ANISOU 176 CD1 LEU A 175 4996 6023 5553 675 1051 1302 C | ANISOU 221 NH2 ARG A 180 9774 14822 9574 2048 1687 980 N |
| ATOM 177 CD2 LEU A 175 177.785 44.579 −5.867 1.00 48.55 C | ATOM 222 C ARG A 180 187.936 46.479 −10.019 1.00 63.20 C |
| ANISOU 177 CD2 LEU A 175 5645 6641 6161 849 1008 853 C | ANISOU 222 C ARG A 180 6557 9780 7675 1073 1633 1926 C |
| ATOM 178 C LEU A 175 180.048 46.608 −8.827 1.00 56.12 C | ATOM 223 O ARG A 180 189.132 46.195 −10.045 1.00 69.21 O |
| ANISOU 178 C LEU A 175 6337 8351 6634 1052 1309 1376 C | ANISOU 223 O ARG A 180 7206 10615 8477 1086 1676 1953 O |
| ATOM 179 O LEU A 175 181.137 46.765 −8.251 1.00 54.98 O | ATOM 224 N THR A 181 187.481 47.680 −9.701 1.00 59.04 N |
| ANISOU 179 O LEU A 175 6131 8128 6630 967 1347 1515 O | ANISOU 224 N THR A 181 6091 9106 7237 939 1587 2092 N |
| ATOM 180 N GLN A 176 179.914 45.859 −9.921 1.00 57.81 N | ATOM 225 CA THR A 181 188.355 48.787 −9.363 1.00 60.45 C |
| ANISOU 180 N GLN A 176 6490 8828 6645 1234 1345 1188 N | ANISOU 225 CA THR A 181 6199 9182 7588 793 1581 2295 C |
| ATOM 226 CB THR A 181 187.535 50.065 −9.221 1.00 64.03 C | ATOM 271 CA TYR A 186 194.184 47.498 −3.400 1.00 73.48 C |
| ANISOU 226 CB THR A 181 6728 9467 8132 687 1529 2411 C | ANISOU 271 CA TYR A 186 4687 10033 13197 −165 822 −213 C |
| ATOM 227 OG1 THR A 181 186.779 50.270 −10.422 1.00 71.50 O | ATOM 272 CB TYR A 186 193.062 47.795 −2.398 1.00 77.23 C |
| ANISOU 227 OG1 THR A 181 7702 10595 8870 818 1566 2464 O | ANISOU 272 CB TYR A 186 5654 9664 14026 −251 895 43 C |
| ATOM 228 CG2 THR A 181 188.428 51.265 −8.975 1.00 61.76 C | ATOM 273 CG TYR A 186 192.903 49.276 −2.113 1.00 81.99 C |
| ANISOU 228 CG2 THR A 181 6348 9066 8053 544 1535 2591 C | ANISOU 273 CG TYR A 186 6419 9992 14742 −506 1140 661 C |
| ATOM 229 C THR A 181 189.083 48.538 −8.055 1.00 62.27 C | ATOM 274 CD2 TYR A 186 193.624 49.886 −1.085 1.00 84.01 C |
| ANISOU 229 C THR A 181 6388 9240 8029 674 1530 2252 C | ANISOU 274 CD2 TYR A 186 6857 9699 15363 −618 1114 688 C |

TABLE 8-continued

DMXAA-hSTING<sup>S162A/Q266I</sup> complex

ATOM 230 O THR A 181 190.294 48.767 -7.940 1.00 66.40 O
ANISOU 230 O THR A 181 6790 9797 8643 621 1557 2337 O
ATOM 231 N TYR A 182 188.333 48.077 -7.059 1.00 55.44 N
ANISOU 231 N TYR A 182 5614 8211 7238 635 1456 2126 N
ATOM 232 CA TYR A 182 188.908 47.788 -5.762 1.00 51.41 C
ANISOU 232 CA TYR A 182 5059 7572 6903 542 1393 2088 C
ATOM 233 CB TYR A 182 187.862 47.251 -4.783 1.00 51.61 C
ANISOU 233 CB TYR A 182 5190 7441 6976 525 1319 1968 C
ATOM 234 CG TYR A 182 188.451 47.077 -3.412 1.00 52.63 C
ANISOU 234 CG TYR A 182 5257 7477 7263 433 1241 1958 C
ATOM 235 CD1 TYR A 182 188.452 48.120 -2.501 1.00 53.21 C
ANISOU 235 CD1 TYR A 182 5330 7426 7460 261 1149 1987 C
ATOM 236 CE1 TYR A 182 189.013 47.969 -1.256 1.00 56.47 C
ANISOU 236 CE1 TYR A 182 5658 7819 7981 189 1072 1967 C
ATOM 237 CZ TYR A 182 189.597 46.759 -0.915 1.00 56.67 C
ANISOU 237 CZ TYR A 182 5603 7929 7999 300 1084 1952 C
ATOM 238 OH TYR A 182 190.184 46.565 0.322 1.00 52.52 O
ANISOU 238 OH TYR A 182 4972 7430 7554 255 1000 1954 O
ATOM 239 CE2 TYR A 182 189.606 45.720 -1.821 1.00 56.74 C
ANISOU 239 CE2 TYR A 182 5620 8013 7925 474 1178 1925 C
ATOM 240 CD2 TYR A 182 189.034 45.885 -3.048 1.00 53.18 C
ANISOU 240 CD2 TYR A 182 5248 7600 7358 534 1256 1910 C
ATOM 241 C TYR A 182 190.007 46.765 -5.923 1.00 54.62 C
ANISOU 241 C TYR A 182 5343 8122 7286 649 1450 2048 C
ATOM 242 O TYR A 182 191.080 46.876 -5.325 1.00 59.92 O
ANISOU 242 O TYR A 182 5904 8790 8074 581 1430 2099 O
ATOM 243 N ASN A 183 189.732 45.772 -6.756 1.00 53.60 N
ANISOU 243 N ASN A 183 5225 8130 7011 825 1517 1930 N
ATOM 244 CA ASN A 183 190.646 44.665 -6.942 1.00 53.00 C
ANISOU 244 CA ASN A 183 5041 8167 6928 955 1567 1837 C
ATOM 245 CB ASN A 183 189.962 43.542 -7.698 1.00 46.46 C
ANISOU 245 CB ASN A 183 4252 7418 5981 1144 1609 1614 C
ATOM 246 CG ASN A 183 189.160 42.670 -6.801 1.00 50.13 C
ANISOU 246 CG ASN A 183 4785 7677 6584 1174 1552 1475 C
ATOM 247 OD1 ASN A 183 189.393 42.643 -5.596 1.00 53.02 O
ANISOU 247 OD1 ASN A 183 5139 7887 7119 1088 1490 1552 O
ATOM 248 ND2 ASN A 183 188.191 41.952 -7.363 1.00 51.38 N
ANISOU 248 ND2 ASN A 183 5007 7837 6680 1298 1563 1261 N
ATOM 249 C ASN A 183 191.914 45.059 -7.666 1.00 63.84 C
ANISOU 249 C ASN A 183 6282 9724 8248 962 1636 1948 C
ATOM 250 O ASN A 183 192.806 44.238 -7.830 1.00 63.31 O
ANISOU 250 O ASN A 183 6112 9762 8183 1063 1678 1878 O
ATOM 251 N GLN A 184 191.971 46.306 -8.135 1.00 71.57 N
ANISOU 251 N GLN A 184 7260 10734 9199 865 1651 2122 N
ATOM 252 CA GLN A 184 193.142 46.814 -8.846 1.00 72.56 C
ANISOU 252 CA GLN A 184 7251 11024 9295 860 1727 2264 C
ATOM 253 CB GLN A 184 192.741 47.603 -10.082 1.00 77.47 C
ANISOU 253 CB GLN A 184 7892 11768 9758 900 1786 2392 C
ATOM 254 CG GLN A 184 193.816 47.645 -11.115 1.00 89.42 C
ANISOU 254 CG GLN A 184 9261 13555 11159 981 1891 2493 C
ATOM 255 CD GLN A 184 193.420 46.872 -12.347 1.00 99.01 C
ANISOU 255 CD GLN A 184 10484 15045 12089 1191 1950 2367 C
ATOM 256 OE1 GLN A 184 192.223 46.698 -12.617 1.00 102.65 O
ANISOU 256 OE1 GLN A 184 11061 15509 12431 1255 1914 2264 O
ATOM 257 NE2 GLN A 184 194.414 46.390 -13.103 1.00 99.98 N
ANISOU 257 NE2 GLN A 184 10475 15416 12098 1303 2036 2350 N
ATOM 258 C GLN A 184 193.943 47.718 -7.928 1.00 67.85 C
ANISOU 258 C GLN A 184 6574 10285 8919 671 1680 2393 C
ATOM 259 O GLN A 184 195.121 47.500 -7.705 1.00 69.36 O
ANISOU 259 O GLN A 184 6629 10544 9179 659 1702 2412 O
ATOM 260 N HIS A 185 193.283 48.724 -7.375 1.00 66.88 N
ANISOU 260 N HIS A 185 6528 9967 8915 524 1611 2452 N
ATOM 261 C HIS A 185 194.528 49.038 -5.239 1.00 64.41 C
ANISOU 261 C HIS A 185 6065 9470 8938 291 1483 2416 C
ATOM 262 O HIS A 185 195.565 49.466 -4.741 1.00 67.11 O
ANISOU 262 O HIS A 185 6265 9815 9418 184 1469 2454 O
ATOM 263 CA HIS A 185 193.957 49.672 -6.502 1.00 70.84 C
ANISOU 263 CA HIS A 185 6946 10328 9642 335 1561 2524 C
ATOM 264 CB HIS A 185 193.009 50.815 -6.111 1.00 82.67 C
ANISOU 264 CB HIS A 185 8545 11610 11256 201 1496 2554 C
ATOM 265 CG HIS A 185 192.687 51.749 -7.236 1.00 96.48 C
ANISOU 265 CG HIS A 185 10310 13384 12963 219 1568 2716 C
ATOM 266 ND1 HIS A 185 192.488 51.319 -8.528 1.00 101.42 N
ANISOU 266 ND1 HIS A 185 10949 14227 13360 391 1655 2775 N
ATOM 267 CE1 HIS A 185 192.224 52.366 -9.301 1.00 102.33 C
ANISOU 267 CE1 HIS A 185 11057 14338 13485 382 1701 2952 C
ATOM 268 NE2 HIS A 185 192.244 53.449 -8.556 1.00 101.32 N
ANISOU 268 NE2 HIS A 185 10917 13968 13612 208 1653 2998 N
ATOM 275 CE2 TYR A 186 193.500 51.241 -0.835 1.00 86.12 C
ANISOU 275 CE2 TYR A 186 7398 9728 15594 -794 1307 1190 C
ATOM 276 CZ TYR A 186 192.643 52.014 -1.619 1.00 86.21 C
ANISOU 276 CZ TYR A 186 7482 10044 15231 -824 1494 1621 C
ATOM 277 OH TYR A 186 192.524 53.368 -1.358 1.00 84.17 O
ANISOU 277 OH TYR A 186 7514 9580 14886 -899 1618 1983 O
ATOM 278 CE1 TYR A 186 191.921 51.429 -2.658 1.00 83.80 C
ANISOU 278 CE1 TYR A 186 6972 10268 14602 -754 1509 1606 C
ATOM 279 CD1 TYR A 186 192.059 50.068 -2.896 1.00 82.09 C
ANISOU 279 CD1 TYR A 186 6492 10303 14396 -614 1348 1155 C
ATOM 280 C TYR A 186 194.509 46.016 -3.430 1.00 69.53 C
ANISOU 280 C TYR A 186 4176 9656 12587 126 552 -909 C
ATOM 281 O TYR A 186 194.486 45.341 -2.411 1.00 66.10 O
ANISOU 281 O TYR A 186 4217 8603 12293 267 325 -1275 O
ATOM 282 N ASN A 187 194.823 45.520 -4.620 1.00 72.65 N
ANISOU 282 N ASN A 187 4243 10828 12532 213 562 -1032 N
ATOM 283 CA ASN A 187 195.232 44.135 -4.798 1.00 77.73 C
ANISOU 283 CA ASN A 187 4922 11652 12961 487 344 -1668 C
ATOM 284 CB ASN A 187 195.418 43.856 -6.294 1.00 87.96 C
ANISOU 284 CB ASN A 187 5909 13749 13763 493 452 -1583 C
ATOM 285 CG ASN A 187 196.187 42.568 -6.572 1.00 94.75 C
ANISOU 285 CG ASN A 187 6785 14838 14379 753 277 -2204 C
ATOM 286 OD1 ASN A 187 197.261 42.592 -7.184 1.00 97.40 O
ANISOU 286 OD1 ASN A 187 6883 15567 14558 788 301 -2227 O
ATOM 287 ND2 ASN A 187 195.640 41.436 -6.121 1.00 95.95 N
ANISOU 287 ND2 ASN A 187 7236 14712 14508 943 108 -2701 N
ATOM 288 C ASN A 187 196.514 43.803 -4.015 1.00 80.60 C
ANISOU 288 C ASN A 187 5348 11774 13501 641 123 -2079 C
ATOM 289 O ASN A 187 196.698 42.687 -3.528 1.00 82.25 O
ANISOU 289 O ASN A 187 5795 11742 13712 884 -104 -2629 O
ATOM 290 N ASN A 188 197.413 44.773 -3.902 1.00 80.08 N
ANISOU 290 N ASN A 188 5079 11784 13562 495 188 -1791 N
ATOM 291 CA ASN A 188 198.638 44.572 -3.128 1.00 79.06 C
ANISOU 291 CA ASN A 188 4978 11438 13623 598 -20 -2108 C
ATOM 292 CB ASN A 188 199.709 45.602 -3.515 1.00 78.83 C
ANISOU 292 CB ASN A 188 4593 11802 13557 427 94 -1736 C
ATOM 293 CG ASN A 188 200.261 45.380 -4.932 1.00 80.94 C
ANISOU 293 CG ASN A 188 4510 12853 13389 494 205 -1650 C
ATOM 294 OD1 ASN A 188 200.393 44.234 -5.403 1.00 79.45 O
ANISOU 294 OD1 ASN A 188 4346 12882 12960 718 123 -2058 O
ATOM 295 ND2 ASN A 188 200.567 46.486 -5.627 1.00 78.94 N
ANISOU 295 ND2 ASN A 188 3965 12955 13072 295 400 -1108 N
ATOM 296 C ASN A 188 198.390 44.571 -1.616 1.00 75.93 C
ANISOU 296 C ASN A 188 4994 10146 13711 598 -202 -2272 C
ATOM 297 O ASN A 188 199.138 43.971 -0.851 1.00 77.52 O
ANISOU 297 O ASN A 188 5366 10058 14029 753 -450 -2664 O
ATOM 298 N LEU A 189 197.328 45.250 -1.202 1.00 74.42 N
ANISOU 298 N LEU A 189 5136 9474 13665 401 -64 -1872 N
ATOM 299 CA LEU A 189 196.952 45.339 0.207 1.00 74.28 C
ANISOU 299 CA LEU A 189 5746 8524 13955 348 -191 -1883 C
ATOM 300 CB LEU A 189 196.158 46.618 0.468 1.00 69.37 C
ANISOU 300 CB LEU A 189 5297 7534 13528 46 74 -1256 C
ATOM 301 CG LEU A 189 195.568 46.750 1.872 1.00 63.47 C
ANISOU 301 CG LEU A 189 5245 5791 13081 -25 -1 -1218 C
ATOM 302 CD1 LEU A 189 196.680 46.688 2.959 1.00 53.27 C
ANISOU 302 CD1 LEU A 189 4159 4074 12006 -34 -257 -1501 C
ATOM 303 CD2 LEU A 189 194.732 48.034 1.970 1.00 58.82 C
ANISOU 303 CD2 LEU A 189 4789 4900 12658 -308 329 -555 C
ATOM 304 C LEU A 189 196.096 44.158 0.631 1.00 76.72 C
ANISOU 304 C LEU A 189 6522 8430 14196 568 -362 -2271 C
ATOM 305 O LEU A 189 196.007 43.651 1.741 1.00 79.34 O
ANISOU 305 O LEU A 189 7311 8127 14709 666 -591 -2577 O
ATOM 306 N LEU A 190 195.217 43.744 -0.263 1.00 76.74 N
ANISOU 306 N LEU A 190 6415 8811 13931 627 -248 -2239 N
ATOM 307 CA LEU A 190 194.313 42.650 0.012 1.00 76.66 C
ANISOU 307 CA LEU A 190 6826 8482 13820 810 -387 -2568 C
ATOM 308 CB LEU A 190 193.137 42.728 -0.948 1.00 80.46 C
ANISOU 308 CB LEU A 190 7177 9332 14060 725 -176 -2256 C
ATOM 309 CG LEU A 190 191.986 41.783 -0.659 1.00 82.98 C
ANISOU 309 CG LEU A 190 7956 9288 14285 847 -284 -2468 C
ATOM 310 CD1 LEU A 190 191.358 42.118 0.703 1.00 80.85 C
ANISOU 310 CD1 LEU A 190 8294 8079 14348 769 -331 -2301 C
ATOM 311 CD2 LEU A 190 190.992 41.956 -1.763 1.00 85.13 C
ANISOU 311 CD2 LEU A 190 7981 10074 14290 724 -69 -2106 C
ATOM 312 C LEU A 190 195.005 41.297 -0.138 1.00 74.98 C
ANISOU 312 C LEU A 190 6567 8511 13411 1120 -627 -3234 C
ATOM 313 O LEU A 190 194.738 40.373 0.622 1.00 74.17 O
ANISOU 313 O LEU A 190 6997 8019 13164 1161 -849 -3456 O

TABLE 8-continued

DMXAA-hSTING$^{S162A/Q266I}$ complex

| ATOM 269 CD2 HIS A 185 192.534 53.099 −7.254 1.00100.08 C | ATOM 314 N ARG A 191 195.893 41.202 −1.126 1.00 76.78 N |
|---|---|
| ANISOU 269 CD2 HIS A 185 10756 13684 13587 98 1566 2837 C | ANISOU 314 N ARG A 191 6248 9499 13424 1184 −573 −3339 N |
| ATOM 270 N TYR A 186 193.843 48.028 −4.714 1.00 79.81 N | ATOM 315 CA ARG A 191 196.549 39.949 −1.515 1.00 74.92 C |
| ANISOU 270 N TYR A 186 5238 11580 13504 −283 1014 164 N | ANISOU 315 CA ARG A 191 5957 9609 12902 1448 −727 −3886 C |
| ATOM 316 CB ARG A 191 197.569 39.520 −0.480 1.00 71.91 C | ATOM 361 NE ARG A 197 176.188 35.645 −8.150 1.00 71.00 N |
| ANISOU 316 CB ARG A 191 5850 8826 12647 1524 −986 −4165 C | ANISOU 361 NE ARG A 197 7146 10864 8967 −617 −151 −274 N |
| ATOM 317 CG ARG A 191 198.486 40.631 −0.111 1.00 78.51 C | ATOM 362 CZ ARG A 197 175.052 35.130 −8.644 1.00 72.31 C |
| ANISOU 317 CG ARG A 191 6381 9627 13824 1414 −950 −3928 C | ANISOU 362 CZ ARG A 197 7367 11307 8801 −828 −216 −64 C |
| ATOM 318 CD ARG A 191 199.356 40.258 1.053 1.00 80.75 C | ATOM 363 NH1 ARG A 197 174.716 33.867 −8.389 1.00 68.80 N |
| ANISOU 318 CD ARG A 191 6969 9448 14265 1451 −1224 −4163 C | ANISOU 363 NH1 ARG A 197 7368 10660 8114 −760 −460 −605 N |
| ATOM 319 NE ARG A 191 200.745 40.162 0.640 1.00 87.19 N | ATOM 364 NH2 ARG A 197 174.251 35.877 −9.399 1.00 70.80 N |
| ANISOU 319 NE ARG A 191 7359 10759 15012 1558 −1251 −4304 N | ANISOU 364 NH2 ARG A 197 6781 11604 8514 −1116 −38 700 N |
| ATOM 320 CZ ARG A 191 201.755 40.020 1.484 1.00 88.94 C | ATOM 365 C ARG A 197 178.149 40.262 −5.055 1.00 57.06 C |
| ANISOU 320 CZ ARG A 191 7648 10740 15406 1590 −1461 −4459 C | ANISOU 365 C ARG A 197 5271 7129 9277 −283 547 948 C |
| ATOM 321 NH1 ARG A 191 201.500 39.963 2.784 1.00 90.54 N | ATOM 366 O ARG A 197 179.034 40.414 −4.239 1.00 51.66 O |
| ANISOU 321 NH1 ARG A 191 8331 10278 15791 1458 −1671 −4424 N | ANISOU 366 O ARG A 197 4783 5969 8879 −120 496 628 O |
| ATOM 322 NH2 ARG A 191 203.003 39.951 1.029 1.00 84.26 N | ATOM 367 N LEU A 198 176.949 40.771 −4.870 1.00 44.55 N |
| ANISOU 322 NH2 ARG A 191 6663 10638 14716 1680 −1453 −4521 N | ANISOU 367 N LEU A 198 4735 5178 7014 151 −71 −712 N |
| ATOM 323 C ARG A 191 195.516 38.865 −1.735 1.00 70.49 C | ATOM 368 CA LEU A 198 176.587 41.332 −3.586 1.00 45.83 C |
| ANISOU 323 C ARG A 191 5753 8982 12048 1539 −787 −4121 C | ANISOU 368 CA LEU A 198 4882 5420 7110 176 −155 −605 C |
| ATOM 324 O ARG A 191 195.642 37.738 −1.267 1.00 71.89 O | ATOM 369 CB LEU A 198 175.699 42.538 −3.785 1.00 38.51 C |
| ANISOU 324 O ARG A 191 6330 8961 12024 1595 −1020 −4386 O | ANISOU 369 CB LEU A 198 4112 4443 6076 65 −125 −587 C |
| ATOM 325 N GLY A 192 194.491 39.230 −2.469 1.00 68.29 N | ATOM 370 CG LEU A 198 175.448 43.567 −2.687 1.00 44.18 C |
| ANISOU 325 N GLY A 192 5287 8968 11693 1452 −586 −3857 N | ANISOU 370 CG LEU A 198 4847 5228 6712 36 −134 −576 C |
| ATOM 326 CA GLY A 192 193.364 38.359 −2.702 1.00 72.34 C | ATOM 371 CD1 LEU A 198 173.938 43.767 −2.548 1.00 44.36 C |
| ANISOU 326 CA GLY A 192 6099 9421 11966 1513 −619 −4025 C | ANISOU 371 CD1 LEU A 198 4983 5141 6729 75 −145 −445 C |
| ATOM 327 C GLY A 192 192.430 39.101 −3.633 1.00 76.79 C | ATOM 372 CD2 LEU A 198 176.073 43.239 −1.352 1.00 45.55 C |
| ANISOU 327 C GLY A 192 6411 10403 12364 1255 −367 −3474 C | ANISOU 372 CD2 LEU A 198 4874 5584 6847 94 −209 −571 C |
| ATOM 328 O GLY A 192 192.726 40.211 −4.076 1.00 85.31 O | ATOM 373 C LEU A 198 175.808 40.253 −2.877 1.00 44.85 C |
| ANISOU 328 O GLY A 192 7094 11804 13514 1062 −173 −3015 O | ANISOU 373 C LEU A 198 4749 5232 7062 311 −244 −436 C |
| ATOM 329 N ALA A 193 191.308 38.481 −3.949 1.00 73.37 N | ATOM 374 O LEU A 198 174.880 39.666 −3.429 1.00 44.45 O |
| ANISOU 329 N ALA A 193 6194 9984 11698 1244 −370 −3506 N | ANISOU 374 O LEU A 198 4794 5034 7061 314 −245 −381 O |
| ATOM 330 CA ALA A 193 190.294 39.132 −4.751 1.00 72.20 C | ATOM 375 N TYR A 199 176.203 39.969 −1.655 1.00 43.41 N |
| ANISOU 330 CA ALA A 193 5846 10187 11401 991 −150 −2951 C | ANISOU 375 N TYR A 199 4441 5179 6876 400 −325 −342 N |
| ATOM 331 CB ALA A 193 190.137 38.448 −6.105 1.00 58.81 C | ATOM 376 CA TYR A 199 175.521 38.928 −0.919 1.00 38.79 C |
| ANISOU 331 CB ALA A 193 3848 9290 9208 987 −90 −3113 C | ANISOU 376 CA TYR A 199 3844 4538 6357 517 −403 −138 C |
| ATOM 332 C ALA A 193 189.017 39.038 −3.952 1.00 65.68 C | ATOM 377 CB TYR A 199 176.528 37.970 −0.310 1.00 35.56 C |
| ANISOU 332 C ALA A 193 5540 8690 10726 943 −202 −2784 C | ANISOU 377 CB TYR A 199 3248 4195 6067 664 −473 −39 C |
| ATOM 333 O ALA A 193 188.763 38.029 −3.286 1.00 63.96 O | ATOM 378 CG TYR A 199 177.166 37.157 −1.381 1.00 40.62 C |
| ANISOU 333 O ALA A 193 5778 8021 10504 1123 −415 −3233 O | ANISOU 378 CG TYR A 199 3845 4664 6924 733 −395 −146 C |
| ATOM 334 N VAL A 194 188.220 40.096 −3.985 1.00 62.09 N | ATOM 379 CD1 TYR A 199 178.279 37.642 −2.082 1.00 43.95 C |
| ANISOU 334 N VAL A 194 5025 8148 10418 709 2 −2128 N | ANISOU 379 CD1 TYR A 199 4175 5169 7355 691 −315 −350 C |
| ATOM 335 CA VAL A 194 186.891 39.982 −3.456 1.00 57.00 C | ATOM 380 CE1 TYR A 199 178.870 36.881 −3.070 1.00 48.80 C |
| ANISOU 335 CA VAL A 194 4807 6994 9855 654 −8 −1911 C | ANISOU 380 CE1 TYR A 199 4741 5639 8161 755 −204 −481 C |
| ATOM 336 CB VAL A 194 186.368 41.310 −2.911 1.00 59.54 C | ATOM 381 CZ TYR A 199 178.318 35.643 −3.386 1.00 51.40 C |
| ANISOU 336 CB VAL A 194 5193 6884 10545 462 206 −1233 C | ANISOU 381 CZ TYR A 199 5139 5703 8688 851 −176 −430 C |
| ATOM 337 CG1 VAL A 194 187.485 42.059 −2.217 1.00 59.14 C | ATOM 382 OH TYR A 199 178.883 34.872 −4.366 1.00 55.33 O |
| ANISOU 337 CG1 VAL A 194 5115 6529 10826 469 216 −1239 C | ANISOU 382 OH TYR A 199 5603 6034 9385 909 −34 −609 O |
| ATOM 338 CG2 VAL A 194 185.821 42.137 −4.004 1.00 64.87 C | ATOM 383 CE2 TYR A 199 177.211 35.157 −2.718 1.00 47.17 C |
| ANISOU 338 CG2 VAL A 194 5405 8175 11066 229 484 −608 C | ANISOU 383 CE2 TYR A 199 4702 5060 8160 874 −268 −219 C |
| ATOM 339 C VAL A 194 186.023 39.448 −4.584 1.00 55.58 C | ATOM 384 CD2 TYR A 199 176.641 35.920 −1.726 1.00 42.53 C |
| ANISOU 339 C VAL A 194 4451 7423 9244 563 43 −1831 C | ANISOU 384 CD2 TYR A 199 4141 4652 7366 818 −375 −69 C |
| ATOM 340 O VAL A 194 186.301 39.681 −5.759 1.00 63.32 O | ATOM 385 C TYR A 199 174.597 39.508 0.122 1.00 30.77 C |
| ANISOU 340 O VAL A 194 4931 9181 9948 454 179 −1686 O | ANISOU 385 C TYR A 199 2883 3622 5185 483 −440 −31 C |
| ATOM 341 N SER A 195 184.991 38.706 −4.217 1.00 52.74 N | ATOM 386 O TYR A 199 175.015 40.266 0.988 1.00 30.62 O |
| ANISOU 341 N SER A 195 4513 6711 8815 600 −77 −1939 N | ANISOU 386 O TYR A 199 2812 3803 5017 441 −462 −68 O |
| ATOM 342 CA SER A 195 184.047 38.165 −5.178 1.00 60.35 C | ATOM 387 N ILE A 200 173.336 39.143 0.014 1.00 33.04 N |
| ANISOU 342 CA SER A 195 5379 8184 9368 481 −53 −1843 C | ANISOU 387 N ILE A 200 3266 3782 5506 485 −434 80 N |
| ATOM 343 CB SER A 195 183.164 37.144 −4.484 1.00 62.44 C | ATOM 388 CA ILE A 200 172.293 39.746 0.829 1.00 36.10 C |
| ANISOU 343 CB SER A 195 6212 7910 9601 586 −259 −2144 C | ANISOU 388 CA ILE A 200 3703 4248 5766 453 −423 157 C |
| ATOM 344 OG SER A 195 183.932 36.434 −3.539 1.00 67.30 O | ATOM 389 CB ILE A 200 171.144 40.278 −0.028 1.00 37.90 C |
| ANISOU 344 OG SER A 195 7191 8001 10379 852 −480 −2771 O | ANISOU 389 CB ILE A 200 4040 4340 6019 391 −364 131 C |
| ATOM 345 C SER A 195 183.190 39.283 −5.743 1.00 66.73 C | ATOM 390 CG1 ILE A 200 171.669 41.270 −1.047 1.00 38.94 C |
| ANISOU 345 C SER A 195 5879 9268 10208 204 215 −1025 C | ANISOU 390 CG1 ILE A 200 4231 4429 6135 314 −308 −44 C |
| ATOM 346 O SER A 195 183.070 40.365 −6.105 1.00 61.40 O | ATOM 391 CD1 ILE A 200 170.590 41.839 −1.914 1.00 38.68 C |
| ANISOU 346 O SER A 195 5229 8181 9920 132 371 −547 O | ANISOU 391 CD1 ILE A 200 4287 4289 6120 265 −277 −17 C |
| ATOM 347 N GLN A 196 182.552 39.019 −6.879 1.00 72.27 N | ATOM 392 CG2 ILE A 200 170.174 41.006 0.835 1.00 39.79 C |
| ANISOU 347 N GLN A 196 6313 10644 10502 38 275 −847 N | ANISOU 392 CG2 ILE A 200 4297 4661 6160 387 −319 183 C |
| ATOM 348 CA GLN A 196 181.906 40.109 −7.599 1.00 76.29 C | ATOM 393 C ILE A 200 171.765 38.689 1.763 1.00 32.03 C |
| ANISOU 348 CA GLN A 196 6417 11564 11006 −229 544 −58 C | ANISOU 393 C ILE A 200 3142 3758 5271 524 −482 390 C |
| ATOM 349 CB GLN A 196 182.222 40.042 −9.090 1.00 83.04 C | ATOM 394 O ILE A 200 171.202 37.675 1.335 1.00 32.54 O |
| ANISOU 349 CB GLN A 196 6726 13420 11408 −377 631 −29 C | ANISOU 394 O ILE A 200 3229 3647 5487 548 −494 501 O |
| ATOM 350 CG GLN A 196 182.975 41.256 −9.590 1.00 91.02 C | ATOM 395 N LEU A 201 171.992 38.915 3.046 1.00 32.87 N |
| ANISOU 350 CG GLN A 196 7214 14819 12550 −479 868 371 C | ANISOU 395 N LEU A 201 3187 4093 5210 534 −516 463 N |
| ATOM 351 CD GLN A 196 184.056 40.876 −10.575 1.00103.44 C | ATOM 396 CA LEU A 201 171.582 37.971 4.068 1.00 30.50 C |
| ANISOU 351 CD GLN A 196 8405 17117 13781 −446 850 −34 C | ANISOU 396 CA LEU A 201 2839 3869 4880 586 −572 727 C |
| ATOM 352 OE1 GLN A 196 185.199 41.357 −10.500 1.00107.61 O | ATOM 397 CB LEU A 201 172.417 38.160 5.313 1.00 31.52 C |
| ANISOU 352 OE1 GLN A 196 8825 17586 14476 −351 884 −142 O | ANISOU 397 CB LEU A 201 2867 4313 4794 590 −650 785 C |

TABLE 8-continued

DMXAA-hSTING$^{S162A/Q266I}$ complex

ATOM 353 NE2 GLN A 196 183.708 39.992 −11.508 1.00108.52 N
ANISOU 353 NE2 GLN A 196 8991 18307 13935 −519 778 −254 N
ATOM 354 C GLN A 196 180.406 40.274 −7.380 1.00 73.93 C
ANISOU 354 C GLN A 196 6326 10996 10769 −369 605 471 C
ATOM 355 O GLN A 196 179.790 41.210 −7.909 1.00 82.14 O
ANISOU 355 O GLN A 196 7040 12330 11840 −582 844 1186 O
ATOM 356 N ARG A 197 179.806 39.378 −6.615 1.00 59.52 N
ANISOU 356 N ARG A 197 5026 8624 8965 −248 400 149 N
ATOM 357 CA ARG A 197 178.393 39.518 −6.371 1.00 57.55 C
ANISOU 357 CA ARG A 197 4975 8106 8788 −370 456 659 C
ATOM 358 CB ARG A 197 177.712 38.156 −6.390 1.00 57.63 C
ANISOU 358 CB ARG A 197 5335 8092 8471 −334 203 229 C
ATOM 359 CG ARG A 197 177.949 37.357 −7.667 1.00 59.69 C
ANISOU 359 CG ARG A 197 5308 9217 8156 −436 121 −96 C
ATOM 360 CD ARG A 197 176.651 37.022 −8.377 1.00 63.39 C
ANISOU 360 CD ARG A 197 5724 10086 8277 −684 116 272 C
ATOM 406 CG LEU A 202 167.102 38.050 2.513 1.00 47.00 C
ANISOU 406 CG LEU A 202 5099 5555 7205 430 −370 833 C
ATOM 407 CD1 LEU A 202 167.223 37.393 1.176 1.00 51.53 C
ANISOU 407 CD1 LEU A 202 5713 5909 7956 395 −420 778 C
ATOM 408 CD2 LEU A 202 165.825 38.840 2.588 1.00 52.64 C
ANISOU 408 CD2 LEU A 202 5792 6321 7886 404 −284 835 C
ATOM 409 C LEU A 202 167.602 36.300 5.880 1.00 36.93 C
ANISOU 409 C LEU A 202 3691 4686 5653 493 −445 1395 C
ATOM 410 O LEU A 202 167.137 35.191 5.608 1.00 40.92 O
ANISOU 410 O LEU A 202 4201 4998 6351 484 −467 1577 O
ATOM 411 N PRO A 203 167.870 36.687 7.129 1.00 39.37 N
ANISOU 411 N PRO A 203 3965 5302 5693 482 −440 1449 N
ATOM 412 CA PRO A 203 167.459 35.800 8.224 1.00 37.69 C
ANISOU 412 CA PRO A 203 3713 5225 5380 461 −454 1777 C
ATOM 413 CB PRO A 203 168.193 36.363 9.440 1.00 39.77 C
ANISOU 413 CB PRO A 203 3938 5881 5291 439 −490 1770 C
ATOM 414 CG PRO A 203 168.535 37.822 9.072 1.00 41.48 C
ANISOU 414 CG PRO A 203 4189 6156 5414 409 −422 1369 C
ATOM 415 CD PRO A 203 168.699 37.823 7.574 1.00 39.28 C
ANISOU 415 CD PRO A 203 3947 5527 5450 464 −438 1225 C
ATOM 416 C PRO A 203 165.948 35.914 8.391 1.00 37.63 C
ANISOU 416 C PRO A 203 3708 5229 5361 378 −309 1823 C
ATOM 417 O PRO A 203 165.424 37.009 8.560 1.00 38.75 O
ANISOU 417 O PRO A 203 3851 5233 5505 5367 347 −186 1620 O
ATOM 418 N LEU A 204 165.244 34.793 8.321 1.00 39.73 N
ANISOU 418 N LEU A 204 3961 5334 5799 342 −311 2081 N
ATOM 419 CA LEU A 204 163.787 34.823 8.405 1.00 47.52 C
ANISOU 419 CA LEU A 204 4908 6338 6807 248 −177 2137 C
ATOM 420 CB LEU A 204 163.211 33.497 7.921 1.00 54.03 C
ANISOU 420 CB LEU A 204 5731 6883 7916 182 −211 2366 C
ATOM 421 CG LEU A 204 163.504 33.260 6.450 1.00 50.88 C
ANISOU 421 CG LEU A 204 5383 6149 7802 202 −299 2243 C
ATOM 422 CD1 LEU A 204 162.843 31.990 6.023 1.00 49.99 C
ANISOU 422 CD1 LEU A 204 5276 5762 7958 92 −300 2361 C
ATOM 423 CD2 LEU A 204 163.016 34.457 5.631 1.00 47.99 C
ANISOU 423 CD2 LEU A 204 5000 5817 7419 200 −242 1895 C
ATOM 424 C LEU A 204 163.243 35.138 9.808 1.00 49.90 C
ANISOU 424 C LEU A 204 5162 7004 6794 186 −51 2251 C
ATOM 425 O LEU A 204 162.093 35.559 9.955 1.00 54.08 O
ANISOU 425 O LEU A 204 5629 7621 7298 130 106 2208 O
ATOM 426 N ASP A 205 164.033 34.893 10.845 1.00 47.20 N
ANISOU 426 N ASP A 205 4830 6900 6205 190 −115 2411 N
ATOM 427 CA ASP A 205 163.648 35.354 12.183 1.00 53.52 C
ANISOU 427 CA ASP A 205 5600 8115 6621 106 13 2455 C
ATOM 428 CB ASP A 205 164.446 34.644 13.280 1.00 57.82 C
ANISOU 428 CB ASP A 205 6143 8915 6909 83 −112 2778 C
ATOM 429 CG ASP A 205 165.951 34.809 13.113 1.00 76.39 C
ANISOU 429 CG ASP A 205 8506 11284 9233 180 −311 2691 C
ATOM 430 OD1 ASP A 205 166.470 34.591 11.983 1.00 84.11 O
ANISOU 430 OD1 ASP A 205 9499 11912 10546 284 −406 2596 O
ATOM 431 OD2 ASP A 205 166.613 35.163 14.114 1.00 82.62 O
ANISOU 431 OD2 ASP A 205 9275 12468 9648 135 −367 2708 O
ATOM 432 C ASP A 205 163.814 36.895 12.282 1.00 52.25 C
ANISOU 432 C ASP A 205 5458 8131 6265 119 123 2031 C
ATOM 433 O ASP A 205 163.511 37.510 13.320 1.00 57.47 O
ANISOU 433 O ASP A 205 6108 9134 6596 43 271 1945 O
ATOM 434 N CYS A 206 164.307 37.500 11.199 1.00 42.26 N
ANISOU 434 N CYS A 206 4230 6622 5205 201 67 1765 N
ATOM 435 CA CYS A 206 164.399 38.963 11.064 1.00 51.67 C
ANISOU 435 CA CYS A 206 5455 7861 6318 215 183 1371 C
ATOM 436 CB CYS A 206 163.012 39.628 11.122 1.00 54.26 C
ANISOU 436 CB CYS A 206 5734 8195 6689 212 422 1257 C
ATOM 398 CG LEU A 201 173.909 37.941 5.129 1.00 33.16 C
ANISOU 398 CG LEU A 201 2947 4585 5066 651 −745 746 C
ATOM 399 CD1 LEU A 201 174.678 38.668 6.253 1.00 33.71 C
ANISOU 399 CD1 LEU A 201 2919 5043 4847 577 −819 698 C
ATOM 400 CD2 LEU A 201 174.152 36.442 5.181 1.00 30.89 C
ANISOU 400 CD2 LEU A 201 2581 4164 4993 801 −829 1028 C
ATOM 401 C LEU A 201 170.129 38.235 4.404 1.00 33.91 C
ANISOU 401 C LEU A 201 3336 4303 5245 531 −491 790 C
ATOM 402 O LEU A 201 169.746 39.370 4.652 1.00 30.78 O
ANISOU 402 O LEU A 201 2976 4008 4720 475 −406 645 O
ATOM 403 N LEU A 202 169.316 37.187 4.389 1.00 36.73 N
ANISOU 403 N LEU A 202 3698 4530 5729 545 −499 999 N
ATOM 404 CA LEU A 202 167.921 37.287 4.777 1.00 33.21 C
ANISOU 404 CA LEU A 202 3267 4116 5236 490 −420 1094 C
ATOM 405 CB LEU A 202 167.015 37.006 3.599 1.00 35.24 C
ANISOU 405 CB LEU A 202 3560 4133 5696 448 −398 1070 C
ATOM 451 N PRO A 209 171.621 42.301 13.457 1.00 54.01 N
ANISOU 451 N PRO A 209 5738 9464 5318 −218 −389 281 N
ATOM 452 CA PRO A 209 172.518 42.844 14.487 1.00 56.06 C
ANISOU 452 CA PRO A 209 5948 10189 5162 −418 −474 107 C
ATOM 453 CB PRO A 209 173.649 41.819 14.541 1.00 55.46 C
ANISOU 453 CB PRO A 209 5694 10289 5087 −347 −785 456 C
ATOM 454 CG PRO A 209 173.680 41.264 13.132 1.00 55.68 C
ANISOU 454 CG PRO A 209 5714 9816 5625 −134 −806 574 C
ATOM 455 CD PRO A 209 172.264 41.264 12.638 1.00 51.40 C
ANISOU 455 CD PRO A 209 5312 8931 5285 −57 −590 571 C
ATOM 456 C PRO A 209 173.040 44.178 13.988 1.00 61.24 C
ANISOU 456 C PRO A 209 6669 10705 5894 −534 −374 −367 C
ATOM 457 O PRO A 209 173.034 44.443 12.771 1.00 55.77 O
ANISOU 457 O PRO A 209 6020 9588 5583 −430 −320 −453 O
ATOM 458 N ASP A 210 173.484 45.016 14.914 1.00 70.14 N
ANISOU 458 N ASP A 210 7811 12191 6649 −772 −343 −675 N
ATOM 459 CA ASP A 210 174.008 46.331 14.557 1.00 78.15 C
ANISOU 459 CA ASP A 210 8898 13070 7727 −930 −231 −1146 C
ATOM 460 CB ASP A 210 174.034 47.249 15.772 1.00 90.37 C
ANISOU 460 CB ASP A 210 10514 14993 8830 −1215 −106 −1532 C
ATOM 461 CG ASP A 210 172.642 47.548 16.281 1.00100.89 C
ANISOU 461 CG ASP A 210 11987 16263 10084 −1187 196 −1644 C
ATOM 462 OD1 ASP A 210 171.727 46.740 15.984 1.00102.43 O
ANISOU 462 OD1 ASP A 210 12172 16289 10458 −967 227 −1303 O
ATOM 463 OD2 ASP A 210 172.461 48.590 16.954 1.00106.91 O
ANISOU 463 OD2 ASP A 210 12862 17133 10626 −1390 418 −2089 O
ATOM 464 C ASP A 210 175.362 46.251 13.879 1.00 77.18 C
ANISOU 464 C ASP A 210 8639 12930 7755 −948 −448 −1129 C
ATOM 465 O ASP A 210 175.708 47.099 13.064 1.00 75.95 O
ANISOU 465 O ASP A 210 8543 12480 7836 −999 −354 −1401 O
ATOM 466 N ASN A 211 176.119 45.218 14.213 1.00 81.47 N
ANISOU 466 N ASN A 211 8987 13786 8179 −897 −728 −785 N
ATOM 467 CA ASN A 211 177.344 44.923 13.496 1.00 83.47 C
ANISOU 467 CA ASN A 211 9064 14011 8641 −848 −927 −701 C
ATOM 468 CB ASN A 211 178.584 45.347 14.280 1.00 91.00 C
ANISOU 468 CB ASN A 211 9846 15472 9259 −1104 −1112 −862 C
ATOM 469 CG ASN A 211 178.868 46.819 14.127 1.00 97.74 C
ANISOU 469 CG ASN A 211 10811 16239 10088 −1377 −939 −1401 C
ATOM 470 OD1 ASN A 211 179.308 47.272 13.058 1.00 95.98 O
ANISOU 470 OD1 ASN A 211 10595 15678 10197 −1365 −876 −1547 O
ATOM 471 ND2 ASN A 211 178.588 47.591 15.182 1.00102.97 N
ANISOU 471 ND2 ASN A 211 11579 17186 10360 −1638 −836 −1712 N
ATOM 472 C ASN A 211 177.443 43.479 13.067 1.00 81.48 C
ANISOU 472 C ASN A 211 8678 13657 8622 −569 −1099 −215 C
ATOM 473 O ASN A 211 177.563 42.578 13.888 1.00 83.10 O
ANISOU 473 O ASN A 211 8763 14182 8628 −517 −1278 132 O
ATOM 474 N LEU A 212 177.401 43.289 11.755 1.00 72.02 N
ANISOU 474 N LEU A 212 10603 8647 8116 151 663 255 N
ATOM 475 CA LEU A 212 177.526 41.982 11.148 1.00 74.96 C
ANISOU 475 CA LEU A 212 10657 9214 8610 22 660 319 C
ATOM 476 CB LEU A 212 177.577 42.153 9.634 1.00 71.49 C
ANISOU 476 CB LEU A 212 10020 8812 8329 −198 645 374 C
ATOM 477 CG LEU A 212 178.036 40.968 8.797 1.00 61.88 C
ANISOU 477 CG LEU A 212 8571 7731 7208 −381 623 385 C
ATOM 478 CD1 LEU A 212 177.249 39.743 9.142 1.00 53.11 C
ANISOU 478 CD1 LEU A 212 7348 6741 6091 −265 692 511 C
ATOM 479 CD2 LEU A 212 177.860 41.330 7.323 1.00 60.95 C
ANISOU 479 CD2 LEU A 212 8393 7597 7167 −569 638 458 C
ATOM 480 C LEU A 212 178.790 41.298 11.653 1.00 81.24 C
ANISOU 480 C LEU A 212 11438 10032 9397 −91 480 176 C
ATOM 481 O LEU A 212 178.814 40.085 11.934 1.00 79.10 O
ANISOU 481 O LEU A 212 11031 9883 9138 −72 490 208 O

TABLE 8-continued

DMXAA-hSTING$^{S162A/Q266I}$ complex

| ATOM 437 SG CYS A 206 161.955 39.293 9.713 1.00 49.38 S | ATOM 482 N SER A 213 179.831 42.115 11.795 1.00 87.74 N |
|---|---|
| ANISOU 437 SG CYS A 206 5050 7214 6499 272 413 1338 S | ANISOU 482 N SER A 213 12366 10713 10230 −212 289 44 N |
| ATOM 438 C CYS A 206 165.307 39.643 12.088 1.00 56.73 C | ATOM 483 CA SER A 213 181.140 41.687 12.276 1.00 89.64 C |
| ANISOU 438 C CYS A 206 6128 8841 6588 150 181 1205 C | ANISOU 483 CA SER A 213 12600 10918 10542 −346 57 −52 C |
| ATOM 439 O CYS A 206 165.205 40.854 12.268 1.00 62.15 O | ATOM 484 CB SER A 213 182.083 42.890 12.295 1.00 90.28 C |
| ANISOU 439 O CYS A 206 6850 9595 7170 124 335 872 O | ANISOU 484 CB SER A 213 12825 10797 10681 −494 −174 −134 C |
| ATOM 440 N GLY A 207 166.157 38.872 12.772 1.00 51.40 N | ATOM 485 OG SER A 213 181.653 43.879 11.370 1.00 87.46 O |
| ANISOU 440 N GLY A 207 5432 8377 5720 116 11 1440 N | ANISOU 485 OG SER A 213 12471 10404 10356 −533 −68 −104 O |
| ATOM 441 CA GLY A 207 167.140 39.431 13.684 1.00 46.91 C | ATOM 486 C SER A 213 181.078 41.053 13.668 1.00 90.15 C |
| ANISOU 441 CA GLY A 207 4867 8176 4780 27 −48 1301 C | ANISOU 486 C SER A 213 12866 10962 10427 −195 −20 −78 C |
| ATOM 442 C GLY A 207 168.324 40.024 12.926 1.00 51.15 C | ATOM 487 O SER A 213 182.059 40.476 14.132 1.00 87.69 O |
| ANISOU 442 C GLY A 207 5417 8578 5439 63 −170 1051 C | ANISOU 487 O SER A 213 12496 10627 10196 −300 −234 −120 O |
| ATOM 443 O GLY A 207 169.102 39.307 12.282 1.00 54.48 O | ATOM 488 N MET A 214 179.927 41.178 14.329 1.00 93.51 N |
| ANISOU 443 O GLY A 207 5796 8833 6072 153 −356 1212 O | ANISOU 488 N MET A 214 13525 11376 10628 54 167 −28 N |
| ATOM 444 N VAL A 208 168.450 41.348 12.975 1.00 52.62 N | ATOM 489 CA MET A 214 179.741 40.689 15.697 1.00 92.02 C |
| ANISOU 444 N VAL A 208 5661 8813 5520 −12 −39 643 N | ANISOU 489 CA MET A 214 13617 11143 10202 226 150 −40 C |
| ATOM 445 CA VAL A 208 169.529 42.026 12.263 1.00 52.80 C | ATOM 490 CB MET A 214 179.187 41.789 16.605 1.00 95.79 C |
| ANISOU 445 CA VAL A 208 5697 8709 5655 −17 −122 389 C | ANISOU 490 CB MET A 214 14618 11400 10377 444 230 −87 C |
| ATOM 446 CB VAL A 208 169.020 43.031 11.218 1.00 46.33 C | ATOM 491 CG MET A 214 180.076 43.026 16.691 1.00 99.58 C |
| ANISOU 446 CB VAL A 208 4963 7519 5120 29 47 103 C | ANISOU 491 CG MET A 214 15390 11628 10818 305 −63 −231 C |
| ATOM 447 CG1 VAL A 208 170.214 43.707 10.534 1.00 42.09 C | ATOM 492 SD MET A 214 181.803 42.652 17.092 1.00 123.79 S |
| ANISOU 447 CG1 VAL A 208 4442 6876 4673 −10 −33 −130 C | ANISOU 492 SD MET A 214 18432 14595 14007 1 −581 −321 S |
| ATOM 448 CG2 VAL A 208 168.145 42.334 10.214 1.00 38.22 C | ATOM 493 CE MET A 214 182.529 44.294 17.009 1.00 90.59 C |
| ANISOU 448 CG2 VAL A 208 3930 6161 4433 167 51 320 C | ANISOU 493 CE MET A 214 14539 10078 9804 −152 −891 −420 C |
| ATOM 449 C VAL A 208 170.377 42.757 13.267 1.00 55.06 C | ATOM 494 C MET A 214 178.832 39.472 15.766 1.00 87.07 C |
| ANISOU 449 C VAL A 208 5975 9389 5555 −191 −147 158 C | ANISOU 494 C MET A 214 12782 10718 9582 363 382 108 C |
| ATOM 450 O VAL A 208 169.904 43.690 13.888 1.00 64.15 O | ATOM 495 O MET A 214 178.939 38.675 16.686 1.00 89.43 O |
| ANISOU 450 O VAL A 208 7199 10669 6507 −305 52 −130 O | ANISOU 495 O MET A 214 13183 11037 9760 428 331 114 O |
| ATOM 496 N ALA A 215 177.942 39.328 14.791 1.00 84.78 N | ATOM 541 C ARG A 220 185.329 41.014 9.041 1.00 45.06 C |
| ANISOU 496 N ALA A 215 12213 10558 9442 385 596 248 N | ANISOU 541 C ARG A 220 5911 5291 5920 −1130 6 −3 C |
| ATOM 497 CA ALA A 215 176.979 38.214 14.764 1.00 84.02 C | ATOM 542 O ARG A 220 185.486 40.658 7.863 1.00 43.25 O |
| ANISOU 497 CA ALA A 215 11894 10629 9400 492 780 438 C | ANISOU 542 O ARG A 220 5513 5129 5791 −1208 247 37 O |
| ATOM 498 CB ALA A 215 175.975 38.393 13.614 1.00 80.60 C | ATOM 543 N PHE A 221 185.121 42.266 9.419 1.00 42.21 N |
| ANISOU 498 CB ALA A 215 11211 10261 9151 482 937 617 C | ANISOU 543 N PHE A 221 5787 4799 5450 −1133 −154 −31 N |
| ATOM 499 C ALA A 215 177.609 36.817 14.689 1.00 82.11 C | ATOM 544 CA PHE A 221 185.214 43.379 8.503 1.00 46.16 C |
| ANISOU 499 C ALA A 215 11416 10521 9260 355 638 427 C | ANISOU 544 CA PHE A 221 6304 5228 6006 −1259 −103 −1 C |
| ATOM 500 O ALA A 215 177.112 35.868 15.286 1.00 84.87 O | ATOM 545 CB PHE A 221 184.749 44.649 9.228 1.00 45.92 C |
| ANISOU 500 O ALA A 215 11725 10956 9566 464 708 538 O | ANISOU 545 CB PHE A 221 6620 5034 5794 −1196 −305 −52 C |
| ATOM 501 N ASP A 216 178.667 36.681 13.901 1.00 73.77 N | ATOM 546 CG PHE A 221 185.047 45.921 8.479 1.00 43.47 C |
| ANISOU 501 N ASP A 216 10191 9473 8366 127 468 315 N | ANISOU 546 CG PHE A 221 6337 4600 5578 −1350 −347 −17 C |
| ATOM 502 CA ASP A 216 179.448 35.465 13.908 1.00 60.81 C | ATOM 547 CD1 PHE A 221 184.170 46.385 7.498 1.00 42.22 C |
| ANISOU 502 CA ASP A 216 8357 7906 6841 17 339 284 C | ANISOU 547 CD1 PHE A 221 6225 4496 5321 −1341 −142 19 C |
| ATOM 503 CB ASP A 216 179.281 34.700 12.597 1.00 59.38 C | ATOM 548 CE1 PHE A 221 184.422 47.574 6.794 1.00 40.98 C |
| ANISOU 503 CB ASP A 216 7890 7832 6839 −104 416 350 C | ANISOU 548 CE1 PHE A 221 6107 4220 5244 −1492 −189 62 C |
| ATOM 504 CG ASP A 216 180.061 33.362 12.571 1.00 63.17 C | ATOM 549 CZ PHE A 221 185.581 48.284 7.061 1.00 41.93 C |
| ANISOU 504 CG ASP A 216 8183 8365 7453 −188 323 318 C | ANISOU 549 CZ PHE A 221 6195 4168 5569 −1658 −438 80 C |
| ATOM 505 OD1 ASP A 216 181.121 33.247 13.216 1.00 69.78 O | ATOM 550 CE2 PHE A 221 186.483 47.814 8.048 1.00 41.87 C |
| ANISOU 505 OD1 ASP A 216 9024 9140 8349 −229 163 226 O | ANISOU 550 CE2 PHE A 221 6122 4093 5695 −1681 −673 64 C |
| ATOM 506 OD2 ASP A 216 179.627 32.414 11.877 1.00 59.47 O | ATOM 551 CD2 PHE A 221 186.208 46.638 8.734 1.00 40.72 C |
| ANISOU 506 OD2 ASP A 216 7571 7973 7052 −220 387 400 O | ANISOU 551 CD2 PHE A 221 5957 4066 5446 −1527 −624 11 C |
| ATOM 507 C ASP A 216 180.867 35.936 14.078 1.00 57.66 C | ATOM 552 C PHE A 221 186.683 43.510 8.052 1.00 48.57 C |
| ANISOU 507 C ASP A 216 8002 7383 6523 −132 111 133 C | ANISOU 552 C PHE A 221 6331 5449 6675 −1469 −159 72 C |
| ATOM 508 O ASP A 216 181.282 36.881 13.413 1.00 62.08 O | ATOM 553 O PHE A 221 187.612 43.426 8.868 1.00 39.77 O |
| ANISOU 508 O ASP A 216 8560 7866 7160 −239 91 76 O | ANISOU 553 O PHE A 221 5130 4223 5757 −1528 −422 95 O |
| ATOM 509 N PRO A 217 181.613 35.304 14.997 1.00 53.53 N | ATOM 554 N LEU A 222 186.918 43.717 6.761 1.00 47.04 N |
| ANISOU 509 N PRO A 217 7511 6822 6006 −149 −90 97 N | ANISOU 554 N LEU A 222 5994 5285 6594 −1589 83 139 N |
| ATOM 510 CA PRO A 217 183.036 35.658 15.131 1.00 50.42 C | ATOM 555 CA LEU A 222 188.281 44.066 6.388 1.00 52.68 C |
| ANISOU 510 CA PRO A 217 7084 6285 5787 −322 −364 12 C | ANISOU 555 CA LEU A 222 6443 5889 7686 −1775 56 252 C |
| ATOM 511 CB PRO A 217 183.479 34.878 16.382 1.00 47.90 C | ATOM 556 CB LEU A 222 189.024 42.912 5.705 1.00 56.36 C |
| ANISOU 511 CB PRO A 217 6871 5915 5413 −301 −604 21 C | ANISOU 556 CB LEU A 222 6584 6432 8398 −1792 365 326 C |
| ATOM 512 CG PRO A 217 182.443 33.740 16.509 1.00 46.76 C | ATOM 557 CG LEU A 222 188.340 42.119 4.620 1.00 59.61 C |
| ANISOU 512 CG PRO A 217 6658 5950 5158 −150 −395 112 C | ANISOU 557 CG LEU A 222 7065 6986 8599 −1725 760 291 C |
| ATOM 513 CD PRO A 217 181.157 34.389 16.062 1.00 45.32 C | ATOM 558 CD1 LEU A 222 187.983 43.055 3.503 1.00 71.12 C |
| ANISOU 513 CD PRO A 217 6576 5833 4812 −14 −103 161 C | ANISOU 558 CD1 LEU A 222 8681 8418 9923 −1833 915 326 C |
| ATOM 514 C PRO A 217 183.900 35.287 13.899 1.00 48.46 C | ATOM 559 CD2 LEU A 222 189.299 41.098 4.120 1.00 56.17 C |
| ANISOU 514 C PRO A 217 6447 6077 5888 −493 −313 14 C | ANISOU 559 CD2 LEU A 222 6343 6555 8445 −1728 1048 363 C |
| ATOM 515 O PRO A 217 185.002 35.798 13.727 1.00 56.63 O | ATOM 560 C LEU A 222 188.458 45.419 5.691 1.00 52.54 C |
| ANISOU 515 O PRO A 217 7385 6990 7142 −641 −467 −9 O | ANISOU 560 C LEU A 222 6483 5758 7721 −1930 37 317 C |
| ATOM 516 N ASN A 218 183.411 34.401 13.046 1.00 42.40 N | ATOM 561 O LEU A 222 189.480 46.096 5.877 1.00 56.19 O |
| ANISOU 516 N ASN A 218 5482 5452 5176 −473 −91 60 N | ANISOU 561 O LEU A 222 6800 6062 8486 −2086 −167 421 O |
| ATOM 517 CA ASN A 218 184.142 34.033 11.828 1.00 41.56 C | ATOM 562 N ASP A 223 187.452 45.836 4.940 1.00 48.10 N |
| ANISOU 517 CA ASN A 218 5102 5355 5333 −600 35 54 C | ANISOU 562 N ASP A 223 6131 5256 6890 −1902 201 282 N |
| ATOM 518 CB ASN A 218 183.901 32.563 11.492 1.00 38.76 C | ATOM 563 CA ASP A 223 187.563 47.109 4.245 1.00 45.52 C |
| ANISOU 518 CB ASN A 218 4598 5100 5031 −559 149 93 C | ANISOU 563 CA ASP A 223 5875 4820 6600 −2053 179 350 C |
| ATOM 519 CG ASN A 218 184.624 31.638 12.434 1.00 43.16 C | ATOM 564 CB ASP A 223 188.658 47.023 3.167 1.00 49.29 C |
| ANISOU 519 CG ASN A 218 5037 5628 5732 −541 −37 104 C | ANISOU 564 CB ASP A 223 6070 5285 7373 −2227 443 500 C |
| ATOM 520 OD1 ASN A 218 185.804 31.820 12.727 1.00 48.51 O | ATOM 565 CG ASP A 223 189.242 48.385 2.833 1.00 61.44 C |
| ANISOU 520 OD1 ASN A 218 5584 6193 6656 −626 −194 97 O | ANISOU 565 CG ASP A 223 7587 6660 9096 −2421 307 618 C |

TABLE 8-continued

DMXAA-hSTING$^{S162A/Q266I}$ complex

| | |
|---|---|
| ATOM 521 ND2 ASN A 218 183.899 30.684 12.973 1.00 41.31 N | ATOM 566 OD1 ASP A 223 188.687 49.357 3.372 1.00 66.54 O |
| ANISOU 521 ND2 ASN A 218 4844 5482 5369 −441 −56 152 N | ANISOU 566 OD1 ASP A 223 8481 7205 9595 −2411 8 555 O |
| ATOM 522 C ASN A 218 183.845 34.920 10.606 1.00 41.71 C | ATOM 567 OD2 ASP A 223 190.216 48.487 2.044 1.00 66.63 O |
| ANISOU 522 C ASN A 218 5151 5370 5328 −671 222 48 C | ANISOU 567 OD2 ASP A 223 7994 7276 10044 −2570 517 784 O |
| ATOM 523 O ASN A 218 184.177 34.577 9.470 1.00 38.32 O | ATOM 568 C ASP A 223 186.257 47.593 3.627 1.00 40.46 C |
| ANISOU 523 O ASN A 218 4586 4950 5023 −753 401 52 O | ANISOU 568 C ASP A 223 5504 4222 5646 −2001 274 315 C |
| ATOM 524 N ILE A 219 183.198 36.047 10.848 1.00 40.26 N | ATOM 569 O ASP A 223 185.325 46.834 3.459 1.00 43.19 O |
| ANISOU 524 N ILE A 219 5182 5152 4964 −630 191 43 N | ANISOU 569 O ASP A 223 5932 4694 5783 −1878 415 275 O |
| ATOM 525 CA ILE A 219 182.997 37.058 9.819 1.00 38.43 C | ATOM 570 N LYS A 224 186.214 48.854 3.237 1.00 47.58 N |
| ANISOU 525 CA ILE A 219 4994 4886 4721 −712 307 46 C | ANISOU 570 N LYS A 224 6522 5001 6556 −2114 176 363 N |
| ATOM 526 CB ILE A 219 181.509 37.271 9.523 1.00 37.87 C | ATOM 571 CA LYS A 224 185.067 49.374 2.507 1.00 53.26 C |
| ANISOU 526 CB ILE A 219 5059 4880 4450 −613 426 122 C | ANISOU 571 CA LYS A 224 7456 5733 7047 −2098 254 376 C |
| ATOM 527 CG1 ILE A 219 180.874 36.011 8.972 1.00 37.84 C | ATOM 572 CB LYS A 224 184.726 50.788 2.972 1.00 58.17 C |
| ANISOU 527 CG1 ILE A 219 4953 4985 4437 −599 532 202 C | ANISOU 572 CB LYS A 224 8288 6175 7638 −2091 −11 360 C |
| ATOM 528 CD1 ILE A 219 179.336 36.066 8.988 1.00 38.26 C | ATOM 573 CG LYS A 224 184.207 50.835 4.397 1.00 66.42 C |
| ANISOU 528 CD1 ILE A 219 5085 5088 4364 −488 584 349 C | ANISOU 573 CG LYS A 224 9518 7158 8561 −1867 −212 240 C |
| ATOM 529 CG2 ILE A 219 181.298 38.356 8.513 1.00 36.09 C | ATOM 574 CD LYS A 224 182.890 51.563 4.482 1.00 70.47 C |
| ANISOU 529 CG2 ILE A 219 4896 4598 4219 −710 499 139 C | ANISOU 574 CD LYS A 224 10286 7602 8888 −1710 −223 230 C |
| ATOM 530 C ILE A 219 183.581 38.359 10.344 1.00 42.50 C | ATOM 575 CE LYS A 224 182.288 51.446 5.875 1.00 74.74 C |
| ANISOU 530 C ILE A 219 5640 5255 5254 −761 127 −4 C | ANISOU 575 CE LYS A 224 11042 8085 9270 −1438 −304 123 C |
| ATOM 531 O ILE A 219 183.030 38.942 11.266 1.00 47.93 O | ATOM 576 NZ LYS A 224 181.414 50.237 6.022 1.00 78.08 N |
| ANISOU 531 O ILE A 219 6577 5886 5748 −646 26 −24 O | ANISOU 576 NZ LYS A 224 11380 8702 9585 −1256 −94 137 N |
| ATOM 532 N ARG A 220 184.711 38.784 9.784 1.00 40.51 N | ATOM 577 C LYS A 224 185.374 49.394 1.029 1.00 56.63 C |
| ANISOU 532 N ARG A 220 5236 4918 5240 −927 94 −8 N | ANISOU 577 C LYS A 224 7834 6186 7498 −2286 512 487 C |
| ATOM 533 CA ARG A 220 185.372 40.016 10.182 1.00 44.61 C | ATOM 578 O LYS A 224 186.522 49.525 0.633 1.00 64.42 O |
| ANISOU 533 CA ARG A 220 5856 5267 5828 −1019 −128 −27 C | ANISOU 578 O LYS A 224 8638 7127 8711 −2436 606 571 O |
| ATOM 534 CB ARG A 220 186.836 39.782 10.523 1.00 48.60 C | ATOM 579 N LEU A 225 184.337 49.269 0.215 1.00 49.72 N |
| ANISOU 534 CB ARG A 220 6130 5663 6672 −1155 −332 15 C | ANISOU 579 N LEU A 225 4801 5833 8256 −365 527 1010 N |
| ATOM 535 CG ARG A 220 187.091 39.039 11.809 1.00 60.63 C | ATOM 580 CA LEU A 225 184.433 49.552 −1.223 1.00 52.36 C |
| ANISOU 535 CG ARG A 220 7698 7151 8186 −1094 −587 7 C | ANISOU 580 CA LEU A 225 5104 6215 8573 −333 708 1222 C |
| ATOM 536 CD ARG A 220 188.144 37.951 11.572 1.00 67.11 C | ATOM 581 CB LEU A 225 183.189 49.046 −1.950 1.00 47.89 C |
| ANISOU 536 CD ARG A 220 8126 7994 9399 −1165 −560 87 C | ANISOU 581 CB LEU A 225 4694 5789 7715 −257 744 1262 C |
| ATOM 537 NE ARG A 220 189.254 37.955 12.525 1.00 67.76 N | ATOM 582 CG LEU A 225 183.139 47.597 −2.374 1.00 41.47 C |
| ANISOU 537 NE ARG A 220 8113 7891 9742 −1274 −959 162 N | ANISOU 582 CG LEU A 225 3963 5144 6651 −189 756 1212 C |
| ATOM 538 CZ ARG A 220 190.536 37.896 12.175 1.00 69.11 C | ATOM 583 CD1 LEU A 225 181.944 47.427 −3.271 1.00 39.36 C |
| ANISOU 538 CZ ARG A 220 7901 7952 10405 −1424 −1021 299 C | ANISOU 583 CD1 LEU A 225 3803 5001 6153 −116 808 1263 C |
| ATOM 539 NH1 ARG A 220 191.476 37.899 13.116 1.00 77.92 N | ATOM 584 CD2 LEU A 225 184.417 47.246 −3.091 1.00 44.24 C |
| ANISOU 539 NH1 ARG A 220 8940 8878 11790 −1541 −1461 405 N | ANISOU 584 CD2 LEU A 225 4208 5544 7056 −162 865 1307 C |
| ATOM 540 NH2 ARG A 220 190.882 37.833 10.890 1.00 62.23 N | ATOM 585 C LEU A 225 184.547 51.046 −1.496 1.00 53.26 C |
| ANISOU 540 NH2 ARG A 220 6738 7139 9768 −1458 −642 355 N | ANISOU 585 C LEU A 225 5114 6175 8946 −382 788 1353 C |
| ATOM 586 O LEU A 225 184.123 51.853 −0.680 1.00 57.16 O | ATOM 631 N ARG A 232 170.259 61.057 −8.616 1.00 80.13 N |
| ANISOU 586 O LEU A 225 5606 6540 9573 −434 694 1274 O | ANISOU 631 N ARG A 232 9479 10116 10852 1012 1610 2888 N |
| ATOM 587 N PRO A 226 185.105 51.424 −2.659 1.00 60.76 N | ATOM 632 CA ARG A 232 168.967 60.531 −8.988 1.00 72.26 C |
| ANISOU 587 N PRO A 226 5980 7135 9972 −354 972 1562 N | ANISOU 632 CA ARG A 232 8561 9413 9483 1149 1521 2779 C |
| ATOM 588 CA PRO A 226 185.086 52.856 −2.996 1.00 62.43 C | ATOM 633 CB ARG A 232 169.026 59.020 −8.882 1.00 72.82 C |
| ANISOU 588 CA PRO A 226 6108 7185 10428 −387 1081 1716 C | ANISOU 633 CB ARG A 232 8624 9666 9380 1077 1383 2546 C |
| ATOM 589 CB PRO A 226 185.830 52.927 −4.326 1.00 60.37 C | ATOM 634 CG ARG A 232 168.592 58.275 −10.091 1.00 78.81 C |
| ANISOU 589 CB PRO A 226 5759 6979 10199 −326 1303 1957 C | ANISOU 634 CG ARG A 232 9389 10761 9795 1274 1427 2550 C |
| ATOM 590 CG PRO A 226 185.745 51.531 −4.897 1.00 59.96 C | ATOM 635 CD ARG A 232 168.649 56.800 −9.785 1.00 80.61 C |
| ANISOU 590 CG PRO A 226 5804 7163 9815 −228 1304 1934 C | ANISOU 635 CD ARG A 232 9607 11108 9913 1165 1278 2290 C |
| ATOM 591 CD PRO A 226 185.750 50.617 −3.706 1.00 61.73 C | ATOM 636 NE ARG A 232 167.968 55.961 −10.769 1.00 86.47 N |
| ANISOU 591 CD PRO A 226 6081 7407 9967 −279 1101 1676 C | ANISOU 636 NE ARG A 232 10356 12186 10314 1335 1264 2201 N |
| ATOM 592 C PRO A 226 183.647 53.319 −3.157 1.00 63.26 C | ATOM 637 CZ ARG A 232 166.650 55.912 −10.940 1.00 87.60 C |
| ANISOU 592 C PRO A 226 6352 7307 10376 −338 1068 1752 C | ANISOU 637 CZ ARG A 232 10540 12523 10223 1438 1184 2087 C |
| ATOM 593 O PRO A 226 182.759 52.576 −3.603 1.00 57.45 O | ATOM 638 NH1 ARG A 232 165.855 56.672 −10.203 1.00 88.15 N |
| ANISOU 593 O PRO A 226 5754 6746 9329 −252 1057 1744 O | ANISOU 638 NH1 ARG A 232 10657 12485 10350 1396 1119 2068 N |
| ATOM 594 N GLN A 227 183.417 54.557 −2.757 1.00 68.31 N | ATOM 639 NH2 ARG A 232 166.127 55.105 −11.856 1.00 89.07 N |
| ANISOU 594 N GLN A 227 6948 7759 11246 −395 1065 1775 N | ANISOU 639 NH2 ARG A 232 10709 13016 10117 1591 1164 1978 N |
| ATOM 595 CA GLN A 227 182.078 55.090 −2.654 1.00 65.90 C | ATOM 640 C ARG A 232 167.988 61.035 −7.954 1.00 67.72 C |
| ANISOU 595 CA GLN A 227 6768 7447 10825 −358 1023 1776 C | ANISOU 640 C ARG A 232 8052 8738 8939 1077 1371 2642 C |
| ATOM 596 CB GLN A 227 182.123 56.367 −1.830 1.00 66.47 C | ATOM 641 O ARG A 232 168.386 61.408 −6.845 1.00 68.33 O |
| ANISOU 596 CB GLN A 227 6764 7274 11216 −449 973 1730 C | ANISOU 641 O ARG A 232 8114 8557 9293 899 1291 2563 O |
| ATOM 597 CG GLN A 227 182.686 56.144 −0.471 1.00 67.98 C | ATOM 642 N ALA A 233 166.705 61.003 −8.287 1.00 57.64 N |
| ANISOU 597 CG GLN A 227 6891 7384 11554 −543 781 1478 C | ANISOU 642 N ALA A 233 6842 7684 7374 1221 1323 2593 N |
| ATOM 598 CD GLN A 227 183.030 57.434 0.215 1.00 75.79 C | ATOM 643 CA ALA A 233 165.688 61.414 −7.331 1.00 54.38 C |
| ANISOU 598 CD GLN A 227 7475 7838 12635 −635 747 1424 C | ANISOU 643 CA ALA A 233 6493 7208 6960 1168 1178 2458 C |
| ATOM 599 OE1 GLN A 227 183.237 58.464 −0.433 1.00 75.79 O | ATOM 644 CB ALA A 233 164.323 61.289 −7.936 1.00 57.37 C |
| ANISOU 599 OE1 GLN A 227 7677 7973 13146 −652 910 1604 O | ANISOU 644 CB ALA A 233 6925 7881 6991 1355 1147 2417 C |
| ATOM 600 NE2 GLN A 227 183.081 57.396 1.538 1.00 75.81 N | ATOM 645 C ALA A 233 165.750 60.628 −6.021 1.00 56.23 C |
| ANISOU 600 NE2 GLN A 227 7744 8071 12991 −682 541 1173 N | ANISOU 645 C ALA A 233 6727 7352 7284 947 973 2189 C |
| ATOM 601 C GLN A 227 181.385 55.357 −3.989 1.00 62.96 C | ATOM 646 O ALA A 233 165.770 59.393 −6.013 1.00 62.51 O |
| ANISOU 601 C GLN A 227 6463 7185 10274 −233 1196 2004 C | ANISOU 646 O ALA A 233 7509 8296 7944 895 890 2026 O |
| ATOM 602 O GLN A 227 182.012 55.517 −5.059 1.00 56.53 O | ATOM 647 N GLY A 234 165.764 61.363 −4.907 1.00 50.91 N |
| ANISOU 602 O GLN A 227 5576 6400 9502 −173 1387 2213 O | ANISOU 647 N GLY A 234 6070 6433 6841 831 897 2144 N |
| ATOM 603 N GLN A 228 180.068 55.424 −3.891 1.00 61.54 N | ATOM 648 CA GLY A 234 165.740 60.794 −3.579 1.00 43.85 C |
| ANISOU 603 N GLN A 228 6418 7074 9890 −180 1127 1960 N | ANISOU 648 CA GLY A 234 5183 5450 6026 658 708 1906 C |
| ATOM 604 CA GLN A 228 179.244 55.806 −5.008 1.00 67.96 C | ATOM 649 C GLY A 234 167.116 60.476 −2.997 1.00 53.59 C |
| ANISOU 604 CA GLN A 228 7298 7996 10525 −44 1261 2146 C | ANISOU 649 C GLY A 234 6346 6495 7522 496 691 1863 C |

TABLE 8-continued

DMXAA-hSTING$^{S162A/Q266I}$ complex

| | |
|---|---|
| ATOM 605 CB GLN A 228 178.360 54.632 -5.427 1.00 72.12 C | ATOM 650 O GLY A 234 167.269 60.272 -1.770 1.00 52.04 O |
| ANISOU 605 CB GLN A 228 7950 8787 10667 51 1201 2058 C | ANISOU 650 O GLY A 234 6149 6176 7448 366 546 1690 O |
| ATOM 606 CG GLN A 228 177.754 54.738 -6.824 1.00 74.95 C | ATOM 651 N ILE A 235 168.134 60.411 -3.855 1.00 48.99 N |
| ANISOU 606 CG GLN A 228 8353 9331 10792 229 1350 2241 C | ANISOU 651 N ILE A 235 5696 5900 7018 517 839 2015 N |
| ATOM 607 CD GLN A 228 176.840 53.554 -7.134 1.00 74.88 C | ATOM 652 CA ILE A 235 169.476 60.148 -3.358 1.00 46.84 C |
| ANISOU 607 CD GLN A 228 8448 9574 10427 308 1262 2097 C | ANISOU 652 CA ILE A 235 5340 5456 7000 372 831 1977 C |
| ATOM 608 OE1 GLN A 228 176.901 52.518 -6.462 1.00 70.75 O | ATOM 653 CB ILE A 235 169.916 58.718 -3.667 1.00 47.15 C |
| ANISOU 608 OE1 GLN A 228 7953 9081 9847 230 1130 1897 O | ANISOU 653 CB ILE A 235 5359 5669 6885 347 807 1885 C |
| ATOM 609 NE2 GLN A 228 175.985 53.705 -8.146 1.00 75.08 N | ATOM 654 CG1 ILE A 235 169.858 58.455 -5.176 1.00 48.51 C |
| ANISOU 609 NE2 GLN A 228 8525 9780 10221 472 1339 2193 N | ANISOU 654 CG1 ILE A 235 5526 6056 6848 507 964 2048 C |
| ATOM 610 C GLN A 228 178.405 56.993 -4.546 1.00 67.50 C | ATOM 655 CD1 ILE A 235 170.676 57.243 -5.602 1.00 47.21 C |
| ANISOU 610 C GLN A 228 7280 7791 10577 -58 1232 2161 C | ANISOU 655 CD1 ILE A 235 5316 6007 6615 482 982 2002 C |
| ATOM 611 O GLN A 228 177.930 57.035 -3.397 1.00 67.53 O | ATOM 656 CG2 ILE A 235 169.078 57.733 -2.869 1.00 43.74 C |
| ANISOU 611 O GLN A 228 7327 7721 10612 -136 1054 1967 O | ANISOU 656 CG2 ILE A 235 4992 5356 6270 298 627 1645 C |
| ATOM 612 N THR A 229 178.232 57.961 -5.438 1.00 68.06 N | ATOM 657 C ILE A 235 170.521 61.124 -3.894 1.00 49.60 C |
| ANISOU 612 N THR A 229 7336 7821 10701 34 1413 2398 N | ANISOU 657 C ILE A 235 5605 5611 7629 377 1014 2201 C |
| ATOM 613 CA THR A 229 177.398 59.130 -5.144 1.00 68.55 C | ATOM 658 O ILE A 235 171.722 60.844 -3.844 1.00 49.59 O |
| ANISOU 613 CA THR A 229 7443 7748 10855 46 1412 2441 C | ANISOU 658 O ILE A 235 5513 5514 7814 286 1051 2209 O |
| ATOM 614 CB THR A 229 178.138 60.437 -5.436 1.00 72.60 C | ATOM 659 N LYS A 236 170.064 62.251 -4.432 1.00 49.16 N |
| ANISOU 614 CB THR A 229 7839 8010 11735 23 1598 2651 C | ANISOU 659 N LYS A 236 5575 5499 7606 491 1141 2389 N |
| ATOM 615 OG1 THR A 229 179.230 60.581 -4.521 1.00 74.09 O | ATOM 660 CA LYS A 236 170.982 63.228 -5.001 1.00 57.34 C |
| ANISOU 615 OG1 THR A 229 7897 7992 12261 -146 1522 2512 O | ANISOU 660 CA LYS A 236 6529 6333 8923 509 1349 2630 C |
| ATOM 616 CG2 THR A 229 177.203 61.616 -5.278 1.00 74.79 C | ATOM 661 CB LYS A 236 170.238 64.454 -5.521 1.00 60.71 C |
| ANISOU 616 CG2 THR A 229 8179 8161 12077 64 1618 2716 C | ANISOU 661 CB LYS A 236 7010 6708 9348 659 1484 2833 C |
| ATOM 617 C THR A 229 176.099 59.099 -5.947 1.00 65.14 C | ATOM 662 CG LYS A 236 170.823 64.993 -6.790 1.00 69.34 C |
| ANISOU 617 C THR A 229 7140 7527 10084 218 1452 2525 C | ANISOU 662 CG LYS A 236 8055 7786 10505 795 1762 3150 C |
| ATOM 618 O THR A 229 176.119 58.778 -7.138 1.00 59.32 O | ATOM 663 CD LYS A 236 169.883 64.721 -7.950 1.00 80.28 C |
| ANISOU 618 O THR A 229 6410 6974 9156 362 1594 2684 O | ANISOU 663 CD LYS A 236 9522 9502 11480 1042 1840 3264 C |
| ATOM 619 N GLY A 230 174.981 59.419 -5.289 1.00 68.21 N | ATOM 664 CE LYS A 236 170.597 64.863 -9.296 1.00 87.79 C |
| ANISOU 619 N GLY A 230 7621 7904 10391 215 1322 2409 N | ANISOU 664 CE LYS A 236 10402 10556 12399 1190 2051 3435 C |
| ATOM 620 CA GLY A 230 173.667 59.369 -5.907 1.00 68.15 C | ATOM 665 NZ LYS A 236 169.649 64.836 -10.453 1.00 90.14 N |
| ANISOU 620 CA GLY A 230 7728 8106 10062 371 1328 2446 C | ANISOU 665 NZ LYS A 236 10765 11165 12321 1463 2126 3525 N |
| ATOM 621 C GLY A 230 173.418 60.605 -6.758 1.00 73.08 C | ATOM 666 C LYS A 236 172.033 63.657 -3.966 1.00 61.62 C |
| ANISOU 621 C GLY A 230 8352 8672 10742 509 1527 2716 C | ANISOU 666 C LYS A 236 6971 6568 9874 313 1292 2535 C |
| ATOM 622 O GLY A 230 173.611 61.736 -6.312 1.00 68.15 O | ATOM 667 O LYS A 236 171.682 64.100 -2.859 1.00 60.83 O |
| ANISOU 622 O GLY A 230 7693 7793 10407 451 1571 2787 O | ANISOU 667 O LYS A 236 6892 6323 9897 229 1141 2373 O |
| ATOM 623 N ASP A 231 173.008 60.387 -8.002 1.00 83.59 N | ATOM 668 N ASP A 237 173.309 63.507 -4.339 1.00 62.20 N |
| ANISOU 623 N ASP A 231 9720 10242 11799 706 1653 2866 N | ANISOU 668 N ASP A 237 6930 6558 10146 254 1408 2625 N |
| ATOM 624 CA ASP A 231 172.624 61.482 -8.893 1.00 92.32 C | ATOM 669 CA ASP A 237 174.464 63.799 -3.476 1.00 65.66 C |
| ANISOU 624 CA ASP A 231 10845 11342 12890 888 1852 3137 C | ANISOU 669 CA ASP A 237 7240 6732 10976 73 1361 2523 C |
| ATOM 625 CB ASP A 231 173.674 61.689 -9.993 1.00 103.54 C | ATOM 670 CB ASP A 237 174.521 65.290 -3.125 1.00 74.50 C |
| ANISOU 625 CB ASP A 231 12176 12771 14392 989 2065 3342 C | ANISOU 670 CB ASP A 237 8316 7559 12433 41 1419 2574 C |
| ATOM 626 CG ASP A 231 173.926 60.426 -10.831 1.00 109.80 C | ATOM 671 CG ASP A 237 174.971 66.159 -4.307 1.00 84.88 C |
| ANISOU 626 CG ASP A 231 12963 13854 14902 1086 2080 3331 C | ANISOU 671 CG ASP A 237 9574 8854 13822 157 1665 2794 C |
| ATOM 627 OD1 ASP A 231 173.472 59.327 -10.423 1.00 110.93 O | ATOM 672 OD2 ASP A 237 174.134 66.965 -4.794 1.00 86.07 O |
| ANISOU 627 OD1 ASP A 231 13153 14155 14841 1028 1912 3123 O | ANISOU 672 OD2 ASP A 237 9801 9019 13883 289 1760 2924 O |
| ATOM 628 OD2 ASP A 231 174.587 60.549 -11.895 1.00 112.19 O | ATOM 673 OD1 ASP A 237 176.149 66.022 -4.740 1.00 88.75 O |
| ANISOU 628 OD2 ASP A 231 13210 14225 15192 1227 2207 3464 O | ANISOU 673 OD1 ASP A 237 9946 9320 14456 125 1762 2836 O |
| ATOM 629 C ASP A 231 171.245 61.192 -9.492 1.00 88.71 C | ATOM 674 C ASP A 237 174.579 62.945 -2.203 1.00 64.36 C |
| ANISOU 629 C ASP A 231 10494 11187 12026 1081 1808 3106 C | ANISOU 674 C ASP A 237 7076 6593 10786 -58 1103 2208 C |
| ATOM 630 O ASP A 231 171.078 61.085 -10.704 1.00 91.37 O | ATOM 675 O ASP A 237 175.279 63.313 -1.264 1.00 62.37 O |
| ANISOU 630 O ASP A 231 10840 11747 12131 1296 1947 3265 O | ANISOU 675 O ASP A 237 6731 6131 10835 -189 1014 2071 O |
| ATOM 676 N ARG A 238 173.883 61.812 -2.180 1.00 63.93 N | ATOM 721 CA SER A 243 181.688 46.703 3.310 1.00 38.08 C |
| ANISOU 676 N ARG A 238 7118 6796 10376 -12 988 2092 N | ANISOU 721 CA SER A 243 3762 4501 6205 -253 145 522 C |
| ATOM 677 CA ARG A 238 173.946 60.878 -1.062 1.00 57.81 C | ATOM 722 CB SER A 243 181.245 46.539 4.759 1.00 44.38 C |
| ANISOU 677 CA ARG A 238 6356 6070 9539 -107 773 1824 C | ANISOU 722 CB SER A 243 4623 5270 6969 -220 7 371 C |
| ATOM 678 CB ARG A 238 172.667 60.056 -0.996 1.00 51.32 C | ATOM 723 OG SER A 243 181.128 47.785 5.403 1.00 53.30 O |
| ANISOU 678 CB ARG A 238 5669 5486 8344 -33 667 1722 C | ANISOU 723 OG SER A 243 5693 6294 8263 -251 -83 331 O |
| ATOM 679 CG ARG A 238 172.590 59.093 0.175 1.00 46.30 C | ATOM 724 C SER A 243 182.126 45.371 2.747 1.00 36.00 C |
| ANISOU 679 CG ARG A 238 5063 4901 7629 -109 466 1470 C | ANISOU 724 C SER A 243 3535 4346 5798 -209 222 535 C |
| ATOM 680 CD ARG A 238 171.246 59.283 0.800 1.00 51.91 C | ATOM 725 O SER A 243 181.309 44.574 2.285 1.00 32.42 O |
| ANISOU 680 CD ARG A 238 5881 5661 8324 -68 348 1370 C | ANISOU 725 O SER A 243 3189 3969 5158 -182 267 537 O |
| ATOM 681 NE ARG A 238 170.476 58.060 0.876 1.00 54.99 N | ATOM 726 N ILE A 244 183.428 45.119 2.827 1.00 35.98 N |
| ANISOU 681 NE ARG A 238 6351 6267 8275 -40 273 1257 N | ANISOU 726 N ILE A 244 3432 4345 5892 -201 230 527 N |
| ATOM 682 CZ ARG A 238 169.219 58.003 1.289 1.00 49.90 C | ATOM 727 CA ILE A 244 183.976 43.836 2.440 1.00 35.60 C |
| ANISOU 682 CZ ARG A 238 5796 5711 7453 3 185 1173 C | ANISOU 727 CA ILE A 244 3415 4392 5720 -148 292 526 C |
| ATOM 683 NH1 ARG A 238 168.585 59.125 1.653 1.00 43.26 N | ATOM 728 CB ILE A 244 185.205 44.028 1.575 1.00 37.60 C |
| ANISOU 683 NH1 ARG A 238 4985 4769 6682 33 156 1195 N | ANISOU 728 CB ILE A 244 3532 4667 6087 -159 382 627 C |
| ATOM 684 NH2 ARG A 238 168.618 56.818 1.334 1.00 48.41 N | ATOM 729 CG1 ILE A 244 184.847 44.936 0.409 1.00 36.47 C |
| ANISOU 684 NH2 ARG A 238 5660 5701 7031 14 134 1068 N | ANISOU 729 CG1 ILE A 244 3352 4518 5988 -193 485 782 C |
| ATOM 685 C ARG A 238 175.135 59.943 -1.256 1.00 58.98 C | ATOM 730 CD1 ILE A 244 186.053 45.305 -0.425 1.00 40.22 C |
| ANISOU 685 C ARG A 238 6417 6268 9726 -165 798 1802 C | ANISOU 730 CD1 ILE A 244 3678 4997 6605 -201 593 909 C |
| ATOM 686 O ARG A 238 175.433 59.523 -2.379 1.00 61.86 O | ATOM 731 CG2 ILE A 244 185.686 42.713 1.009 1.00 31.42 C |
| ANISOU 686 O ARG A 238 6768 6760 9976 -95 946 1959 O | ANISOU 731 CG2 ILE A 244 2789 3992 5155 -95 456 636 C |
| ATOM 687 N VAL A 239 175.821 59.603 -0.169 1.00 54.77 N | ATOM 732 C ILE A 244 184.293 43.056 3.696 1.00 36.97 C |
| ANISOU 687 N VAL A 239 5823 5647 9340 -274 654 1606 N | ANISOU 732 C ILE A 244 3626 4567 5853 -90 199 390 C |
| ATOM 688 CA VAL A 239 176.994 58.750 -0.305 1.00 53.85 C | ATOM 733 O ILE A 244 184.788 43.619 4.662 1.00 46.78 O |
| ANISOU 688 CA VAL A 239 5617 5573 9269 -324 675 1581 C | ANISOU 733 O ILE A 244 4794 5756 7225 -87 98 312 O |

TABLE 8-continued

DMXAA-hSTING$^{S162A/Q266I}$ complex

| | |
|---|---|
| ATOM 689 CB VAL A 239 178.221 59.402 0.292 1.00 50.09 C | ATOM 734 N TYR A 245 183.975 41.772 3.688 1.00 31.91 N |
| ANISOU 689 CB VAL A 239 4980 4867 9184 −435 664 1528 C | ANISOU 734 N TYR A 245 3102 3987 5036 −33 237 358 N |
| ATOM 690 CG1 VAL A 239 179.400 58.444 0.191 1.00 44.19 C | ATOM 735 CA TYR A 245 184.223 40.912 4.837 1.00 33.02 C |
| ANISOU 690 CG1 VAL A 239 4143 4189 8458 −476 675 1491 C | ANISOU 735 CA TYR A 245 3298 4134 5115 50 178 255 C |
| ATOM 691 CG2 VAL A 239 178.503 60.719 −0.469 1.00 44.58 C | ATOM 736 CB TYR A 245 182.900 40.422 5.432 1.00 32.35 C |
| ANISOU 691 CG2 VAL A 239 4201 3980 8759 −434 862 1753 C | ANISOU 736 CB TYR A 245 3363 4031 4898 75 163 204 C |
| ATOM 692 C VAL A 239 176.792 57.349 0.252 1.00 53.32 C | ATOM 737 CG TYR A 245 182.085 41.533 6.035 1.00 33.04 C |
| ANISOU 692 C VAL A 239 5623 5685 8953 −325 531 1397 C | ANISOU 737 CG TYR A 245 3449 4059 5044 39 73 179 C |
| ATOM 693 O VAL A 239 176.536 57.199 1.441 1.00 53.63 O | ATOM 738 CD1 TYR A 245 181.179 42.267 5.257 1.00 36.26 C |
| ANISOU 693 O VAL A 239 5691 5690 8996 −361 359 1202 O | ANISOU 738 CD1 TYR A 245 3867 4453 5457 −38 101 241 C |
| ATOM 694 N TYR A 240 176.852 56.347 −0.640 1.00 53.62 N | ATOM 739 CE1 TYR A 245 180.451 43.321 5.807 1.00 40.76 C |
| ANISOU 694 N TYR A 240 5692 5912 8770 −268 611 1465 N | ANISOU 739 CE1 TYR A 245 4436 4965 6083 −65 19 219 C |
| ATOM 695 CA TYR A 240 176.723 54.920 −0.286 1.00 46.69 C | ATOM 740 CZ TYR A 245 180.627 43.627 7.159 1.00 40.60 C |
| ANISOU 695 CA TYR A 240 4879 5195 7666 −264 512 1313 C | ANISOU 740 CZ TYR A 245 4406 4908 6114 −13 −99 124 C |
| ATOM 696 CB TYR A 240 175.832 54.173 −1.290 1.00 41.59 C | ATOM 741 OH TYR A 245 179.933 44.650 7.744 1.00 43.41 O |
| ANISOU 696 CB TYR A 240 4329 4770 6702 −166 576 1371 C | ANISOU 741 OH TYR A 245 4762 5209 6524 −28 −187 90 O |
| ATOM 697 CG TYR A 240 174.355 54.473 −1.144 1.00 40.56 C | ATOM 742 CE2 TYR A 245 181.514 42.910 7.944 1.00 40.21 C |
| ANISOU 697 CG TYR A 240 4306 4698 6407 −117 519 1335 C | ANISOU 742 CE2 TYR A 245 4342 4886 6050 75 −133 56 C |
| ATOM 698 CD1 TYR A 240 173.611 53.854 −0.149 1.00 30.59 C | ATOM 743 CD2 TYR A 245 182.244 41.872 7.372 1.00 36.38 C |
| ANISOU 698 CD1 TYR A 240 3123 3472 5029 −143 370 1149 C | ANISOU 743 CD2 TYR A 245 3858 4453 5510 98 −44 89 C |
| ATOM 699 CE1 TYR A 240 172.277 54.121 0.008 1.00 34.17 C | ATOM 744 C TYR A 245 185.116 39.708 4.535 1.00 41.92 C |
| ANISOU 699 CE1 TYR A 240 3661 3981 5340 −100 320 1114 C | ANISOU 744 C TYR A 245 4432 5326 6170 116 249 259 C |
| ATOM 700 CZ TYR A 240 171.670 55.064 −0.817 1.00 41.88 C | ATOM 745 O TYR A 245 185.195 39.211 3.410 1.00 41.03 O |
| ANISOU 700 CZ TYR A 240 4650 4979 6284 −24 409 1261 C | ANISOU 745 O TYR A 245 4330 5262 5996 104 350 324 O |
| ATOM 701 OH TYR A 240 170.345 55.362 −0.649 1.00 44.82 O | ATOM 746 N GLU A 246 185.779 39.249 5.587 1.00 43.49 N |
| ANISOU 701 OH TYR A 240 5102 5415 6515 25 355 1222 O | ANISOU 746 N GLU A 246 4625 5534 6365 205 189 181 N |
| ATOM 702 CE2 TYR A 240 172.378 55.713 −1.819 1.00 41.64 C | ATOM 747 CA GLU A 246 186.558 38.040 5.574 1.00 32.25 C |
| ANISOU 702 CE2 TYR A 240 4552 4911 6359 17 564 1457 C | ANISOU 747 CA GLU A 246 3229 4166 4857 295 246 172 C |
| ATOM 703 CD2 TYR A 240 173.718 55.417 −1.973 1.00 40.00 C | ATOM 748 CB GLU A 246 187.702 38.267 6.524 1.00 41.94 C |
| ANISOU 703 CD2 TYR A 240 4253 4642 6303 −34 622 1496 C | ANISOU 748 CB GLU A 246 4349 5420 6166 371 152 101 C |
| ATOM 704 C TYR A 240 178.084 54.239 −0.291 1.00 54.08 C | ATOM 749 CG GLU A 246 188.957 37.513 6.238 1.00 52.80 C |
| ANISOU 704 C TYR A 240 5717 6128 8702 −309 534 1291 C | ANISOU 749 CG GLU A 246 5667 6869 7527 441 200 111 C |
| ATOM 705 O TYR A 240 178.884 54.421 −1.215 1.00 62.56 O | ATOM 750 CD GLU A 246 190.093 37.923 7.205 1.00 61.18 C |
| ANISOU 705 O TYR A 240 6706 7196 9866 −296 682 1448 O | ANISOU 750 CD GLU A 246 6588 7970 8688 515 85 17 C |
| ATOM 706 N SER A 241 178.368 53.463 0.736 1.00 54.06 N | ATOM 751 OE1 GLU A 246 191.279 37.631 6.885 1.00 61.76 O |
| ANISOU 706 N SER A 241 5724 6134 8681 −346 397 1106 N | ANISOU 751 OE1 GLU A 246 6559 8109 8709 799 550 111 24 O |
| ATOM 707 CA SER A 241 179.548 52.619 0.685 1.00 61.88 C | ATOM 752 OE2 GLU A 246 189.779 38.536 8.276 1.00 61.68 O |
| ANISOU 707 CA SER A 241 6641 7163 9707 −365 415 1078 C | ANISOU 752 OE2 GLU A 246 6638 8009 8788 546 −35 −75 O |
| ATOM 708 CB SER A 241 180.555 53.018 1.766 1.00 71.91 C | ATOM 753 C GLU A 246 185.664 36.943 6.146 1.00 37.40 C |
| ANISOU 708 CB SER A 241 7794 8287 11243 −436 315 955 C | ANISOU 753 C GLU A 246 4052 4800 5358 366 281 135 C |
| ATOM 709 OG SER A 241 179.905 53.208 3.013 1.00 77.21 O | ATOM 754 O GLU A 246 184.950 37.161 7.120 1.00 40.60 O |
| ANISOU 709 OG SER A 241 8523 8911 11903 −440 150 786 O | ANISOU 754 O GLU A 246 4516 5167 5744 395 219 88 O |
| ATOM 710 C SER A 241 179.078 51.196 0.898 1.00 56.59 C | ATOM 755 N LEU A 247 185.674 35.762 5.542 1.00 36.83 N |
| ANISOU 710 C SER A 241 6083 6651 8767 −324 355 966 C | ANISOU 755 N LEU A 247 4058 4747 5188 397 390 157 N |
| ATOM 711 O SER A 241 177.921 50.973 1.230 1.00 56.74 O | ATOM 756 CA LEU A 247 185.000 34.614 6.123 1.00 31.28 C |
| ANISOU 711 O SER A 241 6214 6723 8622 −299 290 898 O | ANISOU 756 CA LEU A 247 3505 4005 4376 471 448 124 C |
| ATOM 712 N ASN A 242 179.984 50.242 0.731 1.00 50.25 N | ATOM 757 CB LEU A 247 184.104 33.961 5.097 1.00 34.20 C |
| ANISOU 712 N ASN A 242 5244 5913 7935 −318 381 946 N | ANISOU 757 CB LEU A 247 3954 4354 4686 405 552 136 C |
| ATOM 713 CA ASN A 242 179.691 48.856 1.008 1.00 43.74 C | ATOM 758 CG LEU A 247 183.099 34.920 4.470 1.00 38.29 C |
| ANISOU 713 CA ASN A 242 4515 5207 6897 −283 335 836 C | ANISOU 758 CG LEU A 247 4448 4867 5232 287 524 150 C |
| ATOM 714 CB ASN A 242 179.417 48.103 −0.283 1.00 49.20 C | ATOM 759 CD1 LEU A 247 182.364 34.190 3.395 1.00 44.84 C |
| ANISOU 714 CB ASN A 242 5252 6050 7392 −226 451 921 C | ANISOU 759 CD1 LEU A 247 5336 5707 5996 245 618 135 C |
| ATOM 715 CG ASN A 242 178.136 48.561 −0.964 1.00 54.41 C | ATOM 760 CD2 LEU A 247 182.117 35.418 5.501 1.00 38.58 C |
| ANISOU 715 CG ASN A 242 5982 6773 7919 −187 489 984 C | ANISOU 760 CD2 LEU A 247 4536 4846 5276 280 459 120 C |
| ATOM 716 OD1 ASN A 242 178.039 49.705 −1.430 1.00 62.64 O | ATOM 761 C LEU A 247 186.032 33.610 6.615 1.00 40.39 C |
| ANISOU 716 OD1 ASN A 242 6981 7763 9058 −181 548 1111 O | ANISOU 761 C LEU A 247 4677 5190 5480 609 482 112 C |
| ATOM 717 ND2 ASN A 242 177.139 47.668 −1.017 1.00 45.05 N | ATOM 762 O LEU A 247 186.896 33.175 5.847 1.00 44.71 O |
| ANISOU 717 ND2 ASN A 242 4899 5698 6520 −156 459 892 N | ANISOU 762 O LEU A 247 5179 5786 6023 620 535 137 O |
| ATOM 718 C ASN A 242 180.876 48.243 1.690 1.00 46.66 C | ATOM 763 N LEU A 248 185.934 33.235 7.889 1.00 38.75 N |
| ANISOU 718 C ASN A 242 4820 5555 7353 −296 286 748 C | ANISOU 763 N LEU A 248 4538 4963 5223 731 458 79 N |
| ATOM 719 O ASN A 242 182.015 48.646 1.470 1.00 55.03 O | ATOM 764 CA LEU A 248 186.919 32.339 8.478 1.00 39.41 C |
| ANISOU 719 O ASN A 242 5752 6563 8596 −323 330 802 O | ANISOU 764 CA LEU A 248 4641 5088 5246 893 487 72 C |
| ATOM 720 N SER A 243 180.620 47.248 2.514 1.00 42.16 N | ATOM 765 CB LEU A 248 187.325 32.784 9.885 1.00 36.66 C |
| ANISOU 720 N SER A 243 4335 5031 6655 −266 205 615 N | ANISOU 765 CB LEU A 248 4256 4786 4886 1031 372 21 C |
| ATOM 766 CG LEU A 248 187.850 34.205 10.062 1.00 40.38 C | ATOM 811 O ARG A 253 190.954 31.576 4.122 1.00 47.33 O |
| ANISOU 766 CG LEU A 248 4560 5308 5476 974 216 −36 C | ANISOU 811 O ARG A 253 5295 6363 6324 813 675 212 O |
| ATOM 767 CD1 LEU A 248 188.338 34.337 11.509 1.00 44.76 C | ATOM 812 N ALA A 254 188.816 32.095 4.409 1.00 47.77 N |
| ANISOU 767 CD1 LEU A 248 5087 5930 5989 1159 106 −116 C | ANISOU 812 N ALA A 254 5482 6292 6378 688 652 189 N |
| ATOM 768 CD2 LEU A 248 188.994 34.498 9.096 1.00 34.68 C | ATOM 813 CA ALA A 254 188.299 31.058 3.532 1.00 45.10 C |
| ANISOU 768 CD2 LEU A 248 3690 4638 4847 903 214 −22 C | ANISOU 813 CA ALA A 254 5246 5930 5959 681 768 190 C |
| ATOM 769 C LEU A 248 186.421 30.915 8.537 1.00 41.46 C | ATOM 814 CB ALA A 254 187.364 30.145 4.344 1.00 33.43 C |
| ANISOU 769 C LEU A 248 5058 5280 5415 966 633 96 C | ANISOU 814 CB ALA A 254 3926 4352 4423 732 817 147 C |
| ATOM 770 O LEU A 248 185.251 30.658 8.804 1.00 43.27 O | ATOM 815 C ALA A 254 187.549 31.655 2.333 1.00 48.17 C |
| ANISOU 770 O LEU A 248 5389 5425 5626 940 684 100 O | ANISOU 815 C ALA A 254 5603 6335 6365 554 782 215 C |
| ATOM 771 N GLU A 249 187.344 29.995 8.314 1.00 43.16 N | ATOM 816 O ALA A 254 187.140 30.987 1.427 1.00 51.69 O |
| ANISOU 771 N GLU A 249 5285 5526 5587 1060 704 110 N | ANISOU 816 O ALA A 254 6102 6787 6748 543 862 198 O |
| ATOM 772 CA GLU A 249 187.132 28.586 8.557 1.00 41.96 C | ATOM 817 N GLY A 255 187.352 32.999 2.359 1.00 48.58 N |
| ANISOU 772 CA GLU A 249 5277 5303 5364 1167 847 132 C | ANISOU 817 N GLY A 255 5567 6393 6499 471 705 246 N |

TABLE 8-continued

DMXAA-hSTING$^{S162A/Q266I}$ complex

| | |
|---|---|
| ATOM 773 CB GLU A 249 187.012 27.831 7.242 1.00 43.73 C | ATOM 818 CA GLY A 255 186.634 33.712 1.312 1.00 49.97 C |
| ANISOU 773 CB GLU A 249 5531 5486 5598 1078 958 133 C | ANISOU 818 CA GLY A 255 5712 6592 6684 375 719 285 C |
| ATOM 774 CG GLU A 249 186.039 26.692 7.244 1.00 53.18 C | ATOM 819 C GLY A 255 186.546 35.188 1.666 1.00 50.63 C |
| ANISOU 774 CG GLU A 249 6872 6545 6786 1082 1106 130 C | ANISOU 819 C GLY A 255 5701 6653 6882 303 631 322 C |
| ATOM 775 CD GLU A 249 185.737 26.187 5.822 1.00 67.77 C | ATOM 820 O GLY A 255 186.704 35.562 2.835 1.00 48.70 O |
| ANISOU 775 CD GLU A 249 8723 8365 8661 965 1179 89 C | ANISOU 820 O GLY A 255 5443 6364 6697 320 547 284 O |
| ATOM 776 OE1 GLU A 249 186.693 25.916 5.054 1.00 75.01 O | ATOM 821 N THR A 256 186.315 36.017 0.652 1.00 54.30 N |
| ANISOU 776 OE1 GLU A 249 9591 9355 9556 990 1190 90 O | ANISOU 821 N THR A 256 6101 7155 7377 238 654 394 N |
| ATOM 777 OE2 GLU A 249 184.541 26.070 5.466 1.00 73.89 O | ATOM 822 CA THR A 256 186.234 37.472 0.809 1.00 54.70 C |
| ANISOU 777 OE2 GLU A 249 9541 9058 9476 858 1222 48 O | ANISOU 822 CA THR A 256 6058 7170 7557 165 594 445 C |
| ATOM 778 C GLU A 249 188.389 28.180 9.300 1.00 43.37 C | ATOM 823 CB THR A 256 187.467 38.169 0.261 1.00 54.57 C |
| ANISOU 778 C GLU A 249 5433 5565 5479 1364 831 138 C | ANISOU 823 CB THR A 256 5882 7189 7665 155 622 537 C |
| ATOM 779 O GLU A 249 189.525 28.431 8.849 1.00 38.87 O | ATOM 824 OG1 THR A 256 188.616 37.712 0.968 1.00 66.88 O |
| ANISOU 779 O GLU A 249 4748 5093 4926 1371 779 126 O | ANISOU 824 OG1 THR A 256 7387 8756 9267 211 591 492 O |
| ATOM 780 N ASN A 250 188.190 27.571 10.456 1.00 45.70 N | ATOM 825 CG2 THR A 256 187.349 39.658 0.452 1.00 52.31 C |
| ANISOU 780 N ASN A 250 5834 5830 5701 1536 880 159 N | ANISOU 825 CG2 THR A 256 5497 6835 7542 75 573 584 C |
| ATOM 781 CA ASN A 250 189.312 27.116 11.258 1.00 49.49 C | ATOM 826 C THR A 256 185.066 38.009 0.009 1.00 53.41 C |
| ANISOU 781 CA ASN A 250 6306 6404 6094 1762 870 164 C | ANISOU 826 C THR A 256 5928 7017 7348 112 620 483 C |
| ATOM 782 CB ASN A 250 189.997 25.907 10.597 1.00 53.24 C | ATOM 827 O THR A 256 184.992 37.781 −1.194 1.00 64.56 O |
| ANISOU 782 CB ASN A 250 6834 6862 6534 1824 1004 199 C | ANISOU 827 O THR A 256 7336 8511 8683 130 702 534 O |
| ATOM 783 CG ASN A 250 189.070 24.727 10.465 1.00 53.56 C | ATOM 828 N CYS A 257 184.163 38.746 0.636 1.00 42.89 N |
| ANISOU 783 CG ASN A 250 7045 6735 6571 1826 1194 248 C | ANISOU 828 N CYS A 257 4625 5619 6052 62 551 458 N |
| ATOM 784 OD1 ASN A 250 188.628 24.143 11.475 1.00 54.11 O | ATOM 829 CA CYS A 257 182.978 39.162 −0.107 1.00 39.87 C |
| ANISOU 784 OD1 ASN A 250 7232 6738 6588 1977 1283 299 O | ANISOU 829 CA CYS A 257 4283 5262 5604 27 575 484 C |
| ATOM 785 ND2 ASN A 250 188.730 24.385 9.211 1.00 51.11 N | ATOM 830 CB CYS A 257 181.972 38.013 −0.185 1.00 39.45 C |
| ANISOU 785 ND2 ASN A 250 6744 6352 6324 1662 1264 231 N | ANISOU 830 CB CYS A 257 4355 5230 5405 47 600 387 C |
| ATOM 786 C ASN A 250 190.345 28.218 11.522 1.00 45.83 C | ATOM 831 SG CYS A 257 181.117 37.740 1.371 1.00 62.74 S |
| ANISOU 786 C ASN A 250 5661 6095 5658 1783 686 96 C | ANISOU 831 SG CYS A 257 7405 8075 8359 35 523 285 S |
| ATOM 787 O ASN A 250 191.540 27.967 11.503 1.00 48.32 O | ATOM 832 C CYS A 257 182.291 40.402 0.442 1.00 38.97 C |
| ANISOU 787 O ASN A 250 5905 6512 5943 1889 665 79 O | ANISOU 832 C CYS A 257 4153 5076 5575 −30 502 498 C |
| ATOM 788 N GLY A 251 189.880 29.441 11.735 1.00 48.08 N | ATOM 833 O CYS A 257 182.448 40.760 1.626 1.00 37.05 O |
| ANISOU 788 N GLY A 251 5864 6390 6015 1677 555 48 N | ANISOU 833 O CYS A 257 3901 4755 5420 −42 414 447 O |
| ATOM 789 CA GLY A 251 190.762 30.549 12.083 1.00 47.56 C | ATOM 834 N VAL A 258 181.507 41.034 −0.437 1.00 31.20 N |
| ANISOU 789 CA GLY A 251 5616 6444 6010 1688 378 −38 C | ANISOU 834 N VAL A 258 3169 4132 4552 −49 538 560 N |
| ATOM 790 C GLY A 251 191.492 31.197 10.910 1.00 50.43 C | ATOM 835 CA VAL A 258 180.677 42.160 −0.057 1.00 35.87 C |
| ANISOU 790 C GLY A 251 5820 6840 6503 1516 338 −49 C | ANISOU 835 CA VAL A 258 3764 4664 5201 −93 480 576 C |
| ATOM 791 O GLY A 251 192.290 32.111 11.094 1.00 50.50 O | ATOM 836 CB VAL A 258 180.384 43.074 −1.239 1.00 36.20 C |
| ANISOU 791 O GLY A 251 5655 6929 6602 1504 207 −122 O | ANISOU 836 CB VAL A 258 3757 4758 5238 −89 550 702 C |
| ATOM 792 N GLN A 252 191.228 30.730 9.690 1.00 45.66 N | ATOM 837 CG2 VAL A 258 181.690 43.414 −1.993 1.00 28.11 C |
| ANISOU 792 N GLN A 252 5263 5635 5914 1390 456 19 N | ANISOU 837 CG2 VAL A 258 2615 3752 4313 −71 636 831 C |
| ATOM 793 CA GLN A 252 191.912 31.268 8.526 1.00 41.57 C | ATOM 838 CG1 VAL A 258 179.678 44.330 −0.731 1.00 31.65 C |
| ANISOU 793 CA GLN A 252 4603 5694 5499 1253 445 34 C | ANISOU 838 CG1 VAL A 258 3178 4097 4751 −132 490 725 C |
| ATOM 794 CB GLN A 252 192.767 30.180 7.880 1.00 44.63 C | ATOM 839 C VAL A 258 179.369 41.626 0.515 1.00 40.20 C |
| ANISOU 794 CB GLN A 252 5012 5788 6126 5821 1329 552 74 C | ANISOU 839 C VAL A 258 4430 5207 5639 −98 434 468 C |
| ATOM 795 CG GLN A 252 193.831 29.564 8.817 1.00 43.77 C | ATOM 840 O VAL A 258 178.633 40.909 −0.159 1.00 43.05 O |
| ANISOU 795 CG GLN A 252 4887 6116 5629 1552 529 37 C | ANISOU 840 O VAL A 258 4847 5643 5865 −80 481 429 O |
| ATOM 796 CD GLN A 252 195.008 30.531 9.158 1.00 52.64 C | ATOM 841 N LEU A 259 179.064 42.002 1.752 1.00 39.97 N |
| ANISOU 796 CD GLN A 252 5788 6849 7183 1573 383 −39 C | ANISOU 841 N LEU A 259 4427 5091 5670 −117 343 411 N |
| ATOM 797 OE1 GLN A 252 195.194 31.575 8.510 1.00 53.74 O | ATOM 842 CA LEU A 259 178.033 41.324 2.510 1.00 37.53 C |
| ANISOU 797 OE1 GLN A 252 5778 7503 7139 1408 328 −44 O | ANISOU 842 CA LEU A 259 4223 4763 5271 −109 311 313 C |
| ATOM 798 NE2 GLN A 252 195.808 30.163 10.172 1.00 48.08 N | ATOM 843 CB LEU A 259 178.705 40.391 3.520 1.00 42.73 C |
| ANISOU 798 NE2 GLN A 252 5184 6891 6192 1784 328 −101 N | ANISOU 843 CB LEU A 259 4915 5383 5937 −62 294 249 C |
| ATOM 799 C GLN A 252 190.919 31.829 7.537 1.00 40.28 C | ATOM 844 CG LEU A 259 178.007 39.173 4.108 1.00 47.75 C |
| ANISOU 799 C GLN A 252 4454 5450 5402 1053 476 76 C | ANISOU 844 CG LEU A 259 5661 6002 6479 −30 323 169 C |
| ATOM 800 O GLN A 252 189.766 31.424 7.518 1.00 45.76 O | ATOM 845 CD1 LEU A 259 177.508 38.258 3.004 1.00 46.75 C |
| ANISOU 800 O GLN A 252 5284 6058 6044 1021 539 93 O | ANISOU 845 CD1 LEU A 259 5568 5932 6262 −45 418 146 C |
| ATOM 801 N ARG A 253 191.352 32.784 6.725 1.00 46.55 N | ATOM 846 CD2 LEU A 259 179.000 38.433 5.026 1.00 47.44 C |
| ANISOU 801 N ARG A 253 5099 6274 6315 927 437 94 N | ANISOU 846 CD2 LEU A 259 5635 5934 6457 46 317 142 C |
| ATOM 802 CA ARG A 253 190.474 33.328 5.698 1.00 44.28 C | ATOM 847 C LEU A 259 177.171 42.333 3.240 1.00 34.99 C |
| ANISOU 802 CA ARG A 253 4820 5932 6073 764 475 147 C | ANISOU 847 C LEU A 259 3919 4387 4989 −133 229 301 C |
| ATOM 803 CB ARG A 253 191.109 34.528 5.016 1.00 43.48 C | ATOM 848 O LEU A 259 177.681 43.233 3.906 1.00 39.40 O |
| ANISOU 803 CB ARG A 253 4534 5863 6123 655 433 181 C | ANISOU 848 O LEU A 259 4422 4880 5668 −139 157 312 O |
| ATOM 804 CG ARG A 253 190.319 35.032 3.815 1.00 49.44 C | ATOM 849 N GLU A 260 175.859 42.196 3.121 1.00 34.03 N |
| ANISOU 804 CG ARG A 253 5297 6587 6901 521 494 257 C | ANISOU 849 N GLU A 260 3865 4292 4772 −145 235 266 N |
| ATOM 805 CD ARG A 253 190.975 36.289 3.228 1.00 50.67 C | ATOM 850 CA GLU A 260 174.989 42.988 3.969 1.00 39.69 C |
| ANISOU 805 CD ARG A 253 5267 6758 7227 429 474 315 C | ANISOU 850 CA GLU A 260 4612 4960 5508 −154 155 243 C |
| ATOM 806 NE ARG A 253 191.429 37.164 4.302 1.00 54.86 N | ATOM 851 CB GLU A 260 174.808 44.407 3.425 1.00 38.71 C |
| ANISOU 806 NE ARG A 253 5685 7264 7897 428 348 239 N | ANISOU 851 CB GLU A 260 4431 4831 5446 −179 136 324 C |
| ATOM 807 CZ ARG A 253 192.291 38.167 4.160 1.00 60.69 C | ATOM 852 CG GLU A 260 174.310 44.497 2.018 1.00 48.57 C |
| ANISOU 807 CZ ARG A 253 6232 8002 8827 368 314 250 C | ANISOU 852 CG GLU A 260 5669 6178 6608 −180 214 384 C |
| ATOM 808 NH1 ARG A 253 192.812 38.434 2.963 1.00 59.91 N | ATOM 853 CD GLU A 260 174.415 45.932 1.484 1.00 61.93 C |
| ANISOU 808 NH1 ARG A 253 6038 7928 8798 309 414 363 N | ANISOU 853 CD GLU A 260 7298 7849 8384 −184 220 500 C |
| ATOM 809 NH2 ARG A 253 192.624 38.891 5.231 1.00 62.31 N | ATOM 854 OE1 GLU A 260 175.548 46.477 1.417 1.00 67.69 O |
| ANISOU 809 NH2 ARG A 253 6336 8182 9158 375 184 142 N | ANISOU 854 OE1 GLU A 260 7947 8517 9255 −195 234 572 O |
| ATOM 810 C ARG A 253 190.103 32.254 4.658 1.00 44.13 C | ATOM 855 OE2 GLU A 260 173.359 46.526 1.172 1.00 63.44 O |
| ANISOU 810 C ARG A 253 4910 5900 5956 755 612 191 C | ANISOU 855 OE2 GLU A 260 7516 8078 8512 −173 216 520 O |
| ATOM 856 C GLU A 260 173.645 42.340 4.222 1.00 40.15 C | ATOM 901 CD1 ILE A 266 168.361 47.078 9.639 1.00 31.49 C |
| ANISOU 856 C GLU A 260 4756 5040 5459 −155 168 172 C | ANISOU 901 CD1 ILE A 266 3854 3773 4336 −8 −320 35 C |

TABLE 8-continued

DMXAA-hSTING$^{S162A/Q266I}$ complex

| | |
|---|---|
| ATOM 857 O GLU A 260 173.217 41.467 3.481 1.00 39.26 O | ATOM 902 CG2 ILE A 266 165.769 47.638 11.250 1.00 20.19 C |
| ANISOU 857 O GLU A 260 4666 4987 5265 −163 240 138 O | ANISOU 902 CG2 ILE A 266 2535 2386 2751 94 −397 −19 C |
| ATOM 858 N TYR A 261 172.996 42.793 5.294 1.00 40.09 N | ATOM 903 C ILE A 266 163.384 46.137 10.480 1.00 30.65 C |
| ANISOU 858 N TYR A 261 4786 4983 5462 −142 97 141 N | ANISOU 903 C ILE A 266 3901 3839 3904 24 −219 −41 C |
| ATOM 859 CA TYR A 261 171.683 42.317 5.673 1.00 36.80 C | ATOM 904 O ILE A 266 162.851 46.191 11.590 1.00 28.64 O |
| ANISOU 859 CA TYR A 261 4440 4576 4965 −143 110 83 C | ANISOU 904 O ILE A 266 3689 3574 3621 95 −246 −51 O |
| ATOM 860 CB TYR A 261 171.457 42.542 7.161 1.00 35.89 C | ATOM 905 N THR A 267 162.756 46.513 9.375 1.00 28.23 N |
| ANISOU 860 CB TYR A 261 4368 4398 4870 −92 39 56 C | ANISOU 905 N THR A 267 3561 3602 3564 −32 −204 −39 N |
| ATOM 861 CG TYR A 261 172.019 41.474 8.084 1.00 38.36 C | ATOM 906 CA THR A 267 161.402 47.027 9.469 1.00 26.25 C |
| ANISOU 861 CG TYR A 261 4726 4673 5178 −27 68 26 C | ANISOU 906 CA THR A 267 3317 3412 3244 −17 −226 −54 C |
| ATOM 862 CD1 TYR A 261 171.315 40.294 8.316 1.00 41.21 C | ATOM 907 CB THR A 267 160.988 47.658 8.144 1.00 30.07 C |
| ANISOU 862 CD1 TYR A 261 5153 5021 5482 −16 159 −6 C | ANISOU 907 CB THR A 267 3756 3983 3684 −50 −224 −40 C |
| ATOM 863 CE1 TYR A 261 171.805 39.335 9.180 1.00 46.64 C | ATOM 908 OG1 THR A 267 161.706 48.877 8.008 1.00 25.90 O |
| ANISOU 863 CE1 TYR A 261 5891 5667 6165 64 205 −11 C | ANISOU 908 OG1 THR A 267 3223 3407 3211 −25 −292 27 O |
| ATOM 864 CZ TYR A 261 173.016 39.552 9.817 1.00 42.02 C | ATOM 909 CG2 THR A 267 159.452 47.977 8.086 1.00 19.90 C |
| ANISOU 864 CZ TYR A 261 5282 5074 5609 143 143 1 C | ANISOU 909 CG2 THR A 267 2463 2791 2305 −35 −232 −74 C |
| ATOM 865 OH TYR A 261 173.484 38.600 10.654 1.00 41.83 O | ATOM 910 C THR A 267 160.372 45.964 9.957 1.00 33.02 C |
| ANISOU 865 OH TYR A 261 5310 5026 5559 247 192 2 O | ANISOU 910 C THR A 267 4189 4294 4061 −23 −146 −105 C |
| ATOM 866 CE2 TYR A 261 173.740 40.705 9.623 1.00 40.80 C | ATOM 911 O THR A 267 159.531 46.218 10.853 1.00 30.10 O |
| ANISOU 866 CE2 TYR A 261 5047 4936 5519 124 39 9 C | ANISOU 911 O THR A 267 3848 3931 3657 30 −168 −106 O |
| ATOM 867 CD2 TYR A 261 173.236 41.666 8.750 1.00 39.10 C | ATOM 912 N LEU A 268 160.452 44.772 9.376 1.00 28.90 N |
| ANISOU 867 CD2 TYR A 261 4788 4739 5330 34 10 30 C | ANISOU 912 N LEU A 268 3644 3779 3557 −85 −46 −145 N |
| ATOM 868 C TYR A 261 170.649 43.104 4.883 1.00 31.16 C | ATOM 913 CA LEU A 268 159.563 43.660 9.790 1.00 32.30 C |
| ANISOU 868 C TYR A 261 3710 3924 4205 −175 103 100 C | ANISOU 913 CA LEU A 268 4075 4202 3995 −106 56 −195 C |
| ATOM 869 O TYR A 261 170.844 44.260 4.587 1.00 34.20 O | ATOM 914 CB LEU A 268 159.798 42.366 8.988 1.00 31.99 C |
| ANISOU 869 O TYR A 261 4052 4306 4635 −179 63 164 O | ANISOU 914 CB LEU A 268 3999 4151 4003 −185 165 −257 C |
| ATOM 870 N ALA A 262 169.548 42.477 4.538 1.00 34.81 N | ATOM 915 CG LEU A 268 159.392 42.437 7.515 1.00 37.02 C |
| ANISOU 870 N ALA A 262 4201 4439 4585 −193 148 40 N | ANISOU 915 CG LEU A 268 4561 4901 4603 −249 161 −333 C |
| ATOM 871 CA ALA A 262 168.494 43.186 3.815 1.00 33.08 C | ATOM 916 CD1 LEU A 268 159.681 41.124 6.818 1.00 34.64 C |
| ANISOU 871 CA ALA A 262 3964 4302 4302 −205 136 43 C | ANISOU 916 CD1 LEU A 268 4223 4582 4355 −313 260 −415 C |
| ATOM 872 CB ALA A 262 167.532 42.203 3.166 1.00 23.66 C | ATOM 917 CD2 LEU A 268 157.894 42.754 7.420 1.00 37.29 C |
| ANISOU 872 CB ALA A 262 2772 3190 3027 −227 198 −56 C | ANISOU 917 CD2 LEU A 268 4551 5029 4588 −260 151 −394 C |
| ATOM 873 C ALA A 262 167.759 44.053 4.814 1.00 34.49 C | ATOM 918 C LEU A 268 159.691 43.376 11.278 1.00 29.78 C |
| ANISOU 873 C ALA A 262 4173 4437 4494 −191 59 49 C | ANISOU 918 C LEU A 268 3820 3803 3693 −21 73 −149 C |
| ATOM 874 O ALA A 262 167.095 43.543 5.702 1.00 34.14 O | ATOM 919 O LEU A 268 158.726 43.099 11.978 1.00 28.79 O |
| ANISOU 874 O ALA A 262 4175 4264 4436 −186 58 −6 O | ANISOU 919 O LEU A 268 3706 3677 3554 6 123 −151 O |
| ATOM 875 N THR A 263 167.867 45.366 4.659 1.00 38.05 N | ATOM 920 N PHE A 269 160.915 43.438 11.766 1.00 25.98 N |
| ANISOU 875 N THR A 263 4598 4882 4979 −178 5 120 N | ANISOU 920 N PHE A 269 3374 3260 3236 36 36 −106 N |
| ATOM 876 CA THR A 263 167.260 46.294 5.601 1.00 32.91 C | ATOM 921 CA PHE A 269 161.125 43.152 13.142 1.00 30.76 C |
| ANISOU 876 CA THR A 263 3973 4182 4348 −156 −77 122 C | ANISOU 921 CA PHE A 269 4038 3813 3835 149 48 −67 C |
| ATOM 877 CB THR A 263 167.618 47.734 5.239 1.00 37.37 C | ATOM 922 CB PHE A 269 162.602 42.968 13.398 1.00 33.35 C |
| ANISOU 877 CB THR A 263 4498 4716 4984 −147 −117 209 C | ANISOU 922 CB PHE A 269 4385 4092 4195 198 21 −46 C |
| ATOM 878 OG1 THR A 263 167.194 48.014 3.900 1.00 42.95 O | ATOM 923 CG PHE A 269 162.886 42.549 14.782 1.00 26.90 C |
| ANISOU 878 OG1 THR A 263 5178 5523 5619 −142 −57 262 O | ANISOU 923 CG PHE A 269 3627 3242 3353 343 41 −9 C |
| ATOM 879 CG2 THR A 263 169.134 47.951 5.400 1.00 22.85 C | ATOM 924 CD1 PHE A 269 162.894 41.194 15.098 1.00 31.54 C |
| ANISOU 879 CG2 THR A 263 2610 2789 3283 −156 −128 249 C | ANISOU 924 CD1 PHE A 269 4247 3778 3958 368 195 20 C |
| ATOM 880 C THR A 263 165.749 46.164 5.867 1.00 30.46 C | ATOM 925 CE1 PHE A 269 163.131 40.753 16.394 1.00 35.98 C |
| ANISOU 880 C THR A 263 3701 3928 3945 −151 −82 65 C | ANISOU 925 CE1 PHE A 269 4871 4321 4479 533 236 74 C |
| ATOM 881 O THR A 263 165.315 46.464 6.981 1.00 36.89 O | ATOM 926 CZ PHE A 269 163.311 41.709 17.417 1.00 37.65 C |
| ANISOU 881 O THR A 263 4553 4695 4769 −121 −139 46 O | ANISOU 926 CZ PHE A 269 5104 4581 4621 681 101 76 C |
| ATOM 882 N PRO A 264 164.949 45.745 4.866 1.00 28.89 N | ATOM 927 CE2 PHE A 269 163.310 43.100 17.106 1.00 32.32 C |
| ANISOU 882 N PRO A 264 3482 3838 3656 −169 −27 29 N | ANISOU 927 CE2 PHE A 269 4389 3948 3944 641 −68 23 C |
| ATOM 883 CA PRO A 264 163.520 45.660 5.212 1.00 34.23 C | ATOM 928 CD2 PHE A 269 163.085 43.504 15.782 1.00 30.78 C |
| ANISOU 883 CA PRO A 264 4178 4564 4264 −168 −37 −35 C | ANISOU 928 CD2 PHE A 269 4139 3754 3800 470 −86 −7 C |
| ATOM 884 CB PRO A 264 162.861 45.134 3.925 1.00 35.89 C | ATOM 929 C PHE A 269 160.548 44.271 14.027 1.00 29.15 C |
| ANISOU 884 CB PRO A 264 4341 4510 4385 −185 20 −99 C | ANISOU 929 C PHE A 269 3859 3642 3573 243 −58 −51 C |
| ATOM 885 CG PRO A 264 163.749 45.669 2.806 1.00 36.87 C | ATOM 930 O PHE A 269 159.909 44.026 15.025 1.00 32.93 O |
| ANISOU 885 CG PRO A 264 4429 5080 4501 −159 33 −17 C | ANISOU 930 O PHE A 269 4375 4122 4015 329 −19 −27 O |
| ATOM 886 CD PRO A 264 165.171 45.668 3.398 1.00 30.68 C | ATOM 931 N ALA A 270 160.741 45.504 13.619 1.00 31.66 N |
| ANISOU 886 CD PRO A 264 3660 4165 3832 −170 27 50 C | ANISOU 931 N ALA A 270 4155 3986 3887 230 −181 −60 N |
| ATOM 887 C PRO A 264 163.207 44.704 6.364 1.00 31.81 C | ATOM 932 CA ALA A 270 160.251 46.629 14.389 1.00 28.71 C |
| ANISOU 887 C PRO A 264 3914 4191 3981 −175 −13 −94 C | ANISOU 932 CA ALA A 270 3804 3635 3469 319 −291 −58 C |
| ATOM 888 O PRO A 264 162.135 44.797 6.950 1.00 31.84 O | ATOM 933 CB ALA A 270 160.836 47.898 13.852 1.00 23.93 C |
| ANISOU 888 O PRO A 264 3937 4210 3952 −164 −26 −125 O | ANISOU 933 CB ALA A 270 3170 3016 2905 296 −410 −64 C |
| ATOM 889 N LEU A 265 164.110 43.774 6.640 1.00 29.12 N | ATOM 934 C ALA A 270 158.733 46.671 14.388 1.00 35.95 C |
| ANISOU 889 N LEU A 265 3587 3784 3692 −184 34 −100 N | ANISOU 934 C ALA A 270 4718 4616 4325 309 −250 −62 C |
| ATOM 890 CA LEU A 265 163.946 42.824 7.753 1.00 35.90 C | ATOM 935 O ALA A 270 158.126 46.956 15.404 1.00 41.09 O |
| ANISOU 890 CA LEU A 265 4494 4570 4576 −166 81 −129 C | ANISOU 935 O ALA A 270 5404 5286 4923 411 −277 −50 O |
| ATOM 891 CB LEU A 265 165.011 41.719 7.742 1.00 30.23 C | ATOM 936 N MET A 271 158.110 46.361 13.254 1.00 31.54 N |
| ANISOU 891 CB LEU A 265 3786 3794 3905 −169 151 −132 C | ANISOU 936 N MET A 271 4111 4106 3768 196 −186 −88 N |
| ATOM 892 CG LEU A 265 164.866 40.883 6.471 1.00 38.08 C | ATOM 937 CA MET A 271 156.656 46.290 13.221 1.00 31.16 C |
| ANISOU 892 CG LEU A 265 4737 4843 4887 −234 229 −198 C | ANISOU 937 CA MET A 271 4040 4129 3672 181 −141 −110 C |
| ATOM 893 CD1 LEU A 265 165.784 39.725 6.463 1.00 38.86 C | ATOM 938 CB MET A 271 156.115 46.067 11.805 1.00 26.65 C |
| ANISOU 893 CD1 LEU A 265 4853 4881 5032 −234 308 −209 C | ANISOU 938 CB MET A 271 3395 3632 3097 66 −99 −168 C |
| ATOM 894 CD2 LEU A 265 163.427 40.375 6.259 1.00 32.74 C | ATOM 939 CG MET A 271 156.346 47.253 10.865 1.00 23.58 C |
| ANISOU 894 CD2 LEU A 265 4040 4209 4192 −280 281 −291 C | ANISOU 939 CG MET A 271 2988 3297 2673 58 −198 −158 C |
| ATOM 895 C LEU A 265 163.961 43.576 9.080 1.00 38.25 C | ATOM 940 SD MET A 271 155.811 46.796 9.201 1.00 31.04 S |
| ANISOU 895 C LEU A 265 4835 4814 4882 −91 1 −88 C | ANISOU 940 SD MET A 271 3845 4361 3589 −37 −140 −234 S |

TABLE 8-continued

DMXAA-hSTING$^{S162A/Q266I}$ complex

| | |
|---|---|
| ATOM 896 O LEU A 265 163.263 43.212 10.020 1.00 37.89 O | ATOM 941 CE MET A 271 154.013 46.892 9.317 1.00 41.06 C |
| ANISOU 896 O LEU A 265 4829 4747 4821 −53 26 −100 O | ANISOU 941 CE MET A 271 5067 5747 4787 −29 −127 −298 C |
| ATOM 897 N ILE A 266 164.758 44.641 9.139 1.00 33.90 N | ATOM 942 C MET A 271 156.104 45.222 14.167 1.00 34.55 C |
| ANISOU 897 N ILE A 266 4271 4244 4366 −65 −91 −43 N | ANISOU 942 C MET A 271 4488 4528 4112 219 −21 −95 C |
| ATOM 898 CA ILE A 266 164.762 45.544 10.278 1.00 26.69 C | ATOM 943 O MET A 271 155.030 45.385 14.715 1.00 33.73 O |
| ANISOU 898 CA ILE A 266 3384 3292 3466 11 −191 −31 C | ANISOU 943 O MET A 271 4382 4467 3966 263 −4 −88 O |
| ATOM 899 CB ILE A 266 165.798 46.639 10.089 1.00 22.47 C | ATOM 944 N SER A 272 156.817 44.114 14.342 1.00 27.46 N |
| ANISOU 899 CB ILE A 266 2808 2718 3012 14 −278 −1 C | ANISOU 944 N SER A 272 3605 3554 3275 209 77 −80 N |
| ATOM 900 CG1 ILE A 266 167.182 45.998 9.981 1.00 22.54 C | ATOM 945 CA SER A 272 156.346 43.102 15.289 1.00 24.33 C |
| ANISOU 900 CG1 ILE A 266 2792 2690 3083 9 −251 4 C | ANISOU 945 CA SER A 272 3232 3109 2901 264 216 −39 C |
| ATOM 946 CB SER A 272 157.043 41.741 15.077 1.00 36.15 C | ATOM 991 N GLY A 278 150.312 46.884 14.382 1.00 39.41 N |
| ANISOU 946 CB SER A 272 4733 4516 4488 216 353 −35 C | ANISOU 991 N GLY A 278 4947 5527 4500 258 −25 −186 N |
| ATOM 947 OG SER A 272 158.449 41.812 15.317 1.00 39.69 O | ATOM 992 CA GLY A 278 149.262 45.883 14.252 1.00 31.13 C |
| ANISOU 947 OG SER A 272 5229 4924 4929 281 293 −4 O | ANISOU 992 CA GLY A 278 3810 4507 3512 181 114 −239 C |
| ATOM 948 C SER A 272 156.526 43.620 16.758 1.00 36.59 C | ATOM 993 C GLY A 278 149.798 44.622 13.610 1.00 36.70 C |
| ANISOU 948 C SER A 272 4860 4663 4381 451 157 31 C | ANISOU 993 C GLY A 278 4470 5135 4337 60 226 −291 C |
| ATOM 949 O SER A 272 155.879 43.155 17.678 1.00 35.78 O | ATOM 994 O GLY A 278 149.200 44.068 12.713 1.00 45.21 O |
| ANISOU 949 O SER A 272 4781 4554 4260 538 254 85 O | ANISOU 994 O GLY A 278 5447 6263 5468 −49 281 −398 O |
| ATOM 950 N GLN A 273 157.385 44.601 16.983 1.00 31.67 N | ATOM 995 N PHE A 279 150.975 44.186 14.040 1.00 38.94 N |
| ANISOU 950 N GLN A 273 4265 4051 3718 521 1 25 N | ANISOU 995 N PHE A 279 4828 5305 4663 89 251 −229 N |
| ATOM 951 CA GLN A 273 157.627 45.035 18.368 1.00 36.43 C | ATOM 996 CA PHE A 279 151.720 43.184 13.303 1.00 37.78 C |
| ANISOU 951 CA GLN A 273 4928 4666 4248 714 −67 61 C | ANISOU 996 CA PHE A 279 4654 5087 4613 −13 326 −277 C |
| ATOM 952 CB GLN A 273 159.098 45.361 18.605 1.00 36.99 C | ATOM 997 CB PHE A 279 152.834 43.907 12.581 1.00 35.12 C |
| ANISOU 952 CB GLN A 273 5016 4707 4332 779 −177 39 C | ANISOU 997 CB PHE A 279 4352 4766 4225 −13 198 −274 C |
| ATOM 953 CG GLN A 273 159.969 44.191 18.358 1.00 43.09 C | ATOM 998 CG PHE A 279 153.454 43.136 11.477 1.00 33.62 C |
| ANISOU 953 CG GLN A 273 5793 5420 5160 746 −67 60 C | ANISOU 998 CG PHE A 279 4117 4556 4100 −118 244 −344 C |
| ATOM 954 CD GLN A 273 159.440 43.540 19.197 1.00 58.66 C | ATOM 999 CD1 PHE A 279 152.778 42.996 10.266 1.00 37.69 C |
| ANISOU 954 CD GLN A 273 7809 7368 7110 842 111 139 C | ANISOU 999 CD1 PHE A 279 4533 5174 4612 −206 247 −463 C |
| ATOM 955 OE1 GLN A 273 159.407 43.050 20.436 1.00 67.33 O | ATOM 1000 CE1 PHE A 279 153.347 42.325 9.223 1.00 40.78 C |
| ANISOU 955 OE1 GLN A 273 8957 8502 8125 1034 106 184 O | ANISOU 1000 CE1 PHE A 279 4881 5565 5048 −284 277 −539 C |
| ATOM 956 NE2 GLN A 273 159.304 41.831 18.516 1.00 57.30 N | ATOM 1001 CZ PHE A 279 154.652 41.759 9.371 1.00 42.69 C |
| ANISOU 956 NE2 GLN A 273 7616 7135 7019 719 277 154 N | ANISOU 1001 CZ PHE A 279 5184 5692 5346 −283 313 −486 C |
| ATOM 957 C GLN A 273 156.765 46.223 18.753 1.00 37.67 C | ATOM 1002 CE2 PHE A 279 155.344 41.901 10.576 1.00 37.69 C |
| ANISOU 957 C GLN A 273 5089 4892 4331 779 −179 46 C | ANISOU 1002 CE2 PHE A 279 4646 4957 4716 −198 310 −366 C |
| ATOM 958 O GLN A 273 156.557 46.513 19.928 1.00 40.34 O | ATOM 1003 CD2 PHE A 279 154.726 42.591 11.625 1.00 32.19 C |
| ANISOU 958 O GLN A 273 5471 5264 4592 950 −216 71 O | ANISOU 1003 CD2 PHE A 279 3989 4273 3969 −111 273 −301 C |
| ATOM 959 N TYR A 274 156.257 46.918 17.752 1.00 35.08 N | ATOM 1004 C PHE A 279 152.320 42.197 14.297 1.00 40.89 C |
| ANISOU 959 N TYR A 274 4716 4596 4016 660 −233 5 N | ANISOU 1004 C PHE A 279 5109 5345 5082 36 452 −195 C |
| ATOM 960 CA TYR A 274 155.437 48.096 18.013 1.00 32.17 C | ATOM 1005 O PHE A 279 153.166 42.568 15.105 1.00 41.72 O |
| ANISOU 960 CA TYR A 274 4353 4290 3580 718 −340 −9 C | ANISOU 1005 O PHE A 279 5304 5411 5136 153 396 −108 O |
| ATOM 961 CB TYR A 274 155.803 49.260 17.106 1.00 32.83 C | ATOM 1006 N SER A 280 151.873 40.945 14.236 1.00 42.12 N |
| ANISOU 961 CB TYR A 274 4412 4370 3692 647 −467 −49 C | ANISOU 1006 N SER A 280 5209 5430 5365 −43 624 −228 N |
| ATOM 962 CG TYR A 274 157.145 49.841 17.408 1.00 41.09 C | ATOM 1007 CA SER A 280 152.262 39.931 15.212 1.00 41.57 C |
| ANISOU 962 CG TYR A 274 5474 5349 4790 698 −583 −73 C | ANISOU 1007 CA SER A 280 5195 5225 5376 19 781 −132 C |
| ATOM 963 CD1 TYR A 274 157.416 50.373 18.654 1.00 50.76 C | ATOM 1008 CB SER A 280 151.094 38.987 15.460 1.00 37.73 C |
| ANISOU 963 CD1 TYR A 274 6738 6571 5978 862 −685 −95 C | ANISOU 1008 CB SER A 280 4629 4685 5022 −41 974 −148 C |
| ATOM 964 CE1 TYR A 274 158.663 50.890 18.937 1.00 58.15 C | ATOM 1009 OG SER A 280 150.820 38.248 14.299 1.00 41.29 O |
| ANISOU 964 CE1 TYR A 274 7667 7448 6979 907 −800 −146 C | ANISOU 1009 OG SER A 280 4972 5117 5601 −212 1031 −296 O |
| ATOM 965 CZ TYR A 274 159.647 50.901 17.945 1.00 58.66 C | ATOM 1010 C SER A 280 153.498 39.144 14.767 1.00 45.95 C |
| ANISOU 965 CZ TYR A 274 7687 7449 7154 778 −799 −153 C | ANISOU 1010 C SER A 280 5779 5684 5995 −22 821 −141 C |
| ATOM 966 OH TYR A 274 160.897 51.410 18.179 1.00 66.21 O | ATOM 1011 O SER A 280 153.826 39.131 13.578 1.00 53.79 O |
| ANISOU 966 OH TYR A 274 8616 8342 8199 807 −905 −209 O | ANISOU 1011 O SER A 280 6723 6710 7006 −130 764 −244 O |
| ATOM 967 CE2 TYR A 274 159.404 50.371 16.711 1.00 50.67 C | ATOM 1012 N ARG A 281 154.180 38.492 15.712 1.00 48.13 N |
| ANISOU 967 CE2 TYR A 274 6647 6442 6164 626 −691 −112 C | ANISOU 1012 N ARG A 281 7352 6684 4251 −506 −879 −110 N |
| ATOM 968 CD2 TYR A 274 158.161 49.841 16.448 1.00 46.70 C | ATOM 1013 CA ARG A 281 155.290 37.584 15.387 1.00 53.77 C |
| ANISOU 968 CD2 TYR A 274 6150 6005 5591 590 −590 −82 C | ANISOU 1013 CA ARG A 281 8116 7253 5060 −402 −978 47 C |
| ATOM 969 C TYR A 274 153.948 47.857 17.901 1.00 35.66 C | ATOM 1014 CB ARG A 281 155.775 36.829 16.618 1.00 57.87 C |
| ANISOU 969 C TYR A 274 4765 4800 3983 686 −251 2 C | ANISOU 1014 CB ARG A 281 8844 7743 5400 −366 −1017 267 C |
| ATOM 970 O TYR A 274 153.467 47.357 16.889 1.00 40.53 O | ATOM 1015 CG ARG A 281 156.665 37.647 17.525 1.00 69.29 C |
| ANISOU 970 O TYR A 274 5323 5434 4641 547 −170 −24 O | ANISOU 1015 CG ARG A 281 10296 9357 6674 −304 −1248 311 C |
| ATOM 971 N SER A 275 153.232 48.267 18.945 1.00 36.12 N | ATOM 1016 CD ARG A 281 156.647 37.091 18.947 1.00 83.15 C |
| ANISOU 971 N SER A 275 4857 4908 3960 827 −276 30 N | ANISOU 1016 CD ARG A 281 12259 11195 8138 −334 −1251 501 C |
| ATOM 972 CA SER A 275 151.783 48.098 19.044 1.00 35.13 C | ATOM 1017 NE ARG A 281 157.986 36.822 19.473 1.00 93.63 N |
| ANISOU 972 CA SER A 275 4699 4855 3795 822 −192 47 C | ANISOU 1017 NE ARG A 281 13586 12601 9386 −211 −1480 754 N |
| ATOM 973 CB SER A 275 151.234 48.754 20.311 1.00 28.33 C | ATOM 1018 CZ ARG A 281 158.239 36.038 20.520 1.00 99.97 C |
| ANISOU 973 CB SER A 275 3888 4050 2826 1016 −251 82 C | ANISOU 1018 CZ ARG A 281 14533 13474 9977 −180 −1500 1040 C |
| ATOM 974 OG SER A 275 151.848 48.110 21.389 1.00 37.34 O | ATOM 1019 NH1 ARG A 281 159.491 35.851 20.932 1.00 100.22 N |
| ANISOU 974 OG SER A 275 5082 5156 3952 1155 −196 138 O | ANISOU 1019 NH1 ARG A 281 14505 13628 9945 −60 −1731 1311 N |
| ATOM 975 C SER A 275 151.114 48.696 17.857 1.00 32.61 C | ATOM 1020 NH2 ARG A 281 157.238 35.433 21.149 1.00 103.35 N |
| ANISOU 975 C SER A 275 4320 4597 3475 699 −237 −10 C | ANISOU 1020 NH2 ARG A 281 15143 13865 10261 −261 −1284 1085 N |
| ATOM 976 O SER A 275 150.280 48.091 17.215 1.00 36.34 O | ATOM 1021 C ARG A 281 154.949 36.572 14.295 1.00 57.29 C |
| ANISOU 976 O SER A 275 4722 5110 3976 594 −136 −35 O | ANISOU 1021 C ARG A 281 8542 7546 5678 −460 −822 35 C |
| ATOM 977 N GLN A 276 151.492 49.924 17.581 1.00 29.32 N | ATOM 1022 O ARG A 281 155.793 36.263 13.448 1.00 60.48 O |
| ANISOU 977 N GLN A 276 3926 4187 3027 724 −390 −34 N | ANISOU 1022 O ARG A 281 8893 7836 6251 −372 −872 70 O |
| ATOM 978 CA GLN A 276 150.796 50.692 16.587 1.00 28.30 C | ATOM 1023 N GLU A 282 153.718 36.066 14.299 1.00 53.65 N |
| ANISOU 978 CA GLN A 276 3754 4131 2867 659 −439 −67 C | ANISOU 1023 N GLU A 282 8126 7084 5175 −630 −617 −31 N |
| ATOM 979 CB GLN A 276 151.389 52.080 16.563 1.00 37.83 C | ATOM 1024 CA GLU A 282 153.291 35.134 13.243 1.00 52.18 C |
| ANISOU 979 CB GLN A 276 5006 5306 4064 719 −596 −71 C | ANISOU 1024 CA GLU A 282 7919 6783 5123 −760 −450 −101 C |

TABLE 8-continued

DMXAA-hSTING$^{S162A/Q266I}$ complex

| | |
|---|---|
| ATOM 980 CG GLN A 276 150.394 53.099 16.181 1.00 53.00 C | ATOM 1025 CB GLU A 282 151.995 34.397 13.607 1.00 51.84 C |
| ANISOU 980 CG GLN A 276 6916 7311 5910 746 −656 −79 C | ANISOU 1025 CB GLU A 282 7965 6723 5008 −971 −215 −139 C |
| ATOM 981 CD GLN A 276 151.000 54.455 16.087 1.00 69.55 C | ATOM 1026 CG GLU A 282 152.118 33.493 14.838 1.00 62.24 C |
| ANISOU 981 CD GLN A 276 9053 9347 8027 797 −790 −78 C | ANISOU 1026 CG GLU A 282 9540 7874 6233 −941 −107 54 C |
| ATOM 982 OE1 GLN A 276 152.136 54.678 16.529 1.00 78.92 O | ATOM 1027 CD GLU A 282 152.274 34.257 16.187 1.00 84.70 C |
| ANISOU 982 OE1 GLN A 276 10270 10427 9289 825 −853 −85 O | ANISOU 1027 CD GLU A 282 12459 10858 8865 −832 −238 159 C |
| ATOM 983 NE2 GLN A 276 150.250 55.390 15.509 1.00 74.27 N | ATOM 1028 OE1 GLU A 282 152.904 33.686 17.126 1.00 83.47 O |
| ANISOU 983 NE2 GLN A 276 9643 10006 8569 814 −831 −73 N | ANISOU 1028 OE1 GLU A 282 12482 10620 8613 −730 −254 380 O |
| ATOM 984 C GLN A 276 150.868 50.103 15.181 1.00 24.09 C | ATOM 1029 OE2 GLU A 282 151.768 35.410 16.298 1.00 82.54 O |
| ANISOU 984 C GLN A 276 3151 3616 2388 499 −371 −107 C | ANISOU 1029 OE2 GLU A 282 12064 10782 8517 −855 −301 31 O |
| ATOM 985 O GLN A 276 150.202 50.585 14.298 1.00 30.13 O | ATOM 1030 C GLU A 282 153.152 35.851 11.895 1.00 54.50 C |
| ANISOU 985 O GLN A 276 3870 4468 3110 459 −393 −138 O | ANISOU 1030 C GLU A 282 7965 7217 5526 −786 −507 −263 C |
| ATOM 986 N ALA A 277 151.723 49.114 14.967 1.00 21.60 N | ATOM 1031 O GLU A 282 153.541 35.315 10.845 1.00 50.57 O |
| ANISOU 986 N ALA A 277 2828 3226 2153 429 −295 −109 N | ANISOU 1031 O GLU A 282 7438 6625 5149 −814 −470 −312 O |
| ATOM 987 CA ALA A 277 151.927 48.533 13.630 1.00 32.33 C | ATOM 1032 N ASP A 283 152.594 37.063 11.924 1.00 55.20 N |
| ANISOU 987 CA ALA A 277 4123 4603 3560 292 −239 −157 C | ANISOU 1032 N ASP A 283 7875 7528 5572 −774 −566 −333 N |
| ATOM 988 CB ALA A 277 153.382 47.964 13.450 1.00 20.34 C | ATOM 1033 CA ASP A 283 152.600 37.919 10.745 1.00 57.32 C |
| ANISOU 988 CB ALA A 277 2627 2979 2121 252 −220 −142 C | ANISOU 1033 CA ASP A 283 7882 7954 5943 −737 −635 −418 C |
| ATOM 989 C ALA A 277 150.891 47.465 13.330 1.00 36.29 C | ATOM 1034 CB ASP A 283 152.065 39.332 11.067 1.00 67.20 C |
| ANISOU 989 C ALA A 277 4544 5158 4087 212 −110 −215 C | ANISOU 1034 CB ASP A 283 8958 9398 7179 −672 −650 −437 C |
| ATOM 990 O ALA A 277 150.624 47.169 12.175 1.00 38.84 O | ATOM 1035 CG ASP A 283 150.570 39.364 11.372 1.00 75.62 C |
| ANISOU 990 O ALA A 277 4792 5546 4421 118 −85 −290 O | ANISOU 1035 CG ASP A 283 9953 10610 8168 −831 −477 −455 C |
| ATOM 1036 OD1 ASP A 283 149.878 38.396 11.010 1.00 84.12 O | ATOM 1081 O ALA A 288 160.631 36.638 3.742 1.00 27.78 O |
| ANISOU 1036 OD1 ASP A 283 11043 11704 9214 −1019 −376 −483 O | ANISOU 1081 O ALA A 288 3995 3207 3353 100 −794 −317 O |
| ATOM 1037 OD2 ASP A 283 150.093 40.372 11.964 1.00 73.39 O | ATOM 1082 N LYS A 289 159.081 35.345 4.716 1.00 32.97 N |
| ANISOU 1037 OD2 ASP A 283 9596 10415 7872 −778 −418 −446 O | ANISOU 1082 N LYS A 289 4890 3848 3787 −234 −597 −398 N |
| ATOM 1038 C ASP A 283 154.045 38.044 10.207 1.00 53.01 C | ATOM 1083 CA LYS A 289 159.212 34.371 3.642 1.00 40.64 C |
| ANISOU 1038 C ASP A 283 7330 7289 5524 −556 −786 −380 C | ANISOU 1083 CA LYS A 289 5978 4645 4820 −374 −354 −522 C |
| ATOM 1039 O ASP A 283 154.296 38.018 8.992 1.00 52.20 O | ATOM 1084 CB LYS A 289 158.454 33.095 3.962 1.00 45.73 C |
| ANISOU 1039 O ASP A 283 7103 7209 5520 −554 −795 −434 O | ANISOU 1084 CB LYS A 289 6839 5133 5404 −627 −97 −603 C |
| ATOM 1040 N ARG A 284 154.992 38.179 11.128 1.00 46.40 N | ATOM 1085 CG LYS A 289 158.947 32.367 5.166 1.00 53.34 C |
| ANISOU 1040 N ARG A 284 6617 6346 4667 −414 −904 −277 N | ANISOU 1085 CG LYS A 289 7985 5805 6478 −491 −25 −372 C |
| ATOM 1041 CA ARG A 284 156.377 38.486 10.779 1.00 42.64 C | ATOM 1086 CD LYS A 289 158.071 31.172 5.411 1.00 60.77 C |
| ANISOU 1041 CA ARG A 284 6095 5785 4321 −230 −1064 −217 C | ANISOU 1086 CD LYS A 289 9125 6593 7372 −756 268 −468 C |
| ATOM 1042 CB ARG A 284 157.195 38.798 12.027 1.00 39.49 C | ATOM 1087 CE LYS A 289 158.309 30.557 6.764 1.00 65.86 C |
| ANISOU 1042 CB ARG A 284 5795 5374 3836 −128 −1216 −106 C | ANISOU 1087 CE LYS A 289 9923 7024 8076 −620 328 −209 C |
| ATOM 1043 CG ARG A 284 158.564 39.326 11.680 1.00 34.59 C | ATOM 1088 NZ LYS A 289 157.026 29.967 7.298 1.00 70.20 N |
| ANISOU 1043 CG ARG A 284 5068 4714 3361 44 −1397 −54 C | ANISOU 1088 NZ LYS A 289 10577 7607 8489 −883 492 −303 N |
| ATOM 1044 CD ARG A 284 159.388 39.590 12.890 1.00 33.51 C | ATOM 1089 C LYS A 289 158.682 34.962 2.330 1.00 40.56 C |
| ANISOU 1044 CD ARG A 284 4999 4626 3107 100 −1572 54 C | ANISOU 1089 C LYS A 289 5787 4930 4695 −511 −375 −716 C |
| ATOM 1045 NE ARG A 284 159.851 38.361 13.510 1.00 33.84 N | ATOM 1090 O LYS A 289 159.265 34.771 1.260 1.00 44.17 O |
| ANISOU 1045 NE ARG A 284 5205 4564 3090 132 −1578 284 N | ANISOU 1090 O LYS A 289 6256 5306 5222 −507 −277 −786 O |
| ATOM 1046 CZ ARG A 284 160.102 38.219 14.803 1.00 34.87 C | ATOM 1091 N LEU A 290 157.558 35.664 2.439 1.00 38.93 N |
| ANISOU 1046 CZ ARG A 284 5449 4792 3007 120 −1678 422 C | ANISOU 1091 N LEU A 290 5407 5077 4307 −627 −486 −777 N |
| ATOM 1047 NH1 ARG A 284 160.532 37.043 15.255 1.00 37.78 N | ATOM 1092 CA LEU A 290 156.888 36.273 1.290 1.00 39.99 C |
| ANISOU 1047 NH1 ARG A 284 5936 5060 3357 186 −1652 693 N | ANISOU 1092 CA LEU A 290 5315 5581 4299 −756 −523 −898 C |
| ATOM 1048 NH2 ARG A 284 159.928 39.245 15.633 1.00 36.36 N | ATOM 1093 CB LEU A 290 155.508 36.775 1.676 1.00 39.79 C |
| ANISOU 1048 NH2 ARG A 284 5632 5180 3002 39 −1778 299 N | ANISOU 1093 CB LEU A 290 5115 5904 4098 −901 −590 −911 C |
| ATOM 1049 C ARG A 284 157.102 37.385 9.979 1.00 45.63 C | ATOM 1094 CG LEU A 290 154.759 37.524 0.588 1.00 42.28 C |
| ANISOU 1049 C ARG A 284 6545 5957 4837 −202 −1011 −157 C | ANISOU 1094 CG LEU A 290 5128 6671 4265 −997 −651 −948 C |
| ATOM 1050 O ARG A 284 157.802 37.665 8.990 1.00 42.08 O | ATOM 1095 CD1 LEU A 290 154.625 36.633 −0.667 1.00 39.70 C |
| ANISOU 1050 O ARG A 284 5976 5475 4536 −106 −1062 −179 O | ANISOU 1095 CD1 LEU A 290 4859 6431 3794 −1293 −515 −1150 C |
| ATOM 1051 N LEU A 285 156.960 36.136 10.411 1.00 42.10 N | ATOM 1096 CD2 LEU A 290 153.386 37.905 1.160 1.00 43.89 C |
| ANISOU 1051 N LEU A 285 6298 5340 4358 −277 −871 −74 N | ANISOU 1096 CD2 LEU A 290 5161 7174 4343 −1123 −681 −911 C |
| ATOM 1052 CA LEU A 285 157.719 35.072 9.754 1.00 46.17 C | ATOM 1097 C LEU A 290 157.712 37.413 0.702 1.00 37.64 C |
| ANISOU 1052 CA LEU A 285 6906 5597 5038 −238 −756 −3 C | ANISOU 1097 C LEU A 290 4824 5366 4113 −484 −668 −799 C |
| ATOM 1053 CB LEU A 285 157.795 33.806 10.618 1.00 50.99 C | ATOM 1098 O LEU A 290 157.747 37.599 −0.502 1.00 35.35 O |
| ANISOU 1053 CB LEU A 285 7748 5985 5641 −247 −596 180 C | ANISOU 1098 O LEU A 290 4423 5243 3765 −533 −641 −869 O |
| ATOM 1054 CG LEU A 285 158.369 32.580 9.888 1.00 61.78 C | ATOM 1099 N PHE A 291 158.423 38.143 1.559 1.00 35.96 N |
| ANISOU 1054 CG LEU A 285 9233 7024 7218 −238 −357 236 C | ANISOU 1099 N PHE A 291 4578 5032 4054 −211 −809 −640 N |
| ATOM 1055 CD1 LEU A 285 159.839 32.795 9.394 1.00 48.71 C | ATOM 1100 CA PHE A 291 159.389 39.144 1.098 1.00 37.04 C |
| ANISOU 1055 CD1 LEU A 285 7493 5251 5763 5 −468 378 C | ANISOU 1100 CA PHE A 291 4557 5163 4353 54 −916 −547 C |
| ATOM 1056 CD2 LEU A 285 158.239 31.309 10.736 1.00 64.56 C | ATOM 1101 CB PHE A 291 160.013 39.834 2.301 1.00 32.88 C |
| ANISOU 1056 CD2 LEU A 285 9807 7136 −256 −122 C | ANISOU 1101 CB PHE A 291 4018 4518 3958 266 −1066 −414 C |
| ATOM 1057 C LEU A 285 157.115 34.763 8.376 1.00 47.74 C | ATOM 1102 CG PHE A 291 161.158 40.752 1.971 1.00 28.86 C |
| ANISOU 1057 C LEU A 285 7044 5806 5287 −415 −597 −211 C | ANISOU 1102 CG PHE A 291 3369 3939 3659 522 −1161 −326 C |
| ATOM 1058 O LEU A 285 157.793 34.379 7.428 1.00 49.85 O | ATOM 1103 CD1 PHE A 291 160.921 42.039 1.508 1.00 24.80 C |
| ANISOU 1058 O LEU A 285 7316 5926 5698 −381 −526 −234 O | ANISOU 1103 CD1 PHE A 291 2606 3638 3180 622 −1203 −314 C |
| ATOM 1059 N GLU A 286 155.810 34.925 8.294 1.00 45.36 N | ATOM 1104 CE1 PHE A 291 161.969 42.936 1.260 1.00 23.28 C |
| ANISOU 1059 N GLU A 286 6681 5704 4849 −623 −533 −358 N | ANISOU 1104 CE1 PHE A 291 2354 3315 3177 746 −1112 −198 C |
| ATOM 1060 CA GLU A 286 155.094 34.682 7.071 1.00 41.70 C | ATOM 1105 CZ PHE A 291 163.272 42.524 1.414 1.00 22.73 C |
| ANISOU 1060 CA GLU A 286 6126 5353 4365 −844 −415 −554 C | ANISOU 1105 CZ PHE A 291 2382 3002 3252 836 −1122 −137 C |
| ATOM 1061 CB GLU A 286 155.598 34.746 5.598 1.00 48.17 C | ATOM 1106 CE2 PHE A 291 163.533 41.205 1.875 1.00 34.84 C |
| ANISOU 1061 CB GLU A 286 6875 6399 5027 −1072 −348 −646 C | ANISOU 1106 CE2 PHE A 291 4074 4349 4813 891 −1272 −145 C |
| ATOM 1062 CG GLU A 286 152.737 34.232 6.258 1.00 67.13 C | ATOM 1107 CD2 PHE A 291 162.461 40.339 2.155 1.00 33.79 C |
| ANISOU 1062 CG GLU A 286 9195 8947 7364 −1377 −213 −843 C | ANISOU 1107 CD2 PHE A 291 4091 4279 4468 671 −1187 −227 C |
| ATOM 1063 CD GLU A 286 151.441 35.023 6.117 1.00 84.13 C | ATOM 1108 C PHE A 291 160.504 38.516 0.252 1.00 41.72 C |
| ANISOU 1063 CD GLU A 286 11081 11501 9385 −1509 −271 −886 C | ANISOU 1108 C PHE A 291 5261 5503 5086 123 −813 −554 C |

TABLE 8-continued

DMXAA-hSTING$^{S162A/Q266I}$ complex

ATOM 1064 OE1 GLU A 286 150.558 34.589 5.327 1.00 91.17 O
ANISOU 1064 OE1 GLU A 286 11868 12593 10179 −1808 −179 −1033 O
ATOM 1065 OE2 GLU A 286 151.319 36.074 6.798 1.00 88.67 O
ANISOU 1065 OE2 GLU A 286 11543 12192 9955 −1325 −391 −768 O
ATOM 1066 C GLU A 286 155.509 35.754 6.060 1.00 40.93 C
ANISOU 1066 C GLU A 286 5794 5444 4312 −727 −568 −597 C
ATOM 1067 O GLU A 286 155.829 35.437 4.916 1.00 45.09 O
ANISOU 1067 O GLU A 286 6300 5943 4890 −785 −501 −690 O
ATOM 1068 N GLN A 287 155.546 37.018 6.506 1.00 39.93 N
ANISOU 1068 N GLN A 287 5508 5488 4176 −563 −744 −529 N
ATOM 1069 CA GLN A 287 155.860 38.147 5.630 1.00 38.77 C
ANISOU 1069 CA GLN A 287 5120 5516 4096 −432 −857 −542 C
ATOM 1070 CB GLN A 287 155.527 39.501 6.267 1.00 37.77 C
ANISOU 1070 CB GLN A 287 4828 5565 3958 −313 −956 −492 C
ATOM 1071 CG GLN A 287 154.045 39.809 6.392 1.00 31.08 C
ANISOU 1071 CG GLN A 287 3848 4973 2988 −470 −871 −526 C
ATOM 1072 CD GLN A 287 153.346 39.856 5.058 1.00 37.26 C
ANISOU 1072 CD GLN A 287 4403 6027 3727 −597 −827 −574 C
ATOM 1073 OE1 GLN A 287 153.662 40.693 4.207 1.00 42.82 O
ANISOU 1073 OE1 GLN A 287 4897 6867 4504 −464 −882 −534 O
ATOM 1074 NE2 GLN A 287 152.360 38.981 4.866 1.00 37.40 N
ANISOU 1074 NE2 GLN A 287 4444 6156 3612 −869 −723 −654 N
ATOM 1075 C GLN A 287 157.320 38.126 5.255 1.00 37.62 C
ANISOU 1075 C GLN A 287 5015 5157 4120 −231 −924 −475 C
ATOM 1076 O GLN A 287 157.673 38.564 4.185 1.00 40.38 O
ANISOU 1076 O GLN A 287 5223 5580 4539 −169 −944 −506 O
ATOM 1077 N ALA A 288 158.180 37.615 6.127 1.00 33.83 N
ANISOU 1077 N ALA A 288 4713 4432 3710 −121 −954 −353 N
ATOM 1078 CA ALA A 288 159.603 37.491 5.767 1.00 33.35 C
ANISOU 1078 CA ALA A 288 4670 4160 3841 75 −1001 −251 C
ATOM 1079 CB ALA A 288 160.451 37.154 6.975 1.00 27.03 C
ANISOU 1079 CB ALA A 288 3994 3191 3084 210 −1086 −53 C
ATOM 1080 C ALA A 288 159.819 36.450 4.656 1.00 32.71 C
ANISOU 1080 C ALA A 288 4688 3902 3839 −13 −798 −319 C
ATOM 1126 O ARG A 293 159.984 36.088 −4.872 1.00 43.46 O
ANISOU 1126 O ARG A 293 5733 5998 4781 −728 −105 −1259 O
ATOM 1127 N THR A 294 159.227 37.325 −3.135 1.00 41.28 N
ANISOU 1127 N THR A 294 5199 5925 4561 −503 −451 −1003 N
ATOM 1128 CA THR A 294 158.891 38.445 −3.990 1.00 42.47 C
ANISOU 1128 CA THR A 294 5046 6493 4597 −438 −572 −944 C
ATOM 1129 CB THR A 294 158.109 39.480 −3.247 1.00 42.63 C
ANISOU 1129 CB THR A 294 4824 6772 4600 −338 −743 −801 C
ATOM 1130 OG1 THR A 294 156.937 38.857 −2.729 1.00 48.86 O
ANISOU 1130 OG1 THR A 294 5661 7698 5206 −626 −714 −900 O
ATOM 1131 CG2 THR A 294 157.673 40.560 −4.187 1.00 42.71 C
ANISOU 1131 CG2 THR A 294 4502 7222 4505 −270 −815 −697 C
ATOM 1132 C THR A 294 160.166 39.058 −4.560 1.00 38.76 C
ANISOU 1132 C THR A 294 4527 5860 4342 −129 −582 −830 C
ATOM 1133 O THR A 294 160.291 39.314 −5.757 1.00 38.60 O
ANISOU 1133 O THR A 294 4408 6036 4223 −144 −537 −857 O
ATOM 1134 N LEU A 295 161.136 39.248 −3.695 1.00 32.38 N
ANISOU 1134 N LEU A 295 3785 4702 3817 136 −636 −698 N
ATOM 1135 CA LEU A 295 162.383 39.869 −4.115 1.00 36.47 C
ANISOU 1135 CA LEU A 295 4231 5047 4580 434 −653 −575 C
ATOM 1136 CB LEU A 295 163.274 40.117 −2.914 1.00 29.51 C
ANISOU 1136 CB LEU A 295 3380 3860 3972 673 −764 −424 C
ATOM 1137 CG LEU A 295 164.565 40.869 −3.137 1.00 33.60 C
ANISOU 1137 CG LEU A 295 3782 4208 4778 979 −813 −281 C
ATOM 1138 CD1 LEU A 295 164.236 42.207 −3.772 1.00 32.42 C
ANISOU 1138 CD1 LEU A 295 3369 4356 4592 1057 −852 −226 C
ATOM 1139 CD2 LEU A 295 165.267 41.056 −1.771 1.00 32.89 C
ANISOU 1139 CD2 LEU A 295 3720 3916 4863 1096 −930 −143 C
ATOM 1140 C LEU A 295 163.120 38.994 −5.134 1.00 44.47 C
ANISOU 1140 C LEU A 295 5428 5844 5625 379 −435 −671 C
ATOM 1141 O LEU A 295 163.733 39.514 −6.072 1.00 41.63 O
ANISOU 1141 O LEU A 295 4967 5518 5331 524 −400 −626 O
ATOM 1142 N GLU A 296 163.063 37.667 −4.927 1.00 42.51 N
ANISOU 1142 N GLU A 296 5458 5346 5348 174 −249 −798 N
ATOM 1143 CA GLU A 296 163.575 36.697 −5.901 1.00 47.34 C
ANISOU 1143 CA GLU A 296 6289 5732 5967 49 41 −943 C
ATOM 1144 CB GLU A 296 163.294 35.255 −5.462 1.00 56.37 C
ANISOU 1144 CB GLU A 296 7736 6586 7096 −203 283 −1085 C
ATOM 1145 CG GLU A 296 164.530 34.494 −5.052 1.00 73.53 C
ANISOU 1145 CG GLU A 296 10109 8203 9628 4 484 −944 C
ATOM 1146 CD GLU A 296 164.996 33.465 −6.098 1.00 92.45 C
ANISOU 1146 CD GLU A 296 12761 10298 12067 −149 897 −1123 C
ATOM 1147 OE1 GLU A 296 164.130 32.766 −6.685 1.00 99.22 O
ANISOU 1147 OE1 GLU A 296 13769 11273 12658 −546 1094 −1423 O
ATOM 1109 O PHE A 291 160.838 38.979 −0.834 1.00 41.53 O
ANISOU 1109 O PHE A 291 5111 5575 5093 191 −800 −570 O
ATOM 1110 N CYS A 292 161.076 37.435 0.758 1.00 40.86 N
ANISOU 1110 N CYS A 292 5389 5061 5074 117 −707 −519 N
ATOM 1111 CA CYS A 292 162.187 36.798 0.075 1.00 38.37 C
ANISOU 1111 CA CYS A 292 5190 4446 4943 210 −559 −492 C
ATOM 1112 CB CYS A 292 162.805 35.730 0.999 1.00 35.67 C
ANISOU 1112 CB CYS A 292 5070 3732 4751 269 −452 −353 C
ATOM 1113 SG CYS A 292 163.858 34.524 0.122 1.00 82.68 S
ANISOU 1113 SG CYS A 292 11230 9247 10939 305 −112 −340 S
ATOM 1114 C CYS A 292 161.763 36.235 −1.325 1.00 42.76 C
ANISOU 1114 C CYS A 292 5804 5077 5365 −28 −346 −709 C
ATOM 1115 O CYS A 292 162.497 36.368 −2.328 1.00 38.32 O
ANISOU 1115 O CYS A 292 5216 4451 4892 62 −270 −723 O
ATOM 1116 N ARG A 293 160.577 35.625 −1.385 1.00 39.54 N
ANISOU 1116 N ARG A 293 5469 4827 4727 −353 −246 −887 N
ATOM 1117 CA ARG A 293 160.037 35.102 −2.651 1.00 41.86 C
ANISOU 1117 CA ARG A 293 5805 5275 4823 −660 −65 −1132 C
ATOM 1118 CB ARG A 293 158.742 34.334 −2.412 1.00 46.88 C
ANISOU 1118 CB ARG A 293 6526 6051 5237 −1041 36 −1316 C
ATOM 1119 CG ARG A 293 158.936 32.883 −2.086 1.00 57.16 C
ANISOU 1119 CG ARG A 293 8157 6916 6647 −1199 350 −1410 C
ATOM 1120 CD ARG A 293 157.589 32.204 −1.812 1.00 69.42 C
ANISOU 1120 CD ARG A 293 9767 8621 7990 −1591 449 −1599 C
ATOM 1121 NE ARG A 293 157.159 32.366 −0.415 1.00 74.96 N
ANISOU 1121 NE ARG A 293 10447 9300 8734 −1478 320 −1424 N
ATOM 1122 CZ ARG A 293 155.900 32.564 −0.023 1.00 76.60 C
ANISOU 1122 CZ ARG A 293 10531 9825 8749 −1679 228 −1479 C
ATOM 1123 NH1 ARG A 293 155.613 32.696 1.277 1.00 73.04 N
ANISOU 1123 NH1 ARG A 293 10094 9312 8345 −1557 142 −1315 N
ATOM 1124 NH2 ARG A 293 154.930 32.629 −0.932 1.00 81.62 N
ANISOU 1124 NH2 ARG A 293 11018 10862 9133 −2009 224 −1684 N
ATOM 1125 C ARG A 293 159.755 36.221 −3.653 1.00 42.39 C
ANISOU 1125 C ARG A 293 5589 5780 4736 −632 −220 −1140 C
ATOM 1171 CD1 LEU A 299 167.690 40.208 −6.110 1.00 45.51 C
ANISOU 1171 CD1 LEU A 299 5412 5086 6794 1360 −334 −192 C
ATOM 1172 CD2 LEU A 299 166.741 42.051 −7.471 1.00 38.90 C
ANISOU 1172 CD2 LEU A 299 4201 4897 5683 1358 −412 −170 C
ATOM 1173 C LEU A 299 165.630 39.150 −10.498 1.00 47.60 C
ANISOU 1173 C LEU A 299 5870 6246 5968 544 214 −817 C
ATOM 1174 O LEU A 299 166.419 39.435 −11.383 1.00 49.81 O
ANISOU 1174 O LEU A 299 6133 6457 6337 699 333 −767 O
ATOM 1175 N ALA A 300 164.895 38.043 −10.519 1.00 47.91 N
ANISOU 1175 N ALA A 300 6130 6312 5762 166 348 −1062 N
ATOM 1176 CA ALA A 300 165.064 37.060 −11.585 1.00 52.71 C
ANISOU 1176 CA ALA A 300 7001 6825 6201 −101 673 −1314 C
ATOM 1177 CB ALA A 300 164.106 35.902 −11.410 1.00 55.88 C
ANISOU 1177 CB ALA A 300 7623 7263 6344 −556 809 −1603 C
ATOM 1178 C ALA A 300 164.880 37.687 −12.962 1.00 59.63 C
ANISOU 1178 C ALA A 300 7729 8154 6772 −161 674 −1347 C
ATOM 1179 O ALA A 300 165.459 37.225 −13.942 1.00 69.93 O
ANISOU 1179 O ALA A 300 9218 9327 8026 −238 945 −1481 O
ATOM 1180 N ASP A 301 164.082 38.749 −13.032 1.00 78.43 N
ANISOU 1180 N ASP A 301 9138 13383 7279 506 −2196 −37 N
ATOM 1181 CA ASP A 301 163.776 39.365 −14.309 1.00 76.60 C
ANISOU 1181 CA ASP A 301 8775 13780 6549 654 −2224 189 C
ATOM 1182 CB ASP A 301 162.311 39.135 −14.652 1.00 88.45 C
ANISOU 1182 CB ASP A 301 10032 15637 7939 495 −2594 323 C
ATOM 1183 CG ASP A 301 162.090 38.887 −16.139 1.00 99.91 C
ANISOU 1183 CG ASP A 301 11442 17750 8770 522 −2856 168 C
ATOM 1184 OD1 ASP A 301 162.875 38.115 −16.750 1.00 103.81 O
ANISOU 1184 OD1 ASP A 301 12173 18269 9002 520 −2927 −352 O
ATOM 1185 OD2 ASP A 301 161.137 39.482 −16.693 1.00 103.61 O
ANISOU 1185 OD2 ASP A 301 11693 18551 9124 557 −2898 557 O
ATOM 1186 C ASP A 301 164.069 40.859 −14.355 1.00 71.91 C
ANISOU 1186 C ASP A 301 8109 13279 5936 902 −1831 755 C
ATOM 1187 O ASP A 301 163.419 41.594 −15.088 1.00 78.03 O
ANISOU 1187 O ASP A 301 8712 14502 6435 1028 −1848 1154 O
ATOM 1188 N ALA A 302 165.038 41.321 −13.577 1.00 66.10 N
ANISOU 1188 N ALA A 302 7508 12114 5493 964 −1491 806 N
ATOM 1189 CA ALA A 302 165.325 42.759 −13.536 1.00 66.66 C
ANISOU 1189 CA ALA A 302 7557 12167 5605 1146 −1124 1338 C
ATOM 1190 CB ALA A 302 165.374 43.291 −12.090 1.00 55.52 C
ANISOU 1190 CB ALA A 302 6205 10156 4734 1113 −901 1512 C
ATOM 1191 C ALA A 302 166.625 43.070 −14.231 1.00 70.80 C
ANISOU 1191 C ALA A 302 8188 12861 5850 1248 −879 1291 C
ATOM 1192 O ALA A 302 167.625 42.392 −13.972 1.00 74.53 O
ANISOU 1192 O ALA A 302 8783 13150 6385 1193 −834 878 O

TABLE 8-continued

DMXAA-hSTING$^{S162A/Q266I}$ complex

| | |
|---|---|
| ATOM 1148 OE2 GLU A 296 166.229 33.353 −6.326 1.00 97.34 O | ATOM 1193 N PRO A 303 166.634 44.132 −15.069 1.00 71.39 N |
| ANISOU 1148 OE2 GLU A 296 13429 10562 12994 111 1043 −972 O | ANISOU 1193 N PRO A 303 8201 13288 5636 1407 −700 1761 N |
| ATOM 1149 C GLU A 296 162.976 36.919 −7.297 1.00 46.31 C | ATOM 1194 CA PRO A 303 167.805 44.523 −15.875 1.00 69.71 C |
| ANISOU 1149 C GLU A 296 6070 6000 5523 −168 96 −1116 C | ANISOU 1194 CA PRO A 303 8039 13353 5093 1491 −448 1817 C |
| ATOM 1150 O GLU A 296 163.712 36.994 −8.284 1.00 48.13 O | ATOM 1195 CB PRO A 303 167.345 45.822 −16.560 1.00 71.25 C |
| ANISOU 1150 O GLU A 296 6325 6162 5801 −86 225 −1130 O | ANISOU 1195 CB PRO A 303 8156 13829 5086 1648 −295 2496 C |
| ATOM 1151 N ASP A 297 161.640 36.990 −7.369 1.00 47.82 N | ATOM 1196 CG PRO A 303 165.861 45.739 −16.581 1.00 71.68 C |
| ANISOU 1151 N ASP A 297 6154 6628 5386 −454 3 −1231 N | ANISOU 1196 CG PRO A 303 8070 14021 5145 1697 −587 2651 C |
| ATOM 1152 CA ASP A 297 160.923 37.217 −8.638 1.00 50.39 C | ATOM 1197 CD PRO A 303 165.493 45.044 −15.291 1.00 70.35 C |
| ANISOU 1152 CA ASP A 297 6344 7454 5350 −698 9 −1363 C | ANISOU 1197 CD PRO A 303 7928 13327 5475 1535 −721 2318 C |
| ATOM 1153 CB ASP A 297 159.400 37.170 −8.459 1.00 50.69 C | ATOM 1198 C PRO A 303 169.083 44.777 −15.055 1.00 67.25 C |
| ANISOU 1153 CB ASP A 297 6241 7960 5060 −1026 −107 −1453 C | ANISOU 1198 C PRO A 303 7842 12600 5111 1410 −138 1739 C |
| ATOM 1154 CG ASP A 297 158.896 35.804 −8.014 1.00 73.14 C | ATOM 1199 O PRO A 303 170.195 44.509 −15.517 1.00 65.10 O |
| ANISOU 1154 CG ASP A 297 9369 10592 7828 −1394 81 −1705 C | ANISOU 1199 O PRO A 303 7583 12539 4613 1427 −6 1529 O |
| ATOM 1155 OD1 ASP A 297 159.731 34.867 −7.957 1.00 84.86 O | ATOM 1200 N GLU A 304 168.935 45.280 −13.836 1.00 70.91 N |
| ANISOU 1155 OD1 ASP A 297 11169 11568 9506 −1397 338 −1809 O | ANISOU 1200 N GLU A 304 8368 12494 6082 1329 −25 1896 N |
| ATOM 1156 OD2 ASP A 297 157.669 35.675 −7.726 1.00 76.13 O | ATOM 1201 CA GLU A 304 170.113 45.624 −13.039 1.00 74.00 C |
| ANISOU 1156 OD2 ASP A 297 9644 11300 7981 −1670 0 −1779 O | ANISOU 1201 CA GLU A 304 8852 12493 6770 1220 245 1853 C |
| ATOM 1157 C ASP A 297 161.314 38.537 −9.304 1.00 48.34 C | ATOM 1202 CB GLU A 304 169.828 46.825 −12.130 1.00 75.99 C |
| ANISOU 1157 C ASP A 297 5792 7451 5123 −397 −134 −1150 C | ANISOU 1202 CB GLU A 304 9194 12251 7426 1184 449 2274 C |
| ATOM 1158 O ASP A 297 161.571 38.602 −10.511 1.00 52.73 O | ATOM 1203 CG GLU A 304 169.240 48.018 −12.858 1.00 79.46 C |
| ANISOU 1158 O ASP A 297 6333 8175 5528 −447 −36 −1207 O | ANISOU 1203 CG GLU A 304 9626 12857 7709 1328 575 2870 C |
| ATOM 1159 N ILE A 298 161.387 39.589 −8.505 1.00 39.96 N | ATOM 1204 CD GLU A 304 167.710 48.036 −12.830 1.00 83.04 C |
| ANISOU 1159 N ILE A 298 4514 6401 4268 −87 −336 −910 N | ANISOU 1204 CD GLU A 304 9999 13366 8186 1484 367 3052 C |
| ATOM 1160 CA ILE A 298 161.789 40.874 −9.045 1.00 40.43 C | ATOM 1205 OE1 GLU A 304 167.122 49.101 −13.131 1.00 88.63 O |
| ANISOU 1160 CA ILE A 298 4297 6639 4424 220 −427 −694 C | ANISOU 1205 OE1 GLU A 304 10717 14081 8879 1651 482 3577 O |
| ATOM 1161 CB ILE A 298 161.742 41.994 −7.997 1.00 39.00 C | ATOM 1206 OE2 GLU A 304 167.099 46.993 −12.501 1.00 79.39 O |
| ANISOU 1161 CB ILE A 298 3913 6447 4493 504 −606 −476 C | ANISOU 1206 OE2 GLU A 304 9454 12942 7769 1440 90 2694 O |
| ATOM 1162 CG1 ILE A 298 160.319 42.281 −7.556 1.00 34.56 C | ATOM 1207 C GLU A 304 170.670 44.451 −12.221 1.00 68.28 C |
| ANISOU 1162 CG1 ILE A 298 3161 6268 3701 338 −716 −453 C | ANISOU 1207 C GLU A 304 8174 11504 6264 1118 122 1291 C |
| ATOM 1163 CD1 ILE A 298 160.329 43.195 −6.333 1.00 33.00 C | ATOM 1208 O GLU A 304 171.841 44.433 −11.856 1.00 67.78 O |
| ANISOU 1163 CD1 ILE A 298 2913 5849 3776 549 −784 −284 C | ANISOU 1208 O GLU A 304 8133 11318 6305 1054 294 1152 O |
| ATOM 1164 CG2 ILE A 298 162.329 43.278 −8.543 1.00 39.22 C | ATOM 1209 N SER A 305 169.835 43.466 −11.943 1.00 67.66 N |
| ANISOU 1164 CG2 ILE A 298 3675 6540 4688 837 −632 −261 C | ANISOU 1209 N SER A 305 8097 11353 6257 1096 −185 995 N |
| ATOM 1165 C ILE A 298 163.187 40.777 −9.625 1.00 43.20 C | ATOM 1210 CA SER A 305 170.188 42.474 −10.938 1.00 71.97 C |
| ANISOU 1165 C ILE A 298 4776 6627 5011 430 −282 −672 C | ANISOU 1210 CA SER A 305 8719 11517 7108 996 −299 569 C |
| ATOM 1166 O ILE A 298 163.429 41.230 −10.741 1.00 49.83 O | ATOM 1211 CB SER A 305 169.003 42.234 −10.016 1.00 79.79 C |
| ANISOU 1166 O ILE A 298 5504 7665 5762 497 −225 −625 O | ANISOU 1211 CB SER A 305 9711 12186 8418 903 −485 612 C |
| ATOM 1167 N LEU A 299 164.095 40.162 −8.875 1.00 40.86 N | ATOM 1212 OG SER A 305 167.880 41.779 −10.757 1.00 87.03 O |
| ANISOU 1167 N LEU A 299 4700 5815 5011 537 −212 −679 N | ANISOU 1212 OG SER A 305 10539 13421 9109 912 −765 599 O |
| ATOM 1168 CA LEU A 299 165.474 40.075 −9.302 1.00 43.31 C | ATOM 1213 C SER A 305 170.575 41.152 −11.553 1.00 71.29 C |
| ANISOU 1168 CA LEU A 299 5104 5745 5607 766 −68 −614 C | ANISOU 1213 C SER A 305 8667 11648 6772 1045 −510 49 C |
| ATOM 1169 CB LEU A 299 166.409 39.644 −8.171 1.00 40.43 C | ATOM 1214 O SER A 305 170.432 40.095 −10.917 1.00 67.98 O |
| ANISOU 1169 CB LEU A 299 4873 4880 5608 946 −69 −513 C | ANISOU 1214 O SER A 305 8330 10936 6565 974 −724 −309 O |
| ATOM 1170 CG LEU A 299 166.555 40.632 −7.013 1.00 44.72 C | ATOM 1215 N GLN A 306 171.025 41.204 −12.804 1.00 69.49 N |
| ANISOU 1170 CG LEU A 299 5211 5427 6354 1178 −331 −324 C | ANISOU 1215 N GLN A 306 8395 11927 6081 1178 −452 13 N |
| ATOM 1216 CA GLN A 306 171.371 39.991 −13.510 1.00 74.70 C | ATOM 1261 CD1 LEU A 311 166.665 37.238 −3.148 1.00 43.00 C |
| ANISOU 1216 CA GLN A 306 9120 12824 6439 1279 −641 −517 C | ANISOU 1261 CD1 LEU A 311 5309 5345 5682 4 −1410 −196 C |
| ATOM 1217 CB GLN A 306 171.060 40.120 −15.009 1.00 83.63 C | ATOM 1262 CD2 LEU A 311 168.652 38.614 −2.408 1.00 36.53 C |
| ANISOU 1217 CB GLN A 306 10194 14604 6977 1402 −700 −472 C | ANISOU 1262 CD2 LEU A 311 4612 4360 4909 225 −924 −149 C |
| ATOM 1218 CG GLN A 306 170.159 39.016 −15.601 1.00 89.94 C | ATOM 1263 C LEU A 311 170.442 34.929 −0.897 1.00 43.86 C |
| ANISOU 1218 CG GLN A 306 11074 15559 7538 1376 −1117 −882 C | ANISOU 1263 C LEU A 311 5921 4486 6259 171 −1428 −970 C |
| ATOM 1219 CD GLN A 306 168.741 38.993 −15.019 1.00 91.37 C | ATOM 1264 O LEU A 311 170.256 33.767 −1.315 1.00 37.66 O |
| ANISOU 1219 CD GLN A 306 11211 15496 8010 1169 −1387 −705 C | ANISOU 1264 O LEU A 311 5252 3566 5489 145 −1682 −1213 O |
| ATOM 1220 OE1 GLN A 306 168.349 39.872 −14.244 1.00 90.84 O | ATOM 1265 N ILE A 312 170.839 35.201 0.336 1.00 37.83 N |
| ANISOU 1220 OE1 GLN A 306 11053 15185 8277 1104 −1243 −637 O | ANISOU 1265 N ILE A 312 5161 3549 5664 153 −1309 −832 N |
| ATOM 1221 NE2 GLN A 306 167.973 37.967 −15.381 1.00 91.36 N | ATOM 1266 CA ILE A 312 171.115 34.122 1.269 1.00 43.01 C |
| ANISOU 1221 NE2 GLN A 306 11274 15561 7879 1060 −1780 −1074 N | ANISOU 1266 CA ILE A 312 5937 3877 6528 126 −1465 −916 C |
| ATOM 1222 C GLN A 306 172.848 39.714 −13.257 1.00 78.44 C | ATOM 1267 CB ILE A 312 172.530 34.254 1.828 1.00 48.67 C |
| ANISOU 1222 C GLN A 306 9604 13240 6958 1378 −427 −757 C | ANISOU 1267 CB ILE A 312 6657 4574 7260 288 −1343 −1000 C |
| ATOM 1223 O GLN A 306 173.719 40.409 −13.786 1.00 82.44 O | ATOM 1268 CG1 ILE A 312 173.509 34.573 0.700 1.00 52.31 C |
| ANISOU 1223 O GLN A 306 10002 14080 7242 1461 −138 −557 O | ANISOU 1268 CG1 ILE A 312 7056 5312 7506 482 −1236 −1203 C |
| ATOM 1224 N ASN A 307 173.101 38.736 −12.388 1.00 75.88 N | ATOM 1269 CD1 ILE A 312 174.946 34.652 1.145 1.00 54.27 C |
| ANISOU 1224 N ASN A 307 9388 12494 6947 1359 −565 −1130 N | ANISOU 1269 CD1 ILE A 312 7241 5620 7759 636 −1130 −1283 C |
| ATOM 1225 CA ASN A 307 174.433 38.186 −12.151 1.00 74.32 C | ATOM 1270 CG2 ILE A 312 172.941 33.002 2.567 1.00 45.06 C |
| ANISOU 1225 CA ASN A 307 9194 12258 6787 1509 −436 −1437 C | ANISOU 1270 CG2 ILE A 312 6335 3799 6986 339 −1534 −1105 C |
| ATOM 1226 CB ASN A 307 175.174 38.001 −13.470 1.00 81.17 C | ATOM 1271 C ILE A 312 170.066 34.093 2.394 1.00 34.28 C |
| ANISOU 1226 CB ASN A 307 10003 13720 7116 1759 −317 −1637 C | ANISOU 1271 C ILE A 312 4810 2616 5601 −81 −1495 −630 C |
| ATOM 1227 CG ASN A 307 175.782 36.638 −13.600 1.00 89.46 C | ATOM 1272 O ILE A 312 170.191 34.790 3.396 1.00 37.23 O |
| ANISOU 1227 CG ASN A 307 11186 14716 8089 1999 −448 −2242 C | ANISOU 1272 O ILE A 312 5142 2987 6018 −92 −1322 −441 O |
| ATOM 1228 OD1 ASN A 307 176.499 36.179 −12.702 1.00 88.33 O | ATOM 1273 N ALA A 313 169.027 33.298 2.205 1.00 35.64 N |
| ANISOU 1228 OD1 ASN A 307 11055 14235 8272 2055 −415 −2396 O | ANISOU 1273 N ALA A 313 5001 2687 5855 −257 −1714 −604 N |
| ATOM 1229 ND2 ASN A 307 175.494 35.962 −14.720 1.00 95.35 N | ATOM 1274 CA ALA A 313 167.946 33.153 3.187 1.00 40.07 C |
| ANISOU 1229 ND2 ASN A 307 12050 15790 8388 2163 −611 −2605 N | ANISOU 1274 CA ALA A 313 5495 3158 6571 −476 −1748 −305 C |
| ATOM 1230 C ASN A 307 175.333 38.936 −11.166 1.00 67.14 C | ATOM 1275 CB ALA A 313 166.599 32.963 2.504 1.00 36.67 C |
| ANISOU 1230 C ASN A 307 8170 11138 6202 1425 −164 −1174 C | ANISOU 1275 CB ALA A 313 4940 2871 6122 −681 −1903 −210 C |
| ATOM 1231 O ASN A 307 176.548 38.716 −11.142 1.00 71.83 O | ATOM 1276 C ALA A 313 168.244 31.939 4.035 1.00 44.56 C |
| ANISOU 1231 O ASN A 307 8675 11863 6754 1559 −5 −1330 O | ANISOU 1276 C ALA A 313 6224 3369 7340 −546 −1918 −330 C |

TABLE 8-continued

DMXAA-hSTING$^{S162A/Q266I}$ complex

| ATOM 1232 N ASN A 308 174.765 39.826 −10.366 1.00 56.85 N
| ANISOU 1232 N ASN A 308 6860 9537 5203 1214 −109 −787 N
| ATOM 1233 CA ASN A 308 175.606 40.594 −9.445 1.00 53.96 C
| ANISOU 1233 CA ASN A 308 6416 8969 5119 1094 127 −565 C
| ATOM 1234 CB ASN A 308 175.910 41.994 −9.994 1.00 59.55 C
| ANISOU 1234 CB ASN A 308 7011 9941 5674 1012 420 −105 C
| ATOM 1235 CG ASN A 308 174.704 42.639 −10.584 1.00 61.09 C
| ANISOU 1235 CG ASN A 308 7257 10219 5737 996 376 213 C
| ATOM 1236 OD1 ASN A 308 173.589 42.204 −10.310 1.00 53.33 O
| ANISOU 1236 OD1 ASN A 308 6362 9039 4861 989 140 139 O
| ATOM 1237 ND2 ASN A 308 174.908 43.650 −11.438 1.00 71.64 N
| ANISOU 1237 ND2 ASN A 308 8515 11883 6821 995 596 596 N
| ATOM 1238 C ASN A 308 175.049 40.689 −8.039 1.00 51.21 C
| ANISOU 1238 C ASN A 308 6164 8077 5217 921 38 −481 C
| ATOM 1239 O ASN A 308 175.435 41.566 −7.259 1.00 49.27 O
| ANISOU 1239 O ASN A 308 5892 7634 5193 775 213 −241 O
| ATOM 1240 N CYS A 309 174.164 39.753 −7.715 1.00 42.56 N
| ANISOU 1240 N CYS A 309 5184 6749 4238 923 −240 −695 N
| ATOM 1241 CA CYS A 309 173.419 39.797 −6.488 1.00 44.26 C
| ANISOU 1241 CA CYS A 309 5475 6528 4815 771 −329 −583 C
| ATOM 1242 CB CYS A 309 172.133 40.566 −6.713 1.00 48.09 C
| ANISOU 1242 CB CYS A 309 5948 7047 5277 706 −337 −246 C
| ATOM 1243 SG CYS A 309 171.250 40.861 −5.210 1.00 94.69 S
| ANISOU 1243 SG CYS A 309 11906 12496 11578 564 −358 −51 S
| ATOM 1244 C CYS A 309 173.094 38.377 −6.118 1.00 46.10 C
| ANISOU 1244 C CYS A 309 5816 6531 5171 787 −620 −933 C
| ATOM 1245 O CYS A 309 172.869 37.543 −6.983 1.00 47.55 O
| ANISOU 1245 O CYS A 309 6050 6873 5145 876 −803 −1201 O
| ATOM 1246 N ARG A 310 173.060 38.088 −4.825 1.00 37.20 N
| ANISOU 1246 N ARG A 310 4746 5016 4373 690 −672 −934 N
| ATOM 1247 CA ARG A 310 172.754 36.741 −4.418 1.00 41.58 C
| ANISOU 1247 CA ARG A 310 5424 5299 5077 681 −945 −1209 C
| ATOM 1248 CB ARG A 310 174.015 35.890 −4.344 1.00 49.83 C
| ANISOU 1248 CB ARG A 310 6514 6291 6127 865 −962 −1535 C
| ATOM 1249 CG ARG A 310 173.741 34.397 −4.368 1.00 68.20 C
| ANISOU 1249 CG ARG A 310 9028 8351 8535 917 −1263 −1877 C
| ATOM 1250 CD ARG A 310 173.191 33.945 −5.714 1.00 88.72 C
| ANISOU 1250 CD ARG A 310 11699 11170 10840 965 −1422 −2111 C
| ATOM 1251 NE ARG A 310 173.214 32.487 −5.889 1.00 101.67 N
| ANISOU 1251 NE ARG A 310 13571 12532 12527 1052 −1696 −2532 N
| ATOM 1252 CZ ARG A 310 172.302 31.656 −5.385 1.00 105.52 C
| ANISOU 1252 CZ ARG A 310 14216 12622 13254 841 −1976 −2573 C
| ATOM 1253 NH1 ARG A 310 172.402 30.347 −5.594 1.00 106.99 N
| ANISOU 1253 NH1 ARG A 310 14661 12497 13495 919 −2224 −2968 N
| ATOM 1254 NH2 ARG A 310 171.293 32.141 −4.667 1.00 105.33 N
| ANISOU 1254 NH2 ARG A 310 14093 12507 13420 556 −1998 −2211 N
| ATOM 1255 C ARG A 310 172.080 36.798 −3.082 1.00 42.01 C
| ANISOU 1255 C ARG A 310 5509 5006 5448 507 −988 −1013 C
| ATOM 1256 O ARG A 310 172.563 37.443 −2.165 1.00 42.68 O
| ANISOU 1256 O ARG A 310 5565 4976 5675 471 −818 −858 O
| ATOM 1257 N LEU A 311 170.944 36.124 −2.980 1.00 49.64 N
| ANISOU 1257 N LEU A 311 6524 5835 6503 281 −1219 −1020 N
| ATOM 1258 CA LEU A 311 170.134 36.148 −1.765 1.00 44.50 C
| ANISOU 1258 CA LEU A 311 5868 4925 6116 212 −1251 −795 C
| ATOM 1259 CB LEU A 311 168.637 36.143 −2.092 1.00 37.98 C
| ANISOU 1259 CB LEU A 311 4954 4208 5270 65 −1393 −623 C
| ATOM 1260 CG LEU A 311 168.190 37.285 −2.987 1.00 43.55 C
| ANISOU 1260 CG LEU A 311 5524 5275 5749 139 −1251 −402 C
| ATOM 1306 C GLU A 316 167.375 28.572 13.332 1.00 101.68 C
| ANISOU 1306 C GLU A 316 14116 9026 15494 −2022 1426 1843 C
| ATOM 1307 O GLU A 316 166.288 28.880 13.842 1.00 104.26 O
| ANISOU 1307 O GLU A 316 14121 9455 16037 −2452 1838 1847 O
| ATOM 1308 N PRO A 317 167.854 27.316 13.325 1.00 111.81 N
| ANISOU 1308 N PRO A 317 15956 9825 16699 −1874 1288 2226 N
| ATOM 1309 CA PRO A 317 167.211 26.354 14.219 1.00 125.33 C
| ANISOU 1309 CA PRO A 317 17979 11174 18466 −2222 1743 2748 C
| ATOM 1310 CB PRO A 317 168.072 25.093 14.059 1.00 125.43 C
| ANISOU 1310 CB PRO A 317 18710 10650 18296 −1846 1527 3136 C
| ATOM 1311 CG PRO A 317 168.716 25.239 12.711 1.00 117.18 C
| ANISOU 1311 CG PRO A 317 17599 9496 17428 −1499 899 2694 C
| ATOM 1312 CD PRO A 317 168.969 26.714 12.569 1.00 109.55 C
| ANISOU 1312 CD PRO A 317 16073 9295 16255 −1367 781 2239 C
| ATOM 1313 C PRO A 317 167.332 26.926 15.629 1.00 133.53 C
| ANISOU 1313 C PRO A 317 18966 12907 18863 −2172 2175 2994 C
| ATOM 1314 O PRO A 317 168.434 27.300 16.040 1.00 131.52 O
| ANISOU 1314 O PRO A 317 18840 13203 17929 −1687 2036 3000 O
| ATOM 1315 N ALA A 318 166.212 27.045 16.337 1.00 142.34 N
| ANISOU 1315 N ALA A 318 19828 14085 20169 −2663 2681 3133 N
| ATOM 1277 O ALA A 313 168.694 30.915 3.525 1.00 47.39 O
| ANISOU 1277 O ALA A 313 6712 3617 7676 −475 −2048 −556 O
| ATOM 1278 N TYR A 314 167.988 32.060 5.328 1.00 45.45 N
| ANISOU 1278 N TYR A 314 6282 3478 7510 −610 −1796 −51 N
| ATOM 1279 CA TYR A 314 168.285 30.983 6.261 1.00 47.66 C
| ANISOU 1279 CA TYR A 314 6647 3625 7835 −612 −1836 13 C
| ATOM 1280 CB TYR A 314 169.755 30.980 6.672 1.00 40.06 C
| ANISOU 1280 CB TYR A 314 5761 2650 6809 −368 −1746 −126 C
| ATOM 1281 CG TYR A 314 170.206 32.304 7.203 1.00 36.63 C
| ANISOU 1281 CG TYR A 314 5247 2377 6292 −290 −1530 −61 C
| ATOM 1282 CD1 TYR A 314 170.550 33.345 6.335 1.00 32.71 C
| ANISOU 1282 CD1 TYR A 314 4711 1987 5729 −201 −1435 −202 C
| ATOM 1283 CE1 TYR A 314 170.970 34.590 6.849 1.00 34.97 C
| ANISOU 1283 CE1 TYR A 314 4954 2379 5953 −155 −1229 −140 C
| ATOM 1284 CZ TYR A 314 171.022 34.767 8.242 1.00 36.24 C
| ANISOU 1284 CZ TYR A 314 5122 2551 6098 −194 −1139 28 C
| ATOM 1285 OH TYR A 314 171.443 35.969 8.763 1.00 43.14 O
| ANISOU 1285 OH TYR A 314 5986 3525 6882 −168 −943 45 O
| ATOM 1286 CE2 TYR A 314 170.695 33.737 9.100 1.00 28.94 C
| ANISOU 1286 CE2 TYR A 314 4227 1547 5222 −263 −1245 165 C
| ATOM 1287 CD2 TYR A 314 170.300 32.523 8.589 1.00 35.45 C
| ANISOU 1287 CD2 TYR A 314 5084 2255 6128 −314 −1429 136 C
| ATOM 1288 C TYR A 314 167.415 31.118 7.484 1.00 46.93 C
| ANISOU 1288 C TYR A 314 6455 3581 7795 −780 −1758 363 C
| ATOM 1289 O TYR A 314 167.003 32.212 7.843 1.00 50.49 O
| ANISOU 1289 O TYR A 314 6789 4179 8215 −795 −1594 529 O
| ATOM 1290 N GLN A 315 167.104 29.993 8.106 1.00 72.93 N
| ANISOU 1290 N GLN A 315 9353 5038 13321 −1300 −20 237 N
| ATOM 1291 CA GLN A 315 166.370 30.034 9.351 1.00 75.77 C
| ANISOU 1291 CA GLN A 315 9664 5509 13614 −1762 501 463 C
| ATOM 1292 CB GLN A 315 165.041 29.320 9.196 1.00 77.06 C
| ANISOU 1292 CB GLN A 315 9599 5350 14329 −2268 642 439 C
| ATOM 1293 CG GLN A 315 163.916 29.937 9.984 1.00 80.01 C
| ANISOU 1293 CG GLN A 315 9559 6063 14779 −2675 1166 437 C
| ATOM 1294 CD GLN A 315 162.566 29.411 9.522 1.00 87.78 C
| ANISOU 1294 CD GLN A 315 10152 6953 16248 −3095 1214 249 C
| ATOM 1295 OE1 GLN A 315 162.462 28.804 8.454 1.00 89.01 O
| ANISOU 1295 OE1 GLN A 315 10277 6914 16631 −3004 820 5 O
| ATOM 1296 NE2 GLN A 315 161.528 29.636 10.320 1.00 91.88 N
| ANISOU 1296 NE2 GLN A 315 10372 7766 16774 −3495 1667 326 N
| ATOM 1297 C GLN A 315 167.216 29.388 10.436 1.00 77.20 C
| ANISOU 1297 C GLN A 315 10394 5661 13279 −1721 605 907 C
| ATOM 1298 O GLN A 315 167.675 28.263 10.282 1.00 74.85 O
| ANISOU 1298 O GLN A 315 10546 4932 12963 −1620 381 1147 O
| ATOM 1299 N GLU A 316 167.457 30.132 11.509 1.00 80.87 N
| ANISOU 1299 N GLU A 316 10823 6621 13281 −1734 948 991 N
| ATOM 1300 CA GLU A 316 168.211 29.620 12.635 1.00 88.80 C
| ANISOU 1300 CA GLU A 316 12265 7785 13689 −1626 1087 1399 C
| ATOM 1301 CB GLU A 316 168.551 30.746 13.615 1.00 90.73 C
| ANISOU 1301 CB GLU A 316 12319 8744 13408 −1582 1392 1274 C
| ATOM 1302 CG GLU A 316 169.971 31.293 13.482 1.00 92.92 C
| ANISOU 1302 CG GLU A 316 12718 9460 13169 −1139 1113 1055 C
| ATOM 1303 CD GLU A 316 170.120 32.722 13.990 1.00 94.83 C
| ANISOU 1303 CD GLU A 316 12575 10300 13158 −1201 1393 655 C
| ATOM 1304 OE1 GLU A 316 170.648 32.911 15.113 1.00 96.96 O
| ANISOU 1304 OE1 GLU A 316 12906 11124 12812 −1159 1597 701 O
| ATOM 1305 OE2 GLU A 316 169.708 33.650 13.253 1.00 93.08 O
| ANISOU 1305 OE2 GLU A 316 12032 9995 13340 −1260 1428 283 O
| ATOM 1351 CG PHE A 323 172.947 28.556 11.936 1.00 70.29 C
| ANISOU 1351 CG PHE A 323 11023 6043 9641 184 −205 1599 C
| ATOM 1352 CD1 PHE A 323 172.712 28.110 10.641 1.00 67.70 C
| ANISOU 1352 CD1 PHE A 323 10726 5123 9873 246 −568 1471 C
| ATOM 1353 CE1 PHE A 323 172.631 29.006 9.570 1.00 59.38 C
| ANISOU 1353 CE1 PHE A 323 9249 4136 9175 265 −772 1009 C
| ATOM 1354 CZ PHE A 323 172.771 30.375 9.798 1.00 62.30 C
| ANISOU 1354 CZ PHE A 323 9216 5056 9400 178 −560 686 C
| ATOM 1355 CE2 PHE A 323 173.011 30.842 11.096 1.00 65.39 C
| ANISOU 1355 CE2 PHE A 323 9582 5985 9278 45 −196 744 C
| ATOM 1356 CD2 PHE A 323 173.095 29.925 12.158 1.00 68.69 C
| ANISOU 1356 CD2 PHE A 323 10368 6443 9288 68 −44 1193 C
| ATOM 1357 C PHE A 323 175.533 28.080 12.976 1.00 75.85 C
| ANISOU 1357 C PHE A 323 12197 7910 8711 1201 −509 1891 C
| ATOM 1358 O PHE A 323 175.892 28.894 13.833 1.00 73.30 O
| ANISOU 1358 O PHE A 323 11597 8366 7887 1150 −290 1703 O
| ATOM 1359 N SER A 324 176.028 28.060 11.741 1.00 70.66 N
| ANISOU 1359 N SER A 324 11514 7051 8282 1449 −962 1660 N
| ATOM 1360 CA SER A 324 177.138 28.903 11.332 1.00 63.86 C
| ANISOU 1360 CA SER A 324 10344 6870 7051 1710 −1221 1250 C

TABLE 8-continued

DMXAA-hSTING$^{S162A/Q266I}$ complex

| ATOM 1316 CA ALA A 318 166.219 27.644 17.666 1.00 147.02 C |
| ANISOU 1316 CA ALA A 318 20308 15393 20159 −2616 3102 3313 C |
| ATOM 1317 CB ALA A 318 164.836 28.172 18.023 1.00 147.57 C |
| ANISOU 1317 CB ALA A 318 19861 15613 20597 −3171 3542 3204 C |
| ATOM 1318 C ALA A 318 166.688 26.626 18.700 1.00 156.57 C |
| ANISOU 1318 C ALA A 318 22116 16552 20821 −2372 3386 4024 C |
| ATOM 1319 O ALA A 318 166.961 26.975 19.850 1.00 158.12 O |
| ANISOU 1319 O ALA A 318 22304 17435 20340 −2159 3679 4226 O |
| ATOM 1320 N ASP A 319 166.787 25.368 18.272 1.00 162.56 N |
| ANISOU 1320 N ASP A 319 23408 16500 21857 −2356 3315 4390 N |
| ATOM 1321 CA ASP A 319 167.133 24.256 19.159 1.00 170.73 C |
| ANISOU 1321 CA ASP A 319 25117 17297 22453 −2091 3663 5160 C |
| ATOM 1322 CB ASP A 319 166.742 22.906 18.525 1.00 177.95 C |
| ANISOU 1322 CB ASP A 319 26548 17039 24027 −2367 3723 5461 C |
| ATOM 1323 CG ASP A 319 167.491 22.611 17.219 1.00 175.99 C |
| ANISOU 1323 CG ASP A 319 26501 16351 24018 −2054 3064 5102 C |
| ATOM 1324 OD1 ASP A 319 168.713 22.851 17.129 1.00 174.11 O |
| ANISOU 1324 OD1 ASP A 319 26418 16579 23159 −1362 2666 5038 O |
| ATOM 1325 OD2 ASP A 319 166.853 22.120 16.267 1.00 176.59 O |
| ANISOU 1325 OD2 ASP A 319 26437 15833 24826 −2471 2804 4754 O |
| ATOM 1326 C ASP A 319 168.606 24.238 19.578 1.00 168.61 C |
| ANISOU 1326 C ASP A 319 25204 17617 21242 −1243 3412 5333 C |
| ATOM 1327 O ASP A 319 168.931 23.928 20.726 1.00 174.27 O |
| ANISOU 1327 O ASP A 319 26214 18751 21249 −883 3772 5871 O |
| ATOM 1328 N ASP A 320 169.492 24.551 18.635 1.00 159.54 N |
| ANISOU 1328 N ASP A 320 24000 16563 20054 −895 2802 4880 N |
| ATOM 1329 CA ASP A 320 170.930 24.506 18.886 1.00 153.95 C |
| ANISOU 1329 CA ASP A 320 23562 16464 18468 −98 2506 4968 C |
| ATOM 1330 CB ASP A 320 171.624 23.423 18.025 1.00 152.48 C |
| ANISOU 1330 CB ASP A 320 23981 15572 18384 326 2132 5172 C |
| ATOM 1331 CG ASP A 320 171.911 23.883 16.582 1.00 143.02 C |
| ANISOU 1331 CG ASP A 320 22484 14190 17669 285 1511 4509 C |
| ATOM 1332 OD2 ASP A 320 171.357 23.301 15.624 1.00 142.07 O |
| ANISOU 1332 OD2 ASP A 320 22497 13172 18311 −16 1371 4423 O |
| ATOM 1333 OD1 ASP A 320 172.719 24.809 16.391 1.00 136.60 O |
| ANISOU 1333 OD1 ASP A 320 21301 14145 16457 565 1174 4062 O |
| ATOM 1334 C ASP A 320 171.556 25.870 18.638 1.00 144.58 C |
| ANISOU 1334 C ASP A 320 21780 16152 16999 12 2148 4254 C |
| ATOM 1335 O ASP A 320 170.948 26.746 18.017 1.00 140.48 O |
| ANISOU 1335 O ASP A 320 20756 15569 17052 −444 2063 3718 O |
| ATOM 1336 N SER A 321 172.787 26.036 19.108 1.00 142.06 N |
| ANISOU 1336 N SER A 321 21528 16660 15788 637 1965 4243 N |
| ATOM 1337 CA SER A 321 173.571 27.213 18.762 1.00 133.22 C |
| ANISOU 1337 CA SER A 321 19909 16298 14411 741 1610 3539 C |
| ATOM 1338 CB SER A 321 174.093 27.920 20.014 1.00 133.33 C |
| ANISOU 1338 CB SER A 321 19640 17496 13523 952 1830 3402 C |
| ATOM 1339 OG SER A 321 173.207 28.952 20.409 1.00 130.98 O |
| ANISOU 1339 OG SER A 321 18855 17395 13516 393 2161 3037 O |
| ATOM 1340 C SER A 321 174.722 26.849 17.826 1.00 129.19 C |
| ANISOU 1340 C SER A 321 19611 15745 13732 1257 1044 3423 C |
| ATOM 1341 O SER A 321 175.621 27.658 17.589 1.00 126.90 O |
| ANISOU 1341 O SER A 321 18977 16155 13086 1443 751 2916 O |
| ATOM 1342 N SER A 322 174.682 25.629 17.294 1.00 127.09 N |
| ANISOU 1342 N SER A 322 19911 14642 13735 1466 922 3875 N |
| ATOM 1343 CA SER A 322 175.718 25.141 16.384 1.00 119.83 C |
| ANISOU 1343 CA SER A 322 19257 13615 12658 2015 392 3822 C |
| ATOM 1344 CB SER A 322 175.543 23.643 16.114 1.00 123.71 C |
| ANISOU 1344 CB SER A 322 20507 13113 13383 2257 421 4431 C |
| ATOM 1345 OG SER A 322 176.138 23.283 14.879 1.00 119.94 O |
| ANISOU 1345 OG SER A 322 20193 12251 13129 2567 −117 4225 O |
| ATOM 1346 C SER A 322 175.757 25.889 15.053 1.00 107.81 C |
| ANISOU 1346 C SER A 322 17317 11916 11730 1778 −37 3178 C |
| ATOM 1347 O SER A 322 176.824 25.979 14.440 1.00 105.30 O |
| ANISOU 1347 O SER A 322 16973 11947 11090 2232 −477 2955 O |
| ATOM 1348 N PHE A 323 174.606 26.410 14.615 1.00 98.66 N |
| ANISOU 1348 N PHE A 323 15823 10275 11387 1123 112 2907 N |
| ATOM 1349 CA PHE A 323 174.464 27.016 13.283 1.00 85.21 C |
| ANISOU 1349 CA PHE A 323 13767 8303 10304 949 −239 2382 C |
| ATOM 1350 CB PHE A 323 173.048 27.578 13.075 1.00 79.20 C |
| ANISOU 1350 CB PHE A 323 12605 7142 10303 278 44 2161 C |
| ATOM 1361 CB SER A 324 178.307 28.020 10.908 1.00 67.94 C |
| ANISOU 1361 CB SER A 324 11211 7520 7081 2386 −1677 1442 C |
| ATOM 1362 OG SER A 324 179.476 28.775 10.702 1.00 72.60 O |
| ANISOU 1362 OG SER A 324 11475 8924 7184 2630 −1883 1072 O |
| ATOM 1363 C SER A 324 176.702 29.772 10.168 1.00 60.64 C |
| ANISOU 1363 C SER A 324 9548 6175 7317 1472 −1319 819 C |
| ATOM 1364 O SER A 324 176.383 29.270 9.103 1.00 54.58 O |
| ANISOU 1364 O SER A 324 8884 4817 7038 1580 −1605 840 O |
| ATOM 1365 N LEU A 325 176.675 31.081 10.386 1.00 47.50 N |
| ANISOU 1365 N LEU A 325 3856 5727 8465 −131 1773 752 N |
| ATOM 1366 CA LEU A 325 176.357 32.031 9.330 1.00 49.10 C |
| ANISOU 1366 CA LEU A 325 3824 6036 8795 −152 1371 587 C |
| ATOM 1367 CB LEU A 325 176.217 33.446 9.899 1.00 50.45 C |
| ANISOU 1367 CB LEU A 325 3969 6512 8688 154 1205 504 C |
| ATOM 1368 CG LEU A 325 175.763 34.480 8.860 1.00 54.85 C |
| ANISOU 1368 CG LEU A 325 4345 7186 9311 146 785 376 C |
| ATOM 1369 CD1 LEU A 325 174.428 34.067 8.216 1.00 54.33 C |
| ANISOU 1369 CD1 LEU A 325 3916 7128 9599 −180 656 342 C |
| ATOM 1370 CD2 LEU A 325 175.839 35.875 9.469 1.00 57.04 C |
| ANISOU 1370 CD2 LEU A 325 4649 7699 9323 412 650 272 C |
| ATOM 1371 C LEU A 325 177.473 32.018 8.315 1.00 49.16 C |
| ANISOU 1371 C LEU A 325 4096 5920 8661 −76 1201 539 C |
| ATOM 1372 O LEU A 325 177.245 32.088 7.104 1.00 49.87 O |
| ANISOU 1372 O LEU A 325 4180 5993 8776 −195 793 400 O |
| ATOM 1373 N SER A 326 178.687 31.945 8.849 1.00 49.02 N |
| ANISOU 1373 N SER A 326 4459 5872 8294 188 1432 643 N |
| ATOM 1374 CA SER A 326 179.910 31.837 8.080 1.00 47.68 C |
| ANISOU 1374 CA SER A 326 4747 5620 7748 339 1270 655 C |
| ATOM 1375 CB SER A 326 181.041 31.517 9.038 1.00 52.27 C |
| ANISOU 1375 CB SER A 326 5679 6160 8021 574 1650 806 C |
| ATOM 1376 OG SER A 326 182.081 32.433 8.862 1.00 60.63 O |
| ANISOU 1376 OG SER A 326 6958 7328 8750 794 1356 843 O |
| ATOM 1377 C SER A 326 179.842 30.714 7.057 1.00 48.45 C |
| ANISOU 1377 C SER A 326 5127 5489 7794 100 1092 534 C |
| ATOM 1378 O SER A 326 180.204 30.879 5.895 1.00 52.63 O |
| ANISOU 1378 O SER A 326 5806 6079 8112 194 739 460 O |
| ATOM 1379 N GLN A 327 179.424 29.544 7.524 1.00 49.29 N |
| ANISOU 1379 N GLN A 327 5301 5332 8094 −163 1336 530 N |
| ATOM 1380 CA GLN A 327 179.339 28.352 6.683 1.00 50.98 C |
| ANISOU 1380 CA GLN A 327 5798 5224 8349 −393 1137 352 C |
| ATOM 1381 CB GLN A 327 179.073 27.129 7.544 1.00 49.95 C |
| ANISOU 1381 CB GLN A 327 5721 4746 8513 −646 1512 471 C |
| ATOM 1382 CG GLN A 327 180.305 26.696 8.310 1.00 47.82 C |
| ANISOU 1382 CG GLN A 327 5890 4418 7863 −391 1940 683 C |
| ATOM 1383 CD GLN A 327 181.397 26.178 7.395 1.00 50.32 C |
| ANISOU 1383 CD GLN A 327 6788 4593 7737 −211 1740 546 C |
| ATOM 1384 OE1 GLN A 327 181.153 25.323 6.529 1.00 59.71 O |
| ANISOU 1384 OE1 GLN A 327 8164 5483 9038 −381 1435 297 O |
| ATOM 1385 NE2 GLN A 327 182.602 26.725 7.547 1.00 44.62 N |
| ANISOU 1385 NE2 GLN A 327 6334 4104 6552 168 1868 693 N |
| ATOM 1386 C GLN A 327 178.247 28.488 5.651 1.00 51.53 C |
| ANISOU 1386 C GLN A 327 5553 5313 8713 −627 652 96 C |
| ATOM 1387 O GLN A 327 178.397 28.076 4.500 1.00 54.83 O |
| ANISOU 1387 O GLN A 327 6211 5654 8968 −611 259 −152 O |
| ATOM 1388 N GLU A 328 177.145 29.078 6.081 1.00 55.32 N |
| ANISOU 1388 N GLU A 328 5484 5941 9594 −794 675 147 N |
| ATOM 1389 CA GLU A 328 176.029 29.364 5.194 1.00 60.12 C |
| ANISOU 1389 CA GLU A 328 5706 6634 10502 −1004 227 −65 C |
| ATOM 1390 CB GLU A 328 174.877 30.025 5.956 1.00 65.13 C |
| ANISOU 1390 CB GLU A 328 5718 7465 11563 −1141 381 80 C |
| ATOM 1391 CG GLU A 328 173.598 30.128 5.148 1.00 77.21 C |
| ANISOU 1391 CG GLU A 328 6803 9046 13487 −1426 −46 −110 C |
| ATOM 1392 CD GLU A 328 172.939 28.778 4.916 1.00 92.31 C |
| ANISOU 1392 CD GLU A 328 8683 10537 15856 −1872 −186 −240 C |
| ATOM 1393 OE1 GLU A 328 172.781 28.381 3.737 1.00 96.59 O |
| ANISOU 1393 OE1 GLU A 328 9345 10956 16399 −1973 −703 −588 O |
| ATOM 1394 OE2 GLU A 328 172.578 28.118 5.921 1.00 100.14 O |
| ANISOU 1394 OE2 GLU A 328 9568 11350 17131 −2050 200 18 O |
| ATOM 1395 C GLU A 328 176.491 30.265 4.051 1.00 52.40 C |
| ANISOU 1395 C GLU A 328 4813 5959 9137 −701 −176 −176 C |
| ATOM 1396 O GLU A 328 176.229 30.006 2.885 1.00 62.88 O |
| ANISOU 1396 O GLU A 328 6186 7300 10406 −736 −619 −431 O |
| ATOM 1397 N VAL A 329 177.205 31.318 4.376 1.00 43.86 N |
| ANISOU 1397 N VAL A 329 3734 5127 7803 −369 −40 32 N |
| ATOM 1398 CA VAL A 329 177.678 32.222 3.329 1.00 44.46 C |
| ANISOU 1398 CA VAL A 329 3817 5492 7583 −66 −385 60 C |
| ATOM 1399 CB VAL A 329 178.251 33.510 3.940 1.00 41.13 C |
| ANISOU 1399 CB VAL A 329 3243 5257 7225 225 −239 327 C |
| ATOM 1441 N ARG A 334 180.960 29.365 −2.673 1.00 73.05 N |
| ANISOU 1441 N ARG A 334 9408 9770 8576 1503 −1846 −642 N |
| ATOM 1442 CA ARG A 334 181.733 28.398 −3.435 1.00 75.97 C |
| ANISOU 1442 CA ARG A 334 10320 10181 8364 1898 −2009 −864 C |
| ATOM 1443 CB ARG A 334 182.038 27.177 −2.573 1.00 74.03 C |
| ANISOU 1443 CB ARG A 334 10510 9329 8288 1632 −1740 −1052 C |
| ATOM 1444 CG ARG A 334 183.164 27.415 −1.606 1.00 69.26 C |
| ANISOU 1444 CG ARG A 334 10095 8676 7544 1716 −1187 −555 C |

TABLE 8-continued

DMXAA-hSTING$^{S162A/Q266I}$ complex

| | |
|---|---|
| ATOM 1400 CG1 VAL A 329 178.903 34.399 2.878 1.00 40.20 C | ATOM 1445 CD ARG A 334 182.987 26.586 −0.365 1.00 72.23 C |
| ANISOU 1400 CG1 VAL A 329 5396 5414 7053 136 −544 −3 C | ANISOU 1445 CD ARG A 334 10611 8461 8373 1269 −828 −629 C |
| ATOM 1401 CG2 VAL A 329 177.118 34.256 4.615 1.00 38.47 C | ATOM 1446 NE ARG A 334 184.094 26.758 0.571 1.00 73.01 N |
| ANISOU 1401 CG2 VAL A 329 2370 5005 7233 104 −195 307 C | ANISOU 1446 NE ARG A 334 10908 8547 8285 1394 −319 −195 N |
| ATOM 1402 C VAL A 329 178.664 31.523 2.396 1.00 44.09 C | ATOM 1447 CZ ARG A 334 184.043 26.420 1.858 1.00 73.65 C |
| ANISOU 1402 C VAL A 329 4284 5414 7053 136 −544 −3 C | ANISOU 1447 CZ ARG A 334 10993 8274 8717 1083 105 −82 C |
| ATOM 1403 O VAL A 329 178.602 31.652 1.176 1.00 45.57 O | ATOM 1448 NH1 ARG A 334 182.924 25.900 2.353 1.00 78.15 N |
| ANISOU 1403 O VAL A 329 4469 5817 7029 287 −939 −112 O | ANISOU 1448 NH1 ARG A 334 11344 8474 9874 617 107 −302 N |
| ATOM 1404 N LEU A 330 179.560 30.749 2.986 1.00 41.98 N | ATOM 1449 NH2 ARG A 334 185.100 26.605 2.649 1.00 65.04 N |
| ANISOU 1404 N LEU A 330 4453 4920 6576 185 −226 69 N | ANISOU 1449 NH2 ARG A 334 10085 7233 7395 1260 521 283 N |
| ATOM 1405 CA LEU A 330 180.551 30.025 2.206 1.00 39.11 C | ATOM 1450 C ARG A 334 181.047 27.948 −4.711 1.00 86.29 C |
| ANISOU 1405 CA LEU A 330 4609 4532 5721 428 −331 18 C | ANISOU 1450 C ARG A 334 11630 11684 9473 2084 −2617 −1395 C |
| ATOM 1406 CB LEU A 330 181.568 29.369 3.131 1.00 39.36 C | ATOM 1451 O ARG A 334 180.798 26.752 −4.857 1.00 91.93 O |
| ANISOU 1406 CB LEU A 330 5059 4332 5565 495 112 181 C | ANISOU 1451 O ARG A 334 12665 12003 10261 1969 −2851 −1926 O |
| ATOM 1407 CG LEU A 330 182.552 30.327 3.780 1.00 43.39 C | ATOM 1452 N GLN A 335 180.747 28.912 −5.600 1.00 87.58 N |
| ANISOU 1407 CG LEU A 330 5555 5036 5894 776 365 547 C | ANISOU 1452 N GLN A 335 11417 12438 9423 2384 −2886 −1246 N |
| ATOM 1408 CD1 LEU A 330 183.276 29.646 4.980 1.00 44.13 C | ATOM 1453 CA GLN A 335 180.170 28.742 −6.954 1.00 87.87 C |
| ANISOU 1408 CD1 LEU A 330 5966 4901 5902 776 848 673 C | ANISOU 1453 CA GLN A 335 11383 12860 9144 2706 −3459 −1670 C |
| ATOM 1409 CD2 LEU A 330 183.560 30.791 2.726 1.00 37.18 C | ATOM 1454 CB GLN A 335 179.095 27.665 −7.022 1.00 90.28 C |
| ANISOU 1409 CD2 LEU A 330 4938 4549 4640 1187 141 746 C | ANISOU 1454 CB GLN A 335 11747 12685 9872 2310 −3914 −2446 C |
| ATOM 1410 C LEU A 330 179.923 28.976 1.294 1.00 45.41 C | ATOM 1455 CG GLN A 335 177.881 28.007 −6.206 1.00 88.26 C |
| ANISOU 1410 C LEU A 330 5542 5158 6555 272 −700 −398 C | ANISOU 1455 CG GLN A 335 10979 12076 10480 1596 −3838 −2450 C |
| ATOM 1411 O LEU A 330 180.461 28.656 0.225 1.00 44.05 O | ATOM 1456 CD GLN A 335 177.590 26.982 −5.121 1.00 91.28 C |
| ANISOU 1411 O LEU A 330 5679 5130 5929 579 −988 −536 O | ANISOU 1456 CD GLN A 335 11521 11658 11502 995 −3630 −2652 C |
| ATOM 1412 N ARG A 331 178.806 28.413 1.740 1.00 43.86 N | ATOM 1457 OE1 GLN A 335 176.433 26.764 −4.768 1.00 96.56 O |
| ANISOU 1412 N ARG A 331 5103 4655 6908 −174 −703 −592 N | ANISOU 1457 OE1 GLN A 335 11834 11989 12866 456 −3773 −2872 O |
| ATOM 1413 CA ARG A 331 178.094 27.424 0.946 1.00 50.07 C | ATOM 1458 NE2 GLN A 335 178.632 26.343 −4.595 1.00 90.37 N |
| ANISOU 1413 CA ARG A 331 5945 5189 7890 −384 −1128 −1031 C | ANISOU 1458 NE2 GLN A 335 11906 11258 11100 1100 −3279 −2525 N |
| ATOM 1414 CB ARG A 331 176.869 26.912 1.698 1.00 55.85 C | ATOM 1459 C GLN A 335 179.538 30.052 −7.398 1.00 83.01 C |
| ANISOU 1414 CB ARG A 331 6289 5554 9378 −931 −1041 −1082 C | ANISOU 1459 C GLN A 335 10183 12615 8741 2623 −3360 −1298 C |
| ATOM 1415 CG ARG A 331 176.263 25.621 1.161 1.00 63.99 C | ATOM 1460 O GLN A 335 180.012 30.697 −8.325 1.00 82.36 O |
| ANISOU 1415 CG ARG A 331 7417 6109 10788 −1233 −1435 −1508 C | ANISOU 1460 O GLN A 335 10049 12888 8354 2898 −3109 −926 O |
| ATOM 1416 CD ARG A 331 174.723 25.600 1.377 1.00 104.65 C | TER 1461 GLN A 335 |
| ANISOU 1416 CD ARG A 331 11926 11117 16720 −1742 −1597 −1561 C | ATOM 1461 N SER B 154 148.849 45.994 3.869 1.00 61.24 N |
| ATOM 1417 NE ARG A 331 174.344 26.087 2.704 1.00 102.73 N | ANISOU 1461 N SER B 154 7667 7421 8180 −452 −1039 158 N |
| ANISOU 1417 NE ARG A 331 11283 10943 16807 −1927 −1033 −1085 N | ATOM 1462 CA SER B 154 148.821 46.818 2.655 1.00 62.18 C |
| ATOM 1418 CZ ARG A 331 173.970 25.311 3.715 1.00 106.52 C | ANISOU 1462 CA SER B 154 7904 7529 8192 −597 −1236 209 C |
| ANISOU 1418 CZ ARG A 331 11610 11039 17824 −2268 −673 −843 C | ATOM 1463 CB SER B 154 147.769 47.936 2.754 1.00 63.13 C |
| ATOM 1419 NH1 ARG A 331 173.884 23.996 3.547 1.00 113.86 N | ANISOU 1463 CB SER B 154 7769 7644 8574 −584 −1380 415 C |
| ANISOU 1419 NH1 ARG A 331 12731 11387 19143 −2540 −848 −1027 N | ATOM 1464 OG SER B 154 148.239 48.999 3.570 1.00 57.09 O |
| ATOM 1420 NH2 ARG A 331 173.668 25.855 4.890 1.00 103.69 N | ANISOU 1464 OG SER B 154 6881 6936 7874 −386 −1183 383 O |
| ANISOU 1420 NH2 ARG A 331 10882 10887 17629 −2298 −155 −405 N | ATOM 1465 C SER B 154 150.192 47.452 2.385 1.00 54.84 C |
| ATOM 1421 C ARG A 331 177.676 28.051 −0.379 1.00 53.80 C | ANISOU 1465 C SER B 154 7135 6654 7046 −528 −1086 66 C |
| ANISOU 1421 C ARG A 331 6218 6073 8151 −175 −1671 −1246 C | ATOM 1466 O SER B 154 151.064 47.518 3.277 1.00 47.88 O |
| ATOM 1422 O ARG A 331 177.869 27.476 −1.443 1.00 60.61 O | ANISOU 1466 O SER B 154 6204 5830 6158 −355 −859 −33 O |
| ANISOU 1422 O ARG A 331 7366 6973 8691 45 −2082 −1588 O | ATOM 1467 N VAL B 155 150.353 47.963 1.158 1.00 43.13 N |
| ATOM 1423 N HIS A 332 177.108 29.252 −0.305 1.00 51.62 N | ANISOU 1467 N VAL B 155 5842 5145 5400 −675 −1231 78 N |
| ANISOU 1423 N HIS A 332 5445 6134 8035 −189 −1676 −1046 N | ATOM 1468 CA VAL B 155 151.638 48.468 0.734 1.00 32.52 C |
| ATOM 1424 CA HIS A 332 176.729 29.995 −1.501 1.00 54.98 C | ANISOU 1468 CA VAL B 155 4671 3826 3857 −631 −1084 −44 C |
| ANISOU 1424 CA HIS A 332 5619 7018 8254 51 −2133 −1145 C | ATOM 1469 CB VAL B 155 151.657 48.752 −0.776 1.00 43.29 C |
| ATOM 1425 CB HIS A 332 175.819 31.179 −1.134 1.00 53.62 C | ANISOU 1469 CB VAL B 155 6320 5124 5005 −841 −1255 −26 C |
| ANISOU 1425 CB HIS A 332 4825 7066 8481 −107 −2089 −941 C | ATOM 1470 CG1 VAL B 155 152.878 49.611 −1.148 1.00 38.57 C |
| ATOM 1426 CG HIS A 332 174.473 30.767 −0.661 1.00 60.75 C | ANISOU 1470 CG1 VAL B 155 5836 4552 4268 −766 −1095 −113 C |
| ANISOU 1426 CG HIS A 332 5343 7712 10028 −618 −2136 −1138 C | ATOM 1471 CG2 VAL B 155 151.663 47.430 −1.548 1.00 46.08 C |
| ATOM 1427 ND1 HIS A 332 174.263 30.160 0.578 1.00 62.39 N | ANISOU 1471 CG2 VAL B 155 6997 5361 5151 −1027 −1278 −96 C |
| ANISOU 1427 ND1 HIS A 332 5535 7520 10649 −967 −1728 −1037 N | ATOM 1472 C VAL B 155 151.991 49.711 1.508 1.00 31.39 C |
| ATOM 1428 CE1 HIS A 332 172.994 29.878 0.719 1.00 68.23 C | ANISOU 1472 C VAL B 155 4323 3769 3837 −453 −984 −30 C |
| ANISOU 1428 CE1 HIS A 332 5841 8126 11958 −1374 −1863 −1164 C | ATOM 1473 O VAL B 155 153.060 49.824 2.066 1.00 38.82 O |
| ATOM 1429 NE2 HIS A 332 172.343 30.257 −0.382 1.00 65.54 N | ANISOU 1473 O VAL B 155 5261 4752 4736 −322 −782 −131 O |
| ANISOU 1429 NE2 HIS A 332 5248 8062 11593 −1326 −2374 −1405 N | ATOM 1474 N ALA B 156 151.078 50.666 1.529 1.00 35.88 N |
| ATOM 1430 CD2 HIS A 332 173.253 30.802 −1.252 1.00 60.87 C | ANISOU 1474 N ALA B 156 4718 4345 4572 −459 −1130 115 N |
| ANISOU 1430 CD2 HIS A 332 4939 7820 10368 −837 −2540 −1391 C | ATOM 1475 CA ALA B 156 151.347 51.956 2.147 1.00 32.65 C |
| ATOM 1431 C HIS A 332 177.951 30.493 −2.263 1.00 53.44 C | ANISOU 1475 CA ALA B 156 4157 3986 4264 −313 −1030 131 C |
| ANISOU 1431 C HIS A 332 5707 7231 7365 636 −2172 −912 C | ATOM 1476 CB ALA B 156 150.141 52.858 1.981 1.00 34.00 C |
| ATOM 1432 O HIS A 332 178.017 30.405 −3.486 1.00 57.61 O | ANISOU 1476 CB ALA B 156 4142 4123 4654 −345 −1194 330 C |
| ANISOU 1432 O HIS A 332 6320 8084 7486 972 −2580 −1097 O | ATOM 1477 C ALA B 156 151.690 51.793 3.637 1.00 32.13 C |
| ATOM 1433 N LEU A 333 178.901 31.045 −1.529 1.00 48.63 N | ANISOU 1477 C ALA B 156 3964 3956 4288 −132 −809 61 C |
| ANISOU 1433 N LEU A 333 5199 6643 6634 788 −1757 −479 N | ATOM 1478 O ALA B 156 152.512 52.502 4.215 1.00 34.92 O |
| ATOM 1434 CA LEU A 333 180.111 31.573 −2.134 1.00 60.37 C | ANISOU 1478 O ALA B 156 4308 4350 4608 −25 −673 −6 O |
| ANISOU 1434 CA LEU A 333 6877 8502 7559 1316 −1744 −125 C | ATOM 1479 N HIS B 157 151.045 50.848 4.264 1.00 32.63 N |
| ATOM 1435 CB LEU A 333 181.116 32.001 −1.070 1.00 58.85 C | ANISOU 1479 N HIS B 157 3946 3994 4458 −115 −789 88 N |
| ANISOU 1435 CB LEU A 333 6795 8181 7383 1368 −1281 297 C | ATOM 1480 CA HIS B 157 151.190 50.694 5.704 1.00 35.60 C |
| ATOM 1436 CG LEU A 333 181.275 33.510 −0.922 1.00 64.22 C | ANISOU 1480 CA HIS B 157 4224 4387 4916 39 −597 47 C |
| ANISOU 1436 CG LEU A 333 7041 9112 8249 1515 −1250 740 C | ATOM 1481 CB HIS B 157 150.170 49.654 6.196 1.00 34.17 C |
| ATOM 1437 CD1 LEU A 333 182.617 33.828 −0.281 1.00 64.06 C | ANISOU 1481 CB HIS B 157 3939 4155 4890 35 −605 117 C |
| ANISOU 1437 CD1 LEU A 333 7333 8883 8124 1507 −866 1003 C | ATOM 1482 CG HIS B 157 150.342 49.250 7.607 1.00 34.58 C |
| ATOM 1438 CD2 LEU A 333 181.168 34.209 −2.264 1.00 66.79 C | ANISOU 1482 CG HIS B 157 3943 4212 4983 172 −406 69 C |
| ANISOU 1438 CD2 LEU A 333 7275 9654 8448 1576 −1472 812 C | ATOM 1483 ND1 HIS B 157 150.119 50.116 8.665 1.00 34.37 N |

TABLE 8-continued

DMXAA-hSTING$^{S162A/Q266I}$ complex

| | |
|---|---|
| ATOM 1439 C LEU A 333 180.789 30.609 −3.097 1.00 69.76 C | ANISOU 1483 ND1 HIS B 157 3843 4160 5056 291 −260 100 N |
| ANISOU 1439 C LEU A 333 8563 9799 8144 1681 −1954 −338 C | ATOM 1484 CE1 HIS B 157 150.339 49.496 9.808 1.00 33.86 C |
| ATOM 1440 O LEU A 333 181.145 30.986 −4.206 1.00 75.74 O | ANISOU 1484 CE1 HIS B 157 3802 4094 4971 374 −110 49 C |
| ANISOU 1440 O LEU A 333 9301 11052 8424 2158 −2209 −212 O | ATOM 1485 NE2 HIS B 157 150.709 48.246 9.541 1.00 34.91 N |
| ANISOU 1485 NE2 HIS B 157 3983 4258 5021 327 −151 −6 N | ANISOU 1530 CE1 TYR B 163 3722 3703 3469 160 −243 −276 C |
| ATOM 1486 CD2 HIS B 157 150.721 48.067 8.179 1.00 32.57 C | ATOM 1531 CZ TYR B 163 160.538 59.947 4.428 1.00 28.27 C |
| ANISOU 1486 CD2 HIS B 157 3733 3970 4672 202 −318 −2 C | ANISOU 1531 CZ TYR B 163 3656 3650 3436 166 −292 −272 C |
| ATOM 1487 C HIS B 157 152.632 50.271 6.002 1.00 31.36 C | ATOM 1532 OH TYR B 163 160.932 61.233 4.197 1.00 32.54 O |
| ANISOU 1487 C HIS B 157 3813 3904 4198 88 −465 −100 C | ANISOU 1532 OH TYR B 163 4203 4173 3986 155 −297 −262 O |
| ATOM 1488 O HIS B 157 153.313 50.874 6.822 1.00 31.54 O | ATOM 1533 CE2 TYR B 163 159.369 59.768 5.159 1.00 26.60 C |
| ANISOU 1488 O HIS B 157 3821 3962 4201 182 −355 −143 O | ANISOU 1533 CE2 TYR B 163 3421 3432 3255 190 −306 −268 C |
| ATOM 1489 N GLY B 158 153.102 49.242 5.307 1.00 30.84 N | ATOM 1534 CD2 TYR B 163 158.941 58.478 5.462 1.00 23.25 C |
| ANISOU 1489 N GLY B 158 3880 3826 4011 11 −477 −161 N | ANISOU 1534 CD2 TYR B 163 2983 3020 2832 201 −300 −275 C |
| ATOM 1490 CA GLY B 158 154.491 48.812 5.431 1.00 25.71 C | ATOM 1535 C TYR B 163 160.524 55.701 7.473 1.00 26.39 C |
| ANISOU 1490 CA GLY B 158 3323 3200 3245 57 −337 −258 C | ANISOU 1535 C TYR B 163 3330 3468 3230 239 −226 −291 C |
| ATOM 1491 C GLY B 158 155.493 49.890 5.044 1.00 33.08 C | ATOM 1536 O TYR B 163 161.564 56.336 7.670 1.00 27.97 O |
| ANISOU 1491 C GLY B 158 4304 4164 4103 73 −310 −286 C | ANISOU 1536 O TYR B 163 3516 3671 3439 219 −248 −268 O |
| ATOM 1492 O GLY B 158 156.557 50.009 5.651 1.00 32.77 O | ATOM 1537 N TYR B 164 159.631 55.504 8.431 1.00 24.02 N |
| ANISOU 1492 O GLY B 158 4240 4156 4054 148 −206 −317 O | ANISOU 1537 N TYR B 164 3039 3162 2927 261 −225 −301 N |
| ATOM 1493 N LEU B 159 155.145 50.720 4.053 1.00 22.02 N | ATOM 1538 CA TYR B 164 159.949 55.867 9.817 1.00 27.38 C |
| ANISOU 1493 N LEU B 159 2957 2747 2661 −6 −423 −254 N | ANISOU 1538 CA TYR B 164 3508 3581 3316 251 −239 −297 C |
| ATOM 1494 CA LEU B 159 156.053 51.753 3.543 1.00 27.46 C | ATOM 1539 CB TYR B 164 158.769 55.592 10.693 1.00 29.36 C |
| ANISOU 1494 CA LEU B 159 3702 3454 3279 0 −397 −275 C | ANISOU 1539 CB TYR B 164 3799 3793 3562 286 −181 −310 C |
| ATOM 1495 CB LEU B 159 155.536 52.317 2.210 1.00 32.75 C | ATOM 1540 CG TYR B 164 159.099 55.663 12.137 1.00 32.24 C |
| ANISOU 1495 CB LEU B 159 4484 4087 3874 −124 −540 −231 C | ANISOU 1540 CG TYR B 164 4272 4133 3844 259 −183 −310 C |
| ATOM 1496 CG LEU B 159 155.790 51.492 0.964 1.00 37.07 C | ATOM 1541 CD1 TYR B 164 159.400 56.875 12.738 1.00 33.93 C |
| ANISOU 1496 CG LEU B 159 5282 4555 4246 −255 −542 −271 C | ANISOU 1541 CD1 TYR B 164 4616 4299 3977 205 −197 −328 C |
| ATOM 1497 CD1 LEU B 159 155.476 52.380 −0.215 1.00 39.69 C | ATOM 1542 CE1 TYR B 164 159.642 56.950 14.062 1.00 38.24 C |
| ANISOU 1497 CD1 LEU B 159 5738 4860 4484 −373 −690 −217 C | ANISOU 1542 CE1 TYR B 164 5328 4799 4403 147 −211 −331 C |
| ATOM 1498 CD2 LEU B 159 157.241 51.052 0.950 1.00 35.04 C | ATOM 1543 CZ TYR B 164 159.608 55.786 14.815 1.00 46.86 C |
| ANISOU 1498 CD2 LEU B 159 5116 4271 3925 −190 −412 −356 C | ANISOU 1543 CZ TYR B 164 6433 5906 5467 153 −215 −303 C |
| ATOM 1499 C LEU B 159 156.232 52.902 4.545 1.00 28.73 C | ATOM 1544 OH TYR B 164 159.859 55.831 16.160 1.00 49.68 O |
| ANISOU 1499 C LEU B 159 3729 3664 3524 98 −368 −259 C | ANISOU 1544 OH TYR B 164 6996 6208 5672 73 −247 −295 O |
| ATOM 1500 O LEU B 159 157.314 53.468 4.701 1.00 26.38 O | ATOM 1545 CE2 TYR B 164 159.306 54.564 14.242 1.00 49.26 C |
| ANISOU 1500 O LEU B 159 3441 3389 3194 136 −302 −289 O | ANISOU 1545 CE2 TYR B 164 6574 6264 5879 226 −188 −281 C |
| ATOM 1501 N ALA B 160 155.137 53.283 5.194 1.00 21.13 N | ATOM 1546 CD2 TYR B 164 159.047 54.520 12.911 1.00 42.81 C |
| ANISOU 1501 N ALA B 160 2655 2696 2679 129 −410 −199 N | ANISOU 1546 CD2 TYR B 164 5617 5481 5169 272 −171 −291 C |
| ATOM 1502 CA ALA B 160 155.194 54.351 6.170 1.00 23.35 C | ATOM 1547 C TYR B 164 161.165 55.126 10.389 1.00 29.31 C |
| ANISOU 1502 CA ALA B 160 2869 2985 3020 208 −348 −192 C | ANISOU 1547 C TYR B 164 3719 3852 3566 227 −281 −250 C |
| ATOM 1503 CB ALA B 160 153.799 54.727 6.623 1.00 25.38 C | ATOM 1548 O TYR B 164 162.105 55.714 10.929 1.00 33.26 O |
| ANISOU 1503 CB ALA B 160 3017 3186 3439 239 −350 −99 C | ANISOU 1548 O TYR B 164 4238 4352 4048 171 −358 −213 O |
| ATOM 1504 C ALA B 160 156.069 53.899 7.347 1.00 22.52 C | ATOM 1549 N ILE B 165 161.181 53.815 10.188 1.00 26.46 N |
| ANISOU 1504 C ALA B 160 2778 2907 2873 267 −248 −250 C | ANISOU 1549 N ILE B 165 3298 3503 3251 259 −239 −230 N |
| ATOM 1505 O ALA B 160 156.904 54.651 7.860 1.00 32.99 O | ATOM 1550 CA ILE B 165 162.238 52.991 10.770 1.00 27.93 C |
| ANISOU 1505 O ALA B 160 4130 4249 4157 286 −219 −275 O | ANISOU 1550 CA ILE B 165 3421 3702 3490 249 −265 −150 C |
| ATOM 1506 N TRP B 161 155.866 52.670 7.785 1.00 25.95 N | ATOM 1551 CB ILE B 165 161.769 51.537 10.947 1.00 26.50 C |
| ANISOU 1506 N TRP B 161 3199 3341 3322 281 −217 −257 N | ANISOU 1551 CB ILE B 165 3209 3518 3340 296 −195 −146 C |
| ATOM 1507 CA TRP B 161 156.726 52.080 8.818 1.00 27.65 C | ATOM 1552 CG1 ILE B 165 160.927 51.476 12.211 1.00 33.14 C |
| ANISOU 1507 CA TRP B 161 3425 3581 3501 321 −151 −284 C | ANISOU 1552 CG1 ILE B 165 4130 4357 4103 297 −217 −165 C |
| ATOM 1508 CB TRP B 161 156.168 50.735 9.275 1.00 25.21 C | ATOM 1553 CD1 ILE B 165 159.788 50.636 12.060 1.00 45.03 C |
| ANISOU 1508 CB TRP B 161 3088 3258 3234 341 −113 −275 C | ANISOU 1553 CD1 ILE B 165 5633 5850 5628 347 −135 −205 C |
| ATOM 1509 CG TRP B 161 155.099 50.971 10.320 1.00 25.58 C | ATOM 1554 CG2 ILE B 165 163.010 50.516 11.068 1.00 24.02 C |
| ANISOU 1509 CG TRP B 161 3105 3264 3352 390 −62 −244 C | ANISOU 1554 CG2 ILE B 165 2781 3196 3149 305 −176 −31 C |
| ATOM 1510 CD1 TRP B 161 153.734 50.969 10.138 1.00 25.33 C | ATOM 1555 C ILE B 165 163.618 53.101 10.073 1.00 37.62 C |
| ANISOU 1510 CD1 TRP B 161 3002 3176 3446 396 −62 −186 C | ANISOU 1555 C ILE B 165 4551 4919 4824 234 −263 −71 C |
| ATOM 1511 NE1 TRP B 161 153.103 51.248 11.331 1.00 29.84 N | ATOM 1556 O ILE B 165 163.081 50.721 10.724 1.00 34.98 O |
| ANISOU 1511 NE1 TRP B 161 3572 3686 4078 463 57 −158 N | ANISOU 1556 O ILE B 165 4144 4585 4564 193 −346 40 O |
| ATOM 1512 CE2 TRP B 161 154.048 51.454 12.306 1.00 29.97 C | ATOM 1557 N GLY B 166 163.568 53.186 8.756 1.00 33.98 N |
| ANISOU 1512 CE2 TRP B 161 3701 3724 3962 479 107 −210 C | ANISOU 1557 N GLY B 166 4096 4433 4383 257 −169 −110 N |
| ATOM 1513 CD2 TRP B 161 155.321 51.312 11.700 1.00 24.86 C | ATOM 1558 CA GLY B 166 164.730 53.257 7.924 1.00 25.09 C |
| ANISOU 1513 CD2 TRP B 161 3203 3356 3216 431 12 −250 C | ANISOU 1558 CA GLY B 166 2902 3262 3371 264 −87 −40 C |
| ATOM 1514 CE3 TRP B 161 156.469 51.472 12.490 1.00 25.57 C | ATOM 1559 C GLY B 166 165.231 54.604 7.548 1.00 32.79 C |
| ANISOU 1514 CE3 TRP B 161 3240 3276 3197 416 −1 −268 C | ANISOU 1559 C GLY B 166 3875 4234 4349 226 −141 −29 C |
| ATOM 1515 CZ3 TRP B 161 156.314 51.796 13.869 1.00 22.68 C | ATOM 1560 O GLY B 166 166.191 54.688 6.863 1.00 39.19 O |
| ANISOU 1515 CZ3 TRP B 161 2992 2860 2764 426 64 −267 C | ANISOU 1560 O GLY B 166 4617 4995 5279 234 −64 46 O |
| ATOM 1516 CH2 TRP B 161 155.027 51.953 14.433 1.00 30.80 C | ATOM 1561 N TYR B 167 164.555 55.654 7.950 1.00 31.76 N |
| ANISOU 1516 CH2 TRP B 161 4052 3796 3856 479 201 −254 C | ANISOU 1561 N TYR B 167 3820 4138 4109 191 −247 −93 N |
| ATOM 1517 CZ2 TRP B 161 153.889 51.804 13.672 1.00 33.70 C | ATOM 1562 CA TYR B 167 165.041 56.984 7.697 1.00 32.07 C |
| ANISOU 1517 CZ2 TRP B 161 4285 4130 4388 517 233 −214 C | ANISOU 1562 CA TYR B 167 3865 4167 4154 151 −295 −84 C |
| ATOM 1518 C TRP B 161 158.190 51.971 8.422 1.00 27.74 C | ATOM 1563 CB TYR B 167 164.531 57.492 6.353 1.00 32.26 C |
| ANISOU 1518 C TRP B 161 3460 3620 3460 304 −143 −300 C | ANISOU 1563 CB TYR B 167 3955 4172 4129 175 −212 −150 C |
| ATOM 1519 O TRP B 161 159.089 52.336 9.197 1.00 29.74 O | ATOM 1564 CG TYR B 167 165.023 58.833 6.000 1.00 26.29 C |
| ANISOU 1519 O TRP B 161 3781 3709 3894 3699 153 −145 −287 O | ANISOU 1564 CG TYR B 167 3203 3400 3385 142 −244 −139 C |
| ATOM 1520 N ALA B 162 158.426 51.509 7.195 1.00 25.01 N | ATOM 1565 CD1 TYR B 167 166.335 59.037 5.772 1.00 30.21 C |
| ANISOU 1520 N ALA B 162 3155 3254 3093 265 −132 −312 N | ANISOU 1565 CD1 TYR B 167 3606 3863 4011 126 −225 −44 C |
| ATOM 1521 CA ALA B 162 159.794 51.407 6.677 1.00 20.92 C | ATOM 1566 CE1 TYR B 167 166.806 60.255 5.439 1.00 32.16 C |
| ANISOU 1521 CA ALA B 162 2656 2725 2566 262 −66 −307 C | ANISOU 1566 CE1 TYR B 167 3848 4088 4282 93 −252 −28 C |
| ATOM 1522 CB ALA B 162 159.830 50.798 5.319 1.00 20.66 C | ATOM 1567 CZ TYR B 167 165.970 61.277 5.350 1.00 33.93 C |

TABLE 8-continued

DMXAA-hSTING$^{S162A/Q266I}$ complex

| | |
|---|---|
| ANISOU 1522 CB ALA B 162 2738 2630 2484 213 −5 −332 C | ANISOU 1567 CZ TYR B 167 4172 4325 4395 80 −292 −110 C |
| ATOM 1523 C ALA B 162 160.427 52.777 6.612 1.00 27.98 C | ATOM 1568 OH TYR B 167 166.490 62.468 5.035 1.00 47.66 O |
| ANISOU 1523 C ALA B 162 3538 3639 3454 256 −105 −295 C | ANISOU 1568 OH TYR B 167 5905 6035 6169 48 −309 −89 O |
| ATOM 1524 O ALA B 162 161.627 52.937 6.808 1.00 31.83 O | ATOM 1569 CE2 TYR B 167 164.647 61.115 5.576 1.00 27.99 C |
| ANISOU 1524 O ALA B 162 3980 4127 3987 266 −75 −255 O | ANISOU 1569 CE2 TYR B 167 3502 3599 3535 103 −300 −189 C |
| ATOM 1525 N TYR B 163 159.629 53.778 6.273 1.00 23.24 N | ATOM 1570 CD2 TYR B 167 164.182 59.889 5.906 1.00 27.51 C |
| ANISOU 1525 N TYR B 163 2963 3042 2824 234 −172 −308 N | ANISOU 1570 CD2 TYR B 167 3436 3560 3457 132 −281 −201 C |
| ATOM 1526 CA TYR B 163 160.180 55.110 6.096 1.00 26.46 C | ATOM 1571 C TYR B 167 164.835 57.996 8.800 1.00 31.73 C |
| ANISOU 1526 CA TYR B 163 3372 3458 3225 224 −198 −301 C | ANISOU 1571 C TYR B 167 3897 4135 4025 88 −424 −109 C |
| ATOM 1527 CB TYR B 163 159.166 55.998 5.385 1.00 25.88 C | ATOM 1572 O TYR B 167 165.748 58.565 9.274 1.00 31.83 O |
| ANISOU 1527 CB TYR B 163 3328 3370 3136 198 −258 −297 C | ANISOU 1572 O TYR B 167 3882 4135 4075 14 −530 −37 O |
| ATOM 1528 CG TYR B 163 159.670 57.379 5.079 1.00 21.09 C | ATOM 1573 N LEU B 168 163.593 58.279 9.099 1.00 33.53 N |
| ANISOU 1528 CG TYR B 163 2729 2760 2523 188 −273 −290 C | ANISOU 1573 N LEU B 168 4230 4363 4148 106 −405 −196 N |
| ATOM 1529 CD1 TYR B 163 160.847 57.573 4.328 1.00 30.99 C | ATOM 1574 CA LEU B 168 163.237 59.338 10.000 1.00 31.15 C |
| ANISOU 1529 CD1 TYR B 163 4013 4005 3758 171 −231 −288 C | ANISOU 1574 CA LEU B 168 4053 4028 3755 54 −453 −235 C |
| ATOM 1530 CE1 TYR B 163 161.308 58.858 4.012 1.00 28.67 C | ATOM 1575 CB LEU B 168 161.748 59.556 9.976 1.00 28.01 C |
| ANISOU 1530 CE1 TYR B 163 3731 3599 3314 110 −358 −304 C | ATOM 1576 CG LEU B 168 161.126 60.100 8.709 1.00 35.64 C |
| ANISOU 1576 CG LEU B 168 4648 4563 4331 154 −308 −316 C | ATOM 1620 CD PRO B 173 8370 7656 7213 −645 −1255 34 C |
| ATOM 1577 CD1 LEU B 168 159.656 60.278 8.928 1.00 34.19 C | ATOM 1621 C PRO B 173 168.217 64.189 16.568 1.00 66.54 C |
| ANISOU 1577 CD1 LEU B 168 4489 4333 4168 204 −232 −330 C | ANISOU 1621 C PRO B 173 9599 8110 7571 −1144 −1660 47 C |
| ATOM 1578 CD2 LEU B 168 161.747 61.393 8.265 1.00 22.45 C | ATOM 1622 O PRO B 173 168.258 65.132 17.352 1.00 72.82 O |
| ANISOU 1578 CD2 LEU B 168 2992 2872 2668 116 −333 −311 C | ANISOU 1622 O PRO B 173 10725 8788 8156 −1328 −1746 −5 O |
| ATOM 1579 C LEU B 168 163.689 59.166 11.419 1.00 32.58 C | ATOM 1623 N GLU B 174 169.113 64.009 15.609 1.00 65.05 N |
| ANISOU 1579 C LEU B 168 4312 4195 3871 −29 −558 −197 C | ANISOU 1623 N GLU B 174 9057 7997 7660 −1091 −1725 178 N |
| ATOM 1580 O LEU B 168 164.153 60.077 12.005 1.00 31.87 O | ATOM 1624 CA GLU B 174 170.276 64.873 15.501 1.00 66.84 C |
| ANISOU 1580 O LEU B 168 4322 4066 3721 −127 −650 −188 O | ANISOU 1624 CA GLU B 174 9220 8184 7991 −1255 −1940 298 C |
| ATOM 1581 N ARG B 169 163.557 57.978 11.971 1.00 33.20 N | ATOM 1625 CB GLU B 174 171.468 64.072 14.993 1.00 75.01 C |
| ANISOU 1581 N ARG B 169 4371 4297 3947 −7 −557 −171 N | ANISOU 1625 CB GLU B 174 9857 9285 9359 −1235 −2072 570 C |
| ATOM 1582 CA ARG B 169 164.013 57.765 13.358 1.00 33.77 C | ATOM 1626 CG GLU B 174 172.751 64.422 15.709 1.00 88.99 C |
| ANISOU 1582 CA ARG B 169 4548 4351 3933 −106 −681 −119 C | ANISOU 1626 CG GLU B 174 11603 11000 11208 −1502 −2446 761 C |
| ATOM 1583 CB ARG B 169 163.517 56.418 13.905 1.00 32.35 C | ATOM 1627 CD GLU B 174 172.638 64.256 17.232 1.00 101.41 C |
| ANISOU 1583 CB ARG B 169 4355 4192 3744 −54 −638 −105 C | ANISOU 1627 CD GLU B 174 13517 12521 12492 −1733 −2700 779 C |
| ATOM 1584 CG ARG B 169 164.574 55.351 13.997 1.00 37.97 C | ATOM 1628 OE1 GLU B 174 172.530 65.285 17.946 1.00 104.06 O |
| ANISOU 1584 CG ARG B 169 4905 4943 4580 −70 −729 32 C | ANISOU 1628 OE1 GLU B 174 14213 12749 12574 −1909 −2771 691 O |
| ATOM 1585 CD ARG B 169 164.009 54.013 13.670 1.00 39.72 C | ATOM 1629 OE2 GLU B 174 172.657 63.095 17.714 1.00 107.22 O |
| ANISOU 1585 CD ARG B 169 5033 5190 4869 40 −602 21 C | ANISOU 1629 OE2 GLU B 174 14178 13305 13254 −1715 −2765 881 O |
| ATOM 1586 NE ARG B 169 163.623 53.254 14.840 1.00 44.18 N | ATOM 1630 C GLU B 174 170.036 66.088 14.599 1.00 61.60 C |
| ANISOU 1586 NE ARG B 169 5686 5748 5351 24 −627 41 N | ANISOU 1630 C GLU B 174 8565 7484 7357 −1188 −1777 185 C |
| ATOM 1587 CZ ARG B 169 163.968 51.991 15.069 1.00 43.78 C | ATOM 1631 O GLU B 174 170.914 66.931 14.407 1.00 64.70 O |
| ANISOU 1587 CZ ARG B 169 5524 5717 5392 53 −630 133 C | ANISOU 1631 O GLU B 174 8908 7834 7843 −1310 −1919 266 O |
| ATOM 1588 NH1 ARG B 169 163.550 51.416 16.181 1.00 45.14 N | ATOM 1632 N LEU B 175 168.843 66.170 14.036 1.00 59.61 N |
| ANISOU 1588 NH1 ARG B 169 5807 5879 5465 32 −653 147 N | ANISOU 1632 N LEU B 175 8358 7244 7046 −1000 −1489 18 N |
| ATOM 1589 NH2 ARG B 169 164.726 51.312 14.206 1.00 41.98 N | ATOM 1633 CA LEU B 175 168.555 67.194 13.045 1.00 56.22 C |
| ANISOU 1589 NH2 ARG B 169 5094 5500 5357 104 −582 216 N | ANISOU 1633 CA LEU B 175 7891 6792 6677 −911 −1325 −63 C |
| ATOM 1590 C ARG B 169 165.552 57.931 13.477 1.00 30.97 C | ATOM 1634 CB LEU B 175 167.150 66.954 12.427 1.00 57.22 C |
| ANISOU 1590 C ARG B 169 4095 4005 3667 −214 −864 20 C | ANISOU 1634 CB LEU B 175 8012 6948 6783 −702 −1048 −190 C |
| ATOM 1591 O ARG B 169 166.093 58.143 14.550 1.00 35.97 O | ATOM 1635 CG LEU B 175 166.707 68.024 11.455 1.00 59.28 C |
| ANISOU 1591 O ARG B 169 4839 4611 4217 −350 −1035 86 O | ANISOU 1635 CG LEU B 175 8255 7175 7093 −612 −882 −261 C |
| ATOM 1592 N LEU B 170 166.248 57.851 12.343 1.00 35.89 N | ATOM 1636 CD1 LEU B 175 167.372 67.844 10.092 1.00 57.54 C |
| ANISOU 1592 N LEU B 170 4520 4650 4467 −162 −825 79 N | ANISOU 1636 CD1 LEU B 175 7748 7035 7081 −523 −870 −177 C |
| ATOM 1593 CA LEU B 170 167.713 57.934 12.278 1.00 35.74 C | ATOM 1637 CD2 LEU B 175 165.184 67.991 11.338 1.00 55.19 C |
| ANISOU 1593 CA LEU B 170 4340 4620 4619 −238 −956 248 C | ANISOU 1637 CD2 LEU B 175 7818 6633 6518 −469 −652 −365 C |
| ATOM 1594 CB LEU B 170 168.262 57.022 11.166 1.00 41.55 C | ATOM 1638 C LEU B 175 168.533 68.527 13.726 1.00 58.36 C |
| ANISOU 1594 CB LEU B 170 4850 5358 5581 −124 −806 330 C | ANISOU 1638 C LEU B 175 8472 6930 6773 −1078 −1373 −138 C |
| ATOM 1595 CG LEU B 170 167.827 55.555 11.118 1.00 39.07 C | ATOM 1639 O LEU B 175 169.133 69.489 13.259 1.00 59.43 O |
| ANISOU 1595 CG LEU B 170 4485 5059 5300 −27 −682 329 C | ANISOU 1639 O LEU B 175 8563 7027 6989 −1138 −1421 −111 O |
| ATOM 1596 CD1 LEU B 170 168.341 54.916 9.833 1.00 39.17 C | ATOM 1640 N GLN B 176 167.832 68.586 14.849 1.00 60.35 N |
| ANISOU 1596 CD1 LEU B 170 4350 5029 5502 74 −477 379 C | ANISOU 1640 N GLN B 176 9064 7090 6776 −1157 −1337 −234 N |
| ATOM 1597 CD2 LEU B 170 168.301 54.765 12.340 1.00 33.70 C | ATOM 1641 CA GLN B 176 167.639 69.857 15.508 1.00 64.55 C |
| ANISOU 1597 CD2 LEU B 170 3755 4387 4663 −92 −833 470 C | ANISOU 1641 CA GLN B 176 9966 7453 7107 −1308 −1306 −334 C |
| ATOM 1598 C LEU B 170 168.218 59.328 11.995 1.00 39.25 C | ATOM 1642 CB GLN B 176 166.600 69.769 16.618 1.00 72.10 C |
| ANISOU 1598 C LEU B 170 4815 5031 5067 −317 −1027 248 C | ANISOU 1642 CB GLN B 176 11314 8284 7798 −1333 −1142 −457 C |
| ATOM 1599 O LEU B 170 169.376 59.648 12.270 1.00 49.62 O | ATOM 1643 CG GLN B 176 165.680 70.980 16.636 1.00 79.14 C |
| ANISOU 1599 O LEU B 170 6034 6319 6501 −428 −1196 400 O | ANISOU 1643 CG GLN B 176 12468 9002 8599 −1290 −842 −602 C |
| ATOM 1600 N ILE B 171 167.383 60.167 11.409 1.00 39.73 N | ATOM 1644 CD GLN B 176 164.204 70.608 16.718 1.00 79.33 C |
| ANISOU 1600 N ILE B 171 4984 5082 5028 −266 −909 102 N | ANISOU 1644 CD GLN B 176 12547 8977 8619 −1084 −494 −687 C |
| ATOM 1601 CA ILE B 171 167.885 61.456 10.974 1.00 34.91 C | ATOM 1645 OE1 GLN B 176 163.733 70.126 17.755 1.00 82.90 O |
| ANISOU 1601 CA ILE B 171 4382 4436 4446 −323 −947 104 C | ANISOU 1645 OE1 GLN B 176 13273 9342 8884 −1131 −424 −728 O |
| ATOM 1602 CB ILE B 171 167.608 61.715 9.462 1.00 47.78 C | ATOM 1646 NE2 GLN B 176 163.467 70.826 15.622 1.00 75.00 N |
| ANISOU 1602 CB ILE B 171 5930 6073 6150 −201 −762 50 C | ANISOU 1646 NE2 GLN B 176 11735 8473 8288 −863 −284 −693 N |
| ATOM 1603 CG1 ILE B 171 168.561 62.769 8.913 1.00 55.82 C | ATOM 1647 C GLN B 176 168.960 70.417 16.020 1.00 66.67 C |
| ANISOU 1603 CG1 ILE B 171 6879 7053 7279 −253 −800 115 C | ANISOU 1647 C GLN B 176 10322 7667 7341 −1587 −1641 −226 C |
| ATOM 1604 CD1 ILE B 171 169.188 62.401 7.583 1.00 59.72 C | ATOM 1648 O GLN B 176 169.160 71.624 16.012 1.00 71.77 O |
| ANISOU 1604 CD1 ILE B 171 7204 7534 7952 −162 −652 186 C | ANISOU 1648 O GLN B 176 11136 8201 7933 −1697 −1643 −274 O |
| ATOM 1605 CG2 ILE B 171 166.206 62.235 9.240 1.00 47.62 C | ATOM 1649 N ALA B 177 169.879 69.549 16.434 1.00 58.25 N |
| ANISOU 1605 CG2 ILE B 171 6058 6050 5984 −141 −655 −99 C | ANISOU 1649 N ALA B 177 9122 6673 6336 −1706 −1935 −58 N |
| ATOM 1606 C ILE B 171 167.321 62.568 11.839 1.00 37.31 C | ATOM 1650 CA ALA B 177 171.208 70.031 16.810 1.00 53.97 C |
| | ANISOU 1650 CA ALA B 177 8584 6085 5837 −1980 −2300 104 C |
| | ATOM 1651 CB ALA B 177 172.028 68.944 17.441 1.00 48.14 C |

TABLE 8-continued

DMXAA-hSTING$^{S162A/Q266I}$ complex

| | |
|---|---|
| ANISOU 1606 C ILE B 171 4942 4685 4547 −423 −1006 4 C | ANISOU 1651 CB ALA B 177 7694 5413 5182 −2072 −2568 325 C |
| ATOM 1607 O ILE B 171 167.951 63.620 12.026 1.00 41.72 O | ATOM 1652 C ALA B 177 171.932 70.602 15.588 1.00 51.40 C |
| ANISOU 1607 O ILE B 171 5561 5194 5097 −541 −1118 31 O | ANISOU 1652 C ALA B 177 7903 5805 5822 −1902 −2290 190 C |
| ATOM 1608 N LEU B 172 166.119 62.347 12.357 1.00 41.71 N | ATOM 1653 O ALA B 177 172.542 71.672 15.645 1.00 55.18 O |
| ANISOU 1608 N LEU B 172 5663 5231 4954 −376 −907 −107 N | ANISOU 1653 O ALA B 177 8477 6189 6299 −2078 −2428 217 O |
| ATOM 1609 CA LEU B 172 165.449 63.361 13.177 1.00 48.20 C | ATOM 1654 N ARG B 178 171.858 69.886 14.473 1.00 47.23 N |
| ANISOU 1609 CA LEU B 172 6765 5960 5590 −448 −878 −208 C | ANISOU 1654 N ARG B 178 6991 5404 5548 −1646 −2116 231 N |
| ATOM 1610 CB LEU B 172 163.966 63.054 13.385 1.00 43.37 C | ATOM 1655 CA ARG B 178 172.541 70.342 13.254 1.00 50.99 C |
| ANISOU 1610 CB LEU B 172 6257 5320 4901 −334 −677 −310 C | ANISOU 1655 CA ARG B 178 7149 5910 6315 −1557 −2064 318 C |
| ATOM 1611 CG LEU B 172 163.153 63.228 12.097 1.00 46.31 C | ATOM 1656 CB ARG B 178 172.388 69.324 12.127 1.00 53.34 C |
| ANISOU 1611 CG LEU B 172 6481 5721 5394 −184 −517 −347 C | ANISOU 1656 CB ARG B 178 7107 6328 6834 −1289 −1851 355 C |
| ATOM 1612 CD1 LEU B 172 161.677 63.092 12.391 1.00 44.18 C | ATOM 1657 CG ARG B 178 173.271 68.113 12.223 1.00 57.18 C |
| ANISOU 1612 CD1 LEU B 172 6294 5394 5097 −91 −337 −406 C | ANISOU 1657 CG ARG B 178 7312 6871 7543 −1296 −1994 573 C |
| ATOM 1613 CD2 LEU B 172 163.417 64.574 11.405 1.00 51.32 C | ATOM 1658 CD ARG B 178 172.670 66.985 11.375 1.00 56.47 C |
| ANISOU 1613 CD2 LEU B 172 7117 6317 6066 −204 −504 −360 C | ANISOU 1658 CD ARG B 178 7048 6872 7534 −1037 −1725 528 C |
| ATOM 1614 C LEU B 172 166.115 63.755 14.510 1.00 54.45 C | ATOM 1659 NE ARG B 178 172.934 67.111 9.938 1.00 58.22 N |
| ANISOU 1614 C LEU B 172 7786 6678 6224 −657 −1075 −170 C | ANISOU 1659 NE ARG B 178 7046 7104 7971 −873 −1509 552 N |
| ATOM 1615 O LEU B 172 166.154 64.945 14.825 1.00 60.35 O | ATOM 1660 CZ ARG B 178 172.117 66.678 8.973 1.00 59.84 C |
| ANISOU 1615 O LEU B 172 8737 7329 6863 −762 −1089 −224 O | ANISOU 1660 CZ ARG B 178 7231 7357 8147 −671 −1241 435 C |
| ATOM 1616 N PRO B 173 166.629 62.784 15.291 1.00 58.69 N | ATOM 1661 NH1 ARG B 178 170.962 66.103 9.293 1.00 60.03 N |
| ANISOU 1616 N PRO B 173 8314 7246 6741 −735 −1235 −71 N | ANISOU 1661 NH1 ARG B 178 7405 7429 7974 −599 −1159 295 N |
| ATOM 1617 CA PRO B 173 167.090 63.174 16.639 1.00 60.84 C | ATOM 1662 NH2 ARG B 178 172.454 66.817 7.689 1.00 56.18 N |
| ANISOU 1617 CA PRO B 173 8880 7430 6807 −967 −1444 −37 C | ANISOU 1662 NH2 ARG B 178 6616 6881 7850 −555 −1058 469 N |
| ATOM 1618 CB PRO B 173 167.629 61.869 17.245 1.00 56.11 C | ATOM 1663 C ARG B 178 172.078 71.720 12.745 1.00 51.79 C |
| ANISOU 1618 CB PRO B 173 8177 6892 6248 −1014 −1618 111 C | ANISOU 1663 C ARG B 178 7401 5933 6345 −1528 −1889 168 C |
| ATOM 1619 CG PRO B 173 167.082 60.755 16.381 1.00 57.75 C | ATOM 1664 O ARG B 178 172.868 72.494 12.178 1.00 53.43 O |
| ANISOU 1619 CG PRO B 173 8111 7198 6632 −777 −1416 96 C | ANISOU 1664 O ARG B 178 7472 6105 6722 −1580 −1949 250 O |
| ATOM 1620 CD PRO B 173 166.935 61.370 15.001 1.00 61.16 C | ATOM 1665 N ILE B 179 170.791 72.014 12.916 1.00 47.96 N |
| ANISOU 1665 N ILE B 179 7173 5408 5643 −1433 −1653 −32 N | ANISOU 1710 O ASN B 183 10654 6715 7649 −2497 −1907 −253 O |
| ATOM 1666 CA ILE B 179 170.261 73.280 12.429 1.00 51.34 C | ATOM 1711 N GLN B 184 174.032 79.142 14.299 1.00 73.30 N |
| ANISOU 1666 CA ILE B 179 7726 5749 6033 −1385 −1457 −155 C | ANISOU 1711 N GLN B 184 11379 7858 8612 −2580 −2307 −12 N |
| ATOM 1667 CB ILE B 179 168.746 73.208 12.200 1.00 49.51 C | ATOM 1712 CA GLN B 184 174.948 79.884 15.138 1.00 82.13 C |
| ANISOU 1667 CB ILE B 179 7591 5513 5706 −1178 −1137 −309 C | ANISOU 1712 CA GLN B 184 12671 8898 9636 −2810 −2535 101 C |
| ATOM 1668 CG1 ILE B 179 168.443 72.253 11.047 1.00 45.65 C | ATOM 1713 CB GLN B 184 175.150 79.186 16.482 1.00 91.25 C |
| ANISOU 1668 CG1 ILE B 179 6765 5178 5401 −943 −1018 −265 C | ANISOU 1713 CB GLN B 184 14043 10061 10565 −2947 −2729 196 C |
| ATOM 1669 CD1 ILE B 179 166.948 71.995 10.853 1.00 44.85 C | ATOM 1714 CG GLN B 184 174.084 79.545 17.531 1.00101.96 C |
| ANISOU 1669 CD1 ILE B 179 6718 5080 5241 −760 −762 −371 C | ANISOU 1714 CG GLN B 184 15942 11286 11513 −2986 −2506 1 C |
| ATOM 1670 CG2 ILE B 179 168.166 74.586 11.903 1.00 45.73 C | ATOM 1715 CD GLN B 184 172.658 79.754 16.965 1.00106.22 C |
| ANISOU 1670 CG2 ILE B 179 7273 4909 5192 −1151 −936 −413 C | ANISOU 1715 CD GLN B 184 16583 11780 11998 −2761 −2074 −251 C |
| ATOM 1671 C ILE B 179 170.665 74.442 13.365 1.00 60.56 C | ATOM 1716 OE1 GLN B 184 172.368 80.749 16.285 1.00109.16 O |
| ANISOU 1671 C ILE B 179 9242 6746 7022 −1657 −1608 −191 C | ANISOU 1716 OE1 GLN B 184 16971 12068 12436 −2702 −1879 −359 O |
| ATOM 1672 O ILE B 179 171.000 75.563 12.906 1.00 58.94 O | ATOM 1717 NE2 GLN B 184 171.761 78.821 17.278 1.00105.45 N |
| ANISOU 1672 O ILE B 179 9041 6468 6884 −1702 −1587 −199 O | ANISOU 1717 NE2 GLN B 184 16554 11721 11792 −2635 −1920 −328 N |
| ATOM 1673 N ARG B 180 170.686 74.164 14.669 1.00 66.48 N | ATOM 1718 C GLN B 184 176.256 80.101 14.418 1.00 80.15 C |
| ANISOU 1673 N ARG B 180 10304 7422 7535 −1858 −1771 −205 N | ANISOU 1718 C GLN B 184 12019 8692 9741 −2864 −2761 324 C |
| ATOM 1674 CA ARG B 180 171.163 75.166 15.637 1.00 69.06 C | ATOM 1719 O GLN B 184 176.783 81.207 14.375 1.00 82.41 O |
| ANISOU 1674 CA ARG B 180 11026 7567 7647 −2172 −1961 −228 C | ANISOU 1719 O GLN B 184 12376 8884 10051 −2981 −2817 348 O |
| ATOM 1675 CB ARG B 180 170.896 74.746 17.062 1.00 75.44 C | ATOM 1720 N HIS B 185 176.786 79.066 13.828 1.00 75.86 N |
| ANISOU 1675 CB ARG B 180 12178 8320 8168 −2281 −1995 −234 C | ANISOU 1720 N HIS B 185 11044 8282 9496 −2762 −2859 497 N |
| ATOM 1676 CG ARG B 180 169.562 74.122 17.178 1.00 82.90 C | ATOM 1721 CA HIS B 185 178.049 79.195 13.178 1.00 74.68 C |
| ANISOU 1676 CG ARG B 180 13252 9258 8989 −2104 −1706 −391 C | ANISOU 1721 CA HIS B 185 10473 8162 9739 −2777 −3022 748 C |
| ATOM 1677 CD ARG B 180 168.622 74.866 18.089 1.00 91.41 C | ATOM 1722 CB HIS B 185 178.551 77.841 12.772 1.00 77.52 C |
| ANISOU 1677 CD ARG B 180 14795 10145 9790 −2119 −1413 −532 C | ANISOU 1722 CB HIS B 185 10412 8651 10392 −2650 −3082 950 C |
| ATOM 1678 NE ARG B 180 169.129 74.968 19.456 1.00100.91 N | ATOM 1723 CG HIS B 185 179.149 77.080 13.899 1.00 88.03 C |
| ANISOU 1678 NE ARG B 180 16315 11264 10761 −2343 −1573 −441 N | ANISOU 1723 CG HIS B 185 11789 9999 11660 −2778 −3359 1147 C |
| ATOM 1679 CZ ARG B 180 169.443 73.937 20.246 1.00103.16 C | ATOM 1724 ND1 HIS B 185 179.135 77.551 15.190 1.00 93.29 N |
| ANISOU 1679 CZ ARG B 180 16615 11608 10973 −2421 −1766 −325 C | ANISOU 1724 ND1 HIS B 185 12851 10573 12022 −3002 −3550 1147 N |
| ATOM 1680 NH1 ARG B 180 169.887 74.169 21.481 1.00106.20 N | ATOM 1725 CE1 HIS B 185 179.719 76.676 15.980 1.00 97.67 C |
| ANISOU 1680 NH1 ARG B 180 17341 11878 11131 −2650 −1909 −236 N | ANISOU 1725 CE1 HIS B 185 13359 11147 12602 −3089 −3788 1370 C |
| ATOM 1681 NH2 ARG B 180 169.322 72.682 19.815 1.00 98.28 N | ATOM 1726 NE2 HIS B 185 180.104 75.650 15.246 1.00 97.08 N |
| ANISOU 1681 NH2 ARG B 180 15690 11149 10501 −2284 −1818 −288 N | ANISOU 1726 NE2 HIS B 185 12864 11175 12849 −2910 −3731 1501 N |
| ATOM 1682 C ARG B 180 172.637 75.428 15.462 1.00 60.80 C | ATOM 1727 CD2 HIS B 185 179.769 75.883 13.940 1.00 90.14 C |
| ANISOU 1682 C ARG B 180 9743 6551 6807 −2339 −2292 −15 C | ANISOU 1727 CD2 HIS B 185 11758 10345 12146 −2712 −3458 1366 C |
| ATOM 1683 O ARG B 180 173.079 76.566 15.548 1.00 57.56 O | ATOM 1728 C HIS B 185 178.042 80.071 11.976 1.00 72.41 C |
| ANISOU 1683 O ARG B 180 9460 6038 6372 −2462 −2329 −10 O | ANISOU 1728 C HIS B 185 10028 7824 9659 −2694 −2837 688 C |
| ATOM 1684 N THR B 181 173.391 74.373 15.189 1.00 57.39 N | ATOM 1729 O HIS B 185 179.011 80.716 11.674 1.00 80.31 O |
| ANISOU 1684 N THR B 181 8938 6255 6611 −2315 −2492 181 N | ANISOU 1729 O HIS B 185 10906 8768 10839 −2781 −2944 820 O |
| ATOM 1685 CA THR B 181 174.795 74.556 14.870 1.00 59.91 C | ATOM 1730 N TYR B 186 176.943 80.076 11.274 1.00 72.02 N |
| ANISOU 1685 CA THR B 181 8944 6598 7222 −2411 −2738 428 C | ANISOU 1730 N TYR B 186 9985 7808 9570 −2478 −2519 501 N |
| ATOM 1686 CB THR B 181 175.523 73.230 14.599 1.00 66.32 C | ATOM 1731 CA TYR B 186 176.873 80.634 9.954 1.00 71.52 C |
| ANISOU 1686 CB THR B 181 9331 7539 8330 −2337 −2878 662 C | ANISOU 1731 CA TYR B 186 9724 7758 9693 −2262 −2234 471 C |
| ATOM 1687 OG1 THR B 181 175.603 72.481 15.816 1.00 73.88 O | ATOM 1732 CB TYR B 186 176.359 79.551 9.030 1.00 75.47 C |
| ANISOU 1687 OG1 THR B 181 10457 8499 9114 −2430 −3025 745 O | ANISOU 1732 CB TYR B 186 9949 8416 10312 −1926 −1955 465 C |
| ATOM 1688 CG2 THR B 181 176.947 73.498 14.086 1.00 62.18 C | ATOM 1733 CG TYR B 186 177.374 78.926 8.142 1.00 84.72 C |
| ANISOU 1688 CG2 THR B 181 8440 7006 8180 −2390 −3049 935 C | ANISOU 1733 CG TYR B 186 10677 9649 11864 −1849 −1995 710 C |
| ATOM 1689 C THR B 181 174.908 75.477 13.669 1.00 52.36 C | ATOM 1734 CD2 TYR B 186 177.670 79.485 6.930 1.00 88.16 C |

TABLE 8-continued

DMXAA-hSTING$^{S162A/Q266I}$ complex

| | |
|---|---|
| ANISOU 1689 C THR B 181 7812 5615 6469 −2333 −2603 386 C | ANISOU 1734 CD2 TYR B 186 10885 10073 12540 −1701 −1792 772 C |
| ATOM 1690 O THR B 181 175.606 76.470 13.708 1.00 57.02 O | ATOM 1735 CE2 TYR B 186 178.587 78.916 6.089 1.00 92.39 C |
| ANISOU 1690 O THR B 181 8440 6117 7108 −2479 −2720 449 O | ANISOU 1735 CE2 TYR B 186 11040 10625 13438 −1615 −1759 1001 C |
| ATOM 1691 N TYR B 182 174.187 75.161 12.606 1.00 51.70 N | ATOM 1736 CZ TYR B 186 179.205 77.766 6.452 1.00 96.59 C |
| ANISOU 1691 N TYR B 182 7527 5630 6486 −2013 −2259 296 N | ANISOU 1736 CZ TYR B 186 11380 11191 14130 −1673 −1939 1188 C |
| ATOM 1692 CA TYR B 182 174.224 75.977 11.396 1.00 50.09 C | ATOM 1737 OH TYR B 186 180.111 77.224 5.594 1.00 102.22 O |
| ANISOU 1692 CA TYR B 182 7150 5422 6460 −1864 −2051 272 C | ANISOU 1737 OH TYR B 186 11706 11885 15248 −1572 −1849 1436 O |
| ATOM 1693 CB TYR B 182 173.351 75.356 10.309 1.00 46.79 C | ATOM 1738 CE1 TYR B 186 178.928 77.178 7.648 1.00 93.23 C |
| ANISOU 1693 CB TYR B 182 6547 5122 6109 −1538 −1719 192 C | ANISOU 1738 CE1 TYR B 186 11154 10796 13473 −1827 −2182 1141 C |
| ATOM 1694 CG TYR B 182 173.556 75.997 8.969 1.00 50.20 C | ATOM 1739 CD1 TYR B 186 178.007 77.756 8.488 1.00 89.24 C |
| ANISOU 1694 CG TYR B 182 6769 5562 6744 −1392 −1539 215 C | ANISOU 1739 CD1 TYR B 186 11064 10271 12572 −1917 −2205 895 C |
| ATOM 1695 CD1 TYR B 182 172.789 77.099 8.588 1.00 53.00 C | ATOM 1740 C TYR B 186 175.902 81.785 9.931 1.00 64.14 C |
| ANISOU 1695 CD1 TYR B 182 7291 5850 6996 −1329 −1341 69 C | ANISOU 1740 C TYR B 186 9138 6710 8523 −2247 −2010 241 C |
| ATOM 1696 CE1 TYR B 182 172.979 77.721 7.373 1.00 54.48 C | ATOM 1741 O TYR B 186 175.281 82.029 8.942 1.00 61.93 O |
| ANISOU 1696 CE1 TYR B 182 7308 6040 7353 −1209 −1189 100 C | ANISOU 1741 O TYR B 186 8761 6463 8307 −2009 −1705 164 O |
| ATOM 1697 CZ TYR B 182 173.945 77.240 6.508 1.00 55.96 C | ATOM 1742 N ASN B 187 175.763 82.478 11.039 1.00 62.32 N |
| ANISOU 1697 CZ TYR B 182 7175 6281 7808 −1145 −1200 268 C | ANISOU 1742 N ASN B 187 9334 6328 8017 −2511 −2154 143 N |
| ATOM 1698 OH TYR B 182 174.075 77.899 5.296 1.00 58.47 O | ATOM 1743 CA ASN B 187 174.815 83.559 11.123 1.00 67.81 C |
| ANISOU 1698 OH TYR B 182 7372 6583 8261 −1027 −1022 289 O | ANISOU 1743 CA ASN B 187 10402 6871 8490 −2510 −1905 −71 C |
| ATOM 1699 CE2 TYR B 182 174.740 76.135 6.863 1.00 51.93 C | ATOM 1744 CB ASN B 187 174.679 83.976 12.561 1.00 78.04 C |
| ANISOU 1699 CE2 TYR B 182 6479 5818 7433 −1194 −1362 422 C | ANISOU 1744 CB ASN B 187 12167 8034 9453 −2770 −2046 −140 C |
| ATOM 1700 CD2 TYR B 182 174.536 75.527 8.093 1.00 51.75 C | ATOM 1745 CG ASN B 187 173.505 84.876 12.787 1.00 84.41 C |
| ANISOU 1700 CD2 TYR B 182 6608 5807 7246 −1320 −1547 399 C | ANISOU 1745 CG ASN B 187 13399 8677 9997 −2718 −1697 −373 C |
| ATOM 1701 C TYR B 182 173.771 77.415 11.657 1.00 52.92 C | ATOM 1746 OD1 ASN B 187 172.619 85.002 11.948 1.00 86.04 O |
| ANISOU 1701 C TYR B 182 7853 5631 6624 −1967 −1967 111 C | ANISOU 1746 OD1 ASN B 187 13577 8858 10257 −2505 −1379 −490 O |
| ATOM 1702 O TYR B 182 174.367 78.359 11.136 1.00 51.49 O | ATOM 1747 ND2 ASN B 187 173.493 85.519 13.926 1.00 85.00 N |
| ANISOU 1702 O TYR B 182 7590 5500 5389 6586 −2020 −1987 160 O | ANISOU 1747 ND2 ASN B 187 13857 8637 9801 −2892 −1729 −413 N |
| ATOM 1703 N ASN B 183 172.724 77.574 12.468 1.00 54.55 N | ATOM 1748 C ASN B 187 175.186 84.759 10.276 1.00 68.04 C |
| ANISOU 1703 N ASN B 183 8447 5758 6521 −1992 −1844 −73 N | ANISOU 1748 C ASN B 187 10310 6831 8711 −2465 −1781 −54 C |
| ATOM 1704 CA ASN B 183 172.195 78.906 12.788 1.00 57.74 C | ATOM 1749 O ASN B 187 174.344 85.483 9.799 1.00 64.82 O |
| ANISOU 1704 CA ASN B 183 9221 5981 6736 −2078 −1698 −233 C | ANISOU 1749 O ASN B 187 9985 6379 8266 −2283 −1448 −188 O |
| ATOM 1705 CB ASN B 183 170.885 78.824 13.580 1.00 55.14 C | ATOM 1750 N ASN B 188 176.469 84.958 10.090 1.00 69.05 N |
| ANISOU 1705 CB ASN B 183 9274 5559 6116 −2032 −1460 −418 C | ANISOU 1750 N ASN B 188 10230 6938 9067 −2638 −2054 133 N |
| ATOM 1706 CG ASN B 183 169.674 78.672 12.674 1.00 56.88 C | ATOM 1751 CA ASN B 188 176.944 86.043 9.271 1.00 71.48 C |
| ANISOU 1706 CG ASN B 183 9328 5849 6436 −1697 −1085 −499 C | ANISOU 1751 CA ASN B 188 10403 7177 9579 −2606 −1951 170 C |
| ATOM 1707 OD1 ASN B 183 169.761 78.933 11.458 1.00 57.99 O | ATOM 1752 CB ASN B 188 178.460 86.061 9.288 1.00 76.31 C |
| ANISOU 1707 OD1 ASN B 183 9159 6072 6802 −1532 −990 −449 O | ANISOU 1752 CB ASN B 188 10765 7759 10470 −2829 −2302 419 C |
| ATOM 1708 ND2 ASN B 183 168.535 78.247 13.251 1.00 50.75 N | ATOM 1753 CG ASN B 188 179.009 86.591 10.567 1.00 83.08 C |
| ANISOU 1708 ND2 ASN B 183 8757 5027 5497 −1607 −877 −606 N | ANISOU 1753 CG ASN B 188 11918 8568 11082 −3066 −2548 430 C |
| ATOM 1709 C ASN B 183 173.179 79.783 13.522 1.00 65.45 C | ATOM 1754 OD1 ASN B 188 178.295 87.161 11.355 1.00 89.66 O |
| ANISOU 1709 C ASN B 183 10428 6806 7635 −2424 −1996 −178 C | ANISOU 1754 OD1 ASN B 188 13199 9292 11574 −3143 −2440 232 O |
| ATOM 1710 O ASN B 183 173.167 81.008 13.404 1.00 65.84 O | ATOM 1755 ND2 ASN B 188 180.276 86.390 10.786 1.00 82.66 N |
| ANISOU 1755 ND2 ASN B 188 11627 8574 11206 −3179 −2865 685 N | ANISOU 1800 O VAL B 194 8028 4902 5535 −992 −272 −639 O |
| ATOM 1756 C ASN B 188 176.470 85.965 7.843 1.00 66.95 C | ATOM 1801 N SER B 195 164.443 77.521 9.840 1.00 42.07 N |
| ANISOU 1756 C ASN B 188 9517 6728 9194 −2239 −1602 166 C | ANISOU 1801 N SER B 195 6867 4165 4952 −617 57 −597 N |
| ATOM 1757 O ASN B 188 176.148 86.962 7.261 1.00 67.49 O | ATOM 1802 CA SER B 195 163.552 76.840 10.766 1.00 52.48 C |
| ANISOU 1757 O ASN B 188 9636 6725 9283 −2144 −1375 90 O | ANISOU 1802 CA SER B 195 8347 5429 6166 −586 176 −647 C |
| ATOM 1758 N LEU B 189 176.465 84.771 7.285 1.00 61.56 N | ATOM 1803 CB SER B 195 162.170 76.712 10.131 1.00 60.75 C |
| ANISOU 1758 N LEU B 189 8531 6217 8640 −2049 −1569 257 N | ANISOU 1803 CB SER B 195 9230 6474 7379 −367 412 −601 C |
| ATOM 1759 CA LEU B 189 176.128 84.548 5.895 1.00 62.09 C | ATOM 1804 OG SER B 195 161.732 78.018 9.787 1.00 69.72 O |
| ANISOU 1759 CA LEU B 189 8331 6393 8866 −1742 −1282 276 C | ANISOU 1804 OG SER B 195 10413 7460 8618 −321 614 −592 O |
| ATOM 1760 CB LEU B 189 176.511 83.127 5.495 1.00 61.64 C | ATOM 1805 C SER B 195 164.064 75.484 11.234 1.00 51.84 C |
| ANISOU 1760 CB LEU B 189 7971 6485 8965 −1617 −1313 410 C | ANISOU 1805 C SER B 195 8215 5485 5996 −645 −39 −630 C |
| ATOM 1761 CG LEU B 189 177.470 82.897 4.332 1.00 62.17 C | ATOM 1806 O SER B 195 164.925 74.879 10.602 1.00 42.86 O |
| ANISOU 1761 CG LEU B 189 7663 6583 9376 −1500 −1236 606 C | ANISOU 1806 O SER B 195 6838 4509 4939 −651 −243 −557 O |
| ATOM 1762 CD1 LEU B 189 177.618 81.404 4.133 1.00 62.87 C | ATOM 1807 N GLN B 196 163.480 74.987 12.316 1.00 64.16 N |
| ANISOU 1762 CD1 LEU B 189 7543 6788 9555 −1378 −1219 701 C | ANISOU 1807 N GLN B 196 10002 6966 7410 −672 44 −687 N |
| ATOM 1763 CD2 LEU B 189 176.984 83.562 3.060 1.00 57.30 C | ATOM 1808 CA GLN B 196 164.055 73.855 13.039 1.00 72.80 C |
| ANISOU 1763 CD2 LEU B 189 7021 5966 8785 −1294 −929 547 C | ANISOU 1808 CA GLN B 196 11130 8149 8381 −774 −170 −672 C |
| ATOM 1764 C LEU B 189 174.634 84.678 5.739 1.00 62.94 C | ATOM 1809 CB GLN B 196 163.972 74.078 14.546 1.00 80.99 C |
| ANISOU 1764 C LEU B 189 8642 6519 8754 −1557 −1001 82 C | ANISOU 1809 CB GLN B 196 12621 9001 9149 −951 −138 −757 C |
| ATOM 1765 O LEU B 189 174.133 85.388 4.861 1.00 61.02 O | ATOM 1810 CG GLN B 196 165.316 74.343 15.193 1.00 95.59 C |
| ANISOU 1765 O LEU B 189 8375 6256 8552 −1405 −768 42 O | ANISOU 1810 CG GLN B 196 14648 10827 10844 −1229 −457 −736 C |
| ATOM 1766 N LEU B 190 173.946 83.959 6.618 1.00 62.94 N | ATOM 1811 CD GLN B 196 165.674 75.830 15.239 1.00 108.14 C |
| ANISOU 1766 N LEU B 190 8826 6548 8542 −1035 −11 N | ANISOU 1811 CD GLN B 196 16464 12247 12378 −1367 −425 −787 C |
| ATOM 1767 CA LEU B 190 172.509 83.727 6.555 1.00 63.15 C | ATOM 1812 OE1 GLN B 196 166.392 76.280 16.142 1.00 110.78 O |
| ANISOU 1767 CA LEU B 190 8984 6606 8406 −1390 −786 −151 C | ANISOU 1812 OE1 GLN B 196 17129 12459 12502 −1637 −608 −808 O |
| ATOM 1768 CB LEU B 190 172.129 82.742 7.643 1.00 67.75 C | ATOM 1813 NE2 GLN B 196 165.174 76.600 14.260 1.00 112.63 N |
| ANISOU 1768 CB LEU B 190 9723 7219 8798 −1457 −898 −206 C | ANISOU 1813 NE2 GLN B 196 16864 12799 13132 −1199 −207 −796 N |
| ATOM 1769 CG LEU B 190 171.276 81.566 7.219 1.00 74.45 C | ATOM 1814 C GLN B 196 163.509 72.463 12.711 1.00 70.84 C |
| ANISOU 1769 CG LEU B 190 10432 8218 9636 −1232 −759 −221 C | ANISOU 1814 C GLN B 196 10643 8054 8219 −618 −163 −628 C |
| ATOM 1770 CD1 LEU B 190 171.050 80.704 8.472 1.00 77.34 C | ATOM 1815 O GLN B 196 163.999 71.467 13.245 1.00 76.13 O |
| ANISOU 1770 CD1 LEU B 190 10987 8988 9811 −1340 −886 −269 C | ANISOU 1815 O GLN B 196 11308 8803 8813 −687 −334 −601 O |
| ATOM 1771 CD2 LEU B 190 169.958 82.026 6.591 1.00 73.51 C | ATOM 1816 N ARG B 197 162.508 72.374 11.852 1.00 59.95 N |
| ANISOU 1771 CD2 LEU B 190 10355 8081 9496 −1027 −459 −304 C | ANISOU 1816 N ARG B 197 9069 6708 7002 −424 16 −605 N |
| ATOM 1772 C LEU B 190 171.660 84.976 6.744 1.00 61.83 C | ATOM 1817 CA ARG B 197 161.961 71.056 11.539 1.00 49.55 C |
| ANISOU 1772 C LEU B 190 9091 6274 8126 −1388 −573 −282 C | ANISOU 1817 CA ARG B 197 7550 5520 5758 −301 10 −563 C |
| ATOM 1773 O LEU B 190 170.708 85.197 6.003 1.00 56.91 O | ATOM 1818 CB ARG B 197 160.438 71.021 11.711 1.00 53.83 C |

TABLE 8-continued

DMXAA-hSTING$^{S162A/Q266I}$ complex

| | |
|---|---|
| ANISOU 1773 O LEU B 190 8414 5670 7538 -1180 -324 -312 O | ANISOU 1818 CB ARG B 197 8120 5962 6373 -163 275 -566 C |
| ATOM 1774 N ARG B 191 172.014 85.788 7.738 1.00 68.47 N | ATOM 1819 CG ARG B 197 159.874 72.262 12.354 1.00 64.15 C |
| ANISOU 1774 N ARG B 191 10238 6938 8839 -1634 -674 -342 N | ANISOU 1819 CG ARG B 197 9690 7037 7647 -180 523 -615 C |
| ATOM 1775 CA ARG B 191 171.209 86.949 8.119 1.00 74.22 C | ATOM 1820 CD ARG B 197 158.752 72.003 13.355 1.00 68.99 C |
| ANISOU 1775 CA ARG B 191 11298 7462 9441 -1655 -435 -477 C | ANISOU 1820 CD ARG B 197 10495 7485 8232 -122 790 -639 C |
| ATOM 1776 CB ARG B 191 171.350 88.090 7.109 1.00 74.04 C | ATOM 1821 NE ARG B 197 158.929 72.811 14.570 1.00 80.52 N |
| ANISOU 1776 CB ARG B 191 11145 7383 9603 -1573 -288 -438 C | ANISOU 1821 NE ARG B 197 12398 8719 9478 -259 934 -738 N |
| ATOM 1777 CG ARG B 191 172.740 88.712 7.108 1.00 75.92 C | ATOM 1822 CZ ARG B 197 158.862 74.147 14.633 1.00 86.32 C |
| ANISOU 1777 CG ARG B 191 11337 7563 9945 -1796 -533 -353 C | ANISOU 1822 CZ ARG B 197 13318 9265 10213 -292 1114 -773 C |
| ATOM 1778 CD ARG B 191 172.757 90.056 6.420 1.00 79.96 C | ATOM 1823 NH1 ARG B 197 159.057 74.768 15.793 1.00 91.37 N |
| ANISOU 1778 CD ARG B 191 11847 7953 10581 -1758 -355 -353 C | ANISOU 1823 NH1 ARG B 197 14425 9682 10610 -447 1239 -877 N |
| ATOM 1779 NE ARG B 191 173.104 91.147 7.335 1.00 89.29 N | ATOM 1824 NH2 ARG B 197 158.606 74.869 13.548 1.00 84.76 N |
| ANISOU 1779 NE ARG B 191 13402 8892 11634 -2034 -411 -436 N | ANISOU 1824 NH2 ARG B 197 12874 9088 10244 -184 1169 -702 N |
| ATOM 1780 CZ ARG B 191 172.425 92.291 7.463 1.00 88.21 C | ATOM 1825 C ARG B 197 162.345 70.607 10.146 1.00 44.78 C |
| ANISOU 1780 CZ ARG B 191 13536 8548 11431 -2024 -136 -546 C | ANISOU 1825 C ARG B 197 6627 5082 5304 -221 -102 -489 C |
| ATOM 1781 NH1 ARG B 191 171.333 92.505 6.733 1.00 88.25 N | ATOM 1826 O ARG B 197 162.632 71.413 9.264 1.00 48.26 O |
| ANISOU 1781 NH1 ARG B 191 13440 8569 11521 -1741 203 -560 N | ANISOU 1826 O ARG B 197 6980 5527 5829 -207 -104 -462 O |
| ATOM 1782 NH2 ARG B 191 172.842 93.220 8.326 1.00 84.38 N | ATOM 1827 N LEU B 198 162.348 69.301 9.930 1.00 41.67 N |
| ANISOU 1782 NH2 ARG B 191 13431 7823 10804 -2310 -204 -626 N | ANISOU 1827 N LEU B 198 6087 4812 4935 -172 -178 -456 N |
| ATOM 1783 C ARG B 191 169.759 86.529 8.274 1.00 73.97 C | ATOM 1828 CA LEU B 198 162.463 68.791 8.575 1.00 41.75 C |
| ANISOU 1783 C ARG B 191 11365 7431 9311 -1460 -161 -567 C | ANISOU 1828 CA LEU B 198 5858 4942 5063 -90 -223 -396 C |
| ATOM 1784 O ARG B 191 168.854 87.141 7.717 1.00 77.21 O | ATOM 1829 CB LEU B 198 162.963 67.366 8.608 1.00 37.38 C |
| ANISOU 1784 O ARG B 191 11758 7781 9798 -1283 125 -588 O | ANISOU 1829 CB LEU B 198 5205 4496 4502 -90 -326 -369 C |
| ATOM 1785 N GLY B 192 169.569 85.445 9.018 1.00 70.73 N | ATOM 1830 CG LEU B 198 163.005 66.664 7.259 1.00 41.71 C |
| ANISOU 1785 N GLY B 192 11027 7088 8760 -1493 -263 -592 N | ANISOU 1830 CG LEU B 198 5576 5136 5137 -15 -332 -322 C |
| ATOM 1786 CA GLY B 192 168.259 84.914 9.309 1.00 71.86 C | ATOM 1831 CD1 LEU B 198 164.036 67.316 6.311 1.00 38.71 C |
| ANISOU 1786 CA GLY B 192 11261 7224 8820 -1331 -28 -662 C | ANISOU 1831 CD1 LEU B 198 5126 4766 4818 -41 -365 -280 C |
| ATOM 1787 C GLY B 192 168.454 83.629 10.075 1.00 76.87 C | ATOM 1832 CD2 LEU B 198 163.310 65.171 7.472 1.00 36.17 C |
| ANISOU 1787 C GLY B 192 11927 7962 9319 -1408 -230 -660 C | ANISOU 1832 CD2 LEU B 198 4807 4505 4430 -5 -380 -303 C |
| ATOM 1788 O GLY B 192 169.567 83.326 10.507 1.00 85.87 O | ATOM 1833 C LEU B 198 161.090 68.855 7.879 1.00 44.48 C |
| ANISOU 1788 O GLY B 192 13070 9139 10418 -1612 -542 -607 O | ANISOU 1833 C LEU B 198 6124 5271 5505 32 -94 -368 C |
| ATOM 1789 N ALA B 193 167.375 82.875 10.251 1.00 70.09 N | ATOM 1834 O LEU B 198 160.102 68.354 8.425 1.00 50.79 O |
| ANISOU 1789 N ALA B 193 11074 7140 8417 -1249 -60 -697 N | ANISOU 1834 O LEU B 198 6949 6034 6314 84 -7 -371 O |
| ATOM 1790 CA ALA B 193 167.443 81.577 10.900 1.00 57.93 C | ATOM 1835 N TYR B 199 161.014 69.517 6.720 1.00 36.43 N |
| ANISOU 1790 CA ALA B 193 9539 5708 6765 -1288 -220 -690 C | ANISOU 1835 N TYR B 199 5009 4262 4570 67 -87 -320 N |
| ATOM 1791 CB ALA B 193 166.814 81.629 12.279 1.00 54.00 C | ATOM 1836 CA TYR B 199 159.753 69.591 5.955 1.00 34.46 C |
| ANISOU 1791 CB ALA B 193 9495 5018 6006 -1404 -98 -811 C | ANISOU 1836 CA TYR B 199 4660 3998 4435 156 -23 -246 C |
| ATOM 1792 C ALA B 193 166.671 80.625 10.035 1.00 57.55 C | ATOM 1837 CB TYR B 199 159.447 71.013 5.497 1.00 33.63 C |
| ANISOU 1792 C ALA B 193 9166 5837 6863 -1025 -113 -636 C | ANISOU 1837 CB TYR B 199 4555 3801 4420 175 59 -201 C |
| ATOM 1793 O ALA B 193 165.511 80.879 9.707 1.00 59.23 O | ATOM 1838 CG TYR B 199 159.161 71.921 6.666 1.00 42.42 C |
| ANISOU 1793 O ALA B 193 9366 5996 7142 -851 158 -655 O | ANISOU 1838 CG TYR B 199 5828 4757 5532 167 225 -249 C |
| ATOM 1794 N VAL B 194 167.298 79.523 9.650 1.00 53.72 N | ATOM 1839 CD1 TYR B 199 160.206 72.425 7.464 1.00 43.64 C |
| ANISOU 1794 N VAL B 194 8418 5546 6447 -1004 -323 -551 N | ANISOU 1839 CD1 TYR B 199 6160 4867 5555 63 206 -343 C |
| ATOM 1795 CA VAL B 194 166.524 78.480 9.037 1.00 50.37 C | ATOM 1840 CE1 TYR B 199 159.948 73.236 8.544 1.00 44.58 C |
| ANISOU 1795 CA VAL B 194 7770 5266 6101 -797 -237 -519 C | ANISOU 1840 CE1 TYR B 199 6501 4813 5625 27 367 -401 C |
| ATOM 1796 CB VAL B 194 167.408 77.467 8.283 1.00 47.68 C | ATOM 1841 CZ TYR B 199 158.620 73.567 8.857 1.00 46.43 C |
| ANISOU 1796 CB VAL B 194 7119 5115 5880 -765 -427 -412 C | ANISOU 1841 CZ TYR B 199 6761 4902 5979 126 606 -359 C |
| ATOM 1797 CG1 VAL B 194 166.853 77.887 8.368 1.00 50.34 C | ATOM 1842 OH TYR B 199 158.344 74.384 9.954 1.00 48.34 O |
| ANISOU 1797 CG1 VAL B 194 7418 5435 6273 -941 -644 -342 C | ANISOU 1842 OH TYR B 199 7277 4928 6164 92 833 -423 O |
| ATOM 1798 CG2 VAL B 194 167.199 76.065 8.777 1.00 39.36 C | ATOM 1843 CE2 TYR B 199 157.570 73.054 8.093 1.00 44.08 C |
| ANISOU 1798 CG2 VAL B 194 6031 4160 4764 -739 -498 -407 C | ANISOU 1843 CE2 TYR B 199 6228 4652 5867 245 625 -238 C |
| ATOM 1799 C VAL B 194 165.680 77.874 10.160 1.00 46.53 C | ATOM 1844 CD2 TYR B 199 157.852 72.235 7.010 1.00 42.22 C |
| ANISOU 1799 C VAL B 194 7511 4717 5452 -806 -151 -595 C | ANISOU 1844 CD2 TYR B 199 5796 4604 5642 250 409 -188 C |
| ATOM 1800 O VAL B 194 166.131 77.793 11.296 1.00 48.60 O | ATOM 1845 C TYR B 199 159.683 68.588 4.799 1.00 32.02 C |
| ANISOU 1845 C TYR B 199 4230 3801 4137 173 -129 -195 C | ANISOU 1890 OD2 ASP B 205 9630 8506 8412 -1231 -2583 1443 O |
| ATOM 1846 O TYR B 199 160.528 68.569 3.904 1.00 32.01 O | ATOM 1891 OD1 ASP B 205 152.471 63.935 -7.962 1.00 55.03 O |
| ANISOU 1846 O TYR B 199 4207 3856 4101 144 -196 -188 O | ANISOU 1891 OD1 ASP B 205 7775 6685 6449 -1032 -2167 1052 O |
| ATOM 1847 N ILE B 200 158.669 67.735 4.847 1.00 26.37 N | ATOM 1892 C ASP B 205 151.460 61.361 -7.557 1.00 54.03 C |
| ANISOU 1847 N ILE B 200 3458 3096 3465 213 -129 -156 N | ANISOU 1892 C ASP B 205 7732 6535 6264 -1209 -2361 1014 C |
| ATOM 1848 CA ILE B 200 158.608 66.578 3.969 1.00 28.90 C | ATOM 1893 O ASP B 205 151.650 60.588 -8.496 1.00 54.35 O |
| ANISOU 1848 CA ILE B 200 3723 3504 3753 201 -232 -129 C | ANISOU 1893 O ASP B 205 8141 6520 5992 -1410 -2472 964 O |
| ATOM 1849 CB ILE B 200 158.457 65.306 4.803 1.00 33.30 C | ATOM 1894 N CYS B 206 152.313 61.466 -6.535 1.00 55.64 N |
| ANISOU 1849 CB ILE B 200 4284 4092 4276 211 -228 -172 C | ANISOU 1894 N CYS B 206 7815 6792 6535 -979 -2027 823 N |
| ATOM 1850 CG1 ILE B 200 159.714 65.132 5.652 1.00 39.48 C | ATOM 1895 CA CYS B 206 153.575 60.706 -6.452 1.00 56.34 C |
| ANISOU 1850 CG1 ILE B 200 5136 4897 4968 177 -225 -253 C | ANISOU 1895 CA CYS B 206 8137 6884 6385 -929 -1767 570 C |
| ATOM 1851 CD1 ILE B 200 159.619 64.067 6.703 1.00 41.48 C | ATOM 1896 CB CYS B 206 153.349 59.202 -6.616 1.00 58.58 C |
| ANISOU 1851 CD1 ILE B 200 5411 5165 5183 183 -215 -287 C | ANISOU 1896 CB CYS B 206 8611 7126 6518 -1057 -1827 507 C |
| ATOM 1852 CG2 ILE B 200 158.231 64.093 3.926 1.00 23.10 C | ATOM 1897 SG CYS B 206 152.425 58.494 -5.309 1.00 44.15 S |
| ANISOU 1852 CG2 ILE B 200 2958 2862 2955 191 -314 -145 C | ANISOU 1897 SG CYS B 206 6452 5339 4982 -963 -1849 548 S |
| ATOM 1853 C ILE B 200 157.476 66.717 2.973 1.00 27.65 C | ATOM 1898 C CYS B 206 154.666 61.153 -7.426 1.00 55.92 C |
| ANISOU 1853 C ILE B 200 3487 3329 3690 207 -290 -8 C | ANISOU 1898 C CYS B 206 8383 6792 6073 -970 -1652 484 C |
| ATOM 1854 O ILE B 200 156.283 66.619 3.324 1.00 30.64 O | ATOM 1899 O CYS B 206 155.628 60.420 -7.658 1.00 63.05 O |
| ANISOU 1854 O ILE B 200 3788 3656 4199 245 -264 70 O | ANISOU 1899 O CYS B 206 9530 7654 6773 -972 -1451 320 O |
| ATOM 1855 N LEU B 201 157.861 66.984 1.731 1.00 26.69 N | ATOM 1900 N GLY B 207 154.531 62.346 -7.986 1.00 47.28 N |
| ANISOU 1855 N LEU B 201 3388 3236 3516 163 -369 28 N | ANISOU 1900 N GLY B 207 7262 5693 5008 -994 -1749 608 N |
| ATOM 1856 CA LEU B 201 156.897 67.079 0.648 1.00 31.08 C | ATOM 1901 CA GLY B 207 155.577 62.887 -8.832 1.00 45.91 C |
| ANISOU 1856 CA LEU B 201 3902 3780 4129 127 -484 164 C | ANISOU 1901 CA GLY B 207 7346 5478 4621 -1009 -1609 536 C |
| ATOM 1857 CB LEU B 201 157.549 67.681 -0.591 1.00 36.06 C | ATOM 1902 C GLY B 207 156.695 63.517 -8.020 1.00 49.99 C |

TABLE 8-continued

DMXAA-hSTING$^{S162A/Q266I}$ complex

| | |
|---|---|
| ANISOU 1857 CB LEU B 201 4614 4420 4667 74 −536 188 C | ANISOU 1902 C GLY B 207 7691 6041 5264 −786 −1300 406 C |
| ATOM 1858 CG LEU B 201 157.997 69.132 −0.381 1.00 38.64 C | ATOM 1903 O GLY B 207 156.581 64.643 −7.536 1.00 59.06 O |
| ANISOU 1858 CG LEU B 201 4920 4699 5061 115 −440 185 C | ANISOU 1903 O GLY B 207 8594 7230 6615 −677 −1290 470 O |
| ATOM 1859 CD1 LEU B 201 158.874 69.532 −1.545 1.00 35.08 C | ATOM 1904 N VAL B 208 157.791 62.784 −7.884 1.00 44.26 N |
| ANISOU 1859 CD1 LEU B 201 4567 4263 4501 66 −465 187 C | ANISOU 1904 N VAL B 208 7102 5288 4427 −729 −1047 237 N |
| ATOM 1860 CD2 LEU B 201 156.817 70.089 −0.262 1.00 36.75 C | ATOM 1905 CA VAL B 208 159.029 63.311 −7.332 1.00 39.76 C |
| ANISOU 1860 CD2 LEU B 201 4564 4380 5021 156 −427 325 C | ANISOU 1905 CA VAL B 208 6420 4737 3952 −562 −778 138 C |
| ATOM 1861 C LEU B 201 156.247 65.727 0.329 1.00 28.35 C | ATOM 1906 CB VAL B 208 159.672 62.269 −6.450 1.00 36.82 C |
| ANISOU 1861 C LEU B 201 3556 3466 3749 78 −596 197 C | ANISOU 1906 CB VAL B 208 5982 4377 3632 −468 −592 14 C |
| ATOM 1862 O LEU B 201 156.924 64.757 0.084 1.00 27.03 O | ATOM 1907 CG1 VAL B 208 160.931 62.832 −5.831 1.00 27.01 C |
| ANISOU 1862 O LEU B 201 3487 3345 3437 41 −607 112 O | ANISOU 1907 CG1 VAL B 208 4593 3150 2521 −322 −369 −46 C |
| ATOM 1863 N LEU B 202 154.919 65.672 0.349 1.00 29.08 N | ATOM 1908 CG2 VAL B 208 158.642 61.789 −5.395 1.00 30.42 C |
| ANISOU 1863 N LEU B 202 3529 3517 4003 78 −668 337 N | ANISOU 1908 CG2 VAL B 208 4945 3641 2973 −439 −733 38 C |
| ATOM 1864 CA LEU B 202 154.187 64.475 −0.015 1.00 26.99 C | ATOM 1909 C VAL B 208 160.031 63.656 −8.425 1.00 49.15 C |
| ANISOU 1864 CA LEU B 202 3257 3269 3729 7 −810 396 C | ANISOU 1909 C VAL B 208 7882 5833 4960 −601 −617 110 C |
| ATOM 1865 CB LEU B 202 153.418 63.988 1.195 1.00 34.82 C | ATOM 1910 O VAL B 208 160.427 62.779 −9.188 1.00 57.69 O |
| ANISOU 1865 CB LEU B 202 4120 4227 4884 85 −719 410 C | ANISOU 1910 O VAL B 208 9278 6813 5827 −690 −507 53 O |
| ATOM 1866 CG LEU B 202 154.268 63.364 2.288 1.00 46.17 C | ATOM 1911 N PRO B 209 160.445 64.930 −8.509 1.00 54.29 N |
| ANISOU 1866 CG LEU B 202 5630 5702 6212 145 −570 230 C | ANISOU 1911 N PRO B 209 8432 6498 5698 −535 −573 152 N |
| ATOM 1867 CD1 LEU B 202 153.869 63.865 3.636 1.00 52.42 C | ATOM 1912 CA PRO B 209 161.442 65.311 −9.523 1.00 54.08 C |
| ANISOU 1867 CD1 LEU B 202 6355 6420 7143 248 −387 224 C | ANISOU 1912 CA PRO B 209 8652 6371 5526 −557 −387 136 C |
| ATOM 1868 CD2 LEU B 202 153.984 61.910 2.241 1.00 55.81 C | ATOM 1913 CB PRO B 209 161.362 66.845 −9.557 1.00 49.15 C |
| ANISOU 1868 CD2 LEU B 202 6866 6956 7383 100 −645 214 C | ANISOU 1913 CB PRO B 209 7864 5784 5024 −511 −458 226 C |
| ATOM 1869 C LEU B 202 153.201 64.765 −1.098 1.00 30.78 C | ATOM 1914 CG PRO B 209 160.147 67.211 −8.711 1.00 56.32 C |
| ANISOU 1869 C LEU B 202 3686 3714 4295 −90 −1018 600 C | ANISOU 1914 CG PRO B 209 8484 6791 6122 −488 −692 307 C |
| ATOM 1870 O LEU B 202 151.997 64.856 −0.816 1.00 39.87 O | ATOM 1915 CD PRO B 209 159.987 66.089 −7.725 1.00 56.05 C |
| ANISOU 1870 O LEU B 202 4651 4807 5689 −73 −1069 770 O | ANISOU 1915 CD PRO B 209 8339 6801 6155 −442 −669 223 C |
| ATOM 1871 N PRO B 203 153.683 64.929 −2.337 1.00 32.30 N | ATOM 1916 C PRO B 209 162.847 64.879 −9.086 1.00 57.93 C |
| ANISOU 1871 N PRO B 203 4041 3925 4306 −197 −1139 609 N | ANISOU 1916 C PRO B 209 9099 6815 6099 −431 −62 31 C |
| ATOM 1872 CA PRO B 203 152.747 65.054 −3.474 1.00 38.44 C | ATOM 1917 O PRO B 209 163.077 64.561 −7.909 1.00 51.36 O |
| ANISOU 1872 CA PRO B 203 4820 4668 5117 −340 −1404 822 C | ANISOU 1917 O PRO B 209 8009 6053 5455 −324 −22 −15 O |
| ATOM 1873 CB PRO B 203 153.656 65.256 −4.682 1.00 29.90 C | ATOM 1918 N ASP B 210 163.784 64.893 −10.026 1.00 64.29 N |
| ANISOU 1873 CB PRO B 203 4006 3599 3757 −442 −1451 763 C | ANISOU 1918 N ASP B 210 10157 7489 6782 −448 173 16 N |
| ATOM 1874 CG PRO B 203 154.925 64.593 −4.286 1.00 37.83 C | ATOM 1919 CA ASP B 210 165.180 64.634 −9.711 1.00 69.95 C |
| ANISOU 1874 CG PRO B 203 5154 4641 4578 −382 −1241 524 C | ANISOU 1919 CA ASP B 210 10794 8135 7647 −323 499 −28 C |
| ATOM 1875 CD PRO B 203 155.083 64.880 −2.788 1.00 32.85 C | ATOM 1920 CB ASP B 210 165.980 64.638 −10.993 1.00 80.39 C |
| ANISOU 1875 CD PRO B 203 4320 4030 4132 −211 −1045 444 C | ANISOU 1920 CB ASP B 210 12493 9260 8791 −369 792 −31 C |
| ATOM 1876 C PRO B 203 151.942 63.772 −3.656 1.00 37.98 C | ATOM 1921 CG ASP B 210 165.926 62.971 −11.457 1.00 93.92 C |
| ANISOU 1876 C PRO B 203 4778 4604 5046 −457 −1588 886 C | ANISOU 1921 CG ASP B 210 14530 10845 10309 −448 937 −97 C |
| ATOM 1877 O PRO B 203 152.504 62.697 −3.851 1.00 42.09 O | ATOM 1922 OD1 ASP B 210 164.825 62.489 −11.813 1.00 99.26 O |
| ANISOU 1877 O PRO B 203 5500 5151 5340 −519 −1576 740 O | ANISOU 1922 OD1 ASP B 210 15417 11540 10755 −600 702 −111 O |
| ATOM 1878 N LEU B 204 150.622 63.898 −3.587 1.00 34.80 N | ATOM 1923 OD2 ASP B 210 166.995 62.325 −11.447 1.00 100.19 O |
| ANISOU 1878 N LEU B 204 4153 4150 4918 −487 −1747 1123 N | ANISOU 1923 OD2 ASP B 210 15355 11508 11205 −361 1291 −118 O |
| ATOM 1879 CA LEU B 204 149.722 62.761 −3.715 1.00 38.40 C | ATOM 1924 C ASP B 210 165.759 65.801 −8.941 1.00 67.48 C |
| ANISOU 1879 CA LEU B 204 4581 4587 5422 −609 −1950 1226 C | ANISOU 1924 C ASP B 210 10145 7899 7596 −205 501 8 C |
| ATOM 1880 CB LEU B 204 148.303 63.181 −3.370 1.00 40.15 C | ATOM 1925 O ASP B 210 166.547 65.626 −8.017 1.00 65.35 O |
| ANISOU 1880 CB LEU B 204 4457 4730 6068 −584 −2052 1524 C | ANISOU 1925 O ASP B 210 9635 7650 7543 −103 607 −4 O |
| ATOM 1881 CG LEU B 204 148.316 63.585 −1.899 1.00 45.77 C | ATOM 1926 N ASN B 211 165.346 66.997 −9.339 1.00 69.44 N |
| ANISOU 1881 CG LEU B 204 4969 5414 7008 −341 −1700 1446 C | ANISOU 1926 N ASN B 211 10390 8177 7817 −236 367 67 N |
| ATOM 1882 CD1 LEU B 204 146.967 64.050 −1.469 1.00 51.30 C | ATOM 1927 CA ASN B 211 165.870 68.231 −8.792 1.00 69.04 C |
| ANISOU 1882 CD1 LEU B 204 5325 5997 8169 −278 −1700 1742 C | ANISOU 1927 CA ASN B 211 10084 8169 7977 −149 377 100 C |
| ATOM 1883 CD2 LEU B 204 148.817 62.433 −0.980 1.00 31.72 C | ATOM 1928 CB ASN B 211 166.590 68.999 −9.894 1.00 79.65 C |
| ANISOU 1883 CD2 LEU B 204 3283 3682 5087 −275 −1528 1208 C | ANISOU 1928 CB ASN B 211 11598 9400 9264 −159 545 150 C |
| ATOM 1884 C LEU B 204 149.752 62.085 −5.095 1.00 48.36 C | ATOM 1929 CG ASN B 211 167.768 69.792 −9.378 1.00 88.10 C |
| ANISOU 1884 C LEU B 204 6138 5844 6391 −863 −2241 1256 C | ANISOU 1929 CG ASN B 211 12430 10451 10591 −58 694 175 C |
| ATOM 1885 O LEU B 204 149.519 60.882 −5.196 1.00 55.98 O | ATOM 1930 OD1 ASN B 211 167.611 70.743 −8.598 1.00 89.43 O |
| ANISOU 1885 O LEU B 204 7217 6802 7251 −975 −2344 1218 O | ANISOU 1930 OD1 ASN B 211 12365 10704 10911 −25 557 188 O |
| ATOM 1886 N ASP B 205 150.025 62.843 −6.152 1.00 43.11 N | ATOM 1931 ND2 ASN B 211 168.967 69.404 −9.814 1.00 91.26 N |
| ANISOU 1886 N ASP B 205 5631 5168 5582 −966 −2365 1323 N | ANISOU 1931 ND2 ASN B 211 12899 10718 11058 −14 991 193 N |
| ATOM 1887 CA ASP B 205 150.189 62.255 −7.499 1.00 49.50 C | ATOM 1932 C ASN B 211 164.751 69.092 −8.182 1.00 60.90 C |
| ANISOU 1887 CA ASP B 205 6822 5946 6039 −1225 −2603 1325 C | ANISOU 1932 C ASN B 211 8871 7254 7014 −155 110 136 C |
| ATOM 1888 CB ASP B 205 150.185 63.320 −8.638 1.00 39.30 C | ATOM 1933 O ASN B 211 163.932 69.709 −8.888 1.00 54.95 O |
| ANISOU 1888 CB ASP B 205 5650 4624 4657 −1345 −2786 1484 C | ANISOU 1933 O ASN B 211 8215 6501 6163 −224 −36 209 O |
| ATOM 1889 CG ASP B 205 151.448 64.235 −8.631 1.00 62.09 C | ATOM 1934 N LEU B 212 164.726 69.119 −6.857 1.00 57.88 N |
| ANISOU 1889 CG ASP B 205 8626 7541 7424 −1187 −2483 1305 C | ANISOU 1934 N LEU B 212 8233 6949 6808 −87 61 99 N |
| ATOM 1890 OD2 ASP B 205 151.412 65.278 −9.333 1.00 69.87 O | ATOM 1935 CA LEU B 212 163.735 69.890 −6.125 1.00 58.26 C |
| ANISOU 1935 CA LEU B 212 8115 7069 6951 −73 −114 127 C | ANISOU 1980 OD1 ASN B 218 5283 4571 6423 230 −52 1139 O |
| ATOM 1936 CB LEU B 212 163.974 69.758 −4.625 1.00 51.05 C | ATOM 1981 ND2 ASN B 218 156.926 81.935 −6.728 1.00 39.75 N |
| ANISOU 1936 CB LEU B 212 7699 7217 7287 46 −219 137 C | ANISOU 1981 ND2 ASN B 218 4714 4199 6188 215 −281 1401 N |
| ATOM 1937 CG LEU B 212 162.782 69.985 −3.688 1.00 52.03 C | ATOM 1982 C ASN B 218 160.686 79.571 −4.754 1.00 36.46 C |
| ANISOU 1937 CG LEU B 212 7002 6379 6388 7 −235 72 C | ANISOU 1982 C ASN B 218 4682 3996 5173 159 −74 609 C |
| ATOM 1938 CD1 LEU B 212 163.220 69.677 −2.288 1.00 58.44 C | ATOM 1983 O ASN B 218 160.653 79.921 −3.590 1.00 37.89 O |
| ANISOU 1938 CD1 LEU B 212 7699 7217 7287 46 −203 −2 C | ANISOU 1983 O ASN B 218 4832 4119 5445 195 37 529 O |
| ATOM 1939 CD2 LEU B 212 162.184 71.368 −3.720 1.00 42.24 C | ATOM 1984 N ILE B 219 161.244 78.438 −5.117 1.00 38.14 N |
| ANISOU 1939 CD2 LEU B 212 5700 5114 5236 20 −277 141 C | ANISOU 1984 N ILE B 219 4980 4295 5217 113 −143 541 N |
| ATOM 1940 C LEU B 212 163.708 71.380 −6.538 1.00 62.91 C | ATOM 1985 CA ILE B 219 162.016 77.683 −4.143 1.00 42.83 C |
| ANISOU 1940 C LEU B 212 8674 7632 7596 −67 −129 198 C | ANISOU 1985 CA ILE B 219 5590 4924 5758 112 −93 381 C |
| ATOM 1941 O LEU B 212 162.639 71.928 −6.818 1.00 67.47 O | ATOM 1986 CB ILE B 219 161.518 76.263 −3.956 1.00 46.97 C |

TABLE 8-continued

DMXAA-hSTING$^{S162A/Q266I}$ complex

| | |
|---|---|
| ANISOU 1941 O LEU B 212 9243 8221 8173 −97 −270 282 O | ANISOU 1986 CB ILE B 219 6124 5520 6201 97 −180 356 C |
| ATOM 1942 N SER B 213 164.873 72.021 −6.568 1.00 61.43 N | ATOM 1987 CG1 ILE B 219 160.057 76.277 −3.544 1.00 48.18 C |
| ANISOU 1942 N SER B 213 8453 7401 7488 −30 15 186 N | ANISOU 1987 CG1 ILE B 219 6182 5649 6475 128 −227 449 C |
| ATOM 1943 CA SER B 213 164.987 73.452 −6.897 1.00 66.12 C | ATOM 1988 CD1 ILE B 219 159.515 74.913 −3.197 1.00 48.92 C |
| ANISOU 1943 CA SER B 213 9012 7960 8150 −19 25 245 C | ANISOU 1988 CD1 ILE B 219 6268 5803 6516 116 −305 423 C |
| ATOM 1944 CB SER B 213 166.458 73.869 −6.925 1.00 67.57 C | ATOM 1989 CG2 ILE B 219 162.368 75.544 −2.897 1.00 43.26 C |
| ANISOU 1944 CB SER B 213 9155 8082 8434 13 199 233 C | ANISOU 1989 CG2 ILE B 219 5660 5082 5697 96 −131 211 C |
| ATOM 1945 OG SER B 213 167.259 72.882 −6.295 1.00 70.73 O | ATOM 1990 C ILE B 219 163.446 77.654 −4.636 1.00 48.06 C |
| ANISOU 1945 OG SER B 213 9492 8486 8896 34 277 182 O | ANISOU 1990 C ILE B 219 6321 5595 6344 83 −39 324 C |
| ATOM 1946 C SER B 213 164.322 73.872 −8.219 1.00 67.75 C | ATOM 1991 O ILE B 219 163.725 77.265 −5.764 1.00 49.93 O |
| ANISOU 1946 C SER B 213 9389 8133 8219 −80 −44 345 C | ANISOU 1991 O ILE B 219 6651 5848 6473 56 −54 367 O |
| ATOM 1947 O SER B 213 163.975 75.039 −8.391 1.00 59.99 O | ATOM 1992 N ARG B 220 164.365 78.114 −3.807 1.00 52.69 N |
| ANISOU 1947 O SER B 213 8350 7136 7307 −72 −90 419 O | ANISOU 1992 N ARG B 220 6877 6147 6994 79 33 242 N |
| ATOM 1948 N MET B 214 164.142 72.925 −9.143 1.00 74.01 N | ATOM 1993 CA ARG B 220 165.726 78.279 −4.286 1.00 47.28 C |
| ANISOU 1948 N MET B 214 10411 8900 8808 −154 −57 355 N | ANISOU 1993 CA ARG B 220 6209 5443 6313 57 97 233 C |
| ATOM 1949 CA MET B 214 163.585 73.233 −10.470 1.00 77.45 C | ATOM 1994 CB ARG B 220 166.006 79.752 −4.493 1.00 51.25 C |
| ANISOU 1949 CA MET B 214 11076 9290 9063 −253 −152 461 C | ANISOU 1994 CB ARG B 220 6695 5865 6912 57 159 272 C |
| ATOM 1950 CB MET B 214 164.104 72.251 −11.518 1.00 81.35 C | ATOM 1995 CG ARG B 220 165.644 80.201 −5.896 1.00 60.94 C |
| ANISOU 1950 CB MET B 214 11911 9694 9305 −334 −29 427 C | ANISOU 1995 CG ARG B 220 7981 7077 8097 74 172 384 C |
| ATOM 1951 CG MET B 214 165.618 72.193 −11.593 1.00 83.59 C | ATOM 1996 CD ARG B 220 165.094 81.593 −5.909 1.00 63.66 C |
| ANISOU 1951 CG MET B 214 12223 9890 9647 −254 290 361 C | ANISOU 1996 CD ARG B 220 8288 7349 8550 96 200 449 C |
| ATOM 1952 SD MET B 214 166.339 73.817 −11.900 1.00 135.11 S | ATOM 1997 NE ARG B 220 165.875 82.496 −5.067 1.00 68.52 N |
| ANISOU 1952 SD MET B 214 18655 16370 16312 −194 397 430 S | ANISOU 1997 NE ARG B 220 8866 7891 9277 78 277 381 N |
| ATOM 1953 CE MET B 214 168.085 73.411 −11.919 1.00 97.04 C | ATOM 1998 CZ ARG B 220 166.240 83.725 −5.426 1.00 65.63 C |
| ANISOU 1953 CE MET B 214 13832 11427 11612 −109 771 383 C | ANISOU 1998 CZ ARG B 220 8495 7443 8999 79 352 425 C |
| ATOM 1954 C MET B 214 162.066 73.227 −10.487 1.00 74.60 C | ATOM 1999 NH1 ARG B 220 166.947 84.494 −4.596 1.00 62.09 N |
| ANISOU 1954 C MET B 214 10671 8980 8694 −324 −430 569 C | ANISOU 1999 NH1 ARG B 220 8035 6903 6916 8640 35 400 358 N |
| ATOM 1955 O MET B 214 161.434 73.816 −11.384 1.00 73.18 O | ATOM 2000 NH2 ARG B 220 165.890 84.176 −6.622 1.00 64.54 N |
| ANISOU 1955 O MET B 214 10592 8774 8440 −408 −578 709 O | ANISOU 2000 NH2 ARG B 220 8381 7294 8848 107 364 545 N |
| ATOM 1956 N ALA B 215 161.497 72.552 −9.487 1.00 72.41 N | ATOM 2001 C ARG B 220 166.731 77.653 −3.352 1.00 42.62 C |
| ANISOU 1956 N ALA B 215 10233 8768 8513 −294 −502 525 N | ANISOU 2001 C ARG B 220 5572 4868 5755 26 97 156 C |
| ATOM 1957 CA ALA B 215 160.044 72.372 −9.370 1.00 73.76 C | ATOM 2002 O ARG B 220 166.598 77.752 −2.138 1.00 43.73 O |
| ANISOU 1957 CA ALA B 215 10316 8973 8734 −351 −747 643 C | ANISOU 2002 O ARG B 220 5692 5000 5925 1 56 94 O |
| ATOM 1958 CB ALA B 215 159.700 71.484 −8.177 1.00 71.88 C | ATOM 2003 N PHE B 221 167.727 76.988 −3.925 1.00 43.65 N |
| ANISOU 1958 CB ALA B 215 9921 8792 8599 −296 −746 559 C | ANISOU 2003 N PHE B 221 5701 5001 5883 22 152 177 N |
| ATOM 1959 C ALA B 215 159.271 73.683 −9.275 1.00 73.99 C | ATOM 2004 CA PHE B 221 168.744 76.344 −3.119 1.00 45.53 C |
| ANISOU 1959 C ALA B 215 10152 8995 8967 −317 −842 799 C | ANISOU 2004 CA PHE B 221 5855 5243 6202 −8 141 155 C |
| ATOM 1960 O ALA B 215 158.138 73.792 −9.758 1.00 78.31 O | ATOM 2005 CB PHE B 221 169.642 75.480 −3.987 1.00 44.56 C |
| ANISOU 1960 O ALA B 215 10673 9533 9547 −400 −1065 982 O | ANISOU 2005 CB PHE B 221 5732 5098 6102 17 262 211 C |
| ATOM 1961 N ASP B 216 159.889 74.671 −8.636 1.00 67.69 N | ATOM 2006 CG PHE B 221 170.776 74.846 −3.229 1.00 46.85 C |
| ANISOU 1961 N ASP B 216 9211 8184 8324 −204 −673 745 N | ANISOU 2006 CG PHE B 221 5885 5373 6543 −9 258 242 C |
| ATOM 1962 CA ASP B 216 159.248 75.954 −8.413 1.00 60.18 C | ATOM 2007 CD1 PHE B 221 170.551 73.735 −2.405 1.00 46.88 C |
| ANISOU 1962 CA ASP B 216 8077 7199 7592 −151 −695 875 C | ANISOU 2007 CD1 PHE B 221 5859 5437 6515 −16 180 204 C |
| ATOM 1963 CB ASP B 216 158.592 75.920 −7.024 1.00 59.93 C | ATOM 2008 CE1 PHE B 221 171.603 73.129 −1.701 1.00 45.40 C |
| ANISOU 1963 CB ASP B 216 7823 7170 7778 −61 −649 849 C | ANISOU 2008 CE1 PHE B 221 5527 5232 6491 −48 154 269 C |
| ATOM 1964 CG ASP B 216 157.637 77.075 −6.777 1.00 59.77 C | ATOM 2009 CZ PHE B 221 172.915 73.654 −1.830 1.00 48.53 C |
| ANISOU 1964 CG ASP B 216 7611 7077 8021 −4 −649 1020 C | ANISOU 2009 CZ PHE B 221 5784 5542 7115 −76 201 390 C |
| ATOM 1965 OD1 ASP B 216 157.812 78.144 −7.382 1.00 63.91 O | ATOM 2010 CE2 PHE B 221 173.137 74.777 −2.647 1.00 51.22 C |
| ANISOU 1965 OD1 ASP B 216 8141 7556 8588 0 −628 1108 O | ANISOU 2010 CE2 PHE B 221 6153 5817 7491 −66 291 417 C |
| ATOM 1966 OD2 ASP B 216 156.719 76.902 −5.945 1.00 63.19 O | ATOM 2011 CD2 PHE B 221 172.064 75.365 −3.329 1.00 47.63 C |
| ANISOU 1966 OD2 ASP B 216 7886 7484 8638 47 −640 1072 O | ANISOU 2011 CD2 PHE B 221 5865 5389 6843 −31 321 336 C |
| ATOM 1967 C ASP B 216 160.287 77.086 −8.551 1.00 47.10 C | ATOM 2012 C PHE B 221 169.589 77.393 −2.412 1.00 44.95 C |
| ANISOU 1967 C ASP B 216 6434 5498 5963 −96 −524 829 C | ANISOU 2012 C PHE B 221 5707 5106 6265 −69 113 164 C |
| ATOM 1968 O ASP B 216 161.370 77.038 −7.968 1.00 43.08 O | ATOM 2013 O PHE B 221 170.036 78.350 −3.036 1.00 55.86 O |
| ANISOU 1968 O ASP B 216 5925 4992 5451 −46 −360 675 O | ANISOU 2013 O PHE B 221 7081 6425 7718 −69 179 213 O |
| ATOM 1969 N PRO B 217 159.965 78.120 −9.327 1.00 45.65 N | ATOM 2014 N LEU B 222 169.826 77.168 −1.136 1.00 41.12 N |
| ANISOU 1969 N PRO B 217 6251 5268 5827 −116 −576 984 N | ANISOU 2014 N LEU B 222 5191 4627 5804 −137 3 122 N |
| ATOM 1970 CA PRO B 217 160.890 79.264 −9.380 1.00 44.12 C | ATOM 2015 CA LEU B 222 170.728 77.974 −0.349 1.00 45.43 C |
| ANISOU 1970 CA PRO B 217 6049 5024 5693 −59 −406 946 C | ANISOU 2015 CA LEU B 222 5694 5101 6465 −242 −71 142 C |
| ATOM 1971 CB PRO B 217 160.237 80.217 −10.388 1.00 42.96 C | ATOM 2016 CB LEU B 222 170.058 78.402 0.938 1.00 39.34 C |
| ANISOU 1971 CB PRO B 217 5910 4828 5584 −99 −517 1163 C | ANISOU 2016 CB LEU B 222 5038 4306 5603 −325 −175 49 C |
| ATOM 1972 CG PRO B 217 159.288 79.394 −11.181 1.00 41.49 C | ATOM 2017 CG LEU B 222 169.010 79.472 0.926 1.00 40.36 C |
| ANISOU 1972 CG PRO B 217 5826 4671 5267 −220 −770 1306 C | ANISOU 2017 CG LEU B 222 5289 4380 5667 −292 −93 −11 C |
| ATOM 1973 CD PRO B 217 158.805 78.294 −10.213 1.00 43.97 C | ATOM 2018 CD1 LEU B 222 168.805 79.969 2.326 1.00 43.40 C |
| ANISOU 1973 CD PRO B 217 6044 5039 5624 −202 −806 1219 C | ANISOU 2018 CD1 LEU B 222 5829 4684 5977 −400 −149 −98 C |
| ATOM 1974 C PRO B 217 161.010 79.973 −8.021 1.00 46.42 C | ATOM 2019 CD2 LEU B 222 169.416 80.600 0.022 1.00 46.26 C |
| ANISOU 1974 C PRO B 217 6153 5283 6203 42 −261 861 C | ANISOU 2019 CD2 LEU B 222 6003 5061 6514 −283 −15 46 C |
| ATOM 1975 O PRO B 217 161.979 80.678 −7.764 1.00 47.99 O | ATOM 2020 C LEU B 222 171.989 77.233 0.018 1.00 46.04 C |
| ANISOU 1975 O PRO B 217 6350 5443 6440 75 −116 777 O | ANISOU 2020 C LEU B 222 5630 5176 6688 −293 −128 232 C |
| ATOM 1976 N ASN B 218 160.014 79.807 −7.163 1.00 45.31 N | ATOM 2021 O LEU B 222 173.043 77.639 −0.337 1.00 51.56 O |
| ANISOU 1976 N ASN B 218 5874 5137 6205 80 −293 892 N | ANISOU 2021 O LEU B 222 6214 5811 7566 −323 −102 336 O |
| ATOM 1977 CA ASN B 218 160.065 80.422 −5.846 1.00 39.22 C | ATOM 2022 N ASP B 223 171.874 76.153 0.761 1.00 46.95 N |
| ANISOU 1977 CA ASN B 218 4999 4304 5598 157 −131 803 C | ANISOU 2022 N ASP B 223 5735 5353 6749 −297 −199 210 N |
| ATOM 1978 CB ASN B 218 158.674 80.872 −5.445 1.00 33.16 C | ATOM 2023 CA ASP B 223 173.032 75.531 1.354 1.00 48.82 C |
| ANISOU 1978 CB ASN B 218 4078 3459 5061 211 −125 958 C | ANISOU 2023 CA ASP B 223 5834 5578 7139 −377 −309 311 C |
| ATOM 1979 CG ASN B 218 158.178 82.005 −6.303 1.00 39.55 C | ATOM 2024 CB ASP B 223 173.372 76.297 2.620 1.00 57.59 C |
| ANISOU 1979 CG ASN B 218 4818 4197 6013 221 −146 1168 C | ANISOU 2024 CB ASP B 223 6998 6636 8250 −548 −511 302 C |
| ATOM 1980 OD1 ASN B 218 158.922 82.942 −6.585 1.00 42.84 O | ATOM 2025 CG ASP B 223 174.817 76.277 2.951 1.00 61.92 C |

TABLE 8-continued

DMXAA-hSTING$^{S162A/Q266I}$ complex

| | |
|---|---|
| ANISOU 2025 CG ASP B 223 7369 7143 9014 −663 −662 465 C | ANISOU 2070 C GLN B 228 15252 16449 18937 −290 −3158 553 C |
| ATOM 2026 OD1 ASP B 223 175.629 76.531 2.085 1.00 68.73 O | ATOM 2071 O GLN B 228 175.194 61.638 8.192 1.00130.89 O |
| ANISOU 2026 OD1 ASP B 223 8054 8015 10048 −570 −549 580 O | ANISOU 2071 O GLN B 228 14910 16176 18644 −220 −2851 565 O |
| ATOM 2027 OD2 ASP B 223 175.142 76.020 4.098 1.00 57.53 O | ATOM 2072 N THR B 229 176.629 61.324 9.899 1.00138.46 N |
| ANISOU 2027 OD2 ASP B 223 6856 6530 8474 −847 −877 495 O | ANISOU 2072 N THR B 229 15882 17020 19708 −277 −3362 649 N |
| ATOM 2028 C ASP B 223 172.799 74.100 1.721 1.00 44.61 C | ATOM 2073 CA THR B 229 176.977 59.983 9.465 1.00140.17 C |
| ANISOU 2028 C ASP B 223 5272 5116 6561 −348 −343 308 C | ANISOU 2073 CA THR B 229 15967 17164 20126 −182 −3288 784 C |
| ATOM 2029 O ASP B 223 171.696 73.657 1.810 1.00 47.55 O | ATOM 2074 CB THR B 229 178.503 59.788 9.416 1.00143.45 C |
| ANISOU 2029 O ASP B 223 5767 5551 6750 −305 −340 196 O | ANISOU 2074 CB THR B 229 16118 17387 21000 −161 −3374 845 C |
| ATOM 2030 N LYS B 224 173.870 73.387 1.981 1.00 44.55 N | ATOM 2075 OG1 THR B 229 179.113 60.946 8.829 1.00143.52 O |
| ANISOU 2030 N LYS B 224 5084 5086 6756 −374 −375 452 N | ANISOU 2075 OG1 THR B 229 15933 17317 21280 −194 −3271 754 O |
| ATOM 2031 CA LYS B 224 173.763 72.106 2.610 1.00 42.31 C | ATOM 2076 CG2 THR B 229 178.856 58.561 8.596 1.00142.57 C |
| ANISOU 2031 CA LYS B 224 4757 4857 6464 −380 −452 474 C | ANISOU 2076 CG2 THR B 229 15823 17177 21171 −56 −3188 954 C |
| ATOM 2032 CB LYS B 224 174.841 71.190 2.144 1.00 42.88 C | ATOM 2077 C THR B 229 176.332 58.964 10.398 1.00140.42 C |
| ANISOU 2032 CB LYS B 224 4608 4880 6806 −327 −342 656 C | ANISOU 2077 C THR B 229 16268 17277 19808 −177 −3442 869 C |
| ATOM 2033 CG LYS B 224 174.779 70.883 0.680 1.00 51.87 C | ATOM 2078 O THR B 229 176.459 59.057 11.625 1.00143.15 O |
| ANISOU 2033 CG LYS B 224 5780 5985 7944 −172 −37 641 C | ANISOU 2078 O THR B 229 16811 17639 19940 −241 −3706 874 O |
| ATOM 2034 CD LYS B 224 173.568 70.056 0.328 1.00 59.96 C | ATOM 2079 N GLY B 230 175.631 58.002 9.807 1.00136.83 N |
| ANISOU 2034 CD LYS B 224 6957 7084 8742 −90 42 510 C | ANISOU 2079 N GLY B 230 15832 16864 19294 −104 −3263 936 N |
| ATOM 2035 CE LYS B 224 173.700 69.459 −1.053 1.00 63.11 C | ATOM 2080 CA GLY B 230 174.880 57.021 10.570 1.00134.41 C |
| ANISOU 2035 CE LYS B 224 7452 7423 9102 23 329 500 C | ANISOU 2080 CA GLY B 230 15788 16632 18648 −100 −3354 1020 C |
| ATOM 2036 NZ LYS B 224 172.989 68.165 −1.136 1.00 68.23 N | ATOM 2081 C GLY B 230 175.730 56.029 11.344 1.00133.18 C |
| ANISOU 2036 NZ LYS B 224 8238 8127 9560 73 381 400 N | ANISOU 2081 C GLY B 230 15627 16369 18606 −78 −3571 1149 C |
| ATOM 2037 C LYS B 224 173.898 72.265 4.073 1.00 40.20 C | ATOM 2082 O GLY B 230 176.748 55.538 10.853 1.00134.02 O |
| ANISOU 2037 C LYS B 224 4532 4594 6147 −548 −727 478 C | ANISOU 2082 O GLY B 230 15470 16329 19124 −18 −3550 1214 O |
| ATOM 2038 O LYS B 224 174.599 73.096 4.536 1.00 50.06 O | ATOM 2083 N ASP B 231 175.293 55.722 12.560 1.00130.93 N |
| ANISOU 2038 O LYS B 224 5757 5778 7486 −691 −883 550 O | ANISOU 2083 N ASP B 231 15646 16147 17956 −129 −3763 1187 N |
| ATOM 2039 N LEU B 225 173.183 71.463 4.812 1.00 51.00 N | ATOM 2084 CA ASP B 231 176.062 54.885 13.470 1.00131.82 C |
| ANISOU 2039 N LEU B 225 4907 5974 8497 −493 −1634 −269 N | ANISOU 2084 CA ASP B 231 15796 16161 18128 −124 −4012 1308 C |
| ATOM 2040 CA LEU B 225 173.382 71.348 6.244 1.00 53.84 C | ATOM 2085 CB ASP B 231 176.667 55.764 14.550 1.00135.01 C |
| ANISOU 2040 CA LEU B 225 5354 6368 8734 −568 −1987 −311 C | ANISOU 2085 CB ASP B 231 16304 16547 18446 −217 −4294 1252 C |
| ATOM 2041 CB LEU B 225 172.225 70.559 6.856 1.00 54.51 C | ATOM 2086 CG ASP B 231 175.693 56.818 15.026 1.00134.22 C |
| ANISOU 2041 CB LEU B 225 5702 6611 8398 −539 −2008 −305 C | ANISOU 2086 CG ASP B 231 16481 16593 17924 −304 −4262 1115 C |
| ATOM 2042 CG LEU B 225 171.188 71.199 7.768 1.00 49.85 C | ATOM 2087 OD1 ASP B 231 174.836 56.496 15.878 1.00134.90 O |
| ANISOU 2042 CG LEU B 225 5394 6107 7439 −590 −2050 −426 C | ANISOU 2087 OD1 ASP B 231 16901 16767 17588 −342 −4290 1132 O |
| ATOM 2043 CD1 LEU B 225 170.575 70.104 8.617 1.00 46.67 C | ATOM 2088 OD2 ASP B 231 175.762 57.957 14.517 1.00132.74 O |
| ANISOU 2043 CD1 LEU B 225 5190 5820 6723 −580 −2161 −382 C | ANISOU 2088 OD2 ASP B 231 16178 16423 17834 −335 −4181 990 O |
| ATOM 2044 CD2 LEU B 225 171.837 72.236 8.638 1.00 51.88 C | ATOM 2089 C ASP B 231 175.148 53.861 14.124 1.00128.60 C |
| ANISOU 2044 CD2 LEU B 225 5664 6283 7765 −701 −2292 −535 C | ANISOU 2089 C ASP B 231 15684 15822 17357 −119 −4021 1401 C |
| ATOM 2045 C LEU B 225 174.654 70.538 6.402 1.00 55.85 C | ATOM 2090 O ASP B 231 175.219 53.634 15.337 1.00129.44 O |
| ANISOU 2045 C LEU B 225 5374 6536 9312 −570 −2190 −211 C | ANISOU 2090 O ASP B 231 16024 15929 17230 −169 −4243 1449 O |
| ATOM 2046 O LEU B 225 174.841 69.545 5.703 1.00 58.87 O | ATOM 2091 N ARG B 232 174.285 53.255 13.312 1.00122.29 N |
| ANISOU 2046 O LEU B 225 5645 6911 9813 −489 −2055 −102 O | ANISOU 2091 N ARG B 232 14880 15072 16512 −61 −3771 1428 N |
| ATOM 2047 N PRO B 226 175.533 70.947 7.313 1.00 59.12 N | ATOM 2092 CA ARG B 232 173.296 52.294 13.791 1.00114.35 C |
| ANISOU 2047 N PRO B 226 5708 6874 9882 −663 −2521 −249 N | ANISOU 2092 CA ARG B 232 14148 14126 15172 −59 −3726 1515 C |
| ATOM 2048 CA PRO B 226 176.680 70.093 7.620 1.00 64.45 C | ATOM 2093 CB ARG B 232 171.931 52.970 13.944 1.00107.41 C |
| ANISOU 2048 CA PRO B 226 6161 7467 10861 −661 −2772 −144 C | ANISOU 2093 CB ARG B 232 13538 13410 13861 −128 −3583 1411 C |
| ATOM 2049 CB PRO B 226 177.338 70.819 8.777 1.00 65.22 C | ATOM 2094 CG ARG B 232 171.068 52.349 15.015 1.00107.31 C |
| ANISOU 2049 CB PRO B 226 6322 7508 10951 −761 −3089 −215 C | ANISOU 2094 CG ARG B 232 13896 13455 13421 −176 −3603 1473 C |
| ATOM 2050 CG PRO B 226 177.080 72.266 8.450 1.00 65.45 C | ATOM 2095 CD ARG B 232 169.673 52.085 14.493 1.00104.52 C |
| ANISOU 2050 CG PRO B 226 6350 7493 11027 −832 −2971 −355 C | ANISOU 2095 CD ARG B 232 13677 13200 12837 −178 −3330 1461 C |
| ATOM 2051 CD PRO B 226 175.653 72.272 7.941 1.00 64.64 C | ATOM 2096 NE ARG B 232 168.687 52.949 15.135 1.00104.18 N |
| ANISOU 2051 CD PRO B 226 6470 7523 10570 −772 −2667 −388 C | ANISOU 2096 NE ARG B 232 13925 13279 12379 −274 −3250 1341 N |
| ATOM 2052 C PRO B 226 176.213 68.701 8.025 1.00 73.83 C | ATOM 2097 CZ ARG B 232 167.921 52.595 16.166 1.00102.14 C |
| ANISOU 2052 C PRO B 226 7487 8763 11803 −597 −2850 −44 C | ANISOU 2097 CZ ARG B 232 14005 13061 11743 −332 −3212 1367 C |
| ATOM 2053 O PRO B 226 175.205 68.550 8.719 1.00 71.30 O | ATOM 2098 NH1 ARG B 232 167.056 53.468 16.672 1.00 99.70 N |
| ANISOU 2053 O PRO B 226 7470 8576 11050 −610 −2896 −83 O | ANISOU 2098 NH1 ARG B 232 13933 12847 11101 −414 −3094 1238 N |
| ATOM 2054 N GLN B 227 176.946 67.691 7.573 1.00 86.84 N | ATOM 2099 NH2 ARG B 232 168.011 51.373 16.686 1.00102.28 N |
| ANISOU 2054 N GLN B 227 8920 10340 13737 −525 −2829 85 N | ANISOU 2099 NH2 ARG B 232 14123 13013 11728 −306 −3270 1520 N |
| ATOM 2055 CA GLN B 227 176.398 66.344 7.502 1.00 98.10 C | ATOM 2100 C ARG B 232 173.207 51.114 12.821 1.00106.74 C |
| ANISOU 2055 CA GLN B 227 10439 11850 14984 −442 −2772 187 C | ANISOU 2100 C ARG B 232 13016 13091 14449 45 −3543 1618 C |
| ATOM 2056 CB GLN B 227 177.110 65.522 6.428 1.00100.05 C | ATOM 2101 O ARG B 232 173.828 51.146 11.751 1.00105.67 O |
| ANISOU 2056 CB GLN B 227 10408 11987 15619 −348 −2564 296 C | ANISOU 2101 O ARG B 232 12570 12872 14708 112 −3422 1602 O |
| ATOM 2057 CG GLN B 227 176.401 65.576 5.098 1.00 99.95 C | ATOM 2102 N ALA B 233 172.446 50.082 13.198 1.00 99.06 N |
| ANISOU 2057 CG GLN B 227 10442 12005 15186 −281 −2111 276 C | ANISOU 2102 N ALA B 233 12257 12137 13244 55 −3503 1720 N |
| ATOM 2058 CD GLN B 227 177.341 65.775 3.929 1.00100.74 C | ATOM 2103 CA ALA B 233 172.237 48.917 12.340 1.00 94.25 C |
| ANISOU 2058 CD GLN B 227 10252 11941 16082 −246 −1858 304 C | ANISOU 2103 CA ALA B 233 11529 11452 12828 147 −3322 1817 C |
| ATOM 2059 OE1 GLN B 227 178.484 65.299 3.944 1.00 97.83 O | ATOM 2104 CB ALA B 233 171.274 47.942 12.989 1.00 92.74 C |
| ANISOU 2059 OE1 GLN B 227 9632 11634 16104 −227 −1945 379 O | ANISOU 2104 CB ALA B 233 11640 11292 12305 126 −3292 1921 C |
| ATOM 2060 NE2 GLN B 227 176.865 66.499 2.903 1.00101.26 N | ATOM 2105 C ALA B 233 171.705 49.338 10.966 1.00 90.32 C |
| ANISOU 2060 NE2 GLN B 227 10379 12009 16087 −235 −1520 247 N | ANISOU 2105 C ALA B 233 10887 11002 12429 175 −2973 1690 C |
| ATOM 2061 C GLN B 227 176.332 65.560 8.798 1.00106.25 C | ATOM 2106 O ALA B 233 170.774 50.143 10.875 1.00 87.78 O |
| ANISOU 2061 C GLN B 227 11666 12941 15761 −461 −3093 242 C | ANISOU 2106 O ALA B 233 10712 10818 11822 110 −2803 1552 O |
| ATOM 2062 O GLN B 227 176.810 65.989 9.863 1.00102.24 O | ATOM 2107 N GLY B 234 172.300 48.788 9.909 1.00 89.52 N |
| ANISOU 2062 O GLN B 227 11261 12407 15178 −532 −3353 208 O | ANISOU 2107 N GLY B 234 10517 10777 12718 267 −2810 1708 N |
| ATOM 2063 N GLN B 228 175.705 64.398 8.662 1.00115.69 N | ATOM 2108 CA GLY B 234 171.874 49.057 8.546 1.00 89.09 C |
| ANISOU 2063 N GLN B 228 12948 14213 16798 −391 −3022 330 N | ANISOU 2108 CA GLY B 234 10360 10747 12742 290 −2426 1568 C |
| ATOM 2064 CA GLN B 228 175.504 63.462 9.747 1.00127.55 C | ATOM 2109 C GLY B 234 172.413 50.339 7.917 1.00 95.51 C |

TABLE 8-continued

DMXAA-hSTING$^{S162A/Q266I}$ complex

| ANISOU 2064 CA GLN B 228 14661 15770 18032 -393 -3250 407 C
| ATOM 2065 CB GLN B 228 174.077 63.571 10.282 1.00 127.77 C
| ANISOU 2065 CB GLN B 228 15042 15959 17546 -428 -3203 340 C
| ATOM 2066 CG GLN B 228 173.657 62.396 11.146 1.00 128.19 C
| ANISOU 2066 CG GLN B 228 15312 16074 17319 -416 -3359 444 C
| ATOM 2067 CD GLN B 228 172.176 62.401 11.481 1.00 125.37 C
| ANISOU 2067 CD GLN B 228 15292 15860 16482 -434 -3172 379 C
| ATOM 2068 OE1 GLN B 228 171.473 63.405 11.292 1.00 124.27 O
| ANISOU 2068 OE1 GLN B 228 15248 15777 16193 -467 -2990 245 O
| ATOM 2069 NE2 GLN B 228 171.690 61.271 11.978 1.00 124.63 N
| ANISOU 2069 NE2 GLN B 228 15371 15814 16168 -411 -3207 480 N
| ATOM 2070 C GLN B 228 175.761 62.054 9.213 1.00 133.27 C
| ANISOU 2115 CD1 ILE B 235 7834 8395 9461 -52 -2946 1090 C
| ATOM 2116 CG2 ILE B 235 171.301 53.476 7.596 1.00 64.72 C
| ANISOU 2116 CG2 ILE B 235 7231 7949 9408 125 -2186 1098 C
| ATOM 2117 C ILE B 235 174.955 52.942 8.652 1.00 100.35 C
| ANISOU 2117 C ILE B 235 11160 12087 14883 206 -2921 1373 C
| ATOM 2118 O ILE B 235 175.172 54.140 8.860 1.00 97.76 O
| ANISOU 2118 O ILE B 235 10820 11801 14525 137 -2997 1272 O
| ATOM 2119 N LYS B 236 175.898 52.024 8.812 1.00 102.12 N
| ANISOU 2119 N LYS B 236 11256 12163 15383 255 -2996 1473 N
| ATOM 2120 CA LYS B 236 177.237 52.484 9.114 1.00 104.61 C
| ANISOU 2120 CA LYS B 236 11384 12359 16005 229 -3154 1463 C
| ATOM 2121 CB LYS B 236 178.146 51.361 9.607 1.00 103.46 C
| ANISOU 2121 CB LYS B 236 11157 12061 16090 268 -3313 1595 C
| ATOM 2122 CG LYS B 236 179.303 51.869 10.464 1.00 104.39 C
| ANISOU 2122 CG LYS B 236 11199 12092 16373 208 -3614 1602 C
| ATOM 2123 CD LYS B 236 180.521 50.960 10.361 1.00 100.91 C
| ANISOU 2123 CD LYS B 236 10516 11443 16381 264 -3664 1706 C
| ATOM 2124 CE LYS B 236 181.797 51.705 10.707 1.00 99.40 C
| ANISOU 2124 CE LYS B 236 10138 11128 16500 212 -3864 1684 C
| ATOM 2125 NZ LYS B 236 182.991 51.004 10.156 1.00 101.07 N
| ANISOU 2125 NZ LYS B 236 10037 11117 17247 273 -3788 1755 N
| ATOM 2126 C LYS B 236 177.791 53.152 7.856 1.00 108.39 C
| ANISOU 2126 C LYS B 236 11582 12758 16844 259 -2887 1376 C
| ATOM 2127 O LYS B 236 177.848 52.543 6.779 1.00 105.29 O
| ANISOU 2127 O LYS B 236 11042 12283 16679 341 -2602 1392 O
| ATOM 2128 N ASP B 237 178.114 54.436 8.006 1.00 113.54 N
| ANISOU 2128 N ASP B 237 12195 13434 17510 187 -2960 1279 N
| ATOM 2129 CA ASP B 237 178.807 55.246 7.000 1.00 114.51 C
| ANISOU 2129 CA ASP B 237 12066 13464 17979 193 -2741 1198 C
| ATOM 2130 CB ASP B 237 180.224 54.717 6.773 1.00 123.72 C
| ANISOU 2130 CB ASP B 237 12970 14410 19626 230 -2730 1264 C
| ATOM 2131 CG ASP B 237 181.076 54.805 8.023 1.00 133.75 C
| ANISOU 2131 CG ASP B 237 14248 15618 20953 171 -3121 1314 C
| ATOM 2132 OD2 ASP B 237 181.480 53.745 8.547 1.00 137.12 O
| ANISOU 2132 OD2 ASP B 237 14671 15965 21463 203 -3276 1427 O
| ATOM 2133 OD1 ASP B 237 181.325 55.941 8.484 1.00 136.94 O
| ANISOU 2133 OD1 ASP B 237 14669 16047 21315 92 -3276 1240 O
| ATOM 2134 C ASP B 237 178.100 55.533 5.661 1.00 109.08 C
| ANISOU 2134 C ASP B 237 11330 12822 17292 238 -2360 1126 C
| ATOM 2135 O ASP B 237 178.771 55.809 4.673 1.00 114.75 O
| ANISOU 2135 O ASP B 237 11839 13418 18343 267 -2102 1090 O
| ATOM 2136 N ARG B 238 176.837 55.641 5.709 1.00 92.77 N
| ANISOU 2136 N ARG B 238 9473 10920 14856 240 -2314 1107 N
| ATOM 2137 CA ARG B 238 176.095 56.182 4.644 1.00 72.55 C
| ANISOU 2137 CA ARG B 238 7018 8441 12108 224 -1956 977 C
| ATOM 2138 CB ARG B 238 174.700 55.881 4.928 1.00 71.64 C
| ANISOU 2138 CB ARG B 238 7236 8499 11484 198 -1885 938 C
| ATOM 2139 CG ARG B 238 173.853 55.445 3.827 1.00 64.38 C
| ANISOU 2139 CG ARG B 238 6420 7605 10437 244 -1519 901 C
| ATOM 2140 CD ARG B 238 172.684 54.824 4.523 1.00 57.89 C
| ANISOU 2140 CD ARG B 238 5873 6917 9203 218 -1591 918 C
| ATOM 2141 NE ARG B 238 171.742 54.199 3.676 1.00 54.62 N
| ANISOU 2141 NE ARG B 238 5591 6539 8623 247 -1315 891 N
| ATOM 2142 CZ ARG B 238 171.870 53.006 3.170 1.00 52.58 C
| ANISOU 2142 CZ ARG B 238 5278 6179 8522 313 -1178 950 C
| ATOM 2143 NH1 ARG B 238 170.901 52.535 2.454 1.00 50.95 N
| ANISOU 2143 NH1 ARG B 238 5216 6013 8132 321 -953 906 N
| ATOM 2144 NH2 ARG B 238 173.029 52.446 3.086 1.00 61.54 N
| ANISOU 2144 NH2 ARG B 238 6206 7159 10018 371 -1265 1045 N
| ATOM 2145 C ARG B 238 176.220 57.584 5.020 1.00 64.40 C
| ANISOU 2145 C ARG B 238 5957 7445 11069 140 -2100 892 C
| ATOM 2146 O ARG B 238 176.257 57.831 6.164 1.00 65.01 O
| ANISOU 2146 O ARG B 238 6093 7559 11050 79 -2460 911 O
| ATOM 2147 N VAL B 239 176.254 58.496 4.073 1.00 58.88 N
| ANISOU 2147 N VAL B 239 5187 6725 10460 130 -1831 798 N
| ATOM 2148 CA VAL B 239 176.345 59.905 4.408 1.00 50.22 C
| ANISOU 2109 C GLY B 234 10986 11573 13730 279 -2367 1442 C
| ATOM 2110 O GLY B 234 172.206 50.568 6.718 1.00 92.33 O
| ANISOU 2110 O GLY B 234 10494 11167 13418 305 -2057 1340 O
| ATOM 2111 N ILE B 235 173.098 51.181 8.700 1.00 101.20 N
| ANISOU 2111 N ILE B 235 11661 12298 14490 235 -2664 1448 N
| ATOM 2112 CA ILE B 235 173.570 52.475 8.183 1.00 100.91 C
| ANISOU 2112 CA ILE B 235 11460 12270 14611 210 -2612 1325 C
| ATOM 2113 CB ILE B 235 172.553 53.629 8.456 1.00 72.53 C
| ANISOU 2113 CB ILE B 235 8092 8849 10617 117 -2552 1183 C
| ATOM 2114 CG1 ILE B 235 172.219 53.738 9.952 1.00 72.39 C
| ANISOU 2114 CG1 ILE B 235 8338 8909 10257 39 -2859 1223 C
| ATOM 2115 CD1 ILE B 235 172.033 55.190 10.429 1.00 67.61 C
| ANISOU 2160 CZ TYR B 240 5615 6569 7732 25 -1684 659 C
| ATOM 2161 OH TYR B 240 169.877 56.351 5.763 1.00 52.02 O
| ANISOU 2161 OH TYR B 240 5661 6531 7575 56 -1652 737 O
| ATOM 2162 CE2 TYR B 240 171.072 58.162 6.706 1.00 55.45 C
| ANISOU 2162 CE2 TYR B 240 5980 6936 8152 -27 -1983 669 C
| ATOM 2163 CD2 TYR B 240 171.576 59.440 6.601 1.00 53.71 C
| ANISOU 2163 CD2 TYR B 240 5659 6691 8057 -67 -2017 585 C
| ATOM 2164 C TYR B 240 173.278 63.215 3.954 1.00 62.02 C
| ANISOU 2164 C TYR B 240 6193 7512 9862 -104 -1559 344 C
| ATOM 2165 O TYR B 240 173.920 63.947 4.708 1.00 67.37 O
| ANISOU 2165 O TYR B 240 6798 8151 10651 -169 -1792 313 O
| ATOM 2166 N SER B 241 172.748 63.655 2.826 1.00 62.05 N
| ANISOU 2166 N SER B 241 6236 7523 9818 -76 -1252 298 N
| ATOM 2167 CA SER B 241 172.854 65.059 2.455 1.00 65.37 C
| ANISOU 2167 CA SER B 241 6623 7907 10308 -118 -1163 216 C
| ATOM 2168 CB SER B 241 173.310 65.167 1.011 1.00 74.35 C
| ANISOU 2168 CB SER B 241 7637 8930 11682 -70 -846 237 C
| ATOM 2169 OG SER B 241 173.412 63.867 0.466 1.00 84.33 O
| ANISOU 2169 OG SER B 241 8874 10166 13000 -0 -726 315 O
| ATOM 2170 C SER B 241 171.509 65.760 2.619 1.00 58.09 C
| ANISOU 2170 C SER B 241 5941 7115 9016 -142 -1111 129 C
| ATOM 2171 O SER B 241 170.495 65.306 2.099 1.00 51.46 O
| ANISOU 2171 O SER B 241 5244 6354 7956 -99 -949 133 O
| ATOM 2172 N ASN B 242 171.501 66.865 3.350 1.00 52.89 N
| ANISOU 2172 N ASN B 242 5320 6465 8309 -212 -1253 46 N
| ATOM 2173 CA ASN B 242 170.278 67.620 3.496 1.00 50.50 C
| ANISOU 2173 CA ASN B 242 5222 6260 7708 -229 -1182 -42 C
| ATOM 2174 CB ASN B 242 169.809 67.618 4.946 1.00 53.51 C
| ANISOU 2174 CB ASN B 242 5771 6730 7832 -287 -1419 -92 C
| ATOM 2175 CG ASN B 242 169.458 66.239 5.425 1.00 51.48 C
| ANISOU 2175 CG ASN B 242 5602 6547 7411 -260 -1495 -14 C
| ATOM 2176 OD1 ASN B 242 170.297 65.537 6.001 1.00 52.06 O
| ANISOU 2176 OD1 ASN B 242 5601 6582 7599 -270 -1702 56 O
| ATOM 2177 ND2 ASN B 242 168.218 65.819 5.153 1.00 44.81 N
| ANISOU 2177 ND2 ASN B 242 4904 5797 6324 -222 -1330 -17 N
| ATOM 2178 C ASN B 242 170.447 69.035 3.021 1.00 46.81 C
| ANISOU 2178 C ASN B 242 4706 5719 7361 -257 -1080 -114 C
| ATOM 2179 O ASN B 242 171.425 69.686 3.346 1.00 49.05 O
| ANISOU 2179 O ASN B 242 4856 5907 7875 -313 -1203 -140 O
| ATOM 2180 N SER B 243 169.464 69.517 2.280 1.00 42.99 N
| ANISOU 2180 N SER B 243 4333 5272 6728 -222 -869 -144 N
| ATOM 2181 CA SER B 243 169.556 70.838 1.695 1.00 43.43 C
| ANISOU 2181 CA SER B 243 4359 5246 6897 -238 -745 -195 C
| ATOM 2182 CB SER B 243 169.291 70.785 0.183 1.00 49.14 C
| ANISOU 2182 CB SER B 243 5087 5930 7653 -170 -465 -136 C
| ATOM 2183 OG SER B 243 170.467 70.450 -0.532 1.00 48.90 O
| ANISOU 2183 OG SER B 243 4886 5781 7913 -159 -369 -67 O
| ATOM 2184 C SER B 243 168.640 71.848 2.380 1.00 38.77 C
| ANISOU 2184 C SER B 243 3920 4707 6103 -274 -791 -303 C
| ATOM 2185 O SER B 243 167.522 71.524 2.779 1.00 31.78 O
| ANISOU 2185 O SER B 243 3190 3932 4952 -255 -791 -327 O
| ATOM 2186 N ILE B 244 169.135 73.080 2.486 1.00 40.88 N
| ANISOU 2186 N ILE B 244 4132 4877 6523 -327 -811 -369 N
| ATOM 2187 CA ILE B 244 168.366 74.227 2.948 1.00 38.48 C
| ANISOU 2187 CA ILE B 244 3956 4580 6084 -356 -807 -479 C
| ATOM 2188 C ILE B 244 167.889 75.046 1.743 1.00 40.59 C
| ANISOU 2188 C ILE B 244 4232 4786 6403 -304 -566 -461 C
| ATOM 2189 O ILE B 244 168.643 75.310 0.793 1.00 44.25 O
| ANISOU 2189 O ILE B 244 4578 5142 7092 -295 -444 -402 O
| ATOM 2190 CB ILE B 244 169.228 75.111 3.824 1.00 41.58 C
| ANISOU 2190 CB ILE B 244 4294 4883 6621 -454 -992 -569 C
| ATOM 2191 CG1 ILE B 244 169.989 74.256 4.828 1.00 42.93 C
| ANISOU 2191 CG1 ILE B 244 4427 5083 6803 -506 -1262 -554 C
| ATOM 2192 CG2 ILE B 244 168.392 76.117 4.539 1.00 43.79 C
| ANISOU 2192 CG2 ILE B 244 4741 5176 6722 -489 -1006 -700 C
| ATOM 2193 CD1 ILE B 244 171.019 75.023 5.608 1.00 38.69 C

TABLE 8-continued

DMXAA-hSTING$^{S162A/Q266I}$ complex

| | |
|---|---|
| ANISOU 2148 CA VAL B 239 4090 5663 9329 46 -1938 705 C | ANISOU 2193 CD1 ILE B 244 3808 4440 6452 -611 -1491 -631 C |
| ATOM 2149 CB VAL B 239 177.618 60.575 3.844 1.00 53.39 C | ATOM 2194 N TYR B 245 166.638 75.455 1.783 1.00 37.04 N |
| ANISOU 2149 CB VAL B 239 4165 5892 10228 42 -1876 696 C | ANISOU 2194 N TYR B 245 3925 4395 5755 -270 -493 -507 N |
| ATOM 2150 CG1 VAL B 239 177.830 61.913 4.501 1.00 45.35 C | ATOM 2195 CA TYR B 245 166.070 76.231 0.695 1.00 37.78 C |
| ANISOU 2150 CG1 VAL B 239 3143 4895 9195 -58 -2089 613 C | ANISOU 2195 CA TYR B 245 4047 4429 5878 -215 -301 -480 C |
| ATOM 2151 CG2 VAL B 239 178.836 59.687 4.098 1.00 47.18 C | ATOM 2196 CB TYR B 245 164.967 75.430 0.008 1.00 38.34 C |
| ANISOU 2151 CG2 VAL B 239 3199 4942 9786 82 -1984 797 C | ANISOU 2196 CB TYR B 245 4204 4597 5767 -132 -203 -412 C |
| ATOM 2152 C VAL B 239 175.101 60.520 3.839 1.00 48.36 C | ATOM 2197 CG TYR B 245 165.463 74.217 -0.717 1.00 32.77 C |
| ANISOU 2152 C VAL B 239 4091 5560 8724 27 -1680 601 C | ANISOU 2197 CG TYR B 245 3449 3915 5088 -103 -162 -308 C |
| ATOM 2153 O VAL B 239 174.877 60.467 2.637 1.00 51.23 O | ATOM 2198 CD2 TYR B 245 165.500 72.970 -0.090 1.00 35.12 C |
| ANISOU 2153 O VAL B 239 4445 5894 9125 73 -1345 578 O | ANISOU 2198 CD2 TYR B 245 3744 4308 5291 -109 -268 -292 C |
| ATOM 2154 N TYR B 240 174.256 61.049 4.715 1.00 53.25 N | ATOM 2199 CE2 TYR B 245 165.967 71.841 -0.766 1.00 34.82 C |
| ANISOU 2154 N TYR B 240 4939 6316 8977 -37 -1838 541 N | ANISOU 2199 CE2 TYR B 245 3659 4273 5297 -79 -217 -202 C |
| ATOM 2155 CA TYR B 240 173.040 61.739 4.288 1.00 54.34 C | ATOM 2200 CZ TYR B 245 166.407 71.972 -2.080 1.00 36.42 C |
| ANISOU 2155 CA TYR B 240 5285 6573 8791 -56 -1626 441 C | ANISOU 2200 CZ TYR B 245 3834 4383 5621 -46 -44 -134 C |
| ATOM 2156 CB TYR B 240 171.933 61.606 5.343 1.00 51.32 C | ATOM 2201 OH TYR B 245 166.871 70.866 -2.769 1.00 40.88 O |
| ANISOU 2156 CB TYR B 240 5179 6338 7984 -98 -1769 416 C | ANISOU 2201 OH TYR B 245 4370 4935 6228 -16 36 -58 O |
| ATOM 2157 CG TYR B 240 171.372 60.200 5.455 1.00 52.21 C | ATOM 2202 CE1 TYR B 245 166.377 73.206 -2.714 1.00 28.49 C |
| ANISOU 2157 CG TYR B 240 5400 6495 7945 -51 -1743 501 C | ANISOU 2202 CE1 TYR B 245 2850 3287 4689 -43 65 -141 C |
| ATOM 2158 CD1 TYR B 240 170.664 59.628 4.396 1.00 43.99 C | ATOM 2203 CD1 TYR B 245 165.898 74.311 -2.033 1.00 33.37 C |
| ANISOU 2158 CD1 TYR B 240 4398 5473 6842 6 -1453 502 C | ANISOU 2203 CD1 TYR B 245 3498 3902 5280 -69 -1 -224 C |
| ATOM 2159 CE1 TYR B 240 170.173 58.352 4.489 1.00 48.82 C | ATOM 2204 C TYR B 245 165.482 77.549 1.173 1.00 31.68 C |
| ANISOU 2159 CE1 TYR B 240 5100 6108 7339 40 -1429 573 C | ANISOU 2204 C TYR B 245 3347 3607 5082 -235 -292 -587 C |
| ATOM 2160 CZ TYR B 240 170.375 57.625 5.648 1.00 52.42 C | ATOM 2205 O TYR B 245 164.971 77.651 2.288 1.00 35.07 O |
| ANISOU 2205 O TYR B 245 3863 4092 5368 -267 -388 -687 O | ATOM 2250 C GLY B 251 5196 3940 7369 184 621 -430 C |
| ATOM 2206 N GLU B 246 165.515 78.554 0.315 1.00 35.99 N | ATOM 2251 O GLY B 251 162.065 88.457 -4.108 1.00 47.51 O |
| ANISOU 2206 N GLU B 246 3875 4037 5761 -214 -160 -565 N | ANISOU 2251 O GLY B 251 5679 4381 7990 104 663 -419 O |
| ATOM 2207 CA GLU B 246 164.744 79.774 0.607 1.00 41.36 C | ATOM 2252 N GLN B 252 160.328 88.146 -2.741 1.00 42.77 N |
| ANISOU 2207 CA GLU B 246 4633 4663 6421 -209 -120 -654 C | ANISOU 2252 N GLN B 252 5088 3934 7231 169 562 -587 N |
| ATOM 2208 CB GLU B 246 165.515 81.054 0.322 1.00 43.01 C | ATOM 2253 CA GLN B 252 161.084 88.429 -1.516 1.00 37.73 C |
| ANISOU 2208 CB GLU B 246 4780 4598 6863 -253 -70 -678 C | ANISOU 2253 CA GLN B 252 4416 3277 6643 55 523 -763 C |
| ATOM 2209 CG GLU B 246 165.638 81.402 -1.140 1.00 49.08 C | ATOM 2254 CB GLN B 252 160.363 89.482 -0.674 1.00 39.00 C |
| ANISOU 2209 CG GLU B 246 5530 5370 7748 -198 108 -552 C | ANISOU 2254 CB GLN B 252 4608 3333 6876 67 560 -911 C |
| ATOM 2210 CD GLU B 246 166.307 82.788 -1.373 1.00 60.08 C | ATOM 2255 CG GLN B 252 159.794 90.602 -1.506 1.00 40.00 C |
| ANISOU 2210 CD GLU B 246 6875 6573 9381 -246 179 -577 C | ANISOU 2255 CG GLN B 252 4752 3280 7164 157 659 -826 C |
| ATOM 2211 OE1 GLU B 246 166.835 82.981 -2.509 1.00 58.32 O | ATOM 2256 CD GLN B 252 160.864 91.318 -2.310 1.00 47.39 C |
| ANISOU 2211 OE1 GLU B 246 6620 6247 9290 -228 327 -465 O | ANISOU 2256 CD GLN B 252 5680 4055 8270 112 716 -735 C |
| ATOM 2212 OE2 GLU B 246 166.300 83.649 -0.422 1.00 56.19 O | ATOM 2257 OE1 GLN B 252 161.969 91.573 -1.815 1.00 44.45 O |
| ANISOU 2212 OE2 GLU B 246 6391 6025 8935 -305 99 -710 O | ANISOU 2257 OE1 GLN B 252 5271 3629 7991 -5 700 -823 O |
| ATOM 2213 C GLU B 246 163.443 79.760 -0.163 1.00 39.95 C | ATOM 2258 NE2 GLN B 252 160.550 91.631 -3.563 1.00 50.93 N |
| ANISOU 2213 C GLU B 246 4534 4522 6124 -110 -2 -595 C | ANISOU 2258 NE2 GLN B 252 6168 4418 8765 199 779 -552 N |
| ATOM 2214 O GLU B 246 163.366 79.249 -1.283 1.00 37.53 O | ATOM 2259 C GLN B 252 161.233 87.178 -0.693 1.00 49.39 C |
| ANISOU 2214 O GLU B 246 4226 4225 5808 -54 79 -477 O | ANISOU 2259 C GLN B 252 5880 4946 7940 6 417 -829 C |
| ATOM 2215 N LEU B 247 162.400 80.259 0.478 1.00 38.14 N | ATOM 2260 O GLN B 252 160.370 86.294 -0.718 1.00 50.14 O |
| ANISOU 2215 N LEU B 247 4379 4311 5802 -91 1 -684 N | ANISOU 2260 O GLN B 252 5994 5181 7878 67 394 -794 O |
| ATOM 2216 CA LEU B 247 161.105 80.334 -0.153 1.00 36.98 C | ATOM 2261 N ARG B 253 162.320 87.106 0.061 1.00 47.02 N |
| ANISOU 2216 CA LEU B 247 4279 4184 5586 2 87 -636 C | ANISOU 2261 N ARG B 253 5546 4644 7676 -109 338 -923 N |
| ATOM 2217 CB LEU B 247 160.091 79.730 0.780 1.00 42.06 C | ATOM 2262 CA ARG B 253 162.496 85.981 0.962 1.00 44.93 C |
| ANISOU 2217 CB LEU B 247 4974 4945 6063 11 55 -707 C | ANISOU 2262 CA ARG B 253 5285 4546 7241 -161 215 -987 C |
| ATOM 2218 CG LEU B 247 160.582 78.331 1.108 1.00 51.57 C | ATOM 2263 CB ARG B 253 163.866 85.977 1.626 1.00 37.47 C |
| ANISOU 2218 CG LEU B 247 6170 6272 7151 -25 -33 -673 C | ANISOU 2263 CB ARG B 253 4286 3568 6383 -289 94 -1062 C |
| ATOM 2219 CD1 LEU B 247 159.903 77.902 2.373 1.00 54.10 C | ATOM 2264 CG ARG B 253 164.058 84.755 2.501 1.00 44.88 C |
| ANISOU 2219 CD1 LEU B 247 6563 6682 7310 -53 -69 -769 C | ANISOU 2264 CG ARG B 253 5240 4672 7139 -334 -55 -1100 C |
| ATOM 2220 CD2 LEU B 247 160.296 77.328 -0.017 1.00 49.84 C | ATOM 2265 CD ARG B 253 165.465 84.726 3.094 1.00 50.42 C |
| ANISOU 2220 CD2 LEU B 247 5933 6114 6889 37 -2 -539 C | ANISOU 2265 CD ARG B 253 5866 5330 7959 -458 -215 -1155 C |
| ATOM 2221 C LEU B 247 160.733 81.770 -0.454 1.00 37.47 C | ATOM 2266 NE ARG B 253 166.504 84.546 2.081 1.00 48.30 N |
| ANISOU 2221 C LEU B 247 4357 4104 5778 33 170 -662 C | ANISOU 2266 NE ARG B 253 5449 4999 7905 -464 -177 -1023 N |
| ATOM 2222 O LEU B 247 160.689 82.604 0.443 1.00 39.46 O | ATOM 2267 CZ ARG B 253 167.796 84.430 2.356 1.00 48.61 C |
| ANISOU 2222 O LEU B 247 4628 4294 6070 -7 164 -789 O | ANISOU 2267 CZ ARG B 253 5366 4984 8118 -559 -300 -1035 C |
| ATOM 2223 N LEU B 248 160.473 82.055 -1.721 1.00 39.20 N | ATOM 2268 NH1 ARG B 253 168.680 84.295 1.363 1.00 47.84 N |
| ANISOU 2223 N LEU B 248 4583 4258 6052 103 244 -745 N | ANISOU 2268 NH1 ARG B 253 5124 4811 8241 -557 -212 -913 N |
| ATOM 2224 CA LEU B 248 160.137 83.411 -2.142 1.00 41.84 C | ATOM 2269 NH2 ARG B 253 168.186 84.448 3.629 1.00 50.29 N |
| ANISOU 2224 CA LEU B 248 4936 4438 6522 142 319 -534 C | ANISOU 2269 NH2 ARG B 253 5609 5211 8288 -657 -512 -1170 N |
| ATOM 2225 CB LEU B 248 160.729 83.731 -3.508 1.00 41.93 C | ATOM 2270 C ARG B 253 161.406 85.950 2.031 1.00 36.67 C |
| ANISOU 2225 CB LEU B 248 4967 4345 6621 165 394 -389 C | ANISOU 2270 C ARG B 253 4329 3566 6036 -144 208 -1119 C |
| ATOM 2226 CG LEU B 248 162.239 83.724 -3.686 1.00 46.82 C | ATOM 2271 O ARG B 253 161.225 86.892 2.782 1.00 38.21 O |
| ANISOU 2226 CG LEU B 248 5536 4901 7353 82 428 -370 C | ANISOU 2271 O ARG B 253 4581 3663 6275 -179 232 -1261 O |
| ATOM 2227 CD1 LEU B 248 162.543 84.079 -5.155 1.00 47.73 C | ATOM 2272 N ALA B 254 160.681 84.850 2.098 1.00 35.42 N |
| ANISOU 2227 CD1 LEU B 248 5711 4898 7526 120 551 -213 C | ANISOU 2272 N ALA B 254 4192 3566 5701 -95 194 -1076 N |
| ATOM 2228 CD2 LEU B 248 162.924 84.694 -2.725 1.00 44.14 C | ATOM 2273 CA ALA B 254 159.596 84.715 3.051 1.00 36.89 C |
| ANISOU 2228 CD2 LEU B 248 5138 4459 7174 -3 408 -503 C | ANISOU 2273 CA ALA B 254 4458 3813 5744 -77 226 -1187 C |
| ATOM 2229 C LEU B 248 158.635 83.643 -2.205 1.00 46.97 C | ATOM 2274 CB ALA B 254 158.287 84.425 2.310 1.00 34.99 C |
| ANISOU 2229 C LEU B 248 5611 5097 7189 235 336 -533 C | ANISOU 2274 CB ALA B 254 4189 3614 5492 46 318 -1089 C |
| ATOM 2230 O LEU B 248 157.875 82.784 -2.609 1.00 43.36 O | ATOM 2275 C ALA B 254 159.893 83.621 4.091 1.00 38.55 C |
| ANISOU 2230 O LEU B 248 5160 4739 6575 289 304 -465 O | ANISOU 2275 C ALA B 254 4729 4168 5749 -152 114 -1245 C |
| ATOM 2231 N GLU B 249 158.224 84.844 -1.829 1.00 52.36 N | ATOM 2276 O ALA B 254 159.267 83.553 5.131 1.00 37.96 O |
| ANISOU 2231 N GLU B 249 6294 5656 7943 253 386 -609 N | ANISOU 2276 O ALA B 254 4759 4129 5535 -173 138 -1364 O |
| ATOM 2232 CA GLU B 249 156.854 85.271 -1.950 1.00 49.95 C | ATOM 2277 N GLY B 255 160.832 82.739 3.789 1.00 42.34 N |

TABLE 8-continued

DMXAA-hSTING$^{S162A/Q266I}$ complex

| | |
|---|---|
| ANISOU 2232 CA GLU B 249 5984 5314 7682 351 416 −601 C | ANISOU 2277 N GLY B 255 5152 4722 6213 −188 3 −1154 N |
| ATOM 2233 CB GLU B 249 156.177 85.167 −0.597 1.00 49.67 C | ATOM 2278 CA GLY B 255 161.196 81.711 4.739 1.00 45.42 C |
| ANISOU 2233 CB GLU B 249 5939 5334 7600 332 440 −765 C | ANISOU 2278 CA GLY B 255 5599 5232 6427 −256 −127 −1190 C |
| ATOM 2234 CG GLU B 249 154.720 85.515 −0.629 1.00 56.49 C | ATOM 2279 C GLY B 255 162.438 80.963 4.331 1.00 44.27 C |
| ANISOU 2234 CG GLU B 249 6761 6154 8547 434 492 −768 C | ANISOU 2279 C GLY B 255 5354 5118 6349 −295 −251 −1090 C |
| ATOM 2235 CD GLU B 249 154.034 85.296 0.718 1.00 67.69 C | ATOM 2280 O GLY B 255 162.902 81.067 3.202 1.00 42.72 O |
| ANISOU 2235 CD GLU B 249 8183 7627 9909 411 562 −931 C | ANISOU 2280 O GLY B 255 5052 4869 6313 −259 −200 −980 O |
| ATOM 2236 OE1 GLU B 249 154.429 85.999 1.693 1.00 70.85 O | ATOM 2281 N THR B 256 162.958 80.184 5.266 1.00 49.96 N |
| ANISOU 2236 OE1 GLU B 249 8641 7955 10323 347 622 −1084 O | ANISOU 2281 N THR B 256 6121 5916 6946 −365 −407 −1123 N |
| ATOM 2237 OE2 GLU B 249 153.121 84.415 0.778 1.00 70.22 O | ATOM 2282 CA THR B 256 164.116 79.328 5.022 1.00 53.43 C |
| ANISOU 2237 OE2 GLU B 249 8460 8051 10168 449 560 −905 O | ANISOU 2282 CA THR B 256 6452 6385 7463 −398 −539 −1028 C |
| ATOM 2238 C GLU B 249 156.871 86.723 −2.424 1.00 49.85 C | ATOM 2283 CB THR B 256 165.419 79.985 5.467 1.00 56.96 C |
| ANISOU 2238 C GLU B 249 5981 5098 7860 388 482 −577 C | ANISOU 2283 CB THR B 256 6837 6721 8083 −500 −692 −1092 C |
| ATOM 2239 O GLU B 249 157.385 87.628 −1.724 1.00 46.80 O | ATOM 2284 OG1 THR B 256 165.682 81.120 4.648 1.00 59.40 O |
| ANISOU 2239 O GLU B 249 5600 4605 7579 331 530 −695 O | ANISOU 2284 OG1 THR B 256 7060 6888 8620 −490 −576 −1089 O |
| ATOM 2240 N ASN B 250 156.310 86.934 −3.615 1.00 49.08 N | ATOM 2285 CG2 THR B 256 166.560 79.022 5.306 1.00 56.15 C |
| ANISOU 2240 N ASN B 250 5902 4939 7806 481 471 −420 N | ANISOU 2285 CG2 THR B 256 6603 6644 8089 −527 −832 −992 C |
| ATOM 2241 CA ASN B 250 156.260 88.262 −4.220 1.00 37.16 C | ATOM 2286 C THR B 256 163.988 78.014 5.774 1.00 44.20 C |
| ANISOU 2241 CA ASN B 250 4418 3227 6475 530 525 −358 C | ANISOU 2286 C THR B 256 5356 5353 6086 −412 −651 −1004 C |
| ATOM 2242 CB ASN B 250 155.487 89.199 −3.283 1.00 38.40 C | ATOM 2287 O THR B 256 163.910 77.996 7.002 1.00 48.12 O |
| ANISOU 2242 CB ASN B 250 4526 3283 6781 563 585 −499 C | ANISOU 2287 O THR B 256 5990 5876 6416 −479 −761 −1105 O |
| ATOM 2243 CG ASN B 250 154.974 90.449 −3.967 1.00 40.02 C | ATOM 2288 N CYS B 257 163.980 76.918 5.046 1.00 42.53 N |
| ANISOU 2243 CG ASN B 250 4739 3279 7188 656 621 −412 C | ANISOU 2288 N CYS B 257 5070 5216 5873 −354 −621 −872 N |
| ATOM 2244 OD1 ASN B 250 154.598 90.441 −5.140 1.00 48.59 O | ATOM 2289 CA CYS B 257 163.762 75.618 5.683 1.00 45.66 C |
| ANISOU 2244 OD1 ASN B 250 5860 4328 8276 736 561 −229 O | ANISOU 2289 CA CYS B 257 5535 5734 6078 −359 −707 −835 C |
| ATOM 2245 ND2 ASN B 250 154.957 91.543 −3.221 1.00 46.00 N | ATOM 2290 CB CYS B 257 162.281 75.280 5.735 1.00 46.98 C |
| ANISOU 2245 ND2 ASN B 250 5480 3888 8110 646 714 −544 N | ANISOU 2290 CB CYS B 257 5806 5985 6060 −302 −564 −844 C |
| ATOM 2246 C ASN B 250 157.700 88.759 −4.484 1.00 37.55 C | ATOM 2291 SG CYS B 257 161.616 75.095 4.114 1.00 62.00 S |
| ANISOU 2246 C ASN B 250 4504 3178 6583 443 583 −341 C | ANISOU 2291 SG CYS B 257 7603 7891 8063 −193 −389 −729 S |
| ATOM 2247 O ASN B 250 158.046 89.920 −4.256 1.00 38.85 O | ATOM 2292 C CYS B 257 164.484 74.503 4.970 1.00 39.83 C |
| ANISOU 2247 O ASN B 250 4669 3177 6916 420 652 −394 O | ANISOU 2292 C CYS B 257 4672 5025 5439 −330 −745 −698 C |
| ATOM 2248 N GLY B 251 158.556 87.844 −4.917 1.00 36.55 N | ATOM 2293 O CYS B 257 164.843 74.628 3.810 1.00 40.80 O |
| ANISOU 2248 N GLY B 251 4397 3148 6341 388 566 −276 N | ANISOU 2293 O CYS B 257 4675 5091 5735 −287 −646 −624 O |
| ATOM 2249 CA GLY B 251 159.947 88.154 −5.173 1.00 41.22 C | ATOM 2294 N VAL B 258 164.696 73.410 5.687 1.00 39.33 N |
| ANISOU 2249 CA GLY B 251 4993 3652 7016 301 634 −257 C | ANISOU 2294 N VAL B 258 4651 5036 5257 −355 −879 −663 N |
| ATOM 2250 C GLY B 251 160.868 88.269 −3.951 1.00 43.44 C | ATOM 2295 CA VAL B 258 165.297 72.214 5.114 1.00 40.46 C |
| ANISOU 2295 CA VAL B 258 4684 5202 5485 −321 −908 −536 C | ATOM 2340 C THR B 263 3954 4567 4016 58 −186 196 C |
| ATOM 2296 CB VAL B 258 166.183 71.461 6.139 1.00 48.74 C | ATOM 2341 O THR B 263 160.106 57.143 −2.415 1.00 26.24 O |
| ANISOU 2296 CB VAL B 258 5739 6265 6515 −380 −1152 −513 C | ANISOU 2341 O THR B 263 3130 3657 3184 77 −106 194 O |
| ATOM 2297 CG1 VAL B 258 165.498 71.423 7.473 1.00 56.92 C | ATOM 2342 N PRO B 264 159.297 57.105 −0.275 1.00 23.79 N |
| ANISOU 2297 CG1 VAL B 258 6993 7368 7266 −432 −1243 −592 C | ANISOU 2342 N PRO B 264 2823 3464 2753 22 −233 203 N |
| ATOM 2298 CG2 VAL B 258 166.509 70.046 5.658 1.00 42.15 C | ATOM 2343 CA PRO B 264 158.442 55.975 −0.642 1.00 23.99 C |
| ANISOU 2298 CG2 VAL B 258 4820 5463 5732 −330 −1157 −381 C | ANISOU 2343 CA PRO B 264 2894 3484 2739 6 −191 214 C |
| ATOM 2299 C VAL B 258 164.154 71.340 4.606 1.00 41.64 C | ATOM 2344 CB PRO B 264 157.684 55.660 0.659 1.00 25.99 C |
| ANISOU 2299 C VAL B 258 4891 5444 5486 −250 −765 −478 C | ANISOU 2344 CB PRO B 264 3179 3798 2899 −39 −224 227 C |
| ATOM 2300 O VAL B 258 163.217 70.998 5.334 1.00 38.18 O | ATOM 2345 CG PRO B 264 158.747 56.024 1.772 1.00 27.24 C |
| ANISOU 2300 O VAL B 258 4586 5083 4836 −256 −756 −512 O | ANISOU 2345 CG PRO B 264 3333 3961 3056 −39 −316 264 C |
| ATOM 2301 N LEU B 259 164.241 70.992 3.331 1.00 39.75 N | ATOM 2346 CD PRO B 264 159.354 57.298 1.195 1.00 25.38 C |
| ANISOU 2301 N LEU B 259 4557 5184 5364 −189 −644 −393 N | ANISOU 2346 CD PRO B 264 3040 3715 2889 −10 −319 216 C |
| ATOM 2302 CA LEU B 259 163.125 70.470 2.592 1.00 31.26 C | ATOM 2347 C PRO B 264 157.464 56.290 −1.765 1.00 30.10 C |
| ANISOU 2302 CA LEU B 259 3526 4168 4185 −125 −505 −352 C | ANISOU 2347 C PRO B 264 3693 4261 3482 7 −143 160 C |
| ATOM 2303 CB LEU B 259 162.796 71.496 1.532 1.00 39.05 C | ATOM 2348 O PRO B 264 156.970 55.348 −2.383 1.00 32.88 O |
| ANISOU 2303 CB LEU B 259 4488 5087 5260 −84 −368 −358 C | ANISOU 2348 O PRO B 264 4083 4582 3827 −6 −118 161 O |
| ATOM 2304 CG LEU B 259 161.373 71.757 1.120 1.00 41.85 C | ATOM 2349 N LEU B 265 157.168 57.576 −1.991 1.00 27.06 N |
| ANISOU 2304 CG LEU B 259 4909 5477 5513 −34 −263 −372 C | ANISOU 2349 N LEU B 265 3293 3906 3084 19 −147 116 N |
| ATOM 2305 CD1 LEU B 259 160.587 71.925 2.390 1.00 43.90 C | ATOM 2350 CA LEU B 265 156.313 57.983 −3.108 1.00 32.44 C |
| ANISOU 2305 CD1 LEU B 259 5253 5793 5635 −65 −297 −464 C | ANISOU 2350 CA LEU B 265 4004 4579 3744 27 −136 79 C |
| ATOM 2306 CD2 LEU B 259 161.363 73.041 0.286 1.00 44.12 C | ATOM 2351 CB LEU B 265 155.934 59.470 −3.070 1.00 32.33 C |
| ANISOU 2306 CD2 LEU B 259 5175 5667 5921 −6 −176 −379 C | ANISOU 2351 CB LEU B 265 3960 4593 3731 44 −150 43 C |
| ATOM 2307 C LEU B 259 163.536 69.195 1.882 1.00 34.91 C | ATOM 2352 CG LEU B 265 155.079 59.748 −1.826 1.00 40.02 C |
| ANISOU 2307 C LEU B 259 3931 4642 4693 −90 −485 −247 C | ANISOU 2352 CG LEU B 265 4888 5632 4686 16 −161 16 C |
| ATOM 2308 O LEU B 259 164.651 69.104 1.389 1.00 40.66 O | ATOM 2353 CD1 LEU B 265 154.844 61.219 −1.589 1.00 41.69 C |
| ANISOU 2308 O LEU B 259 4552 5295 5601 −90 −490 −199 O | ANISOU 2353 CD1 LEU B 265 5067 5858 4917 36 −158 −27 C |
| ATOM 2309 N GLU B 260 162.643 68.211 1.837 1.00 35.80 N | ATOM 2354 CD2 LEU B 265 153.749 59.027 −1.844 1.00 41.60 C |
| ANISOU 2309 N GLU B 260 4107 4833 4663 −64 −451 −214 N | ANISOU 2354 CD2 LEU B 265 5073 5850 4883 −14 −160 7 C |
| ATOM 2310 CA GLU B 260 162.806 67.089 0.927 1.00 35.84 C | ATOM 2355 C LEU B 265 156.909 57.563 −4.457 1.00 30.89 C |
| ANISOU 2310 CA GLU B 260 4079 4835 4703 −24 −392 −127 C | ANISOU 2355 C LEU B 265 3877 4301 3557 49 −91 89 C |
| ATOM 2311 CB GLU B 260 163.848 66.112 1.448 1.00 45.20 C | ATOM 2356 O LEU B 265 156.191 57.184 −5.374 1.00 33.58 O |
| ANISOU 2311 CB GLU B 260 5206 6007 5960 −42 −502 −73 C | ANISOU 2356 O LEU B 265 4286 4619 3853 38 −101 71 O |
| ATOM 2312 CG GLU B 260 163.593 65.573 2.820 1.00 59.71 C | ATOM 2357 N ILE B 266 158.232 57.589 −4.545 1.00 31.47 N |
| ANISOU 2312 CG GLU B 260 7122 7915 7652 −84 −640 −83 C | ANISOU 2357 N ILE B 266 3938 4321 3697 75 −39 116 N |
| ATOM 2313 CD GLU B 260 164.648 64.522 3.207 1.00 70.97 C | ATOM 2358 CA ILE B 266 158.966 57.063 −5.694 1.00 26.90 C |
| ANISOU 2313 CD GLU B 260 8484 9310 9171 −90 −767 −4 C | ANISOU 2358 CA ILE B 266 3431 3645 3144 96 53 124 C |
| ATOM 2314 OE1 GLU B 260 165.715 64.893 3.758 1.00 74.16 O | ATOM 2359 CB ILE B 266 160.440 57.269 −5.485 1.00 30.86 C |
| ANISOU 2314 OE1 GLU B 260 8815 9660 9702 −123 −912 −5 O | ANISOU 2359 CB ILE B 266 3860 4088 3779 125 115 157 C |
| ATOM 2315 OE2 GLU B 260 164.422 63.325 2.909 1.00 75.77 O | ATOM 2360 CG1 ILE B 266 160.698 58.764 −5.346 1.00 30.99 C |
| ANISOU 2315 OE2 GLU B 260 9103 9935 9750 −60 −727 62 O | ANISOU 2360 CG1 ILE B 266 3829 4125 3821 135 102 145 C |
| ATOM 2316 C GLU B 260 161.505 66.363 0.640 1.00 33.53 C | ATOM 2361 CD1 ILE B 266 162.201 59.094 −4.964 1.00 28.43 C |

TABLE 8-continued

DMXAA-hSTING$^{S162A/Q266I}$ complex

| | |
|---|---|
| ANISOU 2316 C GLU B 260 3863 4615 4262 4 −328 −114 C | ANISOU 2361 CD1 ILE B 266 3392 3738 3674 153 136 175 C |
| ATOM 2317 O GLU B 260 160.517 66.557 1.330 1.00 33.91 O | ATOM 2362 CG2 ILE B 266 161.297 56.621 −4.939 1.00 33.73 C |
| ANISOU 2317 O GLU B 260 3975 4722 4190 −10 −333 −164 O | ANISOU 2362 CG2 ILE B 266 4291 4326 4201 150 263 163 C |
| ATOM 2318 N TYR B 261 161.529 65.552 −0.418 1.00 32.17 N | ATOM 2363 C ILE B 266 158.690 55.582 −5.916 1.00 33.07 C |
| ANISOU 2318 N TYR B 261 3684 4423 4116 40 −257 −53 N | ANISOU 2363 C ILE B 266 4266 4390 3909 76 70 128 C |
| ATOM 2319 CA TYR B 261 160.434 64.665 −0.821 1.00 25.97 C | ATOM 2364 O ILE B 266 158.493 55.106 −7.031 1.00 37.16 O |
| ANISOU 2319 CA TYR B 261 2959 3690 3220 58 −216 −34 C | ANISOU 2364 O ILE B 266 4899 4846 4373 72 119 103 O |
| ATOM 2320 CB TYR B 261 160.552 64.370 −2.295 1.00 25.81 C | ATOM 2365 N THR B 267 158.619 54.848 −4.826 1.00 24.61 N |
| ANISOU 2320 CB TYR B 261 2956 3613 3237 95 −124 8 C | ANISOU 2365 N THR B 267 3131 3351 2869 59 23 158 N |
| ATOM 2321 CG TYR B 261 159.986 65.482 −3.154 1.00 31.93 C | ATOM 2366 CA THR B 267 158.275 53.451 −4.939 1.00 24.29 C |
| ANISOU 2321 CG TYR B 261 3768 4358 4005 120 −72 −10 C | ANISOU 2366 CA THR B 267 3136 3269 2824 35 37 165 C |
| ATOM 2322 CD2 TYR B 261 160.850 66.472 −3.687 1.00 30.01 C | ATOM 2367 CB THR B 267 158.540 52.768 −3.615 1.00 25.03 C |
| ANISOU 2322 CD2 TYR B 261 3504 4030 3868 130 −15 −3 C | ANISOU 2367 CB THR B 267 3161 3382 2969 26 −5 225 C |
| ATOM 2323 CE2 TYR B 261 160.343 67.512 −4.499 1.00 31.76 C | ATOM 2368 OG1 THR B 267 159.940 52.872 −3.345 1.00 29.83 O |
| ANISOU 2323 CE2 TYR B 261 3777 4210 4079 156 30 −4 C | ANISOU 2368 OG1 THR B 267 3703 3937 3692 70 12 271 O |
| ATOM 2324 CZ TYR B 261 158.959 67.570 −4.766 1.00 33.66 C | ATOM 2369 CG2 THR B 267 158.077 51.260 −3.645 1.00 23.99 C |
| ANISOU 2324 CZ TYR B 261 4072 4495 4222 178 −5 −13 C | ANISOU 2369 CG2 THR B 267 3076 3198 2843 −4 13 239 C |
| ATOM 2325 OH TYR B 261 158.533 68.599 −5.554 1.00 41.27 O | ATOM 2370 C THR B 267 156.799 53.222 −5.378 1.00 30.28 C |
| ANISOU 2325 OH TYR B 261 5084 5403 5193 209 15 2 O | ANISOU 2370 C THR B 267 3954 4060 3493 −12 −13 119 C |
| ATOM 2326 CE1 TYR B 261 158.048 66.624 −4.245 1.00 27.71 C | ATOM 2371 O THR B 267 156.506 52.350 −6.180 1.00 31.27 O |
| ANISOU 2326 CE1 TYR B 261 3315 3824 3389 166 −62 −28 C | ANISOU 2371 O THR B 267 4165 4122 3596 −33 8 93 O |
| ATOM 2327 CD1 TYR B 261 158.578 65.580 −3.409 1.00 26.38 C | ATOM 2372 N LEU B 268 155.858 53.968 −4.807 1.00 26.83 N |
| ANISOU 2327 CD1 TYR B 261 3111 3698 3213 134 −84 −28 C | ANISOU 2372 N LEU B 268 3461 3710 3022 −32 −81 105 N |
| ATOM 2328 C TYR B 261 160.460 63.339 −0.116 1.00 31.67 C | ATOM 2373 CA LEU B 268 154.448 53.866 −5.228 1.00 25.13 C |
| ANISOU 2328 C TYR B 261 3694 4453 3887 38 −270 1 C | ANISOU 2373 CA LEU B 268 3261 3514 2773 −73 −142 64 C |
| ATOM 2329 O TYR B 261 161.529 62.825 0.160 1.00 35.76 O | ATOM 2374 CB LEU B 268 153.548 54.794 −4.419 1.00 26.03 C |
| ANISOU 2329 O TYR B 261 4167 4936 4485 32 −321 42 O | ANISOU 2374 CB LEU B 268 3280 3712 2899 −82 −183 53 C |
| ATOM 2330 N ALA B 262 159.284 62.782 0.171 1.00 35.14 N | ATOM 2375 CG LEU B 268 153.350 54.415 −2.969 1.00 32.17 C |
| ANISOU 2330 N ALA B 262 4186 4954 4211 28 −259 −8 N | ANISOU 2375 CG LEU B 268 3995 4535 3694 −110 −154 81 C |
| ATOM 2331 CA ALA B 262 159.202 61.513 0.882 1.00 36.34 C | ATOM 2376 CD1 LEU B 268 152.591 55.496 −2.201 1.00 32.36 C |
| ANISOU 2331 CA ALA B 262 4367 5137 4302 5 −297 33 C | ANISOU 2376 CD1 LEU B 268 3945 4625 3725 −112 −153 57 C |
| ATOM 2332 CB ALA B 262 157.830 61.329 1.449 1.00 32.04 C | ATOM 2377 CD2 LEU B 268 152.574 53.136 −2.952 1.00 39.04 C |
| ANISOU 2332 CB ALA B 262 3874 4654 3645 −19 −264 3 C | ANISOU 2377 CD2 LEU B 268 4869 5373 4592 −164 −149 86 C |
| ATOM 2333 C ALA B 262 159.518 60.405 −0.135 1.00 35.00 C | ATOM 2378 C LEU B 268 154.272 54.206 −6.691 1.00 29.99 C |
| ANISOU 2333 C ALA B 262 4188 4922 4190 31 −255 89 C | ANISOU 2378 C LEU B 268 3982 4082 3332 −65 −169 26 C |
| ATOM 2334 O ALA B 262 158.768 60.200 −1.081 1.00 29.79 O | ATOM 2379 O LEU B 268 153.493 53.568 −7.412 1.00 33.46 O |
| ANISOU 2334 O ALA B 262 3554 4257 3508 45 −195 81 O | ANISOU 2379 O LEU B 268 4487 4485 3743 −104 −224 −7 O |
| ATOM 2335 N THR B 263 160.622 59.693 0.056 1.00 29.50 N | ATOM 2380 N PHE B 269 154.989 55.231 −7.140 1.00 25.77 N |
| ANISOU 2335 N THR B 263 3456 4179 3575 37 −294 144 N | ANISOU 2380 N PHE B 269 3479 3539 2775 −19 −137 31 N |
| ATOM 2336 CA THR B 263 161.078 58.744 −0.960 1.00 31.40 C | ATOM 2381 CA PHE B 269 154.948 55.551 −8.537 1.00 28.93 C |
| ANISOU 2336 CA THR B 263 3685 4349 3896 67 −224 186 C | ANISOU 2381 CA PHE B 269 4022 3880 3091 −11 −147 8 C |
| ATOM 2337 CB THR B 263 162.460 58.179 −0.619 1.00 29.43 C | ATOM 2382 CB PHE B 269 155.734 56.807 −8.835 1.00 31.31 C |
| ANISOU 2337 CB THR B 263 3357 4029 3796 82 −270 247 C | ANISOU 2382 CB PHE B 269 4340 4171 3386 37 −92 27 C |
| ATOM 2338 OG1 THR B 263 162.403 57.620 0.698 1.00 32.35 O | ATOM 2383 CG PHE B 269 155.532 57.301 −10.248 1.00 31.43 C |
| ANISOU 2338 OG1 THR B 263 3746 4441 4105 54 −395 285 O | ANISOU 2383 CG PHE B 269 4530 4127 3286 43 −112 17 C |
| ATOM 2339 CG2 THR B 263 163.512 59.292 −0.666 1.00 24.96 C | ATOM 2384 CD2 PHE B 269 156.396 56.888 −11.276 1.00 35.94 C |
| ANISOU 2339 CG2 THR B 263 2699 3415 3369 90 −287 233 C | ANISOU 2384 CD2 PHE B 269 5275 4596 3786 49 11 11 C |
| ATOM 2340 C THR B 263 160.106 57.594 −1.275 1.00 33.00 C | ATOM 2385 CE2 PHE B 269 156.214 57.312 −12.604 1.00 32.55 C |
| ANISOU 2385 CE2 PHE B 269 5060 4101 3208 47 −1 5 C | ANISOU 2430 O TYR B 274 4999 3458 3132 −328 −46 −298 O |
| ATOM 2386 CZ PHE B 269 155.095 58.141 −12.926 1.00 32.53 C | ATOM 2431 N SER B 275 154.243 46.093 −14.372 1.00 33.54 N |
| ANISOU 2386 CZ PHE B 269 5080 4136 3143 43 −182 14 C | ANISOU 2431 N SER B 275 5824 3640 3279 −373 29 −437 N |
| ATOM 2387 CE1 PHE B 269 154.188 58.523 −11.901 1.00 33.96 C | ATOM 2432 CA SER B 275 153.157 45.126 −14.348 1.00 38.44 C |
| ANISOU 2387 CE1 PHE B 269 5050 4415 3438 43 −310 18 C | ANISOU 2432 CA SER B 275 6444 4228 3933 −467 −120 −492 C |
| ATOM 2388 CD1 PHE B 269 154.432 58.095 −10.563 1.00 28.26 C | ATOM 2433 CB SER B 275 152.951 44.504 −15.724 1.00 36.20 C |
| ANISOU 2388 CD1 PHE B 269 4135 3757 2847 40 −255 14 C | ANISOU 2433 CB SER B 275 6478 3806 3471 −538 −152 −611 C |
| ATOM 2389 C PHE B 269 155.466 54.376 −9.396 1.00 35.93 C | ATOM 2434 OG SER B 275 154.201 44.078 −16.157 1.00 37.28 O |
| ANISOU 2389 C PHE B 269 5051 4666 3933 −26 −72 −11 C | ANISOU 2434 OG SER B 275 6766 3821 3575 −487 111 −637 O |
| ATOM 2390 O PHE B 269 154.783 53.880 −10.302 1.00 40.51 O | ATOM 2435 C SER B 275 153.362 44.016 −13.319 1.00 34.79 C |
| ANISOU 2390 O PHE B 269 5761 5203 4430 −64 −135 −50 O | ANISOU 2435 C SER B 275 5820 3732 3665 −469 −25 −458 C |
| ATOM 2391 N ALA B 270 156.670 53.918 −9.084 1.00 33.88 N | ATOM 2436 O SER B 275 152.409 43.425 −12.845 1.00 36.81 O |
| ANISOU 2391 N ALA B 270 4768 4361 3745 1 57 14 N | ANISOU 2436 O SER B 275 5976 3999 4011 −539 −142 −464 O |
| ATOM 2392 CA ALA B 270 157.275 52.816 −9.826 1.00 35.16 C | ATOM 2437 N GLN B 276 154.606 43.698 −13.003 1.00 34.65 N |
| ANISOU 2392 CA ALA B 270 5053 4408 3898 −3 167 −7 C | ANISOU 2437 N GLN B 276 5781 3655 3728 −395 188 −417 N |
| ATOM 2393 CB ALA B 270 158.713 52.527 −9.343 1.00 27.84 C | ATOM 2438 CA GLN B 276 154.853 42.642 −12.032 1.00 40.23 C |
| ANISOU 2393 CB ALA B 270 4040 3423 3113 45 309 35 C | ANISOU 2438 CA GLN B 276 6350 4315 4619 −389 264 −367 C |
| ATOM 2394 C ALA B 270 156.423 51.558 −9.768 1.00 35.07 C | ATOM 2439 CB GLN B 276 156.333 42.370 −11.941 1.00 48.12 C |
| ANISOU 2394 C ALA B 270 5070 4379 3875 −58 103 −37 C | ANISOU 2439 CB GLN B 276 7347 5223 5715 −296 488 −328 C |
| ATOM 2395 O ALA B 270 156.322 50.827 −10.746 1.00 31.94 O | ATOM 2440 CG GLN B 276 156.702 40.981 −12.212 1.00 61.35 C |
| ANISOU 2395 O ALA B 270 4837 3891 3406 −86 134 −87 O | ANISOU 2440 CG GLN B 276 9117 6771 6719 7475 −309 618 −373 C |
| ATOM 2396 N MET B 271 155.812 51.288 −8.623 1.00 25.27 N | ATOM 2441 CD GLN B 276 158.029 40.626 −11.568 1.00 74.49 C |
| ANISOU 2396 N MET B 271 3686 3214 2703 −82 25 −10 N | ANISOU 2441 CD GLN B 276 10655 8310 9338 −208 795 −285 C |
| ATOM 2397 CA MET B 271 154.918 50.132 −8.544 1.00 34.49 C | ATOM 2442 OE1 GLN B 276 158.056 40.060 −10.463 1.00 79.33 O |
| ANISOU 2397 CA MET B 271 4868 4357 3881 −144 −30 −35 C | ANISOU 2442 OE1 GLN B 276 11105 8931 10105 −194 763 −192 O |
| ATOM 2398 CB MET B 271 154.431 49.875 −7.108 1.00 32.35 C | ATOM 2443 NE2 GLN B 276 159.145 40.960 −12.249 1.00 75.54 N |
| ANISOU 2398 CB MET B 271 4438 4159 3693 −165 −66 14 C | ANISOU 2443 NE2 GLN B 276 10862 8359 9480 −137 982 −307 N |
| ATOM 2399 CG MET B 271 155.475 49.172 −6.256 1.00 30.03 C | ATOM 2444 C GLN B 276 154.351 43.003 −10.628 1.00 37.41 C |
| ANISOU 2399 CG MET B 271 4096 3830 3484 −134 21 78 C | ANISOU 2444 C GLN B 276 5742 4101 4373 −384 169 −264 C |
| ATOM 2400 SD MET B 271 155.011 48.980 −4.513 1.00 31.26 S | ATOM 2445 O GLN B 276 154.017 42.123 −9.857 1.00 41.62 O |

TABLE 8-continued

DMXAA-hSTING$^{S162A/Q266I}$ complex

| | |
|---|---|
| ANISOU 2400 SD MET B 271 4124 4068 3685 −159 −15 150 S | ANISOU 2445 O GLN B 276 6185 4607 5021 −418 165 −228 O |
| ATOM 2401 CE MET B 271 154.005 47.503 −4.530 1.00 25.78 C | ATOM 2446 N ALA B 277 154.320 44.292 −10.299 1.00 30.82 N |
| ANISOU 2401 CE MET B 271 3459 3308 3029 −238 −17 138 C | ANISOU 2446 N ALA B 277 4812 3402 3497 −345 110 −219 N |
| ATOM 2402 C MET B 271 153.721 50.217 −9.523 1.00 34.08 C | ATOM 2447 CA ALA B 277 153.905 44.746 −8.965 1.00 35.75 C |
| ANISOU 2402 C MET B 271 4914 4297 3738 −199 −157 −99 C | ANISOU 2447 CA ALA B 277 5228 4154 4202 −339 47 −132 C |
| ATOM 2403 O MET B 271 153.232 49.215 −10.058 1.00 34.62 O | ATOM 2448 CB ALA B 277 154.442 46.179 −8.639 1.00 27.95 C |
| ANISOU 2403 O MET B 271 5072 4293 3789 −255 −191 −147 O | ANISOU 2448 CB ALA B 277 4162 3279 3179 −267 48 −84 C |
| ATOM 2404 N SER B 272 153.229 51.420 −9.747 1.00 29.67 N | ATOM 2449 C ALA B 277 152.395 44.701 −8.825 1.00 41.92 C |
| ANISOU 2404 N SER B 272 4335 3802 3135 −185 −247 −99 N | ANISOU 2449 C ALA B 277 5949 4985 4994 −426 −102 −162 C |
| ATOM 2405 CA SER B 272 152.139 51.565 −10.699 1.00 33.42 C | ATOM 2450 O ALA B 277 151.887 44.808 −7.717 1.00 42.80 O |
| ANISOU 2405 CA SER B 272 4900 4261 3543 −230 −405 −147 C | ANISOU 2450 O ALA B 277 5907 5173 5184 −440 −123 −103 O |
| ATOM 2406 CB SER B 272 151.354 52.867 −10.458 1.00 26.95 C | ATOM 2451 N GLY B 278 151.690 44.553 −9.955 1.00 46.93 N |
| ANISOU 2406 CB SER B 272 3965 3526 2748 −210 −523 −125 C | ANISOU 2451 N GLY B 278 6711 5567 5554 −488 −205 −255 N |
| ATOM 2407 OG SER B 272 152.160 54.000 −10.707 1.00 33.08 O | ATOM 2452 CA GLY B 278 150.237 44.428 −9.979 1.00 47.95 C |
| ANISOU 2407 OG SER B 272 4787 4315 3465 −145 −461 −96 O | ANISOU 2452 CA GLY B 278 6770 5715 5735 −580 −370 −293 C |
| ATOM 2408 C SER B 272 152.658 51.478 −12.154 1.00 33.85 C | ATOM 2453 C GLY B 278 149.556 45.561 −9.231 1.00 47.85 C |
| ANISOU 2408 C SER B 272 5215 4214 3431 −230 −379 −188 C | ANISOU 2453 C GLY B 278 6569 5839 5772 −562 −444 −242 C |
| ATOM 2409 O SER B 272 151.867 51.405 −13.065 1.00 38.55 O | ATOM 2454 O GLY B 278 148.781 45.331 −8.310 1.00 53.63 O |
| ANISOU 2409 O SER B 272 5940 4773 3936 −277 −526 −232 O | ANISOU 2454 O GLY B 278 7139 6604 6632 −604 −449 −209 O |
| ATOM 2410 N GLN B 273 153.976 51.535 −12.384 1.00 40.89 N | ATOM 2455 N PHE B 279 149.851 46.793 −9.632 1.00 41.02 N |
| ANISOU 2410 N GLN B 273 6191 5055 4291 −179 −194 −174 N | ANISOU 2455 N PHE B 279 5733 5040 4810 −502 −479 −237 N |
| ATOM 2411 CA GLN B 273 154.547 51.444 −13.757 1.00 37.54 C | ATOM 2456 CA PHE B 279 149.463 47.965 −8.879 1.00 39.38 C |
| ANISOU 2411 CA GLN B 273 6040 4517 3704 −179 −111 −216 C | ANISOU 2456 CA PHE B 279 5361 4952 4649 −465 −509 −188 C |
| ATOM 2412 CB GLN B 273 155.847 52.222 −13.872 1.00 45.99 C | ATOM 2457 CB PHE B 279 150.726 48.504 −8.215 1.00 46.38 C |
| ANISOU 2412 CB GLN B 273 7131 5564 4780 −109 82 −175 C | ANISOU 2457 CB PHE B 279 6233 5887 5500 −378 −365 −125 C |
| ATOM 2413 CG GLN B 273 155.701 53.708 −13.695 1.00 59.01 C | ATOM 2458 CG PHE B 279 150.494 49.319 −6.991 1.00 47.78 C |
| ANISOU 2413 CG GLN B 273 8702 7294 6424 −71 14 −124 C | ANISOU 2458 CG PHE B 279 6243 6171 5740 −351 −341 −72 C |
| ATOM 2414 CD GLN B 273 155.001 54.356 −14.867 1.00 77.94 C | ATOM 2459 CD1 PHE B 279 150.135 48.703 −5.814 1.00 46.78 C |
| ANISOU 2414 CD GLN B 273 11312 9667 8635 −92 −117 −138 C | ANISOU 2459 CD1 PHE B 279 6011 6060 5701 −386 −282 −31 C |
| ATOM 2415 OE1 GLN B 273 153.781 54.586 −14.832 1.00 86.19 O | ATOM 2460 CE1 PHE B 279 149.952 49.438 −4.684 1.00 43.88 C |
| ANISOU 2415 OE1 GLN B 273 12310 10767 9670 −123 −341 −141 O | ANISOU 2460 CE1 PHE B 279 5532 5780 5362 −367 −240 9 C |
| ATOM 2416 NE2 GLN B 273 155.765 54.641 −15.934 1.00 82.74 N | ATOM 2461 CZ PHE B 279 150.161 50.833 −4.713 1.00 42.99 C |
| ANISOU 2416 NE2 GLN B 273 12161 10176 9100 −78 24 −142 N | ANISOU 2461 CZ PHE B 279 5392 5736 5205 −309 −263 5 C |
| ATOM 2417 C GLN B 273 154.873 50.030 −14.141 1.00 35.25 C | ATOM 2462 CE2 PHE B 279 150.524 51.462 −5.874 1.00 40.56 C |
| ANISOU 2417 C GLN B 273 5877 4112 3403 −215 −11 −274 C | ANISOU 2462 CE2 PHE B 279 5169 5412 4831 −272 −326 −27 C |
| ATOM 2418 O GLN B 273 154.896 49.671 −15.320 1.00 36.24 O | ATOM 2463 CD2 PHE B 279 150.691 50.703 −7.009 1.00 45.04 C |
| ANISOU 2418 O GLN B 273 6267 4135 3370 −248 11 −338 O | ANISOU 2463 CD2 PHE B 279 5867 5894 5351 −294 −362 −62 C |
| ATOM 2419 N TYR B 274 155.154 49.204 −13.144 1.00 29.70 N | ATOM 2464 C PHE B 279 148.935 48.974 −9.880 1.00 33.96 C |
| ANISOU 2419 N TYR B 274 5007 3414 2863 −209 58 −251 N | ANISOU 2464 C PHE B 279 4731 4283 3889 −458 −667 −224 C |
| ATOM 2420 CA TYR B 274 155.589 47.856 −13.437 1.00 30.65 C | ATOM 2465 O PHE B 279 149.671 49.442 −10.726 1.00 40.84 O |
| ANISOU 2420 CA TYR B 274 5231 3408 3008 −230 179 −299 C | ANISOU 2465 O PHE B 279 5764 5132 4622 −415 −653 −236 O |
| ATOM 2421 CB TYR B 274 156.706 47.415 −12.519 1.00 30.01 C | ATOM 2466 N SER B 280 147.658 49.331 −9.789 1.00 39.95 N |
| ANISOU 2421 CB TYR B 274 4990 3301 3110 −168 348 −238 C | ANISOU 2466 N SER B 280 5354 5071 4754 −499 −813 −235 N |
| ATOM 2422 CG TYR B 274 157.988 48.143 −12.751 1.00 50.31 C | ATOM 2467 CA SER B 280 147.071 50.286 −10.726 1.00 41.59 C |
| ANISOU 2422 CG TYR B 274 7566 5838 5711 −92 524 −205 C | ANISOU 2467 CA SER B 280 5605 5284 4915 −490 −1001 −255 C |
| ATOM 2423 CD1 TYR B 274 158.656 48.036 −13.953 1.00 57.73 C | ATOM 2468 CB SER B 280 145.569 50.035 −10.831 1.00 45.42 C |
| ANISOU 2423 CD1 TYR B 274 8730 6646 6560 −81 699 −261 C | ANISOU 2468 CB SER B 280 5948 5742 5566 −568 −1194 −286 C |
| ATOM 2424 CE1 TYR B 274 159.841 48.723 −14.155 1.00 68.53 C | ATOM 2469 OG SER B 280 144.876 50.516 −9.688 1.00 51.97 O |
| ANISOU 2424 CE1 TYR B 274 10082 7969 7989 −15 887 −228 C | ANISOU 2469 OG SER B 280 6516 6638 6593 −557 −1142 −248 O |
| ATOM 2425 CZ TYR B 274 160.364 49.521 −13.131 1.00 64.60 C | ATOM 2470 C SER B 280 147.346 51.762 −10.349 1.00 43.47 C |
| ANISOU 2425 CZ TYR B 274 9334 7562 7648 37 866 −141 C | ANISOU 2470 C SER B 280 5764 5608 5143 −402 −966 −203 C |
| ATOM 2426 OH TYR B 274 161.539 50.203 −13.296 1.00 66.25 O | ATOM 2471 O SER B 280 147.709 52.075 −9.200 1.00 41.15 O |
| ANISOU 2426 OH TYR B 274 9499 7718 7957 94 1043 −108 O | ANISOU 2471 O SER B 280 5342 5381 4911 −363 −820 −163 O |
| ATOM 2427 CE2 TYR B 274 159.711 49.639 −11.940 1.00 57.11 C | ATOM 2472 N ARG B 281 147.139 52.668 −11.310 1.00 44.16 N |
| ANISOU 2427 CE2 TYR B 274 8191 6749 6761 25 676 −93 C | ANISOU 2472 N ARG B 281 5944 5685 5149 −375 −1112 −205 N |
| ATOM 2428 CD2 TYR B 274 158.534 48.950 −11.755 1.00 52.53 C | ATOM 2473 CA ARG B 281 147.216 54.104 −11.034 1.00 50.88 C |
| ANISOU 2428 CD2 TYR B 274 7633 6208 6116 −37 523 −122 C | ANISOU 2473 CA ARG B 281 6714 6599 6019 −298 −1104 −159 C |
| ATOM 2429 C TYR B 274 154.487 46.872 −13.310 1.00 31.20 C | ATOM 2474 CB ARG B 281 146.887 54.901 −12.279 1.00 60.59 C |
| ANISOU 2429 C TYR B 274 5292 3463 3098 −313 38 −343 C | ANISOU 2474 CB ARG B 281 8083 7787 7150 −281 −1299 −153 C |
| ATOM 2430 O TYR B 274 153.899 46.767 −12.254 1.00 30.50 O | ATOM 2475 CG ARG B 281 148.088 55.500 −12.931 1.00 76.27 C |
| ANISOU 2475 CG ARG B 281 10286 9755 8936 −225 −1199 −129 C | ATOM 2476 CD ARG B 281 147.682 56.665 −13.850 1.00 87.95 C |
| ANISOU 2476 CD ARG B 281 11861 11210 10347 −189 −1376 −93 C | ATOM 2477 NE ARG B 281 148.470 57.870 −13.566 1.00 94.73 N |
| ANISOU 2477 NE ARG B 281 12706 12100 11185 −108 −1241 −42 N | ATOM 2478 CZ ARG B 281 148.047 59.120 −13.753 1.00 94.24 C |
| ANISOU 2478 CZ ARG B 281 12603 12040 11164 −57 −1346 6 C | ATOM 2479 NH1 ARG B 281 148.838 60.155 −13.458 1.00 90.45 N |
| ANISOU 2479 NH1 ARG B 281 12114 11579 10675 9 −1204 45 N | ATOM 2480 NH2 ARG B 281 146.830 59.330 −14.230 1.00 95.49 N |
| ANISOU 2480 NH2 ARG B 281 12717 12169 11394 −72 −1602 17 N | ATOM 2481 C ARG B 281 146.240 54.520 −9.933 1.00 51.83 C |
| ANISOU 2481 C ARG B 281 6775 6359 −297 −1106 −144 C | ATOM 2482 O ARG B 281 146.480 55.457 −9.156 1.00 50.26 O |
| ANISOU 2482 O ARG B 281 6257 6635 6203 −239 −1004 −115 O | ATOM 2483 N GLU B 282 145.121 53.818 −9.884 1.00 50.97 N |
| ANISOU 2483 N GLU B 282 6332 6634 6401 −368 −1212 −172 N | ATOM 2484 CA GLU B 282 144.092 54.074 −8.887 1.00 54.35 C |
| ANISOU 2520 CA GLU B 286 5353 6593 6507 −306 −267 −100 C | ATOM 2521 CB GLU B 286 143.971 54.044 −3.012 1.00 58.43 C |
| ANISOU 2521 CB GLU B 286 6562 7783 7855 −387 −319 −102 C | ATOM 2522 CG GLU B 286 143.091 53.422 −1.956 1.00 75.50 C |
| ANISOU 2522 CG GLU B 286 8600 9921 10167 −454 −159 −99 C | ATOM 2523 CD GLU B 286 142.750 51.955 −2.288 1.00 89.29 C |
| ANISOU 2523 CD GLU B 286 10349 11601 11976 −541 −198 −94 C | ATOM 2524 OE1 GLU B 286 141.551 51.578 −2.180 1.00 94.04 O |
| ANISOU 2524 OE1 GLU B 286 10780 12143 12808 −605 −185 −111 O | ATOM 2525 OE2 GLU B 286 143.689 51.196 −2.664 1.00 91.51 O |
| ANISOU 2525 OE2 GLU B 286 10796 11877 12098 −546 −236 −76 O | ATOM 2526 C GLU B 286 145.764 55.130 −1.611 1.00 42.01 C |
| ANISOU 2526 C GLU B 286 4645 5810 5506 −300 −121 −70 C | ATOM 2527 O GLU B 286 145.635 55.509 −0.451 1.00 35.30 O |
| ANISOU 2527 O GLU B 286 3770 4988 4655 −301 26 −72 O | ATOM 2528 N GLN B 287 146.865 54.527 −2.054 1.00 35.94 N |
| ANISOU 2528 N GLN B 287 4017 5040 4598 −292 −166 −44 N | ATOM 2529 CA GLN B 287 147.975 54.193 −1.175 1.00 34.78 C |

TABLE 8-continued

DMXAA-hSTING$^{S162A/Q266I}$ complex

| | |
|---|---|
| ANISOU 2484 CA GLU B 282 6492 7090 7069 -379 -1184 -165 C | ANISOU 2529 CA GLN B 287 3976 4921 4317 -286 -74 -3 C |
| ATOM 2485 CB GLU B 282 142.792 53.366 -9.265 1.00 63.19 C | ATOM 2530 CB GLN B 287 148.926 53.178 -1.830 1.00 38.60 C |
| ANISOU 2485 CB GLU B 282 7495 8141 8373 -465 -1362 -198 C | ANISOU 2530 CB GLN B 287 4573 5366 4727 -288 -123 26 C |
| ATOM 2486 CG GLU B 282 142.103 53.972 -10.469 1.00 75.97 C | ATOM 2531 CG GLN B 287 148.325 51.791 -2.049 1.00 38.43 C |
| ANISOU 2486 CG GLU B 282 9143 9709 10012 -460 -1654 -202 C | ANISOU 2531 CG GLN B 287 4546 5282 4773 -356 -125 32 C |
| ATOM 2487 CD GLU B 282 142.995 54.012 -11.719 1.00 85.87 C | ATOM 2532 CD GLN B 287 147.817 51.169 -0.752 1.00 43.76 C |
| ANISOU 2487 CD GLU B 282 10720 10935 10970 -444 -1751 -206 C | ANISOU 2532 CD GLN B 287 5184 5958 5485 -410 3 68 C |
| ATOM 2488 OE1 GLU B 282 143.430 52.924 -12.183 1.00 86.63 O | ATOM 2533 OE1 GLN B 287 148.592 50.656 0.065 1.00 50.64 O |
| ANISOU 2488 OE1 GLU B 282 10995 10987 10933 -503 -1741 -248 O | ANISOU 2533 OE1 GLN B 287 6140 6832 6270 -409 69 126 O |
| ATOM 2489 OE2 GLU B 282 143.273 55.136 -12.212 1.00 89.09 O | ATOM 2534 NE2 GLN B 287 146.519 51.241 -0.544 1.00 42.04 N |
| ANISOU 2489 OE2 GLU B 282 11211 11356 11284 -371 -1813 -168 O | ANISOU 2534 NE2 GLN B 287 4841 5727 5404 -457 40 40 N |
| ATOM 2490 C GLU B 282 144.541 53.615 -7.503 1.00 55.29 C | ATOM 2535 C GLN B 287 148.741 55.446 -0.762 1.00 35.15 C |
| ANISOU 2490 C GLU B 282 6538 7257 7213 -384 -937 -150 C | ANISOU 2535 C GLN B 287 4054 5018 4283 -226 -54 -10 C |
| ATOM 2491 O GLU B 282 144.324 54.306 -6.501 1.00 54.94 O | ATOM 2536 O GLN B 287 149.270 55.517 0.341 1.00 30.91 O |
| ANISOU 2491 O GLU B 282 6353 7261 7261 -352 -820 -134 O | ANISOU 2536 O GLN B 287 3567 4511 3665 -229 25 11 O |
| ATOM 2492 N ASP B 283 145.146 52.434 -7.451 1.00 54.67 N | ATOM 2537 N ALA B 288 148.812 56.429 -1.651 1.00 34.10 N |
| ANISOU 2492 N ASP B 283 6569 7153 7050 -427 -862 -156 N | ANISOU 2537 N ALA B 288 3907 4884 4165 -176 -137 -36 N |
| ATOM 2493 CA ASP B 283 145.719 51.938 -6.209 1.00 60.33 C | ATOM 2538 CA ALA B 288 149.504 57.667 -1.308 1.00 36.04 C |
| ANISOU 2493 CA ASP B 283 7261 7905 7757 -428 -654 -124 C | ANISOU 2538 CA ALA B 288 4174 5163 4358 -125 -117 -47 C |
| ATOM 2494 CB ASP B 283 146.422 50.584 -6.415 1.00 70.84 C | ATOM 2539 CB ALA B 288 149.597 58.631 -2.493 1.00 24.00 C |
| ANISOU 2494 CB ASP B 283 8731 9180 9005 -468 -607 -125 C | ANISOU 2539 CB ALA B 288 2650 3615 2852 -73 -212 -60 C |
| ATOM 2495 CG ASP B 283 145.449 49.439 -6.718 1.00 79.90 C | ATOM 2540 C ALA B 288 148.797 58.313 -0.125 1.00 33.10 C |
| ANISOU 2495 CG ASP B 283 9835 10247 10276 -566 -682 -161 C | ANISOU 2540 C ALA B 288 3735 4815 4026 -136 -10 -78 C |
| ATOM 2496 OD1 ASP B 283 144.220 49.644 -6.556 1.00 83.36 O | ATOM 2541 O ALA B 288 149.434 58.799 0.789 1.00 30.08 O |
| ANISOU 2496 OD1 ASP B 283 10100 10678 10893 -607 -750 -176 O | ANISOU 2541 O ALA B 288 3408 4461 3558 -129 49 -84 O |
| ATOM 2497 OD2 ASP B 283 145.937 48.338 -7.113 1.00 81.92 O | ATOM 2542 N LYS B 289 147.467 58.288 -0.118 1.00 29.63 N |
| ANISOU 2497 OD2 ASP B 283 10221 10434 10471 -601 -667 -177 O | ANISOU 2542 N LYS B 289 3177 4354 3725 -157 21 -103 N |
| ATOM 2498 C ASP B 283 146.727 52.947 -5.692 1.00 57.39 C | ATOM 2543 CA LYS B 289 146.744 58.952 0.948 1.00 35.47 C |
| ANISOU 2498 C ASP B 283 6928 7601 7276 -345 -552 -93 C | ANISOU 2543 CA LYS B 289 3852 5098 4526 -163 163 -143 C |
| ATOM 2499 O ASP B 283 146.865 53.163 -4.481 1.00 58.73 O | ATOM 2544 CB LYS B 289 145.281 59.113 0.573 1.00 40.07 C |
| ANISOU 2499 O ASP B 283 7030 7820 7466 -334 -416 -68 O | ANISOU 2544 CB LYS B 289 4255 5633 5335 -166 167 -169 C |
| ATOM 2500 N ARG B 284 147.418 53.577 -6.635 1.00 49.18 N | ATOM 2545 CG LYS B 289 145.080 60.252 -0.383 1.00 50.62 C |
| ANISOU 2500 N ARG B 284 6013 6557 6116 -294 -620 -96 N | ANISOU 2545 CG LYS B 289 5522 6946 6766 -99 44 -186 C |
| ATOM 2501 CA ARG B 284 148.479 54.495 -6.290 1.00 44.91 C | ATOM 2546 CD LYS B 289 144.069 59.890 -1.445 1.00 60.11 C |
| ANISOU 2501 CA ARG B 284 5514 6063 5487 -223 -532 -70 C | ANISOU 2546 CD LYS B 289 6597 8097 8147 -107 -102 -175 C |
| ATOM 2502 CB ARG B 284 149.217 54.966 -7.529 1.00 44.99 C | ATOM 2547 CE LYS B 289 142.666 59.918 -0.936 1.00 66.69 C |
| ANISOU 2502 CB ARG B 284 5684 6038 5372 -183 -590 -72 C | ANISOU 2547 CE LYS B 289 7228 8881 9231 -109 -6 -203 C |
| ATOM 2503 CG ARG B 284 150.564 55.583 -7.157 1.00 46.17 C | ATOM 2548 NZ LYS B 289 141.767 59.151 -1.870 1.00 75.65 N |
| ANISOU 2503 CG ARG B 284 5878 6213 5453 -124 -470 -43 C | ANISOU 2548 NZ LYS B 289 8245 9963 10536 -168 -171 -187 N |
| ATOM 2504 CD ARG B 284 151.245 56.118 -8.359 1.00 44.55 C | ATOM 2549 C LYS B 289 146.901 58.175 2.237 1.00 36.05 C |
| ANISOU 2504 CD ARG B 284 5800 5935 5116 -87 -490 -41 C | ANISOU 2549 C LYS B 289 4010 5189 4497 -220 302 -124 C |
| ATOM 2505 NE ARG B 284 150.495 57.197 -8.970 1.00 46.36 N | ATOM 2550 O LYS B 289 147.015 58.738 3.334 1.00 41.82 O |
| ANISOU 2505 NE ARG B 284 6051 6190 5375 -66 -611 -41 N | ANISOU 2550 O LYS B 289 4803 5937 5151 -225 422 -151 O |
| ATOM 2506 CZ ARG B 284 150.525 57.454 -10.266 1.00 52.50 C | ATOM 2551 N LEU B 290 146.909 56.867 2.081 1.00 35.90 N |
| ANISOU 2506 CZ ARG B 284 6994 6909 6046 -58 -694 -39 C | ANISOU 2551 N LEU B 290 4016 5156 4468 -265 283 -76 N |
| ATOM 2507 NH1 ARG B 284 149.839 58.467 -10.753 1.00 58.36 N | ATOM 2552 CA LEU B 290 147.001 55.964 3.207 1.00 36.96 C |
| ANISOU 2507 NH1 ARG B 284 7729 7644 6801 -33 -822 -23 N | ANISOU 2552 CA LEU B 290 4242 5291 4508 -323 403 -37 C |
| ATOM 2508 NH2 ARG B 284 151.239 56.685 -11.070 1.00 52.19 N | ATOM 2553 CB LEU B 290 146.723 54.530 2.744 1.00 45.99 C |
| ANISOU 2508 NH2 ARG B 284 7139 6806 5886 -76 -643 -52 N | ANISOU 2553 CB LEU B 290 5368 6394 5713 -372 372 10 C |
| ATOM 2509 C ARG B 284 148.022 55.720 -5.491 1.00 44.78 C | ATOM 2554 CG LEU B 290 146.826 53.395 3.766 1.00 57.05 C |
| ANISOU 2509 C ARG B 284 5363 6103 5550 -187 -500 -66 C | ANISOU 2554 CG LEU B 290 6872 7775 7029 -434 483 73 C |
| ATOM 2510 O ARG B 284 148.691 56.162 -4.521 1.00 32.80 O | ATOM 2555 CD1 LEU B 290 145.879 53.645 4.912 1.00 60.61 C |
| ANISOU 2510 O ARG B 284 3832 4631 3998 -159 -386 -50 O | ANISOU 2555 CD1 LEU B 290 7309 8214 7504 -478 693 55 C |
| ATOM 2511 N LEU B 285 146.910 56.304 -5.929 1.00 43.40 N | ATOM 2556 CD2 LEU B 290 146.450 52.070 3.118 1.00 59.94 C |
| ANISOU 2511 N LEU B 285 5093 5912 5485 -186 -612 -84 N | ANISOU 2556 CD2 LEU B 290 7195 8082 7499 -481 445 105 C |
| ATOM 2512 CA LEU B 285 146.419 57.484 -5.247 1.00 44.90 C | ATOM 2557 C LEU B 290 148.390 56.116 3.855 1.00 36.56 C |
| ANISOU 2512 CA LEU B 285 5150 6133 5776 -145 -569 -88 C | ANISOU 2557 C LEU B 290 4357 5280 4255 -305 368 -5 C |
| ATOM 2513 CB LEU B 285 145.348 58.202 -6.056 1.00 45.22 C | ATOM 2558 O LEU B 290 148.536 56.176 5.077 1.00 37.37 O |
| ANISOU 2513 CB LEU B 285 5101 6132 5947 -126 -733 -95 C | ANISOU 2558 O LEU B 290 4568 5396 4235 -333 466 3 O |
| ATOM 2514 CG LEU B 285 144.798 59.411 -5.304 1.00 53.58 C | ATOM 2559 N PHE B 291 149.400 56.201 3.011 1.00 25.99 N |
| ANISOU 2514 CG LEU B 285 6006 7205 7148 -77 -662 -104 C | ANISOU 2559 N PHE B 291 3039 3949 2888 -261 226 12 N |
| ATOM 2515 CD1 LEU B 285 145.949 60.394 -4.954 1.00 60.00 C | ATOM 2560 CA PHE B 291 150.774 56.421 3.425 1.00 31.73 C |
| ANISOU 2515 CD1 LEU B 285 6915 8055 7829 -18 -564 -97 C | ANISOU 2560 CA PHE B 291 3874 4698 3484 -238 161 41 C |
| ATOM 2516 CD2 LEU B 285 143.698 60.103 -6.110 1.00 58.14 C | ATOM 2561 CB PHE B 291 151.700 56.515 2.193 1.00 24.44 C |
| ANISOU 2516 CD2 LEU B 285 6468 7723 7898 -49 -844 -98 C | ANISOU 2561 CB PHE B 291 2930 3759 2597 -187 38 51 C |
| ATOM 2517 C LEU B 285 145.879 57.068 -3.869 1.00 48.22 C | ATOM 2562 CG PHE B 291 153.135 56.944 2.524 1.00 24.11 C |
| ANISOU 2517 C LEU B 285 5449 6578 6294 -185 -417 -97 C | ANISOU 2562 CG PHE B 291 2951 3726 2484 -159 -30 73 C |
| ATOM 2518 O LEU B 285 146.009 57.783 -2.870 1.00 47.51 O | ATOM 2563 CD1 PHE B 291 154.040 56.024 3.042 1.00 24.36 C |
| ANISOU 2518 O LEU B 285 5320 6524 6207 -160 -291 -104 O | ANISOU 2563 CD1 PHE B 291 3050 3741 2464 -170 -73 145 C |
| ATOM 2519 N GLU B 286 145.268 55.895 -3.843 1.00 44.30 N | ATOM 2564 CE1 PHE B 291 155.344 56.404 3.379 1.00 24.68 C |
| ANISOU 2519 N GLU B 286 4913 6051 5870 -255 -423 -100 N | ANISOU 2564 CE1 PHE B 291 3120 3778 2479 -148 -160 169 C |
| ATOM 2520 CA GLU B 286 144.658 55.358 -2.645 1.00 48.57 C | ATOM 2565 CZ PHE B 291 155.758 57.753 3.182 1.00 24.04 C |
| ANISOU 2565 CZ PHE B 291 3006 3709 2419 -120 -189 112 C | ATOM 2566 CE2 PHE B 291 154.862 58.680 2.659 1.00 23.70 C |
| ANISOU 2566 CE2 PHE B 291 2912 3681 2411 -107 -131 42 C | ANISOU 2610 CB GLU B 296 5770 5784 3263 -509 683 -290 O |
| ATOM 2567 CD2 PHE B 291 153.551 58.274 2.346 1.00 23.77 C | ATOM 2611 N ASP B 297 150.134 59.341 11.915 1.00 41.75 N |
| ANISOU 2567 CD2 PHE B 291 2887 3695 2451 -123 -59 26 C | ANISOU 2611 N ASP B 297 6136 5999 3727 -494 818 -172 N |
| ATOM 2568 C PHE B 291 150.900 57.702 4.275 1.00 34.71 C | ATOM 2612 CA ASP B 297 149.846 58.652 13.167 1.00 45.15 C |
| | ANISOU 2612 CA ASP B 297 6812 6406 3936 -570 955 -128 C |
| | ATOM 2613 CB ASP B 297 148.836 57.546 12.925 1.00 51.05 C |

TABLE 8-continued

DMXAA-hSTING$^{S162A/Q266I}$ complex

| | |
|---|---|
| ANISOU 2568 C PHE B 291 4292 5105 3791 −228 203 −14 C | ANISOU 2613 CB ASP B 297 7461 7123 4814 −592 1124 −62 C |
| ATOM 2569 O PHE B 291 151.507 57.705 5.356 1.00 32.48 O | ATOM 2614 CG ASP B 297 147.451 58.090 12.581 1.00 71.66 C |
| ANISOU 2569 O PHE B 291 4132 4838 3371 −251 208 4 O | ANISOU 2614 CG ASP B 297 9878 9697 7651 −579 1372 −156 C |
| ATOM 2570 N CYS B 292 150.325 58.795 3.777 1.00 26.71 N | ATOM 2615 OD1 ASP B 297 147.250 59.332 12.680 1.00 76.91 O |
| ANISOU 2570 N CYS B 292 3186 4090 2872 −194 221 −80 N | ANISOU 2615 OD1 ASP B 297 10523 10354 8344 −553 1441 −271 O |
| ATOM 2571 CA CYS B 292 150.389 60.068 4.499 1.00 34.60 C | ATOM 2616 OD2 ASP B 297 146.562 57.270 12.230 1.00 79.94 O |
| ANISOU 2571 CA CYS B 292 4220 5100 3826 −182 273 −146 C | ANISOU 2616 OD2 ASP B 297 10790 10713 8872 −597 1494 −114 O |
| ATOM 2572 CB CYS B 292 149.831 61.211 3.636 1.00 33.07 C | ATOM 2617 C ASP B 297 151.083 58.100 13.876 1.00 44.80 C |
| ANISOU 2572 CB CYS B 292 3904 4884 3777 −129 265 −202 C | ANISOU 2617 C ASP B 297 6997 6376 3648 −601 736 −34 C |
| ATOM 2573 SG CYS B 292 149.785 62.749 4.555 1.00 67.72 S | ATOM 2618 O ASP B 297 151.174 58.100 15.104 1.00 49.70 O |
| ANISOU 2573 SG CYS B 292 8333 9263 8136 −117 358 −295 S | ANISOU 2618 O ASP B 297 7904 6980 4001 −665 785 −31 O |
| ATOM 2574 C CYS B 292 149.647 59.990 5.870 1.00 31.78 C | ATOM 2619 N ILE B 298 152.029 57.625 13.083 1.00 40.14 N |
| ANISOU 2574 C CYS B 292 3941 4742 3391 −236 444 −175 C | ANISOU 2619 N ILE B 298 6285 5807 3159 −557 493 45 N |
| ATOM 2575 O CYS B 292 150.101 60.454 6.943 1.00 34.22 O | ATOM 2620 CA ILE B 298 153.303 57.172 13.609 1.00 40.93 C |
| ANISOU 2575 O CYS B 292 4391 5062 3550 −259 479 −204 O | ANISOU 2620 CA ILE B 298 6540 5909 3103 −570 244 139 C |
| ATOM 2576 N ARG B 293 148.490 59.385 5.844 1.00 28.30 N | ATOM 2621 CB ILE B 298 154.192 56.546 12.510 1.00 34.52 C |
| ANISOU 2576 N ARG B 293 3421 4278 3053 −262 557 −170 N | ANISOU 2621 CB ILE B 298 5527 5100 2490 −508 37 223 C |
| ATOM 2577 CA ARG B 293 147.753 59.292 7.094 1.00 35.43 C | ATOM 2622 CG1 ILE B 298 153.591 55.246 11.988 1.00 33.70 C |
| ANISOU 2577 CA ARG B 293 4404 5165 3895 −315 763 −195 C | ANISOU 2622 CG1 ILE B 298 5333 4971 2501 −504 134 311 C |
| ATOM 2578 CB ARG B 293 146.328 58.878 6.832 1.00 37.06 C | ATOM 2623 CD1 ILE B 298 154.352 54.689 10.784 1.00 32.05 C |
| ANISOU 2578 CB ARG B 293 4449 5326 4308 −335 899 −205 C | ANISOU 2623 CD1 ILE B 298 4927 4750 2500 −440 −21 368 C |
| ATOM 2579 CG ARG B 293 145.623 59.790 5.892 1.00 49.81 C | ATOM 2624 CG2 ILE B 298 155.572 56.256 13.043 1.00 35.00 C |
| ANISOU 2579 CG ARG B 293 5862 6914 6150 −277 867 −260 C | ANISOU 2624 CG2 ILE B 298 5705 5147 2446 −512 −236 311 C |
| ATOM 2580 CD ARG B 293 144.194 59.402 5.889 1.00 69.65 C | ATOM 2625 C ILE B 298 154.040 58.334 14.281 1.00 36.85 C |
| ANISOU 2580 CD ARG B 293 8208 9368 8886 −305 1012 −272 C | ANISOU 2625 C ILE B 298 6168 5401 2431 −589 115 55 C |
| ATOM 2581 NE ARG B 293 143.483 59.517 4.609 1.00 79.48 N | ATOM 2626 O ILE B 298 154.479 58.219 15.425 1.00 38.80 O |
| ANISOU 2581 NE ARG B 293 9232 10581 10385 −268 881 −273 N | ANISOU 2626 O ILE B 298 6689 5635 2419 −647 30 87 O |
| ATOM 2582 CZ ARG B 293 143.041 58.479 3.887 1.00 81.59 C | ATOM 2627 N LEU B 299 154.140 59.450 13.581 1.00 35.84 N |
| ANISOU 2582 CZ ARG B 293 9403 10828 10769 −302 790 −228 C | ANISOU 2627 N LEU B 299 5875 5287 2456 −545 99 −51 N |
| ATOM 2583 NH1 ARG B 293 143.253 57.221 4.286 1.00 77.93 N | ATOM 2628 CA LEU B 299 154.880 60.620 14.073 1.00 41.44 C |
| ANISOU 2583 NH1 ARG B 293 9033 10370 10207 −368 832 −175 N | ANISOU 2628 CA LEU B 299 6686 5993 3065 −563 −33 −143 C |
| ATOM 2584 NH2 ARG B 293 142.382 58.696 2.754 1.00 83.46 N | ATOM 2629 CB LEU B 299 155.061 61.654 12.978 1.00 34.65 C |
| ANISOU 2584 NH2 ARG B 293 9461 11030 11222 −271 643 −235 N | ANISOU 2629 CB LEU B 299 5583 5137 2445 −500 −61 −226 C |
| ATOM 2585 C ARG B 293 148.398 58.374 8.137 1.00 35.22 C | ATOM 2630 CG LEU B 299 155.920 61.154 11.824 1.00 43.21 C |
| ANISOU 2585 C ARG B 293 4584 5152 3647 −373 774 −128 C | ANISOU 2630 CG LEU B 299 6447 6228 3743 −439 −237 −136 C |
| ATOM 2586 O ARG B 293 148.290 58.610 9.351 1.00 38.86 O | ATOM 2631 CD1 LEU B 299 156.041 62.234 10.744 1.00 41.03 C |
| ANISOU 2586 O ARG B 293 5208 5606 3951 −415 907 −154 O | ANISOU 2631 CD1 LEU B 299 5966 5945 3679 −383 −234 −214 C |
| ATOM 2587 N THR B 294 149.042 57.311 7.658 1.00 31.72 N | ATOM 2632 CD2 LEU B 299 157.334 60.724 12.298 1.00 35.27 C |
| ANISOU 2587 N THR B 294 4148 4715 3189 −375 639 −39 N | ANISOU 2632 CD2 LEU B 299 5520 5209 2670 −459 −519 −50 C |
| ATOM 2588 CA THR B 294 149.717 56.370 8.530 1.00 30.38 C | ATOM 2633 C LEU B 299 154.254 61.279 15.270 1.00 50.93 C |
| ANISOU 2588 CA THR B 294 4161 4546 2837 −419 611 47 C | ANISOU 2633 C LEU B 299 8187 7174 4025 −630 135 −246 C |
| ATOM 2589 CB THR B 294 150.065 55.060 7.827 1.00 39.52 C | ATOM 2634 O LEU B 299 154.951 61.844 16.125 1.00 59.15 O |
| ANISOU 2589 CB THR B 294 5272 5683 4062 −417 510 140 C | ANISOU 2634 O LEU B 299 9406 8202 4868 −680 −8 −293 O |
| ATOM 2590 OG1 THR B 294 148.870 54.472 7.313 1.00 34.69 O | ATOM 2635 N ALA B 300 152.929 61.217 15.321 1.00 51.13 N |
| ANISOU 2590 OG1 THR B 294 4529 5036 3616 −443 621 133 O | ANISOU 2635 N ALA B 300 8162 7184 4079 −635 445 −289 N |
| ATOM 2591 CG2 THR B 294 150.724 54.079 8.824 1.00 30.66 C | ATOM 2636 CA ALA B 300 152.209 61.780 16.441 1.00 55.44 C |
| ANISOU 2591 CG2 THR B 294 4342 4544 2762 −458 481 245 C | ANISOU 2636 CA ALA B 300 8960 7693 4411 −697 677 −393 C |
| ATOM 2592 C THR B 294 150.975 57.019 9.078 1.00 30.35 C | ATOM 2637 CB ALA B 300 150.733 61.684 16.212 1.00 58.52 C |
| ANISOU 2592 C THR B 294 4297 4571 2666 −405 470 44 C | ANISOU 2637 CB ALA B 300 9227 8055 4953 −684 1027 −432 C |
| ATOM 2593 O THR B 294 151.264 56.981 10.288 1.00 31.72 O | ATOM 2638 C ALA B 300 152.594 61.111 17.767 1.00 61.76 C |
| ANISOU 2593 O THR B 294 4675 4744 2634 −450 492 62 O | ANISOU 2638 C ALA B 300 10136 8478 4850 −784 618 −323 C |
| ATOM 2594 N LEU B 295 151.723 57.657 8.193 1.00 30.18 N | ATOM 2639 O ALA B 300 152.700 61.779 18.799 1.00 64.02 O |
| ANISOU 2594 N LEU B 295 4174 4564 2730 −348 322 19 N | ANISOU 2639 O ALA B 300 10716 8735 4875 −847 646 −413 O |
| ATOM 2595 CA LEU B 295 152.927 58.350 8.656 1.00 29.13 C | ATOM 2640 N ASP B 301 152.798 59.795 17.733 1.00 62.76 N |
| ANISOU 2595 CA LEU B 295 4137 4445 2485 −339 178 9 C | ANISOU 2640 N ASP B 301 8683 8633 6532 15 1371 1184 N |
| ATOM 2596 CB LEU B 295 153.655 58.976 7.500 1.00 27.69 C | ATOM 2641 CA ASP B 301 153.134 59.034 18.929 1.00 69.90 C |
| ANISOU 2596 CB LEU B 295 3812 4264 2446 −277 54 −12 C | ANISOU 2641 CA ASP B 301 9789 9618 7151 23 1415 1451 C |
| ATOM 2597 CG LEU B 295 155.051 59.498 7.803 1.00 33.67 C | ATOM 2642 CB ASP B 301 152.460 57.659 18.901 1.00 86.46 C |
| ANISOU 2597 CG LEU B 295 4622 5018 3152 −270 −117 −6 C | ANISOU 2642 CB ASP B 301 11695 11635 9522 21 1696 1695 C |
| ATOM 2598 CD1 LEU B 295 155.948 58.394 8.281 1.00 28.37 C | ATOM 2643 CG ASP B 301 150.959 57.748 19.051 1.00100.69 C |
| ANISOU 2598 CD1 LEU B 295 4031 4334 2415 −287 −247 103 C | ANISOU 2643 CG ASP B 301 13425 13416 11415 67 2106 1640 C |
| ATOM 2599 CD2 LEU B 295 155.623 60.121 6.518 1.00 26.48 C | ATOM 2644 OD1 ASP B 301 150.426 58.860 18.823 1.00105.45 O |
| ANISOU 2599 CD2 LEU B 295 3555 4093 2415 −210 −183 −25 C | ANISOU 2644 OD1 ASP B 301 14044 14037 11986 113 2155 1387 O |
| ATOM 2600 C LEU B 295 152.606 59.403 9.755 1.00 34.10 C | ATOM 2645 OD2 ASP B 301 150.326 56.716 19.393 1.00104.46 O |
| ANISOU 2600 C LEU B 295 4905 5080 2973 −374 275 −83 C | ANISOU 2645 OD2 ASP B 301 13815 13847 12030 60 2384 1867 O |
| ATOM 2601 O LEU B 295 153.287 59.502 10.781 1.00 35.13 O | ATOM 2646 C ASP B 301 154.621 58.831 19.117 1.00 64.09 C |
| ANISOU 2601 O LEU B 295 5224 5211 2912 −413 199 −74 O | ANISOU 2646 C ASP B 301 9129 8928 6294 −28 1030 1587 C |
| ATOM 2602 N GLU B 296 151.532 60.154 9.530 1.00 32.69 N | ATOM 2647 O ASP B 301 155.050 58.318 20.146 1.00 69.18 O |
| ANISOU 2602 N GLU B 296 4636 4890 2894 −361 442 −172 N | ANISOU 2647 O ASP B 301 9969 9659 6659 −22 982 1824 O |
| ATOM 2603 CA GLU B 296 151.013 61.107 10.507 1.00 39.87 C | ATOM 2648 N ALA B 302 155.412 59.198 18.119 1.00 55.81 N |
| ANISOU 2603 CA GLU B 296 5665 5783 3700 −391 596 −274 C | ANISOU 2648 N ALA B 302 7912 7821 5474 −76 760 1470 N |
| ATOM 2604 CB GLU B 296 149.653 61.594 10.043 1.00 50.68 C | ATOM 2649 CA ALA B 302 156.836 58.878 18.176 1.00 54.16 C |
| ANISOU 2604 CB GLU B 296 6867 7122 5266 −363 796 −344 C | ANISOU 2649 CA ALA B 302 7676 7633 5269 −119 419 1642 C |
| ATOM 2605 CG GLU B 296 149.482 63.062 9.967 1.00 64.40 C | ATOM 2650 CB ALA B 302 157.418 58.732 16.793 1.00 44.24 C |
| ANISOU 2605 CG GLU B 296 8558 8833 7076 −327 845 −458 C | ANISOU 2650 CB ALA B 302 6119 6250 4442 −146 305 1585 C |
| ATOM 2606 CD GLU B 296 148.068 63.435 9.516 1.00 77.16 C | ATOM 2651 C ALA B 302 157.602 59.923 18.961 1.00 65.37 C |
| ANISOU 2606 CD GLU B 296 9984 10404 8929 −293 1034 −510 C | ANISOU 2651 C ALA B 302 9367 9180 6289 −166 110 1560 C |
| ATOM 2607 OE1 GLU B 296 147.348 62.538 8.994 1.00 75.78 O | ATOM 2652 O ALA B 302 157.466 61.126 18.685 1.00 65.07 O |

TABLE 8-continued

DMXAA-hSTING$^{S162A/Q266I}$ complex

| | |
|---|---|
| ANISOU 2607 OE1 GLU B 296 9676 10225 8890 −294 1069 −450 O | ANISOU 2652 O ALA B 302 9411 9136 6175 −191 49 1275 O |
| ATOM 2608 OE2 GLU B 296 147.687 64.622 9.701 1.00 84.25 O | ATOM 2653 N PRO B 303 158.426 59.465 19.928 1.00 71.85 N |
| ANISOU 2608 OE2 GLU B 296 10859 11257 9894 −267 1140 −611 O | ANISOU 2653 N PRO B 303 10331 10103 6865 −187 −111 1818 N |
| ATOM 2609 C GLU B 296 150.834 60.471 11.885 1.00 39.90 C | ATOM 2654 CA PRO B 303 159.165 60.356 20.834 1.00 73.88 C |
| ANISOU 2609 C GLU B 296 5919 5777 3464 −468 703 −246 C | ANISOU 2654 CA PRO B 303 10890 10493 6690 −263 −458 1762 C |
| ATOM 2610 O GLU B 296 151.298 60.992 12.900 1.00 39.99 O | ATOM 2655 CB PRO B 303 159.747 59.394 21.882 1.00 74.10 C |
| ANISOU 2610 O GLU B 296 5836 5466 4171 −467 −711 34 N | ANISOU 2655 CB PRO B 303 11033 10628 6492 −257 −610 2144 C |
| ATOM 2656 CG PRO B 303 159.909 58.078 21.162 1.00 71.42 C | ATOM 2701 CA CYS B 309 158.996 67.190 11.439 1.00 40.83 C |
| ANISOU 2656 CG PRO B 303 10323 10168 6645 −191 −482 2412 C | ANISOU 2701 CA CYS B 309 5608 5425 4479 −408 −546 80 C |
| ATOM 2657 CD PRO B 303 158.763 58.041 20.149 1.00 72.76 C | ATOM 2702 CB CYS B 309 158.925 65.678 11.579 1.00 38.15 C |
| ANISOU 2657 CD PRO B 303 10314 10195 7136 −146 −79 2192 C | ANISOU 2702 CB CYS B 309 5140 5149 4207 −369 −431 279 C |
| ATOM 2658 C PRO B 303 160.286 61.078 20.095 1.00 76.72 C | ATOM 2703 SG CYS B 309 158.884 64.918 9.998 1.00 65.78 S |
| ANISOU 2658 C PRO B 303 11072 10813 7265 −358 −831 1654 C | ANISOU 2703 SG CYS B 309 8384 8557 8052 −344 −302 328 S |
| ATOM 2659 O PRO B 303 160.534 62.271 20.312 1.00 78.51 O | ATOM 2704 C CYS B 309 157.629 67.719 10.988 1.00 45.94 C |
| ANISOU 2659 O PRO B 303 11493 11069 7270 −442 −1035 1420 O | ANISOU 2704 C CYS B 309 6289 6018 5150 −310 −335 −87 C |
| ATOM 2660 N GLU B 304 160.945 60.343 19.205 1.00 79.38 N | ATOM 2705 O CYS B 309 156.670 67.745 11.782 1.00 50.04 O |
| ANISOU 2660 N GLU B 304 11042 11062 8056 −343 −885 1824 N | ANISOU 2705 O CYS B 309 6935 6575 5503 −236 −175 −148 O |
| ATOM 2661 CA GLU B 304 162.111 60.830 18.470 1.00 80.85 C | ATOM 2706 N ARG B 310 157.522 68.120 9.717 1.00 38.07 N |
| ANISOU 2661 CA GLU B 304 11001 11204 8515 −420 −1194 1799 C | ANISOU 2706 N ARG B 310 5169 4931 4364 −300 −323 −139 N |
| ATOM 2662 CB GLU B 304 162.877 59.646 17.899 1.00 84.06 C | ATOM 2707 CA ARG B 310 156.211 68.485 9.170 1.00 36.65 C |
| ANISOU 2662 CB GLU B 304 11060 11531 9348 −362 −1203 2102 C | ANISOU 2707 CA ARG B 310 4963 4706 4257 −202 −158 −246 C |
| ATOM 2663 CG GLU B 304 161.995 58.747 17.073 1.00 86.41 C | ATOM 2708 CB ARG B 310 156.039 69.998 9.064 1.00 48.13 C |
| ANISOU 2663 CG GLU B 304 11206 11688 9937 −262 −790 2094 C | ANISOU 2708 CB ARG B 310 6549 6056 5681 −177 −208 −406 C |
| ATOM 2664 CD GLU B 304 162.050 57.317 17.550 1.00 92.56 C | ATOM 2709 CG ARG B 310 155.996 70.693 10.428 1.00 62.11 C |
| ANISOU 2664 CD GLU B 304 11925 12438 10805 −180 −683 2442 C | ANISOU 2709 CG ARG B 310 8577 7824 7196 −169 −209 −523 C |
| ATOM 2665 OE1 GLU B 304 161.539 57.024 18.653 1.00 96.31 O | ATOM 2710 CD ARG B 310 154.646 70.468 11.167 1.00 97.31 C |
| ANISOU 2665 OE1 GLU B 304 12375 12983 11234 −177 −954 2734 O | ANISOU 2710 CD ARG B 310 13090 12327 11556 −34 58 −569 C |
| ATOM 2666 OE2 GLU B 304 162.590 56.479 16.813 1.00 92.84 O | ATOM 2711 NE ARG B 310 154.800 70.505 12.627 1.00 97.30 N |
| ANISOU 2666 OE2 GLU B 304 11933 12373 10971 −123 −343 2439 O | ANISOU 2711 NE ARG B 310 13355 12383 11231 −46 84 −615 N |
| ATOM 2667 C GLU B 304 161.726 61.732 17.305 1.00 74.78 C | ATOM 2712 CZ ARG B 310 154.973 71.614 13.346 1.00 96.18 C |
| ANISOU 2667 C GLU B 304 10131 10322 7961 −436 −1070 1480 C | ANISOU 2712 CZ ARG B 310 13505 12160 10878 −56 37 −792 C |
| ATOM 2668 O GLU B 304 162.526 61.980 16.409 1.00 77.24 O | ATOM 2713 NH1 ARG B 310 155.120 71.529 14.667 1.00 92.91 N |
| ANISOU 2668 O GLU B 304 10204 10559 8585 −476 −1202 1469 O | ANISOU 2713 NH1 ARG B 310 13372 11814 10114 −79 50 −831 N |
| ATOM 2669 N SER B 305 160.494 62.205 17.295 1.00 69.17 N | ATOM 2714 NH2 ARG B 310 155.003 72.805 12.746 1.00 95.74 N |
| ANISOU 2669 N SER B 305 9586 9593 7101 −393 −798 1246 N | ANISOU 2714 NH2 ARG B 310 13487 11941 10947 −46 −24 −931 N |
| ATOM 2670 CA SER B 305 160.002 62.964 16.166 1.00 70.29 C | ATOM 2715 C ARG B 310 155.939 67.837 7.836 1.00 38.44 C |
| ANISOU 2670 CA SER B 305 9622 9624 7460 −386 −668 985 C | ANISOU 2715 C ARG B 310 4994 4905 4705 −196 −109 −190 C |
| ATOM 2671 CB SER B 305 159.486 62.008 15.111 1.00 77.40 C | ATOM 2716 O ARG B 310 156.730 67.954 6.895 1.00 36.60 O |
| ANISOU 2671 CB SER B 305 10258 10423 8729 −314 −403 1045 C | ANISOU 2716 O ARG B 310 4707 4620 4579 −248 −202 −158 O |
| ATOM 2672 OG SER B 305 160.463 61.015 14.850 1.00 85.81 O | ATOM 2717 N LEU B 311 154.804 67.144 7.765 1.00 39.68 N |
| ANISOU 2672 OG SER B 305 11114 11456 10035 −313 −499 1299 O | ANISOU 2717 N LEU B 311 5057 5092 4927 −140 46 −178 N |
| ATOM 2673 C SER B 305 158.893 63.860 16.637 1.00 68.21 C | ATOM 2718 CA LEU B 311 154.355 66.545 6.527 1.00 36.13 C |
| ANISOU 2673 C SER B 305 9626 9374 6915 −353 −494 736 C | ANISOU 2718 CA LEU B 311 4458 4611 4660 −152 68 −158 C |
| ATOM 2674 O SER B 305 157.799 63.874 16.082 1.00 64.85 O | ATOM 2719 CB LEU B 311 153.427 65.392 6.822 1.00 37.31 C |
| ANISOU 2674 O SER B 305 9130 8886 6623 −276 −206 620 O | ANISOU 2719 CB LEU B 311 4494 4798 4883 −144 217 −100 C |
| ATOM 2675 N GLN B 306 159.182 64.572 17.715 1.00 71.84 N | ATOM 2720 CG LEU B 311 154.105 64.293 7.617 1.00 42.09 C |
| ANISOU 2675 N GLN B 306 10401 9912 6982 −410 −674 664 N | ANISOU 2720 CG LEU B 311 5115 5440 5437 −184 266 29 C |
| ATOM 2676 CA GLN B 306 158.214 65.449 18.341 1.00 77.82 C | ATOM 2721 CD1 LEU B 311 153.166 63.095 7.677 1.00 44.63 C |
| ANISOU 2676 CA GLN B 306 11476 10668 7425 −364 −485 424 C | ANISOU 2721 CD1 LEU B 311 5311 5758 5890 −197 422 96 C |
| ATOM 2677 CB GLN B 306 158.117 65.144 19.835 1.00 86.72 C | ATOM 2722 CD2 LEU B 311 155.469 63.915 6.998 1.00 40.38 C |
| ANISOU 2677 CB GLN B 306 12960 11927 8062 −360 −476 521 C | ANISOU 2722 CD2 LEU B 311 4894 5179 5271 −243 158 95 C |
| ATOM 2678 CG GLN B 306 157.449 63.825 20.146 1.00 92.23 C | ATOM 2723 C LEU B 311 153.604 67.556 5.699 1.00 38.65 C |
| ANISOU 2678 CG GLN B 306 13578 12682 8785 −262 −177 774 C | ANISOU 2723 C LEU B 311 4758 4876 5050 −98 31 −250 C |
| ATOM 2679 CD GLN B 306 155.932 63.905 20.013 1.00 94.45 C | ATOM 2724 O LEU B 311 152.619 68.101 6.156 1.00 37.25 O |
| ANISOU 2679 CD GLN B 306 13855 12908 9125 −135 300 647 C | ANISOU 2724 O LEU B 311 4574 4702 4878 −12 112 −304 O |
| ATOM 2680 OE1 GLN B 306 155.318 64.885 20.440 1.00 97.56 O | ATOM 2725 N ILE B 312 154.066 67.799 4.475 1.00 33.52 N |
| ANISOU 2680 OE1 GLN B 306 14507 13281 9279 −90 448 410 O | ANISOU 2725 N ILE B 312 4104 4172 4460 −137 −73 −249 N |
| ATOM 2681 NE2 GLN B 306 155.325 62.884 19.410 1.00 90.99 N | ATOM 2726 CA ILE B 312 153.330 68.667 3.569 1.00 26.20 C |
| ANISOU 2681 NE2 GLN B 306 13112 12427 9033 −79 542 803 N | ANISOU 2726 CA ILE B 312 3160 3197 3599 −85 −134 −295 C |
| ATOM 2682 C GLN B 306 158.653 66.889 18.123 1.00 76.96 C | ATOM 2727 CB ILE B 312 154.233 69.735 3.030 1.00 31.21 C |
| ANISOU 2682 C GLN B 306 11496 10476 7272 −451 −703 159 C | ANISOU 2727 CB ILE B 312 3908 3752 4200 −101 −234 −303 C |
| ATOM 2683 O GLN B 306 159.639 67.339 18.709 1.00 75.44 O | ATOM 2728 CG1 ILE B 312 155.068 70.297 4.160 1.00 33.66 C |
| ANISOU 2683 O GLN B 306 11467 10320 6875 −583 −1057 152 O | ANISOU 2728 CG1 ILE B 312 4325 4044 4419 −121 −244 −331 C |
| ATOM 2684 N ASN B 307 157.923 67.598 17.263 1.00 74.46 N | ATOM 2729 CD1 ILE B 312 155.904 71.457 3.709 1.00 47.36 C |
| ANISOU 2684 N ASN B 307 11091 10035 7167 −385 −512 −42 N | ANISOU 2729 CD1 ILE B 312 6156 5672 6166 −156 −344 −339 C |
| ATOM 2685 CA ASN B 307 158.190 69.008 16.965 1.00 72.89 C | ATOM 2730 CG2 ILE B 312 153.418 70.824 2.359 1.00 32.87 C |
| ANISOU 2685 CA ASN B 307 11011 9711 6973 −448 −660 −293 C | ANISOU 2730 CG2 ILE B 312 4123 3897 4470 −17 −291 −329 C |
| ATOM 2686 CB ASN B 307 158.341 69.877 18.227 1.00 80.72 C | ATOM 2731 C ILE B 312 152.752 67.849 2.432 1.00 28.24 C |
| ANISOU 2686 CB ASN B 307 12463 10707 7500 −514 −783 −477 C | ANISOU 2731 C ILE B 312 3319 3464 3945 −126 −168 −272 C |
| ATOM 2687 CG ASN B 307 157.015 70.261 18.827 1.00 90.27 C | ATOM 2732 O ILE B 312 153.456 67.463 1.494 1.00 32.26 O |
| ANISOU 2687 CG ASN B 307 13942 11882 8474 −359 −390 −656 C | ANISOU 2732 O ILE B 312 3880 3945 4432 −194 −213 −251 O |
| ATOM 2688 OD1 ASN B 307 155.975 70.132 18.173 1.00 90.81 O | ATOM 2733 N ALA B 313 151.477 67.527 2.567 1.00 27.73 N |
| ANISOU 2688 OD1 ASN B 307 13808 11898 8797 −210 −58 −666 O | ANISOU 2733 N ALA B 313 3178 3117 3435 3984 −93 −133 −276 N |
| ATOM 2689 ND2 ASN B 307 157.036 70.746 20.078 1.00 94.65 N | ATOM 2734 CA ALA B 313 150.755 66.701 1.592 1.00 35.88 C |
| ANISOU 2689 ND2 ASN B 307 14960 12460 8542 −393 −421 −797 N | ANISOU 2734 CA ALA B 313 4045 4475 5115 −162 −206 −267 C |
| ATOM 2690 C ASN B 307 159.404 69.209 16.093 1.00 62.08 C | ATOM 2735 CB ALA B 313 149.931 65.616 2.283 1.00 25.02 C |
| ANISOU 2690 C ASN B 307 9402 8289 5896 −578 −973 −227 C | ANISOU 2735 CB ALA B 313 2509 3136 3861 −195 −90 −240 C |
| ATOM 2691 O ASN B 307 159.990 70.297 16.080 1.00 66.11 O | ATOM 2736 C ALA B 313 149.856 67.550 0.714 1.00 36.74 C |

TABLE 8-continued

DMXAA-hSTING$^{S162A/Q266I}$ complex

| | |
|---|---|
| ANISOU 2691 O ASN B 307 10031 8707 6381 −689 −1195 −380 O | ANISOU 2736 C ALA B 313 4091 4574 5294 −111 −357 −265 C |
| ATOM 2692 N ASN B 308 159.807 68.173 15.374 1.00 44.89 N | ATOM 2737 O ALA B 313 149.158 68.421 1.194 1.00 41.56 O |
| ANISOU 2692 N ASN B 308 6897 6149 4009 −567 −976 O N | ANISOU 2737 O ALA B 313 4622 5181 5987 6 −328 −256 O |
| ATOM 2693 CA ASN B 308 160.903 68.398 14.462 1.00 47.01 C | ATOM 2738 N TYR B 314 149.857 67.292 −0.582 1.00 38.85 N |
| ANISOU 2693 CA ASN B 308 6927 6352 4582 −667 −1196 65 C | ANISOU 2738 N TYR B 314 4409 4829 5525 −189 −515 −266 N |
| ATOM 2694 CB ASN B 308 162.194 67.806 15.006 1.00 48.95 C | ATOM 2739 CA TYR B 314 149.088 68.142 −1.481 1.00 37.70 C |
| ANISOU 2694 CB ASN B 308 7084 6691 4823 −776 −1507 298 C | ANISOU 2739 CA TYR B 314 4226 4681 5418 −141 −706 −230 C |
| ATOM 2695 CG ASN B 308 162.049 66.372 15.350 1.00 53.67 C | ATOM 2740 CB TYR B 314 149.881 69.386 −1.813 1.00 39.04 C |
| ANISOU 2695 CG ASN B 308 7584 7392 5416 −689 −1390 544 C | ANISOU 2740 CB TYR B 314 4569 4792 5474 −67 −731 −206 C |
| ATOM 2696 OD1 ASN B 308 160.992 65.774 15.085 1.00 63.72 O | ATOM 2741 CG TYR B 314 151.289 69.093 −2.302 1.00 39.16 C |
| ANISOU 2696 OD1 ASN B 308 8831 8656 6722 −564 −1066 533 O | ANISOU 2741 CG TYR B 314 4795 4773 5312 −151 −682 −221 C |
| ATOM 2697 ND2 ASN B 308 163.097 65.781 15.938 1.00 52.30 N | ATOM 2742 CD1 TYR B 314 152.357 68.958 −1.402 1.00 29.43 C |
| ANISOU 2697 ND2 ASN B 308 7335 7307 5231 −756 −1660 787 N | ANISOU 2742 CD1 TYR B 314 3610 3521 4051 −161 −523 −239 C |
| ATOM 2698 C ASN B 308 160.633 67.911 13.053 1.00 44.16 C | ATOM 2743 CE1 TYR B 314 153.661 68.705 −1.866 1.00 28.38 C |
| ANISOU 2698 C ASN B 308 6266 5923 4590 −588 −997 122 C | ANISOU 2743 CE1 TYR B 314 3614 3843 3349 3820 −225 −463 −222 C |
| ATOM 2699 O ASN B 308 161.558 67.706 12.281 1.00 49.48 O | ATOM 2744 CZ TYR B 314 153.884 68.570 −3.244 1.00 39.66 C |
| ANISOU 2699 O ASN B 308 6713 6560 5527 −641 −1103 242 O | ANISOU 2744 CZ TYR B 314 5179 4753 5138 −274 −516 −205 C |
| ATOM 2700 N CYS B 309 159.367 67.763 12.715 1.00 40.72 N | ATOM 2745 OH TYR B 314 155.167 68.344 −3.737 1.00 41.74 O |
| ANISOU 2745 OH TYR B 314 5568 4965 5324 −318 −398 −176 O | ANISOU 2790 CB ASP B 320 17086 16418 15230 −164 −3890 1111 C |
| ATOM 2746 CE2 TYR B 314 152.828 68.693 −4.151 1.00 41.72 C | ATOM 2791 CG ASP B 320 145.248 75.182 −14.415 1.00 127.99 C |
| ANISOU 2746 CE2 TYR B 314 5453 5040 5361 −276 −688 −205 C | ANISOU 2791 CG ASP B 320 16893 16253 15483 87 −3720 1304 C |
| ATOM 2747 CD2 TYR B 314 151.547 68.950 −3.672 1.00 43.14 C | ATOM 2792 OD2 ASP B 320 144.896 75.327 −13.223 1.00 127.99 O |
| ANISOU 2747 CD2 TYR B 314 5450 5263 5677 −219 −792 −204 C | ANISOU 2792 OD2 ASP B 320 16525 16200 15907 196 −3545 1252 O |
| ATOM 2748 C TYR B 314 148.744 67.449 −2.765 1.00 38.73 C | ATOM 2793 OD1 ASP B 320 145.718 76.114 −15.110 1.00 127.48 O |
| ANISOU 2748 C TYR B 314 4390 4826 5501 −265 −902 −239 C | ANISOU 2793 OD1 ASP B 320 17094 16125 15219 172 −3724 1497 O |
| ATOM 2749 O TYR B 314 149.355 66.460 −3.151 1.00 42.85 O | ATOM 2794 C ASP B 320 147.383 73.272 −14.117 1.00 122.69 C |
| ANISOU 2749 O TYR B 314 5037 5327 5918 −383 −867 −297 O | ANISOU 2794 C ASP B 320 16689 15560 14370 −206 −3091 807 C |
| ATOM 2750 N GLN B 315 147.754 67.992 −3.443 1.00 46.91 N | ATOM 2795 O ASP B 320 147.484 72.360 −13.297 1.00 123.82 O |
| ANISOU 2750 N GLN B 315 5324 5886 6612 −235 −1117 −180 N | ANISOU 2795 O ASP B 320 16674 15706 14665 −280 −2915 603 O |
| ATOM 2751 CA GLN B 315 147.364 67.467 −4.721 1.00 49.23 C | ATOM 2796 N SER B 321 148.074 74.396 −14.000 1.00 117.23 N |
| ANISOU 2751 CA GLN B 315 5686 6202 6819 −366 −1369 −190 C | ANISOU 2796 N SER B 321 16075 14756 13709 −63 −2885 948 N |
| ATOM 2752 CB GLN B 315 145.935 67.007 −4.643 1.00 56.69 C | ATOM 2797 CA SER B 321 149.110 74.492 −12.996 1.00 109.59 C |
| ANISOU 2752 CB GLN B 315 6327 7196 8016 −416 −1527 −156 C | ANISOU 2797 CA SER B 321 15058 13682 12898 −25 −2462 837 C |
| ATOM 2753 CG GLN B 315 145.711 65.691 −5.330 1.00 71.15 C | ATOM 2798 CB SER B 321 150.467 74.386 −13.673 1.00 110.55 C |
| ANISOU 2753 CG GLN B 315 8210 9023 9800 −636 −1671 −246 C | ANISOU 2798 CB SER B 321 15564 13755 12686 −98 −2206 824 C |
| ATOM 2754 CD GLN B 315 144.427 65.031 −4.858 1.00 82.29 C | ATOM 2799 OG SER B 321 150.414 73.420 −14.705 1.00 113.85 O |
| ANISOU 2754 CD GLN B 315 9261 10462 11543 −713 −1740 −215 C | ANISOU 2799 OG SER B 321 16265 14266 12728 −245 −2332 742 O |
| ATOM 2755 OE1 GLN B 315 143.801 65.489 −3.890 1.00 85.10 O | ATOM 2800 C SER B 321 149.005 75.769 −12.186 1.00 106.35 C |
| ANISOU 2755 OE1 GLN B 315 9332 10845 12157 −580 −1603 −124 O | ANISOU 2800 C SER B 321 14437 13147 12824 164 −2369 962 C |
| ATOM 2756 NE2 GLN B 315 144.025 63.954 −5.535 1.00 84.05 N | ATOM 2801 O SER B 321 149.957 76.547 −12.100 1.00 107.41 O |
| ANISOU 2756 NE2 GLN B 315 9501 10663 11769 −934 −1936 −293 N | ANISOU 2801 O SER B 321 14709 13153 12948 212 −2143 1025 O |
| ATOM 2757 C GLN B 315 147.509 68.555 −5.759 1.00 51.29 C | ATOM 2802 N SER B 322 147.836 75.982 −11.593 1.00 100.39 N |
| ANISOU 2757 C GLN B 315 6111 6454 6924 −304 −1552 −109 C | ANISOU 2802 N SER B 322 13343 12411 12388 267 −2532 997 N |
| ATOM 2758 O GLN B 315 146.927 69.625 −5.628 1.00 54.45 O | ATOM 2803 CA SER B 322 147.669 77.044 −10.611 1.00 91.19 C |
| ANISOU 2758 O GLN B 315 6380 6852 7456 −163 −1624 −3 O | ANISOU 2803 CA SER B 322 11970 11104 11574 453 −2385 1051 C |
| ATOM 2759 N GLU B 316 148.306 68.292 −6.783 1.00 60.87 N | ATOM 2804 CB SER B 322 146.218 77.476 −10.555 1.00 91.91 C |
| ANISOU 2759 N GLU B 316 7622 7646 7858 −395 −1595 −147 N | ANISOU 2804 CB SER B 322 11748 11214 11959 601 −2643 1198 C |
| ATOM 2760 CA GLU B 316 148.424 69.240 −7.878 1.00 72.31 C | ATOM 2805 OG SER B 322 145.433 76.515 −11.224 1.00 93.78 O |
| ANISOU 2760 CA GLU B 316 9264 9090 9119 −352 −1768 −46 C | ANISOU 2805 OG SER B 322 11912 11628 12093 474 −2959 1199 O |
| ATOM 2761 CB GLU B 316 149.667 68.980 −8.739 1.00 77.10 C | ATOM 2806 C SER B 322 148.109 76.490 −9.261 1.00 79.29 C |
| ANISOU 2761 CB GLU B 316 10238 9652 9403 −425 −1655 −91 C | ANISOU 2806 C SER B 322 10326 9580 10221 420 −2083 820 C |
| ATOM 2762 CG GLU B 316 150.990 69.377 −8.090 1.00 80.83 C | ATOM 2807 O SER B 322 147.348 76.472 −8.280 1.00 80.75 O |
| ANISOU 2762 CG GLU B 316 10777 10052 9882 −356 −1340 −87 C | ANISOU 2807 O SER B 322 10225 9763 10696 509 −2035 763 O |
| ATOM 2763 CD GLU B 316 152.032 69.872 −9.112 1.00 87.76 C | ATOM 2808 N PHE B 323 149.336 75.992 −9.232 1.00 61.95 N |
| ANISOU 2763 CD GLU B 316 11967 10877 10501 −358 −1261 −21 C | ANISOU 2808 N PHE B 323 8336 7377 7824 294 −1872 703 N |
| ATOM 2764 OE1 GLU B 316 151.646 70.574 −10.089 1.00 93.02 O | ATOM 2809 CA PHE B 323 149.869 75.480 −8.011 1.00 53.48 C |
| ANISOU 2764 OE1 GLU B 316 12772 11557 11015 −336 −1455 87 O | ANISOU 2809 CA PHE B 323 7164 6294 6864 256 −1619 519 C |
| ATOM 2765 OE2 GLU B 316 153.232 69.548 −8.936 1.00 83.38 O | ATOM 2810 CB PHE B 323 150.014 73.980 −8.081 1.00 48.51 C |
| ANISOU 2765 OE2 GLU B 316 11506 10267 9908 −379 −999 −55 O | ANISOU 2810 CB PHE B 323 6545 5789 6097 99 −1599 375 C |
| ATOM 2766 C GLU B 316 147.168 69.138 −8.715 1.00 72.08 C | ATOM 2811 CG PHE B 323 150.498 73.381 −6.809 1.00 43.27 C |
| ANISOU 2766 C GLU B 316 9146 9133 9108 −413 −2139 12 C | ANISOU 2811 CG PHE B 323 5768 5124 5550 68 −1362 221 C |
| ATOM 2767 O GLU B 316 146.686 68.030 −8.956 1.00 69.46 O | ATOM 2812 CD1 PHE B 323 149.693 73.412 −5.662 1.00 39.66 C |
| ANISOU 2767 O GLU B 316 8783 8833 8777 −573 −2260 −85 O | ANISOU 2812 CD1 PHE B 323 5056 4676 5336 151 −1319 171 C |
| ATOM 2768 N PRO B 317 146.610 70.294 −9.124 1.00 78.33 N | ATOM 2813 CE1 PHE B 323 150.152 72.865 −4.437 1.00 38.79 C |
| ANISOU 2768 N PRO B 317 9879 9939 9946 −290 −2338 182 N | ANISOU 2813 CE1 PHE B 323 4878 4572 5287 124 −1105 46 C |
| ATOM 2769 CA PRO B 317 145.564 70.191 −10.141 1.00 91.70 C | ATOM 2814 CZ PHE B 323 151.422 72.265 −4.379 1.00 38.91 C |
| ANISOU 2769 CA PRO B 317 11536 11709 11598 −368 −2756 265 C | ANISOU 2814 CZ PHE B 323 5039 4583 5160 14 −965 −13 C |
| ATOM 2770 CB PRO B 317 145.228 71.651 −10.456 1.00 92.44 C | ATOM 2815 CE2 PHE B 323 152.239 72.235 −5.553 1.00 42.10 C |
| ANISOU 2770 CB PRO B 317 11585 11783 11756 −178 −2896 492 C | ANISOU 2815 CE2 PHE B 323 5659 4967 5370 −59 −986 40 C |
| ATOM 2771 CG PRO B 317 145.728 72.429 −9.254 1.00 87.59 C | ATOM 2816 CD2 PHE B 323 151.754 72.798 −6.747 1.00 39.61 C |
| ANISOU 2771 CG PRO B 317 10859 11068 11355 2 −2538 491 C | ANISOU 2816 CD2 PHE B 323 5449 4647 4954 −32 −1171 149 C |
| ATOM 2772 CD PRO B 317 146.943 71.691 −8.798 1.00 78.80 C | ATOM 2817 C PHE B 323 151.210 76.118 −7.755 1.00 51.72 C |
| ANISOU 2772 CD PRO B 317 9938 9922 10081 −95 −2222 309 C | ANISOU 2817 C PHE B 323 7111 5941 6602 242 −1393 516 C |
| ATOM 2773 C PRO B 317 146.212 69.503 −11.335 1.00 102.17 C | ATOM 2818 O PHE B 323 152.061 76.241 −8.648 1.00 53.18 O |
| ANISOU 2773 C PRO B 317 13284 13046 12491 −543 −2845 168 C | ANISOU 2818 O PHE B 323 7525 6096 6584 176 −1354 596 O |
| ATOM 2774 O PRO B 317 147.330 69.869 −11.706 1.00 102.61 O | ATOM 2819 N SER B 324 151.393 76.538 −6.516 1.00 44.10 N |
| ANISOU 2774 O PRO B 317 13653 13046 12288 −508 −2648 170 O | ANISOU 2819 N SER B 324 6033 4890 5832 298 −1239 428 N |
| ATOM 2775 N ALA B 318 145.536 68.506 −11.896 1.00 111.55 N | ATOM 2820 CA SER B 324 152.677 77.023 −6.090 1.00 38.30 C |

TABLE 8-continued

DMXAA-hSTING$^{S162A/Q266I}$ complex

| | |
|---|---|
| ANISOU 2775 N ALA B 318 14484 14287 13614 −737 −3115 76 N | ANISOU 2820 CA SER B 324 5418 4038 5098 245 −1056 400 C |
| ATOM 2776 CA ALA B 318 146.181 67.524 −12.775 1.00118.14 C | ATOM 2821 CB SER B 324 152.576 78.457 −5.610 1.00 36.64 C |
| ANISOU 2776 CA ALA B 318 15734 15094 14060 −925 −3106 −102 C | ANISOU 2821 CB SER B 324 5216 3631 5075 362 −1031 445 C |
| ATOM 2777 CB ALA B 318 145.151 66.551 −13.327 1.00120.34 C | ATOM 2822 OG SER B 324 153.856 78.910 −5.234 1.00 44.39 O |
| ANISOU 2777 CB ALA B 318 15971 15419 14332 −1153 −3490 −198 C | ANISOU 2822 OG SER B 324 6307 4489 6069 270 −893 416 O |
| ATOM 2778 C ALA B 318 147.026 68.100 −13.911 1.00123.29 C | ATOM 2823 C SER B 324 153.148 76.114 −4.969 1.00 36.87 C |
| ANISOU 2778 C ALA B 318 16852 15734 14257 −898 −3091 −46 C | ANISOU 2823 C SER B 324 5144 3926 4940 166 −915 229 C |
| ATOM 2779 O ALA B 318 148.210 67.760 −14.055 1.00122.79 O | ATOM 2824 O SER B 324 152.519 76.040 −3.916 1.00 39.61 O |
| ANISOU 2779 O ALA B 318 17087 15594 13973 −909 −2755 −151 O | ANISOU 2824 O SER B 324 5349 4288 5413 229 −884 132 O |
| ATOM 2780 N ASP B 319 146.415 68.969 −14.711 1.00126.19 N | ATOM 2825 N LEU B 325 154.256 75.414 −5.201 1.00 39.54 N |
| ANISOU 2780 N ASP B 319 17268 16173 14505 −854 −3442 147 N | ANISOU 2825 N LEU B 325 5565 4301 5159 40 −813 213 N |
| ATOM 2781 CA ASP B 319 147.056 69.453 −15.925 1.00127.28 C | ATOM 2826 CA LEU B 325 154.831 74.549 −4.182 1.00 34.07 C |
| ANISOU 2781 CA ASP B 319 17877 16312 14173 −848 −3463 226 C | ANISOU 2826 CA LEU B 325 4786 3664 4494 −31 −694 94 C |
| ATOM 2782 CB ASP B 319 146.210 69.096 −17.139 1.00132.16 C | ATOM 2827 CB LEU B 325 156.017 73.783 −4.754 1.00 35.34 C |
| ANISOU 2782 CB ASP B 319 18610 17014 14589 −965 −3761 217 C | ANISOU 2827 CB LEU B 325 5028 3850 4552 −142 −579 125 C |
| ATOM 2783 CG ASP B 319 147.051 68.702 −18.328 1.00134.08 C | ATOM 2828 CG LEU B 325 156.580 72.684 −3.860 1.00 38.32 C |
| ANISOU 2783 CG ASP B 319 19405 17230 14308 −1050 −3617 114 C | ANISOU 2828 CG LEU B 325 5301 4293 4965 −205 −474 42 C |
| ATOM 2784 OD2 ASP B 319 146.648 69.024 −19.467 1.00139.53 O | ATOM 2829 CD1 LEU B 325 155.435 71.759 −3.388 1.00 37.85 C |
| ANISOU 2784 OD2 ASP B 319 20286 17990 14737 −1069 −3839 211 O | ANISOU 2829 CD1 LEU B 325 5130 4339 4911 −177 −524 −51 C |
| ATOM 2785 OD1 ASP B 319 148.117 68.078 −18.116 1.00130.25 O | ATOM 2830 CD2 LEU B 325 157.607 71.885 −4.660 1.00 37.28 C |
| ANISOU 2785 OD1 ASP B 319 19157 16649 13682 −1088 −3264 −56 O | ANISOU 2830 CD2 LEU B 325 5243 4165 4756 −278 −335 91 C |
| ATOM 2786 C ASP B 319 147.318 70.949 −15.894 1.00126.86 C | ATOM 2831 C LEU B 325 155.277 75.372 −2.980 1.00 34.56 C |
| ANISOU 2786 C ASP B 319 17793 16235 14174 −633 −3408 492 C | ANISOU 2831 C LEU B 325 4825 3624 4682 −18 −640 37 C |
| ATOM 2787 O ASP B 319 148.441 71.394 −16.147 1.00126.91 O | ATOM 2832 O LEU B 325 155.180 74.936 −1.833 1.00 35.76 O |
| ANISOU 2787 O ASP B 319 18077 16168 13975 −570 −3098 532 O | ANISOU 2832 O LEU B 325 4895 3826 4868 −21 −596 −69 O |
| ATOM 2788 N ASP B 320 146.277 71.723 −15.601 1.00127.03 N | ATOM 2833 N SER B 326 155.790 76.573 −3.264 1.00 32.96 N |
| ANISOU 2788 N ASP B 320 17460 16027 14508 −519 −3687 685 N | ANISOU 2833 N SER B 326 4724 3266 4534 −16 −645 111 N |
| ATOM 2789 CA ASP B 320 146.450 73.142 −15.323 1.00126.24 C | ATOM 2834 CA SER B 326 156.291 77.462 −2.229 1.00 41.01 C |
| ANISOU 2789 CA ASP B 320 17259 16125 14582 −293 −3583 919 C | ANISOU 2834 CA SER B 326 5769 4147 5665 −36 −621 41 C |
| ATOM 2790 CB ASP B 320 145.102 73.804 −15.040 1.00128.26 C | ATOM 2835 CB SER B 326 157.049 78.643 −2.834 1.00 46.45 C |
| ANISOU 2835 CB SER B 326 6574 4645 6429 −79 −620 155 C | ANISOU 2880 NH2 ARG B 331 11322 11826 13432 823 244 −298 N |
| ATOM 2836 OG SER B 326 156.592 78.877 −4.139 1.00 53.45 O | ATOM 2881 C ARG B 331 151.607 77.041 5.916 1.00 56.57 C |
| ANISOU 2836 OG SER B 326 7526 5524 7258 −13 −654 307 O | ANISOU 2881 C ARG B 331 7732 6246 7517 523 41 −827 C |
| ATOM 2837 C SER B 326 155.187 77.993 −1.332 1.00 45.22 C | ATOM 2882 O ARG B 331 151.097 77.338 6.999 1.00 58.75 O |
| ANISOU 2837 C SER B 326 6277 4632 6274 97 −635 −68 C | ANISOU 2882 O ARG B 331 8124 6474 7723 621 222 −951 O |
| ATOM 2838 O SER B 326 155.412 78.223 −0.145 1.00 50.42 O | ATOM 2883 N HIS B 332 152.408 75.996 5.800 1.00 51.38 N |
| ANISOU 2838 O SER B 326 6963 5242 6953 76 −598 −198 O | ANISOU 2883 N HIS B 332 7024 5743 6754 364 −60 −763 N |
| ATOM 2839 N GLN B 327 154.013 78.240 −1.907 1.00 45.11 N | ATOM 2884 CA HIS B 332 152.699 75.178 6.963 1.00 44.61 C |
| ANISOU 2839 N GLN B 327 6218 4618 6302 236 −687 −7 N | ANISOU 2884 CA HIS B 332 6235 5010 5706 300 6 −812 C |
| ATOM 2840 CA GLN B 327 152.844 78.649 −1.132 1.00 40.63 C | ATOM 2885 CB HIS B 332 153.231 73.819 6.548 1.00 37.46 C |
| ANISOU 2840 CA GLN B 327 5578 4008 5850 396 −654 −86 C | ANISOU 2885 CB HIS B 332 5179 4271 4783 180 −72 −684 C |
| ATOM 2841 CB GLN B 327 151.690 78.985 −2.055 1.00 41.27 C | ATOM 2886 CG HIS B 332 152.181 72.856 6.152 1.00 45.89 C |
| ANISOU 2841 CB GLN B 327 5573 4084 6026 542 −753 53 C | ANISOU 2886 CG HIS B 332 6027 5446 5962 244 24 −601 C |
| ATOM 2842 CG GLN B 327 151.829 80.336 −2.738 1.00 45.21 C | ATOM 2887 ND1 HIS B 332 151.504 72.920 4.938 1.00 47.90 N |
| ANISOU 2842 CG GLN B 327 6195 4368 6615 612 −803 183 C | ANISOU 2887 ND1 HIS B 332 6120 5683 6394 292 −31 −531 N |
| ATOM 2843 CD GLN B 327 151.718 81.506 −1.746 1.00 52.86 C | ATOM 2888 CE1 HIS B 332 150.650 71.927 4.855 1.00 43.87 C |
| ANISOU 2843 CD GLN B 327 7240 5095 7750 718 −687 77 C | ANISOU 2888 CE1 HIS B 332 5424 5276 5968 306 36 −473 C |
| ATOM 2844 OE1 GLN B 327 151.812 81.812 −1.268 1.00 60.46 O | ATOM 2889 NE2 HIS B 332 150.724 71.216 5.969 1.00 47.12 N |
| ANISOU 2844 OE1 GLN B 327 8100 6009 8864 902 −628 46 O | ANISOU 2889 NE2 HIS B 332 5868 5763 6271 284 169 −488 N |
| ATOM 2845 NE2 GLN B 327 152.868 82.126 −1.386 1.00 47.83 N | ATOM 2890 CD2 HIS B 332 151.665 71.777 6.793 1.00 49.15 C |
| ANISOU 2845 NE2 GLN B 327 6780 4296 7096 595 −641 9 N | ANISOU 2890 CD2 HIS B 332 6351 5980 6343 251 154 −565 C |
| ATOM 2846 C GLN B 327 152.419 77.524 −0.202 1.00 40.23 C | ATOM 2891 C HIS B 332 153.724 75.838 7.858 1.00 53.06 C |
| ANISOU 2846 C GLN B 327 5406 4127 5752 387 −579 −200 C | ANISOU 2891 C HIS B 332 7570 5994 6597 195 −76 −936 C |
| ATOM 2847 O GLN B 327 152.113 77.749 0.960 1.00 41.33 O | ATOM 2892 O HIS B 332 153.569 75.863 9.079 1.00 57.74 O |
| ANISOU 2847 O GLN B 327 5558 4226 5921 449 −471 −324 O | ANISOU 2892 O HIS B 332 8339 6600 6998 217 24 −1049 O |
| ATOM 2848 N GLU B 328 152.418 76.300 −0.720 1.00 40.01 N | ATOM 2893 N LEU B 333 154.775 76.365 7.231 1.00 50.28 N |
| ANISOU 2848 N GLU B 328 5290 4273 5640 306 −620 −159 N | ANISOU 2893 N LEU B 333 7251 5551 6301 69 −262 −907 N |
| ATOM 2849 CA GLU B 328 152.123 75.136 0.126 1.00 41.48 C | ATOM 2894 CA LEU B 333 155.878 76.985 7.927 1.00 56.12 C |
| ANISOU 2849 CA GLU B 328 5365 4603 5792 276 −539 −241 C | ANISOU 2894 CA LEU B 333 8198 6200 6925 −81 −408 −1002 C |
| ATOM 2850 CB GLU B 328 152.059 73.822 −0.676 1.00 33.20 C | ATOM 2895 CB LEU B 333 156.791 77.614 6.901 1.00 62.16 C |
| ANISOU 2850 CB GLU B 328 4236 3699 4679 183 −597 −191 C | ANISOU 2895 CB LEU B 333 8914 6841 7862 −192 −563 −921 C |
| ATOM 2851 CG GLU B 328 150.607 73.393 −0.963 1.00 49.41 C | ATOM 2896 CG LEU B 333 158.168 77.023 6.708 1.00 63.00 C |
| ANISOU 2851 CG GLU B 328 6104 5831 6841 253 −659 −159 C | ANISOU 2896 CG LEU B 333 8918 7033 7985 −385 −733 −799 C |
| ATOM 2852 CD GLU B 328 149.628 73.552 0.246 1.00 66.48 C | ATOM 2897 CD2 LEU B 333 159.156 77.699 7.618 1.00 54.08 C |
| ANISOU 2852 CD GLU B 328 8121 7993 9146 377 −525 −214 C | ANISOU 2897 CD2 LEU B 333 7963 5806 6779 −558 −916 −901 C |
| ATOM 2853 OE1 GLU B 328 149.577 72.621 1.093 1.00 59.28 O | ATOM 2898 CD1 LEU B 333 158.526 77.267 5.279 1.00 66.92 C |
| ANISOU 2853 OE1 GLU B 328 7147 7165 8214 331 −404 −268 O | ANISOU 2898 CD1 LEU B 333 9282 7461 8684 −404 −746 −655 C |
| ATOM 2854 OE2 GLU B 328 148.913 74.600 0.329 1.00 72.15 O | ATOM 2899 C LEU B 333 155.396 78.092 8.848 1.00 66.65 C |
| ANISOU 2854 OE2 GLU B 328 8795 8615 10003 530 −515 −188 O | ANISOU 2899 C LEU B 333 9808 7356 8159 −5 −316 −1215 C |
| ATOM 2855 C GLU B 328 153.067 74.986 1.327 1.00 43.83 C | ATOM 2900 O LEU B 333 156.017 78.405 9.863 1.00 72.53 O |
| ANISOU 2855 C GLU B 328 5752 4897 6005 197 −449 −343 C | ANISOU 2900 O LEU B 333 10792 8060 8707 −118 −408 −1349 O |
| ATOM 2856 O GLU B 328 152.653 74.622 2.439 1.00 50.63 O | ATOM 2901 N ARG B 334 154.282 78.703 8.481 1.00 64.64 N |
| ANISOU 2856 O GLU B 328 6581 5811 6845 232 −346 −424 O | ANISOU 2901 N ARG B 334 9530 6983 8047 190 −141 −1246 N |
| ATOM 2857 N VAL B 329 154.348 75.227 1.084 1.00 32.45 N | ATOM 2902 CA ARG B 334 153.808 79.844 9.211 1.00 68.23 C |
| ANISOU 2857 N VAL B 329 4415 3401 4514 81 −491 −317 N | ANISOU 2902 CA ARG B 334 10249 7217 8460 294 −9 −1448 C |
| ATOM 2858 CA VAL B 329 155.347 75.116 2.134 1.00 34.31 C | ATOM 2903 CB ARG B 334 152.976 80.731 8.301 1.00 62.76 C |
| ANISOU 2858 CA VAL B 329 4716 3637 4684 −19 −474 −383 C | ANISOU 2903 CB ARG B 334 9462 6334 8051 478 91 −1402 C |
| ATOM 2859 CB VAL B 329 156.742 75.013 1.524 1.00 35.27 C | ATOM 2904 CG ARG B 334 153.828 81.762 7.609 1.00 62.47 C |

TABLE 8-continued

DMXAA-hSTING$^{S162A/Q266I}$ complex

```
ANISOU 2859 CB  VAL B 329 4852 3736 4812 -158 -524 -292 C
ATOM   2860 CG1 VAL B 329 157.777 74.992 2.580 1.00 31.60 C
ANISOU 2860 CG1 VAL B 329 4419 3269 4319 -270 -564 -332 C
ATOM   2861 CG2 VAL B 329 156.824 73.720 0.703 1.00 38.33 C
ANISOU 2861 CG2 VAL B 329 5142 4251 5170 -186 -485 -208 C
ATOM   2862 C   VAL B 329 155.225 76.298 3.091 1.00 42.27 C
ANISOU 2862 C   VAL B 329 5864 4501 5698 27 -461 -505 C
ATOM   2863 O   VAL B 329 155.322 76.154 4.317 1.00 43.88 O
ANISOU 2863 O   VAL B 329 6139 4734 5801 8 -426 -610 O
ATOM   2864 N   LEU B 330 154.996 77.477 2.519 1.00 39.18 N
ANISOU 2864 N   LEU B 330 5540 3936 5408 92 -484 -488 N
ATOM   2865 CA  LEU B 330 154.841 78.663 3.340 1.00 41.36 C
ANISOU 2865 CA  LEU B 330 5980 4022 5712 145 -451 -621 C
ATOM   2866 CB  LEU B 330 154.751 79.921 2.483 1.00 36.44 C
ANISOU 2866 CB  LEU B 330 5423 3180 5244 204 -484 -554 C
ATOM   2867 CG  LEU B 330 156.120 80.388 2.011 1.00 35.19 C
ANISOU 2867 CG  LEU B 330 5337 2914 5120 22 -584 -485 C
ATOM   2868 CD1 LEU B 330 156.002 81.455 0.931 1.00 33.80 C
ANISOU 2868 CD1 LEU B 330 5209 2540 5092 82 -602 -353 C
ATOM   2869 CD2 LEU B 330 156.882 80.936 3.185 1.00 33.37 C
ANISOU 2869 CD2 LEU B 330 5267 2559 4852 -104 -626 -651 C
ATOM   2870 C   LEU B 330 153.644 78.561 4.295 1.00 44.93 C
ANISOU 2870 C   LEU B 330 6432 4505 6134 305 -300 -738 C
ATOM   2871 O   LEU B 330 153.710 78.973 5.446 1.00 45.94 O
ANISOU 2871 O   LEU B 330 6732 4557 6166 308 -233 -899 O
ATOM   2872 N   ARG B 331 152.543 78.014 3.807 1.00 42.62 N
ANISOU 2872 N   ARG B 331 5951 4319 5925 432 -242 -654 N
ATOM   2873 CA  ARG B 331 151.358 77.881 4.631 1.00 47.47 C
ANISOU 2873 CA  ARG B 331 6507 4961 6567 592 -60 -726 C
ATOM   2874 CB  ARG B 331 150.240 77.301 3.782 1.00 49.41 C
ANISOU 2874 CB  ARG B 331 6482 5318 6975 691 -68 -584 C
ATOM   2875 CG  ARG B 331 149.163 76.603 4.564 1.00 60.76 C
ANISOU 2875 CG  ARG B 331 7766 6865 8456 792 119 -606 C
ATOM   2876 CD  ARG B 331 148.127 76.049 3.605 1.00 71.86 C
ANISOU 2876 CD  ARG B 331 8873 8370 10061 845 42 -452 C
ATOM   2877 NE  ARG B 331 147.486 74.836 4.099 1.00 83.28 N
ANISOU 2877 NE  ARG B 331 10134 9980 11530 821 153 -432 N
ATOM   2878 CZ  ARG B 331 146.363 74.325 3.594 1.00 94.04 C
ANISOU 2878 CZ  ARG B 331 11202 11420 13109 868 125 -319 C
ATOM   2879 NH1 ARG B 331 145.756 74.921 2.573 1.00 98.26 N
ANISOU 2879 NH1 ARG B 331 11599 11903 13833 950 -40 -208 N
ATOM   2880 NH2 ARG B 331 145.842 73.220 4.111 1.00 96.27 N
HETATM 2929 CAB DRG C 1 168.248 51.869 5.487 1.00 23.50 C
HETATM 2930 CAT DRG C 1 166.056 50.821 5.426 1.00 31.37 C
HETATM 2931 OAL DRG C 1 166.098 51.093 4.116 1.00 29.82 O
HETATM 2932 CAU DRG C 1 165.125 50.661 3.280 1.00 23.20 C
HETATM 2933 CAR DRG C 1 164.030 49.989 3.787 1.00 24.45 C
HETATM 2934 CAI DRG C 1 163.050 49.542 2.893 1.00 23.70 C
HETATM 2935 CAF DRG C 1 163.148 49.831 1.533 1.00 24.90 C
HETATM 2936 CAG DRG C 1 164.257 50.533 1.042 1.00 24.70 C
HETATM 2937 CAP DRG C 1 165.250 50.993 1.925 1.00 29.90 C
HETATM 2938 CAK DRG C 1 166.386 51.724 1.462 1.00 26.20 C
HETATM 2939 CAM DRG C 1 167.789 51.131 1.752 1.00 39.78 C
HETATM 2940 OAE DRG C 1 167.893 49.935 2.148 1.00 40.47 O
HETATM 2941 OAC DRG C 1 168.731 51.931 1.552 1.00 41.66 O
HETATM 2942 OAD DRG C 2 160.821 53.562 -0.957 1.00 29.91 O
HETATM 2943 CAQ DRG C 2 161.917 53.977 -0.557 1.00 27.38 C
HETATM 2944 CAS DRG C 2 162.812 54.579 -1.407 1.00 20.36 C
HETATM 2945 CAJ DRG C 2 162.507 54.745 -2.761 1.00 19.81 C
HETATM 2946 CAH DRG C 2 163.441 55.403 -3.591 1.00 24.49 C
HETATM 2947 CAN DRG C 2 164.687 55.855 -3.089 1.00 28.71 C
HETATM 2948 CAA DRG C 2 165.671 56.485 -3.925 1.00 28.17 C
HETATM 2949 CAO DRG C 2 164.978 55.677 -1.721 1.00 26.46 C
HETATM 2950 CAB DRG C 2 166.188 56.089 -1.114 1.00 18.84 C
HETATM 2951 CAT DRG C 2 164.038 55.032 -0.924 1.00 24.41 C
HETATM 2952 OAL DRG C 2 164.378 54.935 0.369 1.00 27.02 O
HETATM 2953 CAU DRG C 2 163.488 54.378 1.221 1.00 27.07 C
HETATM 2954 CAR DRG C 2 162.274 53.883 0.769 1.00 24.72 C
HETATM 2955 CAI DRG C 2 161.376 53.311 1.662 1.00 23.42 C
HETATM 2956 CAF DRG C 2 161.750 53.230 2.996 1.00 24.17 C
HETATM 2957 CAG DRG C 2 162.974 53.719 3.444 1.00 24.73 C
HETATM 2958 CAP DRG C 2 163.876 54.296 2.556 1.00 29.50 C
HETATM 2959 CAK DRG C 2 165.123 54.798 3.007 1.00 31.35 C
HETATM 2960 CAM DRG C 2 165.455 56.308 2.721 1.00 33.32 C
HETATM 2961 OAE DRG C 2 164.570 57.125 2.437 1.00 34.51 O
HETATM 2962 OAC DRG C 2 166.634 56.666 2.839 1.00 40.95 O
HETATM 2963 O   HOH S 1 168.713 53.789 -0.291 1.00 35.33 O
HETATM 2964 O   HOH S 2 161.892 53.727 16.866 1.00 49.67 O
ANISOU 2904 CG  ARG B 334 9512 6074 8151 364 -89 -1390 C
ATOM   2905 CD  ARG B 334 153.159 82.263 6.362 1.00 62.02 C
ANISOU 2905 CD  ARG B 334 9278 5913 8375 519 -59 -1227 C
ATOM   2906 NE  ARG B 334 153.974 83.269 5.691 1.00 67.63 N
ANISOU 2906 NE  ARG B 334 10085 6394 9220 412 -202 -1187 N
ATOM   2907 CZ  ARG B 334 153.754 83.710 4.453 1.00 72.71 C
ANISOU 2907 CZ  ARG B 334 10604 6951 10073 486 -241 -996 C
ATOM   2908 NH1 ARG B 334 152.742 83.209 3.749 1.00 75.45 N
ANISOU 2908 NH1 ARG B 334 10721 7439 10508 658 -192 -840 N
ATOM   2909 NH2 ARG B 334 154.552 84.641 3.919 1.00 71.15 N
ANISOU 2909 NH2 ARG B 334 10514 6527 9995 375 -344 -947 N
ATOM   2910 C   ARG B 334 153.074 79.446 10.490 1.00 82.51 C
ANISOU 2910 C   ARG B 334 12204 9109 10039 401 222 -1574 C
ATOM   2911 O   ARG B 334 151.916 79.817 10.702 1.00 84.62 O
ANISOU 2911 O   ARG B 334 12479 9289 10384 622 494 -1632 O
ATOM   2912 N   GLN B 335 153.767 78.664 11.324 1.00 88.39 N
ANISOU 2912 N   GLN B 335 13052 10024 10510 250 122 -1587 N
ATOM   2913 CA  GLN B 335 153.413 78.453 12.730 1.00 90.10 C
ANISOU 2913 CA  GLN B 335 13537 10296 10402 294 296 -1729 C
ATOM   2914 CB  GLN B 335 152.178 77.573 12.878 1.00 86.04 C
ANISOU 2914 CB  GLN B 335 12828 9936 9926 486 608 -1625 C
ATOM   2915 CG  GLN B 335 151.932 76.676 11.682 1.00 84.23 C
ANISOU 2915 CG  GLN B 335 12170 9850 9985 493 549 -1384 C
ATOM   2916 CD  GLN B 335 150.587 76.950 11.040 1.00 86.54 C
ANISOU 2916 CD  GLN B 335 12230 10073 10579 716 772 -1332 C
ATOM   2917 OE1 GLN B 335 149.777 76.036 10.860 1.00 86.21 O
ANISOU 2917 OE1 GLN B 335 11924 10175 10655 788 906 -1195 O
ATOM   2918 NE2 GLN B 335 150.328 78.215 10.718 1.00 86.38 N
ANISOU 2918 NE2 GLN B 335 12295 9818 10708 824 807 -1428 N
ATOM   2919 C   GLN B 335 154.593 77.838 13.465 1.00 90.04 C
ANISOU 2919 C   GLN B 335 13668 10439 10104 63 37 -1715 C
ATOM   2920 O   GLN B 335 155.623 78.484 13.627 1.00 90.66 O
ANISOU 2920 O   GLN B 335 13924 10409 10114 -122 -230 -1808 O
TER    2922     GLN B 335
HETATM 2921 OAD DRG C 1 162.991 49.038 5.565 1.00 28.90 O
HETATM 2922 CAQ DRG C 1 163.951 49.693 5.137 1.00 31.88 C
HETATM 2923 CAS DRG C 1 165.012 50.082 5.948 1.00 28.82 C
HETATM 2924 CAJ DRG C 1 165.024 49.798 7.306 1.00 26.98 C
HETATM 2925 CAH DRG C 1 166.130 50.171 8.071 1.00 28.53 C
HETATM 2926 CAN DRG C 1 167.237 50.842 7.499 1.00 31.26 C
HETATM 2927 CAA DRG C 1 168.386 51.246 8.285 1.00 24.52 C
HETATM 2928 CAO DRG C 1 167.200 51.163 6.135 1.00 30.95 C
HETATM 2982 O   HOH S 20 171.080 57.987 13.953 1.00 45.06 O
HETATM 2983 O   HOH S 21 148.067 47.124 -0.587 1.00 45.29 O
HETATM 2984 O   HOH S 22 143.902 55.932 -14.363 1.00 63.60 O
HETATM 2986 O   HOH S 24 150.530 40.637 7.539 1.00 55.40 O
HETATM 2987 O   HOH S 25 166.897 51.082 11.483 1.00 49.70 O
HETATM 2988 O   HOH S 26 182.591 60.441 -1.208 1.00 53.67 O
HETATM 2989 O   HOH S 27 172.503 46.354 5.924 1.00 51.32 O
HETATM 2991 O   HOH S 29 197.473 47.430 -5.671 1.00 56.88 O
HETATM 2992 O   HOH S 30 154.281 64.868 15.755 1.00 61.97 O
HETATM 2993 O   HOH S 31 194.426 33.302 6.916 1.00 47.03 O
HETATM 2994 O   HOH S 32 163.586 73.804 8.275 1.00 40.52 O
HETATM 2995 O   HOH S 33 181.340 40.097 -2.774 1.00 48.13 O
HETATM 2996 O   HOH S 34 184.998 42.705 12.196 1.00 50.78 O
HETATM 2997 O   HOH S 35 151.669 47.690 -11.983 1.00 33.83 O
HETATM 2998 O   HOH S 36 171.381 82.460 13.092 1.00 72.55 O
HETATM 2999 O   HOH S 37 164.720 55.181 -7.543 1.00 35.15 O
HETATM 3000 O   HOH S 38 152.216 75.299 -11.371 1.00 64.67 O
HETATM 3001 O   HOH S 39 162.728 61.240 2.446 1.00 52.37 O
HETATM 3002 O   HOH S 40 157.809 85.373 -5.397 1.00 49.67 O
HETATM 3003 O   HOH S 41 160.833 54.824 -11.983 1.00 53.47 O
HETATM 3004 O   HOH S 42 172.438 36.666 11.131 1.00 50.31 O
HETATM 3005 O   HOH S 43 143.215 55.825 1.242 1.00 51.98 O
HETATM 3006 O   HOH S 44 178.194 34.813 -9.692 1.00 61.99 O
HETATM 3007 O   HOH S 45 160.209 55.971 -9.794 1.00 51.89 O
HETATM 3009 O   HOH S 47 170.559 46.042 2.157 1.00 40.56 O
HETATM 3011 O   HOH S 49 176.760 53.698 2.889 1.00 56.49 O
HETATM 3012 O   HOH S 50 168.790 62.275 2.328 1.00 60.56 O
HETATM 3013 O   HOH S 51 167.855 55.504 4.837 1.00 40.62 O
HETATM 3014 O   HOH S 52 177.579 50.250 -7.113 1.00 55.88 O
HETATM 3015 O   HOH S 53 155.929 68.342 -6.155 1.00 42.77 O
HETATM 3016 O   HOH S 54 187.365 29.710 12.394 1.00 49.65 O
HETATM 3017 O   HOH S 55 185.843 27.691 12.218 1.00 51.08 O
HETATM 3018 O   HOH S 56 190.462 26.460 7.158 1.00 50.01 O
HETATM 3019 O   HOH S 57 163.171 48.532 17.270 1.00 48.75 O
HETATM 3020 O   HOH S 58 164.548 48.001 15.528 1.00 60.23 O
HETATM 3021 O   HOH S 59 143.593 59.258 12.238 1.00 63.87 O
```

TABLE 8-continued

DMXAA-hSTING$^{S162A/Q266I}$ complex

| | |
|---|---|
| HETATM 2965 O HOH S 3 164.969 59.956 2.543 1.00 37.40 O | HETATM 3022 O HOH S 60 144.484 59.906 14.347 1.00 71.48 O |
| HETATM 2966 O HOH S 4 153.816 51.547 −17.356 1.00 35.89 O | HETATM 3023 O HOH S 61 152.669 45.115 16.448 1.00 43.47 O |
| HETATM 2967 O HOH S 5 173.955 67.623 4.394 1.00 44.22 O | HETATM 3024 O HOH S 62 160.263 38.016 17.761 1.00 48.84 O |
| HETATM 2968 O HOH S 6 160.329 36.676 11.944 1.00 55.15 O | HETATM 3025 O HOH S 63 152.484 64.476 18.117 1.00 65.15 O |
| HETATM 2969 O HOH S 7 167.121 68.307 2.491 1.00 43.22 O | HETATM 3026 O HOH S 64 149.649 67.575 5.246 1.00 53.28 O |
| HETATM 2970 O HOH S 8 174.241 45.104 7.023 1.00 39.35 O | HETATM 3028 O HOH S 66 154.393 85.153 −5.360 1.00 42.89 O |
| HETATM 2971 O HOH S 9 147.991 51.757 8.039 1.00 42.30 O | HETATM 3029 O HOH S 67 163.677 82.527 −9.406 1.00 55.89 O |
| HETATM 2972 O HOH S 10 150.720 42.063 5.341 1.00 55.82 O | HETATM 3030 O HOH S 68 163.984 77.274 −8.161 1.00 46.95 O |
| HETATM 2973 O HOH S 11 155.127 75.108 −8.066 1.00 54.25 O | HETATM 3031 O HOH S 69 176.278 65.478 13.005 1.00 69.67 O |
| HETATM 2974 O HOH S 12 154.172 39.544 −3.767 1.00 53.24 O | HETATM 3033 O HOH S 71 149.765 70.612 2.125 1.00 53.58 O |
| HETATM 2975 O HOH S 13 165.300 57.764 −7.952 1.00 41.58 O | HETATM 3039 S SO4 E 1 190.873 52.635 2.687 1.00209.77 S |
| HETATM 2976 O HOH S 14 162.850 89.254 −6.796 1.00 52.78 O | HETATM 3040 O1 SO4 E 1 191.344 51.848 1.550 1.00208.46 O |
| HETATM 2977 O HOH S 15 154.964 70.741 −7.727 1.00 45.98 O | HETATM 3041 O2 SO4 E 1 189.413 52.472 2.690 1.00210.80 O |
| HETATM 2978 O HOH S 16 164.131 62.771 −1.020 1.00 51.78 O | HETATM 3042 O3 SO4 E 1 191.451 52.156 3.943 1.00210.05 O |
| HETATM 2979 O HOH S 17 152.520 70.191 15.623 1.00 58.84 O | HETATM 3043 O4 SO4 E 1 191.281 54.037 2.527 1.00209.37 O |
| HETATM 2980 O HOH S 18 166.251 62.142 0.998 1.00 47.15 O | END |

TABLE 9

DMXAA-hSTING$^{S162A/G230I/Q266I}$ complex

REMARK 3
REMARK 3 REFINEMENT.
REMARK 3 PROGRAM:
PHENIX (phenix. refine: 1.8.2_1309)
REMARK 3 AUTHORS:
Adams, Afonine, Bumley, Chen, Davis, Echols,
REMARK 3: Gildea, Gopal, Gros,
Grosse-Kunstleve, Headd, Hung,
REMARK 3: Immormino, Ioerger,
McCoy, McKee, Moriarty, Pai, Read,
REMARK 3: Richardson, Richardson, Romo, Sacchettini, Sauter, Smith,
REMARK 3: Storoni, Terwilliger, Zwart
REMARK 3
REMARK 3 REFINEMENT TARGET: ML
REMARK 3
REMARK 3 DATA USED IN REFINEMENT.

REMARK 3 RESOLUTION RANGE HIGH (ANGSTROMS): 2.370
REMARK 3 RESOLUTION RANGE LOW (ANGSTROMS): 128.671
REMARK 3 MIN(FOBS(SIGMA FOBS): 1.35
REMARK 3 COMPLETENESS FOR RANGE (%): 99.91
REMARK 3 NUMBER OF REFLECTIONS: 19048
REMARK 3 NUMBER OF REFLECTIONS (NON-ANOMALOUS): 19048
REMARK 3
REMARK 3 FIT TO DATA USED IN REFINEMENT.
REMARK 3 R VALUE (WORKING + TEST SET): 0.1893
REMARK 3 R VALUE (WORKING SET): 0.1870
REMARK 3 FREE R VALUE: 0.2310
REMARK 3 FREE R VALUE TEST SET SIZE (%): 5.15
REMARK 3 FREE R VALUE TEST SET COUNT: 981
REMARK 3
REMARK 3 FIT TO DATA USED IN REFINEMENT (IN BINS).

REMARK 3 BIN RESOLUTION RANGE COMPL. NWORK NFREE RWORK RFREE
REMARK 3 1 128.8606-4.5338 1.00 2698 133 0.1721 0.2114
REMARK 3 2 4.5338-3.5985 1.00 2593 146 0.1554 0.1881
REMARK 3 3 3.5985-3.1436 1.00 2587 136 0.1775 0.2098
REMARK 3 4 3.1436-2.8562 1.00 2551 135 0.2056 0.2800
REMARK 3 5 2.8562-2.6514 1.00 2559 140 0.2293 0.2668
REMARK 3 6 2.6514-2.4951 1.00 2546 142 0.2922 0.3880
REMARK 3 7 2.4951-2.3701 1.00 2533 149 0.2916 0.3274
REMARK 3
REMARK 3 BULK SOLVENT MODELLING.
REMARK 3 METHOD USED: FLAT BULK SOLVENT MODEL
REMARK 3 SOLVENT RADIUS: 1.11
REMARK 3 SHRINKAGE RADIUS: 0.90
REMARK 3 GRID STEP FACTOR: 4.00

REMARK 3
REMARK 3 ERROR ESTIMATES.
REMARK 3 COORDINATE ERROR (MAXIMUM-LIKELIHOOD BASED): 0.30
REMARK 3 PHASE ERROR (DEGREES, MAXIMUM-LIKELIHOOD BASED): 22.08

REMARK 3 ORIGIN FOR THE GROUP (A): 119.7412 −45.6180 0.9079
REMARK 3 T TENSOR
REMARK 3 T11: 0.4193 T22: 0.4961
REMARK 3 T33: 0.3419 T12: 0.1443
REMARK 3 T13: 0.0895 T23: 0.1533
REMARK 3 L TENSOR
REMARK 3 L11: 4.6250 L22: 6.8599
REMARK 3 L33: 2.9736 L12: −3.3531
REMARK 3 L13: 0.4680 L23: −0.1759
REMARK 3 S TENSOR
REMARK 3 S11: −0.8048 S12: −0.9653 S13: −0.5231
REMARK 3 S21: 1.3663 S22: 0.5796 S23: 0.1655
REMARK 3 S31: 0.2873 S32: 0.2438 S33: 0.2232
REMARK 3 TLS GROUP: 2
REMARK 3 SELECTION: chain 'A' and (resid 186 through 211 )
REMARK 3 ORIGIN FOR THE GROUP (A): 129.3530 −48.7083 −7.1009
REMARK 3 T TENSOR
REMARK 3 T11: 0.4212 T22: 0.6459
REMARK 3 T33: 0.6367 T12: 0.1380
REMARK 3 T13: 0.0329 T23: −0.0528
REMARK 3 LTENSOR
REMARK 3 L11: 3.5990 L22: 9.5628
REMARK 3 L33: 2.8698 L12: −3.6331
REMARK 3 L13: 1.0100 L23: −0.5546
REMARK 3 S TENSOR
REMARK 3 S11: −0.0638 S12: 0.2429 S13: −0.8055
REMARK 3 S21: 0.1232 S22: 0.2133 S23: −0.3000
REMARK 3 S31: 0.5832 S32: 0.3737 S33: −0.0249
REMARK 3 TLS GROUP: 3
REMARK 3 SELECTION: chain 'A' and (resid 212 through 227 )
REMARK 3 ORIGIN FOR THE GROUP (A): 129.1486 −52.5547 −12.8258
REMARK 3 T TENSOR
REMARK 3 T11: 0.4393 T22: 0.5281
REMARK 3 T33: 0.5919 T12: 0.0322
REMARK 3 T13: −0.0127 T23: 0.1194
REMARK 3 L TENSOR
REMARK 3 L11: 5.8586 L22: 9.3215
REMARK 3 L33: 8.1146 L12: 6.4837
REMARK 3 L13: −6.5623 L23: −5.5758
REMARK 3 S TENSOR
REMARK 3 S11: −0.8869 S12: 1.2379 S13: −0.7595
REMARK 3 S21: −0.4167 S22: 1.1681 S23: 0.6136
REMARK 3 S31: 0.0975 S32: −1.4546 S33: −0.1067
REMARK 3 TLS GROUP: 4
REMARK 3 SELECTION: chain 'A' and (resid 228 through 242 )
REMARK 3 ORIGIN FOR THE GROUP (A): 100.4692 −51.7135 −1.3574
REMARK 3 T TENSOR
REMARK 3 T11: 0.7933 T22: 0.5352
REMARK 3 T33: 0.8596 T12: −0.0041
REMARK 3 T13: 0.2322 T23: 0.1112
REMARK 3 L TENSOR
REMARK 3 L11: 7.5537 L22: 2.8609

TABLE 9-continued

DMXAA-hSTING$^{S162A/G230I/Q266I}$ complex

REMARK 3
REMARK 3 STRUCTURE FACTORS CALCULATION ALGORITHM: FFT
REMARK 3
REMARK 3 DEVIATIONS FROM IDEAL VALUES.
REMARK 3 RMSD MAX COUNT
REMARK 3 BOND: 0.007 0.040 3034
REMARK 3 ANGLE: 1.203 8.976 4122
REMARK 3 CHIRALITY: 0.075 0.371 448
REMARK 3 PLANARITY: 0.004 0.039 542
REMARK 3 DIHEDRAL: 18.321 82.369 1138
REMARK 3 MIN NONBONDED DISTANCE: 1.922
REMARK 3
REMARK 3 MOLPROBITY STATISTICS.
REMARK 3 ALL-ATOM CLASHSCORE: 7.67
REMARK 3 RAMACHANDRAN PLOT:
REMARK 3 OUTLIERS: 0.56%
REMARK 3 ALLOWED: 3.89%
REMARK 3 FAVORED: 95.56%
REMARK 3 ROTAMER OUTLIERS: 11.71%
REMARK 3 CBETA DEVIATIONS: 0
REMARK 3
REMARK 3 ATOMIC DISPLACEMENT PARAMETERS.
REMARK 3 WILSON B: 52.20
REMARK 3 RMS(B_ISO_OR_EQUIVALENT_BONDED): 8.54
REMARK 3 ATOMS NUMBER OF ATOMS
REMARK 3 ISO. ANISO.
REMARK 3 ALL: 3033 2928
REMARK 3 ALL (NO H): 3033 2928
REMARK 3 SOLVENT: 58 0
REMARK 3 NON-SOLVENT: 2975 2928
REMARK 3 HYDROGENS: 0 0
REMARK 3
REMARK 3 TLS DETAILS.
REMARK 3 NUMBER OF TLS GROUPS: 19
REMARK 3 ORIGIN: CENTER OF MASS
REMARK 3 TLS GROUP: 1
REMARK 3 SELECTION: chain 'A' and (resid 154 through 185)
REMARK 3 ORIGIN FOR THE GROUP (A): 136.1529 −33.2184 −19.3637
REMARK 3 T TENSOR
REMARK 3 T11: 1.2099 T22: 1.0982
REMARK 3 T33: 1.0451 T12: −0.0360
REMARK 3 T13: 0.0766 T23: 0.2092
REMARK 3 L TENSOR
REMARK 3 L11: 7.4924 L22: 8.3097
REMARK 3 L33: 3.9134 L12: −7.5601
REMARK 3 L13: −2.5458 L23: 3.9627
REMARK 3 S TENSOR
REMARK 3 S11: 1.0706 S12: 0.5115 S13: 0.7413
REMARK 3 S21: −2.3931 S22: 0.2034 S23: −0.4202
REMARK 3 S31: −1.4970 S32: 1.0416 S33: −1.1149
REMARK 3 TLS GROUP: 8
REMARK 3 SELECTION: chain 'A' and (resid 325 through 335)
REMARK 3 ORIGIN FOR THE GROUP (A): 138.2183 −41.3718 −6.6489
REMARK 3 T TENSOR
REMARK 3 T11: 0.4830 T22: 0.6805
REMARK 3 T33: 0.7524 T12: 0.0984
REMARK 3 T13: 0.0045 T23: −0.1937
REMARK 3 L TENSOR
REMARK 3 L11: 3.9316 L22: 9.9442
REMARK 3 L33: 4.3889 L12: 0.7967
REMARK 3 L13: −3.5976 L23: 2.5293
REMARK 3 S TENSOR
REMARK 3 S11: −0.0798 S12: −1.5666 S13: 2.2980
REMARK 3 S21: 0.1616 S22: 0.8716 S23: 0.0533
REMARK 3 S31: −0.9688 S32: 1.3146 S33: −0.7372
REMARK 3 TLS GROUP: 9
REMARK 3 SELECTION: chain 'B' and (resid 154 through 185)
REMARK 3 ORIGIN FOR THE GROUP (A): 102.7779 −46.2422 −15.6896
REMARK 3 T TENSOR
REMARK 3 T11: 0.3790 T22: 0.4564
REMARK 3 T33: 0.4948 T12: −0.0780
REMARK 3 T13: 0.1193 T23: −0.1808
REMARK 3 L TENSOR
REMARK 3 L11: 5.0670 L22: 9.2284
REMARK 3 L33: 1.9220 L12: 6.1333
REMARK 3 L33: 1.4922 L12: −4.5153
REMARK 3 L13: −2.2277 L23: 1.0483
REMARK 3 S TENSOR
REMARK 3 S11: −0.9886 S12: −1.1618 S13: −1.8144
REMARK 3 S21: 0.0203 S22: 0.2433 S23: 0.9635
REMARK 3 S31: −0.0130 S32: −0.0466 S33: 0.4012
REMARK 3 TLS GROUP: 5
REMARK 3 SELECTION: chain 'A' and (resid 243 through 280 )
REMARK 3 ORIGIN FOR THE GROUP (A): 124.7540 −41.4323 −13.6540
REMARK 3 T TENSOR
REMARK 3 T11: 0.3074 T22: 0.3011
REMARK 3 T33: 0.2748 T12: −0.0078
REMARK 3 T13: 0.0100 T23: 0.0303
REMARK 3 L TENSOR
REMARK 3 L11: 3.6448 L22: 2.3155
REMARK 3 L33: 1.7574 L12: −1.9552
REMARK 3 L13: −0.0407 L23: −0.1114
REMARK 3 S TENSOR
REMARK 3 S11: −0.1020 S12: −0.0173 S13: −0.1125
REMARK 3 S21: 0.1136 S22: 0.0133 S23: −0.1586
REMARK 3 S31: 0.0827 S32: 0.2233 S33: 0.0722
REMARK 3 TLS GROUP: 6
REMARK 3 SELECTION: chain 'A' and (resid 281 through 314 )
REMARK 3 ORIGIN FOR THE GROUP (A): 123.3640 −32.6276 −3.4192
REMARK 3 T TENSOR
REMARK 3 T11: 0.4307 T22: 0.4987
REMARK 3 T33: 0.3607 T12: 0.0528
REMARK 3 T13: −0.0232 T23: −0.0691
REMARK 3 L TENSOR
REMARK 3 L11: 5.0093 L22: 6.6833
REMARK 3 L33: 6.8768 L12: −2.5420
REMARK 3 L13: −0.4223 L23: −1.0414
REMARK 3 S TENSOR
REMARK 3 S11: −0.3563 S12: −0.7204 S13: −0.0370
REMARK 3 S21: 1.1416 S22: 0.4752 S23: −0.2161
REMARK 3 S31: −0.6150 S32: 0.5594 S33: −0.1028
REMARK 3 TLS GROUP: 7
REMARK 3 SELECTION: chain 'A' and (resid 315 through 324 )
REMARK 3 ORIGIN FOR THE GROUP (A): 85.9333 −53.1198 −4.2411
REMARK 3 T TENSOR
REMARK 3 T11: 0.3714 T22: 0.2747
REMARK 3 T33: 0.5722 T12: −0.0192
REMARK 3 T13: −0.0126 T23: −0.0928
REMARK 3 L TENSOR
REMARK 3 L11: 3.3449 L22: 2.0165
REMARK 3 L33: 5.6917 L12: −1.8933
REMARK 3 L13: 1.8124 L23: 0.8956
REMARK 3 S TENSOR
REMARK 3 S11: 0.4190 S12: 1.2640 S13: −1.7916
REMARK 3 S21: −0.2402 S22: −0.4122 S23: 0.0219
REMARK 3 S31: −0.1884 S32: −0.4293 S33: 0.0260
REMARK 3 TLS GROUP: 14
REMARK 3 SELECTION: chain 'B' and (resid 252 through 262 )
REMARK 3 ORIGIN FOR THE GROUP (A): 90.2196 −50.5140 −6.8148
REMARK 3 T TENSOR
REMARK 3 T11: 0.3741 T22: 0.3438
REMARK 3 T33: 0.5056 T12: 0.0020
REMARK 3 T13: 0.0368 T23: −0.0219
REMARK 3 L TENSOR
REMARK 3 L11: 6.9716 L22: 3.5972
REMARK 3 L33: 0.3302 L12: 4.8886
REMARK 3 L13: −0.2250 L23: −0.4021
REMARK 3 S TENSOR
REMARK 3 S11: −0.6307 S12: 0.1548 S13: −0.3940
REMARK 3 S21: −0.4735 S22: 0.4279 S23: −0.0522
REMARK 3 S31: 0.1429 S32: −0.0110 S33: 0.1038
REMARK 3 TLS GROUP: 15
REMARK 3 SELECTION: chain 'B' and (resid 263 through 280 )
REMARK 3 ORIGIN FOR THE GROUP (A): 107.3523 −32.3148 3.4381
REMARK 3 T TENSOR
REMARK 3 T11: 0.3575 T22: 0.4111
REMARK 3 T33: 0.2047 T12: 0.0400
REMARK 3 T13: −0.0095 T23: −0.0117
REMARK 3 L TENSOR
REMARK 3 L11: 4.1938 L22: 7.9005
REMARK 3 L33: 7.0490 L12: 3.5052

TABLE 9-continued

DMXAA-hSTING$^{S162A/G230I/Q266I}$ complex

REMARK 3 L13: −0.3197 L23: −1.2094
REMARK 3 S TENSOR
REMARK 3 S11: −0.7388 S12: 0.8656 S13: −0.5878
REMARK 3 S21: −0.7892 S22: 0.2346 S23: 0.4003
REMARK 3 S31: 0.4546 S32: −0.3021 S33: 0.5353
REMARK 3 TLS GROUP: 10
REMARK 3 SELECTION: chain 'B' and (resid 186 through 197)
REMARK 3 ORIGIN FOR THE GROUP (A): 89.4343 −60.0520 −14.5866
REMARK 3 T TENSOR
REMARK 3 T11: 0.7926 T22: 0.8090
REMARK 3 T33: 0.7893 T12: −0.2621
REMARK 3 T13: 0.0833 T23: −0.0286
REMARK 3 L TENSOR
REMARK 3 L11: 4.1177 L22: 2.1948
REMARK 3 L33: 4.0533 L12: 3.0564
REMARK 3 L13: −1.0144 L23: −0.7338
REMARK 3 S TENSOR
REMARK 3 S11: −0.2529 S12: 0.1725 S13: −0.4022
REMARK 3 S21: −0.9500 S22: 0.4807 S23: −0.1411
REMARK 3 S31: 1.0844 S32: −1.4521 S33: −0.1682
REMARK 3 TLS GROUP: 11
REMARK 3 SELECTION: chain 'B' and (resid 198 through 227)
REMARK 3 ORIGIN FOR THE GROUP (A): 94.8966 −48.5955 −2.3933
REMARK 3 T TENSOR
REMARK 3 T11: 0.3729 T22: 0.3587
REMARK 3 T33: 0.5199 T12: −0.0317
REMARK 3 T13: 0.0514 T23: −0.0067
REMARK 3 L TENSOR
REMARK 3 L11: 3.2456 L22: 4.8310
REMARK 3 L33: 3.6015 L12: 1.6632
REMARK 3 L13: 0.0335 L23: −0.3002
REMARK 3 S TENSOR
REMARK 3 S11: 0.0959 S12: −0.1614 S13: −0.6866
REMARK 3 S21: 0.3321 S22: −0.1757 S23: −0.1693
REMARK 3 S31: 0.4177 S32: 0.1672 S33: 0.1094
REMARK 3 TLS GROUP: 12
REMARK 3 SELECTION: chain 'B' and (resid 228 through 242)
REMARK 3 ORIGIN FOR THE GROUP (A): 112.4208 −51.6896 −13.1983
REMARK 3 T TENSOR
REMARK 3 T11: 0.7790 T22: 0.5122
REMARK 3 T33: 1.0026 T12: 0.1648
REMARK 3 T13: 0.1659 T23: −0.1220
REMARK 3 L TENSOR
REMARK 3 L11: 3.7366 L22: 2.5001
REMARK 3 L33: 0.7851 L12: 3.0397
REMARK 3 L13: 1.3074 L23: 1.0241
REMARK 3 S TENSOR
REMARK 3 S11: 0.1534 S12: 0.8507 S13: −1.6972
REMARK 3 S21: −0.4068 S22: 0.1129 S23: −0.7964
REMARK 3 S31: −0.8144 S32: −0.0429 S33: −0.2444
REMARK 3 TLS GROUP: 13
REMARK 3 SELECTION: chain 'B' and (resid 243 through 251 )
REMARK 3 ORIGIN FOR THE GROUP (A): 84.2902 −43.4926 −8.6366
REMARK 3 T TENSOR
REMARK 3 T11: 0.4372 T22: 0.4478
REMARK 3 T33: 0.5271 T12: −0.0293
REMARK 3 T13: 0.0374 T23: 0.0203
REMARK 3 L TENSOR
REMARK 3 L11: 2.9969 L22: 9.0584
REMARK 3 L33: 2.9310 L12: 2.4391
REMARK 3 L13: 2.1374 L23: −1.3556
REMARK 3 S TENSOR
REMARK 3 S11: −0.3830 S12: 0.6242 S13: 0.6931
REMARK 3 S21: −0.3255 S22: 0.2273 S23: 0.9659
REMARK 3 S31: −0.6838 S32: −0.4201 S33: 0.0795
REMARK 3
CRYST1 148.576 148.576 36.202 90.00 90.00 120.00 P 6
SCALE1 0.006731 0.003886 0.000000 0.00000
SCALE2 0.000000 0.007772 0.000000 0.00000
SCALE3 0.000000 0.000000 0.027623 0.00000
ATOM 1 N SER A 154 111.359 −23.888 −5.719 1.00 72.94 N
ANISOU 1 N SER A 154 9351 8569 9792 361 −1470 −975 N
ATOM 2 CA SER A 154 112.507 −24.367 −6.476 1.00 64.85 C
ANISOU 2 CA SER A 154 8208 7554 8878 89 −1489 −800 C
ATOM 3 CB SER A 154 113.799 −24.176 −5.687 1.00 67.42 C
ANISOU 3 CB SER A 154 8581 7816 9221 15 −1696 −885 C
ATOM 4 OG SER A 154 114.906 −24.681 −6.410 1.00 72.11 O
REMARK 3 L13: 2.3469 L23: 5.1477
REMARK 3 S TENSOR
REMARK 3 S11: −0.0007 S12: −0.7426 S13: 0.1759
REMARK 3 S21: 0.2832 S22: −0.1936 S23: −0.0761
REMARK 3 S31: −0.2331 S32: −0.0177 S33: 0.2045
REMARK 3 TLS GROUP: 16
REMARK 3 SELECTION: chain 'B' and (resid 281 through 300 )
REMARK 3 ORIGIN FOR THE GROUP (A): 99.3068 −29.4630 −6.9766
REMARK 3 T TENSOR
REMARK 3 T11: 0.3660 T22: 0.3222
REMARK 3 T33: 0.3279 T12: 0.0265
REMARK 3 T13: 0.0158 T23: 0.0473
REMARK 3 L TENSOR
REMARK 3 L11: 5.4311 L22: 8.2757
REMARK 3 L33: 4.2934 L12: −1.9276
REMARK 3 L13: −1.7369 L23: 5.9517
REMARK 3 S TENSOR
REMARK 3 S11: −0.0824 S12: −0.1743 S13: 0.1487
REMARK 3 S21: −0.2388 S22: −0.3192 S23: 0.1127
REMARK 3 S31: −0.9197 S32: −0.8060 S33: 0.2108
REMARK 3 TLS GROUP: 17
REMARK 3 SELECTION: chain 'B' and (resid 301 through 314 )
REMARK 3 ORIGIN FOR THE GROUP (A): 96.0561 −40.1387 −17.0384
REMARK 3 T TENSOR
REMARK 3 T11: 0.5710 T22: 0.5758
REMARK 3 T33: 0.3773 T12: −0.0341
REMARK 3 T13: −0.0190 T23: 0.0308
REMARK 3 L TENSOR
REMARK 3 L11: 9.0583 L22: 4.4916
REMARK 3 L33: 4.0786 L12: 0.9703
REMARK 3 L13: −6.1633 L23: −0.3551
REMARK 3 S TENSOR
REMARK 3 S11: −0.5655 S12: 1.7341 S13: −0.0968
REMARK 3 S21: −0.9309 S22: 0.3457 S23: −0.0561
REMARK 3 S31: 0.6964 S32: −1.2850 S33: 0.1675
REMARK 3 TLS GROUP: 18
REMARK 3 SELECTION: chain 'B' and (resid 315 through 324 )
REMARK 3 ORIGIN FOR THE GROUP (A): 85.7637 −36.4903 5.1908
REMARK 3 T TENSOR
REMARK 3 T11: 0.9311 T22: 0.7813
REMARK 3 T33: 0.7808 T12: 0.0715
REMARK 3 T13: 0.1264 T23: −0.2422
REMARK 3 L TENSOR
REMARK 3 L11: 9.5457 L22: 5.3768
REMARK 3 L33: 8.6160 L12: 7.1404
REMARK 3 L13: −0.7572 L23: −0.6912
REMARK 3 S TENSOR
REMARK 3 S11: 0.9085 S12: −1.4752 S13: 1.2802
REMARK 3 S21: 2.8252 S22: 0.2965 S23: −0.1022
REMARK 3 S31: −1.1428 S32: 0.4070 S33: −1.0872
REMARK 3 TLS GROUP: 19
REMARK 3 SELECTION: chain 'B' and (resid 325 through 335 )
ATOM 37 CD2 LEU A 159 114.661 −32.262 −9.760 1.00 41.60 C
ANISOU 37 CD2 LEU A 159 4488 5498 5821 −412 −498 −6 C
ATOM 38 CD1 LEU A 159 112.535 −33.109 −8.789 1.00 40.55 C
ANISOU 38 CD1 LEU A 159 4288 5399 5721 −227 −312 −119 C
ATOM 39 C LEU A 159 114.724 −33.670 −5.030 1.00 35.97 C
ANISOU 39 C LEU A 159 3963 5020 4686 35 −298 −88 C
ATOM 40 O LEU A 159 114.826 −34.892 −4.941 1.00 37.43 O
ANISOU 40 O LEU A 159 4091 5265 4866 49 −126 24 O
ATOM 41 N ALA A 160 115.433 −32.830 −4.286 1.00 32.34 N
ANISOU 41 N ALA A 160 3625 4547 4117 96 −520 −190 N
ATOM 42 CA ALA A 160 116.391 −33.302 −3.299 1.00 31.84 C
ANISOU 42 CA ALA A 160 3639 4569 3891 208 −602 −185 C
ATOM 43 CB ALA A 160 117.279 −32.169 −2.826 1.00 31.17 C
ANISOU 43 CB ALA A 160 3633 4413 3798 211 −963 −352 C
ATOM 44 C ALA A 160 115.671 −33.945 −2.120 1.00 34.93 C
ANISOU 44 C ALA A 160 4183 5056 4034 478 −386 −145 C
ATOM 45 O ALA A 160 116.087 −34.991 −1.619 1.00 32.90 O
ANISOU 45 O ALA A 160 3950 4884 3666 571 −276 −26 O
ATOM 46 N TRP A 161 114.596 −33.304 −1.672 1.00 33.86 N
ANISOU 46 N TRP A 161 4155 4899 3811 628 −302 −223 N
ATOM 47 CA TRP A 161 113.769 −33.868 −0.613 1.00 40.67 C
ANISOU 47 CA TRP A 161 5148 5849 4454 905 −4 −138 C
ATOM 48 CB TRP A 161 112.747 −32.853 −0.108 1.00 32.52 C
ANISOU 48 CB TRP A 161 4244 4793 3318 1101 38 −268 C
ATOM 49 CG TRP A 161 113.380 −31.898 0.825 1.00 33.73 C TABLE 9-continued DMXAA-hSTING$^{S162A/G230I/Q266I}$ complex

```
ANISOU 4 OG SER A 154 9011 8432 9954 -232 -1673 -698 O
ATOM 5 C SER A 154 112.352 -25.838 -6.840 1.00 64.20 C
ANISOU 5 C SER A 154 7963 7714 8716 47 -1234 -654 C
ATOM 6 O SER A 154 111.976 -26.667 -6.008 1.00 54.17 O
ANISOU 6 O SER A 154 6679 6610 7293 183 -1077 -690 O
ATOM 7 N VAL A 155 112.663 -26.148 -8.092 1.00 49.48 N
ANISOU 7 N VAL A 155 5996 5850 6954 -123 -1186 -482 N
ATOM 8 CA VAL A 155 112.566 -27.503 -8.597 1.00 44.82 C
ANISOU 8 CA VAL A 155 5269 5442 6319 -166 -990 -371 C
ATOM 9 CB VAL A 155 112.836 -27.531 -10.105 1.00 56.19 C
ANISOU 9 CB VAL A 155 6672 6848 7830 -288 -983 -215 C
ATOM 10 CG1 VAL A 155 113.122 -28.948 -10.578 1.00 38.85 C
ANISOU 10 CG1 VAL A 155 4361 4816 5583 -340 -826 -127 C
ATOM 11 CG2 VAL A 155 111.660 -26.930 -10.848 1.00 54.16 C
ANISOU 11 CG2 VAL A 155 6460 6512 7605 -182 -1036 -244 C
ATOM 12 C VAL A 155 113.542 -28.425 -7.879 1.00 35.93 C
ANISOU 12 C VAL A 155 4095 4441 5115 -213 -931 -342 C
ATOM 13 O VAL A 155 113.189 -29.530 -7.466 1.00 41.33 O
ANISOU 13 O VAL A 155 4719 5270 5717 -143 -760 -326 O
ATOM 14 N ALA A 156 114.774 -27.953 -7.726 1.00 37.14 N
ANISOU 14 N ALA A 156 4260 4517 5335 -328 -1082 -325 N
ATOM 15 CA ALA A 156 115.835 -28.774 -7.162 1.00 39.89 C
ANISOU 15 CA ALA A 156 4540 4976 5641 -369 -1075 -292 C
ATOM 16 CB ALA A 156 117.172 -28.110 -7.348 1.00 42.00 C
ANISOU 16 CB ALA A 156 4741 5116 6103 -539 -1258 -252 C
ATOM 17 C ALA A 156 115.586 -29.035 -5.685 1.00 56.44 C
ANISOU 17 C ALA A 156 6748 7157 7538 -166 -1097 -434 C
ATOM 18 O ALA A 156 115.878 -30.115 -5.166 1.00 56.09 O
ANISOU 18 O ALA A 156 6677 7262 7374 -105 -986 -385 O
ATOM 19 N HIS A 157 115.068 -28.017 -5.013 1.00 51.70 N
ANISOU 19 N HIS A 157 6303 6454 6888 -31 -1238 -604 N
ATOM 20 CA HIS A 157 114.783 -28.102 -3.592 1.00 55.14 C
ANISOU 20 CA HIS A 157 6911 6970 7071 231 -1254 -750 C
ATOM 21 CB HIS A 157 114.165 -26.785 -3.115 1.00 57.97 C
ANISOU 21 CB HIS A 157 7452 7174 7400 387 -1422 -957 C
ATOM 22 CG HIS A 157 113.896 -26.742 -1.644 1.00 63.55 C
ANISOU 22 CG HIS A 157 8394 7962 7789 720 -1447 -1131 C
ATOM 23 ND1 HIS A 157 114.900 -26.800 -0.700 1.00 57.21 N
ANISOU 23 ND1 HIS A 157 7720 7186 6832 816 -1690 -1255 N
ATOM 24 CE1 HIS A 157 114.366 -26.728 0.508 1.00 62.29 C
ANISOU 24 CE1 HIS A 157 8625 7917 7126 1183 -1653 -1398 C
ATOM 25 NE2 HIS A 157 113.055 -26.628 0.379 1.00 68.89 N
ANISOU 25 NE2 HIS A 157 9467 8782 7927 1309 -1358 -1353 N
ATOM 26 CD2 HIS A 157 112.733 -26.635 -0.957 1.00 68.39 C
ANISOU 26 CD2 HIS A 157 9149 8644 8193 1017 -1255 -1200 C
ATOM 27 C HIS A 157 113.846 -29.279 -3.323 1.00 53.97 C
ANISOU 27 C HIS A 157 6730 7006 6771 374 -903 -641 C
ATOM 28 O HIS A 157 114.069 -30.068 -2.408 1.00 49.08 O
ANISOU 28 O HIS A 157 6182 6519 5949 524 -808 -613 O
ATOM 29 N GLY A 158 112.813 -29.414 -4.146 1.00 37.40 N
ANISOU 29 N GLY A 158 4514 4896 4801 328 -722 -568 N
ATOM 30 CA GLY A 158 111.844 -30.479 -3.969 1.00 44.70 C
ANISOU 30 CA GLY A 158 5345 5938 5702 425 -398 -464 C
ATOM 31 C GLY A 158 112.340 -31.826 -4.474 1.00 45.00 C
ANISOU 31 C GLY A 158 5236 6053 5811 278 -266 -301 C
ATOM 32 O GLY A 158 111.915 -32.875 -4.007 1.00 48.19 O
ANISOU 32 O GLY A 158 5590 6536 6185 361 -14 -198 O
ATOM 33 N LEU A 159 113.243 -31.794 -5.445 1.00 31.81 N
ANISOU 33 N LEU A 159 3497 4341 4249 73 -414 -264 N
ATOM 34 CA LEU A 159 113.779 -33.016 -6.032 1.00 34.05 C
ANISOU 34 CA LEU A 159 3657 4685 4594 -43 -307 -133 C
ATOM 35 CB LEU A 159 114.551 -32.695 -7.313 1.00 43.51 C
ANISOU 35 CB LEU A 159 4792 5829 5909 -230 -437 -94 C
ATOM 36 CG LEU A 159 114.045 -33.149 -8.684 1.00 52.71 C
ANISOU 36 CG LEU A 159 5868 6976 7185 -307 -369 -48 C
ATOM 82 CE1 TYR A 164 116.767 -38.833 4.598 1.00 56.67 C
ANISOU 82 CE1 TYR A 164 8169 8423 4941 2261 409 646 C
ATOM 83 CZ TYR A 164 115.851 -38.162 5.389 1.00 64.24 C
ANISOU 83 CZ TYR A 164 9364 9432 5611 2538 570 601 C
ATOM 84 OH TYR A 164 115.771 -38.464 6.723 1.00 75.84 O
ANISOU 84 OH TYR A 164 11222 11026 6569 3019 723 722 O
ATOM 85 CE2 TYR A 164 115.022 -37.192 4.844 1.00 49.80 C
ANISOU 85 CE2 TYR A 164 7404 7535 3982 2375 588 442 C
ATOM 86 CD2 TYR A 164 115.119 -36.898 3.498 1.00 41.28 C
ANISOU 86 CD2 TYR A 164 5982 6338 3363 1939 436 344 C
ATOM 87 C TYR A 164 114.639 -39.219 0.879 1.00 34.16 C
ANISOU 87 C TYR A 164 4349 5193 3439 1204 918 736 C
ATOM 88 O TYR A 164 114.787 -40.337 1.363 1.00 44.10 O
ANISOU 49 CG TRP A 161 4675 4951 3189 1309 -278 -485 C
ATOM 50 CD1 TRP A 161 113.864 -30.649 0.533 1.00 34.67 C
ANISOU 50 CD1 TRP A 161 4834 4938 3401 1210 -667 -710 C
ATOM 51 NE1 TRP A 161 114.412 -30.085 1.659 1.00 47.90 N
ANISOU 51 NE1 TRP A 161 6792 6626 4780 1471 -941 -912 N
ATOM 52 CE2 TRP A 161 114.299 -30.975 2.700 1.00 43.24 C
ANISOU 52 CE2 TRP A 161 6383 6209 3837 1778 -716 -801 C
ATOM 53 CD2 TRP A 161 113.664 -32.131 2.203 1.00 39.35 C
ANISOU 53 CD2 TRP A 161 5680 5782 3488 1666 -273 -508 C
ATOM 54 CE3 TRP A 161 113.423 -33.199 3.075 1.00 46.01 C
ANISOU 54 CE3 TRP A 161 6650 6766 4065 1926 65 -300 C
ATOM 55 CZ3 TRP A 161 113.824 -33.081 4.402 1.00 48.63 C
ANISOU 55 CZ3 TRP A 161 7350 7205 3924 2328 -47 -387 C
ATOM 56 CH2 TRP A 161 114.460 -31.920 4.866 1.00 46.40 C
ANISOU 56 CH2 TRP A 161 7288 6874 3467 2456 -540 -725 C
ATOM 57 CZ2 TRP A 161 114.704 -30.858 4.033 1.00 52.29 C
ANISOU 57 CZ2 TRP A 161 7878 7446 4543 2165 -881 -938 C
ATOM 58 C TRP A 161 113.079 -35.146 -1.061 1.00 44.81 C
ANISOU 58 C TRP A 161 5482 6377 5165 823 361 82 C
ATOM 59 O TRP A 161 112.957 -36.096 -0.296 1.00 32.05 O
ANISOU 59 O TRP A 161 3934 4823 3422 986 617 249 O
ATOM 60 N ALA A 162 112.636 -35.165 -2.313 1.00 38.90 N
ANISOU 60 N ALA A 162 4511 5541 4729 583 366 79 N
ATOM 61 CA ALA A 162 111.962 -36.340 -2.848 1.00 32.10 C
ANISOU 61 CA ALA A 162 3446 4635 4114 484 635 230 C
ATOM 62 CB ALA A 162 111.342 -36.045 -4.204 1.00 29.26 C
ANISOU 62 CB ALA A 162 2889 4180 4049 282 544 147 C
ATOM 63 C ALA A 162 112.934 -37.518 -2.940 1.00 28.12 C
ANISOU 63 C ALA A 162 2926 4149 3609 420 658 356 C
ATOM 64 O ALA A 162 112.562 -38.672 -2.727 1.00 43.67 O
ANISOU 64 O ALA A 162 4827 6083 5681 446 923 521 O
ATOM 65 N TYR A 163 114.182 -37.219 -3.265 1.00 35.69 N
ANISOU 65 N TYR A 163 3926 5142 4492 337 387 288 N
ATOM 66 CA TYR A 163 115.191 -38.263 -3.410 1.00 37.74 C
ANISOU 66 CA TYR A 163 4154 5425 4761 297 387 391 C
ATOM 67 CB TYR A 163 116.431 -37.706 -4.095 1.00 38.32 C
ANISOU 67 CB TYR A 163 4181 5518 4860 160 100 305 C
ATOM 68 CG TYR A 163 117.442 -38.751 -4.494 1.00 44.80 C
ANISOU 68 CG TYR A 163 4918 6362 5743 112 113 401 C
ATOM 69 CD1 TYR A 163 117.067 -39.863 -5.243 1.00 40.62 C
ANISOU 69 CD1 TYR A 163 4289 5766 5378 45 299 480 C
ATOM 70 CE1 TYR A 163 117.997 -40.811 -5.620 1.00 38.72 C
ANISOU 70 CE1 TYR A 163 3991 5536 5186 34 312 551 C
ATOM 71 CZ TYR A 163 119.320 -40.647 -5.246 1.00 43.29 C
ANISOU 71 CZ TYR A 163 4570 6207 5672 85 148 562 C
ATOM 72 OH TYR A 163 120.264 -41.579 -5.611 1.00 50.07 O
ANISOU 72 OH TYR A 163 5349 7082 6592 102 171 634 O
ATOM 73 CE2 TYR A 163 119.709 -39.547 -4.507 1.00 43.52 C
ANISOU 73 CE2 TYR A 163 4662 6296 5577 129 -66 479 C
ATOM 74 CD2 TYR A 163 118.777 -38.609 -4.141 1.00 35.51 C
ANISOU 74 CD2 TYR A 163 3746 5256 4492 145 -88 391 C
ATOM 75 C TYR A 163 115.549 -38.845 -2.044 1.00 38.96 C
ANISOU 75 C TYR A 163 4484 5659 4660 543 487 506 C
ATOM 76 O TYR A 163 115.807 -40.033 -1.901 1.00 41.43 O
ANISOU 76 O TYR A 163 4783 5959 4999 581 644 664 O
ATOM 77 N TYR A 164 115.545 -37.991 -1.035 1.00 46.11 N
ANISOU 77 N TYR A 164 5587 6635 5298 742 383 420 N
ATOM 78 CA TYR A 164 115.822 -38.433 0.319 1.00 42.19 C
ANISOU 78 CA TYR A 164 5326 6231 4471 1050 457 515 C
ATOM 79 CB TYR A 164 116.127 -37.237 1.217 1.00 35.48 C
ANISOU 79 CB TYR A 164 4714 5453 3313 1260 172 312 C
ATOM 80 CG TYR A 164 116.033 -37.561 2.685 1.00 37.98 C
ANISOU 80 CG TYR A 164 5349 5880 3201 1671 297 398 C
ATOM 81 CD1 TYR A 164 116.852 -38.529 3.256 1.00 44.12 C
ANISOU 81 CD1 TYR A 164 6236 6725 3801 1833 288 542 C
ATOM 127 CZ ARG A 169 110.751 -40.536 5.196 1.00 73.48 C
ANISOU 127 CZ ARG A 169 9892 10168 7859 2342 2580 1598 C
ATOM 128 NH1 ARG A 169 111.080 -39.747 6.194 1.00 65.58 N
ANISOU 128 NH1 ARG A 169 9251 9327 6338 2708 2434 1478 N
ATOM 129 NH2 ARG A 169 109.488 -40.738 4.889 1.00 74.99 N
ANISOU 129 NH2 ARG A 169 9827 10208 8459 2186 2847 1697 N
ATOM 130 C ARG A 169 115.383 -44.385 3.716 1.00 58.53 C
ANISOU 130 C ARG A 169 7942 8201 6094 1998 2023 1935 C
ATOM 131 O ARG A 169 115.185 -44.908 4.766 1.00 65.30 O
ANISOU 131 O ARG A 169 8993 9016 6800 2265 2206 2100 O
ATOM 132 N LEU A 170 115.026 -44.935 2.579 1.00 64.83 N
ANISOU 132 N LEU A 170 8415 8816 7401 1645 2099 1934 N
ATOM 133 CA LEU A 170 114.442 -46.270 2.522 1.00 66.72 C
```

TABLE 9-continued

DMXAA-hSTING$^{S162A/G230I/Q266I}$ complex

| | |
|---|---|
| ANISOU 88 O TYR A 164 5666 6451 4638 1324 1136 956 O | ANISOU 133 CA LEU A 170 8536 8788 8027 1561 2373 2135 C |
| ATOM 89 N ILE A 165 113.460 −38.623 0.795 1.00 38.35 N | ATOM 134 CB LEU A 170 113.403 −46.378 1.413 1.00 61.59 C |
| ANISOU 89 N ILE A 165 4823 5687 4063 1200 1079 695 N | ANISOU 134 CB LEU A 170 7554 7930 7916 1209 2420 2026 C |
| ATOM 90 CA ILE A 165 112.250 −39.226 1.333 1.00 48.87 C | ATOM 135 CG LEU A 170 112.508 −45.194 1.087 1.00 71.61 C |
| ANISOU 90 CA ILE A 165 6130 6986 5453 1340 1550 914 C | ANISOU 135 CG LEU A 170 8705 9260 9243 1101 2378 1842 C |
| ATOM 91 CB ILE A 165 111.073 −38.225 1.292 1.00 50.77 C | ATOM 136 CD1 LEU A 170 111.586 −45.585 −0.051 1.00 68.42 C |
| ANISOU 91 CB ILE A 165 6306 7216 5770 1375 1640 802 C | ANISOU 136 CD1 LEU A 170 7995 8624 9378 783 2351 1731 C |
| ATOM 92 CG1 ILE A 165 111.337 −37.082 2.265 1.00 44.29 C | ATOM 137 CD2 LEU A 170 111.712 −44.780 2.307 1.00 80.57 C |
| ANISOU 92 CG1 ILE A 165 5812 6519 4499 1678 1458 628 C | ANISOU 137 CD2 LEU A 170 10009 10444 10158 1362 2602 1955 C |
| ATOM 93 CD1 ILE A 165 111.586 −37.560 3.697 1.00 39.10 C | ATOM 138 C LEU A 170 115.515 −47.308 2.240 1.00 69.65 C |
| ANISOU 93 CD1 ILE A 165 5490 5984 3380 2084 1659 792 C | ANISOU 138 C LEU A 170 8919 9103 8441 1559 2294 2235 C |
| ATOM 94 CG2 ILE A 165 109.747 −38.901 1.620 1.00 36.02 C | ATOM 139 O LEU A 170 115.288 −48.508 2.366 1.00 73.24 O |
| ANISOU 94 CG2 ILE A 165 4283 5283 4121 1452 2162 1048 C | ANISOU 139 O LEU A 170 9342 9342 9144 1564 2485 2402 O |
| ATOM 95 C ILE A 165 111.861 −40.515 0.609 1.00 45.97 C | ATOM 140 N ILE A 171 116.680 −46.842 1.825 1.00 62.81 N |
| ANISOU 95 C ILE A 165 5495 6467 5505 1121 1798 1107 C | ANISOU 140 N ILE A 171 8068 8400 7397 1538 1937 2067 N |
| ATOM 96 O ILE A 165 111.359 −41.459 1.219 1.00 50.30 O | ATOM 141 CA ILE A 171 117.687 −47.747 1.310 1.00 54.15 C |
| ANISOU 96 O ILE A 165 6046 6960 6105 1241 2190 1376 O | ANISOU 141 CA ILE A 171 6908 7231 6434 1489 1796 2085 C |
| ATOM 97 N GLY A 166 112.038 −40.538 −0.695 1.00 44.97 N | ATOM 142 CB ILE A 171 117.963 −47.458 −0.177 1.00 52.72 C |
| ANISOU 97 N GLY A 166 5153 6256 5680 816 1571 972 N | ANISOU 142 CB ILE A 171 6448 7015 6569 1155 1551 1813 C |
| ATOM 98 CA GLY A 166 111.595 −41.651 −1.494 1.00 46.42 C | ATOM 143 CG1 ILE A 171 117.425 −48.598 −1.044 1.00 62.70 C |
| ANISOU 98 CA GLY A 166 5078 6264 6296 609 1734 1068 C | ANISOU 143 CG1 ILE A 171 7536 8004 8283 965 1756 1885 C |
| ATOM 99 C GLY A 166 112.585 −42.674 −1.962 1.00 49.67 C | ATOM 144 CD1 ILE A 171 118.507 −49.561 −1.529 1.00 57.89 C |
| ANISOU 99 C GLY A 166 5480 6621 6769 510 1629 1113 C | ANISOU 144 CD1 ILE A 171 6904 7327 7763 989 1642 1893 C |
| ATOM 100 O GLY A 166 112.254 −43.542 −2.717 1.00 53.06 O | ATOM 145 CG2 ILE A 171 119.448 −47.210 −0.425 1.00 47.41 C |
| ANISOU 100 O GLY A 166 5720 6885 7556 335 1676 1125 O | ANISOU 145 CG2 ILE A 171 5763 6496 5757 1191 1178 1665 C |
| ATOM 101 N TYR A 167 113.828 −42.530 −1.579 1.00 50.40 N | ATOM 146 C ILE A 171 118.962 −47.701 2.147 1.00 54.13 C |
| ANISOU 101 N TYR A 167 5773 6844 6533 638 1456 1111 N | ANISOU 146 C ILE A 171 7132 7413 6022 1790 1530 2094 C |
| ATOM 102 CA TYR A 167 114.816 −43.511 −1.956 1.00 48.12 C | ATOM 147 O ILE A 171 119.615 −48.719 2.362 1.00 63.95 O |
| ANISOU 102 CA TYR A 167 5471 6516 6297 591 1379 1168 C | ANISOU 147 O ILE A 171 8446 8593 7258 1932 1560 2262 O |
| ATOM 103 CB TYR A 167 115.468 −43.187 −3.298 1.00 38.31 C | ATOM 148 N LEU A 172 119.304 −46.515 2.634 1.00 47.71 N |
| ANISOU 103 CB TYR A 167 4095 5280 5182 373 1082 962 C | ANISOU 148 N LEU A 172 6432 6809 4889 1902 1240 1899 N |
| ATOM 104 CG TYR A 167 116.491 −44.174 −3.702 1.00 31.13 C | ATOM 149 CA LEU A 172 120.481 −46.363 3.483 1.00 55.03 C |
| ANISOU 104 CG TYR A 167 3158 4335 4333 353 1032 1011 C | ANISOU 149 CA LEU A 172 7560 7907 5442 2203 906 1855 C |
| ATOM 105 CD1 TYR A 167 116.136 −45.410 −4.137 1.00 48.17 C | ATOM 150 CB LEU A 172 120.769 −44.890 3.787 1.00 51.97 C |
| ANISOU 105 CD1 TYR A 167 5228 6304 6772 296 1215 1103 C | ANISOU 150 CB LEU A 172 7228 7691 4825 2239 517 1552 C |
| ATOM 106 CE1 TYR A 167 117.051 −46.306 −4.489 1.00 29.30 C | ATOM 151 CG LEU A 172 121.240 −44.075 2.593 1.00 60.79 C |
| ANISOU 106 CE1 TYR A 167 2832 3867 4435 312 1174 1135 C | ANISOU 151 CG LEU A 172 8021 8805 6273 1871 225 1277 C |
| ATOM 107 CZ TYR A 167 118.347 −45.996 −4.425 1.00 32.82 C | ATOM 152 CD1 LEU A 172 121.711 −42.716 3.066 1.00 63.38 C |
| ANISOU 107 CZ TYR A 167 3322 4479 4669 384 966 1094 C | ANISOU 152 CD1 LEU A 172 8423 9256 6403 1942 −202 998 C |
| ATOM 108 OH TYR A 167 119.252 −46.919 −4.782 1.00 41.47 O | ATOM 153 CD2 LEU A 172 122.343 −44.817 1.861 1.00 56.04 C |
| ANISOU 108 OH TYR A 167 4392 5536 5827 429 943 1128 O | ANISOU 153 CD2 LEU A 172 7197 8175 5919 1760 96 1295 C |
| ATOM 109 CE2 TYR A 167 118.735 −44.792 −3.976 1.00 33.13 C | ATOM 154 C LEU A 172 120.473 −47.183 4.785 1.00 65.71 C |
| ANISOU 109 CE2 TYR A 167 3411 4700 4478 415 772 1010 C | ANISOU 154 C LEU A 172 9263 9274 6429 2632 1112 2153 C |
| ATOM 110 CD2 TYR A 167 117.812 −43.884 −3.629 1.00 35.52 C | ATOM 155 O LEU A 172 121.486 −47.819 5.101 1.00 73.94 O |
| ANISOU 110 CD2 TYR A 167 3759 5027 4712 401 797 960 C | ANISOU 155 O LEU A 172 10359 10336 7397 2788 927 2172 O |
| ATOM 111 C TYR A 167 115.842 −43.763 −0.887 1.00 37.61 C | ATOM 156 N PRO A 173 119.359 −47.157 5.551 1.00 63.91 N |
| ANISOU 111 C TYR A 167 4374 5314 4602 841 1308 1265 C | ANISOU 156 N PRO A 173 9182 8994 6108 2741 1464 2243 N |
| ATOM 112 O TYR A 167 119.198 −44.841 −0.408 1.00 54.20 O | ATOM 157 CA PRO A 173 119.343 −47.849 6.847 1.00 72.40 C |
| ANISOU 112 O TYR A 167 6559 7357 6679 981 1512 1486 O | ANISOU 157 CA PRO A 173 10522 10049 6939 3086 1637 2389 C |
| ATOM 113 N LEU A 168 116.588 −42.733 −0.580 1.00 44.24 N | ATOM 158 CB PRO A 173 117.858 −47.878 7.197 1.00 65.42 C |
| ANISOU 113 N LEU A 168 5316 6308 5186 905 994 1095 N | ANISOU 158 CB PRO A 173 9635 9040 6184 3085 2101 2538 C |
| ATOM 114 CA LEU A 168 117.719 −42.803 0.289 1.00 39.59 C | ATOM 159 CG PRO A 173 117.347 −46.601 6.632 1.00 61.93 C |
| ANISOU 114 CA LEU A 168 4913 5843 4285 1135 800 1115 C | ANISOU 159 CG PRO A 173 9081 8684 5764 2899 1985 2328 C |
| ATOM 115 CB LEU A 168 118.400 −41.456 0.341 1.00 47.60 C | ATOM 160 CD PRO A 173 118.106 −46.403 5.343 1.00 64.47 C |
| ANISOU 115 CB LEU A 168 5966 6970 5148 1134 394 864 C | ANISOU 160 CD PRO A 173 9175 9037 6281 2597 1689 2202 C |
| ATOM 116 CG LEU A 168 119.233 −41.056 −0.857 1.00 44.06 C | ATOM 161 C PRO A 173 119.890 −49.271 6.823 1.00 75.75 C |
| ANISOU 116 CG LEU A 168 5267 6494 4978 839 160 721 C | ANISOU 161 C PRO A 173 10928 10333 7519 3125 1751 2598 C |
| ATOM 117 CD1 LEU A 168 119.778 −39.714 −0.676 1.00 40.81 C | ATOM 162 O PRO A 173 120.603 −49.661 7.746 1.00 69.85 O |
| ANISOU 117 CD1 LEU A 168 4872 6139 4496 820 −216 502 C | ANISOU 162 O PRO A 173 10408 9657 6476 3430 1634 2625 O |
| ATOM 118 CD2 LEU A 168 120.359 −42.025 −1.031 1.00 39.25 C | ATOM 163 N GLU A 174 119.574 −50.033 5.784 1.00 71.87 N |
| ANISOU 118 CD2 LEU A 168 4554 5889 4471 830 132 819 C | ANISOU 163 N GLU A 174 10180 9635 7494 2829 1952 2717 N |
| ATOM 119 C LEU A 168 117.433 −43.219 1.695 1.00 51.39 C | ATOM 164 CA GLU A 174 119.989 −51.424 5.750 1.00 77.47 C |
| ANISOU 119 C LEU A 168 6698 7393 5478 1484 1044 1329 C | ANISOU 164 CA GLU A 174 10879 10170 8387 2868 2083 2907 C |
| ATOM 120 O LEU A 168 118.185 −43.944 2.269 1.00 53.79 O | ATOM 165 CB GLU A 174 118.806 −52.335 5.433 1.00 70.91 C |
| ANISOU 120 O LEU A 168 7112 7701 5626 1672 1059 1486 O | ANISOU 165 CB GLU A 174 9887 9034 8020 2679 2533 3099 C |
| ATOM 121 N ARG A 169 116.360 −42.735 2.272 1.00 49.82 N | ATOM 166 CG GLU A 174 117.692 −52.247 6.445 1.00 76.28 C |
| ANISOU 121 N ARG A 169 6594 7196 5139 1604 1255 1355 N | ANISOU 166 CG GLU A 174 10687 9682 8616 2845 2871 3235 C |
| ATOM 122 CA ARG A 169 116.081 −43.062 3.641 1.00 58.82 C | ATOM 167 CD GLU A 174 118.102 −52.781 7.800 1.00 106.62 C |
| ANISOU 122 CA ARG A 169 8044 8402 5903 1998 1521 1575 C | ANISOU 167 CD GLU A 174 14852 13588 12071 3264 2965 3408 C |
| ATOM 123 CB ARG A 169 115.277 −41.978 4.323 1.00 62.17 C | ATOM 168 OE1 GLU A 174 119.003 −53.649 7.853 1.00 116.02 O |
| ANISOU 123 CB ARG A 169 8633 8916 6074 2189 1601 1480 C | ANISOU 168 OE1 GLU A 174 16115 14740 13226 3359 2875 3486 O |
| ATOM 124 CG ARG A 169 113.825 −42.185 4.234 1.00 66.31 C | ATOM 169 OE2 GLU A 174 117.524 −52.331 8.815 1.00 111.19 O |
| ANISOU 124 CG ARG A 169 8984 9327 6885 2097 2077 1642 C | ANISOU 169 OE2 GLU A 174 15623 14251 12374 3520 3126 3464 O |
| ATOM 125 CD ARG A 169 113.106 −40.999 4.735 1.00 71.86 C | ATOM 170 C GLU A 174 121.100 −51.675 4.752 1.00 70.07 C |
| ANISOU 125 CD ARG A 169 9823 10112 7367 2285 2094 1497 C | ANISOU 170 C GLU A 174 9776 9235 7613 2735 1778 2820 C |
| ATOM 126 NE ARG A 169 111.689 −41.138 4.494 1.00 73.35 N | ATOM 171 O GLU A 174 121.312 −52.807 4.327 1.00 67.57 O |
| ANISOU 126 NE ARG A 169 9773 10134 7962 2140 2420 1597 N | ANISOU 171 O GLU A 174 9378 8720 7575 2678 1900 2947 O |
| ATOM 172 N LEU A 175 121.815 −50.628 4.370 1.00 66.42 N | ATOM 217 CD ARG A 180 128.430 −55.323 8.896 1.00104.25 C |

TABLE 9-continued

DMXAA-hSTING$^{S162A/G230I/Q266I}$ complex

| | |
|---|---|
| ANISOU 172 N LEU A 175 9245 8981 7009 2700 1375 2597 N | ANISOU 217 CD ARG A 180 14944 13973 10694 4509 188 2870 C |
| ATOM 173 CA LEU A 175 122.786 −50.788 3.303 1.00 68.74 C | ATOM 218 NE ARG A 180 129.208 −54.366 9.677 1.00117.14 C |
| ANISOU 173 CA LEU A 175 9304 9274 7539 2573 1111 2515 C | ANISOU 218 NE ARG A 180 16654 15840 12014 4697 −305 2605 N |
| ATOM 174 CB LEU A 175 123.215 −49.449 2.718 1.00 68.07 C | ATOM 219 CZ ARG A 180 129.199 −54.309 11.006 1.00126.76 C |
| ANISOU 174 CB LEU A 175 9007 9377 7477 2359 733 2150 C | ANISOU 219 CZ ARG A 180 18228 17147 12788 5052 −352 2618 C |
| ATOM 175 CG LEU A 175 124.122 −49.686 1.513 1.00 71.76 C | ATOM 220 NH1 ARG A 180 129.938 −53.405 11.636 1.00128.69 N |
| ANISOU 175 CG LEU A 175 9156 9821 8290 2143 555 1995 C | ANISOU 220 NH1 ARG A 180 18520 17576 12802 5203 −846 2328 N |
| ATOM 176 CD1 LEU A 175 123.326 −50.325 0.383 1.00 69.95 C | ATOM 221 NH2 ARG A 180 128.459 −55.158 11.705 1.00127.17 N |
| ANISOU 176 CD1 LEU A 175 8768 9360 8452 1857 862 2024 C | ANISOU 221 NH2 ARG A 180 18580 17087 12651 5265 98 2916 N |
| ATOM 177 CD2 LEU A 175 124.756 −48.395 1.065 1.00 68.69 C | ATOM 222 C ARG A 180 128.144 −58.234 5.012 1.00 87.42 C |
| ANISOU 177 CD2 LEU A 175 8560 9610 7929 1976 187 1697 C | ANISOU 222 C ARG A 180 12093 11064 10059 3799 888 3183 C |
| ATOM 178 C LEU A 175 124.015 −51.556 3.759 1.00 65.89 C | ATOM 223 O ARG A 180 128.988 −59.127 5.034 1.00 94.84 O |
| ANISOU 178 C LEU A 175 9011 8949 7076 2807 904 2530 C | ANISOU 223 O ARG A 180 13038 11929 11068 3960 791 3231 O |
| ATOM 179 O LEU A 175 124.388 −52.564 3.158 1.00 69.49 O | ATOM 224 N THR A 181 126.866 −58.451 4.740 1.00 86.09 N |
| ANISOU 179 O LEU A 175 9354 9244 7805 2764 986 2621 O | ANISOU 224 N THR A 181 11947 10691 10072 3599 1291 3316 N |
| ATOM 180 N GLN A 176 124.641 −51.066 4.822 1.00 70.35 N | ATOM 225 CA THR A 181 126.356 −59.771 4.418 1.00 85.37 C |
| ANISOU 180 N GLNA 176 9761 9708 7259 3057 615 2413 N | ANISOU 225 CA THR A 181 11877 10246 10313 3527 1631 3511 C |
| ATOM 181 CA GLN A 176 125.846 −51.681 5.358 1.00 74.29 C | ATOM 226 CB THR A 181 124.822 −59.762 4.401 1.00 88.62 C |
| ANISOU 181 CA GLN A 176 10324 10257 7646 3288 362 2398 C | ANISOU 226 CB THR A 181 12289 10472 10911 3305 2045 3634 C |
| ATOM 182 CB GLN A 176 126.271 −50.977 6.632 1.00 74.33 C | ATOM 227 OG1 THR A 181 124.342 −59.442 5.713 1.00 90.82 O |
| ANISOU 182 CB GLN A 176 10570 10451 7223 3555 52 2239 C | ANISOU 227 OG1 THR A 181 12807 10883 10816 3505 2191 3775 O |
| ATOM 183 CG GLN A 176 126.088 −49.491 6.565 1.00 81.07 C | ATOM 228 CG2 THR A 181 124.259 −61.106 3.970 1.00 79.42 C |
| ANISOU 183 CG GLN A 176 11365 11450 7989 3441 −207 1973 C | ANISOU 228 CG2 THR A 181 11085 8901 10592 3176 2351 3791 C |
| ATOM 184 CD GLN A 176 127.229 −48.750 7.209 1.00106.05 C | ATOM 229 C THR A 181 126.907 −60.281 3.085 1.00 91.37 C |
| ANISOU 184 CD GLN A 176 14535 14768 10990 3576 −765 1684 C | ANISOU 229 C THR A 181 12396 10852 11469 3386 1530 3376 C |
| ATOM 185 OE1 GLN A 176 128.292 −48.586 6.611 1.00119.42 O | ATOM 230 O THR A 181 127.056 −61.486 2.880 1.00 99.93 O |
| ANISOU 185 OE1 GLN A 176 15926 16500 12951 3450 −1110 1538 O | ANISOU 230 O THR A 181 13515 11672 12782 3429 1646 3478 O |
| ATOM 186 NE2 GLN A 176 127.025 −48.311 8.445 1.00114.32 N | ATOM 231 N TYR A 182 127.221 −59.363 2.179 1.00 86.87 N |
| ANISOU 186 NE2 GLN A 176 15909 15889 11639 3841 −844 1595 N | ANISOU 231 N TYR A 182 11584 10443 10978 3238 1318 3139 N |
| ATOM 187 C GLN A 176 125.631 −53.151 5.654 1.00 71.28 C | ATOM 232 CA TYR A 182 127.757 −59.771 0.889 1.00 76.62 C |
| ANISOU 187 C GLN A 176 10083 9667 7334 3407 715 2679 C | ANISOU 232 CA TYR A 182 10057 9032 10022 3144 1244 2982 C |
| ATOM 188 O GLN A 176 126.494 −53.978 5.381 1.00 82.45 O | ATOM 233 CB TYR A 182 127.691 −58.644 −0.130 1.00 78.14 C |
| ANISOU 188 O GLN A 176 11416 11018 8892 3466 614 2715 O | ANISOU 233 CB TYR A 182 9988 9383 10317 2933 1128 2754 C |
| ATOM 189 N ALA A 177 124.472 −53.466 6.219 1.00 79.72 N | ATOM 234 CG TYR A 182 128.133 −59.095 −1.500 1.00 64.81 C |
| ANISOU 189 N ALA A 177 11337 10618 8334 3443 1136 2871 N | ANISOU 234 CG TYR A 182 8089 7578 8959 2858 1113 2575 C |
| ATOM 190 CA ALA A 177 124.161 −54.837 6.594 1.00 86.84 C | ATOM 235 CD1 TYR A 182 127.226 −59.678 −2.371 1.00 72.08 C |
| ANISOU 190 CA ALA A 177 12361 11297 9338 3547 1496 3149 C | ANISOU 235 CD1 TYR A 182 9003 8169 10215 2668 1334 2537 C |
| ATOM 191 CB ALA A 177 122.863 −54.907 7.367 1.00 62.05 C | ATOM 236 CE1 TYR A 182 127.611 −60.104 −3.619 1.00 79.90 C |
| ANISOU 191 CB ALA A 177 9383 8074 6121 3609 1934 3329 C | ANISOU 236 CE1 TYR A 182 9852 9055 11451 2640 1306 2327 C |
| ATOM 192 C ALA A 177 124.083 −55.708 5.354 1.00 83.93 C | ATOM 237 CZ TYR A 182 128.930 −59.958 −4.010 1.00 75.04 C |
| ANISOU 192 C ALA A 177 11746 10671 9473 3283 1647 3217 C | ANISOU 237 CZ TYR A 182 9071 8683 10756 2793 1115 2189 C |
| ATOM 193 O ALA A 177 124.414 −56.887 5.392 1.00 82.55 O | ATOM 238 OH TYR A 182 129.326 −60.381 −5.254 1.00 70.06 O |
| ANISOU 193 O ALA A 177 11613 10320 9433 3367 1751 3366 O | ANISOU 238 OH TYR A 182 8325 7977 10316 2797 1125 1973 O |
| ATOM 194 N ARG A 178 123.633 −55.122 4.252 1.00 74.77 N | ATOM 239 CE2 TYR A 182 129.860 −59.388 −3.159 1.00 65.52 C |
| ANISOU 194 N ARG A 178 10342 9475 8590 2979 1647 3095 N | ANISOU 239 CE2 TYR A 182 7811 7793 9290 2944 903 2244 C |
| ATOM 195 CA ARG A 178 123.541 −55.858 3.000 1.00 77.3 C | ATOM 240 CD2 TYR A 182 129.457 −58.962 −1.912 1.00 59.62 C |
| ANISOU 195 CA ARG A 178 10441 9544 9393 2740 1753 3101 C | ANISOU 240 CD2 TYR A 182 7232 7129 8290 2982 873 2419 C |
| ATOM 196 CB ARG A 178 122.688 −55.099 2.003 1.00 70.71 C | ATOM 241 C TYR A 182 129.199 −60.182 1.050 1.00 73.36 C |
| ANISOU 196 CB ARG A 178 9394 8658 8815 2421 1818 2983 C | ANISOU 241 C TYR A 182 9603 8742 9528 3399 970 2927 C |
| ATOM 197 CG ARG A 178 121.235 −55.179 2.331 1.00 70.83 C | ATOM 242 O TYR A 182 129.660 −61.154 0.451 1.00 71.50 O |
| ANISOU 197 CG ARG A 178 9426 8515 8971 2286 2188 3091 C | ANISOU 242 O TYR A 182 9317 8321 9530 3451 998 2904 O |
| ATOM 198 CD ARG A 178 120.451 −54.248 1.460 1.00 63.52 C | ATOM 243 N ASN A 183 129.908 −59.427 1.879 1.00 75.52 N |
| ANISOU 198 CD ARG A 178 8303 7593 8240 1990 2187 2937 C | ANISOU 243 N ASN A 183 9894 9318 9482 3561 682 2880 N |
| ATOM 199 NE ARG A 178 120.408 −54.682 0.071 1.00 54.03 N | ATOM 244 CA ASN A 183 131.330 −59.631 2.092 1.00 69.08 C |
| ANISOU 199 NE ARG A 178 6879 6161 7488 1733 2161 2833 N | ANISOU 244 CA ASN A 183 8979 8648 8621 3787 357 2794 C |
| ATOM 200 CZ ARG A 178 120.571 −53.870 −0.966 1.00 60.81 C | ATOM 245 CB ASN A 183 131.906 −58.503 2.939 1.00 64.57 C |
| ANISOU 200 CZ ARG A 178 7533 7161 8411 1504 1907 2490 C | ANISOU 245 CB ASN A 183 8386 8395 7752 3884 −8 2678 C |
| ATOM 201 NH1 ARG A 178 120.797 −52.582 −0.759 1.00 62.71 N | ATOM 246 CG ASN A 183 132.200 −57.271 2.126 1.00 72.76 C |
| ANISOU 201 NH1 ARG A 178 7770 7707 8349 1502 1700 2333 N | ANISOU 246 CG ASN A 183 9081 9637 8927 3668 −202 2431 C |
| ATOM 202 NH2 ARG A 178 120.511 −54.344 −2.207 1.00 62.39 N | ATOM 247 OD1 ASN A 183 132.154 −57.309 0.899 1.00 77.79 O |
| ANISOU 202 NH2 ARG A 178 7557 7179 8969 1301 1857 2304 N | ANISOU 247 OD1 ASN A 183 9484 10216 9858 3487 −68 2348 O |
| ATOM 203 C ARG A 178 124.917 −56.081 2.422 1.00 76.19 C | ATOM 248 ND2 ASN A 183 132.519 −56.170 2.801 1.00 75.78 N |
| ANISOU 203 C ARG A 178 10179 9475 9296 2822 1423 2977 C | ANISOU 248 ND2 ASN A 183 9437 10249 9107 3688 −522 2301 N |
| ATOM 204 O ARG A 178 125.188 −57.090 1.777 1.00 71.95 O | ATOM 249 C ASN A 183 131.663 −60.965 2.729 1.00 81.86 C |
| ANISOU 204 O ARG A 178 9563 8721 9055 2788 1493 3009 O | ANISOU 249 C ASN A 183 10818 10075 10210 4039 425 2988 C |
| ATOM 205 N ILE A 179 125.780 −55.109 2.659 1.00 69.81 N | ATOM 250 O ASN A 183 132.805 −61.217 3.100 1.00 79.94 O |
| ANISOU 205 N ILE A 179 9332 8969 8224 2930 1049 2805 N | ANISOU 250 O ASN A 183 10529 9936 9910 4267 152 2949 O |
| ATOM 206 CA ILE A 179 127.132 −55.157 2.158 1.00 64.05 C | ATOM 251 N GLN A 184 130.651 −61.812 2.850 1.00 98.06 N |
| ANISOU 206 CA ILE A 179 8408 8354 7574 2999 716 2654 C | ANISOU 251 N GLN A 184 13084 11832 12344 3986 788 3197 N |
| ATOM 207 CB ILE A 179 127.735 −53.763 2.131 1.00 52.00 C | ATOM 252 CA GLN A 184 130.783 −63.098 3.496 1.00107.67 C |
| ANISOU 207 CB ILE A 179 6717 7128 5910 2966 332 2414 C | ANISOU 252 CA GLN A 184 14534 12827 13549 4203 908 3421 C |
| ATOM 208 CG1 ILE A 179 127.131 −52.974 0.972 1.00 55.85 C | ATOM 253 CB GLN A 184 129.845 −63.171 4.689 1.00 93.19 C |
| ANISOU 208 CG1 ILE A 179 6964 7618 6641 2634 404 2275 C | ANISOU 253 CB GLN A 184 13011 10950 11449 4270 1158 3675 C |
| ATOM 209 CD1 ILE A 179 127.736 −51.607 0.785 1.00 57.56 C | ATOM 254 CG GLN A 184 130.441 −63.860 5.876 1.00116.71 C |
| ANISOU 209 CD1 ILE A 179 6966 8087 6818 2505 49 2002 C | ANISOU 254 CG GLN A 184 16254 13943 14149 4629 1085 3864 C |
| ATOM 210 CG2 ILE A 179 129.243 −53.838 2.014 1.00 60.05 C | ATOM 255 CD GLN A 184 130.816 −62.879 6.956 1.00130.90 C |
| ANISOU 210 CG2 ILE A 179 7537 8283 6998 3078 −27 2268 C | ANISOU 255 CD GLN A 184 18178 16087 15471 4835 818 3801 C |
| ATOM 211 C ILE A 179 127.969 −56.090 3.021 1.00 74.21 C | ATOM 256 OE1 GLN A 184 130.085 −62.710 7.930 1.00137.40 O |

TABLE 9-continued

DMXAA-hSTING<sup>S162A/G230I/Q266I</sup> complex

| | |
|---|---|
| ANISOU 211 C ILE A 179 9866 9625 8705 3289 626 2753 C | ANISOU 256 OE1 GLN A 184 19262 16946 15997 4934 1018 3959 O |
| ATOM 212 O ILE A 179 128.676 −56.964 2.508 1.00 74.73 O | ATOM 257 NE2 GLN A 184 131.951 −62.210 6.784 1.00 131.97 N |
| ANISOU 212 O ILE A 179 9826 9581 8985 3338 601 2760 O | ANISOU 257 NE2 GLN A 184 18113 16472 15558 4902 364 3553 N |
| ATOM 213 N ARG A 180 127.874 −55.897 4.334 1.00 74.18 N | ATOM 258 C GLN A 184 130.416 −64.214 2.537 1.00 116.25 C |
| ANISOU 213 N ARG A 180 10139 9729 8319 3502 581 2819 N | ANISOU 258 C GLN A 184 15577 13535 15060 4073 1146 3449 C |
| ATOM 214 CA ARG A 180 128.508 −56.784 5.303 1.00 80.62 C | ATOM 259 O GLN A 184 131.260 −65.020 2.146 1.00 124.03 O |
| ANISOU 214 CA ARG A 180 11173 10521 8939 3809 527 2947 C | ANISOU 259 O GLN A 184 16506 14415 16206 4215 1038 3401 O |
| ATOM 215 CB ARG A 180 128.054 −56.445 6.719 1.00 85.92 C | ATOM 260 N HIS A 185 129.139 −64.252 2.171 1.00 110.66 N |
| ANISOU 215 CB ARG A 180 12183 11301 9161 4036 574 3023 C | ANISOU 260 N HIS A 185 14884 12608 14552 3806 1452 3504 N |
| ATOM 216 CG ARG A 180 128.933 −55.468 7.468 1.00 91.95 C | ATOM 261 C HIS A 185 129.383 −65.406 0.017 1.00 92.33 C |
| ANISOU 216 CG ARG A 180 12994 12342 9601 4219 84 2787 C | ANISOU 261 C HIS A 185 12318 9864 12900 3635 1469 3216 C |
| ATOM 262 O HIS A 185 129.521 −66.485 −0.550 1.00 98.64 O | ATOM 307 CA LEU A 190 134.820 −61.671 −4.986 1.00 95.91 C |
| ANISOU 262 O HIS A 185 13138 10359 13983 3667 1510 3178 O | ANISOU 307 CA LEU A 190 11460 10243 14740 3450 −524 −1121 C |
| ATOM 263 CA HIS A 185 128.615 −65.303 1.318 1.00 104.80 C | ATOM 308 CB LEU A 190 134.059 −60.637 −4.161 1.00 87.74 C |
| ANISOU 263 CA HIS A 185 14115 11454 14250 3652 1655 3503 C | ANISOU 308 CB LEU A 190 10475 9357 13507 3235 −462 −822 C |
| ATOM 264 CB HIS A 185 127.139 −65.062 1.013 1.00 112.81 C | ATOM 309 CG LEU A 190 134.612 −59.218 −4.144 1.00 92.31 C |
| ANISOU 264 CB HIS A 185 15091 12281 15489 3324 1935 3529 C | ANISOU 309 CG LEU A 190 10820 10362 13892 3202 −451 −846 C |
| ATOM 265 CG HIS A 185 126.246 −65.249 2.193 1.00 126.75 C | ATOM 310 CD1 LEU A 190 133.896 −58.331 −5.146 1.00 86.41 C |
| ANISOU 265 CG HIS A 185 17047 13979 17133 3539 2220 3828 C | ANISOU 310 CD1 LEU A 190 9935 9875 13020 2917 −276 −940 C |
| ATOM 266 ND1 HIS A 185 126.578 −64.797 3.455 1.00 131.78 N | ATOM 311 CD2 LEU A 190 134.456 −58.672 −2.758 1.00 97.93 C |
| ANISOU 266 ND1 HIS A 185 17870 14903 17298 3592 2178 3979 N | ANISOU 311 CD2 LEU A 190 11710 11065 14436 3242 −543 −546 C |
| ATOM 267 CE1 HIS A 185 125.611 −65.104 4.297 1.00 133.99 C | ATOM 312 C LEU A 190 136.321 −61.547 −4.736 1.00 101.40 C |
| ANISOU 267 CE1 HIS A 185 18294 15058 17557 3587 2513 4234 C | ANISOU 312 C LEU A 190 11962 11085 15481 3764 −636 −1224 C |
| ATOM 268 NE2 HIS A 185 124.662 −65.741 3.630 1.00 135.39 N | ATOM 313 O LEU A 190 137.007 −60.772 −5.406 1.00 107.19 O |
| ANISOU 268 NE2 HIS A 185 18348 14872 18224 3310 2756 4257 N | ANISOU 313 O LEU A 190 12395 12145 16186 3782 −548 −1390 O |
| ATOM 269 CD2 HIS A 185 125.037 −65.845 2.314 1.00 131.80 C | ATOM 314 N ARG A 191 136.823 −62.322 −3.775 1.00 102.35 N |
| ANISOU 269 CD2 HIS A 185 17704 14302 18072 3152 2554 3989 C | ANISOU 314 N ARG A 191 12243 10934 15711 4020 −830 −1108 N |
| ATOM 270 N TYR A 186 129.888 −64.273 −0.451 1.00 97.02 N | ATOM 315 CA ARG A 191 138.241 −62.311 −3.423 1.00 92.68 C |
| ANISOU 270 N TYR A 186 12866 8573 15423 3009 47 783 N | ANISOU 315 CA ARG A 191 10820 9781 14614 4348 −1021 −1202 C |
| ATOM 271 CA TYR A 186 130.601 −64.247 −1.715 1.00 95.33 C | ATOM 316 CB ARG A 191 139.070 −62.902 −4.549 1.00 82.16 C |
| ANISOU 271 CA TYR A 186 12399 8574 15249 3003 −192 278 C | ANISOU 316 CB ARG A 191 9253 8467 13495 4543 −934 −1528 C |
| ATOM 272 CB TYR A 186 129.839 −63.409 −2.733 1.00 98.17 C | ATOM 317 CG ARG A 191 138.862 −64.381 −4.694 1.00 92.03 C |
| ANISOU 272 CB TYR A 186 12474 9203 15622 2672 −134 91 C | ANISOU 317 CG ARG A 191 10784 9297 14886 4699 −989 −1602 C |
| ATOM 273 CG TYR A 186 128.475 −63.961 −3.053 1.00 109.28 C | ATOM 318 CD ARG A 191 138.932 −64.798 −6.139 1.00 85.99 C |
| ANISOU 273 CG TYR A 186 13823 10238 17462 2362 −43 209 C | ANISOU 318 CD ARG A 191 9943 8559 14170 4746 −801 −1933 C |
| ATOM 274 CD1 TYR A 186 128.331 −65.017 −3.935 1.00 107.32 C | ATOM 319 NE ARG A 191 139.533 −66.117 −6.261 1.00 98.85 N |
| ANISOU 274 CD1 TYR A 186 13548 9632 17598 2305 −239 −55 C | ANISOU 319 NE ARG A 191 11687 9851 16021 5090 −914 −2097 N |
| ATOM 275 CE1 TYR A 186 127.093 −65.536 −4.236 1.00 108.04 C | ATOM 320 CZ ARG A 191 140.827 −66.354 −6.078 1.00 112.46 C |
| ANISOU 275 CE1 TYR A 186 13541 9324 18185 2007 −237 30 C | ANISOU 320 CZ ARG A 191 13216 11667 17849 5318 −939 −2112 C |
| ATOM 276 CZ TYR A 186 125.969 −64.996 −3.654 1.00 111.82 C | ATOM 321 NH1 ARG A 191 141.302 −67.586 −6.203 1.00 104.32 N |
| ANISOU 276 CZ TYR A 186 13903 9779 18806 1761 30 414 C | ANISOU 321 NH1 ARG A 191 12332 10363 16942 5534 −997 −2201 N |
| ATOM 277 OH TYR A 186 124.734 −65.519 −3.964 1.00 113.56 O | ATOM 322 NH2 ARG A 191 141.648 −65.361 −5.766 1.00 120.30 N |
| ANISOU 277 OH TYR A 186 13941 9566 19641 1451 18 506 O | ANISOU 322 NH2 ARG A 191 13851 13000 18856 5312 −921 −2030 N |
| ATOM 278 CE2 TYR A 186 126.219 −63.939 −2.768 1.00 108.67 C | ATOM 323 C ARG A 191 138.706 −60.903 −3.099 1.00 99.97 C |
| ANISOU 278 CE2 TYR A 186 13559 9758 17974 1843 291 695 C | ANISOU 323 C ARG A 191 11480 11061 15441 4282 −1079 −1157 C |
| ATOM 279 CD2 TYR A 186 127.330 −63.429 −2.471 1.00 108.19 C | ATOM 324 O ARG A 191 139.677 −60.403 −3.665 1.00 100.88 O |
| ANISOU 279 CD2 TYR A 186 13640 10074 17392 2142 220 576 C | ANISOU 324 O ARG A 191 11198 11411 15722 4363 −1053 −1338 O |
| ATOM 280 C TYR A 186 132.019 −63.730 −1.573 1.00 88.95 C | ATOM 325 N GLY A 192 137.979 −60.268 −2.191 1.00 97.78 N |
| ANISOU 280 C TYR A 186 11556 8110 14130 3307 −379 80 C | ANISOU 325 N GLY A 192 11432 10798 14923 4142 −1134 −901 N |
| ATOM 281 O TYR A 186 132.646 −63.346 −2.558 1.00 79.91 O | ATOM 326 CA GLY A 192 138.250 −58.906 −1.790 1.00 92.08 C |
| ANISOU 281 O TYR A 186 10159 7254 12948 3310 −476 −285 O | ANISOU 326 CA GLY A 192 10543 10359 14083 4067 −1236 −852 C |
| ATOM 282 N ASN A 187 132.522 −63.715 −0.344 1.00 94.49 N | ATOM 327 C GLY A 192 137.107 −58.429 −0.924 1.00 101.10 C |
| ANISOU 282 N ASN A 187 12515 8757 14629 3581 −431 330 N | ANISOU 327 C GLY A 192 12056 11461 14896 3918 −1200 −565 C |
| ATOM 283 CA ASN A 187 133.897 −63.300 −0.102 1.00 100.37 C | ATOM 328 O GLY A 192 136.419 −59.231 −0.292 1.00 106.23 O |
| ANISOU 283 CA ASN A 187 13199 9752 15186 3887 −692 148 C | ANISOU 328 O GLY A 192 13090 11818 15455 3977 −1160 −356 O |
| ATOM 284 CB ASN A 187 134.194 −63.283 1.396 1.00 107.63 C | ATOM 329 N ALA A 193 136.881 −57.124 −0.914 1.00 99.06 N |
| ANISOU 284 CB ASN A 187 14510 10537 15846 4200 −800 467 C | ANISOU 329 N ALA A 193 11682 11476 14479 3733 −1174 −535 N |
| ATOM 285 CG ASN A 187 135.670 −63.413 1.701 1.00 114.91 C | ATOM 330 CA ALA A 193 135.786 −56.563 −0.146 1.00 92.70 C |
| ANISOU 285 CG ASN A 187 15406 11504 16752 4586 −1183 271 C | ANISOU 330 CA ALA A 193 11211 10661 13349 3617 −1094 −272 C |
| ATOM 286 OD1 ASN A 187 136.466 −62.528 1.387 1.00 111.24 O | ATOM 331 CB ALA A 193 136.239 −56.239 1.268 1.00 85.64 C |
| ANISOU 286 OD1 ASN A 187 14625 11390 16252 4610 −1357 30 O | ANISOU 331 CB ALA A 193 10620 9667 12252 3914 −1438 −133 C |
| ATOM 287 ND2 ASN A 187 136.045 −64.525 2.327 1.00 121.75 N | ATOM 332 C ALA A 193 135.260 −55.317 −0.834 1.00 82.52 C |
| ANISOU 287 ND2 ASN A 187 16583 11983 17693 4893 −1323 390 N | ANISOU 332 C ALA A 193 9700 9692 11962 3302 −913 −318 C |
| ATOM 288 C ASN A 187 134.878 −64.206 −0.840 1.00 102.41 C | ATOM 333 O ALA A 193 136.031 −54.500 −1.331 1.00 84.82 O |
| ANISOU 288 C ASN A 187 13316 9898 15696 4082 −877 −186 C | ANISOU 333 O ALA A 193 9647 10216 12364 3256 −994 −489 O |
| ATOM 289 O ASN A 187 135.930 −63.760 −1.297 1.00 113.67 O | ATOM 334 N VAL A 194 133.944 −55.176 −0.876 1.00 67.94 N |
| ANISOU 289 O ASN A 187 14465 11610 17113 4217 −1016 −463 O | ANISOU 334 N VAL A 194 8027 7835 9954 3087 −658 −148 N |
| ATOM 290 N ASN A 188 134.519 −65.479 −0.963 1.00 93.40 N | ATOM 335 CA VAL A 194 133.371 −53.956 −1.400 1.00 69.10 C |
| ANISOU 290 N ASN A 188 12352 8316 14820 4101 −857 −147 N | ANISOU 335 CA VAL A 194 8018 8262 9975 2821 −519 −166 C |
| ATOM 291 CA ASN A 188 135.336 −66.437 −1.697 1.00 101.81 C | ATOM 336 CB VAL A 194 131.990 −54.192 −2.040 1.00 63.56 C |
| ANISOU 291 CA ASN A 188 13336 9222 16127 4308 −1017 −472 C | ANISOU 336 CB VAL A 194 7347 7519 9283 2553 −224 −92 C |
| ATOM 292 CB ASN A 188 134.932 −67.872 −1.346 1.00 102.42 C | ATOM 337 CG1 VAL A 194 131.949 −55.557 −2.694 1.00 58.36 C |
| ANISOU 292 CB ASN A 188 13733 8706 16476 4384 −1043 −307 C | ANISOU 337 CG1 VAL A 194 6670 6625 8881 2563 −173 −202 C |
| ATOM 293 CG ASN A 188 135.496 −68.324 −0.020 1.00 110.24 C | ATOM 338 CG2 VAL A 194 130.893 −54.095 −1.012 1.00 78.10 C |
| ANISOU 293 CG ASN A 188 15056 9462 17367 4735 −1177 −19 C | ANISOU 338 CG2 VAL A 194 9501 9220 10954 2549 −89 236 C |
| ATOM 294 OD1 ASN A 188 136.561 −67.874 0.400 1.00 114.87 O | ATOM 339 C VAL A 194 133.304 −52.956 −0.252 1.00 68.18 C |
| ANISOU 294 OD1 ASN A 188 15584 10284 17776 5024 −1386 −102 O | ANISOU 339 C VAL A 194 8123 8202 9581 2921 −671 −1 C |
| ATOM 295 ND2 ASN A 188 134.785 −69.225 0.651 1.00 96.05 N | ATOM 340 O VAL A 194 133.091 −53.330 0.905 1.00 70.06 O |

TABLE 9-continued

DMXAA-hSTING$^{S162A/G230I/Q266I}$ complex

ANISOU 295 ND2 ASN A 188 13615 7167 15712 4725 -1073 333 N
ATOM 296 C ASN A 188 135.243 -66.232 -3.202 1.00 84.41 C
ANISOU 296 C ASN A 188 10844 7225 14004 4133 -947 -860 C
ATOM 297 O ASN A 188 136.102 -66.672 -3.959 1.00 88.71 O
ANISOU 297 O ASN A 188 11265 7791 14649 4351 -1030 -1187 O
ATOM 298 N LEU A 189 134.182 -65.560 -3.625 1.00 92.06 N
ANISOU 298 N LEU A 189 11736 8334 14910 3776 -786 -814 N
ATOM 299 CA LEU A 189 133.913 -65.354 -5.041 1.00 95.19 C
ANISOU 299 CA LEU A 189 11957 8887 15326 3619 -744 -1159 C
ATOM 300 CB LEU A 189 132.409 -65.404 -5.294 1.00 88.17 C
ANISOU 300 CB LEU A 189 11124 7793 14585 3248 -679 -1047 C
ATOM 301 CG LEU A 189 131.920 -64.906 -6.650 1.00 83.74 C
ANISOU 301 CG LEU A 189 10426 7430 13960 3061 -682 -1363 C
ATOM 302 CD1 LEU A 189 132.484 -65.766 -7.773 1.00 81.76 C
ANISOU 302 CD1 LEU A 189 10252 7028 13785 3290 -829 -1794 C
ATOM 303 CD2 LEU A 189 130.402 -64.890 -6.692 1.00 78.74 C
ANISOU 303 CD2 LEU A 189 9796 6570 13554 2691 -673 -1205 C
ATOM 304 C LEU A 189 134.476 -64.020 -5.515 1.00 104.41 C
ANISOU 304 C LEU A 189 12847 10608 16216 3602 -650 -1299 C
ATOM 305 O LEU A 189 135.013 -63.908 -6.619 1.00 103.93 O
ANISOU 305 O LEU A 189 12643 10736 16110 3698 -609 -1623 O
ATOM 306 N LEU A 190 134.340 -63.006 -4.669 1.00 103.74 N
ANISOU 306 N LEU A 190 12716 10757 15943 3499 -596 -1038 N
ATOM 352 OE1 GLN A 196 131.505 -52.981 5.539 1.00 131.50 O
ANISOU 352 OE1 GLN A 196 18420 15455 16088 4126 -678 1202 O
ATOM 353 NE2 GLN A 196 130.490 -51.867 7.206 1.00 139.63 N
ANISOU 353 NE2 GLN A 196 20266 16448 16341 4524 -490 1584 N
ATOM 354 C GLN A 196 129.672 -48.796 2.598 1.00 96.40 C
ANISOU 354 C GLN A 196 12760 12066 11802 2921 -267 787 C
ATOM 355 O GLN A 196 128.565 -48.804 3.132 1.00 105.45 O
ANISOU 355 O GLN A 196 14161 13133 12773 2970 54 1058 O
ATOM 356 N ARG A 197 130.077 -47.801 1.818 1.00 74.18 N
ANISOU 356 N ARG A 197 9617 9488 9081 2715 -421 561 N
ATOM 357 CA ARG A 197 129.212 -46.655 1.585 1.00 65.60 C
ANISOU 357 CA ARG A 197 8499 8575 7852 2547 -266 606 C
ATOM 358 CB ARG A 197 129.997 -45.349 1.706 1.00 78.79 C
ANISOU 358 CB ARG A 197 10127 10376 9435 2574 -627 432 C
ATOM 359 CG ARG A 197 130.910 -45.302 2.922 1.00 86.12 C
ANISOU 359 CG ARG A 197 11394 11139 10188 2946 -1055 401 C
ATOM 360 CD ARG A 197 130.852 -43.954 3.628 1.00 98.27 C
ANISOU 360 CD ARG A 197 13203 12701 11433 3083 -1308 376 C
ATOM 361 NE ARG A 197 131.678 -42.934 2.985 1.00 111.48 N
ANISOU 361 NE ARG A 197 14490 14493 13375 2876 -1615 140 N
ATOM 362 CZ ARG A 197 131.689 -41.650 3.331 1.00 110.43 C
ANISOU 362 CZ ARG A 197 14483 14374 13101 2908 -1868 73 C
ATOM 363 NH1 ARG A 197 132.476 -40.796 2.691 1.00 112.62 N
ANISOU 363 NH1 ARG A 197 14356 14716 13718 2688 -2115 -109 N
ATOM 364 NH2 ARG A 197 130.930 -41.218 4.314 1.00 95.25 N
ANISOU 364 NH2 ARG A 197 13098 12379 10712 3176 -1847 202 N
ATOM 365 C ARG A 197 128.520 -46.746 0.230 1.00 60.72 C
ANISOU 365 C ARG A 197 7503 8088 7481 2186 2 545 C
ATOM 366 O ARG A 197 128.893 -47.552 -0.617 1.00 60.04 O
ANISOU 366 O ARG A 197 7172 7984 7657 2070 17 411 O
ATOM 367 N LEU A 198 127.499 -45.918 0.039 1.00 53.27 N
ANISOU 367 N LEU A 198 6547 7257 6435 2048 187 630 N
ATOM 368 CA LEU A 198 126.854 -45.814 -1.255 1.00 59.13 C
ANISOU 368 CA LEU A 198 6969 8125 7374 1738 345 540 C
ATOM 369 CB LEU A 198 125.347 -45.638 -1.105 1.00 62.03 C
ANISOU 369 CB LEU A 198 7383 8456 7729 1665 635 752 C
ATOM 370 CG LEU A 198 124.412 -46.093 -2.233 1.00 57.38 C
ANISOU 370 CG LEU A 198 6486 8510 7850 7442 1397 780 708 C
ATOM 371 CD1 LEU A 198 123.314 -45.059 -2.436 1.00 61.47 C
ANISOU 371 CD1 LEU A 198 6959 8487 7910 1287 898 784 C
ATOM 372 CD2 LEU A 198 125.127 -46.373 -3.550 1.00 49.71 C
ANISOU 372 CD2 LEU A 198 5311 6971 6607 1246 614 413 C
ATOM 373 C LEU A 198 127.437 -44.595 -1.938 1.00 54.18 C
ANISOU 373 C LEU A 198 6163 7726 6698 1613 176 352 C
ATOM 374 O LEU A 198 127.406 -43.495 -1.394 1.00 58.50 O
ANISOU 374 O LEU A 198 6844 8340 7042 1678 78 391 O
ATOM 375 N TYR A 199 127.970 -44.794 -3.133 1.00 48.96 N
ANISOU 375 N TYR A 199 5225 7158 6219 1455 160 160 N
ATOM 376 CA TYR A 199 128.545 -43.689 -3.867 1.00 47.41 C
ANISOU 376 CA TYR A 199 4847 7153 6014 1333 78 30 C
ATOM 377 CB TYR A 199 129.894 -44.078 -4.435 1.00 45.79 C
ANISOU 377 CB TYR A 199 4415 6969 6015 1355 -2 -134 C
ATOM 378 CG TYR A 199 130.883 -44.256 -3.329 1.00 52.57 C
ANISOU 378 CG TYR A 199 5336 7703 6935 1568 -261 -129 C
ATOM 379 CD1 TYR A 199 131.008 -45.480 -2.673 1.00 59.93 C
ANISOU 340 O VAL A 194 8749 8231 9640 3145 -738 210 O
ATOM 341 N SER A 195 133.521 -51.687 -0.574 1.00 62.31 N
ANISOU 341 N SER A 195 7170 7718 8787 2789 -730 -97 N
ATOM 342 CA SER A 195 133.480 -50.635 0.426 1.00 66.35 C
ANISOU 342 CA SER A 195 7899 8274 9039 2890 -925 7 C
ATOM 343 CB SER A 195 133.952 -49.319 -0.179 1.00 65.76 C
ANISOU 343 CB SER A 195 7486 8453 9046 2711 -1018 -151 C
ATOM 344 OG SER A 195 134.845 -49.562 -1.243 1.00 76.90 O
ANISOU 344 OG SER A 195 8462 9955 10800 2629 -985 -353 O
ATOM 345 C SER A 195 132.055 -50.507 0.951 1.00 78.03 C
ANISOU 345 C SER A 195 9723 9700 10227 2841 -653 272 C
ATOM 346 O SER A 195 131.102 -50.967 0.316 1.00 72.71 O
ANISOU 346 O SER A 195 8980 9006 9641 2634 -332 341 O
ATOM 347 N GLN A 196 131.902 -49.867 2.102 1.00 75.77 N
ANISOU 347 N GLN A 196 9804 9369 9615 3051 -789 415 N
ATOM 348 CA GLN A 196 130.637 -49.963 2.815 1.00 95.27 C
ANISOU 348 CA GLN A 196 12658 11728 11812 3115 -472 725 C
ATOM 349 CB GLN A 196 130.886 -50.181 4.307 1.00 107.29 C
ANISOU 349 CB GLN A 196 14754 13030 12983 3563 -650 904 C
ATOM 350 CG GLN A 196 129.989 -51.235 4.926 1.00 117.21 C
ANISOU 350 CG GLN A 196 16367 14021 14147 3700 -255 1260 C
ATOM 351 CD GLN A 196 130.726 -52.107 5.920 1.00 131.08 C
ANISOU 351 CD GLN A 196 18557 15855 15502 4122 -492 1348 C
ATOM 397 CB LEU A 201 127.619 -40.653 -10.148 1.00 52.73 C
ANISOU 397 CB LEU A 201 5143 8533 6357 671 588 -332 C
ATOM 398 CG LEU A 201 128.661 -41.745 -9.991 1.00 51.94 C
ANISOU 398 CG LEU A 201 4934 8362 6440 785 623 -411 C
ATOM 399 CD1 LEU A 201 128.547 -42.706 -11.158 1.00 40.25 C
ANISOU 399 CD1 LEU A 201 3528 6863 4902 854 720 -576 C
ATOM 400 CD2 LEU A 201 130.033 -41.109 -9.943 1.00 47.80 C
ANISOU 400 CD2 LEU A 201 4209 7891 6601 797 686 -373 C
ATOM 401 C LEU A 201 126.384 -38.714 -9.246 1.00 50.88 C
ANISOU 401 C LEU A 201 5031 8352 5951 556 449 -130 C
ATOM 402 O LEU A 201 125.201 -38.949 -9.483 1.00 36.89 O
ANISOU 402 O LEU A 201 3332 6560 4127 535 434 -136 O
ATOM 403 N LEU A 202 126.913 -37.497 -9.299 1.00 56.46 N
ANISOU 403 N LEU A 202 5711 9118 6624 502 440 -70 N
ATOM 404 CA LEU A 202 126.125 -36.319 -9.620 1.00 34.24 C
ANISOU 404 CA LEU A 202 3003 6362 3646 432 419 -6 C
ATOM 405 CB LEU A 202 125.970 -35.446 -8.399 1.00 40.78 C
ANISOU 405 CB LEU A 202 3898 7132 4466 459 265 88 C
ATOM 406 CG LEU A 202 124.996 -35.957 -7.365 1.00 54.27 C
ANISOU 406 CG LEU A 202 5717 8772 6131 566 225 137 C
ATOM 407 CD1 LEU A 202 125.599 -35.774 -5.999 1.00 60.13 C
ANISOU 407 CD1 LEU A 202 6550 9414 6884 697 76 177 C
ATOM 408 CD2 LEU A 202 123.724 -35.159 -7.497 1.00 52.67 C
ANISOU 408 CD2 LEU A 202 5610 8604 5797 553 232 200 C
ATOM 409 C LEU A 202 126.765 -35.491 -10.713 1.00 37.34 C
ANISOU 409 C LEU A 202 3369 6828 3990 361 548 15 C
ATOM 410 O LEU A 202 127.434 -34.496 -10.430 1.00 44.17 O
ANISOU 410 O LEU A 202 4167 7667 4950 302 519 99 O
ATOM 411 N PRO A 203 126.581 -35.912 -11.967 1.00 46.49 N
ANISOU 411 N PRO A 203 4605 8049 5009 386 687 -57 N
ATOM 412 CA PRO A 203 127.074 -35.119 -13.096 1.00 46.65 C
ANISOU 412 CA PRO A 203 4684 8135 4908 367 883 5 C
ATOM 413 CB PRO A 203 126.863 -36.040 -14.295 1.00 39.98 C
ANISOU 413 CB PRO A 203 4001 7329 3860 490 995 -130 C
ATOM 414 CG PRO A 203 125.775 -36.991 -13.870 1.00 38.12 C
ANISOU 414 CG PRO A 203 3803 7031 3648 513 756 -262 C
ATOM 415 CD PRO A 203 125.997 -37.195 -12.392 1.00 36.53 C
ANISOU 415 CD PRO A 203 3410 6766 3704 462 665 -200 C
ATOM 416 C PRO A 203 126.244 -33.852 -13.255 1.00 43.70 C
ANISOU 416 C PRO A 203 4467 7776 4363 306 794 99 C
ATOM 417 O PRO A 203 125.024 -33.921 -13.421 1.00 44.20 O
ANISOU 417 O PRO A 203 4676 7849 4268 337 647 41 O
ATOM 418 N LEU A 204 126.916 -32.705 -13.205 1.00 52.75 N
ANISOU 418 N LEU A 204 5554 8894 5596 221 866 243 N
ATOM 419 CA LEU A 204 126.239 -31.415 -13.250 1.00 50.34 C
ANISOU 419 CA LEU A 204 5398 8569 5161 168 766 343 C
ATOM 420 CB LEU A 204 127.192 -30.290 -12.859 1.00 61.50 C
ANISOU 420 CB LEU A 204 6672 9876 6819 48 787 491 C
ATOM 421 CG LEU A 204 127.599 -30.326 -11.389 1.00 57.99 C
ANISOU 421 CG LEU A 204 6061 9327 6647 25 534 447 C
ATOM 422 CD1 LEU A 204 128.215 -29.000 -10.980 1.00 47.40 C
ANISOU 422 CD1 LEU A 204 4645 7824 5541 -89 412 557 C
ATOM 423 CD2 LEU A 204 126.396 -30.648 -10.518 1.00 43.15 C
ANISOU 423 CD2 LEU A 204 4336 7469 4592 125 317 360 C
ATOM 424 C LEU A 204 125.604 -31.132 -14.605 1.00 51.32 C

TABLE 9-continued

DMXAA-hSTING$^{S162A/G230I/Q266I}$ complex

| | |
|---|---|
| ANISOU 379 CD1 TYR A 199 6415 8452 7904 1754 -303 -90 C | ANISOU 424 C LEU A 204 5790 8756 4953 235 866 355 C |
| ATOM 380 CE1 TYR A 199 131.898 -45.638 -1.640 1.00 64.77 C | ATOM 425 O LEU A 204 124.617 -30.404 -14.702 1.00 49.91 O |
| ANISOU 380 CE1 TYR A 199 7136 8931 8541 1993 -598 -94 C | ANISOU 425 O LEU A 204 5780 8572 4611 245 709 378 O |
| ATOM 381 CZ TYR A 199 132.662 -44.556 -1.235 1.00 67.32 C | ATOM 426 N ASP A 205 126.170 -31.715 -15.653 1.00 44.62 N |
| ANISOU 381 CZ TYR A 199 7394 9286 8897 2033 -898 -158 C | ANISOU 426 N ASP A 205 5014 7956 3983 323 1118 335 N |
| ATOM 382 OH TYR A 199 133.558 -44.706 -0.208 1.00 80.49 O | ATOM 427 CA ASP A 205 125.586 -31.612 -16.990 1.00 48.53 C |
| ANISOU 382 OH TYR A 199 9180 10788 10613 2295 -1290 -197 O | ANISOU 427 CA ASP A 205 5863 8496 4081 466 1179 312 C |
| ATOM 383 CE2 TYR A 199 132.545 -43.331 -1.863 1.00 63.93 C | ATOM 428 CB ASP A 205 126.604 -32.012 -18.052 1.00 46.12 C |
| ANISOU 383 CE2 TYR A 199 6789 9017 8483 1820 -850 -189 C | ANISOU 428 CB ASP A 205 5655 8224 3645 597 1578 357 C |
| ATOM 384 CD2 TYR A 199 131.651 -43.186 -2.896 1.00 59.32 C | ATOM 429 CG ASP A 205 127.179 -33.391 -17.799 1.00111.60 C |
| ANISOU 384 CD2 TYR A 199 6130 8583 7825 1597 -512 -162 C | ANISOU 429 CG ASP A 205 13765 16534 12104 657 1636 200 C |
| ATOM 385 C TYR A 199 127.585 -43.202 -4.930 1.00 46.13 C | ATOM 430 OD1 ASP A 205 128.050 -33.509 -16.908 1.00113.45 O |
| ANISOU 385 C TYR A 199 4598 7116 5811 1127 238 10 C | ANISOU 430 OD1 ASP A 205 13641 16737 12727 539 1698 255 O |
| ATOM 386 O TYR A 199 127.218 -43.929 -5.845 1.00 44.02 O | ATOM 431 OD2 ASP A 205 126.750 -34.354 -18.469 1.00108.99 O |
| ANISOU 386 O TYR A 199 4247 6834 5644 1042 339 -73 O | ANISOU 431 OD2 ASP A 205 13659 16220 11531 834 1568 5 O |
| ATOM 387 N ILE A 200 127.155 -41.961 -4.761 1.00 45.87 N | ATOM 432 C ASP A 205 124.358 -32.514 -17.096 1.00 41.86 C |
| ANISOU 387 N ILE A 200 4623 7180 5624 1077 215 73 N | ANISOU 432 C ASP A 205 5142 7661 3102 563 869 85 C |
| ATOM 388 CA ILE A 200 126.173 -41.375 -5.640 1.00 46.13 C | ATOM 433 O ASP A 205 123.716 -32.582 -18.145 1.00 47.54 O |
| ANISOU 388 CA ILE A 200 4610 7319 5499 971 321 69 C | ANISOU 433 O ASP A 205 6174 8386 3501 712 781 -2 O |
| ATOM 389 CB ILE A 200 125.079 -40.694 -4.846 1.00 46.93 C | ATOM 434 N CYS A 206 124.067 -33.229 -16.009 1.00 45.24 N |
| ANISOU 389 CB ILE A 200 4867 7403 5563 959 364 234 C | ANISOU 434 N CYS A 206 5329 8059 3801 491 696 -3 N |
| ATOM 390 CG1 ILE A 200 124.409 -41.706 -3.930 1.00 39.39 C | ATOM 435 CA CYS A 206 122.873 -34.066 -15.891 1.00 42.51 C |
| ANISOU 390 CG1 ILE A 200 4026 6271 4670 1083 493 393 C | ANISOU 435 CA CYS A 206 4991 7670 3492 533 413 -173 C |
| ATOM 391 CD1 ILE A 200 123.399 -41.100 -3.017 1.00 41.61 C | ATOM 436 CB CYS A 206 121.609 -33.207 -15.929 1.00 38.59 C |
| ANISOU 391 CD1 ILE A 200 4478 6520 4811 1193 620 595 C | ANISOU 436 CB CYS A 206 4586 7155 2922 529 176 -146 C |
| ATOM 392 CG2 ILE A 200 124.067 -40.075 -5.785 1.00 37.87 C | ATOM 437 SG CYS A 206 121.490 -32.044 -14.559 1.00 48.70 S |
| ANISOU 392 CG2 ILE A 200 3641 6352 4396 808 428 217 C | ANISOU 437 SG CYS A 206 5700 8427 4375 412 172 43 S |
| ATOM 393 C ILE A 200 126.831 -40.376 -6.574 1.00 46.59 C | ATOM 438 C CYS A 206 122.785 -35.158 -16.948 1.00 45.62 C |
| ANISOU 393 C ILE A 200 4549 7532 5622 808 292 -28 C | ANISOU 438 C CYS A 206 5568 8037 3727 683 367 -376 C |
| ATOM 394 O ILE A 200 127.385 -39.372 -6.139 1.00 45.64 O | ATOM 439 O CYS A 206 121.700 -35.652 -17.243 1.00 70.57 O |
| ANISOU 394 O ILE A 200 4438 7441 5463 819 179 0 O | ANISOU 439 O CYS A 206 8796 11121 6896 732 69 -531 O |
| ATOM 395 N LEU A 201 126.780 -40.688 -7.864 1.00 37.61 N | ATOM 440 N GLY A 207 123.920 -35.504 -17.541 1.00 52.22 N |
| ANISOU 395 N LEU A 201 3326 6461 4505 723 392 -139 N | ANISOU 440 N GLY A 207 6484 8914 4444 775 648 -379 N |
| ATOM 396 CA LEU A 201 127.345 -39.838 -8.895 1.00 44.66 C | ATOM 441 CA GLY A 207 123.960 -36.591 -18.498 1.00 46.68 C |
| ANISOU 396 CA LEU A 201 4146 7486 5337 647 458 -190 C | ANISOU 441 CA GLY A 207 6007 8172 3556 970 620 -593 C |
| ATOM 442 C GLY A 207 124.056 -37.913 -17.754 1.00 58.59 C | ATOM 487 O SER A 213 131.061 -49.313 -18.911 1.00 91.58 O |
| ANISOU 442 C GLY A 207 7276 9597 5390 928 529 -725 C | ANISOU 487 O SER A 213 11498 12915 10385 -1297 -936 665 O |
| ATOM 443 O GLY A 207 125.078 -38.220 -17.140 1.00 63.85 O | ATOM 488 N MET A 214 129.086 -48.292 -19.251 1.00106.88 N |
| ANISOU 443 O GLY A 207 7722 10288 6251 886 756 -652 O | ANISOU 488 N MET A 214 12792 15761 12056 -1169 -1455 1782 N |
| ATOM 444 N VAL A 208 122.975 -38.687 -17.787 1.00 52.82 N | ATOM 489 CA MET A 214 129.434 -47.781 -20.570 1.00100.93 C |
| ANISOU 444 N VAL A 208 6568 8734 4765 938 175 -909 N | ANISOU 489 CA MET A 214 12223 15322 10803 -1680 -1675 1718 C |
| ATOM 445 CA VAL A 208 122.959 -39.983 -17.132 1.00 46.21 C | ATOM 490 CB MET A 214 128.275 -48.012 -21.537 1.00113.49 C |
| ANISOU 445 CA VAL A 208 5532 7767 4261 899 82 -1016 C | ANISOU 490 CB MET A 214 13386 17726 12008 -2403 -2121 2191 C |
| ATOM 446 CB VAL A 208 121.832 -40.095 -16.116 1.00 53.16 C | ATOM 491 CG MET A 214 127.606 -49.373 -21.387 1.00126.03 C |
| ANISOU 446 CB VAL A 208 6151 8536 5511 729 -143 -957 C | ANISOU 491 CG MET A 214 14750 19473 13662 -2973 -2119 2023 C |
| ATOM 447 CG1 VAL A 208 121.841 -41.481 -15.477 1.00 56.27 C | ATOM 492 SD MET A 214 128.517 -50.735 -22.140 1.00157.08 S |
| ANISOU 447 CG1 VAL A 208 6369 8756 6255 698 -195 -1028 C | ANISOU 492 SD MET A 214 19295 23060 17327 -4014 -1779 961 S |
| ATOM 448 CG2 VAL A 208 121.977 -39.015 -15.065 1.00 45.69 C | ATOM 493 CE MET A 214 128.777 -51.803 -20.729 1.00105.49 C |
| ANISOU 448 CG2 VAL A 208 5029 7705 4625 602 25 -701 C | ANISOU 493 CE MET A 214 12781 15799 11503 -3486 -1264 575 C |
| ATOM 449 C VAL A 208 122.828 -41.084 -18.167 1.00 53.32 C | ATOM 494 C MET A 214 129.796 -46.296 -20.533 1.00 96.96 C |
| ANISOU 449 C VAL A 208 6692 8534 5034 1092 -101 -1302 C | ANISOU 494 C MET A 214 11883 14720 10237 -1067 -1664 2050 C |
| ATOM 450 O VAL A 208 121.869 -41.111 -18.931 1.00 64.85 O | ATOM 495 O MET A 214 130.165 -45.716 -21.552 1.00 91.46 O |
| ANISOU 450 O VAL A 208 8364 9894 6382 1171 -443 -1470 O | ANISOU 495 O MET A 214 11382 14228 9139 -1387 -1820 2027 O |
| ATOM 451 N PRO A 209 123.811 -41.992 -18.199 1.00 50.33 N | ATOM 496 N ALA A 215 129.681 -45.679 -19.360 1.00111.58 N |
| ANISOU 451 N PRO A 209 6313 8132 4679 1197 87 -1378 N | ANISOU 496 N ALA A 215 13723 16223 12448 -244 -1420 2344 N |
| ATOM 452 CA PRO A 209 123.884 -43.032 -19.223 1.00 59.62 C | ATOM 497 CA ALA A 215 130.025 -44.262 -19.200 1.00107.97 C |
| ANISOU 452 CA PRO A 209 7803 9175 5673 1441 -50 -1669 C | ANISOU 497 CA ALA A 215 13536 15552 11935 326 -1256 2620 C |
| ATOM 453 CB PRO A 209 125.335 -43.508 -19.131 1.00 60.97 C | ATOM 498 CB ALA A 215 129.447 -43.715 -17.907 1.00106.55 C |
| ANISOU 453 CB PRO A 209 7916 9423 5827 1560 360 -1630 C | ANISOU 498 CB ALA A 215 13305 15026 12155 1078 -897 3020 C |
| ATOM 454 CG PRO A 209 125.688 -43.293 -17.706 1.00 64.35 C | ATOM 499 C ALA A 215 131.537 -44.066 -19.224 1.00 92.13 C |
| ANISOU 454 CG PRO A 209 7903 9901 6644 1317 491 -1396 C | ANISOU 499 C ALA A 215 12125 13085 9795 259 -1078 1935 C |
| ATOM 455 CD PRO A 209 124.975 -42.026 -17.301 1.00 46.90 C | ATOM 500 O ALA A 215 132.047 -43.073 -19.736 1.00 79.93 O |
| ANISOU 455 CD PRO A 209 5604 7786 4430 1128 423 -1206 C | ANISOU 500 O ALA A 215 10876 11503 7990 328 -1053 1961 O |
| ATOM 456 C PRO A 209 122.949 -44.203 -18.973 1.00 53.38 C | ATOM 501 N ASP A 216 132.239 -45.022 -18.631 1.00 79.82 N |
| ANISOU 456 C PRO A 209 6928 8107 5249 1379 -481 -1875 C | ANISOU 501 N ASP A 216 10690 11176 8460 143 -935 1394 N |
| ATOM 457 O PRO A 209 122.583 -44.527 -17.841 1.00 56.65 O | ATOM 502 CA ASP A 216 133.684 -45.089 -18.678 1.00 66.06 C |
| ANISOU 457 O PRO A 209 6987 8430 6109 1162 -528 -1754 O | ANISOU 502 CA ASP A 216 9346 9056 6699 6 -783 812 C |
| ATOM 458 N ASP A 210 122.580 -44.828 -20.081 1.00 58.64 N | ATOM 503 CB ASP A 216 134.294 -44.525 -17.389 1.00 65.42 C |
| ANISOU 458 N ASP A 210 7959 8608 5712 1601 -793 -2183 N | ANISOU 503 CB ASP A 216 9539 8543 6774 510 -560 837 C |
| ATOM 459 CA ASP A 210 121.848 -46.079 -20.114 1.00 79.31 C | ATOM 504 CG ASP A 216 135.828 -44.647 -17.340 1.00 70.81 C |
| ANISOU 459 CA ASP A 210 10558 10893 8683 1592 -1243 -2442 C | ANISOU 504 CG ASP A 216 10500 8909 7496 342 -456 359 C |
| ATOM 460 CB ASP A 210 121.899 -46.590 -21.542 1.00 93.89 C | ATOM 505 OD1 ASP A 216 136.381 -45.682 -17.750 1.00 74.00 O |
| ANISOU 460 CB ASP A 210 12963 12612 10101 1955 -1507 -2807 C | ANISOU 505 OD1 ASP A 216 10776 9234 8107 -2 -412 -7 O |
| ATOM 461 CG ASP A 210 123.154 -46.128 -22.264 1.00106.02 C | ATOM 506 OD2 ASP A 216 136.479 -43.690 -16.862 1.00 61.37 O |
| ANISOU 461 CG ASP A 210 14853 14408 11024 2253 -1004 -2753 C | ANISOU 506 OD2 ASP A 216 9651 7523 6143 540 -362 388 O |
| ATOM 462 OD2 ASP A 210 123.089 -45.087 -22.957 1.00103.95 O | ATOM 507 C ASP A 216 133.961 -46.570 -18.809 1.00 67.30 C |
| ANISOU 462 OD2 ASP A 210 14874 14310 10314 2376 -911 -2680 O | ANISOU 507 C ASP A 216 9372 9111 7088 -437 -713 365 C |
| ATOM 463 OD1 ASP A 210 124.210 -46.782 -22.109 1.00100.76 O | ATOM 508 O ASP A 216 133.339 -47.379 -18.123 1.00 67.08 O |

TABLE 9-continued

DMXAA-hSTING$^{S162A/G230I/Q266I}$ complex

| | |
|---|---|
| ANISOU 463 OD1 ASP A 210 14155 13769 10362 2365 -669 -2754 O | ANISOU 508 O ASP A 216 9086 9061 7340 -358 -680 466 O |
| ATOM 464 C ASP A 210 122.498 -47.102 -19.192 1.00 82.20 C | ATOM 509 N PRO A 217 134.882 -46.941 -19.706 1.00 66.02 N |
| ANISOU 464 C ASP A 210 10650 11163 9421 1507 -1055 -2384 C | ANISOU 509 N PRO A 217 9420 8830 6834 -911 -599 -130 N |
| ATOM 465 O ASP A 210 121.834 -47.724 -18.363 1.00 68.23 O | ATOM 510 CA PRO A 217 135.176 -48.368 -19.827 1.00 64.08 C |
| ANISOU 465 O ASP A 210 8573 9176 8176 1297 -1239 -2336 O | ANISOU 510 CA PRO A 217 9116 8350 6883 -1313 -340 -551 C |
| ATOM 466 N ASN A 211 123.805 -47.277 -19.353 1.00 90.27 N | ATOM 511 CB PRO A 217 135.888 -48.464 -21.173 1.00 48.60 C |
| ANISOU 466 N ASN A 211 11784 12328 10185 1691 -668 -2371 N | ANISOU 511 CB PRO A 217 7463 6347 4654 -1938 -174 -1014 C |
| ATOM 467 CA ASN A 211 124.582 -48.145 -18.478 1.00 91.11 C | ATOM 512 CG PRO A 217 136.568 -47.138 -21.307 1.00 59.06 C |
| ANISOU 467 CA ASN A 211 11646 12371 10602 1652 -471 -2302 C | ANISOU 512 CG PRO A 217 9013 7671 5756 -1645 -285 -928 C |
| ATOM 468 CB ASN A 211 124.858 -49.495 -19.139 1.00103.18 C | ATOM 513 CD PRO A 217 135.602 -46.143 -20.714 1.00 60.33 C |
| ANISOU 468 CB ASN A 211 13438 13650 12116 1902 -645 -2627 C | ANISOU 513 CD PRO A 217 9020 8151 5751 -1145 -614 -321 C |
| ATOM 469 CG ASN A 211 123.642 -50.394 -19.140 1.00110.52 C | ATOM 514 C PRO A 217 136.084 -48.884 -18.709 1.00 63.77 C |
| ANISOU 469 CG ASN A 211 14359 14191 13442 1793 -1195 -2829 C | ANISOU 514 C PRO A 217 9035 7806 7389 -926 -71 -659 C |
| ATOM 470 OD1 ASN A 211 122.837 -50.366 -20.070 1.00113.40 O | ATOM 515 O PRO A 217 136.365 -50.077 -18.673 1.00 75.95 O |
| ANISOU 470 OD1 ASN A 211 15002 14416 13669 1888 -1603 -3075 O | ANISOU 515 O PRO A 217 10495 9060 9303 -1134 241 -919 O |
| ATOM 471 ND2 ASN A 211 123.496 -51.192 -18.087 1.00109.03 N | ATOM 516 N ASN A 218 136.551 -48.011 -17.824 1.00 58.53 N |
| ANISOU 471 ND2 ASN A 211 13849 13794 13782 1599 -1227 -2715 N | ANISOU 516 N ASN A 218 8446 7036 6757 -433 -161 -426 N |
| ATOM 472 C ASN A 211 125.878 -47.487 -18.027 1.00 86.33 C | ATOM 517 CA ASN A 218 137.290 -48.472 -16.651 1.00 57.92 C |
| ANISOU 472 C ASN A 211 10878 12051 9873 1672 39 -2059 C | ANISOU 517 CA ASN A 218 8269 6617 7121 -144 -31 -365 C |
| ATOM 473 O ASN A 211 126.714 -47.099 -18.843 1.00 78.01 O | ATOM 518 CB ASN A 218 138.402 -47.496 -16.269 1.00 51.91 C |
| ANISOU 473 O ASN A 211 10028 11165 8448 1891 331 -2080 O | ANISOU 518 CB ASN A 218 7721 5747 6256 27 -80 -310 C |
| ATOM 474 N LEU A 212 126.013 -47.361 -16.712 1.00 95.19 N | ATOM 519 CG ASN A 218 139.519 -47.476 -17.274 1.00 56.93 C |
| ANISOU 474 N LEU A 212 10128 14488 11554 495 -1249 3688 N | ANISOU 519 CG ASN A 218 8447 6253 6932 -265 99 -655 C |
| ATOM 475 CA LEU A 212 127.161 -46.730 -16.080 1.00 95.93 C | ATOM 520 OD1 ASN A 218 139.944 -48.518 -17.760 1.00 57.84 O |
| ANISOU 475 CA LEU A 212 10852 13931 11664 946 -919 3289 C | ANISOU 520 OD1 ASN A 218 8408 6135 7433 -494 408 -906 O |
| ATOM 476 CB LEU A 212 127.042 -46.883 -14.567 1.00 93.98 C | ATOM 521 ND2 ASN A 218 139.988 -46.277 -17.618 1.00 60.95 N |
| ANISOU 476 CB LEU A 212 10752 13167 11791 1472 -519 3285 C | ANISOU 521 ND2 ASN A 218 9250 6855 7054 -270 -2 -680 N |
| ATOM 477 CG LEU A 212 128.290 -46.769 -13.704 1.00 80.74 C | ATOM 522 C ASN A 218 136.364 -48.698 -15.467 1.00 51.59 C |
| ANISOU 477 CG LEU A 212 9712 10871 10095 1658 -263 2763 C | ANISOU 522 C ASN A 218 7309 5852 6439 178 -128 -14 C |
| ATOM 478 CD1 LEU A 212 128.974 -45.427 -13.906 1.00 82.58 C | ATOM 523 O ASN A 218 136.807 -48.853 -14.335 1.00 51.21 O |
| ANISOU 478 CD1 LEU A 212 10387 10897 10091 1814 -122 2675 C | ANISOU 523 O ASN A 218 7233 5606 6620 413 -112 158 O |
| ATOM 479 CD2 LEU A 212 127.877 -46.939 -12.263 1.00 76.72 C | ATOM 524 N ILE A 219 135.071 -48.695 -15.748 1.00 53.47 N |
| ANISOU 479 CD2 LEU A 212 9312 9974 9864 1925 90 2733 C | ANISOU 524 N ILE A 219 7431 6381 6503 140 -239 141 N |
| ATOM 480 C LEU A 212 128.426 -47.402 -16.560 1.00101.92 C | ATOM 525 CA ILE A 219 134.069 -48.994 -14.747 1.00 47.84 C |
| ANISOU 480 C LEU A 212 12023 14495 12207 434 -987 2476 C | ANISOU 525 CA ILE A 219 6537 5699 5942 412 -262 461 C |
| ATOM 481 O LEU A 212 129.452 -46.763 -16.803 1.00101.04 O | ATOM 526 CB ILE A 219 133.148 -47.801 -14.501 1.00 56.94 C |
| ANISOU 481 O LEU A 212 12333 14146 11913 496 -923 2195 O | ANISOU 526 CB ILE A 219 7753 7063 6819 744 -356 889 C |
| ATOM 482 N SER A 213 128.320 -48.714 -16.706 1.00110.74 N | ATOM 527 CG1 ILE A 219 133.968 -46.593 -14.070 1.00 53.02 C |
| ANISOU 482 N SER A 213 13007 15688 13381 -84 -1045 2124 N | ANISOU 527 CG1 ILE A 219 7676 6368 6099 981 -293 933 C |
| ATOM 483 CA SER A 213 129.394 -49.551 -17.201 1.00108.19 C | ATOM 528 CD1 ILE A 219 133.121 -45.397 -13.681 1.00 52.89 C |
| ANISOU 483 CA SER A 213 13017 15118 12974 -596 -956 1401 C | ANISOU 528 CD1 ILE A 219 7831 6379 5887 1363 -169 1365 C |
| ATOM 484 CB SER A 213 128.859 -50.970 -17.357 1.00103.95 C | ATOM 529 CG2 ILE A 219 132.127 -48.122 -13.426 1.00 52.12 C |
| ANISOU 484 CB SER A 213 12287 14695 12513 -1179 -922 1174 C | ANISOU 529 CG2 ILE A 219 6967 6415 6419 1033 -276 1218 C |
| ATOM 485 OG SER A 213 127.614 -51.105 -16.692 1.00 91.43 O | ATOM 530 C ILE A 219 133.268 -50.179 -15.245 1.00 54.28 C |
| ANISOU 485 OG SER A 213 10259 13360 11122 -952 -1005 1685 O | ANISOU 530 C ILE A 219 7070 6656 6898 54 -221 343 C |
| ATOM 486 C SER A 213 129.922 -49.042 -18.539 1.00101.82 C | ATOM 531 O ILE A 219 132.538 -50.070 -16.227 1.00 49.64 O |
| ANISOU 486 C SER A 213 12421 14545 11719 -1058 -1124 1227 C | ANISOU 531 O ILE A 219 6385 6448 6026 -281 -366 373 O |
| ATOM 532 N ARG A 220 133.437 -51.318 -14.578 1.00 52.26 N | ATOM 577 C LYS A 224 124.581 -57.612 -6.087 1.00 61.88 C |
| ANISOU 532 N ARG A 220 6696 6109 7052 60 -22 241 N | ANISOU 577 C LYS A 224 6350 6786 10376 1114 1117 2043 C |
| ATOM 533 CA ARG A 220 132.825 -52.567 -15.009 1.00 50.66 C | ATOM 578 O LYS A 224 125.084 -58.649 -5.677 1.00 79.58 O |
| ANISOU 533 CA ARG A 220 6322 5932 6995 -359 137 44 C | ANISOU 578 O LYS A 224 8721 8686 12830 1012 1274 1843 O |
| ATOM 534 CB ARG A 220 133.894 -53.609 -15.309 1.00 63.82 C | ATOM 579 N LEU A 225 124.096 -56.673 -5.283 1.00 68.38 N |
| ANISOU 534 CB ARG A 220 8077 7136 9034 -606 557 -360 C | ANISOU 579 N LEU A 225 7268 7563 11151 1526 1203 2402 N |
| ATOM 535 CG ARG A 220 134.474 -53.532 -16.697 1.00 76.30 C | ATOM 580 CA LEU A 225 123.941 -56.898 -3.853 1.00 68.91 C |
| ANISOU 535 CG ARG A 220 9888 8715 10386 -1116 717 -766 C | ANISOU 580 CA LEU A 225 7622 7278 11283 1717 1448 2491 C |
| ATOM 536 CD ARG A 220 135.968 -53.766 -16.654 1.00 76.49 C | ATOM 581 CB LEU A 225 123.782 -55.567 -3.120 1.00 68.40 C |
| ANISOU 536 CD ARG A 220 9990 8230 10842 -977 1090 -943 C | ANISOU 581 CB LEU A 225 7909 7268 10811 1852 1549 2539 C |
| ATOM 537 NE ARG A 220 136.386 -54.937 -17.413 1.00 83.48 N | ATOM 582 CG LEU A 225 125.045 -54.815 -2.728 1.00 58.28 C |
| ANISOU 537 NE ARG A 220 11006 8688 12026 -1449 1725 -1376 N | ANISOU 582 CG LEU A 225 7121 5890 9132 1795 1397 2308 C |
| ATOM 538 CZ ARG A 220 136.970 -56.008 -16.885 1.00 85.77 C | ATOM 583 CD1 LEU A 225 124.669 -53.663 -1.823 1.00 54.77 C |
| ANISOU 538 CZ ARG A 220 11164 8425 13000 -1276 2248 -1366 C | ANISOU 583 CD1 LEU A 225 7025 5370 8416 1902 1670 2372 C |
| ATOM 539 NH1 ARG A 220 137.314 -57.031 -17.662 1.00 95.16 N | ATOM 584 CD2 LEU A 225 126.007 -55.751 -2.021 1.00 61.54 C |
| ANISOU 539 NH1 ARG A 220 12547 9173 14437 -1706 2971 -1764 N | ANISOU 584 CD2 LEU A 225 7722 6109 9552 1632 1261 2151 C |
| ATOM 540 NH2 ARG A 220 137.210 -56.063 -15.583 1.00 69.97 N | ATOM 585 C LEU A 225 122.714 -57.776 -3.604 1.00 76.72 C |
| ANISOU 540 NH2 ARG A 220 8857 6328 11400 -687 2084 -911 N | ANISOU 585 C LEU A 225 8255 8306 12590 1655 1653 2635 C |
| ATOM 541 C ARG A 220 131.885 -53.121 -13.957 1.00 50.13 C | ATOM 586 O LEU A 225 121.908 -57.986 -4.513 1.00 83.49 O |
| ANISOU 541 C ARG A 220 6036 5858 7155 -128 144 315 C | ANISOU 586 O LEU A 225 8638 9600 13483 1389 1550 2676 O |
| ATOM 542 O ARG A 220 132.194 -53.117 -12.765 1.00 46.16 O | ATOM 587 N PRO A 226 122.566 -58.299 -2.374 1.00 78.29 N |
| ANISOU 542 O ARG A 220 5553 5089 6895 293 190 507 O | ANISOU 587 N PRO A 226 8707 8191 12847 1708 1882 2634 N |
| ATOM 543 N PHE A 221 130.743 -53.615 -14.410 1.00 45.38 N | ATOM 588 CA PRO A 226 121.321 -59.007 -2.060 1.00 81.39 C |
| ANISOU 543 N PHE A 221 5231 5579 6433 -487 88 349 N | ANISOU 588 CA PRO A 226 8775 8586 13562 1694 2134 2814 C |
| ATOM 544 CA PHE A 221 129.805 -54.256 -13.516 1.00 51.00 C | ATOM 589 CB PRO A 226 121.573 -59.574 -0.659 1.00 75.37 C |
| ANISOU 544 CA PHE A 221 5715 6286 7377 -344 140 569 C | ANISOU 589 CB PRO A 226 8452 7482 12703 1672 2316 2686 C |
| ATOM 545 CB PHE A 221 128.479 -54.512 -14.229 1.00 65.56 C | ATOM 590 CG PRO A 226 122.683 -58.741 -0.099 1.00 79.28 C |
| ANISOU 545 CB PHE A 221 7268 8671 8971 -832 -37 706 C | ANISOU 590 CG PRO A 226 9438 7991 12693 1671 2115 2509 C |
| ATOM 546 CG PHE A 221 127.575 -55.445 -13.488 1.00 59.67 C | ATOM 591 CD PRO A 226 123.544 -58.411 -1.279 1.00 80.52 C |
| ANISOU 546 CG PHE A 221 6292 7898 8483 -853 92 818 C | ANISOU 591 CD PRO A 226 9497 8278 12818 1631 1832 2408 C |
| ATOM 547 CD1 PHE A 221 126.753 -54.972 -12.478 1.00 60.92 C | ATOM 592 C PRO A 226 120.129 -58.057 -2.034 1.00 83.17 C |

TABLE 9-continued

DMXAA-hSTING$^{S162A/G230I/Q266I}$ complex

| | |
|---|---|
| ANISOU 547 CD1 PHE A 221 6222 8136 8790 −322 17 1304 C | ANISOU 592 C PRO A 226 8712 9065 13825 1929 2300 3224 C |
| ATOM 548 CE1 PHE A 221 125.919 −55.829 −11.786 1.00 58.77 C | ATOM 593 O PRO A 226 120.241 −56.911 −1.600 1.00 84.84 O |
| ANISOU 548 CE1 PHE A 221 5744 7826 8759 −349 159 1402 C | ANISOU 593 O PRO A 226 9271 9276 13688 2047 2394 3232 O |
| ATOM 549 CZ PHE A 221 125.908 −57.180 −12.102 1.00 58.77 C | ATOM 594 N GLN A 227 118.988 −58.552 −2.492 1.00 81.13 N |
| ANISOU 549 CZ PHE A 221 5788 7703 8841 −922 378 1003 C | ANISOU 594 N GLN A 227 7853 9178 13794 1740 2316 3406 N |
| ATOM 550 CE2 PHE A 221 126.734 −57.665 −13.109 1.00 65.13 C | ATOM 595 CA GLN A 227 117.816 −57.716 −2.663 1.00 87.79 C |
| ANISOU 550 CE2 PHE A 221 6873 8370 9503 −1465 529 504 C | ANISOU 595 CA GLN A 227 8191 10348 14817 1983 2456 3967 C |
| ATOM 551 CD2 PHE A 221 127.558 −56.797 −13.793 1.00 58.19 C | ATOM 596 CB GLN A 227 116.797 −58.424 −3.534 1.00 87.19 C |
| ANISOU 551 CD2 PHE A 221 6176 7535 8398 −1422 385 417 C | ANISOU 596 CB GLN A 227 7349 10919 14861 1497 2230 4131 C |
| ATOM 552 C PHE A 221 130.392 −55.567 −13.005 1.00 56.52 C | ATOM 597 CG GLN A 227 117.308 −58.689 −4.919 1.00 87.65 C |
| ANISOU 552 C PHE A 221 6480 6473 8520 −401 525 293 C | ANISOU 597 CG GLN A 227 7247 11452 14602 929 1726 3858 C |
| ATOM 553 O PHE A 221 130.897 −56.378 −13.775 1.00 52.12 O | ATOM 598 CD GLN A 227 116.409 −59.620 −5.679 1.00 95.42 C |
| ANISOU 553 O PHE A 221 6048 5706 8047 −856 828 −112 O | ANISOU 598 CD GLN A 227 7657 13039 15559 197 1516 3898 C |
| ATOM 554 N LEU A 222 130.321 −55.763 −11.697 1.00 62.61 N | ATOM 599 OE1 GLN A 227 115.568 −60.302 −5.092 1.00 88.00 O |
| ANISOU 554 N LEU A 222 7201 7004 9585 50 579 544 N | ANISOU 599 OE1 GLN A 227 6499 12083 14854 98 1744 4006 O |
| ATOM 555 CA LEU A 222 130.802 −56.987 −11.089 1.00 64.09 C | ATOM 600 NE2 GLN A 227 116.570 −59.654 −6.997 1.00 98.48 N |
| ANISOU 555 CA LEU A 222 7389 6716 10246 75 932 436 C | ANISOU 600 NE2 GLN A 227 7835 13979 15603 −410 1088 3808 N |
| ATOM 556 CB LEU A 222 131.618 −56.685 −9.836 1.00 64.99 C | ATOM 601 C GLN A 227 117.172 −57.293 −1.356 1.00 90.29 C |
| ANISOU 556 CB LEU A 222 7566 6552 10577 585 870 747 C | ANISOU 601 C GLN A 227 8902 10264 15140 2216 2954 4135 C |
| ATOM 557 CG LEU A 222 133.117 −56.490 −10.030 1.00 69.45 C | ATOM 602 O GLN A 227 117.273 −57.975 −0.335 1.00 77.69 O |
| ANISOU 557 CG LEU A 222 8202 6882 11304 656 920 706 C | ANISOU 602 O GLN A 227 7658 8284 13578 2191 3201 3924 O |
| ATOM 558 CD2 LEU A 222 133.673 −57.553 −10.968 1.00 42.04 C | ATOM 603 N GLN A 228 116.505 −56.150 −1.414 1.00 77.76 N |
| ANISOU 558 CD2 LEU A 222 4693 3085 8195 330 1391 348 C | ANISOU 603 N GLN A 228 10247 7639 11657 16 3681 2587 N |
| ATOM 559 CD1 LEU A 222 133.810 −56.551 −8.682 1.00 64.59 C | ATOM 604 CA GLN A 228 115.783 −55.635 −0.276 1.00 77.20 C |
| ANISOU 559 CD1 LEU A 222 7558 6052 10930 997 839 1120 C | ANISOU 604 CA GLN A 228 10045 7953 11335 306 3718 2785 C |
| ATOM 560 C LEU A 222 129.642 −57.889 −10.719 1.00 72.27 C | ATOM 605 CB GLN A 228 116.422 −54.346 0.218 1.00 81.32 C |
| ANISOU 560 C LEU A 222 8266 7798 11359 −84 1061 474 C | ANISOU 605 CB GLN A 228 10794 9022 11081 427 3334 2626 C |
| ATOM 561 O LEU A 222 129.511 −59.002 −11.226 1.00 72.79 O | ATOM 606 CG GLN A 228 115.781 −53.786 1.468 1.00 88.52 C |
| ANISOU 561 O LEU A 222 8350 7698 11609 −531 1403 166 O | ANISOU 606 CG GLN A 228 11561 10419 11655 785 3349 2805 C |
| ATOM 562 N ASP A 223 128.795 −57.393 −9.830 1.00 68.75 N | ATOM 607 CD GLN A 228 116.645 −52.741 2.132 1.00 92.39 C |
| ANISOU 562 N ASP A 223 7710 7534 10878 250 863 841 N | ANISOU 607 CD GLN A 228 12171 11497 11436 977 3046 2674 C |
| ATOM 563 CA ASP A 223 127.782 −58.227 −9.222 1.00 62.67 C | ATOM 608 OE1 GLN A 228 117.699 −52.374 1.615 1.00 95.36 O |
| ANISOU 563 CA ASP A 223 6779 6747 10284 196 1007 937 C | ANISOU 608 OE1 GLN A 228 12743 11873 11618 802 2823 2436 O |
| ATOM 564 CB ASP A 223 128.443 −59.128 −8.175 1.00 69.82 C | ATOM 609 NE2 GLN A 228 116.207 −52.258 3.288 1.00 90.21 N |
| ANISOU 564 CB ASP A 223 7794 7108 11625 434 1289 966 C | ANISOU 609 NE2 GLN A 228 11748 11729 10797 1354 3042 2804 N |
| ATOM 565 CG ASP A 223 127.536 −60.248 −7.702 1.00 79.32 C | ATOM 610 C GLN A 228 114.357 −55.380 −0.712 1.00 77.10 C |
| ANISOU 565 CG ASP A 223 8887 8197 13052 282 1546 956 C | ANISOU 610 C GLN A 228 9991 7653 11649 154 3582 2469 C |
| ATOM 566 OD1 ASP A 223 126.316 −60.185 −7.956 1.00 87.51 O | ATOM 611 O GLN A 228 114.115 −54.766 −1.752 1.00 78.09 O |
| ANISOU 566 OD1 ASP A 223 9744 9603 13901 −81 1503 894 O | ANISOU 611 O GLN A 228 10357 7582 11732 −119 3190 1951 O |
| ATOM 567 OD2 ASP A 223 128.058 −61.195 −7.079 1.00 81.50 O | ATOM 612 N THR A 229 113.413 −55.867 0.082 1.00 72.46 N |
| ANISOU 567 OD2 ASP A 223 9232 8043 13690 496 1775 1063 O | ANISOU 612 N THR A 229 9081 7055 11395 366 3933 2803 N |
| ATOM 568 C ASP A 223 126.687 −57.377 −8.585 1.00 60.35 C | ATOM 613 CA THR A 229 112.008 −55.659 −0.211 1.00 86.25 C |
| ANISOU 568 C ASP A 223 6333 6754 9844 515 814 1362 C | ANISOU 613 CA THR A 229 10731 8554 13486 252 3836 2524 C |
| ATOM 569 O ASP A 223 126.847 −56.172 −8.404 1.00 49.51 O | ATOM 614 CB THR A 229 111.200 −56.928 0.020 1.00 98.72 C |
| ANISOU 569 O ASP A 223 5064 5468 8281 851 655 1589 O | ANISOU 614 CB THR A 229 11861 9715 15935 307 4391 2845 C |
| ATOM 570 N LYS A 224 125.570 −58.014 −8.261 1.00 54.11 N | ATOM 615 OG1 THR A 229 112.053 −58.067 −0.143 1.00 102.25 O |
| ANISOU 570 N LYS A 224 5312 6076 9172 394 915 1474 N | ANISOU 615 OG1 THR A 229 12180 10020 16652 354 4584 2973 O |
| ATOM 571 CA LYS A 224 124.482 −57.340 −7.579 1.00 67.24 C | ATOM 616 CG2 THR A 229 110.051 −57.005 −0.971 1.00 97.67 C |
| ANISOU 571 CA LYS A 224 6786 7933 10830 732 879 1925 C | ANISOU 616 CG2 THR A 229 11634 9099 16376 6 4216 2305 C |
| ATOM 572 CB LYS A 224 123.136 −57.840 −8.100 1.00 79.72 C | ATOM 617 C THR A 229 111.494 −54.551 0.686 1.00 85.87 C |
| ANISOU 572 CB LYS A 224 7895 9982 12412 328 833 2063 C | ANISOU 617 C THR A 229 10753 9002 12871 490 3627 2545 C |
| ATOM 573 CG LYS A 224 122.806 −57.387 −9.501 1.00 89.53 C | ATOM 618 O THR A 229 111.907 −54.431 1.839 1.00 79.18 O |
| ANISOU 573 CG LYS A 224 8845 11840 13333 −117 507 2136 C | ANISOU 618 O THR A 229 9827 8638 11620 853 3793 2958 O |
| ATOM 574 CD LYS A 224 122.770 −55.881 −9.551 1.00 91.80 C | ATOM 619 N ILE A 230 110.597 −53.732 0.156 1.00 94.96 N |
| ANISOU 574 CD LYS A 224 9068 12298 13512 380 350 2572 C | ANISOU 619 N ILE A 230 12043 10070 13968 322 3254 2082 N |
| ATOM 575 CE LYS A 224 121.471 −55.372 −10.129 1.00 94.90 C | ATOM 620 CA ILE A 230 110.200 −52.537 0.879 1.00 105.12 C |
| ANISOU 575 CE LYS A 224 8831 13364 13862 269 131 3181 C | ANISOU 620 CA ILE A 230 13449 11816 14676 512 2984 2013 C |
| ATOM 576 NZ LYS A 224 121.041 −54.144 −9.407 1.00 96.27 N | ATOM 621 C ILE A 230 108.769 −52.585 1.373 1.00 107.19 C |
| ANISOU 576 NZ LYS A 224 8924 13410 14244 1037 329 3763 N | ANISOU 621 C ILE A 230 13460 12036 15231 640 3134 2104 C |
| ATOM 622 O ILE A 230 107.856 −53.005 0.660 1.00 107.09 O | ATOM 667 CD LYS A 236 100.598 −52.449 −1.207 1.00 111.37 C |
| ANISOU 622 O ILE A 230 13315 11539 15797 430 3165 1872 O | ANISOU 667 CD LYS A 236 12914 10977 18423 −29 2646 107 C |
| ATOM 623 CB ILE A 230 110.426 −51.286 0.051 1.00 107.83 C | ATOM 668 CE LYS A 236 100.180 −51.487 −0.105 1.00 113.51 C |
| ANISOU 623 CB ILE A 230 14193 12202 14576 289 2422 1455 C | ANISOU 668 CE LYS A 236 13299 11714 18117 243 2601 410 C |
| ATOM 624 CG1 ILE A 230 111.719 −51.434 −0.722 1.00 107.90 C | ATOM 669 NZ LYS A 236 98.967 −51.970 0.613 1.00 115.08 N |
| ANISOU 624 CG1 ILE A 230 14414 12089 14496 101 2332 1344 C | ANISOU 669 NZ LYS A 236 13036 11775 18915 378 2686 661 N |
| ATOM 625 CG2 ILE A 230 110.525 −50.077 0.959 1.00 112.84 C | ATOM 670 C LYS A 236 104.972 −53.286 −1.910 1.00 89.98 C |
| ANISOU 625 CG2 ILE A 230 14946 13370 14559 518 2181 1429 C | ANISOU 670 C LYS A 236 10882 8355 14950 −191 2730 558 C |
| ATOM 626 CD1 ILE A 230 112.956 −51.437 0.152 1.00 110.78 C | ATOM 671 O LYS A 236 104.772 −53.029 −3.100 1.00 77.11 O |
| ANISOU 626 CD1 ILE A 230 14767 12860 14464 318 2447 1666 C | ANISOU 671 O LYS A 236 9400 6556 13340 −389 2365 −16 O |
| ATOM 627 N ASP A 231 108.598 −52.124 2.606 1.00 110.83 N | ATOM 672 N ASP A 237 105.656 −54.351 −1.496 1.00 91.80 N |
| ANISOU 627 N ASP A 231 13839 12998 15272 1012 3209 2410 N | ANISOU 672 N ASP A 237 10898 8438 15545 −139 3190 1004 N |
| ATOM 628 CA ASP A 231 107.360 −52.282 3.346 1.00 116.69 C | ATOM 673 CA ASP A 237 106.115 −55.404 −2.402 1.00 95.15 C |
| ANISOU 628 CA ASP A 231 14294 13784 16261 1241 3468 2665 C | ANISOU 673 CA ASP A 237 11191 8408 16554 −355 3329 827 C |
| ATOM 629 CB ASP A 231 107.620 −53.164 4.571 1.00 133.15 C | ATOM 674 CB ASP A 237 104.928 −56.186 −2.968 1.00 104.62 C |
| ANISOU 629 CB ASP A 231 16048 16128 18415 1698 4061 3410 C | ANISOU 674 CB ASP A 237 11959 9100 18692 −508 3462 469 C |
| ATOM 630 CG ASP A 231 108.717 −52.605 5.486 1.00 138.60 C | ATOM 675 CG ASP A 237 104.312 −57.136 −1.955 1.00 119.66 C |
| ANISOU 630 CG ASP A 231 16865 17521 18274 2067 3947 3591 C | ANISOU 675 CG ASP A 237 13346 10767 21353 −357 4113 1010 C |
| ATOM 631 OD1 ASP A 231 109.623 −53.378 5.859 1.00 135.24 O | ATOM 676 OD1 ASP A 237 104.162 −56.744 −0.779 1.00 124.16 O |

TABLE 9-continued

DMXAA-hSTING$^{S162A/G230I/Q266I}$ complex

| | |
|---|---|
| ANISOU 631 OD1 ASP A 231 16323 17215 17847 2271 4284 4010 O | ANISOU 676 OD1 ASP A 237 13914 11692 21568 −75 4308 1537 O |
| ATOM 632 OD2 ASP A 231 108.680 −51.407 5.849 1.00141.48 O | ATOM 677 OD2 ASP A 237 103.981 −58.278 −2.343 1.00118.27 O |
| ANISOU 632 OD2 ASP A 231 17416 18330 18010 2176 3528 3296 O | ANISOU 677 OD2 ASP A 237 12744 10043 22150 −495 4449 903 O |
| ATOM 633 C ASP A 231 106.821 −50.946 3.821 1.00103.91 C | ATOM 678 C ASP A 237 106.980 −54.907 −3.556 1.00 91.77 C |
| ANISOU 633 C ASP A 231 12842 12591 14047 1381 3078 2422 C | ANISOU 678 C ASP A 237 11179 8020 15671 −539 2872 377 C |
| ATOM 634 O ASP A 231 106.187 −50.861 4.868 1.00113.64 O | ATOM 679 O ASP A 237 106.742 −55.236 −4.714 1.00 94.08 O |
| ANISOU 634 O ASP A 231 13874 14146 15158 1743 3278 2747 O | ANISOU 679 O ASP A 237 11433 8004 16309 −728 2691 −141 O |
| ATOM 635 N ARG A 232 107.104 −49.894 3.075 1.00 90.06 N | ATOM 680 N ARG A 238 107.987 −54.114 −3.233 1.00 92.74 N |
| ANISOU 635 N ARG A 232 11449 10847 11923 1130 2550 1877 N | ANISOU 680 N ARG A 238 11668 8535 15033 −452 2697 560 N |
| ATOM 636 CA ARG A 232 106.747 −48.565 3.524 1.00 84.45 C | ATOM 681 CA ARG A 238 108.866 −53.577 −4.252 1.00 81.27 C |
| ANISOU 636 CA ARG A 232 10908 10529 10652 1261 2180 1625 C | ANISOU 681 CA ARG A 238 10608 7122 13149 −595 2323 217 C |
| ATOM 637 CB ARG A 232 107.794 −47.560 3.052 1.00 86.13 C | ATOM 682 CB ARG A 238 108.889 −52.059 −4.158 1.00 73.09 C |
| ANISOU 637 CB ARG A 232 11477 10867 10382 1103 1748 1225 C | ANISOU 682 CB ARG A 238 9947 6466 11358 −529 1911 62 C |
| ATOM 638 CG ARG A 232 108.805 −47.142 4.063 1.00 88.53 C | ATOM 683 CG ARG A 238 109.509 −51.365 −5.343 1.00 73.97 C |
| ANISOU 638 CG ARG A 232 11769 11727 10140 1407 1711 1353 C | ANISOU 683 CG ARG A 238 10447 6566 11093 −651 1535 −326 C |
| ATOM 639 CD ARG A 232 108.377 −45.821 4.631 1.00 99.52 C | ATOM 684 CD ARG A 238 108.553 −50.322 −5.883 1.00 67.88 C |
| ANISOU 639 CD ARG A 232 13251 13494 11069 1569 1373 1061 C | ANISOU 684 CD ARG A 238 9848 5867 10075 −634 1162 −739 C |
| ATOM 640 NE ARG A 232 109.487 −45.080 5.203 1.00106.19 N | ATOM 685 NE ARG A 238 109.168 −49.007 −5.968 1.00 65.06 N |
| ANISOU 640 NE ARG A 232 14153 14783 11413 1732 1156 887 N | ANISOU 685 NE ARG A 238 9885 5756 9080 −595 889 −788 N |
| ATOM 641 CZ ARG A 232 109.384 −44.328 6.291 1.00110.50 C | ATOM 686 CZ ARG A 238 108.552 −47.920 −6.421 1.00 75.03 C |
| ANISOU 641 CZ ARG A 232 14594 15886 11504 2097 1016 807 C | ANISOU 686 CZ ARG A 238 11363 7105 10038 −547 583 −1082 C |
| ATOM 642 NH1 ARG A 232 108.219 −44.232 6.915 1.00106.89 N | ATOM 687 NH1 ARG A 238 107.293 −47.990 −6.833 1.00 52.39 N |
| ANISOU 642 NH1 ARG A 232 14002 15209 11004 2342 1094 948 N | ANISOU 687 NH1 ARG A 238 8366 4155 7387 −521 470 −1377 N |
| ATOM 643 NH2 ARG A 232 110.443 −43.677 6.755 1.00111.84 N | ATOM 688 NH2 ARG A 238 109.202 −46.766 −6.463 1.00 49.24 N |
| ANISOU 643 NH2 ARG A 232 14767 16444 11285 2232 797 554 N | ANISOU 688 NH2 ARG A 238 8419 3997 6293 −516 407 −1089 N |
| ATOM 644 C ARG A 232 105.388 −48.196 2.966 1.00 82.28 C | ATOM 689 C ARG A 238 110.249 −54.142 −3.998 1.00 75.31 C |
| ANISOU 644 C ARG A 232 10644 9980 10638 1094 2011 1314 C | ANISOU 689 C ARG A 238 9901 6405 12310 −576 2562 590 C |
| ATOM 645 O ARG A 232 104.746 −48.994 2.282 1.00 92.01 O | ATOM 690 O ARG A 238 110.682 −54.223 −2.852 1.00 72.82 O |
| ANISOU 645 O ARG A 232 11719 10754 12487 896 2177 1272 O | ANISOU 690 O ARG A 238 9502 6357 11811 −376 2821 1088 O |
| ATOM 646 N ALA A 233 104.954 −46.979 3.266 1.00 73.11 N | ATOM 691 N VAL A 239 110.942 −54.549 −5.053 1.00 59.22 N |
| ANISOU 646 N ALA A 233 9645 9110 9025 1187 1676 1060 N | ANISOU 691 N VAL A 239 7892 4137 10383 −742 2478 349 N |
| ATOM 647 CA ALA A 233 103.758 −46.433 2.651 1.00 69.97 C | ATOM 692 CA VAL A 239 112.260 −55.138 −4.865 1.00 58.90 C |
| ANISOU 647 CA ALA A 233 9318 8497 8769 1032 1441 703 C | ANISOU 692 CA VAL A 239 7976 4113 10292 −731 2711 694 C |
| ATOM 648 CB ALA A 233 103.304 −45.206 3.392 1.00 60.26 C | ATOM 693 CB VAL A 239 112.363 −56.510 −5.508 1.00 61.22 C |
| ANISOU 648 CB ALA A 233 8188 7685 7023 1253 1186 578 C | ANISOU 693 CB VAL A 239 8009 3944 11307 −859 2990 637 C |
| ATOM 649 C ALA A 233 104.075 −46.087 1.205 1.00 74.76 C | ATOM 694 CG1 VAL A 239 113.670 −57.158 −5.114 1.00 61.20 C |
| ANISOU 649 C ALA A 233 10230 8754 9422 674 1117 230 C | ANISOU 694 CG1 VAL A 239 8009 3985 11259 −804 3295 1087 C |
| ATOM 650 O ALA A 233 105.183 −45.653 0.889 1.00 69.64 O | ATOM 695 CG2 VAL A 239 111.184 −57.376 −5.091 1.00 65.00 C |
| ANISOU 650 O ALA A 233 9829 8161 8472 588 947 110 O | ANISOU 695 CG2 VAL A 239 8013 4113 12573 −833 3342 717 C |
| ATOM 651 N GLY A 234 103.092 −46.279 0.332 1.00 73.78 N | ATOM 696 C VAL A 239 113.365 −54.256 −5.413 1.00 55.71 C |
| ANISOU 651 N GLY A 234 10063 8294 9678 503 1042 −43 N | ANISOU 696 C VAL A 239 7999 3917 9252 −788 2380 545 C |
| ATOM 652 CA GLY A 234 103.243 −45.975 −1.077 1.00 66.19 C | ATOM 697 O VAL A 239 113.400 −53.965 −6.606 1.00 59.88 O |
| ANISOU 652 CA GLY A 234 9364 7058 8727 255 744 −490 C | ANISOU 697 O VAL A 239 8737 4304 9710 −915 2095 121 O |
| ATOM 653 C GLY A 234 104.168 −46.939 −1.791 1.00 74.82 C | ATOM 698 N TYR A 240 114.267 −53.842 −4.528 1.00 84.46 N |
| ANISOU 653 C GLY A 234 10444 7875 10108 81 889 −458 C | ANISOU 698 N TYR A 240 11737 7909 12444 −658 2436 892 N |
| ATOM 654 O GLY A 234 104.506 −46.738 −2.956 1.00 87.48 O | ATOM 699 CA TYR A 240 115.387 −52.978 −4.896 1.00 77.39 C |
| ANISOU 654 O GLY A 234 12278 9299 11662 −76 668 −786 O | ANISOU 699 CA TYR A 240 11188 7198 11018 −709 2173 780 C |
| ATOM 655 N ILE A 235 104.566 −48.005 −1.107 1.00 74.41 N | ATOM 700 CB TYR A 240 115.518 −51.822 −3.921 1.00 51.23 C |
| ANISOU 655 N ILE A 235 10121 7802 10363 146 1286 −41 N | ANISOU 700 CB TYR A 240 7970 4322 7174 −555 2013 859 C |
| ATOM 656 CA ILE A 235 105.611 −48.862 −1.639 1.00 77.16 C | ATOM 701 CG TYR A 240 114.507 −50.734 −4.114 1.00 64.11 C |
| ANISOU 656 CA ILE A 235 10470 7928 10919 7 1439 38 C | ANISOU 701 CG TYR A 240 9737 5998 8622 −565 1701 531 C |
| ATOM 657 CB ILE A 235 106.970 −48.134 −1.548 1.00 74.77 C | ATOM 702 CD1 TYR A 240 114.735 −49.704 −5.006 1.00 60.79 C |
| ANISOU 657 CB ILE A 235 10490 7877 10042 20 1269 72 C | ANISOU 702 CD1 TYR A 240 9645 5529 7924 −674 1376 189 C |
| ATOM 658 CG1 ILE A 235 108.119 −48.954 −2.107 1.00 86.24 C | ATOM 703 CE1 TYR A 240 113.811 −48.700 −5.175 1.00 60.29 C |
| ANISOU 658 CG1 ILE A 235 11973 9129 11664 −117 1413 159 C | ANISOU 703 CE1 TYR A 240 9707 5508 7692 −653 1119 −79 C |
| ATOM 659 CD1 ILE A 235 109.442 −48.277 −1.864 1.00 91.15 C | ATOM 704 CZ TYR A 240 112.639 −48.720 −4.448 1.00 65.08 C |
| ANISOU 659 CDI ILE A 235 12842 10011 11778 −86 1288 219 C | ANISOU 704 CZ TYR A 240 10111 6217 8399 −543 1155 −37 C |
| ATOM 660 CG2 ILE A 235 107.257 −47.726 −0.138 1.00 75.09 C | ATOM 705 OH TYR A 240 111.708 −47.725 −4.613 1.00 61.22 O |
| ANISOU 660 CG2 ILE A 235 10459 8372 9699 294 1365 404 C | ANISOU 705 OH TYR A 240 9745 5777 7738 −513 900 −303 O |
| ATOM 661 C ILE A 235 105.604 −50.247 −0.975 1.00 86.08 C | ATOM 706 CE2 TYR A 240 112.394 −49.734 −3.550 1.00 73.96 C |
| ANISOU 661 C ILE A 235 11190 8912 12603 89 1959 495 C | ANISOU 706 CE2 TYR A 240 10902 7390 9810 −436 1482 305 C |
| ATOM 662 O ILE A 235 106.509 −50.637 −0.235 1.00 96.17 O | ATOM 707 CD2 TYR A 240 113.329 −50.733 −3.393 1.00 74.48 C |
| ANISOU 662 O ILE A 235 12415 10372 13752 233 2215 915 O | ANISOU 707 CD2 TYR A 240 10845 7402 10052 −438 1766 600 C |
| ATOM 663 N LYS A 236 104.538 −50.983 −1.247 1.00 82.69 N | ATOM 708 C TYR A 240 116.706 −53.716 −4.877 1.00 75.28 C |
| ANISOU 663 N LYS A 236 10441 8147 12830 20 2134 404 N | ANISOU 708 C TYR A 240 10907 6914 10781 −719 2395 1050 C |
| ATOM 664 CA LYS A 236 104.439 −52.363 −0.816 1.00 92.51 C | ATOM 709 O TYR A 240 117.012 −54.437 −3.930 1.00 83.55 O |
| ANISOU 664 CA LYS A 236 11254 9111 14783 62 2679 797 C | ANISOU 709 O TYR A 240 11717 8088 11942 −560 2734 1478 O |
| ATOM 665 CB LYS A 236 102.984 −52.699 −0.520 1.00102.01 C | ATOM 710 N SER A 241 117.507 −53.509 −5.908 1.00 64.59 N |
| ANISOU 665 CB LYS A 236 12069 10118 16570 101 2883 798 C | ANISOU 710 N SER A 241 9809 5433 9298 −865 2223 832 N |
| ATOM 666 CG LYS A 236 102.037 −52.223 −1.606 1.00104.79 C | ATOM 711 CA SER A 241 118.841 −54.068 −5.899 1.00 78.88 C |
| ANISOU 666 CG LYS A 236 12479 10290 17047 −92 2459 110 C | ANISOU 711 CA SER A 241 11635 7260 11076 −876 2399 1072 C |
| ATOM 712 CB SER A 241 119.007 −55.117 −6.997 1.00 90.36 C | ATOM 757 C GLU A 246 135.520 −51.428 −11.149 1.00 48.85 C |
| ANISOU 712 CB SER A 241 13061 8312 12959 −1015 2514 950 C | ANISOU 757 C GLU A 246 5888 6427 6245 1125 158 694 C |
| ATOM 713 OG SER A 241 119.087 −54.504 −8.266 1.00 96.85 O | ATOM 758 O GLU A 246 135.039 −51.015 −12.198 1.00 50.43 O |
| ANISOU 713 OG SER A 241 14176 9015 13606 −1124 2203 547 O | ANISOU 758 O GLU A 246 6090 6600 6470 1011 197 610 O |
| ATOM 714 C SER A 241 119.844 −52.944 −6.086 1.00 70.46 C | ATOM 759 N LEU A 247 136.498 −50.797 −10.510 1.00 51.24 N |
| ANISOU 714 C SER A 241 10863 6399 9510 −910 2145 959 C | ANISOU 759 N LEU A 247 6081 6895 6494 1159 55 715 N |
| ATOM 715 O SER A 241 119.499 −51.852 −6.520 1.00 73.40 O | ATOM 760 CA LEU A 247 137.141 −49.625 −11.096 1.00 38.62 C |

TABLE 9-continued

DMXAA-hSTING$^{S162A/G230I/Q266I}$ complex

| | |
|---|---|
| ANISOU 715 O SER A 241 11451 6790 9651 -954 1856 669 O | ANISOU 760 CA LEU A 247 4337 5428 4908 1046 1 650 C |
| ATOM 716 N ASN A 242 121.089 -53.225 -5.743 1.00 70.78 N | ATOM 761 CB LEU A 247 137.228 -48.488 -10.096 1.00 38.08 C |
| ANISOU 716 N ASN A 242 10885 6579 9430 -876 2283 1197 N | ANISOU 761 CB LEU A 247 4226 5457 4785 984 -138 636 C |
| ATOM 717 CA ASN A 242 122.160 -52.283 -5.963 1.00 54.31 C | ATOM 762 CG LEU A 247 135.914 -48.101 -9.444 1.00 42.78 C |
| ANISOU 717 CA ASN A 242 9019 4624 6991 -930 2092 1082 C | ANISOU 762 CG LEU A 247 4972 5976 5308 920 -149 636 C |
| ATOM 718 CB ASN A 242 122.653 -51.712 -4.643 1.00 62.00 C | ATOM 763 CD1 LEU A 247 136.193 -47.165 -8.296 1.00 48.05 C |
| ANISOU 718 CB ASN A 242 9857 6054 7644 -754 2074 1215 C | ANISOU 763 CD1 LEU A 247 5598 6757 5901 924 -307 605 C |
| ATOM 719 CG ASN A 242 121.621 -50.840 -3.971 1.00 71.36 C | ATOM 764 CD2 LEU A 247 135.003 -47.438 -10.466 1.00 47.25 C |
| ANISOU 719 CG ASN A 242 11003 7444 8668 -649 1900 1075 C | ANISOU 764 CD2 LEU A 247 5578 6465 5911 750 -82 580 C |
| ATOM 720 OD1 ASN A 242 120.672 -51.336 -3.355 1.00 73.27 O | ATOM 765 C LEU A 247 138.536 -50.008 -11.545 1.00 48.91 C |
| ANISOU 720 OD1 ASN A 242 11052 7755 9033 -513 2036 1236 O | ANISOU 765 C LEU A 247 5484 6838 6262 1150 6 659 C |
| ATOM 721 ND2 ASN A 242 121.794 -49.526 -4.090 1.00 60.48 N | ATOM 766 O LEU A 247 139.318 -50.554 -10.770 1.00 52.80 O |
| ANISOU 721 ND2 ASN A 242 9790 6136 7052 -704 1623 781 N | ANISOU 766 O LEU A 247 5928 7392 6740 1296 -49 709 O |
| ATOM 722 C ASN A 242 123.284 -53.011 -6.655 1.00 66.02 C | ATOM 767 N LEU A 248 138.844 -49.714 -12.799 1.00 42.05 N |
| ANISOU 722 C ASN A 242 10565 5934 8588 -1021 2233 1184 C | ANISOU 767 N LEU A 248 4531 6004 5441 1092 78 619 N |
| ATOM 723 O ASN A 242 123.385 -54.234 -6.571 1.00 74.94 O | ATOM 768 CA LEU A 248 140.098 -50.146 -13.366 1.00 37.95 C |
| ANISOU 723 O ASN A 242 11428 7066 9981 -947 2396 1349 O | ANISOU 768 CA LEU A 248 3860 5589 4968 1205 117 635 C |
| ATOM 724 N SER A 243 124.136 -52.261 -7.333 1.00 43.84 N | ATOM 769 CB LEU A 248 139.897 -50.721 -14.763 1.00 48.54 C |
| ANISOU 724 N SER A 243 5896 4842 5919 675 745 1234 N | ANISOU 769 CB LEU A 248 5240 6886 6315 1246 255 589 C |
| ATOM 725 CA SER A 243 125.180 -52.889 -8.107 1.00 47.87 C | ATOM 770 CG LEU A 248 138.936 -51.887 -14.968 1.00 57.93 C |
| ANISOU 725 CA SER A 243 6383 5303 6504 703 699 1144 C | ANISOU 770 CG LEU A 248 6621 7890 7500 1317 317 540 C |
| ATOM 726 CB SER A 243 125.067 -52.500 -9.567 1.00 60.70 C | ATOM 771 CD1 LEU A 248 139.121 -52.358 -16.391 1.00 58.89 C |
| ANISOU 726 CB SER A 243 7964 6912 8185 564 626 916 C | ANISOU 771 CD1 LEU A 248 6728 8028 7619 1395 422 463 C |
| ATOM 727 OG SER A 243 123.978 -53.173 -10.135 1.00 68.49 O | ATOM 772 CD2 LEU A 248 139.185 -53.027 -13.978 1.00 40.68 C |
| ANISOU 727 OG SER A 243 8935 7696 9394 471 688 871 O | ANISOU 772 CD2 LEU A 248 4491 5621 5343 1474 293 599 C |
| ATOM 728 C SER A 243 126.553 -52.564 -7.592 1.00 46.65 C | ATOM 773 C LEU A 248 141.097 -49.016 -13.441 1.00 42.46 C |
| ANISOU 728 C SER A 243 6230 5334 6162 835 614 1167 C | ANISOU 773 C LEU A 248 4212 6321 5600 1121 57 648 C |
| ATOM 729 O SER A 243 126.809 -51.474 -7.092 1.00 45.37 O | ATOM 774 O LEU A 248 140.742 -47.863 -13.664 1.00 48.42 O |
| ANISOU 729 O SER A 243 6070 5362 5807 846 529 1145 O | ANISOU 774 O LEU A 248 4937 7082 6379 954 38 632 O |
| ATOM 730 N ILE A 244 127.436 -53.535 -7.747 1.00 57.68 N | ATOM 775 N GLU A 249 142.358 -49.382 -13.278 1.00 47.07 N |
| ANISOU 730 N ILE A 244 7616 6662 7638 937 630 1197 N | ANISOU 775 N GLU A 249 4631 7023 6230 1242 32 682 N |
| ATOM 731 CA ILE A 244 128.815 -53.388 -7.351 1.00 49.88 C | ATOM 776 CA GLU A 249 143.466 -48.465 -13.426 1.00 52.66 C |
| ANISOU 731 CA ILE A 244 6604 5842 6508 1071 546 1212 C | ANISOU 776 CA GLU A 249 5084 7881 7045 1175 -13 702 C |
| ATOM 732 CB ILE A 244 129.272 -54.603 -6.571 1.00 41.30 C | ATOM 777 CB GLU A 249 143.935 -47.978 -12.061 1.00 59.35 C |
| ANISOU 732 CB ILE A 244 5548 4674 5470 1262 625 1401 C | ANISOU 777 CB GLU A 249 5839 8794 7915 1165 -212 681 C |
| ATOM 733 CG1 ILE A 244 128.400 -54.778 -5.332 1.00 45.71 C | ATOM 778 CG GLU A 249 144.424 -46.544 -12.043 1.00 76.50 C |
| ANISOU 733 CG1 ILE A 244 6174 5211 5983 1339 728 1618 C | ANISOU 778 CG GLU A 249 7808 11032 10228 982 -301 655 C |
| ATOM 734 CD1 ILE A 244 128.660 -56.085 -4.583 1.00 40.06 C | ATOM 779 CD GLU A 249 144.712 -46.040 -10.638 1.00 94.55 C |
| ANISOU 734 CD1 ILE A 244 5496 4374 5349 1533 847 1854 C | ANISOU 779 CD GLU A 249 10033 13371 12521 979 -534 581 C |
| ATOM 735 CG2 ILE A 244 130.712 -54.450 -6.159 1.00 42.72 C | ATOM 780 OE1 GLU A 249 145.351 -46.778 -9.855 1.00108.42 O |
| ANISOU 735 CG2 ILE A 244 5686 5047 5498 1413 521 1407 C | ANISOU 780 OE1 GLU A 249 11750 15220 14226 1156 -625 582 O |
| ATOM 736 C ILE A 244 129.637 -53.269 -8.611 1.00 47.66 C | ATOM 781 OE2 GLU A 249 144.292 -44.907 -10.317 1.00 88.03 O |
| ANISOU 736 C ILE A 244 6254 5587 6267 1016 477 1033 C | ANISOU 781 OE2 GLU A 249 9203 12499 11745 816 -630 515 O |
| ATOM 737 O ILE A 244 129.478 -54.059 -9.535 1.00 45.90 O | ATOM 782 C GLU A 249 144.544 -49.285 -14.106 1.00 53.35 C |
| ANISOU 737 O ILE A 244 6039 5215 6221 986 525 961 O | ANISOU 782 C GLU A 249 5036 8067 7167 1341 84 744 C |
| ATOM 738 N TYR A 245 130.510 -52.272 -8.649 1.00 45.91 N | ATOM 783 O GLU A 249 144.938 -50.332 -13.601 1.00 52.21 O |
| ANISOU 738 N TYR A 245 5970 5569 5903 1009 364 960 N | ANISOU 783 O GLU A 249 4919 7928 6990 1523 61 756 O |
| ATOM 739 CA TYR A 245 131.357 -52.080 -9.809 1.00 42.18 C | ATOM 784 N ASN A 250 144.992 -48.824 -15.268 1.00 53.02 N |
| ANISOU 739 CA TYR A 245 5416 5151 5458 971 320 824 C | ANISOU 784 N ASN A 250 4855 8105 7185 1296 207 780 N |
| ATOM 740 CB TYR A 245 131.110 -50.725 -10.458 1.00 46.75 C | ATOM 785 CA ASN A 250 145.932 -49.575 -16.087 1.00 56.11 C |
| ANISOU 740 CB TYR A 245 5955 5832 5976 815 259 707 C | ANISOU 785 CA ASN A 250 5126 8604 7589 1470 331 819 C |
| ATOM 741 CG TYR A 245 129.739 -50.614 -11.047 1.00 47.21 C | ATOM 786 CB ASN A 250 147.318 -49.574 -15.453 1.00 64.54 C |
| ANISOU 741 CG TYR A 245 6070 5772 6095 689 312 650 C | ANISOU 786 CB ASN A 250 5936 9821 8766 1544 243 864 C |
| ATOM 742 CD1 TYR A 245 128.654 -50.262 -10.249 1.00 41.72 C | ATOM 787 CG ASN A 250 147.893 -48.194 -15.355 1.00 68.44 C |
| ANISOU 742 CD1 TYR A 245 5438 5045 5369 644 329 712 C | ANISOU 787 CG ASN A 250 6182 10400 9422 1353 181 902 C |
| ATOM 743 CE1 TYR A 245 127.388 -50.169 -10.775 1.00 55.30 C | ATOM 788 OD1 ASN A 250 148.170 -47.557 -16.372 1.00 71.32 O |
| ANISOU 743 CE1 TYR A 245 7190 6664 7158 532 373 660 C | ANISOU 788 OD1 ASN A 250 6411 10825 9864 1276 318 974 O |
| ATOM 744 CZ TYR A 245 127.193 -50.440 -12.117 1.00 54.69 C | ATOM 789 ND2 ASN A 250 148.061 -47.705 -14.128 1.00 59.14 N |
| ANISOU 744 CZ TYR A 245 7089 6522 7170 472 383 529 C | ANISOU 789 ND2 ASN A 250 4942 9224 8303 1281 -25 855 N |
| ATOM 745 OH TYR A 245 125.930 -50.347 -12.646 1.00 57.29 O | ATOM 790 C ASN A 250 145.014 -51.014 -16.362 1.00 55.12 C |
| ANISOU 745 OH TYR A 245 7436 6765 7568 370 404 460 O | ANISOU 790 C ASN A 250 5200 8384 7359 1666 403 770 C |
| ATOM 746 CE2 TYR A 245 128.256 -50.801 -12.932 1.00 59.41 C | ATOM 791 O ASN A 250 146.357 -51.902 -16.422 1.00 55.68 O |
| ANISOU 746 CE2 TYR A 245 7639 7157 7776 531 367 460 C | ANISOU 791 O ASN A 250 5199 8518 7441 1860 437 785 O |
| ATOM 747 CD2 TYR A 245 129.520 -50.889 -12.391 1.00 47.48 C | ATOM 792 N GLY A 251 144.216 -51.239 -16.510 1.00 60.10 N |
| ANISOU 747 CD2 TYR A 245 6089 5741 6209 635 341 529 C | ANISOU 792 N GLY A 251 6072 8852 7913 1614 422 705 N |
| ATOM 748 C TYR A 245 132.824 -52.223 -9.499 1.00 45.55 C | ATOM 793 CA GLY A 251 143.715 -52.544 -16.896 1.00 55.11 C |
| ANISOU 748 C TYR A 245 5764 5713 5832 1106 259 854 C | ANISOU 793 CA GLY A 251 5622 8092 7227 1771 490 637 C |
| ATOM 749 O TYR A 245 133.273 -52.022 -8.374 1.00 41.16 O | ATOM 794 C GLY A 251 143.413 -53.484 -15.741 1.00 63.57 C |
| ANISOU 749 O TYR A 245 5200 5268 5269 1205 198 939 O | ANISOU 794 C GLY A 251 6828 9019 8307 1860 408 643 C |
| ATOM 750 N GLU A 246 133.553 -52.561 -10.549 1.00 55.77 N | ATOM 795 O GLY A 251 142.845 -54.553 -15.945 1.00 64.09 O |
| ANISOU 750 N GLU A 246 6991 7009 7191 1122 272 773 N | ANISOU 795 O GLY A 251 7057 8923 8372 1961 457 589 O |
| ATOM 751 CA GLU A 246 134.985 -52.700 -10.521 1.00 56.36 C | ATOM 796 N GLN A 252 143.790 -53.097 -14.527 1.00 54.87 N |
| ANISOU 751 CA GLU A 246 6958 7214 7241 1242 225 784 C | ANISOU 796 N GLN A 252 5656 7973 7220 1832 284 708 N |
| ATOM 752 CB GLU A 246 135.347 -53.881 -11.404 1.00 62.62 C | ATOM 797 CA GLN A 252 143.572 -53.959 -13.375 1.00 44.68 C |
| ANISOU 752 CB GLU A 246 7752 7896 8147 1337 305 748 C | ANISOU 797 CA GLN A 252 4486 6578 5914 1949 220 751 C |
| ATOM 753 CG GLU A 246 136.669 -54.532 -11.134 1.00 83.10 C | ATOM 798 CB GLN A 252 144.889 -54.274 -12.673 1.00 50.42 C |
| ANISOU 753 CG GLU A 246 10266 10565 10741 1523 289 804 C | ANISOU 798 CB GLN A 252 5046 7454 6658 2118 145 818 C |
| ATOM 754 CD GLU A 246 136.916 -55.681 -12.094 1.00 95.97 C | ATOM 799 CG GLN A 252 146.029 -54.672 -13.602 1.00 49.88 C |

TABLE 9-continued

DMXAA-hSTING$^{S162A/G230I/Q266I}$ complex

| | |
|---|---|
| ANISOU 754 CD GLU A 246 11911 12066 12488 1623 373 742 C | ANISOU 799 CG GLN A 252 4808 7505 6640 2254 231 814 C |
| ATOM 755 OE1 GLU A 246 137.880 −56.444 −11.878 1.00 96.93 O | ATOM 800 CD GLN A 252 145.885 −56.080 −14.176 1.00 59.65 C |
| ANISOU 755 OE1 GLU A 246 11988 12208 12634 1802 380 796 O | ANISOU 800 CD GLN A 252 129.008 −47.189 −8.280 1.00 51.44 C |
| ATOM 756 OE2 GLU A 246 136.135 −55.817 −13.062 1.00 96.30 O | ATOM 801 OE1 GLN A 252 145.065 −56.877 −13.714 1.00 59.49 O |
| ANISOU 756 OE2 GLU A 246 12007 11990 12593 1537 421 626 O | ANISOU 801 OE1 GLN A 252 6364 8371 7869 2496 352 792 O |
| ATOM 802 NE2 GLN A 252 146.693 −56.390 −15.189 1.00 86.03 N | ATOM 847 CB LEU A 259 129.008 −47.189 −8.280 1.00 51.44 C |
| ANISOU 802 NE2 GLN A 252 7125 9756 8969 2571 446 756 N | ANISOU 847 CB LEU A 259 6653 6638 6253 616 94 698 C |
| ATOM 803 C GLN A 252 142.609 −53.317 −12.392 1.00 49.03 C | ATOM 848 CG LEU A 259 129.582 −45.924 −8.894 1.00 62.42 C |
| ANISOU 803 C GLN A 252 5149 7065 6417 1809 127 765 C | ANISOU 848 CG LEU A 259 7963 8116 7639 509 −3 585 C |
| ATOM 804 O GLN A 252 142.416 −52.103 −12.390 1.00 50.15 O | ATOM 849 CD1 LEU A 259 130.145 −45.051 −7.797 1.00 65.76 C |
| ANISOU 804 O GLN A 252 5230 7275 6550 1631 71 738 O | ANISOU 849 CD1 LEU A 259 8361 8664 7959 560 −137 559 C |
| ATOM 805 N ARG A 253 142.009 −54.149 −11.556 1.00 60.02 N | ATOM 850 CD2 LEU A 259 130.663 −46.299 −9.890 1.00 58.33 C |
| ANISOU 805 N ARG A 253 6702 8320 7783 1901 121 819 N | ANISOU 850 CD2 LEU A 259 7347 7613 7202 506 6 556 C |
| ATOM 806 CA ARG A 253 141.120 −53.659 −10.522 1.00 65.27 C | ATOM 851 C LEU A 259 126.549 −46.860 −8.103 1.00 50.61 C |
| ANISOU 806 CA ARG A 253 7476 8942 8380 1815 49 852 C | ANISOU 851 C LEU A 259 6667 6408 6155 508 208 730 C |
| ATOM 807 CB ARG A 253 140.506 −54.822 −9.759 1.00 68.74 C | ATOM 852 O LEU A 259 126.047 −47.780 −8.747 1.00 48.96 O |
| ANISOU 807 CB ARG A 253 8087 9215 8815 1955 97 951 C | ANISOU 852 O LEU A 259 6462 6065 6076 476 299 745 O |
| ATOM 808 CG ARG A 253 139.560 −54.393 −8.663 1.00 74.55 C | ATOM 853 N GLU A 260 126.016 −45.646 −8.054 1.00 44.73 N |
| ANISOU 808 CG ARG A 253 8938 9924 9462 1901 50 1011 C | ANISOU 853 N GLU A 260 5934 5718 5344 433 155 663 N |
| ATOM 809 CD ARG A 253 138.892 −55.606 −8.071 1.00 78.34 C | ATOM 854 CA GLU A 260 124.886 −45.318 −8.905 1.00 43.78 C |
| ANISOU 809 CD ARG A 253 9579 10215 9973 2033 145 1143 C | ANISOU 854 CA GLU A 260 5822 5521 5290 311 203 611 C |
| ATOM 810 NE ARG A 253 138.380 −56.489 −9.114 1.00 78.20 N | ATOM 855 CB GLU A 260 123.586 −45.918 −8.360 1.00 44.32 C |
| ANISOU 810 NE ARG A 253 9633 9970 10108 2006 274 1096 N | ANISOU 855 CB GLU A 260 5940 5506 5392 331 312 705 C |
| ATOM 811 CZ ARG A 253 137.801 −57.662 −8.881 1.00 79.41 C | ATOM 856 CG GLU A 260 123.180 −45.451 −6.976 1.00 47.56 C |
| ANISOU 811 CZ ARG A 253 9909 9895 10369 2097 376 1191 C | ANISOU 856 CG GLU A 260 6406 6003 5659 429 314 786 C |
| ATOM 812 NH1 ARG A 253 137.662 −58.092 −7.635 1.00 65.59 N | ATOM 857 CD GLU A 260 122.004 −46.249 −6.430 1.00 73.21 C |
| ANISOU 812 NH1 ARG A 253 8225 8125 8570 2232 389 1375 N | ANISOU 857 CD GLU A 260 9682 9169 8967 467 461 929 C |
| ATOM 813 NH2 ARG A 253 137.363 −58.404 −9.896 1.00 73.08 N | ATOM 858 OE1 GLU A 260 122.096 −47.496 −6.404 1.00 87.23 O |
| ANISOU 813 NH2 ARG A 253 9157 8882 9728 2063 465 1100 N | ANISOU 858 OE1 GLU A 260 11446 10836 10860 505 551 1032 O |
| ATOM 814 C ARG A 253 141.880 −52.757 −9.557 1.00 46.24 C | ATOM 859 OE2 GLU A 260 120.985 −45.632 −6.057 1.00 81.40 O |
| ANISOU 814 C ARG A 253 4925 6733 5911 1814 −113 864 C | ANISOU 859 OE2 GLU A 260 10740 10236 9952 457 493 943 O |
| ATOM 815 O ARG A 253 142.989 −53.072 −9.142 1.00 51.02 O | ATOM 860 C GLU A 260 124.747 −43.823 −9.127 1.00 49.13 C |
| ANISOU 815 O ARG A 253 5403 7467 6516 1966 −177 899 O | ANISOU 860 C GLU A 260 6493 6268 5908 230 120 519 C |
| ATOM 816 N ALA A 254 141.276 −51.632 −9.204 1.00 53.21 N | ATOM 861 O GLU A 260 125.290 −43.009 −8.376 1.00 47.87 O |
| ANISOU 816 N ALA A 254 5826 7640 6751 1649 −189 818 N | ANISOU 861 O GLU A 260 6333 6197 5659 268 26 494 O |
| ATOM 817 CA ALA A 254 141.905 −50.708 −8.279 1.00 61.18 C | ATOM 862 N TYR A 261 124.029 −43.484 −10.191 1.00 47.32 N |
| ANISOU 817 CA ALA A 254 6707 8820 7718 1639 −368 786 C | ANISOU 862 N TYR A 261 6253 5991 5736 127 147 461 N |
| ATOM 818 CB ALA A 254 142.315 −49.441 −8.997 1.00 49.86 C | ATOM 863 CA TYR A 261 123.708 −42.107 −10.503 1.00 40.20 C |
| ANISOU 818 CB ALA A 254 5099 7459 6385 1441 −409 699 C | ANISOU 863 CA TYR A 261 5350 5125 4798 54 92 397 C |
| ATOM 819 C ALA A 254 140.954 −50.387 −7.142 1.00 66.62 C | ATOM 864 CB TYR A 261 123.388 −41.964 −11.979 1.00 42.64 C |
| ANISOU 819 C ALA A 254 7549 9484 8279 1637 −441 797 C | ANISOU 864 CB TYR A 261 5627 5405 5168 −29 120 344 C |
| ATOM 820 O ALA A 254 141.312 −49.697 −6.194 1.00 69.58 O | ATOM 865 CG TYR A 261 124.596 −41.918 −12.869 1.00 50.21 C |
| ANISOU 820 O ALA A 254 7858 9996 8584 1664 −609 751 O | ANISOU 865 CG TYR A 261 6518 6404 6155 −42 101 323 C |
| ATOM 821 N GLY A 255 139.730 −50.881 −7.255 1.00 61.93 N | ATOM 866 CD1 TYR A 261 125.237 −40.711 −13.125 1.00 41.41 C |
| ANISOU 821 N GLY A 255 7151 8721 7660 1612 −316 848 N | ANISOU 866 CD1 TYR A 261 5359 5336 5038 −88 48 312 C |
| ATOM 822 CA GLY A 255 138.712 −50.586 −6.273 1.00 52.05 C | ATOM 867 CE1 TYR A 261 126.336 −40.652 −13.944 1.00 49.19 C |
| ANISOU 822 CA GLY A 255 6044 7443 6289 1611 −347 878 C | ANISOU 867 CE1 TYR A 261 6262 6365 6062 −97 55 322 C |
| ATOM 823 C GLY A 255 137.405 −51.265 −6.611 1.00 45.40 C | ATOM 868 CZ TYR A 261 126.815 −41.813 −14.522 1.00 46.48 C |
| ANISOU 823 C GLY A 255 5381 6293 5478 1570 −180 945 C | ANISOU 868 CZ TYR A 261 5892 6033 5734 −41 107 323 C |
| ATOM 824 O GLY A 255 137.177 −51.692 −7.741 1.00 48.88 O | ATOM 869 OH TYR A 261 127.917 −41.749 −15.339 1.00 56.84 O |
| ANISOU 824 O GLY A 255 5831 6705 6035 1494 −69 918 O | ANISOU 869 OH TYR A 261 7115 7409 7072 −29 129 342 O |
| ATOM 825 N THR A 256 136.545 −51.353 −5.611 1.00 51.64 N | ATOM 870 CE2 TYR A 261 126.195 −43.031 −14.284 1.00 50.48 C |
| ANISOU 825 N THR A 256 6301 7158 6163 1631 −168 1029 N | ANISOU 870 CE2 TYR A 261 6454 6477 6248 8 144 310 C |
| ATOM 826 CA THR A 256 135.270 −52.018 −5.751 1.00 61.33 C | ATOM 871 CD2 TYR A 261 125.091 −43.077 −13.460 1.00 50.53 C |
| ANISOU 826 CA THR A 256 7675 8183 7442 1596 −11 1114 C | ANISOU 871 CD2 TYR A 261 6531 6427 6242 −1 145 319 C |
| ATOM 827 CB THR A 256 135.332 −53.424 −5.158 1.00 63.03 C | ATOM 872 C TYR A 261 122.494 −41.680 −9.705 1.00 41.89 C |
| ANISOU 827 CB THR A 256 7965 8308 7677 1805 88 1295 C | ANISOU 872 C TYR A 261 5626 5336 4955 72 112 417 C |
| ATOM 828 OG1 THR A 256 136.433 −54.136 −5.732 1.00 74.47 O | ATOM 873 O TYR A 261 121.621 −42.488 −9.412 1.00 43.11 O |
| ANISOU 828 OG1 THR A 256 9328 9754 9214 1895 89 1282 O | ANISOU 873 O TYR A 261 5802 5441 5136 98 199 480 O |
| ATOM 829 CG2 THR A 256 134.056 −54.173 −5.430 1.00 57.25 C | ATOM 874 N ALA A 262 122.440 −40.403 −9.354 1.00 42.04 N |
| ANISOU 829 CG2 THR A 256 7352 7328 7073 1743 257 1377 C | ANISOU 874 N ALA A 262 5665 5399 4911 61 37 366 N |
| ATOM 830 C THR A 256 134.277 −51.194 −4.963 1.00 61.39 C | ATOM 875 CA ALA A 262 121.255 −39.871 −8.705 1.00 38.91 C |
| ANISOU 830 C THR A 256 7765 8230 7328 1545 −39 1120 C | ANISOU 875 CA ALA A 262 5325 5010 4449 91 59 372 C |
| ATOM 831 O THR A 256 134.575 −50.783 −3.850 1.00 69.11 O | ATOM 876 CB ALA A 262 121.563 −38.572 −8.003 1.00 34.70 C |
| ANISOU 831 O THR A 256 8744 9370 8143 1669 −146 1141 O | ANISOU 876 CB ALA A 262 4821 4526 3838 122 −53 296 C |
| ATOM 832 N CYS A 257 133.103 −50.935 −5.524 1.00 53.53 N | ATOM 877 C ALA A 262 120.181 −39.662 −9.763 1.00 38.08 C |
| ANISOU 832 N CYS A 257 6836 7103 6401 1382 45 1088 N | ANISOU 877 C ALA A 262 5205 4853 4410 4 112 351 C |
| ATOM 833 CA CYS A 257 132.154 −50.096 −4.807 1.00 49.19 C | ATOM 878 O ALA A 262 120.383 −38.933 −10.729 1.00 31.85 O |
| ANISOU 833 CA CYS A 257 6357 6600 5734 1342 23 1088 C | ANISOU 878 O ALA A 262 4391 4056 3656 −66 74 298 O |
| ATOM 834 CB CYS A 257 132.606 −48.629 −4.828 1.00 46.30 C | ATOM 879 N THR A 263 119.035 −40.303 −9.570 1.00 37.56 N |
| ANISOU 834 CB CYS A 257 5910 6383 5297 1245 −145 922 C | ANISOU 879 N THR A 263 5144 4758 4368 19 202 404 N |
| ATOM 835 SG CYS A 257 132.342 −47.808 −6.413 1.00 61.31 S | ATOM 880 CA THR A 263 117.941 −40.260 −10.543 1.00 39.32 C |
| ANISOU 835 SG CYS A 257 7749 8198 7347 985 −130 775 S | ANISOU 880 CA THR A 263 5334 4942 4665 −52 241 373 C |
| ATOM 836 C CYS A 257 130.722 −50.188 −5.315 1.00 49.36 C | ATOM 881 CB THR A 263 116.840 −41.265 −10.170 1.00 41.91 C |
| ANISOU 836 C CYS A 257 6456 6449 5849 1204 154 1105 C | ANISOU 881 CB THR A 263 5635 5220 5071 −40 346 446 C |
| ATOM 837 O CYS A 257 130.464 −50.511 −6.479 1.00 41.68 O | ATOM 882 OG1 THR A 263 116.357 −40.986 −8.846 1.00 38.62 O |
| ANISOU 837 O CYS A 257 5464 5339 5031 1082 217 1043 O | ANISOU 882 OG1 THR A 263 5259 4852 4562 52 392 527 O |
| ATOM 838 N VAL A 258 129.798 −49.885 −4.409 1.00 36.44 N | ATOM 883 CG2 THR A 263 117.401 −42.674 −10.235 1.00 24.77 C |

TABLE 9-continued

DMXAA-hSTING$^{S162A/G230I/Q266I}$ complex

```
ANISOU 838 N VAL A 258 4900 4840 4107 1242 185 1180 N
ATOM 839 CA VAL A 258 128.404 -49.750 -4.766 1.00 44.98 C
ANISOU 839 CA VAL A 258 6032 5793 5264 1110 289 1187 C
ATOM 840 CB VAL A 258 127.488 -49.987 -3.570 1.00 49.65 C
ANISOU 840 CB VAL A 258 6708 6398 5758 1231 388 1362 C
ATOM 841 CG2 VAL A 258 127.825 -51.324 -2.933 1.00 46.49 C
ANISOU 841 CG2 VAL A 258 6338 5941 5388 1417 494 1572 C
ATOM 842 CG1 VAL A 258 126.033 -49.959 -4.008 1.00 43.15 C
ANISOU 842 CG1 VAL A 258 5908 5429 5058 1086 507 1377 C
ATOM 843 C VAL A 258 128.223 -48.350 -5.319 1.00 48.92 C
ANISOU 843 C VAL A 258 6498 6361 5728 950 184 1008 C
ATOM 844 O VAL A 258 128.511 -47.352 -4.656 1.00 48.72 O
ANISOU 844 O VAL A 258 6469 6486 5557 985 64 945 O
ATOM 845 N LEU A 259 127.750 -48.290 -6.551 1.00 45.19 N
ANISOU 845 N LEU A 259 6001 5773 5396 785 225 922 N
ATOM 846 CA LEU A 259 127.833 -47.072 -7.316 1.00 45.45 C
ANISOU 846 CA LEU A 259 5987 5860 5422 644 137 771 C
ATOM 894 CA LEU A 265 119.262 -35.598 -12.722 1.00 50.24 C
ANISOU 894 CA LEU A 265 6725 6349 6014 -188 8 216 C
ATOM 895 CB LEU A 265 120.760 -35.868 -12.665 1.00 46.07 C
ANISOU 895 CB LEU A 265 6154 5826 5524 -207 -27 224 C
ATOM 896 CG LEU A 265 121.381 -35.385 -11.364 1.00 38.99 C
ANISOU 896 CG LEU A 265 5278 4925 4612 -175 -114 184 C
ATOM 897 CD1 LEU A 265 122.825 -35.793 -11.307 1.00 52.56 C
ANISOU 897 CD1 LEU A 265 6930 6663 6377 -187 -154 189 C
ATOM 898 CD2 LEU A 265 121.257 -33.873 -11.269 1.00 39.29 C
ANISOU 898 CD2 LEU A 265 5335 4906 4689 -199 -181 138 C
ATOM 899 C LEU A 265 118.700 -36.029 -14.072 1.00 45.73 C
ANISOU 899 C LEU A 265 6120 5798 5456 -208 62 225 C
ATOM 900 O LEU A 265 118.782 -35.302 -15.061 1.00 51.66 O
ANISOU 900 O LEU A 265 6856 6557 6214 -225 62 241 O
ATOM 901 N ILE A 266 118.150 -37.234 -14.105 1.00 43.38 N
ANISOU 901 N ILE A 266 5807 5508 5168 -197 106 216 N
ATOM 902 CA ILE A 266 117.415 -37.682 -15.267 1.00 38.42 C
ANISOU 902 CA ILE A 266 5143 4901 4554 -203 129 182 C
ATOM 903 CB ILE A 266 116.915 -39.107 -15.094 1.00 34.90 C
ANISOU 903 CB ILE A 266 4666 4421 4174 -204 165 158 C
ATOM 904 CG1 ILE A 266 118.098 -40.054 -14.979 1.00 45.29 C
ANISOU 904 CG1 ILE A 266 5974 5714 5521 -197 175 169 C
ATOM 905 CD1 ILE A 266 117.727 -41.437 -14.501 1.00 41.97 C
ANISOU 905 CD1 ILE A 266 5533 5219 5194 -194 221 175 C
ATOM 906 CG2 ILE A 266 116.038 -39.514 -16.268 1.00 27.36 C
ANISOU 906 CG2 ILE A 266 3661 3486 3249 -208 157 79 C
ATOM 907 C ILE A 266 116.229 -36.747 -15.462 1.00 42.72 C
ANISOU 907 C ILE A 266 5699 5462 5069 -191 121 173 C
ATOM 908 O ILE A 266 115.934 -36.306 -16.568 1.00 36.17 O
ANISOU 908 O ILE A 266 4855 4677 4213 -178 111 159 O
ATOM 909 N THR A 267 115.570 -36.425 -14.359 1.00 33.13 N
ANISOU 909 N THR A 267 4514 4227 3846 -172 129 188 N
ATOM 910 CA THR A 267 114.407 -35.566 -14.408 1.00 30.75 C
ANISOU 910 CA THR A 267 4221 3942 3519 -145 127 181 C
ATOM 911 CB THR A 267 113.633 -35.587 -13.088 1.00 33.04 C
ANISOU 911 CB THR A 267 4530 4227 3795 -103 161 201 C
ATOM 912 OG1 THR A 267 113.045 -36.879 -12.919 1.00 33.06 O
ANISOU 912 OG1 THR A 267 4471 4223 3865 -118 222 217 O
ATOM 913 CG2 THR A 267 112.539 -34.506 -13.077 1.00 22.10 C
ANISOU 913 CG2 THR A 267 3159 2863 2377 -56 156 191 C
ATOM 914 C THR A 267 114.789 -34.136 -14.809 1.00 39.63 C
ANISOU 914 C THR A 267 5387 5057 4615 -135 87 195 C
ATOM 915 O THR A 267 114.108 -33.509 -15.628 1.00 36.59 O
ANISOU 915 O THR A 267 4993 4608 4212 -110 83 198 O
ATOM 916 N LEU A 268 115.891 -33.636 -14.252 1.00 34.13 N
ANISOU 916 N LEU A 268 4723 4315 3929 -151 54 206 N
ATOM 917 CA LEU A 268 116.391 -32.311 -14.632 1.00 41.26 C
ANISOU 917 CA LEU A 268 5646 5168 4862 -161 21 230 C
ATOM 918 CB LEU A 268 117.632 -31.917 -13.827 1.00 31.47 C
ANISOU 918 CB LEU A 268 4415 3866 3674 -192 -35 214 C
ATOM 919 CG LEU A 268 117.405 -31.509 -12.379 1.00 45.22 C
ANISOU 919 CG LEU A 268 6215 5581 5386 -143 -92 144 C
ATOM 920 CD1 LEU A 268 118.726 -31.172 -11.722 1.00 55.89 C
ANISOU 920 CD1 LEU A 268 7555 6884 6797 -171 -177 100 C
ATOM 921 CD2 LEU A 268 116.463 -30.321 -12.303 1.00 47.05 C
ANISOU 921 CD2 LEU A 268 6497 5765 5616 -97 -107 122 C
ATOM 922 C LEU A 268 116.713 -32.249 -16.123 1.00 36.09 C
ANISOU 883 CG2 THR A 263 3436 2975 3000 -37 392 491 C
ATOM 884 C THR A 263 117.307 -38.897 -10.867 1.00 29.26 C
ANISOU 884 C THR A 263 4076 3696 3344 -74 198 318 C
ATOM 885 O THR A 263 116.885 -38.682 -12.006 1.00 45.79 O
ANISOU 885 O THR A 263 6137 5781 5481 -129 192 274 O
ATOM 886 N PRO A 264 117.205 -37.985 -9.877 1.00 37.40 N
ANISOU 886 N PRO A 264 5161 4766 4282 -13 164 315 N
ATOM 887 CA PRO A 264 116.598 -36.690 -10.218 1.00 39.64 C
ANISOU 887 CA PRO A 264 5464 5053 4544 -26 125 262 C
ATOM 888 CB PRO A 264 116.688 -35.905 -8.907 1.00 41.04 C
ANISOU 888 CB PRO A 264 5709 5266 4617 69 77 238 C
ATOM 889 CG PRO A 264 116.664 -36.968 -7.843 1.00 40.43 C
ANISOU 889 CG PRO A 264 5644 5235 4483 156 143 316 C
ATOM 890 CD PRO A 264 117.445 -38.104 -8.423 1.00 32.06 C
ANISOU 890 CD PRO A 264 4534 4138 3507 96 165 355 C
ATOM 891 C PRO A 264 117.315 -35.911 -11.322 1.00 36.77 C
ANISOU 891 C PRO A 264 5083 4663 4224 -97 63 218 C
ATOM 892 O PRO A 264 116.735 -34.978 -11.884 1.00 38.64 O
ANISOU 892 O PRO A 264 5327 4888 4466 -110 50 199 O
ATOM 893 N LEU A 265 118.559 -36.263 -11.625 1.00 40.12 N
ANISOU 893 N LEU A 265 5479 5083 4682 -129 35 221 N
ATOM 937 CB ALA A 270 113.300 -35.395 -18.728 1.00 38.08 C
ANISOU 937 CB ALA A 270 5035 5071 4363 -73 67 81 C
ATOM 938 C ALA A 270 113.446 -32.982 -19.346 1.00 36.08 C
ANISOU 938 C ALA A 270 4857 4830 4021 4 74 223 C
ATOM 939 O ALA A 270 112.927 -32.568 -20.384 1.00 43.81 O
ANISOU 939 O ALA A 270 5824 5893 4928 82 65 237 O
ATOM 940 N MET A 271 113.394 -32.311 -18.201 1.00 41.65 N
ANISOU 940 N MET A 271 5607 5445 4774 -23 76 246 N
ATOM 941 CA MET A 271 112.701 -31.029 -18.121 1.00 38.79 C
ANISOU 941 CA MET A 271 5282 5055 4402 30 69 285 C
ATOM 942 CB MET A 271 112.669 -30.495 -16.696 1.00 34.05 C
ANISOU 942 CB MET A 271 4734 4358 3846 15 58 268 C
ATOM 943 CG MET A 271 111.765 -31.276 -15.775 1.00 25.98 C
ANISOU 943 CG MET A 271 3688 3368 2816 23 70 208 C
ATOM 944 SD MET A 271 111.843 -30.648 -14.097 1.00 40.35 S
ANISOU 944 SD MET A 271 5583 5115 4634 52 59 185 S
ATOM 945 CE MET A 271 110.878 -29.152 -14.233 1.00 42.12 C
ANISOU 945 CE MET A 271 5848 5309 4847 144 44 189 C
ATOM 946 C MET A 271 113.316 -29.994 -19.053 1.00 30.50 C
ANISOU 946 C MET A 271 4256 3989 3345 63 88 390 C
ATOM 947 O MET A 271 112.623 -29.125 -19.572 1.00 45.40 O
ANISOU 947 O MET A 271 6159 5891 5201 141 91 439 O
ATOM 948 N SER A 272 114.621 -30.087 -19.268 1.00 33.34 N
ANISOU 948 N SER A 272 4609 4318 3741 13 112 443 N
ATOM 949 CA SER A 272 115.280 -29.148 -20.163 1.00 33.40 C
ANISOU 949 CA SER A 272 4619 4305 3768 40 158 579 C
ATOM 950 CB SER A 272 116.791 -29.00 -19.909 1.00 32.18 C
ANISOU 950 CB SER A 272 4438 4068 3719 -48 181 632 C
ATOM 951 OG SER A 272 117.427 -30.312 -20.239 1.00 35.55 O
ANISOU 951 OG SER A 272 4819 4591 4096 -62 196 598 O
ATOM 952 C SER A 272 114.995 -29.521 -21.623 1.00 41.58 C
ANISOU 952 C SER A 272 5625 5505 4670 143 191 620 C
ATOM 953 O SER A 272 115.211 -28.724 -22.534 1.00 46.64 O
ANISOU 953 O SER A 272 6270 6169 5282 215 247 759 O
ATOM 954 N GLN A 273 114.519 -30.740 -21.848 1.00 36.29 N
ANISOU 954 N GLN A 273 4922 4946 3921 161 155 497 N
ATOM 955 CA GLN A 273 114.224 -31.178 -23.208 1.00 41.96 C
ANISOU 955 CA GLN A 273 5610 5836 4496 278 155 485 C
ATOM 956 CB GLN A 273 114.628 -32.637 -23.431 1.00 41.92 C
ANISOU 956 CB GLN A 273 5564 5899 4464 260 132 362 C
ATOM 957 CG GLN A 273 116.120 -32.871 -23.342 1.00 54.73 C
ANISOU 957 CG GLN A 273 7181 7482 6132 206 193 430 C
ATOM 958 CD GLN A 273 116.930 -31.817 -24.094 1.00 74.29 C
ANISOU 958 CD GLN A 273 9663 9981 8584 261 283 624 C
ATOM 959 OE1 GLN A 273 116.672 -31.534 -25.270 1.00 76.76 O
ANISOU 959 OE1 GLN A 273 9975 10432 8757 400 314 688 O
ATOM 960 NE2 GLN A 273 117.908 -31.223 -23.409 1.00 58.93 N
ANISOU 960 NE2 GLN A 273 7712 7900 6780 160 325 723 N
ATOM 961 C GLN A 273 112.762 -30.964 -23.600 1.00 43.54 C
ANISOU 961 C GLN A 273 5802 6124 4619 375 100 428 C
ATOM 962 O GLN A 273 112.441 -30.846 -24.781 1.00 45.57 O
ANISOU 962 O GLN A 273 6046 6530 4737 511 93 450 O
ATOM 963 N TYR A 274 111.875 -30.917 -22.613 1.00 36.43 N
ANISOU 963 N TYR A 274 4898 5149 3795 322 60 358 N
ATOM 964 CA TYR A 274 110.453 -30.750 -22.906 1.00 28.45 C
ANISOU 964 CA TYR A 274 3852 4225 2732 408 5 298 C
ATOM 965 CB TYR A 274 109.591 -31.682 -22.059 1.00 26.63 C
ANISOU 965 CB TYR A 274 3557 3972 2588 333 -40 156 C
ATOM 966 CG TYR A 274 109.815 -33.130 -22.395 1.00 41.07 C
ANISOU 966 CG TYR A 274 5324 5847 4434 291 -76 29 C
ATOM 967 CD1 TYR A 274 109.300 -33.668 -23.560 1.00 58.75 C
```

TABLE 9-continued

DMXAA-hSTING$^{S162A/G230I/Q266I}$ complex

| | |
|---|---|
| ANISOU 922 C LEU A 268 4950 4548 4214 −174 53 286 C | ANISOU 967 CD1 TYR A 274 7500 8232 6591 382 −151 −80 C |
| ATOM 923 O LEU A 268 116.436 −31.256 −16.799 1.00 31.94 O | ATOM 968 CE1 TYR A 274 109.513 −34.984 −23.885 1.00 77.16 C |
| ANISOU 923 O LEU A 268 4435 4007 3694 −150 61 335 O | ANISOU 968 CE1 TYR A 274 9776 10583 8957 350 −198 −223 C |
| ATOM 924 N PHE A 269 117.316 −33.312 −16.632 1.00 23.63 N | ATOM 969 CZ TYR A 274 110.257 −35.783 −23.039 1.00 72.59 C |
| ANISOU 924 N PHE A 269 3328 3021 2628 −190 76 285 N | ANISOU 969 CZ TYR A 274 9209 9875 8498 227 −153 −229 C |
| ATOM 925 CA PHE A 269 117.644 −33.349 −18.048 1.00 35.81 C | ATOM 970 OH TYR A 274 110.466 −37.100 −23.370 1.00 71.71 O |
| ANISOU 925 CA PHE A 269 4835 4630 4141 −167 112 331 C | ANISOU 970 OH TYR A 274 9045 9758 8441 203 −197 −371 O |
| ATOM 926 CB PHE A 269 118.478 −34.582 −18.391 1.00 32.84 C | ATOM 971 CE2 TYR A 274 110.790 −35.267 −21.872 1.00 59.23 C |
| ANISOU 926 CB PHE A 269 4416 4301 3758 −173 132 309 C | ANISOU 971 CE2 TYR A 274 7579 8059 6868 145 −75 −105 C |
| ATOM 927 CG PHE A 269 119.047 −34.525 −19.766 1.00 37.72 C | ATOM 972 CD2 TYR A 274 110.571 −33.947 −21.561 1.00 55.88 C |
| ANISOU 927 CG PHE A 269 5000 5004 4327 −125 177 364 C | ANISOU 972 CD2 TYR A 274 7206 7618 6406 177 −45 9 C |
| ATOM 928 CD1 PHE A 269 120.199 −33.790 −20.009 1.00 36.51 C | ATOM 973 C TYR A 274 109.949 −29.319 −22.782 1.00 43.31 C |
| ANISOU 928 CD1 PHE A 269 4815 4833 4224 −146 216 473 C | ANISOU 973 C TYR A 274 5783 6057 4614 477 27 412 C |
| ATOM 929 CE1 PHE A 269 120.731 −33.714 −21.266 1.00 39.02 C | ATOM 974 O TYR A 274 110.124 −28.675 −21.752 1.00 45.27 O |
| ANISOU 929 CE1 PHE A 269 5095 5247 4485 −82 285 557 C | ANISOU 974 O TYR A 274 6080 6157 4962 413 53 450 O |
| ATOM 930 CZ PHE A 269 120.100 −34.370 −22.324 1.00 48.35 C | ATOM 975 N SER A 275 109.312 −28.854 −23.852 1.00 39.73 N |
| ANISOU 930 CZ PHE A 269 6284 6558 5529 23 295 501 C | ANISOU 975 N SER A 275 5318 5734 4042 626 8 453 N |
| ATOM 931 CE2 PHE A 269 118.936 −35.102 −22.095 1.00 44.60 C | ATOM 976 CA SER A 275 108.706 −27.529 −23.922 1.00 47.48 C |
| ANISOU 931 CE2 PHE A 269 5836 6090 5020 33 228 358 C | ANISOU 976 CA SER A 275 6342 6684 5013 726 27 567 C |
| ATOM 932 CD2 PHE A 269 118.415 −35.167 −20.818 1.00 31.93 C | ATOM 977 CB SER A 275 107.915 −27.383 −25.222 1.00 30.05 C |
| ANISOU 932 CD2 PHE A 269 4255 4374 3501 −49 181 306 C | ANISOU 977 CB SER A 275 4100 4681 2637 916 −15 582 C |
| ATOM 933 C PHE A 269 116.383 −33.332 −18.908 1.00 30.08 C | ATOM 978 OG SER A 275 108.776 −27.447 −26.329 1.00 50.82 O |
| ANISOU 933 C PHE A 269 4109 3979 3341 −102 116 308 C | ANISOU 978 OG SER A 275 6750 7413 5147 998 29 678 O |
| ATOM 934 O PHE A 269 116.265 −32.554 −19.851 1.00 35.59 O | ATOM 979 C SER A 275 107.763 −27.265 −22.764 1.00 39.47 C |
| ANISOU 934 O PHE A 269 4808 4718 3995 −50 136 374 O | ANISOU 979 C SER A 275 5321 5582 4093 688 1 497 C |
| ATOM 935 N ALA A 270 115.440 −34.200 −18.567 1.00 38.93 N | ATOM 980 O SER A 275 107.732 −26.173 −22.206 1.00 51.70 O |
| ANISOU 935 N ALA A 270 5216 5119 4458 −100 98 222 N | ANISOU 980 O SER A 275 6935 6999 5708 703 34 577 O |
| ATOM 936 CA ALA A 270 114.193 −34.310 −19.316 1.00 34.22 C | ATOM 981 N GLN A 276 106.976 −28.276 −22.433 1.00 35.92 N |
| ANISOU 936 CA ALA A 270 4591 4598 3813 −43 79 170 C | ANISOU 981 N GLN A 276 4784 5205 3658 649 −55 346 N |
| ATOM 982 CA GLN A 276 105.928 −28.124 −21.447 1.00 50.59 C | ATOM 1027 N GLU A 282 120.033 −23.369 −19.061 1.00 57.06 N |
| ANISOU 982 CA GLN A 276 6609 7027 5587 641 −64 291 C | ANISOU 1027 N GLU A 282 8241 6824 6614 273 907 270 N |
| ATOM 983 CB GLN A 276 105.093 −29.386 −21.364 1.00 59.82 C | ATOM 1028 CA GLU A 282 120.709 −22.572 −18.045 1.00 59.16 C |
| ANISOU 983 CB GLN A 276 7645 8290 6793 596 −116 145 C | ANISOU 1028 CA GLU A 282 8661 6786 7033 −10 995 226 C |
| ATOM 984 CG GLN A 276 103.709 −29.194 −21.890 1.00 77.52 C | ATOM 1029 CB GLU A 282 120.654 −21.081 −18.383 1.00 65.32 C |
| ANISOU 984 CG GLN A 276 9786 10668 9001 712 −178 96 C | ANISOU 1029 CB GLU A 282 9883 7175 7758 3 1177 427 C |
| ATOM 985 CD GLN A 276 102.693 −29.937 −21.075 1.00 82.36 C | ATOM 1030 CG GLU A 282 121.460 −20.689 −19.611 1.00 78.28 C |
| ANISOU 985 CD GLN A 276 10269 11287 9737 647 −184 1 C | ANISOU 1030 CG GLU A 282 11622 8808 9314 −126 1388 652 C |
| ATOM 986 OE1 GLN A 276 102.540 −31.148 −21.217 1.00 94.25 O | ATOM 1031 CD GLU A 282 120.865 −21.215 −20.912 1.00 92.75 C |
| ANISOU 986 OE1 GLN A 276 11666 12824 11319 565 −224 −110 O | ANISOU 1031 CD GLU A 282 13414 10948 10879 228 1367 784 C |
| ATOM 987 NE2 GLN A 276 102.000 −29.223 −20.195 1.00 81.23 N | ATOM 1032 OE1 GLU A 282 121.644 −21.504 −21.849 1.00 95.00 O |
| ANISOU 987 NE2 GLN A 276 10131 11105 9629 688 −136 49 N | ANISOU 1032 OE1 GLU A 282 13627 11413 11056 146 1507 886 O |
| ATOM 988 C GLN A 276 106.459 −27.798 −20.068 1.00 40.32 C | ATOM 1033 OE2 GLU A 282 119.623 −21.337 −20.997 1.00 97.16 O |
| ANISOU 988 C GLN A 276 5382 5554 4383 549 −13 312 C | ANISOU 1033 OE2 GLU A 282 14001 11587 11328 600 1204 782 O |
| ATOM 989 O GLN A 276 105.746 −27.258 −19.240 1.00 41.86 O | ATOM 1034 C GLU A 282 120.050 −22.823 −16.702 1.00 61.91 C |
| ANISOU 989 O GLN A 276 5588 5706 4611 585 −1 303 O | ANISOU 1034 C GLU A 282 8955 7093 7475 74 862 57 C |
| ATOM 990 N ALA A 277 107.713 −28.150 −19.830 1.00 41.85 N | ATOM 1035 O GLU A 282 120.714 −22.906 −15.667 1.00 52.99 O |
| ANISOU 990 N ALA A 277 5621 5667 4611 448 12 328 N | ANISOU 1035 O GLU A 282 7779 5897 6455 −163 819 −97 O |
| ATOM 991 CA ALA A 277 108.318 −27.992 −18.518 1.00 42.30 C | ATOM 1036 N ASP A 283 118.728 −22.936 −16.733 1.00 61.93 N |
| ANISOU 991 CA ALA A 277 5739 5586 4746 368 36 319 C | ANISOU 1036 N ASP A 283 8951 7159 7418 431 798 102 N |
| ATOM 992 CB ALA A 277 109.478 −28.963 −18.349 1.00 36.84 C | ATOM 1037 CA ASP A 283 117.976 −23.321 −15.556 1.00 52.27 C |
| ANISOU 992 CB ALA A 277 5043 4871 4083 255 44 298 C | ANISOU 1037 CA ASP A 283 7622 5964 6273 565 727 −7 C |
| ATOM 993 C ALA A 277 108.779 −26.555 −18.274 1.00 44.78 C | ATOM 1038 CB ASP A 283 116.482 −23.427 −15.870 1.00 57.22 C |
| ANISOU 993 C ALA A 277 6150 5759 5105 402 46 397 C | ANISOU 1038 CB ASP A 283 8151 6718 6872 964 680 101 C |
| ATOM 994 O ALA A 277 109.032 −26.170 −17.136 1.00 45.54 O | ATOM 1039 CG ASP A 283 115.847 −22.081 −16.175 1.00 77.24 C |
| ANISOU 994 O ALA A 277 6300 5745 5258 375 41 359 O | ANISOU 1039 CG ASP A 283 11051 8999 9297 1243 794 271 C |
| ATOM 995 N GLY A 278 108.900 −25.776 −19.348 1.00 45.02 N | ATOM 1040 OD1 ASP A 283 116.478 −21.047 −15.878 1.00 87.58 O |
| ANISOU 995 N GLY A 278 6199 5791 5115 471 60 503 N | ANISOU 1040 OD1 ASP A 283 12745 9954 10577 1114 926 277 O |
| ATOM 996 CA GLY A 278 109.313 −24.381 −19.258 1.00 46.08 C | ATOM 1041 OD2 ASP A 283 114.709 −22.065 −16.704 1.00 74.73 O |
| ANISOU 996 CA GLY A 278 6412 5760 5336 501 78 597 C | ANISOU 1041 OD2 ASP A 283 10631 8825 8940 1595 735 399 O |
| ATOM 997 C GLY A 278 110.633 −24.218 −18.522 1.00 38.88 C | ATOM 1042 C ASP A 283 118.495 −24.662 −15.045 1.00 62.44 C |
| ANISOU 997 C GLY A 278 5538 4686 4548 379 75 588 C | ANISOU 1042 C ASP A 283 8558 7498 7667 384 616 −163 C |
| ATOM 998 O GLY A 278 110.755 −23.459 −17.565 1.00 60.48 O | ATOM 1043 O ASP A 283 118.592 −24.889 −13.841 1.00 61.88 O |
| ANISOU 998 O GLY A 278 8331 7270 7380 369 45 540 O | ANISOU 1043 O ASP A 283 8467 7394 7650 333 597 −271 O |
| ATOM 999 N PHE A 279 111.635 −24.948 −18.984 1.00 39.91 N | ATOM 1044 N ARG A 284 118.847 −25.541 −15.977 1.00 56.52 N |
| ANISOU 999 N PHE A 279 5629 4858 4676 297 96 620 N | ANISOU 1044 N ARG A 284 7577 6982 6915 325 548 −170 N |
| ATOM 1000 CA PHE A 279 112.846 −25.144 −18.221 1.00 40.74 C | ATOM 1045 CA ARG A 284 119.276 −26.885 −15.616 1.00 56.20 C |
| ANISOU 1000 CA PHE A 279 5738 4858 4883 177 78 582 C | ANISOU 1045 CA ARG A 284 7229 7145 6979 212 449 −302 C |
| ATOM 1001 CB PHE A 279 112.742 −26.482 −17.497 1.00 47.68 C | ATOM 1046 CB ARG A 284 119.418 −27.783 −16.843 1.00 46.88 C |
| ANISOU 1001 CB PHE A 279 6588 5835 5692 130 52 458 C | ANISOU 1046 CB ARG A 284 5875 6182 5755 242 376 −322 C |
| ATOM 1002 CG PHE A 279 113.749 −26.663 −16.416 1.00 57.08 C | ATOM 1047 CG ARG A 284 119.637 −29.240 −16.475 1.00 42.76 C |
| ANISOU 1002 CG PHE A 279 7792 6938 6959 42 14 392 C | ANISOU 1047 CG ARG A 284 5077 5809 5360 190 269 −456 C |
| ATOM 1003 CD1 PHE A 279 113.635 −25.960 −15.228 1.00 55.52 C | ATOM 1048 CD ARG A 284 119.893 −30.075 −17.701 1.00 37.32 C |
| ANISOU 1003 CD1 PHE A 279 7651 6633 6809 60 −41 308 C | ANISOU 1048 CD ARG A 284 4298 5286 4596 233 202 −522 C |
| ATOM 1004 CE1 PHE A 279 114.557 −26.131 −14.217 1.00 50.65 C | ATOM 1049 NE ARG A 284 121.192 −29.782 −18.290 1.00 42.99 N |
| ANISOU 1004 CE1 PHE A 279 7044 5959 6241 4 −99 228 C | ANISOU 1049 NE ARG A 284 5072 6056 5207 119 344 −501 N |
| ATOM 1005 CZ PHE A 279 115.612 −27.026 −14.390 1.00 54.57 C | ATOM 1050 CZ ARG A 284 121.469 −29.887 −19.583 1.00 47.12 C |
| ANISOU 1005 CZ PHE A 279 7485 6498 6750 −79 −92 247 C | ANISOU 1050 CZ ARG A 284 5658 6702 5544 210 387 −487 C |
| ATOM 1006 CE2 PHE A 279 115.727 −27.743 −15.573 1.00 39.80 C | ATOM 1051 NH1 ARG A 284 122.688 −29.597 −20.028 1.00 51.32 N |

TABLE 9-continued

DMXAA-hSTING$^{S162A/G230I/Q266I}$ complex

| | |
|---|---|
| ANISOU 1006 CE2 PHE A 279 5560 4723 4839 −99 −24 337 C | ANISOU 1051 NH1 ARG A 284 6199 7297 6005 102 583 −424 N |
| ATOM 1007 CD2 PHE A 279 114.798 −27.556 −16.577 1.00 49.04 C | ATOM 1052 NH2 ARG A 284 120.527 −30.271 −20.428 1.00 51.49 N |
| ANISOU 1007 CD2 PHE A 279 6727 5957 5949 −35 23 400 C | ANISOU 1052 NH2 ARG A 284 6256 7332 5976 413 233 −531 N |
| ATOM 1008 C PHE A 279 114.007 −25.174 −19.192 1.00 51.53 C | ATOM 1053 C ARG A 284 120.576 −26.915 −14.810 1.00 53.69 C |
| ANISOU 1008 C PHE A 279 7065 6223 6292 131 134 710 C | ANISOU 1053 C ARG A 284 6893 6789 6718 −62 466 −402 C |
| ATOM 1009 O PHE A 279 114.105 −26.075 −20.023 1.00 46.48 O | ATOM 1054 O ARG A 284 120.671 −27.601 −13.790 1.00 48.95 O |
| ANISOU 1009 O PHE A 279 6379 5736 5544 148 165 732 O | ANISOU 1054 O ARG A 284 6167 6244 6188 −84 398 −491 O |
| ATOM 1010 N SER A 280 114.877 −24.177 −19.091 1.00 34.46 N | ATOM 1055 N LEU A 285 121.581 −26.183 −15.269 1.00 51.78 N |
| ANISOU 1010 N SER A 280 4911 3884 4299 80 147 790 N | ANISOU 1055 N LEU A 285 6756 6466 6453 −270 554 −367 N |
| ATOM 1011 CA SER A 280 115.967 −24.039 −20.043 1.00 39.56 C | ATOM 1056 CA LEU A 285 122.870 −26.221 −14.595 1.00 50.63 C |
| ANISOU 1011 CA SER A 280 5501 4518 5011 45 227 954 C | ANISOU 1056 CA LEU A 285 6506 6334 6398 −558 527 −463 C |
| ATOM 1012 CB SER A 280 116.271 −22.569 −20.303 1.00 38.02 C | ATOM 1057 CB LEU A 285 123.973 −25.575 −15.433 1.00 50.95 C |
| ANISOU 1012 CB SER A 280 5318 4120 5010 47 272 1105 C | ANISOU 1057 CB LEU A 285 6547 6347 6466 −810 663 −373 C |
| ATOM 1013 OG SER A 280 116.895 −21.991 −19.174 1.00 52.77 O | ATOM 1058 CG LEU A 285 125.336 −25.539 −14.737 1.00 67.37 C |
| ANISOU 1013 OG SER A 280 7188 5773 7090 −62 193 1005 O | ANISOU 1058 CG LEU A 285 8435 8470 8692 −1145 604 −469 C |
| ATOM 1014 C SER A 280 117.246 −24.735 −19.590 1.00 49.26 C | ATOM 1059 CD1 LEU A 285 125.806 −26.947 −14.359 1.00 65.69 C |
| ANISOU 1014 C SER A 280 6670 5733 6315 −78 210 907 C | ANISOU 1059 CD1 LEU A 285 7863 8573 8524 −1075 481 −573 C |
| ATOM 1015 O SER A 280 117.397 −25.136 −18.433 1.00 57.66 O | ATOM 1060 CD2 LEU A 285 126.356 −24.847 −15.613 1.00 70.27 C |
| ANISOU 1015 O SER A 280 7745 6762 7403 −140 125 752 O | ANISOU 1060 CD2 LEU A 285 8752 8808 9139 −1421 793 −330 C |
| ATOM 1016 N ARG A 281 118.171 −24.835 −20.536 1.00 52.94 N | ATOM 1061 C LEU A 285 122.787 −25.566 −13.220 1.00 50.19 C |
| ANISOU 1016 N ARG A 281 7439 6822 5852 847 555 242 N | ANISOU 1061 C LEU A 285 6651 6070 6350 −622 458 −564 C |
| ATOM 1017 CA ARG A 281 119.492 −25.390 −20.312 1.00 50.01 C | ATOM 1062 O LEU A 285 123.423 −26.018 −12.267 1.00 56.94 O |
| ANISOU 1017 CA ARG A 281 6937 6496 5568 532 648 134 C | ANISOU 1062 O LEU A 285 7381 7010 7242 −733 334 −689 O |
| ATOM 1018 CB ARG A 281 120.290 −25.288 −21.606 1.00 56.68 C | ATOM 1063 N GLU A 286 121.995 −24.504 −13.112 1.00 47.02 N |
| ANISOU 1018 CB ARG A 281 7897 7449 6191 530 799 250 C | ANISOU 1063 N GLU A 286 6591 5396 5878 −505 529 −514 N |
| ATOM 1019 CG ARG A 281 121.391 −26.290 −21.714 1.00 73.20 C | ATOM 1064 CA GLU A 286 121.859 −23.820 −11.833 1.00 53.04 C |
| ANISOU 1019 CG ARG A 281 9750 9736 8328 354 843 117 C | ANISOU 1064 CA GLU A 286 7631 5927 6594 −510 478 −640 C |
| ATOM 1020 CD ARG A 281 122.554 −25.765 −22.535 1.00 81.07 C | ATOM 1065 CB GLU A 286 121.171 −22.448 −11.969 1.00 61.87 C |
| ANISOU 1020 CD ARG A 281 10854 10749 9200 236 1145 298 C | ANISOU 1065 CB GLU A 286 9192 6673 7643 −385 602 −572 C |
| ATOM 1021 NE ARG A 281 123.817 −26.313 −22.051 1.00 91.66 N | ATOM 1066 CG GLU A 286 119.653 −22.492 −12.099 1.00 89.48 C |
| ANISOU 1021 NE ARG A 281 11910 12185 10732 −35 1244 205 N | ANISOU 1066 CG GLU A 286 12746 10195 11056 60 692 −452 C |
| ATOM 1022 CZ ARG A 281 124.162 −27.596 −22.130 1.00 91.29 C | ATOM 1067 CD GLU A 286 118.989 −21.152 −11.830 1.00111.37 C |
| ANISOU 1022 CZ ARG A 281 11617 12380 10689 31 1159 22 C | ANISOU 1067 CD GLU A 286 15995 12583 13740 264 808 −422 C |
| ATOM 1023 NH1 ARG A 281 125.333 −27.998 −21.652 1.00 85.14 N | ATOM 1068 OE1 GLU A 286 119.659 −20.249 −11.283 1.00114.93 O |
| ANISOU 1023 NH1 ARG A 281 10564 11105 11695 10090 −176 1255 −29 N | ANISOU 1068 OE1 GLU A 286 16788 12698 14181 48 793 −552 O |
| ATOM 1024 NH2 ARG A 281 123.342 −28.481 −22.684 1.00 87.43 N | ATOM 1069 OE2 GLU A 286 117.793 −21.004 −12.168 1.00115.73 O |
| ANISOU 1024 NH2 ARG A 281 11155 12028 10038 307 959 −119 N | ANISOU 1069 OE2 GLU A 286 16574 13157 14242 647 901 −275 O |
| ATOM 1025 C ARG A 281 120.253 −24.674 −19.186 1.00 54.25 C | ATOM 1070 C GLU A 286 121.100 −24.711 −10.847 1.00 51.37 C |
| ANISOU 1025 C ARG A 281 7557 6772 6283 246 785 126 C | ANISOU 1070 C GLU A 286 7317 5877 6324 −255 422 −693 C |
| ATOM 1026 O ARG A 281 121.030 −25.287 −18.454 1.00 59.98 O | ATOM 1071 O GLU A 286 121.416 −24.749 −9.659 1.00 47.88 O |
| ANISOU 1026 O ARG A 281 8076 7558 7157 20 760 −18 O | ANISOU 1071 O GLU A 286 6964 5414 5816 −290 327 −832 O |
| ATOM 1072 N GLN A 287 120.105 −25.439 −11.348 1.00 42.68 N | ATOM 1117 SG CYS A 292 125.052 −31.770 −7.150 1.00 80.54 S |
| ANISOU 1072 N GLN A 287 6028 4942 5247 −6 474 −575 N | ANISOU 1117 SG CYS A 292 9573 10925 10105 −177 −314 −893 S |
| ATOM 1073 CA GLN A 287 119.291 −26.262 −10.480 1.00 37.21 C | ATOM 1118 C CYS A 292 123.891 −30.465 −3.413 1.00 41.93 C |
| ANISOU 1073 CA GLN A 287 5215 4375 4548 215 479 −566 C | ANISOU 1118 C CYS A 292 5622 5847 4463 238 −425 −1018 C |
| ATOM 1074 CB GLN A 287 117.971 −26.641 −11.141 1.00 54.31 C | ATOM 1119 O CYS A 292 124.062 −31.168 −2.418 1.00 46.09 O |
| ANISOU 1074 CB GLN A 287 7209 6642 6785 467 544 −418 C | ANISOU 1119 O CYS A 292 6199 6508 4804 438 −495 −968 O |
| ATOM 1075 CG GLN A 287 116.986 −25.494 −11.232 1.00 40.90 C | ATOM 1120 N ARG A 293 123.844 −29.141 −3.365 1.00 51.13 N |
| ANISOU 1075 CG GLN A 287 5760 4769 5013 722 665 −325 C | ANISOU 1120 N ARG A 293 7060 6826 5541 109 −466 −1183 N |
| ATOM 1076 CD GLN A 287 116.608 −24.946 −9.871 1.00 49.59 C | ATOM 1121 CA ARG A 293 123.970 −28.419 −2.107 1.00 52.73 C |
| ANISOU 1076 CD GLN A 287 7125 5720 5995 902 776 −368 C | ANISOU 1121 CA ARG A 293 7666 6963 5407 193 −621 −1367 C |
| ATOM 1077 OE1 GLN A 287 116.041 −25.657 −9.041 1.00 57.21 O | ATOM 1122 CB ARG A 293 123.996 −26.918 −2.355 1.00 50.13 C |
| ANISOU 1077 OE1 GLN A 287 7942 6821 6973 1052 840 −330 O | ANISOU 1122 CB ARG A 293 7634 6338 5075 −19 −665 −1569 C |
| ATOM 1078 NE2 GLN A 287 116.924 −23.676 −9.632 1.00 61.68 N | ATOM 1123 CG ARG A 293 125.325 −26.421 −2.858 1.00 66.91 C |
| ANISOU 1078 NE2 GLN A 287 9086 6949 7401 895 816 −445 N | ANISOU 1123 CG ARG A 293 9563 8464 7394 −467 −940 −1736 C |
| ATOM 1079 C GLN A 287 117.503 −27.503 −10.052 1.00 39.52 C | ATOM 1124 CD ARG A 293 125.309 −24.922 −3.035 1.00 90.67 C |
| ANISOU 1079 C GLN A 287 5240 4876 4898 91 369 −630 C | ANISOU 1124 CD ARG A 293 12931 11099 10421 −696 −963 −1917 C |
| ATOM 1080 O GLN A 287 119.861 −28.007 −8.952 1.00 51.16 O | ATOM 1125 NE ARG A 293 124.939 −24.540 −4.394 1.00102.36 N |
| ANISOU 1080 O GLN A 287 6716 6400 6322 198 365 −645 O | ANISOU 1125 NE ARG A 293 14300 12418 12173 −816 −708 −1754 N |
| ATOM 1081 N ALA A 288 120.920 −27.994 −10.927 1.00 38.41 N | ATOM 1126 CZ ARG A 293 124.160 −23.508 −4.694 1.00106.89 C |
| ANISOU 1081 N ALA A 288 4893 4860 4842 −91 305 −647 N | ANISOU 1126 CZ ARG A 293 15243 12642 12728 −754 −526 −1751 C |
| ATOM 1082 CA ALA A 288 121.717 −29.174 −10.602 1.00 42.79 C | ATOM 1127 NH1 ARG A 293 123.882 −23.231 −5.962 1.00103.74 N |
| ANISOU 1082 CA ALA A 288 5199 5604 5457 −162 209 −698 C | ANISOU 1127 NH1 ARG A 293 14732 12141 12544 −831 −319 −1573 N |
| ATOM 1083 CB ALA A 288 122.464 −29.677 −11.811 1.00 40.86 C | ATOM 1128 NH2 ARG A 293 123.658 −22.755 −3.725 1.00113.36 N |
| ANISOU 1083 CB ALA A 288 4738 5495 5291 −272 199 −698 C | ANISOU 1128 NH2 ARG A 293 16574 13216 13281 −567 −547 −1922 N |
| ATOM 1084 C ALA A 288 122.692 −28.881 −9.469 1.00 49.91 C | ATOM 1129 C ARG A 293 122.848 −28.760 −1.131 1.00 58.02 C |
| ANISOU 1084 C ALA A 288 6183 6500 6279 −291 94 −813 C | ANISOU 1129 C ARG A 293 8611 7630 5806 613 −395 −1231 C |
| ATOM 1085 O ALA A 288 122.952 −29.733 −8.618 1.00 42.56 O | ATOM 1130 O ARG A 293 123.069 −28.895 0.075 1.00 57.30 O |
| ANISOU 1085 O ALA A 288 5158 5692 5322 −218 14 −831 O | ANISOU 1130 O ARG A 293 8764 7634 5374 807 −518 −1297 O |
| ATOM 1086 N LYS A 289 123.234 −27.669 −9.467 1.00 42.44 N | ATOM 1131 N THR A 294 121.638 −28.891 −1.660 1.00 48.76 N |
| ANISOU 1086 N LYS A 289 5428 5399 5296 −487 66 −888 N | ANISOU 1131 N THR A 294 7381 6368 4776 764 −60 −1030 N |
| ATOM 1087 CA LYS A 289 124.145 −27.260 −8.415 1.00 46.34 C | ATOM 1132 CA THR A 294 120.489 −29.133 −0.811 1.00 44.14 C |
| ANISOU 1087 CA LYS A 289 6015 5872 5719 −652 −111 −1043 C | ANISOU 1132 CA THR A 294 6996 5786 3991 1149 227 −858 C |
| ATOM 1088 CB LYS A 289 124.819 −25.943 −8.764 1.00 60.14 C | ATOM 1133 CB THR A 294 119.174 −28.883 −1.542 1.00 47.37 C |
| ANISOU 1088 CB LYS A 289 7921 7405 7524 −968 −136 −1117 C | ANISOU 1133 CB THR A 294 7308 6081 4610 1257 550 −686 C |
| ATOM 1089 CG LYS A 289 125.754 −26.015 −9.944 1.00 74.27 C | ATOM 1134 OG1 THR A 294 119.208 −27.588 −2.147 1.00 51.55 O |
| ANISOU 1089 CG LYS A 289 9406 9313 9500 −1217 −79 −1036 C | ANISOU 1134 OG1 THR A 294 8025 6392 5167 1127 496 −861 O |
| ATOM 1090 CD LYS A 289 126.266 −24.628 −10.259 1.00 80.93 C | ATOM 1135 CG2 THR A 294 118.002 −28.957 −0.560 1.00 41.42 C |

TABLE 9-continued

DMXAA-hSTING^{S162A/G230I/Q266I} complex

| | |
|---|---|
| ANISOU 1090 CD LYS A 289 10445 9874 10431 −1548 −47 −1057 C | ANISOU 1135 CG2 THR A 294 6750 5347 3641 1671 887 −503 C |
| ATOM 1091 CE LYS A 289 127.138 −24.608 −11.492 1.00 84.18 C | ATOM 1136 C THR A 294 120.522 −30.556 −0.287 1.00 40.40 C |
| ANISOU 1091 CE LYS A 289 10566 10400 11019 −1781 96 −913 C | ANISOU 1136 C THR A 294 6331 5516 3504 1305 285 −634 C |
| ATOM 1092 NZ LYS A 289 127.295 −23.213 −11.996 1.00 88.82 N | ATOM 1137 O THR A 294 120.199 −30.820 0.870 1.00 50.45 O |
| ANISOU 1092 NZ LYS A 289 11424 10629 11694 −2052 226 −843 N | ANISOU 1137 O THR A 294 7849 6856 4462 1609 400 −537 O |
| ATOM 1093 C LYS A 289 123.386 −27.105 −7.106 1.00 49.67 C | ATOM 1138 N LEU A 295 120.925 −31.472 −1.153 1.00 37.85 N |
| ANISOU 1093 C LYS A 289 6739 6201 5933 −419 −128 −1100 C | ANISOU 1138 N LEU A 295 5607 5269 3506 1119 223 −543 N |
| ATOM 1094 O LYS A 289 123.873 −27.471 −6.037 1.00 56.99 O | ATOM 1139 CA LEU A 295 121.016 −32.873 −0.773 1.00 48.68 C |
| ANISOU 1094 O LYS A 289 7684 7237 6732 −390 −291 −1195 O | ANISOU 1139 CA LEU A 295 6813 6765 4920 1251 276 −325 C |
| ATOM 1095 N LEU A 290 122.186 −26.551 −7.206 1.00 40.29 N | ATOM 1140 CB LEU A 295 121.273 −33.752 −1.993 1.00 38.11 C |
| ANISOU 1095 N LEU A 290 5789 4832 4688 −212 51 −1027 N | ANISOU 1140 CB LEU A 295 5068 5429 3985 1047 245 −265 C |
| ATOM 1096 CA LEU A 290 121.362 −26.305 −6.037 1.00 38.30 C | ATOM 1141 CG LEU A 295 121.290 −35.246 −1.706 1.00 43.40 C |
| ANISOU 1096 CA LEU A 290 5843 4490 4220 69 117 −1054 C | ANISOU 1141 CG LEU A 295 5599 6135 4756 1181 324 −33 C |
| ATOM 1097 CB LEU A 290 120.198 −25.388 −6.399 1.00 36.13 C | ATOM 1142 CD1 LEU A 295 119.971 −35.656 −1.068 1.00 50.64 C |
| ANISOU 1097 CB LEU A 290 5815 3989 3923 275 326 −975 C | ANISOU 1142 CD1 LEU A 295 6601 6969 5671 1391 678 250 C |
| ATOM 1098 CG LEU A 290 119.167 −25.024 −5.338 1.00 52.76 C | ATOM 1143 CD2 LEU A 295 121.527 −36.018 −2.993 1.00 40.05 C |
| ANISOU 1098 CG LEU A 290 8237 6000 5807 648 486 −967 C | ANISOU 1143 CD2 LEU A 295 4842 5665 4710 994 280 −41 C |
| ATOM 1099 CD1 LEU A 290 119.844 −24.496 −4.081 1.00 51.15 C | ATOM 1144 C LEU A 295 122.107 −33.083 0.279 1.00 40.58 C |
| ANISOU 1099 CD1 LEU A 290 8424 5681 5330 618 327 −1213 C | ANISOU 1144 C LEU A 295 5955 5901 3562 1355 4 −414 C |
| ATOM 1100 CD2 LEU A 290 118.237 −23.977 −5.920 1.00 56.81 C | ATOM 1145 O LEU A 295 121.937 −33.857 1.223 1.00 68.34 O |
| ANISOU 1100 CD2 LEU A 290 8966 6277 6340 836 669 −892 C | ANISOU 1145 O LEU A 295 9595 9498 6874 1634 104 −216 O |
| ATOM 1101 C LEU A 290 120.863 −27.627 −5.448 1.00 44.57 C | ATOM 1146 N GLU A 296 123.226 −32.387 0.106 1.00 59.18 N |
| ANISOU 1101 C LEU A 290 6434 5514 4987 305 183 −922 C | ANISOU 1146 N GLU A 296 8301 8313 5872 1129 −344 −693 N |
| ATOM 1102 O LEU A 290 120.674 −27.760 −4.240 1.00 55.20 O | ATOM 1147 CA GLU A 296 124.305 −32.402 1.088 1.00 54.90 C |
| ANISOU 1102 O LEU A 290 7974 6888 6112 500 191 −946 O | ANISOU 1147 CA GLU A 296 7888 7960 5013 1198 −694 −834 C |
| ATOM 1103 N PHE A 291 120.667 −28.606 −6.319 1.00 38.51 N | ATOM 1148 CB GLU A 296 125.433 −31.460 0.676 1.00 62.30 C |
| ANISOU 1103 N PHE A 291 5308 4889 4435 287 234 −781 N | ANISOU 1148 CB GLU A 296 8723 8922 6027 833 −1062 −1154 C |
| ATOM 1104 CA PHE A 291 120.258 −29.941 −5.911 1.00 34.50 C | ATOM 1149 CG GLU A 296 126.691 −32.166 0.242 1.00 83.26 C |
| ANISOU 1104 CA PHE A 291 4592 4537 3981 445 299 −639 C | ANISOU 1149 CG GLU A 296 10937 11809 8888 688 −1318 −1157 C |
| ATOM 1105 CB PHE A 291 119.939 −30.779 −7.155 1.00 38.37 C | ATOM 1150 CD GLU A 296 127.875 −31.848 1.130 1.00 103.45 C |
| ANISOU 1105 CB PHE A 291 4748 5092 4739 382 332 −541 C | ANISOU 1150 CD GLU A 296 13523 14587 11195 645 −1790 −1381 C |
| ATOM 1106 CG PHE A 291 119.667 −32.226 −6.858 1.00 30.11 C | ATOM 1151 OE1 GLU A 296 127.991 −30.685 1.575 1.00 112.17 O |
| ANISOU 1106 CG PHE A 291 3492 4134 3814 471 374 −413 C | ANISOU 1151 OE1 GLU A 296 14915 15588 12116 486 −1992 −1654 O |
| ATOM 1107 CD1 PHE A 291 118.412 −32.640 −6.435 1.00 28.88 C | ATOM 1152 OE2 GLU A 296 128.687 −32.765 1.388 1.00 111.35 O |
| ANISOU 1107 CD1 PHE A 291 3288 3953 3733 645 564 −234 C | ANISOU 1152 OE2 GLU A 296 14268 15855 12184 782 −1982 −1292 O |
| ATOM 1108 CE1 PHE A 291 118.156 −33.982 −6.164 1.00 29.10 C | ATOM 1153 C GLU A 296 123.794 −31.990 2.463 1.00 53.69 C |
| ANISOU 1108 CE1 PHE A 291 3138 4000 3921 682 626 −89 C | ANISOU 1153 C GLU A 296 8239 7803 4359 1523 −647 −854 C |
| ATOM 1109 CZ PHE A 291 119.174 −34.925 −6.313 1.00 32.34 C | ATOM 1154 O GLU A 296 124.059 −32.657 3.462 1.00 60.30 O |
| ANISOU 1109 CZ PHE A 291 3461 4445 4384 599 485 −138 C | ANISOU 1154 O GLU A 296 9218 8811 4882 1807 −725 −747 O |
| ATOM 1110 CE2 PHE A 291 120.435 −34.513 −6.740 1.00 40.72 C | ATOM 1155 N ASP A 297 123.064 −30.879 2.500 1.00 55.94 N |
| ANISOU 1110 CE2 PHE A 291 4543 5578 5350 476 296 −322 C | ANISOU 1155 N ASP A 297 8824 7888 4541 1524 −506 −985 N |
| ATOM 1111 CD2 PHE A 291 120.671 −33.170 −7.011 1.00 35.92 C | ATOM 1156 CA ASP A 297 122.544 −30.348 3.755 1.00 63.40 C |
| ANISOU 1111 CD2 PHE A 291 4071 4962 4616 385 246 −450 C | ANISOU 1156 CA ASP A 297 10308 8808 4972 1870 −428 −1046 C |
| ATOM 1112 C PHE A 291 121.351 −30.614 −5.066 1.00 46.79 C | ATOM 1157 CB ASP A 297 121.808 −29.029 3.541 1.00 69.36 C |
| ANISOU 1112 C PHE A 291 6119 6231 5427 408 124 −703 C | ANISOU 1157 CB ASP A 297 11365 9291 5699 1849 −273 −1221 C |
| ATOM 1113 O PHE A 291 121.070 −31.207 −4.025 1.00 49.14 O | ATOM 1158 CG ASP A 297 122.731 −27.903 3.151 1.00 99.54 C |
| ANISOU 1113 O PHE A 291 6497 6589 5585 616 180 −612 O | ANISOU 1158 CG ASP A 297 15271 12961 9589 1459 −667 −1613 C |
| ATOM 1114 N CYS A 292 122.599 −30.510 −5.518 1.00 41.14 N | ATOM 1159 OD1 ASP A 297 123.961 −28.072 3.278 1.00 110.44 O |
| ANISOU 1114 N CYS A 292 5274 5587 4770 168 −76 −832 N | ANISOU 1159 OD1 ASP A 297 16501 14496 10965 1230 −1092 −1781 O |
| ATOM 1115 CA CYS A 292 123.730 −31.085 −4.794 1.00 46.08 C | ATOM 1160 OD2 ASP A 297 122.215 −26.844 2.726 1.00 109.93 O |
| ANISOU 1115 CA CYS A 292 5812 6390 5309 146 −289 −896 C | ANISOU 1160 OD2 ASP A 297 16794 13995 10981 1387 −542 −1734 O |
| ATOM 1116 CB CYS A 292 125.036 −30.921 −5.574 1.00 44.22 C | ATOM 1161 C ASP A 297 121.529 −31.331 4.420 1.00 54.00 C |
| ANISOU 1116 CB CYS A 292 5316 6261 5225 −138 −458 −1004 C | ANISOU 1161 C ASP A 297 9182 7704 3633 2284 −17 −656 C |
| ATOM 1162 O ASP A 297 121.615 −31.505 5.630 1.00 66.19 O | ATOM 1207 CG GLU A 304 117.079 −42.904 7.920 1.00 99.39 C |
| ANISOU 1162 O ASP A 297 11089 9371 4689 2632 −20 −612 O | ANISOU 1207 CG GLU A 304 14390 12928 10447 3840 3265 3634 C |
| ATOM 1163 N ILE A 298 120.766 −31.966 3.610 1.00 54.21 N | ATOM 1208 CD GLU A 304 116.443 −41.521 8.013 1.00 100.29 C |
| ANISOU 1163 N ILE A 298 8857 7659 4082 2233 335 −366 N | ANISOU 1208 CD GLU A 304 14523 13230 10352 3865 3332 3379 C |
| ATOM 1164 CA ILE A 298 119.820 −32.929 4.131 1.00 51.45 C | ATOM 1209 OE1 GLU A 304 115.216 −41.448 8.231 1.00 98.49 O |
| ANISOU 1164 CA ILE A 298 8490 7349 3708 2541 761 43 C | ANISOU 1209 OE1 GLU A 304 14123 12925 10373 3845 3744 3565 O |
| ATOM 1165 CB ILE A 298 118.871 −33.421 3.046 1.00 51.13 C | ATOM 1210 OE2 GLU A 304 117.168 −40.513 7.862 1.00 100.65 O |
| ANISOU 1165 CB ILE A 298 8013 7190 4222 2374 1073 279 C | ANISOU 1210 OE2 GLU A 304 14738 13479 10027 3899 2941 2974 O |
| ATOM 1166 CG1 ILE A 298 117.975 −32.280 2.591 1.00 47.60 C | ATOM 1211 C GLU A 304 120.911 −42.497 7.442 1.00 89.63 C |
| ANISOU 1166 CG1 ILE A 298 7620 6614 3852 2364 1250 176 C | ANISOU 1211 C GLU A 304 13327 12146 8582 3960 1677 2705 C |
| ATOM 1167 CD1 ILE A 298 117.042 −32.659 1.474 1.00 46.35 C | ATOM 1212 O GLU A 304 121.421 −43.504 6.962 1.00 78.68 O |
| ANISOU 1167 CD1 ILE A 298 7010 6379 4220 2200 1475 368 C | ANISOU 1212 O GLU A 304 11775 10601 7521 3906 1584 2809 O |
| ATOM 1168 CG2 ILE A 298 118.014 −34.568 3.568 1.00 60.58 C | ATOM 1213 N SER A 305 121.446 −41.290 7.320 1.00 85.74 N |
| ANISOU 1168 CG2 ILE A 298 9122 8408 5489 2603 1489 727 C | ANISOU 1213 N SER A 305 12848 11888 7842 3869 1288 2236 N |
| ATOM 1169 C ILE A 298 120.531 −34.113 4.767 1.00 52.33 C | ATOM 1214 CA SER A 305 122.467 −41.022 6.322 1.00 87.73 C |
| ANISOU 1169 C ILE A 298 8583 7623 3674 2685 641 227 C | ANISOU 1214 CA SER A 305 12775 12204 8355 3568 805 1829 C |
| ATOM 1170 O ILE A 298 120.211 −34.515 5.882 1.00 61.86 O | ATOM 1215 CB SER A 305 122.027 −39.862 5.445 1.00 95.11 C |
| ANISOU 1170 O ILE A 298 10088 8919 4497 3062 842 452 O | ANISOU 1215 CB SER A 305 13514 13099 9523 3191 774 1478 C |
| ATOM 1171 N LEU A 299 121.514 −34.654 4.060 1.00 57.38 N | ATOM 1216 OG SER A 305 122.247 −38.645 6.132 1.00 100.27 O |
| ANISOU 1171 N LEU A 299 8895 8310 4598 2428 331 148 N | ANISOU 1216 OG SER A 305 14466 13955 9678 3295 567 1198 O |
| ATOM 1172 CA LEU A 299 122.212 −35.848 4.521 1.00 51.71 C | ATOM 1217 C SER A 305 123.813 −40.652 6.909 1.00 89.66 C |
| ANISOU 1172 CA LEU A 299 8118 7725 3804 2591 217 345 C | ANISOU 1217 C SER A 305 13155 12776 8136 3756 263 1572 C |
| ATOM 1173 CB LEU A 299 123.093 −36.432 3.421 1.00 48.81 C | ATOM 1218 O SER A 305 124.580 −39.915 6.287 1.00 81.56 O |
| ANISOU 1173 CB LEU A 299 7306 7365 3874 2302 −24 270 C | ANISOU 1218 O SER A 305 11905 11877 7208 3487 −135 1166 O |
| ATOM 1174 CG LEU A 299 122.363 −36.971 2.200 1.00 66.13 C | ATOM 1219 N GLN A 306 124.098 −41.135 8.109 1.00 86.88 N |

TABLE 9-continued

DMXAA-hSTING$^{S162A/G230I/Q266I}$ complex

| | |
|---|---|
| ANISOU 1174 CG LEU A 299 9155 9351 6621 2078 249 409 C | ANISOU 1219 N GLN A 306 13159 12575 7275 4212 239 1818 N |
| ATOM 1175 CD1 LEU A 299 123.325 -37.735 1.310 1.00 63.97 C | ATOM 1220 CA GLN A 306 125.373 -40.818 8.724 1.00 88.90 C |
| ANISOU 1175 CD1 LEU A 299 8537 9103 6665 1918 33 355 C | ANISOU 1220 CA GLN A 306 13520 13186 7071 4412 -339 1572 C |
| ATOM 1176 CD2 LEU A 299 121.208 -37.862 2.634 1.00 58.44 C | ATOM 1221 CB GLN A 306 125.223 -40.565 10.227 1.00 106.68 C |
| ANISOU 1176 CD2 LEU A 299 8242 8238 5726 2279 697 814 C | ANISOU 1221 CB GLN A 306 16223 15550 8761 4738 -295 1591 C |
| ATOM 1177 C LEU A 299 123.061 -35.587 5.755 1.00 63.98 C | ATOM 1222 CG GLN A 306 125.659 -39.164 10.673 1.00 122.35 C |
| ANISOU 1177 C LEU A 299 10042 9504 4762 2858 -120 206 C | ANISOU 1222 CG GLN A 306 18365 17726 10398 4623 -718 1078 C |
| ATOM 1178 O LEU A 299 123.257 -36.475 6.579 1.00 70.06 O | ATOM 1223 CD GLN A 306 124.735 -38.051 10.183 1.00 136.76 C |
| ANISOU 1178 O LEU A 299 10956 10393 5271 3185 -91 463 O | ANISOU 1223 CD GLN A 306 20271 19405 12288 4382 -504 881 C |
| ATOM 1179 N ALA A 300 123.578 -34.370 5.867 1.00 64.53 N | ATOM 1224 OE1 GLN A 306 123.668 -38.307 9.626 1.00 142.59 O |
| ANISOU 1179 N ALA A 300 10282 9618 4619 2713 -463 -202 N | ANISOU 1224 OE1 GLN A 306 20950 19941 13286 4336 -3 1155 O |
| ATOM 1180 CA ALA A 300 124.483 -34.035 6.956 1.00 72.54 C | ATOM 1225 NE2 GLN A 306 125.147 -36.805 10.399 1.00 138.57 N |
| ANISOU 1180 CA ALA A 300 11622 10856 5084 2900 -904 -424 C | ANISOU 1225 NE2 GLN A 306 20623 19709 12318 4209 -880 408 N |
| ATOM 1181 CB ALA A 300 124.997 -32.619 6.814 1.00 62.85 C | ATOM 1226 C GLN A 306 126.388 -41.914 8.424 1.00 88.57 C |
| ANISOU 1181 CB ALA A 300 10519 9576 3784 2595 -1285 -918 C | ANISOU 1226 C GLN A 306 13215 13198 7240 4532 -574 1705 C |
| ATOM 1182 C ALA A 300 123.805 -34.222 8.309 1.00 83.96 C | ATOM 1227 O GLN A 306 126.257 -43.052 8.881 1.00 87.25 O |
| ANISOU 1182 C ALA A 300 13605 12371 5925 3426 -651 -214 C | ANISOU 1227 O GLN A 306 13169 12886 7096 4800 -314 2092 O |
| ATOM 1183 O ALA A 300 124.443 -34.604 9.290 1.00 88.19 O | ATOM 1228 N ASN A 307 127.369 -41.551 7.602 1.00 87.94 N |
| ANISOU 1183 O ALA A 300 14294 13079 6134 3660 -891 -188 O | ANISOU 1228 N ASN A 307 12719 13263 7431 4245 -997 1343 N |
| ATOM 1184 N ASP A 301 122.505 -33.961 8.354 1.00 76.83 N | ATOM 1229 CA ASN A 307 128.536 -42.376 7.306 1.00 89.61 C |
| ANISOU 1184 N ASP A 301 12878 11291 5025 3561 -124 -40 N | ANISOU 1229 CA ASN A 307 12624 13619 7803 4387 -1301 1383 C |
| ATOM 1185 CA ASP A 301 121.778 -34.046 9.609 1.00 75.30 C | ATOM 1230 CB ASN A 307 129.231 -42.804 8.595 1.00 102.12 C |
| ANISOU 1185 CA ASP A 301 13036 11068 4638 3957 202 175 C | ANISOU 1230 CB ASN A 307 14429 15409 8962 4755 -1504 1474 C |
| ATOM 1186 CB ASP A 301 121.098 -32.708 9.929 1.00 95.50 C | ATOM 1231 CG ASN A 307 130.720 -42.874 8.436 1.00 113.55 C |
| ANISOU 1186 CB ASP A 301 15894 13447 6944 3974 312 -78 C | ANISOU 1231 CG ASN A 307 15478 17161 10504 4729 -2016 1246 C |
| ATOM 1187 CG ASP A 301 121.805 -31.941 11.037 1.00 120.84 C | ATOM 1232 OD1 ASN A 307 131.289 -43.952 8.270 1.00 119.30 O |
| ANISOU 1187 CG ASP A 301 19495 16700 9719 6134 3660 -107 -425 C | ANISOU 1232 OD1 ASN A 307 16042 17858 11427 4934 -1993 1452 O |
| ATOM 1188 OD1 ASP A 301 123.053 -31.965 11.087 1.00 128.34 O | ATOM 1233 ND2 ASN A 307 131.365 -41.715 8.445 1.00 121.33 N |
| ANISOU 1188 OD1 ASP A 301 20373 17799 10592 3887 -654 -674 O | ANISOU 1233 ND2 ASN A 307 16288 18413 11400 4444 -2457 821 N |
| ATOM 1189 OD2 ASP A 301 121.102 -31.317 11.863 1.00 128.05 O | ATOM 1234 C ASN A 307 128.343 -43.592 6.390 1.00 81.26 C |
| ANISOU 1189 OD2 ASP A 301 20764 17506 10382 4330 109 -441 O | ANISOU 1234 C ASN A 307 11345 12227 7305 4360 -973 1646 C |
| ATOM 1190 C ASP A 301 120.739 -35.166 9.637 1.00 71.55 C | ATOM 1235 O ASN A 307 129.138 -44.532 6.424 1.00 88.95 O |
| ANISOU 1190 C ASP A 301 12425 10533 4226 4170 814 737 C | ANISOU 1235 O ASN A 307 12218 13259 8319 4660 -1110 1813 O |
| ATOM 1191 O ASP A 301 119.971 -35.278 10.582 1.00 87.78 O | ATOM 1236 N ASN A 308 127.311 -43.577 5.560 1.00 73.11 N |
| ANISOU 1191 O ASP A 301 14694 12542 6118 4477 1169 965 O | ANISOU 1236 N ASN A 308 10240 10840 6700 4021 -572 1665 N |
| ATOM 1192 N ALA A 302 120.706 -35.997 8.604 1.00 73.18 N | ATOM 1237 CA ASN A 308 127.097 -44.695 4.650 1.00 75.76 C |
| ANISOU 1192 N ALA A 302 12245 10710 4852 3973 934 962 N | ANISOU 1237 CA ASN A 308 10402 10820 7564 3954 -309 1846 C |
| ATOM 1193 CA ALA A 302 119.666 -37.019 8.538 1.00 71.92 C | ATOM 1238 CB ASN A 308 126.024 -45.626 5.200 1.00 79.22 C |
| ANISOU 1193 CA ALA A 302 11904 10420 5002 4064 1516 1488 C | ANISOU 1238 CB ASN A 308 11169 10892 8039 4134 179 2322 C |
| ATOM 1194 CB ALA A 302 119.262 -37.292 7.104 1.00 60.51 C | ATOM 1239 CG ASN A 308 124.826 -44.874 5.730 1.00 83.81 C |
| ANISOU 1194 CB ALA A 302 9898 8763 4328 3608 1608 1501 C | ANISOU 1239 CG ASN A 308 11968 11438 8438 4020 484 2392 C |
| ATOM 1195 C ALA A 302 120.060 -38.313 9.241 1.00 86.36 C | ATOM 1240 OD1 ASN A 308 124.714 -43.664 5.548 1.00 61.56 O |
| ANISOU 1195 C ALA A 302 13798 12291 6725 4315 1561 1854 C | ANISOU 1240 OD1 ASN A 308 9072 8802 5516 3786 342 2056 O |
| ATOM 1196 O ALA A 302 121.096 -38.901 8.929 1.00 87.89 O | ATOM 1241 ND2 ASN A 308 123.926 -45.585 6.398 1.00 95.78 N |
| ANISOU 1196 O ALA A 302 13858 12552 6983 4247 1190 1810 O | ANISOU 1241 ND2 ASN A 308 13761 12708 9923 4203 934 2852 N |
| ATOM 1197 N PRO A 303 119.223 -38.754 10.199 1.00 90.87 N | ATOM 1242 C ASN A 308 126.707 -44.223 3.267 1.00 65.05 C |
| ANISOU 1197 N PRO A 303 14508 12782 7237 4584 2004 2185 N | ANISOU 1242 C ASN A 308 8722 9300 6693 3459 -229 1559 C |
| ATOM 1198 CA PRO A 303 119.346 -39.984 10.993 1.00 95.18 C | ATOM 1243 O ASN A 308 126.101 -44.954 2.488 1.00 63.44 O |
| ANISOU 1198 CA PRO A 303 15137 13299 7728 4838 2173 2566 C | ANISOU 1243 O ASN A 308 8447 8738 6921 3315 48 1666 O |
| ATOM 1199 CB PRO A 303 117.906 -40.241 11.447 1.00 83.53 C | ATOM 1244 N CYS A 309 127.064 -42.984 2.973 1.00 55.06 N |
| ANISOU 1199 CB PRO A 303 13619 11663 6456 4945 2822 2941 C | ANISOU 1244 N CYS A 309 7290 8288 5342 3199 -491 1188 N |
| ATOM 1200 CG PRO A 303 118.892 -38.892 11.421 1.00 80.65 C | ATOM 1245 CA CYS A 309 126.673 -42.362 1.736 1.00 50.64 C |
| ANISOU 1200 CG PRO A 303 13319 11330 5996 4931 2879 2672 C | ANISOU 1245 CA CYS A 309 6479 7608 5152 2763 -417 933 C |
| ATOM 1201 CD PRO A 303 118.129 -37.910 10.704 1.00 87.77 C | ATOM 1246 CB CYS A 309 125.306 -41.706 1.899 1.00 55.78 C |
| ANISOU 1201 CD PRO A 303 14250 12335 6763 4709 2340 2163 C | ANISOU 1246 CB CYS A 309 7323 8091 5781 2596 -118 975 C |
| ATOM 1202 C PRO A 303 119.839 -41.197 10.208 1.00 90.58 C | ATOM 1247 SG CYS A 309 124.592 -41.092 0.370 1.00 109.82 S |
| ANISOU 1202 C PRO A 303 14281 12599 7537 4674 2120 2807 C | ANISOU 1247 SG CYS A 309 13897 14750 13079 2128 10 742 S |
| ATOM 1203 O PRO A 303 120.660 -41.961 10.711 1.00 87.61 O | ATOM 1248 C CYS A 309 127.720 -41.323 1.391 1.00 62.38 C |
| ANISOU 1203 O PRO A 303 14015 12278 6994 4871 1921 2899 O | ANISOU 1248 C CYS A 309 7714 9419 6568 2568 -806 567 C |
| ATOM 1204 N GLU A 304 119.335 -41.373 8.993 1.00 85.28 N | ATOM 1249 O CYS A 309 128.319 -40.719 2.275 1.00 61.60 O |
| ANISOU 1204 N GLU A 304 13260 11744 7398 4332 2289 2905 N | ANISOU 1249 O CYS A 309 9710 9600 6094 2674 -1105 463 O |
| ATOM 1205 CA GLU A 304 119.609 -42.584 8.231 1.00 95.23 C | ATOM 1250 N ARG A 310 127.946 -41.117 0.104 1.00 59.92 N |
| ANISOU 1205 CA GLU A 304 14249 12770 9164 4150 2287 3131 C | ANISOU 1250 N ARG A 310 7089 9066 6614 2275 -807 372 N |
| ATOM 1206 CB GLU A 304 118.454 -42.883 7.269 1.00 93.31 C | ATOM 1251 CA ARG A 310 128.938 -40.150 -0.317 1.00 53.28 C |
| ANISOU 1206 CB GLU A 304 13592 12223 9639 3745 2661 3267 C | ANISOU 1251 CA ARG A 310 5967 8503 5776 2043 -1113 72 C |
| ATOM 1252 CB ARG A 310 130.322 -40.781 -0.335 1.00 62.68 C | ATOM 1297 CG GLN A 315 130.827 -28.728 -14.453 1.00 90.47 C |
| ANISOU 1252 CB ARG A 310 6849 9973 6995 2251 -1373 77 C | ANISOU 1297 CG GLN A 315 12046 10035 12292 -175 41 3173 C |
| ATOM 1253 CG ARG A 310 131.428 -39.807 -0.681 1.00 90.54 C | ATOM 1298 CD GLN A 315 130.637 -27.372 -13.810 1.00 93.01 C |
| ANISOU 1253 CG ARG A 310 10009 13828 10566 1987 -1692 -197 C | ANISOU 1298 CD GLN A 315 12461 10118 12762 -349 350 3165 C |
| ATOM 1254 CD ARG A 310 131.357 -38.554 0.181 1.00 111.87 C | ATOM 1299 OE1 GLN A 315 131.018 -27.164 -12.656 1.00 89.11 O |
| ANISOU 1254 CD ARG A 310 12907 16637 12963 1800 -1940 -385 C | ANISOU 1299 OE1 GLN A 315 11435 9905 12517 -458 452 2878 O |
| ATOM 1255 NE ARG A 310 132.663 -37.907 0.275 1.00 121.45 N | ATOM 1300 NE2 GLN A 315 130.048 -26.438 -14.551 1.00 94.84 N |
| ANISOU 1255 NE ARG A 310 13757 18213 14175 1632 -2362 -599 N | ANISOU 1300 NE2 GLN A 315 13385 9837 12813 -307 487 3452 N |
| ATOM 1256 CZ ARG A 310 133.278 -37.618 1.417 1.00 115.83 C | ATOM 1301 C GLN A 315 132.660 -31.460 -15.058 1.00 85.58 C |
| ANISOU 1256 CZ ARG A 310 13105 17775 13131 1750 -2783 -688 C | ANISOU 1301 C GLN A 315 10745 10280 11491 -159 -133 2667 C |
| ATOM 1257 NH1 ARG A 310 132.697 -37.897 2.574 1.00 109.86 N | ATOM 1302 O GLN A 315 133.872 -31.346 -14.887 1.00 87.44 O |
| ANISOU 1257 NH1 ARG A 310 12816 16973 11953 2082 -2802 -569 N | ANISOU 1302 O GLN A 315 10754 10784 11686 -458 292 2283 O |
| ATOM 1258 NH2 ARG A 310 134.471 -37.039 1.401 1.00 115.15 N | ATOM 1303 N GLU A 316 132.122 -31.948 -16.167 1.00 93.06 N |

TABLE 9-continued

DMXAA-hSTING$^{S162A/G230I/Q266I}$ complex

| | |
|---|---|
| ANISOU 1258 NH2 ARG A 310 12115 17482 12636 1514 −3161 −882 N | ANISOU 1303 N GLU A 316 12110 11010 12238 87 −449 2879 N |
| ATOM 1259 C ARG A 310 128.582 −39.615 −1.687 1.00 57.20 C | ATOM 1304 CA GLU A 316 132.944 −32.378 −17.282 1.00105.24 C |
| ANISOU 1259 C ARG A 310 6279 8856 6600 1676 −959 −94 C | ANISOU 1304 CA GLU A 316 13941 12627 13416 48 −282 2736 C |
| ATOM 1260 O ARG A 310 128.325 −40.379 −2.612 1.00 67.02 O | ATOM 1305 CB GLU A 316 132.120 −33.240 −18.235 1.00114.41 C |
| ANISOU 1260 O ARG A 310 7420 9918 8127 1676 −764 −34 O | ANISOU 1305 CB GLU A 316 15363 13652 14455 500 −893 2893 C |
| ATOM 1261 N LEU A 311 128.568 −38.293 −1.806 1.00 55.60 N | ATOM 1306 CG GLU A 316 132.753 −34.573 −18.582 1.00122.92 C |
| ANISOU 1261 N LEU A 311 6078 8714 6333 1380 −1060 −310 N | ANISOU 1306 CG GLU A 316 16147 15063 15495 591 −1104 2657 C |
| ATOM 1262 CA LEU A 311 128.183 −37.653 −3.050 1.00 53.04 C | ATOM 1307 CD GLU A 316 131.724 −35.676 −18.747 1.00123.98 C |
| ANISOU 1262 CA LEU A 311 5637 8256 6260 1061 −910 −437 C | ANISOU 1307 CD GLU A 316 16060 15103 15943 1008 −1852 2711 C |
| ATOM 1263 CB LEU A 311 127.413 −36.367 −2.791 1.00 44.67 C | ATOM 1308 OE1 GLU A 316 131.525 −36.142 −19.889 1.00123.64 O |
| ANISOU 1263 CB LEU A 311 4830 7081 5062 865 −875 −549 C | ANISOU 1308 OE1 GLU A 316 16358 14968 15652 1322 −2192 2638 O |
| ATOM 1264 CG LEU A 311 126.277 −36.458 −1.787 1.00 56.43 C | ATOM 1309 OE2 GLU A 316 131.115 −36.076 −17.731 1.00119.92 O |
| ANISOU 1264 CG LEU A 311 6687 8427 6329 1074 −709 −401 C | ANISOU 1309 OE2 GLU A 316 15014 14589 15959 1055 −2075 2803 O |
| ATOM 1265 CD1 LEU A 311 125.512 −35.146 −1.793 1.00 47.92 C | ATOM 1310 C GLU A 316 133.463 −31.157 −18.014 1.00109.60 C |
| ANISOU 1265 CD1 LEU A 311 5829 7216 5162 908 −631 −530 C | ANISOU 1310 C GLU A 316 15117 12873 13653 −194 381 2771 C |
| ATOM 1266 CD2 LEU A 311 125.367 −37.635 −2.115 1.00 56.93 C | ATOM 1311 O GLU A 316 132.674 −30.320 −18.457 1.00113.83 O |
| ANISOU 1266 CD2 LEU A 311 6739 8292 6600 1215 −411 −156 C | ANISOU 1311 O GLU A 316 16227 12983 14038 −35 395 3075 O |
| ATOM 1267 C LEU A 311 129.399 −37.321 −3.876 1.00 55.70 C | ATOM 1312 N PRO A 317 134.796 −31.031 −18.125 1.00111.73 N |
| ANISOU 1267 C LEU A 311 5595 8808 6760 873 −1065 −589 C | ANISOU 1312 N PRO A 317 15265 13325 13864 −561 985 2455 N |
| ATOM 1268 O LEU A 311 130.354 −36.717 −3.392 1.00 56.50 O | ATOM 1313 CA PRO A 317 135.320 −29.971 −18.987 1.00120.18 C |
| ANISOU 1268 O LEU A 311 5556 9150 6761 780 −1347 −710 O | ANISOU 1313 CA PRO A 317 16968 14005 14689 −768 1748 2540 C |
| ATOM 1269 N ILE A 312 129.344 −37.699 −5.142 1.00 53.76 N | ATOM 1314 CB PRO A 317 136.828 −30.205 −18.945 1.00119.13 C |
| ANISOU 1269 N ILE A 312 5178 8481 6766 811 −877 −586 N | ANISOU 1314 CB PRO A 317 16423 14183 14659 −1174 2309 2077 C |
| ATOM 1270 CA ILE A 312 130.425 −37.393 −6.045 1.00 57.69 C | ATOM 1315 CG PRO A 317 137.060 −30.809 −17.601 1.00110.79 C |
| ANISOU 1270 CA ILE A 312 5312 9187 7421 656 −926 −687 C | ANISOU 1315 CG PRO A 317 14465 13637 13996 −1270 1934 1685 C |
| ATOM 1271 CB ILE A 312 131.071 −38.668 −6.565 1.00 48.70 C | ATOM 1316 CD PRO A 317 135.864 −31.697 −17.360 1.00106.48 C |
| ANISOU 1271 CB ILE A 312 3949 8140 6417 939 −858 −605 C | ANISOU 1316 CD PRO A 317 13857 13183 13418 −798 1078 1990 C |
| ATOM 1272 CG1 ILE A 312 131.506 −39.515 −5.374 1.00 56.76 C | ATOM 1317 C PRO A 317 134.795 −30.149 −20.404 1.00127.42 C |
| ANISOU 1272 CG1 ILE A 312 4991 9276 7300 1281 −1036 −482 C | ANISOU 1317 C PRO A 317 18712 14665 15039 −290 1592 2901 C |
| ATOM 1273 CD1 ILE A 312 132.106 −40.845 −5.741 1.00 66.54 C | ATOM 1318 O PRO A 317 134.416 −31.255 −20.787 1.00130.44 O |
| ANISOU 1273 CD1 ILE A 312 6074 10552 6775 1642 −965 −378 C | ANISOU 1318 O PRO A 317 19028 15274 15261 91 939 2897 O |
| ATOM 1274 CG2 ILE A 312 132.270 −38.335 −7.432 1.00 55.83 C | ATOM 1319 N ALA A 318 134.757 −29.066 −21.167 1.00135.01 N |
| ANISOU 1274 CG2 ILE A 312 4426 9320 7465 821 −865 −679 C | ANISOU 1319 N ALA A 318 20452 15141 15705 −245 2186 3191 N |
| ATOM 1275 C ILE A 312 129.921 −36.500 −7.169 1.00 44.64 C | ATOM 1320 CA ALA A 318 134.265 −29.136 −22.533 1.00144.52 C |
| ANISOU 1275 C ILE A 312 3690 7392 5878 358 −749 −771 C | ANISOU 1320 CA ALA A 318 22543 16124 16244 366 2063 3528 C |
| ATOM 1276 O ILE A 312 129.451 −36.972 −8.199 1.00 48.88 O | ATOM 1321 CB ALA A 318 133.292 −28.005 −22.800 1.00144.93 C |
| ANISOU 1276 O ILE A 312 4239 7801 6532 402 −545 −747 O | ANISOU 1321 CB ALA A 318 23324 15649 16095 667 2151 3940 C |
| ATOM 1277 N ALA A 313 130.001 −35.195 −6.934 1.00 43.74 N | ATOM 1322 C ALA A 318 135.436 −29.077 −23.502 1.00155.29 C |
| ANISOU 1277 N ALA A 313 3633 7282 5705 71 −848 −875 N | ANISOU 1322 C ALA A 318 24319 17450 17233 299 2881 3522 C |
| ATOM 1278 CA ALA A 313 129.573 −34.213 −7.918 1.00 57.72 C | ATOM 1323 O ALA A 318 135.313 −29.458 −24.665 1.00156.58 O |
| ANISOU 1278 CA ALA A 313 5473 8902 7556 −194 −686 −922 C | ANISOU 1323 O ALA A 318 25121 17609 16763 871 2760 3699 O |
| ATOM 1279 CB ALA A 313 129.016 −32.980 −7.241 1.00 50.83 C | ATOM 1324 N ASP A 319 136.572 −28.598 −23.004 1.00164.45 N |
| ANISOU 1279 CB ALA A 313 4908 7857 6550 −377 −764 −1007 C | ANISOU 1324 N ASP A 319 25077 18591 18815 −365 3714 3270 N |
| ATOM 1280 C ALA A 313 130.756 −33.841 −8.787 1.00 43.87 C | ATOM 1325 CA ASP A 319 137.777 −28.445 −23.812 1.00174.36 C |
| ANISOU 1280 C ALA A 313 3354 7351 5964 −397 −664 −947 C | ANISOU 1325 CA ASP A 319 26611 19754 19884 −538 4665 3234 C |
| ATOM 1281 O ALA A 313 131.873 −33.713 −8.303 1.00 48.80 O | ATOM 1326 CB ASP A 319 138.796 −27.551 −23.098 1.00176.94 C |
| ANISOU 1281 O ALA A 313 3693 8216 6633 −485 −863 −986 O | ANISOU 1326 CB ASP A 319 26440 19871 20918 −1328 5629 2910 C |
| ATOM 1282 N TYR A 314 130.514 −33.670 −10.078 1.00 52.80 N | ATOM 1327 CG ASP A 319 138.650 −27.587 −21.584 1.00170.39 C |
| ANISOU 1282 N TYR A 314 4475 8409 7177 −462 −422 −910 N | ANISOU 1327 CG ASP A 319 24650 19336 20753 −1725 5120 2467 C |
| ATOM 1283 CA TYR A 314 131.604 −33.358 −10.988 1.00 59.38 C | ATOM 1328 OD2 ASP A 319 139.444 −28.288 −20.921 1.00164.19 O |
| ANISOU 1283 CA TYR A 314 4963 9445 8152 −623 −311 −881 C | ANISOU 1328 OD2 ASP A 319 23021 19069 20293 −2021 4963 1922 O |
| ATOM 1284 CB TYR A 314 132.372 −34.618 −11.378 1.00 46.79 C | ATOM 1329 OD ASP A 319 137.743 −26.908 −21.058 1.00170.65 O |
| ANISOU 1284 CB TYR A 314 3056 8101 6621 −326 −245 −832 C | ANISOU 1329 OD1 ASP A 319 24803 19101 20937 −1670 4881 2663 O |
| ATOM 1285 CG TYR A 314 131.514 −35.693 −12.010 1.00 47.08 C | ATOM 1330 C ASP A 319 138.404 −29.787 −24.182 1.00175.38 C |
| ANISOU 1285 CG TYR A 314 3315 7979 6593 −11 −92 −823 C | ANISOU 1330 C ASP A 319 26406 20445 19784 −403 4303 2948 C |
| ATOM 1286 CD1 TYR A 314 130.844 −36.623 −11.219 1.00 47.08 C | ATOM 1331 O ASP A 319 138.652 −30.063 −25.356 1.00179.26 O |
| ANISOU 1286 CD1 TYR A 314 3511 7836 6541 226 −201 −823 C | ANISOU 1331 O ASP A 319 27527 20911 19672 19 4527 3145 O |
| ATOM 1287 CE1 TYR A 314 130.064 −37.605 −11.786 1.00 56.71 C | ATOM 1332 N ASP A 320 138.666 −30.620 −23.180 1.00169.60 N |
| ANISOU 1287 CE1 TYR A 314 4922 8865 7761 446 −89 −830 C | ANISOU 1332 N ASP A 320 24722 20225 19495 −693 3761 2491 N |
| ATOM 1288 CZ TYR A 314 129.950 −37.672 −13.162 1.00 52.64 C | ATOM 1333 CA ASP A 320 139.199 −31.953 −23.439 1.00162.15 C |
| ANISOU 1288 CZ TYR A 314 4433 8329 7239 471 96 −875 C | ANISOU 1333 CA ASP A 320 23426 19811 18372 −543 3347 2209 C |
| ATOM 1289 OH TYR A 314 129.172 −38.654 −13.725 1.00 64.37 O | ATOM 1334 CB ASP A 320 140.477 −32.211 −22.624 1.00154.29 C |
| ANISOU 1289 OH TYR A 314 6127 9606 8725 663 145 −934 O | ANISOU 1334 CB ASP A 320 21538 19212 17872 −1132 3716 1629 C |
| ATOM 1290 CE2 TYR A 314 130.612 −36.765 −13.974 1.00 45.51 C | ATOM 1335 CG ASP A 320 140.195 −32.517 −21.160 1.00140.41 C |
| ANISOU 1290 CE2 TYR A 314 3367 7602 6323 300 −320 −859 C | ANISOU 1335 CG ASP A 320 18937 17780 16633 −1309 3124 1322 C |
| ATOM 1291 CD2 TYR A 314 131.386 −35.785 −13.397 1.00 41.71 C | ATOM 1336 OD1 ASP A 320 139.993 −31.568 −20.374 1.00134.61 O |
| ANISOU 1291 CD2 TYR A 314 2665 7282 5899 42 156 −815 C | ANISOU 1336 OD1 ASP A 320 18030 16823 16294 −1597 3353 1281 O |
| ATOM 1292 C TYR A 314 131.117 −32.637 −12.226 1.00 52.45 C | ATOM 1337 OD2 ASP A 320 140.174 −33.713 −20.801 1.00131.89 O |
| ANISOU 1292 C TYR A 314 4237 8415 7276 −763 −55 −833 C | ANISOU 1337 OD2 ASP A 320 17395 17166 15551 −1107 2456 1135 O |
| ATOM 1293 O TYR A 314 129.976 −32.799 −12.659 1.00 53.17 O | ATOM 1338 C ASP A 320 138.136 −33.015 −23.166 1.00156.49 C |
| ANISOU 1293 O TYR A 314 4627 8305 7270 −629 41 −826 O | ANISOU 1338 C ASP A 320 22479 19354 17626 −97 2170 2232 C |
| ATOM 1294 N GLN A 315 132.004 −31.835 −12.789 1.00 73.26 N | ATOM 1339 O ASP A 320 137.556 −33.072 −22.080 1.00152.48 O |
| ANISOU 1294 N GLN A 315 8269 9110 10457 141 −456 2692 N | ANISOU 1339 O ASP A 320 21451 18919 17564 −218 1719 2167 O |
| ATOM 1295 CA GLN A 315 131.682 −31.071 −13.970 1.00 75.45 C | ATOM 1340 N SER A 321 137.865 −33.850 −24.162 1.00155.79 N |
| ANISOU 1295 CA GLN A 315 9227 8921 10520 5 −355 2863 C | ANISOU 1340 N SER A 321 22770 19372 17050 454 1703 2309 N |
| ATOM 1296 CB GLN A 315 131.782 −29.587 −13.667 1.00 77.58 C | ATOM 1341 CA SER A 321 136.912 −34.938 −23.984 1.00148.13 C |
| ANISOU 1296 CB GLN A 315 9717 8958 10803 −265 73 2800 C | ANISOU 1341 CA SER A 321 21503 18582 16198 857 631 2243 C |
| ATOM 1342 CB SER A 321 136.269 −35.331 −25.316 1.00152.02 C | ATOM 1387 CD GLN A 327 142.638 −42.363 −12.073 1.00 51.89 C |

TABLE 9-continued

DMXAA-hSTING$^{S162A/G230I/Q266I}$ complex

| | |
|---|---|
| ANISOU 1342 CB SER A 321 22697 18968 16095 1607 146 2375 C | ANISOU 1387 CD GLN A 327 5503 6448 7764 −693 463 −999 C |
| ATOM 1343 OG SER A 321 134.886 −35.022 −25.325 1.00150.99 O | ATOM 1388 OE1 GLN A 327 143.172 −41.750 −11.144 1.00 57.63 O |
| ANISOU 1343 OG SER A 321 22817 18534 16020 2000 −450 2573 O | ANISOU 1388 OE1 GLN A 327 5794 7460 8640 −727 482 −1712 O |
| ATOM 1344 C SER A 321 137.605 −36.140 −23.355 1.00139.27 C | ATOM 1389 NE2 GLN A 327 142.793 −43.671 −12.255 1.00 51.46 N |
| ANISOU 1344 C SER A 321 19565 17956 15395 653 363 1848 C | ANISOU 1389 NE2 GLN A 327 5466 6838 7248 −467 363 −651 N |
| ATOM 1345 O SER A 321 137.255 −37.286 −23.631 1.00117.43 O | ATOM 1390 CA GLN A 327 139.107 −40.706 −10.476 1.00 51.08 C |
| ANISOU 1345 O SER A 321 19169 17894 15154 1018 −332 1729 O | ANISOU 1390 CA GLN A 327 5588 5492 8328 4 173 −833 C |
| ATOM 1346 N SER A 322 138.595 −35.862 −22.512 1.00134.09 N | ATOM 1391 O GLN A 327 139.614 −40.573 −9.363 1.00 63.13 O |
| ANISOU 1346 N SER A 322 18387 17516 15045 106 914 1599 N | ANISOU 1391 O GLN A 327 6739 7520 9726 76 205 −1483 O |
| ATOM 1347 CA SER A 322 139.367 −36.898 −21.837 1.00124.46 C | ATOM 1392 N GLU A 328 138.005 −40.072 −10.851 1.00 56.97 N |
| ANISOU 1347 CA SER A 322 16413 16805 14070 −41 738 1198 C | ANISOU 1392 N GLU A 328 6587 5554 9506 52 149 −475 N |
| ATOM 1348 CB SER A 322 140.782 −36.974 −22.410 1.00125.86 C | ATOM 1393 CA GLU A 328 137.294 −39.186 −9.945 1.00 67.32 C |
| ANISOU 1348 CB SER A 322 16587 17235 14000 −264 1379 898 C | ANISOU 1393 CA GLU A 328 7726 6626 11226 195 239 −835 C |
| ATOM 1349 OG SER A 322 141.628 −37.737 −21.569 1.00121.45 O | ATOM 1394 CB GLU A 328 136.176 −38.447 −10.684 1.00 55.41 C |
| ANISOU 1349 OG SER A 322 15247 17188 13711 −452 1301 443 O | ANISOU 1394 CB GLU A 328 6519 4231 10304 222 198 −331 C |
| ATOM 1350 C SER A 322 139.427 −36.670 −20.327 1.00114.51 C | ATOM 1395 CG GLU A 328 135.508 −37.357 −9.869 1.00 72.04 C |
| ANISOU 1350 C SER A 322 14458 15717 13333 −350 751 1020 C | ANISOU 1395 CG GLU A 328 8455 5935 12983 316 387 −718 C |
| ATOM 1351 O SER A 322 140.499 −36.490 −19.751 1.00117.25 O | ATOM 1396 CD GLU A 328 136.427 −36.182 −9.603 1.00 92.77 C |
| ANISOU 1351 O SER A 322 14345 16365 13840 −700 1196 622 O | ANISOU 1396 CD GLU A 328 10997 8350 15903 −82 739 −1378 C |
| ATOM 1352 N PHE A 323 138.257 −36.666 −19.701 1.00 98.14 N | ATOM 1397 OE1 GLU A 328 136.622 −35.838 −8.416 1.00 98.81 O |
| ANISOU 1352 N PHE A 323 12304 13459 11525 −161 255 1278 N | ANISOU 1397 OE1 GLU A 328 11445 9428 16668 −70 920 −2077 O |
| ATOM 1353 CA PHE A 323 138.142 −36.610 −18.256 1.00 90.65 C | ATOM 1398 OE2 GLU A 328 136.951 −35.601 −10.580 1.00103.16 O |
| ANISOU 1353 CA PHE A 323 10743 12699 11000 −267 166 1173 C | ANISOU 1398 OE2 GLU A 328 12597 9165 17434 −431 864 −1219 O |
| ATOM 1354 CB PHE A 323 136.985 −35.680 −17.878 1.00 81.28 C | ATOM 1399 C GLU A 328 136.721 −40.008 −8.791 1.00 67.22 C |
| ANISOU 1354 CB PHE A 323 9788 11097 9997 −237 72 1529 C | ANISOU 1399 C GLU A 328 7484 7207 10850 642 137 −969 C |
| ATOM 1355 CG PHE A 323 136.132 −36.180 −16.747 1.00 77.40 C | ATOM 1400 O GLU A 328 136.815 −39.625 −7.625 1.00 67.33 O |
| ANISOU 1355 CG PHE A 323 8840 10672 9894 4 −398 1673 C | ANISOU 1400 O GLU A 328 7250 7484 10848 718 262 −1581 O |
| ATOM 1356 CD2 PHE A 323 136.348 −35.732 −15.454 1.00 80.07 C | ATOM 1401 N VAL A 329 136.133 −41.149 −9.128 1.00 50.73 N |
| ANISOU 1356 CD2 PHE A 323 8731 11228 10463 −103 −218 1522 C | ANISOU 1401 N VAL A 329 5528 5305 8443 911 −53 −408 N |
| ATOM 1357 CE2 PHE A 323 135.564 −36.177 −14.410 1.00 73.12 C | ATOM 1402 CA VAL A 329 135.567 −42.031 −8.118 1.00 50.22 C |
| ANISOU 1357 CE2 PHE A 323 7494 10402 9888 204 −554 1723 C | ANISOU 1402 CA VAL A 329 5332 5743 8006 1331 −73 −474 C |
| ATOM 1358 CZ PHE A 323 134.541 −37.076 −14.655 1.00 71.61 C | ATOM 1403 CB VAL A 329 134.715 −43.143 −8.748 1.00 44.05 C |
| ANISOU 1358 CZ PHE A 323 7327 9974 9908 535 −1030 2064 C | ANISOU 1403 CB VAL A 329 4741 4938 7057 1557 −227 217 C |
| ATOM 1359 CE1 PHE A 323 134.309 −37.530 −15.943 1.00 72.94 C | ATOM 1404 CG1 VAL A 329 134.264 −44.134 −7.685 1.00 48.29 C |
| ANISOU 1359 CE1 PHE A 323 7862 9910 9941 601 −1280 2120 C | ANISOU 1404 CG1 VAL A 329 5192 6000 7157 1966 −146 117 C |
| ATOM 1360 CD1 PHE A 323 135.093 −37.073 −16.981 1.00 75.71 C | ATOM 1405 CG2 VAL A 329 133.503 −42.532 −9.433 1.00 41.12 C |
| ANISOU 1360 CD1 PHE A 323 8637 10275 9854 379 −989 1936 C | ANISOU 1405 CG2 VAL A 329 4484 3797 7344 1559 −325 627 C |
| ATOM 1361 C PHE A 323 137.896 −38.043 −17.798 1.00 78.80 C | ATOM 1406 C VAL A 329 136.660 −42.615 −7.220 1.00 54.37 C |
| ANISOU 1361 C PHE A 323 8792 11471 9679 72 −411 1148 C | ANISOU 1406 C VAL A 329 5660 7097 7901 1410 −64 −962 C |
| ATOM 1362 O PHE A 323 137.410 −38.862 −18.574 1.00 78.84 O | ATOM 1407 O VAL A 329 136.498 −42.721 −6.004 1.00 45.85 O |
| ANISOU 1362 O PHE A 323 8994 11346 9615 363 −837 1277 O | ANISOU 1407 O VAL A 329 4460 6389 6573 1661 1 −1368 O |
| ATOM 1363 N SER A 324 138.221 −38.354 −16.550 1.00 76.66 N | ATOM 1408 N LEU A 330 137.783 −42.980 −7.824 1.00 46.41 N |
| ANISOU 1363 N SER A 324 7929 11553 9646 98 −416 963 N | ANISOU 1408 N LEU A 330 4633 6359 6642 1202 −131 −931 N |
| ATOM 1364 CA SER A 324 138.120 −39.735 −16.096 1.00 86.20 C | ATOM 1409 CA LEU A 330 138.899 −43.505 −7.056 1.00 55.29 C |
| ANISOU 1364 CA SER A 324 8743 12992 11019 457 −816 971 C | ANISOU 1409 CA LEU A 330 5503 8263 7241 1056 −194 −1388 C |
| ATOM 1365 CB SER A 324 139.505 −40.310 −15.804 1.00 75.19 C | ATOM 1410 CB LEU A 330 139.995 −44.038 −7.971 1.00 54.46 C |
| ANISOU 1365 CB SER A 324 6950 12173 9445 429 −614 484 C | ANISOU 1410 CB LEU A 330 5374 8336 6982 1078 −228 −1214 C |
| ATOM 1366 OG SER A 324 139.434 −41.708 −15.608 1.00 81.29 O | ATOM 1411 CG LEU A 330 139.686 −45.380 −8.675 1.00 56.73 C |
| ANISOU 1366 OG SER A 324 7464 13098 10323 810 −968 532 O | ANISOU 1411 CG LEU A 330 5905 8749 6899 1291 −276 −534 C |
| ATOM 1367 C SER A 324 137.213 −39.905 −14.884 1.00 79.88 C | ATOM 1412 CD1 LEU A 330 140.641 −45.619 −9.758 1.00 53.07 C |
| ANISOU 1367 C SER A 324 7631 12116 10603 736 −1025 1258 C | ANISOU 1412 CD1 LEU A 330 5500 8198 6467 944 −201 −341 C |
| ATOM 1368 O SER A 324 137.592 −39.579 −13.760 1.00 75.64 O | ATOM 1413 CD2 LEU A 330 139.812 −46.483 −7.573 1.00 51.48 C |
| ANISOU 1368 O SER A 324 6754 11893 10092 778 −827 1102 O | ANISOU 1413 CD2 LEU A 330 5132 8823 5603 1778 −364 −622 C |
| ATOM 1369 N LEU A 325 136.015 −40.425 −15.131 1.00 60.54 N | ATOM 1414 C LEU A 330 139.468 −42.433 −6.141 1.00 57.39 C |
| ANISOU 1369 N LEU A 325 8649 4434 9918 −162 −384 1802 N | ANISOU 1414 C LEU A 330 5486 8649 7671 1129 −136 −2203 C |
| ATOM 1370 CA LEU A 325 135.062 −40.708 −14.071 1.00 59.04 C | ATOM 1415 O LEU A 330 139.975 −42.730 −5.061 1.00 63.33 O |
| ANISOU 1370 CA LEU A 325 8051 4428 9952 254 −549 1741 C | ANISOU 1415 O LEU A 330 6037 10055 7971 1333 −246 −2678 O |
| ATOM 1371 CB LEU A 325 133.762 −41.238 −14.661 1.00 61.51 C | ATOM 1416 N ARG A 331 139.387 −41.185 −6.586 1.00 54.75 N |
| ANISOU 1371 CB LEU A 325 8508 5067 9797 450 −714 1932 C | ANISOU 1416 N ARG A 331 5169 7669 7965 752 36 −2366 N |
| ATOM 1372 CG LEU A 325 132.661 −41.391 −13.621 1.00 67.24 C | ATOM 1417 CA ARG A 331 139.896 −40.072 −5.798 1.00 64.26 C |
| ANISOU 1372 CG LEU A 325 8863 5932 10755 782 −784 1807 C | ANISOU 1417 CA ARG A 331 6120 8892 9405 511 162 −3176 C |
| ATOM 1373 CD1 LEU A 325 132.447 −40.052 −12.940 1.00 64.62 C | ATOM 1418 CB ARG A 331 139.832 −38.764 −6.588 1.00 67.85 C |
| ANISOU 1373 CD1 LEU A 325 8330 5070 11151 844 −696 1593 C | ANISOU 1418 CB ARG A 331 6681 8494 10603 66 428 −3211 C |
| ATOM 1374 CD2 LEU A 325 131.382 −41.873 −14.271 1.00 68.04 C | ATOM 1419 CG ARG A 331 139.639 −37.542 −5.719 1.00 87.83 C |
| ANISOU 1374 CD2 LEU A 325 9071 6291 6235 10546 866 −892 1916 C | ANISOU 1419 CG ARG A 331 9803 10770 13517 −84 661 −3885 C |
| ATOM 1375 C LEU A 325 135.644 −41.755 −13.135 1.00 50.75 C | ATOM 1420 CD ARG A 331 139.642 −36.251 −6.518 1.00 98.56 C |
| ANISOU 1375 C LEU A 325 6643 4106 8532 416 −481 1465 C | ANISOU 1420 CD ARG A 331 10587 11239 15622 −513 982 −3907 C |
| ATOM 1376 O LEU A 325 135.478 −41.701 −11.919 1.00 52.59 O | ATOM 1421 NE ARG A 331 138.468 −35.422 −6.244 1.00108.78 N |
| ANISOU 1376 O LEU A 325 6502 4681 8800 661 −393 1008 O | ANISOU 1421 NE ARG A 331 12029 11870 17433 −402 1183 −3845 N |
| ATOM 1377 N SER A 326 136.329 −42.710 −13.744 1.00 50.97 N | ATOM 1422 CZ ARG A 331 138.194 −34.852 −5.071 1.00112.55 C |
| ANISOU 1377 N SER A 326 6839 4463 8062 276 −478 1686 N | ANISOU 1422 CZ ARG A 331 12344 12422 17999 −363 1361 −4467 C |
| ATOM 1378 CA SER A 326 137.016 −43.768 −13.032 1.00 53.85 C | ATOM 1423 NH1 ARG A 331 139.002 −35.018 −4.030 1.00107.37 N |
| ANISOU 1378 CA SER A 326 6923 5627 7911 432 −389 1407 C | ANISOU 1423 NH1 ARG A 331 11405 12520 16872 −421 1296 −5206 N |
| ATOM 1379 CB SER A 326 137.823 −44.606 −14.018 1.00 52.10 C | ATOM 1424 NH2 ARG A 331 137.099 −34.115 −4.937 1.00116.88 N |
| ANISOU 1379 CB SER A 326 6967 5539 7289 182 −320 1724 C | ANISOU 1424 NH2 ARG A 331 13021 12277 19112 −257 1597 −4358 N |
| ATOM 1380 OG SER A 326 137.857 −45.951 −13.610 1.00 76.36 O | ATOM 1425 C ARG A 331 139.125 −39.947 −4.483 1.00 82.42 C |
| ANISOU 1380 OG SER A 326 9910 9235 9869 470 −335 1817 O | ANISOU 1425 C ARG A 331 8406 11367 11544 816 197 −3512 C |
| ATOM 1381 C SER A 326 137.956 −43.191 −11.980 1.00 52.20 C | ATOM 1426 O ARG A 331 139.704 −39.666 −3.433 1.00 98.29 O |

TABLE 9-continued

DMXAA-hSTING$^{S162A/G230I/Q266I}$ complex

| | |
|---|---|
| ANISOU 1381 C SER A 326 6308 5780 7746 390 −202 656 C | ANISOU 1426 O ARG A 331 10200 13848 13298 793 165 −4224 O |
| ATOM 1382 O SER A 326 137.951 −43.607 −10.818 1.00 51.82 O | ATOM 1427 N HIS A 332 137.817 −40.166 −4.540 1.00 75.79 N |
| ANISOU 1382 O SER A 326 5945 6293 7452 706 −216 308 O | ANISOU 1427 N HIS A 332 7801 10141 10853 1087 270 −3025 N |
| ATOM 1383 N GLN A 327 138.766 −42.229 −12.406 1.00 44.35 N | ATOM 1428 CA HIS A 332 137.010 −40.170 −3.329 1.00 66.73 C |
| ANISOU 1383 N GLN A 327 5357 4444 7050 −20 −19 383 N | ANISOU 1428 CA HIS A 332 6692 9106 9556 1382 395 −3300 C |
| ATOM 1384 CA GLN A 327 139.746 −41.596 −11.530 1.00 48.33 C | ATOM 1429 CB HIS A 332 135.526 −40.028 −3.659 1.00 67.38 C |
| ANISOU 1384 CA GLN A 327 5451 5257 7655 −156 155 −408 C | ANISOU 1429 CB HIS A 332 6943 8490 10167 1548 561 −2806 C |
| ATOM 1385 CB GLN A 327 140.732 −40.777 −12.354 1.00 52.93 C | ATOM 1430 CG HIS A 332 135.154 −38.666 −4.151 1.00 80.98 C |
| ANISOU 1385 CB GLN A 327 6157 5404 8548 −697 437 −601 C | ANISOU 1430 CG HIS A 332 8649 9378 12744 1259 756 −2871 C |
| ATOM 1386 CG GLN A 327 141.742 −41.643 −13.058 1.00 50.52 C | ATOM 1431 ND1 HIS A 332 135.535 −38.196 −5.387 1.00 93.26 N |
| ANISOU 1386 CG GLN A 327 5894 5379 7921 −894 534 −477 C | ANISOU 1431 ND1 HIS A 332 10274 10483 14679 959 684 −2552 N |
| ATOM 1432 CE1 HIS A 332 135.073 −36.966 −5.545 1.00 95.60 C | HETATM 1488 CAS DRG C 2 108.520 −40.709 −3.521 1.00 43.19 C |
| ANISOU 1432 CE1 HIS A 332 10592 10025 15705 791 915 −2663 C | HETATM 1489 CAJ DRG C 2 108.227 −40.522 −2.176 1.00 31.16 C |
| ATOM 1433 NE2 HIS A 332 134.416 −36.625 −4.454 1.00 93.80 N | HETATM 1490 CAH DRG C 2 108.129 −41.637 −1.347 1.00 32.15 C |
| ANISOU 1433 NE2 HIS A 332 10268 9751 15620 953 1149 −3070 N | HETATM 1491 CAN DRG C 2 108.311 −42.932 −1.845 1.00 47.34 C |
| ATOM 1434 CD2 HIS A 332 134.454 −37.670 −3.560 1.00 86.16 C | HETATM 1492 CAA DRG C 2 108.213 −44.057 −1.015 1.00 30.55 C |
| ANISOU 1434 CD2 HIS A 332 9267 9531 13939 1232 1063 −3217 C | HETATM 1493 CAO DRG C 2 108.594 −43.114 −3.197 1.00 44.08 C |
| ATOM 1435 C HIS A 332 137.234 −41.443 −2.529 1.00 67.50 C | HETATM 1494 CAB DRG C 2 108.784 −44.373 −3.763 1.00 31.60 C |
| ANISOU 1435 C HIS A 332 6838 10015 8795 1781 225 −3299 C | HETATM 1495 CAT DRG C 2 108.702 −42.002 −4.005 1.00 44.81 C |
| ATOM 1436 O HIS A 332 137.463 −41.396 −1.322 1.00 69.48 O | HETATM 1496 OAL DRG C 2 108.961 −42.249 −5.314 1.00 40.22 O |
| ANISOU 1436 O HIS A 332 7066 10714 8618 1903 235 −3861 O | HETATM 1497 CAU DRG C 2 109.053 −41.199 −6.163 1.00 34.93 C |
| ATOM 1437 N LEU A 333 137.162 −42.575 −3.223 1.00 63.88 N | HETATM 1498 CAR DRG C 2 108.884 −39.890 −5.703 1.00 42.08 C |
| ANISOU 1437 N LEU A 333 6496 9712 8065 1979 82 −2658 N | HETATM 1499 CAI DRG C 2 108.976 −38.828 −6.597 1.00 36.30 C |
| ATOM 1438 CA LEU A 333 137.325 −43.892 −2.612 1.00 74.05 C | HETATM 1500 CAF DRG C 2 109.251 −39.098 −7.930 1.00 38.45 C |
| ANISOU 1438 CA LEU A 333 7893 11682 8561 2398 −34 −2526 C | HETATM 1501 CAG DRG C 2 109.418 −40.405 −8.378 1.00 43.73 C |
| ATOM 1439 CB LEU A 333 137.459 −44.967 −3.690 1.00 69.09 C | HETATM 1502 CAP DRG C 2 109.326 −41.476 −7.499 1.00 34.19 C |
| ANISOU 1439 CB LEU A 333 7355 11111 7785 2470 −148 −1833 C | HETATM 1503 CAK DRG C 2 109.511 −42.771 −7.991 1.00 41.63 C |
| ATOM 1440 CG LEU A 333 136.282 −45.907 −3.924 1.00 73.24 C | HETATM 1504 CAM DRG C 2 108.391 −43.779 −7.682 1.00 52.21 C |
| ANISOU 1440 CG LEU A 333 8146 11437 8246 2764 −16 −1218 C | HETATM 1505 OAE DRG C 2 107.239 −43.341 −7.449 1.00 53.23 O |
| ATOM 1441 CD1 LEU A 333 136.734 −47.344 −3.775 1.00 81.65 C | HETATM 1506 OAC DRG C 2 108.735 −44.980 −7.713 1.00 50.44 O |
| ANISOU 1441 CD1 LEU A 333 9440 12971 8612 2889 −138 −869 C | ATOM 1507 N SERB 154 109.380 −24.066 −8.178 1.00 59.21 N |
| ATOM 1442 CD2 LEU A 333 135.169 −45.619 −2.955 1.00 75.23 C | ANISOU 1507 N SER B 154 8214 7141 7141 −67 −526 997 N |
| ANISOU 1442 CD2 LEU A 333 8537 11425 8624 2879 218 −1382 C | ATOM 1508 CA SER B 154 108.231 −24.663 −7.508 1.00 59.32 C |
| ATOM 1443 C LEU A 333 138.525 −43.981 −1.675 1.00 82.19 C | ANISOU 1508 CA SER B 154 8128 6918 7492 −96 −101 651 C |
| ANISOU 1443 C LEU A 333 8752 13481 8997 2462 −251 −3141 C | ATOM 1509 CB SER B 154 106.967 −24.499 −8.351 1.00 61.82 C |
| ATOM 1444 O LEU A 333 138.441 −44.549 −0.587 1.00 89.91 O | ANISOU 1509 CB SER B 154 7950 7074 8464 137 −192 514 C |
| ANISOU 1444 O LEU A 333 9904 14840 9419 2726 −323 −3194 O | ATOM 1510 OG SER B 154 105.850 −25.104 −7.726 1.00 66.10 O |
| ATOM 1445 N ARG A 334 139.646 −43.421 −2.102 1.00 75.04 N | ANISOU 1510 OG SER B 154 8348 7382 9384 112 240 177 O |
| ANISOU 1445 N ARG A 334 7536 12681 8297 2109 −403 −3472 N | ATOM 1511 C SER B 154 108.484 −26.143 −7.259 1.00 62.75 C |
| ATOM 1446 CA ARG A 334 140.856 −43.479 −1.300 1.00 86.72 C | ANISOU 1511 C SER B 154 8644 7550 7646 −177 −8 653 C |
| ANISOU 1446 CA ARG A 334 8741 14906 9302 2144 −689 −4099 C | ATOM 1512 O SER B 154 108.929 −26.861 −8.158 1.00 53.14 O |
| ATOM 1447 CB ARG A 334 142.073 −43.093 −2.142 1.00 79.76 C | ANISOU 1512 O SER B 154 7288 6606 6298 −61 −286 817 O |
| ANISOU 1447 CB ARG A 334 7469 14055 8782 1734 −799 −4300 C | ATOM 1513 N VAL B 155 108.195 −26.610 −6.049 1.00 47.86 N |
| ATOM 1448 CG ARG A 334 142.540 −44.219 −3.038 1.00 71.60 C | ANISOU 1513 N VAL B 155 7000 5505 5681 −413 406 460 N |
| ANISOU 1448 CG ARG A 334 6425 13204 7575 1872 −901 −3710 C | ATOM 1514 CA VAL B 155 108.467 −28.004 −5.756 1.00 42.30 C |
| ATOM 1449 CD ARG A 334 142.931 −43.711 −4.406 1.00 78.55 C | ANISOU 1514 CA VAL B 155 6380 4949 4742 −515 452 512 C |
| ANISOU 1449 CD ARG A 334 7218 13530 9098 1370 −716 −3528 C | ATOM 1515 CB VAL B 155 108.588 −28.294 −4.234 1.00 62.29 C |
| ATOM 1450 NE ARG A 334 143.455 −44.775 −5.257 1.00 79.10 N | ANISOU 1515 CB VAL B 155 9366 7333 6968 −935 800 445 C |
| ANISOU 1450 NE ARG A 334 7290 13766 8998 1452 −755 −3027 N | ATOM 1516 CG2 VAL B 155 107.236 −28.588 −3.609 1.00 50.37 C |
| ATOM 1451 CZ ARG A 334 143.721 −44.629 −6.550 1.00 84.77 C | ANISOU 1516 CG2 VAL B 155 7802 5561 5775 −1037 1306 19 C |
| ANISOU 1451 CZ ARG A 334 8077 13998 10136 1065 −553 −2716 C | ATOM 1517 CG1 VAL B 155 109.261 −27.125 −3.530 1.00 48.01 C |
| ATOM 1452 NH1 ARG A 334 143.501 −43.461 −7.139 1.00 93.59 N | ANISOU 1517 CG1 VAL B 155 7957 5430 4853 −1197 815 551 C |
| ANISOU 1452 NH1 ARG A 334 9290 14426 11845 605 −324 −2816 N | ATOM 1518 C VAL B 155 107.453 −28.916 −6.449 1.00 42.87 C |
| ATOM 1453 NH2 ARG A 334 144.200 −45.650 −7.251 1.00 63.69 N | ANISOU 1518 C VAL B 155 6060 5037 5190 −311 495 315 C |
| ANISOU 1453 NH2 ARG A 334 5432 11492 7275 1140 −542 −2298 N | ATOM 1519 O VAL B 155 107.811 −29.985 −6.934 1.00 49.65 O |
| ATOM 1454 C ARG A 334 140.765 −42.597 −0.053 1.00106.79 C | ANISOU 1519 O VAL B 155 6838 6094 5933 −248 348 423 O |
| ANISOU 1454 C ARG A 334 11265 17540 11770 2063 −659 −4808 C | ATOM 1520 N ALA B 156 106.198 −28.481 −6.524 1.00 38.64 N |
| ATOM 1455 O ARG A 334 141.549 −41.661 0.094 1.00120.52 O | ANISOU 1520 N ALA B 156 5258 4264 5158 −215 695 33 N |
| ANISOU 1455 O ARG A 334 12685 19344 13764 1690 −715 −5470 O | ATOM 1521 CA ALA B 156 105.155 −29.313 −7.118 1.00 46.04 C |
| ATOM 1456 N GLN A 335 139.790 −42.919 0.807 1.00106.24 N | ANISOU 1521 CA ALA B 156 5817 5192 6484 −67 716 −137 C |
| ANISOU 1456 N GLN A 335 11563 17353 11451 2318 −531 −4541 N | ATOM 1522 CB ALA B 156 103.788 −28.716 −6.886 1.00 40.11 C |
| ATOM 1457 CA GLN A 335 139.553 −42.335 2.141 1.00109.47 C | ANISOU 1522 CB ALA B 156 4766 4085 6388 −15 1012 −439 C |
| ANISOU 1457 CA GLN A 335 12109 17782 11704 2260 −455 −4970 C | ATOM 1523 C ALA B 156 105.398 −29.502 −8.609 1.00 37.09 C |
| ATOM 1458 CB GLN A 335 139.856 −40.839 2.213 1.00106.86 C | ANISOU 1523 C ALA B 156 4426 4318 5347 136 221 70 C |
| ANISOU 1458 CB GLN A 335 11521 17201 11878 −789 −310 −5741 C | ATOM 1524 O ALA B 156 105.096 −30.543 −9.183 1.00 35.58 O |
| ATOM 1459 CG GLN A 335 138.927 −39.988 1.380 1.00100.18 C | ANISOU 1524 O ALA B 156 4079 4255 5185 178 152 30 O |
| ANISOU 1459 CG GLN A 335 10712 15519 11833 1588 131 −5734 C | ATOM 1525 N HIS B 157 105.945 −28.472 −9.230 1.00 37.65 N |
| ATOM 1460 CD GLN A 335 139.678 −39.126 0.389 1.00105.46 C | ANISOU 1525 N HIS B 157 4496 4459 5351 209 −105 281 N |
| ANISOU 1460 CD GLN A 335 11038 15898 13134 1133 156 −6015 C | ATOM 1526 CA HIS B 157 106.222 −28.514 −10.655 1.00 48.59 C |
| ATOM 1461 OE1 GLN A 335 139.183 −38.088 −0.048 1.00113.37 O | ANISOU 1526 CA HIS B 157 5718 6092 6651 301 −565 479 C |
| ANISOU 1461 OE1 GLN A 335 12049 16138 14888 827 490 −6049 O | ATOM 1527 CB HIS B 157 106.718 −27.139 −11.112 1.00 49.34 C |
| ATOM 1462 NE2 GLN A 335 140.884 −39.548 0.033 1.00103.48 N | ANISOU 1527 CB HIS B 157 5844 6191 6711 334 −884 704 C |
| ANISOU 1462 NE2 GLN A 335 10504 16175 12640 1055 −178 −6101 N | ATOM 1528 CG HIS B 157 107.091 −27.075 −12.565 1.00 34.29 C |
| ATOM 1463 C GLN A 335 138.098 −42.552 2.541 1.00110.98 C | ANISOU 1528 CG HIS B 157 3856 4553 4620 329 −1359 926 C |
| ANISOU 1463 C GLN A 335 12751 17492 11923 2440 −78 −4603 C | ATOM 1529 ND1 HIS B 157 108.357 −26.779 −12.980 1.00 44.41 N |
| ATOM 1464 O GLN A 335 137.744 −43.571 3.133 1.00109.72 O | ANISOU 1529 ND1 HIS B 157 5403 6038 5433 275 −1345 986 N |
| ANISOU 1464 O GLN A 335 12908 17475 11306 2730 −97 −4162 O | ATOM 1530 CE1 HIS B 157 108.386 −26.771 −14.314 1.00 40.71 C |
| TER 1465 GLN A 335 | ANISOU 1530 CE1 HIS B 157 4907 5692 4869 236 −1437 919 C |

TABLE 9-continued

DMXAA-hSTING$^{S162A/G230I/Q266I}$ complex

| | |
|---|---|
| HETATM 1465 OAD DRG C 1 113.462 −38.019 −10.559 1.00 29.78 O | ATOM 1531 NE2 HIS B 157 107.182 −27.055 −14.747 1.00 41.99 N |
| HETATM 1466 CAQ DRG C 1 113.397 −39.177 −10.166 1.00 40.86 C | ANISOU 1531 NE2 HIS B 157 4825 5799 5329 211 −1634 927 N |
| HETATM 1467 CAS DRG C 1 113.580 −40.249 −11.022 1.00 40.22 C | ATOM 1532 CD2 HIS B 157 106.334 −27.254 −13.677 1.00 29.33 C |
| HETATM 1468 CAJ DRG C 1 113.855 −40.035 −12.369 1.00 32.92 C | ANISOU 1532 CD2 HIS B 157 2991 3973 4181 307 −1638 933 C |
| HETATM 1469 CAH DRG C 1 114.057 −41.134 −13.196 1.00 29.54 C | ATOM 1533 C HIS B 157 107.265 −29.588 −10.924 1.00 41.92 C |
| HETATM 1470 CAN DRG C 1 113.982 −42.436 −12.689 1.00 41.38 C | ANISOU 1533 C HIS B 157 5056 5536 5334 246 −592 584 C |
| HETATM 1471 CAA DRG C 1 114.183 −43.537 −13.518 1.00 29.25 C | ATOM 1534 O HIS B 157 107.106 −30.418 −11.822 1.00 49.38 O |
| HETATM 1472 CAO DRG C 1 113.710 −42.644 −11.336 1.00 32.01 C | ANISOU 1534 O HIS B 157 5875 6636 6253 253 −709 553 O |
| HETATM 1473 CAB DRG C 1 113.622 −43.906 −10.750 1.00 33.55 C | ATOM 1535 N GLY B 158 108.329 −29.572 −10.132 1.00 29.40 N |
| HETATM 1474 CAT DRG C 1 113.499 −41.553 −10.532 1.00 36.06 C | ANISOU 1535 N GLY B 158 3763 3988 3421 161 −477 711 N |
| HETATM 1475 OAL DRG C 1 113.267 −41.828 −9.235 1.00 35.96 O | ATOM 1536 CA GLY B 158 109.407 −30.533 −10.283 1.00 38.06 C |
| HETATM 1476 CAU DRG C 1 113.112 −40.793 −8.373 1.00 29.79 C | ANISOU 1536 CA GLY B 158 4966 5275 4218 122 −488 851 C |
| HETATM 1477 CAR DRG C 1 113.191 −39.466 −8.835 1.00 38.79 C | ATOM 1537 C GLY B 158 108.967 −31.929 −9.875 1.00 38.76 C |
| HETATM 1478 CAI DRG C 1 113.048 −38.423 −7.930 1.00 35.14 C | ANISOU 1537 C GLY B 158 5013 5304 4409 89 −237 684 C |
| HETATM 1479 CAF DRG C 1 112.818 −38.723 −6.595 1.00 40.44 C | ATOM 1538 O GLY B 158 109.416 −32.930 −10.421 1.00 37.24 O |
| HETATM 1480 CAG DRG C 1 112.741 −40.042 −6.150 1.00 36.18 C | ANISOU 1538 O GLY B 158 4761 5227 4161 110 −238 703 O |
| HETATM 1481 CAP DRG C 1 112.879 −41.100 −7.040 1.00 36.02 C | ATOM 1539 N LEU B 159 108.061 −31.994 −8.910 1.00 29.75 N |
| HETATM 1482 CAK DRG C 1 112.792 −42.415 −6.569 1.00 35.27 C | ANISOU 1539 N LEU B 159 3906 3954 3445 17 22 496 N |
| HETATM 1483 CAM DRG C 1 114.002 −43.331 −6.858 1.00 42.08 C | ATOM 1540 CA LEU B 159 107.623 −33.272 −8.373 1.00 31.76 C |
| HETATM 1484 OAE DRG C 1 115.083 −42.798 −7.202 1.00 51.70 O | ANISOU 1540 CA LEU B 159 4161 4131 3775 −60 267 352 C |
| HETATM 1485 OAC DRG C 1 113.797 −44.559 −6.713 1.00 41.96 O | ATOM 1541 CB LEU B 159 106.827 −33.073 −7.083 1.00 28.85 C |
| HETATM 1486 OAD DRG C 2 108.474 −38.473 −3.971 1.00 36.96 O | ANISOU 1541 CB LEU B 159 3939 3521 3503 −237 606 165 C |
| HETATM 1487 CAQ DRG C 2 108.627 −39.628 −4.372 1.00 49.22 C | ATOM 1542 CG LEU B 159 107.459 −33.468 −5.751 1.00 46.24 C |
| ANISOU 1542 CG LEU B 159 6523 5642 5404 −537 764 293 C | ATOM 1587 CD1 TYR B 164 4663 6212 4724 −684 −458 −619 C |
| ATOM 1543 CD2 LEU B 159 106.741 −32.721 −4.652 1.00 45.94 C | ATOM 1588 CE1 TYR B 164 104.921 −38.952 −19.000 1.00 52.04 C |
| ANISOU 1543 CD2 LEU B 159 6701 5371 5384 −774 1116 73 C | ANISOU 1588 CE1 TYR B 164 6235 7769 5767 −1035 −582 −704 C |
| ATOM 1544 CD1 LEU B 159 108.940 −33.159 −5.699 1.00 54.73 C | ATOM 1589 CZ TYR B 164 105.891 −38.321 −19.762 1.00 57.32 C |
| ANISOU 1544 CD1 LEU B 159 7794 6840 6162 −595 483 677 C | ANISOU 1589 CZ TYR B 164 7106 8610 6063 −1183 −657 −610 C |
| ATOM 1545 C LEU B 159 106.771 −33.993 −9.415 1.00 34.06 C | ATOM 1590 OH TYR B 164 105.974 −38.562 −21.110 1.00 66.85 O |
| ANISOU 1545 C LEU B 159 4156 4484 4300 59 222 167 C | ANISOU 1590 OH TYR B 164 8569 9985 6847 −1631 −735 −721 O |
| ATOM 1546 O LEU B 159 106.878 −35.206 −9.605 1.00 33.81 O | ATOM 1591 CE2 TYR B 164 106.785 −37.443 −19.178 1.00 53.77 C |
| ANISOU 1546 O LEU B 159 4095 4495 4256 47 294 124 O | ANISOU 1591 CE2 TYR B 164 6639 8165 5627 −943 −642 −411 C |
| ATOM 1547 N ALA B 160 105.922 −33.227 −10.089 1.00 29.30 N | ATOM 1592 CD2 TYR B 164 106.708 −37.200 −17.831 1.00 49.78 C |
| ANISOU 1547 N ALA B 160 3333 3857 3943 145 75 81 N | ANISOU 1592 CD2 TYR B 164 5960 7492 5463 −599 −553 −313 C |
| ATOM 1548 CA ALA B 160 105.052 −33.767 −11.118 1.00 33.09 C | ATOM 1593 C TYR B 164 107.324 −39.409 −15.280 1.00 40.21 C |
| ANISOU 1548 CA ALA B 160 3545 4392 4634 184 −60 −42 C | ANISOU 1593 C TYR B 164 4641 5838 4801 −184 297 −483 C |
| ATOM 1549 CB ALA B 160 104.076 −32.714 −11.606 1.00 28.13 C | ATOM 1594 O TYR B 164 107.243 −40.521 −15.804 1.00 37.31 O |
| ANISOU 1549 CB ALA B 160 2647 3652 4388 242 −281 −49 C | ANISOU 1594 O TYR B 164 4291 5434 4452 −291 499 −697 O |
| ATOM 1550 C ALA B 160 105.875 −34.325 −12.283 1.00 38.04 C | ATOM 1595 N ILE B 165 108.462 −38.752 −15.180 1.00 30.92 N |
| ANISOU 1550 C ALA B 160 4223 5270 4960 161 −263 57 C | ANISOU 1595 N ILE B 165 3529 4712 3507 −113 275 −281 N |
| ATOM 1551 O ALA B 160 105.629 −35.430 −12.770 1.00 31.69 O | ATOM 1596 CA ILE B 165 109.696 −39.275 −15.703 1.00 31.32 C |
| ANISOU 1551 O ALA B 160 3368 4518 4154 111 −199 −73 O | ANISOU 1596 CA ILE B 165 3629 4780 3490 −151 497 −299 C |
| ATOM 1552 N TRP B 161 106.852 −33.551 −12.731 1.00 30.18 N | ATOM 1597 CB ILE B 165 110.793 −38.200 −15.709 1.00 33.02 C |
| ANISOU 1552 N TRP B 161 3343 4413 3712 168 −463 261 N | ANISOU 1597 CB ILE B 165 3889 5094 3562 −96 368 −34 C |
| ATOM 1553 CA TRP B 161 107.751 −34.033 −13.763 1.00 36.31 C | ATOM 1598 CG1 ILE B 165 110.470 −37.098 −16.706 1.00 35.79 C |
| ANISOU 1553 CA TRP B 161 4195 5402 4199 102 −544 316 C | ANISOU 1598 CG1 ILE B 165 4333 5673 3593 −242 45 −3 C |
| ATOM 1554 CB TRP B 161 108.682 −32.927 −14.240 1.00 34.27 C | ATOM 1599 CD1 ILE B 165 110.094 −37.550 −18.016 1.00 30.89 C |
| ANISOU 1554 CB TRP B 161 4043 5282 3696 87 −778 544 C | ANISOU 1599 CD1 ILE B 165 3822 5188 2728 −534 92 −246 C |
| ATOM 1555 CG TRP B 161 107.969 −32.038 −15.169 1.00 24.91 C | ATOM 1600 CG2 ILE B 165 112.142 −38.783 −15.962 1.00 26.33 C |
| ANISOU 1555 CG TRP B 161 2762 4152 2551 15 −1150 599 C | ANISOU 1600 CG2 ILE B 165 3006 4189 2810 −97 672 −29 C |
| ATOM 1556 CD1 TRP B 161 107.358 −30.854 −14.875 1.00 29.59 C | ATOM 1601 C ILE B 165 110.202 −40.535 −15.024 1.00 39.00 C |
| ANISOU 1556 CD1 TRP B 161 3250 4604 3391 82 −1357 700 C | ANISOU 1601 C ILE B 165 4520 5510 4789 −56 826 −330 C |
| ATOM 1557 NE1 TRP B 161 106.771 −30.339 −16.000 1.00 32.70 N | ATOM 1602 O ILE B 165 110.686 −41.435 −15.667 1.00 47.32 O |
| ANISOU 1557 NE1 TRP B 161 3575 5001 3848 −12 −1640 717 N | ANISOU 1602 O ILE B 165 5550 6484 5945 −118 1123 −510 O |
| ATOM 1558 CE2 TRP B 161 106.977 −31.208 −17.047 1.00 33.34 C | ATOM 1603 N GLY B 166 110.100 −40.567 −13.712 1.00 40.03 N |
| ANISOU 1558 CE2 TRP B 161 3753 5261 3652 −195 −1662 641 C | ANISOU 1603 N GLY B 166 4619 5493 5098 54 783 −152 N |
| ATOM 1559 CD2 TRP B 161 107.720 −32.293 −16.546 1.00 40.53 C | ATOM 1604 CA GLY B 166 110.625 −41.640 −12.925 1.00 36.59 C |
| ANISOU 1559 CD2 TRP B 161 4737 6301 4363 −188 −1381 572 C | ANISOU 1604 CA GLY B 166 4110 4803 4991 108 982 −58 C |
| ATOM 1560 CE3 TRP B 161 108.073 −33.331 −17.420 1.00 26.85 C | ATOM 1605 C GLY B 166 109.706 −42.758 −12.547 1.00 40.38 C |
| ANISOU 1560 CE3 TRP B 161 3113 4721 2366 −374 −1249 424 C | ANISOU 1605 C GLY B 166 4563 5121 5657 70 1120 −238 C |
| ATOM 1561 CZ3 TRP B 161 107.675 −33.251 −18.742 1.00 37.79 C | ATOM 1606 O GLY B 166 110.115 −43.643 −11.873 1.00 43.27 O |
| ANISOU 1561 CZ3 TRP B 161 4569 6222 3567 −656 −1518 416 C | ANISOU 1606 O GLY B 166 4876 5247 6316 88 1229 −114 O |
| ATOM 1562 CH2 TRP B 161 106.932 −32.154 −19.213 1.00 41.76 C | ATOM 1607 N TYR B 167 108.455 −42.676 −12.935 1.00 31.17 N |
| ANISOU 1562 CH2 TRP B 161 5014 6560 4292 −635 −1803 533 C | ANISOU 1607 N TYR B 167 3417 4065 4361 −4 1079 −491 N |
| ATOM 1563 CZ2 TRP B 161 106.576 −31.122 −18.382 1.00 37.46 C | ATOM 1608 CA TYR B 167 107.505 −43.715 −12.650 1.00 39.43 C |
| ANISOU 1563 CZ2 TRP B 161 4319 5834 4082 −396 −1863 637 C | ANISOU 1608 CA TYR B 167 4429 4969 5583 −60 1221 −681 C |
| ATOM 1564 C TRP B 161 108.548 −35.254 −13.328 1.00 34.70 C | ATOM 1609 CB TYR B 167 106.820 −43.484 −11.323 1.00 28.55 C |
| ANISOU 1564 C TRP B 161 4073 5172 3940 107 −245 280 C | ANISOU 1609 CB TYR B 167 3086 3508 4253 −71 1158 −563 C |
| ATOM 1565 O TRP B 161 108.729 −36.192 −14.098 1.00 32.00 O | ATOM 1610 CG TYR B 167 105.890 −44.568 −10.958 1.00 34.39 C |
| ANISOU 1565 O TRP B 161 3712 4896 3550 44 −146 156 O | ANISOU 1610 CG TYR B 167 3796 4100 5172 −153 1315 −741 C |
| ATOM 1566 N ALA B 162 109.029 −35.241 −12.093 1.00 28.82 N | ATOM 1611 CD1 TYR B 167 106.352 −45.820 −10.638 1.00 41.93 C |
| ANISOU 1566 N ALA B 162 3426 4299 3224 141 −109 403 N | ANISOU 1611 CD1 TYR B 167 4740 4829 6362 −171 1485 −710 C |
| ATOM 1567 CA ALA B 162 109.778 −36.380 −11.572 1.00 29.10 C | ATOM 1612 CE1 TYR B 167 105.513 −46.806 −10.317 1.00 30.94 C |
| ANISOU 1567 CA ALA B 162 3499 4249 3309 128 94 458 C | ANISOU 1612 CE1 TYR B 167 3336 3295 5124 −267 1619 −864 C |
| ATOM 1568 CB ALA B 162 110.371 −36.060 −10.219 1.00 27.34 C | ATOM 1613 CZ TYR B 167 104.189 −46.571 −10.310 1.00 40.47 C |
| ANISOU 1568 CB ALA B 162 3440 3905 3045 69 102 702 C | ANISOU 1613 CZ TYR B 167 4518 4595 6263 −346 1604 −1061 C |
| ATOM 1569 C ALA B 162 108.896 −37.634 −11.483 1.00 31.94 C | ATOM 1614 OH TYR B 167 103.337 −47.567 −9.970 1.00 50.37 O |
| ANISOU 1569 C ALA B 162 3772 4499 3865 105 294 220 C | ANISOU 1614 OH TYR B 167 5752 5717 7670 −460 1746 −1216 O |

TABLE 9-continued

DMXAA-hSTING$^{S162A/G230I/Q266I}$ complex

| | |
|---|---|
| ATOM 1570 O ALA B 162 109.353 −38.754 −11.702 1.00 46.58 O | ATOM 1615 CE2 TYR B 167 103.699 −45.345 −10.614 1.00 36.07 C |
| ANISOU 1570 O ALA B 162 5582 6299 5818 103 447 182 O | ANISOU 1615 CE2 TYR B 167 3918 4230 5555 −313 1445 −1087 C |
| ATOM 1571 N TYR B 163 107.632 −37.438 −11.138 1.00 33.94 N | ATOM 1616 CD2 TYR B 167 104.542 −44.358 −10.939 1.00 39.25 C |
| ANISOU 1571 N TYR B 163 3977 4685 4233 85 316 57 N | ANISOU 1616 CD2 TYR B 167 4356 4764 5791 −218 1291 −923 C |
| ATOM 1572 CA TYR B 163 106.722 −38.560 −10.979 1.00 36.48 C | ATOM 1617 C TYR B 167 106.501 −44.020 −13.752 1.00 39.73 C |
| ANISOU 1572 CA TYR B 163 4215 4901 4743 42 499 −163 C | ANISOU 1617 C TYR B 167 4455 5126 5516 −192 1212 −995 C |
| ATOM 1573 CB TYR B 163 105.448 −38.111 −10.268 1.00 27.18 C | ATOM 1618 O TYR B 167 106.489 −45.079 −14.286 1.00 49.78 O |
| ANISOU 1573 CB TYR B 163 2977 3601 3750 9 577 −303 C | ANISOU 1618 O TYR B 167 5733 6312 6869 −281 1422 −1216 O |
| ATOM 1574 CG TYR B 163 104.498 −39.234 −9.938 1.00 35.21 C | ATOM 1619 N LEU B 168 105.650 −43.069 −14.059 1.00 38.42 N |
| ANISOU 1574 CG TYR B 163 3914 4498 4967 −61 790 −517 C | ANISOU 1619 N LEU B 168 4266 5126 5205 −231 951 −994 N |
| ATOM 1575 CD1 TYR B 163 104.943 −40.378 −9.274 1.00 44.03 C | ATOM 1620 CA LEU B 168 104.580 −43.235 −14.996 1.00 43.70 C |
| ANISOU 1575 CD1 TYR B 163 5156 5515 6059 −140 967 −479 C | ANISOU 1620 CA LEU B 168 4899 5896 5809 −408 819 −1197 C |
| ATOM 1576 CE1 TYR B 163 104.073 −41.407 −8.967 1.00 35.72 C | ATOM 1621 CB LEU B 168 103.733 −41.984 −15.022 1.00 35.81 C |
| ANISOU 1576 CE1 TYR B 163 4046 4349 5178 −225 1155 −666 C | ANISOU 1621 CB LEU B 168 3785 5003 4818 −408 467 −1082 C |
| ATOM 1577 CZ TYR B 163 102.739 −41.290 −9.323 1.00 36.72 C | ATOM 1622 CG LEU B 168 102.958 −41.719 −13.757 1.00 49.06 C |
| ANISOU 1577 CZ TYR B 163 3964 4468 5522 −226 1179 −900 C | ANISOU 1622 CG LEU B 168 5326 6527 6789 −282 526 −1041 C |
| ATOM 1578 OH TYR B 163 101.861 −42.295 −9.025 1.00 44.92 O | ATOM 1623 CD1 LEU B 168 102.083 −40.540 −13.960 1.00 52.56 C |
| ANISOU 1578 OH TYR B 163 4932 5397 6738 −324 1368 −1085 O | ANISOU 1623 CD1 LEU B 168 5572 6998 7399 −283 223 −971 C |
| ATOM 1579 CE2 TYR B 163 102.278 −40.159 −9.981 1.00 41.54 C | ATOM 1624 CD2 LEU B 168 102.148 −42.900 −13.390 1.00 47.62 C |
| ANISOU 1579 CE2 TYR B 163 4403 5154 6225 −144 980 −913 C | ANISOU 1624 CD2 LEU B 168 5087 6197 6809 −343 756 −1233 C |
| ATOM 1580 CD2 TYR B 163 103.154 −39.144 −10.283 1.00 32.94 C | ATOM 1625 C LEU B 168 104.998 −43.560 −16.408 1.00 46.97 C |
| ANISOU 1580 CD2 TYR B 163 3398 4172 4946 −64 782 −720 C | ANISOU 1625 C LEU B 168 5452 6424 5969 −620 869 −1363 C |
| ATOM 1581 C TYR B 163 106.416 −39.157 −12.352 1.00 42.75 C | ATOM 1626 O LEU B 168 104.392 −44.352 −17.051 1.00 42.91 O |
| ANISOU 1581 C TYR B 163 4894 5812 5537 22 445 −339 C | ANISOU 1626 O LEU B 168 4986 5889 5430 −823 955 −1599 O |
| ATOM 1582 O TYR B 163 106.279 −40.373 −12.519 1.00 36.33 O | ATOM 1627 N ARG B 169 106.029 −42.934 −16.907 1.00 44.92 N |
| ANISOU 1582 O TYR B 163 4055 4934 4813 −21 617 −486 O | ANISOU 1627 N ARG B 169 5291 6281 5495 −627 845 −1264 N |
| ATOM 1583 N TYR B 164 106.339 −38.282 −13.344 1.00 39.30 N | ATOM 1628 CA ARG B 169 106.448 −43.261 −18.265 1.00 51.77 C |
| ANISOU 1583 N TYR B 164 4423 5535 4973 3 192 −311 N | ANISOU 1628 CA ARG B 169 6345 7255 6068 −915 963 −1469 C |
| ATOM 1584 CA TYR B 164 106.093 −38.716 −14.702 1.00 38.13 C | ATOM 1629 CB ARG B 169 107.262 −42.140 −18.904 1.00 47.70 C |
| ANISOU 1584 CA TYR B 164 4256 5521 4711 −136 96 −451 C | ANISOU 1629 CB ARG B 169 5942 6938 5244 −989 804 −1317 C |
| ATOM 1585 CB TYR B 164 105.678 −37.534 −15.568 1.00 37.79 C | ATOM 1630 CG ARG B 169 108.733 −42.167 −18.591 1.00 48.59 C |
| ANISOU 1585 CB TYR B 164 4173 5618 4566 −221 −297 −347 C | ANISOU 1630 CG ARG B 169 6032 6960 5470 −810 1118 −1243 C |
| ATOM 1586 CG TYR B 164 105.746 −37.817 −17.043 1.00 45.68 C | ATOM 1631 CD ARG B 169 109.431 −41.113 −19.415 1.00 54.09 C |
| ANISOU 1586 CG TYR B 164 5275 6799 5280 −485 −443 −426 C | ANISOU 1631 CD ARG B 169 6869 7877 5806 −964 976 −1141 C |
| ATOM 1587 CD1 TYR B 164 104.855 −38.696 −17.646 1.00 41.06 C | ATOM 1632 NE ARG B 169 110.850 −41.013 −19.107 1.00 63.98 N |
| ANISOU 1632 NE ARG B 169 8050 9045 7216 −791 1245 −1030 N | ANISOU 1677 O GLU B 174 10278 9517 10782 −2082 2794 −3464 O |
| ATOM 1633 CZ ARG B 169 111.715 −40.276 −19.792 1.00 60.86 C | ATOM 1678 N LEU B 175 101.427 −51.535 −19.206 1.00 58.22 N |
| ANISOU 1633 CZ ARG B 169 7759 8802 6562 −921 1255 −972 C | ANISOU 1678 N LEU B 175 7398 7131 7591 −2072 2125 −3231 N |
| ATOM 1634 NH1 ARG B 169 111.303 −39.568 −20.832 1.00 49.23 N | ATOM 1679 CA LEU B 175 100.394 −51.754 −18.205 1.00 59.56 C |
| ANISOU 1634 NH1 ARG B 169 6515 7583 4609 −1258 985 −1003 N | ANISOU 1679 CA LEU B 175 7330 7233 8065 −1918 1957 −3105 C |
| ATOM 1635 NH2 ARG B 169 112.994 −40.253 −19.436 1.00 58.96 N | ATOM 1680 CB LEU B 175 99.976 −50.447 −17.542 1.00 57.85 C |
| ANISOU 1635 NH2 ARG B 169 7386 8447 6569 −748 1506 −851 N | ANISOU 1680 CB LEU B 175 6882 7185 7913 −1699 1564 −2771 C |
| ATOM 1636 C ARG B 169 107.197 −44.600 −18.308 1.00 48.60 C | ATOM 1681 CG LEU B 175 98.934 −50.659 −16.447 1.00 64.25 C |
| ANISOU 1636 C ARG B 169 5973 6632 5859 −912 1484 −1706 C | ANISOU 1681 CG LEU B 175 7449 7894 9069 −1571 1506 −2694 C |
| ATOM 1637 O ARG B 169 107.495 −45.130 −19.377 1.00 52.89 O | ATOM 1682 CD1 LEU B 175 99.555 −51.412 −15.279 1.00 71.52 C |
| ANISOU 1637 O ARG B 169 6691 7190 6213 −1190 1738 −1981 O | ANISOU 1682 CD1 LEU B 175 8359 8557 10258 −1332 1862 −2669 C |
| ATOM 1638 N LEU B 170 107.479 −45.151 −17.133 1.00 40.85 N | ATOM 1683 CD2 LEU B 175 98.362 −49.337 −15.991 1.00 55.00 C |
| ANISOU 1638 N LEU B 170 4830 5415 5278 −637 1647 −1596 N | ANISOU 1683 CD2 LEU B 175 6043 6853 8000 −1432 1174 −2446 C |
| ATOM 1639 CA LEU B 170 108.114 −46.457 −17.049 1.00 47.41 C | ATOM 1684 C LEU B 175 99.163 −52.435 −18.795 1.00 69.82 C |
| ANISOU 1639 CA LEU B 170 5611 5952 6450 −600 2094 −1763 C | ANISOU 1684 C LEU B 175 8693 8559 9275 −2292 1820 −3293 C |
| ATOM 1640 CB LEU B 170 109.108 −46.521 −15.892 1.00 53.57 C | ATOM 1685 O LEU B 175 98.629 −53.389 −18.225 1.00 68.12 O |
| ANISOU 1640 CB LEU B 170 6211 6509 7634 −313 2184 −1449 C | ANISOU 1685 O LEU B 175 8402 8155 9326 −2267 1978 −3392 O |
| ATOM 1641 CG LEU B 170 110.097 −45.373 −15.710 1.00 66.77 C | ATOM 1686 N GLN B 176 98.708 −51.932 −19.937 1.00 64.96 N |
| ANISOU 1641 CG LEU B 170 7851 8301 9217 −194 1992 −1146 C | ANISOU 1686 N GLN B 176 8229 8177 8276 −2684 1482 −3307 N |
| ATOM 1642 CD1 LEU B 170 111.146 −45.791 −14.706 1.00 70.69 C | ATOM 1687 CA GLN B 176 97.522 −52.481 −20.571 1.00 69.72 C |
| ANISOU 1642 CD1 LEU B 170 8158 8504 10196 4 2080 −844 C | ANISOU 1687 CA GLN B 176 8898 8824 8767 −3117 1247 −3420 C |
| ATOM 1643 CD2 LEU B 170 110.744 −44.956 −17.016 1.00 73.81 C | ATOM 1688 CB GLN B 176 97.018 −51.579 −21.695 1.00 75.31 C |
| ANISOU 1643 CD2 LEU B 170 8847 9352 9847 −358 2148 −1323 C | ANISOU 1688 CB GLN B 176 9713 9816 9084 −3507 679 −3217 C |
| ATOM 1644 C LEU B 170 107.084 −47.565 −16.869 1.00 51.00 C | ATOM 1689 CG GLN B 176 96.046 −50.522 −21.210 1.00 91.17 C |
| ANISOU 1644 C LEU B 170 6061 6262 7055 −684 2185 −1972 C | ANISOU 1689 CG GLN B 176 11299 11921 11419 −3375 117 −2869 C |
| ATOM 1645 O LEU B 170 107.252 −48.677 −17.360 1.00 70.42 O | ATOM 1690 CD GLN B 176 95.520 −49.646 −22.327 1.00 103.56 C |
| ANISOU 1645 O LEU B 170 8563 8526 9668 −802 2553 −2255 O | ANISOU 1690 CD GLN B 176 12935 13709 12706 −3779 −538 −2589 C |
| ATOM 1646 N ILE B 171 106.017 −47.257 −16.153 1.00 45.67 N | ATOM 1691 OE1 GLN B 176 96.021 −49.686 −23.451 1.00105.79 O |
| ANISOU 1646 N ILE B 171 5326 5657 6370 −635 1891 −1850 N | ANISOU 1691 OE1 GLN B 176 13637 14101 12459 −4079 −549 −2590 O |
| ATOM 1647 CA ILE B 171 105.061 −48.283 −15.781 1.00 49.10 C | ATOM 1692 NE2 GLN B 176 94.499 −48.849 −22.024 1.00102.03 N |
| ANISOU 1647 CA ILE B 171 5723 5940 6992 −694 1975 −2002 C | ANISOU 1692 NE2 GLN B 176 12303 13533 12931 −3721 −1061 −2277 N |
| ATOM 1648 CB ILE B 171 104.490 −48.060 −14.356 1.00 52.70 C | ATOM 1693 C GLN B 176 97.769 −53.895 −21.075 1.00 66.42 C |
| ANISOU 1648 CB ILE B 171 6063 6330 7632 −535 1822 −1772 C | ANISOU 1693 C GLN B 176 8748 8250 8237 −3259 1689 −3652 C |
| ATOM 1649 CG1 ILE B 171 104.171 −49.392 −13.688 1.00 60.42 C | ATOM 1694 O GLN B 176 96.835 −54.673 −21.233 1.00 72.91 O |
| ANISOU 1649 CG1 ILE B 171 7006 7035 8916 −549 2038 −1852 C | ANISOU 1694 O GLN B 176 9587 9034 9084 −3456 1615 −3705 O |
| ATOM 1650 CD1 ILE B 171 105.350 −49.985 −12.959 1.00 64.40 C | ATOM 1695 N ALA B 177 99.032 −54.226 −21.319 1.00 70.71 N |
| ANISOU 1650 CD1 ILE B 171 7470 7257 9741 −408 2211 −1650 C | ANISOU 1695 N ALA B 177 9453 8688 8727 −3157 2155 −3765 N |
| ATOM 1651 CG2 ILE B 171 103.253 −47.167 −14.380 1.00 59.21 C | ATOM 1696 CA ALA B 177 99.380 −55.580 −21.725 1.00 75.96 C |
| ANISOU 1651 CG2 ILE B 171 6827 7354 8315 −599 1513 −1760 C | ANISOU 1696 CA ALA B 177 10273 9151 9438 −3264 2635 −3964 C |
| ATOM 1652 C ILE B 171 103.921 −48.394 −16.792 1.00 50.43 C | ATOM 1697 CB ALA B 177 100.761 −55.625 −22.350 1.00 66.79 C |
| ANISOU 1652 C ILE B 171 5985 6272 6902 −996 1834 −2246 C | ANISOU 1697 CB ALA B 177 9253 7919 8207 −3285 3059 −4044 C |

TABLE 9-continued

DMXAA-hSTING$^{S162A/G230I/Q266I}$ complex

| | |
|---|---|
| ATOM 1653 O ILE B 171 103.399 -49.482 -17.031 1.00 66.95 O | ATOM 1698 C ALA B 177 99.315 -56.490 -20.509 1.00 70.57 C |
| ANISOU 1653 O ILE B 171 8121 8236 9078 -1153 2010 -2485 O | ANISOU 1698 C ALA B 177 9334 8182 9297 -2911 2861 -3944 C |
| ATOM 1654 N LEU B 172 103.542 -47.270 -17.390 1.00 46.26 N | ATOM 1699 O ALA B 177 98.792 -57.604 -20.572 1.00 73.01 O |
| ANISOU 1654 N LEU B 172 5487 6008 6080 -1109 1476 -2151 N | ANISOU 1699 O ALA B 177 9686 8361 9694 -3036 3009 -4062 O |
| ATOM 1655 CA LEU B 172 102.349 -47.229 -18.242 1.00 50.22 C | ATOM 1700 N ARG B 178 99.851 -56.000 -19.397 1.00 64.80 N |
| ANISOU 1655 CA LEU B 172 6032 6659 6390 -1430 1186 -2258 C | ANISOU 1700 N ARG B 178 8361 7359 8902 -2498 2859 -3760 N |
| ATOM 1656 CB LEU B 172 101.850 -45.795 -18.449 1.00 40.37 C | ATOM 1701 CA ARG B 178 99.839 -56.752 -18.150 1.00 73.39 C |
| ANISOU 1656 CB LEU B 172 4685 5623 5029 -1447 682 -1997 C | ANISOU 1701 CA ARG B 178 9230 8187 10466 -2202 2995 -3642 C |
| ATOM 1657 CG LEU B 172 101.233 -45.088 -17.243 1.00 47.35 C | ATOM 1702 CB ARG B 178 100.587 -55.999 -17.051 1.00 78.71 C |
| ANISOU 1657 CG LEU B 172 5283 6438 6268 -1147 529 -1783 C | ANISOU 1702 CB ARGB 178 9717 8800 11391 -1823 2937 -3374 C |
| ATOM 1658 CD1 LEU B 172 100.701 -43.735 -17.671 1.00 50.62 C | ATOM 1703 CG ARG B 178 102.080 -56.233 -17.029 1.00 77.77 C |
| ANISOU 1658 CD1 LEU B 172 5573 7000 6662 -1202 42 -1556 C | ANISOU 1703 CG ARG B 178 9568 8477 11503 -1648 3197 -3259 C |
| ATOM 1659 CD2 LEU B 172 100.125 -45.923 -16.591 1.00 51.57 C | ATOM 1704 CD ARG B 178 102.759 -55.204 -16.133 1.00 75.05 C |
| ANISOU 1659 CD2 LEU B 172 5651 6817 7127 -1146 626 -1902 C | ANISOU 1704 CD ARG B 178 9097 8154 11263 -1343 3036 -2969 C |
| ATOM 1660 C LEU B 172 102.434 -47.940 -19.592 1.00 52.94 C | ATOM 1705 NE ARG B 178 102.770 -55.582 -14.718 1.00 65.21 N |
| ANISOU 1660 C LEU B 172 6660 7050 6403 -1859 1328 -2559 C | ANISOU 1705 NE ARG B 178 7704 6691 10380 -1140 3006 -2729 N |
| ATOM 1661 O LEU B 172 101.421 -48.466 -20.054 1.00 64.79 O | ATOM 1706 CZ ARG B 178 102.641 -54.718 -13.717 1.00 65.38 C |
| ANISOU 1661 O LEU B 172 8209 8570 7838 -2151 1192 -2691 O | ANISOU 1706 CZ ARG B 178 7662 6784 10397 -982 2810 -2517 C |
| ATOM 1662 N PRO B 173 103.616 -47.930 -20.252 1.00 69.07 N | ATOM 1707 NH1 ARG B 178 102.474 -53.432 -13.978 1.00 75.96 N |
| ANISOU 1662 N PRO B 173 8908 9107 8229 -1952 1615 -2678 N | ANISOU 1707 NH1 ARG B 178 9018 8408 11437 -951 2623 -2513 N |
| ATOM 1663 CA PRO B 173 103.661 -48.552 -21.580 1.00 65.54 C | ATOM 1708 NH2 ARG B 178 102.672 -55.140 -12.456 1.00 66.60 N |
| ANISOU 1663 CA PRO B 173 8804 8699 7398 -2463 1818 -3022 C | ANISOU 1708 NH2 ARG B 178 7752 6710 10842 -892 2824 -2321 N |
| ATOM 1664 CB PRO B 173 105.138 -48.449 -21.958 1.00 60.37 C | ATOM 1709 C ARG B 178 98.418 -57.030 -17.681 1.00 73.50 C |
| ANISOU 1664 CB PRO B 173 8274 7993 6672 -2436 2257 -3137 C | ANISOU 1709 C ARG B 178 9158 8238 10530 -2295 2775 -3665 C |
| ATOM 1665 CG PRO B 173 105.592 -47.229 -21.283 1.00 58.34 C | ATOM 1710 O ARG B 178 98.140 -58.063 -17.089 1.00 79.88 O |
| ANISOU 1665 CG PRO B 173 7812 7855 6498 -2075 1961 -2746 C | ANISOU 1710 O ARG B 178 9899 8851 11600 -2241 2929 -3662 O |
| ATOM 1666 CD PRO B 173 104.876 -47.216 -19.965 1.00 64.01 C | ATOM 1711 N ILE B 179 97.514 -56.102 -17.933 1.00 62.83 N |
| ANISOU 1666 CD PRO B 173 8223 8476 7621 -1692 1733 -2509 C | ANISOU 1711 N ILE B 179 7772 7120 8978 -2456 2384 -3658 N |
| ATOM 1667 C PRO B 173 103.226 -50.011 -21.602 1.00 68.20 C | ATOM 1712 CA ILE B 179 96.158 -56.274 -17.449 1.00 71.25 C |
| ANISOU 1667 C PRO B 173 9201 8801 7913 -2595 2165 -3337 C | ANISOU 1712 CA ILE B 179 8663 8203 10205 -2541 2158 -3632 C |
| ATOM 1668 O PRO B 173 102.507 -50.404 -22.513 1.00 81.18 O | ATOM 1713 CB ILE B 179 95.443 -54.925 -17.314 1.00 65.73 C |
| ANISOU 1668 O PRO B 173 11047 10538 9261 -3017 2041 -3425 O | ANISOU 1713 CB ILE B 179 7729 7703 9544 -2572 1720 -3486 C |
| ATOM 1669 N GLU B 174 103.648 -50.802 -20.624 1.00 68.37 N | ATOM 1714 CG1 ILE B 179 95.988 -54.192 -16.090 1.00 60.28 C |
| ANISOU 1669 N GLU B 174 9005 8525 8450 -2209 2503 -3321 N | ANISOU 1714 CG1 ILE B 179 6854 6973 9077 -2138 1800 -3251 C |
| ATOM 1670 CA GLU B 174 103.288 -52.215 -20.620 1.00 73.99 C | ATOM 1715 CD1 ILE B 179 95.409 -52.812 -15.887 1.00 59.09 C |
| ANISOU 1670 CA GLU B 174 9711 9000 9401 -2283 2767 -3462 C | ANISOU 1715 CD1 ILE B 179 6440 7012 9000 -2035 1437 -3008 C |
| ATOM 1671 CB GLU B 174 104.510 -53.097 -20.349 1.00 77.89 C | ATOM 1716 CG2 ILE B 179 93.937 -55.110 -17.199 1.00 56.99 C |
| ANISOU 1671 CB GLU B 174 10088 9154 10354 -2066 3216 -3429 C | ANISOU 1716 CG2 ILE B 179 6394 6637 8624 -2740 1452 -3434 C |
| ATOM 1672 CG GLU B 174 105.588 -53.013 -21.418 1.00 97.84 C | ATOM 1717 C ILE B 179 95.393 -57.269 -18.322 1.00 81.45 C |
| ANISOU 1672 CG GLU B 174 12772 11666 12736 -2273 3506 -3539 C | ANISOU 1717 C ILE B 179 10125 9508 11315 -2894 2140 -3785 C |
| ATOM 1673 CD GLU B 174 105.165 -53.638 -22.742 1.00121.13 C | ATOM 1718 O ILE B 179 94.633 -58.109 -17.822 1.00 76.25 O |
| ANISOU 1673 CD GLU B 174 16029 14678 15317 -2805 3698 -3828 C | ANISOU 1718 O ILE B 179 9376 8734 10860 -2906 2191 -3808 O |
| ATOM 1674 OE1 GLU B 174 104.366 -54.601 -22.726 1.00129.64 O | ATOM 1719 N ARG B 180 95.630 -57.197 -19.626 1.00 89.48 N |
| ANISOU 1674 OE1 GLU B 174 17134 15665 16458 -2927 3758 -3949 O | ANISOU 1719 N ARG B 180 11422 10661 11915 -3209 2083 -3882 N |
| ATOM 1675 OE2 GLU B 174 105.637 -53.164 -23.800 1.00125.30 O | ATOM 1720 CA ARG B 180 95.027 -58.141 -20.557 1.00 90.84 C |
| ANISOU 1675 OE2 GLU B 174 16790 15349 15471 -3131 3789 -3917 O | ANISOU 1720 CA ARG B 180 11836 10840 11839 -3599 2089 -4025 C |
| ATOM 1676 C GLU B 174 102.180 -52.544 -19.621 1.00 77.17 C | ATOM 1721 CB ARG B 180 95.281 -57.728 -21.999 1.00 93.73 C |
| ANISOU 1676 C GLU B 174 9931 9331 10061 -2139 2576 -3424 C | ANISOU 1721 CB ARG B 180 12543 11408 11662 -4006 1950 -4061 C |
| ATOM 1677 O GLU B 174 102.010 -53.698 -19.232 1.00 80.47 O | ATOM 1722 CG ARG B 180 94.506 -56.502 -22.397 1.00 99.35 C |
| ANISOU 1722 CG ARG B 180 13166 12380 12201 -4212 1280 -3807 C | ATOM 1767 C HIS B 185 12734 10354 15229 -2939 3793 -4232 C |
| ATOM 1723 CD ARG B 180 94.511 -56.305 -23.887 1.00116.30 C | ATOM 1768 O HIS B 185 94.040 -67.867 -15.533 1.00 95.59 O |
| ANISOU 1723 CD ARG B 180 15704 14718 13768 -4181 1066 -3777 C | ANISOU 1768 O HIS B 185 11077 9458 14787 -2956 3934 -4255 O |
| ATOM 1724 NE ARG B 180 93.754 -55.121 -24.266 1.00123.66 N | ATOM 1769 CA HIS B 185 94.997 -66.425 -17.194 1.00 99.08 C |
| ANISOU 1724 NE ARG B 180 16497 15864 14624 -4896 332 -3426 N | ANISOU 1769 CA HIS B 185 12681 10195 14771 -3067 3965 -4409 C |
| ATOM 1725 CZ ARG B 180 93.266 -54.910 -25.482 1.00130.00 C | ATOM 1770 CB HIS B 185 96.499 -66.349 -16.931 1.00110.66 C |
| ANISOU 1725 CZ ARG B 180 17556 16830 15009 -5382 -88 -3258 C | ANISOU 1770 CB HIS B 185 14033 11454 16557 -2791 4224 -4305 C |
| ATOM 1726 NH1 ARG B 180 93.452 -55.812 -26.437 1.00119.89 N | ATOM 1771 CG HIS B 185 97.322 -66.215 -18.165 1.00130.05 C |
| ANISOU 1726 NH1 ARG B 180 16728 15547 13276 -5784 212 -3459 N | ANISOU 1771 CG HIS B 185 16644 13929 18838 -2945 4489 -4497 C |
| ATOM 1727 NH2 ARG B 180 92.586 -53.802 -25.743 1.00138.81 N | ATOM 1772 ND1 HIS B 185 96.759 -66.074 -19.429 1.00137.01 N |
| ANISOU 1727 NH2 ARG B 180 18456 18085 16200 -5470 -790 -2866 N | ANISOU 1772 ND1 HIS B 185 17811 15031 19214 -3339 4466 -4733 N |
| ATOM 1728 C ARG B 180 95.532 -59.554 -20.316 1.00 77.93 C | ATOM 1773 CE1 HIS B 185 97.709 -65.978 -20.324 1.00140.50 C |
| ANISOU 1728 C ARG B 180 10281 8932 10398 -3496 2620 -4195 C | ANISOU 1773 CE1 HIS B 185 18375 15439 19570 -3455 4773 -4870 C |
| ATOM 1729 O ARG B 180 94.776 -60.517 -20.407 1.00 73.54 O | ATOM 1774 NE2 HIS B 185 98.884 -66.053 -19.708 1.00138.79 N |
| ANISOU 1729 O ARG B 180 9780 8296 9866 -3672 2647 -4286 O | ANISOU 1774 NE2 HIS B 185 17918 14972 19845 -3127 4992 -4734 N |
| ATOM 1730 N THR B 181 96.817 -59.669 -20.011 1.00 76.75 N | ATOM 1775 CD2 HIS B 185 98.657 -66.202 -18.365 1.00132.42 C |
| ANISOU 1730 N THR B 181 10101 8620 10439 -3221 3005 -4200 N | ANISOU 1775 CD2 HIS B 185 16870 14050 19395 -2814 4788 -4485 C |
| ATOM 1731 CA THR B 181 97.389 -60.967 -19.704 1.00 84.43 C | ATOM 1776 N TYR B 186 93.765 -65.658 -15.242 1.00 92.09 N |
| ANISOU 1731 CA THR B 181 11052 9284 11742 -3102 3455 -4281 C | ANISOU 1776 N TYR B 186 13438 8920 12630 -3015 1796 -991 N |
| ATOM 1732 CB THR B 181 98.907 -60.897 -19.502 1.00 85.82 C | ATOM 1777 CA TYR B 186 93.012 -65.832 -14.008 1.00 88.87 C |
| ANISOU 1732 CB THR B 181 11138 9278 12194 -2839 3780 -4210 C | ANISOU 1777 CA TYR B 186 12741 8837 12189 -3077 1542 -708 C |
| ATOM 1733 OG1 THR B 181 99.547 -60.747 -20.775 1.00 89.45 O | ATOM 1778 CB TYR B 186 93.629 -65.012 -12.880 1.00 90.65 C |
| ANISOU 1733 OG1 THR B 181 11837 9810 12342 -3115 3992 -4384 O | ANISOU 1778 CB TYR B 186 12572 9210 12659 -2626 1504 -557 C |
| ATOM 1734 CG2 THR B 181 99.414 -62.170 -18.838 1.00 69.58 C | ATOM 1779 CG TYR B 186 94.946 -65.571 -12.407 1.00 99.96 C |
| ANISOU 1734 CG2 THR B 181 8933 6848 10657 -2657 4116 -4188 C | ANISOU 1779 CG TYR B 186 13836 9864 14281 -2356 1687 -556 C |
| ATOM 1735 C THR B 181 96.728 -61.548 -18.464 1.00 78.25 C | ATOM 1780 CD2 TYR B 186 94.995 -66.482 -11.360 1.00 99.50 C |
| ANISOU 1735 C THR B 181 10046 8352 11333 -2892 3393 -4166 C | ANISOU 1780 CD2 TYR B 186 13732 9656 14416 -2417 1598 -333 C |
| ATOM 1736 O THR B 181 96.349 -62.718 -18.434 1.00 91.21 O | ATOM 1781 CE2 TYR B 186 96.192 -67.005 -10.930 1.00107.20 C |
| ANISOU 1736 O THR B 181 11729 9828 13096 -2988 3560 -4268 O | ANISOU 1781 CE2 TYR B 186 14749 10161 15820 -2157 1746 -278 C |

TABLE 9-continued

DMXAA-hSTING$^{S162A/G230I/Q266I}$ complex

```
ATOM   1737 N   TYR B 182  96.574 -60.715 -17.444 1.00 65.42           N
ANISOU 1737 N   TYR B 182  8204  6785  9868 -2640  3165 -3957          N
ATOM   1738 CA  TYR B 182  95.981 -61.170 -16.195 1.00 65.09           C
ANISOU 1738 CA  TYR B 182  7978  6614 10140 -2485  3132 -3828          C
ATOM   1739 CB  TYR B 182  96.085 -60.090 -15.123 1.00 62.91           C
ANISOU 1739 CB  TYR B 182  7510  6397  9994 -2237  2962 -3601          C
ATOM   1740 CG  TYR B 182  95.529 -60.536 -13.799 1.00 70.58           C
ANISOU 1740 CG  TYR B 182  8348  7241 11227 -2143  2973 -3461          C
ATOM   1741 CD1 TYR B 182  96.340 -61.170 -12.865 1.00 74.18           C
ANISOU 1741 CD1 TYR B 182  8794  7438 11954 -1969  3144 -3287          C
ATOM   1742 CE1 TYR B 182  95.834 -61.582 -11.659 1.00 70.79           C
ANISOU 1742 CE1 TYR B 182  8317  6901 11681 -1955  3134 -3147          C
ATOM   1743 CZ  TYR B 182  94.494 -61.366 -11.384 1.00 73.73           C
ANISOU 1743 CZ  TYR B 182  8611  7431 11971 -2090  3020 -3207          C
ATOM   1744 OH  TYR B 182  93.947 -61.771 -10.196 1.00 75.59           O
ANISOU 1744 OH  TYR B 182  8831  7581 12307 -2121  3050 -3086          O
ATOM   1745 CE2 TYR B 182  93.676 -60.746 -12.296 1.00 67.69           C
ANISOU 1745 CE2 TYR B 182  7780  6896 11043 -2223  2857 -3371          C
ATOM   1746 CD2 TYR B 182  94.190 -60.337 -13.490 1.00 64.00           C
ANISOU 1746 CD2 TYR B 182  7398  6531 10389 -2265  2798 -3483          C
ATOM   1747 C   TYR B 182  94.521 -61.577 -16.391 1.00 70.13           C
ANISOU 1747 C   TYR B 182  8623  7343 10678 -2744  2943 -3929          C
ATOM   1748 O   TYR B 182  94.052 -62.560 -15.816 1.00 74.03           O
ANISOU 1748 O   TYR B 182  9080  7682 11367 -2746  3046 -3931          O
ATOM   1749 N   ASN B 183  93.808 -60.813 -17.211 1.00 66.39           N
ANISOU 1749 N   ASN B 183  8187  7114  9923 -2987  2620 -3976          N
ATOM   1750 CA  ASN B 183  92.408 -61.092 -17.485 1.00 66.46           C
ANISOU 1750 CA  ASN B 183  8157  7210  9885 -3269  2347 -4006          C
ATOM   1751 CB  ASN B 183  91.748 -59.914 -18.191 1.00 75.57           C
ANISOU 1751 CB  ASN B 183  9235  8623 10856 -3488  1859 -3907          C
ATOM   1752 CG  ASN B 183  91.284 -58.850 -17.227 1.00 70.44           C
ANISOU 1752 CG  ASN B 183  8196  8035 10532 -3258  1658 -3709          C
ATOM   1753 OD1 ASN B 183  91.136 -59.101 -16.030 1.00 69.33           O
ANISOU 1753 OD1 ASN B 183  7878  7765 10698 -3018  1864 -3665          O
ATOM   1754 ND2 ASN B 183  91.045 -57.648 -17.744 1.00 73.30           N
ANISOU 1754 ND2 ASN B 183  8430  8589 10833 -3354  1257 -3567          N
ATOM   1755 C   ASN B 183  92.226 -62.346 -18.318 1.00 77.56           C
ANISOU 1755 C   ASN B 183  9833  8526 11109 -3559  2504 -4199          C
ATOM   1756 O   ASN B 183  91.109 -62.822 -18.523 1.00 75.62           O
ANISOU 1756 O   ASN B 183  9582  8309 10840 -3810  2306 -4220          O
ATOM   1757 N   GLN B 184  93.343 -62.868 -18.802 1.00 78.87           N
ANISOU 1757 N   GLN B 184 10212  8569 11186 -3535  2878 -4333          N
ATOM   1758 CA  GLN B 184  93.341 -64.069 -19.605 1.00 85.17           C
ANISOU 1758 CA  GLN B 184 11274  9246 11841 -3808  3136 -4548          C
ATOM   1759 CB  GLN B 184  94.504 -64.036 -20.592 1.00 97.79           C
ANISOU 1759 CB  GLN B 184 13110 10828 13216 -3912  3457 -4694          C
ATOM   1760 CG  GLN B 184  94.217 -64.700 -21.911 1.00109.17           C
ANISOU 1760 CG  GLN B 184 14922 12307 14250 -4407  3569 -4924          C
ATOM   1761 CD  GLN B 184  93.268 -63.878 -22.753 1.00112.28           C
ANISOU 1761 CD  GLN B 184 15483 13020 14159 -4810  3025 -4846          C
ATOM   1762 OE1 GLN B 184  92.870 -62.776 -22.364 1.00114.09           O
ANISOU 1762 OE1 GLN B 184 15057 13324 14423 -4690  2577 -4626          O
ATOM   1763 NE2 GLN B 184  92.900 -64.404 -23.915 1.00 99.14           N
ANISOU 1763 NE2 GLN B 184 14184 11416 12068 -5319  3038 -4994          N
ATOM   1764 C   GLN B 184  93.504 -65.273 -18.704 1.00 82.18           C
ANISOU 1764 C   GLN B 184 10785  8565 11874 -3596  3451 -4557          C
ATOM   1765 O   GLN B 184  92.702 -66.206 -18.724 1.00 85.55           O
ANISOU 1765 O   GLN B 184 11272  8913 12321 -3774  3452 -4642          O
ATOM   1766 N   HIS B 185  94.555 -65.236 -17.900 1.00 78.95           N
ANISOU 1766 N   HIS B 185 10212  7980 11805 -3235  3671 -4433          N
ATOM   1767 C   HIS B 185  94.223 -66.709 -15.909 1.00100.85           C
ATOM   1782 CZ  TYR B 186  97.365 -66.623 -11.551 1.00111.75           C
ANISOU 1782 CZ  TYR B 186 15405 10422 16632 -1831  2005  -475          C
ATOM   1783 OH  TYR B 186  98.561 -67.147 -11.119 1.00118.66           O
ANISOU 1783 OH  TYR B 186 16276 10854 17956 -1555  2152  -395          O
ATOM   1784 CE1 TYR B 186  97.345 -65.724 -12.599 1.00106.05           C
ANISOU 1784 CE1 TYR B 186 14751  9844 15700 -1790  2110  -729          C
ATOM   1785 CD1 TYR B 186  96.139 -65.206 -13.023 1.00104.61           C
ANISOU 1785 CD1 TYR B 186 14536 10118 15094 -2053  1943  -754          C
ATOM   1786 C   TYR B 186  91.546 -65.481 -14.205 1.00 85.90           C
ANISOU 1786 C   TYR B 186 12209  9058 11371 -3404  1290  -604          C
ATOM   1787 O   TYR B 186  90.873 -65.002 -13.295 1.00 82.87           O
ANISOU 1787 O   TYR B 186 11448  9134 10905 -3350  1081  -398          O
ATOM   1788 N   ASN B 187  91.063 -65.736 -15.413 1.00 88.63           N
ANISOU 1788 N   ASN B 187 12838  9410 11428 -3763  1322  -753          N
ATOM   1789 CA  ASN B 187  89.694 -65.419 -15.784 1.00 94.92           C
ANISOU 1789 CA  ASN B 187 13489 10789 11788 -4101  1083  -642          C
ATOM   1790 CB  ASN B 187  89.539 -65.529 -17.296 1.00103.73           C
ANISOU 1790 CB  ASN B 187 14945 11853 12616 -4443  1175  -841          C
ATOM   1791 CG  ASN B 187  88.137 -65.231 -17.754 1.00107.80           C
ANISOU 1791 CG  ASN B 187 15296 12999 12666 -4821   912  -688          C
ATOM   1792 OD1 ASN B 187  87.414 -64.459 -17.124 1.00108.18           O
ANISOU 1792 OD1 ASN B 187 14898 13560 12646 -4661   690  -457          O
ATOM   1793 ND2 ASN B 187  87.736 -65.849 -18.859 1.00113.17           N
ANISOU 1793 ND2 ASN B 187 16323 13657 13019 -5343   946  -817          N
ATOM   1794 C   ASN B 187  88.662 -66.307 -15.088 1.00 93.03           C
ANISOU 1794 C   ASN B 187 13200 10767 11379 -4490   881  -463          C
ATOM   1795 O   ASN B 187  87.596 -65.841 -14.682 1.00 92.57           O
ANISOU 1795 O   ASN B 187 12790 11296 11085 -4582   640  -270          O
ATOM   1796 N   ASN B 188  88.977 -67.591 -14.969 1.00 80.71           N
ANISOU 1796 N   ASN B 188 11994  8723  9951 -4721   993  -528          N
ATOM   1797 CA  ASN B 188  88.124 -68.517 -14.243 1.00 93.86           C
ANISOU 1797 CA  ASN B 188 13655 10520 11487 -5099   817  -352          C
ATOM   1798 CB  ASN B 188  88.709 -69.924 -14.299 1.00102.50           C
ANISOU 1798 CB  ASN B 188 15226 10914 12803 -5303  1009  -460          C
ATOM   1799 CG  ASN B 188  88.572 -70.548 -15.656 1.00105.14           C
ANISOU 1799 CG  ASN B 188 16043 10993 12913 -5740  1181  -729          C
ATOM   1800 OD1 ASN B 188  87.574 -70.341 -16.341 1.00116.01           O
ANISOU 1800 OD1 ASN B 188 17406 12836 13835 -6133  1043  -736          O
ATOM   1801 ND2 ASN B 188  89.580 -71.311 -16.066 1.00 95.53           N
ANISOU 1801 ND2 ASN B 188 15242  9042 12011 -5688  1495  -952          N
ATOM   1802 C   ASN B 188  87.975 -68.102 -12.793 1.00 92.41           C
ANISOU 1802 C   ASN B 188 13016 10654 11441 -4832   639   -96          C
ATOM   1803 O   ASN B 188  86.952 -68.334 -12.154 1.00 99.12           O
ANISOU 1803 O   ASN B 188 13664 11930 12066 -5111   417    90          O
ATOM   1804 N   LEU B 189  89.025 -67.482 -12.285 1.00 91.36           N
ANISOU 1804 N   LEU B 189 12723 10330 11660 -4319   752  -100          N
ATOM   1805 CA  LEU B 189  89.099 -67.114 -10.889 1.00 91.12           C
ANISOU 1805 CA  LEU B 189 12298 10538 11785 -4074   631   112          C
ATOM   1806 CB  LEU B 189  90.559 -66.931 -10.505 1.00 86.21           C
ANISOU 1806 CB  LEU B 189 11687  9468 11601 -3612   821    76          C
ATOM   1807 CG  LEU B 189  90.891 -66.449  -9.106 1.00 82.39           C
ANISOU 1807 CG  LEU B 189 10809  9204 11293 -3339   735   274          C
ATOM   1808 CD1 LEU B 189  90.139 -67.276  -8.079 1.00 70.59           C
ANISOU 1808 CD1 LEU B 189  9220  7907  9694 -3682   526   516          C
ATOM   1809 CD2 LEU B 189  92.385 -66.577  -8.912 1.00 77.56           C
ANISOU 1809 CD2 LEU B 189 10292  8070 11108 -2975   929   251          C
ATOM   1810 C   LEU B 189  88.345 -65.821 -10.658 1.00 88.18           C
ANISOU 1810 C   LEU B 189 11466 10834 11204 -3928   487   179          C
ATOM   1811 O   LEU B 189  87.726 -65.612  -9.615 1.00 91.88           O
ANISOU 1811 O   LEU B 189 11584 11729 11599 -3960   326   352          O
ATOM   1812 N   LEU B 190  88.407 -64.944 -11.647 1.00 81.52           N
ANISOU 1812 N   LEU B 190 10626 10072 10277 -3770   561    40          N
ATOM   1813 CA  LEU B 190  87.856 -63.616 -11.484 1.00 85.25           C
ANISOU 1813 CA  LEU B 190 10671 11079 10640 -3540   467   101          C
ATOM   1814 CB  LEU B 190  88.553 -62.632 -12.411 1.00 82.74           C
ANISOU 1814 CB  LEU B 190 10418 10612 10407 -3214   621   -54          C
ATOM   1815 CG  LEU B 190  88.942 -61.384 -11.635 1.00 91.81           C
ANISOU 1815 CG  LEU B 190 11193 11945 11746 -2748   662   -23          C
ATOM   1816 CD1 LEU B 190  90.444 -61.357 -11.449 1.00 95.82           C
ANISOU 1816 CD1 LEU B 190 11859 11957 12590 -2429   878  -142          C
ATOM   1817 CD2 LEU B 190  88.436 -60.139 -12.341 1.00 89.58           C
ANISOU 1817 CD2 LEU B 190 10716 11992 11330 -2587   626   -23          C
ATOM   1818 C   LEU B 190  86.355 -63.568 -11.715 1.00 86.28           C
ANISOU 1818 C   LEU B 190 10607 11784 10392 -3887   246   223          C
ATOM   1819 O   LEU B 190  85.632 -62.887 -10.986 1.00 80.46           O
ANISOU 1819 O   LEU B 190  9435 11547  9590 -3790   124   352          O
ATOM   1820 N   ARG B 191  85.895 -64.301 -12.724 1.00100.06           N
ANISOU 1820 N   ARG B 191 12666 13469 11884 -4308   211   174          N
ATOM   1857 CD  GLN B 196 15693 16129 15118 -1566   876   -49          C
ATOM   1858 OE1 GLN B 196  90.038 -50.610 -21.699 1.00126.09           O
ANISOU 1858 OE1 GLN B 196 15722 16699 15485 -1349   733   211          O
ATOM   1859 NE2 GLN B 196  90.743 -52.458 -22.766 1.00124.70           N
ANISOU 1859 NE2 GLN B 196 16171 16240 14967 -2026   868  -140          N
ATOM   1860 C   GLN B 196  93.302 -50.189 -17.674 1.00 85.07           C
ANISOU 1860 C   GLN B 196 10386 10587 11349  -224  1519  -497          C
ATOM   1861 O   GLN B 196  94.516 -50.305 -17.820 1.00 88.19           O
ANISOU 1861 O   GLN B 196 11019 10666 11825  -178  1712  -700          O
ATOM   1862 N   ARG B 197  92.757 -49.160 -17.038 1.00 79.93           N
ANISOU 1862 N   ARG B 197  9413 10127 10828    52  1488  -369          N
ATOM   1863 CA  ARG B 197  93.562 -48.006 -16.644 1.00 78.97           C
ANISOU 1863 CA  ARG B 197  9257  9833 10913   392  1679  -461          C
ATOM   1864 CB  ARG B 197  92.709 -46.737 -16.661 1.00 72.37           C
ANISOU 1864 CB  ARG B 197  8155  9187 10156   630  1608  -263          C
ATOM   1865 CG  ARG B 197  92.229 -46.344 -18.046 1.00 73.78           C
ANISOU 1865 CG  ARG B 197  8435  9432 10165   523  1440   -57          C
```

TABLE 9-continued

DMXAA-hSTING$^{S162A/G230I/Q266I}$ complex

| | |
|---|---|
| ATOM 1821 CA ARG B 191 84.513 −64.203 −13.179 1.00 106.19 C | ATOM 1866 CD ARG B 197 91.120 −45.318 −17.970 1.00 83.46 C |
| ANISOU 1821 CA ARG B 191 13265 14816 12266 −4662 O 297 C | ANISOU 1866 CD ARG B 197 9317 10895 11499 752 1321 214 C |
| ATOM 1822 CB ARG B 191 83.556 −64.881 −12.192 1.00 101.06 C | ATOM 1867 NE ARG B 197 91.340 −44.201 −18.885 1.00 106.05 N |
| ANISOU 1822 CB ARG B 191 12418 14522 11460 −4988 −184 468 C | ANISOU 1867 NE ARG B 197 12285 13622 14387 890 1315 347 N |
| ATOM 1823 CG ARG B 191 83.827 −66.366 −11.998 1.00 101.30 C | ATOM 1868 CZ ARG B 197 90.589 −43.106 −18.920 1.00 110.68 C |
| ANISOU 1823 CG ARG B 191 12873 14111 11506 −5367 −144 430 C | ANISOU 1868 CZ ARG B 197 12610 14306 15136 1159 1250 595 C |
| ATOM 1824 CD ARG B 191 82.698 −67.069 −11.265 1.00 107.76 C | ATOM 1869 NH1 ARG B 197 90.863 −42.135 −19.783 1.00 100.40 N |
| ANISOU 1824 CD ARG B 191 13536 15343 12065 −5813 −356 609 C | ANISOU 1869 NH1 ARG B 197 11442 12845 13859 1262 1237 737 N |
| ATOM 1825 NE ARG B 191 82.033 −68.059 −12.114 1.00 122.15 N | ATOM 1870 NH2 ARG B 197 89.563 −42.984 −18.093 1.00 116.41 N |
| ANISOU 1825 NE ARG B 191 15706 17159 13545 −6421 −416 579 N | ANISOU 1870 NH2 ARG B 197 12934 15283 16011 1324 1207 706 N |
| ATOM 1826 CZ ARG B 191 80.789 −67.948 −12.572 1.00 115.66 C | ATOM 1871 C ARG B 197 94.262 −48.149 −15.290 1.00 74.83 C |
| ANISOU 1826 CZ ARG B 191 14695 16940 12309 −6793 −607 681 C | ANISOU 1871 C ARG B 197 8629 9219 10583 538 1853 −626 C |
| ATOM 1827 NH1 ARG B 191 80.276 −68.900 −13.340 1.00 116.23 N | ATOM 1872 O ARG B 197 93.941 −49.028 −14.497 1.00 80.15 O |
| ANISOU 1827 NH1 ARG B 191 15127 16980 12056 −7393 −643 637 N | ANISOU 1872 O ARG B 197 9185 10011 11259 420 1801 −621 O |
| ATOM 1828 NH2 ARG B 191 80.056 −66.890 −12.257 1.00 110.51 N | ATOM 1873 N LEU B 198 95.229 −47.272 −15.046 1.00 65.47 N |
| ANISOU 1828 NH2 ARG B 191 13488 16927 11575 −6575 −751 827 N | ANISOU 1873 N LEU B 198 8102 8167 8604 −545 849 −1462 N |
| ATOM 1829 C ARG B 191 84.166 −62.728 −13.366 1.00 105.34 C | ATOM 1874 CA LEU B 198 95.825 −47.128 −13.727 1.00 60.80 C |
| ANISOU 1829 C ARG B 191 12743 15134 12147 −4303 −56 371 C | ANISOU 1874 CA LEU B 198 7354 7554 8192 −412 868 −1313 C |
| ATOM 1830 O ARG B 191 83.151 −62.240 −12.875 1.00 107.31 O | ATOM 1875 CB LEU B 198 97.296 −46.739 −13.831 1.00 57.48 C |
| ANISOU 1830 O ARG B 191 12561 15943 12271 −4307 −220 538 O | ANISOU 1875 CB LEU B 198 6846 7234 7759 −343 1010 −1307 C |
| ATOM 1831 N GLY B 192 85.053 −62.018 −14.053 1.00 94.81 N | ATOM 1876 CG LEU B 198 98.280 −47.200 −12.746 1.00 53.82 C |
| ANISOU 1831 N GLY B 192 11541 13508 10973 −3981 101 242 N | ANISOU 1876 CG LEU B 198 6216 6712 7522 −184 1066 −1220 C |
| ATOM 1832 CA GLY B 192 84.883 −60.604 −14.310 1.00 91.69 C | ATOM 1877 CD1 LEU B 198 99.415 −46.191 −12.608 1.00 46.13 C |
| ANISOU 1832 CA GLY B 192 10819 13403 10615 −3615 76 309 C | ANISOU 1877 CD1 LEU B 198 5116 5908 6504 −181 1105 −1129 C |
| ATOM 1833 C GLY B 192 86.065 −60.117 −15.112 1.00 98.42 C | ATOM 1878 CD2 LEU B 198 97.620 −47.456 −11.394 1.00 45.39 C |
| ANISOU 1833 C GLY B 192 11952 13810 11633 −3352 276 133 C | ANISOU 1878 CD2 LEU B 198 5119 5539 6590 −148 931 −1072 C |
| ATOM 1834 O GLY B 192 86.650 −60.875 −15.885 1.00 112.65 O | ATOM 1879 C LEU B 198 95.087 −46.002 −13.026 1.00 56.37 C |
| ANISOU 1834 O GLY B 192 14192 15219 13389 −3578 390 −27 O | ANISOU 1879 C LEU B 198 6753 7066 7598 −454 714 −1144 C |
| ATOM 1835 N ALA B 193 86.422 −58.853 −14.926 1.00 86.23 N | ATOM 1880 O LEU B 198 94.959 −44.909 −13.573 1.00 57.67 O |
| ANISOU 1835 N ALA B 193 10161 12318 10282 −2888 339 145 N | ANISOU 1880 O LEU B 198 6961 7349 7603 −529 651 −1104 O |
| ATOM 1836 CA ALA B 193 87.583 −58.291 −15.597 1.00 77.82 C | ATOM 1881 N TYR B 199 94.607 −46.263 −11.818 1.00 48.98 N |
| ANISOU 1836 CA ALA B 193 9332 10857 9378 −2623 531 −17 C | ANISOU 1881 N TYR B 199 5751 6046 6813 −406 664 −1044 N |
| ATOM 1837 CB ALA B 193 87.293 −58.039 −17.066 1.00 68.40 C | ATOM 1882 CA TYR B 199 93.933 −45.228 −11.054 1.00 45.02 C |
| ANISOU 1837 CB ALA B 193 8314 9751 7926 −2834 471 1 C | ANISOU 1882 CA TYR B 199 5213 5597 6297 −430 567 −912 C |
| ATOM 1838 C ALA B 193 88.019 −57.005 −14.925 1.00 83.28 C | ATOM 1883 CB TYR B 199 92.578 −45.712 −10.553 1.00 50.83 C |
| ANISOU 1838 C ALA B 193 9723 11585 10333 −2106 619 −7 C | ANISOU 1883 CB TYR B 199 5930 6245 7139 −467 505 −897 C |
| ATOM 1839 O ALA B 193 87.217 −56.098 −14.700 1.00 84.05 O | ATOM 1884 CG TYR B 199 91.584 −45.889 −11.674 1.00 56.59 C |
| ANISOU 1839 O ALA B 193 9448 12074 10411 −1944 513 146 O | ANISOU 1884 CG TYR B 199 6702 6978 7820 −566 416 −990 C |
| ATOM 1840 N VAL B 194 89.303 −56.940 −14.604 1.00 81.14 N | ATOM 1885 CD1 TYR B 199 91.568 −47.053 −12.436 1.00 59.62 C |
| ANISOU 1840 N VAL B 194 9612 10836 10318 −1854 828 −175 N | ANISOU 1885 CD1 TYR B 199 7162 7279 8212 −615 442 −1131 C |
| ATOM 1841 CA VAL B 194 89.907 −55.712 −14.134 1.00 70.74 C | ATOM 1886 CE1 TYR B 199 90.666 −47.214 −13.469 1.00 56.61 C |
| ANISOU 1841 CA VAL B 194 8097 9552 9228 −1408 952 −210 C | ANISOU 1886 CE1 TYR B 199 6839 6913 7757 −742 329 −1218 C |
| ATOM 1842 CB VAL B 194 91.371 −55.939 −13.788 1.00 65.98 C | ATOM 1887 CZ TYR B 199 89.772 −46.195 −13.755 1.00 66.18 C |
| ANISOU 1842 CB VAL B 194 7703 8496 8871 −1228 1171 −388 C | ANISOU 1887 CZ TYR B 199 8002 8228 8916 −797 169 −1138 C |
| ATOM 1843 CG1 VAL B 194 91.958 −54.709 −13.131 1.00 59.23 C | ATOM 1888 OH TYR B 199 88.870 −46.349 −14.782 1.00 63.33 O |
| ANISOU 1843 CG1 VAL B 194 6627 7657 8222 −822 1298 −425 C | ANISOU 1888 OH TYR B 199 7685 7894 8482 −935 8 −1199 O |
| ATOM 1844 CG2 VAL B 194 91.499 −57.138 −12.874 1.00 76.21 C | ATOM 1889 CE2 TYR B 199 89.777 −45.024 −13.015 1.00 61.23 C |
| ANISOU 1844 CG2 VAL B 194 9034 9684 10240 −1398 1156 −372 C | ANISOU 1889 CE2 TYR B 199 7287 7661 8316 −715 158 −996 C |
| ATOM 1845 C VAL B 194 89.817 −54.670 −15.239 1.00 64.76 C | ATOM 1890 CD2 TYR B 199 90.682 −44.878 −11.986 1.00 51.36 C |
| ANISOU 1845 C VAL B 194 7361 8853 8394 −1286 943 −181 C | ANISOU 1890 CD2 TYR B 199 6011 6393 7111 −613 290 −938 C |
| ATOM 1846 O VAL B 194 89.892 −55.000 −16.421 1.00 65.28 O | ATOM 1891 C TYR B 199 94.814 −44.727 −9.924 1.00 44.46 C |
| ANISOU 1846 O VAL B 194 7715 8806 8282 −1518 925 −217 O | ANISOU 1891 C TYR B 199 5077 5559 6258 −366 594 −791 C |
| ATOM 1847 N SER B 195 89.655 −53.413 −14.850 1.00 69.37 N | ATOM 1892 O TYR B 199 95.241 −45.483 −9.055 1.00 37.82 O |
| ANISOU 1847 N SER B 195 7646 9605 9107 −944 964 −114 N | ANISOU 1892 O TYR B 199 4196 4644 5531 −303 626 −744 O |
| ATOM 1848 CA SER B 195 89.638 −52.316 −15.805 1.00 66.53 C | ATOM 1893 N ILE B 200 95.097 −43.434 −9.970 1.00 42.16 N |
| ANISOU 1848 CA SER B 195 7293 9263 8724 −782 958 −52 C | ANISOU 1893 N ILE B 200 4793 5369 5856 −398 561 −733 N |
| ATOM 1849 CB SER B 195 89.080 −51.065 −15.141 1.00 69.69 C | ATOM 1894 CA ILE B 200 96.022 −42.822 −9.040 1.00 32.22 C |
| ANISOU 1849 CB SER B 195 7284 9909 9286 −430 958 64 C | ANISOU 1894 CA ILE B 200 3491 4159 4593 −380 568 −633 C |
| ATOM 1850 OG SER B 195 88.063 −51.425 −14.230 1.00 75.90 O | ATOM 1895 CB ILE B 200 97.070 −42.029 −9.779 1.00 39.12 C |
| ANISOU 1850 OG SER B 195 7741 11051 10046 −512 848 166 O | ANISOU 1895 CB ILE B 200 4357 5147 5359 −423 598 −636 C |
| ATOM 1851 C SER B 195 91.040 −52.052 −16.344 1.00 59.01 C | ATOM 1896 CG1 ILE B 200 97.812 −42.953 −10.734 1.00 45.54 C |
| ANISOU 1851 C SER B 195 6670 7878 7872 −652 1165 −250 C | ANISOU 1896 CG1 ILE B 200 5131 5978 6196 −389 709 −744 C |
| ATOM 1852 O SER B 195 92.037 −52.414 −15.722 1.00 61.64 O | ATOM 1897 CD1 ILE B 200 98.732 −42.234 −11.650 1.00 55.86 C |
| ANISOU 1852 O SER B 195 7115 7935 8370 −562 1334 −422 O | ANISOU 1897 CD1 ILE B 200 6434 7413 7378 −459 781 −767 C |
| ATOM 1853 N GLN B 196 91.102 −51.402 −17.498 1.00 74.21 N | ATOM 1898 CG2 ILE B 200 98.031 −41.382 −8.792 1.00 32.64 C |
| ANISOU 1853 N GLN B 196 8728 9775 9693 −654 1140 −203 N | ANISOU 1898 CG2 ILE B 200 3480 4381 4540 −437 577 −532 C |
| ATOM 1854 CA GLN B 196 92.349 −51.245 −18.237 1.00 86.68 C | ATOM 1899 C ILE B 200 95.305 −41.908 −8.066 1.00 36.74 C |
| ANISOU 1854 CA GLN B 196 10652 10986 11298 −623 1322 −393 C | ANISOU 1899 C ILE B 200 4098 4719 5144 −408 512 −554 C |
| ATOM 1855 CB GLN B 196 92.051 −50.937 −19.706 1.00 98.27 C | ATOM 1900 O ILE B 200 94.636 −40.953 −8.470 1.00 39.12 O |
| ANISOU 1855 CB GLN B 196 12294 12531 12514 −836 1212 −292 C | ANISOU 1900 O ILE B 200 4446 5031 5387 −442 467 −555 O |
| ATOM 1856 CG GLN B 196 91.459 −52.102 −20.478 1.00 111.75 C | ATOM 1901 N LEU B 201 95.451 −42.209 −6.781 1.00 35.53 N |
| ANISOU 1856 CG GLN B 196 14192 14350 13916 −1328 1082 −274 C | ANISOU 1901 N LEU B 201 3933 4530 5037 −392 516 −483 N |
| ATOM 1857 CD GLN B 196 90.683 −51.659 −21.704 1.00 123.54 C | ATOM 1902 CA LEU B 201 94.785 −41.441 −5.743 1.00 34.83 C |
| ANISOU 1902 CA LEU B 201 3900 4422 4911 −426 508 −437 C | ANISOU 1947 CA GLY B 207 5825 5564 4776 −1226 259 −48 C |
| ATOM 1903 CB LEU B 201 94.546 −42.305 −4.515 1.00 43.80 C | ATOM 1948 C GLY B 207 97.568 −39.547 3.152 1.00 39.71 C |
| ANISOU 1903 CB LEU B 201 5049 5501 6093 −426 534 −379 C | ANISOU 1948 C GLY B 207 5262 5202 4625 −1078 227 49 C |
| ATOM 1904 CG LEU B 201 93.553 −43.426 −4.773 1.00 41.07 C | ATOM 1949 O GLY B 207 96.541 −40.096 2.760 1.00 55.79 O |
| ANISOU 1904 CG LEU B 201 4674 5070 5862 −409 571 −419 C | ANISOU 1949 O GLY B 207 7254 7168 6775 −980 368 −2 O |

TABLE 9-continued

DMXAA-hSTING$^{S162A/G230I/Q266I}$ complex

| ATOM | 1905 | CD1 | LEU | B | 201 | 93.647 | −44.434 | −3.664 | 1.00 | 38.22 | C |
|---|---|---|---|---|---|---|---|---|---|---|---|
| ANISOU | 1905 | CD1 | LEU | B | 201 | 4344 | 4640 | 5539 | −422 | 589 | −331 | C |
| ATOM | 1906 | CD2 | LEU | B | 201 | 92.156 | −42.855 | −4.854 | 1.00 | 44.79 | C |
| ANISOU | 1906 | CD2 | LEU | B | 201 | 5132 | 5530 | 6357 | −433 | 602 | −467 | C |
| ATOM | 1907 | C | LEU | B | 201 | 95.595 | −40.211 | −5.365 | 1.00 | 40.53 | C |
| ANISOU | 1907 | C | LEU | B | 201 | 4669 | 5205 | 5525 | −479 | 477 | −392 | C |
| ATOM | 1908 | O | LEU | B | 201 | 96.786 | −40.310 | −5.083 | 1.00 | 35.98 | O |
| ANISOU | 1908 | O | LEU | B | 201 | 4058 | 4687 | 4927 | −499 | 448 | −339 | O |
| ATOM | 1909 | N | LEU | B | 202 | 94.932 | −39.058 | −5.354 | 1.00 | 29.97 | N |
| ANISOU | 1909 | N | LEU | B | 202 | 3403 | 3842 | 4143 | −503 | 475 | −411 | N |
| ATOM | 1910 | CA | LEU | B | 202 | 95.571 | −37.795 | −5.019 | 1.00 | 27.75 | C |
| ANISOU | 1910 | CA | LEU | B | 202 | 3204 | 3577 | 3761 | −574 | 447 | −384 | C |
| ATOM | 1911 | CB | LEU | B | 202 | 95.606 | −36.902 | −6.244 | 1.00 | 45.84 | C |
| ANISOU | 1911 | CB | LEU | B | 202 | 5522 | 5873 | 6022 | −592 | 410 | −394 | C |
| ATOM | 1912 | CG | LEU | B | 202 | 96.581 | −37.346 | −7.319 | 1.00 | 61.91 | C |
| ANISOU | 1912 | CG | LEU | B | 202 | 7487 | 8006 | 8029 | −618 | 405 | −389 | C |
| ATOM | 1913 | CD1 | LEU | B | 202 | 96.067 | −36.976 | −8.692 | 1.00 | 72.29 | C |
| ANISOU | 1913 | CD1 | LEU | B | 202 | 8843 | 9317 | 9308 | −623 | 376 | −408 | C |
| ATOM | 1914 | CD2 | LEU | B | 202 | 97.886 | −36.663 | −7.055 | 1.00 | 66.93 | C |
| ANISOU | 1914 | CD2 | LEU | B | 202 | 8127 | 8713 | 8592 | −720 | 388 | −338 | C |
| ATOM | 1915 | C | LEU | B | 202 | 94.854 | −37.062 | −3.897 | 1.00 | 37.45 | C |
| ANISOU | 1915 | C | LEU | B | 202 | 4541 | 4729 | 4959 | −593 | 491 | −403 | C |
| ATOM | 1916 | O | LEU | B | 202 | 94.128 | −36.092 | −4.147 | 1.00 | 42.77 | O |
| ANISOU | 1916 | O | LEU | B | 202 | 5269 | 5326 | 5654 | −568 | 507 | −441 | O |
| ATOM | 1917 | N | PRO | B | 203 | 95.027 | −37.532 | −2.655 | 1.00 | 45.89 | N |
| ANISOU | 1917 | N | PRO | B | 203 | 5651 | 5808 | 5978 | −634 | 517 | −376 | N |
| ATOM | 1918 | CA | PRO | B | 203 | 94.434 | −36.812 | −1.525 | 1.00 | 50.82 | C |
| ANISOU | 1918 | CA | PRO | B | 203 | 6413 | 6368 | 6527 | −678 | 597 | −419 | C |
| ATOM | 1919 | CB | PRO | B | 203 | 94.665 | −37.750 | −0.340 | 1.00 | 29.70 | C |
| ANISOU | 1919 | CB | PRO | B | 203 | 3779 | 3732 | 3775 | −738 | 607 | −360 | C |
| ATOM | 1920 | CG | PRO | B | 203 | 95.810 | −38.620 | −0.755 | 1.00 | 38.03 | C |
| ANISOU | 1920 | CG | PRO | B | 203 | 4722 | 4865 | 4862 | −732 | 483 | −264 | C |
| ATOM | 1921 | CD | PRO | B | 203 | 95.664 | −38.790 | −2.239 | 1.00 | 42.42 | C |
| ANISOU | 1921 | CD | PRO | B | 203 | 5148 | 5420 | 5550 | −637 | 482 | −304 | C |
| ATOM | 1922 | C | PRO | B | 203 | 95.149 | −35.487 | −1.307 | 1.00 | 41.70 | C |
| ANISOU | 1922 | C | PRO | B | 203 | 5391 | 5194 | 5257 | −773 | 552 | −434 | C |
| ATOM | 1923 | O | PRO | B | 203 | 96.365 | −35.440 | −1.130 | 1.00 | 37.45 | O |
| ANISOU | 1923 | O | PRO | B | 203 | 4863 | 4736 | 4632 | −873 | 450 | −372 | O |
| ATOM | 1924 | N | LEU | B | 204 | 94.380 | −34.409 | −1.332 | 1.00 | 40.98 | N |
| ANISOU | 1924 | N | LEU | B | 204 | 5391 | 4987 | 5192 | −742 | 623 | −515 | N |
| ATOM | 1925 | CA | LEU | B | 204 | 94.949 | −33.079 | −1.253 | 1.00 | 50.46 | C |
| ANISOU | 1925 | CA | LEU | B | 204 | 6744 | 6120 | 6308 | −834 | 584 | −540 | C |
| ATOM | 1926 | CB | LEU | B | 204 | 93.904 | −32.034 | −1.615 | 1.00 | 57.77 | C |
| ANISOU | 1926 | CB | LEU | B | 204 | 7729 | 6873 | 7347 | −730 | 659 | −617 | C |
| ATOM | 1927 | CG | LEU | B | 204 | 93.551 | −32.085 | −3.095 | 1.00 | 59.91 | C |
| ANISOU | 1927 | CG | LEU | B | 204 | 7865 | 7141 | 7757 | −624 | 579 | −558 | C |
| ATOM | 1928 | CD1 | LEU | B | 204 | 92.730 | −30.868 | −3.465 | 1.00 | 65.80 | C |
| ANISOU | 1928 | CD1 | LEU | B | 204 | 8683 | 7696 | 8621 | −530 | 594 | −592 | C |
| ATOM | 1929 | CD2 | LEU | B | 204 | 94.823 | −32.154 | −3.971 | 1.00 | 47.90 | C |
| ANISOU | 1929 | CD2 | LEU | B | 204 | 6319 | 5731 | 6151 | −730 | 453 | −467 | C |
| ATOM | 1930 | C | LEU | B | 204 | 95.575 | −32.770 | 0.104 | 1.00 | 49.58 | C |
| ANISOU | 1930 | C | LEU | B | 204 | 6810 | 6021 | 6007 | −994 | 585 | −564 | C |
| ATOM | 1931 | O | LEU | B | 204 | 96.436 | −31.907 | 0.211 | 1.00 | 55.16 | O |
| ANISOU | 1931 | O | LEU | B | 204 | 7630 | 6713 | 6615 | −1130 | 504 | −561 | O |
| ATOM | 1932 | N | ASP | B | 205 | 95.138 | −33.474 | 1.140 | 1.00 | 39.52 | N |
| ANISOU | 1932 | N | ASP | B | 205 | 5575 | 4776 | 4665 | −1007 | 670 | −583 | N |
| ATOM | 1933 | CA | ASP | B | 205 | 95.722 | −33.301 | 2.463 | 1.00 | 53.70 | C |
| ANISOU | 1933 | CA | ASP | B | 205 | 7567 | 6605 | 6233 | −1187 | 648 | −592 | C |
| ATOM | 1934 | CB | ASP | B | 205 | 94.779 | −33.840 | 3.541 | 1.00 | 47.75 | C |
| ANISOU | 1934 | CB | ASP | B | 205 | 6906 | 5837 | 5399 | −1187 | 820 | −647 | C |
| ATOM | 1935 | CG | ASP | B | 205 | 94.300 | −35.246 | 3.237 | 1.00 | 80.95 | C |
| ANISOU | 1935 | CG | ASP | B | 205 | 10916 | 10109 | 9733 | −1079 | 839 | −556 | C |
| ATOM | 1936 | OD1 | ASP | B | 205 | 93.397 | −35.393 | 2.380 | 1.00 | 98.48 | O |
| ANISOU | 1936 | OD1 | ASP | B | 205 | 12978 | 12278 | 12161 | −923 | 922 | −593 | O |
| ATOM | 1937 | OD2 | ASP | B | 205 | 94.835 | −36.203 | 3.836 | 1.00 | 84.14 | O |
| ANISOU | 1937 | OD2 | ASP | B | 205 | 11327 | 10604 | 10037 | −1158 | 750 | −438 | O |
| ATOM | 1938 | C | ASP | B | 205 | 97.063 | −34.032 | 2.541 | 1.00 | 48.89 | C |
| ANISOU | 1938 | C | ASP | B | 205 | 6867 | 6154 | 5555 | −1290 | 440 | −439 | C |
| ATOM | 1939 | O | ASP | B | 205 | 97.747 | −33.984 | 3.561 | 1.00 | 43.58 | O |
| ANISOU | 1939 | O | ASP | B | 205 | 6328 | 5541 | 4689 | −1461 | 345 | −401 | O |
| ATOM | 1940 | N | CYS | B | 206 | 97.413 | −34.725 | 1.459 | 1.00 | 48.43 | N |
| ANISOU | 1940 | N | CYS | B | 206 | 6577 | 6162 | 5661 | −1182 | 370 | −354 | N |
| ATOM | 1941 | CA | CYS | B | 206 | 98.654 | −35.488 | 1.362 | 1.00 | 46.42 | C |
| ANISOU | 1941 | CA | CYS | B | 206 | 6171 | 6045 | 5422 | −1223 | 201 | −216 | C |
| ATOM | 1942 | CB | CYS | B | 206 | 99.877 | −34.577 | 1.504 | 1.00 | 45.91 | C |
| ANISOU | 1942 | CB | CYS | B | 206 | 6143 | 6042 | 5260 | −1403 | 57 | −185 | C |
| ATOM | 1943 | SG | CYS | B | 206 | 99.936 | −33.240 | 0.327 | 1.00 | 52.90 | S |
| ANISOU | 1943 | SG | CYS | B | 206 | 7044 | 6850 | 6204 | −1421 | 100 | −262 | S |
| ATOM | 1950 | N | VAL | B | 208 | 98.770 | −40.103 | 3.042 | 1.00 | 46.67 | N |
| ANISOU | 1950 | N | VAL | B | 208 | 6010 | 6151 | 5572 | −1065 | 39 | 185 | N |
| ATOM | 1951 | CA | VAL | B | 208 | 98.952 | −41.422 | 2.457 | 1.00 | 45.89 | C |
| ANISOU | 1951 | CA | VAL | B | 208 | 5732 | 6018 | 5687 | −913 | 11 | 266 | C |
| ATOM | 1952 | CB | VAL | B | 208 | 100.157 | −41.451 | 1.525 | 1.00 | 45.13 | C |
| ANISOU | 1952 | CB | VAL | B | 208 | 5403 | 5990 | 5753 | −833 | −88 | 292 | C |
| ATOM | 1953 | CG1 | VAL | B | 208 | 100.336 | −42.840 | 0.938 | 1.00 | 34.08 | C |
| ANISOU | 1953 | CG1 | VAL | B | 208 | 3838 | 4523 | 4587 | −660 | −85 | 345 | C |
| ATOM | 1954 | CG2 | VAL | B | 208 | 99.971 | −40.428 | 0.429 | 1.00 | 46.87 | C |
| ANISOU | 1954 | CG2 | VAL | B | 208 | 5587 | 6231 | 5990 | −825 | 21 | 140 | C |
| ATOM | 1955 | C | VAL | B | 208 | 99.125 | −42.475 | 3.539 | 1.00 | 48.15 | C |
| ANISOU | 1955 | C | VAL | B | 208 | 6091 | 6279 | 5925 | −950 | −102 | 447 | C |
| ATOM | 1956 | O | VAL | B | 208 | 100.089 | −42.428 | 4.300 | 1.00 | 48.14 | O |
| ANISOU | 1956 | O | VAL | B | 208 | 6111 | 6352 | 5829 | −1041 | −303 | 588 | O |
| ATOM | 1957 | N | PRO | B | 209 | 98.171 | −43.420 | 3.620 | 1.00 | 49.81 | N |
| ANISOU | 1957 | N | PRO | B | 209 | 6347 | 6381 | 6196 | −898 | 11 | 457 | N |
| ATOM | 1958 | CA | PRO | B | 209 | 98.207 | −44.515 | 4.596 | 1.00 | 52.41 | C |
| ANISOU | 1958 | CA | PRO | B | 209 | 6777 | 6651 | 6484 | −940 | −83 | 650 | C |
| ATOM | 1959 | CB | PRO | B | 209 | 96.817 | −45.156 | 4.468 | 1.00 | 41.71 | C |
| ANISOU | 1959 | CB | PRO | B | 209 | 5481 | 5181 | 5184 | −923 | 128 | 581 | C |
| ATOM | 1960 | CG | PRO | B | 209 | 96.386 | −44.829 | 3.075 | 1.00 | 57.39 | C |
| ANISOU | 1960 | CG | PRO | B | 209 | 7300 | 7153 | 7353 | −796 | 255 | 389 | C |
| ATOM | 1961 | CD | PRO | B | 209 | 96.954 | −43.459 | 2.792 | 1.00 | 52.69 | C |
| ANISOU | 1961 | CD | PRO | B | 209 | 6678 | 6672 | 6668 | −822 | 222 | 297 | C |
| ATOM | 1962 | C | PRO | B | 209 | 99.272 | −45.539 | 4.242 | 1.00 | 60.41 | C |
| ANISOU | 1962 | C | PRO | B | 209 | 7604 | 7620 | 7727 | −796 | −265 | 802 | C |
| ATOM | 1963 | O | PRO | B | 209 | 99.697 | −45.632 | 3.087 | 1.00 | 62.46 | O |
| ANISOU | 1963 | O | PRO | B | 209 | 7653 | 7873 | 8206 | −644 | −236 | 715 | O |
| ATOM | 1964 | N | ASP | B | 210 | 99.680 | −46.311 | 5.242 | 1.00 | 61.65 | N |
| ANISOU | 1964 | N | ASP | B | 210 | 7851 | 7739 | 7834 | −843 | −442 | 1031 | N |
| ATOM | 1965 | CA | ASP | B | 210 | 100.645 | −47.383 | 5.050 | 1.00 | 71.27 | C |
| ANISOU | 1965 | CA | ASP | B | 210 | 8895 | 8875 | 9309 | −681 | −626 | 1205 | C |
| ATOM | 1966 | CB | ASP | B | 210 | 101.076 | −47.947 | 6.402 | 1.00 | 82.95 | C |
| ANISOU | 1966 | CB | ASP | B | 210 | 10528 | 10337 | 10654 | −787 | −877 | 1498 | C |
| ATOM | 1967 | CG | ASP | B | 210 | 101.898 | −46.963 | 7.202 | 1.00 | 102.87 | C |
| ANISOU | 1967 | CG | ASP | B | 210 | 13098 | 13052 | 12934 | −960 | −1091 | 1580 | C |
| ATOM | 1968 | OD1 | ASP | B | 210 | 102.881 | −46.419 | 6.651 | 1.00 | 100.05 | O |
| ANISOU | 1968 | OD1 | ASP | B | 210 | 12501 | 12805 | 12707 | −896 | −1189 | 1542 | O |
| ATOM | 1969 | OD2 | ASP | B | 210 | 101.553 | −46.727 | 8.381 | 1.00 | 115.08 | O |
| ANISOU | 1969 | OD2 | ASP | B | 210 | 14932 | 14645 | 14148 | −1185 | −1150 | 1674 | O |
| ATOM | 1970 | C | ASP | B | 210 | 100.063 | −48.500 | 4.195 | 1.00 | 66.88 | C |
| ANISOU | 1970 | C | ASP | B | 210 | 8269 | 8125 | 9019 | −511 | −478 | 1141 | C |
| ATOM | 1971 | O | ASP | B | 210 | 100.760 | −49.094 | 3.375 | 1.00 | 66.93 | O |
| ANISOU | 1971 | O | ASP | B | 210 | 8064 | 8060 | 9309 | −316 | −507 | 1130 | O |
| ATOM | 1972 | N | ASN | B | 211 | 98.784 | −48.790 | 4.398 | 1.00 | 59.75 | N |
| ANISOU | 1972 | N | ASN | B | 211 | 7542 | 7134 | 8026 | −599 | −307 | 1086 | N |
| ATOM | 1973 | CA | ASN | B | 211 | 98.123 | −49.837 | 3.636 | 1.00 | 72.51 | C |
| ANISOU | 1973 | CA | ASN | B | 211 | 9121 | 8559 | 9870 | −490 | −175 | 1016 | C |
| ATOM | 1974 | CB | ASN | B | 211 | 97.995 | −51.124 | 4.456 | 1.00 | 94.72 | C |
| ANISOU | 1974 | CB | ASN | B | 211 | 12080 | 11179 | 12731 | −515 | −268 | 1250 | C |
| ATOM | 1975 | CG | ASN | B | 211 | 98.905 | −52.222 | 3.949 | 1.00 | 111.75 | C |
| ANISOU | 1975 | CG | ASN | B | 211 | 14090 | 13150 | 15221 | −289 | −395 | 1343 | C |
| ATOM | 1976 | OD1 | ASN | B | 211 | 98.567 | −52.939 | 3.006 | 1.00 | 108.78 | O |
| ANISOU | 1976 | OD1 | ASN | B | 211 | 13651 | 12607 | 15072 | −172 | −268 | 1209 | O |
| ATOM | 1977 | ND2 | ASN | B | 211 | 100.075 | −52.355 | 4.569 | 1.00 | 116.87 | N |
| ANISOU | 1977 | ND2 | ASN | B | 211 | 14677 | 13820 | 15910 | −227 | −649 | 1568 | N |
| ATOM | 1978 | C | ASN | B | 211 | 96.769 | −49.415 | 3.093 | 1.00 | 66.72 | C |
| ANISOU | 1978 | C | ASN | B | 211 | 8428 | 7841 | 9081 | −562 | 69 | 796 | C |
| ATOM | 1979 | O | ASN | B | 211 | 95.852 | −49.084 | 3.842 | 1.00 | 64.14 | O |
| ANISOU | 1979 | O | ASN | B | 211 | 8258 | 7554 | 8559 | −726 | 170 | 797 | O |
| ATOM | 1980 | N | LEU | B | 212 | 96.662 | −49.437 | 1.772 | 1.00 | 73.48 | N |
| ANISOU | 1980 | N | LEU | B | 212 | 9133 | 8671 | 10114 | −439 | 162 | 609 | N |
| ATOM | 1981 | CA | LEU | B | 212 | 95.457 | −49.016 | 1.084 | 1.00 | 77.24 | C |
| ANISOU | 1981 | CA | LEU | B | 212 | 9603 | 9171 | 10574 | −489 | 342 | 411 | C |
| ATOM | 1982 | CB | LEU | B | 212 | 95.701 | −49.037 | −0.423 | 1.00 | 76.05 | C |
| ANISOU | 1982 | CB | LEU | B | 212 | 9299 | 9010 | 10587 | −356 | 381 | 234 | C |
| ATOM | 1983 | CG | LEU | B | 212 | 94.558 | −48.641 | −1.346 | 1.00 | 68.59 | C |
| ANISOU | 1983 | CG | LEU | B | 212 | 8326 | 8091 | 9644 | −395 | 508 | 43 | C |
| ATOM | 1984 | CD1 | LEU | B | 212 | 93.884 | −47.383 | −0.846 | 1.00 | 65.79 | C |
| ANISOU | 1984 | CD1 | LEU | B | 212 | 8010 | 7874 | 9114 | −496 | 564 | 13 | C |
| ATOM | 1985 | CD2 | LEU | B | 212 | 95.125 | −48.414 | −2.726 | 1.00 | 68.54 | C |
| ANISOU | 1985 | CD2 | LEU | B | 212 | 8207 | 8125 | 9711 | −290 | 512 | −102 | C |
| ATOM | 1986 | C | LEU | B | 212 | 94.274 | −49.911 | 1.452 | 1.00 | 78.38 | C |
| ANISOU | 1986 | C | LEU | B | 212 | 9852 | 9177 | 10750 | −588 | 442 | 441 | C |
| ATOM | 1987 | O | LEU | B | 212 | 93.123 | −49.474 | 1.473 | 1.00 | 74.00 | O |
| ANISOU | 1987 | O | LEU | B | 212 | 9315 | 8673 | 10130 | −691 | 582 | 343 | O |
| ATOM | 1988 | N | SER | B | 213 | 94.572 | −51.168 | 1.752 | 1.00 | 88.86 | N |
| ANISOU | 1988 | N | SER | B | 213 | 11239 | 10321 | 12203 | −558 | 368 | 586 | N |

TABLE 9-continued

DMXAA-hSTING$^{S162A/G230I/Q266I}$ complex

| | |
|---|---|
| ATOM 1944 C CYS B 206 98.732 −36.603 2.395 1.00 52.46 C | ATOM 1989 CA SER B 213 93.551 −52.138 2.128 1.00 91.14 C |
| ANISOU 1944 C CYS B 206 6952 6861 6119 −1246 148 −117 C | ANISOU 1989 CA SER B 213 11643 10451 12535 −678 451 644 C |
| ATOM 1945 O CYS B 206 99.825 −37.019 2.784 1.00 51.74 O | ATOM 1990 CB SER B 213 94.194 −53.505 2.313 1.00 89.16 C |
| ANISOU 1945 O CYS B 206 6792 6869 5996 −1320 −30 11 O | ANISOU 1990 CB SER B 213 11458 9955 12463 −597 328 816 C |
| ATOM 1946 N GLY B 207 97.574 −37.080 2.845 1.00 45.94 N | ATOM 1991 OG SER B 213 95.270 −53.659 1.405 1.00 85.53 O |
| ANISOU 1946 N GLY B 207 6207 5967 5282 −1190 294 −160 N | ANISOU 1991 OG SER B 213 10851 9452 12194 −377 247 744 O |
| ATOM 1947 CA GLY B 207 97.528 −38.172 3.802 1.00 42.54 C | ATOM 1992 C SER B 213 92.837 −51.724 3.411 1.00 99.55 C |
| ANISOU 1992 C SER B 213 12861 11609 13353 −883 530 748 C | ANISOU 2037 O ILE B 219 8088 7008 9293 −1045 914 254 O |
| ATOM 1993 O SER B 213 91.668 −52.046 3.615 1.00 104.42 O | ATOM 2038 N ARG B 220 88.946 −53.473 −1.051 1.00 55.58 N |
| ANISOU 1993 O SER B 213 13525 12185 13966 −1026 683 723 O | ANISOU 2038 N ARG B 220 6886 5738 8493 −993 861 25 N |
| ATOM 1994 N MET B 214 93.550 −51.008 4.274 1.00 102.99 N | ATOM 2039 CA ARG B 220 89.508 −54.734 −0.608 1.00 53.58 C |
| ANISOU 1994 N MET B 214 13374 12177 13580 −915 436 855 N | ANISOU 2039 CA ARG B 220 6786 5240 8331 −986 809 169 C |
| ATOM 1995 CA MET B 214 93.000 −50.578 5.556 1.00 101.30 C | ATOM 2040 CB ARG B 220 88.401 −55.766 −0.421 1.00 54.31 C |
| ANISOU 1995 CA MET B 214 13350 12058 13081 −1123 522 940 C | ANISOU 2040 CB ARG B 220 6939 5164 8531 −1195 881 200 C |
| ATOM 1996 CB MET B 214 94.116 −50.419 6.593 1.00 109.32 C | ATOM 2041 CG ARG B 220 87.702 −55.672 0.916 1.00 75.74 C |
| ANISOU 1996 CB MET B 214 14510 13133 13896 −1166 307 1153 C | ANISOU 2041 CG ARG B 220 9718 7941 11117 −1386 994 371 C |
| ATOM 1997 CG MET B 214 95.015 −51.628 6.728 1.00 112.85 C | ATOM 2042 CD ARG B 220 86.227 −55.947 0.760 1.00 89.26 C |
| ANISOU 1997 CG MET B 214 14976 13403 14500 −1073 73 1395 C | ANISOU 2042 CD ARG B 220 11337 9661 12916 −1611 1124 297 C |
| ATOM 1998 SD MET B 214 94.078 −53.141 7.007 1.00 158.88 S | ATOM 2043 NE ARG B 220 85.723 −56.910 1.735 1.00 103.07 N |
| ANISOU 1998 SD MET B 214 20954 18975 20439 −1175 162 1535 S | ANISOU 2043 NE ARG B 220 13238 11255 14670 −1831 1207 485 N |
| ATOM 1999 CE MET B 214 95.400 −54.289 7.379 1.00 83.56 C | ATOM 2044 CZ ARG B 220 84.991 −57.974 1.421 1.00 98.10 C |
| ANISOU 1999 CE MET B 214 11464 9225 11058 −1040 −175 1862 C | ANISOU 2044 CZ ARG B 220 12630 10430 14212 −2008 1230 474 C |
| ATOM 2000 C MET B 214 92.251 −49.257 5.451 1.00 87.09 C | ATOM 2045 NH1 ARG B 220 84.572 −58.798 2.371 1.00 110.35 N |
| ANISOU 2000 C MET B 214 11502 10430 11157 −1175 711 726 C | ANISOU 2045 NH1 ARG B 220 14340 11841 15748 −2228 1314 670 N |
| ATOM 2001 O MET B 214 91.491 −48.896 6.347 1.00 92.67 O | ATOM 2046 NH2 ARG B 220 84.678 −58.212 0.154 1.00 81.87 N |
| ANISOU 2001 O MET B 214 12341 11204 11665 −1342 876 722 O | ANISOU 2046 NH2 ARG B 220 10462 8319 12325 −1991 1164 269 N |
| ATOM 2002 N ALA B 215 92.479 −48.537 4.359 1.00 77.21 N | ATOM 2047 C ARG B 220 90.554 −55.253 −1.566 1.00 48.99 C |
| ANISOU 2002 N ALA B 215 10070 9240 10025 −1029 697 551 N | ANISOU 2047 C ARG B 220 6207 4520 7886 −796 717 82 C |
| ATOM 2003 CA ALA B 215 92.026 −47.153 4.239 1.00 69.38 C | ATOM 2048 O ARG B 220 90.339 −55.306 −2.774 1.00 51.15 O |
| ANISOU 2003 CA ALA B 215 9040 8387 8932 −1041 821 375 C | ANISOU 2048 O ARG B 220 6419 4783 8234 −773 726 −122 O |
| ATOM 2004 CB ALA B 215 92.651 −46.495 3.019 1.00 68.13 C | ATOM 2049 N PHE B 221 91.693 −55.632 −1.008 1.00 42.61 N |
| ANISOU 2004 CB ALA B 215 8716 8274 8894 −883 731 252 C | ANISOU 2049 N PHE B 221 5469 3611 7108 −665 629 240 N |
| ATOM 2005 C ALA B 215 90.509 −46.992 4.203 1.00 73.10 C | ATOM 2050 CA PHE B 221 92.751 −56.223 −1.796 1.00 59.57 C |
| ANISOU 2005 C ALA B 215 9462 8864 9450 −1112 1064 248 C | ANISOU 2050 CA PHE B 221 7599 5603 9431 −459 574 168 C |
| ATOM 2006 O ALA B 215 89.971 −45.985 4.658 1.00 82.88 O | ATOM 2051 CB PHE B 221 93.986 −56.433 −0.935 1.00 60.69 C |
| ANISOU 2006 O ALA B 215 10734 10190 10565 −1163 1214 147 O | ANISOU 2051 CB PHE B 221 7765 5686 9610 −313 451 395 C |
| ATOM 2007 N ASP B 216 89.829 −47.985 3.645 1.00 71.81 N | ATOM 2052 CG PHE B 221 95.091 −57.123 −1.651 1.00 67.18 C |
| ANISOU 2007 N ASP B 216 9205 8597 9483 −1113 1103 245 N | ANISOU 2052 CG PHE B 221 8531 6324 10669 −74 417 334 C |
| ATOM 2008 CA ASP B 216 88.377 −47.964 3.516 1.00 66.32 C | ATOM 2053 CD1 PHE B 221 95.800 −56.462 −2.643 1.00 63.47 C |
| ANISOU 2008 CA ASP B 216 8400 7911 8886 −1187 1309 128 C | ANISOU 2053 CD1 PHE B 221 7902 6007 10205 69 461 144 C |
| ATOM 2009 CB ASP B 216 87.973 −47.329 2.175 1.00 79.26 C | ATOM 2054 CE1 PHE B 221 96.826 −57.089 −3.314 1.00 53.24 C |
| ANISOU 2009 CB ASP B 216 9820 9590 10707 −1055 1287 −39 C | ANISOU 2054 CE1 PHE B 221 6535 4554 9139 293 479 63 C |
| ATOM 2010 CG ASP B 216 86.450 −47.223 1.986 1.00 81.72 C | ATOM 2055 CZ PHE B 221 97.153 −58.403 −2.996 1.00 73.02 C |
| ANISOU 2010 CG ASP B 216 9958 9928 11164 −1116 1463 −141 C | ANISOU 2055 CZ PHE B 221 9130 6714 11902 405 434 174 C |
| ATOM 2011 OD1 ASP B 216 85.719 −48.190 2.270 1.00 76.61 O | ATOM 2056 CE2 PHE B 221 96.446 −59.077 −2.007 1.00 77.20 C |
| ANISOU 2011 OD1 ASP B 216 9294 9220 10596 −1249 1552 −88 O | ANISOU 2056 CE2 PHE B 221 9840 7065 12427 260 358 387 C |
| ATOM 2012 OD2 ASP B 216 85.993 −46.155 1.529 1.00 86.81 O | ATOM 2057 CD2 PHE B 221 95.420 −58.434 −1.342 1.00 75.02 C |
| ANISOU 2012 OD2 ASP B 216 10469 10604 11865 −1030 1503 −264 O | ANISOU 2057 CD2 PHE B 221 9635 6981 11891 8 360 464 C |
| ATOM 2013 C ASP B 216 87.897 −49.403 3.594 1.00 46.66 C | ATOM 2058 C PHE B 221 92.305 −57.566 −2.343 1.00 65.47 C |
| ANISOU 2013 C ASP B 216 5932 5282 6514 −1293 1328 242 C | ANISOU 2058 C PHE B 221 8452 6040 10382 −501 608 88 C |
| ATOM 2014 O ASP B 216 88.457 −50.281 2.941 1.00 58.77 O | ATOM 2059 O PHE B 221 91.792 −58.403 −1.602 1.00 69.10 O |
| ANISOU 2014 O ASP B 216 7460 6688 8183 −1223 1175 286 O | ANISOU 2059 O PHE B 221 9048 6310 10898 −630 602 242 O |
| ATOM 2015 N PRO B 217 86.852 −49.656 4.395 1.00 49.67 N | ATOM 2060 N LEU B 222 92.499 −57.783 −3.636 1.00 55.94 N |
| ANISOU 2015 N PRO B 217 6345 5674 6852 −1472 1536 272 N | ANISOU 2060 N LEU B 222 7211 4772 9272 −415 649 −155 N |
| ATOM 2016 CA PRO B 217 86.333 −51.026 4.487 1.00 57.96 C | ATOM 2061 CA LEU B 222 92.231 −59.110 −4.164 1.00 68.04 C |
| ANISOU 2016 CA PRO B 217 7429 6576 8019 −1612 1563 380 C | ANISOU 2061 CA LEU B 222 8879 5968 11004 −446 679 −253 C |
| ATOM 2017 CB PRO B 217 85.338 −50.955 5.649 1.00 46.04 C | ATOM 2062 CB LEU B 222 90.978 −59.146 −5.051 1.00 76.03 C |
| ANISOU 2017 CB PRO B 217 5984 5140 6371 −1833 1838 421 C | ANISOU 2062 CB LEU B 222 9903 7013 11971 −665 730 −470 C |
| ATOM 2018 CG PRO B 217 84.946 −49.505 5.723 1.00 59.16 C | ATOM 2063 CG LEU B 222 90.785 −58.221 −6.245 1.00 80.72 C |
| ANISOU 2018 CG PRO B 217 7531 6981 7966 −1760 1991 242 C | ANISOU 2063 CG LEU B 222 10387 7857 12425 −673 748 −708 C |
| ATOM 2019 CD PRO B 217 86.171 −48.736 5.324 1.00 46.05 C | ATOM 2064 CD1 LEU B 222 91.619 −58.685 −7.416 1.00 94.02 C |
| ANISOU 2019 CD PRO B 217 5920 5352 6226 −1568 1776 212 C | ANISOU 2064 CD1 LEU B 222 12131 9409 14185 −524 798 −936 C |
| ATOM 2020 C PRO B 217 85.623 −51.488 3.212 1.00 62.27 C | ATOM 2065 CD2 LEU B 222 89.320 −58.216 −6.626 1.00 77.29 C |
| ANISOU 2020 C PRO B 217 7754 7056 8850 −1582 1535 251 C | ANISOU 2065 CD2 LEU B 222 9939 7481 11948 −939 736 −801 C |
| ATOM 2021 O PRO B 217 85.326 −52.671 3.070 1.00 69.37 O | ATOM 2066 C LEU B 222 93.429 −59.821 −4.797 1.00 71.25 C |
| ANISOU 2021 O PRO B 217 8685 7795 9875 −1688 1515 318 O | ANISOU 2066 C LEU B 222 9307 6149 11616 −193 696 −350 C |
| ATOM 2022 N ASN B 218 85.345 −50.565 2.301 1.00 53.65 N | ATOM 2067 O LEU B 222 93.618 −61.001 −4.561 1.00 74.79 O |
| ANISOU 2022 N ASN B 218 6463 6074 7849 −1456 1519 74 N | ANISOU 2067 O LEU B 222 9890 6251 12278 −143 683 −283 O |
| ATOM 2023 CA ASN B 218 84.740 −50.935 1.034 1.00 44.98 C | ATOM 2068 N ASP B 223 94.247 −59.118 −5.573 1.00 66.22 N |
| ANISOU 2023 CA ASN B 218 5176 4933 6981 −1441 1444 −44 C | ANISOU 2068 N ASP B 223 8536 5691 10931 −31 738 −500 N |
| ATOM 2024 CB ASN B 218 83.655 −49.945 0.630 1.00 41.84 C | ATOM 2069 CA ASP B 223 95.335 −59.798 −6.270 1.00 59.33 C |
| ANISOU 2024 CB ASN B 218 4525 4687 6684 −1422 1538 −183 C | ANISOU 2069 CA ASP B 223 7658 4613 10271 210 809 −635 C |
| ATOM 2025 CG ASN B 218 82.390 −50.120 1.431 1.00 55.11 C | ATOM 2070 CB ASP B 223 94.774 −60.584 −7.456 1.00 59.87 C |
| ANISOU 2025 CG ASN B 218 6096 6414 8428 −1605 1779 −164 C | ANISOU 2070 CB ASP B 223 7880 4473 10396 124 920 −938 C |
| ATOM 2026 OD1 ASN B 218 81.997 −51.239 1.765 1.00 58.75 O | ATOM 2071 CG ASP B 223 95.583 −61.829 −7.767 1.00 74.59 C |
| ANISOU 2026 OD1 ASN B 218 6606 6774 8941 −1791 1833 −77 O | ANISOU 2071 CG ASP B 223 9836 5940 12566 338 1001 −1030 C |
| ATOM 2027 ND2 ASN B 218 81.747 −49.004 1.761 1.00 44.50 N | ATOM 2072 OD1 ASP B 223 96.762 −61.893 −7.376 1.00 82.90 O |
| ANISOU 2027 ND2 ASN B 218 4603 5213 7092 −1557 1943 −246 N | ANISOU 2072 OD1 ASP B 223 10813 6864 13819 561 946 −822 O |

TABLE 9-continued

DMXAA-hSTING$^{S162A/G230I/Q266I}$ complex

| | |
|---|---|
| ATOM 2028 C ASN B 218 85.750 −51.086 −0.090 1.00 44.92 C | ATOM 2073 OD2 ASP B 223 95.025 −62.754 −8.391 1.00 86.26 O |
| ANISOU 2028 C ASN B 218 5195 4857 7017 −1278 1229 −100 C | ANISOU 2073 OD2 ASP B 223 11467 7222 14087 280 1111 −1312 O |
| ATOM 2029 O ASN B 218 85.390 −51.307 −1.239 1.00 50.77 O | ATOM 2074 C ASP B 223 96.432 −58.861 −6.758 1.00 70.26 C |
| ANISOU 2029 O ASN B 218 5821 5572 7896 −1265 1145 −216 O | ANISOU 2074 C ASP B 223 8846 6254 11594 389 855 −709 C |
| ATOM 2030 N ILE B 219 87.021 −50.955 0.245 1.00 53.96 N | ATOM 2075 O ASP B 223 96.220 −57.662 −6.906 1.00 64.39 O |
| ANISOU 2030 N ILE B 219 6486 5985 8033 −1168 1143 −21 N | ANISOU 2075 O ASP B 223 8011 5839 10617 296 843 −728 O |
| ATOM 2031 CA ILE B 219 88.066 −51.251 −0.715 1.00 52.95 C | ATOM 2076 N LYS B 224 97.606 −59.429 −7.008 1.00 70.51 N |
| ANISOU 2031 CA ILE B 219 6377 5781 7960 −1020 982 −66 C | ANISOU 2076 N LYS B 224 8808 6121 11863 646 915 −748 N |
| ATOM 2032 CB ILE B 219 88.979 −50.059 −0.953 1.00 51.96 C | ATOM 2077 CA LYS B 224 98.702 −58.696 −7.620 1.00 62.10 C |
| ANISOU 2032 CB ILE B 219 6228 5798 7717 −872 917 −107 C | ANISOU 2077 CA LYS B 224 7540 5274 10782 810 1005 −853 C |
| ATOM 2033 CG1 ILE B 219 88.164 −48.893 −1.495 1.00 47.28 C | ATOM 2078 CB LYS B 224 100.034 −59.179 −7.070 1.00 65.25 C |
| ANISOU 2033 CG1 ILE B 219 5490 5352 7121 −862 963 −238 C | ANISOU 2078 CB LYS B 224 7771 5534 11486 1101 968 −693 C |
| ATOM 2034 CD1 ILE B 219 89.008 −47.738 −1.954 1.00 58.34 C | ATOM 2079 CG LYS B 224 100.210 −58.921 −5.615 1.00 73.13 C |
| ANISOU 2034 CD1 ILE B 219 6879 6863 8426 −735 889 −287 C | ANISOU 2079 CG LYS B 224 8710 6597 12479 1093 732 −321 C |
| ATOM 2035 CG2 ILE B 219 90.076 −50.417 −1.940 1.00 46.64 C | ATOM 2080 CD LYS B 224 101.192 −57.805 −5.389 1.00 74.58 C |
| ANISOU 2035 CG2 ILE B 219 5556 5060 7107 −732 795 −157 C | ANISOU 2080 CD LYS B 224 8637 7112 12586 1164 674 −224 C |
| ATOM 2036 C ILE B 219 88.847 −52.453 −0.213 1.00 60.04 C | ATOM 2081 CE LYS B 224 100.803 −57.048 −4.143 1.00 82.74 C |
| ANISOU 2036 C ILE B 219 7438 6484 8891 −1017 918 85 C | ANISOU 2081 CE LYS B 224 9706 8341 13391 987 465 53 C |
| ATOM 2037 O ILE B 219 89.316 −52.475 0.920 1.00 64.19 O | ATOM 2082 NZ LYS B 224 101.882 −56.169 −3.643 1.00 94.62 N |
| ANISOU 2082 NZ LYS B 224 10981 10100 14871 1054 344 209 N | ANISOU 2127 C ILE B 230 11003 8961 13729 1363 2158 −2282 C |
| ATOM 2083 C LYS B 224 98.705 −58.926 −9.118 1.00 66.42 C | ATOM 2128 O ILE B 230 114.834 −52.194 −15.044 1.00 84.49 O |
| ANISOU 2083 C LYS B 224 8155 5778 11303 814 1217 −1220 C | ANISOU 2128 O ILE B 230 10391 8183 13527 1275 2088 −2076 O |
| ATOM 2084 O LYS B 224 98.303 −59.984 −9.592 1.00 81.46 O | ATOM 2129 CB ILE B 230 111.848 −51.128 −15.165 1.00 98.08 C |
| ANISOU 2084 O LYS B 224 10244 7378 13329 799 1296 −1385 O | ANISOU 2129 CB ILE B 230 12833 10318 14114 1711 1912 −1660 C |
| ATOM 2085 N LEU B 225 99.175 −57.935 −9.860 1.00 64.32 N | ATOM 2130 CG1 ILE B 230 110.335 −51.236 −15.323 1.00 97.19 C |
| ANISOU 2085 N LEU B 225 7766 5810 10862 814 1312 −1347 N | ANISOU 2130 CG1 ILE B 230 12803 10352 13772 1933 1793 −1609 C |
| ATOM 2086 CA LEU B 225 99.482 −58.150 −11.259 1.00 70.84 C | ATOM 2131 CG2 ILE B 230 112.318 −49.949 −15.991 1.00 93.96 C |
| ANISOU 2086 CA LEU B 225 8648 6612 11656 845 1542 −1685 C | ANISOU 2131 CG2 ILE B 230 12738 9999 12964 1605 2108 −1725 C |
| ATOM 2087 CB LEU B 225 99.605 −56.820 −11.996 1.00 71.30 C | ATOM 2132 CD1 ILE B 230 109.891 −51.216 −16.779 1.00 91.06 C |
| ANISOU 2087 CB LEU B 225 8629 7056 11406 729 1596 −1770 C | ANISOU 2132 CD1 ILE B 230 12085 9855 12659 1942 1923 −1964 C |
| ATOM 2088 CG LEU B 225 98.321 −56.174 −12.496 1.00 67.37 C | ATOM 2133 N ASP B 231 114.292 −52.030 −17.233 1.00 102.37 N |
| ANISOU 2088 CG LEU B 225 8294 6722 10580 440 1508 −1836 C | ANISOU 2133 N ASP B 231 12776 10940 15182 1241 2396 −2688 N |
| ATOM 2089 CD1 LEU B 225 98.667 −55.064 −13.470 1.00 57.97 C | ATOM 2134 CA ASP B 231 115.650 −51.931 −17.750 1.00 121.49 C |
| ANISOU 2089 CD1 LEU B 225 7063 5840 9121 363 1600 −1954 C | ANISOU 2134 CA ASP B 231 15077 13362 17720 988 2623 −3002 C |
| ATOM 2090 CD2 LEU B 225 97.438 −57.215 −13.164 1.00 70.99 C | ATOM 2135 CB ASP B 231 115.845 −53.015 −18.803 1.00 134.17 C |
| ANISOU 2090 CD2 LEU B 225 9004 6927 11042 318 1546 −2055 C | ANISOU 2135 CB ASP B 231 16187 15055 19738 880 2778 −3621 C |
| ATOM 2091 C LEU B 225 100.805 −58.895 −11.325 1.00 68.45 C | ATOM 2136 CG ASP B 231 114.577 −53.277 −19.606 1.00 142.54 C |
| ANISOU 2091 C LEU B 225 8201 6111 11696 1159 1694 −1735 C | ANISOU 2136 CG ASP B 231 17298 16375 20487 1000 2765 −3768 C |
| ATOM 2092 O LEU B 225 101.602 −58.820 −10.392 1.00 71.97 O | ATOM 2137 OD1 ASP B 231 114.134 −52.374 −20.351 1.00 145.88 O |
| ANISOU 2092 O LEU B 225 8436 6570 12341 1335 1589 −1485 O | ANISOU 2137 OD1 ASP B 231 18169 17105 20155 960 2858 −3736 O |
| ATOM 2093 N PRO B 226 101.051 −59.625 −12.424 1.00 70.55 N | ATOM 2138 OD2 ASP B 231 114.017 −54.387 −19.486 1.00 142.66 O |
| ANISOU 2093 N PRO B 226 8577 6190 12039 1232 1941 −2063 N | ANISOU 2138 OD2 ASP B 231 16903 16276 21024 1126 2640 −3899 O |
| ATOM 2094 CA PRO B 226 102.406 −60.162 −12.549 1.00 78.63 C | ATOM 2139 C ASP B 231 115.924 −50.573 −18.399 1.00 123.54 C |
| ANISOU 2094 CA PRO B 226 9400 7069 13409 1562 2130 −2129 C | ANISOU 2139 C ASP B 231 15884 13889 17166 855 2805 −2952 C |
| ATOM 2095 CB PRO B 226 102.320 −61.084 −13.763 1.00 66.61 C | ATOM 2140 O ASP B 231 115.877 −50.446 −19.620 1.00 131.14 O |
| ANISOU 2095 CB PRO B 226 8111 5323 11874 1561 2381 −2503 C | ANISOU 2140 O ASP B 231 16914 15143 17771 718 2991 −3301 O |
| ATOM 2096 CG PRO B 226 101.226 −60.545 −14.557 1.00 64.39 C | ATOM 2141 N ARG B 232 116.224 −49.560 −17.596 1.00 111.30 N |
| ANISOU 2096 CG PRO B 226 8071 5189 11204 1235 2397 −2704 C | ANISOU 2141 N ARG B 232 14723 12246 15320 866 2744 −2519 N |
| ATOM 2097 CD PRO B 226 100.211 −60.000 −13.571 1.00 75.76 C | ATOM 2142 CA ARG B 232 116.472 −48.236 −18.151 1.00 107.25 C |
| ANISOU 2097 CD PRO B 226 9529 6760 12497 1033 2067 −2390 C | ANISOU 2142 CA ARG B 232 14743 11956 14053 741 2879 −2429 C |
| ATOM 2098 C PRO B 226 103.378 −59.023 −12.806 1.00 75.65 C | ATOM 2143 CB ARG B 232 115.217 −47.376 −18.073 1.00 97.93 C |
| ANISOU 2098 C PRO B 226 8733 7078 12933 1612 2220 −2107 C | ANISOU 2143 CB ARG B 232 14039 10899 12270 942 2724 −2072 C |
| ATOM 2099 O PRO B 226 103.097 −58.075 −13.545 1.00 70.96 O | ATOM 2144 CG ARG B 232 114.249 −47.566 −19.209 1.00 104.03 C |
| ANISOU 2099 O PRO B 226 8190 6786 11984 1404 2285 −2226 O | ANISOU 2144 CG ARG B 232 14847 11947 12732 976 2737 −2309 C |
| ATOM 2100 N GLN B 227 104.530 −59.137 −12.168 1.00 83.72 N | ATOM 2145 CD ARG B 232 112.938 −46.921 −18.845 1.00 115.18 C |
| ANISOU 2100 N GLN B 227 9444 8078 14285 1883 2204 −1933 N | ANISOU 2145 CD ARG B 232 16616 13382 13764 1232 2520 −1930 C |
| ATOM 2101 CA GLN B 227 105.486 −58.057 −12.099 1.00 96.43 C | ATOM 2146 NE ARG B 232 112.423 −46.043 −19.890 1.00 120.63 N |
| ANISOU 2101 CA GLN B 227 10732 10053 15854 1917 2221 −1828 C | ANISOU 2146 NE ARG B 232 17976 14596 14022 1172 2527 −1934 N |
| ATOM 2102 CB GLN B 227 106.650 −58.469 −11.218 1.00 101.85 C | ATOM 2147 CZ ARG B 232 112.880 −44.818 −20.135 1.00 121.90 C |
| ANISOU 2102 CB GLN B 227 11075 10637 16986 2229 2130 −1595 C | ANISOU 2147 CZ ARG B 232 18338 14581 13396 1030 2564 −1760 C |
| ATOM 2103 CG GLN B 227 106.222 −58.821 −9.827 1.00 105.43 C | ATOM 2148 NH1 ARG B 232 113.880 −44.324 −19.417 1.00 117.50 N |
| ANISOU 2103 CG GLN B 227 11586 10929 17542 2235 1768 −1238 C | ANISOU 2148 NH1 ARG B 232 17878 13865 12904 945 2629 −1591 N |
| ATOM 2104 CD GLN B 227 107.067 −59.915 −9.237 1.00 119.40 C | ATOM 2149 NH2 ARG B 232 112.343 −44.091 −21.106 1.00 122.16 N |
| ANISOU 2104 CD GLN B 227 13189 12390 19786 2564 1696 −1084 C | ANISOU 2149 NH2 ARG B 232 18730 14846 12840 957 2517 −1741 N |
| ATOM 2105 OE1 GLN B 227 107.463 −60.853 −9.930 1.00 130.45 O | ATOM 2150 C ARG B 232 117.612 −47.519 −17.455 1.00 104.78 C |
| ANISOU 2105 OE1 GLN B 227 14650 13607 21307 2705 1879 −1276 O | ANISOU 2150 C ARG B 232 14599 11483 13729 612 2927 −2205 C |
| ATOM 2106 NE2 GLN B 227 107.363 −59.799 −7.950 1.00 121.33 N | ATOM 2151 O ARG B 232 118.258 −48.073 −16.571 1.00 111.40 O |
| ANISOU 2106 NE2 GLN B 227 13280 12642 20180 2628 1374 −700 N | ANISOU 2151 O ARG B 232 15127 12039 15159 603 2858 −2134 O |
| ATOM 2107 C GLN B 227 106.022 −57.594 −13.438 1.00 104.22 C | ATOM 2152 N ALA B 233 117.855 −46.279 −17.862 1.00 91.19 N |
| ANISOU 2107 C GLN B 227 11674 11254 16670 1874 2552 −2132 C | ANISOU 2152 N ALA B 233 13375 9937 11337 497 3024 −2080 N |
| ATOM 2108 O GLN B 227 105.692 −58.126 −14.501 1.00 108.64 O | ATOM 2153 CA ALA B 233 118.847 −45.460 −17.190 1.00 86.90 C |
| ANISOU 2108 O GLN B 227 12491 11721 17068 1796 2742 −2414 O | ANISOU 2153 CA ALA B 233 13059 9258 10699 387 3062 −1827 C |
| ATOM 2109 N GLN B 228 106.878 −56.591 −13.466 1.00 93.61 N | ATOM 2154 CB ALA B 233 119.032 −44.144 −17.911 1.00 84.49 C |
| ANISOU 2109 N GLN B 228 10600 9446 15523 2340 917 −1613 N | ANISOU 2154 CB ALA B 233 13295 9192 9615 234 3173 −1754 C |
| ATOM 2110 CA GLN B 228 107.514 −56.000 −14.494 1.00 86.82 C | ATOM 2155 C ALA B 233 118.366 −45.223 −15.772 1.00 88.14 C |
| ANISOU 2110 CA GLN B 228 9901 8736 14349 2298 1170 −1914 C | ANISOU 2155 C ALA B 233 13341 9172 10975 602 2829 −1325 C |
| ATOM 2111 CB GLN B 228 106.707 −54.792 −14.958 1.00 85.38 C | ATOM 2156 O ALA B 233 117.165 −45.093 −15.530 1.00 83.02 O |
| ANISOU 2111 CB GLN B 228 10238 8831 13373 2431 1262 −1824 C | ANISOU 2156 O ALA B 233 12850 8559 10137 818 2670 −1118 O |

TABLE 9-continued

DMXAA-hSTING$^{S162A/G230I/Q266I}$ complex

| | |
|---|---|
| ATOM 2112 CG GLN B 228 106.961 −54.372 −16.389 1.00 89.04 C | ATOM 2157 N GLY B 234 119.304 −45.195 −14.831 1.00 87.94 N |
| ANISOU 2112 CG GLN B 228 10847 9525 13461 2385 1482 −2172 C | ANISOU 2157 N GLY B 234 13227 8908 11276 521 2810 −1148 N |
| ATOM 2113 CD GLN B 228 106.183 −53.131 −16.764 1.00 92.22 C | ATOM 2158 CA GLY B 234 118.976 −44.946 −13.441 1.00 80.20 C |
| ANISOU 2113 CD GLN B 228 11773 10151 13116 2499 1504 −2015 C | ANISOU 2158 CA GLY B 234 12367 7718 10386 650 2606 −678 C |
| ATOM 2114 OE1 GLN B 228 105.145 −52.837 −16.174 1.00103.63 O | ATOM 2159 C GLY B 234 118.126 −46.036 −12.825 1.00 79.87 C |
| ANISOU 2114 OE1 GLN B 228 13377 11611 14388 2674 1360 −1760 O | ANISOU 2159 C GLY B 234 11966 7546 10835 813 2403 −625 C |
| ATOM 2115 NE2 GLN B 228 106.689 −52.386 −17.739 1.00 96.81 N | ATOM 2160 O GLY B 234 117.729 −45.959 −11.663 1.00 80.49 O |
| ANISOU 2115 NE2 GLN B 228 12615 10902 13267 2383 1674 −2170 N | ANISOU 2160 O GLY B 234 12106 7480 10995 891 2226 −257 O |
| ATOM 2116 C GLN B 228 108.881 −55.565 −14.001 1.00 84.86 C | ATOM 2161 N ILE B 235 117.842 −47.072 −13.595 1.00 88.05 N |
| ANISOU 2116 C GLN B 228 9704 8308 14231 2110 1226 −1792 C | ANISOU 2161 N ILE B 235 12617 8643 12196 839 2430 −1002 N |
| ATOM 2117 O GLN B 228 108.990 −54.751 −13.088 1.00 93.99 O | ATOM 2162 CA ILE B 235 117.014 −48.135 −13.071 1.00 91.27 C |
| ANISOU 2117 O GLN B 228 11170 9413 15129 2084 1171 −1409 O | ANISOU 2162 CA ILE B 235 12679 8930 13068 985 2228 −959 C |
| ATOM 2118 N THR B 229 109.927 −56.140 −14.573 1.00 81.28 N | ATOM 2163 CB ILE B 235 115.506 −47.840 −13.313 1.00110.98 C |
| ANISOU 2118 N THR B 229 8919 7752 14212 1970 1333 −2136 N | ANISOU 2163 CB ILE B 235 15428 11625 15114 1207 2153 −867 C |
| ATOM 2119 CA THR B 229 111.269 −55.713 −14.242 1.00 79.42 C | ATOM 2164 CG1 ILE B 235 114.640 −48.518 −12.260 1.00107.58 C |
| ANISOU 2119 CA THR B 229 8718 7358 14101 1788 1407 −2073 C | ANISOU 2164 CG1 ILE B 235 14805 11050 15020 1343 1912 −620 C |
| ATOM 2120 CB THR B 229 112.264 −56.862 −14.382 1.00 88.46 C | ATOM 2165 CD1 ILE B 235 113.213 −48.646 −12.691 1.00107.37 C |
| ANISOU 2120 CB THR B 229 9283 8254 16076 1643 1380 −2385 C | ANISOU 2165 CD1 ILE B 235 14840 11203 14752 1554 1850 −676 C |
| ATOM 2121 OG1 THR B 229 111.609 −58.094 −14.065 1.00 90.20 O | ATOM 2166 CG2 ILE B 235 115.066 −48.185 −14.725 1.00119.64 C |
| ANISOU 2121 OG1 THR B 229 9155 8442 16676 1623 1099 −2312 O | ANISOU 2166 CG2 ILE B 235 16435 12963 16059 1231 2277 −1288 C |
| ATOM 2122 CG2 THR B 229 113.443 −56.660 −13.447 1.00 91.06 C | ATOM 2167 C ILE B 235 117.501 −49.495 −13.578 1.00 94.55 C |
| ANISOU 2122 CG2 THR B 229 9568 8289 16742 1483 1301 −2139 C | ANISOU 2167 C ILE B 235 12492 9244 14190 907 2256 −1387 C |
| ATOM 2123 C THR B 229 111.603 −54.609 −15.226 1.00 88.04 C | ATOM 2168 O ILE B 235 117.456 −49.810 −14.766 1.00101.51 O |
| ANISOU 2123 C THR B 229 10206 8714 14530 1741 1685 −2244 C | ANISOU 2168 O ILE B 235 13240 10311 15018 875 2421 −1819 O |
| ATOM 2124 O THR B 229 111.261 −54.708 −16.401 1.00 94.87 O | ATOM 2169 N LYS B 236 118.042 −50.288 −12.671 1.00 86.81 N |
| ANISOU 2124 O THR B 229 11060 9814 15174 1759 1837 −2606 O | ANISOU 2169 N LYS B 236 11134 7955 13894 846 2089 −1276 N |
| ATOM 2125 N ILE B 230 112.244 −53.545 −14.759 1.00 83.19 N | ATOM 2170 CA LYS B 236 118.524 −51.584 −13.090 1.00 97.56 C |
| ANISOU 2125 N ILE B 230 9957 8078 13574 1659 1740 −1975 N | ANISOU 2170 CA LYS B 236 11887 9165 16015 781 2082 −1684 C |
| ATOM 2126 CA ILE B 230 112.514 −52.424 −15.652 1.00 90.88 C | ATOM 2171 CB LYS B 236 120.056 −51.633 −13.158 1.00100.49 C |
| ANISOU 2126 CA ILE B 230 11349 9303 13879 1597 1969 −2085 C | ANISOU 2171 CB LYS B 236 12033 9365 16784 563 2199 −1882 C |
| ATOM 2127 C ILE B 230 113.997 −52.207 −15.947 1.00 88.68 C | ATOM 2172 CG LYS B 236 120.764 −52.015 −11.878 1.00102.42 C |
| ANISOU 2172 CG LYS B 236 12047 9225 17641 473 1947 −1550 C | ANISOU 2217 CA SER B 241 10488 8519 13613 2346 443 −111 C |
| ATOM 2173 CD LYS B 236 122.237 −51.735 −12.014 1.00 99.28 C | ATOM 2218 CB SER B 241 104.354 −55.608 −7.596 1.00 93.06 C |
| ANISOU 2173 CD LYS B 236 11554 8711 17458 268 2098 −1720 C | ANISOU 2218 CB SER B 241 11102 9260 14999 2131 199 146 C |
| ATOM 2174 CE LYS B 236 122.893 −52.677 −13.013 1.00102.27 C | ATOM 2219 OG SER B 241 104.571 −54.861 −6.416 1.00 98.91 O |
| ANISOU 2174 CE LYS B 236 11372 9042 18445 180 2252 −2368 C | ANISOU 2219 OG SER B 241 12095 9981 15507 1955 171 497 C |
| ATOM 2175 NZ LYS B 236 124.104 −52.048 −13.607 1.00100.60 N | ATOM 2220 C SER B 241 103.155 −53.700 −8.629 1.00 76.19 C |
| ANISOU 2175 NZ LYS B 236 11226 8914 18084 −19 2544 −2656 N | ANISOU 2220 C SER B 241 9620 7508 11821 2511 498 −33 C |
| ATOM 2176 C LYS B 236 117.947 −52.672 −12.213 1.00 95.84 C | ATOM 2221 O SER B 241 103.314 −52.613 −8.082 1.00 77.14 O |
| ANISOU 2176 C LYS B 236 11304 8705 16406 865 1771 −1495 C | ANISOU 2221 O SER B 241 10080 7654 11575 2472 568 159 O |
| ATOM 2177 O LYS B 236 117.988 −52.590 −10.981 1.00 98.10 O | ATOM 2222 N ASN B 242 101.987 −54.102 −9.103 1.00 70.47 N |
| ANISOU 2177 O LYS B 236 11653 8794 16827 831 1549 −1045 O | ANISOU 2222 N ASN B 242 8796 6924 11055 2696 462 −197 N |
| ATOM 2178 N ASP B 237 117.362 −53.662 −12.879 1.00 91.49 N | ATOM 2223 CA ASN B 242 100.792 −53.321 −8.885 1.00 60.34 C |
| ANISOU 2178 N ASP B 237 10392 8194 16174 953 1757 −1838 N | ANISOU 2223 CA ASN B 242 7773 5817 9337 2856 480 −145 C |
| ATOM 2179 CA ASP B 237 116.823 −54.837 −12.225 1.00 95.99 C | ATOM 2224 CB ASN B 242 100.332 −52.679 −10.187 1.00 66.79 C |
| ANISOU 2179 CA ASP B 237 10555 8538 17379 1017 1462 −1731 C | ANISOU 2224 CB ASN B 242 8805 6785 9789 3099 593 −386 C |
| ATOM 2180 CB ASP B 237 117.963 −55.762 −11.807 1.00105.52 C | ATOM 2225 CG ASN B 242 101.357 −51.718 −10.743 1.00 70.58 C |
| ANISOU 2180 CB ASP B 237 11221 9356 19516 857 1313 −1829 C | ANISOU 2225 CG ASN B 242 9583 7239 9997 3061 738 −396 C |
| ATOM 2181 CG ASP B 237 118.515 −56.561 −12.968 1.00114.21 C | ATOM 2226 OD1 ASN B 242 102.406 −52.133 −11.239 1.00 78.16 O |
| ANISOU 2181 CG ASP B 237 11859 10529 21005 772 1468 −2438 C | ANISOU 2226 OD1 ASN B 242 10406 8115 11175 2943 798 −509 O |
| ATOM 2182 OD1 ASP B 237 119.007 −55.946 −13.939 1.00116.12 O | ATOM 2227 ND2 ASN B 242 101.072 −50.423 −10.647 1.00 53.57 N |
| ANISOU 2182 OD1 ASP B 237 12245 10939 20936 734 1816 −2821 O | ANISOU 2227 ND2 ASN B 242 7821 5147 7387 3149 791 −289 N |
| ATOM 2183 OD2 ASP B 237 118.452 −57.806 −12.904 1.00115.88 O | ATOM 2228 C ASN B 242 99.697 −54.184 −8.290 1.00 67.60 C |
| ANISOU 2183 OD2 ASP B 237 11579 10673 21775 691 1231 −2518 O | ANISOU 2228 C ASN B 242 8435 6790 10460 2860 327 −112 C |
| ATOM 2184 C ASP B 237 115.963 −54.475 −11.023 1.00 93.55 C | ATOM 2229 O ASN B 242 99.581 −55.360 −8.615 1.00 74.28 O |
| ANISOU 2184 C ASP B 237 10545 8408 16791 1088 1228 −1161 C | ANISOU 2229 O ASN B 242 8928 7591 11703 2855 227 −237 O |
| ATOM 2185 O ASP B 237 116.207 −54.932 −9.908 1.00 99.80 O | ATOM 2230 N SER B 243 98.902 −53.594 −7.408 1.00 59.32 N |
| ANISOU 2185 O ASP B 237 11156 8727 18037 987 959 −834 O | ANISOU 2230 N SER B 243 5998 7665 8876 −134 596 −1377 N |
| ATOM 2186 N ARG B 238 114.980 −53.616 −11.250 1.00 76.68 N | ATOM 2231 CA SER B 243 97.854 −54.342 −6.739 1.00 52.84 C |
| ANISOU 2186 N ARG B 238 8868 6365 13904 1233 1326 −1049 N | ANISOU 2231 CA SER B 243 5275 6302 8498 −89 391 −1463 C |
| ATOM 2187 CA ARG B 238 114.047 −53.272 −10.197 1.00 69.57 C | ATOM 2232 CB SER B 243 98.272 −54.917 −5.251 1.00 63.15 C |
| ANISOU 2187 CA ARG B 238 8230 5488 12724 1303 1143 −593 C | ANISOU 2232 CB SER B 243 6853 7101 10042 −341 337 −985 C |
| ATOM 2188 CB ARG B 238 113.797 −51.777 −10.156 1.00 70.10 C | ATOM 2233 OG SER B 243 98.998 −54.463 −4.620 1.00 81.25 O |
| ANISOU 2188 CB ARG B 238 8899 5768 11970 1357 1293 −387 C | ANISOU 2233 OG SER B 243 8983 9267 12621 −373 290 −958 O |
| ATOM 2189 CG ARG B 238 113.268 −51.311 −8.833 1.00 67.37 C | ATOM 2234 C SER B 243 96.496 −54.082 −7.360 1.00 52.84 C |
| ANISOU 2189 CG ARG B 238 8794 5384 11420 1340 1128 88 C | ANISOU 2234 C SER B 243 5421 6386 8269 O 386 −1569 C |
| ATOM 2190 CD ARG B 238 114.172 −50.240 −8.288 1.00 67.24 C | ATOM 2235 O SER B 243 96.218 −52.994 −7.853 1.00 46.24 O |
| ANISOU 2190 CD ARG B 238 9114 5316 11119 1201 1207 333 C | ANISOU 2235 O SER B 243 4794 5862 6914 −48 535 −1365 O |
| ATOM 2191 NE ARG B 238 113.574 −48.918 −8.410 1.00 63.62 N | ATOM 2236 N ILE B 244 95.648 −55.100 −7.313 1.00 57.53 N |
| ANISOU 2191 NE ARG B 238 9181 5075 9916 1321 1339 443 N | ANISOU 2236 N ILE B 244 5912 6686 9261 126 197 −1892 N |
| ATOM 2192 CZ ARG B 238 114.216 −47.781 −8.173 1.00 63.81 C | ATOM 2237 CA ILE B 244 94.307 −55.003 −7.852 1.00 47.95 C |
| ANISOU 2192 CZ ARG B 238 9576 5108 9561 1242 1449 608 C | ANISOU 2237 CA ILE B 244 4775 5545 7897 219 155 −2054 C |
| ATOM 2193 NH1 ARG B 238 115.486 −47.803 −7.798 1.00 56.77 N | ATOM 2238 CB ILE B 244 93.994 −56.186 −8.741 1.00 59.70 C |
| ANISOU 2193 NH1 ARG B 238 8595 4035 8939 1040 1456 687 N | ANISOU 2238 CB ILE B 244 5947 7103 9633 489 −9 −2687 C |
| ATOM 2194 NH2 ARG B 238 113.581 −46.627 −8.301 1.00 56.26 N | ATOM 2239 CG1 ILE B 244 95.138 −56.437 −9.710 1.00 59.82 C |
| ANISOU 2194 NH2 ARG B 238 9066 4324 7986 1366 1534 696 N | ANISOU 2239 CG1 ILE B 244 5691 7571 9467 715 53 −3013 C |
| ATOM 2195 C ARG B 238 112.755 −53.993 −10.487 1.00 74.07 C | ATOM 2240 CD1 ILE B 244 94.917 −57.652 −10.559 1.00 51.94 C |
| ANISOU 2195 C ARG B 238 8637 6168 13339 1476 1049 −705 C | ANISOU 2240 CD1 ILE B 244 4391 6621 8723 1029 −151 −3677 C |

TABLE 9-continued

DMXAA-hSTING$^{S162A/G230I/Q266I}$ complex

| | |
|---|---|
| ATOM 2196 O ARG B 238 112.357 −54.119 −11.642 1.00 85.97 O | ATOM 2241 CG2 ILE B 244 92.718 −55.944 −9.514 1.00 58.22 C |
| ANISOU 2196 O ARG B 238 10111 7866 14689 1589 1203 −1072 O | ANISOU 2241 CG2 ILE B 244 5802 7137 9183 615 −34 −2897 C |
| ATOM 2197 N VAL B 239 112.097 −54.476 −9.444 1.00 71.98 N | ATOM 2242 C ILE B 244 93.309 −54.994 −6.713 1.00 55.72 C |
| ANISOU 2197 N VAL B 239 8273 5800 13277 1468 795 −389 N | ANISOU 2242 C ILE B 244 5976 6044 9152 34 63 −1760 C |
| ATOM 2198 CA VAL B 239 110.855 −55.194 −9.649 1.00 62.35 C | ATOM 2243 O ILE B 244 93.399 −55.805 −5.795 1.00 51.52 O |
| ANISOU 2198 CA VAL B 239 6889 4681 12121 1622 693 −481 C | ANISOU 2243 O ILE B 244 5395 5043 9138 −61 −66 −1717 O |
| ATOM 2199 CB VAL B 239 110.853 −56.539 −8.930 1.00 72.47 C | ATOM 2244 N TYR B 245 92.347 −54.083 −6.785 1.00 50.99 N |
| ANISOU 2199 CB VAL B 239 7681 5695 14160 1514 389 −375 C | ANISOU 2244 N TYR B 245 5619 5579 8177 7 126 −1559 N |
| ATOM 2200 CG1 VAL B 239 109.843 −57.459 −9.577 1.00 60.93 C | ATOM 2245 CA TYR B 245 91.394 −53.921 −5.705 1.00 43.63 C |
| ANISOU 2200 CG1 VAL B 239 5949 4333 14689 1671 341 −642 C | ANISOU 2245 CA TYR B 245 4887 4286 7404 −146 65 −1248 C |
| ATOM 2201 CG2 VAL B 239 112.238 −57.155 −8.999 1.00 62.14 C | ATOM 2246 CB TYR B 245 91.556 −52.555 −5.060 1.00 46.69 C |
| ANISOU 2201 CG2 VAL B 239 5996 4110 13503 1330 337 −514 C | ANISOU 2246 CB TYR B 245 5658 4697 7385 −282 186 −699 C |
| ATOM 2202 C VAL B 239 109.682 −54.350 −9.201 1.00 60.71 C | ATOM 2247 CG TYR B 245 92.882 −52.387 −4.376 1.00 52.34 C |
| ANISOU 2202 C VAL B 239 7100 4692 11273 1747 694 −224 C | ANISOU 2247 CG TYR B 245 6424 5253 8211 −437 236 −414 C |
| ATOM 2203 O VAL B 239 109.561 −53.997 −8.030 1.00 56.77 O | ATOM 2248 CD1 TYR B 245 93.999 −51.957 −5.082 1.00 52.62 C |
| ANISOU 2203 O VAL B 239 6760 4141 10669 1644 570 158 O | ANISOU 2248 CD1 TYR B 245 6403 5628 7963 −431 361 −440 C |
| ATOM 2204 N TYR B 240 108.834 −54.006 −10.159 1.00 66.99 N | ATOM 2249 CE1 TYR B 245 95.220 −51.810 −4.457 1.00 50.43 C |
| ANISOU 2204 N TYR B 240 8067 5736 11648 1951 835 −454 N | ANISOU 2249 CE1 TYR B 245 6125 5243 7794 −586 398 −203 C |
| ATOM 2205 CA TYR B 240 107.634 −53.246 −9.878 1.00 69.02 C | ATOM 2250 CZ TYR B 245 95.329 −52.102 −3.108 1.00 52.64 C |
| ANISOU 2205 CA TYR B 240 8675 6191 11359 2103 831 −281 C | ANISOU 2250 CZ TYR B 245 6490 5050 8461 −712 296 54 C |
| ATOM 2206 CB TYR B 240 107.432 −52.162 −10.924 1.00 72.04 C | ATOM 2251 OH TYR B 245 96.537 −51.964 −2.470 1.00 59.11 O |
| ANISOU 2206 CB TYR B 240 9444 6795 11133 2244 1037 −447 C | ANISOU 2251 OH TYR B 245 7297 5774 9387 −843 310 263 O |
| ATOM 2207 CG TYR B 240 108.358 −50.991 −10.766 1.00 69.93 C | ATOM 2252 CE2 TYR B 245 94.231 −52.535 −2.389 1.00 56.61 C |
| ANISOU 2207 CG TYR B 240 9539 6506 10527 2141 1164 −300 C | ANISOU 2252 CE2 TYR B 245 7076 5202 9232 −706 183 106 C |
| ATOM 2208 CD1 TYR B 240 108.059 −49.967 −9.876 1.00 56.94 C | ATOM 2253 CD2 TYR B 245 93.019 −52.678 −3.024 1.00 56.85 C |
| ANISOU 2208 CD1 TYR B 240 8255 4879 8503 2150 1142 20 C | ANISOU 2253 CD2 TYR B 245 7075 5363 9162 −588 160 −124 C |
| ATOM 2209 CE1 TYR B 240 108.894 −48.891 −9.728 1.00 62.14 C | ATOM 2254 C TYR B 245 89.956 −54.115 −6.141 1.00 47.73 C |
| ANISOU 2209 CE1 TYR B 240 9245 5510 8856 2058 1253 155 C | ANISOU 2254 C TYR B 245 5349 4896 7889 −43 −19 −1499 C |
| ATOM 2210 CZ TYR B 240 110.050 −48.823 −10.475 1.00 64.12 C | ATOM 2255 O TYR B 245 89.575 −53.781 −7.257 1.00 49.86 O |
| ANISOU 2210 CZ TYR B 240 9475 5727 9161 1945 1390 −24 C | ANISOU 2255 O TYR B 245 5585 5585 7774 151 13 −1766 O |
| ATOM 2211 OH TYR B 240 110.883 −47.744 −10.325 1.00 56.47 O | ATOM 2256 N GLU B 246 89.174 −54.667 −5.227 1.00 50.03 N |
| ANISOU 2211 OH TYR B 240 8842 4735 7878 1845 1497 118 O | ANISOU 2256 N GLU B 246 5620 4809 8581 −179 −125 −1402 N |
| ATOM 2212 CE2 TYR B 240 110.373 −49.834 −11.369 1.00 69.67 C | ATOM 2257 CA GLU B 246 87.739 −54.776 −5.381 1.00 48.26 C |
| ANISOU 2212 CE2 TYR B 240 9809 6426 10237 1920 1430 −368 C | ANISOU 2257 CA GLU B 246 5333 4659 8344 −146 −199 −1555 C |
| ATOM 2213 CD2 TYR B 240 109.530 −50.905 −11.509 1.00 65.13 C | ATOM 2258 CB GLU B 246 87.264 −56.047 −4.695 1.00 70.53 C |
| ANISOU 2213 CD2 TYR B 240 8898 5865 9981 2022 1317 −507 C | ANISOU 2258 CB GLU B 246 7940 7024 11833 −315 −351 −1658 C |
| ATOM 2214 C TYR B 240 106.417 −54.151 −9.862 1.00 78.62 C | ATOM 2259 CG GLU B 246 85.778 −56.266 −4.698 1.00 86.28 C |
| ANISOU 2214 C TYR B 240 9642 7469 12760 2226 687 −345 C | ANISOU 2259 CG GLU B 246 9811 9074 13898 −356 −430 −1788 C |
| ATOM 2215 O TYR B 240 106.264 −55.027 −10.713 1.00 74.15 O | ATOM 2260 CD GLU B 246 85.394 −57.518 −3.925 1.00 95.68 C |
| ANISOU 2215 O TYR B 240 8772 6917 12485 2293 692 −655 O | ANISOU 2260 CD GLU B 246 10856 10003 15495 −497 −511 −1651 C |
| ATOM 2216 N SER B 241 105.549 −53.926 −8.888 1.00 79.96 N | ATOM 2261 OE1 GLU B 246 84.559 −58.297 −4.432 1.00 101.97 O |
| ANISOU 2216 N SER B 241 9938 7688 12755 2238 573 −71 N | ANISOU 2261 OE1 GLU B 246 11412 10833 16501 −490 −625 −1986 O |
| ATOM 2217 CA SER B 241 104.311 −54.671 −8.795 1.00 85.85 C | ATOM 2262 OE2 GLU B 246 85.930 −57.725 −2.814 1.00 83.50 O |
| ANISOU 2262 OE2 GLU B 246 9476 8317 13934 −569 −452 −1198 O | ATOM 2307 OE1 GLN B 252 5311 5371 7733 97 326 379 O |
| ATOM 2263 C GLU B 246 87.115 −53.572 −4.694 1.00 46.20 C | ATOM 2308 NE2 GLN B 252 75.026 −56.869 −1.515 1.00 40.28 N |
| ANISOU 2263 C GLU B 246 5402 4477 7675 −189 −112 −1092 C | ANISOU 2308 NE2 GLN B 252 4036 4516 6752 214 279 303 N |
| ATOM 2264 O GLU B 246 87.529 −53.191 −3.603 1.00 50.39 O | ATOM 2309 C GLN B 252 79.430 −55.306 −4.249 1.00 54.78 C |
| ANISOU 2264 O GLU B 246 6144 4748 8253 −336 −68 −644 O | ANISOU 2309 C GLN B 252 6252 6190 8373 108 223 208 C |
| ATOM 2265 N LEU B 247 86.132 −52.960 −5.338 1.00 36.17 N | ATOM 2310 O GLN B 252 79.715 −54.110 −4.252 1.00 55.07 O |
| ANISOU 2265 N LEU B 247 4186 3576 5981 −23 −108 −1219 N | ANISOU 2310 O GLN B 252 6258 6251 8416 128 120 177 O |
| ATOM 2266 CA LEU B 247 85.415 −51.852 −4.733 1.00 40.20 C | ATOM 2311 N ARG B 253 80.094 −56.218 −4.949 1.00 54.78 N |
| ANISOU 2266 CA LEU B 247 5010 4184 6082 1 −64 −838 C | ANISOU 2311 N ARG B 253 6534 6119 8342 21 344 184 N |
| ATOM 2267 CB LEU B 247 85.445 −50.659 −5.664 1.00 46.44 C | ATOM 2312 CA ARG B 253 81.185 −55.836 −5.828 1.00 47.37 C |
| ANISOU 2267 CB LEU B 247 6070 5403 6174 230 10 −841 C | ANISOU 2312 CA ARG B 253 5513 5153 7330 −82 367 106 C |
| ATOM 2268 CG LEU B 247 86.857 −50.403 −6.176 1.00 58.80 C | ATOM 2313 CB ARG B 253 81.846 −57.055 −6.453 1.00 54.90 C |
| ANISOU 2268 CG LEU B 247 7717 7017 7607 206 115 −793 C | ANISOU 2313 CB ARG B 253 6528 6001 8330 −187 585 12 C |
| ATOM 2269 CD1 LEU B 247 86.784 −49.502 −7.364 1.00 59.30 C | ATOM 2314 CG ARG B 253 82.962 −56.693 −7.413 1.00 62.33 C |
| ANISOU 2269 CD1 LEU B 247 7965 7540 7028 437 184 −901 C | ANISOU 2314 CG ARG B 253 7563 6928 9189 −342 652 −122 C |
| ATOM 2270 CD2 LEU B 247 87.707 −49.771 −5.084 1.00 47.38 C | ATOM 2315 CD ARG B 253 83.685 −57.933 −7.900 1.00 66.37 C |
| ANISOU 2270 CD2 LEU B 247 6565 5277 6161 4 174 −266 C | ANISOU 2315 CD ARG B 253 8075 7296 9847 −439 938 −284 C |
| ATOM 2271 C LEU B 247 83.978 −52.264 −4.468 1.00 52.15 C | ATOM 2316 NE ARG B 253 84.199 −58.733 −6.792 1.00 70.49 N |
| ANISOU 2271 C LEU B 247 6335 5734 7745 −1 −155 −969 C | ANISOU 2316 NE ARG B 253 8427 7708 10647 −192 1051 −190 N |
| ATOM 2272 O LEU B 247 83.276 −52.702 −5.377 1.00 49.19 O | ATOM 2317 CZ ARG B 253 85.023 −59.764 −6.936 1.00 73.56 C |
| ANISOU 2272 O LEU B 247 5709 5607 7372 124 −230 −1417 O | ANISOU 2317 CZ ARG B 253 8722 7903 11325 −200 1295 −287 C |
| ATOM 2273 N LEU B 248 83.542 −52.131 −3.220 1.00 47.06 N | ATOM 2318 NH1 ARG B 253 85.433 −60.114 −8.145 1.00 76.44 N |
| ANISOU 2273 N LEU B 248 5791 4870 7218 −142 −151 −584 N | ANISOU 2318 NH1 ARG B 253 9161 8175 11707 −453 1509 −561 N |
| ATOM 2274 CA LEU B 248 82.192 −52.538 −2.856 1.00 48.85 C | ATOM 2319 NH2 ARG B 253 85.443 −60.438 −5.869 1.00 67.09 N |
| ANISOU 2274 CA LEU B 248 5798 5165 7599 −187 −215 −660 C | ANISOU 2319 NH2 ARG B 253 7707 6982 10804 7 1328 −107 N |
| ATOM 2275 CB LEU B 248 82.159 −53.202 −1.486 1.00 65.81 C | ATOM 2320 C ARG B 253 80.664 −54.916 −6.923 1.00 53.87 C |
| ANISOU 2275 CB LEU B 248 5341 4351 7708 −465 −214 −327 C | ANISOU 2320 C ARG B 253 6415 5990 8062 −291 178 118 C |
| ATOM 2276 CG LEU B 248 83.064 −54.373 −1.171 1.00 58.11 C | ATOM 2321 O ARG B 253 79.709 −55.237 −7.623 1.00 52.06 O |
| ANISOU 2276 CG LEU B 248 6748 5426 9903 −690 −250 −360 C | ANISOU 2321 O ARG B 253 6233 5742 7804 −473 112 158 O |
| ATOM 2277 CD1 LEU B 248 82.969 −54.607 0.319 1.00 47.09 C | ATOM 2322 N ALA B 254 81.300 −53.764 −7.063 1.00 50.63 N |
| ANISOU 2277 CD1 LEU B 248 8261 6737 11267 −785 −198 96 C | ANISOU 2322 N ALA B 254 6003 5615 7618 −288 66 120 N |
| ATOM 2278 CD2 LEU B 248 82.628 −55.607 −1.934 1.00 53.15 C | ATOM 2323 CA ALA B 254 80.839 −52.765 −8.003 1.00 51.58 C |
| ANISOU 2278 CD2 LEU B 248 5724 4748 9723 −769 −372 −871 C | ANISOU 2323 CA ALA B 254 6147 5742 7708 −496 −173 210 C |
| ATOM 2279 C LEU B 248 81.249 −51.357 −2.806 1.00 53.88 C | ATOM 2324 CB ALA B 254 80.459 −51.496 −7.266 1.00 56.68 C |
| ANISOU 2279 C LEU B 248 6660 6188 7624 37 −199 −514 C | ANISOU 2324 CB ALA B 254 6625 6362 8548 −327 −344 273 C |

TABLE 9-continued

DMXAA-hSTING$^{S162A/G230I/Q266I}$ complex

| | |
|---|---|
| ATOM 2280 O LEU B 248 81.626 -50.257 -2.409 1.00 46.37 O | ATOM 2325 C ALA B 254 81.928 -52.478 -9.018 1.00 60.20 C |
| ANISOU 2280 O LEU B 248 6113 5256 6249 139 -147 -155 O | ANISOU 2325 C ALA B 254 7368 6883 8622 -712 -164 155 C |
| ATOM 2281 N GLU B 249 80.005 -51.614 -3.177 1.00 50.45 N | ATOM 2326 O ALA B 254 81.681 -51.887 -10.064 1.00 56.75 O |
| ANISOU 2281 N GLU B 249 5959 6053 7158 114 -266 -808 N | ANISOU 2326 O ALA B 254 6985 6491 8088 -1002 -359 256 O |
| ATOM 2282 CA GLU B 249 78.949 -50.645 -2.991 1.00 48.20 C | ATOM 2327 N GLY B 255 83.144 -52.891 -8.702 1.00 59.44 N |
| ANISOU 2282 CA GLU B 249 5822 6256 6151 6341 344 -275 -695 C | ANISOU 2327 N GLY B 255 7303 6786 8497 -599 50 18 N |
| ATOM 2283 CB GLU B 249 78.628 -49.948 -4.302 1.00 59.95 C | ATOM 2328 CA GLY B 255 84.248 -52.653 -9.601 1.00 49.63 C |
| ANISOU 2283 CB GLU B 249 7413 8099 7267 697 -317 -1039 C | ANISOU 2328 CA GLY B 255 6166 5588 7102 -801 105 -78 C |
| ATOM 2284 CG GLU B 249 77.681 -48.790 -4.153 1.00 73.78 C | ATOM 2329 C GLY B 255 85.532 -53.306 -9.156 1.00 49.48 C |
| ANISOU 2284 CG GLU B 249 9418 8377 1011 -349 -912 C | ANISOU 2329 C GLY B 255 6132 5517 7152 -648 375 -229 C |
| ATOM 2285 CD GLU B 249 77.440 -48.074 -5.461 1.00 96.99 C | ATOM 2330 O GLY B 255 85.707 -53.659 -7.992 1.00 41.45 O |
| ANISOU 2285 CD GLU B 249 12523 13599 10730 1388 -397 -1228 C | ANISOU 2330 O GLY B 255 5003 4452 6293 -360 450 -192 O |
| ATOM 2286 OE1 GLU B 249 77.527 -48.729 -6.523 1.00 105.41 O | ATOM 2331 N THR B 256 86.432 -53.463 -10.112 1.00 57.87 N |
| ANISOU 2286 OE1 GLU B 249 13319 14783 11949 1411 -428 -1673 O | ANISOU 2331 N THR B 256 7288 6596 8105 -885 515 -387 N |
| ATOM 2287 OE2 GLU B 249 77.176 -46.854 -5.424 1.00 105.18 O | ATOM 2332 CA THR B 256 87.754 -53.988 -9.851 1.00 65.81 C |
| ANISOU 2287 OE2 GLU B 249 13986 14841 11139 1684 -419 -1031 O | ANISOU 2332 CA THR B 256 8246 7514 9247 -772 770 -536 C |
| ATOM 2288 C GLU B 249 77.729 -51.383 -2.480 1.00 48.37 C | ATOM 2333 CB THR B 256 87.862 -55.449 -10.273 1.00 69.36 C |
| ANISOU 2288 C GLU B 249 5439 6260 6681 195 -319 -785 C | ANISOU 2333 CB THR B 256 8680 7828 9847 -899 1090 -740 C |
| ATOM 2289 O GLU B 249 77.292 -52.364 -3.090 1.00 48.07 O | ATOM 2334 OG1 THR B 256 87.021 -56.250 -9.438 1.00 68.47 O |
| ANISOU 2289 O GLU B 249 4989 6260 7013 80 -393 -1204 O | ANISOU 2334 OG1 THR B 256 8473 7626 9918 -697 1095 -623 O |
| ATOM 2290 N ASN B 250 77.206 -50.920 -1.348 1.00 49.06 N | ATOM 2335 CG2 THR B 256 89.287 -55.923 -10.147 1.00 70.16 C |
| ANISOU 2290 N ASN B 250 5635 6380 6626 188 -278 -388 N | ANISOU 2335 CG2 THR B 256 8681 7787 10188 -816 1357 -896 C |
| ATOM 2291 CA ASN B 250 76.014 -51.503 -0.745 1.00 43.22 C | ATOM 2336 C THR B 256 88.750 -53.168 -10.652 1.00 62.48 C |
| ANISOU 2291 CA ASN B 250 4507 5794 6122 33 -286 -394 C | ANISOU 2336 C THR B 256 7905 7177 8655 -968 758 -629 C |
| ATOM 2292 CB ASN B 250 74.801 -51.247 -1.651 1.00 46.23 C | ATOM 2337 O THR B 256 88.592 -53.002 -11.858 1.00 61.14 O |
| ANISOU 2292 CB ASN B 250 4653 6764 6148 287 -371 -829 C | ANISOU 2337 O THR B 256 7860 7116 8254 -1359 738 -713 O |
| ATOM 2293 CG ASN B 250 73.474 -51.393 -0.922 1.00 41.47 C | ATOM 2338 N CYS B 257 89.774 -52.647 -9.990 1.00 55.13 N |
| ANISOU 2293 CG ASN B 250 3716 6488 5551 221 -362 -753 C | ANISOU 2338 N CYS B 257 6905 6228 7813 -740 758 -600 N |
| ATOM 2294 OD1 ASN B 250 73.378 -51.167 0.282 1.00 45.28 O | ATOM 2339 CA CYS B 257 90.733 -51.812 -10.691 1.00 53.17 C |
| ANISOU 2294 OD1 ASN B 250 4298 6892 6012 148 -280 -299 O | ANISOU 2339 CA CYS B 257 6729 6066 7406 -910 734 -676 C |
| ATOM 2295 ND2 ASN B 250 72.439 -51.779 -1.662 1.00 45.40 N | ATOM 2340 CB CYS B 257 90.239 -50.369 -10.750 1.00 63.85 C |
| ANISOU 2295 ND2 ASN B 250 3791 7392 6067 254 -448 -1212 N | ANISOU 2340 CB CYS B 257 8116 7542 8600 -937 377 -475 C |
| ATOM 2296 C ASN B 250 76.211 -53.006 -0.489 1.00 42.69 C | ATOM 2341 SG CYS B 257 90.235 -49.558 -9.139 1.00 69.92 S |
| ANISOU 2296 C ASN B 250 4059 5301 6860 -405 -292 -476 C | ANISOU 2341 SG CYS B 257 8736 8282 9548 -487 220 -307 S |
| ATOM 2297 O ASN B 250 75.294 -53.812 -0.657 1.00 41.49 O | ATOM 2342 C CYS B 257 92.109 -51.849 -10.055 1.00 47.80 C |
| ANISOU 2297 O ASN B 250 3469 5274 7021 -585 -344 -736 O | ANISOU 2342 C CYS B 257 5951 5304 6906 -684 884 -729 C |
| ATOM 2298 N GLY B 251 77.432 -53.371 -0.118 1.00 37.96 N | ATOM 2343 O CYS B 257 92.261 -52.213 -8.890 1.00 49.64 O |
| ANISOU 2298 N GLY B 251 3641 4192 6591 -570 -259 -268 N | ANISOU 2343 O CYS B 257 6049 5453 7358 -374 908 -618 O |
| ATOM 2299 CA GLY B 251 77.765 -54.748 0.185 1.00 42.65 C | ATOM 2344 N VAL B 258 93.108 -51.464 -10.843 1.00 48.03 N |
| ANISOU 2299 CA GLY B 251 3974 4305 7925 -944 -287 -308 C | ANISOU 2344 N VAL B 258 6040 5379 6829 -882 970 -877 N |
| ATOM 2300 C GLY B 251 78.122 -55.607 -1.022 1.00 55.81 C | ATOM 2345 CA VAL B 258 94.462 -51.280 -10.342 1.00 49.66 C |
| ANISOU 2300 C GLY B 251 5420 5863 9923 -978 -407 -855 C | ANISOU 2345 CA VAL B 258 6154 5522 7193 -693 1071 -905 C |
| ATOM 2301 O GLY B 251 78.469 -56.772 -0.867 1.00 60.68 O | ATOM 2346 CB VAL B 258 95.503 -51.479 -11.438 1.00 49.79 C |
| ANISOU 2301 O GLY B 251 5867 6043 11146 -1248 -469 -935 O | ANISOU 2346 CB VAL B 258 6213 5529 7176 -991 1328 -1191 C |
| ATOM 2302 N GLN B 252 78.037 -55.044 -2.225 1.00 57.71 N | ATOM 2347 CG2 VAL B 258 95.360 -52.863 -12.043 1.00 51.67 C |
| ANISOU 2302 N GLN B 252 6371 6718 8837 269 228 206 N | ANISOU 2347 CG2 VAL B 258 6413 5626 7594 -1193 1679 -1464 C |
| ATOM 2303 CA GLN B 252 78.251 -55.824 -3.445 1.00 47.13 C | ATOM 2348 CG1 VAL B 258 96.905 -51.272 -10.877 1.00 46.87 C |
| ANISOU 2303 CA GLN B 252 5182 5256 7468 162 238 251 C | ANISOU 2348 CG1 VAL B 258 5720 5071 7016 -775 1418 -1193 C |
| ATOM 2304 CB GLN B 252 77.011 -55.806 -4.341 1.00 35.35 C | ATOM 2349 C VAL B 258 94.569 -49.869 -9.786 1.00 51.60 C |
| ANISOU 2304 CB GLN B 252 3722 3678 6030 25 121 284 C | ANISOU 2349 C VAL B 258 6413 5891 7300 -537 771 -707 C |
| ATOM 2305 CG GLN B 252 75.704 -55.814 -3.586 1.00 42.44 C | ATOM 2350 O VAL B 258 94.215 -48.897 -10.446 1.00 53.05 O |
| ANISOU 2305 CG GLN B 252 4482 4598 7044 81 94 301 C | ANISOU 2350 O VAL B 258 6701 6202 7252 -730 562 -658 O |
| ATOM 2306 CD GLN B 252 75.534 -57.055 -2.731 1.00 46.86 C | ATOM 2351 N LEU B 259 95.078 -49.769 -8.570 1.00 51.23 N |
| ANISOU 2306 CD GLN B 252 5017 5227 7563 142 240 334 C | ANISOU 2351 N LEU B 259 6239 5806 7419 -220 748 -583 N |
| ATOM 2307 OE1 GLN B 252 75.869 -58.165 -3.150 1.00 48.46 O | ATOM 2352 CA LEU B 259 94.884 -48.583 -7.778 1.00 45.06 C |
| ANISOU 2307 OE1 GLN B 252 5439 5133 6550 -54 495 -423 C | ANISOU 2352 CA LEU B 259 4977 4742 3737 497 195 250 C |
| | ATOM 2397 C PRO B 264 104.956 -35.763 -2.580 1.00 40.47 C |
| ATOM 2353 CB LEU B 259 93.711 -48.845 -6.845 1.00 51.48 C | ATOM 2398 O PRO B 264 104.956 -35.763 -2.580 1.00 40.47 C |
| ANISOU 2353 CB LEU B 259 6181 5954 7425 99 409 -302 C | ANISOU 2398 O PRO B 264 5633 5403 4343 500 139 210 O |
| ATOM 2354 CG LEU B 259 92.928 -47.726 -6.191 1.00 49.50 C | ATOM 2399 N LEU B 265 103.175 -37.107 -2.903 1.00 34.84 N |
| ANISOU 2354 CG LEU B 259 5895 5791 7122 191 184 -215 C | ANISOU 2399 N LEU B 265 4814 4750 3675 542 195 180 N |
| ATOM 2355 CD1 LEU B 259 92.333 -46.868 -7.271 1.00 59.28 C | ATOM 2400 CA LEU B 265 102.416 -36.503 -1.811 1.00 43.01 C |
| ANISOU 2355 CD1 LEU B 259 7220 7035 8268 -14 2 -214 C | ANISOU 2400 CA LEU B 265 5720 5939 4682 590 171 14 C |
| ATOM 2356 CD2 LEU B 259 91.833 -48.350 -5.349 1.00 57.62 C | ATOM 2401 CB LEU B 265 100.955 -36.949 -1.840 1.00 40.16 C |
| ANISOU 2356 CD2 LEU B 259 6844 6821 8228 294 194 -154 C | ANISOU 2401 CB LEU B 265 5196 5689 4374 594 208 -169 C |
| ATOM 2357 C LEU B 259 96.127 -48.317 -6.947 1.00 46.73 C | ATOM 2402 CG LEU B 265 100.206 -36.452 -3.072 1.00 46.21 C |
| ANISOU 2357 C LEU B 259 5551 5350 6853 135 530 -372 C | ANISOU 2402 CG LEU B 265 5992 6294 5274 732 -6 -301 C |
| ATOM 2358 O LEU B 259 96.697 -49.243 -6.382 1.00 51.04 O | ATOM 2403 CD1 LEU B 265 98.808 -37.026 -3.111 1.00 46.11 C |
| ANISOU 2358 O LEU B 259 5976 5804 7613 249 683 -333 O | ANISOU 2403 CD1 LEU B 265 5733 6429 5359 730 29 -537 C |
| ATOM 2359 N GLU B 260 96.544 -47.059 -6.864 1.00 42.49 N | ATOM 2404 CD2 LEU B 265 100.149 -34.926 -3.083 1.00 48.20 C |
| ANISOU 2359 N GLU B 260 5043 4910 6191 153 371 -344 N | ANISOU 2404 CD2 LEU B 265 6313 6410 5589 905 -266 -461 C |
| ATOM 2360 CA GLU B 260 97.584 -46.684 -5.914 1.00 52.74 C | ATOM 2405 C LEU B 265 103.060 -36.815 -0.457 1.00 29.42 C |
| ANISOU 2360 CA GLU B 260 6244 6253 7540 326 366 -270 C | ANISOU 2405 C LEU B 265 3967 4371 2839 503 264 99 C |
| ATOM 2361 CB GLU B 260 98.954 -47.186 -6.367 1.00 53.94 C | ATOM 2406 O LEU B 265 102.961 -36.041 0.495 1.00 39.52 O |
| ANISOU 2361 CB GLU B 260 6367 6316 7812 289 553 -341 C | ANISOU 2406 O LEU B 265 5198 5769 4048 504 251 -28 O |
| ATOM 2362 CG GLU B 260 99.379 -46.736 -7.745 1.00 60.18 C | ATOM 2407 N ILE B 266 103.720 -37.964 -0.385 1.00 40.28 N |
| ANISOU 2362 CG GLU B 260 7290 7113 8464 49 593 -514 C | ANISOU 2407 N ILE B 266 5399 5715 4192 435 317 299 N |
| ATOM 2363 CD GLU B 260 100.622 -47.460 -8.207 1.00 88.97 C | ATOM 2408 CA ILE B 266 104.473 -38.355 0.802 1.00 40.42 C |
| ANISOU 2363 CD GLU B 260 10872 10636 12296 -12 859 -655 C | ANISOU 2408 CA ILE B 266 5469 5799 4089 373 287 424 C |

TABLE 9-continued

DMXAA-hSTING$^{S162A/G230I/Q266I}$ complex

| ATOM 2364 OE1 GLU B 260 100.622 −48.712 −8.179 1.00 98.16 O
| ANISOU 2364 OE1 GLU B 260 11930 11637 13730 3 1076 −712 O
| ATOM 2365 OE2 GLU B 260 101.606 −46.778 −8.564 1.00 96.06 O
| ANISOU 2365 OE2 GLU B 260 11798 11579 13123 −72 860 −714 O
| ATOM 2366 C GLU B 260 97.634 −45.186 −5.633 1.00 49.13 C
| ANISOU 2366 C GLU B 260 5805 5909 6953 357 164 −248 C
| ATOM 2367 O GLU B 260 97.057 −44.384 −6.361 1.00 42.11 O
| ANISOU 2367 O GLU B 260 4991 5027 5983 235 19 −275 O
| ATOM 2368 N TYR B 261 98.324 −44.832 −4.555 1.00 43.08 N
| ANISOU 2368 N TYR B 261 4945 5225 6197 497 147 −179 N
| ATOM 2369 CA TYR B 261 98.510 −43.445 −4.176 1.00 34.37 C
| ANISOU 2369 CA TYR B 261 3831 4217 5010 525 2 −198 C
| ATOM 2370 CB TYR B 261 98.760 −43.330 −2.683 1.00 39.73 C
| ANISOU 2370 CB TYR B 261 4387 5041 5667 630 7 −134 C
| ATOM 2371 CG TYR B 261 97.520 −43.403 −1.831 1.00 54.69 C
| ANISOU 2371 CG TYR B 261 6211 7010 7561 645 −8 −152 C
| ATOM 2372 CD1 TYR B 261 96.721 −42.276 −1.642 1.00 45.87 C
| ANISOU 2372 CD1 TYR B 261 5057 5906 6466 630 −93 −285 C
| ATOM 2373 CE1 TYR B 261 95.584 −42.332 −0.853 1.00 56.76 C
| ANISOU 2373 CE1 TYR B 261 6344 7342 7878 624 −65 −353 C
| ATOM 2374 CZ TYR B 261 95.238 −43.527 −0.237 1.00 54.20 C
| ANISOU 2374 CZ TYR B 261 5989 7100 7503 622 20 −252 C
| ATOM 2375 OH TYR B 261 94.115 −43.592 0.550 1.00 58.38 O
| ANISOU 2375 OH TYR B 261 6429 7714 8039 586 61 −334 O
| ATOM 2376 CE2 TYR B 261 96.019 −44.660 −0.409 1.00 55.68 C
| ANISOU 2376 CE2 TYR B 261 6207 7266 7683 643 71 −73 C
| ATOM 2377 CD2 TYR B 261 97.154 −44.593 −1.201 1.00 57.17 C
| ANISOU 2377 CD2 TYR B 261 6462 7361 7899 660 71 −41 C
| ATOM 2378 C TYR B 261 99.690 −42.835 −4.922 1.00 39.48 C
| ANISOU 2378 C TYR B 261 4543 4853 5605 462 −12 −235 C
| ATOM 2379 O TYR B 261 100.658 −43.526 −5.243 1.00 44.83 O
| ANISOU 2379 O TYR B 261 5221 5482 6329 446 128 −237 O
| ATOM 2380 N ALA B 262 99.602 −41.534 −5.184 1.00 38.29 N
| ANISOU 2380 N ALA B 262 4416 4726 5406 419 −175 −266 N
| ATOM 2381 CA ALA B 262 100.711 −40.792 −5.777 1.00 36.25 C
| ANISOU 2381 CA ALA B 262 4210 4484 5080 353 −218 −284 C
| ATOM 2382 CB ALA B 262 100.226 −39.478 −6.349 1.00 33.76 C
| ANISOU 2382 CB ALA B 262 3910 4144 4774 253 −441 −274 C
| ATOM 2383 C ALA B 262 101.788 −40.545 −4.727 1.00 43.22 C
| ANISOU 2383 C ALA B 262 5013 5456 5953 488 −173 −258 C
| ATOM 2384 O ALA B 262 101.588 −39.777 −3.791 1.00 40.65 O
| ANISOU 2384 O ALA B 262 4611 5211 5625 559 −245 −270 O
| ATOM 2385 N THR B 263 102.935 −41.191 −4.896 1.00 38.65 N
| ANISOU 2385 N THR B 263 5349 5034 4300 356 491 413 N
| ATOM 2386 CA THR B 263 104.028 −41.086 −3.928 1.00 42.76 C
| ANISOU 2386 CA THR B 263 5842 5580 4824 397 473 492 C
| ATOM 2387 CB THR B 263 105.189 −42.018 −4.288 1.00 38.33 C
| ANISOU 2387 CB THR B 263 5272 4888 4404 428 499 529 C
| ATOM 2388 OG1 THR B 263 105.640 −41.737 −5.620 1.00 43.17 O
| ANISOU 2388 OG1 THR B 263 5897 5442 5063 377 586 411 O
| ATOM 2389 CG2 THR B 263 104.745 −43.451 −4.179 1.00 30.88 C
| ANISOU 2389 CG2 THR B 263 4395 3835 3502 403 510 613 C
| ATOM 2390 C THR B 263 104.604 −39.697 −3.620 1.00 35.14 C
| ANISOU 2390 C THR B 263 4863 4671 3817 436 403 439 C
| ATOM 2391 O THR B 263 105.086 −39.485 −2.507 1.00 35.41 O
| ANISOU 2391 O THR B 263 4855 4786 3813 460 358 477 O
| ATOM 2392 N PRO B 264 104.596 −38.759 −4.593 1.00 31.58 N
| ANISOU 2392 N PRO B 264 4508 4147 3343 410 368 361 N
| ATOM 2393 CA PRO B 264 105.191 −37.467 −4.231 1.00 34.29 C
| ANISOU 2393 CA PRO B 264 4893 4500 3636 406 296 319 C
| ATOM 2394 CB PRO B 264 105.153 −36.675 −5.541 1.00 28.58 C
| ANISOU 2394 CB PRO B 264 4414 3609 2836 301 238 278 C
| ATOM 2395 CG PRO B 264 105.182 −37.709 −6.602 1.00 32.01 C
| ANISOU 2395 CG PRO B 264 4888 3991 3285 211 358 294 C
| ATOM 2396 CD PRO B 264 104.346 −38.840 −6.043 1.00 30.64 C
| ANISOU 2396 CD PRO B 264 4538 3900 3202 330 379 329 C
| ATOM 2397 C PRO B 264 104.419 −36.711 −3.159 1.00 35.41 C
| ANISOU 2442 CA ALA B 270 5503 6202 3670 298 −114 209 C
| ATOM 2443 CB ALA B 270 108.351 −35.815 4.305 1.00 37.17 C
| ANISOU 2443 CB ALA B 270 5055 5651 3417 379 −233 385 C
| ATOM 2444 C ALA B 270 107.990 −33.411 4.893 1.00 38.88 C
| ANISOU 2444 C ALA B 270 5248 5998 3528 318 −168 43 C
| ATOM 2445 O ALA B 270 108.531 −32.983 5.903 1.00 44.00 O
| ANISOU 2445 O ALA B 270 5925 6762 4047 253 −267 −1 O
| ATOM 2446 N MET B 271 107.913 −32.705 3.774 1.00 30.86 N
| ANISOU 2446 N MET B 271 4215 4828 2681 370 −125 −41 N
| ATOM 2447 CA MET B 271 108.488 −31.375 3.711 1.00 35.37 C
| ANISOU 2447 CA MET B 271 4823 5330 3286 331 −181 −183 C
| ATOM 2409 CB ILE B 266 105.012 −39.777 0.669 1.00 40.60 C
| ANISOU 2409 CB ILE B 266 5584 5688 4154 358 251 621 C
| ATOM 2410 CG1 ILE B 266 103.855 −40.765 0.694 1.00 45.98 C
| ANISOU 2410 CG1 ILE B 266 6341 6380 4748 210 371 652 C
| ATOM 2411 CD1 ILE B 266 104.236 −42.162 0.275 1.00 37.46 C
| ANISOU 2411 CD1 ILE B 266 5389 5087 3758 215 319 820 C
| ATOM 2412 CG2 ILE B 266 105.999 −40.102 1.790 1.00 36.79 C
| ANISOU 2412 CG2 ILE B 266 5202 5192 3585 358 73 758 C
| ATOM 2413 C ILE B 266 105.619 −37.375 1.041 1.00 31.18 C
| ANISOU 2413 C ILE B 266 4278 4623 2946 438 178 400 C
| ATOM 2414 O ILE B 266 105.906 −36.975 2.165 1.00 39.97 O
| ANISOU 2414 O ILE B 266 5410 5850 3927 397 121 388 O
| ATOM 2415 N THR B 267 106.253 −36.967 −0.045 1.00 30.03 N
| ANISOU 2415 N THR B 267 4114 4354 2942 484 170 370 N
| ATOM 2416 CA THR B 267 107.335 −36.007 0.044 1.00 37.75 C
| ANISOU 2416 CA THR B 267 5069 5330 3946 470 112 306 C
| ATOM 2417 CB THR B 267 108.117 −35.941 −1.260 1.00 36.41 C
| ANISOU 2417 CB THR B 267 4901 5041 3892 405 183 264 C
| ATOM 2418 OG1 THR B 267 108.875 −37.145 −1.394 1.00 46.07 O
| ANISOU 2418 OG1 THR B 267 5991 6258 5257 446 202 295 O
| ATOM 2419 CG2 THR B 267 109.058 −34.737 −1.262 1.00 29.75 C
| ANISOU 2419 CG2 THR B 267 4071 4199 3034 290 173 151 C
| ATOM 2420 C THR B 267 106.841 −34.614 0.472 1.00 36.14 C
| ANISOU 2420 C THR B 267 4920 5156 3655 467 64 171 C
| ATOM 2421 O THR B 267 107.432 −33.979 1.349 1.00 45.07 O
| ANISOU 2421 O THR B 267 6030 6369 4727 441 4 121 O
| ATOM 2422 N LEU B 268 105.744 −34.164 −0.130 1.00 33.93 N
| ANISOU 2422 N LEU B 268 4705 4792 3394 518 49 81 N
| ATOM 2423 CA LEU B 268 105.091 −32.917 0.275 1.00 32.75 C
| ANISOU 2423 CA LEU B 268 4586 4624 3233 587 −54 −113 C
| ATOM 2424 CB LEU B 268 103.822 −32.654 −0.541 1.00 28.79 C
| ANISOU 2424 CB LEU B 268 4248 4118 3992 2831 712 −162 −244 C
| ATOM 2425 CG LEU B 268 103.999 −32.226 −1.991 1.00 41.80 C
| ANISOU 2425 CG LEU B 268 6034 5345 4504 693 −309 −167 C
| ATOM 2426 CD1 LEU B 268 102.649 −31.984 −2.643 1.00 43.30 C
| ANISOU 2426 CD1 LEU B 268 6250 5396 4804 870 −529 −318 C
| ATOM 2427 CD2 LEU B 268 104.851 −30.970 −2.068 1.00 44.86 C
| ANISOU 2427 CD2 LEU B 268 6664 5547 4832 603 −421 −172 C
| ATOM 2428 C LEU B 268 104.723 −32.933 1.751 1.00 43.95 C
| ANISOU 2428 C LEU B 268 5872 6282 4546 574 5 −226 C
| ATOM 2429 O LEU B 268 104.898 −31.943 2.462 1.00 48.04 O
| ANISOU 2429 O LEU B 268 6398 6832 5022 579 −51 −372 O
| ATOM 2430 N PHE B 269 104.189 −34.053 2.214 1.00 33.23 N
| ANISOU 2430 N PHE B 269 4436 5081 3107 507 130 −172 N
| ATOM 2431 CA PHE B 269 103.848 −34.146 3.622 1.00 35.51 C
| ANISOU 2431 CA PHE B 269 4683 5609 3199 380 226 −272 C
| ATOM 2432 CB PHE B 269 103.114 −35.444 3.925 1.00 39.82 C
| ANISOU 2432 CB PHE B 269 5232 6281 3616 216 385 −202 C
| ATOM 2433 CG PHE B 269 102.636 −35.524 5.338 1.00 49.03 C
| ANISOU 2433 CG PHE B 269 6426 7709 4493 −29 536 −337 C
| ATOM 2434 CD1 PHE B 269 101.497 −34.838 5.728 1.00 48.61 C
| ANISOU 2434 CD1 PHE B 269 6162 7857 4449 −71 697 −758 C
| ATOM 2435 CE1 PHE B 269 101.049 −34.891 7.029 1.00 42.52 C
| ANISOU 2435 CE1 PHE B 269 5415 7374 3367 −380 909 −950 C
| ATOM 2436 CZ PHE B 269 101.749 −35.641 7.965 1.00 50.97 C
| ANISOU 2436 CZ PHE B 269 6821 8484 4059 −659 897 −642 C
| ATOM 2437 CE2 PHE B 269 102.897 −36.331 7.585 1.00 50.48 C
| ANISOU 2437 CE2 PHE B 269 6984 8167 4027 −547 638 −193 C
| ATOM 2438 CD2 PHE B 269 103.336 −36.261 6.279 1.00 40.10 C
| ANISOU 2438 CD2 PHE B 269 5545 6615 3077 −230 492 −83 C
| ATOM 2439 C PHE B 269 105.104 −34.057 4.492 1.00 34.85 C
| ANISOU 2439 C PHE B 269 4703 5569 2972 305 138 −129 C
| ATOM 2440 O PHE B 269 105.151 −33.328 5.481 1.00 42.26 O
| ANISOU 2440 O PHE B 269 5646 6639 3772 240 135 −279 O
| ATOM 2441 N ALA B 270 106.124 −34.814 4.114 1.00 35.80 N
| ANISOU 2441 N ALA B 270 4873 5581 3148 324 47 114 N
| ATOM 2442 CA ALA B 270 107.367 −34.807 4.867 1.00 40.47 C
| ANISOU 2487 N GLN B 276 6058 7444 4534 −229 −856 −781 N
| ATOM 2488 CA GLN B 276 115.070 −27.732 7.277 1.00 42.29 C
| ANISOU 2488 CA GLN B 276 5217 6738 4115 −355 −805 −896 C
| ATOM 2489 CB GLN B 276 115.999 −28.931 7.247 1.00 54.96 C
| ANISOU 2489 CB GLN B 276 6516 8463 5903 −244 −967 −863 C
| ATOM 2490 CG GLN B 276 117.382 −28.668 6.744 1.00 74.49 C
| ANISOU 2490 CG GLN B 276 8654 11017 8632 −404 −950 −1128 C
| ATOM 2491 CD GLN B 276 118.296 −29.842 7.011 1.00 92.77 C
| ANISOU 2491 CD GLN B 276 10604 13458 11185 −199 −1234 −1186 C
| ATOM 2492 OE1 GLN B 276 117.839 −30.923 7.389 1.00100.03 O
| ANISOU 2492 OE1 GLN B 276 11614 14330 12062 54 −1437 −957 O

TABLE 9-continued

DMXAA-hSTING$^{S162A/G230I/Q266I}$ complex

| | |
|---|---|
| ATOM 2448 CB MET B 271 108.464 −30.821 2.292 1.00 30.14 C | ATOM 2493 NE2 GLN B 276 119.595 −29.637 6.827 1.00 96.97 N |
| ANISOU 2448 CB MET B 271 4275 4426 2749 316 −164 −199 C | ANISOU 2493 NE2 GLN B 276 10724 14136 11985 −315 −1276 −1528 N |
| ATOM 2449 CG MET B 271 109.551 −31.419 1.397 1.00 26.56 C | ATOM 2494 C GLN B 276 114.547 −27.452 5.866 1.00 51.26 C |
| ANISOU 2449 CG MET B 271 3767 3935 2391 212 −94 −108 C | ANISOU 2494 C GLN B 276 6495 7638 5343 −415 −563 −861 C |
| ATOM 2450 SD MET B 271 109.342 −30.946 −0.321 1.00 39.72 S | ATOM 2495 O GLN B 276 115.208 −26.810 5.054 1.00 52.96 O |
| ANISOU 2450 SD MET B 271 5687 5328 4076 87 −36 −101 S | ANISOU 2495 O GLN B 276 6718 7759 5644 −651 −442 −985 O |
| ATOM 2451 CE MET B 271 110.352 −29.479 −0.419 1.00 34.88 C | ATOM 2496 N ALA B 277 113.348 −27.948 5.586 1.00 42.04 N |
| ANISOU 2451 CE MET B 271 5256 4599 3396 −184 −51 −227 C | ANISOU 2496 N ALA B 277 5470 6378 4125 −245 −504 −702 N |
| ATOM 2452 C MET B 271 107.820 −30.413 4.685 1.00 40.64 C | ATOM 2497 CA ALA B 277 112.751 −27.840 4.266 1.00 37.47 C |
| ANISOU 2452 C MET B 271 5525 6078 3840 336 −200 −391 C | ANISOU 2497 CA ALA B 277 5056 5568 3611 −263 −358 −641 C |
| ATOM 2453 O MET B 271 108.469 −29.522 5.233 1.00 37.95 O | ATOM 2498 CB ALA B 277 111.755 −28.967 4.041 1.00 32.84 C |
| ANISOU 2453 O MET B 271 5212 5753 3456 269 −271 −498 O | ANISOU 2498 CB ALA B 277 4459 4988 3030 −53 −326 −467 C |
| ATOM 2454 N SER B 272 106.526 −30.597 4.913 1.00 35.02 N | ATOM 2499 C ALA B 277 112.081 −26.488 4.034 1.00 47.35 C |
| ANISOU 2454 N SER B 272 4775 5437 3093 396 −120 −507 N | ANISOU 2499 C ALA B 277 6623 6567 4801 −321 −377 −738 C |
| ATOM 2455 CA SER B 272 105.831 −29.730 5.857 1.00 36.53 C | ATOM 2500 O ALA B 277 111.840 −26.100 2.896 1.00 54.14 O |
| ANISOU 2455 CA SER B 272 4930 5741 3207 398 −94 −813 C | ANISOU 2500 O ALA B 277 7722 7166 5683 −409 −338 −701 O |
| ATOM 2456 CB SER B 272 104.319 −29.727 5.627 1.00 37.08 C | ATOM 2501 N GLY B 278 111.765 −25.786 5.118 1.00 63.33 N |
| ANISOU 2456 CB SER B 272 4869 5836 3385 512 −13 −1068 C | ANISOU 2501 N GLY B 278 8686 8641 6737 −270 −472 −876 N |
| ATOM 2457 OG SER B 272 103.752 −30.989 5.911 1.00 49.49 O | ATOM 2502 CA GLY B 278 111.169 −24.460 5.032 1.00 59.75 C |
| ANISOU 2457 OG SER B 272 6365 7613 4825 389 166 −983 O | ANISOU 2502 CA GLY B 278 8515 7909 6279 −270 −556 −1035 C |
| ATOM 2458 C SER B 272 106.151 −30.095 7.315 1.00 34.75 C | ATOM 2503 C GLY B 278 109.834 −24.449 4.307 1.00 57.23 C |
| ANISOU 2458 C SER B 272 4719 5795 2689 211 −36 −806 C | ANISOU 2503 C GLY B 278 8354 7353 6039 −50 −612 −1016 C |
| ATOM 2459 O SER B 272 105.932 −29.294 8.217 1.00 52.91 O | ATOM 2504 O GLY B 278 109.608 −23.669 3.387 1.00 65.52 O |
| ANISOU 2459 O SER B 272 7011 8216 4877 152 −6 −1070 O | ANISOU 2504 O GLY B 278 9728 8031 7134 −87 −731 −1019 O |
| ATOM 2460 N GLN B 273 106.656 −31.303 7.551 1.00 40.74 N | ATOM 2505 N PHE B 279 108.933 −25.316 4.747 1.00 62.01 N |
| ANISOU 2460 N GLN B 273 5542 6628 3310 113 −55 −518 N | ANISOU 2505 N PHE B 279 8755 8162 6644 156 −558 −1012 N |
| ATOM 2461 CA GLN B 273 106.995 −31.709 8.917 1.00 35.92 C | ATOM 2506 CA PHE B 279 107.711 −25.603 4.016 1.00 44.23 C |
| ANISOU 2461 CA GLN B 273 5066 6221 2361 −90 −95 −455 C | ANISOU 2506 CA PHE B 279 6537 5768 4501 363 −597 −1013 C |
| ATOM 2462 CB GLN B 273 106.833 −33.215 9.119 1.00 41.55 C | ATOM 2507 CB PHE B 279 107.890 −26.950 3.331 1.00 55.14 C |
| ANISOU 2462 CB GLN B 273 5931 6960 2898 −210 −97 −177 C | ANISOU 2507 CB PHE B 279 7811 7261 5878 332 −468 −750 C |
| ATOM 2463 CG GLN B 273 105.458 −33.749 8.785 1.00 55.27 C | ATOM 2508 CG PHE B 279 106.993 −27.166 2.160 1.00 54.39 C |
| ANISOU 2463 CG GLN B 273 7620 8756 4624 −284 166 −270 C | ANISOU 2508 CG PHE B 279 7832 6949 5885 456 −536 −696 C |
| ATOM 2464 CD GLN B 273 104.368 −33.161 9.664 1.00 82.05 C | ATOM 2509 CD1 PHE B 279 107.236 −26.520 0.960 1.00 55.03 C |
| ANISOU 2464 CD GLN B 273 10955 12415 7805 −488 424 −653 C | ANISOU 2509 CD1 PHE B 279 8255 6678 5977 357 −665 −618 C |
| ATOM 2465 OE1 GLN B 273 103.658 −32.234 9.261 1.00 80.01 O | ATOM 2510 CE1 PHE B 279 106.423 −26.732 −0.132 1.00 48.80 C |
| ANISOU 2465 OE1 GLN B 273 10450 12168 7780 −335 525 −1008 O | ANISOU 2510 CE1 PHE B 279 7625 5673 5243 460 −789 −554 C |
| ATOM 2466 NE2 GLN B 273 104.230 −33.698 10.877 1.00 86.40 N | ATOM 2511 CZ PHE B 279 105.356 −27.621 −0.033 1.00 53.59 C |
| ANISOU 2466 NE2 GLN B 273 11751 13154 7923 −842 508 −612 N | ANISOU 2511 CZ PHE B 279 6448 5944 678 −756 −601 C |
| ATOM 2467 C GLN B 273 108.418 −31.303 9.285 1.00 37.30 C | ATOM 2512 CE2 PHE B 279 105.113 −28.285 1.162 1.00 50.79 C |
| ANISOU 2467 C GLN B 273 5272 6369 2532 −85 −337 −374 C | ANISOU 2512 CE2 PHE B 279 7262 6458 5578 733 −570 −692 C |
| ATOM 2468 O GLN B 273 108.720 −31.045 10.443 1.00 50.96 O | ATOM 2513 CD2 PHE B 279 105.934 −28.056 2.246 1.00 49.48 C |
| ANISOU 2468 O GLN B 273 7113 8255 3996 −235 −419 −432 O | ANISOU 2513 CD2 PHE B 279 7015 6476 5308 616 −474 −720 C |
| ATOM 2469 N TYR B 274 109.298 −31.267 8.292 1.00 46.42 N | ATOM 2514 C PHE B 279 106.577 −25.691 5.020 1.00 45.23 C |
| ANISOU 2469 N TYR B 274 6317 7350 3971 50 −441 −279 N | ANISOU 2514 C PHE B 279 6456 6100 4629 538 −556 −1270 C |
| ATOM 2470 CA TYR B 274 110.703 −30.974 8.546 1.00 37.77 C | ATOM 2515 O PHE B 279 106.591 −26.547 5.898 1.00 58.42 O |
| ANISOU 2470 CA TYR B 274 5158 6261 2933 38 −656 −269 C | ANISOU 2515 O PHE B 279 7940 8107 6151 468 −397 −1233 O |
| ATOM 2471 CB TYR B 274 111.619 −31.813 7.653 1.00 39.92 C | ATOM 2516 N SER B 280 105.603 −24.798 4.897 1.00 40.10 N |
| ANISOU 2471 CB TYR B 274 5281 6420 3469 148 −758 −128 C | ANISOU 2516 N SER B 280 5857 5235 4145 744 −716 −1564 N |
| ATOM 2472 CG TYR B 274 111.542 −33.285 7.976 1.00 47.25 C | ATOM 2517 CA SER B 280 104.515 −24.734 5.862 1.00 37.26 C |
| ANISOU 2472 CG TYR B 274 6300 7331 4322 208 −905 108 C | ANISOU 2517 CA SER B 280 5230 5103 3824 880 −632 −1954 C |
| ATOM 2473 CD1 TYR B 274 111.898 −33.749 9.238 1.00 60.08 C | ATOM 2518 CB SER B 280 104.022 −23.296 6.025 1.00 53.38 C |
| ANISOU 2473 CD1 TYR B 274 8098 9035 5697 151 −1188 216 C | ANISOU 2518 CB SER B 280 7352 6860 6071 1082 −868 −2370 C |
| ATOM 2474 CE1 TYR B 274 111.814 −35.088 9.549 1.00 72.23 C | ATOM 2519 OG SER B 280 103.224 −22.914 4.923 1.00 60.97 O |
| ANISOU 2474 CE1 TYR B 274 9841 10474 7129 178 −1389 464 C | ANISOU 2519 OG SER B 280 8427 7430 7310 1361 −1175 −2449 O |
| ATOM 2475 CZ TYR B 274 111.364 −35.985 8.598 1.00 70.01 C | ATOM 2520 C SER B 280 103.347 −25.629 5.454 1.00 40.92 C |
| ANISOU 2475 CZ TYR B 274 9535 10038 7027 273 −1265 577 C | ANISOU 2520 C SER B 280 5468 5685 4395 1017 −553 −2018 C |
| ATOM 2476 OH TYR B 274 111.286 −37.318 8.921 1.00 75.36 O | ATOM 2521 O SER B 280 103.287 −26.146 4.337 1.00 58.09 O |
| ANISOU 2476 OH TYR B 274 10474 10559 7600 284 −1492 827 O | ANISOU 2521 O SER B 280 7734 7693 6643 1067 −634 −1767 O |
| ATOM 2477 CE2 TYR B 274 110.993 −35.550 7.337 1.00 55.52 C | ATOM 2522 N ARG B 281 102.396 −25.774 6.369 1.00 58.87 N |
| ANISOU 2477 CE2 TYR B 274 7480 8171 5446 334 −953 450 C | ANISOU 2522 N ARG B 281 8326 8383 5659 1120 −812 −887 N |
| ATOM 2478 CD2 TYR B 274 111.080 −34.204 7.033 1.00 50.56 C | ATOM 2523 CA ARG B 281 101.235 −26.607 6.123 1.00 70.75 C |
| ANISOU 2478 CD2 TYR B 274 6704 7619 4888 297 −794 232 C | ANISOU 2523 CA ARG B 281 9909 9979 6992 1011 −459 −575 C |
| ATOM 2479 C TYR B 274 111.031 −29.494 8.423 1.00 36.33 C | ATOM 2524 CB ARG B 281 100.511 −26.891 7.427 1.00 86.15 C |
| ANISOU 2479 C TYR B 274 4934 6035 2833 −8 −625 −508 C | ANISOU 2524 CB ARG B 281 12102 12238 8391 1134 −289 −585 C |
| ATOM 2480 O TYR B 274 110.680 −28.849 7.442 1.00 46.63 O | ATOM 2525 CG ARG B 281 100.183 −28.348 7.605 1.00 101.97 C |
| ANISOU 2480 O TYR B 274 6245 7164 4306 30 −509 −590 O | ANISOU 2525 CG ARG B 281 14348 14284 10112 1060 −6 −192 C |
| ATOM 2481 N SER B 275 111.722 −28.968 9.426 1.00 46.56 N | ATOM 2526 CD ARG B 281 98.703 −28.489 7.883 1.00 107.82 C |
| ANISOU 2481 N SER B 275 4976 6192 2721 −112 −771 −610 N | ANISOU 2526 CD ARG B 281 15104 15175 10687 949 478 −209 C |
| ATOM 2482 CA SER B 275 111.990 −27.538 9.497 1.00 48.21 C | ATOM 2527 NE ARG B 281 98.343 −29.316 9.039 1.00 113.76 N |
| ANISOU 2482 CA SER B 275 6464 7618 4235 −198 −751 −857 C | ANISOU 2527 NE ARG B 281 16275 16081 10868 994 793 −33 N |
| ATOM 2483 CB SER B 275 112.393 −27.148 10.919 1.00 43.66 C | ATOM 2528 CZ ARG B 281 98.924 −29.303 10.240 1.00 119.33 C |
| ANISOU 2483 CB SER B 275 5947 7044 3399 −330 −897 −978 C | ANISOU 2528 CZ ARG B 281 17373 16937 11029 1244 616 −36 C |
| ATOM 2484 OG SER B 275 113.543 −27.860 11.314 1.00 61.31 O | ATOM 2529 NH1 ARG B 281 98.459 −30.105 11.188 1.00 126.50 N |
| ANISOU 2484 OG SER B 275 8086 9584 5624 −342 −1166 −848 O | ANISOU 2529 NH1 ARG B 281 18751 17936 11376 1272 1003 182 N |
| ATOM 2485 C SER B 275 113.071 −27.096 8.506 1.00 53.01 C | ATOM 2530 NH2 ARG B 281 99.958 −28.514 10.515 1.00 113.49 N |
| ANISOU 2485 C SER B 275 6956 8087 5099 −258 −765 −890 C | ANISOU 2530 NH2 ARG B 281 16584 16246 10290 1478 80 −280 N |
| ATOM 2486 O SER B 275 113.089 −25.957 8.043 1.00 43.72 O | ATOM 2531 C ARG B 281 100.293 −25.943 5.128 1.00 68.75 C |

TABLE 9-continued

DMXAA-hSTING$^{S162A/G230I/Q266I}$ complex

| ANISOU 2486 O SER B 275 5879 6741 3991 -355 -697 -1041 O | ANISOU 2531 C ARG B 281 9456 9608 7057 907 -283 -635 C |
| --- | --- |
| ATOM 2487 N GLN B 276 113.972 -28.013 8.186 1.00 47.47 N | ATOM 2532 O ARG B 281 99.464 -26.594 4.497 1.00 72.07 O |
| ATOM 2532 O ARG B 281 99.821 10037 7527 794 -39 -450 O | ANISOU 2577 O GLU B 286 6905 5862 6001 661 -77 150 O |
| ATOM 2533 N GLU B 282 100.433 -24.633 4.991 1.00 69.45 N | ATOM 2578 N GLN B 287 100.606 -26.493 -2.857 1.00 42.52 N |
| ANISOU 2533 N GLU B 282 9441 9570 7375 977 -425 -930 N | ANISOU 2578 N GLN B 287 5937 5034 5183 385 -48 154 N |
| ATOM 2534 CA GLU B 282 99.634 -23.881 4.044 1.00 59.33 C | ATOM 2579 CA GLN B 287 101.494 -27.274 -3.706 1.00 39.34 C |
| ANISOU 2534 CA GLU B 282 8047 8124 6370 971 -337 -992 C | ANISOU 2579 CA GLN B 287 5530 4488 4929 178 18 324 C |
| ATOM 2535 CB GLU B 282 99.539 -22.410 4.446 1.00 67.43 C | ATOM 2580 CB GLN B 287 102.814 -27.553 -2.994 1.00 39.44 C |
| ANISOU 2535 CB GLU B 282 9028 9077 7517 1114 -450 -1367 C | ANISOU 2580 CB GLN B 287 5491 4427 5068 24 -35 286 C |
| ATOM 2536 CG GLU B 282 98.709 -22.168 5.693 1.00 86.43 C | ATOM 2581 CG GLN B 287 103.701 -26.323 -2.893 1.00 43.54 C |
| ANISOU 2536 CG GLU B 282 11418 11822 9600 1236 -383 -1621 C | ANISOU 2581 CG GLN B 287 6111 4651 5780 7 -69 84 C |
| ATOM 2537 CD GLU B 282 99.280 -22.849 6.933 1.00 95.29 C | ATOM 2582 CD GLN B 287 104.124 -25.806 -4.259 1.00 50.36 C |
| ANISOU 2537 CD GLU B 282 12688 13223 10295 1269 -431 -1611 C | ANISOU 2582 CD GLN B 287 7154 5142 6838 -109 105 142 C |
| ATOM 2538 OE1 GLU B 282 98.500 -23.489 7.671 1.00 99.31 O | ATOM 2583 OE1 GLN B 287 104.876 -26.471 -4.972 1.00 68.26 O |
| ANISOU 2538 OE1 GLU B 282 13303 14017 10415 1275 -207 -1555 O | ANISOU 2583 OE1 GLN B 287 9379 7292 9265 -315 210 215 O |
| ATOM 2539 OE2 GLU B 282 100.507 -22.753 7.154 1.00 97.80 O | ATOM 2584 NE2 GLN B 287 103.631 -24.629 -4.637 1.00 42.48 N |
| ANISOU 2539 OE2 GLU B 282 13034 13458 10669 1305 -681 -1684 O | ANISOU 2584 NE2 GLN B 287 6395 3935 5808 36 157 113 N |
| ATOM 2540 C GLU B 282 100.282 -24.002 2.682 1.00 59.46 C | ATOM 2585 C GLN B 287 100.861 -28.576 -4.183 1.00 42.81 C |
| ANISOU 2540 C GLU B 282 8057 7811 6724 847 -365 -794 C | ANISOU 2585 C GLN B 287 5803 5135 5328 118 108 452 C |
| ATOM 2541 O GLU B 282 99.603 -24.094 1.660 1.00 58.58 O | ATOM 2586 O GLN B 287 101.124 -29.034 -5.287 1.00 47.47 O |
| ANISOU 2541 O GLU B 282 7923 7609 6726 834 -269 -669 O | ANISOU 2586 O GLN B 287 6395 5626 6015 22 164 551 O |
| ATOM 2542 N ASP B 283 101.609 -24.001 2.676 1.00 58.22 N | ATOM 2587 N ALA B 288 100.028 -29.175 -3.344 1.00 45.27 N |
| ANISOU 2542 N ASP B 283 7913 7483 6723 771 -501 -819 N | ANISOU 2587 N ALA B 288 5972 5719 5509 156 167 418 N |
| ATOM 2543 CA ASP B 283 102.340 -24.235 1.449 1.00 58.57 C | ATOM 2588 CA ALA B 288 99.344 -30.405 -3.723 1.00 37.77 C |
| ANISOU 2543 CA ASP B 283 7959 7219 7074 605 -462 -653 C | ANISOU 2588 CA ALA B 288 4825 4934 4591 73 322 472 C |
| ATOM 2544 CB ASP B 283 103.848 -24.182 1.687 1.00 76.12 C | ATOM 2589 CB ALA B 288 98.655 -31.035 -2.528 1.00 34.71 C |
| ANISOU 2544 CB ASP B 283 10116 9284 9523 519 -607 -830 C | ANISOU 2589 CB ALA B 288 4354 4762 4071 51 497 443 C |
| ATOM 2545 CG ASP B 283 104.351 -22.777 1.925 1.00 96.28 C | ATOM 2590 C ALA B 288 98.343 -30.178 -4.856 1.00 29.67 C |
| ANISOU 2545 CG ASP B 283 12630 11604 12346 551 -655 -1215 C | ANISOU 2590 C ALA B 288 3708 3966 3599 219 295 335 C |
| ATOM 2546 OD1 ASP B 283 103.641 -21.819 1.550 1.00 108.82 O | ATOM 2591 O ALA B 288 98.193 -31.015 -5.739 1.00 38.34 O |
| ANISOU 2546 OD1 ASP B 283 14309 13033 14007 610 -544 -1247 O | ANISOU 2591 O ALA B 288 4665 5104 4800 145 357 356 O |
| ATOM 2547 OD2 ASP B 283 105.465 -22.636 2.483 1.00 95.53 O | ATOM 2592 N LYS B 289 97.643 -29.050 -4.810 1.00 39.21 N |
| ANISOU 2547 OD2 ASP B 283 12400 11471 12425 536 -815 -1526 O | ANISOU 2592 N LYS B 289 4990 5187 4720 467 170 155 N |
| ATOM 2548 C ASP B 283 101.959 -25.600 0.892 1.00 62.66 C | ATOM 2593 CA LYS B 289 96.711 -28.694 -5.874 1.00 35.85 C |
| ANISOU 2548 C ASP B 283 8464 7857 7485 504 -343 -322 C | ANISOU 2593 CA LYS B 289 4531 4806 4286 721 41 -14 C |
| ATOM 2549 O ASP B 283 101.898 -25.798 -0.318 1.00 64.84 O | ATOM 2594 CB LYS B 289 95.947 -27.432 -5.519 1.00 35.55 C |
| ANISOU 2549 O ASP B 283 8748 7959 7928 409 -248 -162 O | ANISOU 2594 CB LYS B 289 4570 4766 4169 1027 -121 -238 C |
| ATOM 2550 N ARG B 284 101.682 -26.532 1.796 1.00 53.69 N | ATOM 2595 CG LYS B 289 94.896 -27.584 -4.461 1.00 47.66 C |
| ANISOU 2550 N ARG B 284 7340 7005 6054 536 -323 -232 N | ANISOU 2595 CG LYS B 289 5808 6578 5722 1052 -15 -526 C |
| ATOM 2551 CA ARG B 284 101.449 -27.909 1.409 1.00 49.47 C | ATOM 2596 CD LYS B 289 94.315 -26.216 -4.150 1.00 44.17 C |
| ANISOU 2551 CA ARG B 284 6789 6540 5467 419 -175 56 C | ANISOU 2596 CD LYS B 289 5456 6090 5239 1360 -205 -762 C |
| ATOM 2552 CB ARG B 284 101.394 -28.822 2.631 1.00 52.96 C | ATOM 2597 CE LYS B 289 93.598 -26.191 -2.823 1.00 51.37 C |
| ANISOU 2552 CB ARG B 284 7364 7205 5552 478 -136 161 C | ANISOU 2597 CE LYS B 289 6139 7234 6145 1313 -39 -1030 C |
| ATOM 2553 CG ARG B 284 101.430 -30.292 2.261 1.00 45.17 C | ATOM 2598 NZ LYS B 289 93.470 -24.796 -2.308 1.00 65.38 N |
| ANISOU 2553 CG ARG B 284 6388 6191 4583 345 20 465 C | ANISOU 2598 NZ LYS B 289 8051 8904 7888 1540 -207 -1198 N |
| ATOM 2554 CD ARG B 284 101.369 -31.155 3.494 1.00 43.81 C | ATOM 2599 C LYS B 289 97.475 -28.433 -7.166 1.00 41.91 C |
| ANISOU 2554 CD ARG B 284 6474 6163 4010 437 104 620 C | ANISOU 2599 C LYS B 289 5574 5320 5030 744 -45 167 C |
| ATOM 2555 NE ARG B 284 100.024 -31.210 4.042 1.00 54.85 N | ATOM 2600 O LYS B 289 97.028 -28.769 -8.262 1.00 50.27 O |
| ANISOU 2555 NE ARG B 284 7934 7744 5163 423 459 600 N | ANISOU 2600 O LYS B 289 6602 6442 6056 869 -116 110 O |
| ATOM 2556 CZ ARG B 284 99.751 -31.465 5.313 1.00 58.27 C | ATOM 2601 N LEU B 290 98.631 -27.804 -7.012 1.00 37.60 N |
| ANISOU 2556 CZ ARG B 284 8670 8328 5143 531 599 647 C | ANISOU 2601 N LEU B 290 5300 4482 4502 623 -17 337 N |
| ATOM 2557 NH1 ARG B 284 98.489 -31.500 5.730 1.00 60.64 N | ATOM 2602 CA LEU B 290 99.471 -27.437 -8.135 1.00 41.11 C |
| ANISOU 2557 NH1 ARG B 284 8985 8770 5285 459 1012 571 N | ANISOU 2602 CA LEU B 290 6068 4614 4938 584 17 500 C |
| ATOM 2558 NH2 ARG B 284 100.739 -31.680 6.163 1.00 57.40 N | ATOM 2603 CB LEU B 290 100.554 -26.468 -7.652 1.00 49.46 C |
| ANISOU 2558 NH2 ARG B 284 8853 8228 4730 730 328 731 N | ANISOU 2603 CB LEU B 290 7362 5331 6099 463 92 547 C |
| ATOM 2559 C ARG B 284 100.186 -28.111 0.578 1.00 51.26 C | ATOM 2604 CG LEU B 290 101.642 -25.958 -8.586 1.00 57.21 C |
| ANISOU 2559 C ARG B 284 6917 6819 5739 387 33 118 C | ANISOU 2604 CG LEU B 290 8697 5888 7153 319 269 675 C |
| ATOM 2560 O ARG B 284 100.183 -28.855 -0.410 1.00 37.73 O | ATOM 2605 CD1 LEU B 290 101.047 -25.551 -9.915 1.00 47.75 C |
| ANISOU 2560 O ARG B 284 5126 5030 4179 267 115 278 O | ANISOU 2605 CD1 LEU B 290 7877 4563 5704 587 243 779 C |
| ATOM 2561 N LEU B 285 99.099 -27.474 0.989 1.00 47.68 N | ATOM 2606 CD2 LEU B 290 102.305 -24.767 -7.920 1.00 58.82 C |
| ANISOU 2561 N LEU B 285 6430 6516 5171 513 100 -71 N | ANISOU 2606 CD2 LEU B 290 9067 5772 7510 276 337 584 C |
| ATOM 2562 CA LEU B 285 97.849 -27.670 0.278 1.00 47.01 C | ATOM 2607 C LEU B 290 100.080 -28.696 -8.753 1.00 37.59 C |
| ANISOU 2562 CA LEU B 285 6185 6516 5162 534 248 -131 C | ANISOU 2607 C LEU B 290 5468 4218 4597 315 147 610 C |
| ATOM 2563 CB LEU B 285 96.657 -27.142 1.072 1.00 50.69 C | ATOM 2608 O LEU B 290 100.195 -28.829 -9.979 1.00 35.56 O |
| ANISOU 2563 CB LEU B 285 6563 7198 5500 659 355 -418 C | ANISOU 2608 O LEU B 290 5370 3875 4265 343 173 673 O |
| ATOM 2564 CG LEU B 285 95.343 -27.319 0.305 1.00 63.69 C | ATOM 2609 N PHE B 291 100.455 -29.630 -7.889 1.00 30.95 N |
| ANISOU 2564 CG LEU B 285 7956 8941 7302 718 461 -608 C | ANISOU 2609 N PHE B 291 4346 3511 3904 82 224 627 N |
| ATOM 2565 CD1 LEU B 285 94.990 -28.802 0.131 1.00 58.52 C | ATOM 2610 CA PHE B 291 101.006 -30.906 -8.329 1.00 36.22 C |
| ANISOU 2565 CD1 LEU B 285 7154 8389 6692 510 758 -495 C | ANISOU 2610 CA PHE B 291 4822 4215 4725 -164 337 708 C |
| ATOM 2566 CD2 LEU B 285 94.223 -26.563 0.983 1.00 60.14 C | ATOM 2611 CB PHE B 291 101.418 -31.750 -7.116 1.00 34.95 C |
| ANISOU 2566 CD2 LEU B 285 7368 8664 6817 869 520 -996 C | ANISOU 2611 CB PHE B 291 4458 4138 4682 -334 382 753 C |
| ATOM 2567 C LEU B 285 97.923 -26.992 -1.089 1.00 50.47 C | ATOM 2612 CG PHE B 291 101.689 -33.187 -7.456 1.00 29.81 C |
| ANISOU 2567 C LEU B 285 6634 6727 5816 615 98 -138 C | ANISOU 2612 CG PHE B 291 3577 3539 4210 -535 493 820 C |
| ATOM 2568 O LEU B 285 97.437 -27.517 -2.091 1.00 56.28 O | ATOM 2613 CD1 PHE B 291 102.925 -33.570 -7.952 1.00 29.81 C |
| ANISOU 2568 O LEU B 285 7267 7472 6644 608 140 -96 O | ANISOU 2613 CD1 PHE B 291 3573 3345 4409 -739 522 874 C |
| ATOM 2569 N GLU B 286 98.541 -25.817 -1.110 1.00 42.73 N | ATOM 2614 CE1 PHE B 291 103.177 -34.892 -8.283 1.00 27.32 C |
| ANISOU 2569 N GLU B 286 5809 5525 4902 702 -59 -210 N | ANISOU 2614 CE1 PHE B 291 3072 3086 4223 -869 577 841 C |
| ATOM 2570 CA GLU B 286 98.719 -25.069 -2.339 1.00 52.03 C | ATOM 2615 CZ PHE B 291 102.174 -35.848 -8.115 1.00 30.12 C |

TABLE 9-continued

DMXAA-hSTING[S162A/G230I/Q266I] complex

| | |
|---|---|
| ANISOU 2570 CA GLU B 286 7140 6401 6228 788 −142 −169 C | ANISOU 2615 CZ PHE B 291 3242 3632 4571 −843 661 811 C |
| ATOM 2571 CB GLU B 286 99.444 −23.760 −2.047 1.00 57.33 C | ATOM 2616 CE2 PHE B 291 100.934 −35.468 −7.625 1.00 35.87 C |
| ANISOU 2571 CB GLU B 286 7989 6783 7008 837 −217 −285 C | ANISOU 2616 CE2 PHE B 291 3893 4520 5217 −724 737 823 C |
| ATOM 2572 CG GLU B 286 99.940 −23.030 −3.273 1.00 83.87 C | ATOM 2617 CD2 PHE B 291 100.696 −34.147 −7.301 1.00 28.40 C |
| ANISOU 2572 CG GLU B 286 11629 9716 10520 859 −192 −176 C | ANISOU 2617 CD2 PHE B 291 3159 3574 4057 −534 606 776 C |
| ATOM 2573 CD GLU B 286 100.840 −21.865 −2.916 1.00103.03 C | ATOM 2618 C PHE B 291 99.975 −9.179 1.00 42.91 C |
| ANISOU 2573 CD GLU B 286 14201 11794 13152 814 −161 −322 C | ANISOU 2618 C PHE B 291 5471 5294 5536 −66 336 609 C |
| ATOM 2574 OE1 GLU B 286 100.465 −20.710 −3.216 1.00103.70 O | ATOM 2619 O PHE B 291 100.282 −32.202 −10.238 1.00 38.58 O |
| ANISOU 2574 OE1 GLU B 286 14505 11606 13292 1010 −173 −393 O | ANISOU 2619 O PHE B 291 4910 4719 5030 −150 385 632 O |
| ATOM 2575 OE2 GLU B 286 101.920 −22.107 −2.330 1.00105.76 O | ATOM 2620 N CYS B 292 98.742 −31.686 −8.694 1.00 29.28 N |
| ANISOU 2575 OE2 GLU B 286 14428 12126 13632 603 −135 −405 O | ANISOU 2620 N CYS B 292 3559 3808 3759 112 290 433 N |
| ATOM 2576 C GLU B 286 99.518 −25.905 −3.340 1.00 50.59 C | ATOM 2621 CA CYS B 292 97.654 −32.361 −9.384 1.00 37.25 C |
| ANISOU 2576 C GLU B 286 6998 6080 6144 594 −77 74 C | ANISOU 2621 CA CYS B 292 4283 5064 4808 228 276 202 C |
| ATOM 2577 O GLU B 286 99.150 −26.033 −4.509 1.00 49.40 O | ATOM 2622 CB CYS B 292 96.392 −32.323 −8.522 1.00 30.38 C |
| ANISOU 2622 CB CYS B 292 3154 4422 3968 357 303 −64 C | ANISOU 2667 C ASP B 297 7624 5999 4605 911 105 431 C |
| ATOM 2623 SG CYS B 292 94.895 −32.847 −9.370 1.00 79.76 S | ATOM 2668 O ASP B 297 99.683 −32.037 −19.876 1.00 43.96 O |
| ANISOU 2623 SG CYS B 292 8981 10986 10340 583 230 −545 S | ANISOU 2668 O ASP B 297 7470 5518 3715 1101 82 415 O |
| ATOM 2624 C CYS B 292 97.362 −31.736 −10.756 1.00 41.82 C | ATOM 2669 N ILE B 298 100.556 −32.636 −17.900 1.00 38.67 N |
| ANISOU 2624 C CYS B 292 5080 5620 5188 527 66 119 C | ANISOU 2669 N ILE B 298 6094 4715 3883 391 385 510 N |
| ATOM 2625 O CYS B 292 97.132 −32.424 −11.750 1.00 38.69 O | ATOM 2670 CA ILE B 298 101.586 −33.463 −18.495 1.00 48.88 C |
| ANISOU 2625 O CYS B 292 4542 5349 4808 557 42 −1 O | ANISOU 2670 CA ILE B 298 7292 5937 5342 −9 675 526 C |
| ATOM 2626 N ARG B 293 97.358 −30.416 −10.808 1.00 41.69 N | ATOM 2671 CB ILE B 298 102.581 −33.962 −17.452 1.00 40.21 C |
| ANISOU 2626 N ARG B 293 5447 5433 4963 780 −89 173 N | ANISOU 2671 CB ILE B 298 5832 4677 4769 −495 896 599 C |
| ATOM 2627 CA ARG B 293 97.061 −29.738 −12.056 1.00 32.22 C | ATOM 2672 CG1 ILE B 298 103.377 −32.794 −16.890 1.00 44.24 C |
| ANISOU 2627 CA ARG B 293 4596 4158 3489 1139 −296 146 C | ANISOU 2672 CG1 ILE B 298 6739 4786 5285 −599 1050 806 C |
| ATOM 2628 CB ARG B 293 96.725 −28.284 −11.794 1.00 44.75 C | ATOM 2673 CD1 ILE B 298 104.380 −33.218 −15.841 1.00 47.74 C |
| ANISOU 2628 CB ARG B 293 6549 5558 4897 1476 −472 154 C | ANISOU 2673 CD1 ILE B 298 6823 5098 6218 −988 1172 800 C |
| ATOM 2629 CG ARG B 293 95.439 −28.153 −11.064 1.00 54.97 C | ATOM 2674 CG2 ILE B 298 103.542 −34.975 −18.072 1.00 40.72 C |
| ANISOU 2629 CG ARG B 293 7486 7128 6272 1718 −644 −196 C | ANISOU 2674 CG2 ILE B 298 5678 4708 5086 −879 1145 524 C |
| ATOM 2630 CD ARG B 293 95.009 −26.736 −10.991 1.00 91.56 C | ATOM 2675 C ILE B 298 100.975 −34.666 −19.207 1.00 46.53 C |
| ANISOU 2630 CD ARG B 293 12471 11578 10741 2123 −874 −239 C | ANISOU 2675 C ILE B 298 6557 6034 5089 56 553 221 C |
| ATOM 2631 NE ARG B 293 93.968 −26.578 −9.985 1.00108.10 N | ATOM 2676 O ILE B 298 101.329 −34.981 −20.343 1.00 58.33 O |
| ANISOU 2631 NE ARG B 293 14167 13912 12993 2243 −956 −594 N | ANISOU 2676 O ILE B 298 8224 7557 6383 31 653 166 O |
| ATOM 2632 CZ ARG B 293 94.134 −25.922 −8.844 1.00102.89 C | ATOM 2677 N LEU B 299 100.047 −35.329 −18.530 1.00 39.73 N |
| ANISOU 2632 CZ ARG B 293 13525 13154 12414 2140 −864 −572 C | ANISOU 2677 N LEU B 299 5126 5464 4505 125 378 −13 N |
| ATOM 2633 NH1 ARG B 293 93.134 −25.837 −7.980 1.00 99.36 N | ATOM 2678 CA LEU B 299 99.469 −36.563 −19.044 1.00 40.75 C |
| ANISOU 2633 NH1 ARG B 293 12707 12948 12095 2237 −896 −936 N | ANISOU 2678 CA LEU B 299 4716 5936 4830 120 319 −378 C |
| ATOM 2634 NH2 ARG B 293 95.298 −25.342 −8.579 1.00 96.55 N | ATOM 2679 CB LEU B 299 98.721 −37.321 −17.950 1.00 35.84 C |
| ANISOU 2634 NH2 ARG B 293 13085 12015 11585 1937 −722 −247 N | ANISOU 2679 CB LEU B 299 3465 5480 4675 14 323 −572 C |
| ATOM 2635 C ARG B 293 98.192 −29.847 −13.069 1.00 46.65 C | ATOM 2680 CG LEU B 299 99.515 −37.784 −16.729 1.00 51.31 C |
| ANISOU 2635 C ARG B 293 6770 5740 5214 964 −152 399 C | ANISOU 2680 CG LEU B 299 5245 7205 7047 −422 587 −317 C |
| ATOM 2636 O ARG B 293 97.958 −29.937 −14.269 1.00 49.04 O | ATOM 2681 CD1 LEU B 299 98.539 −38.354 −15.707 1.00 40.79 C |
| ANISOU 2636 O ARG B 293 7257 6089 5288 1180 −257 356 O | ANISOU 2681 CD1 LEU B 299 3450 6022 6026 −433 622 −497 C |
| ATOM 2637 N THR B 294 99.421 −29.834 −12.576 1.00 39.86 N | ATOM 2682 CD2 LEU B 299 100.579 −38.820 −17.086 1.00 45.08 C |
| ANISOU 2637 N THR B 294 5992 4628 4524 587 88 614 N | ANISOU 2682 CD2 LEU B 299 4263 6298 6566 −816 819 −276 C |
| ATOM 2638 CA THR B 294 100.570 −29.946 −13.452 1.00 42.36 C | ATOM 2683 C LEU B 299 98.524 −36.300 −20.208 1.00 54.10 C |
| ANISOU 2638 CA THR B 294 6579 4688 4829 351 302 785 C | ANISOU 2683 C LEU B 299 6574 7912 6068 642 −5 −671 C |
| ATOM 2639 CB THR B 294 101.872 −29.689 −12.707 1.00 42.27 C | ATOM 2684 O LEU B 299 98.267 −37.178 −21.021 1.00 63.33 O |
| ANISOU 2639 CB THR B 294 6601 4379 5080 −15 524 900 C | ANISOU 2684 O LEU B 299 7433 9348 7282 671 −54 −999 O |
| ATOM 2640 OG1 THR B 294 101.811 −28.405 −12.076 1.00 44.36 O | ATOM 2685 N ALA B 300 97.981 −35.095 −20.269 1.00 49.93 N |
| ANISOU 2640 OG1 THR B 294 7136 4429 5288 137 480 925 O | ANISOU 2685 N ALA B 300 6529 7333 5109 1098 −264 −591 N |
| ATOM 2641 CG2 THR B 294 103.044 −29.736 −13.679 1.00 30.60 C | ATOM 2686 CA ALA B 300 97.076 −34.761 −21.352 1.00 58.46 C |
| ANISOU 2641 CG2 THR B 294 5380 2605 3641 −283 807 994 C | ANISOU 2686 CA ALA B 300 7846 8672 5694 1709 −663 −874 C |
| ATOM 2642 C THR B 294 100.628 −31.335 −14.075 1.00 36.59 C | ATOM 2687 CB ALA B 300 96.430 −33.414 −21.113 1.00 56.31 C |
| ANISOU 2642 C THR B 294 5498 4188 4215 170 364 697 C | ANISOU 2687 CB ALA B 300 8056 8285 5056 2221 −971 −775 C |
| ATOM 2643 O THR B 294 100.810 −31.497 −15.282 1.00 32.95 O | ATOM 2688 C ALA B 300 97.821 −34.764 −22.681 1.00 68.16 C |
| ANISOU 2643 O THR B 294 5247 3700 3571 210 411 709 O | ANISOU 2688 C ALA B 300 9616 9824 6459 1734 −551 −741 C |
| ATOM 2644 N LEU B 295 100.465 −32.338 −13.228 1.00 36.55 N | ATOM 2689 O ALA B 300 97.268 −35.126 −23.719 1.00 82.19 O |
| ANISOU 2644 N LEU B 295 4990 4393 4505 −21 386 607 N | ANISOU 2689 O ALA B 300 11378 11922 7928 2099 −816 −1082 O |
| ATOM 2645 CA LEU B 295 100.498 −33.723 −13.670 1.00 39.13 C | ATOM 2690 N ASP B 301 99.086 −34.366 −22.639 1.00 72.40 N |
| ANISOU 2645 CA LEU B 295 4931 4902 5034 −215 473 503 C | ANISOU 2690 N ASP B 301 9533 10764 7212 747 309 2417 N |
| ATOM 2646 CB LEU B 295 100.369 −34.661 −12.482 1.00 29.39 C | ATOM 2691 CA ASP B 301 99.865 −34.183 −23.855 1.00 79.42 C |
| ANISOU 2646 CB LEU B 295 3269 3781 4117 −417 555 477 C | ANISOU 2691 CA ASP B 301 10585 11781 7808 745 556 2545 C |
| ATOM 2647 CG LEU B 295 100.553 −36.124 −12.854 1.00 38.69 C | ATOM 2692 CB ASP B 301 100.628 −32.863 −23.779 1.00101.48 C |
| ANISOU 2647 CG LEU B 295 4066 5051 5458 −658 696 396 C | ANISOU 2692 CB ASP B 301 13287 14125 11148 1181 856 2956 C |
| ATOM 2648 CD1 LEU B 295 101.923 −36.352 −13.491 1.00 26.99 C | ATOM 2693 CG ASP B 301 100.669 −32.134 −25.103 1.00128.45 C |
| ANISOU 2648 CD1 LEU B 295 2700 3346 4209 −917 811 510 C | ANISOU 2693 CG ASP B 301 16668 17969 14170 1334 1022 3494 C |
| ATOM 2649 CD2 LEU B 295 100.389 −36.970 −11.616 1.00 44.70 C | ATOM 2694 OD1 ASP B 301 100.183 −32.681 −26.115 1.00137.19 O |
| ANISOU 2649 CD2 LEU B 295 4571 5848 6566 −802 795 419 C | ANISOU 2694 OD1 ASP B 301 17833 19793 14501 1075 870 3519 O |
| ATOM 2650 C LEU B 295 99.375 −34.009 −14.669 1.00 39.86 C | ATOM 2695 OD2 ASP B 301 101.192 −30.999 −25.120 1.00137.22 O |
| ANISOU 2650 C LEU B 295 4910 5282 4953 89 305 246 C | ANISOU 2695 OD2 ASP B 301 17679 18710 15746 1703 1338 3888 O |
| ATOM 2651 O LEU B 295 99.567 −34.678 −15.681 1.00 42.15 O | ATOM 2696 C ASP B 301 100.867 −35.309 −24.052 1.00 68.04 C |
| ANISOU 2651 O LEU B 295 5131 5649 5234 30 348 159 O | ANISOU 2696 C ASP B 301 8191 9504 10022 6326 450 772 1969 C |
| ATOM 2652 N GLU B 296 98.193 −33.504 −14.343 1.00 37.31 N | ATOM 2697 O ASP B 301 101.744 −35.222 −24.901 1.00 69.68 O |
| ANISOU 2652 N GLU B 296 4526 5135 4515 430 94 60 N | ANISOU 2697 O ASP B 301 9894 10156 6424 447 1058 1983 O |
| ATOM 2653 CA GLU B 296 97.043 −33.523 −15.237 1.00 40.92 C | ATOM 2698 N ALA B 302 100.749 −36.360 −23.252 1.00 63.48 N |
| ANISOU 2653 CA GLU B 296 4887 5872 4789 840 −170 −280 C | ANISOU 2698 N ALA B 302 9022 9214 5884 226 694 1496 N |
| ATOM 2654 CB GLU B 296 95.962 −32.623 −14.645 1.00 42.77 C | ATOM 2699 CA ALA B 302 101.793 −37.372 −23.222 1.00 55.49 C |

TABLE 9-continued

DMXAA-hSTING$^{S162A/G230I/Q266I}$ complex

| | |
|---|---|
| ANISOU 2654 CB GLU B 296 5128 6196 4926 1218 -410 -463 C | ANISOU 2699 CA ALA B 302 8307 7738 5038 43 984 1020 C |
| ATOM 2655 CG GLU B 296 94.609 -32.687 -15.281 1.00 59.21 C | ATOM 2700 CB ALA B 302 102.111 -37.772 -21.798 1.00 47.46 C |
| ANISOU 2655 CG GLU B 296 6952 8611 6933 1681 -740 -956 C | ANISOU 2700 CB ALA B 302 7267 6152 4613 166 966 807 C |
| ATOM 2656 CD GLU B 296 93.714 -31.549 -14.808 1.00 84.41 C | ATOM 2701 C ALA B 302 101.481 -38.602 -24.060 1.00 75.31 C |
| ANISOU 2656 CD GLU B 296 10262 11814 9996 2108 -1019 -1120 C | ANISOU 2701 C ALA B 302 11032 10603 6979 -459 1074 596 C |
| ATOM 2657 OE1 GLU B 296 92.542 -31.498 -15.245 1.00 101.08 O | ATOM 2702 O ALA B 302 100.387 -39.166 -23.968 1.00 68.11 O |
| ANISOU 2657 OE1 GLU B 296 12123 14202 12082 2552 -1352 -1610 O | ANISOU 2702 O ALA B 302 10038 10099 5741 -734 852 429 O |
| ATOM 2658 OE2 GLU B 296 94.182 -30.705 -14.009 1.00 63.58 O | ATOM 2703 N PRO B 303 102.461 -39.025 -24.875 1.00 72.71 N |
| ANISOU 2658 OE2 GLU B 296 7932 8913 7312 2017 -925 -817 O | ANISOU 2703 N PRO B 303 10970 10095 6561 -611 1451 375 N |
| ATOM 2659 C GLU B 296 97.437 -33.006 -16.631 1.00 45.45 C | ATOM 2704 CA PRO B 303 102.386 -40.233 -25.702 1.00 83.59 C |
| ANISOU 2659 C GLU B 296 5996 6334 4937 1072 -280 -174 C | ANISOU 2704 CA PRO B 303 12597 11691 7471 -1141 1690 -136 C |
| ATOM 2660 O GLU B 296 97.088 -33.592 -17.657 1.00 48.51 O | ATOM 2705 CB PRO B 303 103.795 -40.341 -26.288 1.00 80.66 C |
| ANISOU 2660 O GLU B 296 6273 6946 5214 1228 -396 -409 O | ANISOU 2705 CB PRO B 303 12489 10851 7309 -1108 2173 -249 C |
| ATOM 2661 N ASP B 297 98.177 -31.903 -16.653 1.00 43.27 N | ATOM 2706 CG PRO B 303 104.287 -38.935 -26.330 1.00 59.10 C |
| ANISOU 2661 N ASP B 297 6326 5693 4420 1090 -206 164 N | ANISOU 2706 CG PRO B 303 9612 8042 4802 -634 2103 304 C |
| ATOM 2662 CA ASP B 297 98.568 -31.261 -17.900 1.00 50.57 C | ATOM 2707 CD PRO B 303 103.714 -38.282 -25.102 1.00 62.98 C |
| ANISOU 2662 CA ASP B 297 7916 6416 4881 1307 -213 329 C | ANISOU 2707 CD PRO B 303 9802 8431 5696 -297 1728 593 C |
| ATOM 2663 CB ASP B 297 99.013 -29.820 -17.655 1.00 51.85 C | ATOM 2708 C PRO B 303 102.076 -41.481 -24.880 1.00 84.86 C |
| ANISOU 2663 CB ASP B 297 8731 6133 4835 1408 -133 641 C | ANISOU 2708 C PRO B 303 12825 11533 7883 -1385 1768 -602 C |
| ATOM 2664 CG ASP B 297 97.857 -28.851 -17.672 1.00 83.05 C | ATOM 2709 O PRO B 303 101.283 -42.301 -25.320 1.00 85.87 O |
| ANISOU 2664 CG ASP B 297 12942 10131 8484 2025 -531 534 C | ANISOU 2709 O PRO B 303 13001 12071 7556 -1859 1782 -981 O |
| ATOM 2665 OD1 ASP B 297 96.761 -29.250 -18.119 1.00 100.07 O | ATOM 2710 N GLU B 304 102.693 -41.627 -23.713 1.00 80.16 N |
| ANISOU 2665 OD1 ASP B 297 14841 12666 10515 2427 -896 194 O | ANISOU 2710 N GLU B 304 12216 10251 7992 -1077 1845 -573 N |
| ATOM 2666 OD2 ASP B 297 98.053 -27.689 -17.248 1.00 88.28 O | ATOM 2711 CA GLU B 304 102.485 -42.820 -22.894 1.00 83.48 C |
| ANISOU 2666 OD2 ASP B 297 14033 10438 9071 2119 -488 737 O | ANISOU 2711 CA GLU B 304 12704 10312 8702 -1234 1994 -920 C |
| ATOM 2667 C ASP B 297 99.656 -32.020 -18.651 1.00 47.97 C | ATOM 2712 CB GLU B 304 103.617 -42.993 -21.881 1.00 90.31 C |
| ANISOU 2712 CB GLU B 304 13580 10431 10302 -854 2195 -827 C | ATOM 2757 CB ARG B 310 5581 5629 4170 -576 -325 -27 C |
| ATOM 2713 CG GLU B 304 104.979 -43.214 -22.495 1.00 102.89 C | ATOM 2758 CB ARG B 310 91.988 -42.391 -14.279 1.00 60.53 C |
| ANISOU 2713 CG GLU B 304 15358 11606 12130 -823 2658 -917 C | ANISOU 2758 CB ARG B 310 8013 8405 6580 -909 -349 -253 C |
| ATOM 2714 CD GLU B 304 105.765 -41.926 -22.639 1.00 111.99 C | ATOM 2759 CG ARG B 310 90.812 -41.458 -14.239 1.00 81.13 C |
| ANISOU 2714 CD GLU B 304 16390 12722 13438 -459 2539 -550 C | ANISOU 2759 CG ARG B 310 10263 11443 9119 -853 -674 30 C |
| ATOM 2715 OE1 GLU B 304 107.009 -42.001 -22.722 1.00 119.36 O | ATOM 2760 CD ARG B 310 90.295 -41.168 -15.630 1.00 95.03 C |
| ANISOU 2715 OE1 GLU B 304 17383 13195 14773 -305 2870 -556 O | ANISOU 2760 CD ARG B 310 11797 13909 10400 -1092 -879 87 C |
| ATOM 2716 OE2 GLU B 304 105.140 -40.843 -22.663 1.00 108.90 O | ATOM 2761 NE ARG B 310 88.857 -40.939 -15.584 1.00 113.74 N |
| ANISOU 2716 OE2 GLU B 304 15823 12733 12821 -323 2164 -251 O | ANISOU 2761 NE ARG B 310 13794 16743 12680 -1209 -1119 198 N |
| ATOM 2717 C GLU B 304 101.162 -42.812 -22.137 1.00 81.29 C | ATOM 2762 CZ ARG B 310 88.303 -39.768 -15.293 1.00 119.62 C |
| ANISOU 2717 C GLU B 304 12218 10345 8325 -1266 1601 -868 C | ANISOU 2762 CZ ARG B 310 14230 17634 13584 -893 -1325 681 C |
| ATOM 2718 O GLU B 304 100.667 -43.857 -21.724 1.00 81.38 O | ATOM 2763 NH1 ARG B 310 86.982 -39.648 -15.255 1.00 119.18 N |
| ANISOU 2718 O GLU B 304 12290 10227 8406 -1515 1740 -1198 O | ANISOU 2763 NH1 ARG B 310 13805 17997 13483 -1003 -1516 786 N |
| ATOM 2719 N SER B 305 100.598 -41.628 -21.949 1.00 87.98 N | ATOM 2764 NH2 ARG B 310 88.716 -38.716 -15.043 1.00 120.92 N |
| ANISOU 2719 N SER B 305 12813 11549 9067 -1004 1176 -444 N | ANISOU 2764 NH2 ARG B 310 14434 17507 14002 -480 -1292 1045 N |
| ATOM 2720 CA SER B 305 99.522 -41.448 -20.984 1.00 85.33 C | ATOM 2765 C ARG B 310 93.660 -41.082 -12.978 1.00 45.85 C |
| ANISOU 2720 CA SER B 305 12252 11352 8819 -913 830 -316 C | ANISOU 2765 C ARG B 310 6244 5932 5243 -193 -354 184 C |
| ATOM 2721 CB SER B 305 99.676 -40.106 -20.284 1.00 94.70 C | ATOM 2766 O ARG B 310 93.970 -41.807 -12.040 1.00 49.88 O |
| ANISOU 2721 CB SER B 305 13217 12427 10337 -428 585 164 C | ANISOU 2766 O ARG B 310 6910 6080 5964 -123 -183 72 O |
| ATOM 2722 OG SER B 305 101.048 -39.772 -20.225 1.00 99.41 O | ATOM 2767 N LEU B 311 93.593 -39.762 -12.878 1.00 49.02 N |
| ANISOU 2722 OG SER B 305 13620 13590 10560 -382 359 517 O | ANISOU 2767 N LEU B 311 6442 6446 5738 48 -534 497 N |
| ATOM 2723 C SER B 305 98.126 -41.470 -21.580 1.00 75.03 C | ATOM 2768 CA LEU B 311 93.890 -39.084 -11.631 1.00 43.12 C |
| ANISOU 2723 C SER B 305 10778 10799 6933 -1241 556 -356 C | ANISOU 2768 CA LEU B 311 5648 5407 5328 340 -539 622 C |
| ATOM 2724 O SER B 305 97.157 -41.202 -20.876 1.00 77.92 O | ATOM 2769 CB LEU B 311 94.539 -37.737 -11.889 1.00 44.46 C |
| ANISOU 2724 O SER B 305 10917 11326 7362 -1157 264 -205 O | ANISOU 2769 CB LEU B 311 5686 5560 5646 575 -561 862 C |
| ATOM 2725 N GLN B 306 97.999 -41.751 -22.869 1.00 72.67 N | ATOM 2770 CG LEU B 311 95.934 -37.814 -12.484 1.00 56.98 C |
| ANISOU 2725 N GLN B 306 10552 11013 6045 -1619 638 -551 N | ANISOU 2770 CG LEU B 311 7425 6994 7229 634 -433 803 C |
| ATOM 2726 CA GLN B 306 96.682 -41.627 -23.480 1.00 83.69 C | ATOM 2771 CD1 LEU B 311 96.606 -36.453 -12.360 1.00 47.40 C |
| ANISOU 2726 CA GLN B 306 11693 13286 6819 -1910 305 -524 C | ANISOU 2771 CD1 LEU B 311 6067 5651 6293 880 -383 984 C |
| ATOM 2727 CB GLN B 306 96.770 -41.348 -24.983 1.00 89.69 C | ATOM 2772 CD2 LEU B 311 96.744 -38.908 -11.794 1.00 51.52 C |
| ANISOU 2727 CB GLN B 306 12464 14757 6855 -2139 304 -473 C | ANISOU 2772 CD2 LEU B 311 6948 6007 6620 636 -301 571 C |
| ATOM 2728 CG GLN B 306 97.738 -40.222 -25.362 1.00 88.91 C | ATOM 2773 C LEU B 311 92.644 -38.874 -10.800 1.00 42.01 C |
| ANISOU 2728 CG GLN B 306 12414 14492 6877 -1680 370 50 C | ANISOU 2773 C LEU B 311 5342 5329 5290 334 -630 684 C |
| ATOM 2729 CD GLN B 306 97.183 -38.826 -25.134 1.00 87.21 C | ATOM 2774 O LEU B 311 91.672 -38.280 -11.253 1.00 44.08 O |
| ANISOU 2729 CD GLN B 306 11843 14560 6733 -1200 16 783 C | ANISOU 2774 O LEU B 311 5364 5894 5492 291 -762 867 O |
| ATOM 2730 OE1 GLN B 306 96.444 -38.299 -25.970 1.00 75.15 O | ATOM 2775 N ILE B 312 92.693 -39.347 -9.566 1.00 41.91 N |
| ANISOU 2730 OE1 GLN B 306 10070 13869 4616 -1234 -230 1135 O | ANISOU 2775 N ILE B 312 5441 5048 5435 400 -542 572 N |
| ATOM 2731 NE2 GLN B 306 97.551 -38.211 -24.006 1.00 63.98 N | ATOM 2776 CA ILE B 312 91.583 -39.157 -8.662 1.00 36.06 C |
| ANISOU 2731 NE2 GLN B 306 8850 10943 4515 -751 26 1029 N | ANISOU 2776 CA ILE B 312 4577 4309 4816 401 -574 611 C |
| ATOM 2732 C GLN B 306 95.820 -42.851 -23.191 1.00 96.38 C | ATOM 2777 CB ILE B 312 91.105 -40.489 -8.120 1.00 47.47 C |
| ANISOU 2732 C GLN B 306 13301 14974 8346 -2391 370 -1080 C | ANISOU 2777 CB ILE B 312 6186 5628 6222 247 -439 411 C |
| ATOM 2733 O GLN B 306 96.202 -43.983 -23.496 1.00 97.12 O | ATOM 2778 CG1 ILE B 312 90.933 -41.467 -9.271 1.00 45.65 C |
| ANISOU 2733 O GLN B 306 13657 14822 8423 -2794 788 -1645 O | ANISOU 2778 CG1 ILE B 312 6026 5543 5777 -52 -377 217 C |
| ATOM 2734 N ASN B 307 94.674 -42.600 -22.562 1.00 99.08 N | ATOM 2779 CD1 ILE B 312 90.289 -42.752 -8.856 1.00 58.25 C |
| ANISOU 2734 N ASN B 307 13340 15588 8717 -2335 22 -914 N | ANISOU 2779 CD1 ILE B 312 7744 6983 7405 -259 -155 -14 C |
| ATOM 2735 CA ASN B 307 93.634 -43.602 -22.362 1.00 97.27 C | ATOM 2780 CG2 ILE B 312 89.792 -40.315 -7.375 1.00 41.61 C |
| ANISOU 2735 CA ASN B 307 13023 15569 8538 -2807 37 -1399 C | ANISOU 2780 CG2 ILE B 312 5296 4919 5596 203 -456 445 C |
| ATOM 2736 CB ASN B 307 93.266 -44.260 -23.695 1.00 115.55 C | ATOM 2781 C ILE B 312 91.995 -38.236 -7.527 1.00 34.48 C |
| ANISOU 2736 CB ASN B 307 15329 18632 9942 -3472 120 -1900 C | ANISOU 2781 C ILE B 312 4329 3923 4850 635 -546 683 C |
| ATOM 2737 CG ASN B 307 91.855 -43.956 -24.121 1.00 132.77 C | ATOM 2782 O ILE B 312 92.630 -38.660 -6.567 1.00 45.48 O |
| ANISOU 2737 CG ASN B 307 17004 21635 11807 -3595 -313 -1726 C | ANISOU 2782 O ILE B 312 5870 5142 6268 727 -469 582 O |
| ATOM 2738 OD1 ASN B 307 91.103 -44.855 -24.503 1.00 138.43 O | ATOM 2783 N ALA B 313 91.651 -36.964 -7.662 1.00 35.57 N |

TABLE 9-continued

DMXAA-hSTING$^{S162A/G230I/Q266I}$ complex

| | |
|---|---|
| ANISOU 2738 OD1 ASN B 307 17574 22601 12423 -4070 -202 -2189 O | ANISOU 2783 N ALA B 313 4234 4124 5156 727 -576 864 N |
| ATOM 2739 ND2 ASN B 307 91.476 -42.688 -24.043 1.00135.98 N | ATOM 2784 CA ALA B 313 91.977 -35.984 -6.637 1.00 44.62 C |
| ANISOU 2739 ND2 ASN B 307 17112 22420 12135 -3143 -745 -1026 N | ANISOU 2784 CA ALA B 313 5308 5090 6557 875 -474 849 C |
| ATOM 2740 C ASN B 307 93.951 -44.681 -21.330 1.00 83.66 C | ATOM 2785 CB ALA B 313 92.466 -34.698 -7.260 1.00 34.12 C |
| ANISOU 2740 C ASN B 307 11549 12992 7248 -2847 443 -1779 C | ANISOU 2785 CB ALA B 313 3804 3732 5430 997 -401 1007 C |
| ATOM 2741 O ASN B 307 93.215 -45.659 -21.211 1.00 79.29 O | ATOM 2786 C ALA B 313 90.766 -35.716 -5.764 1.00 44.06 C |
| ANISOU 2741 O ASN B 307 10976 12485 6664 -3279 606 -2257 O | ANISOU 2786 C ALA B 313 5121 4981 6640 844 -410 871 C |
| ATOM 2742 N ASN B 308 95.028 -44.517 -20.575 1.00 59.59 N | ATOM 2787 O ALA B 313 89.652 -35.593 -6.257 1.00 46.95 O |
| ANISOU 2742 N ASN B 308 8701 9188 4752 -2398 628 -1554 N | ANISOU 2787 O ALA B 313 5307 5481 7049 787 -451 1041 O |
| ATOM 2743 CA ASN B 308 95.424 -45.586 -19.670 1.00 61.32 C | ATOM 2788 N TYR B 314 90.991 -35.614 -4.462 1.00 45.87 N |
| ANISOU 2743 CA ASN B 308 9141 8651 5506 -2392 1052 -1826 C | ANISOU 2788 N TYR B 314 5427 5070 6933 876 -308 701 N |
| ATOM 2744 CB ASN B 308 96.572 -46.370 -20.276 1.00 66.55 C | ATOM 2789 CA TYR B 314 89.894 -35.391 -3.540 1.00 48.33 C |
| ANISOU 2744 CB ASN B 308 10125 8895 6266 -2559 1594 -2145 C | ANISOU 2789 CA TYR B 314 5664 5310 7389 833 -192 684 C |
| ATOM 2745 CG ASN B 308 97.788 -45.508 -20.503 1.00 77.08 C | ATOM 2790 CB TYR B 314 89.212 -36.709 -3.187 1.00 35.91 C |
| ANISOU 2745 CG ASN B 308 11531 10048 7706 -2149 1549 -1767 C | ANISOU 2790 CB TYR B 314 4252 3762 5629 735 -224 631 C |
| ATOM 2746 OD1 ASN B 308 97.709 -44.283 -20.426 1.00 76.57 O | ATOM 2791 CG TYR B 314 90.161 -37.760 -2.650 1.00 34.89 C |
| ANISOU 2746 OD1 ASN B 308 11276 10264 7554 -1815 1127 -1312 O | ANISOU 2791 CG TYR B 314 4393 3612 5251 776 -232 506 C |
| ATOM 2747 ND2 ASN B 308 98.924 -46.139 -20.787 1.00 80.65 N | ATOM 2792 CD1 TYR B 314 90.884 -38.577 -3.516 1.00 30.60 C |
| ANISOU 2747 ND2 ASN B 308 12242 9994 8407 -2173 2043 -1955 N | ANISOU 2792 CD1 TYR B 314 3970 3101 4556 770 -303 514 C |
| ATOM 2748 C ASN B 308 95.816 -45.139 -18.269 1.00 66.14 C | ATOM 2793 CE1 TYR B 314 91.753 -39.529 -3.040 1.00 34.50 C |
| ANISOU 2748 C ASN B 308 9729 8722 6679 -1823 950 -1412 C | ANISOU 2793 CE1 TYR B 314 4669 3542 4899 857 -251 479 C |
| ATOM 2749 O ASN B 308 96.478 -45.877 -17.540 1.00 66.00 O | ATOM 2794 CZ TYR B 314 91.902 -39.692 -1.673 1.00 48.14 C |
| ANISOU 2749 O ASN B 308 9892 8079 7105 -1681 1302 -1481 O | ANISOU 2794 CZ TYR B 314 6473 5270 6546 963 -178 469 C |
| ATOM 2750 N CYS B 309 95.414 -43.937 -17.889 1.00 57.64 N | ATOM 2795 OH TYR B 314 92.762 -40.652 -1.190 1.00 52.05 O |
| ANISOU 2750 N CYS B 309 8409 7910 5581 -1500 504 -975 N | ANISOU 2795 OH TYR B 314 7125 5765 6889 1110 -117 543 O |
| ATOM 2751 CA CYS B 309 95.788 -43.419 -16.590 1.00 54.76 C | ATOM 2796 CE2 TYR B 314 91.197 -38.895 -0.786 1.00 36.52 C |
| ANISOU 2751 CA CYS B 309 8006 7120 5682 -1022 410 -648 C | ANISOU 2796 CE2 TYR B 314 4910 3822 5143 932 -134 414 C |
| ATOM 2752 CB CYS B 309 97.161 -42.763 -16.660 1.00 48.32 C | ATOM 2797 CD2 TYR B 314 90.331 -37.934 -1.278 1.00 33.36 C |
| ANISOU 2752 CB CYS B 309 7269 6026 5065 -681 469 -420 C | ANISOU 2797 CD2 TYR B 314 4315 3387 4972 832 -135 414 C |
| ATOM 2753 SG CYS B 309 97.792 -42.250 -15.068 1.00 71.58 S | ATOM 2798 C TYR B 3 90.355 -34.690 -2.273 1.00 48.00 C |
| ANISOU 2753 SG CYS B 309 10146 8523 8527 -182 390 -139 S | ANISOU 2798 C TYR B 314 5634 5157 7445 859 -28 481 C |
| ATOM 2754 C CYS B 309 94.754 -42.419 -16.107 1.00 64.21 C | ATOM 2799 O TYR B 314 91.491 -34.849 -1.823 1.00 42.97 O |
| ANISOU 2754 C CYS B 309 8904 8648 6844 -861 6 -337 C | ANISOU 2799 O TYR B 314 5108 4574 6644 890 -66 316 O |
| ATOM 2755 O CYS B 309 94.331 -41.543 -16.856 1.00 73.26 O | ATOM 2800 N GLN B 315 89.448 -33.912 -1.705 1.00 59.28 N |
| ANISOU 2755 O CYS B 309 9852 10282 7702 -862 -242 -112 O | ANISOU 2800 N GLN B 315 5285 7275 9962 -655 546 -2539 N |
| ATOM 2756 N ARG B 310 94.348 -42.544 -14.850 1.00 50.79 N | ATOM 2801 CA GLN B 315 89.703 -33.222 -0.460 1.00 57.58 C |
| ANISOU 2756 N ARG B 310 7165 6683 5451 -702 -20 -285 N | ANISOU 2801 CA GLN B 315 5768 6696 9414 -642 589 -2977 C |
| ATOM 2757 CA ARG B 310 93.315 -41.663 -14.343 1.00 40.48 C | ATOM 2802 CB GLN B 315 89.345 -31.750 -0.599 1.00 61.20 C |
| ANISOU 2802 CB GLN B 315 6516 6556 10180 -785 1109 -2953 C | ANISOU 2847 CA SER B 321 16410 14104 11889 624 1371 -2209 C |
| ATOM 2803 CG GLN B 315 90.256 -30.815 0.155 1.00 89.53 C | ATOM 2848 CB SER B 321 85.016 -38.864 8.981 1.00105.77 C |
| ANISOU 2803 CG GLN B 315 10610 9882 13524 -1154 1002 -3613 C | ANISOU 2848 CB SER B 321 16063 13693 10433 296 550 -2265 C |
| ATOM 2804 CD GLN B 315 90.389 -29.473 -0.536 1.00 94.49 C | ATOM 2849 OG SER B 321 85.343 -38.091 10.112 1.00109.17 O |
| ANISOU 2804 CD GLN B 315 11252 10043 14608 -1511 1279 -3599 C | ANISOU 2849 OG SER B 321 17093 14123 10263 -135 660 -2816 O |
| ATOM 2805 OE1 GLN B 315 89.766 -29.230 -1.572 1.00 97.90 O | ATOM 2850 C SER B 321 83.123 -38.891 7.380 1.00106.37 C |
| ANISOU 2805 OE1 GLN B 315 11292 10353 15555 -1464 1525 -3023 O | ANISOU 2850 C SER B 321 15449 13590 11376 932 1622 -1574 C |
| ATOM 2806 NE2 GLN B 315 91.210 -28.594 0.031 1.00 97.65 N | ATOM 2851 O SER B 321 83.075 -40.098 7.608 1.00105.37 O |
| ANISOU 2806 NE2 GLN B 315 12113 10192 14799 -1936 1211 -4193 N | ANISOU 2851 O SER B 321 15389 13738 10908 901 1142 -1224 O |
| ATOM 2807 C GLN B 315 88.831 -33.875 0.595 1.00 58.08 C | ATOM 2852 N SER B 322 82.225 -38.274 6.627 1.00103.49 N |
| ANISOU 2807 C GLN B 315 6297 6678 9091 -204 767 -2828 C | ANISOU 2852 N SER B 322 14748 13040 11533 1200 2347 -1381 N |
| ATOM 2808 O GLN B 315 87.622 -33.983 0.429 1.00 71.31 O | ATOM 2853 CA SER B 322 81.231 -39.056 5.919 1.00 99.85 C |
| ANISOU 2808 O GLN B 315 7977 8210 10908 106 1248 -2339 O | ANISOU 2853 CA SER B 322 13897 12801 11240 1418 2544 -737 C |
| ATOM 2809 N GLU B 316 89.452 -34.321 1.676 1.00 90.11 N | ATOM 2854 CB SER B 322 79.954 -38.249 5.711 1.00102.64 C |
| ANISOU 2809 N GLU B 316 10714 10894 12631 -233 349 -3212 N | ANISOU 2854 CB SER B 322 14086 13017 11895 1678 3486 -554 C |
| ATOM 2810 CA GLU B 316 88.724 -35.019 2.722 1.00 93.60 C | ATOM 2855 OG SER B 322 78.853 -39.113 5.499 1.00104.22 O |
| ANISOU 2810 CA GLU B 316 11616 11348 12600 61 428 -3070 C | ANISOU 2855 OG SER B 322 14091 13580 11927 1775 3694 31 O |
| ATOM 2811 CB GLU B 316 89.582 -36.144 3.300 1.00105.57 C | ATOM 2856 C SER B 322 81.823 -39.476 4.580 1.00 91.47 C |
| ANISOU 2811 CB GLU B 316 13094 13285 13734 35 -356 -3200 C | ANISOU 2856 C SER B 322 12193 11796 10763 1452 2113 -479 C |
| ATOM 2812 CG GLU B 316 88.816 -37.169 4.111 1.00115.39 C | ATOM 2857 O SER B 322 81.146 -40.059 3.734 1.00 78.84 O |
| ANISOU 2812 CG GLU B 316 14680 14624 14540 304 -397 -2875 C | ANISOU 2857 O SER B 322 10176 10394 9386 1540 2248 35 O |
| ATOM 2813 CD GLU B 316 89.676 -38.361 4.501 1.00119.83 C | ATOM 2858 N PHE B 323 83.102 -39.175 4.400 1.00 56.42 N |
| ANISOU 2813 CD GLU B 316 15103 15530 14896 326 -1247 -2859 C | ANISOU 2858 N PHE B 323 7669 7241 6528 1311 1614 -874 N |
| ATOM 2814 OE1 GLU B 316 90.445 -38.849 3.644 1.00119.94 O | ATOM 2859 CA PHE B 323 83.759 -39.411 3.132 1.00 54.89 C |
| ANISOU 2814 OE1 GLU B 316 14482 15730 15359 359 -1653 -2888 O | ANISOU 2859 CA PHE B 323 6840 7121 6896 1274 1283 -775 C |
| ATOM 2815 OE2 GLU B 316 89.586 -38.803 5.665 1.00118.84 O | ATOM 2860 CB PHE B 323 85.122 -38.729 3.103 1.00 53.29 C |
| ANISOU 2815 OE2 GLU B 316 15485 15488 14180 292 -1505 -2812 O | ANISOU 2860 CB PHE B 323 6582 6790 6875 1079 880 -1320 C |
| ATOM 2816 C GLU B 316 88.316 -34.033 3.806 1.00 92.26 C | ATOM 2861 CG PHE B 323 85.891 -38.992 1.852 1.00 53.28 C |
| ANISOU 2816 C GLU B 316 12193 10764 12099 -12 922 -3393 C | ANISOU 2861 CG PHE B 323 5908 6939 7396 972 542 -1317 C |
| ATOM 2817 O GLU B 316 89.149 -33.275 4.305 1.00 95.73 O | ATOM 2862 CD1 PHE B 323 85.511 -38.400 0.658 1.00 46.58 C |
| ANISOU 2817 O GLU B 316 12943 11098 12331 -384 785 -3923 O | ANISOU 2862 CD1 PHE B 323 4572 6071 7056 903 942 -1079 C |
| ATOM 2818 N PRO B 317 87.021 -34.024 4.163 1.00 95.43 N | ATOM 2863 CE1 PHE B 323 86.217 -38.641 -0.507 1.00 46.77 C |
| ANISOU 2818 N PRO B 317 12868 10949 12444 303 1546 -3115 N | ANISOU 2863 CE1 PHE B 323 3975 6317 7480 683 671 -1124 C |
| ATOM 2819 CA PRO B 317 86.580 -33.105 5.211 1.00102.12 C | ATOM 2864 CZ PHE B 323 87.323 -39.484 -0.482 1.00 45.64 C |
| ANISOU 2819 CA PRO B 317 14411 11385 13003 237 2132 -3519 C | ANISOU 2864 CZ PHE B 323 3650 6366 7323 625 37 -1463 C |
| ATOM 2820 CB PRO B 317 85.055 -33.279 5.225 1.00 99.20 C | ATOM 2865 CE2 PHE B 323 87.711 -40.087 0.712 1.00 50.47 C |
| ANISOU 2820 CB PRO B 317 14039 10885 12767 684 2829 -3068 C | ANISOU 2865 CE2 PHE B 323 4710 6940 7528 789 -405 -1640 C |
| ATOM 2821 CG PRO B 317 84.721 -34.108 4.012 1.00 92.31 C | ATOM 2866 CD2 PHE B 323 86.993 -39.838 1.868 1.00 53.46 C |
| ANISOU 2821 CG PRO B 317 12445 10318 12312 918 2615 -2382 C | ANISOU 2866 CD2 PHE B 323 5749 7147 7415 913 -174 -1539 C |
| ATOM 2822 CD PRO B 317 85.937 -34.918 3.727 1.00 85.93 C | ATOM 2867 C PHE B 323 83.915 -40.894 2.864 1.00 51.27 C |

TABLE 9-continued

DMXAA-hSTING<sup>S162A/G230I/Q266I</sup> complex

| | |
|---|---|
| ANISOU 2822 CD PRO B 317 11366 9927 11358 677 1744 −2484 C | ANISOU 2867 C PHE B 323 6207 6926 6347 1281 773 −500 C |
| ATOM 2823 C PRO B 317 87.150 −33.588 6.527 1.00112.78 C | ATOM 2868 O PHE B 323 84.216 −41.676 3.762 1.00 61.61 O |
| ANISOU 2823 C PRO B 317 16298 13054 13501 −68 1692 −3909 C | ANISOU 2868 O PHE B 323 7906 8292 7210 1268 310 −543 O |
| ATOM 2824 O PRO B 317 87.177 −34.796 6.753 1.00114.74 O | ATOM 2869 N SER B 324 83.697 −41.270 1.611 1.00 52.95 N |
| ANISOU 2824 O PRO B 317 16441 13739 13415 19 1188 −3608 O | ANISOU 2869 N SER B 324 5844 7283 6991 1256 867 −200 N |
| ATOM 2825 N ALA B 318 87.605 −32.676 7.376 1.00120.72 N | ATOM 2870 CA SER B 324 83.920 −42.637 1.171 1.00 53.22 C |
| ANISOU 2825 N ALA B 318 17879 13842 14148 −472 1859 −4539 N | ANISOU 2870 CA SER B 324 5667 7485 7068 1227 457 −34 C |
| ATOM 2826 CA ALA B 318 88.154 −33.069 8.668 1.00131.67 C | ATOM 2871 CB SER B 324 82.621 −43.275 0.704 1.00 50.70 C |
| ANISOU 2826 CA ALA B 318 19789 15612 14629 −899 1418 −4878 C | ANISOU 2871 CB SER B 324 5251 7371 6642 1206 884 544 C |
| ATOM 2827 CB ALA B 318 89.649 −32.802 8.714 1.00 62.95 C | ATOM 2872 OG SER B 324 82.895 −44.471 0.002 1.00 62.56 O |
| ANISOU 2827 CB ALA B 318 19451 15578 14193 −1403 706 −5258 C | ANISOU 2872 OG SER B 324 6478 8981 8311 1095 583 628 O |
| ATOM 2828 C ALA B 318 87.443 −32.358 9.818 1.00147.32 C | ATOM 2873 C SER B 324 84.932 −42.650 0.035 1.00 51.81 C |
| ANISOU 2828 C ALA B 318 22552 17316 16106 −1116 2192 −5357 C | ANISOU 2873 C SER B 324 4862 7378 7445 1074 191 −307 C |
| ATOM 2829 O ALA B 318 87.590 −31.149 9.986 1.00150.36 O | ATOM 2874 O SER B 324 84.710 −42.049 −1.012 1.00 43.28 O |
| ANISOU 2829 O ALA B 318 23290 17228 16610 −1373 2705 −5914 O | ANISOU 2874 O SER B 324 3325 6410 6711 899 546 −200 O |
| ATOM 2830 N ASP B 319 86.682 −33.106 10.616 1.00158.28 N | ATOM 2875 N LEU B 325 86.043 −43.344 0.246 1.00 53.65 N |
| ANISOU 2830 N ASP B 319 24226 18992 16920 −1063 2301 −5177 N | ANISOU 2875 N LEU B 325 7977 5221 7187 −189 1536 −759 N |
| ATOM 2831 CA ASP B 319 86.553 −34.551 10.455 1.00162.22 C | ATOM 2876 CA LEU B 325 87.075 −43.425 −0.771 1.00 45.96 C |
| ANISOU 2831 CA ASP B 319 24382 19987 17266 −818 1656 −4513 C | ANISOU 2876 CA LEU B 325 6870 4368 6224 −331 1251 −585 C |
| ATOM 2832 CB ASP B 319 87.586 −35.275 11.330 1.00167.60 C | ATOM 2877 CB LEU B 325 88.379 −43.974 −0.196 1.00 51.17 C |
| ANISOU 2832 CB ASP B 319 25290 21220 17169 −1309 682 −4556 C | ANISOU 2877 CB LEU B 325 7750 4907 6786 −598 1099 −572 C |
| ATOM 2833 CG ASP B 319 87.745 −36.739 10.961 1.00164.73 C | ATOM 2878 CG LEU B 325 89.561 −43.890 −1.160 1.00 48.90 C |
| ANISOU 2833 CG ASP B 319 24478 21224 16889 −1011 −124 −3867 C | ANISOU 2878 CG LEU B 325 7319 4692 6568 −733 869 −390 C |
| ATOM 2834 OD1 ASP B 319 87.355 −37.604 11.773 1.00169.02 O | ATOM 2879 CD1 LEU B 325 89.785 −42.442 −1.565 1.00 39.94 C |
| ANISOU 2834 OD1 ASP B 319 25222 21942 17057 −909 −64 −3482 O | ANISOU 2879 CD1 LEU B 325 6311 3392 5471 −654 731 −224 C |
| ATOM 2835 OD2 ASP B 319 88.263 −37.028 9.861 1.00157.65 O | ATOM 2880 CD2 LEU B 325 90.810 −44.455 −0.521 1.00 54.14 C |
| ANISOU 2835 OD2 ASP B 319 23029 20427 16444 −900 −793 −3738 O | ANISOU 2880 CD2 LEU B 325 8125 5189 7258 −980 705 −366 C |
| ATOM 2836 C ASP B 319 85.144 −35.029 10.811 1.00166.37 C | ATOM 2881 C LEU B 325 86.616 −44.297 −1.938 1.00 42.53 C |
| ANISOU 2836 C ASP B 319 25075 20562 17578 −540 2251 −4203 C | ANISOU 2881 C LEU B 325 5996 4310 5853 −332 1245 −549 C |
| ATOM 2837 O ASP B 319 84.951 −35.697 11.826 1.00171.36 O | ATOM 2882 O LEU B 325 86.960 −44.042 −3.090 1.00 44.88 O |
| ANISOU 2837 O ASP B 319 26132 21587 17391 −830 2045 −4163 O | ANISOU 2882 O LEU B 325 6146 4738 6168 −357 1085 −403 O |
| ATOM 2838 N ASP B 320 84.157 −34.672 9.991 1.00162.47 N | ATOM 2883 N SER B 326 85.851 −45.339 −1.637 1.00 38.02 N |
| ANISOU 2838 N ASP B 320 24229 19716 17786 −35 2971 −3951 N | ANISOU 2883 N SER B 326 5260 3899 5288 −337 1408 −674 N |
| ATOM 2839 CA ASP B 320 82.827 −35.260 10.122 1.00158.27 C | ATOM 2884 CA SER B 326 85.358 −46.219 −2.687 1.00 41.93 C |
| ANISOU 2839 CA ASP B 320 23664 19337 17132 269 3459 −3536 C | ANISOU 2884 CA SER B 326 5390 4711 5830 −355 1362 −646 C |
| ATOM 2840 CB ASP B 320 81.783 −34.451 9.346 1.00157.98 C | ATOM 2885 CB SER B 326 84.818 −47.528 −2.113 1.00 39.92 C |
| ANISOU 2840 CB ASP B 320 23262 18840 17923 773 4387 −3386 C | ANISOU 2885 CB SER B 326 5026 4582 5561 −440 1495 −779 C |
| ATOM 2841 CG ASP B 320 80.381 −34.580 9.933 1.00160.12 C | ATOM 2886 OG SER B 326 83.830 −47.272 −1.143 1.00 57.38 O |
| ANISOU 2841 CG ASP B 320 23687 19221 17932 960 5184 −3297 C | ANISOU 2886 OG SER B 326 7277 6688 7838 −320 1751 −864 O |
| ATOM 2842 OD1 ASP B 320 79.741 −35.636 9.744 1.00157.27 O | ATOM 2887 C SER B 326 84.293 −45.533 −3.554 1.00 48.03 C |
| ANISOU 2842 OD1 ASP B 320 23082 19295 17379 1102 5014 −2702 O | ANISOU 2887 C SER B 326 5924 5558 6767 −161 1318 −539 C |
| ATOM 2843 OD2 ASP B 320 79.918 −33.612 10.575 1.00161.79 O | ATOM 2888 O SER B 326 84.179 −45.823 −4.741 1.00 53.17 O |
| ANISOU 2843 OD2 ASP B 320 24047 19168 18259 907 5697 −3668 O | ANISOU 2888 O SER B 326 6384 6408 7409 −208 1151 −439 O |
| ATOM 2844 C ASP B 320 82.956 −36.662 9.546 1.00145.06 C | ATOM 2889 N GLN B 327 83.509 −44.634 −2.962 1.00 34.97 N |
| ANISOU 2844 C ASP B 320 21570 18082 15464 424 2691 −2844 C | ANISOU 2889 N GLN B 327 4301 3713 5274 50 1456 −563 N |
| ATOM 2845 O ASP B 320 82.335 −37.614 10.021 1.00147.51 O | ATOM 2890 CA GLN B 327 82.537 −43.864 −3.736 1.00 50.89 C |
| ANISOU 2845 O ASP B 320 22039 18743 15265 402 2602 −2500 O | ANISOU 2890 CA GLN B 327 6070 5721 7544 250 1355 −438 C |
| ATOM 2846 N SER B 321 83.802 −36.765 8.523 1.00128.64 N | ATOM 2891 CB GLN B 327 81.669 −42.983 −2.840 1.00 43.63 C |
| ANISOU 2846 N SER B 321 18971 15947 13961 530 2157 −2690 N | ANISOU 2891 CB GLN B 327 5167 4543 6868 519 1599 −530 C |
| ATOM 2847 CA SER B 321 84.242 −38.039 7.953 1.00111.60 C | ATOM 2892 CG GLN B 327 80.448 −43.685 −2.277 1.00 69.58 C |
| ANISOU 2892 CG GLN B 327 8154 7920 10361 615 1908 −644 C | ANISOU 2930 NH2 ARG B 331 12254 10127 12798 −2 −754 1136 N |
| ATOM 2893 CD GLN B 327 79.598 −44.342 −3.357 1.00 76.84 C | ATOM 2931 C ARG B 331 83.488 −42.005 −10.946 1.00 61.47 C |
| ANISOU 2893 CD GLN B 327 8607 9088 11501 598 1706 −496 C | ANISOU 2931 C ARG B 331 7509 7510 8338 −393 −287 695 C |
| ATOM 2894 OE1 GLN B 327 78.858 −43.669 −4.080 1.00 87.42 O | ATOM 2932 O ARG B 331 82.986 −41.671 −12.019 1.00 62.26 O |
| ANISOU 2894 OE1 GLN B 327 9685 10364 13167 762 1523 −348 O | ANISOU 2932 O ARG B 331 7631 7614 8410 −486 −621 908 O |
| ATOM 2895 NE2 GLN B 327 79.707 −45.662 −3.475 1.00 71.13 N | ATOM 2933 N HIS B 332 84.771 −42.292 −10.848 1.00 59.85 N |
| ANISOU 2895 NE2 GLN B 327 7800 8612 10614 383 1686 −522 N | ANISOU 2933 N HIS B 332 7487 7383 7868 −544 −86 619 N |
| ATOM 2896 C GLN B 327 83.261 −42.983 −4.738 1.00 57.49 C | ATOM 2934 CA HIS B 332 85.656 −42.259 −11.992 1.00 56.95 C |
| ANISOU 2896 C GLN B 327 7021 6512 8312 204 1051 −247 C | ANISOU 2934 CA HIS B 332 7331 7158 7150 −822 −152 755 C |
| ATOM 2897 O GLN B 327 82.832 −42.802 −5.879 1.00 56.04 O | ATOM 2935 CB HIS B 332 87.080 −42.058 −11.532 1.00 50.51 C |
| ANISOU 2897 O GLN B 327 6653 6431 8207 207 817 −82 O | ANISOU 2935 CB HIS B 332 6645 6305 6242 −915 65 723 C |
| ATOM 2898 N GLU B 328 84.377 −42.432 −4.290 1.00 55.93 N | ATOM 2936 CG HIS B 332 87.377 −40.661 −11.139 1.00 56.42 C |
| ANISOU 2898 N GLU B 328 7153 6138 7960 125 1028 −247 N | ANISOU 2936 CG HIS B 332 7528 6783 7126 −857 −86 900 C |
| ATOM 2899 CA GLU B 328 85.125 −41.490 −5.098 1.00 58.25 C | ATOM 2937 ND1 HIS B 332 88.018 −39.781 −11.969 1.00 64.51 N |
| ANISOU 2899 CA GLU B 328 7578 6357 8196 57 768 −46 C | ANISOU 2937 ND1 HIS B 332 8741 7788 7983 −1057 −253 1159 N |
| ATOM 2900 CB GLU B 328 86.137 −40.743 −4.237 1.00 43.81 C | ATOM 2938 CE1 HIS B 332 88.131 −38.619 −11.364 1.00 60.89 C |
| ANISOU 2900 CB GLU B 328 6118 4238 6289 13 758 −56 C | ANISOU 2938 CE1 HIS B 332 8384 7036 7716 −956 −407 1277 C |
| ATOM 2901 CG GLU B 328 86.706 −39.521 −4.912 1.00 51.35 C | ATOM 2939 NE2 HIS B 332 87.571 −38.711 −10.179 1.00 54.89 N |
| ANISOU 2901 CG GLU B 328 7214 5045 7251 −23 485 173 C | ANISOU 2939 NE2 HIS B 332 7537 6105 7214 −689 −312 1078 N |
| ATOM 2902 CD GLU B 328 85.628 −38.562 −5.416 1.00 69.56 C | ATOM 2940 CD2 HIS B 332 87.093 −39.977 −10.014 1.00 53.58 C |
| ANISOU 2902 CD GLU B 328 9415 7232 9784 202 343 271 C | ANISOU 2940 CD2 HIS B 332 7181 6142 7036 −634 −100 852 C |
| ATOM 2903 OE1 GLU B 328 85.900 −37.848 −6.403 1.00 69.95 O | ATOM 2941 C HIS B 332 85.592 −43.535 −12.801 1.00 69.45 C |
| ANISOU 2903 OE1 GLU B 328 9487 7273 9817 116 61 509 O | ANISOU 2941 C HIS B 332 8909 9014 8467 −995 −102 660 C |
| ATOM 2904 OE2 GLU B 328 84.517 −38.516 −4.831 1.00 78.20 O | ATOM 2942 O HIS B 332 85.662 −43.518 −13.998 1.00 66.53 O |
| ANISOU 2904 OE2 GLU B 328 10392 8224 11096 452 512 123 O | ANISOU 2942 O HIS B 332 8718 8747 7813 −1206 −267 804 O |
| ATOM 2905 C GLU B 328 85.818 −42.176 −6.272 1.00 57.13 C | ATOM 2943 N LEU B 333 85.440 −44.654 −12.133 1.00 74.71 N |
| ANISOU 2905 C GLU B 328 7349 6499 7861 −181 640 63 C | ANISOU 2943 N LEU B 333 9419 9769 9200 −926 114 416 N |
| ATOM 2906 O GLU B 328 85.968 −41.603 −7.350 1.00 52.82 O | ATOM 2944 CA LEU B 333 85.391 −45.904 −12.828 1.00 79.69 C |

TABLE 9-continued

DMXAA-hSTING$^{S162A/G230I/Q266I}$ complex

| | |
|---|---|
| ANISOU 2906 O GLU B 328 6810 5999 7261 -251 431 258 O | ANISOU 2944 CA LEU B 333 10062 10617 9600 -1071 162 287 C |
| ATOM 2907 N VAL B 329 86.240 -43.411 -6.051 1.00 35.43 N | ATOM 2945 CB LEU B 333 85.286 -47.035 -11.851 1.00 75.72 C |
| ANISOU 2907 N VAL B 329 4545 3919 4997 -315 775 -73 N | ANISOU 2945 CB LEU B 333 9371 10149 9249 -973 360 37 C |
| ATOM 2908 CA VAL B 329 86.878 -44.178 -7.101 1.00 41.84 C | ATOM 2946 CG LEU B 333 86.653 -47.644 -11.683 1.00 91.95 C |
| ANISOU 2908 CA VAL B 329 5282 4981 5636 -513 731 -34 C | ANISOU 2946 CG LEU B 333 11497 12286 11153 -1090 628 -138 C |
| ATOM 2909 CB VAL B 329 87.690 -45.347 -6.522 1.00 44.73 C | ATOM 2947 CD1 LEU B 333 87.063 -47.539 -10.262 1.00106.42 C |
| ANISOU 2909 CB VAL B 329 5643 5401 5952 -642 874 -201 C | ANISOU 2947 CD1 LEU B 333 13228 13977 13230 -977 781 -253 C |
| ATOM 2910 CG1 VAL B 329 88.324 -46.150 -7.623 1.00 38.21 C | ATOM 2948 CD2 LEU B 333 86.593 -49.084 -12.110 1.00 77.02 C |
| ANISOU 2910 CG1 VAL B 329 4732 4807 4981 -808 889 -207 C | ANISOU 2948 CD2 LEU B 333 9611 10560 9093 -1189 653 -312 C |
| ATOM 2911 CG2 VAL B 329 88.767 -44.813 -5.595 1.00 40.56 C | ATOM 2949 C LEU B 333 84.217 -45.910 -13.758 1.00 91.96 C |
| ANISOU 2911 CG2 VAL B 329 5322 4618 5472 -698 873 -183 C | ANISOU 2949 C LEU B 333 11627 12212 11102 -1132 180 428 C |
| ATOM 2912 C VAL B 329 85.817 -44.677 -8.076 1.00 47.35 C | ATOM 2950 O LEU B 333 84.230 -46.563 -14.770 1.00105.03 O |
| ANISOU 2912 C VAL B 329 5785 5888 6318 -496 636 -3 C | ANISOU 2950 O LEU B 333 13499 14002 12407 -1352 -264 449 O |
| ATOM 2913 O VAL B 329 86.004 -44.648 -9.293 1.00 43.12 O | ATOM 2951 N ARG B 334 83.186 -45.174 -13.423 1.00 91.31 N |
| ANISOU 2913 O VAL B 329 5278 5492 5614 -628 505 119 O | ANISOU 2951 N ARG B 334 11320 11988 11387 -942 -378 525 N |
| ATOM 2914 N LEU B 330 84.689 -45.119 -7.531 1.00 47.31 N | ATOM 2952 CA ARG B 334 82.035 -45.205 -14.260 1.00 89.10 C |
| ANISOU 2914 N LEU B 330 5603 5888 6484 -359 696 -97 N | ANISOU 2952 CA ARG B 334 11001 11676 11178 -997 -796 727 C |
| ATOM 2915 CA LEU B 330 83.591 -45.603 -8.359 1.00 51.28 C | ATOM 2953 CB ARG B 334 80.808 -44.804 -13.468 1.00 75.67 C |
| ANISOU 2915 CA LEU B 330 5892 6545 7046 -351 545 -36 C | ANISOU 2953 CB ARG B 334 8925 9791 10033 -724 -913 796 C |
| ATOM 2916 CB LEU B 330 82.451 -46.156 -7.501 1.00 46.75 C | ATOM 2954 CG ARG B 334 80.254 -45.999 -12.721 1.00 73.29 C |
| ANISOU 2916 CB LEU B 330 5074 5962 6725 -212 680 -143 C | ANISOU 2954 CG ARG B 334 8330 9579 9938 -647 -793 638 C |
| ATOM 2917 CG LEU B 330 82.684 -47.558 -6.942 1.00 54.79 C | ATOM 2955 CD ARG B 334 79.775 -45.703 -11.333 1.00 64.53 C |
| ANISOU 2917 CG LEU B 330 6064 7114 7639 -332 840 -329 C | ANISOU 2955 CD ARG B 334 6946 8354 9219 -368 -474 508 C |
| ATOM 2918 CD1 LEU B 330 81.655 -47.889 -5.881 1.00 51.25 C | ATOM 2956 NE ARG B 334 79.520 -46.958 -10.654 1.00 72.05 N |
| ANISOU 2918 CD1 LEU B 330 5424 6622 7424 -216 1039 -415 C | ANISOU 2956 NE ARG B 334 7705 9435 10237 -369 -271 330 N |
| ATOM 2919 CD2 LEU B 330 82.636 -48.579 -8.064 1.00 53.00 C | ATOM 2957 CZ ARG B 334 78.933 -47.079 -9.476 1.00 76.05 C |
| ANISOU 2919 CD2 LEU B 330 5779 7105 7255 -500 656 -314 C | ANISOU 2957 CZ ARG B 334 7962 9875 11057 -184 16 218 C |
| ATOM 2920 C LEU B 330 83.068 -44.524 -9.307 1.00 54.99 C | ATOM 2958 NH1 ARG B 334 78.533 -46.021 -8.821 1.00 78.83 N |
| ANISOU 2920 C LEU B 330 6359 6940 7595 -308 259 201 C | ANISOU 2958 NH1 ARG B 334 8239 10021 11691 50 164 232 N |
| ATOM 2921 O LEU B 330 82.610 -44.819 -10.408 1.00 57.84 O | ATOM 2959 NH2 ARG B 334 78.743 -48.268 -8.957 1.00 66.41 N |
| ANISOU 2921 O LEU B 330 6677 7423 7876 -419 19 321 O | ANISOU 2959 NH2 ARG B 334 6600 8781 9851 -245 164 88 N |
| ATOM 2922 N ARG B 331 83.141 -43.272 -8.873 1.00 44.63 N | ATOM 2960 C ARG B 334 82.300 -44.320 -15.442 1.00102.82 C |
| ANISOU 2922 N ARG B 331 5135 5388 6434 -164 241 276 N | ANISOU 2960 C ARG B 334 13047 13355 12666 -1186 -1072 985 C |
| ATOM 2923 CA ARG B 331 82.640 -42.173 -9.685 1.00 51.18 C | ATOM 2961 O ARG B 334 81.736 -43.262 -15.601 1.00101.63 O |
| ANISOU 2923 CA ARG B 331 5965 6085 7395 -116 -81 517 C | ANISOU 2961 O ARG B 334 12830 12996 12789 -1078 -1323 1191 O |
| ATOM 2924 CB ARG B 331 82.627 -40.871 -8.892 1.00 58.29 C | ATOM 2962 N GLN B 335 83.197 -44.826 -16.277 1.00109.97 N |
| ANISOU 2924 CB ARG B 331 6949 6662 8535 103 -54 533 C | ANISOU 2962 N GLN B 335 14293 14431 13058 -1464 -976 950 N |
| ATOM 2925 CG ARG B 331 81.979 -39.723 -9.635 1.00 73.21 C | ATOM 2963 CA GLN B 335 81.550 -44.255 -17.567 1.00105.58 C |
| ANISOU 2925 CG ARG B 331 8801 8353 10661 189 -428 780 C | ANISOU 2963 CA GLN B 335 14147 13893 12077 -1772 -1207 1177 C |
| ATOM 2926 CD ARG B 331 82.192 -38.401 -8.920 1.00 80.82 C | ATOM 2964 CB GLN B 335 83.440 -42.745 -17.557 1.00 99.33 C |
| ANISOU 2926 CD ARG B 331 9928 8966 11814 384 -423 785 C | ANISOU 2964 CB GLN B 335 13413 12881 11446 -1761 -1520 1490 C |
| ATOM 2927 NE ARG B 331 83.533 -37.869 -9.145 1.00 94.70 N | ATOM 2965 CG GLN B 335 83.642 -42.144 -16.222 1.00101.26 C |
| ANISOU 2927 NE ARG B 331 12034 10698 13251 172 -503 890 N | ANISOU 2965 CG GLN B 335 13508 12996 11969 -1546 -1285 1463 C |
| ATOM 2928 CZ ARG B 331 83.867 -36.590 -8.994 1.00103.81 C | ATOM 2966 CD GLN B 335 82.815 -40.915 -16.039 1.00108.55 C |
| ANISOU 2928 CZ ARG B 331 13398 11548 14497 234 -680 1009 C | ANISOU 2966 CD GLN B 335 14225 13618 13401 -1305 -1639 1647 C |
| ATOM 2929 NH1 ARG B 331 82.956 -35.701 -8.618 1.00109.37 N | ATOM 2967 OE1 GLN B 335 81.608 -40.988 -15.881 1.00108.52 O |
| ANISOU 2929 NH1 ARG B 331 14018 11930 15609 533 -782 1005 N | ANISOU 2967 OE1 GLN B 335 14011 13523 13697 -1202 -1942 1716 O |
| | ATOM 2968 NE2 GLN B 335 83.455 -39.764 -16.085 1.00110.71 N |

ATOM 2930 NH2 ARG B 331 85.115 -36.200 -9.227 1.00 92.59 N
ANISOU 2968 NE2 GLN B 335 14547 13709 13810 -1216 -1618 1735 N
ATOM 2969 C GLN B 335 84.930 -44.716 -18.000 1.00 99.77 C
ANISOU 2969 C GLN B 335 13688 13356 10864 -1980 -778 1016 C
ATOM 2970 O GLN B 335 85.207 -45.909 -18.035 1.00 94.32 O
ANISOU 2970 O GLN B 335 13052 12823 9963 -2046 -563 777 O
TER 2974 GLN B 335
HETATM 2971 O HOH S 1 110.319 -45.601 -9.573 1.00 39.14 O
HETATM 2972 O HOH S 2 112.398 -45.393 -4.628 1.00 48.56 O
HETATM 2973 O HOH S 3 123.141 -29.303 -16.515 1.00 49.19 O
HETATM 2974 O HOH S 4 92.690 -51.029 -13.033 1.00 53.52 O
HETATM 2975 O HOH S 5 93.030 -41.555 0.913 1.00 51.01 O
HETATM 2976 O HOH S 6 128.910 -39.669 -15.753 1.00 51.84 O
HETATM 2977 O HOH S 7 106.614 -30.842 12.237 1.00 54.53 O
HETATM 2978 O HOH S 8 109.156 -39.164 -21.771 1.00 54.08 O
HETATM 2979 O HOH S 9 97.811 -30.595 2.170 1.00 48.71 O
HETATM 2980 O HOH S 10 105.036 -44.979 -7.282 1.00 51.03 O
HETATM 2981 O HOH S 12 103.744 -48.332 -7.113 1.00 59.56 O
HETATM 2982 O HOH S 13 102.856 -40.999 5.206 1.00 60.87 O
HETATM 2983 O HOH S 14 78.716 -40.614 -2.936 1.00 59.21 O
HETATM 2984 O HOH S 15 89.578 -46.058 -20.621 1.00 74.32 O
HETATM 2985 O HOH S 16 114.649 -30.692 -26.795 1.00 49.10 O
HETATM 2986 O HOH S 17 142.633 -40.619 -9.003 1.00 56.67 O
HETATM 2987 O HOH S 18 116.936 -44.379 -7.204 1.00 62.33 O
HETATM 2988 O HOH S 19 96.204 -29.452 4.025 1.00 56.31 O
HETATM 2989 O HOH S 21 115.084 -38.633 -20.997 1.00 70.64 O
HETATM 2990 O HOH S 22 89.198 -28.947 10.760 1.00 66.83 O
HETATM 2991 O HOH S 23 79.979 -40.035 -6.193 1.00 70.41 O
HETATM 2992 O HOH S 24 119.896 -43.181 -7.274 1.00 54.10 O
HETATM 2993 O HOH S 25 119.736 -51.368 1.322 1.00 56.96 O

TABLE 9-continued

DMXAA-hSTING$^{S162A/G230I/Q266I}$ complex

```
HETATM 2994  O    HOH S  26 137.748 -60.377   2.044 1.00  69.09    O
HETATM 2996  O    HOH S  28 130.865 -49.157  -1.725 1.00  56.51    O
HETATM 2997  O    HOH S  29 130.133 -53.659 -16.917 1.00  63.59    O
HETATM 2998  O    HOH S  30 142.632 -49.220 -17.348 1.00  53.78    O
HETATM 2999  O    HOH S  31 145.254 -49.889  -7.093 1.00  70.96    O
HETATM 3000  O    HOH S  32 147.065 -50.187 -11.753 1.00  78.79    O
HETATM 3002  O    HOH S  34 122.353 -45.352 -11.824 1.00  67.53    O
HETATM 3003  O    HOH S  35 111.792 -27.084 -21.446 1.00  48.46    O
HETATM 3004  O    HOH S  38 127.029 -40.326   5.304 1.00  57.55    O
HETATM 3005  O    HOH S  39 107.501 -23.962  -4.417 1.00  55.20    O
HETATM 3006  O    HOH S  40 102.641 -43.919  -7.277 1.00  61.10    O
HETATM 3008  O    HOH S  42 103.070 -51.992 -16.598 1.00  56.67    O
HETATM 3010  O    HOH S  45 101.908 -39.022   4.295 1.00  65.97    O
HETATM 3011  O    HOH S  46 107.409 -38.986   7.075 1.00  71.54    O
HETATM 3012  O    HOH S  47  86.638 -44.011   3.203 1.00  60.81    O
HETATM 3013  O    HOH S  49  98.622 -50.649  -8.050 1.00  74.15    O
HETATM 3014  O    HOH S  50 105.194 -49.981  -7.010 1.00  66.48    O
HETATM 3015  O    HOH S  51  79.285 -43.513  -9.134 1.00  57.17    O
HETATM 3016  O    HOH S  52  80.026 -42.362  -7.039 1.00  57.20    O
HETATM 3017  O    HOH S  54 108.687 -27.481   7.180 1.00  56.18    O
HETATM 3018  O    HOH S  55 103.638 -29.900  10.927 1.00  86.50    O
HETATM 3019  O    HOH S  56  97.777 -23.963  -5.954 1.00  59.40    O
HETATM 3021  O    HOH S  59  95.246 -27.230 -16.402 1.00  87.80    O
HETATM 3025  O    HOH S  63  82.517 -46.956 -18.723 1.00  85.91    O
HETATM 3026  O    HOH S  65 110.613 -30.055  -7.221 1.00  60.49    O
HETATM 3027  O    HOH S  66 146.283 -49.230  -9.611 1.00  99.22    O
HETATM 3028  O    HOH S  67 149.262 -52.143 -12.721 1.00  77.47    O
HETATM 3029  S    SO4 D   1 124.241 -63.786  -7.468 1.00 144.81    S
HETATM 3030  O1   SO4 D   1 125.494 -63.499  -6.774 1.00 140.19    O
HETATM 3031  O2   SO4 D   1 124.514 -64.163  -8.855 1.00 139.55    O
HETATM 3032  O3   SO4 D   1 123.552 -64.891  -6.798 1.00 145.34    O
HETATM 3033  O4   SO4 D   1 123.399 -62.594  -7.442 1.00 141.27    O
END
```

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of designing a stimulator of interferon genes (STING) modulator, comprising:
   providing the structural coordinates on a computer of a human STING$^{H232}$ C-terminal domain in a closed conformation according to Table 1;
   identifying a binding pocket comprising a potential interaction site, wherein the potential interaction site contains amino acid residues corresponding to Ser162, Tyr167, Arg238, Tyr240, and Glu260 of the human STING$^{H232}$ C-terminal domain, as set forth in SEQ ID NO. 1; and
   determining whether a moiety docks with the binding pocket and forms binding interactions with Ser162, Tyr167, Arg238, Tyr240, and Glu260, wherein a moiety that docks with the binding pocket and forms binding interactions with Ser162, Tyr167, Arg238, Tyr240, and Glu260 is a STING modulator structural element, wherein the binding interaction with Arg238 comprises a stacking interaction.

2. The method of claim 1, wherein whether a moiety docks with the binding pocket is determined by assessing one or more features selected from the group consisting of: spatial separation between the moiety and Ser162, Tyr167, Arg238, Tyr240, and Glu260; energy of interaction between the moiety and Ser162, Tyr167, Arg238, Tyr240, and Glu260, and combinations thereof.

3. The method of claim 1, wherein the step of determining whether a moiety docks with the binding pocket comprises a step of providing a new image of the moiety docked with the binding pocket.

4. The method of claim 3, further comprising a step of comparing the new image with a structure of a human $STING^{H232}$ C-terminal domain bound to a known modulator.

5. The method of claim 1, wherein the structural coordinates are obtained from a crystallographic structure determination of the human $STING^{H232}$ C-terminal domain crystallized as a homodimer having c[G(2',5')pA(3',5')p] bound in a binding pocket formed at the interface between the two human $STING^{H232}$ C-terminal domains in the homodimer.

6. The method of claim 1, wherein one of the binding interactions is a water-mediated hydrogen bond.

* * * * *

```
                         SEQUENCE LISTING

<160> NUMBER OF SEQ ID NOS: 103

<210> SEQ ID NO 1
<211> LENGTH: 379
<212> TYPE: PRT
<213> ORGANISM: Homo sapiens

<400> SEQUENCE: 1

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125
```

```
Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                    165                 170                 175

Ala Arg Ile Arg Thr Tyr Asn Gln His Tyr Asn Asn Leu Leu Arg Gly
                180                 185                 190

Ala Val Ser Gln Arg Leu Tyr Ile Leu Pro Leu Asp Cys Gly Val
            195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                    245                 250                 255

Cys Val Leu Glu Tyr Ala Thr Pro Leu Gln Thr Leu Phe Ala Met Ser
                260                 265                 270

Gln Tyr Ser Gln Ala Gly Phe Ser Arg Glu Asp Arg Leu Glu Gln Ala
            275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                    325                 330                 335

Glu Lys Glu Glu Val Thr Val Gly Ser Leu Lys Thr Ser Ala Val Pro
                340                 345                 350

Ser Thr Ser Thr Met Ser Gln Glu Pro Glu Leu Leu Ile Ser Gly Met
            355                 360                 365

Glu Lys Pro Leu Pro Leu Arg Thr Asp Phe Ser
    370                 375

<210> SEQ ID NO 2
<211> LENGTH: 378
<212> TYPE: PRT
<213> ORGANISM: Mus musculus

<400> SEQUENCE: 2

Met Pro Tyr Ser Asn Leu His Pro Ala Ile Pro Arg Pro Arg Gly His
1               5                   10                  15

Arg Ser Lys Tyr Val Ala Leu Ile Phe Leu Val Ala Ser Leu Met Ile
                20                  25                  30

Leu Trp Val Ala Lys Asp Pro Pro Asn His Thr Leu Lys Tyr Leu Ala
            35                  40                  45

Leu His Leu Ala Ser His Glu Leu Gly Leu Leu Leu Lys Asn Leu Cys
        50                  55                  60

Cys Leu Ala Glu Glu Leu Cys His Val Gln Ser Arg Tyr Gln Gly Ser
65                  70                  75                  80

Tyr Trp Lys Ala Val Arg Ala Cys Leu Gly Cys Pro Ile His Cys Met
                85                  90                  95

Ala Met Ile Leu Leu Ser Ser Tyr Phe Tyr Phe Leu Gln Asn Thr Ala
            100                 105                 110

Asp Ile Tyr Leu Ser Trp Met Phe Gly Leu Leu Val Leu Tyr Lys Ser
        115                 120                 125
```

```
Leu Ser Met Leu Leu Gly Leu Gln Ser Leu Thr Pro Ala Glu Val Ser
    130                 135                 140

Ala Val Cys Glu Glu Lys Lys Leu Asn Val Ala His Gly Leu Ala Trp
145                 150                 155                 160

Ser Tyr Tyr Ile Gly Tyr Leu Arg Leu Ile Leu Pro Gly Leu Gln Ala
                165                 170                 175

Arg Ile Arg Met Phe Asn Gln Leu His Asn Asn Met Leu Ser Gly Ala
            180                 185                 190

Gly Ser Arg Arg Leu Tyr Ile Leu Phe Pro Leu Asp Cys Gly Val Pro
        195                 200                 205

Asp Asn Leu Ser Val Val Asp Pro Asn Ile Arg Phe Arg Asp Met Leu
    210                 215                 220

Pro Gln Gln Asn Ile Asp Arg Ala Gly Ile Lys Asn Arg Val Tyr Ser
225                 230                 235                 240

Asn Ser Val Tyr Glu Ile Leu Glu Asn Gly Gln Pro Ala Gly Val Cys
                245                 250                 255

Ile Leu Glu Tyr Ala Thr Pro Leu Gln Thr Leu Phe Ala Met Ser Gln
            260                 265                 270

Asp Ala Lys Ala Gly Phe Ser Arg Glu Asp Arg Leu Glu Gln Ala Lys
        275                 280                 285

Leu Phe Cys Arg Thr Leu Glu Glu Ile Leu Glu Asp Val Pro Glu Ser
    290                 295                 300

Arg Asn Asn Cys Arg Leu Ile Val Tyr Gln Glu Pro Thr Asp Gly Asn
305                 310                 315                 320

Ser Phe Ser Leu Ser Gln Glu Val Leu Arg His Ile Arg Gln Glu Glu
                325                 330                 335

Lys Glu Glu Val Thr Met Asn Ala Pro Met Thr Ser Val Ala Pro Pro
            340                 345                 350

Pro Ser Val Leu Ser Gln Glu Pro Arg Leu Leu Ile Ser Gly Met Asp
        355                 360                 365

Gln Pro Leu Pro Leu Arg Thr Asp Leu Ile
    370                 375

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atatatgtcg acatgccata ctccaacctg catcca                              36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atatatgcgg ccgctcagat gaggtcagtg cggagt                              36

<210> SEQ ID NO 5
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 5
atatatgtcg acaccatgcc ccactccagc ctgca                              35

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atatatgcgg ccgctcaaga gaaatccgtg cggaga                             36

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccaccatgg attacaagga tgacgacgat aaggtcgaca tgccccactc cagcctgca    59

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaattccctt tttcacacac tgcag                                         25

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccagctgag atctctgca                                                19

<210> SEQ ID NO 10
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtggtttgt ccaaactcat cgagctcgat gcggccgcgg tcaagagaaa tccgtgcgga   60
ga                                                                  62

<210> SEQ ID NO 11
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 11
cccaatgtag tatgcccagg ccagcccg                                            28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgggctggcc tgggcatact acattggg                                            28

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggtcatac tacattgggg ccttgcggtt gatcttacca                               40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggtaagatc aaccgcaagg ccccaatgta gtatgaccag                               40

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgaccgtgct ggcatcaaga atgcggttta ttccaacag                                39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgttggaat aaaccgcatt cttgatgcca gcacggtcg                                39

<210> SEQ ID NO 17
<211> LENGTH: 40
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 17
tcgtagacgc tgttggaagc aacccgattc ttgatgccag                          40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggcatcaa gaatcgggtt gcttccaaca gcgtctacga                          40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagaatctcg tagacgctgg cggaataaac ccgattcttg                          40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caagaatcgg gtttattccg ccagcgtcta cgagattctg                          40

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggggtggcg tacgccagga tacagac                                       27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtctgtatcc tggcgtacgc cacccccc                                      27

<210> SEQ ID NO 23
<211> LENGTH: 27
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 23
cctggagtac gccgcccct tgcagac                                            27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtctgcaagg gggcggcgta ctccagg                                           27

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catggcaaac agggcctgca aggggggtgg                                        29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccaccccctt gcaggccctg tttgccatg                                         29

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agatatccga tgtaatatcc ccatgccagc ccatgggc                               38

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcccatgggc tggcatgggg atattacatc ggatatct                               38

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 29
gcccatgggc tggcatggac gtattacatc ggatatctg                           39

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagatatccg atgtaatacg tccatgccag cccatgggc                           39

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatgggctg gcatggttat attacatcgg atatc                              35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatatccgat gtaatataac catgccagcc catgg                              35

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gccaccatgg attacaagga tgacgacgat aaggtcgaca tgccccactc cagcctgca    59

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaattccctt tttcacacac tgcag                                         25

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 35
cccagctgag atctctgca                                              19

<210> SEQ ID NO 36
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgtggtttgt ccaaactcat cgagctcgat gcggccgcgg tcaagagaaa tccgtgcgga   60
ga                                                                 62

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tggcaggatc agccgcag                                               18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctgcggctga tcctgcca                                               18

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acagtccaat gggaggagaa tatacag                                     27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgtatattc tcctcccatt ggactgt                                     27

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 41
tggcgtactc caggacacag g                                          21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cctgtgtcct ggagtacgcc a                                          21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acagcgagaa gctgctgtca t                                          21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atgacagcag cttctcgctg t                                          21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tggcgtactc caggacacag                                            20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agcttctgga gaacgggcag                                            20

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgccatgtca caatacagtc aagct                                           25

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcctgctca agcctatcct c                                               21

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctgccccagc agaccggtga ccgtgctggc atcaaggatc                           40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gatccttgat gccagcacgg tcaccggtct gctggggcag                           40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctgccccagc agaccgctga ccgtgctggc atcaaggatc                           40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatccttgat gccagcacgg tcagcggtct gctggggcag                           40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 53
ctgccccagc agaccggtga ccatgctggc atcaaggatc                                40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gatccttgat gccagcatgg tcaccggtct gctggggcag                                40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctgccccagc agaacggtga ccgtgctggc atcaagaatc                                40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gattcttgat gccagcacgg tcaccgttct gctggggcag                                40

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtgacatggc aaacaaagtt atcaagggggg tggcgtactc c                             41

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggagtacgcc accccccttga taactttgtt tgccatgtca c                             41

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cccatgggct ggcatgggca tattacatcg gatatc                                    36

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gatatccgat gtaatatgcc catgccagcc catggg                                    36

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctgccccagc agaccattga ccatgctggc at                                        32

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atgccagcat ggtcaatggt ctgctggggc ag                                        32

<210> SEQ ID NO 63
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tccttgatgc cagcacggtc aatggtctgc tggggcag                                  38

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctgccccagc agaccattga ccgtgctggc atcaagga                                  38

<210> SEQ ID NO 65
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

```
gggctggcat ggtcatatta cgccggatat ctgcggct                              38
```

<210> SEQ ID NO 66
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

```
agccgcagat atccggcgta atatgaccat gccagccc                              38
```

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
ctggcatggt catattacat cagctatctg cggctgatcc                            40
```

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
ggatcagccg cagatagctg atgtaatatg accatgccag                            40
```

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
agaccggtga ccgtgctggc ctcaaggatc ggg                                   33
```

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
cccgatcctt gaggccagca cggtcaccgg tct                                   33
```

<210> SEQ ID NO 71
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
ggagtacgcc acccccttga taactttgtt tgccatgtca c                          41
```

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgacatggc aaacaaagtt atcaaggggg tggcgtactc c                     41

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgccaccccc ttgctgactt tgtttgccat                                  30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atggcaaaca aagtcagcaa gggggtggcg                                  30

<210> SEQ ID NO 75
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gtacgccacc cccttggtga ctttgtttgc catgt                            35

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acatggcaaa caaagtcacc aagggggtgg cgtac                            35

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
atgctgcccc agcaaaacgg cgaccgtgct gg                               32

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
ccagcacggt cgccgttttg ctggggcagc at          32

<210> SEQ ID NO 79
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
atgctgcccc agcaaaacgc cgaccgtgct gg          32

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
ccagcacggt cggcgttttg ctggggcagc at          32

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
tggagatgac ggagaagatg          20

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
ttggatggca aaggcagt          18

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
gtcaggttgc ctctgtctca          20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
tcagggaaga gtctggaaag                                         20

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
gcccacgtca aggagtattt cta                                     23

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
acacacttgg cggttccttc                                         20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
aggcataacg cactaggttt                                         20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
agctggagtc acagaaggag                                         20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
atcaagaagg tggtgaagca                                         20

<210> SEQ ID NO 90

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
agacaacctg gtcctcagtg t                                            21

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 91

His His His His His His
1               5

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggaccatagt cagagtggaa atcctaag                                     28

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cacttaaaca gcatctgctg gttgaag                                      27

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
accttaaccg ccttattagc ca                                           22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acattcaggg ctccatcaaa tc                                           22

<210> SEQ ID NO 96
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gctacctaca tacaattcca aacacatac                                              29

<210> SEQ ID NO 97
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gtacttaatt acatgttatt ccatgtacac tgaaaac                                     37

<210> SEQ ID NO 98
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ser Val Ala His Gly Leu Ala Trp Ser Tyr Tyr Ile Gly Tyr Leu Arg
1               5                   10                  15

Leu Ile Leu Pro Glu Leu Gln Ala Arg Ile Arg Thr Tyr Asn Gln His
            20                  25                  30

Tyr Asn Asn Leu Leu Arg Gly Ala Val Ser Gln Arg Leu Tyr Ile Leu
        35                  40                  45

Leu Pro Leu Asp Cys Gly Val Pro Asp Asn Leu Ser Met Ala Asp Pro
    50                  55                  60

Asn Ile Arg Phe Arg Asp Met Leu Pro Gln Gln Asn Ile Asp Arg Ala
65                  70                  75                  80

Gly Ile Lys Asn Arg Val Tyr Ser Asn Ser Val Tyr Glu Leu Leu Glu
                85                  90                  95

Asn Gly Gln Arg Ala Gly Thr Cys Val Leu Glu Tyr Ala Thr Pro Leu
            100                 105                 110

Gln Thr Leu Phe Ala Met Ser Gln Tyr Ser Gln Ala Gly Phe Ser Arg
        115                 120                 125

Glu Asp Arg Leu Glu Gln Ala Lys Leu Phe Cys Arg Thr Leu Glu Asp
    130                 135                 140

Ile Leu Ala Asp Ala Pro Glu Ser Gln Asn Asn Cys Arg Leu Ile Ala
145                 150                 155                 160

Tyr Gln Glu Pro Ala Asp Asp Ser Ser Phe Ser Leu Ser Gln Glu Val
                165                 170                 175

Leu Arg His Leu Arg Gln
            180

<210> SEQ ID NO 99
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 99

```
Ser Val Ala His Gly Leu Ala Trp Ser Tyr Tyr Ile Gly Tyr Leu Arg
1               5                   10                  15

Leu Ile Leu Pro Glu Leu Gln Ala Arg Ile Arg Thr Tyr Asn Gln His
            20                  25                  30

Tyr Asn Asn Leu Leu Arg Gly Ala Val Ser Gln Arg Leu Tyr Ile Leu
        35                  40                  45

Leu Pro Leu Asp Cys Gly Val Pro Asp Asn Leu Ser Met Ala Asp Pro
50                  55                  60

Asn Ile Arg Phe Leu Asp Lys Leu Pro Gln Gln Thr Ile Asp Arg Ala
65                  70                  75                  80

Gly Ile Lys Asp Arg Val Tyr Ser Asn Ser Ile Tyr Glu Leu Leu Glu
                85                  90                  95

Asn Gly Gln Arg Ala Gly Thr Cys Val Leu Glu Tyr Ala Thr Pro Leu
                100                 105                 110

Gln Thr Leu Phe Ala Met Ser Gln Tyr Ser Gln Ala Gly Phe Ser Arg
            115                 120                 125

Glu Asp Arg Leu Glu Gln Ala Lys Leu Phe Cys Arg Thr Leu Glu Asp
    130                 135                 140

Ile Leu Ala Asp Ala Pro Glu Ser Gln Asn Asn Cys Arg Leu Ile Ala
145                 150                 155                 160

Tyr Gln Glu Pro Ala Asp Asp Ser Ser Phe Ser Leu Ser Gln Glu Val
                165                 170                 175

Leu Arg His Leu Arg Gln
            180
```

<210> SEQ ID NO 100
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Ser Val Ala His Gly Leu Ala Trp Ala Tyr Tyr Ile Gly Tyr Leu Arg
1               5                   10                  15

Leu Ile Leu Pro Glu Leu Gln Ala Arg Ile Arg Thr Tyr Asn Gln His
            20                  25                  30

Tyr Asn Asn Leu Leu Arg Gly Ala Val Ser Gln Arg Leu Tyr Ile Leu
        35                  40                  45

Leu Pro Leu Asp Cys Gly Val Pro Asp Asn Leu Ser Met Ala Asp Pro
50                  55                  60

Asn Ile Arg Phe Leu Asp Lys Leu Pro Gln Gln Thr Gly Asp Arg Ala
65                  70                  75                  80

Gly Ile Lys Asp Arg Val Tyr Ser Asn Ser Ile Tyr Glu Leu Leu Glu
                85                  90                  95

Asn Gly Gln Arg Ala Gly Thr Cys Val Leu Glu Tyr Ala Thr Pro Leu
                100                 105                 110

Ile Thr Leu Phe Ala Met Ser Gln Tyr Ser Gln Ala Gly Phe Ser Arg
            115                 120                 125

Glu Asp Arg Leu Glu Gln Ala Lys Leu Phe Cys Arg Thr Leu Glu Asp
    130                 135                 140

Ile Leu Ala Asp Ala Pro Glu Ser Gln Asn Asn Cys Arg Leu Ile Ala
145                 150                 155                 160
```

Tyr Gln Glu Pro Ala Asp Asp Ser Ser Phe Ser Leu Ser Gln Glu Val
                165                 170                 175

Leu Arg His Leu Arg Gln
            180

<210> SEQ ID NO 101
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ser Val Ala His Gly Leu Ala Trp Ala Tyr Tyr Ile Gly Tyr Leu Arg
1               5                   10                  15

Leu Ile Leu Pro Glu Leu Gln Ala Arg Ile Arg Thr Tyr Asn Gln His
                20                  25                  30

Tyr Asn Asn Leu Leu Arg Gly Ala Val Ser Gln Arg Leu Tyr Ile Leu
            35                  40                  45

Leu Pro Leu Asp Cys Gly Val Pro Asp Asn Leu Ser Met Ala Asp Pro
50                  55                  60

Asn Ile Arg Phe Leu Asp Lys Leu Pro Gln Gln Thr Ile Asp Arg Ala
65                  70                  75                  80

Gly Ile Lys Asp Arg Val Tyr Ser Asn Ser Ile Tyr Glu Leu Leu Glu
                85                  90                  95

Asn Gly Gln Arg Ala Gly Thr Cys Val Leu Glu Tyr Ala Thr Pro Leu
            100                 105                 110

Ile Thr Leu Phe Ala Met Ser Gln Tyr Ser Gln Ala Gly Phe Ser Arg
        115                 120                 125

Glu Asp Arg Leu Glu Gln Ala Lys Leu Phe Cys Arg Thr Leu Glu Asp
130                 135                 140

Ile Leu Ala Asp Ala Pro Glu Ser Gln Asn Asn Cys Arg Leu Ile Ala
145                 150                 155                 160

Tyr Gln Glu Pro Ala Asp Asp Ser Ser Phe Ser Leu Ser Gln Glu Val
                165                 170                 175

Leu Arg His Leu Arg Gln
            180

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Asp Arg Val Tyr
1               5

<210> SEQ ID NO 103
<211> LENGTH: 379
<212> TYPE: PRT
<213> ORGANISM: Homo sapiens

<400> SEQUENCE: 103

Met Pro His Ser Ser Leu His Pro Ser Ile Pro Cys Pro Arg Gly His
1               5                   10                  15

-continued

```
Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Leu Asn Gly Val Cys
        50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
            130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
            195                 200                 205

Pro Asp Asn Leu Ser Met Ala Asp Pro Asn Ile Arg Phe Leu Asp Lys
            210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
            275                 280                 285

Lys Leu Phe Cys Arg Thr Leu Glu Asp Ile Leu Ala Asp Ala Pro Glu
            290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
            355                 360                 365

Glu Lys Pro Leu Pro Leu Arg Thr Asp Phe Ser
            370                 375
```